United States Patent
Chotani et al.

(10) Patent No.: US 9,752,161 B2
(45) Date of Patent: Sep. 5, 2017

(54) METHODS OF PRODUCING ISOPRENE AND A CO-PRODUCT

(71) Applicants: Danisco US Inc., Palo Alto, CA (US); The Goodyear Tire & Rubber Company, Akron, OH (US)

(72) Inventors: Gopal K. Chotani, Cupertino, CA (US); Joseph C. McAuliffe, Sunnyvale, CA (US); Caroline M. Peres, Palo Alto, CA (US); Karl J. Sanford, Cupertino, CA (US); Derek H. Wells, Palo Alto, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 241 days.

(21) Appl. No.: 14/148,332

(22) Filed: Jan. 6, 2014

(65) Prior Publication Data
US 2014/0127770 A1 May 8, 2014

Related U.S. Application Data

(62) Division of application No. 12/650,332, filed on Dec. 30, 2009, now Pat. No. 8,895,288.

(60) Provisional application No. 61/141,652, filed on Dec. 30, 2008, provisional application No. 61/187,934, filed on Jun. 17, 2009.

(51) Int. Cl.
| | | |
|---|---|---|
| *C12P 5/02* | (2006.01) | |
| *C12P 7/06* | (2006.01) | |
| *C12P 5/00* | (2006.01) | |
| *C12P 7/18* | (2006.01) | |
| *C12N 9/88* | (2006.01) | |

(52) U.S. Cl.
CPC ............... *C12P 5/007* (2013.01); *C12N 9/88* (2013.01); *C12P 7/06* (2013.01); *C12P 7/065* (2013.01); *C12P 7/18* (2013.01); *Y02E 50/17* (2013.01)

(58) Field of Classification Search
CPC ............. C12P 5/007; C12P 7/06; C12P 7/065
See application file for complete search history.

(56) References Cited

U.S. PATENT DOCUMENTS

| | | |
|---|---|---|
| 4,570,029 A | 2/1986 | Kulprathipanja et al. |
| 4,683,202 A | 7/1987 | Mullis |
| 4,703,007 A | 10/1987 | Mulholland et al. |
| 4,740,222 A | 4/1988 | Mehra |
| 5,849,970 A | 12/1998 | Fall et al. |
| 5,874,276 A | 2/1999 | Fowler et al. |
| 6,022,725 A | 2/2000 | Fowler et al. |
| 6,106,888 A | 8/2000 | Dale et al. |
| 6,176,176 B1 | 1/2001 | Dale et al. |
| 6,268,328 B1 | 7/2001 | Mitchinson et al. |
| 7,132,527 B2 | 11/2006 | Payne et al. |
| 7,241,587 B2 | 7/2007 | Dodge et al. |
| 7,262,041 B2 | 8/2007 | Baldwin et al. |
| 7,371,558 B2 | 5/2008 | Cervin et al. |
| 8,895,288 B2 | 11/2014 | Chotani et al. |
| 2008/0038805 A1 | 2/2008 | Melis |
| 2008/0176302 A1 | 7/2008 | Cervin et al. |
| 2008/0293119 A1 | 11/2008 | Gibson et al. |
| 2009/0142843 A1 | 6/2009 | Cervin et al. |
| 2009/0203102 A1 | 8/2009 | Cervin et al. |
| 2011/0046422 A1 | 2/2011 | McAuliffe et al. |
| 2011/0159557 A1 | 6/2011 | Beck et al. |

FOREIGN PATENT DOCUMENTS

| | | |
|---|---|---|
| EP | 0 215 594 A2 | 3/1987 |
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 0 137 280 B1 | 3/1992 |
| WO | WO-95/04134 | 2/1995 |
| WO | WO-96/35796 | 11/1996 |
| WO | WO-98/02550 A2 | 1/1998 |

(Continued)

OTHER PUBLICATIONS

Akhtar, M.K. et al. (2008). "Deletion of iscR stimulates recombinant Clostridia! Fe/Fe hydrogenase activity and $H_2$-accumulation in *Escherichia coli* BL21(DE3)," *Appl. Microbiol. Biotechnol.*, 78(5):853-862.

Alexopoulos, C.J. (1962). Introductory Mycology, Wiley: New York, NY, pp. ix-x, (Table of Contents Only).

Anderson, M.S. et al. (1989). "Isopentenyl Diphosphate: Dimethylallyl Diphosphate Isomerare. An Improved Purification of the Enzyme and Isolation of the Gene From *Saccharomyces cerevisia*," *J. Biol. Chem.* 264(32):19169-19175.

Aon, J. et al. (2008). "Suppressing Posttranslational Gluconoylation of Heterologous Proteins by Metabolic Engineering of *Escherichia coli*," *Applied and Environmental Microbiology*, 74(4):950-958.

Ausubel, F.M. et al. eds. (1987). Current Protocols in Molecular Biology, Supplement 30, section 7.7.18.

(Continued)

*Primary Examiner* — Rebecca Prouty
(74) *Attorney, Agent, or Firm* — Mintz Levin Cohn Ferris Glovsky and Popeo, P.C.

(57) ABSTRACT

The invention features methods producing isoprene and a co-product, such as ethanol, 1,3-propanediol, or hydrogen from cultured cells. The invention also provides compositions that include these cultured cells. The invention provides compositions comprising isoprene and ethanol, isoprene and 1,3-propanediol, and isoprene and hydrogen. Additionally, the invention provides methods of co-producing isoprene and ethanol, isoprene and 1,3-propanediol, and isoprene and hydrogen by culturing cells under conditions suitable for co-production of isoprene and ethanol, isoprene and 1,3-propanediol, and isoprene and hydrogen.

32 Claims, 380 Drawing Sheets

(56) References Cited

FOREIGN PATENT DOCUMENTS

| | | |
|---|---|---|
| WO | WO-98/02550 A3 | 1/1998 |
| WO | WO-2004/033646 A2 | 4/2004 |
| WO | WO-2004/033646 A3 | 4/2004 |
| WO | WO-2005/001036 A2 | 1/2005 |
| WO | WO-2005/001036 C1 | 1/2005 |
| WO | WO-2007/089901 A2 | 8/2007 |
| WO | WO-2007/089901 A3 | 8/2007 |
| WO | WO-2007/089901 C1 | 8/2007 |
| WO | WO-2007/140339 A2 | 12/2007 |
| WO | WO-2007/140339 A3 | 12/2007 |
| WO | WO-2007/140339 A8 | 12/2007 |
| WO | WO-2008/003078 A2 | 1/2008 |
| WO | WO-2008/003078 A3 | 1/2008 |
| WO | WO-2008/003078 A8 | 1/2008 |
| WO | WO-2008/130437 A2 | 10/2008 |
| WO | WO-2008/130437 A3 | 10/2008 |
| WO | WO-2008/137092 A2 | 11/2008 |
| WO | WO-2008/137092 A3 | 11/2008 |
| WO | WO-2010/031076 A2 | 3/2010 |
| WO | WO-2010/031076 A3 | 3/2010 |
| WO | WO-2010/078457 A2 | 7/2010 |
| WO | WO-2010/078457 A3 | 7/2010 |

OTHER PUBLICATIONS

Baba, T. et al. (2006). "Construction of *Escherichia coli* K-12 In-Frame, Single-Gene Knockout Mutants: The Keio Collection," *Mo. Syst. Biol.*, 2(2006.2008):1-11.

Bellion, E. et al. (1993). "Methylamine Utilization in Yeast and Bacteria: Studies Using in vivo NMR," Chapter 32 in Microbial Growth $C_1$ Compounds Muerrell, J.C. et al. eds, Intercept Ltd: Andover, UK, pp. 415-432.

Bennett, J.W. et al. eds. (1991). "Gene Cloning and Analysis," Chapter 3 in More Gene Manipulations in Fungi Academic Press, San Diego, CA pp. 70-76.

Boel, E. et al. (1984). "Two Different Types of Intervening Sequences in the Glucoamylase Gene from *Aspergillus niger*," *The EMBO Journal* 3(7):1581-1585.

Bouvier, F. et al. (2005). "Biogenesis, Molecular Regulation and Function of Plant Isoprenoids," *Progress in Lipid Res.* 44:357-429.

Brown, L. et al. (1996). "Enyzymatic Saccharification of Lignocellulosic Biomass," *NREL standard assay method Lap-009*.

Bunge, M. et al. (2008). "On-Line Monitoring of Microbial V9olatile Metabolites by Proton Transfer Reaction-Mass Spectrometry," *Applied and Environmental Microbiology*, 74(7):2179-2186.

Burgdorf, T. et al. (2005). "[NiFe]-hydrogenases of *Ralstonia eutropha* H16: Modular Enzymes for Oxygen-Tolerant Biological Hydrogen Oxidation," *J. Mol. Microbiol. Biotechnol.* 10(2-4):181-196.

Campbell, E.I. et al. (1989). "Improved Transformation Efficiency of *Aspergillus niger* Using the Homologus niaD Gene for Nitrate Reductase," *Curr. Genet.* 16:53-56.

Cao, Q-N et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.

Chittibabu, G. et al. (2006). "Feasibility Studies on the Fermentative Hydrogen Production by Recombinant *Escherichia coli* BL-21," *Process Biochem.* 41(3):682-688.

Chou, C.J. et al. (2008). "Hydrogenesis in Hyperthermophilic Microorganisms: Implications for Biofuels," *Metabol. Eng.*, 10:394-404.

Conway, T. et al. (1994). "Expression Vector for *Zymomonas Mobilis*," *Appl. Environ. Microbiol.*, 53(2):235-241.

Datsenko, K. et al. (2000). "One-Step Inactivation of Chromosomal Genes in *Escherichia coli* K-12 Using PCR Products," *PNAS*, 97(12):6640-6645.

Dhe-Paganon, S. et al. (1994). "Mechanism of Mevalonate Pyrophosphate Decarboxylase: Evidence for a Carbocationic Transition State," *Biochemistry* 33(45):13355-13362.

Finkelstein, D.B. (1992). "Transformation," Chapter 6 in Biotechnology of Filamentous Fungi Butterworth-Heinemann: Boston, MA, pp. 113-156.

GenBank Accession No. AAQ16588, 2005.

GenBank Accession No. AAQ84170, last updated on Feb. 15, 2005, located at <http://www.ncbi.nlm.nih.gov/protein/AAQ84170>, last visited on Dec. 22, 2011, 2 pages.

GenBank Accession No. ACD70404, 2008.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30934014>, last visited on Jun. 2, 2010, 2 pages.

GenBank Accession No. AY315591, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

GenBank Accession No. BAD98243, 2007.

GenBank Accession No. CAC35696, last updated Apr. 15, 2005, located at <http://www.ncbi.nlm.nih.gov/protein/CAC35696>, last visited on Nov. 1, 2011, 2 pages.

GenBank Accession No. CAJ29303, 2007.

GenBank Accession No. CAL69918, 2008.

GenBank Accession No. D86235, 1997.

GenBank Accession No. NC_003901.1, last updated May 11, 2011, located at <http://www.ncbi.nlm.nih.gov/nuccore/NC_003901.1>, last visited on Oct. 27, 2011, 360 pages.

Gerhardt, P. et al. eds. (1994). Methods for General and Molecular Bacteriology, American Society for Microbiology: Washington, D.C., p. v, (Table of Contents Only).

Goedegebuur, F. et al. (2002). "Cloning and Relational Analysis of 15 Novel Fungal Endoglucanases form Family 12 Glycosyl Hydrolase," *Curr. Genet.* 41:89-98.

Gottschalk, G. (1986). Bacterial Metabolism, Second Edition, Springer Verlag: New York, NY, pp. xi-xiii, (Table of Contents Only).

Grawert, T. et al. (2004, e-pub. Sep. 21, 2004). "IspH Protein of *Escherichia coli*: Studies on Iron-Sulfur Cluster Implementation and Catalysis," *Journal American Chemistry Society* 126:12847-12855.

Greenberg, J.P. et al. (1993). "Sub-Parts Per Billion Detection of Isoprene Using a Reduction Gas Detector with a Portable Gas Chormatograph," *Atmos. Environ.* 27A(16):2689-2692.

Hale, W.G. et al. (1991). The Harper Collins Dictionary of Biology, Ehrlich, E. ed., Harper Perennial: New York, NY, 2 pages.

Harkki, A. et al. (1989). "A Novel Fungal Expression System: Secretion of Active Calf Chymosin From the Filamentous Fungus *Trichoderma ressei*," *Bio. Technol.*7:596-603.

Harkki, A. et al. (1991). "Genetic Engineering of *Trichoderma* to Produce Strains with Novel Cellulase Profiles," *Enzyme Microb. Technol.* 13:277-233.

Hedl, M. et al. (2002). "*Enterococcus faecalis* Acetoacetyl-Coenzyme A Thiolase/3-Hydroxy-3-Methylglutaryl-Coenzyme A Reductase, A Dual-Function Protein of Isopentenyl Diphosphate Biosynthesis," *J. Bacteriol.* 184(8):2116-2122.

Hoeffler, J-F et al. (2002). "Isoprenoid Biosynthesis via the Methylerythritol Phosphate Pathway. Mechanistic Investigations of the 1-Deoxy-$_D$-Xylulose 5-Phosphate Reductiosimerase," *Eur. J. Biochem.* 269:4446-4457.

Hunter, B.K. (1985). "Formaldehyde Metabolism by *Escherichia coli*. Carbon and Solvent Deuterium Incoproration into Glycerol, 1,2-Propanediol, and 1,3-Propanediol," *Biochemistry* 24(15):4148-4155.

Ilmen, M. et al. (1997). "Regulation of Cellulase Gene Expression in the Filamentous Fungus *Trichoderma reesei*," *Appl. Environ. MicrobioL* 63(4):1298-1306.

(56) References Cited

OTHER PUBLICATIONS

Ingram, L. et al. (1987). "Genetic Engineering of Ethanol Production in *Escherichia coli*," *Applied and Environ. Microbio.*, 53(10):2420-2425.

Innis, M.A. et al. (1985). "Expression, Glycosylation, and Secretion of an Aspergillus Glucoamylase by *Saccharomyces cerevisiae*," *Science* 228:21-26.

International Search Report mailed on Sep. 10, 2010, for PCT Patent Application No. PCT/US2009/069862, filed on Dec. 30, 2009, 7 pages.

Jeon, YJ et al. (2005). "Over-Expression of Xylulokinase in a Xylose-Metabolising Recombinant Strain of *Zymomonas Mobilis*," *FEMS Microbiol. Letters*, 244:85-92.

Julsing, M.K. et al. (2007). "Functional Analysis of Genes Involved in the Biosynthesis of Isoprene in *Bacillus subtilis*," *Applied MicrobioL Biotechno*l.75:1377-1384.

Kelly, J.M. et al. (1985). "Transformation of Aspergillus niger by the amdS Gene of *Asperfillus nidulans*," *The EMBO Journal* 4(2):475-479.

King, P. et al. (2006). "Functional Studies of [FeFe] Hydrogenase Maturation in an *Escherichia coli* Biosynthetic System," *J. Bacteriol.*, 188(6):2163-2172.

Kinghorn, J.R. et al. (1992). Applied Molecular Genetics of Filamentous Fungi, Blackie Academic Professional and Chapman and Hall: London, 3 pages, (Table of Contents Only).

Koga, Y. et al. (2007). "Biosynthesis of Ether-Type Polar Lipids in Archaea and Evolutionary Considerations," *Microbiology and Molecular Biology Reviews* 71(1):97-120.

Kovach, M.E. et al. (1994). "pBBR1MCS: A Broad-Host-Range Cloning Vector," *Biotechniques*, 16(5):800-802.

Kovach, M.E. et al. (1995). "Four New Derivatives of The Broad-Host-Range Cloning Vector pBBR1MCS, Carrying Different Antibiotic-Resistance Cassettes," *Gene* 166:175-176.

Kreigler, M. (1990). Gene Transfer and Expression: A Laboratory Manual, W.H. Freeman and Company: New York, NY, pp. vii-x, (Table of Contents Only.).

Ladygina, N. et al. (2006). "A Review on Microbial Synthesis of Hydrocarbons," *Process Biochemistry* 41:1001-1014.

Luttgen, H. et al. (2000). "Biosynthesis of Terpenoids: YchB Protein *Escherichia coli* Phosphorylates the 2-Hydroxy Group of 4-Diphosphocytidy1-2C-Methyl-$_D$-Erythritol," *PNAS* 97(3)1 062-1067.

Maeda, T. et al. (2007) "Enhanced Hydrogen Production From Glucose by Metabolically Engineered *Escherichia coli*," *Appl. MicrobioL*, 77(4):879-890.

Maness, P.C. et al. (2002) "Characterization of the Oxygen Tolerance of a Hydrogenase Linked to a Carbon Monoxide Oxidation Pathway in *Rubrivivax gelatinosus*," *Appl. Environ. MicrobioL*, 68(6):2633-2636.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Nagy, L.E. et al. (2007). "Application of Gene-Shuffling for the Rapid Generation of Novel [FeFe]-Hydrogenase Libraries," *BiotechnoL Letts.*, 29(3):421-430.

Neidhardt, F.C. et al. (1974). "Culture Medium for Enterobacteria," *J. Bacteriology* 119(3):736-747.

Nevalainen, K.M.H. et al. (1992). "The Molecular Biology of *Trichoderma* and its Application to the Expression of Both Homologous and Heterologous Genes," Chapter 6 in Molecular Industrial Mycology, Systems and Applications for Filamentous Fungi, Leong, S.A. et al. eds., Marcel Dekker Inc.: New York, NY, pp. 129-148.

NFPA, (2008) edition. 69 Standard on Explosion Prevention Systems.

Nunberg, J.H. et al. (1984). "Molecular Cloning and Characterization of the Glucoamylase Gene of *Aspergillus awamori*," *Mol. Cell. Biol.* 4(11):2306-2315.

Oulmouden, A. et al. (1991). "Nucleotide Sequence of the ERG12 Gene of *Saccharomyces cerevisiae* Encoding Mevalonate Kinase," *Curr. Genet.* 19:9-14.

Penttila, M. et al. (1987). "A Versatile Transformation System for the Cellulolytic Filamentous Fungus *Trichoderma reesei*," *Gene* 61:155-164.

Perego, M. (1993). "Integrational Vectors for Genetic Manipulation in *Bacillus subtilis*," Chapter 42 in Bacillus subtilis and Other Gram-Positive Bacteria: Biochemistry, Physiology, and Molecular Genetics, Sonenshein et al. eds., American Society for Microbiology: Washington, D.C., pp. 615-624.

Pourquie, J. et al. (1988). "Scale Up of Cellulose Production and Utilization," in Biochemistry and Genetics of Cellulose Degradation Aubert, J.-P. et al. eds., Academic Press: San Diego, CA, pp. 71-86.

Rohdich, F. et al. (1999). "Cytidine 5'-Triphosphate-Dependent Biosynthesis of Isoprenoids: YgbP Protein of *Escherichia coli* Catalyzes the Formation of 4-Diphosphocytidyl-2-C-Methylerythritol," *PNAS* 96(21):11758-11763.

Rohdich, F. et al. (2000). "Biosynthesis of Terpenoids: 4-Diphosphocytidyl-2C-Methyl-$_D$-Erythritol Synthase of *Arabidopsis thaliana*," *PNAS* 97(12):6451-6456.

Sambrook, J. et al. (1989). Molecular Cloning: A Laboratory Manual, 2nd edition, Cold Spring Harbor Laboratory Press: New York, NY, pp. xi-xxxviii (Table of Contents Only).

Sasaki K. et al. (2005). "Gene Expression and Characterization of Isoprene Synthase From *Populus alba*," *FEBS Letters*, 579(11):2514-2518.

Schnitzler, J.-P. et al. (2005, e-pub. Jul. 29, 2005). "Biochemical Properties of Isoprene Synthase in Poplar (*Populus x canescens*)," *Planta* 222(5):777-786.

Seedorf, H. et al. (2008). "The Genome of Clostridium Kluyveri, A Strict Anaerobe With Unique Metabolic Features," *PNAS*, 105(6):2128-2133.

Sharkey, T.D. et al. (2005). "Evolution of the Isoprene Biosynthetic Pathway in Kudzu," *Plant Physiology* 137:700-712.

Sheir-Neiss, G. et al. (1984). "Characterization of the Secreted Ceullulases of *Trichoderma ressei* Wild Type and Mutants During Controlled Fermentations," *AppL Microbiol. Biotechnol.* 20(1):46-53.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (1995). "Characterization of Aspen Isoprene Synthase, an Enzyme Responsible for Leaf Isoprene Emission to the Atmosphere," *The Journal of Biological Chemistry* 270(22):13010-13016.

Sonenshein, A. et al. (ed.), "Bacillus subtilis and other gram-positive bacteria: biochemistry, physiology, and molecular genetics," American Society for Microbiology, Washington, D.C.

Sprenger, G.A. et al. (1997). "Identification of a Thiamin-Dependent Synthase in *Escherichia coli* Required for the Formation of the 1-Deoxy-$_D$-Xylulose 5-Phosphate Precursor to Isoprenoids, Thiamin, and Pyridoxol," *PNAS* 94:12857-12862.

Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.

Sutherlin, A. et al. (2002). "*Enterococcus faecalis* 3-Hydroxy-3-Methylglutaryl Coenzyme A Synthase, an Enzyme of Isopentenyl Diphosphate Biosynthesis," *J. Bacteriol.* 184(15):4065-4070.

Swings, J. et al. (1977). "The Biology of Zymomonas," *Bacteriol. Reviews*, 41(1):1-46.

Teymouri, F. et al. (2005, e-pub. Feb. 24, 2005). "Optimization of the Ammonia Fiber Explosion (AFEX) Treatment Parameters for Enzymeatic Hydrolysis of Corn Stover," *Bioresource Technology* 96:2014-2018.

Tsay, Y.H. et al. (1991). "Cloning and Characterization of ERG8, an Essential Gene of *Saccharomyces cerevisiae* That Encodes Phosphomevalonate Kinase," *Mol. Cell Biol.* 11(2):620-631.

(56) References Cited

OTHER PUBLICATIONS

Van Den Hondel, C. et al. (1991). "Heterologous Gene Expression in Filamentous Fungi," Chapter 18 in *More Gene Manipulations in Fungi* Bennet, J.W. et al. eds., Academic Press, Inc.: San Diego, CA, pp. 396-428.

Vardar-Schara, G. et al. (2008). "Metabolically Engineered Bacteria for Producing Hydrogen Via Fermentation," *Microbial Biotechnology*, 1(2):107-125.

Wagner, W.P. et al. (1999). "Three Distinct Phases of Isoprene Formation During Growth and Sporulation of Bacillus Subtilis," *Journal of Bacteriology*, 181(15):4700-4703.

Ward, M. et al. (1993). "Use of Aspergillus Overproducing Mutants, Cured for Integrated Plasmid, to Overproduce Heterologous Proteins," *AppL Microbiol. Biotechnol.*, 39(6):738-743.

Withers, S.T. et al. (Oct. 2007, e-pub. Aug. 10, 2007). "Identification of Isopentenol Biosynthetic from *Bacillus subtilis* by a Screening Method Based on Isorpenoid Precursor Toxicity," *AppL Environ Microbiol*. 73(19):6277-6283.

Woodward, J. et al. (2000). "Enzymatic Production of Biohydrogen," *Nature*, 405(6790):1014-1015.

World-wide web at "expasy.org", Swiss Institute of Bioinformatics Swiss-Prot group CMU—1 rue Michel Servet CH-1211 Geneva 4, Switzerland, 2012.

World-wide web at "fgsc.net" "Fungal Genetics Stock Center Catalogue of Strains," FGSC, 2006.

World-wide web at genome.jp/kegg/pathway/map/map00100.html, 2012.

Yamada, K. et al. (1989). "Production of Glycerol from Methanol by a Mutant Strain of *Candida boidinii* No. 2201," *Agric. Biol. Chem.* 53(2):541-543.

Yelton, M.M. et al. (Mar. 1984). "Transformation of *Aspergillus nidulans* by Using a trpC Plasmid," *PNAS* 81:1470-1474.

Yoshida, A. et al. (2007). "Efficient Induction of Formate Hydrogen Lyase of Aerobically Grown *Escherichia coli* in a Three-Step Biohydrogen Production Process," *Appl. Microbiol Biotechnol*, 74:754-760.

Zabetakis, M.G. (1965). "Bulletin 627—Flammability Characteristics of Combustible Gases and Vapors," published by the former US Bureau of Mines.

Zepeck, F. et al. (2005, e-pub. Oct. 14, 2005). "Biosynthesis of Isoprenoids. Purification and Properties of IspG Protein from *Escherichia coli*,"*J. Org. Chem.* 70:9168-9174.

Figure 1

1-
*atg*tgtgcgacctcttctcaatttactcagattaccgagcataattcccgtcgttccgcaaactatcagccaaa
cctgtggaatttcgaattcctgcaatccctggagaacgacctgaaagtggaaaagctggaggagaaagc
gaccaaactggaggaagaagttcgctgcatgatcaaccgtgtagacacccagccgctgtccctgctgga
gctgatcgacgatgtgcagcgcctgggtctgacctacaaatttgaaaaagacatcattaaagccctggaa
aacatcgtactgctggacgaaaacaaaaagaacaaatctgacctgcacgcaaccgctctgtctttccgtct
gctgcgtcagcacggtttcgaggttctcaggatgttttgagcgtttcaaggataaagaaggtggtttcagcg
gtgaactgaaaggtgacgtccaaggcctgctgagcctgatgaagcgtcttacctgggttcgagggtgag
aacctgctggaggaggcgcgtaccttttccatcacccacctgaagaacaacctgaaagaaggcattaata
ccaaggttgcagaacaagtgagccacgccctggaactgccatatcaccagcgtctgcaccgtctggagg
cacgttggttcctggataaatacgaaccgaaagaaccgcatcaccagctgctgctggagctggcgaagct
ggattttaacatggtacagaccctgcaccagaaagagctgcaagatctgtcccgctggtggaccgagatg
ggcctggctagcaaactggattttgtacgcgaccgcctgatggaagtttatttctgggcactgggtatggcgc
cagacccgcagtttggtgaatgtcgcaaagctgttactaaaatgtttggtctggtgacgatcatcgatgacgt
gtatgacgtttatggcactctggacgaactgcaactgttcaccgatgctgtagagcgctgggacgttaacgct
attaacaccctgccggactatatgaaactgtgtttcctggcactgtacaacaccgttaacgacacgtcctattc
tattctgaaagagaaaggtcataacaacctgtcctatctgacgaaaagctggcgtgaactgtgcaaagcct
ttctgcaagaggcgaaatggtccaacaacaaaattatcccggctttctccaagtacctggaaaacgccag
cgtttcctcctccggtgtagcgctgctggcgccgtcttacttttccgtatgccagcagcaggaagacatctccg
accacgcgctgcgttccctgaccgacttccatggtctggtgcgttctagctgcgttatcttccgcctgtcaac
gatctggccacctctgcggcggagctggaacgtggcgagactaccaattctatcattagctacatgcacga
aaacgatggtaccagcgaggaacaggcccgcgaagaactgcgtaaactgatcgacgccgaatggaaa
aagatgaatcgtgaacgcgttagcgactccaccctgctgcctaaagcgttcatggaaatcgcagttaacat
ggcacgtgtttcccactgcacctaccagtatggcgatggtctgggtcgcccagactacgcgactgaaaacc
gcatcaaactgctgctgattgaccctttcccgattaaccagctgatgtatgtc
taa*ctgcag*
(SEQ ID NO:1)

Figure 3A 1-
gtttgacagcttatcatcgactgcacggtgcaccaatgcttctggcgtcaggcagccatcggaagctgtggtatg
gctgtgcaggtcgtaaatcactgcataattcgtgtcgctcaaggcgcactcccgttctggataatgtttttgcgcc
gacatcataacggttctggcaaatattctgaaatgagctgttgacaattaatcatccggctcgtataatgtgtgga
attgtgagcggataacaatttcacacaggaaacagcgccgctgagaaaaagcgaagcggcactgctcttta
acaatttatcagacaatctgtgtgggcactcgaccggaattatcgattaactttattattaaaaattaaagaggtat
atattaatgtatcgattaaata<u>aggagg</u>aataaaccATGtgtgcgacctcttctcaatttactcagattaccgag
cataattcccgtcgttccgcaaactatcagccaaacctgtggaatttcgaattcctgcaatccctggagaacga
cctgaaagtggaaaagctggaggagaaagcgaccaaactggaggaagaagttcgctgcatgatcaaccgt
gtagacacccagccgctgtccctgctggagctgatcgacgatgtgcagcgcctgggtctgacctacaaatttg
aaaaagacatcattaaagccctggaaaacatcgtactgctggacgaaaacaaaagaacaaatctgacct
gcacgcaaccgctctgtctttccgtctgctgcgtcagcacggtttcgaggtttctcaggatgttttgagcgtttcaa
ggataaagaaggtggtttcagcggtgaactgaaaggtgacgtccaaggcctgctgagcctgtatgaagcgtct
tacctgggtttcgagggtgagaacctgctggaggaggcgcgtaccttttccatcacccacctgaagaacaacc
tgaaagaaggcattaataccaaggttgcagaacaagtgagccacgccctggaactgccatatcaccagcgt
ctgcaccgtctggaggcacgttggttcctggataaatacgaaccgaaagaaccgcatccagctgctgctg
gagctggcgaagctggattttaacatggtacagaccctgcaccagaaagagctgcaagatctgtcccgctgg
tggaccgagatgggcctggctagcaaactggattttgtacgcgaccgcctgatggaagtttattctgggcactg
ggtatggcgccagacccgcagtttggtgaatgtcgcaaagctgttactaaaatgtttggtctggtgacgatcatc
gatgacgtgtatgacgtttatggcactctggacgaactgcaactgttcaccgatgctgtagagcgctgggacgtt
aacgctattaacaccctgccggactatatgaaactgtgtttcctggcactgtacaacaccgttaacgacacgtc
ctattctattctgaaagagaaaggtcataacaacctgtcctatctgacgaaaagctggcgtgaactgtgcaaag
cctttctgcaagaggcgaaatggtccaacaacaaaattatcccggctttctccaagtacctggaaaacgccag
cgtttcctcctccggtgtagcgctgctggcgccgtcttacttttccgtatgccagcagcaggaagacatctccgac
cacgcgctgcgttccctgaccgacttccatggtctggtgcgttctagctgcgttatcttccgcctgtgcaacgatct
ggccacctctgcggcggagctggaacgtggcgagactaccaattctatcattagctacatgcacgaaaacga
tggtaccagcgaggaacaggcccgcgaagaactgcgtaaactgatcgacgccgaatggaaaaagatgaa
tcgtgaacgcgttagcgactccaccctgctgcctaaagcgttcatggaaatcgcagttaacatggcacgtgtttc
ccactgcacctaccagtatggcgatggtctgggtcgcccagactacgcgactgaaaaccgcatcaaactgct
gctgattgacccttcccgattaaccagctgatgtatgtcTAActgcagctggtaccatatgggaattcgaagct
ttctagaacaaaaactcatctcagaagaggatctgaatagcgccgtcgaccatcatcatcatcatcattgagttt
aaacggtctccagcttggctgttttggcggatgagagaagattttcagcctgatacagattaaatcagaacgca
gaagcggtctgataaaacagaatttgcctggcggcagtagcgcggtggtcccacctgaccccatgccgaact
cagaagtgaaacgccgtagcgccgatggtagtgtggggtctccccatgcgagagtagggaactgccaggc
atcaaataaaacgaaaggctcagtcgaaagactgggcctttcgttttatctgttgtttgtcggtgaacgctctcctg
agtaggacaaatccgccgggagcggatttgaacgttgcgaagcaacggcccgg

Figure 3B agggtggcgggcaggacgcccgccataaactgccaggcatcaaattaagcagaaggccatcctgac
ggatggcctttttgcgtttctacaaactctttttgtttattttctaaatacattcaaatatgtatccgctcatgagac
aataaccctgataaatgcttcaataatattgaaaaaggaagagtatgagtattcaacatttccgtgtcgccc
ttattccctttttttgcggcatttttgccttcctgttttttgctcacccagaaacgctggtgaaagtaaaagatgctga
agatcagttgggtgcacgagtgggttacatcgaactggatctcaacagcggtaagatccttgagagttttc
gccccgaagaacgttttccaatgatgagcacttttaaagttctgctatgtggcgcggtattatcccgtgttgac
gccgggcaagagcaactcggtcgccgcatacactattctcagaatgacttggttgagtactcaccagtca
cagaaaagcatcttacggatggcatgacagtaagagaattatgcagtgctgccataaccatgagtgata
acactgcggccaacttacttctgacaacgatcggaggaccgaaggagctaaccgcttttttgcacaacat
gggggatcatgtaactcgccttgatcgttgggaaccggagctgaatgaagccataccaaacgacgagc
gtgacaccacgatgcctgtagcaatggcaacaacgttgcgcaaactattaactggcgaactacttactct
agcttcccggcaacaattaatagactggatggaggcggataaagttgcaggaccacttctgcgctcggc
ccttccggctggctggtttattgctgataaatctggagccggtgagcgtgggtctcgcggtatcattgcagca
ctggggccagatggtaagccctcccgtatcgtagttatctacacgacggggagtcaggcaactatggatg
aacgaaatagacagatcgctgagataggtgcctcactgattaagcattggtaactgtcagaccaagttta
ctcatatatactttagattgatttaaaacttcattttttaatttaaaaggatctaggtgaagatcctttttgataatct
catgaccaaaatcccttaacgtgagttttcgttccactgagcgtcagaccccgtagaaaagatcaaagga
tcttcttgagatcctttttttctgcgcgtaatctgctgcttgcaaacaaaaaaaccaccgctaccagcggtggt
ttgtttgccggatcaagagctaccaactctttttccgaaggtaactggcttcagcagagcgcagataccaa
atactgtccttctagtgtagccgtagttaggccaccacttcaagaactctgtagcaccgcctacatacctcg
ctctgctaatcctgttaccagtggctgctgccagtggcgataagtcgtgtcttaccgggttggactcaagac
gatagttaccggataaggcgcagcggtcgggctgaacggggggttcgtgcacacagcccagcttggag
cgaacgacctacaccgaactgagatacctacagcgtgagctatgagaaagcgccacgcttcccgaag
ggagaaaggcggacaggtatccggtaagcggcagggtcggaacaggagagcgcacgagggagctt
ccaggggggaaacgcctggtatctttatagtcctgtcgggtttcgccacctctgacttgagcgtcgatttttgtg
atgctcgtcaggggggcggagcctatgaaaaacgccagcaacgcggcctttttacggttcctggcctttt
gctggcctttttgctcacatgttctttcctgcgttatccccgattctgtggataaccgtattaccgcctttgagtga
gctgataccgctcgccgcagccgaacgaccgagcgcagcgagtcagtgagcgaggaagcggaaga
gcgcctgatgcggtattttctccttacgcatctgtgcggtatttcacaccgcatatggtgcactctcagtacaa
tctgctctgatgccgcatagttaagccagtatacactccgctatcgctacgtgactgggtcatggctgcgcc
ccgacacccgccaacacccgctgacgcgccctgacgggcttgtctgctcccggcatccgcttacagaca
agctgtgaccgtctccgggagctgcatgtgtcagaggttttcaccgtcatcaccgaaacgcgcgaggca
gcagatcaattcgcgcgcgaaggcgaagcggcatgcatttacgttgacaccatcgaatggtgcaaaac
ctttcgcggtatggcatgatagcgcccggaagagagtcaattcagggtggtgaatgtgaaaccagtaac
gttatacgatgtcgcagagtatgccggtgtctcttatcagaccgtttcccgcgtggtgaaccaggccagcc
acgtttctgcgaaaacgcgggaaaaagtggaagcggcgatggcggagctgaattacattcccaaccgc
gtggcacaacaactggcgggcaaacagtcgttgctgattggcgttgccacctccagtctggccctgcacg
cgccgtcgcaaattgtcgcggcgattaaatctcgcgccgatcaactgggtgccagcgtggtggtgtcgat
ggtagaacgaagcggcgtcgaagcctgtaaagcggcggtgcacaatcttctcgcgcaacgcgtcagtg
ggctgatcattaactatccgctggatgaccaggatgccattgctgtggaagctgcct

Figure 3C

Gcactaatgttccggcgttatttcttgatgtctctgaccagacacccatcaacagtattattttctc
ccatgaagacggtacgcgactgggcgtggagcatctggtcgcattgggtcaccagcaaat
cgcgctgttagcgggcccattaagttctgtctcggcgcgtctgcgtctggctggctggcataaa
tatctcactcgcaatcaaattcagccgatagcggaacgggaaggcgactggagtgccatgt
ccggttttcaacaaaccatgcaaatgctgaatgagggcatcgttcccactgcgatgctggttg
ccaacgatcagatggcgctggcgcaatgcgcgccattaccgagtccgggctgcgcgttg
gtgcggatatctcggtagtgggatacgacgataccgaagacagctcatgttatatcccgccg
tcaaccaccatcaaacaggattttcgcctgctggggcaaaccagcgtggaccgcttgctgc
aactctctcagggccaggcggtgaagggcaatcagctgttgcccgtctcactggtgaaaag
aaaaaccaccctggcgcccaatacgcaaaccgcctctccccgcgcgttggccgattcatta
atgcagctggcacgacaggtttcccgactggaaagcgggcagtgagcgcaacgcaatta
atgtgagttagcgcgaattgatctg
(SEQ ID NO:2)

Figure 5A 1-
ttctcatgtttgacagcttatcatcgataagctttaatgcggtagtttatcacagttaaattgctaacgcagtca
ggcaccgtgtatgaaatctaacaatgcgctcatcgtcatcctcggcaccgtcaccctggatgctgtaggca
taggcttggttatgccggtactgccgggcctcttgcgggatatccggatatagttcctcctttcagcaaaaaa
cccctcaagacccgtttagaggccccaaggggttatgctagttattgctcagcggtggcagcagccaact
cagcttcctttcgggctttgttagcagccggatccctgcagttagacatacatcagctggttaatcgggaaa
gggtcaatcagcagcagtttgatgcggttttcagtcgcgtagtctgggcgacccagaccatcgccatactg
gtaggtgcagtgggaaacacgtgccatgttaactgcgatttccatgaacgctttaggcagcagggtggag
tcgctaacgcgttcacgattcatcttttccattcggcgtcgatcagtttacgcagttcttcgcgggcctgttcct
cgctggtaccatcgttttcgtgcatgtagctaatgatagaattggtagtctcgccacgttccagctccgccgc
agaggtggccagatcgttgcacaggcggaagataacgcagctagaacgcaccagaccatggaagtc
ggtcagggaacgcagcgcgtggtcggagatgtcttcctgctgctggcatacggaaaagtaagacggcg
ccagcagcgctacaccggaggaggaaacgctggcgttttccaggtacttggagaaagccgggataattt
tgttgttggaccatttcgcctcttgcagaaaggctttgcacagttcacgccagcttttcgtcagataggacag
gttgttatgacctttctctttcagaatagaataggacgtgtcgttaacggtgttgtacagtgccaggaaacac
agtttcatatagtccggcagggtgttaatagcgttaacgtcccagcgctctacagcatcggtgaacagttgc
agttcgtccagagtgccataaacgtcatacacgtcatcgatgatcgtcaccagaccaaacattttagtaac
agctttgcgacattcaccaaactgcgggtctggcgccatacccagtgcccagaaataaacttccatcagg
cggtcgcgtacaaaatccagtttgctagccaggcccatctcggtccaccagcgggacagatcttgcagct
ctttctggtcagggtctgtaccatgttaaaatccagcttcgccagctccagcagcagctggtgatgcggtt
ctttcggttcgtatttatccaggaaccaacgtgcctccagacggtgcagacgctggtgatatggcagttcca
gggcgtggctcacttgttctgcaaccttggtattaatgccttctttcaggttgttcttcaggtgggtgatggaaa
aggtacgcgcctcctccagcaggttctcaccctcgaaacccaggtaagacgcttcatacaggctcagca
ggccttggacgtcacctttcagttcaccgctgaaaccaccttctttatccttgaaacgctcaaaaacatcctg
agaaacctcgaaaccgtgctgacgcagcagacggaaagacagagcggttgcgtgcaggtcagatttgt
tcttttgttttcgtccagcagtacgatgttttccagggctttaatgatgtctttttcaaatttgtaggtcagaccca
ggcgctgcacatcgtcgatcagctccagcagggacagcggctgggtgtctacacggttgatcatgcagc
gaacttcttcctccagtttggtcgctttctcctccagcttttccactttcaggtcgttctccagggattgcaggaat
tcgaaattccacaggtttggctgatagtttgcggaacgacgggaattatgctcggtaatctgagtaaattga
gaagaggtcgcacacatatgacgaccttcgatatggccgctgctgtgatgatgatgatgatgatgatgatg
atggcccatggtatatctccttcttaaagttaaacaaaattattctagaggggaattgttatccgctcacaatt
cccctatagtgagtcgtattaatttcgcgggatcgagatctcgatcctctacgccggacgcatcgtggccgg
catcaccggcgccacaggtgcggttgctggcgcctatatcgccgacatcaccgatggggaagatcggg
ctcgccacttcgggctcatgagcgcttgtttcggcgtgggtatggtggcaggccccgtggccggggact
gttgggcgccatctccttgcatgcaccattccttgcggcggcggtgctcaacggcctcaacctactactgg
gctgcttcctaatgcaggagtcgcataagggagagcgtcgagatcccggacaccatcgaatggcgcaa
aacctttcgcggtatggcatgatagcgcccggaagagagtcaattcagggtggtaatgtgaaaccagt
aacgttatacgatgtcgcagagtatgccggtgtctcttatcagaccgtttcccgcgtggtgaaccaggcca
gccacgtttctgcgaaaacgcgggaaaaagtggaagcggcgatggcggagctgaattacattcccaac
cgcgtggcacaacaactggcgggcaaacagtcgttgctgattggcgttgccacctccagtctggccctgc
acgcgccgtcgcaaattgtcgcggcgattaaatct

Figure 5B cgcgccgatcaactgggtgccagcgtggtggtgtcgatggtagaacgaagcggcgtcgaagcctgta
aagcggcggtgcacaatcttctcgcgcaacgcgtcagtgggctgatcattaactatccgctggatgacc
aggatgccattgctgtggaagctgcctgcactaatgttccggcgttatttcttgatgtctctgaccagacac
ccatcaacagtattattttctcccatgaagacggtacgcgactgggcgtggagcatctggtcgcattgggt
caccagcaaatcgcgctgttagcgggcccattaagttctgtctcggcgcgtctgcgtctggctggctggc
ataaatatctcactcgcaatcaaattcagccgatagcggaacgggaaggcgactggagtgccatgtcc
ggttttcaacaaaccatgcaaatgctgaatgagggcatcgttcccactgcgatgctggttgccaacgatc
agatggcgctgggcgcaatgcgcgccattaccgagtccgggctgcgcgttggtgcggatatctcggta
gtgggatacgacgataccgaagacagctcatgttatatcccgccgttaaccaccatcaaacaggatttt
cgcctgctggggcaaaccagcgtggaccgcttgctgcaactctctcagggccaggcggtgaagggca
atcagctgttgcccgtctcactggtgaaaagaaaaaccaccctggcgcccaatacgcaaaccgcctct
ccccgcgcgttggccgattcattaatgcagctggcacgacaggtttcccgactggaaagcgggcagtg
agcgcaacgcaattaatgtaagttagctcactcattaggcaccgggatctcgaccgatgcccttgagag
ccttcaacccagtcagctccttccggtgggcgcggggcatgactatcgtcgccgcacttatgactgtcttc
tttatcatgcaactcgtaggacaggtgccggcagcgctctgggtcattttcggcgaggaccgctttcgctg
gagcgcgacgatgatcggcctgtcgcttgcggtattcggaatcttgcacgccctcgctcaagccttcgtc
actggtcccgccaccaaacgtttcggcgagaagcaggccattatcgccggcatggcggccgacgcg
ctgggctacgtcttgctggcgttcgcgacgcgaggctggatggccttccccattatgattcttctcgcttccg
gcggcatcgggatgcccgcgttgcaggccatgctgtccaggcaggtagatgacgaccatcagggaca
gcttcaaggatcgctcgcggctcttaccagccaacttcgatcactggaccgctgatcgtcacggcgattt
atgccgcctcggcgagcacatggaacggggttggcatggattgtaggcgccgccctataccttgtctgcct
ccccgcgttgcgtcgcggtgcatggagccgggccacctcgacctgaatggaagccggcggcacctcg
ctaacggattcaccactccaagaattggagccaatcaattcttgcggagaactgtgaatgcgcaaacc
aaccccttggcagaacatatccatcgcgtccgccatctccagcagccgcacgcggcgcatctcgggca
gcgttgggtcctggccacgggtgcgcatgatcgtgctcctgtcgttgaggacccggctaggctggcggg
gttgccttactggttagcagaatgaatcaccgatacgcgagcgaacgtgaagcgactgctgctgcaaa
acgtctgcgacctgagcaacaacatgaatggtcttcggtttccgtgtttcgtaaagtctggaaacgcgga
agtcagcgccctgcaccattatgttccggatctgcatcgcaggatgctgctggctaccctgtggaacacc
tacatctgtattaacgaagcgctggcattgaccctgagtgattttctctggtcccgccgcatccataccgc
cagttgtttaccctcacaacgttccagtaaccgggcatgttcatcatcagtaacccgtatcgtgagcatcct
ctctcgtttcatcggtatcattaccccccatgaacagaaatcccccttacacggaggcatcagtgaccaaa
caggaaaaaaccgcccttaacatggcccgctttatcagaagccagacattaacgcttctggagaaact
caacgagctggacgcggatgaacaggcagacatctgtgaatcgcttcacgaccacgctgatgagcttt
accgcagctgcctcgcgcgtttcggtgatgacggtgaaaacctctgacacatgcagctcccggagacg
gtcacagcttgtctgtaagcggatgccgggagcagacaagcccgtcagggcgcgtcagcgggtgttg
gcgggtgtcggggcgcagccatgacccagtcacgtagcgatagcggagtgtatactggcttaactatg
cggcatcagagcagattgtactgagagtgcaccatatatgcggtgtgaaataccgcacagatgcgtaa
ggagaaaataccgcatcaggcgctcttccgcttcctcgctcactgactcgctgcgctcggtcgttcggctg
cggcgagcggtatcagctcactcaaaggcggtaatacggttatccacagaatcaggggataacgcag
gaaagaacatgtgagcaaaaggccagcaaaaggccaggaaccgtaaaaaggccgcgttgctggc
gtttttccataggctccgcccccctgacgagcatcacaaaaatcgacgctcaagtcaga

Figure 5C ggtggcgaaacccgacaggactataaagataccaggcgtttccccctggaagctccctcgtgcgctctcct
gttccgaccctgccgcttaccggatacctgtccgcctttctcccttcgggaagcgtggcgctttctcatagctca
cgctgtaggtatctcagttcggtgtaggtcgttcgctccaagctgggctgtgtgcacgaaccccccgttcagc
ccgaccgctgcgccttatccggtaactatcgtcttgagtccaacccggtaagacacgacttatcgccactgg
cagcagccactggtaacaggattagcagagcgaggtatgtaggcggtgctacagagttcttgaagtggtg
gcctaactacggctacactagaaggacagtatttggtatctgcgctctgctgaagccagttaccttcggaaa
aagagttggtagctcttgatccggcaaacaaaccaccgctggtagcggtggtttttttgtttgcaagcagcag
attacgcgcagaaaaaaggatctcaagaagatcctttgatcttttctacggggtctgacgctcagtggaac
gaaaactcacgttaagggattttggtcatgagattatcaaaaaggatcttcacctagatccttttaaattaaaa
atgaagttttaaatcaatctaaagtatatatgagtaaacttggtctgacagttaccaatgcttaatcagtgagg
cacctatctcagcgatctgtctatttcgttcatccatagttgcctgactccccgtcgtgtagataactacgatacg
ggagggcttaccatctggccccagtgctgcaatgataccgcgagacccacgctcaccggctccagatttat
cagcaataaaccagccagccggaagggccgagcgcagaagtggtcctgcaactttatccgcctccatcc
agtctattaattgttgccgggaagctagagtaagtagttcgccagttaatagtttgcgcaacgttgttgccattg
ctgcaggcatcgtggtgtcacgctcgtcgtttggtatggcttcattcagctccggttcccaacgatcaaggcg
agttacatgatcccccatgttgtgcaaaaaagcggttagctccttcggtcctccgatcgttgtcagaagtaagt
tggccgcagtgttatcactcatggttatggcagcactgcataattctcttactgtcatgccatccgtaagatgctt
ttctgtgactggtgagtactcaaccaagtcattctgagaatagtgtatgcggcgaccgagttgctcttgcccgg
cgtcaacacgggataataccgcgccacatagcagaactttaaaagtgctcatcattggaaaacgttcttcg
gggcgaaaactctcaaggatcttaccgctgttgagatccagttcgatgtaacccactcgtgcacccaactg
atcttcagcatcttttactttcaccagcgtttctgggtgagcaaaaacaggaaggcaaaatgccgcaaaaa
agggaataagggcgacacggaaatgttgaatactcatactcttccttttcaatattattgaagcatttatcagg
gttattgtctcatgagcggatacatatttgaatgtatttagaaaaataaacaaatagggttccgcgcacattt
ccccgaaaagtgccacctgacgtctaagaaaccattattcatgacattaacctataaaaataggcgtatc
acgaggccctttcgtcttcaagaa (SEQ ID NO:3)

Figure 7A 1-
cccgtcttactgtcgggaattcgcgttggccgattcattaatgcagctggcacgacaggtttcccgactggaa
agcgggcagtgagcgcaacgcaattaatgtgagttagctcactcattaggcaccccaggctttacactttat
gcttccggctcgtatgttgtgtggaattgtgagcggataacaatttcacacaggaaacagctatgaccatgat
tacgccaagcttgtatcgattaaataaggaggaataaaccatgtgtgcgacctcttctcaatttactcagatta
ccgagcataattcccgtcgttccgcaaactatcagccaaacctgtggaatttcgaattcctgcaatccctgga
gaacgacctgaaagtggaaaagctggaggagaaagcgaccaaactggaggaagaagttcgctgcatg
atcaaccgtgtagacacccagccgctgtccctgctggagctgatcgacgatgtgcagcgcctgggtctgac
ctacaaatttgaaaagacatcattaaagccctggaaaacatcgtactgctggacgaaaacaaaaagaa
caaatctgacctgcacgcaaccgctctgtctttccgtctgctgcgtcagcacggtttcgaggtttctcaggatgt
ttttgagcgtttcaaggataaagaaggtggtttcagcggtgaactgaaaggtgacgtccaaggcctgctga
gcctgtatgaagcgtcttacctgggtttcgagggtgagaacctgctggaggaggcgcgtaccttttccatcac
ccacctgaagaacaacctgaaagaaggcattaataccaaggttgcagaacaagtgagccacgccctgg
aactgccatatcaccagcgtctgcaccgtctggaggcacgttggttcctggataaatacgaaccgaaaga
accgcatcaccagctgctgctggagctggcgaagctggattttaacatggtacagaccctgcaccagaaa
gagctgcaagatctgtcccgctggtggaccgagatgggcctggctagcaaactggattttgtacgcgaccg
cctgatgaagtttatttctgggcactgggtatggcgccagacccgcagtttggtgaatgtcgcaaagctgtt
actaaaatgtttggtctggtgacgatcatcgatgacgtgatgacgtttatggcactctggacgaactgcaact
gttcaccgatgctgtagagcgctgggacgttaacgctattaacaccctgccggactatatgaaactgtgtttc
ctggcactgtacaacaccgttaacgacacgtccattctattctgaaagagaaaggtcataacaacctgtcc
tatctgacgaaaagctggcgtgaactgtgcaaagcctttctgcaagaggcgaaatggtccaacaacaaa
attatcccggctttctccaagtacctggaaaacgccagcgtttcctcctccggtgtagcgctgctggcgccgt
cttacttttccgtatgccagcagcaggaagacatctccgaccacgcgctgcgttccctgaccgacttccatg
gtctggtgcgttctagctgcgttatcttccgcctgtgcaacgatctggccacctctgcggcggagctggaacgt
ggcgagactaccaattctatcattagctacatgcacgaaaacgatggtaccagcgaggaacaggcccgc
gaagaactgcgtaaactgatcgacgccgaatggaaaaagatgaatcgtgaacgcgttagcgactccacc
ctgctgcctaaagcgttcatggaaatcgcagttaacatggcacgtgtttcccactgcacctaccagtatggc
gatggtctgggtcgcccagactacgcgactgaaaaccgcatcaaactgctgctgattgacccttcccgatt
aaccagctgatgtatgtctaactgcaggtcgactctagaggatccccgggtaccgagctcgaattcactgg
ccgtcgttttacaacgtcgtgactgggaaaaccctggcgttacccaacttaatcgccttgcagcacatcccc
ctttcgccagctggcgtaatagcgaagaggcccgcaccgatcgcccttcccaacagttgcgcagcctgaa
tggcgaatggcgcctgatgcggtattttctccttacgcatctgtgcggtatttcacaccgcatatggtgcactct
cagtacaatctgctctgatgccgcatagttaagccagccccgacacccgccaacacccgctgacgagctt
agtaaagccctcgctagattttaatgcggatgttgcgattacttcgccaactattgcgataacaagaaaaag
ccagcctttcatgatatatctcccaatttgtgtagggcttattatgcacgcttaaaaataataaaagcagacttg
acctgatagtttggctgtgagcaattatgtgcttagtgcatctaacgcttgagttaagccgcgccgcgaagcg
gcgtcggcttgaacgaattgttagacattatttgccgactaccttggtgatctcgcctttcacgtagtggacaaa
ttcttccaactgatctgcgcgcgaggccaagcgatcttcttcttgtccaagataagcctgtctagcttcaagtat
gacgggctgatactgggccggcaggcgctccattgcccagtcggcagcgacatccttcggcgcgattttgc
cggttactgcgctgtaccaaatgcgggacaacgtaagcactacatttcgctcatcgccagcccagtcgggc
ggcgagttccatag

Figure 7B cgttaaggtttcatttagcgcctcaaatagatcctgttcaggaaccggatcaaagagttcctccgccgctg
gacctaccaaggcaacgctatgttctcttgcttttgtcagcaagatagccagatcaatgtcgatcgtggct
ggctcgaagatacctgcaagaatgtcattgcgctgccattctccaaattgcagttcgcgcttagctggata
acgccacggaatgatgtcgtcgtgcacaacaatggtgacttctacagcgcggagaatctcgctctctcc
aggggaagccgaagtttccaaaaggtcgttgatcaaagctcgccgcgttgtttcatcaagccttacggtc
accgtaaccagcaaatcaatatcactgtgtggcttcaggccgccatccactgcggagccgtacaaatgt
acggccagcaacgtcggttcgagatggcgctcgatgacgccaactacctctgatagttgagtcgatact
tcggcgatcaccgcttccctcatgatgtttaactttgttttagggcgactgccctgctgcgtaacatcgttgct
gctccataacatcaaacatcgacccacggcgtaacgcgcttgctgcttggatgcccgaggcatagact
gtaccccaaaaaaacagtcataacaagccatgaaaaccgccactgcgccgttaccaccgctgcgttc
ggtcaaggttctggaccagttgcgtgagcgcatacgctacttgcattacagcttacgaaccgaacaggc
ttatgtccactgggttcgtgccttcatccgtttccacggtgtgcgtcacccggcaaccttgggcagcagcg
aagtcgaggcatttctgtcctggctggcgaacgagcgcaaggtttcggtctccacgcatcgtcaggcatt
ggcggccttgctgttcttctacggcaaggtgctgtgcacggatctgccctggcttcaggagatcggaaga
cctcggccgtcgcggcgcttgccggtggtgctgaccccggatgaagtggttcgcatcctcggttttctgga
aggcgagcatcgtttgttcgcccagcttctgtatggaacgggcatgcggatcagtgagggtttgcaactg
cgggtcaaggatctggatttcgatcacggcacgatcatcgtgcgggagggcaagggctccaaggatc
gggccttgatgttacccgagagcttggcacccagcctgcgcgagcaggggaattaattcccacggtttt
tgctgcccgcaaacgggctgttctggtgttgctagtttgttatcagaatcgcagatccggcttcagccggttt
gccggctgaaagcgctatttcttccagaattgccatgattttttccccacggggaggcgtcactggctcccgt
gttgtcggcagctttgattcgataagcagcatcgcctgtttcaggctgtctatgtgtgactgttgagctgtaa
caagttgtctcaggtgttcaatttcatgttctagttgctttgttttactggtttcacctgttctattaggtgttacatg
ctgttcatctgttacattgtcgatctgttcatggtgaacagctttgaatgcaccaaaaactcgtaaaagctct
gatgtatctatcttttttacaccgttttcatctgtgcatatggacagttttccctttgatatgtaacggtgaacagt
tgttctactttgtttgttagtcttgatgcttcactgatagatacaagagccataagaacctcagatccttccgt
atttagccagtatgttctctagtgtggttcgttgttttttgcgtgagccatgagaacgaaccattgagatcatac
ttactttgcatgtcactcaaaaattttgcctcaaaactggtgagctgaattttttgcagttaaagcatcgtgtag
tgtttttcttagtccgttatgtaggtaggaatctgatgtaatggttgttggtattttgtcaccattcatttttatctggt
tgttctcaagttcggttacgagatccatttgtctatctagttcaacttggaaaatcaacgtatcagtcgggcg
gcctcgcttatcaaccaccaatttcatattgctgtaagtgtttaaatctttacttattggtttcaaaacccattgg
ttaagccttttaaactcatggtagttattttcaagcattaacatgaacttaaattcatcaaggctaatctctata
tttgccttgtgagttttcttttgtgttagttcttttaataaccactcataaatcctcatagagtatttgttttcaaaag
acttaacatgttccagattatatttttatgaatttttttaactggaaaagataaggcaatatctcttcactaaaa
actaattctaatttttcgcttgagaacttggcatagtttgtccactggaaaatctcaaagcctttaaccaaag
gattcctgatttccacagttctcgtcatcagctctctggttgctttagctaatacaccataagcattttccctact
gatgttcatcatctgagcgtattggttataagtgaacgataccgtccgttctttccttgtagggttttcaatcgt
ggggttgagtagtgccacacagcataaaattagcttggtttcatgctccgttaagtcatagcgactaatcg
ctagttcatttgctttgaaaacaactaattcagacatacatctcaattggtctaggtgattttaatcactatac
caattgagatgggctagtcaatgataattactagtcctttcctttgagttgtgggtatctgta

Figure 7C

Aattctgctagacctttgctggaaaacttgtaaattctgctagaccctctgtaaattccgctagacctttgtg
tgtttttttgtttatattcaagtggttataatttatagaataaagaaagaataaaaaaagataaaaagaat
agatcccagccctgtgtataactcactactttagtcagttccgcagtattacaaaaggatgtcgcaaac
gctgtttgctcctctacaaaacagaccttaaaaccctaaaggcttaagtagcaccctcgcaagctcgg
gcaaatcgctgaatattccttttgtctccgaccatcaggcacctgagtcgctgtcttttcgtgacattcagtt
cgctgcgctcacggctctggcagtgaatgggggtaaatggcactacaggcgccttttatggattcatgc
aaggaaactacccataatacaagaaaagcccgtcacgggcttctcagggcgttttatggcgggtctg
ctatgtggtgctatctgacttttgctgttcagcagttcctgccctctgattttccagtctgaccacttcggatta
tcccgtgacaggtcattcagactggctaatgcacccagtaaggcagcggtatcatcaacaggctta (SEQ ID NO:4)

A.

Figure 12A 1-
gaattgctccattttcttctgctatcaaaataacagactcgtgattttccaaacgagctttcaaaaaagcctctgcc
ccttgcaaatcggatgcctgtctataaaattcccgatattggttaaacagcggcgcaatggcggccgcatctgat
gtctttgcttggcgaatgttcatcttatttcttcctccctctcaataattttttcattctatcccttttctgtaaagtttattttc
agaatactttatcatcatgctttgaaaaaatatcacgataatatccattgttctcacggaagcacacgcaggtca
tttgaacgaattttttcgacaggaatttgccgggactcaggagcatttaacctaaaaaagcatgacatttcagcat
aatgaacatttactcatgtctattttcgttcttttctgtatgaaaatagttatttcgagtctctacggaaatagcgagag
atgatatacctaaatagagataaaatcatctcaaaaaaatgggtctactaaaatattattccatctattacaataa
attcacagaatagtcttttaagtaagtctactctgaattttttaaaaggagagggtaaagagtgtgtgcgacctctt
ctcaatttactcagattaccgagcataattcccgtcgttccgcaaactatcagccaaacctgtggaatttcgaatt
cctgcaatccctggagaacgacctgaaagtggaaaagctggaggagaaagcgaccaaactggaggaag
aagttcgctgcatgatcaaccgtgtagacacccagccgctgtcctgctggagctgatcgacgatgtgcagcg
cctgggtctgacctacaaatttgaaaagacatcattaaagccctggaaaacatcgtactgctggacgaaaa
caaaaagaacaaatctgacctgcacgcaaccgctctgtctttccgtctgctgcgtcagcacggtttcgaggtttc
tcaggatgttttgagcgtttcaaggataaagaaggtggtttcagcggtgaactgaaaggtgacgtccaaggcc
tgctgagcctgtatgaagcgtcttacctgggtttcgagggtgagaacctgctggaggaggcgcgtaccttttcca
tcacccacctgaagaacaacctgaaagaaggcattaataccaaggttgcagaacaagtgagccacgccct
ggaactgccatatcaccagcgtctgcaccgtctggaggcacgttggttcctggataaatacgaaccgaaaga
accgcatcaccagctgctgctggagctggcgaagctggattttaacatggtacagaccctgcaccagaaaga
gctgcaagatctgtcccgctggtggaccgagatgggcctggctagcaaactggattttgtacgcgaccgcctg
atggaagtttatttctgggcactgggtatggcgccagacccgcagtttggtgaatgtcgcaaagctgttactaaa
atgtttggtctggtgacgatcatcgatgacgtgtatgacgtttatggcactctggacgaactgcaactgttcaccg
atgctgtagagcgctgggacgttaacgctattaacaccctgccggactatatgaaactgtgtttcctggcactgt
acaacaccgttaacgacacgtccattctattctgaaagagaaaggtcataacaacctgtcctatctgacgaaa
agctggcgtgaactgtgcaaagcctttctgcaagaggcgaaatggtccaacaacaaaattatcccggctttctc
caagtacctggaaaacgccagcgtttcctcctccggtgtagcgctgctggcgccgtcttactttccgtatgccag
cagcaggaagacatctccgaccacgcgctgcgttccctgaccgacttccatggtctggtgcgttctagctgcgtt
atcttccgcctgtgcaacgatctggccacctctgcggcggagctggaacgtggcgagactaccaattctatcat
tagctacatgcacgaaaacgatggtaccagcgaggaacaggcccgcgaagaactgcgtaaactgatcgac
gccgaatggaaaaagatgaatcgtgaacgcgttagcgactccaccctgctgcctaaagcgttcatggaaatc
gcagttaacatggcacgtgtttcccactgcacctaccagtatggcgatggtctgggtcgcccagactacgcga
ctgaaaaccgcatcaaactgctgctgattgacccttccgattaaccagctgatgtatgtctaaaaaaaaccg
gccttggccccgccggttttttattattttttcttcctccgcatgttcaatccgctccataatcgacggatggctccctct
gaaaattttaacgagaaacggcgggttgacccggctcagtccgtaacggccaagtcctgaaacgtctcaat
cgccgcttcccggtttccggtcagctcaatgccgtaacggtcggcggcgttttcctgataccgggagacggcatt
cgtaatcggatcctctagagtcgacctgcaggcatgcaagcttgcctcgcgcgtttcggtgatgacggtgaaa
acctctgacacatgcagctcccggagacggtcacagcttgtctgtaagcggatgccgggagcagacaagcc
cgtcagggcgcgtcagcgggtgttggcgggtgtcggggcgcagccatgacccagtcacgtagcgata

Figure 12B gcggagtgtatactggcttaactatgcggcatcagagcagattgtactgagagtgcaccatatgcggtgt
gaaataccgcacagatgcgtaaggagaaataccgcatcaggcgctcttccgcttcctcgctcactga
ctcgctgcgctcggtcgttcggctgcggcgagcggtatcagctcactcaaaggcggtaatacggttatcc
acagaatcaggggataacgcaggaaagaacatgtgagcaaaaggccagcaaaaggccaggaac
cgtaaaaaggccgcgttgctggcgttttccataggctccgcccccctgacgagcatcacaaaaatcga
cgctcaagtcagaggtggcgaaacccgacaggactataaagataccaggcgtttccccctggaagct
ccctcgtgcgctctcctgttccgaccctgccgcttaccggatacctgtccgcctttctcccttcgggaagcgt
ggcgctttctcaatgctcacgctgtaggtatctcagttcggtgtaggtcgttcgctccaagctgggctgtgt
cacgaaccccccgttcagcccgaccgctgcgccttatccggtaactatcgtcttgagtccaacccggta
agacacgacttatcgccactggcagcagccactggtaacaggattagcagagcgaggtatgtaggcg
gtgctacagagttcttgaagtggtggcctaactacggctacactagaaggacagtatttggtatctgcgct
ctgctgaagccagttaccttcggaaaaagagttggtagctcttgatccggcaaacaaaccaccgctggt
agcggtggtttttttgtttgcaagcagcagattacgcgcagaaaaaaaggatctcaagaagatcctttgat
cttttctacggggtctgacgctcagtggaacgaaaactcacgttaagggattttggtcatgagattatcaa
aaaggatcgaagtcggttcagaaaagaaggatatggatctggagctgtaatataaaaaccttcttcaa
ctaacggggcaggttagtgacattagaaaaccgactgtaaaaagtacagtcggcattatctcatattata
aaagccagtcattaggcctatctgacaattcctgaatagagttcataaacaatcctgcatgataaccatc
acaaacagaatgatgtacctgtaaagatagcggtaaatatattgaattacctttattaatgaattttcctgct
gtaataatgggtagaaggtaattactattattattgatatttaagttaaacccagtaaatgaagtccatgga
ataatagaaagagaaaaagcattttcaggtataggtgttttgggaaacaatttaaaagaaccattatattt
ctctacatcagaaaggtataaatcataaaactctttgaagtcattctttacaggagtccaaataccagag
aatgttttagatacaccatcaaaaattgtataaagtggctctaacttatcccaataacctaactctccgtcg
ctattgtaaccagttctaaaagctgtatttgagtttatcacccttgtcactaagaaaataaatgcagggtaa
aatttatatccttcttgttttatgtttcggtataaaacactaatatcaatttctgtggttatactaaaagtcgtttgtt
ggttcaaataatgattaaatatctcttttctcttccaattgtctaaatcaatttttattaaagttcatttgatatgcct
cctaaattttatctaaagtgaatttaggaggcttacttgtctgctttcttcattagaatcaatccttttttaaagtc
aatattactgtaacataaatatatattttaaaaatatcccactttatccaatttttcgtttgttgaactaatgggtg
ctttagttgaagaataaagaccacattaaaaaatgtggtcttttgtgttttttaaaggatttgagcgtacgcg
aaaaatcctttctttctttcttatcttgataataagggtaactattgccggttgtccattcatggctgaactctgc
ttcctctgttgacatgacacacatcatctcaatatccgaatagggcccatcagtctgacgaccaagagag
ccataaacaccaatagccttaacatcatccccatatttatccaatattcgttccttaatttcatgaacaatctt
cattctttcttctctagtcattattattggtccattcactattctcattcccttttcagataattttagatttgcttttcta
aataagaatatttggagagcaccgttcttattcagctattaataactcgtcttcctaagcatccttcaatccttt
taataacaattatagcatctaatcttcaacaaactggcccgtttgttgaactactctttaataaaataattttc
cgttcccaattccacattgcaataatagaaaatccatcttcatcggcttttcgtcatcatctgtatgaatcaa
atcgccttcttctgtgtcatcaaggtttaattttttatgtatttctttttaacaaaccaccataggagattaaccttt
acggtgtaaaccttcctccaaatcagacaaacgtttcaaattcttttcttcatcatcggtcataaaatccgta
tcctttacaggatatttgcagtttcgtcaattgccgattgtatatccgatttatatttattttcggtcgaatcattt
gaacttttacatttggatcatagtctaatttcattgccttttccaaaattgaatccattgttt

Figure 12C ttgattcacgtagttttctgttattctaaaataagttggttccacacataccattacatgcatgtgctgattata
agaattatctttattatttattgtcacatccgttgcacgcataaaaccaacaagattttattaattttttatatt
gcatcattcggcgaaatccttgagccatatctgtcaaactcttatttaattcttcgccatcataaacattttta
actgttaatgtgagaaacaaccaacgaactgttggcttttgtttaataacttcagcaacaacctttgtgac
tgaatgccatgtttcattgctctcctccagttgcacattggacaaagcctggatttgcaaaaccacactcg
ataccactttctttcgcctgtttcacgattttgtttatactctaatatttcagcacaatcttttactctttcagccttt
ttaaattcaagaatatgcagaagttcaaagtaatcaacattagcgattttcttttctctccatggtctcacttt
tccacttttgtcttgtccactaaaacccttgattttcatctgaataaatgctactattaggacacataatatt
aaaagaaaccccatctatttagttatttgtttagtcacttataactttaacagatggggttttctgtgcaac
caattttaagggttttcaatactttaaaacacatacataccaacacttcaacgcacctttcagcaactaa
aataaaaatgacgttatttctatatgtatcaagataagaaagaacaagttcaaaaccatcaaaaaaag
acaccttttcaggtgctttttttatttataaaactcattccctgatctcgacttcgttcttttttacctctcggttatg
agttagttcaaattcgttcttttaggttctaaatcgtgttttcttggaattgtgctgttttatcctttaccttgtcta
caaaccccttaaaaacgttttaaaggcttttaagccgtctgtacgttccttaag (SEQ ID NO:5)

Figure 13

ATGTGTGCAACCTCCTCCCAGTTTACTCAGATTACCGAGCATAATTCTCGAC
GATCTGCTAACTACCAGCCGAACCTTTGGAACTTTGAGTTTCTCCAGTCTCT
CGAAAATGACCTGAAGGTGGAAAAGCTCGAGGAGAAGGCGACCAAACTCG
AGGAGGAGGTGCGATGTATGATCAACAGAGTTGACACCCAACCCCTGTCTT
TGCTGGAGCTGATCGACGATGTGCAGCGGTTGGGTTTGACTTATAAATTCG
AGAAGGACATTATCAAGGCACTGGAGAACATTGTGCTCCTCGACGAGAACA
AGAAGAACAAGTCTGATCTTCACGCTACCGCTCTCTTTCCGACTTCTTCG
ACAACACGGCTTCGAGGTGTCGCAGGACGTCTTCGAGAGATTTAAGGACA
AGGAGGGAGGATTTAGCGGCGAGCTGAAGGGAGACGTTCAGGGTCTTCTC
TCCTTGTACGAGGCGTCCTACCTGGGATTCGAGGGAGAGAACCTCCTGGA
GGAAGCTCGTACATTTTCCATCACTCACCTTAAGAATAACCTTAAGGAGGG
AATTAACACCAAGGTGGCCGAGCAGGTTTCTCACGCCCTGGAGCTCCCCT
ACCACCAACGGCTCCATAGACTGGAGGCTCGTTGGTTCCTGGACAAATATG
AGCCAAAGGAGCCTCATCATCAGTTGCTGTTGGAGTTGGCCAAGCTGGACT
TCAATATGGTTCAGACGCTGCACCAAAAGGAGTTGCAGGACCTGTCTCGAT
GGTGGACCGAGATGGGATTGGCCTCGAAGCTGGATTTTGTCCGTGACCGA
CTTATGGAGGTCTATTTTGGGCCCTTGGAATGGCGCCTGACCCCCAGTTC
GGAGAGTGCCGGAAGGCGGTGACGAAGATGTTCGGTCTTGTGACTATCAT
CGACGACGTCTACGATGTCTACGGCACACTCGACGAGTTGCAGCTGTTCA
CTGACGCCGTCGAGCGATGGGATGTGAACGCCATTAATACTCTCCCTGACT
ATATGAAGCTGTGCTTCCTGGCTCTGTACAACACTGTCAACGATACCTCGT
ACTCTATCCTCAAGGAGAAGGGACACAACAATCTCTCCTACTTGACCAAAT
CCTGGCGAGAACTGTGCAAGGCTTTTCTGCAGGAGGCTAAATGGTCCAATA
ACAAGATCATTCCTGCTTTTCTAAATACCTGGAAAATGCCTCGGTGTCGAG
CTCTGGCGTCGCCCTTCTGGCCCCTTCCTACTTCTCCGTCTGCCAGCAGCA
GGAGGATATTTCCGATCATGCTCTTAGATCGCTGACCGATTTTCACGGCCT
CGTGCGATCTTCCTGCGTGATTTTCGGTTGTGTAATGACCTTGCGACCTC
TGCTGCTGAGCTGGAACGAGGCGAGACTACAAATTCCATTATTTCTTACAT
GCACGAAAACGATGGAACATCTGAAGAACAGGCTAGAGAGGAACTGCGAA
AGTTGATCGACGCCGAGTGGAAGAAGATGAACAGAGAGCGGGTGTCCGAC
TCTACCCTGCTTCCCAAGGCCTTCATGGAGATCGCCGTGAACATGGCTCGA
GTTTCCCATTGTACTTACCAGTACGGTGACGGCCTGGGTCGTCCGGACTAC
GCTACAGAGAACCGAATCAAGCTGCTGCTCATCGACCCCTTCCCTATCAAC
CAATTGATGTACGTGTAA (SEQ ID NO:6)

Figure 15A

```
   1 TCGACCGGTG AGAAGAACAG CATCGGGACA AGGGAAGGAA GAACAAAGAC AAAGAAAACA
  61 AAAGAAAGCA ATTGAAAACA AAACAAAACA ATTTTCATTC CTTCTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCCAACC TCCCATTTCC TCCTTACGGC CCGATAGCGA
 301 TCGTCTTTCC CTCGCTATCA CTCGCTACCG GCCCCTCCTC TGCACCGTAA CCTCCTACGT
 361 ATTTACCATA TCATAAAGTT TTTTCCGACG CTTATCGCTG ACCCCCTGTC GCCCTCCTAT
 421 TGGCTTCCGG ATTATCTTCT TGTCCATAAG GTGATCCATG CTTCCTGAAG ATTCCCGAAA
 481 TGTGTCCACT TTGGCGGGGA ATCATTCCAT CCACTTCTTT CTCTCTCGCT TTCCTCATTC
 541 GGCGCTCCCC TTCCGCGTCT CATTGGTCTT CCGCTCCGTT TTTGCTTTGC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG CCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC CTTCGTGTTT ACCAAAGTTG GAACACTTTT GCTAATCCTG ATAGACCCAA
 901 CCTTAAGAAG AGAAATGATA CACCTGCAAG TGGATATCAA GTTGAAAAAG TCGTAATTTT
 961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGAG GCACAAACTC CTATAGATAA
1381 TTTGAATCAA CATTACATCC CCTTTTTAGC TTTAATGAAT ACAACATTAA ATTTAGTAC
1441 TTCTGCCTGG TGCCAAAAAC ACTCTGCTGA TAAATCCTGT GACCTAGGTT TATCCATGCC
1501 TTCTAAATTG TCCATAAAAG ATAATGGTAA CAAGGTCGCA TTGGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAATTCCAG GTTGCAATGA TCAAACAGCC GAGGGTTACT GTCCTCTTTC
2101 CACTTTTACA AGAGTTGTTT CCCAATCTGT TGAACCTGGA TGCCAACTTC AATAATGAGG
2161 ATCCAAGTAA GGGAATGAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTGTTCTTT TATTTCCTTT TTTCCATCTT CAAGGCTTTT CTTTTCTTCC
2461 TCCTCCTCGT TCATCTTGAG GTTGACGTG TCTGTTTAGA ATTTTGAGCT GTTGCAGCAT
2521 CTTATTTTTT GTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTGAGCT ATAGTTAAGT GTAAGGGCCC TACTGCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGACTTGC TCGGCACCTT ACGAGAAATC AAAGTCTTTG GGTTCCGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCGA TAACGACGAG GACCTTAACC TGCTAAATAG CTGGATCAGC
3121 CATTTTGGCT GATCATTAGC TTCTTAGAGG GACTATTGGC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

Figure 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCGGTA
3721 GTCTAATATC TAGCAAAAAT CTTTTGGGTG AAAAGGCTTG CAATTTCACG ACACCGAACT
3781 ATTTGTCATT TTTTAATAAG GAAGTTTTCC ATAAATTCCT GTAATTCTCG GTTGATCTAA
3841 TTGAAAAGAG TAGTTTTGCA TCACGATGAG GAGGGCTTTT GTAGAAAGAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATGTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATTGGATT ATGTCAGGAA AAGAACGACA ATTTTGCATC
4561 CAAATTGTCT AAATTTTAGA GTTGCTGAAA ACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAAGA GACCGCCTCG
5041 TTTCTTTTTC TTCGTCGAAA AAGGCAATAA AAATTTTTAT CACGTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTTCTTT TTTTTCTGTA
5941 CAGACGCGAG CTTCCAGTA AATGTGCCAT CTCGTAGGCA GAAAACGGTT CCCCCGTAGG
6001 GTCTCTCTCT TGGCCTCCTT TCTAGGTCGG GCTGATTGCT CTTGAAGCTC TCTAGGGGGG
6061 CTCACACCAT AGGCAGATAA CGTTCCCCAC CGGCTCGCCT CGTAAGCGCA CAAGGACTGC
6121 TCCCAAAGAT CCTAGGCGGG ATTTTGCCGA TTTCGGCCTA AAGGAACCGG AACACGTAGA
6181 AAGCCAGTCC GCAGAAACGG TGCTGACCCC GGATGAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

Figure 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
```

(SEQ ID NO:7)

Figure 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTGACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GGCTTCGAGG TGTCGCAGGA CGTCTTCGAG AGATTAAGG
 421 ACAAGGAGGG AGGATTTAGC GGCGAGCTGA AGGGAGACGT TCAGGGTCTT CTCTCCTTGT
 481 ACGAGGCGTC CTACCTGGGA TTCGAGGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCGAG
1141 AACTGTGCAA GGCTTTTCTG CAGGAGGCTA AATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTTCCGA TCATGCTCTT AGATCGCTGA
1321 CCGATTTTCA CGGCCTCGTG CGATCTTCCT GCGTGATTTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
```

(SEQ ID NO:8)

Figure 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 GTCGTTGTAT GAGGCCTCGT TCCTGGCTCT TGAGGGCGAG AATATTCTGG ATGAGGCTCG
 541 GGTTTTCGCT ATTTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAG CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGGCAG TGGGTGTGGC CTTTGAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA CAAATCTAC
1201 TCCTACATTT GATGACTACT TCGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
```

(SEQ ID NO:9)

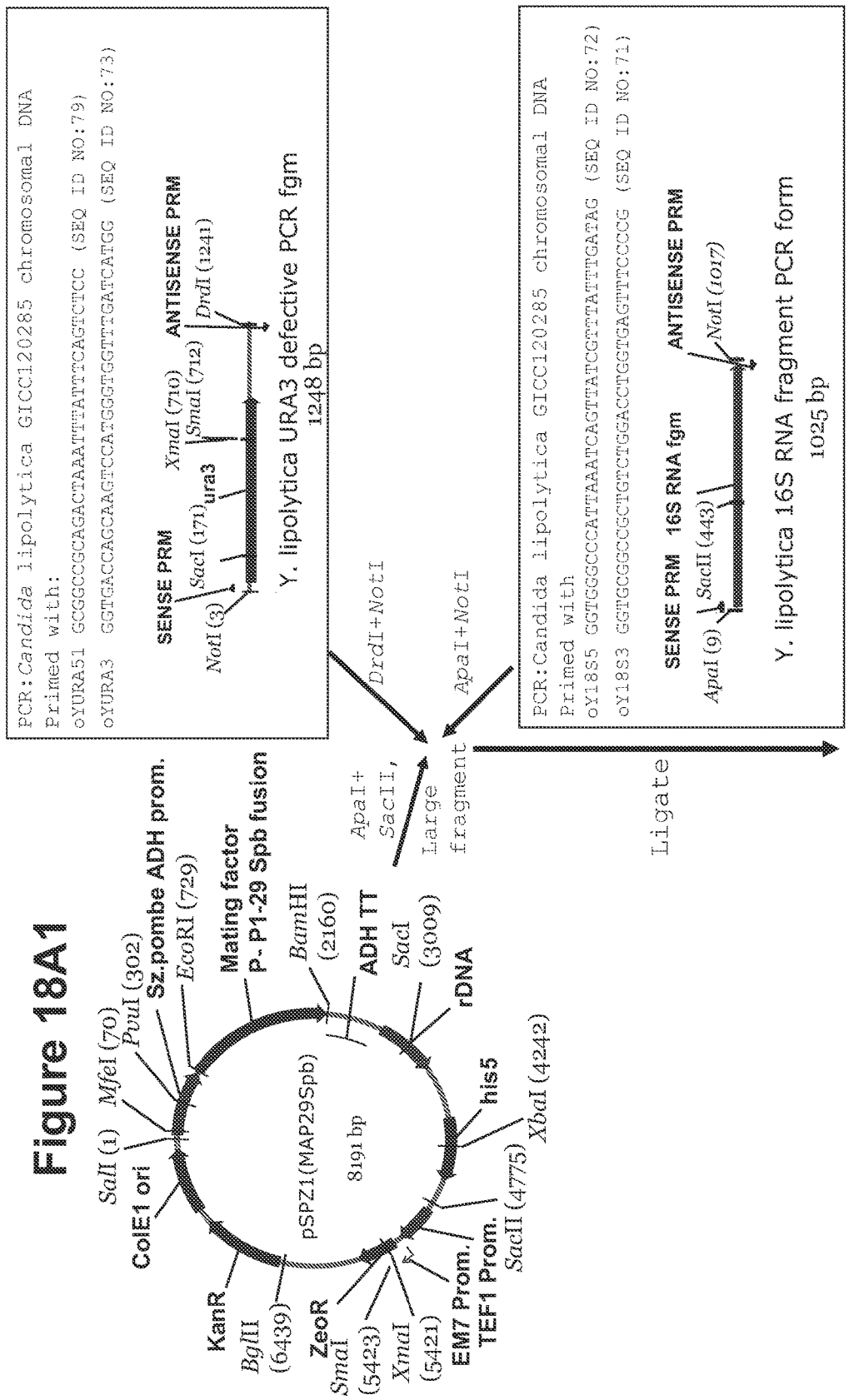

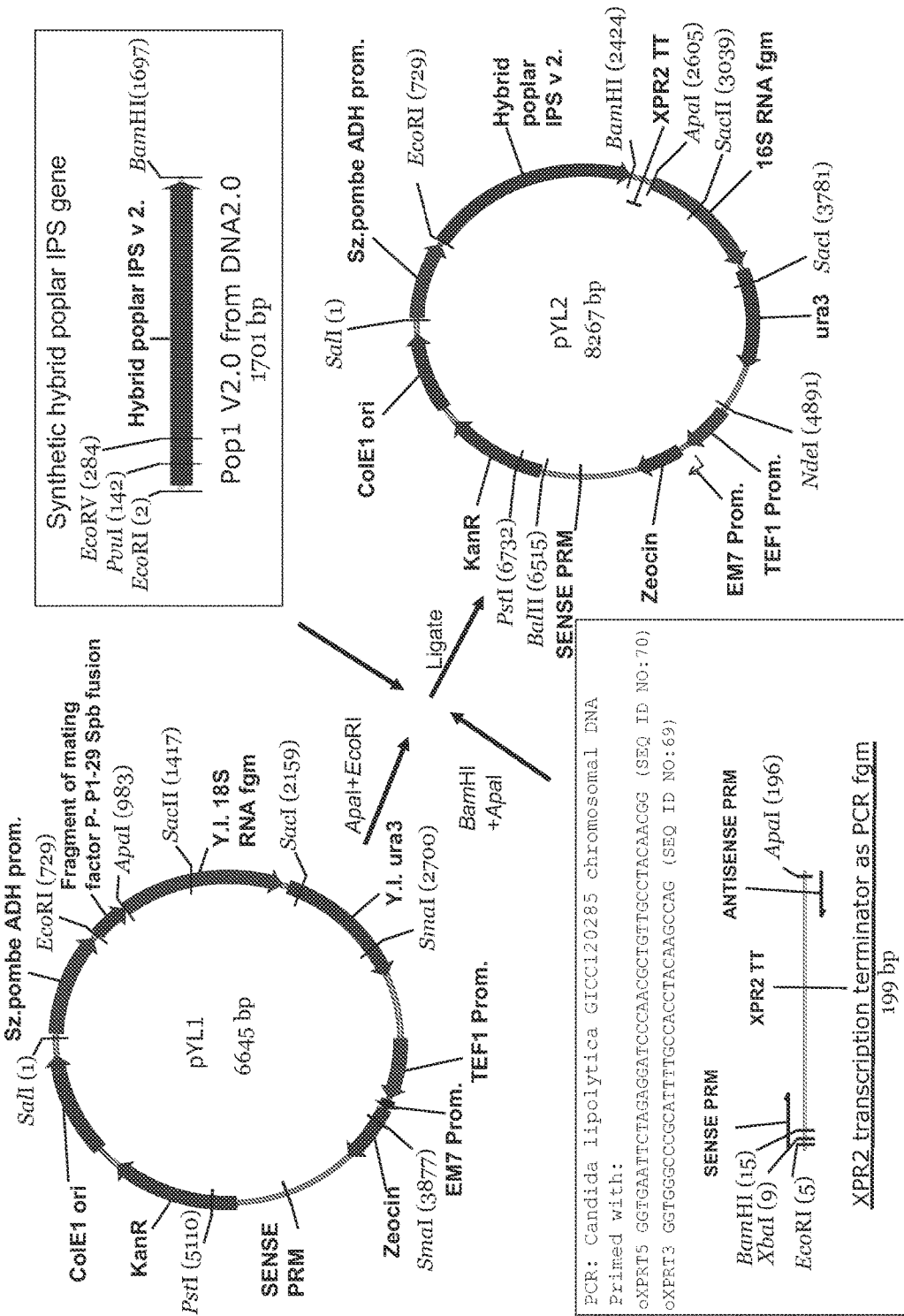
Figure 18A2

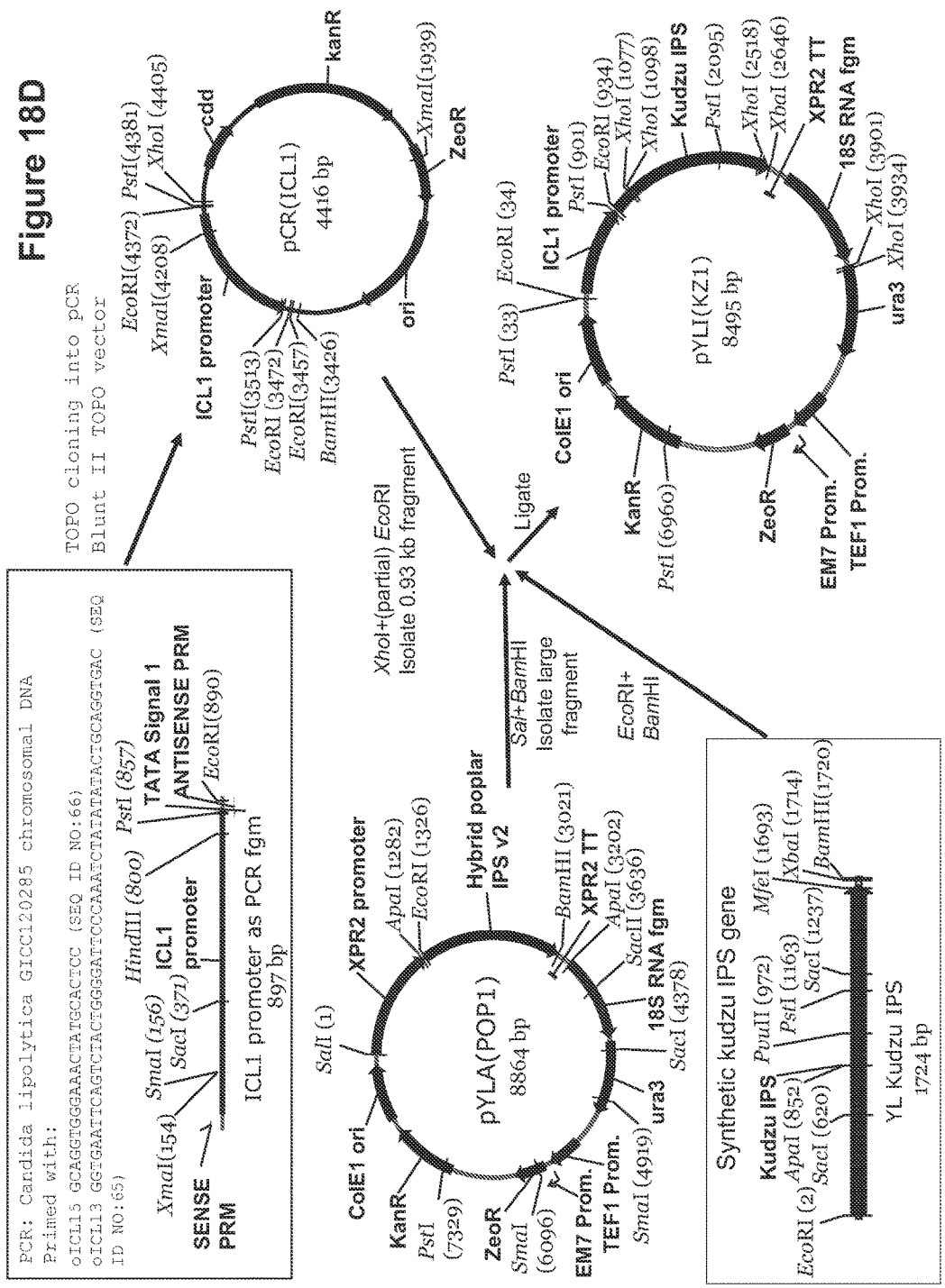

Figure 22A 1-
gctggtaccatatgggaattcgaagctttctagaacaaaaactcatctcagaagaggatctgaatagcgccgtc
gaccatcatcatcatcatcattgagtttaaacggtctccagcttggctgttttggcggatgagagaagattttcagcc
tgatacagattaaatcagaacgcagaagcggtctgataaaacagaatttgcctggcggcagtagcgcggtggt
cccacctgaccccatgccgaactcagaagtgaaacgccgtagcgccgatggtagtgtggggtctcccatgcg
agagtagggaactgccaggcatcaaataaaacgaaaggctcagtcgaagactgggcctttcgttttatctgtt
gtttgtcggtgaacgctctcctgagtaggacaaatccgccgggagcggatttgaacgttgcgaagcaacggcc
cggagggtggcgggcaggacgcccgccataaactgccaggcatcaaattaagcagaaggccatcctgacg
gatggccttttgcgtttctacaaactctttttgtttattttctaaatacattcaaatatgtatccgcttaaccggaattgcc
agctggggcgccctctggtaaggttgggaagccctgcaaagtaaactggatggctttctcgccgccaaggatct
gatggcgcaggggatcaagctctgatcaagagacaggatgaggatcgtttcgcatgattgaacaagatggatt
gcacgcaggttctccggccgcttgggtggagaggctattcggctatgactgggcacaacagacaatcggctgct
ctgatgccgccgtgttccggctgtcagcgcaggggcgcccggttcttttttgtcaagaccgacctgtccggtgccct
gaatgaactgcaagacgaggcagcgcggctatcgtggctggccacgacgggcgttccttgcgcagctgtgctc
gacgttgtcactgaagcgggaagggactggctgctattgggcgaagtgccggggcaggatctcctgtcatctca
ccttgctcctgccgagaaagtatccatcatggctgatgcaatgcggcggctgcatacgcttgatccggctacctg
cccattcgaccaccaagcgaaacatcgcatcgagcgagcacgtactcggatggaagccggtcttgtcgatca
ggatgatctggacgaagagcatcaggggctcgcgccagccgaactgttcgccaggctcaaggcgagcatgc
ccgacggcgaggatctcgtcgtgacccatggcgatgcctgcttgccgaatatcatggtggaaaatggccgcttt
ctggattcatcgactgtggccggctgggtgtggcggaccgctatcaggacatagcgttggctacccgtgatattg
ctgaagagcttggcggcgaatgggctgaccgcttcctcgtgctttacggtatcgccgctcccgattcgcagcgca
tcgccttctatcgccttcttgacgagttcttctgacatgaccaaaatcccttaacgtgagttttcgttccactgagcgtc
agaccccgtagaaaagatcaaaggatcttcttgagatccttttttttctgcgcgtaatctgctgcttgcaaacaaaaa
aaccaccgctaccagcggtggtttgtttgccggatcaagagctaccaactcttttttccgaaggtaactggcttcag
cagagcgcagataccaaatactgtccttctagtgtagccgtagttaggccaccacttcaagaactctgtagcacc
gcctacatacctcgctctgctaatcctgttaccagtggctgctgccagtggcgataagtcgtgtcttaccgggttgg
actcaagacgatagttaccggataaggcgcagcggtcgggctgaacggggggttcgtgcacacagcccagct
tggagcgaacgacctacaccgaactgagatacctacagcgtgagctatgagaaagcgccacgcttcccgaa
gggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgt
caggggggcggagcctatggaaaaacgccagcaacgcggcctttttacggttcctggccttttgctggccttttgc
tcacatgttctttcctgcgttatcccctgattctgtggataaccgtattaccgcctttgagtgagctgataccgctcgcc
gcagccgaacgaccgagcgcagcgagtcagtgagcgaggaagcggaagagcgcctgatgcggtattttctc
cttacgcatctgtgcggtatttcacaccgcatatggtgcactctcagtacaatctgctctgatgccgcatagttaagc
cagtatacactccgctatcgctacgtgactgggtcatgctgcgccccgacacccgccaacacccgctgacgc
gccctgacgggcttgtctgctcccggcatccgcttacagacaagctgtgaccgtctccgggagctgcatgtgtca
gaggttttcaccgtcatcaccgaaacgcgcgaggcagcagatcaattcgcgcgcgaaggcgaagcggcatg
catttacgttgacaccatcgaatggtgcaaaacctttcgcggtatggcatgatagcgcccggaaga

Figure 22B gagtcaattcagggtggtgaatgtgaaaccagtaacgttatacgatgtcgcagagtatgccggtgtctcttatc
agaccgtttcccgcgtggtgaaccaggccagccacgtttctgcgaaaacgcgggaaaaagtggaagcgg
cgatggcggagctgaattacattcccaaccgcgtggcacaacaactggcgggcaaacagtcgttgctgatt
ggcgttgccacctccagtctggccctgcacgcgccgtcgcaaattgtcgcggcgattaaatctcgcgccgat
caactgggtgccagcgtggtggtgtcgatggtagaacgaagcggcgtcgaagcctgtaaagcggcggtgc
acaatcttctcgcgcaacgcgtcagtgggctgatcattaactatccgctggatgaccaggatgccattgctgtg
gaagctgcctgcactaatgttccggcgttatttcttgatgtctctgaccagacacccatcaacagtattatttctc
ccatgaagacggtacgcgactgggcgtggagcatctggtcgcattgggtcaccagcaaatcgcgctgttag
cgggcccattaagttctgtctcggcgcgtctgcgtctggctggctggcataaatatctcactcgcaatcaaattc
agccgatagcggaacgggaaggcgactggagtgccatgtccggttttcaacaaaccatgcaaatgctgaa
tgagggcatcgttcccactgcgatgctggttgccaacgatcagatggcgctgggcgcaatgcgcgccattac
cgagtccgggctgcgcgttggtgcggatatctcggtagtgggatacgacgataccgaagacagctcatgtta
tatcccgccgtcaaccaccatcaaacaggattttcgcctgctggggcaaaccagcgtggaccgcttgctgca
actctctcagggccaggcggtgaagggcaatcagctgttcccgtctcactggtgaaaagaaaaaccacc
ctggcgcccaatacgcaaaccgcctctccccgcgcgttggccgattcattaatgcagctggcacgacaggtt
tcccgactggaaagcgggcagtgagcgcaacgcaattaatgtgagttagcgcgaattgatctggtttgacag
cttatcatcgactgcacggtgcaccaatgcttctggcgtcaggcagccatcggaagctgtggtatggctgtgc
aggtcgtaaatcactgcataattcgtgtcgctcaaggcgcactcccgttctggataatgtttttttgcgccgacatc
ataacggttctggcaaatattctgaaatgagctgttgacaattaatcatccggctcgtataatgtgtggaattgtg
agcggataacaatttcacacaggaaacagcgccgctgagaaaaagcgaagcggcactgctctcttaacaat
ttatcagacaatctgtgtgggcactcgaccggaattatcgattaactttattattaaaaattaaagaggtatatatt
aatgtatcgattaaataaggaggaataaaccatgtgtgcgacctcttctcaatttactcagattaccgagcata
attcccgtcgttccgcaaactatcagccaaacctgtggaatttcgaattcctgcaatccctggagaacgacctg
aaagtggaaaagctggaggagaaagcgaccaaactggaggaagaagttcgctgcatgatcaaccgtgt
agacacccagccgctgtccctgctggagctgatcgacgatgtgcagcgcctgggtctgacctacaaatttga
aaaagacatcattaaagccctggaaaacatcgtactgctggacgaaaacaaaaagaacaaatctgacct
gcacgcaaccgctctgtctttccgtctgctgcgtcagcacggtttcgaggtttctcaggatgtttttgagcgtttca
aggataaagaaggtggtttcagcggtgaactgaaaggtgacgtccaaggcctgctgagcctgtatgaagcg
tcttacctgggtttcgagggtgagaacctgctggaggaggcgcgtacctttccatcacccacctgaagaaca
acctgaaagaaggcattaataccaaggttgcagaacaagtgagccacgccctggaactgccatatcacca
gcgtctgcaccgtctggaggcacgttggttcctggataaatacgaaccgaaagaaccgcatcaccagctgc
tgctggagctggcgaagctggattttaacatggtacagaccctgcaccagaaagagctgcaagatctgtccc
gctggtggaccgagatgggcctggctagcaaactggattttgtacgcgaccgcctgatggaagtttatttctgg
gcactgggtatggcgccagacccgcagtttggtgaatgtcgcaaagctgttactaaaatgtttggtctggtgac
gatcatcgatgacgtgtatgacgtttatggcactctggacgaactgcaactgttcaccgatgctgtagagcgct
gggacgttaacgctattaacaccctgccggactatatgaaactgtgtttcctggcactgtacaacaccgttaac
gacacgtcctattctattctgaaagagaaaggtcataacaacctgtcctatctgacgaaaagctggcgtgaa
ctgtgcaaagcctttctgcaagaggcgaaatggtccaacaacaaaattatcccggctttctccaagtacctgg
aaaacgccagcgtttcctcctccggtgtagcgctgctggcgccgtcttactttccgta

Figure 22C tgccagcagcaggaagacatctccgaccacgcgctgcgttccctgaccgacttccatggtctggtgcgttctag
ctgcgttatcttccgcctgtgcaacgatctggccacctctgcggcggagctggaacgtggcgagactaccaatt
ctatcattagctacatgcacgaaaacgatggtaccagcgaggaacaggcccgcgaagaactgcgtaaactg
atcgacgccgaatggaaaaagatgaatcgtgaacgcgttagcgactccaccctgctgcctaaagcgttcatg
gaaatcgcagttaacatggcacgtgtttccactgcacctaccagtatggcgatggtctgggtcgcccagacta
cgcgactgaaaaccgcatcaaactgctgctgattgacccttccccgattaaccagctgatgtatgtctaactgca
tcgcccttaggaggtaaaaaaaaatgactgccgacaacaatagtatgccccatggtgcagtatctagttacgc
caaattagtgcaaaaccaaacacctgaagacatttggaagagtttcctgaaattattccattacaacaaagac
ctaatacccgatctagtgagacgtcaaatgacgaaagcggagaaacatgttttctggtcatgatgaggagca
aattaagttaatgaatgaaaattgtattgttttggattgggacgataatgctattggtgccggtaccaagaaagttt
gtcatttaatggaaaatattgaaaagggtttactacatcgtgcattctccgtctttattttcaatgaacaaggtgaatt
acttttacaacaaagagccactgaaaaaataactttccctgatctttggactaacacatgctgctctcatccacta
tgtattgatgacgaattaggtttgaagggtaagctagacgataagattaagggcgctattactgcggcggtgag
aaaactagatcatgaattaggtattccagaagatgaaactaagacaaggggtaagtttcacttttaaacagaa
tccattacatggcaccaagcaatgaaccatggggtgaacatgaaattgattacatcctatttataagatcaacg
ctaaagaaaacttgactgtcaacccaaacgtcaatgaagttagagacttcaaatgggtttccaccaaatgatttg
aaaactatgtttgctgacccaagttacaagtttacgccttggtttaagattatttgcgagaattacttattcaactggt
gggagcaattagatgacctttctgaagtggaaaatgacaggcaaattcatagaatgctataacaacgcgtcct
gcattcgcccttaggaggtaaaaaaacatgagttttgatattgccaaatacccgaccctggcactggtcgactc
cacccaggagttacgactgttgccgaaagagagtttaccgaaactctgcgacgaactgcgccgctatttactc
gacagcgtgagccgttccagcgggcacttcgcctccgggctgggcacggtcgaactgaccgtggcgctgca
ctatgtctacaacaccccgtttgaccaattgatttgggatgtggggcatcaggcttatccgcataaaattttgacc
ggacgccgcgacaaaatcggcaccatccgtcagaaaggcggtctgcacccgttcccgtggcgcggcgaaa
gcgaatatgacgtattaagcgtcgggcattcatcaacctccatcagtgccggaattggtattgcggttgctgccg
aaaaagaaggcaaaaatcgccgcaccgtctgtgtcattggcgatggcgcgattaccgcaggcatggcgtttg
aagcgatgaatcacgcgggcgatatccgtcctgatatgctggtgattctcaacgacaatgaaatgtcgatttcc
gaaaatgtcggcgcgctcaacaaccatctggcacagctgctttccggtaagctttactcttcactgcgcgaagg
cgggaaaaaagttttctctggcgtgccgccaattaaagagctgctcaaacgcaccgaagaacatattaaagg
catggtagtgcctggcacgttgtttgaagagctgggctttaactacatcggcccggtggacggtcacgatgtgct
ggggcttatcaccacgctaaagaacatgcgcgacctgaaaggcccgcagttcctgcatatcatgaccaaaa
aaggtcgtggttatgaaccggcagaaaaagacccgatcactttccacgccgtgcctaaatttgatccctccag
cggttgtttgccgaaaagtagcggcggtttgccgagctattcaaaaatctttggcgactggttgtgcgaaacggc
agcgaaagacaacaagctgatggcgattactccggcgatgcgtgaaggttccggcatggtcgagttttcacgt
aaattcccggatcgctacttcgacgtggcaattgccgagcaacacgcggtgacctttgctgcgggtctggcgat
tggtgggtacaaacccattgtcgcgatttactccactttcctgcaacgcgcctatgatcaggtgctgcatgacgtg
gcgattcaaaagcttccggtcctgttcgccatcgaccgcgcgggcattgttggtgctgacggtcaaacccatca
gggtgcttttgatctctcttacctgcgctgcataccggaaatggtcattatgaccccgagcgatgaaaacgaatg
tcgccagatgctctataccggctatcactataacgatggcccgtcagcggtgcgctacccgcgtggcaacgcg
gtcgg

Figure 22D cgtggaactgacgccgctggaaaaactaccaattggcaaaggcattgtgaagcgtcgtggcgagaaactgg
cgatccttaactttggtacgctgatgccagaagcggcgaaagtcgccgaatcgctgaacgccacgctggtcg
atatgcgttttgtgaaaccgcttgatgaagcgttaattctggaaatggccgccagccatgaagcgctggtcacc
gtagaagaaaacgccattatgggcggcgcaggcagcggcgtgaacgaagtgctgatggcccatcgtaaac
cagtacccgtgctgaacattggcctgccggacttctttattccgcaaggaactcaggaagaaatgcgcgccga
actcggcctcgatgccgctggtatggaagccaaaatcaaggcctggctggcataactgca (SEQ ID NO:10)

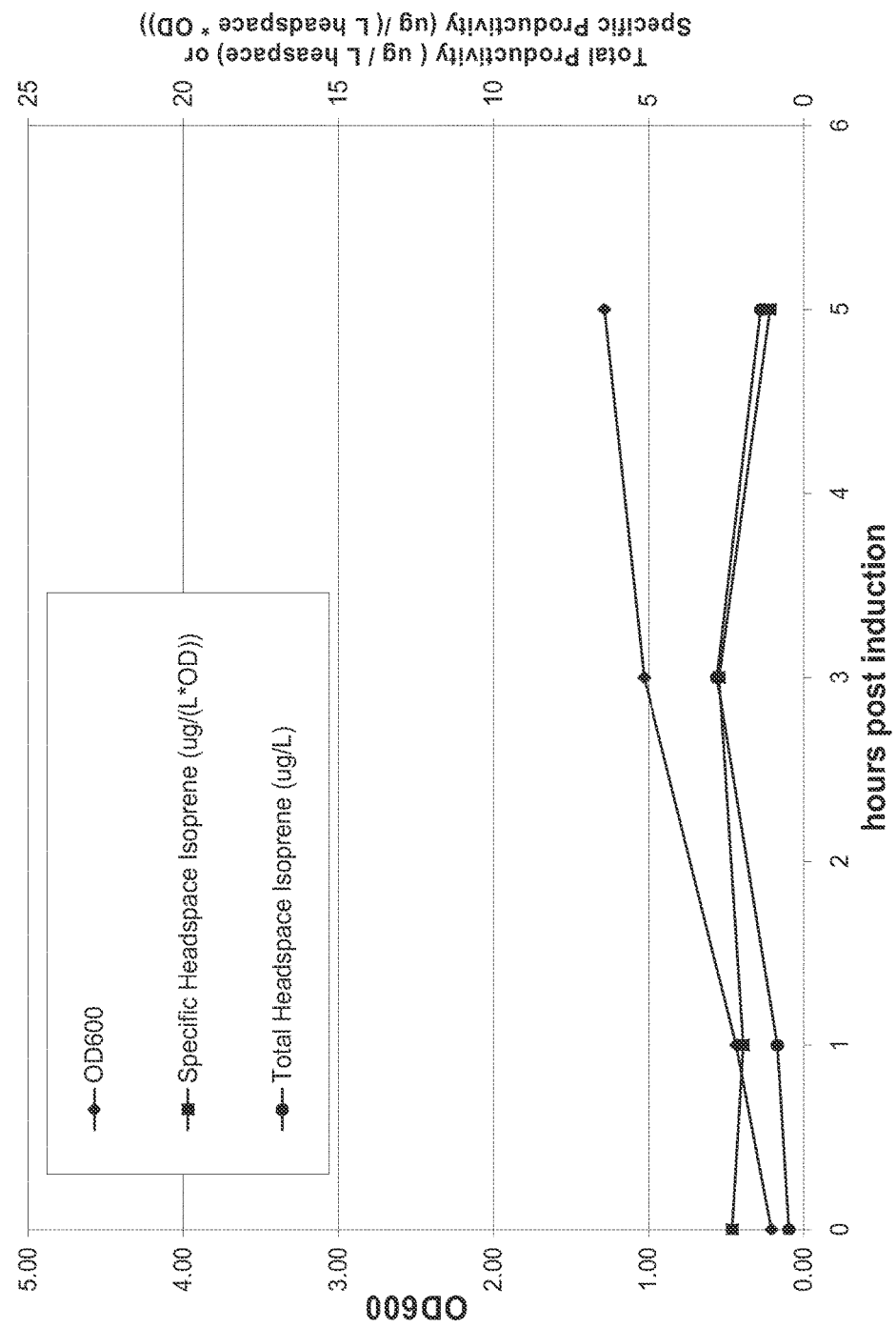

Figure 25A

5'-
gtttgacagcttatcatcgactgcacggtgcaccaatgcttctggcgtcaggcagccatcggaagctgtggtatg
gctgtgcaggtcgtaaatcactgcataattcgtgtcgctcaaggcgcactcccgttctggataatgtttttgcgcc
gacatcataacggttctggcaaatattctgaaatgagctgttgacaattaatcatccggctcgtataatgtgtgga
attgtgagcggataacaatttcacacaggaaacagcgccgctgagaaaaagcgaagcggcactgctctta
acaatttatcagacaatctgtgtgggcactcgaccggaattatcgattaactttattattaaaaattaaagaggtat
atattaatgtatcgattaaataaggaggaataaaccatggatccgagctcggatccactagtaacggccgcca
gtgtgctggaattcgcccttaggaggtaaaaaaacatgtcattaccgttcttaacttctgcaccgggaaaggttat
tattttggtgaacactctgctgtgtacaacaagcctgccgtcgctgctagtgtgtctgcgttgagaacctacctgct
aataagcgagtcatctgcaccagatactattgaattggacttcccggacattagctttaatcataagtggtccatc
aatgatttcaatgccatcaccgaggatcaagtaaactcccaaaaattggccaaggctcaacaagccaccgat
ggcttgtctcaggaactcgttagtctttggatccgttgttagctcaactatccgaatccttccactaccatgcagcg
ttttgtttcctgtatatgtttgtttgcctatgccccatgccaagaatattaagttttctttaaagtctactttacccatcgg
tgctgggttgggctcaagcgcctctatttctgtatcactggccttagctatggccacttgggggggttaataggat
ctaatgacttggaaaagctgtcagaaaacgataagcatatagtgaatcaatgggccttcataggtgaaaagtg
tattcacggtaccccttcaggaatagataacgctgtggccacttatggtaatgccctgctatttgaaaaagactc
acataatggaacaataaacacaaacaattttaagttcttagatgatttcccagccattccaatgatcctaacctat
actagaattccaaggtctacaaaagatcttgttgctcgcgttcgtgtgttggtcaccgagaaatttcctgaagttat
gaagccaattctagatgccatgggtgaatgtgccctacaaggcttagagatcatgactaagttaagtaaatgta
aaggcaccgatgacgaggctgtagaaactaataatgaactgtatgaacaactattggaattgataagaataa
atcatggactgcttgtctcaatcggtgtttctcatcctggattagaacttattaaaaatctgagcgatgatttgagaa
ttggctccacaaaacttaccggtgctggtggcggcggttgctctttgactttgttacgaagagacattactcaaga
gcaaattgacagcttcaaaaagaaattgcaagatgattttagttacgagacatttgaaacagacttgggtggga
ctggctgctgtttgttaagcgcaaaaaatttgaataaagatcttaaaatcaaatccctagtattccaattatttgaa
aataaaactaccacaaagcaacaaattgacgatctattattgccaggaaacacgaatttaccatggacttcat
aagctaatttgcgataggcctgcacccttaaggaggaaaaaaacatgtcagagttgagagccttcagtgccc
cagggaaagcgttactagctggtggatatttagttagatacaaaatatgaagcatttgtagtcggattatcggc
aagaatgcatgctgtagcccatccttacggttcattgcaagggtctgataagtttgaagtgcgtgtgaaaagtaa
acaatttaaagatggggagtggctgtaccatataagtcctaaaagtggcttcattcctgtttcgataggcggatct
aagaacccttcattgaaaaagttatcgctaacgtatttagctactttaaacctaacatggacgactactgcaata
gaaacttgttcgttattgatattttctctgatgatgcctaccattctcaggaggatagcgttaccgaacatcgtggca
acagaagattgagttttcattcgcacagaattgaagaagttcccaaaacagggctgggctcctcggcaggtta
gtcacagttttaactacagctttggcctccttttttgtatcggacctggaaaataatgtagacaaatatagagaagt
tattcataatttagcacaagttgctcattgtcaagctcagggtaaaattggaagcgggtttgatgtagcggcggc
agcatatggatctatcagatatagaagattcccacccgcattaatctctaatttgccagatattggaagtgctactt
acggcagtaaactggcgcatttggttgatgaagaagactggaatattacgattaaaagtaaccatttaccttcg
ggattaactttatggatgggcgatattaagaatggttcagaaacagtaaaactggtccagaaggtaaaaaatt
ggtatgattcgcatatgccagaaagcttgaaaata

Figure 25B tatacagaactcgatcatgcaaattctagatttatggatggactatctaaactagatcgcttacacgagactc
atgacgattacagcgatcagatatttgagtctcttgagaggaatgactgtacctgtcaaaagtatcctgaaat
cacagaagttagagatgcagttgccacaattagacgttcctttagaaaaataactaaagaatctggtgccg
atatcgaacctcccgtacaaactagcttattggatgattgccagaccttaaaaggagttcttacttgcttaatac
ctggtgctggtggttatgacgccattgcagtgattactaagcaagatgttgatcttagggctcaaaccgctaat
gacaaagattttctaaggttcaatggctggatgtaactcaggctgactggggtgttaggaaagaaaaaga
tccggaaacttatcttgataaataacttaaggtagctgcatgcagaattcgcccttaaggaggaaaaaaaa
atgaccgtttacacagcatccgttaccgcacccgtcaacatcgcaacccttaagtattggggaaaaggg
acacgaagttgaatctgcccaccaattcgtccatatcagtgactttatcgcaagatgacctcagaacgttga
cctctgcggctactgcacctgagtttgaacgcgacactttgtggttaaatggagaaccacacagcatcgac
aatgaaagaactcaaaattgtctgcgcgacctacgccaattaagaaaggaaatggaatcgaaggacgc
ctcattgcccacattatctcaatggaaactccacattgtctccgaaaataactttcctacagcagctggtttag
cttcctccgctgctggctttgctgcattggtctctgcaattgctaagttataccaattaccacagtcaacttcaga
aatatctagaatagcaagaaaggggtctggttcagcttgtagatcgttgtttggcggatacgtggcctggga
aatgggaaaagctgaagatggtcatgattccatggcagtacaaatcgcagacagctctgactggcctcag
atgaaagcttgtgtcctagttgtcagcgatattaaaaaggatgtgagttccactcagggtatgcaattgaccgt
ggcaacctccgaactatttaaagaaagaattgaacatgtcgtaccaaagagatttgaagtcatgcgtaaag
ccattgttgaaaaagatttcgccacctttgcaaaggaaacaatgatggattccaactctttccatgccacatgt
ttggactctttccctccaatattctacatgaatgacacttccaagcgtatcatcagttggtgccacaccattaat
cagttttacggagaaacaatcgttgcatacacgtttgatgcaggtccaaatgctgtgttgtactacttagctga
aaatgagtcgaaactctttgcatttatctataaattgtttggctctgttcctggatgggacaagaaatttactact
gagcagcttgaggctttcaaccatcaatttgaatcatctaactttactgcacgtgaattggatcttgagttgcaa
aaggatgttgccagagtgattttaactcaagtcggttcaggcccacaagaaacaaacgaatctttgattgac
gcaaagactggtctaccaaaggaataagatcaattcgctgcatcgcccttaggaggtaaaaaaaatga
ctgccgacaacaatagtatgccccatggtgcagtatctagttacgccaaattagtgcaaaaccaaacacct
gaagacattttggaagagtttcctgaaattattccattacaacaaagacctaatacccgatctagtgagacgt
caaatgacgaaagcggagaaacatgtttttctggtcatgatgaggagcaaattaagttaatgaatgaaaatt
gtattgttttggattgggacgataatgctattggtccggtaccaagaaagtttgtcatttaatggaaaatattga
aaagggtttactacatcgtgcattctccgtctttattttcaatgaacaaggtgaattactttacaacaaagagc
cactgaaaaaataactttccctgatctttggactaacacatgctgctctcatccactatgtattgatgacgaatt
aggtttgaagggtaagctagacgataagattaagggcgctattactgcggcggtgagaaaactagatcat
gaattaggtattccagaagatgaaactaagacaaggggtaagtttcacttttttaaacagaatccattacatg
gcaccaagcaatgaaccatggggtgaacatgaaattgattacatcctatttttataagatcaacgctaaaga
aaacttgactgtcaacccaaacgtcaatgaagttagagacttcaaatggtttcaccaaatgatttgaaaac
tatgtttgctgacccaagttacaagtttacgccttggtttaagattatttgcgagaattacttattcaactggtggg
agcaattagatgacctttctgaagtggaaaatgacaggcaaattcatagaatgctataacaacgcgtcctg
cattcgcccttaggaggtaaaaaaacatgtgtgcgacctcttctcaatttactcagattaccgagcataattcc
cgtcgttccgcaaactatcagccaaacctgtggaatttcgaattcctgcaatccctggagaacgacctgaa
agtggaaaagctggaggagaaagcgaccaaactggaggaagaagttcgctgcatg

Figure 25C atcaaccgtgtagacacccagccgctgtccctgctggagctgatcgacgatgtgcagcgcctgggtctgacc
tacaaatttgaaaaagacatcattaaagccctggaaaacatcgtactgctggacgaaaacaaaaagaaca
aatctgacctgcacgcaaccgctctgtctttccgtctgctgcgtcagcacggtttcgaggtttctcaggatgtttt
gagcgtttcaaggataaagaaggtggtttcagcggtgaactgaaaggtgacgtccaaggcctgctgagcct
gtatgaagcgtcttacctgggtttcgagggtgagaacctgctggaggaggcgcgtaccttttccatcacccac
ctgaagaacaacctgaaagaaggcattaataccaaggttgcagaacaagtgagccacgccctggaactg
ccatatcaccagcgtctgcaccgtctggaggcacgttggttcctggataaatacgaaccgaaagaaccgca
tcaccagctgctgctggagctggcgaagctggattttaacatggtacagaccctgcaccagaaagagctgc
aagatctgtcccgctggtggaccgagatgggcctggctagcaaactggattttgtacgcgaccgcctgatgg
aagtttatttctgggcactgggtatggcgccagacccgcagtttggtgaatgtcgcaaagctgttactaaaatgt
ttggtctggtgacgatcatcgatgacgtgtatgacgtttatggcactctggacgaactgcaactgttcaccgatg
ctgtagagcgctgggacgttaacgctattaacaccctgccggactatatgaaactgtgtttcctggcactgtac
aacaccgttaacgacacgtcctattctattctgaaagagaaaggtcataacaacctgtcctatctgacgaaaa
gctggcgtgaactgtgcaaagcctttctgcaagaggcgaaatggtccaacaacaaaattatcccggctttctc
caagtacctggaaaacgccagcgtttcctcctccggtgtagcgctgctggcgccgtcttacttttccgtatgcca
gcagcaggaagacatctccgaccacgcgctgcgttccctgaccgacttccatggtctggtgcgttctagctgc
gttatcttccgcctgtgcaacgatctggccacctctgcggcggagctggaacgtggcgagactaccaattcta
tcattagctacatgcacgaaaacgatggtaccagcgaggaacaggcccgcgaagaactgcgtaaactgat
cgacgccgaatggaaaaagatgaatcgtgaacgcgttagcgactccaccctgctgcctaaagcgttcatgg
aaatcgcagttaacatggcacgtgtttcccactgcacctaccagtatggcgatggtctgggtcgcccagacta
cgcgactgaaaaccgcatcaaactgctgctgattgaccctttcccgattaaccagctgatgtatgtctaactgc
agctggtaccatatgggaattcgaagctttctagaacaaaaactcatctcagaagaggatctgaatagcgcc
gtcgaccatcatcatcatcatcattgagtttaaacggtctccagcttggctgttttggcggatgagagaagatttt
cagcctgatacagattaaatcagaacgcagaagcggtctgataaaacagaatttgcctggcggcagtagc
gcggtggtcccacctgaccccatgccgaactcagaagtgaaacgccgtagcgccgatggtagtgtgggggt
ctccccatgcgagagtagggaactgccaggcatcaaataaaacgaaaggctcagtcgaaagactgggcc
tttcgttttatctgttgtttgtcggtgaacgctctcctgagtaggacaaatccgccgggagcggatttgaacgttgc
gaagcaacggcccggagggtggcgggcaggacgcccgccataaactgccaggcatcaaattaagcag
aaggccatcctgacggatggcctttttgcgtttctacaaactcttttgtttatttttctaaatacattcaaatatgtatc
cgcttaaccggaattgccagctggggcgccctctggtaaggttgggaagccctgcaaagtaaactggatgg
ctttctcgccgccaaggatctgatggcgcagggatcaagctctgatcaagagacaggatgaggatcgtttc
gcatgattgaacaagatggattgcacgcaggttctccggccgcttgggtggagaggctattcggctatgactg
ggcacaacagacaatcggctgctctgatgccgccgtgttccggctgtcagcgcagggcgcccggttctttt
gtcaagaccgacctgtccggtgccctgaatgaactgcaagacgaggcagcgcggctatcgtggctggcca
cgacgggcgttccttgcgcagctgtgctcgacgttgtcactgaagcgggaagggactggctgctattgggcg
aagtgccggggcaggatctcctgtcatctcaccttgctcctgccgagaaagtatccatcatggctgatgcaat
gcggcggctgcatacgcttgatccggctacctgcccattcgaccaccaagcgaaacatcgcatcgagcga
gcacgtactcggatggaagccggtcttgtcgatcaggatgatctggacgaagagcatcaggggctcgcgcc
agccgaactgttcgccaggctcaaggcgagcatgcccgacggcgaggatctcgtcgtgacccat

Figure 25D ggcgatgcctgcttgccgaatatcatggtggaaaatggccgcttttctggattcatcgactgtggccggctgg
gtgtggcggaccgctatcaggacatagcgttggctacccgtgatattgctgaagagcttggcggcgaatgg
gctgaccgcttcctcgtgctttacggtatcgccgctcccgattcgcagcgcatcgccttctatcgccttcttgac
gagttcttctgacgcatgaccaaaatcccttaacgtgagttttcgttccactgagcgtcagacccgtagaaa
agatcaaaggatcttcttgagatcctttttttctgcgcgtaatctgctgcttgcaaacaaaaaaaccaccgcta
ccagcggtggtttgtttgccggatcaagagctaccaactctttttccgaaggtaactggcttcagcagagcgc
agataccaaatactgtccttctagtgtagccgtagttaggccaccacttcaagaactctgtagcaccgcctac
atacctcgctctgctaatcctgttaccagtggctgctgccagtggcgataagtcgtgtcttaccgggttggact
caagacgatagttaccggataaggcgcagcggtcgggctgaacggggggttcgtgcacacagcccagc
ttggagcgaacgacctacaccgaactgagatacctacagcgtgagctatgagaaagcgccacgcttccc
gaagggagaaaggcggacaggtatccggtaagcggcagggtcggaacaggagagcgcacgaggga
gcttccaggggggaaacgcctggtatctttatagtcctgtcgggtttcgccacctctgacttgagcgtcgattttg
tgatgctcgtcaggggggcggagcctatggaaaaacgccagcaacgcggccttttacggttcctggccttt
tgctggccttttgctcacatgttctttcctgcgttatcccctgattctgtggataaccgtattaccgcctttgagtga
gctgataccgctcgccgcagccgaacgaccgagcgcagcgagtcagtgagcgaggaagcggaagag
cgcctgatgcggtattttctccttacgcatctgtgcggtatttcacaccgcatatggtgcactctcagtacaatct
gctctgatgccgcatagttaagccagtatacactccgctatcgctacgtgactgggtcatggctgcgcccg
acaccgccaacacccgctgacgcgccctgacgggcttgtctgctcccggcatccgcttacagacaagct
gtgaccgtctccgggagctgcatgtgtcagaggttttcaccgtcatcaccgaaacgcgcgaggcagcaga
tcaattcgcgcgcgaaggcgaagcggcatgcatttacgttgacaccatcgaatggtgcaaaacctttcgcg
gtatggcatgatagcgcccggaagagagtcaattcagggtggtgaatgtgaaaccagtaacgttatacgat
gtcgcagagtatgccggtgtctcttatcagaccgtttcccgcgtggtgaaccaggccagccacgttctgcga
aaacgcgggaaaaagtggaagcggcgatggcggagctgaattacattcccaaccgcgtggcacaaca
actggcgggcaaacagtcgttgctgattggcgttgccacctccagtctggccctgcacgcgccgtcgcaaa
ttgtcgcggcgattaaatctcgcgccgatcaactgggtgccagcgtggtggtcgatggtagaacgaagc
ggcgtcgaagcctgaaagcggcggtgcacaatcttctcgcgcaacgcgtcagtgggctgatcattaacta
tccgctggatgaccaggatgccattgctgtggaagctgcctgcactaatgttccggcgttatttcttgatgtctct
gaccagacacccatcaacagtattatttctcccatgaagacggtacgcgactgggcgtggagcatctggt
cgcattgggtcaccagcaaatcgcgctgttagcgggcccattaagttctgtctcggcgcgtctgcgtctggct
ggctggcataaatatctcactcgcaatcaaattcagccgatagcggaacgggaaggcgactggagtgcc
atgtccggttttcaacaaaccatgcaaatgctgaatgagggcatcgttcccactgcgatgctggttgccaac
gatcagatggcgctgggcgcaatgcgcgccattaccgagtccgggctgcgcgttggtgcggatatctcggt
agtgggatacgacgataccgaagacagctcatgttatatccgccgtcaaccaccatcaaacaggattttc
gcctgctggggcaaaccagcgtggaccgcttgctgcaactctctcagggccaggcggtgaagggcaatc
agctgttgcccgtctcactggtgaaaagaaaaaccaccctggcgcccaatacgcaaaccgcctctccccg
cgcgttggccgattcattaatgcagctggcacgacaggtttcccgactggaaagcgggcagtgagcgcaa
cgcaattaatgtgagttagcgcgaattgatctg (SEQ ID NO:11)

Figure 27A

5'-
cccgtcttactgtcgggaattcgcgttggccgattcattaatgcagattctgaaatgagctgttgacaattaatcatc
cggctcgtataatgtgtggaattgtgagcggataacaatttcacacaggaaacagcgccgctgagaaaagcg
aagcggcactgctctttaacaatttatcagacaatctgtgtgggcactcgaccggaattatcgattaactttattatta
aaaattaaagaggtatatattaatgtatcgattaaataaggaggaataaaccatggatccgagctcaggaggta
aaaaaacatgaaaacagtagttattattgatgcattacgaacaccaattggaaaatataaaggcagcttaagtc
aagtaagtgccgtagacttaggaacacatgttacaacacaacttttaaaaagacattccactatttctgaagaaa
ttgatcaagtaatctttggaaatgttttacaagctggaaatggccaaaatcccgcacgacaaatagcaataaac
agcggtttgtctcatgaaattccgcaatgacggttaatgaggtctgcggatcaggaatgaaggccgttattttgg
cgaaacaattgattcaattaggagaagcggaagttttaattgctggcgggattgagaatatgtcccaagcaccta
aattacaacgttttaattacgaaacagaaagctacgatgcgccttttctagtatgatgtatgatggattaacggatg
cctttagtggtcaggcaatgggcttaactgctgaaaatgtggccgaaaagtatcatgtaactagagaagagcaa
gatcaatttctgtacattcacaattaaaagcagctcaagcacaagcagaagggatattcgctgacgaaatagc
cccattagaagtatcaggaacgcttgtggagaaagatgaagggattcgccctaattcgagcgttgagaagcta
ggaacgcttaaaacagttttttaaagaagacggtactgtaacagcagggaatgcatcaaccattaatgatgggg
cttctgctttgattattgcttcacaagaatatgccgaagcacacggtcttccttatttagctattattcgagacagtgtg
gaagtcggtattgatccagcctatatgggaatttcgccgattaaagccattcaaaaactgttagcgcgcaatcaa
cttactacggaagaaattgatctgtatgaaatcaacgaagcatttgcagcaacttcaatcgtggtccaaagaga
actggctttaccagaggaaaaggtcaacatttatggtggcggtatttcattaggtcatgcgattggtgccacaggt
gctcgtttattaacgagtttaagttatcaattaaatcaaaaagaaaagaaatatggagtggcttctttatgtatcggc
ggtggcttaggactcgctatgctactagagagacctcagcaaaaaaaaacagccgatttttatcaaatgagtcc
tgaggaacgcctggcttctcttcttaatgaaggccagatttctgctgatacaaaaaaagaatttgaaaatacggct
ttatcttcgcagattgccaatcatatgattgaaaatcaaatcagtgaaacagaagtgccgatgggcgttggcttac
atttaacagtggacgaaactgattatttggtaccaatggcgacagaagagccctcagttattgcggctttgagtaa
tggtgcaaaaatagcacaaggatttaaaacagtgaatcaacaacgcttaatgcgtggacaaatcgttttttacga
tgttgcagatcccgagtcattgattgataaactacaagtaagagaagcggaagttttcaacaagcagagttaag
ttatccatctatcgttaaacggggcggcggcttaagagatttgcaatatcgtactttgatgaatcatttgtatctgtcg
acttttagtagatgttaaggatgcaatgggggcaaatatcgttaacgctatgttggaaggtgtggccgagttgttcc
gtgaatggtttgcggagcaaaagattttattcagtattttaagtaattatgccacggagtcggttgttacgatgaaaa
cggctattccagtttcacgtttaagtaaggggagcaatggccgggaaattgctgaaaaaattgtttttagcttcacg
ctatgcttcattagatccttatcgggcagtcacgcataacaaaggaatcatgaatggcattgaagctgtagttttag
ctacaggaaatgatacacgcgctgttagcgcttcttgtcatgcttttgcggtgaaggaaggtcgctaccaaggctt
gactagttggacgctggatggcgaacaactaattggtgaaatttcagttccgcttgctttagccacggttggcggtg
ccacaaaagtcttacctaaatctcaagcagctgctgatttgttagcagtgacggatgcaaaagaactaagtcga
gtagtagcggctgttggtttggcacaaaatttagcggcgttacgggccttagtctctgaaggaattcaaaaagga
cacatggctctacaagcacgttctttagcgatgacggtcggagctactggtaaagaagttgaggcagtcgctca
acaattaaaacgtcaaaaaacgatgaaccaagaccgagccatggctattttaaatgatttaagaaaacaataa
aggaggtaaaaaaacatgacaattgggat

Figure 27B tgataaaattagtttttttgtgcccccttattatattgatatgacggcactggctgaagccagaaatgtagaccctgg
aaaatttcatattggtattgggcaagaccaaatggcggtgaacccaatcagccaagatattgtgacatttgcag
ccaatgccgcagaagcgatcttgaccaaagaagataaagaggccattgatatggtgattgtcgggactgagt
ccagtatcgatgagtcaaaagcggccgcagttgtcttacatcgtttaatggggattcaacctttcgctcgctcttc
gaaatcaaggaagcttgttacggagcaacagcaggcttacagttagctaagaatcacgtagccttacatcca
gataaaaagtcttggtcgtagcggcagatattgcaaaatatggcttaaattctggcggtgagcctacacaag
gagctggggcggttgcaatgttagttgctagtgaaccgcgcattttggctttaaaagaggataatgtgatgctga
cgcaagatatctatgactttggcgtccaacaggccacccgtatcctatggtcgatggtcctttgtcaaacgaaa
cctacatccaatctttgcccaagtctgggatgaacataaaaaacgaaccggtcttgattttgcagattatgatgc
tttagcgttccatattccttacacaaaaatgggcaaaaaagccttattagcaaaaatctccgaccaaactgaag
cagaacaggaacgaatttagcccgttatgaagaaagtatcgtctatagtcgtcgcgtaggaaacttgtatacg
ggttcactttatctgggactcatttcccttagaaaatgcaacgactttaaccgcaggcaatcaaattggtttattc
agttatggttctggtgctgtcgctgaattttcactggtgaattagtagctggttatcaaaatcatttacaaaaagaa
actcatttagcactgctggataatcggacagaactttctatcgctgaatatgaagccatgtttgcagaaactttag
acacagacattgatcaaacgttagaagatgaattaaaatatagtatttctgctattaataataccgttcgttcttatc
gaaactaagagatctgcagctggtaccatatgggaattcgaagcttgggcccgaacaaaaactcatctcaga
agaggatctgaatagcgccgtcgaccatcatcatcatcatcattgagtttaaacggtctccagcttggctgttttg
gcggatgagagaagattttcagcctgatacagattaaatcagaacgcagaagcggtctgataaaacagaatt
tgcctggcggcagtagcgcggtggtcccacctgacccatgccgaactcagaagtgaaacgccgtagcgcc
gatggtagtgtggggtctccccatgcgagagtagggaactgccaggcatcaataaaacgaaaggctcagt
cgaaagactgggcctttcgttttatctgttgtttgtcggtgaacgctctcctgagtaggacaaatccgccgggagc
ggatttgaacgttgcgaagcaacggcccggagggtggcgggcaggacgcccgccataaactgccaggcat
caaattaagcagaaggccatcctgacggatggcctttttgcgtttctacaaactcttttgtttatttttctaaatacatt
caaatatgtatccgctcatgagacaataaccctgataaatgcttcaataatctggcgtaatagcgaagaggcc
cgcaccgatcgcccttcccaacagttgcgcagcctgaatggcgaatggcgcctgatgcggtattttctccttacg
catctgtgcggtatttcacaccgcatatggtgcactctcagtacaatctgctctgatgccgcatagttaagccagc
cccgacacccgccaacacccgctgacgagcttagtaaagccctcgctagattttaatgcggatgttgcgattac
ttcgccaactattgcgataacaagaaaaagccagcctttcatgatatatctcccaatttgtgtagggcttattatgc
acgcttaaaaataataaaagcagacttgacctgatagtttggctgtgagcaattatgtgcttagtgcatctaacg
cttgagttaagccgcgccgcgaagcggcgtcggcttgaacgaattgttagacattatttgccgactaccttggtg
atctcgcctttcacgtagtggacaaattcttccaactgatctgcgcgcgaggccaagcgatcttcttcttgtccaa
gataagcctgtctagcttcaagtatgacgggctgatactgggccggcaggcgctccattgcccagtcggcagc
gacatccttcggcgcgattttgccggttactgcgctgtaccaaatgcgggacaacgtaagcactacatttcgctc
atcgccagcccagtcgggcggcgagttccatagcgttaaggtttcatttagcgcctcaaatagatcctgttcagg
aaccggatcaaagagttcctccgccgctggacctaccaaggcaacgctatgttctcttgcttttgtcagcaagat
agccagatcaatgtcgatcgtggctggctcgaagatacctgcaagaatgtcattgcgctgccattctccaaattg
cagttcgcgcttagctggataacgccacggaatgatgtcgtcgtgcacaacaatggtgacttctacagcgcgg
agaatctcgctctctccaggggaagccgaagtttccaaaaggtcgttgat

Figure 27C caaagctcgccgcgttgtttcatcaagccttacggtcaccgtaaccagcaaatcaatatcactgtgtggcttca
ggccgccatccactgcggagccgtacaaatgtacggccagcaacgtcggttcgagatggcgctcgatgac
gccaactacctctgatagttgagtcgatacttcggcgatcaccgcttccctcatgatgtttaactttgttttagggc
gactgccctgctgcgtaacatcgttgctgctccataacatcaaacatcgacccacggcgtaacgcgcttgctg
cttggatgcccgaggcatagactgtaccccaaaaaaacagtcataacaagccatgaaaaccgccactgc
gccgttaccaccgctgcgttcggtcaaggttctggaccagttgcgtgagcgcatacgctacttgcattacagct
tacgaaccgaacaggcttatgtccactgggttcgtgccttcatccgtttccacggtgtgcgtcacccggcaacc
ttgggcagcagcgaagtcgaggcatttctgtcctggctggcgaacgagcgcaaggtttcggtctccacgcat
cgtcaggcattggcggccttgctgttcttctacggcaaggtgctgtgcacggatctgccctggcttcaggagat
cggaagacctcggccgtcgcggcgcttgccggtggtgctgaccccggatgaagtggttcgcatcctcggtttt
ctggaaggcgagcatcgtttgttcgcccagcttctgtatggaacgggcatgcggatcagtgagggtttgcaac
tgcgggtcaaggatctggatttcgatcacggcacgatcatcgtgcgggagggcaagggctccaaggatcg
ggccttgatgttacccgagagcttggcacccagcctgcgcgagcaggggaattaattcccacgggttttgctg
cccgcaaacgggctgttctggtgttgctagtttgttatcagaatcgcagatccggcttcagccggtttgccggct
gaaagcgctatttcttccagaattgccatgattttttccccacgggaggcgtcactggctcccgtgttgtcggca
gctttgattcgataagcagcatcgcctgttcaggctgtctatgtgtgactgttgagctgtaacaagttgtctcagg
tgttcaatttcatgttctagttgctttgttttactggttcacctgttctattaggtgttacatgctgttcatctgttacattgt
cgatctgttcatggtgaacagctttgaatgcaccaaaaactcgtaaaagctctgatgtatctatctttttacacc
gttttcatctgtgcatatggacagttttcccttttgatatgtaacggtgaacagttgttctactttgtttgttagtcttgat
gcttcactgatagatacaagagccataagaacctcagatccttccgtatttagccagtatgttctctagtgtggtt
cgttgttttttgcgtgagccatgagaacgaaccattgagatcatacttactttgcatgtcactcaaaaattttgcctc
aaaactggtgagctgaattttttgcagttaaagcatcgtgtagtgtttttcttagtccgttatgtaggtaggaatctga
tgtaatggttgttggtattttgtcaccattcattttatctggttgttctcaagttcggttacgagatccatttgtctatcta
gttcaacttggaaaatcaacgtatcagtcgggcggcctcgcttatcaaccaccaatttcatattgctgtaagtgtt
taaatctttacttattggtttcaaaacccattggttaagccttttaaactcatggtagttatttttcaagcattaacatg
aacttaaattcatcaaggctaatctctatatttgccttgtgagttttcttttgtgttagttcttttaataaccactcataaa
tcctcatagagtatttgtttttcaaaagacttaacatgttccagattatattttatgaattttttttaactggaaaagataa
ggcaatatctcttcactaaaaactaattctaattttttcgcttgagaacttggcatagtttgtccactggaaaatctc
aaagcctttaaccaaaggattcctgatttccacagttctcgtcatcagctctctggttgctttagctaatacaccat
aagcattttccctactgatgttcatcatctgagcgtattggttataagtgaacgataccgtccgttctttccttgtag
ggttttcaatcgtggggttgagtagtgccacacagcataaaattagcttggtttcatgctccgttaagtcatagcg
actaatcgctagttcatttgctttgaaaacaactaattcagacatacatctcaattggtctaggtgatttaatcact
ataccaattgagatgggctagtcaatgataattactagtccttttcctttgagttgtgggtatctgtaaattctgcta
gacctttgctggaaaacttgtaaattctgctagaccctctgtaaattccgctagacctttgtgtgttttttttgtttatatt
caagtggttataatttatagaataaagaaagaataaaaaagataaaaagaatagatcccagccctgtgtat
aactcactactttagtcagttccgcagtattacaaaaggatgtcgcaaacgctgtttgctcctctacaaaacag
accttaaaaccctaaaggcttaagtagcaccctcgcaagctcgggcaaatcgctgaatattccttttgtctccg
acc

Figure 27D

Atcaggcacctgagtcgctgtcttttcgtgacattcagttcgctgcgctcacggctctggcagtgaatggggg
gtaaatggcactacaggcgcctttatggattcatgcaaggaaactacccataatacaagaaaagcccgt
cacgggcttctcagggcgttttatggcgggtctgctatgtggtgctatctgacttttgctgttcagcagttcctg
ccctctgattttccagtctgaccacttcggattatcccgtgacaggtcattcagactggctaatgcacccagt
aaggcagcggtatcatcaacaggctta (SEQ ID NO:12)

Figure 29A

5'-
tgtaacctttgctttcaaatgagtagaaataatgcacatccatgtttgtatcgtgcaaataaagtgtttcatccgtag
gaaaaaatgactttagtatctgttccgcttttctgatgaaatgtgctccccgacaaaattgaatgaatcatggaca
tttgctggctttgatacagcgaaagcagccgttcctatgttatatatcggatttaacagcaggacaaaaaacacc
atgacagccatcgtcacccacttattcacacgcacataaaccttcctgacttttggaacagatgatagctcatc
aaaaatcccgccattgccaaataaatcgtatatggcattactgcaccataatcttttgagatttgattgggatatgg
cgcaagcagcaagacaagcagtccgataatcagcgtataaaataagcctagtaagatcttatccgttctcca
atacagcttgaaaaacactacattcaacgcaatgggaagagtgatgatgaaaaacagaaacacgaatgca
atcggctccatcccatccgggtattccttccaatacgaaaagaaactaaaaatcatttgtacgatcggcaaact
gacaacagcaaggtcgaacgtataaaacttaccctttccgccatgatcacgcggcatcagcatatagtgaaa
agccgtcagcagcacatatccgtataacaaaaaatgcagcagcggcagcagttcttttccgtcctctcttaagt
aagcgctggtgaagtttgttgattgcacctggtgaataagttcaacagacactcccgccagcagcacaatccg
caatataacacccgccaagaacattgtgcgctgccggtttatttgggatgatgcaccaaaagatataagccc
gccagaacaacaattgaccattgaatcagcaggtgctttgtctgcttaatataaaataacgttcgaaatgcaat
acataatgactgaataactccaacacgaacaacaactccattttcttctgctatcaaaataacagactcgtgattt
tccaaacgagctttcaaaaaagcctctgcccctgcaaatcggatgcctgtctataaaattcccgatattggttaa
acagcggcgcaatggcggccgcatctgatgtctttgcttggcgaatgttcatcttatttcttcctccctctcaataatt
ttttcattctatccctttctgtaaagtttattttcagaatacttttatcatcatgctttgaaaaaatatcacgataatatc
cattgttctcacggaagcacacgcaggtcatttgaacgaatttttcgacaggaatttgccgggactcaggagc
atttaacctaaaaagcatgacatttcagcataatgaacatttactcatgtctatttcgttcttttctgtatgaaaata
gttatttcgagtctctacggaaatagcgagagatgatatacctaaatagagataaaatcatctcaaaaaaatgg
gtctactaaaatattattccatctattacaataaaattcacagaatagtcttttaagtaagtctactctgaatttttttaaa
aggagagggtaaagagtgtcattaccgttcttaacttctgcaccgggaaaggttattattttggtgaacactctg
ctgtgtacaacaagcctgccgtcgctgctagtgtgtctgcgttgagaacctacctgctaataagcgagtcatctg
caccagatactattgaattggacttcccggacattagctttaatcataagtggtccatcaatgatttcaatgccatc
accgaggatcaagtaaactcccaaaaattggccaaggctcaacaagccaccgatggcttgtctcaggaact
cgttagtcttttggatccgttgttagctcaactatccgaatccttccactaccatgcagcgttttgtttcctgtatatgttt
gtttgcctatgcccccatgccaagaatattaagttttctttaaagtctactttacccatcggtgctgggttgggctca
agcgcctctatttctgtatcactggccttagctatggcctacttggggggggttaataggatctaatgacttggaaaa
gctgtcagaaaacgataagcatatagtgaatcaatgggccttcataggtgaaaagtgtattcacggtacccctt
caggaatagataacgctgtggccacttatggtaatgccctgctatttgaaaaagactcacataatggaacaata
aacacaaacaattttaagttcttagatgatttcccagccattccaatgatcctaacctatactagaattccaaggtc
tacaaagatcttgttgctcgcgttcgtgtgttggtcaccgagaaatttcctgaagttatgaagccaattctagatg
ccatgggtgaatgtgccctacaaggcttagagatcatgactaagttaagtaaatgtaaaggcaccgatgacga
ggctgtagaaactaataatgaactgtatgaacaactattggaattgataagaataaatcatggactgcttgtctc
aatcggtgtttctcatcctggattagaacttattaaaaatctgagcgatgatttgagaattggctccacaaaactta
ccggtgctggtggcggcggttgctctttgactttgttacgaagagacattactcaagagcaaattgacagcttca
aaaagaaattgcaagatgattttagt

Figure 29B tacgagacatttgaaacagacttgggtgggactggctgctgtttgttaagcgcaaaaaatttgaataaagat
cttaaaatcaaatccctagtattccaattatttgaaaataaaactaccacaaagcaacaaattgacgatctat
tattgccaggaaacacgaatttaccatggacttcataaaaggagagggtgtcagagttgagagccttcagt
gccccagggaaagcgttactagctggtggatatttagttttagatacaaaatatgaagcatttgtagtcggatt
atcggcaagaatgcatgctgtagcccatccttacggttcattgcaagggtctgataagtttgaagtgcgtgtg
aaaagtaaacaatttaaagatggggagtggctgtaccatataagtcctaaaagtggcttcattcctgtttcga
taggcggatctaagaaccctttcattgaaaaagttatcgctaacgtatttagctactttaaacctaacatggac
gactactgcaatagaaacttgttcgttattgatattttctctgatgatgcctaccattctcaggaggatagcgtta
ccgaacatcgtggcaacagaagattgagttttcattcgcacagaattgaagaagttcccaaaacagggct
gggctcctcggcaggtttagtcacagttttaactacagctttggcctccttttttgtatcggacctggaaaataat
gtagacaaatatagagaagttattcataatttagcacaagttgctcattgtcaagctcagggtaaaattggaa
gcgggtttgatgtagcggcggcagcatatggatctatcagatatagaagattcccacccgcattaatctcta
atttgccagatattggaagtgctacttacggcagtaaactggcgcatttggttgatgaagaagactggaatat
tacgattaaaagtaaccatttaccttcgggattaactttatggatgggcgatattaagaatggttcagaaaca
gtaaaactggtccagaaggtaaaaaattggtatgattcgcatatgccagaaagcttgaaaatatatacaga
actcgatcatgcaaattctagatttatggatggactatctaaactagatcgcttacacgagactcatgacgatt
acagcgatcagatatttgagtctcttgagaggaatgactgtacctgtcaaaagtatcctgaaatcacagaag
ttagagatgcagttgccacaattagacgttcctttagaaaaataactaaagaatcggtgccgatatcgaac
ctcccgtacaaactagcttattggatgattgccagaccttaaaaggagttcttacttgcttaatacctggtgctg
gtggttatgacgccattgcagtgattactaagcaagatgttgatcttagggctcaaaccgctaatgacaaaa
gattttctaaggttcaatggctggatgtaactcaggctgactgggggtgttaggaaagaaaaagatccggaa
acttatcttgataaataaaggagagggtgaccgtttacacagcatccgttaccgcacccgtcaacatcgc
aacccttaagtattgggggaaaagggacacgaagttgaatctgcccaccaattcgtccatatcagtgactt
atcgcaagatgacctcagaacgttgacctctgcggctactgcacctgagtttgaacgcgacactttgtggtta
aatggagaaccacacagcatcgacaatgaaagaactcaaaattgtctgcgcgacctacgccaattaaga
aaggaaatggaatcgaaggacgcctcattgcccacattatctcaatggaaactccacattgtctccgaaaa
taactttcctacagcagctggtttagcttcctccgctgctggctttgctgcattggtctctgcaattgctaagttata
ccaattaccacagtcaacttcagaaatatctagaatagcaagaaaggggtctggttcagcttgtagatcgtt
gtttggcggatacgtggcctgggaaatgggaaaagctgaagatggtcatgattccatggcagtacaaatcg
cagacagctctgactggcctcagatgaaagcttgtgtcctagttgtcagcgatattaaaaaggatgtgagttc
cactcagggtatgcaattgaccgtggcaacctccgaactatttaaagaaagaattgaacatgtcgtaccaa
agagatttgaagtcatgcgtaaagccattgttgaaaaagatttcgccacctttgcaaaggaaacaatgatg
gattccaactctttccatgccacatgtttggactctttcctccaatattctacatgaatgacacttccaagcgtat
catcagttggtgccacaccattaatcagttttacggagaaacaatcgttgcatacacgtttgatgcaggtcca
aatgctgtgttgtactacttagctgaaaatgagtcgaaactctttgcatttatctataaattgtttggctctgttcctg
gatgggacaagaaatttactactgagcagcttgaggctttcaaccatcaatttgaatcatctaactttactgca
cgtgaattggatcttgagttgcaaaaggatgttgccagagtgattttaactcaagtcggttcaggcccacaag
aaacaaacgaatctttgattgacgcaaagactggtctaccaaaggaataaaaggagagggtgactgccg
acaacaatagtatgccccatggtgcagtatctagttacgccaaattagt

Figure 29C gcaaaaccaaacacctgaagacattttggaagagtttcctgaaattattccattacaacaaagacctaatac
ccgatctagtgagacgtcaaatgacgaaagcggagaaacatgtttttctggtcatgatgaggagcaaattaa
gttaatgaatgaaaattgtattgttttggattgggacgataatgctattggtgccggtaccaagaaagtttgtcatt
taatggaaaatattgaaaaggggtttactacatcgtgcattctccgtctttattttcaatgaacaaggtgaattacttt
tacaacaaagagccactgaaaaaataactttccctgatctttggactaacacatgctgctctcatccactatgt
attgatgacgaattaggtttgaagggtaagctagacgataagattaagggcgctattactgcggcggtgaga
aaactagatcatgaattaggtattccagaagatgaaactaagacaaggggtaagtttcactttttaaacagaa
tccattacatggcaccaagcaatgaaccatggggtgaacatgaaattgattacatcctattttataagatcaac
gctaaagaaaacttgactgtcaacccaaacgtcaatgaagttagagacttcaaatgggtttcaccaaatgatt
tgaaaactatgtttgctgacccaagttacaagtttacgccttggtttaagattatttgcgagaattacttattcaact
ggtgggagcaattagatgacctttctgaagtggaaaatgacaggcaaattcatagaatgctataaaaaaaa
ccggccttggccccgccggttttttattattttttcttcctccgcatgttcaatccgctccataatcgacggatggctc
cctctgaaaattttaacgagaaacggcgggttgacccggctcagtcccgtaacggccaagtcctgaaacgt
ctcaatcgccgcttccggtttccggtcagctcaatgccgtaacggtcggcggcgttttcctgataccgggaga
cggcattcgtaatttgaatacatacgaacaaattaataaagtgaaaaaaatacttcggaaacatttaaaaaat
aaccttattggtacttacatgtttggatcaggagttgagagtggactaaaaccaaatagtgatcttgacttttagt
cgtcgtatctgaaccattgacagatcaaagtaaagaaatactatacaaaaaattagacctatttcaaaaaa
aataggagataaaagcaacttacgatatattgaattaacaattattattcagcaagaaatggtaccgtggaat
catcctcccaaacaagaatttatttatggagaatggttacaagagctttatgaacaaggatacattcctcagaa
ggaattaaattcagatttaaccataatgctttaccaagcaaaacgaaaaaataaaagaatatacggaaatta
tgacttagaggaattactacctgatattccattttctgatgtgagaagagccattatggattcgtcagaggaatta
atagataattatcaggatgatgaaaccaactctatattaactttatgccgtatgattttaactatggacacgggta
aaatcataccaaaagatattgcgggaaatgcagtggctgaatcttctccattagaacatagggagagaatttt
gttagcagttcgtagttatcttggagagaatattgaatggactaatgaaaatgtaaatttaactataaactattta
aataacagattaaaaaaattataatgtaacctttgctttcaaatgagtagaaataatgcacatccatgtttgtatc
gtgcaaataaagtgtttcatccgtaggaaaaaatgactttagtatctgttccgcttttctgatgaaatgtgctccc
cgacaaaattgaatgaatcatggacatttgctggctttgatacagcgaaagcagccgttcctatgttatatatcg
gatttaacagcaggacaaaaaacaccatgacagccatcgtcacccacttattcacacgcacataaaccttttc
ctgacttttggaacagatgatagctcatcaaaaatcccgccattgccaaataaatcgtatatggcattactgca
ccataatctttttgagatttgattgggatatggcgcaagcagcaagacaagcagtccgataatcagcgtataaa
ataagcctagtaagatcttatccgttctccaatacagcttgaaaaacactacattcaacgcaatgggaagagt
gatgatgaaaaacagaaacacgaatgcaatcggctccatcccatccgggtattccttccaatacgaaaaga
aactaaaaatcatttgtacgatcggcaaactgacaacagcaaggtcgaacgtataaaacttacccctttccgc
catgatcacgcggcatcagcatatagtgaaaagccgtcagcagcacatatccgtataacaaaaaatgcag
cagcggcagcagttcttttccgtcctctcttaagtaagcgctggtgaagtttgttgattgcacctggtgaataagtt
caacagacactcccgccagcagcacaatccgcaatataacacccgccaagaacattgtgcgctgccggtt
tattttgggatgatgcaccaaaagatataagcccgccagaacaacaattgaccattgaatcagcagggtgct
ttgtctgcttaatataaaataacgttcgaaatgcaatacataatgactgaataactccaacacgaacaacaaa
agtgcgcatttt

Figure 29D

Ataaaagctaatgattcagtccacataattgatagacgaattctgctacaggtcacgtggctatgtgaagg
atcgcgcgtccagttaagagcaaaaacattgacaaaaaaatttatttatgctaaaatttactattaatatattt
gtatgtataataagattctcctggccaggggaatcttattttttgtggaggatcatttcatgaggaaaaatgag
tccagcttaacgtctctaatttcagcttttgcccgtgcatatcacagccgatatgacacacctcttattttgatg
attttatcgcaaaagatctcattaacgaaaagagtttatcgacatcagtaaaaatatgattcaagaaatat
cgttttcaacaaagagatcgccgaacgtcttcaaaatgatcctgaaaaaatattaaaatgggttgcacaa
atccagctgtctccaacgccctagcacgtgcttcttattgtgaaaagtcttgcacaacgaattaatcctgg
gggcaaaacagtatgtcattcttggagcgggactggatactttctgctttcggcatccagaattagaaaac
agcttacaggttttcgaggttgatcatccggccacacagcaattgaaaaaaaataagctgaaggatgca
aatctgacaattccgggtcatcttcattttgttcctatggatttcaccaaaacgttttcgtatgatcctctcttagat
gaaggatttaaaaacacaaaaacattcttcagccttctcggagtgtcttattatgtaacacgggaagaaaa
tgcaagcttgatcagcaatttattttctcatgtcccgcctggaagctctattgttttgattatgcggacgaaac
acttttacagcaaaagggacgtcgaatcgagttgaacatatggtgaagatggctgccgcaagcgggga
accgatgaaatcatgtttcacttatcaagagattgaacatctg (SEQ ID NO:13)

Figure 31A

5'-
tagaaaaaactcatcgagcatcaaatgaaactgcaatttattcatatcaggattatcaataccatattttgaaaa
agccgtttctgtaatgaaggagaaaactcaccgaggcagttccataggatggcaagatcctggtatcggtct
gcgattccgactcgtccaacatcaatacaacctattaatttccctcgtcaaaaataaggttatcaagtgagaa
atcaccatgagtgacgactgaatccggtgagaatggcaaaagtttatgcatttctttccagacttgttcaacag
gccagccattacgctcgtcatcaaaatcactcgcatcaaccaaaccgttattcattcgtgattgcgcctgagcg
aggcgaaatacgcgatcgctgttaaaaggacaattacaaacaggaatcgagtgcaaccggcgcaggaa
cactgccagcgcatcaacaatattttcacctgaatcaggatattcttctaatacctggaacgctgttttccgggg
atcgcagtggtgagtaaccatgcatcatcaggagtacggataaaatgcttgatggtcggaagtggcataaat
tccgtcagccagtttagtctgaccatctcatctgtaacatcattggcaacgctacctttgccatgtttcagaaaca
actctggcgcatcgggcttcccatacaagcgatagattgtcgcacctgattgcccgacattatcgcgagccca
tttatacccatataaatcagcatccatgttggaatttaatcgcggcctcgacgtttcccgttaatatggctcatat
tcttccttttcaatattattgaagcatttatcagggttattgtctcatgagcggatacatatttgaatgtatttagaaa
aataaacaaatagggggtcagtgttacaaccaattaaccaattctgaacattatcgcgagcccatttatacctg
aatatggctcataacaccccttgtttgcctggcggcagtagcgcggtggtcccacctgaccccatgccgaact
cagaagtgaaacgccgtagcgccgatggtagtgtggggactccccatgcgagagtagggaactgccagg
catcaaataaaacgaaaggctcagtcgaaagactgggcctttcgcccgggctaattagggggtgtcgcccttt
tagtcgctgaacatgtgctctgtttctaccgagaacgtttccttcactgagacggaaaccgaggcacgtcgtag
cgcgaactacgagccgaatagctgggactacgatttcctgctgtcttccgatactgacgaatctattgaggtgt
acaaagacaaagcaaagaaactggaggctgaagtgcgccgcgaaattaacaacgagaaagctgaattc
ctgactctgctggagctgatcgataacgtacagcgcctgggtctgggttaccgcttcgaatctgatatccgtcg
cgcactggatcgtttcgtaagcagcggcggtttcgatggcgtgaccaaaacgagcctgcacgctaccgcgc
tgtccttccgtctgctgcgtcagcacggcttcgaagtttctcaggaagcattctccggtttcaaagatcaaaacg
gtaacttcctggaaaacctgaaagaagacactaaggcgatcctgagcctgtatgaggcaagctttctggccc
tggagggtgagaacatcctggatgaggcgcgcgtattcgccatctcccatctgaaagagctgtctgaagag
aaaatcggtaaggaactggcagagcaggttaatcacgcactggaactgccgctgcatcgtcgtacccagc
gtctggaggcggtttggtccatcgaagcgtaccgcaaaaaggaggatgctaaccaggttctgctggaactg
gccatcctggactacaacatgatccagtccgtttaccagcgtgatctgcgtgaaacctcccgttggtggcgcc
gtgtgggcctggcgaccaaactgcacttcgctaaggaccgcctgattgagtcttttactgggcagtcggcgtt
gcgttcgaacctcagtattctgactgccgtaacagcgttgcgaaaatgttcagcttcgttactattatcgacgac
atctacgacgtttacggtactctggacgagctggaactgtttaccgacgctgtcgaacgttgggatgttaacgc
catcaacgatctgcctgactacatgaaactgtgcttcctggcactgtataacacgatcaacgaaattgcatac
gacaacctgaaagacaaaggtgaaaacatcctgccgtacctgactaaagcgtgggcggatctgtgtaacg
cttttctgcaagaagcgaaatggctgtataacaaatccactccgaccttgacgattatttcggcaatgcctgga
aatccagctctggcccgctgcaactgatcttcgcttattttgcggttgtccaaaacatcaaaaaggaggaaatt
gaaaacctgcaaaaataccacgatatcattagccgtccttctcatatctttcgcctgtgcaacgacctggcaa
gcgcgtccgcagagatcgcacgtggcgaaaccgctaactctgtttcctgctacatgcgcaccaagggcattt
ccgaagagctggcaaccgagagcgtaatgaatctgatcgacgaaacctgtaagaaaatgaacaaagaa
aaactgggtggctccctgttcgctaaaccgttcgtagagactgctattaacct

Figure 31B ggcacgtcagagccactgcacctaccacaatggtgacgcacatactagcccggatgaactgactcg
taaacgtgtactgtctgttatcaccgaaccgattctgccgttcgaacgttaactgcagcgtcaatcgaaa
gggcgacacaaaatttattctaaatgcataataaatactgataacatcttatagtttgtattatattttgtatt
atcgttgacatgtataattttgatatcaaaaactgattttcccttattattttcgagatttattttcttaattctcttt
aacaaactagaaatattgtatatacaaaaaatcataaataatagatgaatagtttaattataggtgttcat
caatcgaaaaagcaacgtatcttatttaaagtgcgttgcttttttctcatttataaggttaaataattctcatat
atcaagcaaagtgacaggcgcccttaaatattctgacaaatgctctttccctaaactcccccataaaa
aaacccgccgaagcgggttttttacgttatttgcggattaacgattactcgttatcagaaccgcccaggg
ggcccgagcttaagactggccgtcgttttacaacacagaaagagtttgtagaaacgcaaaaaggcc
atccgtcaggggccttctgcttagtttgatgcctggcagttccctactctcgccttccgcttcctcgctcact
gactcgctgcgctcggtcgttcggctgcggcgagcggtatcagctcactcaaaggcggtaatacggtt
atccacagaatcagggataacgcaggaaagaacatgtgagcaaaaggccagcaaaaggccag
gaaccgtaaaaaggccgcgttgctggcgttttccataggctccgccccctgacgagcatcacaaa
aatcgacgctcaagtcagaggtggcgaaacccgacaggactataaagataccaggcgtttccccct
ggaagctccctcgtgcgctctcctgttccgaccctgccgcttaccggatacctgtccgcctttctcccttcg
ggaagcgtggcgctttctcatagctcacgctgtaggtatctcagttcggtgtaggtcgttcgctccaagct
gggctgtgtgcacgaaccccccgttcagcccgaccgctgcgccttatccggtaactatcgtcttgagtc
caacccggtaagacacgacttatcgccactggcagcagccactggtaacaggattagcagagcga
ggtatgtaggcggtgctacagagttcttgaagtggtgggctaactacggctacactagaagaacagta
tttggtatctgcgctctgctgaagccagttaccttcggaaaaagagttggtagctcttgatccggcaaac
aaaccaccgctggtagcggtggtttttttgtttgcaagcagcagattacgcgcagaaaaaaaggatctc
aagaagatcctttgatcttttctacggggtctgacgctcagtggaacgacgcgcgcgtaactcacgtta
agggattttggtcatgagcttgcgccgtcccgtcaagtcagcgtaatgctctgcttt (SEQ ID NO:14)

Figure 33A

5'-
gtttgacagcttatcatcgactgcacggtgcaccaatgcttctggcgtcaggcagccatcggaagctgtgg
tatggctgtgcaggtcgtaaatcactgcataattcgtgtcgctcaaggcgcactcccgttctggataatgttttt
tgcgccgacatcataacggttctggcaaatattctgaaatgagctgttgacaattaatcatccggctcgtata
atgtgtggaattgtgagcggataacaatttcacacaggaaacagcgccgctgagaaaaagcgaagcg
gcactgctctttaacaatttatcagacaatctgtgtgggcactcgaccggaattatcgattaactttattattaa
aaattaaagaggtatatattaatgtatcgattaaataaggaggaataaaccatgtgctctgtttctaccgag
aacgtttccttcactgagacggaaaccgaggcacgtcgtagcgcgaactacgagccgaatagctggga
ctacgatttcctgctgtcttccgatactgacgaatctattgaggtgtacaaagacaaagcaaagaaactgg
aggctgaagtgcgccgcgaaattaacaacgagaaagctgaattcctgactctgctggagctgatcgata
acgtacagcgcctgggtctgggttaccgcttcgaatctgatatccgtcgcgcactggatcgtttcgtaagca
gcggcggtttcgatggcgtgaccaaaacgagcctgcacgctaccgcgctgtccttccgtctgctgcgtca
gcacggcttcgaagtttctcaggaagcattctccggtttcaaagatcaaaacggtaacttcctggaaaacc
tgaaagaagacactaaggcgatcctgagcctgtatgaggcaagctttctggccctggagggtgagaac
atcctggatgaggcgcgcgtattcgccatctcccatctgaaagagctgtctgaagagaaaatcggtaagg
aactggcagagcaggttaatcacgcactggaactgccgctgcatcgtcgtacccagcgtctggaggcg
gtttggtccatcgaagcgtaccgcaaaaggaggatgctaaccaggttctgctggaactggccatcctgg
actacaacatgatccagtccgtttaccagcgtgatctgcgtgaaacctcccgttggtggcgccgtgtgggc
ctggcgaccaaactgcacttcgctaaggaccgcctgattgagtcttttactgggcagtcggcgttgcgttc
gaacctcagtattctgactgccgtaacagcgttgcgaaaatgttcagcttcgttactattatcgacgacatct
acgacgtttacggtactctggacgagctggaactgtttaccgacgctgtcgaacgttgggatgttaacgcc
atcaacgatctgcctgactacatgaaactgtgcttcctggcactgtataacacgatcaacgaaattgcata
cgacaacctgaaagacaaaggtgaaaacatcctgccgtacctgactaaagcgtgggcggatctgtgta
acgcttttctgcaagaagcgaaatggctgtataacaaatccactccgacctttgacgattatttcggcaatg
cctggaaatccagctctggcccgctgcaactgatcttcgcttattttgcggttgtccaaaacatcaaaaagg
aggaaattgaaaacctgcaaaaataccacgatatcattagccgtccttctcatatctttcgcctgtgcaacg
acctggcaagcgcgtccgcagagatcgcacgtggcgaaaccgctaactctgttcctgctacatgcgca
ccaagggcatttccgaagagctggcaaccgagagcgtaatgaatctgatcgacgaaacctgtaagaaa
atgaacaaagaaaaactgggtggctccctgttcgctaaaccgttcgtagagactgctattaacctggcac
gtcagagccactgcacctaccacaatggtgacgcacatactagcccggatgaactgactcgtaaacgtg
tactgtctgttataccgaaccgattctgccgttcgaacgttaactgcagctggtaccatatgggaattcgaa
gctttctagaacaaaaactcatctcagaagaggatctgaatagcgccgtcgaccatcatcatcatcatcat
tgagtttaaacggtctccagcttggctgttttggcggatgagagaagattttcagcctgatacagattaaatc
agaacgcagaagcggtctgataaaacagaatttgcctggcggcagtagcgcggtggtcccacctgacc
ccatgccgaactcagaagtgaaacgccgtagcgccgatggtagtgtggggtctccccatgcgagagta
gggaactgccaggcatcaaataaaacgaaaggctcagtcgaaagactgggcctttcgttttatctgttgttt
gtcggtgaacgctctcctgagtaggacaaatccgccgggagcggatttgaacgttgcgaagcaacggc
ccggagggtggcgggcaggacgcccgccataaactgccaggcatcaaattaagcagaaggccatcct
gacggatggcctttttgcgtttctacaaactcttttgtttatttttctaaatacattcaaatatgtatccgctcatga
gacaataacccctgataaatgcttcaataatattgaaaaaggaagagtatgagtattcaacatttc

Figure 33B cgtgtcgcccttattccctttttgcggcattttgccttcctgttttgctcacccagaaacgctggtgaaagtaa
aagatgctgaagatcagttgggtgcacgagtgggttacatcgaactggatctcaacagcggtaagatc
cttgagagttttcgccccgaagaacgttttccaatgatgagcacttttaaagttctgctatgtggcgcggtat
tatcccgtgttgacgccgggcaagagcaactcggtcgccgcatacactattctcagaatgacttggttga
gtactcaccagtcacagaaaagcatcttacggatggcatgacagtaagagaattatgcagtgctgccat
aaccatgagtgataacactgcggccaacttacttctgacaacgatcggaggaccgaaggagctaacc
gcttttttgcacaacatgggggatcatgtaactcgccttgatcgttgggaaccggagctgaatgaagccat
accaaacgacgagcgtgacaccacgatgcctgtagcaatggcaacaacgttgcgcaaactattaact
ggcgaactacttactctagcttcccggcaacaattaatagactggatggaggcggataaagttgcagg
accacttctgcgctcggcccttccggctggctggtttattgctgataaatctggagccggtgagcgtgggtc
tcgcggtatcattgcagcactggggccagatggtaagccctcccgtatcgtagttatctacacgacggg
gagtcaggcaactatggatgaacgaaatagacagatcgctgagataggtgcctcactgattaagcatt
ggtaactgtcagaccaagtttactcatatatactttagattgatttaaaacttcattttaatttaaaaggatct
aggtgaagatcctttttgataatctcatgaccaaaatcccttaacgtgagttttcgttccactgagcgtcaga
ccccgtagaaaagatcaaaggatcttcttgagatcctttttttctgcgcgtaatctgctgcttgcaaacaaa
aaaaccaccgctaccagcggtggtttgtttgccggatcaagagctaccaactcttttccgaaggtaact
ggcttcagcagagcgcagataccaaatactgtccttctagtgtagccgtagttaggccaccacttcaag
aactctgtagcaccgcctacatacctcgctctgctaatcctgttaccagtggctgctgccagtggcgataa
gtcgtgtcttaccgggttggactcaagacgatagttaccggataaggcgcagcggtcgggctgaacgg
ggggttcgtgcacacagcccagcttggagcgaacgacctacaccgaactgagatacctacagcgtga
gctatgagaaagcgccacgcttcccgaagggagaaaggcggacaggtatccggtaagcggcaggg
tcggaacaggagagcgcacgagggagcttccaggggaaacgcctggtatctttatagtcctgtcggg
tttcgccacctctgacttgagcgtcgatttgtgatgctcgtcaggggggcggagcctatggaaaaacgc
cagcaacgcggcctttttacggttcctggccttttgctggccttttgctcacatgttctttcctgcgttatcccct
gattctgtggataaccgtattaccgcctttgagtgagctgataccgctcgccgcagccgaacgaccgag
cgcagcgagtcagtgagcgaggaagcggaagagcgcctgatgcggtattttctccttacgcatctgtgc
ggtatttcacaccgcatatggtgcactctcagtacaatctgctctgatgccgcatagttaagccagtatac
actccgctatcgctacgtgactgggtcatggctgcgccccgacacccgccaacacccgctgacgcgcc
ctgacgggcttgtctgctcccggcatccgcttacagacaagctgtgaccgtctccgggagctgcatgtgt
cagaggttttcaccgtcatcaccgaaacgcgcgaggcagcagatcaattcgcgcgcgaaggcgaag
cggcatgcatttacgttgacaccatcgaatggtgcaaaacctttcgcggtatggcatgatagcgcccgg
aagagagtcaattcagggtggtgaatgtgaaaccagtaacgttatacgatgtcgcagagtatgccggtg
tctcttatcagaccgtttcccgcgtggtgaaccaggccagccacgtttctgcgaaaacgcgggaaaaag
tggaagcggcgatggcggagctgaattacattcccaaccgcgtggcacaacaactggcgggcaaac
agtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaag
cctgtaaagcggcggtgcacaatcttctcgcgcaacgcgtcagtgggctgatcattaactatccgctgga
tgaccaggatgccattgctgtggaagctgcctgcactaatgttccggcgttatttcttgatgtctctgaccag
acacccatcaacagtattattttctcccatgaagacggtacgcgactgggcgtggagcatctggtcgcat
tgggtcaccagcaaatcgcgctgttagcgggcccattaagttctgtctcggcgcgtctgcgtctggctggc
tggcataaatatctcactcgcaatc

Figure 33C aaattcagccgatagcggaacgggaaggcgactggagtgccatgtccggttttcaacaaaccatgca
aatgctgaatgagggcatcgttcccactgcgatgctggttgccaacgatcagatggcgctgggcgcaat
gcgcgccattaccgagtccgggctgcgcgttggtgcggatatctcggtagtgggatacgacgataccg
aagacagctcatgttatatcccgccgtcaaccaccatcaaacaggattttcgcctgctggggcaaacca
gcgtggaccgcttgctgcaactctctcagggccaggcggtgaagggcaatcagctgttgcccgtctcac
tggtgaaaagaaaaaccaccctggcgcccaatacgcaaaccgcctctccccgcgcgttggccgattc
attaatgcagctggcacgacaggtttcccgactggaaagcgggcagtgagcgcaacgcaattaatgtg
agttagcgcgaattgatctg (SEQ ID NO:15)

Figure 35A

5'-
ttgtctgctcccggcatccgcttacagacaagctgtgaccgtctccgggagctgcatgtgtcagaggttttca
ccgtcatcaccgaaacgcgcgaggcagcagatcaattcgcgcgcgaaggcgaagcggcatgcattta
cgttgacaccatcgaatggtgcaaaaccttcgcggtatggcatgatagcgcccggaagagagtcaattc
agggtggtgaatgtgaaaccagtaacgttatacgatgtcgcagagtatgccggtgtctcttatcagaccgtt
tcccgcgtggtgaaccaggccagccacgtttctgcgaaaacgcgggaaaaagtggaagcggcgatgg
cggagctgaattacattcccaaccgcgtggcacaacaactggcgggcaaacagtcgttgctgattggcg
ttgccacctccagtctggccctgcacgcgccgtcgcaaattgtcgcggcgattaaatctcgcgccgatcaa
ctgggtgccagcgtggtggtcgatggtagaacgaagcggcgtcgaagcctgtaaagcggcggtgca
caatcttctcgcgcaacgcgtcagtgggctgatcattaactatccgctggatgaccaggatgccattgctgt
ggaagctgcctgcactaatgttccggcgttatttcttgatgtctctgaccagacacccatcaacagtattatttt
ctcccatgaagacggtacgcgactgggcgtggagcatctggtcgcattgggtcaccagcaaatcgcgct
gttagcgggcccattaagttctgtctcggcgcgtctgcgtctggctggctggcataaatatctcactcgcaat
caaattcagccgatagcggaacgggaaggcgactggagtgccatgtccggttttcaacaaaccatgca
aatgctgaatgagggcatcgttcccactgcgatgctggttgccaacgatcagatggcgctgggcgcaatg
cgcgccattaccgagtccgggctgcgcgttggtgcggatatctcggtagtgggatacgacgataccgaa
gacagctcatgttatatcccgccgtcaaccaccatcaaacaggattttcgcctgctggggcaaaccagcg
tggaccgcttgctgcaactctctcagggccaggcggtgaagggcaatcagctgttcccgtctcactggtg
aaaagaaaaaccaccctggcgcccaatacgcaaaccgcctctccccgcgcgttggccgattcattaat
gcagctggcacgacaggtttcccgactggaaagcgggcagtgagcgcaacgcaattaatgtgagttag
cgcgaattgatctggtttgacagcttatcatcgactgcacggtgcaccaatgcttctggcgtcaggcagcc
atcggaagctgtggtatggctgtgcaggtcgtaaatcactgcataattcgtgtcgctcaaggcgcactccc
gttctggataatgttttttgcgccgacatcataacggttctggcaaatattctgaaatgagctgttgacaattaa
tcatccggctcgtataatgtgtggaattgtgagcggataacaatttcacacaggaaacagcgccgctgag
aaaaagcgaagcggcactgctctttaacaatttatcagacaatctgtgtgggcactcgaccggaattatcg
attaactttattattaaaaattaaagaggtatatattaatgtatcgattaaataaggaggaataaaccatgtgt
gcgacctcttctcaatttactcagattaccgagcataattcccgtcgttccgcaaactatcagccaaacctgt
ggaatttcgaattcctgcaatccctggagaacgacctgaaagtggaaaagctggaggagaaagcgac
caaactggaggaagaagttcgctgcatgatcaaccgtgtagacacccagccgctgtccctgctggagct
gatcgacgatgtgcagcgcctgggtctgacctacaaatttgaaaaagacatcattaaagccctggaaaa
catcgtactgctggacgaaaacaaaaagaacaaatctgacctgcacgcaaccgctctgtctttccgtctg
ctgcgtcagcacggtttcgaggtttctcaggatgttttgagcgtttcaaggataaagaaggtggtttcagcg
gtgaactgaaaggtgacgtccaaggcctgctgagcctgtatgaagcgtcttacctggtttcgagggtga
gaacctgctggaggaggcgcgtaccttttccatcacccacctgaagaacaacctgaaagaaggcatta
ataccaaggttgcagaacaagtgagccacgccctggaactgccatatcaccagcgtctgcaccgtctgg
aggcacgttggttcctggataaatacgaaccgaaagaaccgcatcaccagctgctgctggagctggcg
aagctggattttaacatggtacagaccctgcaccagaaagagctgcaagatctgtcccgctggtggacc
gagatgggcctggctagcaaactggattttgtacgcgaccgcctgatgaagtttatttctgggcactgggt
atggcgccagacccgcagtttggtgaatgtcgcaaagctgttactaaaatgtttggtctggtgacgatcatc
gatgacgtgtatgacgt

Figure 35B ttatggcactctggacgaactgcaactgttcaccgatgctgtagagcgctgggacgttaacgctattaacac
cctgccggactatatgaaactgtgtttcctggcactgtacaacaccgttaacgacacgtcctattctattctga
aagagaaaggtcataacaacctgtcctatctgacgaaaagctggcgtgaactgtgcaaagcctttctgca
agaggcgaaatggtccaacaacaaaattatcccggctttctccaagtacctggaaaacgccagcgtttcct
cctccggtgtagcgctgctggcgccgtcttacttttccgtatgccagcagcaggaagacatctccgaccacg
cgctgcgttccctgaccgacttccatggtctggtgcgttctagctgcgttatcttccgcctgtgcaacgatctgg
ccacctctgcggcggagctggaacgtggcgagactaccaattctatcattagctacatgcacgaaaacga
tggtaccagcgaggaacaggcccgcgaagaactgcgtaaactgatcgacgccgaatggaaaaagatg
aatcgtgaacgcgttagcgactccaccctgctgcctaaagcgttcatggaaatcgcagttaacatggcacg
tgtttcccactgcacctaccagtatggcgatggtctgggtcgcccagactacgcgactgaaaaccgcatca
aactgctgctgattgacccttcccgattaaccagctgatgtatgtctaactgcatcgcccttaggaggtaaaa
aaaaatgactgccgacaacaatagtatgccccatggtgcagtatctagttacgccaaattagtgcaaaacc
aaacacctgaagacattttggaagagtttcctgaaattattccattacaacaaagacctaatacccgatcta
gtgagacgtcaaatgacgaaagcggagaaacatgtttttctggtcatgatgaggagcaaattaagttaatg
aatgaaaattgtattgttttggattgggacgataatgctattggtgccggtaccaagaaagtttgtcatttaatgg
aaaatattgaaaagggtttactacatcgtgcattctccgtctttattttcaatgaacaaggtgaattactttaca
acaaagagccactgaaaaaataactttccctgatctttggactaacacatgctgctctcatccactatgtattg
atgacgaattaggtttgaagggtaagctagacgataagattaagggcgctattactgcggcggtgagaaa
actagatcatgaattaggtattccagaagatgaaactaagacaaggggtaagtttcactttttaaacagaat
ccattacatggcaccaagcaatgaaccatggggtgaacatgaaattgattacatcctattttataagatcaa
cgctaaagaaaacttgactgtcaacccaaacgtcaatgaagttagagacttcaaatgggtttcaccaaatg
atttgaaaactatgtttgctgacccaagttacaagtttacgccttggtttaagattatttgcgagaattacttattc
aactggtgggagcaattagatgacctttctgaagtggaaaatgacaggcaaattcatagaatgctataaca
acgcgtcctgcagctggtaccatatgggaattcgaagctttctagaacaaaaactcatctcagaagaggat
ctgaatagcgccgtcgaccatcatcatcatcattgagtttaaacggtctccagcttggctgttttggcggat
gagagaagattttcagcctgatacagattaaatcagaacgcagaagcggtctgataaaacagaatttgcct
ggcggcagtagcgcggtggtcccacctgaccccatgccgaactcagaagtgaaacgccgtagcgccga
tggtagtgtggggtctccccatgcgagagtagggaactgccaggcatcaaataaaacgaaaggctcagt
cgaaagactgggcctttcgttttatctgttgtttgtcggtgaacgctctcctgagtaggacaaatccgccggga
gcggatttgaacgttgcgaagcaacggcccggagggtggcgggcaggacgcccgccataaactgcca
ggcatcaaattaagcagaaggccatcctgacggatggcttttgcgtttctacaaactcttttgtttatttttcta
aatacattcaaatatgtatccgcttaaccggaattgccagctggggcgccctctggtaaggttgggaagccc
tgcaaagtaaactggatggctttctcgccgccaaggatctgatggcgcaggggatcaagctctgatcaag
agacaggatgaggatcgtttcgcatgattgaacaagatggattgcacgcaggttctccggccgcttgggtg
gagaggctattcggctatgactgggcacaacagacaatcggctgctctgatgccgccgtgttccggctgtc
agcgcaggggcgcccggttcttttgtcaagaccgacctgtccggtgccctgaatgaactgcaagacgag
gcagcgcggctatcgtggctggccacgacgggcgttccttgcgcagctgtgctcgacgttgtcactgaagc
gggaagggactggctgctattgggcgaagtgccggggcaggatctcctgtcatctcaccttgctcctgccg
agaaagtatccatcatggctgat

Figure 35C gcaatgcggcggctgcatacgcttgatccggctacctgcccattcgaccaccaagcgaaacatcgca
tcgagcgagcacgtactcggatggaagccggtcttgtcgatcaggatgatctggacgaagagcatca
ggggctcgcgccagccgaactgttcgccaggctcaaggcgagcatgcccgacggcgaggatctcg
tcgtgacccatggcgatgcctgcttgccgaatatcatggtggaaaatggccgcttttctggattcatcga
ctgtggccggctgggtgtggcggaccgctatcaggacatagcgttggctacccgtgatattgctgaag
agcttggcggcgaatgggctgaccgcttcctcgtgctttacggtatcgccgctcccgattcgcagcgca
tcgccttctatcgccttcttgacgagttcttctgacatgaccaaaatcccttaacgtgagttttcgttccactg
agcgtcagaccccgtagaaaagatcaaaggatcttcttgagatccttttttctgcgcgtaatctgctgctt
gcaaacaaaaaaaccaccgctaccagcggtggtttgtttgccggatcaagagctaccaactcttttcc
gaaggtaactggcttcagcagagcgcagataccaaatactgtccttctagtgtagccgtagttaggcc
accacttcaagaactctgtagcaccgcctacatacctcgctctgctaatcctgttaccagtggctgctgc
cagtggcgataagtcgtgtcttaccgggttggactcaagacgatagttaccggataaggcgcagcggt
cgggctgaacggggggttcgtgcacacagcccagcttggagcgaacgacctacaccgaactgaga
tacctacagcgtgagctatgagaaagcgccacgcttcccgaagggagaaaggcggacaggtatcc
ggtaagcggcagggtcggaacaggagagcgcacgagggagcttcaggggggaaacgcctggtat
ctttatagtcctgtcgggtttcgccacctctgacttgagcgtcgatttttgtgatgctcgtcaggggggcgg
agcctatggaaaaacgccagcaacgcggcctttttacggttcctggccttttgctggccttttgctcacat
gttctttcctgcgttatcccctgattctgtggataaccgtattaccgcctttgagtgagctgataccgctcgc
cgcagccgaacgaccgagcgcagcgagtcagtgagcgaggaagcggaagagcgcctgatgcg
gtattttctccttacgcatctgtgcggtatttcacaccgcatatggtgcactctcagtacaatctgctctgatg
ccgcatagttaagccagtatacactccgctatcgctacgtgactgggtcatggctgcgccccgacacc
cgccaacacccgctgacgcgccctgacgggc (SEQ ID NO:16)

Figure 37A

5'-
ttgtctgctcccggcatccgcttacagacaagctgtgaccgtctccgggagctgcatgtgtcagaggttttca
ccgtcatcaccgaaacgcgcgaggcagcagatcaattcgcgcgcgaaggcgaagcggcatgcattta
cgttgacaccatcgaatggtgcaaaaccttcgcggtatggcatgatagcgcccggaagagagtcaattc
agggtggtgaatgtgaaaccagtaacgttatacgatgtcgcagagtatgccggtgtctcttatcagaccgtt
tcccgcgtggtgaaccaggccagccacgtttctgcgaaaacgcgggaaaaagtggaagcggcgatgg
cggagctgaattacattcccaaccgcgtggcacaacaactggcgggcaaacagtcgttgctgattggcg
ttgccacctccagtctggccctgcacgcgccgtcgcaaattgtcgcggcgattaaatcgcgccgatcaa
ctgggtgccagcgtggtggtgtcgatggtagaacgaagcggcgtcgaagcctgtaaagcggcggtgca
caatcttctcgcgcaacgcgtcagtgggctgatcattaactatccgctggatgaccaggatgccattgctgt
ggaagctgcctgcactaatgttccggcgttatttcttgatgtctctgaccagacacccatcaacagtattatttt
ctcccatgaagacggtacgcgactgggcgtggagcatctggtcgcattgggtcaccagcaaatcgcgct
gttagcgggcccattaagttctgtctcggcgcgtctgcgtctggctggctggcataaatatctcactcgcaat
caaattcagccgatagcggaacgggaaggcgactggagtgccatgtccggttttcaacaaaccatgca
aatgctgaatgagggcatcgttcccactgcgatgctggttgccaacgatcagatggcgctgggcgcaatg
cgcgccattaccgagtccgggctgcgcgttggtgcggatatctcggtagtgggatacgacgataccgaa
gacagctcatgttatatcccgccgtcaaccaccatcaaacaggattttcgcctgctggggcaaaccagcg
tggaccgcttgctgcaactctctcagggccaggcggtgaagggcaatcagctgttcccgtctcactggtg
aaaagaaaaaccaccctggcgcccaatacgcaaaccgcctctccccgcgcgttggccgattcattaat
gcagctggcacgacaggttcccgactggaaagcgggcagtgagcgcaacgcaattaatgtgagttag
cgcgaattgatctggtttgacagcttatcatcgactgcacggtgcaccaatgcttctggcgtcaggcagcc
atcggaagctgtggtatggctgtgcaggtcgtaaatcactgcataattcgtgtcgctcaaggcgcactccc
gttctggataatgttttgcgccgacatcataacggttctggcaaatattctgaaatgagctgttgacaattaa
tcatccggctcgtataatgtgtggaattgtgagcggataacaatttcacacaggaaacagcgccgctgag
aaaaagcgaagcggcactgctctttaacaatttatcagacaatctgtgtgggcactcgaccggaattatcg
attaactttattattaaaaattaaagaggtatatattaatgtatcgattaaataaggaggaataaaccatgtgt
gcgacctcttctcaatttactcagattaccgagcataattcccgtcgttccgcaaactatcagccaaacctgt
ggaatttcgaattcctgcaatccctggagaacgacctgaaagtggaaaagctggaggagaaagcgac
caaactggaggaagaagttcgctgcatgatcaaccgtgtagacacccagccgctgtccctgctggagct
gatcgacgatgtgcagcgcctgggtctgacctacaaatttgaaaaagacatcattaaagccctggaaaa
catcgtactgctggacgaaaacaaaaagaacaaatctgacctgcacgcaaccgctctgtcttccgtctg
ctgcgtcagcacggtttcgaggtttctcaggatgtttttgagcgtttcaaggataaagaaggtggtttcagcg
gtgaactgaaaggtgacgtccaaggcctgctgagcctgtatgaagcgtcttacctgggtttcgagggtga
gaacctgctggaggaggcgcgtaccttttccatcacccacctgaagaacaacctgaaagaaggcatta
ataccaaggttgcagaacaagtgagccacgccctggaactgccatatcaccagcgtctgcaccgtctgg
aggcacgttggttcctggataaatacgaaccgaaagaaccgcatcaccagctgctgctggagctggcg
aagctggatttaacatggtacagaccctgcaccagaaagagctgcaagatctgtcccgctggtggacc
gagatgggcctggctagcaaactggattttgtacgcgaccgcctgatggaagtttatttctgggcactgggt
atggcgccagacccgcagtttggtgaatgtcgcaaagctgttactaaaatgtttggtctggtgacgatcatc
gatgacgtgtatgacgtttatggcactctggacgaactgcaactgttcaccgatgctgtagagcgctggga
cgttaacgct

Figure 37B attaacaccctgccggactatatgaaactgtgtttcctggcactgtacaacaccgttaacgacacgtccta
ttctattctgaaagagaaaggtcataacaacctgtcctatctgacgaaaagctggcgtgaactgtgcaa
agcctttctgcaagaggcgaaatggtccaacaacaaaattatcccggctttctccaagtacctggaaaa
cgccagcgtttcctcctccggtgtagcgctgctggcgccgtcttacttttccgtatgccagcagcaggaag
acatctccgaccacgcgctgcgttccctgaccgacttccatggtctggtgcgttctagctgcgttatcttccg
cctgtgcaacgatctggccacctctgcggcggagctggaacgtggcgagactaccaattctatcattag
ctacatgcacgaaaacgatggtaccagcgaggaacaggcccgcgaagaactgcgtaaactgatcg
acgccgaatggaaaaagatgaatcgtgaacgcgttagcgactccaccctgctgcctaaagcgttcatg
gaaatcgcagttaacatggcacgtgtttcccactgcacctaccagtatggcgatggtctgggtcgcccag
actacgcgactgaaaaccgcatcaaactgctgctgattgacccttccccgattaaccagctgatgtatgtc
taactgcattcgcccttaggaggtaaaaaaacatgagttttgatattgccaaatacccgaccctggcact
ggtcgactccacccaggagttacgactgttgccgaaagagagtttaccgaaactctgcgacgaactgc
gccgctatttactcgacagcgtgagccgttccagcgggcacttcgcctccgggctgggcacggtcgaa
ctgaccgtggcgctgcactatgtctacaacacccccgtttgaccaattgatttgggatgtggggcatcagg
cttatccgcataaaattttgaccggacgccgcgacaaaatcggcaccatccgtcagaaaggcggtctg
cacccgttcccgtggcgcggcgaaagcgaatatgacgtattaagcgtcgggcattcatcaacctccatc
agtgccggaattggtattgcggttgctgccgaaaaagaaggcaaaaatcgccgcaccgtctgtgtcatt
ggcgatggcgcgattaccgcaggcatggcgtttgaagcgatgaatcacgcgggcgatatccgtcctga
tatgctggtgattctcaacgacaatgaaatgtcgatttccgaaaatgtcggcgcgctcaacaaccatctg
gcacagctgctttccggtaagctttactcttcactgcgcgaaggcgggaaaaaagttttctctggcgtgcc
gccaattaaagagctgctcaaacgcaccgaagaacatattaaaggcatggtagtgcctggcacgttgtt
tgaagagctgggctttaactacatcggcccggtggacggtcacgatgtgctggggcttatcaccacgct
aaagaacatgcgcgacctgaaaggcccgcagttcctgcatatcatgaccaaaaaaggtcgtggttatg
aaccggcagaaaaagacccgatcactttccacgccgtgcctaaatttgatccctccagcggttgtttgcc
gaaaagtagcggcggtttgccgagctattcaaaaatctttggcgactggttgtgcgaaacggcagcga
aagacaacaagctgatggcgattactccggcgatgcgtgaaggttccggcatggtcgagttttcacgta
aattcccggatcgctacttcgacgtggcaattgccgagcaacacgcggtgacctttgctgcgggtctggc
gattggtgggtacaaacccattgtcgcgatttactccactttcctgcaacgcgcctatgatcaggtgctgca
tgacgtggcgattcaaaagcttccggtcctgttcgccatcgaccgcgcgggcattgttggtgctgacggtc
aaacccatcagggtgcttttgatctctcttacctgcgctgcataccggaaatggtcattatgaccccgagc
gatgaaaacgaatgtcgccagatgctctataccggctatcactataacgatgcccgtcagcggtgcg
ctacccgcgtggcaacgcggtcggcgtggaactgacgccgctggaaaaactaccaattggcaaagg
cattgtgaagcgtcgtggcgagaaactggcgatcccttaactttggtacgctgatgccagaagcggcgaa
agtcgccgaatcgctgaacgccacgctggtcgatatgcgttttgtgaaaccgcttgatgaagcgttaattc
tggaaatggccgccagccatgaagcgctggtcaccgtagaagaaaacgccattatgggcggcgcag
gcagcggcgtgaacgaagtgctgatggcccatcgtaaaccagtacccgtgctgaacattggcctgccg
gacttctttattccgcaaggaactcaggaagaaatgcgcgccgaactcggcctcgatgccgctggtatg
gaagccaaaatcaaggcctggctggcataactgcagctggtaccatatgggaattcgaagcttctaga
acaaaaactcatctcagaagaggatctgaatagcgccgtcgaccatcatcatcatcatcattgagtttaa
acggtctccagcttggctgttttggcggatgagagaagatttcagcctgatacagattaaatcagaacg
cagaagcggtctgataaaacagaatttgcctggcggcagtagcgcg

Figure 37C gtggtcccacctgaccccatgccgaactcagaagtgaaacgccgtagcgccgatggtagtgggggtct
ccccatgcgagagtagggaactgccaggcatcaaataaaacgaaaggctcagtcgaaagactgggc
ctttcgttttatctgttgtttgtcggtgaacgctctcctgagtaggacaaatccgccgggagcggatttgaacg
ttgcgaagcaacggcccggagggtggcgggcaggacgcccgccataaactgccaggcatcaaatta
agcagaaggccatcctgacggatggccttttgcgtttctacaaactcttttgtttattttctaaatacattcaa
atatgtatccgcttaaccggaattgccagctggggcgccctctggtaaggttgggaagccctgcaaagta
aactggatggctttctcgccgccaaggatctgatggcgcaggggatcaagctctgatcaagagacagga
tgaggatcgtttcgcatgattgaacaagatggattgcacgcaggttctccggccgcttgggtggagaggct
attcggctatgactgggcacaacagacaatcggctgctctgatgccgccgtgttccggctgtcagcgcag
gggcgcccggttcttttgtcaagaccgacctgtccggtgccctgaatgaactgcaagacgaggcagcgc
ggctatcgtggctggccacgacgggcgttccttgcgcagctgtgctcgacgttgtcactgaagcgggaag
ggactggctgctattgggcgaagtgccggggcaggatctcctgtcatctcaccttgctcctgccgagaaa
gtatccatcatggctgatgcaatgcggcggctgcatacgcttgatccggctacctgcccattcgaccacca
agcgaaacatcgcatcgagcgagcacgtactcggatggaagccggtcttgtcgatcaggatgatctgga
cgaagagcatcaggggctcgcgccagccgaactgttcgccaggctcaaggcgagcatgcccgacgg
cgaggatctcgtcgtgacccatggcgatgcctgcttgccgaatatcatggtggaaaatggccgcttttctgg
attcatcgactgtggccggctgggtgtggcggaccgctatcaggacatagcgttggctacccgtgatattg
ctgaagagcttggcggcgaatgggctgaccgcttcctcgtgctttacggtatcgccgctcccgattcgcag
cgcatcgccttctatcgccttcttgacgagttcttctgacgcatgaccaaaatcccttaacgtgagttttcgttc
cactgagcgtcagaccccgtagaaaagatcaaaggatcttcttgagatcctttttttctgcgcgtaatctgct
gcttgcaaacaaaaaaaccaccgctaccagcggtggtttgtttgccggatcaagagctaccaactcttttt
ccgaaggtaactggcttcagcagagcgcagataccaaatactgtccttctagtgtagccgtagttaggcc
accacttcaagaactctgtagcaccgcctacatacctcgctctgctaatcctgttaccagtggctgctgcca
gtggcgataagtcgtgtcttaccgggttggactcaagacgatagttaccggataaggcgcagcggtcgg
gctgaacggggggttcgtgcacacagcccagcttggagcgaacgacctacaccgaactgagatacc ta
cagcgtgagctatgagaaagcgccacgcttcccgaagggagaaaggcggacaggtatccggtaagc
ggcagggtcggaacaggagagcgcacgagggagcttccaggggggaaacgcctggtatctttatagtcc
tgtcgggtttcgccacctctgacttgagcgtcgattttgtgatgctcgtcaggggggcggagcctatggaaa
aacgccagcaacgcggccttttacggttcctggccttttgctggccttttgctcacatgttctttcctgcgttatc
ccctgattctgtggataaccgtattaccgcctttgagtgagctgataccgctcgccgcagccgaacgaccg
agcgcagcgagtcagtgagcgaggaagcggaagagcgcctgatgcggtattttctccttacgcatctgtg
cggtatttcacaccgcatatggtgcactctcagtacaatctgctctgatgccgcatagttaagccagtatac
actccgctatcgctacgtgactgggtcatggctgcgccccgacacccgccaacacccgctgacgcgccc
tgacgggc (SEQ ID NO:17)

Figure 39A

5'-
ctggcgtaatagcgaagaggcccgcaccgatcgcccttcccaacagttgcgcagcctgaatggcgaa
tggcgcctgatgcggtattttctccttacgcatctgtgcggtatttcacaccgcatatggtgcactctcagtac
aatctgctctgatgccgcatagttaagccagccccgacacccgccaacacccgctgacgagcttagta
aagccctcgctagattttaatgcggatgttgcgattacttcgccaactattgcgataacaagaaaaagcc
agcctttcatgatatatctcccaatttgtgtagggcttattatgcacgcttaaaaataataaaagcagacttg
acctgatagtttggctgtgagcaattatgtgcttagtgcatcaacgcttgagttaagccgcgccgcgaag
cggcgtcggcttgaacgaattgttagacattatttgccgactaccttggtgatctcgcctttcacgtagtgga
caaattcttccaactgatctgcgcgcgaggccaagcgatcttcttcttgtccaagataagcctgtctagctt
caagtatgacgggctgatactgggccggcaggcgctccattgcccagtcggcagcgacatccttcggc
gcgattttgccggttactgcgctgtaccaaatgcgggacaacgtaagcactacatttcgctcatcgccag
cccagtcgggcggcgagttccatagcgttaaggtttcatttagcgcctcaaatagatcctgttcaggaac
cggatcaaagagttcctccgccgctggacctaccaaggcaacgctatgttctcttgcttttgtcagcaaga
tagccagatcaatgtcgatcgtggctggctcgaagatacctgcaagaatgtcattgcgctgccattctcc
aaattgcagttcgcgcttagctggataacgccacggaatgatgtcgtcgtgcacaacaatggtgacttct
acagcgcggagaatctcgctctctccaggggaagccgaagtttccaaaaggtcgttgatcaaagctcg
ccgcgttgtttcatcaagccttacggtcaccgtaaccagcaaatcaatatcactgtgtggcttcaggccgc
catccactgcggagccgtacaaatgtacggccagcaacgtcggttcgagatggcgctcgatgacgcc
aactacctctgatagttgagtcgatacttcggcgatcaccgcttccctcatgatgtttaactttgttttagggc
gactgccctgctgcgtaacatcgttgctgctccataacatcaaacatcgacccacggcgtaacgcgctt
gctgcttggatgcccgaggcatagactgtaccccaaaaaaacagtcataacaagccatgaaaaccgc
cactgcgccgttaccaccgctgcgttcggtcaaggttctggaccagttgcgtgagcgcatacgctacttg
cattacagcttacgaaccgaacaggcttatgtccactgggttcgtgccttcatccgtttccacggtgtgcgt
cacccggcaaccttgggcagcagcgaagtcgaggcatttctgtcctggctggcgaacgagcgcaagg
tttcggtctccacgcatcgtcaggcattggcggccttgctgttcttctacggcaaggtgctgtgcacggatct
gccctggcttcaggagatcggaagacctcggccgtcgcggcgcttgccggtggtgctgaccccggatg
aagtggttcgcatcctcggttttctggaaggcgagcatcgtttgttcgcccagcttctgtatggaacgggca
tgcggatcagtgagggtttgcaactgcgggtcaaggatctggatttcgatcacggcacgatcatcgtgcg
ggagggcaagggctccaaggatcgggccttgatgttacccgagagcttggcacccagcctgcgcgag
caggggaattaattcccacgggttttgctgcccgcaaacgggctgttctggtgttgctagtttgttatcagaa
tcgcagatccggcttcagccggtttgccggctgaaagcgctatttcttccagaattgccatgatttttcccc
acgggaggcgtcactggctcccgtgttgtcggcagctttgattcgataagcagcatcgcctgtttcaggct
gtctatgtgtgactgttgagctgtaacaagttgtctcaggtgttcaatttcatgttctagttgctttgttttactggtt
tcacctgttctattaggtgttacatgctgttcatctgttacattgtcgatctgttcatggtgaacagctttgaatg
caccaaaaactcgtaaaagctctgatgtatctatcttttttacaccgttttcatctgtgcatatgacagttttc
cctttgatatgtaacggtgaacagttgttctacttttgtttgttagtcttgatgcttcactgatagatacaagagc
cataagaacctcagatccttccgtatttagccagtatgttctctagtgtggttcgttgttttgcgtgagccatg
agaacgaaccattgagatcatacttactttgcatgtcactcaaaaatttgcctcaaaactggtgagctga
attttgcagttaaagcatcgtgtagtgtttttcttagtccgttatgtaggtaggaatctgatgtaatggttgttgg
tatttgtcaccattcatttttatctggttgttctcaagttcgg

Figure 39B ttacgagatccatttgtctatctagttcaacttggaaaatcaacgtatcagtcgggcggcctcgcttatcaacc
accaatttcatattgctgtaagtgtttaaatctttacttattggtttcaaaacccattggttaagccttttaaactcat
ggtagttattttcaagcattaacatgaacttaaattcatcaaggctaatctctatatttgccttgtgagttttcttttgt
gttagttcttttaataaccactcataaatcctcatagagtatttgttttcaaaagacttaacatgttccagattatatt
ttatgaattttttaactggaaaagataaggcaatatctcttcactaaaaactaattctaattttcgcttgagaac
ttggcatagtttgtccactggaaaatctcaaagcctttaaccaaaggattcctgatttccacagttctcgtcatc
agctctctggttgctttagctaatacaccataagcattttccctactgatgttcatcatctgagcgtattggttata
agtgaacgataccgtccgttctttccttgtagggttttcaatcgtggggttgagtagtgccacacagcataaaa
ttagcttggtttcatgctccgttaagtcatagcgactaatcgctagttcatttgctttgaaaacaactaattcaga
catacatctcaattggtctaggtgattttaatcactataccaattgagatgggctagtcaatgataattactagtc
ctttccttttgagttgtgggtatctgtaaattctgctagacctttgctggaaaacttgtaaattctgctagaccctct
gtaaattccgctagacctttgtgtgttttttttgtttatattcaagtggttataatttatagaataaagaaagaataa
aaaaagataaaaagaatagatcccagccctgtgtataactcactactttagtcagttccgcagtattacaaa
aggatgtcgcaaacgctgtttgctcctctacaaaacagaccttaaaaccctaaaggcttaagtagcaccct
cgcaagctcgggcaaatcgctgaatattccttttgtctccgaccatcaggcacctgagtcgctgtcttttcgtg
acattcagttcgctgcgctcacggctctggcagtgaatgggggtaaatggcactacaggcgcctttatggat
tcatgcaaggaaactacccataatacaagaaaagcccgtcacgggcttctcagggcgttttatggcgggtc
tgctatgtggtgctatctgacttttgctgttcagcagttcctgccctctgattttccagtctgaccacttcggattat
cccgtgacaggtcattcagactggctaatgcacccagtaaggcagcggtatcatcaacaggcttacccgtc
ttactgtcgggaattcgcgttggccgattcattaatgcagattctgaaatgagctgttgacaattaatcatccgg
ctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttatt
attaaaaattaaagaggtatatattaatgtatcgattaaataaggaggaataaaccatgtgtgcgacctcttct
caatttactcagattaccgagcataattcccgtcgttccgcaaactatcagccaaacctgtggaatttcgaatt
cctgcaatccctggagaacgacctgaaagtggaaaagctggaggagaaagcgaccaaactggagga
agaagttcgctgcatgatcaaccgtgtagacacccagccgctgtccctgctggagctgatcgacgatgtgc
agcgcctgggtctgacctacaaatttgaaaaagacatcattaaagccctggaaaacatcgtactgctggac
gaaaacaaaagaacaaatctgacctgcacgcaaccgctctgtctttccgtctgctgcgtcagcacggtttc
gaggtttctcaggatgtttttgagcgtttcaaggataaagaaggtggtttcagcggtgaactgaaaggtgacg
tccaaggcctgctgagcctgtatgaagcgtcttacctgggtttcgagggtgagaacctgctggaggaggcg
cgtaccttttccatcacccacctgaagaacaacctgaaagaaggcattaataccaaggttgcagaacaag
tgagccacgccctggaactgccatatcaccagcgtctgcaccgtctggaggcacgttggttcctggataaat
acgaaccgaaagaaccgcatcaccagctgctgctggagctggcgaagctggattttaacatggtacaga
ccctgcaccagaaagagctgcaagatctgtcccgctggtggaccgagatgggcctggctagcaaactgg
attttgtacgcgaccgcctgatggaagtttatttctgggcactgggtatggcgccagacccgcagtttggtga
atgtcgcaaagctgttactaaaatgtttggtctggtgacgatcatcgatgacgtgtatgacgtttatggcactct
ggacgaactgcaactgttcaccgatgctgtagagcgctgggacgttaacgctattaacaccctgccggact
atatgaaactgtgtttcctggcactgtacaacaccgttaacgacacgtcctattctattctgaaagagaaagg
tcataacaacctgtcct

Figure 39C atctgacgaaaagctggcgtgaactgtgcaaagcctttctgcaagaggcgaaatggtccaacaaca
aaattatcccggctttctccaagtacctggaaaacgccagcgtttcctcctccggtgtagcgctgctggc
gccgtcttacttttccgtatgccagcagcaggaagacatctccgaccacgcgctgcgttccctgaccga
cttccatggtctggtgcgttctagctgcgttatcttccgcctgtgcaacgatctggccacctctgcggcgg
agctggaacgtggcgagactaccaattctatcattagctacatgcacgaaaacgatggtaccagcga
ggaacaggcccgcgaagaactgcgtaaactgatcgacgccgaatggaaaaagatgaatcgtgaa
cgcgttagcgactccaccctgctgcctaaagcgttcatggaaatcgcagttaacatggcacgtgtttcc
cactgcacctaccagtatggcgatggtctgggtcgcccagactacgcgactgaaaaccgcatcaaa
ctgctgctgattgaccctttcccgattaaccagctgatgtatgtctaactgcagctggtaccatatgggaa
ttcgaagctttctagaacaaaaactcatctcagaagaggatctgaatagcgccgtcgaccatcatcat
catcatcattgagtttaaacggtctccagcttggctgttttggcggatgagagaagattttcagcctgatac
agattaaatcagaacgcagaagcggtctgataaaacagaatttgcctggcggcagtagcgcggtgg
tcccacctgaccccatgccgaactcagaagtgaaacgccgtagcgccgatggtagtgtggggtctcc
ccatgcgagagtagggaactgccaggcatcaaataaaacgaaaggctcagtcgaaagactgggc
ctttcgttttatctgttgtttgtcggtgaacgctctcctgagtaggacaaatccgccgggagcggatttgaa
cgttgcgaagcaacggcccggagggtggcgggcaggacgcccgccataaactgccaggcatcaa
attaagcagaaggccatcctgacggatggcctttttgcgtttctacaaactcttttgtttattttttctaaatac
attcaaatatgtatccgctcatgagacaataaccctgataaatgcttcaataat (SEQ ID NO:18)

Figure 41A

5'- cccgtcttactgtcgggaattcgcgttggccgattcattaatgcagattattgaagcatttatcagggttattgtctc
atgagcggatacatatttgaatgtatttagaaaaataaacaaaaagagtttgtagaaacgcaaaaaggccat
ccgtcaggatggccttctgcttaatttgatgcctggcagtttatggcgggcgtcctgcccgccaccctccgggc
cgttgcttcgcaacgttcaaatccgctcccggcggatttgtcctactcaggagagcgttcaccgacaaacaac
agataaaacgaaaggcccagtctttcgactgagcctttcgttttatttgatgcctggcagttccctactctcgcat
ggggagaccccacactaccatcggcgctacggcgtttcacttctgagttcggcatggggtcaggtgggacc
accgcgctactgccgccaggcaaattctgttttatcagaccgcttctgcgttctgatttaatctgtatcaggctga
aaatcttctctcatccgccaaaacagccaagctggagaccgtttaaactcaatgatgatgatgatgatggtcg
acggcgctattcagatcctcttctgagatgagttttgttctagaaagcttcgaattcccatatggtaccagctgc
agttagacatacatcagctggttaatcgggaaagggtcaatcagcagcagtttgatgcggttttcagtcgcgta
gtctgggcgacccagaccatcgccatactggtaggtgcagtgggaaacacgtgccatgttaactgcgatttc
catgaacgctttaggcagcagggtggagtcgctaacgcgttcacgattcatcttttccattcggcgtcgatcag
tttacgcagttcttcgcgggcctgttcctcgctggtaccatcgttttcgtgcatgtagctaatgatagaattggtagt
ctcgccacgttccagctccgccgcagaggtggccagatcgttgcacaggcggaagataacgcagctagaa
cgcaccagaccatggaagtcggtcagggaacgcagcgcgtggtcggagatgtcttcctgctgctggcatac
ggaaaagtaagacggcgccagcagcgctacaccggaggaggaaacgctggcgttttccaggtacttgga
gaaagccgggataattttgttgttggaccatttcgcctcttgcagaaaggctttgcacagttcacgccagcttttc
gtcagataggacaggttgttatgacctttctctttcagaatagaataggacgtgtcgttaacggtgttgtacagtg
ccaggaaacacagtttcatatagtccggcagggtgttaatagcgttaacgtcccagcgctctacagcatcggt
gaacagttgcagttcgtccagagtgccataaacgtcatacacgtcatcgatgatcgtcaccagaccaaacat
tttagtaacagctttgcgacattcaccaaactgcgggtctggcgccatacccagtgcccagaaataaacttcc
atcaggcggtcgcgtacaaaatccagtttgctagccaggccatctcggtccaccagcgggacagatcttgc
agctctttctggtgcagggtctgtaccatgttaaaatccagcttcgccagctccagcagcagctggtgatgcgg
ttctttcggttcgtatttatccaggaaccaacgtgcctccagacggtgcagacgctggtgatatggcagttccag
ggcgtggctcacttgttctgcaaccttggtattaatgccttctttcaggttgttcttcaggtgggtgatggaaaaggt
acgcgcctcctccagcaggttctcaccctcgaaacccaggtaagacgcttcatacaggctcagcaggcctt
ggacgtcacctttcagttcaccgctgaaaccaccttctttatccttgaaacgctcaaaaacatcctgagaaacc
tcgaaaccgtgctgacgcagcagacggaaagacagagcggttgcgtgcaggtcagatttgttctttttgttttc
gtccagcagtacgatgttttccagggctttaatgatgtcttttcaaatttgtaggtcagacccaggcgctgcaca
tcgtcgatcagctccagcagggacagcggctgggtgtctacacggttgatcatcagcgaacttcttcctcca
gtttggtcgtttctcctccagcttttccactttcaggtcgttctcagggattgcaggaattcgaaattccacaggt
ttggctgatagtttgcggaacgacgggaattatgctcggtaatctgagtaaattgagaagaggtcgcacacat
ggtttattcctccttatttaatcgatacattaatatatacctctttaattttaataataaagttaatcgataattccggt
cgagtgcccacacagattgtctgataaattgttaaagagcagtgccgcttcgcttttctcagcggcgctgtttcc
tgtgtgaaattgttatccgctcacaattccacacattatacgagccggatgattaattgtcaacagctcatttcag
aatctggcgtaatagcgaagaggcccgcaccgatcgcccttcccaacagttgcgcagcctgaatggcgaa
tggcgcctgatgcggtattttctccttacgcatctgtgcggtatttcacaccgcatatggtgcactctcagtacaat
ctgctc

Figure 41B tgatgccgcatagttaagccagccccgacacccgccaacacccgctgacgagcttagtaaagccctcg
ctagattttaatgcggatgttgcgattacttcgccaactattgcgataacaagaaaaagccagcctttcatg
atatatctcccaatttgtgtagggcttattatgcacgcttaaaaataataaaagcagacttgacctgatagttt
ggctgtgagcaattatgtgcttagtgcatctaacgcttgagttaagccgcgccgcgaagcggcgtcggctt
gaacgaattgttagacattatttgccgactaccttggtgatctcgccttcacgtagtggacaaattcttccaa
ctgatctgcgcgcgaggccaagcgatcttcttcttgtccaagataagcctgtctagcttcaagtatgacggg
ctgatactgggccggcaggcgctccattgcccagtcggcagcgacatcttcggcgcgattttgccggtta
ctgcgctgtaccaaatgcgggacaacgtaagcactacatttcgctcatcgccagcccagtcgggcggcg
agttccatagcgttaaggtttcatttagcgcctcaaatagatcctgttcaggaaccggatcaaagagttcctc
cgccgctggacctaccaaggcaacgctatgttctcttgcttttgtcagcaagatagccagatcaatgtcgat
cgtggctggctcgaagatacctgcaagaatgtcattgcgctgccattctccaaattgcagttcgcgcttagc
tggataacgccacggaatgatgtcgtcgtgcacaacaatggtgacttctacagcgcggagaatctcgctc
tctccaggggaagccgaagtttccaaaaggtcgttgatcaaagctcgccgcgttgtttcatcaagccttac
ggtcaccgtaaccagcaaatcaatatcactgtgtggcttcaggccgccatccactgcggagccgtacaa
atgtacggccagcaacgtcggttcgagatggcgctcgatgacgccaactacctctgatagttgagtcgat
acttcggcgatcaccgcttccctcatgatgtttaactttgttttagggcgactgccctgctgcgtaacatcgttg
ctgctccataacatcaaacatcgacccacggcgtaacgcgcttgctgcttggatgcccgaggcatagact
gtaccccaaaaaaacagtcataacaagccatgaaaaccgccactgcgccgttaccaccgctgcgttcg
gtcaaggttctggaccagttgcgtgagcgcatacgctacttgcattacagcttacgaaccgaacaggctta
tgtccactgggttcgtgccttcatccgtttccacggtgtgcgtcacccggcaaccttgggcagcagcgaagt
cgaggcatttctgtcctggctggcgaacgagcgcaaggtttcggtctccacgcatcgtcaggcattggcg
gccttgctgttcttctacggcaaggtgctgtgcacggatctgccctggcttcaggagatcggaagacctcg
gccgtcgcggcgcttgccggtggtgctgaccccggatgaagtggttcgcatcctcggttttctggaaggcg
agcatcgtttgttcgcccagcttctgtatgaacgggcatgcggatcagtgagggtttgcaactgcgggtca
aggatctggatttcgatcacggcacgatcatcgtgcgggagggcaagggctccaaggatcgggccttga
tgttacccgagagcttggcacccagcctgcgcgagcaggggaattaattcccacgggttttgctgcccgc
aaacgggctgttctggtgttgctagtttgttatcagaatcgcagatccggcttcagccggtttgccggctgaa
agcgctatttcttccagaattgccatgattttttccccacgggaggcgtcactggctcccgtgttgtcggcagc
tttgattcgataagcagcatcgcctgtttcaggctgtctatgtgtgactgttgagctgtaacaagttgtctcagg
tgttcaatttcatgttctagttgctttgttttactggttcacctgttctattaggtgttacatgctgttcatctgttacatt
gtcgatctgttcatggtgaacagctttgaatgcaccaaaaactcgtaaaagctctgatgtatctatcttttttac
accgttttcatctgtgcatatggacagttttccctttgatatgtaacggtgaacagttgttctactttgtttgttagt
cttgatgcttcactgatagatacaagagccataagaacctcagatccttccgtatttagccagtatgttctcta
gtgtggttcgttgttttttgcgtgagccatgagaacgaaccattgagatcatacttactttgcatgtcactcaaa
aattttgcctcaaaactggtgagctgaattttttgcagttaaagcatcgtgtagtgttttcttagtccgttatgtag
gtaggaatctgatgtaatggttgttggtattttgtcaccattcattttatctggttgttctcaagttcggttacgag
atccatttgtctatctagttcaacttggaaaatcaacgtatcagtcgggcggcctcgcttatcaaccaccaat
ttcatattgctgtaagtgtttaaatctttacttattggtttcaaaacccattggttaagccttttaaactcatggtagt
tattttcaagcattaacatgaacttaaattcatcaaggctaatctctatatttgc

Figure 41C cttgtgagttttcttttgtgttagttcttttaataaccactcataaatcctcatagagtatttgttttcaaaagacttaa
catgttccagattatattttatgaattttttaactggaaaagataaggcaatatctcttcactaaaaactaattc
taattttcgcttgagaacttggcatagtttgtccactggaaaatctcaaagcctttaaccaaaggattcctga
tttccacagttctcgtcatcagctctctggttgctttagctaatacaccataagcattttccctactgatgttcatc
atctgagcgtattggttataagtgaacgataccgtccgttctttccttgtagggttttcaatcgtggggttgagta
gtgccacacagcataaaattagcttggtttcatgctccgttaagtcatagcgactaatcgctagttcatttgctt
tgaaaacaactaattcagacatacatctcaattggtctaggtgattttaatcactataccaattgagatgggc
tagtcaatgataattactagtccttttcctttgagttgtgggtatctgtaaattctgctagacctttgctggaaaac
ttgtaaattctgctagaccctctgtaaattccgctagacctttgtgtgttttttttgtttatattcaagtggttataattt
atagaataaagaaagaataaaaaagataaaaagaatagatcccagccctgtgtataactcactacttt
agtcagttccgcagtattacaaaaggatgtcgcaaacgctgtttgctcctctacaaaacagaccttaaaac
cctaaaggcttaagtagcaccctcgcaagctcgggcaaatcgctgaatattccttttgtctccgaccatcag
gcacctgagtcgctgtcttttcgtgacattcagttcgctgcgctcacggctctggcagtgaatgggggtaaa
tggcactacaggcgcctttatggattcatgcaaggaaactacccataatacaagaaaagcccgtcacg
ggcttctcagggcgtttatggcgggtctgctatgtggtgctatctgacttttgctgttcagcagttcctgccctc
tgattttccagtctgaccacttcggattatcccgtgacaggtcattcagactggctaatgcacccagtaagg
cagcggtatcatcaacaggctta (SEQ ID NO:19)

Figure 43A

5'- ctggcgtaatagcgaagaggcccgcaccgatcgcccttcccaacagttgcgcagcctgaatggcgaa
tggcgcctgatgcggtattttctccttacgcatctgtgcggtatttcacaccgcatatggtgcactctcagtac
aatctgctctgatgccgcatagttaagccagccccgacacccgccaacacccgctgacgagcttagta
aagccctcgctagattttaatgcggatgttgcgattacttcgccaactattgcgataacaagaaaaagcc
agcctttcatgatatatctcccaatttgtgtagggcttattatgcacgcttaaaaataataaaagcagacttg
acctgatagtttggctgtgagcaattatgtgcttagtgcatctaacgcttgagttaagccgcgccgcgaag
cggcgtcggcttgaacgaattgttagacattatttgccgactaccttggtgatctcgcctttcacgtagtgga
caaattcttccaactgatctgcgcgcgaggccaagcgatcttcttcttgtccaagataagcctgtctagctt
caagtatgacgggctgatactgggccggcaggcgctccattgcccagtcggcagcgacatccttcggc
gcgattttgccggttactgcgctgtaccaaatgcgggacaacgtaagcactacatttcgctcatcgccag
cccagtcgggcggcgagttccatagcgttaaggtttcatttagcgcctcaaatagatcctgttcaggaac
cggatcaaagagttcctccgccgctggacctaccaaggcaacgctatgttctcttgcttttgtcagcaaga
tagccagatcaatgtcgatcgtggctggctcgaagatacctgcaagaatgtcattgcgctgccattctcc
aaattgcagttcgcgcttagctggataacgccacggaatgatgtcgtcgtcacaacaatggtgacttct
acagcgcggagaatctcgctctctccaggggaagccgaagtttccaaaaggtcgttgatcaaagctcg
ccgcgttgtttcatcaagccttacggtcaccgtaaccagcaaatcaatatcactgtgtggcttcaggccgc
catccactgcggagccgtacaaatgtacggccagcaacgtcggttcgagatggcgctcgatgacgcc
aactacctctgatagttgagtcgatacttcggcgatcaccgcttccctcatgatgtttaactttgttttagggc
gactgccctgctgcgtaacatcgttgctgctccataacatcaaacatcgacccacggcgtaacgcgctt
gctgcttggatgcccgaggcatagactgtaccccaaaaaaacagtcataacaagccatgaaaaccgc
cactgcgccgttaccaccgctgcgttcggtcaaggttctggaccagttgcgtgagcgcatacgctacttg
cattacagcttacgaaccgaacaggcttatgtccactgggttcgtgccttcatccgtttccacggtgtgcgt
cacccggcaaccttgggcagcagcgaagtcgaggcatttctgtcctggctggcgaacgagcgcaagg
tttcggtctccacgcatcgtcaggcattggcggccttgctgttcttctacggcaaggtgctgtgcacggatct
gccctggcttcaggagatcggaagacctcggccgtcgcggcgcttgccggtggtgctgaccccggatg
aagtggttcgcatcctcggttttctggaaggcgagcatcgtttgttcgcccagcttctgtatggaacgggca
tgcggatcagtgagggtttgcaactgcgggtcaaggatctggatttcgatcacggcacgatcatcgtgcg
ggagggcaagggctccaaggatcgggccttgatgttacccgagagcttggcacccagcctgcgcgag
caggggaattaattcccacgggttttgctgccgcaaacgggctgttctggtgttgctagtttgttatcagaa
tcgcagatccggcttcagccggtttgccggctgaaagcgctatttcttccagaattgccatgattttttcccc
acgggaggcgtcactggctcccgtgttgtcggcagctttgattcgataagcagcatcgcctgtttcaggct
gtctatgtgtgactgttgagctgtaacaagttgtctcaggtgttcaatttcatgttctagttgctttgttttactggtt
tcacctgttctattaggtgttacatgctgttcatctgttacattgtcgatctgttcatggtgaacagctttgaatg
caccaaaaactcgtaaaagctctgatgtatctatctttttacaccgttttcatctgtgcatatggacagttttc
cctttgatatgtaacggtgaacagttgttctactttgtttgtagtcttgatgcttcactgatagatacaagagc
cataagaacctcagatccttccgtatttagccagtatgttctctagtgtggttcgttgttttgcgtgagccatg
agaacgaaccattgagatcatacttactttgcatgtcactcaaaaattttgcctcaaaactggtgagctga
attttgcagttaaagcatcgtgtagtgtttttcttagtccgttatgtaggtaggaatctgatgtaatggttgttgg
tattttgtcaccattcattttatctggttgttctcaagttcgg

Figure 43B ttacgagatccatttgtctatctagttcaacttggaaaatcaacgtatcagtcgggcggcctcgcttatcaa
ccaccaatttcatattgctgtaagtgtttaaatctttacttattggtttcaaaacccattggttaagccttttaaa
ctcatggtagttattttcaagcattaacatgaacttaaattcatcaaggctaatctctatatttgccttgtgagtt
ttcttttgtgttagttcttttaataaccactcataaatcctcatagagtatttgttttcaaaagacttaacatgttcc
agattatattttatgaattttttttaactggaaaagataaggcaatatctcttcactaaaaactaattctaattttt
cgcttgagaacttggcatagtttgtccactggaaaatctcaaagcctttaaccaaaggattcctgatttcca
cagttctcgtcatcagctctctggttgctttagctaatacaccataagcattttccctactgatgttcatcatctg
agcgtattggttataagtgaacgataccgtccgttctttccttgtagggttttcaatcgtggggttgagtagtg
ccacacagcataaaattagcttggtttcatgctccgttaagtcatagcgactaatcgctagttcatttgctttg
aaaacaactaattcagacatacatctcaattggtctaggtgattttaatcactataccaattgagatgggct
agtcaatgataattactagtcctttccttttgagttgtgggtatctgtaaattctgctagacctttgctggaaaa
cttgtaaattctgctagaccctctgtaaattccgctagacctttgtgtgttttttttgtttatattcaagtggttataa
tttatagaataaagaaagaataaaaaaagataaaaagaatagatcccagccctgtgtataactcacta
ctttagtcagttccgcagtattacaaaaggatgtcgcaaacgctgtttgctcctctacaaaacagaccta
aaaccctaaaggcttaagtagcaccctcgcaagctcgggcaaatcgctgaatattccttttgtctccgac
catcaggcacctgagtcgctgtcttttcgtgacattcagttcgctgcgctcacggctctggcagtgaatgg
gggtaaatggcactacaggcgccttttatggattcatgcaaggaaactacccataatacaagaaaagc
ccgtcacgggcttctcagggcgttttatggcgggtctgctatgtggtgctatctgacttttgctgttcagcagt
tcctgccctctgattttccagtctgaccacttcggattatcccgtgacaggtcattcagactggctaatgcac
ccagtaaggcagcggtatcatcaacaggcttacccgtcttactgtcgggaattcgcgttggccgattcatt
aatgcagattctgaaatgagctgttgacaattaatcatccggctcgtataatgtgtggaattgtgagcggat
aacaatttcacacaggaaacagcgccgctgagaaaaagcgaagcggcactgctctttaacaatttatc
agacaatctgtgtgggcactcgaccggaattatcgattaactttattattaaaaattaaagaggtatatatt
aatgtatcgattaaataaggaggaataaaccatgtgtgcgacctcttctcaatttactcagattaccgagc
ataattcccgtcgttccgcaaactatcagccaaacctgtggaatttcgaattcctgcaatccctggagaac
gacctgaaagtggaaaagctggaggagaaagcgaccaaactggaggaagaagttcgctgcatgat
caaccgtgtagacacccagccgctgtccctgctggagctgatcgacgatgtgcagcgcctgggtctga
cctacaaatttgaaaaagacatcattaaagccctggaaaacatcgtactgctggacgaaaacaaaaa
gaacaaatctgacctgcacgcaaccgctctgtctttccgtctgctgcgtcagcacggtttcgaggtttctca
ggatgttttgagcgtttcaaggataaagaaggtggtttcagcggtgaactgaaaggtgacgtccaagg
cctgctgagcctgtatgaagcgtcttacctgggtttcgagggtgagaacctgctggaggaggcgcgtac
cttttccatcacccacctgaagaacaacctgaaagaaggcattaataccaaggttgcagaacaagtga
gccacgccctggaactgccatatcaccagcgtctgcaccgtctggaggcacgttggttcctggataaat
acgaaccgaaagaaccgcatcaccagctgctgctggagctggcgaagctggattttaacatggtaca
gaccctgcaccagaaagagctgcaagatctgtcccgctggtggaccgagatgggcctggctagcaaa
ctggattttgtacgcgaccgcctgatggaagtttatttctgggcactgggtatggcgccagacccgcagttt
ggtgaatgtcgcaaagctgttactaaaatgtttggtctggtgacgatcatcgatgacgtgtatgacgtttatg
gcactctggacgaactgcaactgttcaccgatgctgtagagcgctgggacgttaacgctattaacaccct
gccggactatatgaaactgtgtttcctggcactgtacaacaccgttaacgacacgtcctattctattctgaa
agagaaaggtcataacaacctgtcct

Figure 43C atctgacgaaaagctggcgtgaactgtgcaaagcctttctgcaagaggcgaaatggtccaacaa
caaaattatcccggctttctccaagtacctggaaaacgccagcgtttcctcctccggtgtagcgctgc
tggcgccgtcttacttttccgtatgccagcagcaggaagacatctccgaccacgcgctgcgttccct
gaccgacttccatggtctggtgcgttctagctgcgttatcttccgcctgtgcaacgatctggccacctct
gcggcggagctggaacgtggcgagactaccaattctatcattagctacatgcacgaaaacgatg
gtaccagcgaggaacaggcccgcgaagaactgcgtaaactgatcgacgccgaatggaaaaa
gatgaatcgtgaacgcgttagcgactccaccctgctgcctaaagcgttcatggaaatcgcagttaa
catggcacgtgtttcccactgcacctaccagtatggcgatggtctgggtcgcccagactacgcgact
gaaaaccgcatcaaactgctgctgattgacccttccccgattaaccagctgatgtatgtctaactgca
tcgcccttaggaggtaaaaaaaaatgactgccgacaacaatagtatgccccatggtgcagtatct
agttacgccaaattagtgcaaaaccaaacacctgaagacattttggaagagtttcctgaaattattc
cattacaacaaagacctaatacccgatctagtgagacgtcaaatgacgaaagcggagaaacat
gttttctggtcatgatgaggagcaaattaagttaatgaatgaaaattgtattgtttggattgggacgat
aatgctattggtgccggtaccaagaaagtttgtcatttaatggaaaatattgaaaagggtttactacat
cgtgcattctccgtctttattttcaatgaacaaggtgaattacttttacaacaaagagccactgaaaaa
ataactttccctgatctttggactaacacatgctgctctcatccactatgtattgatgacgaattaggttt
gaagggtaagctagacgataagattaagggcgctattactgcggcggtgagaaaactagatcat
gaattaggtattccagaagatgaaactaagacaaggggtaagtttcacttttaaacagaatccatt
acatggcaccaagcaatgaaccatggggtgaacatgaaattgattacatcctattttataagatcaa
cgctaaagaaaacttgactgtcaacccaaacgtcaatgaagttagagacttcaaatgggtttcacc
aaatgatttgaaaactatgtttgctgacccaagttacaagtttacgccttggtttaagattatttgcgag
aattacttattcaactggtgggagcaattagatgacctttctgaagtggaaaatgacaggcaaattc
atagaatgctataacgacgcgtcctgcagctggtaccatatgggaattcgaagctttctagaacga
aaactcatctcagaagaggatctgaatagcgccgtcgaccatcatcatcatcattgagtttaaa
cggtctccagcttggctgttttggcggatgagagaagattttcagcctgatacagattaaatcagaac
gcagaagcggtctgataaacagaatttgcctggcggcagtagcgcggtggtcccacctgaccc
catgccgaactcagaagtgaaacgccgtagcgccgatggtagtgtggggtctccccatgcgaga
gtagggaactgccaggcatcaaataaaacgaaaggctcagtcgaaagactgggcctttcgttttat
ctgttgtttgtcggtgaacgctctcctgagtaggacaaatccgccgggagcggatttgaacgttgcg
aagcaacggcccggagggtggcgggcaggacgcccgccataaactgccaggcatcaaattaa
gcagaaggccatcctgacggatggccttttgcgtttctacaaactcttttgttattttctaaatacatt
caaatatgtatccgctcatgagacaataaccctgataaatgcttcaataat (SEQ ID NO:20)

Figure 45A

5'- cccgtcttactgtcgggaattcgcgttggccgattcattaatgcagattattgaagcatttatcagggttattgt
ctcatgagcggatacatatttgaatgtatttagaaaaataaacaaaaagagtttgtagaaacgcaaaaag
gccatccgtcaggatggccttctgcttaatttgatgcctggcagtttatggcgggcgtcctgcccgccaccct
ccgggccgttgcttcgcaacgttcaaatccgctcccggcggatttgtcctactcaggagagcgttaccga
caaacaacagataaaacgaaaggcccagtctttcgactgagcctttcgttttatttgatgcctggcagttcc
ctactctcgcatggggagaccccacactaccatcggcgctacggcgtttcacttctgagttcggcatgggg
tcaggtgggaccaccgcgctactgccgccaggcaaattctgttttatcagaccgcttctgcgttctgatttaa
tctgtatcaggctgaaaatcttctctcatccgccaaaacagccaagctggagaccgtttaaactcaatgat
gatgatgatgatggtcgacggcgctattcagatcctcttctgagatgagttttgttctagaaagcttcgaattc
ccatatggtaccagctgcagttatgccagccaggccttgattttggcttccataccagcggcatcgaggcc
gagttcggcgcgcatttcttcctgagttccttgcggaataaagaagtccggcaggccaatgttcagcacgg
gtactggtttacgatgggccatcagcacttcgttcacgccgctgcctgcgccgcccataatggcgttttcttct
acggtgaccagcgcttcatggctggcggccatttccagaattaacgcttcatcaagcggtttcacaaaac
gcatatcgaccagcgtggcgttcagcgattcggcgactttcgccgcttctggcatcagcgtaccaaagtta
aggatcgccagtttctcgccacgacgcttcacaatgcctttgccaattggtagtttttccagcggcgtcagttc
cacgccgaccgcgttgccacgcgggtagcgcaccgctgacgggccatcgttatagtgatagccggtata
gagcatctggcgacattcgttttcatcgctcggggtcataatgaccatttccggtatgcagcgcaggtaaga
gagatcaaaagcaccctgatgggtttgaccgtcagcaccaacaatgcccgcgcggtcgatggcgaaca
ggaccggaagcttttgaatcgccacgtcatgcagcacctgatcataggcgcgttgcaggaaagtggagt
aaatcgcgacaatgggtttgtacccaccaatcgccagacccgcagcaaaggtcaccgcgtgttgctcgg
caattgccacgtcgaagtagcgatccgggaatttacgtgaaaactcgaccatgccggaaccttcacgca
tcgccggagtaatcgccatcagcttgttgtctttcgctgccgtttcgcacaaccagtcgccaaagattttga
atagctcggcaaaccgccgctactttcggcaaacaaccgctggagggatcaaatttaggcacggcgtg
gaaagtgatcgggtcttttctgccggttcataaccacgaccttttttggtcatgatatgcaggaactgcgggc
ctttcaggtcgcgcatgttctttagcgtggtgataagccccagcacatcgtgaccgtccaccgggccgatgt
agttaaagcccagctcttcaaacaacgtgccaggcactaccatgcctttaatatgttcttcggtgcgtttgag
cagctctttaattggcggcacgccagagaaaactttttcccgccttcgcgcagtgaagagtaaagcttac
cggaaagcagctgtgccagatggttgttgagcgcgccgacattttcggaaatcgacatttcattgtcgttga
gaataccagcatatcaggacggatatcgcccgcgtgattcatcgcttcaaacgccatgcctgcggtaat
cgcgccatcgccaatgacacagacggtgcggcgattttgccttcttttcggcagcaaccgcaataccaa
ttccggcactgatggaggttgatgaatgcccgacgcttaatacgtcatattcgctttcgccgcgccacggg
aacgggtgcagaccgcctttctgacggatggtgccgattttgtcgcggcgtccggtcaaaattttatgcgga
taagcctgatgccccacatcccaaatcaattggtcaaacggggtgttgtagacatagtgcagcgccacg
gtcagttcgaccgtgcccagcccggaggcgaagtcccgctggaacggctcacgctgtcgagtaaata
gcggcgcagttcgtcgcagagtttcggtaaactctcttcggcaacagtcgtaactcctgggtggagtcga
ccagtgccagggtcgggtatttggcaatatcaaaactcatgttttttacctcctaagggcgaatgcagttag
acatacatcagctggttaatcgggaaagggtcaatcagcagcagtttgatgcggttttcagtcgcgtagtct
gggcgacccagaccatcgccatactggtaggtgcagtgggaaacacgtgccatgttaactgcgatttcc
atgaacgctttaggcagcagggtggagtcgctaacgcgttcacg

Figure 45B attcatctttttccattcggcgtcgatcagtttacgcagttcttcgcgggcctgttcctcgctggtaccatcgttttc
gtgcatgtagctaatgatagaattggtagtctcgccacgttccagctccgccgcagaggtggccagatcgt
tgcacaggcggaagataacgcagctagaacgcaccagaccatggaagtcggtcagggaacgcagc
gcgtggtcggagatgtcttcctgctgctggcatacggaaaagtaagacggcgccagcagcgctacacc
ggaggaggaaacgctggcgttttccaggtacttggagaaagccgggataattttgttgttggaccatttcgc
ctcttgcagaaaggctttgcacagttcacgccagcttttcgtcagataggacaggttgttatgacctttctcttt
cagaatagaataggacgtgtcgttaacggtgttgtacagtgccaggaaacacagtttcatatagtccggc
agggtgttaatagcgttaacgtccagcgctctacagcatcggtgaacagttgcagttcgtccagagtgcc
ataaacgtcatacacgtcatcgatgatcgtcaccagaccaaacattttagtaacagctttgcgacattcac
caaactgcgggtctggcgccatacccagtgcccagaaataaacttccatcaggcggtcgcgtacaaaat
ccagtttgctagccaggcccatctcggtccaccagcgggacagatcttgcagctctttctggtgcagggtct
gtaccatgttaaaatccagcttcgccagctccagcagcagctggtgatgcggttctttcggttcgtatttatcc
aggaaccaacgtgcctccagacggtgcagacgctggtgatatggcagttccagggcgtggctcacttgtt
ctgcaaccttggtattaatgccttctttcaggttgttcttcaggtgggtgatggaaaaggtacgcgcctcctcc
agcaggttctcaccctcgaaacccaggtaagacgcttcatacaggctcagcaggccttggacgtcacctt
tcagttcaccgctgaaaccaccttctttatccttgaaacgctcaaaaacatcctgagaaacctcgaaaccg
tgctgacgcagcagacggaaagacagagcggttgcgtgcaggtcagatttgttcttttttgttttcgtccagc
agtacgatgttttccagggctttaatgatgtcttttcaaatttgtaggtcagacccaggcgctgcacatcgtc
gatcagctccagcagggacagcggctgggtgtctacacggttgatcatgcagcgaacttcttcctccagtt
tggtcgctttctcctccagcttttccactttcaggtcgttctccagggattgcaggaattcgaaattccacaggt
ttggctgatagtttgcggaacgacgggaattatgctcggtaatctgagtaaattgagaagaggtcgcacac
atggtttattcctccttatttaatcgatacattaatatatacctctttaattttaataataaagttaatcgataattcc
ggtcgagtgcccacacagattgtctgataaattgttaaagagcagtgccgcttcgcttttctcagcggcgct
gtttcctgtgtgaaattgttatccgctcacaattccacacattatacgagccggatgattaattgtcaacagct
catttcagaatctggcgtaatagcgaagaggcccgcaccgatcgcccttcccaacagttgcgcagcctg
aatggcgaatggcgcctgatgcggtattttctccttacgcatctgtgcggtatttcacaccgcatatggtgca
ctctcagtacaatctgctctgatgccgcatagttaagccagccccgacacccgccaacacccgctgacg
agcttagtaaagccctcgctagattttaatgcggatgttgcgattacttcgccaactattgcgataacaaga
aaaagccagcctttcatgatatatctcccaatttgtgtagggcttattatgcacgcttaaaaataataaaagc
agacttgacctgatagtttggctgtgagcaattatgtgcttagtgcatctaacgcttgagttaagccgcgccg
cgaagcggcgtcggcttgaacgaattgttagacattatttgccgactaccttggtgatctcgcctttcacgta
gtggacaaattcttccaactgatctgcgcgcgaggccaagcgatcttcttcttgtccaagataagcctgtct
agcttcaagtatgacgggctgatactgggccggcaggcgctccattgcccagtcggcagcgacatcctc
ggcgcgattttgccggttactgcgctgtaccaaatgcgggacaacgtaagcactacatttcgctcatcgcc
agcccagtcgggcggcgagttccatagcgttaaggtttcatttagcgcctcaaatagatcctgttcaggaa
ccggatcaaagagttcctccgccgctggacctaccaaggcaacgctatgttctcttgcttttgtcagcaaga
tagccagatcaatgtcgatcgtggctggctcgaagatacctgcaagaatgtcattgcgctgccattctcca
aattgcagttcgcgcttagctggataacgccacggaatgatgtcgtcgtgcacaacaatggtgacttctac
agcgcggagaatctcgctctctccaggggaagccgaagttccaaaaggtcgttgatcaaagctcgccg
cgttgtttcatcaagc

Figure 45C cttacggtcaccgtaaccagcaaatcaatatcactgtgtggcttcaggccgccatccactgcggagccg
tacaaatgtacggccagcaacgtcggttcgagatggcgctcgatgacgccaactacctctgatagttga
gtcgatacttcggcgatcaccgcttccctcatgatgtttaactttgttttagggcgactgccctgctgcgtaac
atcgttgctgctccataacatcaaacatcgacccacggcgtaacgcgcttgctgcttggatgcccgagg
catagactgtaccccaaaaaaacagtcataacaagccatgaaaaccgccactgcgccgttaccacc
gctgcgttcggtcaaggttctggaccagttgcgtgagcgcatacgctacttgcattacagcttacgaacc
gaacaggcttatgtccactgggttcgtgccttcatccgttccacggtgtgcgtcacccggcaaccttggg
cagcagcgaagtcgaggcatttctgtcctggctggcgaacgagcgcaaggtttcggtctccacgcatcg
tcaggcattggcggccttgctgttcttctacggcaaggtgctgtgcacggatctgccctggcttcaggaga
tcggaagacctcggccgtcgcggcgcttgccggtggtgctgaccccggatgaagtggttcgcatcctcg
gttttctggaaggcgagcatcgtttgttcgcccagcttctgtatggaacgggcatgcggatcagtgagggt
ttgcaactgcgggtcaaggatctggatttcgatcacggcacgatcatcgtgcgggagggcaagggctc
caaggatcgggccttgatgttacccgagagcttggcacccagcctgcgcgagcagggggaattaattcc
cacgggttttgctgcccgcaaacgggctgttctggtgttgctagtttgttatcagaatcgcagatccggcttc
agccggtttgccggctgaaagcgctatttcttccagaattgccatgattttttccccacgggaggcgtcact
ggctcccgtgttgtcggcagctttgattcgataagcagcatcgcctgtttcaggctgtctatgtgactgttg
agctgtaacaagttgtctcaggtgttcaatttcatgttctagttgctttgttttactggtttcacctgttctattaggt
gttacatgctgttcatctgttacattgtcgatctgttcatggtgaacagctttgaatgcaccaaaaactcgta
aaagctctgatgtatctatcttttttacaccgttttcatctgtgcatatggacagttttcccttttgatatgtaacgg
tgaacagttgttctacttttgtttgttagtcttgatgcttcactgatagatacaagagccataagaacctcaga
tccttccgtatttagccagtatgttctctagtgtggttcgttgttttttgcgtgagccatgagaacgaaccattga
gatcatacttactttgcatgtcactcaaaaattttgcctcaaaactggtgagctgaattttgcagttaaagc
atcgtgtagtgtttttcttagtccgttatgtaggtaggaatctgatgtaatggttgttggtattttgtcaccattcat
ttttatctggttgttctcaagttcggttacgagatccatttgtctatctagttcaacttggaaaatcaacgtatca
gtcgggcggcctcgcttatcaaccaccaatttcatattgctgtaagtgtttaaatctttacttattggtttcaaa
acccattggttaagccttttaaactcatggtagttattttcaagcattaacatgaacttaaattcatcaaggct
aatctctatatttgccttgtgagttttcttttgttagttcttttaataaccactcataaatcctcatagagtatttgt
tttcaaaagacttaacatgttccagattatattttatgaattttttaactggaaaagataaggcaatatctctt
cactaaaaactaattctaattttcgcttgagaacttggcatagtttgtccactggaaaatctcaaagccttt
aaccaaaggattcctgatttccacagttctcgtcatcagctctctggttgctttagctaatacaccataagc
attttccctactgatgttcatcatctgagcgtattggttataagtgaacgataccgtccgttctttccttgtaggg
ttttcaatcgtggggttgagtagtgccacacagcataaaattagcttggtttcatgctccgttaagtcatagc
gactaatcgctagttcatttgctttgaaaacaactaattcagacatacatctcaattggtctaggtgatttaa
tcactataccaattgagatgggctagtcaatgataattactagtccttttcctttgagttgtgggtatctgtaaa
ttctgctagacctttgctggaaaacttgtaaattctgctagaccctctgtaaattccgctagacctttgtgtgttt
tttttgtttatattcaagtggttataatttatagaataaagaaagaataaaaaagataaaagaatagatc
ccagccctgtgtataactcactactttagtcagttccgcagtattacaaaaggatgtcgcaaacgctgtttg
ctcctctacaaaacagaccttaaaacccttaaaggcttaagtagcaccctcgcaagctcgggcaaatcg
ctgaatattccttttgtctccgaccatcaggcacctgagtcgctgtcttttc

Figure 45D

Gtgacattcagttcgctgcgctcacggctctggcagtgaatgggggtaaatggcactacaggcgccttttatggattcatgcaaggaaactacccataatacaagaaaagcccgtcacgggcttctcagggcgttttatggcgggtctgctatgtggtgctatctgacttttgctgttcagcagttcctgccctctgattttccagtctgaccacttcggattatcccgtgacaggtcattcagactggctaatgcacccagtaaggcagcggtatcatcaacaggctta (SEQ ID NO:21)

Figure 51A

5'- tcgctgcgctcggtcgttcggctgcggcgagcggtatcagctcactcaaaggcggtaatacggttatcca
cagaatcaggggataacgcaggaaagaacatgtgagcaaaaggccagcaaaaggccaggaacc
gtaaaaaggccgcgttgctggcgttttccataggctccgcccccctgacgagcatcacaaaaatcgac
gctcaagtcagaggtggcgaaacccgacaggactataaagataccaggcgtttccccctggaagctc
cctcgtgcgctctcctgttccgaccctgccgcttaccggatacctgtccgcctttctcccttcgggaagcgt
ggcgctttctcatagctcacgctgtaggtatctcagttcggtgtaggtcgttcgctccaagctgggctgtgtg
cacgaaccccccgttcagcccgaccgctgcgccttatccggtaactatcgtcttgagtccaacccggta
agacacgacttatcgccactggcagcagccactggtaacaggattagcagagcgaggtatgtaggcg
gtgctacagagttcttgaagtggtggcctaactacggctacactagaagaacagtatttggtatctgcgct
ctgctgaagccagttaccttcggaaaaagagttggtagctcttgatccggcaaacaaaccaccgctggt
agcggtggtttttttgtttgcaagcagcagattacgcgcagaaaaaaaggatctcaagaagatcctttgat
cttttctacggggtctgacgctcagtggaacgaaaactcacgttaagggattttggtcatgagattatcaa
aaaggatcttcacctagatccttttaaattaaaaatgaagttttaaatcaatctaaagtatatatgagtaaa
cttggtctgacagttaccaatgcttaatcagtgaggcacctatctcagcgatctgtctatttcgttcatccata
gttgcctgactccccgtcgtgtagataactacgatacgggagggcttaccatctggccccagtgctgcaa
tgataccgcgagacccacgctcaccggctccagatttatcagcaataaaccagccagccggaaggg
ccgagcgcagaagtggtcctgcaactttatccgcctccatccagtctattaattgttgccgggaagctaga
gtaagtagttcgccagttaatagtttgcgcaacgttgttgccattgctacaggcatcgtggtgtcacgctcgt
cgtttggtatggcttcattcagctccggttcccaacgatcaaggcgagttacatgatcccccatgttgtgca
aaaaagcggttagctccttcggtcctccatcgttgtcagaagtaagttggccgcagtgttatcactcatg
gttatggcagcactgcataattctcttactgtcatgccatccgtaagatgcttttctgtgactggtgagtactc
aaccaagtcattctgagaatagtgtatgcggcgaccgagttgctcttgcccggcgtcaatacgggataat
accgcgccacatagcagaactttaaaagtgctcatcattggaaaacgttcttcggggcgaaaactctca
aggatcttaccgctgttgagatccagttcgatgtaacccactcgtgcacccaactgatcttcagcatctttta
ctttcaccagcgtttctgggtgagcaaaaacaggaaggcaaaatgccgcaaaaaagggaataaggg
cgacacggaaatgttgaatactcatactcttcctttttcaatattattgaagcatttatcaggttattgtctcat
gagcggatacatatttgaatgtatttagaaaaataaacaatagggggttccgcgcacatttccccgaaa
agtgccacctgacgtctaagaaaccattattatcatgacattaacctataaaaataggcgtatcacgagg
ccctttcgtctcgcgcgtttcggtgatgacggtgaaaacctctgacacatgcagctcccggagacggtca
cagcttgtctgtaagcggatgccgggagcagacaagcccgtcagggcgcgtcagcgggtgttggcgg
gtgtcggggctggcttaactatgcggcatcagagcagattgtactgagagtgcaccatagatctggagc
tgtaatataaaaaccttcttcaactaacggggcaggttagtgacattagaaaaccgactgtaaaaagta
cagtcggcattatctcatattataaaagccagtcattaggcctatctgacaattcctgaatagagttcataa
acaatcctgcatgataaccatcacaaacagaatgatgtacctgtaaagatagcggtaaatatattgaatt
acctttattaatgaattttcctgctgtaataatgggtagaaggtaattactattattattgatatttaagttaaac
ccagtaaatgaagtccatggaataatagaaagagaaaaagcattttcaggtataggtgttttgggaaac
aatttccccgaaccattatatttctctacatcagaaaggtataaatcataaaactctttgaagtcattctttac
aggagtccaaataccagagaatgttttagatacaccatcaaaaattgtataaagtggctctaacttatcc
caataacctaactctccgtcgctattgtaaccagttctaaaagctgtatttgagtttatcacccttgtcactaa
gaaaataaatgcagggtaaaatttatatccttcttgtttatgtttc

Figure 51B ggtataaaacactaatatcaatttctgtggttatactaaaagtcgtttgttggttcaaataatgattaaatatctc
ttttctcttccaattgtctaaatcaattttattaaagttcatttgatatgcctcctaaattttatctaaagtgaattta
ggaggcttacttgtctgctttcttcattagaatcaatccttttaaaagtcaatattactgtaacataaatatat
tttaaaaatatcccactttatccaattttcgtttgttgaactaatgggtgctttagttgaagaataaaagacctat
gcggtgtgaaataccgcacagatgcgtaaggagaaaataccgcatcaggcgccattcgccattcaggc
tgcgcaactgttgggaagggcgatcggtgcgggcctcttcgctattacgccagctggcgaaaggggat
gtgctgcaaggcgattaagttgggtaacgccaggttttcccagtcacgacgttgtaaaacgacggccag
tgccaagcttgcatgcctgcactccatttcttctgctatcaaaataacagactcgtgatttccaaacgagct
ttcaaaaaagcctctgccccttgcaaatcggatgcctgtctataaaattcccgatattggttaaacagcggc
gcaatggcggccgcatctgatgtctttgcttggcgaatgttcatcttatttcttcctccctctcaataattttttcatt
ctatccctttctgtaaagtttatttttcagaatactttatcatcatgctttgaaaaaatatcacgataatatccatt
gttctcacggaagcacacgcaggtcatttgaacgaatttttcgacaggaatttgccgggactcaggagca
tttaacctaaaaaagcatgacatttcagcataatgaacatttactcatgtctattttcgttcttttctgtatgaaaa
tagttatttcgagtctctacggaaatagcgagagatgatatacctaaatagagataaaatcatctcaaaaa
aatgggtctactaaaatattattccatctattacaataaaattcacagaatagtctttaagtaagtctactctga
attttttttaaaaggagagggtaaagagtgaaaacagtagttattattgatgcattacgaacaccaattggaa
aatataaaggcagcttaagtcaagtaagtgccgtagactaggaacacatgttacaacacaacttttaaa
aagacattccactatttctgaagaaattgatcaagtaatctttggaaatgttttacaagctggaaatggccaa
aatcccgcacgacaaatagcaataaacagcggtttgtctcatgaaattcccgcaatgacggttaatgagg
tctgcggatcaggaatgaaggccgttatttggcgaaacaattgattcaattaggagaagcggaagtttta
attgctggcgggattgagaatatgtcccaagcacctaaattacaacgttttaattacgaaacagaaagcta
cgatgcgccttttctagtatgatgtatgatggattaacggatgcctttagtggtcaggcaatgggcttaactg
ctgaaaatgtggccgaaaagtatcatgtaactagagaagagcaagatcaattttctgtacattcacaatta
aaagcagctcaagcacaagcagaagggatattcgctgacgaaatagccccattagaagtatcaggaa
cgcttgtggagaaagatgaagggattcgccctaattcgagcgttgagaagctaggaacgcttaaaacag
tttttaaagaagacggtactgtaacagcagggaatgcatcaaccattaatgatggggcttctgctttgattatt
gcttcacaagaatatgccgaagcacacggtcttccttatttagctattattcgagacagtgtggaagtcggt
attgatccagcctatatgggaatttcgccgattaaagccattcaaaaactgttagcgcgcaatcaacttact
acggaagaaattgatctgtatgaaatcaacgaagcatttgcagcaacttcaatcgtggtccaaagagaa
ctggctttaccagaggaaaaggtcaacatttatggtggcggtatttcattaggtcatgcgattggtgccaca
ggtgctcgtttattaacgagtttaagttatcaattaaatcaaaaagaaaagaaatatggagtggcttctttatg
tatcggcggtggcttaggactcgctatgctactagagagacctcagcaaaaaaaaaacagccgattttat
caaatgagtcctgaggaacgcctggcttctcttcttaatgaaggccagatttctgctgatacaaaaaaaga
atttgaaaatacggctttatcttcgcagattgccaatcatatgattgaaaatcaaatcagtgaaacagaagt
gccgatgggcgttggcttacatttaacagtggacgaaactgattatttggtaccaatggcgacagaagag
ccctcagttattgcggctttgagtaatggtgcaaaaatagcacaaggatttaaaacagtgaatcaacaac
gcttaatgcgtggacaaatcgttttttacgatgttgcagatcccgagtcattgattgataaactacaagtaag
agaagcggaagttttcaacaagcagagttaagttatccatctatcgttaaacggggcggcggcttaaga
gatttgcaatatcgtactttgatgaatcatttgtatctgtcgacttttagtagatgttaaggatgcaatggggg
caaatatcgttaacgctatgttggaaggtgtg

Figure 51C gccgagttgttccgtgaatggtttgcggagcaaaagattttattcagtattttaagtaattatgccacggag
tcggttgttacgatgaaaacggctattccagtttcacgtttaagtaaggggagcaatggccgggaaatt
gctgaaaaaattgttttagcttcacgctatgcttcattagatccttatcgggcagtcacgcataacaaagg
aatcatgaatggcattgaagctgtagttttagctacaggaaatgatacacgcgctgttagcgcttcttgtc
atgcttttgcggtgaaggaaggtcgctaccaaggcttgactagttggacgctggatggcgaacaacta
attggtgaaatttcagttccgcttgctttagccacggttggcggtgccacaaaagtcttacctaaatctca
agcagctgctgatttgttagcagtgacggatgcaaaagaactaagtcgagtagtagcggctgttggttt
ggcacaaaatttagcggcgttacgggccttagtctctgaaggaattcaaaaaggacacatggctctac
aagcacgttctttagcgatgacggtcggagctactggtaaagaagttgaggcagtcgctcaacaatta
aaacgtcaaaaaacgatgaaccaagaccgagccatggctatttaaatgatttaagaaaacaataa
aaggagagggtgacaattggattgataaaattagttttttttgtgcccccttattatattgatatgacggca
ctggctgaagccagaaatgtagaccctggaaaatttcatattggtattgggcaagaccaaatggcggt
gaacccaatcagccaagatattgtgacatttgcagccaatgccgcagaagcgatcttgaccaaaga
agataaagaggccattgatatggtgattgtcgggactgagtccagtatcgatgagtcaaaagcggcc
gcagttgtcttacatcgtttaatggggattcaacctttcgctcgctctttcgaaatcaaggaagcttgttacg
gagcaacagcaggcttacagttagctaagaatcacgtagccttacatccagataaaaaagtcttggtc
gtagcggcagatattgcaaaatatggcttaaattctggcggtgagcctacacaaggagctggggcgg
ttgcaatgttagttgctagtgaaccgcgcattttggctttaaaagaggataatgtgatgctgacgcaagat
atctatgacttttggcgtccaacaggccacccgtatcctatggtcgatggtcctttgtcaaacgaaaccta
catccaatcttttgcccaagtctgggatgaacataaaaaacgaaccggtcttgattttgcagattatgatg
ctttagcgttccatattccttacacaaaaatgggcaaaaaagccttattagcaaaaatctccgaccaaa
ctgaagcagaacaggaacgaattttagcccgttatgaagaaagtatcgtctatagtcgtcgcgtagga
aacttgtatacgggttcactttatctgggactcatttcccttttagaaaatgcaacgactttaaccgcaggc
aatcaaattggtttattcagttatggttctggtgctgtcgctgaattttcactggtgaattagtagctggttatc
aaaatcatttacaaaaagaaactcatttagcactgctggataatcggacagaactttctatcgctgaat
atgaagccatgtttgcagaaactttagacacagacattgatcaaacgttagaagatgaattaaaatata
gtatttctgctattaataataccgttcgttcttatcgaaactaaaaaaaaccggccttggccccgccggttt
tttattattttttcttcctccgcatgttcaatccgctccataatcgacggatggctccctctgaaaattttaacga
gaaacggcgggttgacccggctcagtccgtaacggccaagtcctgaaacgtcaatcgccgcttc
ccggtttccggtcagctcaatgccgtaacggtcggcggcgttttcctgataccgggagacggcattcgt
aatcgggatccccgggtaccgagctcgaattcgtaatcatgtcatagctgtttcctgtgtgaaattgttatc
cgctcacaattccacacaacatacgagccggaagcataaagtgtaaagcctggggtgcctaatgag
tgagctaactcacattaattgcgttcgctcactgcccgctttccagtcgggaaacctgtcgtgccagct
gcattaatgaatcggccaacgcgcggggagaggcggtttgcgtattgggcgctcttccgcttcctcgct
cactgac (SEQ ID NO:22)

Figure 75A

| Fuel Conc. (wt.%) | Oxidizer Conc. (wt.%) | Fuel Makeup Isoprene (wt. %) | Oxidizer Makeup H₂O (wt. %) | Oxidizer Makeup O₂ (wt. %) | Oxidizer Makeup N₂ (wt. %) | Concentration at Deflagration — Molar Concentration based on 100g of sample | | | | | Concentration at Deflagration — Volumetric Concentrations based on ideal gas law | | | |
|---|---|---|---|---|---|---|---|---|---|---|---|---|---|---|
| | | | | | | Isoprene (mole) | H₂O (mole) | O₂ (mole) | N₂ (mole) | Total (mole) | Isoprene (vol. %) | O₂ (vol. %) | N₂ (vol. %) | H₂O (vol. %) |
| 3.10 | 96.90 | 100 | 0 | 12 | 88 | 4.56 | 0.00 | 36.34 | 304.54 | 345.44 | 1.32 | 10.52 | 88.16 | 0.00 |
| 3.10 | 96.90 | 100 | 0 | 13 | 87 | 4.56 | 0.00 | 39.37 | 301.08 | 345.01 | 1.32 | 11.41 | 87.27 | 0.00 |
| 3.10 | 96.90 | 100 | 0 | 14 | 86 | 4.56 | 0.00 | 42.39 | 297.62 | 344.57 | 1.32 | 12.30 | 86.37 | 0.00 |
| 3.10 | 96.90 | 100 | 0 | 15 | 85 | 4.56 | 0.00 | 45.42 | 294.16 | 344.14 | 1.32 | 13.20 | 85.48 | 0.00 |
| 3.10 | 96.90 | 100 | 0 | 16 | 84 | 4.56 | 0.00 | 48.45 | 290.70 | 343.71 | 1.33 | 14.10 | 84.58 | 0.00 |
| 3.10 | 96.90 | 100 | 0 | 17 | 83 | 4.56 | 0.00 | 51.48 | 287.24 | 343.28 | 1.33 | 15.00 | 83.68 | 0.00 |
| 3.10 | 96.90 | 100 | 0 | 21 | 79 | 4.56 | 0.00 | 63.59 | 273.40 | 341.55 | 1.33 | 18.62 | 80.05 | 0.00 |
| 3.50 | 96.50 | 100 | 0 | 11.1 | 88.9 | 5.15 | 0.00 | 33.47 | 306.39 | 345.01 | 1.49 | 9.70 | 88.81 | 0.00 |
| 4.40 | 95.60 | 100 | 0 | 12 | 88 | 6.47 | 0.00 | 35.85 | 300.46 | 342.78 | 1.89 | 10.46 | 87.65 | 0.00 |
| 5.50 | 94.50 | 100 | 0 | 13 | 87 | 8.09 | 0.00 | 38.39 | 293.63 | 340.10 | 2.38 | 11.29 | 86.33 | 0.00 |
| 6.60 | 93.40 | 100 | 0 | 14 | 86 | 9.71 | 0.00 | 40.86 | 286.87 | 337.44 | 2.88 | 12.11 | 85.01 | 0.00 |
| 7.60 | 92.40 | 100 | 0 | 15 | 85 | 11.18 | 0.00 | 43.31 | 280.50 | 334.99 | 3.34 | 12.93 | 83.73 | 0.00 |
| 8.50 | 91.50 | 100 | 0 | 16 | 84 | 12.50 | 0.00 | 45.75 | 274.50 | 332.75 | 3.76 | 13.75 | 82.49 | 0.00 |
| 9.60 | 90.40 | 100 | 0 | 17 | 83 | 14.12 | 0.00 | 48.03 | 267.97 | 330.11 | 4.28 | 14.55 | 81.18 | 0.00 |
| 13.50 | 86.50 | 100 | 0 | 21 | 79 | 19.85 | 0.00 | 56.77 | 244.05 | 320.67 | 6.19 | 17.70 | 76.11 | 0.00 |

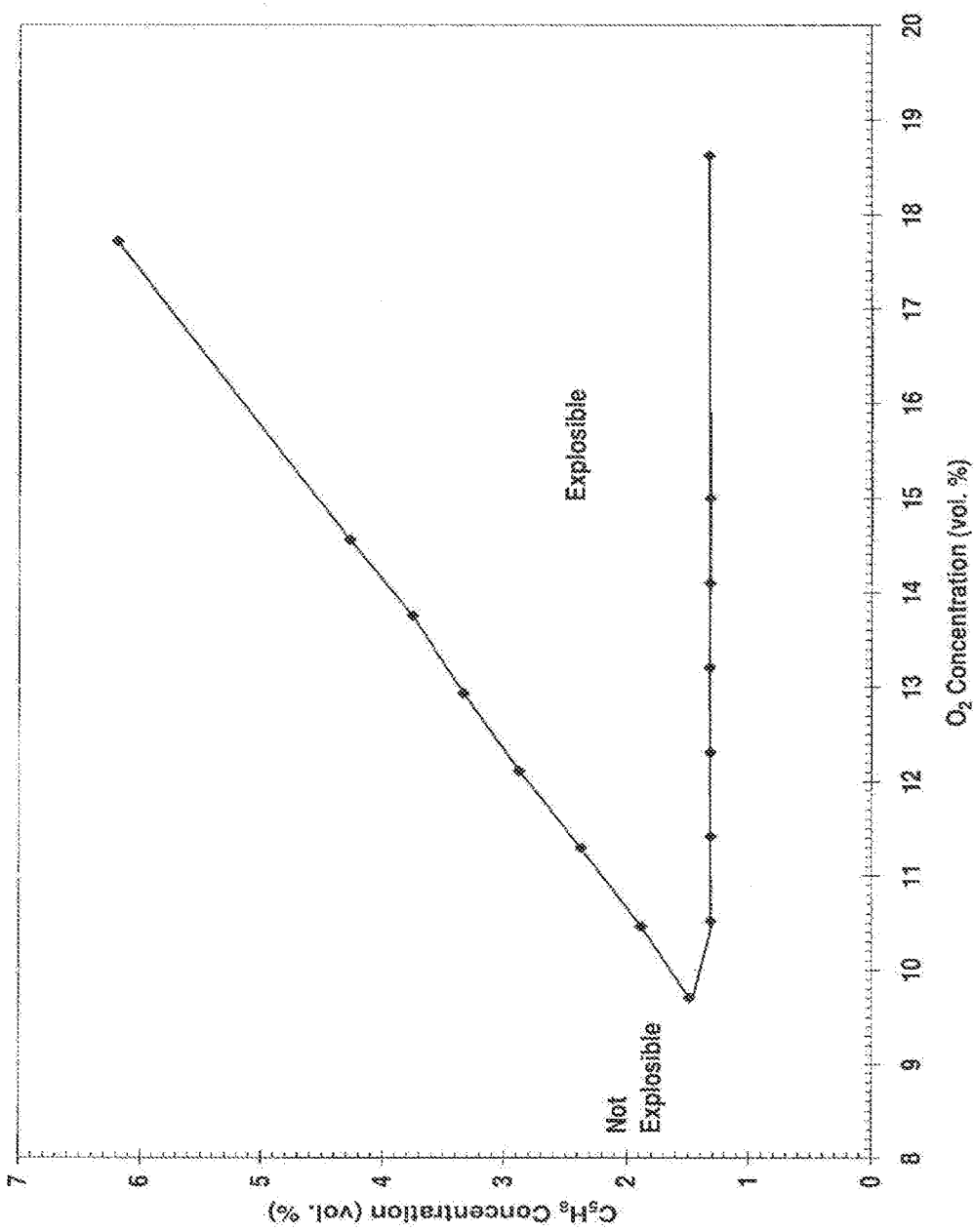

Figure 76A

| Fuel Conc. (wt.%) | Oxidizer Conc. (wt.%) | Fuel Makeup | Oxidizer Makeup | | | Concentration at Deflagration | | | | | | | | |
|---|---|---|---|---|---|---|---|---|---|---|---|---|---|---|
| | | | | | | Molar Concentration based on 100g of sample | | | | | Volumetric Concentrations based on ideal gas law | | | |
| | | Isoprene (wt.%) | H₂O (wt.%) | O₂ (wt.%) | N₂ (wt.%) | Isoprene (mole) | H₂O (mole) | O₂ (mole) | N₂ (mole) | Total (mole) | Isoprene (vol.%) | O₂ (vol.%) | N₂ (vol.%) | H₂O (vol.%) |
| 3.252 | 96.748 | 100 | 4 | 12 | 84 | 4.78 | 21.50 | 36.28 | 290.24 | 352.81 | 1.36 | 10.28 | 82.27 | 6.09 |
| 3.274 | 96.726 | 100 | 4 | 13 | 83 | 4.81 | 21.49 | 39.29 | 286.72 | 352.33 | 1.37 | 11.15 | 81.38 | 6.10 |
| 3.290 | 96.710 | 100 | 4 | 14 | 82 | 4.84 | 21.49 | 42.31 | 283.22 | 351.86 | 1.38 | 12.02 | 80.49 | 6.11 |
| 3.288 | 96.712 | 100 | 4 | 15 | 81 | 4.84 | 21.49 | 45.33 | 279.77 | 351.43 | 1.38 | 12.90 | 79.61 | 6.12 |
| 3.286 | 96.714 | 100 | 4 | 16 | 80 | 4.83 | 21.49 | 48.36 | 276.33 | 351.01 | 1.38 | 13.78 | 78.72 | 6.12 |
| 3.284 | 96.716 | 100 | 4 | 17 | 79 | 4.83 | 21.49 | 51.38 | 272.88 | 350.58 | 1.38 | 14.66 | 77.84 | 6.13 |
| 3.276 | 96.724 | 100 | 4 | 21 | 75 | 4.82 | 21.49 | 63.48 | 259.08 | 348.87 | 1.38 | 18.19 | 74.26 | 6.16 |
| 3.500 | 96.500 | 100 | 4 | 11.5 | 84.5 | 5.15 | 21.44 | 34.68 | 291.22 | 352.49 | 1.46 | 9.84 | 82.62 | 6.08 |
| 4.200 | 95.800 | 100 | 4 | 12 | 84 | 6.18 | 21.29 | 35.93 | 287.40 | 350.79 | 1.76 | 10.24 | 81.93 | 6.07 |
| 5.300 | 94.700 | 100 | 4 | 13 | 83 | 7.79 | 21.04 | 38.47 | 280.72 | 348.03 | 2.24 | 11.05 | 80.66 | 6.05 |
| 6.400 | 93.600 | 100 | 4 | 14 | 82 | 9.41 | 20.80 | 40.95 | 274.11 | 345.28 | 2.73 | 11.86 | 79.39 | 6.02 |
| 7.400 | 92.600 | 100 | 4 | 15 | 81 | 10.88 | 20.58 | 43.41 | 267.88 | 342.74 | 3.18 | 12.66 | 78.16 | 6.00 |
| 8.500 | 91.500 | 100 | 4 | 16 | 80 | 12.50 | 20.33 | 45.75 | 261.43 | 340.01 | 3.68 | 13.46 | 76.89 | 5.98 |
| 9.400 | 90.600 | 100 | 4 | 17 | 79 | 13.82 | 20.13 | 48.13 | 255.62 | 337.71 | 4.09 | 14.25 | 75.69 | 5.96 |
| 13.300 | 86.700 | 100 | 4 | 21 | 75 | 19.56 | 19.27 | 56.90 | 232.23 | 327.96 | 5.96 | 17.35 | 70.81 | 5.87 |

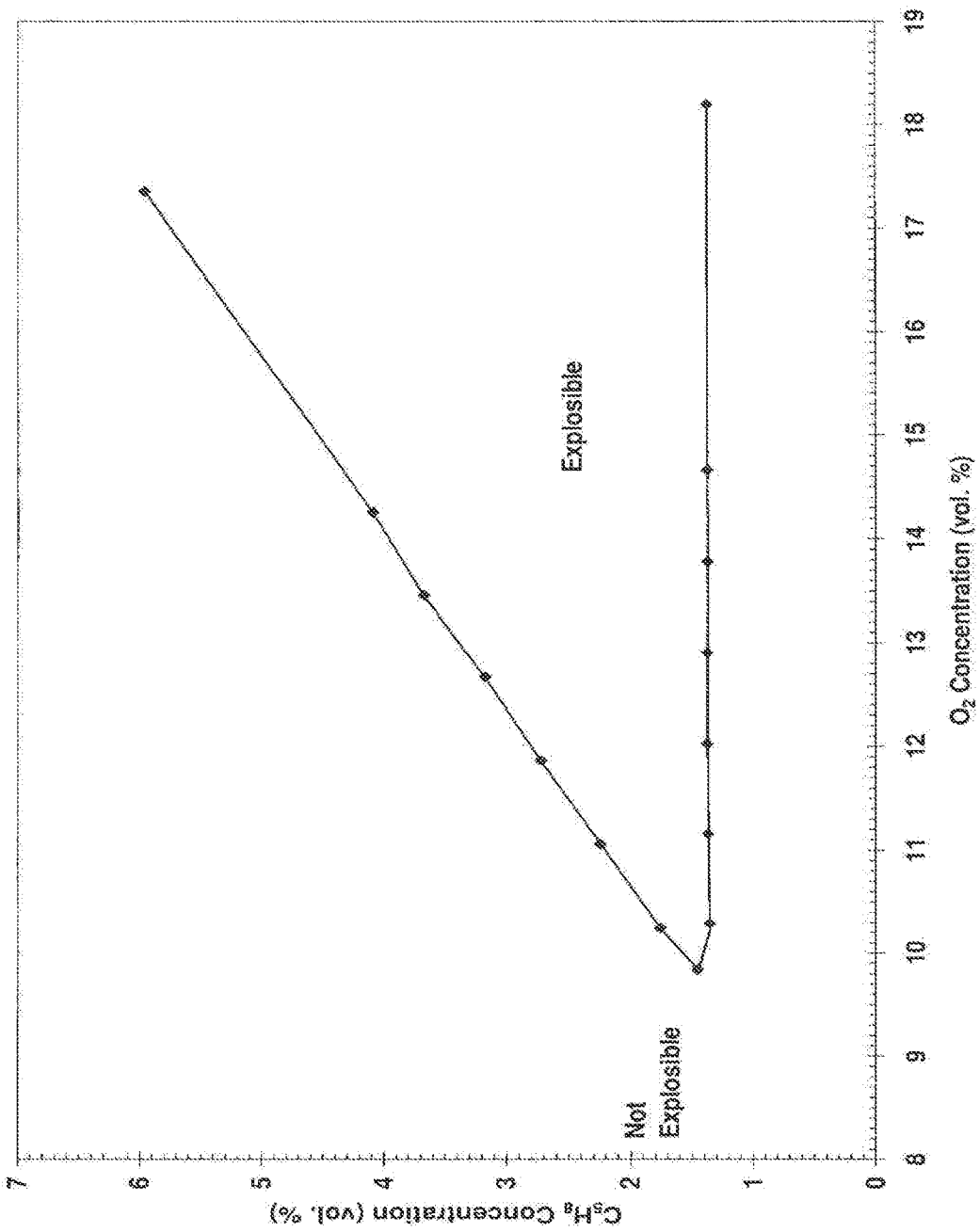

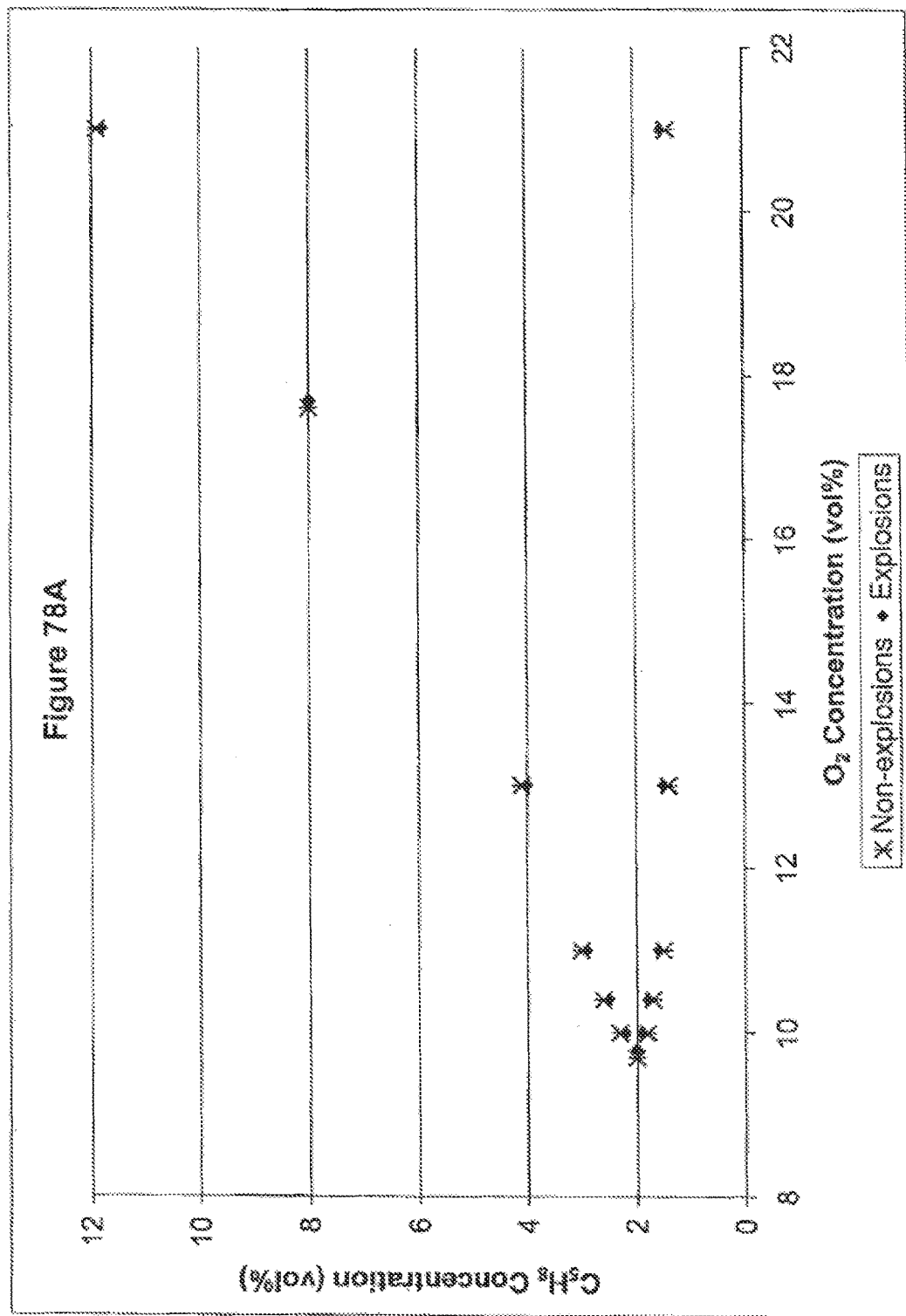

Figure 78B

| Explosions | | Non-explosions | |
|---|---|---|---|
| O₂ Concentration | C₅H₈ Concentration | O₂ Concentration | C₅H₈ Concentration |
| (vol. %) | (vol. %) | (vol. %) | (vol. %) |
| 21.0 | 1.5 | 21.0 | 1.4 |
| 13.0 | 1.5 | 13.0 | 1.4 |
| 11.0 | 1.6 | 11.0 | 1.5 |
| 10.4 | 1.8 | 10.4 | 1.7 |
| 10.0 | 1.9 | 10.0 | 1.8 |
| 9.8 | 2 | 9.7 | 2 |
| 10.0 | 2.2 | 10.0 | 2.3 |
| 10.4 | 2.5 | 10.4 | 2.6 |
| 11.0 | 2.9 | 11.0 | 3.0 |
| 13.0 | 4.0 | 13.0 | 4.1 |
| 17.7 | 8.0 | 17.6 | 8.0 |
| 21.0 | 11.8 | 21.0 | 11.9 |

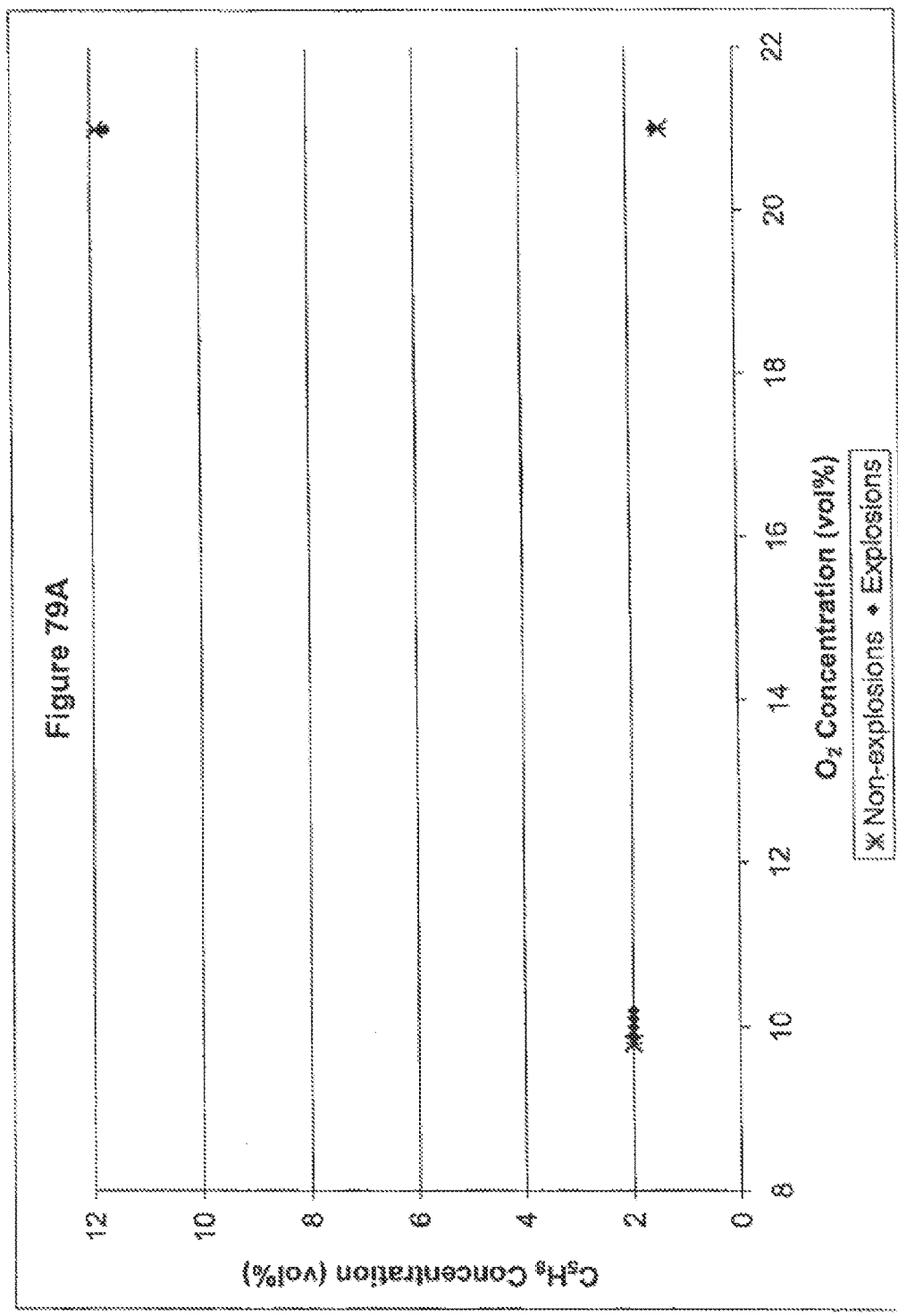

Figure 79B

| Explosions | | Non-explosions | |
|---|---|---|---|
| $O_2$ Concentration (vol. %) | $C_5H_8$ Concentration (vol. %) | $O_2$ Concentration (vol. %) | $C_5H_8$ Concentration (vol. %) |
| 21.0 | 11.7 | 21.0 | 11.9 |
| 21.0 | 11.8 | 21.0 | 11.9 |
| 21.0 | 11.8 | 21.0 | 11.9 |
| 21.0 | 1.5 | 21.0 | 1.4 |
| 21.0 | 1.5 | 21.0 | 1.4 |
| 10.2 | 2.0 | 21.0 | 1.4 |
| 10.1 | 2.0 | 9.8 | 2.0 |
| 10.0 | 2.0 | 9.8 | 2.0 |
| 9.9 | 2.0 | 9.8 | 2.0 |

Figure 80A

TEST SERIES 1

| Test | Data File Name | Temp °C | Initial Pressure bara | Partial Pressures C₃H₈ mbar | N₂ mbar | O₂ mbar | Concentrations C₃H₈ vol. % | N₂ vol. % | O₂ vol. % | Result | Pex bara |
|---|---|---|---|---|---|---|---|---|---|---|---|
| 1 | T11120700 | 40 | 1.012 | 12 | 787 | 213 | 1.2 | 77.8 | 21.0 | Non-Explosion | 1.05 |
| 2 | T11120701 | 40 | 1.016 | 16 | 787 | 213 | 1.6 | 77.5 | 21.0 | Explosion | 5.5 |
| 3 | T11120702 | 40 | 1.015 | 14 | 788 | 213 | 1.4 | 77.6 | 21.0 | Non-Explosion | <1.02 |
| 4 | T11120703 | 40 | 1.014 | 15 | 786 | 213 | 1.5 | 77.5 | 21.0 | Non-Explosion | <1.02 |
| 5 | T11120704 | 40 | 1.014 | 15 | 786 | 213 | 1.5 | 77.5 | 21.0 | Explosion | 4.31 |
| 6 | T11120705 | 40 | 1.017 | 18 | 785 | 214 | 1.8 | 77.2 | 21.0 | Explosion | 5.47 |
| 7 | T11120706 | 40 | 1.014 | 15 | 786 | 213 | 1.5 | 77.5 | 21.0 | Explosion | 4.51 |
| 8 | T11120707 | 40 | 1.014 | 14 | 787 | 213 | 1.4 | 77.6 | 21.0 | Non-Explosion | <1.02 |
| 9 | T11120708 | 40 | 1.014 | 14 | 787 | 213 | 1.4 | 77.6 | 21.0 | Non-Explosion | 1.05 |
| 10 | T11120709 | 40 | 1.015 | 102 | 700 | 213 | 10.0 | 69.0 | 21.0 | Explosion | 1.45 |
| 11 | T11120710 | 40 | 1.014 | 102 | 699 | 213 | 10.1 | 68.9 | 21.0 | Explosion | 1.39 |
| 12 | T11120711 | 40 | 1.014 | 106 | 695 | 213 | 10.5 | 68.5 | 21.0 | Explosion | 1.34 |
| 13 | T11120712 | 40 | 1.014 | 113 | 688 | 213 | 11.1 | 67.9 | 21.0 | Explosion | 1.29 |
| 14 | T11120713 | 40 | 1.014 | 122 | 679 | 213 | 12.0 | 67.0 | 21.0 | Non-Explosion | <1.02 |
| 15 | T11120714 | 40 | 1.014 | 117 | 684 | 213 | 11.5 | 67.5 | 21.0 | Explosion | 1.32 |
| 16 | T11120715 | 40 | 1.014 | 120 | 681 | 213 | 11.8 | 67.2 | 21.0 | Non-Explosion | 1.08 |
| 17 | T11130700 | 40 | 1.014 | 120 | 681 | 213 | 11.8 | 67.2 | 21.0 | Explosion | 1.09 |
| 18 | T11130701 | 40 | 1.014 | 121 | 680 | 213 | 11.9 | 67.1 | 21.0 | Non-Explosion | 1.07 |
| 19 | T11130702 | 40 | 1.015 | 121 | 681 | 213 | 11.9 | 67.1 | 21.0 | Non-Explosion | 1.06 |
| 20 | T11130703 | 40 | 1.015 | 121 | 681 | 213 | 11.9 | 67.1 | 21.0 | Non-Explosion | 1.07 |
| 21 | T11130704 | 40 | 1.015 | 30 | 853 | 132 | 3.0 | 84.0 | 13.0 | Explosion | 1.61 |
| 22 | T11130705 | 40 | 1.014 | 36 | 846 | 132 | 3.6 | 83.4 | 13.0 | Explosion | 1.28 |
| 23 | T11130706 | 40 | 1.014 | 39 | 843 | 132 | 3.8 | 83.1 | 13.0 | Explosion | 1.12 |
| 24 | T11130707 | 40 | 1.015 | 41 | 842 | 132 | 4.0 | 83.0 | 13.0 | Explosion | 1.09 |
| 25 | T11130708 | 40 | 1.014 | 42 | 840 | 132 | 4.1 | 82.8 | 13.0 | Non-Explosion | 1.06 |
| 26 | T11130709 | 40 | 1.015 | 42 | 841 | 132 | 4.1 | 82.9 | 13.0 | Non-Explosion | 1.06 |
| 27 | T11130710 | 40 | 1.014 | 42 | 840 | 132 | 4.1 | 82.8 | 13.0 | Non-Explosion | 1.05 |
| 28 | T11130711 | 40 | 1.014 | 15 | 867 | 132 | 1.5 | 85.5 | 13.0 | Non-Explosion | 1.03 |
| 29 | T11130712 | 40 | 1.014 | 16 | 866 | 132 | 1.6 | 85.4 | 13.0 | Explosion | 4.81 |
| 30 | T11130713 | 40 | 1.014 | 15 | 867 | 132 | 1.5 | 85.5 | 13.0 | Explosion | 4 |
| 31 | T11130714 | 40 | 1.014 | 14 | 868 | 132 | 1.4 | 85.6 | 13.0 | Non-Explosion | 1.03 |
| 32 | T11130715 | 40 | 1.014 | 14 | 868 | 132 | 1.4 | 85.6 | 13.0 | Non-Explosion | <1.02 |
| 33 | T11130716 | 40 | 1.014 | 14 | 868 | 132 | 1.4 | 85.6 | 13.0 | Non-Explosion | 1.03 |
| 34 | T11130717 | 40 | 1.015 | 20 | 883 | 112 | 2.0 | 87.0 | 11.0 | Explosion | 1.7 |
| 35 | T11130718 | 40 | 1.014 | 28 | 874 | 112 | 2.8 | 86.2 | 11.0 | Non-Explosion | 1.08 |
| 36 | T11130719 | 40 | 1.014 | 28 | 874 | 112 | 2.8 | 86.2 | 11.0 | Non-Explosion | 1.08 |
| 37 | T11130720 | 40 | 1.014 | 28 | 874 | 112 | 2.8 | 86.2 | 11.0 | Explosion | 1.13 |
| 38 | T11130721 | 40 | 1.015 | 29 | 874 | 112 | 2.9 | 86.1 | 11.0 | Non-Explosion | 1.08 |
| 39 | T11130722 | 40 | 1.014 | 29 | 873 | 112 | 2.9 | 86.1 | 11.0 | Explosion | 1.1 |

Figure 80B

| Test | Data File Name | Temp °C | Initial Pressure bara | Partial Pressures C$_3$H$_8$ mbar | Partial Pressures N$_2$ mbar | Partial Pressures O$_2$ mbar | Concentrations C$_3$H$_8$ vol. % | Concentrations N$_2$ vol. % | Concentrations O$_2$ vol. % | Result | Pex bara |
|---|---|---|---|---|---|---|---|---|---|---|---|
| 40 | T11130723 | 40 | 1.014 | 30 | 872 | 112 | 3.0 | 86.0 | 11.0 | Non-Explosion | 1.06 |
| 41 | T11130724 | 40 | 1.014 | 30 | 872 | 112 | 3.0 | 86.0 | 11.0 | Non-Explosion | 1.05 |
| 42 | T11130725 | 40 | 1.014 | 30 | 872 | 112 | 3.0 | 86.0 | 11.0 | Non-Explosion | 1.05 |
| 43 | T11130726 | 40 | 1.014 | 15 | 887 | 112 | 1.5 | 87.5 | 11.0 | Non-Explosion | <1.02 |
| 44 | T11130727 | 40 | 1.014 | 15 | 887 | 112 | 1.5 | 87.5 | 11.0 | Non-Explosion | <1.02 |
| 45 | T11140700 | 40 | 1.014 | 16 | 886 | 112 | 1.6 | 87.4 | 11.0 | Non-Explosion | <1.02 |
| 46 | T11140701 | 40 | 1.014 | 17 | 885 | 112 | 1.7 | 87.3 | 11.0 | Explosion | 1.81 |
| 47 | T11140702 | 40 | 1.014 | 16 | 886 | 112 | 1.6 | 87.4 | 11.0 | Explosion | 1.54 |
| 48 | T11140703 | 40 | 1.014 | 15 | 887 | 112 | 1.5 | 87.5 | 11.0 | Non-Explosion | <1.02 |
| 49 | T11140704 | 40 | 1.015 | 20 | 899 | 96 | 2.0 | 88.6 | 9.5 | Non-Explosion | 1.05 |
| 50 | T11140705 | 40 | 1.014 | 20 | 898 | 96 | 2.0 | 88.6 | 9.5 | Non-Explosion | 1.05 |
| 51 | T11140706 | 40 | 1.014 | 23 | 890 | 101 | 2.3 | 87.8 | 10.0 | Non-Explosion | 1.06 |
| 52 | T11140707 | 40 | 1.015 | 23 | 886 | 106 | 2.3 | 87.3 | 10.4 | Explosion | 1.19 |
| 53 | T11140708 | 40 | 1.014 | 25 | 984 | 105 | 2.5 | 87.2 | 10.4 | Explosion | 1.09 |
| 54 | T11140709 | 40 | 1.014 | 26 | 883 | 105 | 2.6 | 87.1 | 10.4 | Non-Explosion | 1.05 |
| 55 | T11140710 | 40 | 1.014 | 26 | 883 | 105 | 2.6 | 87.1 | 10.4 | Non-Explosion | 1.06 |
| 56 | T11140711 | 40 | 1.014 | 26 | 883 | 105 | 2.6 | 87.1 | 10.4 | Non-Explosion | 1.07 |
| 57 | T11140712 | 40 | 1.014 | 20 | 889 | 105 | 2.0 | 87.7 | 10.4 | Explosion | 1.21 |
| 58 | T11140713 | 40 | 1.014 | 17 | 892 | 105 | 1.7 | 88.0 | 10.4 | Non-Explosion | 1.04 |
| 59 | T11140714 | 40 | 1.014 | 18 | 891 | 105 | 1.8 | 87.9 | 10.4 | Explosion | 1.21 |
| 60 | T11140715 | 40 | 1.014 | 17 | 892 | 105 | 1.7 | 88.0 | 10.4 | Non-Explosion | 1.03 |
| 61 | T11140716 | 40 | 1.014 | 17 | 892 | 105 | 1.7 | 88.0 | 10.4 | Non-Explosion | 1.03 |
| 62 | T11140717 | 40 | 1.014 | 21 | 890 | 103 | 2.1 | 87.8 | 10.2 | Explosion | 1.1 |
| 63 | T11140718 | 40 | 1.014 | 21 | 891 | 102 | 2.1 | 87.9 | 10.1 | Explosion | 1.09 |
| 64 | T11140719 | 40 | 1.014 | 21 | 892 | 101 | 2.1 | 88.0 | 10.0 | Explosion | 1.09 |
| 65 | T11140720 | 40 | 1.014 | 22 | 891 | 101 | 2.2 | 87.9 | 10.0 | Explosion | 1.1 |
| 66 | T11140721 | 40 | 1.014 | 23 | 890 | 101 | 2.3 | 87.8 | 10.0 | Non-Explosion | 1.06 |
| 67 | T11140722 | 40 | 1.014 | 23 | 890 | 101 | 2.3 | 87.8 | 10.0 | Non-Explosion | 1.08 |
| 68 | T11140723 | 40 | 1.014 | 19 | 894 | 101 | 1.9 | 88.2 | 10.0 | Explosion | 1.12 |
| 69 | T11140724 | 40 | 1.014 | 18 | 895 | 101 | 1.8 | 88.3 | 10.0 | Non-Explosion | 1.06 |
| 70 | T11140725 | 40 | 1.014 | 18 | 895 | 101 | 1.8 | 88.3 | 10.0 | Non-Explosion | 1.03 |
| 71 | T11140726 | 40 | 1.014 | 18 | 895 | 101 | 1.8 | 88.3 | 10.0 | Non-Explosion | 1.04 |
| 72 | T11140727 | 40 | 1.014 | 20 | 895 | 99 | 2.0 | 88.3 | 9.8 | Non-Explosion | 1.08 |
| 73 | T11140728 | 40 | 1.014 | 20 | 895 | 99 | 2.0 | 88.3 | 9.8 | Explosion | 1.1 |
| 74 | T11140729 | 40 | 1.014 | 20 | 896 | 98 | 2.0 | 88.4 | 9.7 | Non-Explosion | 1.06 |
| 75 | T11140730 | 40 | 1.014 | 20 | 896 | 98 | 2.0 | 88.4 | 9.7 | Non-Explosion | 1.08 |
| 76 | T11140731 | 40 | 1.014 | 20 | 896 | 98 | 2.0 | 88.4 | 9.7 | Non-Explosion | 1.07 |
| 77 | T11140732 | 40 | 1.014 | 81 | 761 | 172 | 8.0 | 75.0 | 17.0 | Non-Explosion | 1.04 |
| 78 | T11140733 | 40 | 1.014 | 81 | 750 | 183 | 8.0 | 74.0 | 18.0 | Explosion | 1.3 |
| 79 | T11140734 | 40 | 1.014 | 81 | 754 | 179 | 8.0 | 74.4 | 17.7 | Explosion | 1.24 |
| 80 | T11140735 | 40 | 1.014 | 81 | 757 | 176 | 8.0 | 74.7 | 17.4 | Non-Explosion | 1.03 |
| 81 | T11140736 | 40 | 1.014 | 81 | 755 | 178 | 8.0 | 74.5 | 17.6 | Non-Explosion | 1.05 |
| 82 | T11140737 | 40 | 1.014 | 81 | 755 | 178 | 8.0 | 74.5 | 17.6 | Non-Explosion | 1.03 |
| 83 | T11140738 | 40 | 1.014 | 81 | 755 | 178 | 8.0 | 74.5 | 17.6 | Non-Explosion | 1.03 |

Figure 81

TEST SERIES 2

| Test | Data File Name | Temp °C | Initial Pressure bara | Partial Pressures | | | | Concentrations | | | | Result | Pex bara |
|---|---|---|---|---|---|---|---|---|---|---|---|---|---|
| | | | | $H_2O$ mbar | $C_3H_8$ mbar | $N_2$ mbar | $O_2$ mbar | $H_2O$ vol. % | $C_3H_8$ vol. % | $N_2$ vol. % | $O_2$ vol. % | | |
| 1 | T11150700 | 40 | 1.014 | 41 | 119 | 641 | 213 | 4.0 | 11.7 | 63.2 | 21.0 | Explosion | 1.33 |
| 2 | T11150701 | 40 | 1.014 | 40 | 121 | 640 | 213 | 3.9 | 11.9 | 63.1 | 21.0 | Non-explosion | 1.07 |
| 3 | T11150702 | 40 | 1.014 | 41 | 120 | 640 | 213 | 4.0 | 11.8 | 63.1 | 21.0 | Explosion | 1.09 |
| 4 | T11150703 | 40 | 1.014 | 40 | 121 | 640 | 213 | 3.9 | 11.9 | 63.1 | 21.0 | Non-explosion | 1.06 |
| 5 | T11150704 | 40 | 1.014 | 40 | 120 | 641 | 213 | 3.9 | 11.8 | 63.2 | 21.0 | Explosion | 1.09 |
| 6 | T11150705 | 40 | 1.014 | 40 | 121 | 640 | 213 | 3.9 | 11.9 | 63.1 | 21.0 | Non-explosion | 1.08 |
| 7 | T11150706 | 40 | 1.014 | 40 | 15 | 746 | 213 | 3.9 | 1.5 | 73.6 | 21.0 | Explosion | 4.68 |
| 8 | T11150707 | 40 | 1.014 | 41 | 15 | 745 | 213 | 4.0 | 1.5 | 73.5 | 21.0 | Explosion | 5.27 |
| 9 | T11150708 | 40 | 1.014 | 41 | 14 | 746 | 213 | 4.0 | 1.4 | 73.6 | 21.0 | Non-explosion | 1.03 |
| 10 | T11150709 | 40 | 1.014 | 42 | 14 | 745 | 213 | 4.1 | 1.4 | 73.5 | 21.0 | Non-explosion | 1.03 |
| 11 | T11160700 | 40 | 1.014 | 41 | 14 | 746 | 213 | 4.0 | 1.4 | 73.6 | 21.0 | Non-explosion | 1.03 |
| 12 | T11160701 | 40 | 1.014 | 41 | 20 | 850 | 103 | 4.0 | 2.0 | 83.8 | 10.2 | Explosion | 1.11 |
| 13 | T11160702 | 40 | 1.014 | 41 | 20 | 851 | 102 | 4.0 | 2.0 | 83.9 | 10.1 | Explosion | 1.11 |
| 14 | T11160703 | 40 | 1.014 | 41 | 20 | 852 | 101 | 4.0 | 2.0 | 84.0 | 10.0 | Explosion | 1.09 |
| 15 | T11160704 | 40 | 1.014 | 41 | 20 | 853 | 100 | 4.0 | 2.0 | 84.1 | 9.9 | Explosion | 1.09 |
| 16 | T11160705 | 40 | 1.014 | 41 | 20 | 854 | 99 | 4.0 | 2.0 | 84.2 | 9.8 | Non-explosion | 1.07 |
| 17 | T11160706 | 40 | 1.014 | 40 | 20 | 855 | 99 | 3.9 | 2.0 | 84.3 | 9.8 | Non-explosion | 1.06 |
| 18 | T11160707 | 40 | 1.014 | 41 | 20 | 854 | 99 | 4.0 | 2.0 | 84.2 | 9.8 | Non-explosion | 1.08 |

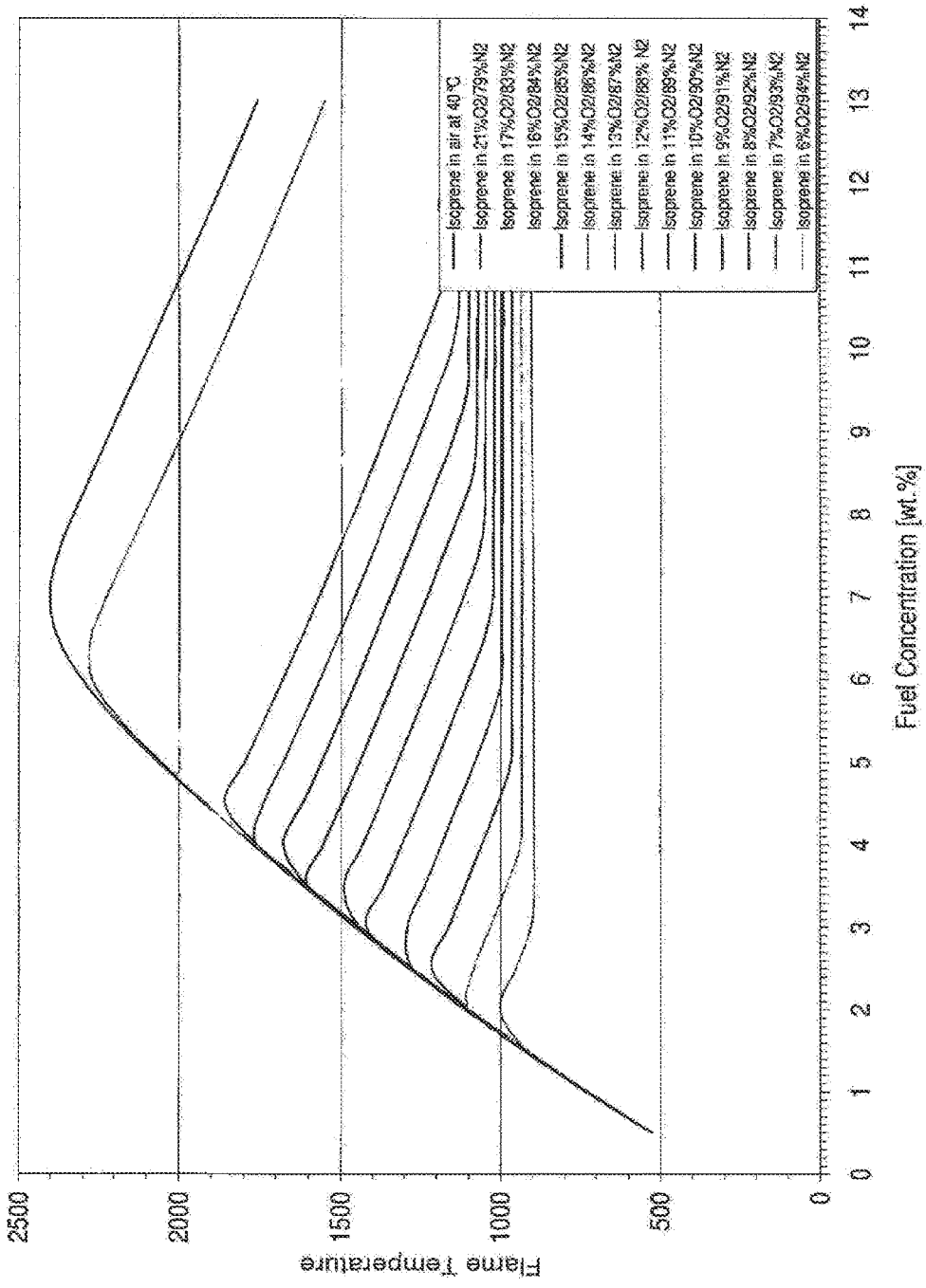

2-methyl-1,3-butadiene standard.

2-methyl-1,3-butadiene from recombinant *E. coli*

Figure 90
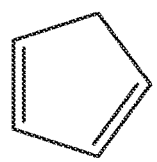
cyclopentadiene
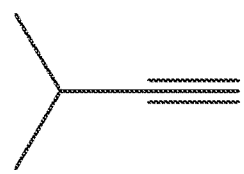
"isopryne" = 3-Me-1-butyne
trans-piperylene
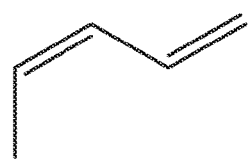
cis-piperylene
1-pentyne
pent-4-ene-1-yne
trans-pent-3-ene-1-yne
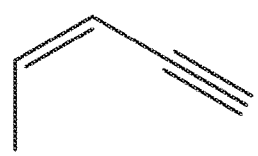
cis-pent-3-ene-1-yne

Figure 92A 1-
gtttgacagcttatcatcgactgcacggtgcaccaatgcttctggcgtcaggcagccatcggaagctgtggtatggctgtgcaggtcgt
aaatcactgcataattcgtgtcgctcaaggcgcactcccgttctggataatgttttttgcgccgacatcataacggttctggcaaatattct
gaaatgagctgttgacaattaatcatccggctcgtataatgtgtggaattgtgagcggataacaatttcacacaggaaacagcgccg
ctgagaaaaagcgaagcggcactgctctttaacaatttatcagacaatctgtgtgggcactcgaccggaattatcgattaactttattatt
aaaaattaaagagggtatatattaatgtatcgattaaataaggaggaataaaccatggatccgagctcaggaggtaaaaaaacatga
aaacagtagttattattgatgcattacgaacaccaattggaaaatataaaggcagcttaagtcaagtaagtgccgtagacttaggaac
acatgttacaacacaactttttaaaaagacattccactatttctgaagaaattgatcaagtaatctttggaaatgttttacaagctggaaat
ggccaaaatcccgcacgacaaatagcaataaacagcggtttgtctcatgaaattcccgcaatgacggttaatgaggtctgcggatc
aggaatgaaggccgttattttggcgaaacaattgattcaattaggagaagcggaagttttaattgctggcgggattgagaatatgtccc
aagcacctaaattacaacgttttaattacgaaacagaaagctacgatgcgcctttttctagtatgatgtatgatggattaacggatgcctt
tagtggtcaggcaatgggcttaactgctgaaaatgtggccgaaaagtatcatgtaactagagaagagcaagatcaattttctgtacatt
cacaattaaaagcagctcaagcacaagcagaagggatattcgctgacgaaatagccccattagaagtatcaggaacgcttgtgga
gaaagatgaagggattcgccctaattcgagcgttgagaagctaggaacgcttaaaacagttttttaaagaagacggtactgtaacag
cagggaatgcatcaaccattaatgatggggcttctgctttgattattgcttcacaagaatatgccgaagcacacggtcttccttatttagct
attattcgagacagtgtggaagtcggtattgatccagcctatatgggaatttcgccgattaaaagccattcaaaaactgttagcgcgcaa
tcaacttactacggaagaaattgatctgtatgaaatcaacgaagcatttgcagcaacttcaatcgtggtccaaagagaactggctttac
cagaggaaaaggtcaacatttatggtggcggtatttcattaggtcatgcgattggtgccacaggtgctcgtttattaacgagtttaagttat
caattaaatcaaaaagaaaagaaatatggagtggcttctttatgtatcggcggtggcttaggactcgctatgctactagagagacctc
agcaaaaaaaaaacagccgattttatcaaatgagtcctgaggaacgcctggcttctcttcttaatgaaggccagattctgctgataca
aaaaaagaatttgaaaatacggctttatcttcgcagattgccaatcatatgattgaaaatcaaatcagtgaaacagaagtgccgatgg
gcgttggcttacatttaacagtggacgaaactgattatttggtaccaatggcgacagaagagccctcagttattgcggctttgagtaatg
gtgcaaaaatagcacaaggatttaaaacagtgaatcaacaacgcttaatgcgtggacaaatcgttttttacgatgttgcagatcccga
gtcattgattgataaactacaagtaagagaagcggaagttttcaacaagcagagttaagttatccatctatcgttaaacggggcggc
ggcttaagagatttgcaatatcgtactttgatgaatcatttgtatctgtcgactttttagtagatgttaaggatgcaatgggggcaaatatc
gttaacgctatgttggaaggtgtggccgagttgttccgtgaatggtttgcggagcaaaagattttattcagtatttaagtaattatgccacg
gagtcggttgttacgatgaaaacggctattccagtttcacgtttaagtaaggggagcaatggccgggaaattgctgaaaaaattgttta
gcttcacgctatgcttcattagatcctatcgggcagtcacgcataacaaaggaatcatgaatggcattgaagctgtagttttagctaca
ggaaatgatacacgcgctgttagcgcttcttgtcatgcttttgcggtgaaggaaggtcgctaccaaggcttgactagttggacgctggat
ggcgaacaactaattggtgaaatttcagttccgcttgctttagccacggttggcggtgccacaaaagtcttacctaaatctcaagcagc
tgctgatttgttagcagtgacggatgcaaaagaactaagtcgagtagtagcggctgttggtttggcacaaaatttagcggcgttacggg
ccttagtctctgaaggaattcaaaaaggacacatggctctacaagcacgttcttagcgatgacggtcggagctactggtaaagaagt
tgaggcagtcgctcaacaattaaaacgtcaaaaaacgatgaaccaagaccgagccatggctattttaaatgatttaagaaaacaat
aaaggagggtaaaaaaacatgacaattgggattgataaaattagttttttttgtgccccccttattatattgatatgacggcactggctgaagc
cagaaatgtagaccctggaaaatttcatattggtattgggcaagaccaaatggcggtgaacccaatcagccaagatattgtgacattt
gcagccaatgccgcagaagcgatcttgaccaaagaagataaagaggccattgatatggtgattgtcgggactgagtccagtatcg
atgagtcaaaagcggccgcagttgtcttacatcgtttaatggggattcaacctttcgctcgctctttcgaaatcaaggaagcttgttacgg
agcaacagcaggcttacagttagctaagaatcacgtagccttacatccagataaaaaagtcttggtcgtagcggcagatattgcaaa
atatggcttaaatctggcggtgagcctacacaaggagctggggcggttgcaatgttagttgctagtgaaccgcgcatttggctttaaa
agaggataatgtgatgctgacgcaagatatctatgactttggcgtccaacaggccaccegtatcctatgtcgatgtcctttgtcaaa
cgaaacctacatccaatctttttgcccaagtctgggatgaacataaaaaacgaaccggtcttgattttgcagattatgatgcttagcgttc
catattccttacacaaaaatgggcaaaaaagcccttattagcaaaaatctccgaccaaactgaagcagaacaggaacgaattttagc
ccgttatgaagaaagtatcgtctatagtcgtcgcgtaggaaacttgtatacgggttcacttatctgggactcatttccctttagaaaatgc
aacgactttaaccgcaggcaatcaaattggtttattcagttatggttctggtgctgtcgctgaattttcactggtgaattag

Figure 92B tagctggttatcaaaatcatttacaaaaagaaactcatttagcactgctggataatcggacagaactttctatcgctgaatatg
aagccatgtttgcagaaactttagacacagacattgatcaaacgttagaagatgaattaaaatatagtatttctgctattaataa
taccgttcgttcttatcgaaactaagagatctgcagctggtaccatatgggaattcgaagcttgggcccgaacaaaaactcat
ctcagaagaggatctgaatagcgccgtcgaccatcatcatcatcattgagtttaaacggtctccagcttggctgttttggc
ggatgagagaagattttcagcctgatacagattaaatcagaacgcagaagcggtctgataaaacagaatttgcctggcgg
cagtagcgcggtggtcccacctgaccccatgccgaactcagaagtgaaacgccgtagcgccgatggtagtgtggggtctc
cccatgcgagagtagggaactgccaggcatcaaataaaacgaaaggctcagtcgaaagactgggcctttcgttttatctgtt
gtttgtcggtgaacgctctcctgagtaggacaaatccgccgggagcggatttgaacgttgcgaagcaacggcccggaggg
tggcgggcaggacgcccgccataaactgccaggcatcaaattaagcagaaggccatcctgacggatggccttttttgcgttt
ctacaaactcttttgtttattttctaaatacattcaaatatgtatccgctcatgagacaataaccctgataaatgcttcaataatatt
gaaaaaggaagagtatgagtattcaacatttccgtgtcgcccttattccctttttgcggcattttgccttcctgtttttgctcaccca
gaaacgctggtgaaagtaaaagatgctgaagatcagttgggtgcacgagtgggttacatcgaactggatctcaacagcgg
taagatccttgagagttttcgccccgaagaacgttttccaatgatgagcacttttaaagttctgctatgtggcgcggtattatccc
gtgttgacgccgggcaagagcaactcggtcgccgcatacactattctcagaatgacttggttgagtactcaccagtcacaga
aaagcatcttacggatggcatgacagtaagagaattatgcagtgctgccataaccatgagtgataacactgcggccaactt
actctgacaacgatcggaggaccgaaggagctaaccgcttttttgcacaacatggggatcatgtaactcgccttgatcgtt
gggaaccggagctgaatgaagccataccaaacgacgagcgtgacaccacgatgcctgtagcaatggcaacaacgttg
cgcaaactattaactggcgaactacttactctagcttcccggcaacaattaatagactggatggaggcggataaagttgcag
gaccacttctgcgctcggcccttccggctggctggtttattgctgataaatctggagccggtgagcgtgggtctcgcggtatcat
tgcagcactggggccagatggtaagccctcccgtatcgtagttatctacacgacggggagtcaggcaactatggatgaac
gaaatagacagatcgctgagataggtgcctcactgattaagcattggtaactgtcagaccaagtttactcatatatactttaga
ttgatttaaaacttcattttttaatttaaaaggatctaggtgaagatcctttttgataatctcatgaccaaaatcccttaacgtgagttt
cgttccactgagcgtcagaccccgtagaaaagatcaaaggatcttcttgagatcctttttttctgcgcgtaatctgctgcttgcaa
acaaaaaaaccaccgctaccagcggtggtttgtttgccggatcaagagctaccaactctttttccgaaggtaactggcttcag
cagagcgcagataccaaatactgtccttctagtgtagccgtagttaggccaccacttcaagaactctgtagcaccgcctaca
tacctcgctctgctaatcctgttaccagtggctgctgccagtggcgataagtcgtgtcttaccgggttggactcaagacgatagt
taccggataaggcgcagcggtcgggctgaacggggggttcgtgcacacagcccagcttggagcgaacgacctacaccg
aactgagatacctacagcgtgagctatgagaaagcgccacgcttcccgaagggagaaaggcggacaggtatccggtaa
gcggcagggtcggaacaggagagcgcacgagggagcttccaggggggaaacgcctggtatctttatagtcctgtcgggttt
cgccacctctgacttgagcgtcgatttttgtgatgctcgtcaggggggcggagcctatggaaaaacgccagcaacgcggcc
tttttacggttcctggccttttgctggccttttgctcacatgttctttcctgcgttatcccctgattctgtggataaccgtattaccgccttt
gagtgagctgataccgctcgccgcagccgaacgaccgagcgcagcgagtcagtgagcgaggaagcggaagagcgcc
tgatgcggtattttctccttacgcatctgtgcggtatttcacaccgcatatggtgcactctcagtacaatctgctctgatgccgcat
agttaagccagtatacactccgctatcgctacgtgactgggtcatggctgcgccccgacacccgccaacacccgctgacg
cgccctgacgggcttgtctgctcccggcatccgcttacagacaagctgtgaccgtctccgggagctgcatgtgtcagaggttt
tcaccgtcatcaccgaaacgcgcgaggcagcagatcaattcgcgcgcgaaggcgaagcggcatgcatttacgttgacac
catcgaatggtgcaaaacctttcgcggtatggcatgatagcgcccggaagagagtcaattcagggtggtgaatgtgaaac
cagtaacgttatacgatgtcgcagagtatgccggtgtctcttatcagaccgtttcccgcgtggtgaaccaggccagccacgttt
ctgcgaaaacgcgggaaaaagtggaagcggcgatggcggagctgaattacattcccaaccgcgtggcacaacaactg
gcgggcaaacagtcgttgctgattggcgttgccacctccagtctggccctgcacgcgccgtcgcaaattgtcgcggcgatta
aatctcgcgccgatcaactgggtgccagcgtggtggtgtcgatggtagaacgaagcggcgtcgaagcctgtaaagcggc
ggtgcacaatcttctcgcgcaacgcgtcagtgggctgatcattaactatccgctggatgaccaggatgccattgctgtggaa
gctgcctgcactaatgttccggcgttatttcttgatgtctctgaccagacacccatcaacagtattatttctcccatgaagacggt
acgcgactgggcgtggagcatctggtcgcattgggtcaccagcaaatcgcgctgttagcgggcccattaagttctgtctcgg
cgcgtctgcgtctggctggctggcataaatatctcactcgcaatcaaattcagccgatagcggaacgggaaggcgactgg
agtgccatgtccggttttcaacaaaccatgcaaatgctgaatgagggcatcg

Figure 92C ttcccactgcgatgctggttgccaacgatcagatggcgctgggcgcaatgcgcgccattaccgagtccgggct
gcgcgttggtgcggatatctcggtagtgggatacgacgataccgaagacagctcatgttatatcccgccgtca
accaccatcaaacaggattttcgcctgctggggcaaaccagcgtggaccgcttgctgcaactctctcagggc
caggcggtgaagggcaatcagctgttgcccgtctcactggtgaaaagaaaaaccaccctggcgcccaatac
gcaaaccgcctctccccgcgcgttggccgattcattaatgcagctggcacgacaggtttcccgactggaaag
cgggcagtgagcgcaacgcaattaatgtgagttagcgcgaattgatctg (SEQ ID NO:23)

Figure 103A cccgtcttactgtcgggaattcgcgttggccgattcattaatgcagattctgaaatgagctgttgacaattaatcatccggctcgtata
atgtgtggaattgtgagcggataacaatttcacacaggaaacagcgccgctgagaaaaagcgaagcggcactgctctttaaca
atttatcagacaatctgtgtgggcactcgaccggaattatcgattaactttattattaaaaattaaagaggtatatattaatgtatcgatt
aaataaggaggaataaaccatggatccgagctcaggaggtaaaaaaacatgaaaacagtagttattattgatgcattacgaac
accaattggaaaatataaaggcagcttaagtcaagtaagtgccgtagacttaggaacacatgttacaacacaacttttaaaaag
acattccactatttctgaagaaattgatcaagtaatctttggaaatgttttacaagctggaaatggccaaaatccgcacgacaaat
agcaataaacagcggtttgtctcatgaaattcccgcaatgacggttaatgaggtctgcggatcaggaatgaaggccgttatttgg
cgaaacaattgattcaattaggagaagcggaagttttaattgctggcgggattgagaatatgtcccaagcacctaaattacaacgt
tttaattacgaaacagaaagctacgatgcgccttttctagtatgatgtatgatggattaacggatgcctttagtggtcaggcaatgg
gcttaactgctgaaaatgtggccgaaaagtatcatgtaactagagaagagcaagatcaattttctgtacattcacaattaaaagca
gctcaagcacaagcagaagggatattcgctgacgaaatagccccattagaagtatcaggaacgcttgtggagaaagatgaag
ggattcgccctaattcgagcgttgagaagctaggaacgcttaaaacagttttaaagaagacggtactgtaacagcagggaatg
catcaaccattaatgatggggcttctgctttgattattgcttcacaagaatatgccgaagcacacggtcttccttatttagctattattcg
agacagtgtggaagtcggtattgatccagcctatatgggaatttcgccgattaaagccattcaaaaactgttagcgcgcaatcaa
cttactacggaagaaattgatctgtatgaaatcaacgaagcatttgcagcaacttcaatcgtggtccaaagagaactggctttacc
agaggaaaaggtcaacattatggtggcggtatttcattaggtcatgcgattggtgccacaggtgctcgtttattaacgagtttaagtt
atcaattaaatcaaaaagaaaagaaatatggagtggcttctttatgtatcggcggtggcttaggactcgctatgctactagagaga
cctcagcaaaaaaaaacagccgattttatcaaatgagtcctgaggaacgcctggcttctcttcttaatgaaggccagatttctgct
gatacaaaaaaagaatttgaaaatacggctttatcttcgcagattgccaatcatatgattgaaaatcaaatcagtgaaacagaag
tgccgatgggcgttggcttacatttaacagtggacgaaactgattatttggtaccaatggcgacagaagagccctcagttattgcg
gctttgagtaatggtgcaaaaatagcacaaggatttaaaacagtgaatcaacaacgcttaatgcgtggacaaatcgttttttacga
tgttgcagatcccgagtcattgattgataaactacaagtaagagaagcggaagttttcaacaagcagagttaagttatccatctat
cgttaaacggggcggcggcttaagagatttgcaatatcgtacttttgatgaatcatttgtatctgtcgactttagtagatgttaaggat
gcaatggggcaaatatcgttaacgctatgttggaaggtgtggccgagttgttccgtgaatggttgcggagcaaaagatttattc
agtattttaagtaattatgccacggagtcggttgttacgatgaaaacggctattccagtttcacgtttaagtaaggggagcaatggcc
gggaaattgctgaaaaaattgttttagcttcacgctatgcttcattagatcctatcgggcagtcacgcataacaaaggaatcatga
atggcattgaagctgtagttttagctacaggaaatgatacacgcgctgttagcgcttcttgtcatgcttttgcggtgaaggaaggtcg
ctaccaaggcttgactagttggacgctggatggcgaacaactaattggtgaaatttcagttccgcttgctttagccacggttggcgg
tgccacaaaagtcttacctaaatctcaagcagctgctgatttgttagcagtgacggatgcaaaagaactaagtcgagtagtagcg
gctgttggtttggcacaaaatttagcggcgttacgggccttagtctctgaaggaattcaaaaaggacacatggctctacaagcac
gttctttagcgatgacggtcggagctactggtaaagaagttgaggcagtcgctcaacaattaaaacgtcaaaaaacgatgaacc
aagaccgagccatggctatttaaatgatttaagaaaacaataaaggaggtaaaaaaacatgacaattgggattgataaaatta
gtttttttgtgccccttattatattgatatgacggcactggctgaagccagaaatgtagaccctggaaaatttcatattggtattgggc
aagaccaaatggcggtgaacccaatcagccaagatattgtgacatttgcagccaatgccgcagaagcgatcttgaccaaaga
agataaagaggccattgatatggtgattgtcgggactgagtccagtatcgatgagtcaaaagcggccgcagttgtcttacatcgttt
aatggggattcaacctttcgctcgctctttcgaaatcaaggaagcttgttacggagcaacagcaggcttacagttagctaagaatc
acgtagccttacatccagataaaaaagtcttggtcgtagcggcagatattgcaaaatatggcttaaattctggcggtgagcctaca
caaggagctggggcggttgcaatgttagttgctagtgaaccgcgcattttggctttaaaagaggataatgtgatgctgacgcaag
atatctatgacttttggcgtccaacaggccacccgtatcctatgtcgatggtcctttgtcaaacgaaacctacatccaatcttttgcc
caagtctgggatgaacataaaaaacgaaccggtcttgattttgcagattatgatgctttagcgttccatattccttacacaaaaatgg
gcaaaaaagccttattagcaaaaatctccgaccaaactgaagcagaacaggaacgaattttagcccgttatgaagaaagtatc
gtctatagtcgtcgcgtaggaaacttgtatacgggttcactttatctgggactcatttcccttttagaaaatgcaacgactttaaccgca
ggcaatcaaatggttattcagttatggttctggtgctgtcgctgaattttcactggtgaattagtagctggttatcaaaatcatttaca
aaaagaaactcatttagcactgctggataatcggacagaacttctatcgctgaatatgaagccatgtttgcagaaactttagaca
cagacattgatcaaacgtta

Figure 103B gaagatgaattaaaatatagtatttctgctattaataataccgttcgttcttatcgaaactaaagatctgcatcctgcattcgcccta
ggaggtaaaaaaacatgtgtgcgacctcttctcaatttactcagattaccgagcataattcccgtcgttccgcaaactatcagcc
aaacctgtggaatttcgaattcctgcaatccctggagaacgacctgaaagtggaaaagctggaggagaaagcgaccaaact
ggaggaagaagttcgctgcatgatcaaccgtgtagacacccagccgctgtccctgctggagctgatcgacgatgtgcagcgc
ctgggtctgacctacaaatttgaaaaagacatcattaaagccctggaaaacatcgtactgctggacgaaaacaaaaagaac
aaatctgacctgcacgcaaccgctctgtctttccgtctgctgcgtcagcacggtttcgaggtttctcaggatgtttttgagcgtttcaa
ggataaagaaggtggtttcagcggtgaactgaaaggtgacgtccaaggcctgctgagcctgtatgaagcgtcttacctgggttt
cgagggtgagaacctgctggaggaggcgcgtaccttccatcacccacctgaagaacaacctgaaagaaggcattaatac
caaggttgcagaacaagtgagccacgccctggaactgccatatcaccagcgtctgcaccgtctggaggcacgttggttcctg
gataaatacgaaccgaaagaaccgcatcaccagctgctgctggagctggcgaagctggattttaacatggtacagaccctgc
accagaaagagctgcaagatctgtcccgctggtggaccgagatgggcctggctagcaaactggattttgtacgcgaccgcct
gatggaagtttatttctgggcactgggtatggcgccagaccgcagtttggtgaatgtcgcaaagctgttactaaaatgtttggtct
ggtgacgatcatcgatgacgtgtatgacgtttatggcactctggacgaactgcaactgttcaccgatgctgtagagcgctggga
cgttaacgctattaacaccctgccggactatatgaaactgtgtttcctggcactgtacaacaccgttaacgacacgtcctattctat
tctgaaagagaaaggtcataacaacctgtcctatctgacgaaaagctggcgtgaactgtgcaaagcctttctgcaagaggcg
aaatggtccaacaacaaaattatcccggctttctccaagtacctggaaaacgccagcgtttcctcctccggtgtagcgctgctgg
cgccgtcttacttttccgtatgccagcagcaggaagacatctccgaccacgcgctgcgttccctgaccgacttccatggtctggt
gcgttctagctgcgttatcttccgcctgtgcaacgatctggccacctctgcggcggagctggaacgtggcgagactaccaattct
atcattagctacatgcacgaaaacgatggtaccagcgaggaacaggcccgcgaagaactgcgtaaactgatcgacgccga
atggaaaagatgaatcgtgaacgcgttagcgactccaccctgctgcctaaagcgttcatggaaatcgcagttaacatggca
cgtgtttcccactgcacctaccagtatggcgatggtctgggtcgcccagactacgcgactgaaaaccgcatcaaactgctgctg
attgacccttcccgattaaccagctgatgtatgtctaactgcagctggtaccatatgggaattcgaagcttgggcccgaacaaa
aactcatctcagaagaggatctgaatagcgccgtcgaccatcatcatcatcatcattgagtttaaacggtctccagcttggctgttt
tggcggatgagagaagattttcagcctgatacagattaaatcagaacgcagaagcggtctgataaaacagaatttgcctggc
ggcagtagcgcggtggtcccacctgacccatgccgaactcagaagtgaaacgccgtagcgccgatggtagtgtggggtct
ccccatgcgagagtagggaactgccaggcatcaaataaaacgaaaggctcagtcgaaagactgggcctttcgttttatctgtt
gtttgtcggtgaacgctctcctgagtaggacaaatccgccgggagcggatttgaacgttgcgaagcaacggcccggagggtg
gcgggcaggacgcccgccataaactgccaggcatcaaattaagcagaaggccatcctgacggatggcctttttgcgtttctac
aaactcttttgtttatttttctaaatacattcaaatatgtatccgctcatgagacaataaccctgataaatgcttcaataatctggcgta
atagcgaagaggcccgcaccgatcgcccttcccaacagttgcgcagcctgaatggcgaatggcgcctgatgcggtattttctc
cttacgcatctgtgcggtatttcacaccgcatatggtgcactctcagtacaatctgctctgatgccgcatagttaagccagccccg
acacccgccaacacccgctgacgagcttagtaaagccctcgctagattttaatgcggatgttgcgattacttcgccaactattgc
gataacaagaaaaagccagcctttcatgatatatctcccaatttgtgtagggcttattatgcacgcttaaaaataataaaagcag
acttgacctgatagtttggctgtgagcaattatgtgcttagtgcatctaacgcttgagttaagccgcgccgcgaagcggcgtcgg
cttgaacgaattgttagacattatttgccgactacccttggtgatctcgcctttcacgtagtgggacaaattcttccaactgatctgcgcg
cgaggccaagcgatcttcttcttgtccaagataagcctgtctagcttcaagtatgacgggctgatactgggccggcaggcgctc
cattgcccagtcggcagcgacatccttcggcgcgattttgccggttactgcgctgtaccaaatgcgggacaacgtaagcactac
atttcgctcatcgccagcccagtcgggcggcgagttccatagcgttaaggtttcatttagcgcctcaaatagatcctgttcaggaa
ccggatcaaagagttcctccgccgctggacctaccaaggcaacgctatgttctcttgcttttgtcagcaagatagccagatcaat
gtcgatcgtggctggctcgaagatacctgcaagaatgtcattgcgctgccattctccaaattgcagttcgcgcttagctggataac
gccacggaatgatgtcgtcgtgcacaacaatggtgacttctacagcgcggagaatctcgctctctccaggggaagccgaagtt
tccaaaaggtcgttgatcaaagctcgccgcgttgtttcatcaagccttacggtcaccgtaaccagcaaatcaatatcactgtgtg
gcttcaggccgccatccactgcggagccgtacaaatgtacggccagcaacgtcggttcgagatggcgctcgatgacgccaa
ctacctctgatagttgagtcgatacttcggcgatcaccgcttccctcatgatgtttaactttgttttagggcgactgccctgctgcgta
acatcgttgctgctccataacatcaaacatcgacccacggcgtaacgcgcttgctgcttggat

Figure 103C gcccgaggcatagactgtaccccaaaaaaacagtcataacaagccatgaaaaccgccactgcgccgttacc
accgctgcgttcggtcaaggttctggaccagttgcgtgagcgcatacgctacttgcattacagcttacgaaccga
acaggcttatgtccactgggttcgtgccttcatccgtttccacggtgtgcgtcacccggcaaccttgggcagcagc
gaagtcgaggcatttctgtcctggctggcgaacgagcgcaaggtttcggtctccacgcatcgtcaggcattggc
ggccttgctgttcttctacggcaaggtgctgtgcacggatctgccctggcttcaggagatcggaagacctcggcc
gtcgcggcgcttgccggtggtgctgaccccggatgaagtggttcgcatcctcggttttctggaaggcgagcatcg
tttgttcgcccagcttctgtatggaacgggcatgcggatcagtgagggtttgcaactgcgggtcaaggatctggatt
tcgatcacggcacgatcatcgtgcgggagggcaagggctccaaggatcgggccttgatgttacccgagagctt
ggcacccagcctgcgcgagcaggggaattaattcccacgggttttgctgcccgcaaacgggctgttctggtgttg
ctagtttgttatcagaatcgcagatccggcttcagccggtttgccggctgaaagcgctatttcttccagaattgccat
gatttttttccccacgggaggcgtcactggctcccgtgttgtcggcagctttgattcgataagcagcatcgcctgtttc
aggctgtctatgtgtgactgttgagctgtaacaagtgtctcaggtgttcaatttcatgttctagttgctttgttttactggtt
tcacctgttctattaggtgttacatgctgttcatctgttacattgtcgatctgttcatggtgaacagcttgaatgcacca
aaaactcgtaaaagctctgatgtatctatctttttttacaccgttttcatctgtgcatatggacagttttcccttgatatgta
acggtgaacagttgttctactttgtttgttagtcttgatgcttcactgatagatacaagagccataagaacctcagat
ccttccgtatttagccagtatgttctctagtgtggttcgttgttttttgcgtgagccatgagaacgaaccattgagatcat
acttactttgcatgtcactcaaaaatttttgcctcaaaactggtgagctgaatttttttgcagttaaagcatcgtgtagtgtt
tttcttagtccgttatgtaggtaggaatctgatgtaatggttgttggtattttgtcaccattcatttttatctggttgttctcaa
gttcggttacgagatccatttgtctatctagttcaacttggaaaatcaacgtatcagtcgggcggcctcgcttatcaa
ccaccaatttcatatttgctgtaagtgtttaaatcttacttattggtttcaaaacccattggttaagcctttaaactcatg
gtagttattttcaagcattaacatgaacttaaattcatcaaggctaatctctatatttgcctgtgagttttctttgtgttag
ttctttaataaccactcataaatcctcatagagtatttgtttcaaaagacttaacatgttccagattatattttatgaatt
ttttttaactggaaaagataaggcaatatctcttcactaaaaactaattctaattttcgcttgagaacttggcatagttt
gtccactggaaaatctcaaagcctttaaccaaaggattcctgatttccacagttctcgtcatcagctctctggttgctt
tagctaatacaccataagcatttttccctactgatgttcatcatctgagcgtattggttataagtgaacgataccgtcc
gttctttccttgtaggggttttcaatcgtggggttgagtagtgccacacagcataaaattagcttggtttcatgctccgtta
agtcatagcgactaatcgctagttcatttgctttgaaaacaactaattcagacatacatctcaattggtctaggtgatt
ttaatcactataccaattgagatgggctagtcaatgataattactagtccttttcctttgagttgtgggtatctgtaaatt
ctgctagacctttgctggaaaacttgtaaattctgctagaccctctgtaaattccgctagacctttgtgtgtttttttgttt
atattcaagtggttataatttatagaataaagaaagaataaaaaaagataaaagaatagatcccagccctgtg
tataactcactacttagtcagttccgcagtattacaaaaggatgtcgcaaacgctgtttgctcctctacaaaacag
accttaaaaccctaaaggcttaagtagcaccctcgcaagctcgggcaaatcgctgaatattcctttgtctccgac
catcaggcacctgagtcgctgtctttttcgtgacattcagttcgctgcgctcacggctctggcagtgaatgggggta
aatggcactacaggcgccttttatggattcatgcaaggaaactacccataatacaagaaaagcccgtcacggg
cttctcagggcgtttatgcgggtctgctatgtggtgctatctgacttttttgctgttcagcagttcctgccctctgatttc
cagtctgaccacttcggattatcccgtgacaggtcattcagactggctaatgcacccagtaaggcagcggtatca
tcaacaggctta (SEQ ID NO:24)

MCM330 - FRT-cm-FRT-gi1.2-KKDyI at attTn7

Figure 108A 1-
caagaaaaatgccccgcttacgcagggcatccatttattactcaaccgtaaccgattttgccaggttacgcggctggtcaacg
tcggtgcctttgatcagcgcgacatggtaagccagcagctgcagcggaacggtgtagaagatcggtgcaatcacctcttcca
catgcggcatctcgatgatgtgcatgttatcgctacttacaaaacccgcatcctgatcggcgaagacatacaactgaccgcc
acgcgcgcgaacttcttcaatgttggatttcagttttccagcaattcgttgttcggtgcaacaacaataaccggcatatcggcat
caattagcgccagcggaccgtgtttcagttcgccagcagcgtaggcttcagcgtgaatgtaagagatctctttcaacttcaatg
cgccttccagcgcgattgggtactgatcgccacggcccaggaacagcgcgtgatgtttgtcagagaaatcttctgccagcgc
ttcaatgcgtttgtcctgagacagcatctgctcaatacggctcggcagcgcctgcagaccatgcacgatgtcatgttcaatgga
ggcatccagacctttcaggcgagacagcttcgccaccagcatcaacagcacagttaactgagtggtgaatgctttagtggat
gccacgccgatttctgtacccgcgttggtcattagcgccagatcggattcgcgcaccagagaagaacccggaacgttacag
attgccagtgaaccaaggtaacccagctctttcgacagacgcaggccagccagggtatccgcggtttcgccagactgtgac
acgatcgcccttcccaacagttgcgcagcctatacgtacggcagtttaaggtttacacctataaaagagagagccgttatcgt
ctgtttgtggatgtacagagtgatattattgacacgccggggcgacggatggtgatcccctggccagtgcacgtctgctgtca
gataaagtctcccgtgaactttaccggtggtgcatatcggggatgaaagctggcgcatgatgaccaccgatatggccagtg
tgccggtctccgttatcggggaagaagtggctgatctcagccaccgcgaaaatgacatcaaaaacgccattaacctgatgtt
ctggggaatataaatgtcaggcatgagattatcaaaaaggatcttcacctagatccttttcacgtagaaagccagtccgcaga
aacggtgctgaccccggatgaatgtcagctactgggctatctggacaagggaaaacgcaagcgcaaagagaaagcagg
tagcttgcagtgggcttacatggcgatagctagactgggcggtttatggacagcaagcgaaccggaattgccagctgggc
gccctctggtaaggttgggaagccctgcaaagtaaactggatggcttctcgccgcaaggatctgatggcgcaggggatc
aagctctgatcaagagacaggatgaggatcgtttcgcatgattgaacaagatggattgcacgcaggttctccggccgcttgg
gtggagaggctattcggctatgactgggcacaacagacaatcggctgctctgatgccgccgtgttccggctgtcagcgcagg
ggcgcccggttcttttttgtcaagaccgacctgtccggtgccctgaatgaactgcaagacgaggcagcgcggctatcgtggct
ggccacgacgggcgttccttgcgcagctgtgctcgacgttgtcactgaagcggggaagggactggctgctattgggcgaagt
gccggggcaggatctcctgtcatctcaccttgctcctgccgagaaagtatccatcatggctgatgcaatgcggcggctgcata
cgcttgatccggctacctgcccattcgaccaccaagcgaaacatcgcatcgagcgagcacgtactcggatggaagccggt
cttgtcgatcaggatgatctggacgaagagcatcaggggctcgcgccagccgaactgttcgccaggctcaaggcgagcat
gcccgacggcgaggatctcgtcgtgacccatggcgatgcctgcttgccgaatatcatggtggaaaatggccgcttttctggatt
catcgactgtggccgctgggtgtggcggaccgctatcaggacatagcgttggctacccgtgatattgctgaagagcttggc
ggcgaatgggctgaccgcttcctcgtgctttacggtatcgccgctcccgattcgcagcgcatcgccttctatcgccttcttgacg
agttcttctgaattattaacgcttacaatttcctgatgcggtattttctccttacgcatctgtgcggtatttcacaccgcatacaggtg
gcacttttcggggaaatgtgcgcggaaccccctatttgtttatttttctaaatacattcaaatatgtatccgctcatgagacaataac
cctgataaatgcttcaataatagcacgtgaggagggccaccatggccaagttgaccagtgccgttccggtgctcaccgcgc
gcgacgtcgccggagcggtcgagttctggaccgaccggctcgggttctcccctagtaacggccgccagtgtgctggaattc
aggcagttcaacctgttgatagtacgtactaagctctcatgtttcacgtactaagctctcatgtttaacgtactaagctctcatgttt
aacgaactaaaccctcatggctaacgtactaagctctcatggctaacgtactaagctctcatgtttcacgtactaagctctcatg
tttgaacaataaaattaatataaatcagcaacttaaatagcctctaaggttttaagttttataagaaaaaaaagaatatataagg
cttttaaagcttttaaggtttaacggttgtggacaacaagccagggatgtaacgcactgagaagcccttagagcctctcaaag
caattttcagtgacacaggaacacttaacggctgacagcctgaattctgcagatatctgttttccactcttcgttcactttcgcca
ggtagctggtgaagacgaaggaagtcccggagccatctgcgcggcgtactacagcaatgtttgtgaaggcagtttcagac
ccggattcagtttggcgatggcttcatcatcccacttcttgatttgcccaggtagatgtcgccgagggtttaccatccagcacc
agttcgccagacttcagccctggaatgttaaccgccagcaccacgcgccaatcacggtcgggaactggaacagaccttc
ctgagccagttttcgtcagacagcggcgcgtcagaggcaccaaaatcaacggtattagcgataatctgttttacgccaccgg
aagaaccgatacccctggtagttaactttattaccggtttctttctggtaagtgtcagcccatttggcatacaccggcgcagggaa
ggttgcacctgcacctgtcaggcttgcttctgcaaacacagagaaagcactcatcgataaggtcgcggcgacaacagttgc
gacggtggtacgcataactttcataatgtctcctgggaggattcataaagcattgtttgttggctacgagaagcaaaataggac
aaacaggtgacagtatatgtaaggaatatgacagttttatgacagagagataaagtcttcagtctgatttaaataagcgttgat
attcagtcaattacaaacattaataacg

Figure 108B aagagatgacagaaaaattttcattctgtgacagagaaaaagtagccgaagatgacggtttgtcacatggagttggcaggatg
tttgattaaaagcaattaaccctcactaaagggcggccgcgaagttcctattctctagaaagtataggaacttcattctaccgggt
aggggaggcgcttttcccaaggcagtctggagcatgcgcttagcagccccgctgggcacttggcgctacacaagtggcctct
ggcctcgcacacattccacatccaccggtaggcgccaaccggctccgttcttggtggccccttcgcgccaccttccactcctcc
cctagtcaggaagttccccccgccccgcagctcgcgtcgtgcaggacgtgacaaatggaagtagcacgtctcactagtctc
gtgcagatggacagcaccgctgagcaatggaagcgggtaggcctttggggcagcggccaatagcagctttgctccttcgcttt
ctgggctcagaggctgggaaggggtggtccggggcgggctcaggggcgggctcaggggcggggcgggcgccgaa
ggtcctccggaggcccggcattctgcacgcttcaaaagcgcacgtctgccgcgctgttctcctcttcctcatctccgggcctttcg
acctgcagcagcacgtgttgacaattaatcatcggcatagtatatcggcatagtataatacgacaaggtgaggaactaaacca
tggagaaaaaaatcactggatataccaccgttgatatatcccaatggcatcgtaaagaacattttgaggcatttcagtcagttgct
caatgtacctataaccagaccgttcagctggatattacggcctttttaaagaccgtaaagaaaaataagcacaagtttatccgg
cctttattcacattcttgcccgcctgatgaatgctcatccggaattccgtatggcaatgaaagacggtgagctggtgatatgggat
agtgttcacccttgttacaccgttttccatgagcaaactgaaacgttttcatcgctctggagtgaataccacgacgatttccggcag
tttctacacatatattcgcaagatgtggcgtgttacggtgaaaacctggcctatttccctaaagggtttattgagaatatgttttcgtct
cagccaatccctgggtgagtttcaccagttttgatttaaacgtggccaatatggacaacttcttcgcccccgttttcaccatgggca
aatattatacgcaaggcgacaaggtgctgatgccgctggcgattcaggttcatcatgccgtttgtgatggcttccatgtcggcag
aatgcttaatgaattacaacagtactgcgatgagtggcagggcggggcgtaagcgggactctggggttcgaataaagaccg
accaagcgacgtctgagagctccctggcgaattcggtaccaataaaagagctttattttcatgatctgtgtgttggttttgtgtgcg
gcgcggaagttcctattctctagaaagtataggaacttcctcgagcccatagtgagtcgtattagcccttgacgatgccacatcc
tgagcaaataattcaaccactaattgtgagcggataacacaaggaggaaacagctatgtcattaccgttcttaacttctgcacc
gggaaaggttattattttttggtgaacactctgctgtgtacaacaagcctgccgtcgctgctagtgtgtctgcgttgagaacctacct
gctaataagcgagtcatctgcaccagatactattgaattggacttccggacattagctttaatcataagtggtccatcaatgattt
caatgccatcaccgaggatcaagtaaactcccaaaaattggccaaggctcaacaagccaccgatggcttgtctcaggaact
cgttagtcttttggatccgttgttagctcaactatccgaatccttccactaccatgcagcgtttgtttcctgtatatgtttgtttgcctatgc
ccccatgccaagaatattaagttttctttaaagtctactttacccatcggtgctgggttgggctcaagcgcctctatttctgtatcactg
gccttagctatggcctacttggggggttaataggatctaatgacttggaaaagctgtcagaaaacgataagcatatagtgaat
caatgggccttcataggtgaaaagtgtattcacggtaccccttcaggaatagataacgctgtggccacttatggtaatgccctgc
tatttgaaaaagactcacataatggaacaataaacacaaacaattttaagttcttagatgatttcccagccattccaatgatccta
acctatactagaattccaaggtctacaaaagatcttgttgctcgcgttcgtgtgttggtcaccgagaaatttcctgaagttatgaag
ccaattctagatgccatgggtgaatgtgccctacaaggcttagagatcatgactaagttaagtaaatgtaaaggcaccgatgac
gaggctgtagaaactaataatgaactgtatgaacaactattggaattgataagaataaatcatggactgcttgtctcaatcggtgt
ttctcatcctggattagaacttattaaaaatctgagcgatgatttgagaattggctccacaaaacttaccggtgctggtggcggcg
gttgctctttgactttgttacgaagagacattactcaagagcaaattgacagcttcaaaaagaaattgcaagatgatttagttacg
agacatttgaaacagacttgggtgggactggctgctgtttgttaagcgcaaaaaatttgaataaagatcttaaaatcaaatccct
agtattccaattatttgaaaataaaactaccacaaagcaacaaattgacgatctattattgccaggaaacacgaattaccatgg
acttcataagctaatttgcgataggcctgcacccttaaggaggaaaaaaacatgtcagagttgagagccttcagtgccccagg
gaaagcgttactagctggtggatatttagtttagatacaaaatatgaagcatttgtagtcggattatcggcaagaatgcatgctgt
agcccatccttacggttcattgcaagggtctgataagtttgaagtgcgtgtgaaaagtaaacaatttaaagatggggagtggctg
taccatataagtcctaaaagtggcttcattcctgtttcgataggcggatctaagaacccttcattgaaaaagttatcgctaacgtat
ttagctactttaaacctaacatggacgactactgcaatagaaacttgttcgttattgatattttctctgatgatgcctaccattctcagg
aggatagcgttaccgaacatcgtggcaacagaagattgagttttcattcgcacagaattgaagaagttcccaaaacagggctg
ggctcctcggcaggtttagtcacagttttaactacagctttggcctccttttttgtatcggacctggaaaataatgtagacaaatata
gagaagttattcataatttagcacaagttgctcattgtcaagctcagggtaaaattggaagcgggtttgatgtagcggcggcagc
atatggatctatcagatatagaagattcccacccgcattaatctctaatttgccagatattggaagtgctacttacggcagtaaact
ggcgcatttggttgatgaagaagactggaatattacgattaaaagtaaccatttaccttc

Figure 108C gggattaactttatggatgggcgatattaagaatggttcagaaacagtaaaactggtccagaaggtaaaaaatt
ggtatgattcgcatatgccagaaagcttgaaaatatatacagaactcgatcatgcaaattctagatttatggatgg
actatctaaactagatcgcttacacgagactcatgacgattacagcgatcagatatttgagtctcttgagaggaat
gactgtacctgtcaaaagtatcctgaaatcacagaagttagagatgcagttgccacaattagacgttcctttaga
aaaataactaaagaatctggtgccgatatcgaacctcccgtacaaactagcttattggatgattgccagaccta
aaaggagttcttactgcttaatacctggtgctggtggttatgacgccattgcagtgattactaagcaagatgttgat
cttagggctcaaaccgctaatgacaaaagattttctaaggttcaatggctggatgtaactcaggctgactgggt
gttaggaaagaaaaagatccggaaacttatcttgataaataacttaaggtagctgcatgcagaattcgcccttaa
ggaggaaaaaaaaatgaccgtttacacagcatccgttaccgcacccgtcaacatcgcaacccttaagtattgg
gggaaaagggacacgaagttgaatctgcccaccaattcgtccatatcagtgacttatcgcaagatgacctcag
aacgttgacctctgcggctactgcacctgagtttgaacgcgacactttgtggttaaatggagaaccacacagcat
cgacaatgaaagaactcaaaattgtctgcgcgacctacgccaattaagaaaggaaatggaatcgaaggacg
cctcattgcccacattatctcaatggaaactccacattgtctccgaaaataactttcctacagcagctggtttagctt
cctccgctgctggcttgctgcattggtctctgcaattgctaagttataccaattaccacagtcaacttcagaaatatc
tagaatagcaagaaaggggtctggttcagcttgtagatcgttgtttggcggatacgtggcctgggaaatgggaa
aagctgaagatggtcatgattccatggcagtacaaatcgcagacagctctgactggcctcagatgaaagcttgt
gtcctagttgtcagcgatattaaaaaggatgtgagttccactcagggtatgcaattgaccgtggcaacctccgaa
ctatttaaagaaagaattgaacatgtcgtaccaaagagatttgaagtcatgcgtaaagccattgttgaaaaagat
ttcgccacctttgcaaaggaaacaatgatggattccaactctttccatgccacatgtttggactctttccctccaatat
tctacatgaatgacacttccaagcgtatcatcagttggtgccacaccattaatcagttttacggagaaacaatcgtt
gcatacacgtttgatgcaggtccaaatgctgtgttgtactacttagctgaaaatgagtcgaaactctttgcatttatct
ataaaattgtttggctctgttcctggatgggacaagaaatttactactgagcagcttgaggctttcaaccatcaatttg
aatcatctaactttactgcacgtgaattggatcttgagttgcaaaaggatgttgccagagtgattttaactcaagtcg
gttcaggcccacaagaaacaaacgaatctttgattgacgcaaagactggtctaccaaaggaataagatcaatt
cgctgcatcgcccttaggaggtaaaaaaaatgactgccgacaacaatagtatgcccatggtgcagtatcta
gttacgccaaattagtgcaaaaccaaacacctgaagacattttggaagagtttcctgaaattattccattacaaca
aagacctaatacccgatctagtgagacgtcaaatgacgaaagcggagaaacatgttttctggtcatgatgagg
agcaaattaagttaatgaatgaaaattgtattgttttggattgggacgataatgctattggtgccggtaccaagaaa
gtttgtcatttaatggaaaatattgaaaagggtttactacatcgtgcattctccgtctttattttcaatgaacaaggtga
attacttttacaacaaagagccactgaaaaaataacttccctgatctttggactaacacatgctgctctcatccact
atgtattgatgacgaattaggtttgaagggtaagctagacgataagattaagggcgctattactgcggcggtgag
aaaactagatcatgaattaggtattccagaagatgaaactaagacaaggggtaagtttcactttttaaacagaat
ccattacatggcaccaagcaatgaaccatggggtgaacatgaaattgattacatcctatttttataagatcaacgct
aaagaaaacttgactgtcaacccaaacgtcaatgaagttagagacttcaaatgggtttcaccaaatgatttgaa
aactatgtttgctgacccaagttacaagtttacgccttggtttaagattatttgcgagaattacttattcaactggtggg
agcaattagatgacctttctgaagtggaaaatgacaggcaaattcatagaatgctataacaacgcgtctacaaa
taaaaaaggcacgtcagatgacgtgccttttttcttggggcc (SEQ ID NO:25)

Figure 110A 1-
gtgcggccgcaagcttgtcgacggagctcgaattcggatccctgcagttagacatacatcagctggttaatcgggaaagggtca
atcagcagcagtttgatgcggttttcagtcgcgtagtctgggcgacccagaccatcgccatactggtaggtgcagtgggaaaca
cgtgccatgttaactgcgatttccatgaacgctttaggcagcagggtggagtcgctaacgcgttcacgattcatcttttccattcgg
cgtcgatcagtttacgcagttcttcgcgggcctgttcctcgctggtaccatcgttttcgtgcatgtagctaatgatagaattggtagtct
cgccacgttccagctccgccgcagaggtggccagatcgttgcacaggcggaagataacgcagctagaacgcaccagacca
tggaagtcggtcagggaacgcagcgcgtggtcggagatgtcttcctgctgctggcatacggaaaagtaagacggcgccagc
agcgctacaccggaggaggaaacgctggcgttttccaggtacttggagaaagccgggataattttgttgttggaccatttcgcct
cttgcagaaaggctttgcacagttcacgccagcttttcgtcagataggacaggttgttatgacctttctctttcagaatagaatagga
cgtgtcgttaacggtgttgtacagtgccaggaaacacagtttcatatagtccggcagggtgttaatagcgttaacgtcccagcgct
ctacagcatcggtgaacagttgcagttcgtccagagtgccataaacgtcatacacgtcatcgatgatcgtcaccagaccaaac
attttagtaacagctttgcgacattcaccaaactgcgggtctggcgccatacccagtgcccagaaataaacttccatcaggcggt
cgcgtacaaaatccagtttgctagccaggcccatctcggtccaccagcgggacagatcttgcagctctttctggtgcagggtctgt
accatgttaaaatccagcttcgccagctccagcagcagctggtgatgcggttctttcggttcgtatttatccaggaaccaacgtgc
ctccagacggtgcagacgctggtgatatggcagttccagggcgtggctcacttgttctgcaaccttggtattaatgccttcttcagg
ttgttcttcaggtgggtgatggaaaaggtacgcgcctcctccagcaggttctcaccctcgaaacccaggtaagacgcttcataca
ggctcagcaggccttggacgtcacctttcagttcaccgctgaaaccaccttctttatccttgaaacgctcaaaaacatcctgagaa
acctcgaaaccgtgctgacgcagcagacggaaagacagagcggttgcgtgcaggtcagatttgttcttttttgtttcgtccagcag
tacgatgttttccagggctttaatgatgtcttttcaaattgtaggtcagacccaggcgctgcacatcgtcgatcagctccagcagg
gacagcggctgggtgtctacacggttgatcatgcagcgaacttcttcctccagtttggtcgctttctcctccagcttttccactttcagg
tcgttctccaggattgcaggaattcgaaattccacaggtttggctgatagtttgcggaacgacgggaattatgctcggtaatctga
gtaaattgagaagaggtcgcacacatggtatatctccttcttaaagttaaacaaaattatttctagaggggaattgttatccgctcac
aattcccctatagtgagtcgtattaatttcgcgggatcgagatctcgatcctctacgccggacgcatcgtggccggcatcaccggc
gccacaggtgcggttgctggcgcctatatcgccgacatcaccgatggggaagatcgggctcgccacttcgggctcatgagcgc
ttgtttcggcgtgggtatggtggcaggccccgtggccgggggactgttgggcgccatctccttgcatgcaccattccttgcggcgg
cggtgctcaacggcctcaacctactactgggctgcttcctaatgcaggagtcgcataagggagagcgtcgagatcccggaca
ccatcgaatggcgcaaaacctttcgcggtatggcatgatagcgcccggaagagagtcaattcagggtggtgaatgtgaaacc
agtaacgttatacgatgtcgcagagtatgccggtgtctcttatcagaccgtttcccgcgtggtgaaccaggccagccacgtttctg
cgaaaacgcgggaaaagtggaagcggcgatggcggagctgaattacattcccaaccgcgtggcacaacaactggcggg
caaacagtcgttgctgattggcgttgccacctccagtctggccctgcacgcgccgtcgcaaattgtcgcggcgattaaatctcgc
gccgatcaactgggtgccagcgtggtggtgtcgatggtagaacgaagcggcgtcgaagcctgtaaagcggcggtgcacaat
cttctcgcgcaacgcgtcagtgggctgatcattaactatccgctggatgaccaggatgccattgctgtggaagctgcctgcacta
atgttccggcgttatttcttgatgtctctgaccagacacccatcaacagtattatttctcccatgaagacggtacgcgactgggcgt
ggagcatctggtcgcattgggtcaccagcaaatcgcgctgttagcgggcccattaagttctgtctcggcgcgtctgcgtctggctg
gctggcataaatatctcactcgcaatcaaattcagccgatagcggaacgggaaggcgactggagtgccatgtccggttttcaac
aaaccatgcaaatgctgaatgagggcatcgttcccactgcgatgctggttgccaacgatcagatgcgctgggcgcaatgcgc
gccattaccgagtccgggctgcgcgttggtgcggatatctcggtagtgggatacgacgataccgaagacagctcatgttatatcc
cgccgttaaccaccatcaaacaggattttcgcctgctggggcaaaccagcgtggaccgcttgctgcaactctctcagggccag
gcggtgaagggcaatcagctgttgcccgtctcactggtgaaaagaaaaaccaccctggcgcccaatacgcaaaccgcctctc
cccgcgcgttggccgattcattaatgcagctggcacgacaggtttcccgactggaaagcgggcagtgagcgcaacgcaatta
atgtaagttagctcactcattaggcaccgggatctcgaccgatgcccttgagagccttcaacccagtcagctccttccggtgggc
gcggggcatgactatcgtcgccgcacttatgactgtcttctttatcatgcaactcgtaggacaggtgccggcagcgctctgggtca
ttttcggcgaggaccgctttcgctggagcgcgacgatgatcggcctgtcgcttgcggtattcggaatcttcacgccctcgctcaa
gccttcgtcactggtcccgccaccaaacgtttcggcgagaagcaggccattatcgccggcatggcggccccacgggtgcgca
tgatcgtgctcctg

Figure 110B tcgttgaggacccggctaggctggcggggttgccttactggttagcagaatgaatcaccgatacgcgagcgaacgtg
aagcgactgctgctgcaaaacgtctgcgacctgagcaacaacatgaatggtcttcggttccgtgtttcgtaaagtctg
gaaacgcggaagtcagcgccctgcaccattatgttccggatctgcatcgcaggatgctgctggctaccctgtggaac
acctacatctgtattaacgaagcgctggcattgaccctgagtgattttctctggtcccgccgcatccataccgccagttg
tttaccctcacaacgttccagtaaccgggcatgttcatcatcagtaacccgtatcgtgagcatcctctctcgtttcatcggt
atcattaccccatgaacagaaatccccttacacggaggcatcagtgaccaaacaggaaaaaaccgcccttaac
atggcccgctttatcagaagccagacattaacgcttctggagaaactcaacgagctggacgcggatgaacaggca
gacatctgtgaatcgcttcacgaccacgctgatgagctttaccgcagctgcctcgcgcgtttcggtgatgacggtgaaa
acctctgacacatgcagctcccggagacggtcacagcttgtctgtaagcggatgccgggagcagacaagcccgtc
agggcgcgtcagcgggtgttggcgggtgtcggggcgcagccatgacccagtcacgtagcgatagcggagtgtata
ctggcttaactatgcggcatcagagcagattgtactgagagtgcaccatatatgcggtgtgaaataccgcacagatgc
gtaaggagaaaataccgcatcaggcgctcttccgcttcctcgctcactgactcgctgcgctcggtcgttcggctgcggc
gagcggtatcagctcactcaaaggcggtaatacggttatccacagaatcaggggataacgcaggaaagaacatgt
gagcaaaaggccagcaaaaggccaggaaccgtaaaaaggccgcgttgctggcgtttttccataggctccgcccc
ctgacgagcatcacaaaaatcgacgctcaagtcagaggtggcgaaacccgacaggactataaagataccaggc
gtttccccctggaagctccctcgtgcgctctcctgttccgaccctgccgcttaccggatacctgtccgcctttctcccttcgg
gaagcgtggcgctttctcatagctcacgctgtaggtatctcagttcggtgtaggtcgttcgctccaagctgggctgtgtgc
acgaaccccccgttcagcccgaccgctgcgccttatccggtaactatcgtcttgagtccaacccggtaagacacgac
ttatcgccactggcagcagccactggtaacaggattagcagagcgaggtatgtaggcggtgctacagagttcttgaa
gtggtggcctaactacggctacactagaaggacagtatttggtatctgcgctctgctgaagccagttaccttcggaaaa
agagttggtagctcttgatccggcaaacaaaccaccgctggtagcggtggtttttttgtttgcaagcagcagattacgcg
cagaaaaaaaggatctcaagaagatcctttgatcttttctacggggtctgacgctcagtggaacgaaaactcacgtta
agggattttggtcatgaacaataaaactgtctgcttacataaacagtaatacaagggggtgttatgagccatattcaacg
ggaaacgtcttgctctaggccgcgattaaattccaacatggatgctgatttatatgggtataaatgggctcgcgataatg
tcgggcaatcaggtgcgacaatctatcgattgtatgggaagcccgatgcgccagagtgtttctgaaacatggcaaag
gtagcgttgccaatgatgttacagatgagatggtcagactaaactggctgacggaatttatgcctcttccgaccatcaa
gcatttatccgtactcctgatgatgcatggttactcaccactgcgatccccgggaaaacagcattccaggtattagaag
aatatcctgattcaggtgaaaatattgttgatgcgctggcagtgttcctgcgccggttgcattcgattcctgtttgtaattgtc
cttttaacagcgatcgcgtatttcgtctcgctcaggcgcaatcacgaatgaataacggtttggttgatgcgagtgattttga
tgacgagcgtaatggctggcctgttgaacaagtctggaaagaaatgcataaactttgccattctcaccggattcagtc
gtcactcatggtgatttctcacttgataaccttatttttgacgaggggaaattaataggttgtattgatgttggacgagtcgg
aatcgcagaccgataccaggatcttgccatcctatggaactgcctcggtgagttttctccttcattacagaaacggctttt
caaaaatatggtattgataatcctgatatgaataaattgcagtttcatttgatgctcgatgagttttctaagaattaattcat
gagcggatacatatttgaatgtatttagaaaaataaacaatagggggttccgcgcacatttccccgaaaagtgccacc
tgaaattgtaaacgttaatattttgttaaaattcgcgttaaattttgttaaatcagctcatttttaaccaataggccgaaatc
ggcaaaatcccttataaatcaaaagaatagaccgagatagggttgagtgttgttccagtttggaacaagagtccacta
ttaaagaacgtggactccaacgtcaaagggcgaaaaaccgtctatcagggcgatggcccactacgtgaaccatca
ccctaatcaagttttttggggtcgaggtgccgtaaagcactaaatcggaaccctaaagggagccccgatttagagct
tgacggggaaagccggcgaacgtggcgagaaaggaagggaagaaagcgaaaggagcgggcgctagggcg
ctggcaagtgtagcggtcacgctgcgcgtaaccaccacacccgccgcgcttaatgcgccgctacagggcgcgtcc
cattcgccaatccggatatagttcctcctttcagcaaaaaacccctcaagacccgtttagaggccccaaggggttatg
ctagttattgctcagcggtggcagcagccaactcagcttcctttcgggctttgttagcagccggatctcagtggtggtggt
ggtggtgctcga (SEQ ID NO:26)

Figure 112B gcggccgcgcccttgacgatgccacatcctgagcaaataattcaaccactaattgtgagcggataacacaaggaggaaa
cagccatggtatcctgttctgcgccgggtaagatttacctgttcggtgaacacgccgtagtttatggcgaaactgcaattgcgt
gtgcggtggaactgcgtacccgtgttcgcgcggaactcaatgactctatcactattcagagccagatcggccgcaccggtct
ggatttcgaaaagcacccttatgtgtctgcggtaattgagaaaatgcgcaaatctattcctattaacggtgttttcttgaccgtcg
attccgacatcccggtgggctccggtctgggtagcagcgcagccgttactatcgcgtctattggtgcgctgaacgagctgttc
ggctttggcctcagcctgcaagaaatcgctaaactgggccacgaaatcgaaattaaagtacagggtgccgcgtccccaac
cgatacgtatgtttctaccttcggcggcgtggttaccatcccggaacgtcgcaaactgaaaactccggactgcggcattgtga
ttggcgataccggcgttttctcctccaccaaagagttagtagctaacgtacgtcagctgcgcgaaagctacccggatttgatc
gaaccgctgatgacctctattggcaaaatctctcgtatcggcgaacaactggttctgtctggcgactacgcatccatcggccg
cctgatgaacgtcaaccagggtctcctggacgccctgggcgttaacatcttagaactgagccagctgatctattccgctcgtg
cggcaggtgcgtttggcgctaaaatcacgggcgctggcggcggtggctgtatggttgcgctgaccgctccggaaaaatgc
aaccaagtggcagaagcggtagcaggcgctggcggtaaagtgactatcactaaaccgaccgagcaaggtctgaaagta
gattaagccttgacttaatagctgcttatttcgcccttatggtacctagtaggaggaaaaaaacatggaaatgcgtcaaccgg
ctgtcgcaggtcaattctacccactgcgttgcgagaacctggaaaacgaactgaaacgctgcttcgaaggcctggagatcc
gcgaacaagaagtgctgggcgcagtctgtccgcacgccggttatatgtactctggcaaagttgcggcgcacgtctatgcca
ctctgccggaagctgatacctacgtaatcttcggcccgaaccacaccggctacggtagccctgtctctgtgagccgtgaaac
ttggaagaccccgttgggcaatatcgatgttgacctggaactggcggacggcttcctgggttccatcgtagatgcggatgaa
ctcggtcacaaatacgaacactctatcgaagttcagctgccgtttctgcaataccgttttgaacgcgatttcaaaattctgccaa
tctgcatgggtatgcaagacgaagaaaccgcggtcgaagtaggtaacctgctggcggatctgatcagcgagtccggtaaa
cgtgctgtgatcatcgcaagctctgatttcacccactatgagacggctgaacgtgccaaagaaatcgattccgaagttattga
ttctatcctgaactttgacatctctggcatgtacgatcgcctgtatcgccgtaacgcctctgtttgcggttacggcccgatcaccg
ctatgctgacggcaagcaaaaagctgggcggctctcgtgcgactttgctgaaatacgcaaacagcggtgacgtgtccggt
gataaagacgctgtgggtgggctacgccgccatcatcgttgagtaagctgattaaaggttgaacagataggatttcgtcatgg
atcctacaaggaggaaaaaaacatgaatgcttctaatgaaccggtgattctgaaactgggtggctctgctattaccgacaa
aggtgcctacgaaggcgtagttaaggaagctgatttgctgcgcatcgcacaggaagttagcggtttccgtggcaagatgat
cgtggttcatggtgctggtagcttcggccatacgtacgcgaagaaatacggcctggaccgtaccttcgacccagagggcgc
aattgttactcatgaatctgttaaaaagctcgcctccaaagttgtaggtgctctgaatagcttcggcgtgccgtgctatcgcggtg
catcctatggactgcgcagtatgccgtaacggtcgtatcgaaacgatgtatctggactccatcaagttaatgctggaaaaag
gtctggtgccggtctgcacggcgacgtcgcaatggatattgaactgggcacttgtatcctgtccggtgatcaaatcgttccta
cctggccaaagaactgggtatctcccgcctcggcctgggcagcgcagaggatggtgtgctggatatggagggcaaacct
gtaccggaaatcaccccagaaactttcgaagagttccgccactgcatcggtggttctggttctactgatgtaaccggtggcat
gctgggcaaagtgctggaacttctggaattgagcaaaaattcttccattactagctacattttcaacgctggtaaagcagaca
acatctaccgctttctgaatggtgagtccatcggcactcgcatcagcccggacaagcgtgtttaagctagttattaacctaaat
gctctaaaccagttatgagctctacaaggaggaaaaaaacatgattaacactaccagccgccgcaaaattgaacacctg
aaactctgcgcagaatccccggttgaagcgcgtcaggtatctgccggctttgaagacgttactctgatccaccgcgctttacc
ggagctgaacatggatgaactggacctcagcgttgatttcctgggtaaacgcatcaaagcgccgttcctgattgcgtctatca
cgggtggtcacccagataccatcccggttaacgctgcgctggcagctgctgctgaggagctgggtgttggcatcggcgttgg
ctctcagcgcgcggccattgatgatccgagccaggaagacagcttccgtgtagtgcgtgatgaagccccagatgcgtttgttt
atggcaacgtcggcgcagcacagatccgtcagtatggtgttgaaggtgttgaaaaactgatcgaaatgattgacgcagatg
ccttggcaatccacctgaacttctgcaagaagcggtccaaccggaaggtgaccgcgacgcgaccggttgcctggacatg
attaccgaaatttgctctcagattaaaactccggtaatcgtgaaagaaaccggtgcaggcattagccgtgaagatgcgattct
gttccagaaagctggcgtgagcgcaatcgacgttggcggcgcgggcggcacctcctgggctggcgtcgaggtctaccgtg
ctaaagaaagccgtgactctgttagcgagcgtttaggtgagctgttttgggatttcggcattccgacggtagcttctctgattga
atcccgcgtttccttgccgctgatcgcaaccggcggtatccgtaacggtctggacattgctaaaagcattgctctcggcgcaa
gcgctgccagcgccgctctgccgttcgttggtccgtccctggagggcaaagaatccgttgtacgtgtgctgagctgcatgctg
gaagaatttaaagcagcaatgttttgtgcggttgcggcaacatcaaaga

Figure 112C cctgcacaactctccagtagtggtaactggttgacccgcgaatacctggagcagcgcggttttaacgttaa
ggacctctccctgccgggcaacgctctgtaagcttaacgcgtctacaaataaaaaaggcacgtcagatga
cgtgccttttttcttgtctaga (SEQ ID NO:27)

Figure 113B gtttgacagcttatcatcgactgcacggtgcaccaatgcttctggcgtcaggcagccatcggaagctgtggtatggctgtgcagg
tcgtaaatcactgcataattcgtgtcgctcaaggcgcactcccgttctggataatgtttttgcgccgacatcataacggttctggca
aatattctgaaatgagctgttgacaattaatcatccggctcgtataatgtgtggaattgtgagcggataacaatttcacacaggaa
acagcgccgctgagaaaaagcgaagcggcactgctctttaacaatttatcagacaatctgtgtgggcactcgaccggaattat
cgattaactttattattaaaaattaaagaggtatatattaatgtatcgattaaataaggaggaataaaccatgtgtgcgacctcttct
caatttactcagattaccgagcataattcccgtcgttccgcaaactatcagccaaacctgtggaatttcgaattcctgcaatccctg
gagaacgacctgaaagtggaaaagctggaggagaaagcgaccaaactggaggaagaagttcgctgcatgatcaaccgt
gtagacacccagccgctgtccctgctggagctgatcgacgatgtgcagcgcctgggtctgacctacaaatttgaaaaagacat
cattaaagccctggaaaacatcgtactgctggacgaaaacaaaaagaacaaatctgacctgcacgcaaccgctctgtctttc
cgtctgctgcgtcagcacggtttcgaggtttctcaggatgtttttgagcgtttcaaggataaagaaggtggtttcagcggtgaactg
aaaggtgacgtccaaggcctgctgagcctgtatgaagcgtcttacctgggtttcgagggtgagaacctgctggaggaggcgc
gtacctttccatcacccacctgaagaacaacctgaaagaaggcattaataccaaggttgcagaacaagtgagccacgccct
ggaactgccatatcaccagcgtctgcaccgtctggaggcacgttggttcctggataaatacgaaccgaaagaaccgcatcac
cagctgctgctggagctggcgaagctggatttttaacatggtacagaccctgcaccagaaagagctgcaagatctgtcccgctg
gtggaccgagatgggcctggctagcaaactggattttgtacgcgaccgcctgatggaagtttatttctgggcactgggtatggcg
ccagacccgcagtttggtgaatgtcgcaaagctgttactaaaatgtttggtctggtgacgatcatcgatgacgtgtatgacgtttat
ggcactctggacgaactgcaactgttcaccgatgctgtagagcgctgggacgttaacgctattaacaccctgccggactatatg
aaactgtgtttcctggcactgtacaacaccgttaacgacacgtcctattctattctgaaagagaaaggtcataacaacctgtccta
tctgacgaaaagctggcgtgaactgtgcaaagccttctgcaagaggcgaaatggtccaacaacaaaattatcccggctttctc
caagtacctggaaaacgccagcgtttcctcctccggtgtagcgctgctggcgccgtcttacttttccgtatgccagcagcaggaa
gacatctccgaccacgcgctgcgttccctgaccgacttccatggtctggtgcgttctagctgcgttatcttccgcctgtgcaacgat
ctggccacctctgcggcggagctggaacgtggcgagactaccaattctatcattagctacatgcacgaaaacgatggtacca
gcgaggaacaggcccgcgaagaactgcgtaaactgatcgacgccgaatggaaaaagatgaatcgtgaacgcgttagcga
ctccaccctgctgcctaaagcgttcatggaaatcgcagttaacatggcacgtgtttcccactgcacctaccagtatggcgatggt
ctgggtcgcccagactacgcgactgaaaaccgcatcaaactgctgctgattgacccttcccgattaaccagctgatgtatgtct
aactgcataaaggaggtaaaaaaacatggtatcctgttctgcgccgggtaagatttacctgttcggtgaacacgccgtagtttat
ggcgaaactgcaattgcgtgtgcggtggaactgcgtacccgtgttcgcgcggaactcaatgactctatcactattcagagccag
atcggccgcaccggtctggatttcgaaaagcacccttatgtgtctgcggtaattgagaaaatgcgcaaatctattcctattaacg
gtgttttcttgaccgtcgattccgacatcccggtgggctccggtctgggtagcagcgcagccgttactatcgcgtctattggtcgc
tgaacgagctgttcggctttggcctcagcctgcaagaaatcgctaaactgggccacgaaatcgaaattaaagtacagggtgc
cgcgtccccaaccgatacgtatgtttctaccttcggcggcgtggttaccatcccggaacgtcgcaaactgaaaactccggactg
cggcattgtgattggcgataccggccgttttctcctccaccaaagagttagtagctaacgtacgtcagctgcgcgaaagctaccc
ggatttgatcgaaccgctgatgacctctattggcaaaatctctcgtatcggcgaacaactggttctgtctggcgactacgcatcca
tcggccgcctgatgaacgtcaaccagggtctcctggacgccctgggcgttaacatcttagaactgagccagctgatctattccg
ctcgtgcggcaggtgcgttggcgctaaaatcacgggcgctggcggcggtggctgtatggttgcgctgaccgctccggaaaaa
tgcaaccaagtggcagaagcggtagcaggcgctggcggtaaagtgactatcactaaaccgaccgagcaaggtctgaaagt
agattaaagtctagttaaagtttaaacggtctccagcttgctgttttggcggatgagagaagattttcagcctgatacagattaaa
tcagaacgcagaagcggtctgataaaacagaatttgcctggcggcagtagcgcggtggtcccacctgaccccatgccgaac
tcagaagtgaaacgccgtagcgccgatggtagtgtggggtctcccatgcgagagtagggaactgccaggcatcaaataaa
acgaaaggctcagtcgaaagactgggcctttcgttttatctgttgtttgtcggtgaacgctctcctgagtaggacaaatccgccgg
gagcggatttgaacgttgcgaagcaacggcccggagggtggcgggcaggacgcccgccataaactgccaggcatcaaatt
aagcagaaggccatcctgacggatggcctttttgcgtttctacaaactctttttgtttattttctaaatacattcaaatatgtatccgctt
aaccggaattgccagctggggcgccctctggtaaggttgggaagccctgcaaagtaaactggatggctttctcgccgccaag
gatctgatggcgcaggggatcaagctctgatcaagagacaggatgaggatcgtttcgcatgattgaacaagatggattgcac
gcaggttctccggccgcttgggtggagaggctattcggctatgactgggcacaa

Figure 113C cagacaatcggctgctctgatgccgccgtgttccggctgtcagcgcaggggcgcccggttcttttgtcaagaccga
cctgtccggtgccctgaatgaactgcaagacgaggcagcgcggctatcgtggctggccacgacgggcgttccttg
cgcagctgtgctcgacgttgtcactgaagcgggaagggactggctgctattgggcgaagtgccggggcaggatct
cctgtcatctcaccttgctcctgccgagaaagtatccatcatggctgatgcaatgcggcggctgcatacgcttgatcc
ggctacctgcccattcgaccaccaagcgaaacatcgcatcgagcgagcacgtactcggatggaagccggtcttgt
cgatcaggatgatctggacgaagagcatcaggggctcgcgccagccgaactgttcgccaggctcaaggcgagc
atgcccgacggcgaggatctcgtcgtgacccatggcgatgcctgcttgccgaatatcatggtggaaaatggccgctt
ttctggattcatcgactgtggccggctgggtgtggcggaccgctatcaggacatagcgttggctacccgtgatattgct
gaagagcttggcggcgaatgggctgaccgcttcctcgtgctttacggtatcgccgctcccgattcgcagcgcatcgc
cttctatcgccttcttgacgagttcttctgacgcatgaccaaaatcccttaacgtgagttttcgttccactgagcgtcaga
ccccgtagaaaagatcaaaggatcttcttgagatccttttttctgcgcgtaatctgctgcttgcaaacaaaaaaacca
ccgctaccagcggtggtttgtttgccggatcaagagctaccaactcttttccgaaggtaactggcttcagcagagcg
cagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgat
agttaccggataaggcgcagcggtcgggctgaacggggggttcgtgcacacagcccagcttggagcgaacgac
ctacaccgaactgagatacctacagcgtgagctatgagaaagcgccacgcttcccgaagggagaaaggcgga
caggtatccggtaagcggcagggtcggaacaggagagcgcacgagggagcttccaggggaaacgcctggt
atctttatagtcctgtcgggtttcgccacctctgactgagcgtcgattttgtgatgctcgtcagggggcggagcctat
ggaaaaacgccagcaacgcggccttttacggttcctggccttttgctggccttttgctcacatgttctttcctgcgttatcc
cctgattctgtggataaccgtattaccgcctttgagtgagctgataccgctcgccgcagccgaacgaccgagcgca
gcgagtcagtgagcgaggaagcggaagagcgcctgatgcggtattttctccttacgcatctgtgcggtatttcacac
cgcatatggtgcactctcagtacaatctgctctgatgccgcatagttaagccagtatacactccgctatcgctacgtga
ctgggtcatggctgcgccccgacacccgccaacacccgctgacgcgccctgacgggcttgtctgctcccggcatc
cgcttacagacaagctgtgaccgtctccgggagctgcatgtgtcagaggttttcaccgtcatcaccgaaacgcgcg
aggcagcagatcaattcgcgcgcgaaggcgaagcggcatgcatttacgttgacaccatcgaatggtgcaaaacc
tttcgcggtatggcatgatagcgcccggaagagagtcaattcagggtggtgaatgtgaaaccagtaacgttatacg
atgtcgcagagtatgccggtgtctcttatcagaccgtttcccgcgtggtgaaccaggccagccacgtttctgcgaaaa
cgcgggaaaaagtggaagcggcgatggcggagctgaattacattcccaaccgcgtggcacaacaactggcgg
gcaaacagtcgttgctgattggcgttgccacctccagtctggccctgcacgcgccgtcgcaaattgtcgcggcgatt
aaatctcgcgccgatcaactgggtgccagcgtggtggtcgatggtagaacgaagcggcgtcgaagcctgtaaa
gcggcggtgcacaatcttctcgcgcaacgcgtcagtgggctgatcattaactatccgctggatgaccaggatgccat
tgctgtggaagctgcctgcactaatgttccggcgttatttcttgatgtctctgaccagacacccatcaacagtattatttct
cccatgaagacggtacgcgactgggcgtggagcatctggtcgcattgggtcaccagcaaatcgcgctgtagcgg
gcccattaagttctgtctcggcgcgtctgcgtctggctggctggcataaatatctcactcgcaatcaaattcagccgat
agcggaacgggaaggcgactggagtgccatgtccggttttcaacaaaccatgcaaatgctgaatgagggcatcg
ttcccactgcgatgctggttgccaacgatcagatggcgctgggcgcaatgcgcgccattaccgagtccgggctgcg
cgttggtgcggatatctcggtagtgggatacgacgataccgaagacagctcatgttatatcccgccgtcaaccacca
tcaaacaggattttcgcctgctggggcaaaccagcgtggaccgcttgctgcaactctctcagggccaggcggtgaa
gggcaatcagctgttgcccgtctcactggtgaaaagaaaaaccaccctggcgcccaatacgcaaaccgcctctcc
ccgcgcgttggccgattcattaatgcagctggcacgacaggtttcccgactggaaagcgggcagtgagcgcaac
gcaattaatgtgagttagcgcgaattgatctg (SEQ ID NO:28)

Figure 114B aagggcgagctcaacgatccggctgctaacaaagcccgaaaggaagctgagttggctgctgccaccgctgagcaata
actagcataaccccttggggcctctaaacgggtcttgaggagttttttgctgaaaggaggaactatatccggatatcccgca
agaggcccggcagtaccggcataaccaagcctatgcctacagcatccagggtgacggtgccgaggatgacgatgagc
gcattgttagatttcatacacggtgcctgactgcgttagcaatttaactgtgataaactaccgcattaaagcttatcgatgataa
gctgtcaaacatgagaattaattcttgaagacgaaagggcctcgtgatacgcctattttataggttaatgtcatgataataatg
gtttcttagacgtcaggtggcacttttcggggaaatgtgcgcggaacccctatttgtttattttctaaatacattcaaatatgtatc
cgctcatgagacaataaccctgataaatgcttcaataatattgaaaaaggaagagtatgattgaacaagatggattgcacg
caggttctccggccgcttgggtggagaggctattcggctatgactgggcacaactgacaatcggctgctctgatgccgccgt
gttccggctgtcagcgcaggggcgcccggttcttttgtcaagaccgacctgtccggtgccctgaatgaactgcaggacga
ggcagcgcggctatcgtggctggccacgacgggcgttcttgcgcagctgtgctcgacgttgtcactgaagcgggaagg
gactggctgctattgggcgaagtgccggggcaggatctcctgtcatctcaccttgctcctgccgagaaagtatccatcatgg
ctgatgcaatgcggcggctgcatacgcttgatccggctacctgcccattcgaccaccaagcgaaacatcgcatcgagcg
ggcacgtactcggatggaagccggtcttgtcgatcaggatgatctggacgaagagcatcaggggctcgcgccagccga
actgttcgccaggctcaaggcgcgcatgcccgacggcgaggatctcgtcgtgacacatggcgatgcctgcttgccgaata
tcatggtggaaaatggccgcttttctggattcatcgactgtggccggctgggtgtggcggaccgctatcaggacatagcgttg
gctacccgtgatattgctgaagagcttggcggcgaatgggctgaccgcttcctcgtgctttacggtatcgccgctcccgattc
gcagcgcatcgccttctatcgccttcttgacgagttcttctgagcgggactctggggttcgaaatgaccgaccaagcgacgc
ctaactgtcagaccaagtttactcatatatactttagattgatttaaaacttcattttaatttaaaaggatctaggtgaagatcctt
ttgataatctcatgaccaaaatcccttaacgtgagttttcgttccactgagcgtcagaccccgtagaaaagatcaaaggatct
tcttgagatcctttttttctgcgcgtaatctgctgcttgcaaacaaaaaaaccaccgctaccagcggtggtttgtttgccggatc
aagagctaccaactctttttccgaaggtaactggcttcagcagagcgcagataccaaatactgtccttctagtgtagccgta
gttaggccaccacttcaagaactctgtagcaccgcctacatacctcgctctgctaatcctgttaccagtggctgctgccagtg
gcgataagtcgtgtcttaccgggttggactcaagacgatagttaccggataaggcgcagcggtcgggctgaacggggggg
ttcgtgcacacagcccagcttggagcgaacgacctacaccgaactgagatacctacagcgtgagctatgagaaagcgc
cacgcttcccgaagggagaaaggcggacaggtatccggtaagcggcagggtcggaacaggagagcgcacgaggga
gcttccaggggggaaacgcctggtatctttatagtcctgtcgggtttcgccacctctgacttgagcgtcgatttttgtgatgctcgt
caggggggcggagcctatggaaaaacgccagcaacgcggcctttttacggttcctggccttttgctggccttttgctcacatg
ttctttcctgcgttatcccctgattctgtggataaccgtattaccgcctttgagtgagctgataccgctcgccgcagccgaacga
ccgagcgcagcgagtcagtgagcgaggaagcggaagagcgcctgatgcggtattttctccttacgcatctgtgcggtattt
cacaccgcaatggtgcactctcagtacaatctgctctgatgccgcatagttaagccagtatacactccgctatcgctacgtg
actgggtcatggctgcgccccgacacccgccaacacccgctgacgcgccctgacgggcttgtctgctcccggcatccgct
tacagacaagctgtgaccgtctccggagctgcatgtgtcagaggttttcaccgtcatcaccgaaacgcgcgaggcagct
gcggtaaagctcatcagcgtggtcgtgaagcgattcacagatgtctgcctgttcatccgcgtccagctcgttgagtttctccag
aagcgttaatgtctggcttctgataaagcgggccatgttaagggcggttttttcctgtttggtcactgatgcctccgtgtaaggg
ggatttctgttcatgggggtaatgataccgatgaaacgagagaggatgctcacgatacgggttactgatgatgaacatgcc
cggttactggaacgttgtgagggtaaacaactggcggtatggatgcggcgggaccagagaaaaatcactcagggtcaat
gccagcgcttcgttaatacagatgtaggtgttccacagggtagccagcagcatcctgcgatgcagatccggaacataatg
gtgcagggcgctgacttccgcgtttccagactttacgaaacacggaaaccgaagaccattcatgttgttgctcaggtcgca
gacgttttgcagcagcagtcgcttcacgttcgctcgcgtatcggtgattcattctgctaaccagtaaggcaacccccgccagc
ctagccgggtcctcaacgacaggagcacgatcatgcgcacccgtggccaggacccaacgctgcccgagatgcgccgc
gtgcggctgctggagatggcggacgcgatggatatgttctgccaagggttggtttgcgcattcacagttctccgcaagaattg
attggctccaattcttggagtggtgaatccgttagcgaggtgccgccggcttccattcaggtcgaggtggcccggctccatgc
accgcgacgcaacgcggggaggcagacaaggtatagggcggcgcctacaatccatgccaacccgttccatgtgctcg
ccgaggcggcataaatcgccgtgacgatcagcggtccaatgatcgaagttaggctggtaagagccgcgagcgatccttg
aagctgtccctgatggtcgtcatctacctgcctggacagcatggcctgcaacgcgggcatcccgatgccgccggaagcg
agaagaatcataatggggaaggccatccagcctcgcgtcgcgaacgccagcaagacgtagcccagcgcgt

Figure 114C cggccgccatgccggcgataatggcctgcttctcgccgaaacgtttggtggcgggaccagtgacgaaggcttg
agcgagggcgtgcaagattccgaataccgcaagcgacaggccgatcatcgtcgcgctccagcgaaagcgg
tcctcgccgaaaatgacccagagcgctgccggcacctgtcctacgagttgcatgataaagaagacagtcataa
gtgcggcgacgatagtcatgccccgcgcccaccggaaggagctgactgggttgaaggctctcaagggcatcg
gtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagg
gtggttttctttcaccagtgagacgggcaacagctgattgcccttcaccgcctggccctgagagagttgcagca
agcggtccacgctggtttgccccagcaggcgaaaatcctgtttgatggtggttaacggcgggataacatgag
ctgtcttcggtatcgtcgtatcccactaccgagatatccgccaccaacgcgcagcccggactcggtaatggcgcg
cattgcgcccagcgccatctgatcgttggcaaccagcatcgcagtgggaacgatgccctcattcagcatttgcat
ggtttgttgaaaaccggacatggcactccagtcgccttcccgttccgctatcggctgaatttgattgcgagtgagat
atttatgccagccagccagacgcagacgcgccgagacagaacttaatgggcccgctaacagcgcgatttgct
ggtgacccaatgcgaccagatgctccacgcccagtcgcgtaccgtcttcatgggagaaaataatactgttgatg
ggtgtctggtcagagacatcaagaaataacgccggaacattagtgcaggcagcttccacagcaatggcatcct
ggtcatccagcggatagttaatgatcagcccactgacgcgttgcgcgagaagattgtgcaccgccgctttacag
gcttcgacgccgcttcgttctaccatcgacaccaccacgctggcacccagttgatcggcgcgagatttaatcgcc
gcgacaatttgcgacggcgcgtgcagggccagactggaggtggcaacgccaatcagcaacgactgtttgccc
gccagtgttgtgccacgcggttgggaatgtaattcagctccgccatcgccgcttccactttttcccgcgttttcgcag
aaacgtggctggcctggttcaccacgcgggaaacggctgataagagacaccggcatactgcgacatcgt
ataacgttactggtttcacattcaccaccctgaattgactctcttccgggcgctatcatgccataccgcgaaaggttt
tgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccg
gccacggggcctgccaccatacccacgccgaaacaagcgctcatgagcccgaagtggcgagcccgatcttc
cccatcggtgatgtcggcgatataggcgccagcaaccgcacctgtggcgccggtgatgccggccacgatgcg
tccggcgtagaggatcgagatctcgatcccgcgaaattaatacgactcactatagggaattgtgagcggata
acaattcccctctagaaataattttgtttaactttaagaaggagatatacatatgcgggttctcatcatcatcatcat
catggtatggctagcatgactggtggacagcaaatgggtcgggatctgtacgacgatgacgataaggatcatc
ccttcaccatggtatcctgttctgcgccgggtaagatttacctgttcggtgaacacgccgtagtttatggcgaaactg
caattgcgtgtcggtggaactgcgtacccgtgttcgcgcggaactcaatgactctatcactattcagagccaga
tcggccgcaccggtctggatttcgaaaagcacccttatgtgtctgcggtaattgagaaaatgcgcaaatctattcc
tattaacggtgtttcttgaccgtcgattccgacatcccggtgggctccggtctgggtagcagcgcagccgttactat
cgcgtctattggtgcgctgaacgagctgttcggctttggcctcagcctgcaagaaatcgctaaactgggccacga
aatcgaaattaaagtacagggtgccgcgtccccaaccgatacgtatgttctaccttcggcggcgtggttaccatc
ccggaacgtcgcaaactgaaaactccggactgcggcattgtgattggcgataccggcgttttctcctccaccaa
agagttaglagctaacgtacgtcagctgcgcgaaagctacccggatttgatcgaaccgctgatgacctctattgg
caaaatctctcgtatcggcgaacaactggtctgtctggcgactacgcatccatcggccgcctgatgaacgtcaa
ccagggtctcctggacgccctgggcgttaacatcttagaactgagccagctgatctattccgctcgtgcggcagg
tgcgtttggcgctaaaatcacgggcgctggcggcggtggctgtatggttgcgctgaccgctccggaaaaatgca
accaagtggcagaagcggtagcaggcgctggcggtaaagtgactatcactaaaccgaccgagcaaggtctg
aaagtagattaa (SEQ ID NO:29)

Figures 115A-B
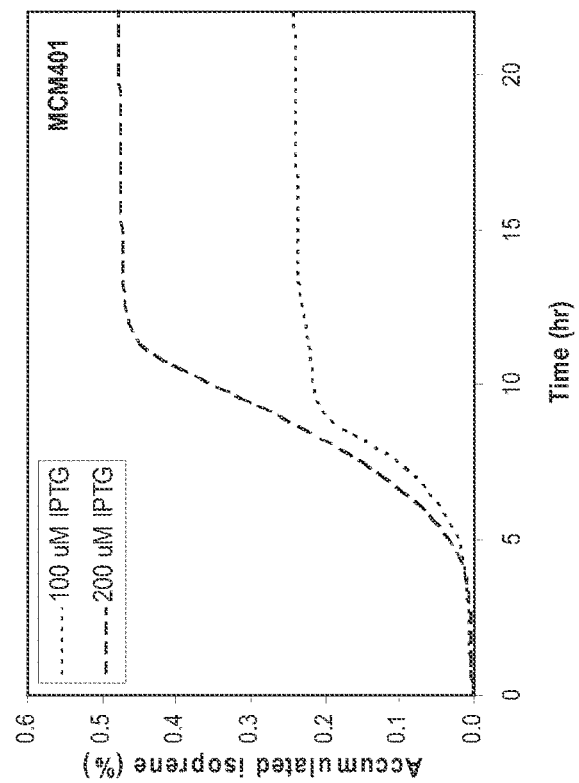
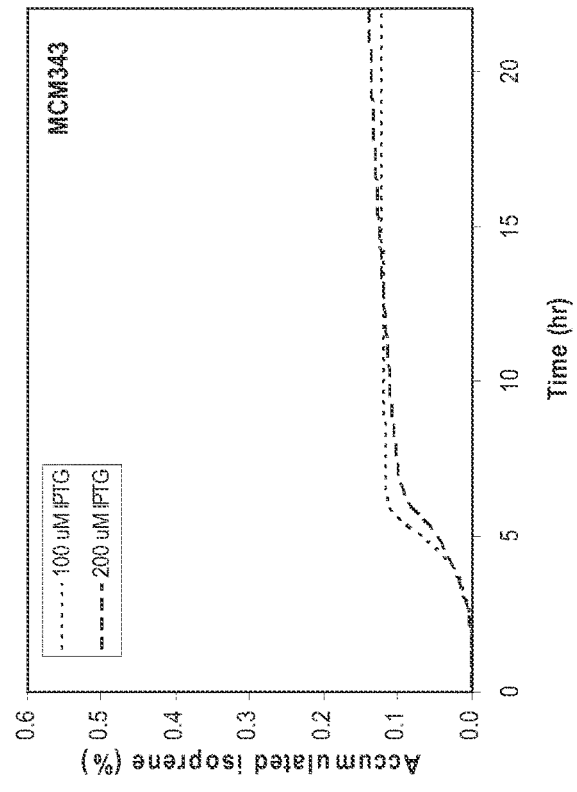

Figures 115C-D
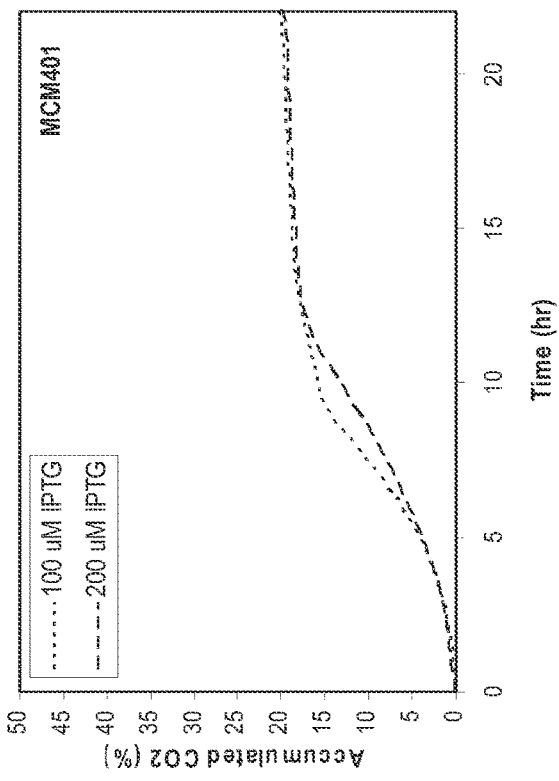
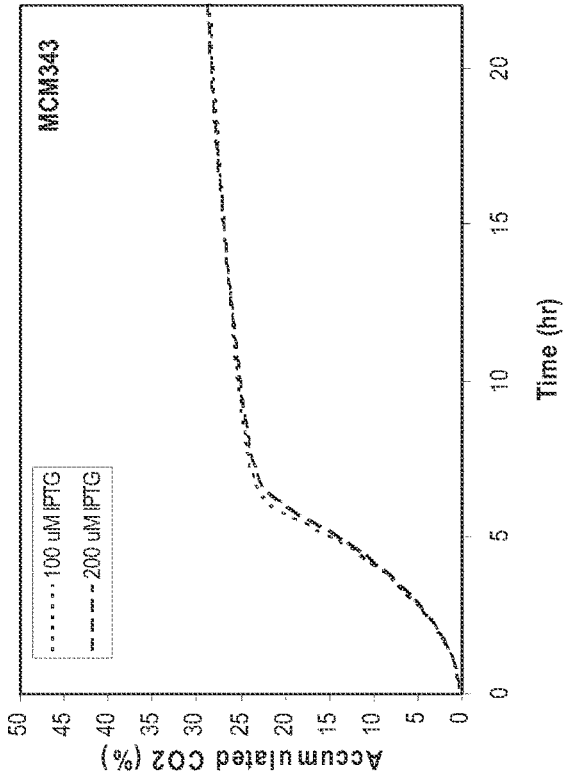

Figure 137A tggcgaatgggacgcgccctgtagcggcgcattaagcgcggcgggtgtggtggttacgcgcagcgtgaccgctacacttgcca
gcgccctagcgcccgctcctttcgctttcttcccttccttctcgccacgttcgccggctttccccgtcaagctctaaatcgggggctcc
ctttagggttccgatttagtgctttacggcacctcgaccccaaaaaactgattagggtgatggttcacgtagtgggccatcgccctg
atagacggttttttcgcccttttgacgttggagtccacgttctttaatagtggactcttgttccaaactggaacaacactcaaccctatctc
ggtctattcttttgatttataagggattttgccgatttcggcctattggtaaaaaatgagctgatttaacaaaaatttaacgcgaatttta
acaaaatattaacgtttacaatttcaggtggcactttttcggggaaatgtgcgcggaacccctatttgtttatttttctaaatacattcaaa
tatgtatccgctcatgaattaattcttagaaaaactcatcgagcatcaaatgaaactgcaatttattcatatcaggattatcaatacca
tatttttgaaaaagccgtttctgtaatgaaggagaaaactcaccgaggcagttccataggatggcaagatcctggtatcggtctgc
gattccgactcgtccaacatcaatacaacctattaatttcccctcgtcaaaaataaggttatcaagtgagaaatcaccatgagtga
cgactgaatccggtgagaatggcaaaagtttatgcatttctttccagacttgttcaacaggccagccattacgctcgtcatcaaaat
cactcgcatcaaccaaaccgttattcatcgtgattgcgcctgagcgagacgaaatacgcgatcgctgttaaaaggacaattaca
aacaggaatcgaatgcaaccggcgcaggaacactgccagcgcatcaacaatatttcacctgaatcaggatattcttctaaatac
ctggaatgctgttttcccggggatcgcagtggtgagtaaccatgcatcatcaggagtacggataaaatgcttgatggtcggaaga
ggcataaattccgtcagccagtttagtctgaccatctcatctgtaacatcattggcaacgctacctttgccatgtttcagaaacaactc
tggcgcatcgggcttcccatacaatcgatagattgtcgcacctgattgcccgacattatcgcgagcccatttatacccatataaatc
agcatccatgttggaatttaatcgcggcctagagcaagacgtttcccgttgaatatggctcataacaccccttgtattactgtttatgta
agcagacagttttattgttcatgaccaaaatcccttaacgtgagttttcgttccactgagcgtcagaccccgtagaaaagatcaaag
gatcttcttgagatccttttttctgcgcgtaatctgctgcttgcaaacaaaaaaaccaccgctaccagcggtggtttgtttgccggatc
aagagctaccaactcttttccgaaggtaactggcttcagcagagcgcagataccaaatactgtccttctagtgtagccgtagttag
gccaccacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcacaca
gcccagcttggagcgaacgacctacaccgaactgagatacctacagcgtgagctatgagaaagcgccacgcttcccgaagg
gagaaaggcggacaggtatccggtaagcggcagggtcggaacaggagagcgcacgagggagcttccaggggggaaacgc
ctggtatctttatagtcctgtcgggtttcgccacctctgacttgagcgtcgatttttgtgatgctcgtcaggggggcggagcctatggaa
aaacgccagcaacgcggccttttacggttcctggccttttgctggccttttgctcacatgttctttcctgcgttatcccctgattctgtgg
ataaccgtattaccgcctttgagtgagctgataccgctcgccgcagccgaacgaccgagcgcagcgagtcagtgagcgagga
agcggaagagcgcctgatgcggtattttctccttacgcatctgtgcggtatttcacaccgcatatatggtgcactctcagtacaatct
gctctgatgccgcatagttaagccagtatacactccgctatcgctacgtgactgggtcatggctgcgccccgacacccgccaac
acccgctgacgcgccctgacgggcttgtctgctcccggcatccgcttacagacaagctgtgaccgtctccgggagctgcatgtgt
cagaggttttcaccgtcatcaccgaaacgcgcgaggcagctgcggtaaagctcatcagcgtggtcgtgaagcgattcacagat
gtctgcctgttcatccgcgtccagctcgttgagtttctccagaagcgttaatgtctggcttctgataaagcgggccatgttaagggcg
gttttttcctgtttggtcactgatgcctccgtgtaagggggatttctgttcatgggggtaatgataccgatgaaacgagagaggatgct
cacgatacggggttactgatgatgaacatgcccggttactggaacgttgtgagggtaaacaactggcggtatggatgcggcggga
ccagagaaaaatcactcagggtcaatgccagcgcttcgttaatacagatgtaggtgttccacagggtagccagcagcatcctgc
gatgcagatccggaacataatggtgcagggcgctgacttccgcgtttccagactttacgaaacacggaaaccgaagaccattc
atgttgttgctcaggtcgcagacgttttgcagcagcagtcgcttcacgttcgctcgcgtatcggtgattcattctgctaaccagtaagg
caaccccgccagcctagccgggtcctcaacgacaggagcacgatcatgcgcacccgtggggccgccatgccggcgataatg
gcctgcttctcgccgaaacgtttggtggcgggaccagtgacgaaggcttgagcgagggcgtgcaagattccgaataccgcaag
cgacaggccgatcatcgtcgcgctccagcgaaagcggtcctcgccgaaaatgacccagagcgctgccggcacctgtcctacg
agttgcatgataaagaagacagtcataagtgcggcgacgatagtcatgccccgcgcccaccggaaggagctgactgggttga
aggctctcaagggcatcggtcgagatcccggtgcctaatgagtgagctaacttacattaattgcgttgcgctcactgcccgctttcc
agtcgggaaacctgtcgtgccagctgcattaatgaatcggccaacgcgcggggagaggcggtttgcgtattgggcgccagggt
ggtttttcttttcaccagtgagacgggcaacagctgattgcccttcaccgcctggccctgagagagttgcagcaagcggtccacgc
tggtttgccccagcaggcgaaaatcctgtttgatggtggttaacggcgggatataacatgagctgtcttcggtatc

Figure 137B gtcgtatcccactaccgagatatccgcaccaacgcgcagcccggactcggtaatggcgcgcattgcgcccagcg
ccatctgatcgttggcaaccagcatcgcagtgggaacgatgccctcattcagcatttgcatggtttgttgaaaaccgg
acatggcactccagtcgccttcccgttccgctatcggctgaatttgattgcgagtgagatatttatgccagccagccag
acgcagacgcgccgagacagaacttaatgggcccgctaacagcgcgatttgctggtgacccaatgcgaccagat
gctccacgcccagtcgcgtaccgtcttcatgggagaaaataatactgttgatgggtgtctggtcagagacatcaaga
aataacgccggaacattagtgcaggcagcttccacagcaatggcatcctggtcatccagcggatagttaatgatca
gcccactgacgcgttgcgcgagaagattgtgcaccgccgctttacaggcttcgacgccgcttcgttctaccatcgac
accaccacgctggcacccagttgatcggcgcgagatttaatcgccgcgacaatttgcgacggcgcgtgcagggc
cagactggaggtggcaacgccaatcagcaacgactgtttgcccgccagttgttgtgccacgcggttgggaatgtaa
ttcagctccgccatcgccgcttccacttttcccgcgttttcgcagaaacgtggctggcctggttcaccacgcgggaaa
cggtctgataagagacaccggcatactctgcgacatcgtataacgttactggtttcacattcaccaccctgaattgact
ctcttccgggcgctatcatgccataccgcgaaaggttttgcgccattcgatggtgtccgggatctcgacgctctccctta
tgcgactcctgcattaggaagcagcccagtagtaggttgaggccgttgagcaccgccgccgcaaggaatggtgc
atgcaaggagatggcgcccaacagtcccccggccacggggcctgccaccatacccacgccgaaacaagcgct
catgagcccgaagtggcgagcccgatcttccccatcggtgatgtcggcgatataggcgccagcaaccgcacctgt
ggcgccggtgatgccggccacgatgcgtccggcgtagaggatcgagatctcgatcccgcgaaattaatacgactc
actataggggaattgtgagcggataacaattcccctctagaaataattttgtttaactttaagaaggagatatacatat
gcgttgtagcgtgtccaccgaaaatgtgtctttcaccgaaactgaaaccgaagctcgtcgttctgcgaactacgaac
ctaacagctgggactatgattacctgctgtcctccgacacggacgagtccatcgaagtatacaaagacaaagcga
aaaagctggaagccgaagttcgtcgcgagattaataacgaaaaagcagaatttctgaccctgctggaactgattg
acaacgtccagcgcctgggcctgggttaccgtttcgagtctgatatccgtggtgcgctggatcgcttcgtttcctccgg
cggcttcgatgcggtaaccaagacttccctgcacggtacggcactgtctttccgtctgctgcgtcaacacggttttgag
gtttctcaggaagcgttcagcggcttcaaagaccaaaacggcaacttcctggagaacctgaaggaagatatcaaa
gctatcctgagcctgtacgaggccagcttcctggctctggaaggcgaaaacatcctggacgaggcgaaggttttcg
caatctctcatctgaaagaactgtctgaagaaaagatcggtaaagagctggcagaacaggtgaaccatgcactg
gaactgccactgcatcgccgtactcagcgtctggaagcagtatggtctatcgaggcctaccgtaaaaaggaggac
gcgaatcaggttctgctggagctggcaattctggattacaacatgatccagtctgtataccagcgtgatctgcgtgaa
acgtcccgttggtggcgtcgtgtgggtctggcgaccaaactgcactttgctcgtgaccgcctgattgagagcttctact
gggccgtgggtgtagcattcgaaccgcaatactccgactgccgtaactccgtcgcaaaaatgttttctttcgtaaccat
tatcgacgatatctacgatgtatacggcaccctggacgaactggagctgttactgatgcagttgagcgttgggacgt
aaacgccatcaacgacctgccggattacatgaaactgtgcttctggctctgtataacactattaacgaaatcgccta
cgacaacctgaaagataaaggtgagaacatcctgccgtatctgaccaaagcctgggctgacctgtgcaacgctttc
ctgcaagaagccaagtggctgtacaacaaatctactccgacctttgacgactacttcggcaacgcatggaaatcct
cttctggcccgctgcaactggtgttcgcttacttcgctgtcgtgcagaacattaaaaaggaagagatcgaaaacctg
caaaaataccatgacaccatctctcgtcctcccatatcttccgtctgtgcaatgacctggctagcgcgtctgcggaaa
ttgcgcgtggtgaaaccgcaaatagcgtttcttgttacatgcgcactaaaggtatctccgaagaactggctaccgaa
agcgtgatgaatctgatcgatgaaacctggaaaaagatgaacaaggaaaaactgggtggtagcctgttcgcgaa
accgttcgtggaaaccgcgatcaacctggcacgtcaatctcactgcacttatcataacggcgacgcgcataccctc
cggatgagctgacccgcaaacgcgttctgtctgtaatcactgaaccgattctgccgtttgaacgctaaggatccgaat
tcgagctccgtcgacaagcttgcggccgcactcgagcaccaccaccaccaccactgagatccggctgctaacaa
agcccgaaaggaagctgagttggctgctgccaccgctgagcaataactagcataaccccttggggcctctaaacg
ggtcttgaggggttttttgctgaaaggaggaactatatccggat (SEQ ID NO:30)

Figure 137C tggcgaatgggacgcgccctgtagcggcgcattaagcgcggcgggtgtggtggttacgcgcagcgtgaccgctacacttgc
cagcgccctagcgcccgctccttttcgctttcttcccttccttttctcgccacgttcgccggctttccccgtcaagctctaaatcggggg
gctcccttttagggttccgatttagtgctttacggcacctcgaccccaaaaaaacttgattagggtgatggttcacgtagtgggcca
tcgccctgatagacggtttttcgccctttgacgttggagtccacgttctttaatagtggactcttgttccaaactggaacaacactc
aaccctatctcggtctattctttttgatttataagggatttttgccgatttcggcctattggttaaaaaatgagctgatttaacaaaaattt
aacgcgaattttaacaaaatattaacgtttacaattttcaggtggcactttttcggggaaatgtgcgcggaaccccctatttgtttatttt
tctaaatacattcaaatatgtatccgctcatgaattaattcttagaaaaactcatcgagcatcaaatgaaactgcaatttattcata
tcaggattatcaataccatattttgaaaaagccgtttctgtaatgaaggagaaaactcaccgaggcagttccataggatggc
aagatcctggtatcggtctgcgattccgactcgtccaacatcaatacaacctattaatttccctcgtcaaaaataaggttatca
agtgagaaatcaccatgagtgacgactgaatccggtgagaatggcaaaagtttatgcatttctttccagacttgttcaacaggc
cagccattacgctcgtcatcaaaatcactcgcatcaaccaaacgttattcattcgtgattgcgcctgagcgagacgaaatac
gcgatcgctgttaaaggacaattacaaacaggaatcgaatgcaaccggcgcaggaacactgccagcgcatcaacaat
atttttcacctgaatcaggatattcttctaatacctggaatgctgttttcccggggatcgcagtggtgagtaaccatgcatcatcag
gagtacggataaaatgcttgatggtcggaagaggcataaaattccgtcagccagtttagtctgaccatctcatctgtaacatcatt
ggcaacgctacctttgccatgtttcagaaacaactctggcgcatcgggcttcccatacaatcgatagattgtcgcacctgattg
cccgacattatcgcgagcccattatacccatataaatcagcatccatgttggaatttaatcgcggcctagagcaagacgttc
ccgttgaatatggctcataacaccccttgtattactgtttatgtaagcagacagtttattgttcatgaccaaaatcccttaacgtga
gttttcgttccactgagcgtcagacccgtagaaaagatcaaaggatcttcttgagatcctttttttctgcgcgtaatctgctgcttg
caaacaaaaaaaccaccgctaccagcggtggtttgtttgccggatcaagagctaccaactcttttccgaaggtaactggctt
cagcagagcgcagataccaaatactgtccttctagtgtagccgtagttaggccaccacttcaagaactctgtagcaccgcct
acatacctcgctctgctaatcctgttaccagtggctgctgccagtggcgataagtcgtgtcttaccggggttggactcaagacgat
agttaccggataaggcgcagcggtcgggctgaacggggggttcgtgcacacagcccagcttggagcgaacgacctacac
cgaactgagatacctacagcgtgagctatgagaaagcgccacgcttcccgaagggagaaaggcggacaggtatccggt
aagcggcagggtcggaacaggagagcgcacgagggagcttccaggggggaaacgcctggtatctttatagtcctgtcgggt
ttcgccacctctgacttgagcgtcgatttttgtgatgctcgtcaggggggcggagcctatgaaaaacgccagcaacgcggc
cttttttacggttcctggcctttgctggccttttgctcacatgttctttcctgcgttatcccctgattctgtggataaccgtattaccgcctt
gagtgagctgataccgctcgccgcagccgaacgaccgagcgcagcgagtcagtgagcgaggaagcggaagagcgcct
gatgcggtatttctccttacgcatctgtgcggtatttcacaccgcatatatggtgcactctcagtacaatctgctctgatgccgcat
agttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttc
accgtcatcaccgaaacgcgcgaggcagctgcggtaaagctcatcagcgtggtcgtgaagcgattcacagatgtctgcctg
ttcatccgcgtccagctcgttgagtttctccagaagcgttaatgtctggcttctgataaagcgggccatgttaagggcggttttttc
ctgtttggtcactgatgcctccgtgtaagggggattctgttcatgggggtaatgataccgatgaaacgagagaggatgctcac
gatacgggttactgatgatgaacatgcccggttactggaacgttgtgagggtaaacaactggcggtatggatgcggcggga
ccagagaaaaatcactcagggtcaatgccagcgcttcgttaatacagatgtaggtgttccacagggtagccagcagcatcc
tgcgatgcagatccggaacataatggtgcagggcgctgacttccgcgtttccagactttacgaaacacggaaaccgaaga
ccattcatgttgttgctcaggtcgcagacgttttgcagcagcagtcgcttcacgttcgctcgcgtatcggtgattcattctgctaac
cagtaaggcaaccccgccagcctagccgggtcctcaacgacaggagcacgatcatgcgcacccgtggggccgccatgc
cggcgataatggcctgcttctcgccgaaacgtttggtggcgggaccagtgacgaaggcttgagcgagggcgtgcaagattc
cgaataccgcaagcgacaggccgatcatcgtcgcgctccagcgaaagcggtcctcgccgaaaatgacccagagcgctg
ccggcacctgtcctacgagttgcatgataaagaagacagtcataagtgcggcgacgatagtcatgccccgcgcccaccgg
aaggagctgactgggttgaaggctctcaagggcatcggtcgagatcccggtgcctaatgagtgagctaacttacattaattgc
gttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctg
agagagttgcagcaagcggtccacgctggtttgccccagcaggcgaaaatcctgtttgatggtggttaacggcgggatataa
catgagctgtcttcggtatc

Figure 137D gtcgtatcccactaccgagatatccgcaccaacgcgcagcccggactcggtaatggcgcgcattgcgcccagcgc
catctgatcgttggcaaccagcatcgcagtgggaacgatgccctcattcagcatttgcatggtttgttgaaaaccggac
atggcactccagtcgccttcccgttccgctatcggctgaatttgattgcgagtgagatatttatgccagccagccagacg
cagacgcgccgagacagaacttaatgggcccgctaacagcgcgatttgctggtgacccaatgcgaccagatgctc
cacgcccagtcgcgtaccgtcttcatgggagaaaataatactgttgatgggtgtctggtcagagacatcaagaaataa
cgccggaacattagtgcaggcagcttccacagcaatggcatcctggtcatccagcggatagttaatgatcagcccac
tgacgcgttgcgcgagaagattgtgcaccgccgctttacaggcttcgacgccgcttcgttctaccatcgacaccacca
cgctggcacccagttgatcggcgcgagatttaatcgccgcgacaatttgcgacggcgcgtgcagggccagactgga
ggtggcaacgccaatcagcaacgactgtttgcccgccagttgttgtgccacgcggttgggaatgtaattcagctccgc
catcgccgcttccactttttcccgcgttttcgcagaaacgtggctggcctggttcaccacgcgggaaacggtctgataa
gagacaccggcatactctgcgacatcgtataacgttactggtttcacattcaccaccctgaattgactctcttccgggcg
ctatcatgccataccgcgaaaggttttgcgccattcgatggtgtccgggatctcgacgctctcccttatgcgactcctgca
ttaggaagcagcccagtagtaggttgaggccgttgagcaccgccgccgcaaggaatggtgcatgcaaggagatg
gcgcccaacagtcccccggccacgggcctgccaccatacccacgccgaaacaagcgctcatgagcccgaagt
ggcgagcccgatcttccccatcggtgatgtcggcgatataggcgccagcaaccgcacctgtggcgccggtgatgcc
ggccacgatgcgtccggcgtagaggatcgagatctcgatcccgcgaaattaatacgactcactatagggggaattgtg
agcggataacaattcccctctagaaataattttgtttaactttaagaaggagatatacatatgcgttgtagcgtgtccacc
gaaaatgtgtctttcaccgaaactgaaaccgaaacgcgtcgttctgcgaactacgaacctaacagctgggactatga
ttacctgctgtcctccgacacggacgagtccatcgaagtatacaaagacaaagcgaaaaagctggaagccgaagt
tcgtcgcgagattaataacgaaaaagcagaatttctgaccctgccggaactgattgacaacgtccagcgcctgggc
ctgggttaccgtttcgagtctgatatccgtcgtgcgctggatcgcttcgtttcctccggcggcttcgatgcggtaaccaag
acttccctgcacgcgacggcactgtctttccgtctgctgcgtcaacacggttttgaggtttctcaggaagcgttcagcgg
cttcaaagaccaaaacggcaacttcctgaaaaacctgaaggaagatatcaaagctatcctgagcctgtacgaggc
cagcttcctggctctggaaggcgaaaacatcctggacgaggcgaaggttttcgcaatctctcatctgaaagaactgtc
tgaagaaaagatcggtaaagatctggcagaacaggtgaaccatgcactggaactgccactgcatcgccgtactca
gcgtctggaagcagtatggtctatcgaggcctaccgtaaaaaggaggacgcggatcaggttctgctggagctggca
attctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaat
actccgactgccgtaactccgtcgcaaaaatgtttctttcgtaaccattatcgacgatatctacgatgtatacggcaccc
tggacgaactggagctgtttactgacgcagttgagcgttgggacgtaaacgccatcgacgatctgccggattacatga
aactgtgctttctggctctgtataacactattaacgaaatcgcctacgacaacctgaaagataaaggtgagaacatcct
gccgtatctgaccaaagcctgggctgacctgtgcaacgctttcctgcaagaagccaagtggctgtacaacaaatcta
ctccgaccttttgacgaatacttcggcaacgcatggaaatcctcttctggccccgctgcaactggtgttcgcttactcgctgt
cgtgcagaacattaaaaaggaagagatcgataacctgcaaaaataccatgacatcatctctcgtccttcccatatcttc
cgtctgtgcaatgacctggctagcgcgtctgcggaaattgcgcgtggtgaaaccgcaaatagcgtttcttgttacatgc
gcactaaaggtatctccgaagaactggcaccgaaagcgtgatgaatctgatcgatgaaacctggaaaagatga
acaaggaaaaactgggtggtagcctgttcgcgaaaccgttcgtggaaaccgcgatcaacctggcacgtcaatctca
ctgcacttatcataacggcgacgcgcatacctctccggatgagctgacccgcaaacgcgttctgtctgtaatcactga
accgattctgccgtttgaacgctaaggatccgaattcgagctccgtcgacaagcttgcggccgcactcgagcaccac
caccaccactgagatccggctgctaacaaagcccgaaaggaagctgagttggctgctgccaccgctgagca
ataactagcataaccccttggggcctctaaacgggtcttgaggggttttttgctgaaaggaggaactatatccggat (SEQ ID NO:31)

Figure 137E tggcgaatgggacgcgccctgtagcggcgcattaagcgcggcgggtgtggtggttacgcgcagcgtgaccgctacacttgc
cagcgccctagcgcccgctccttttcgctttcttcccttccttctcgccacgttcgccggctttccccgtcaagctctaaatcgggg
gctcccttttaggggttccgatttagtgcttttacggcacctcgaccccaaaaaacttgattagggtgatggttcacgtagtgggcca
tcgccctgatagacggttttttcgcccttttgacgttggagtccacgttctttaatagtggactcttgttccaaactggaacaacactc
aaccctatctcggtctattcttttgatttataagggattttgccgatttcggcctattggttaaaaaatgagctgatttaacaaaaattt
aacgcgaattttaacaaaatattaacgtttacaatttcaggtggcacttttcggggaaatgtgcgcggaaccccctatttgtttattt
tctaaatacattcaaatatgtatccgctcatgaattaattcttagaaaaactcatcgagcatcaaatgaaactgcaatttattcata
tcaggattatcaataccatatttttgaaaaagccgtttctgtaatgaaggagaaaactcaccgaggcagttccataggatggc
aagatcctggtatcggtctgcgattccgactcgtccaacatcaatacaacctattaatttcccctcgtcaaaaataaggttatca
agtgagaaatcaccatgagtgacgactgaatccggtgagaatggcaaaagtttatgcatttctttccagacttgttcaacaggc
cagccattacgctcgtcatcaaaatcactcgcatcaaccaaaccgttattcattcgtgattgcgcctgagcgagacgaaatac
gcgatcgctgttaaaaggacaattacaaacaggaatcgaatgcaaccggcgcaggaacactgccagcgcatcaacaat
attttcacctgaatcaggatattcttctaatacctggaatgctgttttcccggggatcgcagtggtgagtaaccatgcatcatcag
gagtacggataaaatgcttgatggtcggaagaggcataaattccgtcagccagtttagtctgaccatctcatctgtaacatcatt
ggcaacgctacctttgccatgttcagaaacaactctggcgcatcgggcttcccatacaatcgatagattgtcgcacctgattg
cccgacattatcgcgagcccatttatacccatataaatcagcatccatgttggaatttaatcgcggcctagagcaagacgtttc
ccgttgaatatggctcataacaccccttgtattactgtttatgtaagcagacagttttattgttcatgaccaaaatcccttaacgtga
gttttcgttccactgagcgtcagaccccgtagaaaagatcaaaggatcttcttgagatcctttttttctgcgcgtaatctgctgcttg
caaacaaaaaaaccaccgctaccagcggtggtttgtttgccggatcaagagctaccaactctttttccgaaggtaactggctt
cagcagagcgcagataccaaatactgtccttcagtgtagccgtagttaggccaccacttcaagaactctgtagcaccgcct
acatacctcgctctgctaatcctgttaccagtggctgctgccagtggcgataagtcgtgtcttaccgggttggactcaagacgat
agttaccggataaggcgcagcggtcgggctgaacggggggttcgtgcacacagcccagcttggagcgaacgacctacac
cgaactgagatacctacagcgtgagctatgagaaagcgccacgcttccgaagggagaaaggcggacaggtatccggt
aagcggcagggtcggaacaggagagcgcacgagggagcttccaggggggaaacgcctggtatctttatagtcctgtcgggt
ttcgccacctctgacttgagcgtcgatttttgtgatgctcgtcaggggggcggagcctatggaaaaacgccagcaacgcggc
cttttttacggttcctggccttttgctggccttttgctcacatgttctttcctgcgttatcccctgattctgtggataaccgtattaccgcctt
gagtgagctgataccgctcgccgcagccgaacgaccgagcgcagcgagtcagtgagcgaggaagcggaagagcgcct
gatgcggtattttctccttacgcatctgtgcggtatttcacaccgcatatatggtgcactctcagtacaatctgctctgatgccgcat
agttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttc
accgtcatcaccgaaacgcgcgaggcagctgcggtaaagctcatcagcgtggtcgtgaagcgattcacagatgtctgcctg
ttcatccgcgtccagctcgttgagtttctccagaagcgttaatgtctggcttctgataaagcgggccatgttaagggcggttttttc
ctgtttggtcactgatgcctccgtgtaagggggatttctgttcatgggggtaatgataccgatgaaacgagagaggatgctcac
gatacgggttactgatgatgaacatgcccggttactggaacgttgtgagggtaaacaactggcggtatggatgcggcggga
ccagagaaaaatcactcagggtcaatgccagcgcttcgttaatacagatgtaggtgttccacagggtagccagcagcatcc
tgcgatgcagatccggaacataatggtgcagggcgctgacttccgcgtttccagactttacgaaacacggaaaccgaaga
ccattcatgttgttgctcaggtcgcagacgttttgcagcagcagtcgcttcacgttcgctcgcgtatcggtgattcattctgctaac
cagtaaggcaaccccgccagcctagccgggtcctcaacgacaggagcacgatcatgcgcacccgtggggccgccatgc
cggcgataatggcctgcttctcgccgaaacgtttggtggcgggaccagtgacgaaggcttgagcgagggcgtgcaagattc
cgaataccgcaagcgacaggccgatcatcgtcgcgctccagcgaaagcggtcctcgccgaaaatgacccagagcgctg
ccggcacctgtcctacgagttgcatgataaagaagacagtcataagtgcggcgacgatagtcatgccccgcgcccaccgg
aaggagctgactgggttgaaggctctcaagggcatcggtcgagatcccggtgcctaatgagtgagctaacttacattaattgc
gttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctg
agagagttgcagcaagcggtccacgctggtttgccccagcaggcgaaaatcctgtttgatggtggttaacggcgggatataa
catgagctgtcttcggtatc

Figure 137F gtcgtatcccactaccgagatatccgcaccaacgcgcagcccggactcggtaatggcgcgcattgcgcccagcg
ccatctgatcgttggcaaccagcatcgcagtgggaacgatgccctcattcagcatttgcatggtttgttgaaaaccgg
acatggcactccagtcgccttcccgttccgctatcggctgaatttgattgcgagtgagatatttatgccagccagccag
acgcagacgcgccgagacagaacttaatgggcccgctaacagcgcgatttgctggtgacccaatgcgaccagat
gctccacgcccagtcgcgtaccgtcttcatgggagaaaataatactgttgatgggtgtctggtcagagacatcaaga
aataacgccggaacattagtgcaggcagcttccacagcaatggcatcctggtcatccagcggatagttaatgatca
gcccactgacgcgttgcgcgagaagattgtgcaccgccgctttacaggcttcgacgccgcttcgttctaccatcgac
accaccacgctggcacccagttgatcggcgcgagatttaatcgccgcgacaatttgcgacggcgcgtgcagggc
cagactggaggtggcaacgccaatcagcaacgactgtttgcccgccagttgttgtgccacgcggttgggaatgtaa
ttcagctccgccatcgccgcttccactttttcccgcgttttcgcagaaacgtggctggcctggttcaccacgcgggaaa
cggtctgataagagacaccggcatactctgcgacatcgtataacgttactggtttcacattcaccaccctgaattgact
ctcttccgggcgctatcatgccataccgcgaaaggttttgcgccattcgatggtgtccgggatctcgacgctctcccta
tgcgactcctgcattaggaagcagcccagtagtaggttgaggccgttgagcaccgccgccgcaaggaatggtgc
atgcaaggagatggcgcccaacagtccccggccacggggcctgccaccatacccacgccgaaacaagcgct
catgagcccgaagtggcgagcccgatcttccccatcggtgatgtcggcgatataggcgccagcaaccgcacctgt
ggcgccggtgatgccggccacgatgcgtccggcgtagaggatcgagatctgatcccgcgaaattaatacgactc
actataggggaattgtgagcggataacaattcccctctagaaataattttgtttaactttaagaaggagatatacatat
gcgttgtagcgtgtccaccgaaaatgtgtctttctctgaaactgaaaccgaaacgcgtcgttctgcgaactacgaacc
taacagctgggactatgattacctgctgtcctccgacacggacgagtccatcgaagtacacaaagacaaagcga
aaaagctggaagccgaagttcgtcgcgagattaataacgaaaaagcagaatttctgaccctgctggaactgattg
acaacgtccagcgcctgggcctgggttaccgtttcgagtctgatatccgtcgtgcgctggatcgcttcgtttcctccggc
ggcttcgatggcgtaaccaagacttcctgcacggtacggcactgtctttccgtctgctgcgtcaacacggttttgagg
tttctcaggaagcgttcagcggcttcaaagaccaaaacggcaacttcctggagaacctgaaggaagatatcaaag
ctatcctgagcctgtacgaggccagcttcctggctctggaaggcgaaaacatcctggacgaggcgaaggttttcgc
aatctctcatctgaaagaactgtctgaagaaaagatcggtaaagagctggcagaacaggtgcccatgcactgga
actgccactgcatcgccgtactcagcgtctggaagcagtatggtctatcgaggcctaccgtaaaaaggaggacgc
gaaccaggttctgctggagctggcaattctggattacaacatgatccagtctgtataccagcgtgatctgcgtgaaac
gtcccgttggtggcgtcgtgtgggtctggcgaccaaactgcactttgctcgtgaccgcctgattgagagcttctactgg
gccgtgggtgtagcattcgaaccgcaatactccgactgccgtaactccgtcgcaaaaatgttttctttcgtaaccattat
cgacgatatctacgatgtatacggcaccctggacgaactggagctgtttactgatgcagttgagcgttgggacgtaa
acgccatcaacgacctgccggattacatgaaactgtgctttctggctctgtataacactattaacgaaatcgcctacg
acaacctgaaagataaaggtgagaacatcctgccgtatctgaccaaagcctgggctgacctgtgcaacgctttcct
gcaagaagccaagtggctgtacaacaaatctactccgacctttgacgactacttcggcaacgcatggaaatcctctt
ctggcccgctgcaactgatcttcgcttacttcgctgtcgtgcagaacattaaaaaggaagagatcgaaaacctgca
aaaataccatgacatcatctctcgtccttcccatatcttccgtctgtgcaatgacctggctagcgcgtctgcggaaattg
cgcgtggtgaaaccgcaaatagcgtttcttgttacatgcgcactaaaggtatctccgaagaactggctaccgaaag
cgtgatgaatctgatcgatgaaacctggaaaagatgaacaaggaaaaactgggtggtagcctgttcgcgaaac
cgttcgtggaaaccgcgatcaacctggcacgtcaatctcactgcacttatcataacggcgacgcgcatacctctccg
gatgagctgacccgcaaacgcgttctgtctgtaatcactgaaccgattctgccgtttgaacgctaaggatccgaattc
gagctccgtcgacaagcttgcggccgcactcgagcaccaccaccaccaccactgagatccggctgctaacaaa
gcccgaaaggaagctgagttggctgctgccaccgctgagcaataactagcataaccccttggggcctctaaacgg
gtcttgaggggttttttgctgaaaggaggaactatatccggat (SEQ ID NO:32)

Figure 137G

MRCSVSTENVSFSETETETRRSANYEPNSWDYDYLLSSDTDESIEVHKDKAK
KLEAEVRREINNEKAEFLTLLELIDNVQRLGLGYRFESDIRRALDRFVSSGGFD
GVTKTSLHGTALSFRLLRQHGFEVSQEAFSGFKDQNGNFLENLKEDIKAILSL
YEASFLALEGENILDEAKVFAISHLKELSEEKIGKELAEQVSHALELPLHRRTQ
RLEAVWSIEAYRKKEDANQVLLELAILDYNMIQSVYQRDLRETSRWWRRVGL
ATKLHFARDRLIESFYWAVGVAFEPQYSDCRNSVAKMFSFVTIIDDIYDVYGTL
DELELFTDAVERWDVNAINDLPDYMKLCFLALYNTINEIAYDNLKDKGENILPY
LTKAWADLCNAFLQEAKWLYNKSTPTFDDYFGNAWKSSSGPLQLIFAYFAVV
QNIKKEEIENLQKYHDIISRPSHIFRLCNDLASASAEIARGETANSVSCYMRTK
GISEELATESVMNLIDETWKKMNKEKLGGSLFAKPFVETAINLARQSHCTYHN
GDAHTSPDELTRKRVLSVITEPILPFER (SEQ ID NO: 33)

Figure 137H tggcgaatgggacgcgccctgtagcggcgcattaagcgcggcgggtgtggtggttacgcgcagcgtgaccgctacactt
gccagcgccctagcgcccgctccttcgctttcttcccttccttctcgccacgttcgccggctttcccgtcaagctctaaatcg
ggggctcccttaggtccgatttagtgctttacggcacctcgaccccaaaaaaacttgattagggtgatggttcacgtagtgg
gccatcgccctgatagacggttttcgcccttgacgttggagtccacgttctttaatagtggactcttgttccaaactggaaca
acactcaaccctatctcggtctattcttttgatttataagggattttgccgatttcggcctattggttaaaaaatgagctgatttaac
aaaaatttaacgcgaattttaacaaaatattaacgtttacaatttcaggtggcacttttcggggaaatgtgcgcggaacccct
atttgtttattttctaaatacattcaaatatgtatccgctcatgaattaattcttagaaaaactcatcgagcatcaaatgaaactg
caatttattcatatcaggattatcaataccatattttgaaaaagccgtttctgtaatgaaggagaaaactcaccgaggcagtt
ccataggatggcaagatcctggtatcggtctgcgattccgactcgtccaacatcaatacaacctattaatttcccctcgtcaa
aaataaggttatcaagtgagaaatcaccatgagtgacgactgaatccggtgagaatggcaaaagtttatgcatttctttcca
gacttgttcaacaggccagccattacgctcgtcatcaaaatcactcgcatcaaccaaaccgttattcattcgtgattgcgcct
gagcgagacgaaatacgcgatcgctgttaaaaggacaattacaaacaggaatcgaatgcaaccggcgcaggaacact
gccagcgcatcaacaatattttcacctgaatcaggatattcttctaatacctggaatgctgttttcccggggatcgcagtggtg
agtaaccatgcatcatcaggagtacggataaaatgcttgatggtcggaagaggcataaattccgtcagccagtttagtctg
accatctcatctgtaacatcattggcaacgctacctttgccatgtttcagaaacaactctggcgcatcgggcttcccatacaat
cgatagattgtcgcacctgattgcccgacattatcgcgagcccatttatacccatataaatcagcatccatgttggaatttaat
cgcggcctagagcaagacgtttcccgttgaatatggctcataacaccccttgtattactgtttatgtaagcagacagttttattgt
tcatgaccaaaatcccttaacgtgagttttcgttccactgagcgtcagaccccgtagaaaagatcaaaggatcttcttgagat
ccttttttctgcgcgtaatctgctgcttgcaaacaaaaaaaccaccgctaccagcggtggtttgtttgccggatcaagagcta
ccaactcttttccgaaggtaactggcttcagcagagcgcagataccaaatactgtccttctagtgtagccgtagttaggcca
ccacttcaagaactctgtagcaccgcctacatacctcgctctgctaatcctgttaccagtggctgctgccagtggcgataagt
cgtgtcttaccgggttggactcaagacgatagttaccggataaggcgcagcggtcgggctgaacggggggtcgtgcaca
cagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccagg
gggaaacgcctggtatctttatagtcctgtcgggtttcgccacctctgacttgagcgtcgatttttgtgatgctcgtcagggggg
cggagcctatggaaaaacgccagcaacgcggccttttacggttcctggccttttgctggccttttgctcacatgttctttcctgc
gttatcccctgattctgtggataaccgtattaccgcctttgagtgagctgataccgctcgccgcagccgaacgaccgagcgc
agcgagtcagtgagcgaggaagcggaagagcgcctgatgcggtattttctccttacgcatctgtgcggtatttcacaccgc
atatatggtgcactctcagtacaatctgctctgatgccgcatagttaagccagtatacactccgctatcgctacgtgactgggt
catggctgcgccccgacacccgccaacacccgctgacgcgccctgacgggcttgtctgctcccggcatccgcttacaga
caagctgtgaccgtctccgggagctgcatgtgtcagaggttttcaccgtcatcaccgaaacgcgcgaggcagctgcggta
aagctcatcagcgtggtcgtgaagcgattcacagatgtctgcctgttcatccgcgtccagctcgttgagtttctccagaagcgt
taatgtctggcttctgataaagcgggccatgttaagggcggttttttcctgtttggtcactgatgcctccgtgtaagggggatttct
gttcatgggggtaatgataccgatgaaacgagagaggatgctcacgatacgggttactgatgatgaacatgcccggttact
ggaacgttgtgagggtaaacaactggcggtatggatgcggcgggaccagagaaaaatcactcagggtcaatgccagc
gcttcgttaatacagatgtaggtgttccacagggtagccagcagcatcctgcgatgcagatccggaacataatggtgcagg
gcgctgacttccgcgtttccagactttacgaaacacggaaaccgaagaccattcatgttgttgctcaggtcgcagacgttttg
cagcagcagtcgcttcacgttcgctcgcgtatcggtgattcattctgctaaccagtaaggcaacccgccagcctagccgg
gtcctcaacgacaggagcacgatcatgcgcacccgtggggccgccatgccggcgataatggcctgcttctcgccgaaac
gtttggtggcgggaccagtgacgaaggcttgagcgagggcgtgcaagattccgaataccgcaagcgacaggccgatca
tcgtcgcgctccagcgaaagcggtcctcgccgaaaatgacccagagcgctgccggcacctgtcctacgagttgcatgat
aaagaagacagtcataagtgcggcgacgatagtcatgccccgcgcccaccggaaggagctgactgggttgaaggctct
caagggcatcggtcgagatcccggtgcctaatgagtgagctaacttacattaattgcgttgcgctcactgcccgctttccagt
cgggaaaccgtcgtgccagctgcattaatgaatcggccaacgcgcggggagaggcggtttgcgtattgggcgccaggg
tggttttcttttcaccagtgagacgggcaacagctgattgcccttcaccgcctggccctgagagagttgcagcaagcggtcc
acgctggtttgccccagcaggcgaaaatcctgtttgatggtggttaacggcgggatataacatgagctgtcttcggtatc

Figure 137I gtcgtatcccactaccgagatatccgcaccaacgcgcagcccggactcggtaatggcgcgcattgcgcccagcgc
catctgatcgttggcaaccagcatcgcagtgggaacgatgccctcattcagcatttgcatggtttgttgaaaaccggac
atggcactccagtcgccttcccgttccgctatcggctgaatttgattgcgagtgagatatttatgccagccagccagacg
cagacgcgccgagacagaacttaatgggcccgctaacagcgcgatttgctggtgacccaatgcgaccagatgctc
cacgcccagtcgcgtaccgtcttcatgggagaaaataatactgttgatgggtgtctggtcagagacatcaagaaata
acgccggaacattagtgcaggcagcttccacagcaatggcatcctggtcatccagcggatagtaatgatcagccc
actgacgcgttgcgcgagaagattgtgcaccgccgctttacaggcttcgacgccgcttcgttctaccatcgacaccac
cacgctggcacccagttgatcggcgcgagatttaatcgccgcgacaatttgcgacggcgcgtgcagggccagact
ggaggtggcaacgccaatcagcaacgactgtttgcccgccagtgttgtgccacgcggttgggaatgtaattcagctc
cgccatcgccgcttccactttttcccgcgttttcgcagaaacgtggctggcctggttcaccacgcgggaaacggtctga
taagagacaccggcatactctgcgacatcgtataacgttactggtttcacattcaccaccctgaattgactctcttccgg
gcgctatcatgccataccgcgaaaggttttgcgccattcgatggtgtccgggatctcgacgctctcccttatgcgactcc
tgcattaggaagcagcccagtagtaggttgaggccgttgagcaccgccgccgcaaggaatggtgcatgcaagga
gatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtga
tgccggccacgatgcgtccggcgtagaggatcgagatctcgatcccgcgaaattaatacgactcactatagggaa
ttgtgagcggataacaattcccctctagaaataattttgtttaactttaagaaggagatatacatatgcatatgcgttgtag
cgtgtccaccgaaaatgtgtctttcaccgaaactgaaaccgaaacgcgtcgttctgcgaactacgaacctaacagct
gggactatgattacctgctgtcctccgacacggacgagtccatcgaagtatacaaagacaaagcgaaaaagctgg
aagccgaagttcgtcgcgagattaataacgaaaaagcagaatttctgaccctgctggaactgattgacaacgtcca
gcgcctgggcctgggttaccgtttcgagtctgatatccgtcgtgcgctggatcgcttcgtttcctccggcggcttcgatgc
ggtaaccaagacttccctgcacgcgacggcactgtctttccgtctgctgcgtcaacacggttttgaggtttctcaggaag
cgttcagcggcttcaaagaccaaaacggcaacttcctggagaacctgaaggaagatatcaaagctatcctgagcct
gtacgaggccagcttcctggctctggaaggcgaaaacatcctggacgaggcgaaggttttcgcaatctctcatctga
aagaactgtctgaagaaagatcggtaaagatctggcagaacaggtgaaccatgcactggaactgccactgcatc
gccgtactcagcgtctggaagcagtactgtctatcgaggcctaccgtaaaaaggaggacgcggatcaggttctgctg
gagctggcaattctggattacaacatgatccagtctgtataccagcgtgatctgcgtgaaacgtcccgttggtggcgtc
gtgtgggtctggcgaccaaactgcactttgctcgtgaccgcctgattgagagcttctactgggccgtgggtgtagcattc
gaaccgcaatactccgactgccgtaactccgtcgcaaaaatgtttctttcgtaaccattatcgacgatatctacgatgt
atacggcaccctggacgaactggagctgttactaacgcagttgagcgttgggacgtaaacgccatcgacgatctgc
cggattacatgaaactgtgctttctggctctgtataacactattaacgaaatcgcctacgacaacctgaaagaaaaag
gtgagaacatcctgccgtatctgaccaaagcctgggctgacctgtgcaacgctttcctgcaagaagccaagtggctg
tacaacaaatctactccgacctttgacgaatacttcggcaacgcatggaaatcctcttctggcccgctgcaactggtgtt
cgcttacttcgctgtcgtgcagaacattaaaaaggaagagatcgaaaacctgcaaaaataccatgacatcatctctc
gtccttcccatatcttccgtctgtgcaatgacctggctagcgcgtctgcggaaattgcgcgtggtgaaaccgcaaatag
cgtttcttgttacatgcgcactaaaggtatctccgaagaactggctaccgaaagcgtgatgaatctgatcgatgaaac
ctggaaaaagatgaacaaggaaaaactgggtgtagcctgttcgcgaaaccgttcgtggaaaccgcgatcaacct
ggcacgtcaatctcactgcacttatcataacggcgacgcgcataccctccggatgagctgacccgcaaacgcgttc
tgtctgtaatcactgaaccgattctgccgtttgaacgctaaggatccgaattcgagctccgtcgacaagcttgcggccg
cactcgagcaccaccaccaccaccactgagatccggctgctaacaaagcccgaaaggaagctgagttggctgct
gccaccgctgagcaataactagcataaccccttggggcctctaaacgggtcttgaggggttttttgctgaaaggagg
aactatatccggat (SEQ ID NO:34)

Figure 137J tggcgaatgggacgcgccctgtagcggcgcattaagcgcggcgggtgtggtggttacgcgcagcgtgaccgctacactt
gccagcgccctagcgcccgctcctttcgctttcttcccttcctttctcgccacgttcgccggctttccccgtcaagctctaaatcg
ggggctcccttagggttccgatttagtgctttacggcacctcgaccccaaaaaaacttgattagggtgatggttcacgtagtgg
gccatcgccctgatagacggttttcgcccttgacgttggagtccacgttctttaatagtggactcttgttccaaactggaaca
acactcaaccctatctcggtctattcttttgatttataagggatttgccgatttcggcctattggtaaaaaatgagctgatttaac
aaaaatttaacgcgaattttaacaaaatattaacgtttacaatttcaggtggcacttttcggggaaatgtgcgcggaacccct
atttgtttattttctaaatacattcaaatatgtatccgctcatgaattaattcttagaaaaactcatcgagcatcaaatgaaactg
caatttattcatatcaggattatcaataccatatttttgaaaaagccgtttctgtaatgaaggagaaaactcaccgaggcagtt
ccataggatggcaagatcctggtatcggtctgcgattccgactcgtccaacatcaatacaacctattaatttcccctcgtcaa
aaataaggttatcaagtgagaaatcaccatgagtgacgactgaatccggtgagaatggcaaaagtttatcatttctttcca
gacttgttcaacaggccagccattacgctcgtcatcaaaatcactcgcatcaaccaaaccgttattcattcgtgattgcgcct
gagcgagacgaaatacgcgatcgctgttaaaaggacaattacaaacaggaatcgaatgcaaccggcgcaggaacact
gccagcgcatcaacaatattttcacctgaatcaggatattcttctaatacctggaatgctgttttccggggatcgcagtggtg
agtaaccatgcatcatcaggagtacggataaaatgcttgatggtcggaagaggcataaattccgtcagccagtttagtctg
accatctcatctgtaacatcattggcaacgctacctttgccatgtttcagaaacaactctggcgcatcgggcttcccatacaat
cgatagattgtcgcacctgattgcccgacattatcgcgagcccatttatacccatataaatcagcatccatgttggaatttaat
cgcggcctagagcaagacgtttcccgttgaatatggctcataacaccccttgtattactgtttatgtaagcagacagttttattgt
tcatgaccaaaatcccttaacgtgagttttcgttccactgagcgtcagacccgtagaaaagatcaaaggatcttcttgagat
ccttttttctcgcgcgtaatctgctgcttgcaaacaaaaaaaccaccgctaccagcggtggtttgtttgccggatcaagagcta
ccaactcttttccgaaggtaactggcttcagcagagcgcagataccaaatactgtccttctagtgtagccgtagttaggcca
ccacttcaagaactctgtagcaccgcctacatacctcgctctgctaatcctgttaccagtggctgctgccagtggcgataagt
cgtgtcttaccgggttggactcaagacgatagttaccggataaggcgcagcggtcgggctgaacggggggttcgtgcaca
cagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccagg
gggaaacgcctggtatctttatagtcctgtcgggtttcgccacctctgacttgagcgtcgatttttgtgatgctcgtcaggggg
cggagcctatggaaaaacgccagcaacgcggcctttttacggttcctggccttttgctggccttttgctcacatgttcttcctgc
gttatcccctgattctgtggataaccgtattaccgcctttgagtgagctgataccgctcgccgcagccgaacgaccgagcgc
agcgagtcagtgagcgaggaagcggaagagcgcctgatgcggtattttctccttacgcatctgtgcggtatttcacaccgc
atatatggtgcactctcagtacaatctgctctgatgccgcatagttaagccagtatacactccgctatcgctacgtgactgggt
catggctgcgccccgacacccgccaacacccgctgacgcgccctgacgggcttgtctgctcccggcatccgcttacaga
caagctgtgaccgtctccgggagctgcatgtgtcagaggttttcaccgtcatcaccgaaacgcgcgaggcagctgcggta
aagctcatcagcgtggtcgtgaagcgattcacagatgtctgcctgttcatccgcgtccagctcgttgagtttctccagaagcgt
taatgtctggcttctgataaagcgggccatgttaagggcggttttttcctgtttggtcactgatgcctccgtgtaaggggatttct
gttcatgggggtaatgataccgatgaaacgagagaggatgctcacgatacgggttactgatgatgaacatgcccggttact
ggaacgttgtgagggtaaacaactggcggtatggatgcggcgggaccagagaaaaatcactcagggtcaatgccagc
gcttcgttaatacagatgtaggtgttccacagggtagccagcagcatcctgcgatgcagatccggaacataatggtgcagg
gcgctgacttccgcgtttccagactttacgaaacacggaaaccgaagaccattcatgttgttgctcaggtcgcagacgttttg
cagcagcagtcgcttcacgttcgctcgcgtatcggtgattcattctgctaaccagtaaggcaaccccgccagcctagccgg
gtcctcaacgacaggagcacgatcatgcgcacccgtggggccgccatgccggcgataatgcctgcttctcgccgaaac
gtttggtggcgggaccagtgacgaaggcttgagcgagggcgtgcaagattccgaataccgcaagcgacaggccgatca
tcgtcgcgctccagcgaaagcggtcctcgccgaaaatgacccagagcgctgccggcacctgtcctacgagttgcatgat
aaagaagacagtcataagtgcggcgacgatagtcatgccccgcgcccaccggaaggagctgactgggttgaaggctct
caagggcatcggtcgagatcccggtgcctaatgagtgagctaacttacattaattgcgttgcgctcactgcccgctttccagt
cgggaaacctgtcgtgccagctgcattaatgaatcggccaacgcgcggggagaggcggtttgcgtattgggcgccaggg
tggtttttcttttcaccagtgagacgggcaacagctgattgcccttcaccgcctggccctgagagagttgcagcaagcggtcc
acgctggtttgccccagcaggcgaaaatcctgtttgatggtggttaacggcgggatataacatgagctgtcttcggtatc

Figure 137K gtcgtatcccactaccgagatatccgcaccaacgcgcagcccggactcggtaatggcgcgcattgcgcccagcgc
catctgatcgttggcaaccagcatcgcagtgggaacgatgccctcattcagcatttgcatggtttgttgaaaaccggac
atggcactccagtcgccttcccgttccgctatcggctgaatttgattgcgagtgagatatttatgccagccagccagacg
cagacgcgccgagacagaacttaatgggcccgctaacagcgcgatttgctggtgacccaatgcgaccagatgctc
cacgcccagtcgcgtaccgtcttcatgggagaaaataatactgttgatgggtgtctggtcagagacatcaagaaataa
cgccggaacattagtgcaggcagcttccacagcaatggcatcctggtcatccagcggatagttaatgatcagcccac
tgacgcgttgcgcgagaagattgtgcaccgccgctttacaggcttcgacgccgcttcgttctaccatcgacaccacca
cgctggcacccagttgatcggcgcgagatttaatcgccgcgacaatttgcgacggcgcgtgcagggccagactgga
ggtggcaacgccaatcagcaacgactgtttgcccgccagttgttgtgccacgcggttgggaatgtaattcagctccgc
catcgccgcttccactttttcccgcgttttcgcagaaacgtggctggcctggttcaccacgcgggaaacggtctgataa
gagacaccggcatactctgcgacatcgtataacgttactggtttcacattcaccaccctgaattgactctcttccgggcg
ctatcatgccataccgcgaaaggttttgcgccattcgatggtgtccgggatctcgacgctctcccttatgcgactcctgca
ttaggaagcagcccagtagtaggttgaggccgttgagcaccgccgcgcaaggaatggtgcatgcaaggagatg
gcgcccaacagtcccccggccacggggcctgccaccatacccacgccgaaacaagcgctcatgagcccgaagt
ggcgagcccgatcttccccatcggtgatgtcggcgatataggcgccagcaaccgcacctgtggcgccggtgatgcc
ggccacgatgcgtccggcgtagaggatcgagatctcgatcccgcgaaattaatacgactcactatagggggaattgtg
agcggataacaattcccctctagaaataattttgtttaactttaagaaggagatatacatatgtgctctgtttctaccgaga
acgtttccttcactgagacggaaaccgaggcacgtcgtagcgcgaactacgagccgaatagctgggactacgattt
cctgctgtcttccgatactgacgaatctattgaggtgtacaaagacaaagcaaagaaactggaggctgaagtgcgcc
gcgaaattaacaacgagaaagctgaattcctgactctgctggagctgatcgataacgtacagcgcctgggtctgggtt
accgcttcgaatctgatatccgtcgcgcactggatcgtttcgtaagcagcggcggtttcgatggcgtgaccaaaacga
gcctgcacgctaccgcgctgtccttccgtctgctgcgtcagcacggcttcgaagtttctcaggaagcattctccggtttca
aagatcaaaacggtaacttcctggaaaacctgaaagaagacactaaggcgatcctgagcctgtatgaggcaagct
ttctggccctggagggtgagaacatcctggatgaggcgcgcgtattctccatctcccatctgaaagagctgtctgaag
agaaaatcggtaaggaactggcagagcaggttaatcacgcactggaactgccgctgcatcgtcgtacccagcgtct
ggaggcggtttggtccatcgaagcgtaccgcaaaaaggaggatgctaaccaggtctgctggaactggccatcctg
gactacaacatgatccagtccgttaccagcgtgatctgcgtgaaacctcccgttggtggcgccgtgtgggcctggcg
accaaactgcacttcgctaaggaccgcctgattgagtctttttactgggcagtcggcgttgcgttcgaacctcagtattct
gactgccgtaacagcgttgcgaaaatgttcagcttcgttactattatcgacgacatctacgacgtttacggtactctgga
cgagctggaactgtttaccgacgctgtcgaacgttgggatgttaacgccatcaacgatctgcctgactacatgaaact
gtgcttcctggcactgtataacacgatcaacgaaattgcatacgacaacctgaaagacaaaggtgaaaacatcctg
ccgtacctgactaaagcgtgggcggatctgtgtaacgcttttctgcaagaagcgaaatggctgtataacaaatccact
ccgaccttgacgattattcggcaatgcctggaaatccagctctggcccgctgcaactgatcttcgcttattttgcggttgt
ccaaaacatcaaaaggaggaaattgaaaacctgcaaaaataccacgatatcattagccgtccttctcatatctttcg
cctgtgcaacgacctggcaagcgcgtccgcagagatcgcacgtggcgaaaccgctaactctgttcctgctacatgc
gcaccaagggcatttccgaagagctggcaaccgagagcgtaatgaatctgatcgacgaaacctgtaagaaaatg
aacaaagaaaaactgggtggctccctgttcgctaaaccgttcgtagagactgctattaacctggcacgtcagagcca
ctgcacctaccacaatggtgacgcacatactagcccggatgaactgactcgtaaacgtgtactgtctgttatcaccga
accgattctgccgttcgaacgttaactgcagctggtaggatccgaattcgagctccgtcgacaagcttgcggccgcac
tcgagcaccaccaccaccaccactgagatccggctgctaacaaagcccgaaaggaagctgagttggctgctgcc
accgctgagcaataactagcataaccccttggggcctctaaacgggtcttgaggggttttttgctgaaaggaggaact
atatccggat (SEQ ID NO:35)

Figure 137M

Plasmid MCM93 = pCR2.1-Kudzu
aagggcgaatactgcagatatccatcacactggcggccgctcgagcatgcatctagagggcccaattcgccctatagtgagtc
gtattacaattcactggccgtcgttttacaacgtcgtgactgggaaaaccctggcgttacccaacttaatcgccttgcagcacatcc
ccctttcgccagctggcgtaatagcgaagaggcccgcaccgatcgcccttcccaacagttgcgcagcctgaatggcgaatgga
cgcgccctgtagcggcgcattaagcgcggcgggtgtggtggttacgcgcagcgtgaccgctacacttgccagcgccctagcgc
ccgctcctttcgctttcttcccttcctttctcgccacgttcgccggctttccccgtcaagctctaaatcgggggctcccctttagggttccga
tttagtgctttacggcacctcgaccccaaaaaacttgattagggtgatggttcacgtagtgggccatcgccctgatagacggttttc
gcccttttgacgttggagtccacgttctttaatagtggactcttgttccaaactggaacaacactcaaccctatctcggtctattctttga
tttataaggattttgccgatttcggcctattggttaaaaaatgagctgatttaacaaaaatttaacgcgaattttaacaaaattcagg
gcgcaagggctgctaaaggaagcggaacacgtagaaagccagtccgcagaaacggtgctgacccggatgaatgtcagct
actgggctatctggacaagggaaaacgcaagcgcaaagagaaagcaggtagcttgcagtgggcttacatggcgatagctag
actgggcggttttatggacagcaagcgaaccggaattgccagctggggcgccctctggtaaggttgggaagccctgcaaagta
aactggatggctttcttgccgccaaggatctgatggcgcagggatcaagatctgatcaagagacaggatgaggatcgtttcgc
atgattgaacaagatggattgcacgcaggttctccggccgcttgggtggagaggctattcggctatgactgggcacaacagaca
atcggctgctctgatgccgccgtgttccggctgtcagcgcaggggcgcccggttcttttttgtcaagaccgacctgtccggtgccctg
aatgaactgcaggacgaggcagcgcggctatcgtggctggccacgacgggcgttccttgcgcagctgtgctcgacgttgtcact
gaagcgggaagggactggctgctattgggcgaagtgccggggcaggatcCcctgtcatcccaccttgctcctgccgagaaag
tatccatcatggctgatgcaatgcggcggctgcatacgcttgatccggctacctgcccattcgaccaccaagcgaaacatcgcat
cgagcgagcacgtactcgatggaagccggtcttgtcgatcaggatgatctggacgaagagcatcagggggctcgcgccagcc
gaactgttcgccaggctcaaggcgcgcatgcccgacggcgaggatctcgtcgtgacccatggcgatgcctgcttgccgaatatc
atggtggaaaatggccgcttttctggattcatcgactgtggccggctgggtgtggcggaccgctatcaggacatagcgttggctac
ccgtgatattgctgaagagcttggcggcgaatgggctgaccgcttcctcgtgctttacggtatcgccgctcccgattcgcagcgcat
cgccttctatcgccttcttgacgagttcttctgaattgaaaaaggaagagtatgagtattcaacatttccgtgtcgcccttattccctttttt
gcggcattttgccttcctgtttttgctcacccagaaacgctggtgaaagtaaaagatgctgaagatcagttgggtgcacgagtgggt
tacatcgaactggatctcaacagcggtaagatccttgagagttttcgccccgaagaacgttttccaatgatgagcacttttaaagttc
tgctatgtggcgcggtattatcccgtattgacgccgggcaagagcaactcggtcgccgcatacactattctcagaatgacttggttg
agtactcaccagtcacagaaaagcatcttacggatggcatgacagtaagagaattatgcagtgctgccataaccatgagtgata
acactgcggccaacttacttctgacaacgatcggaggaccgaaggagctaaccgcttttttgcacaacatgggggatcatgtaa
ctcgccttgatcgttgggaaccggagctgaatgaagccataccaaacgacgagcgtgacaccacgatgcctgtagcaatggc
aacaacgttgcgcaaactattaactggcgaactacttactctagcttcccggcaacaattaatagactggatggaggcggataa
agttgcaggaccacttctgcgctcggcccttccggctggctggtttattgctgataaatctggagccggtgagcgtgggtctcgcgg
tatcattgcagcactggggccagatggtaagccctcccgtatcgtagttatctacacgacggggagtcaggcaactatggatgaa
cgaaatagacagatcgctgagataggtgcctcactgattaagcattggtaactgtcagaccaagtttactcatatatactttagattg
atttaaaacttcattttaatttaaaaggatctaggtgaagatcctttttgataatctcatgaccaaaatcccttaacgtgagttttcgttcc
actgagcgtcagaccccgtagaaaagatcaaaggatcttcttgagatcctttttttctgcgcgtaatctgctgcttgcaaacaaaaa
aaccaccgctaccagcggtggtttgtttgccggatcaagagctaccaactctttttccgaaggtaactggcttcagcagagcgca
gataccaaatactgttcttctagtgtagccgtagttaggccaccacttcaagaactctgtagcaccgcctacatacctcgctctgcta
atcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcg
tgagctatgagaaagcgccacgcttcccgaagggagaaaggcggacaggtatccggtaagcggcagggtcggaacagga
gagcgcacgagggagcttccaggggaaacgcctggtatctttatagtcctgtcgggtttcgccacctctgacttgagcgtcgattt
ttgtgatgctcgtcaggggggcggagcctatggaaaaacgccagcaacgcggcctttttacggttcctggccttttgctggccttttg
ctcacatgttctttcctgcgttatcccctgattctgtggataaccgtattaccgcctttgagtgagctgataccgctcgccgcagccga
acgaccgagcgcagcgagtcagtgagcgaggaagcggaagagcgcccaatacgcaaaccgcctctccccgcgcgttggc
cgattcattaatgcagctggcacgacaggtttcccgactggaaagcgggcagtgagcgcaacgcaattaatgtgagttagctca
ctcattaggcaccccaggctttacactttatgcttccggctcgtatgttgtgtggaattgtgagcggataacaatttcacacaggaaa
cagctatgaccatgattacgccaagcttggtaccgagctcggatccactagtaacggccgccagtgtgctggaattcgcccttgat
catgcattcgcccttaggaggtaaaaaaacatgtgtgcgacctcttctcaatttactcagattaccgagcataattcccgtcgttccg
caaactatcagccaaacctgtggaatttcgaattcctgcaatccctggagaacgacctg

Figure 137N

```
aaagtggaaaagctggaggagaaagcgaccaaactggaggaagaagttcgctgcatgatcaaccgtgtagacaccca
gccgctgtccctgctggagctgatcgacgatgtgcagcgcctgggtctgacctacaaatttgaaaaagacatcatta
aagccctggaaaacatcgtactgctggacgaaaacaaaaagaacaaatctgacctgcacgcaaccgctctgtctttc
cgtctgctgcgtcagcacggtttcgaggtttctcaggatgttttgagcgtttcaaggataaagaaggtggtttcag
cggtgaactgaaaggtgacgtccaaggcctgctgagcctgtatgaagcgtcttacctgggtttcgagggtgagaacc
tgctggaggaggcgcgtacctttccatcacccacctgaagaacaacctgaaagaaggcattaataccaaggttgca
gaacaagtgagccacgccctggaactgccatatcaccagcgtctgcaccgtctggaggcacgttggttcctggataa
atacgaaccgaaagaaccgcatcaccagctgctgctggagctggcgaagctggatttaacatggtacagaccctgc
accagaaagagctgcaagatctgtcccgctggtggaccgagatgggcctggctagcaaactggatttgtacgcgac
cgcctgatggaagtttatttctgggcactgggtatggcgccagacccgcagtttggtgaatgtcgcaaagctgttac
taaaatgtttggtctggtgacgatcatcgatgacgtgtatgacgtttatggcactctggacgaactgcaactgttca
ccgatgctgtagagcgctgggacgttaacgctattaacaccctgccggactatatgaaactgtgtttcctggcactg
tacaacaccgttaacgacacgtcctattctattctgaaagagaaaggtcataacaacctgtcctatctgacgaaaag
ctggcgtgaactgtgcaaagcctttctgcaagaggcgaaatggtccaacaacaaaattatcccggctttctccaagt
acctggaaaacgccagcgtttcctcctccggtgtagcgctgctggcgccgtcttacttttccgtatgccagcagcag
gaagacatctccgaccacgcgctgcgttccctgaccgacttccatggtctggtgcgttctagctgcgttatcttccg
cctgtgcaacgatctggccacctctgcggcggagctggaacgtggcgagactaccaattctatcattagctacatgc
acgaaaacgatggtaccagcgaggaacaggcccgcgaagaactgcgtaaactgatcgacgccgaatggaaaaagatg
aatcgtgaacgcgttagcgactccaccctgctgcctaaagcgttcatggaaatcgcagttaacatggcacgtgtttc
ccactgcacctaccagtatggcgatggtctgggtcgcccagactacgcgactgaaaaccgcatcaaactgctgctga
ttgacccttttcccgattaaccagctgatgtatgtctaactgcagggatccgtcgaccg
```

(SEQ ID NO:36)

Figure 137P

```
pET24D-Kudzu              Kudzu IspS ORF 48-1742 (complementary)
gtgcggccgcaagcttgtcgacggagctcgaattcggatccctgcagttagacatacatcagctggttaatcgggaa
agggtcaatcagcagcagtttgatgcggttttcagtcgcgtagtctgggcgacccagaccatcgccatactggtagg
tgcagtgggaaacacgtgccatgttaactgcgatttccatgaacgctttaggcagcagggtggagtcgctaacgcgt
tcacgattcatcttttttccattcggcgtcgatcagtttacgcagttcttcgcgggctgttcctcgctggtaccatc
gtttttcgtgcatgtagctaatgatagaattggtagtctcgccacgttccagctccgccgcagaggtggccagatcgt
tgcacaggcggaagataacgcagctagaacgcaccagaccatggaagtcggtcagggaacgcagcgcgtggtcggag
atgtcttcctgctgctggcatacggaaaagtaagacggcgccagcagcgctacaccggaggaggaaacgctggcgtt
ttccaggtacttggagaaagccgggataattttgttgttggaccattcgcctcttgcagaaaggctttgcacagtt
cacgccagcttttcgtcagataggacaggttgttatgacctttctctttcagaatagaataggacgtgtcgttaacg
gtgttgtacagtgccaggaaaacacagtttcatatagtccggcagggtgttaatagcgttaacgtcccagcgctctac
agcatcggtgaacagttgcagttcgtccagagtgccataaacgtcatacacgtcatcgatgatcgtcaccagaccaa
acatttagtaacagcttgcgacattcaccaaactgcgggtctggcgccataccccagtgccagaaataaacttcc
atcaggcgtcgcgtacaaaatccagtttgctagccaggccatctcggtccaccagcgggacagatcttgcagctc
tttctggtgcagggtctgtaccatgttaaaatccagcttcgccagctccagcagcagctggtgatgcggttcttcg
gttcgtatttatccaggaaccaacgtgcctccagacggtgcagacgctggtgatatggcagttccagggcgtggctc
acttgttctgcaaccttggtattaatgccttctttcaggttgttcttcaggtgggtgatggaaaaggtacgcgcctc
ctccagcaggttctcacccctcgaaacccaggtaagacgcttcatacaggctcagcaggccttggacgtcacctttca
gttcaccgctgaaaccaccttctttatccttgaaacgctcaaaaacatcctgagaaacctcgaaaccgtgctgacgc
agcagacgaaagacagagcggttgcgtgcaggtcagatttgttctttttgttttcgtccagcagtacgatgttttc
cagggctttaatgatgtctttttcaaatttgtaggtcagacccaggcgctgcacatcgtcgatcagctccagcaggg
acagcggctgggtgtctacacggttgatcatgcagcgaacttcttcctccagtttggtcgctttctcctccagcttt
tccactttcaggtcgttctccagggattgcaggaattcgaaattccacaggtttggctgatagtttgcggaacgacg
ggaattatgctcggtaatctgagtaaattgagaagaggtcgcacacatggtatatctccttcttaaagttaaacaaa
attatttctagaggggaattgttatccgctcacaattccctatagtgagtcgtattaatttcgcgggatcgagatc
tcgatcctctacgccggacgcatcgtggccggcatcaccggcgccacaggtgcggttgctggcgcctatatcgcga
catcaccgatggggaagatcgggctcgccacttcgggctcatgagcgcttgtttcggcgtgggtatggtggcaggcc
ccgtggccgggggactgttgggcgccatcccttgcatgcaccattccttgcggcgggtgctcaacggcctcaac
ctactactgggcgcttcctaatgcaggagtcgcataaggagagcgtcgagatcccggacaccatcgaatgcgca
aaacctttcgcgtatgcatgatagcgcccgaagagagtcaattcagggtggtgaatgtgaaaccagtaacgtta
tacgatgtcgcagagtatgccggtgtctcttatcagaccgtttcccgcgtggtgaaccaggccagccacgtttctgc
gaaaacgcgggaaaaagtggaagcggcgatggcggagctgaattacattcccaaccgcgtggcacaacaactggcgg
gcaaacagtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaagcctgtaaagc
ggcggtgcacaatcttctcgcgcaacgcgtcagtgggctgatcattaactatccgctggatgaccaggatgccattg
ctgtggaagctgcctgcactaatgttccggcgttatttcttgatgtctctgaccagacacccatcaacagtattatt
ttctcccatgaagacggtacgcgactgggcgtggagcatctggtcgcattgggtcaccagcaaatcgcgctgttagc
gggcccattaagttctgtctcggcgcgtctgcgtctggctggctggcataaatatctcactcgcaatcaaattcagc
cgatagcggaacgggaaggcgactggagtgccatgtccggttttcaacaaaccatgcaaatgctgaatgagggcatc
gttcccactgcgatgctggttgccaacgatcagatggcgctgggcgcaatgcgcgccattaccgagtccgggctgcg
cgttggtgcggatatctcggtagtgggatacgacgataccgaagacagctcatgttatatcccgccgttaaccacca
tcaaacaggattttcgcctgctggggcaaaccagcgtggaccgcttgctgcaactctctcagggccaggcggtgaag
ggcaatcagctgttgccgtctcactggtgaaaagaaaaaccaccctggcgcccaatacgcaaaccgcctctccccg
cgcgttggccgattcattaatgcagctggcacgacaggtttcccgactggaaagcgggcagtgagcgcaacgcaatt
aatgtaagttagctcactcattaggcaccgggactcgaccgatgcccttgagagccttcaacccagtcagctcctt
ccggtgggcgcggggcatgactatcgtcgccgcacttatgactgtctttctttatcatgcaactcgtaggacaggtgc
cggcagcgctctgggtcattttcggcgaggaccgctttcgctggagcgcgacgatgatcggcctgtcgcttgcggta
ttcggaatcttgcacgccctcgctcaagccttcgtcactggtcccgccaccaaacgtttcggcgagaagcaggccat
tatcgccggcatggcggccccacgggtgcgcatgatcgtgctcctgtcgttgaggacccggctaggctggcggggtt
gccttactggttagcagaatgaatcaccgatacgcgagcgaacgtgaagcgactgctgctgcaaaacgtctgcgacc
tgagcaacaacatgaatggtcttcggtttccgtgtttcgtaaagtctggaaacgcggaagtcagcgccctgcaccat
tatgttccggatctgcatcgcaggatgctgctggctaccctgtggaacacctacatctgtattaacgaagcgctggc
attgaccctgagtgatttttctctggtcccgccgcatccataccgccagttgtttaccctcacaacgttccagtaac
cgggcatgttcatcatcagtaacccgtatcgtgagcatcctctctcgtttcatcggtatcattaccccatgaacag
```

Figure 137Q

```
aaatccccccttacacggaggcatcagtgaccaaacaggaaaaaaccgcccttaacatggcccgctttatcagaagcc
agacattaacgcttctggagaaactcaacgagctggacgcggatgaacaggcagacatctgtgaatcgcttcacgac
cacgctgatgagctttaccgcagctgcctcgcgcgtttcggtgatgacggtgaaaacctctgacacatgcagctccc
ggagacggtcacagcttgtctgtaagcggatgccgggagcagacaagcccgtcagggcgcgtcagcgggtgttggcg
ggtgtcggggcgcagccatgacccagtcacgtagcgatagcggagtgtatactggcttaactatgcggcatcagagc
agattgtactgagagtgcaccatatatgcggtgtgaaataccgcacagatgcgtaaggagaaaataccgcatcaggc
gctcttccgcttcctcgctcactgactcgctgcgctcggtcgttcggctgcggcgagcggtatcagctcactcaaag
gcggtaatacggttatccacagaatcaggggataacgcaggaaagaacatgtgagcaaaaggccagcaaaaggccag
gaaccgtaaaaaggccgcgttgctggcgtttttccataggctccgcccccctgacgagcatcacaaaaatcgacgct
caagtcagaggtggcgaaacccgacaggactataaagataccaggcgtttccccctggaagctccctcgtgcgctct
cctgttccgaccctgccgcttaccggatacctgtccgcctttctcccttcgggaagcgtggcgctttctcatagctc
acgctgtaggtatctcagttcggtgtaggtcgttcgctccaagctgggctgtgtgcacgaaccccccgttcagcccg
accgctgcgccttatccggtaactatcgtcttgagtccaacccggtaagacacgacttatcgccactggcagcagcc
actggtaacaggattagcagagcgaggtatgtaggcggtgctacagagttcttgaagtggtggcctaactacggcta
cactagaaggacagtatttggtatctgcgctctgctgaagccagttaccttcggaaaaagagttggtagctcttgat
ccggcaaacaaaccaccgctggtagcggtggtttttttgtttgcaagcagcagattacgcgcagaaaaaaaggatct
caagaagatcctttgatcttttctacggggtctgacgctcagtggaacgaaaactcacgttaagggattttggtcat
gaacaataaaactgtctgcttacataaacagtaatacaaggggtgttatgagccatattcaacgggaaacgtcttgc
tctaggccgcgattaaattccaacatggatgctgatttatatgggtataaatgggctcgcgataatgtcgggcaatc
aggtgcgacaatctatcgattgtatgggaagcccgatgcgccagagttgtttctgaaacatggcaaaggtagcgttg
ccaatgatgttacagatgagatggtcagactaaactggctgacggaatttatgcctcttccgaccatcaagcatttt
atccgtactcctgatgatgcatggttactcaccactgcgatcccgggaaaacagcattccaggtattagaagaata
tcctgattcaggtgaaaatattgttgatgcgctggcagtgttcctgcgccggttgcattcgattcctgtttgtaatt
gtcctttaacagcgatcgcgtatttcgtctcgctcaggcgcaatcacgaatgaataacggtttggttgatgcgagt
gattttgatgacgagcgtaatggctggcctgttgaacaagtctggaaagaaatgcataaacttttgccattctcacc
ggattcagtcgtcactcatggtgatttctcacttgataaccttatttttgacgaggggaaattaataggttgtattg
atgttggacgagtcggaatcgcagaccgataccaggatcttgccatcctatggaactgcctcggtgagttttctcct
tcattacagaaacggcttttttcaaaaatatggtattgataatcctgatatgaataaattgcagtttcatttgatgct
cgatgagttttttctaagaattaattcatgagcggatacatatttgaatgtatttagaaaaataaacaaatagggtt
ccgcgcacatttccccgaaaagtgccacctgaaattgtaaacgttaatattttgttaaaattcgcgttaaattttg
ttaaatcagctcattttttaaccaataggccgaaatcggcaaaatcccttataaatcaaaagaatagaccgagatag
ggttgagtgttgttccagtttggaacaagagtccactattaaagaacgtggactccaacgtcaaagggcgaaaaacc
gtctatcaggcgatggcccactacgtgaaccatcacctaatcaagttttttggggtcgaggtgccgtaaagcact
aaatcggaacctaaaggagccccgatttagagcttgacggggaaagccggcgaacgtggcgagaaaggaaggga
agaaagcgaaaggagcgggcgctagggcgctggcaagtgtagcggtcacgctgcgcgtaaccaccacaccgccgcg
cttaatgcgccgctacagggcgcgtcccattcgccaatccggatatagttcctcctttcagcaaaaaacccctcaag
acccgtttagaggccccaaggggttatgctagttattgctcagcggtggcagcagccaactcagcttcctttcgggc
tttgttagcagccggatctcagtggtggtggtggtggtgctcga
```

(SEQ ID NO:37)

Figure 141 gaattcaaaatgtgtgcaacttcatcccaattcactcaaatcacagagcataattctagacgttcagctaactac
caaccaaatctgtggaattttgaatttcttcaatcccttgaaaatgatttgaaagtggaaaagttggaggaaaaa
gccacaaaactagaggaagaagttagatgtatgataaacagagtagatacacaacctctgtcactactaga
attgattgacgatgtccagaggctgggtttaacatataagttcgaaaaggatataatcaaagccttagaaaac
atagtccttctagatgaaaacaagaagaataagtctgacttgcacgcaaccgctctgagttttagattgctgag
acaacatggttttgaagtaagtcaagatgtgtttgaaaggttcaaagacaaagagggaggattctcaggaga
attaaagggagatgtgcagggtctgttgtcattgtacgaggccagttatttggggtttgaaggggaaaatctact
agaggaggccagaaccttctctataacccatctgaagaataacttgaaagaaggcatcaatacaaaagtgg
ctgaacaagtttcacatgcattggaattgccctaccaccaaagacttcatagacttgaagccagatggttttgg
acaagtatgaaccaaaggagcctcaccatcaactttattggaattagcaaaactggatttttaacatggttcag
acattacaccagaaagaattgcaggacctatcaagatggtggacggagatgggtttagccagcaagttagat
ttcgttagagatagattgatggaagtttactttttgggcactgggaatggcaccagatcctcaatttggtgaatgtag
aaaggcagttacaaagatgtttggtctagtaacaatcattgatgatgtttatgatgtgtacggaactttggatgaat
tacaactattcaccgacgcagttgaacgttgggatgaaacgcaataaacacgttgcctgattatatgaagctgt
gttttctggcattgtacaacacagtcaatgacacttcttactccattttaaaggagaaagggcataacaatctatc
ctatttgacaaaatcatggagggagttatgcaaagcattccttcaagaagctaagtggtctaacaataagataa
tcccagcattctccaagtatcttgaaaacgcttccgtatcctcctccggtgtggccctactagcaccatcatatttt
ccgtctgccagcagcaggaagatatctctgatcatgctttgagatccttaacagatttcatggtctagtcagatc
ctcttgcgtgattttcagattgtgcaatgatttggctacttcagccgcagagttagagagggggtgaaaccacgaa
ctcaattattagttatatgcacgagaatgatggaacatccgaagaacaagcccgtgaagaattaagaaaact
gatcgatgctgaatggaagaagatgaatagagaaagagtttccgacagcactttgctgcctaaggcattcatg
gagatagctgttaacatggctagggtttcacactgtacataccaatacggggacggtcttggaaggcccgact
acgccactgaaaatagaattaaactgctactgattgatcctttccccattaaccagttaatgtacgtgtaatagggg
atccgaattc (SEQ ID NO:38)

Figure 142B acggattagaagccgccgagcgggtgacagccctccgaaggaagactctcctccgtgcgtcctcgtcttcaccggtcgcgtt
cctgaaacgcagatgtgcctcgcgccgcactgctccgaacaataaagattctacaatactagcttttatggttatgaagagga
aaaattggcagtaacctggccccacaaaccttcaaatgaacgaatcaaattaacaaccataggatgataatgcgattagtttt
ttagccttatttctggggtaattaatcagcgaagcgatgattttgatctattaacagatatataaatgcaaaaactgcataacca
ctttaactaatactttcaacattttcggtttgtattacttcttattcaaatgtaataaaagtatcaacaaaaaattgttaatatacctcta
tactttaacgtcaaggagaaaaaaccccggatcggactactagcagctgtaatacgactcactatagggaatattaagctat
caaacaagtttgtacaaaaaagcaggctgaattcaaaatgtgtgcaacttcatcccaattcactcaaatcacagagcataatt
ctagacgttcagctaactaccaaccaaatctgtggaattttgaatttcttcaatcccttgaaaatgatttgaaagtggaaaagttg
gaggaaaaagccacaaaactagaggaagaagttagatgtatgataaacagagtagatacacaacctctgtcactactag
aattgattgacgatgtccagaggctgggtttaacatataagttcgaaaaggatataatcaaagccttagaaaacatagtccttc
tagatgaaaacaagaagaataagtctgacttgcacgcaaccgctctgagttttagattgctgagacaacatggttttgaagta
agtcaagatgtgtttgaaaggttcaaagacaaagagggaggattctcaggagaattaaagggagatgtgcagggtctgttgt
cattgtacgaggccagttatttggggtttgaaggggaaaatctactagaggaggccagaaccttctctataacccatctgaag
aataacttgaaagaaggcatcaatacaaaagtggctgaacaagtttcacatgcattggaattgccctaccaccaaagacttc
atagacttgaagccagatggtttttggacaagtatgaaccaaaggagcctcaccatcaactttattggaattagcaaaactg
gatttttaacatggttcagacattacaccagaaagaattgcaggacctatcaagatggtggacggagatgggtttagccagca
agttagatttcgttagagatagattgatggaagtttacttttgggcactgggaatggcaccagatcctcaatttggtgaatgtaga
aaggcagttacaaagatgtttggtctagtaacaatcattgatgatgtttatgatgtgtacggaactttggatgaattacaactattc
accgacgcagttgaacgttgggatgtaaacgcaataaacacgttgcctgattatatgaagctgtgttttctggcattgtacaaca
cagtcaatgacacttcttactccattttaaaggagaaagggcataacaatctatcctatttgacaaaatcatggagggagttat
gcaaagcattccttcaagaagctaagtggtctaacaataagataatcccagcattctccaagtatcttgaaaacgcttccgtat
cctcctccggtgtggccctactagcaccatcatatttttccgtctgccagcagcaggaagatatctctgatcatgctttgagatcct
taacagattttcatggtctagtcagatcctcttgcgtgattttcagattgtgcaatgatttggctacttcagccgcagagttagagag
gggtgaaaccacgaactcaattattagttatatgcacgagaatgatggaacatccgaagaacaagcccgtgaagaattaa
gaaaactgatcgatgctgaatggaagaagatgaatagagaaagagtttccgacagcactttgctgcctaaagcattcatgg
agatagctgttaacatggctagggtttcacactgtacataccaatacggggacggtcttggaaggcccgactacgccactga
aaatagaattaaactgctactgattgatcctttccccattaaccagttaatgtacgtgtaatagggatccgaattcacccagcttt
cttgtacaaagtggttcgatctagagggccccttcgaaggtaagcctatccctaaccctctcctcggtctcgattctacgcgtacc
ggtcatcatcaccatcaccattgagtttaaacccgctgatcctagagggccgcatcatgtaattagttatgtcacgcttacattca
cgccctcccccacatccgctctaaccgaaaaggaaggagttagacaacctgaagtctaggtccctatttatttttttatagttat
gttagtattaagaacgttatttatatttcaaattttctttttttctgtacagacgcgtgtacgcatgtaacattatactgaaaaccttgc
ttgagaaggttttgggacgctcgaaggctttaatttgcaagctgcggccctgcattaatgaatcggccaacgcgcggggaga
ggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagc
aaaagcccaggaaccgtaaaaaggccgcgttgctggcgtttttccataggctccgcccccctgacgagcatcacaaaaat
cgacgctcaagtcagaggtggcgaaacccgacaggactataaagataccaggcgtttccccctggaagctccctcgtgcg
ctctcctgttccgaccctgccgcttaccggatacctgtccgcctttctcccttcgggaagcgtggcgctttctcatagctcacgctg
taggtatctcagttcggtgtaggtcgttcgctccaagctgggctgtgcacgaaccccccgttcagcccgaccgctgcgcctt
atccggtaactatcgtcttgagtccaacccggtaagacacgacttatcgccactggcagcagccactggtaacaggattagc
agagcgaggtatgtaggcggtgctacagagttcttgaagtggtggcctaactacggctacactagaaggacagtatttggtat
ctgcgctctgctgaagccagttaccttcggaaaaagagttggtagctcttgatccggcaaacaaaccaccgctggtagcggt
ggtttttttgtttgcaagcagcagattacgcgcagaaaaaaggatctcaagaagatcctttgatcttttctacggggtctgacgc
tcagtggaacgaaaactcacgttaagggattttggtcatgagattatcaaaaaggatcttcacctagatccttttaaattaaaaa
tgaagttttaaatcaatctaaagtatatatgagtaaacttggtctgacagttaccaatgcttaatcagtgaggcacctatctcagc
gatctgtctatttcgttcatccatagttgcctgactccccgtcgtgtagataactacgatacgggagcgcttaccatctggcccca
gtgctgcaatgataccgcgagacccacgctcaccggctccagatt

Figure 142C tatcagcaataaaccagccagccggaagggccgagcgcagaagtggtcctgcaactttatccgcctccatccagtctatta
attgttgccgggaagctagagtaagtagttcgccagttaatagtttgcgcaacgttgttggcattgctacaggcatcgtggtgtc
actctcgtcgtttggtatggcttcattcagctccggttcccaacgatcaaggcgagttacatgatcccccatgttgtgcaaaaaa
gcggttagctccttcggtcctccgatcgttgtcagaagtaagttggccgcagtgttatcactcatggttatggcagcactgcata
attctcttactgtcatgccatccgtaagatgctttctgtgactggtgagtactcaaccaagtcattctgagaatagtgtatgcggc
gaccgagttgctcttgcccggcgtcaatacgggataatagtgtatcacatagcagaactttaaaagtgctcatcattggaaaa
cgttcttcggggcgaaaactctcaaggatcttaccgctgttgagatccagttcgatgtaacccactcgtgcacccaactgatctt
cagcatcttttactttcaccagcgtttctgggtgagcaaaaacaggaaggcaaaatgccgcaaaaaagggaataagggcg
acacggaaatgttgaatactcatactcttccttttcaatgggtaataactgatataattaaattgaagctctaatttgtgagtttagt
atacatgcatttacttataatacagttttttagttttgctggccgcatcttctcaaatatgcttcccagcctgcttttctgtaacgttcacc
ctctaccttagcatcccttcccttgcaaatagtcctcttccaacaataataatgtcagatcctgtagagaccacatcatccacgg
ttctatactgttgacccaatgcgtctcccttgtcatctaaacccacaccgggtgtcataatcaaccaatcgtaaccttcatctcttc
cacccatgtctctttgagcaataaagccgataacaaaatctttgtcgctcttcgcaatgtcaacagtaccctagtatattctcca
gtagatagggagcccttgcatgacaattctgctaacatcaaaaggcctctaggttcctttgttacttcttctgccgcctgcttcaaa
ccgctaacaatacctgggcccaccacaccgtgtgcattcgtaatgtctgcccattctgctattctgtatacacccgcagagtact
gcaatttgactgtattaccaatgtcagcaaatttctgtcttcgaagagtaaaaaattgtactggcggataatgcctttagcggct
taactgtgccctccatggaaaaatcagtcaagatatccacatgtgtttttagtaaacaaattttgggacctaatgcttcaactaac
tccagtaattccttggtggtacgaacatccaatgaagcacacaagtttgtttgcttttcgtgcatgatattaaatagcttggcagca
acaggactaggatgagtagcagcacgttcctatatgtagctttcgacatgatttatcttcgtttcctgcaggttttgttctgtgcagt
tgggttaagaatactgggcaatttcatgtttcttcaacactacatatgcgtatatataccaatcaagtctgtgctccttccttcgttct
tccttctgttcggagattaccgaatcaaaaaaatttcaaagaaaccgaaatcaaaaaaaagaataaaaaaaaaatgatga
attgaattgaaaagctagcttatcgatgataagctgtcaaagatgagaattaattccacggactatagactatactagatactc
cgtctactgtacgatacacttccgctcaggtccttgtcctttaacgaggccttaccactcttttgttactctattgatccagctcagca
aaggcagtgtgatcaagattctatcttcgcgatgtagtaaaactagctagaccgagaaagagactagaaatgcaaaaggc
acttctacaatggctgccatcattattatccgatgtgacgctgcagcttctcaatgatattcgaatacgctttgaggagatacagc
ctaaatccgacaaactgttttacagatttacgatcgtacttgttacccatcattgaattttgaacatccgaacctgggagttttccc
tgaaacagatagtatatttgaacctgtataataatatatagtctagcgctttacggaagacaatgtatgtatttcggttcctggaga
aactatgcatctattgcataggtaatcttgcacgtcgcatccccggttcattttctgcgttccatcttgcacttcaatagcatatcttt
gttaacgaagcatctgtgcttcattttgtagaacaaaaatgcaacgcgagagcgctaattttcaaacaaagaatctgagctgc
attttttacagaacagaaatgcaacgcgaaagcgctatttaccaacgaagaatctgtgcttcattttgtaaaacaaaaatgca
acgcgacgagagcgctaattttcaaacaaagaatcgagctgcatttttacagaacagaaatgcaacgcgagagcgctatt
ttaccaacaaagaatctatacttcttttttgttctacaaaaatgcatcccgagagcgctatttttctaacaaagcatcttagattactt
ttttttctcctttgtgcgctctataatgcagtctcttgataacttttttgcactgtaggtccgttaaggttagaagaaggctactttggtgtct
attttctcttccataaaaaaagcctgactccactcccgcgtttactgattactagcgaagctgcgggtgcatttttcaagataaa
ggcatccccgattatattctataccgatgtggattgcgcatactttgtgaacagaaagtgatagcgttgatgattcttcattggtca
gaaaattatgaacggttcttctatttttgtctctatatactacgtataggaaatgtttacatttttcgtattgttttcgattcactctatgaat
agttcttactacaattttttttgtctaaagagtaatactagagataaacataaaaaatgtagaggtcgagtttagatgcaagttcaa
ggagcgaaaggtggatgggtaggttatataggatatagcacagagatatatagcaaagagatactttgagcaatgtttgtg
gaagcggtattcgcaatgggaagctccaccccggttgataatcagaaaagccccaaaaacaggaagattgtataagcaa
atatttaaattgtaaacgttaatattttgttaaaattcgcgttaaattttgttaaatcagctcatttttaacgaatagcccgaaatcgg
caaaatcccttataaatcaaaagaatagaccgagatagggttgagtgttgttccagtttccaacaagagtccactattaaaga
acgtggactccaacgtcaaagggcgaaaaaggtctatcagggcgatggcccactacgtgaaccatcaccctaatcaagt
tttttggggtcgaggtgccgtaaagcagtaaatcggaagggtaaacggatgcccccattagagcttgacggggaaagccg
gcgaacgtggcgagaaaggaagggaagaaagcgaaaggagcggggggctagggcggtgggaagtgtaggggtcacg
ctgggcgtaaccaccacaccgccgcgcttaatggggcgctacagggcgcgtggggatgatccactagt (SEQ ID NO:39)

Figures 144A-B
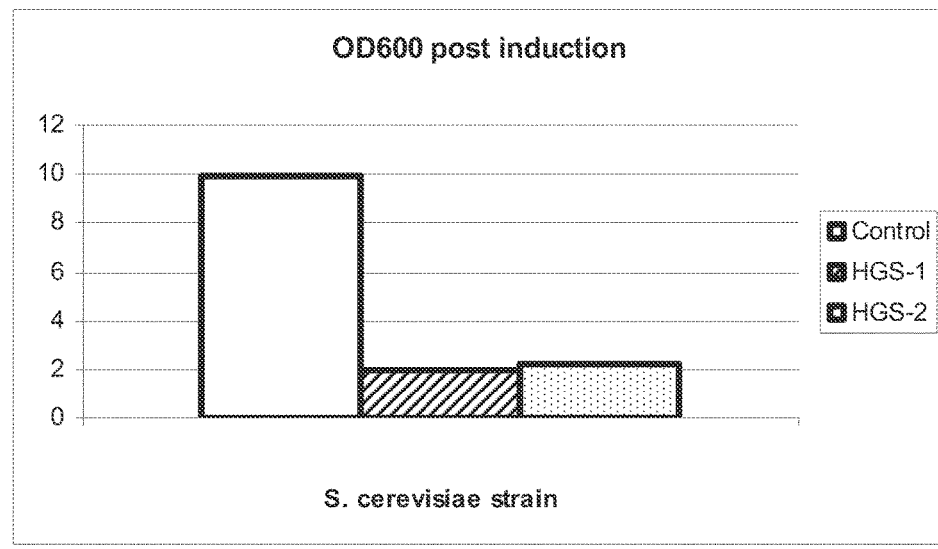
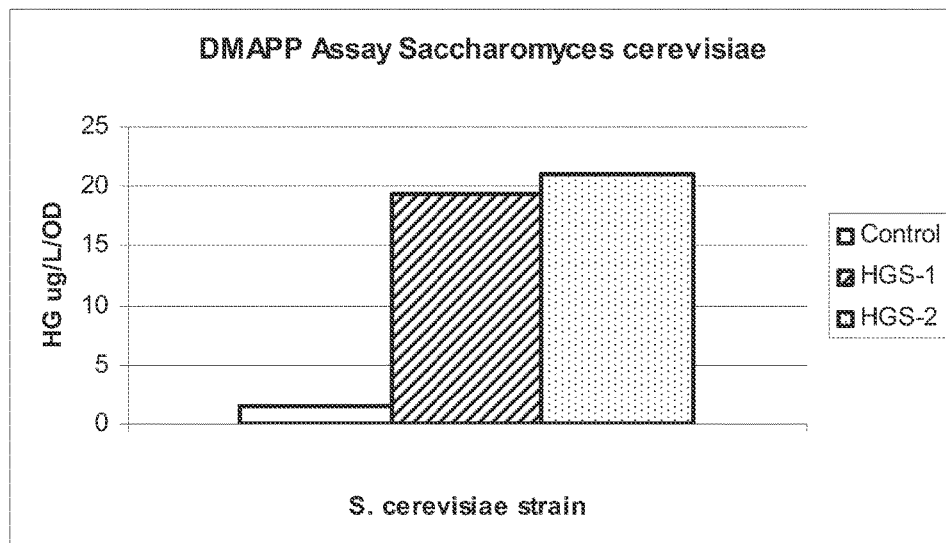

Figure 145B catcttaagcttgtttaactttaagaaggagatatacatatgtgcgccaccagcagccagttcacccagatca
ccgagcataatagccgtcggtccgcgaactaccagcccaacctgtggaacttcgagttcctgcagagcctg
gaaaacgacctgaaggtggagaagctcgaagagaaggccaccaagctggaggaggaggtgcgttgca
tgatcaaccgggtggacacccagcccctgagcctgctggagctcatcgacgacgtgcagcgcctgggcct
gacctacaagtttgagaaagatatcatcaaggcgctggagaacatcgtcctgctggacgagaataagaag
aacaaaagcgatctgcacgcgaccgccctgagcttccgcctgctgcggcagcatggctttgaggtgagcc
aggacgtgttcgagcgcttcaaggacaaagaaggggggcttctccggggaactgaagggtgacgtgcagg
gcctgctgagcctgtacgaggccagctatctcggtttcgaaggcgaaaatctgctggaggaggcccgtacc
ttcagcatcacccatctgaagaacaacctcaaggaggggatcaacacgaaggtggccgagcaggtgtcc
cacgcgctggagctgccgtatcatcaacgcctgcaccgcctggaggcgcggtggtttctggacaagtacga
acccaaggagccgcatcaccagctgctgctggaactggccaaactcgatttcaacatggtccagaccctg
caccaaaaagagctgcaggacctgagccggtggtggaccgagatgggcctcgccagcaagctggatttc
gtgcgggaccgcctgatgaagtgtacttctgggcgctgggcatggcgccggacccgcagttcggcgaat
gccgcaaggccgtcaccaagatgttcggtctggtcaccattatcgatgacgtctatgacgtgtacggtaccct
ggacgaactgcagctcttcaccgacgcggtggaacgctgggacgtgaacgccatcaacacgctgcccga
ctatatgaagctgtgcttcctggccctgtacaacaccgtgaacgacacgtcctactccatcctgaaggagaa
gggccacaataacctgagctatctgaccaaaagctggcgcgaactgtgcaaggccttcctgcaagaagcc
aagtggagcaataacaagatcatccccgccttcagcaagtacctggagaacgccagcgtgtcctccagcg
gggtcgcgctgctggcgccgagctacttctcggtctgccagcagcaggaagatatctcggaccacgccctc
cgctccctgaccgacttccacggcctggtgcgctcgtcctgcgtgatctttcggctgtgcaacgatctggcgac
ctcggcggcggaactcgaacgcggcgaaaccaccaacagcatcatcagctacatgcacgagaacgac
ggcacgagcgaggaacaggcccgcgaagagctgcgcaagctgatcgacgccgagtggaagaaaatg
aaccgcgagcgcgtgtcggacagcaccctgctgccgaaggcgttcatggagatcgccgtgaacatggcc
cgcgtgagccactgcacctaccaatatggggacgggctggccgcccggattacgccaccgagaaccg
catcaagctgctgctcatcgacccgttccccatcaaccagctgatgtacgtgtgaggatcccgtaac (SEQ ID NO:40)

Figure 146B ctcgggccgtctcttgggcttgatcggccttcttgcgcatctcacgcgctcctgcggcggcctgtagggcaggctcatacccctgc
cgaaccgcttttgtcagccggtcggccacggcttccggcgtctcaacgcgctttgagattccagcttttcggccaatccctgcg
gtgcataggcgcgtggctcgaccgcttgcgggctgatggtgacgtggcccactggtggccgctccagggcctcgtagaacgc
ctgaatgcgcgtgtgacgtgccttgctgccctcgatgcccgttgcagccctagatcggccacagcggccgcaaacgtggtct
ggtcgcgggtcatctgcgctttgttgccgatgaactccttggccgacagcctgccgtcctgcgtcagcggcaccacgaacgcg
gtcatgtgcgggctggtttcgtcacggtggatgctggccgtcacgatgcgatccgccccgtactgtccgccagccacttgtgcg
ccttctcgaagaacgccgcctgctgttcttggctggccgacttccaccattccgggctggccgtcatgacgtactcgaccgccaa
cacagcgtccttgcgccgcttctctggcagcaactcgcgcagtcggcccatcgcttcatcggtgctgctggccgccagtgctc
gttctctggcgtcctgctggcgtcagcgttgggcgtctcgcgctcgcggtaggcgtgcttgagactggccgccacgttgcccatttt
cgccagcttcttgcatcgcatgatcgcgtatgccgccatgcctgcccctcccttttggtgtcaaccggctcgacggggggcagcg
caaggcggtgcctccggcgggccactcaatgcttgagtatactcactagactttgcttcgcaaagtcgtgaccgcctacggcgg
ctgcggcgccctacgggcttgctctccgggcttcgccctgcgcggtcgctgcgctcccttgccagcccgtggatatgtggacgat
ggccgcgagcggccaccggctggctcgcttcgctcggcccgtggacaaccctgctggacaagctgatggacaggctgcgc
ctgcccacgagcttgaccacagggattgcccaccggctacccagccttcgaccacatacccaccggctccaactgcgcggc
ctgcggccttgccccatcaatttttttaattttctctggggaaaagcctccggcctgcggcctgcgcgcttcgcttgccggttggaca
ccaagtggaaggcgggtcaaggctcgcgcagcgaccgcgcagcggcttggccttgacgcgcctggaacgacccaagcct
atgcgagtgggggcagtcgaaggcgaagccgccgcctgcccccgagcctcacggcggcgagtgcggggttccaag
ggggcagcgccaccttgggcaaggcgaaggccgcgcagtcgatcaacaagccccggaggggccactttttgccggagg
gggagccgcgccgaaggcgtgggggaaccccgcaggggtgcccttctttgggcaccaaagaactagatatagggcgaaa
tgcgaaagacttaaaaatcaacaacttaaaaaagggggtacgcaacagctcattgcggcaccccccgcaatagctcattg
cgtaggttaaagaaaatctgtaattgactgccactttacgcaacgcataattgttgtcgcgctgccgaaaagttgcagctgattg
cgcatggtgccgcaaccgtgcggcaccctaccgcatggagataagcatggccacgcagtccagagaaatcggcattcaag
ccaagaacaagcccggtcactgggtgcaaacggaacgcaaagcgcatgaggcgtgggccgggcttattgcgaggaaacc
cacggcggcaatgctgctgcatcacctcgtggcgcagatgggccaccagaacgccgtggtggtcagccagaagacactttc
caagctcatcggacgttctttgcggacggtccaatacgcagtcaaggacttggtggccgagcgctggatctccgtcgtgaagct
caacggccccggcaccgtgtcggcctacgtggtcaatgaccgcgtggcgtggggccagccccgcgaccagttgcgcctgtc
ggtgttcagtgccgccgtggtggttgatcacgacgaccaggacgaatcgctgttggggcatggcgacctgcgccgcatcccg
accctgtatccgggcgagcagcaactaccgaccggccccggcgaggagccgcccagccagcccggcattccgggcatgg
aaccagacctgccagccttgaccgaaacggaggaatgggaacggcgcgggcagcagcgcctgccgatgccgatgagc
cgtgttctggacgatggcgagccgttggagccgccgacacgggtcacgctgccgcgccggtagcacttgggttgcgcagc
aacccgtaagtgcgctgttccagactatcggctgtagccgcctcgccgcctataccttgtctgcctccccgcgttgcgtcgcggt
gcatggagccgggccacctcgacctgaatggaagccggcggcacctcgctaacggattcaccgtttttatcaggctctggga
ggcagaataaatgatcatatcgtcaattattacctccacggggagagcctgagcaaactggcctcaggcatttgagaagcac
acggtcacactgcttccggtagtcaataaaccggtaaaccagcaatagacataagcggctatttaacgaccctgccctgaac
cgacgaccgggtcgaatttgctttcgaatttctgccattcatccgcttattatcacttattcaggcgtagcaccaggcgtttaagggc
accaataactgccttaaaaaaattacgccccgccctgccactcatcgcagtcggcctattggttaaaaaatgagctgatttaac
aaaaatttaacgcgaattttaacaaaatattaacgcttacaatttccattcgccattcaggctgcgcaactgttgggaagggcgat
cggtgcgggcctcttcgctattacgccagctggcgaaaggggggatgtgctgcaaggcgattaagttgggtaacgccagggtttt
cccagtcacgacgttgtaaaacgacggccagtgagcgcgcgtaatacgactcactatagggcgaattggagctccaccgcg
gtggcggccgctctagaactagtggatccccgggctgcaggaattcgatatcaagcttatcgataccgtcgacctcgagggg
gggcccggtaccagctttgttccctttagtgagggttaattgcgcgcttggcgtaatcatggtcatagctgtttcctgtgtgaaatt
gttatccgctcacaattccacacaacatacgagccggaagcataaagtgtaaagcctggggtgcctaatgagtgagctaactc
acattaattgcgttgcgctcactgcccgctttccagtcgggaaacctgtcgtgccagctgcattaatgaatcggccaacgcgcgg
ggagaggcggtttgcgtattgggcgcatgcataaaaactgttaattcattaagcattctgccgacatggaagccatcacaaa
cggcatgatgaacctgaatcgccagcggcatcagcac

Figure 146C cttgtcgccttgcgtataatatttgcccatggacgcacaccgtggaaacggatgaaggcacgaacccagttgaca
taagcctgttcggttcgtaaactgtaatgcaagtagcgtatgcgctcacgcaactggtccagaaccttgaccgaac
gcagcggtggtaacggcgcagtggcggttttcatggcttgttatgactgttttttgtacagtctatgcctcgggcatcc
aagcagcaagcgcgttacgccgtgggtcgatgtttgatgttatggagcagcaacgatgttacgcagcagcaacg
atgttacgcagcagggcagtcgccctaaaacaaagttaggtggctcaagtatgggcatcattcgcacatgtaggc
tcggccctgaccaagtcaaatccatgcgggctgctcttgatcttttcggtcgtgagttcggagacgtagccacctact
cccaacatcagccggactccgattacctcgggaacttgctccgtagtaagacattcatcgcgcttgctgccttcgac
caagaagcggttgttggcgctctcgcggcttacgttctgcccaggtttgagcagccgcgtagtgagatctatatctat
gatctcgcagtctccggcgagcaccggaggcagggcattgccaccgcgctcatcaatctcctcaagcatgaggc
caacgcgcttggtgcttatgtgatctacgtgcaagcagattacggtgacgatcccgcagtggctctctatacaaagt
tgggcatacgggaagaagtgatgcactttgatatcgacccaagtaccgccacctaacaattcgttcaagccgag
atcggcttcccggccgcggagttgttcggtaaattgtcacaacgccgccaggtggcacttttcggggaaatgtgcg
cgcccgcgttcctgctggcgctgggcctgttctggcgctggacttcccgctgttccgtcagcagcttttcgcccacgg
ccttgatgatcgcggcggccttggcctgcatatcccgattcaacggccccagggcgtccagaacgggcttcaggc
gctcccgaaggt (SEQ ID NO:41)

Figure 147B ctcgggccgtctcttgggcttgatcggccttcttgcgcatctcacgcgctcctgcggcggcctgtagggcaggctcataccct
gccgaaccgcttttgtcagccggtcggccacggcttccggcgtctcaacgcgctttgagattcccagcttttcggccaatccct
gcggtgcataggcgcgtggctcgaccgcttgcgggctgatggtgacgtggcccactggtggccgctccagggcctcgtaga
acgcctgaatgcgcgtgtgacgtgccttgctgccctcgatgccccgttgcagccctagatcggccacagcggccgcaaacg
tggtctggtcgcgggtcatctgcgctttgttgccgatgaactccttggccgacagcctgccgtcctgcgtcagcggcaccacga
acgcggtcatgtgcgggctggtttcgtcacggtggatgctggccgtcacgatgcgatccgccccgtacttgtccgccagccac
ttgtgcgccttctcgaagaacgccgcctgctgttcttggctggccgacttccaccattccgggctggccgtcatgacgtactcga
ccgccaacacagcgtccttgcgccgctctctggcagcaactcgcgcagtcggcccatcgcttcatcggtgctgctggccgc
ccagtgctcgttctctggcgtcctgctggcgtcagcgttgggcgtctcgcgctcgcggtaggcgtgcttgagactggccgccac
gttgcccattttcgccagcttcttgcatcgcatgatcgcgtatgccgccatgcctgcccctcccttttggtgtccaaccggctcgac
gggggcagcgcaaggcggtgcctccggcgggccactcaatgcttgagtatactcactagactttgcttcgcaaagtcgtgac
cgcctacggcggctgcggcgccctacgggcttgctctccgggcttcgccctgcgcggtcgctgcgctcccttgccagcccgt
ggatatgtggacgatggccgcgagcggccaccggctggctcgcttgctcggcccgtggacaaccctgctggacaagctg
atggacaggctgcgcctgccacgagcttgaccacagggattgcccaccggctacccagccttcgaccacataccaccg
gctccaactcgcgcggcctgcggccttgccccatcaatttttaatttttctctggggaaaagcctccggcctgcggcctgcgcgc
ttcgcttgccggttggacaccaagtggaaggcgggtcaaggctcgcgcagcgaccgcgcagcggcttggccttgacgcgc
ctggaacgacccaagcctatgcgagtgggggcagtcgaaggcgaagcccgcccgcctgccccccgagcctcacggcg
gcgagtgcggggttccaaggggcagcgccaccttgggcaaggccgaaggccgcgcagtcgatcaacaagcccgg
aggggccacttttttgccggaggggggagccgcgccgaaggcgtgggggaaccccgcagggtgcccttctttgggcacca
aagaactagatataggcgaaatgcgaaagacttaaaaatcaacaacttaaaaaaggggggtacgcaacagctcattgc
ggcacccccgcaatagctcattgcgtaggttaaagaaaatctgtaattgactgccactttacgcaacgcataattgttgtcgc
gctgccgaaaagtgcagctgattgcgcatggtgccgcaaccgtgcggcaccctaccgcatggagataagcatggccacg
cagtccagagaaatcggcattcaagccaagaacaagccggtcactgggtgcaaacggaacgcaaagcgcatgaggc
gtgggccgggcttattgcgaggaaacccacggcggcaatgctgctgcatcacctcgtggcgcagatgggccaccagaac
gccgtggtggtcagccagaagacactttccaagctcatcggacgttctttgcggacggtccaatacgcagtcaaggacttggt
ggccgagcgctggatctccgtcgtgaagctcaacggccccggcaccgtgtcggcctacgtggtcaatgaccgcgtggcgtg
gggccagccccgcgaccagttgcgcctgtcggtgttcagtgccgccgtggtggttgatcacgacgaccaggacgaatcgct
gttggggcatggcgacctgcgccgcatcccgaccctgtatccgggcgagcagcaactaccgaccggccccggcgagga
gccgcccagccagcccggcattccgggcatggaaccagacctgccagccttgaccgaaacggaggaatgggaacggc
gcgggcagcagcgcctgccgatgcccgatgagccgtgttttctggacgatggcgagccgttggagccgccgacacgggtc
acgctgccgcgcgggtagcacttggttgcgcagcaaacccgtaagtgcgctgttccagactatcggctgtagccgcctcgcc
gccctataccttgtctgcctccccgcgttgcgtcgcggtgcatggagccgggccacctcgacctgaatggaagccggcggc
acctcgctaacggattcaccgtttttatcaggctctgggaggcagaataaatgatcatatcgtcaattattacctccacgggga
gagcctgagcaaactggcctcaggcatttgagaagcacacggtcacactgcttccggtagtcaataaaccggtaaaccag
caatagacataagcggctatttaacgaccctgccctgaaccgacgaccgggtcgaatttgctttcgaattctgccattcatcc
gcttattatcacttattcaggcgtagcaccaggcgtttaagggcaccaataactgccttaaaaaaattacgccccgccctgcc
actcatcgcagtcggcctattggttaaaaaatgagctgatttaacaaaaatttaacgcgaatttaacaaaatattaacgcttac
aatttccattcgccattcaggctgcgcaactgttgggaagggcgatcggtgcgggcctcttcgctattacgccagctggcgaa
aggggggatgtgctgcaaggcgattaagttgggtaacgccagggttttcccagtcacgacgttgtaaaacgacggccagtga
gcgcgcgtaatacgactcactatagggcgaattggagctccaccgcggtggcggccgctctagaactagtggatcctcaca
cgtacatcagctggttgatggggaacgggtcgatgagcagcagcttgatgcggttctcggtggcgtaatccgggcggccca
gcccgtccccatattggtaggtgcagtggctcacgcgggccatgttcacggcgatctccatgaacgccttcggcagcagggt
gctgtccgacacgcgctcgcggttcattttcttccactcggcgtcgatcagcttgcgcagctcttcgcgggcctgttcctcgctcg
tgccgtcgttctcgtgcatgtagctgatgatgctgttggtggtttcgccgcgttcgagttccgccgccgaggtcgccagatcgttg
cacagccgaaagatcacgcaggacgagcgcaccaggccgtggaagtcggtcagggagcggagggcgtggtccgaga
tatcttcctg

Figure 147C ctgctggcagaccgagaagtagctcggcgccagcagcgcgaccccgctggaggacacgctggcgttctccag
gtacttgctgaaggcggggatgatcttgttattgctccacttggcttcttgcaggaaggccttgcacagttcgcgcca
gcttttggtcagatagctcaggttattgtggcccttctccttcaggatggagtaggacgtgtcgttcacggtgttgtaca
gggccaggaagcacagcttcatatagtcgggcagcgtgttgatggcgttcacgtcccagcgttccaccgcgtcgg
tgaagagctgcagttcgtccagggtaccgtacacgtcatagacgtcatcgataatggtgaccagaccgaacatct
tggtgacggccttgcggcattcgccgaactgcgggtccggcgccatgcccagcgcccagaagtacacttccatc
aggcggtcccgcacgaaatccagcttgctggcgaggcccatctcggtccaccaccggctcaggtcctgcagctc
tttttggtgcagggtctggaccatgttgaaatcgagtttggccagttccagcagcagctggtgatgcggctccttgggt
tcgtacttgtccagaaaccaccgcgcctccaggcggtgcaggcgttgatgatacggcagctccagcgcgtggga
cacctgctcggccaccttcgtgttgatccctccttgaggttgttcttcagatgggtgatgctgaaggtacgggcctcc
tccagcagattttcgccttcgaaaccgagatagctggcctcgtacaggctcagcaggccctgcacgtcacccttca
gttccccggagaagccccccttctttgtccttgaagcgctcgaacacgtcctggctcactcaaagccatgctgccg
cagcaggcggaagctcagggcggtcgcgtgcagatcgcttttgttcttcttattctcgtccagcaggacgatgttctc
cagcgccttgatgatatctttctcaaacttgtaggtcaggcccaggcgctgcacgtcgtcgatgagctccagcagg
ctcaggggctgggtgtccacccggttgatcatgcaacgcacctcctcctccagcttggtggccttctcttcgagcttct
ccaccttcaggtcgttttccaggctctgcaggaactcgaagttccacaggttgggctggtagttcgcggaccgacg
gctattatgctcggtgatctgggtgaactggctgctggtggcgcacatatgtatatctccttcttaaagttaaacaagct
tatcgataccgtcgacctcgagggggggcccggtacccagctttgttccctttagtgagggtaattgcgcgcttgg
cgtaatcatggtcatagctgtttcctgtgtgaaattgttatccgctcacaattccacacaacatacgagccggaagc
ataaagtgtaaagcctggggtgcctaatgagtgagctaactcacattaattgcgttgcgctcactgcccgctttcca
gtcgggaaacctgtcgtgccagctgcattaatgaatcggccaacgcgcggggagaggcggtttgcgtattggc
gcatgcataaaaactgttgtaattcattaagcattctgccgacatggaagccatcacaaacggcatgatgaacctg
aatcgccagcggcatcagcaccttgtcgccttgcgtataatatttgcccatggacgcacaccgtggaaacggatg
aaggcacgaacccagttgacataagcctgttcggttcgtaaactgtaatgcaagtagcgtatgcgctcacgcaac
tggtccagaaccttgaccgaacgcagcggtggtaacggcgcagtggcggttttcatggcttgttatgactgttttttgt
acagtctatgcctcgggcatccaagcagcaagcgcgttacgccgtgggtcgatgtttgatgttatggagcagcaa
cgatgttacgcagcagcaacgatgttacgcagcagggcagtcgccctaaaacaaagttaggtggctcaagtatg
ggcatcattcgcacatgtaggctcggccctgaccaagtcaaatccatgcgggctgctcttgatcttttcggtcgtgag
ttcggagacgtagccacctactcccaacatcagccggactccgattacctcgggaacttgctccgtagtaagaca
ttcatcgcgcttgctgccttcgaccaagaagcggttgttggcgctctcgcggcttacgttctgcccaggtttgagcag
ccgcgtagtgagatctatatctatgatctcgcagtctccggcgagcaccggaggcagggcattgccaccgcgctc
atcaatctcctcaagcatgaggccaacgcgcttggtgcttatgtgatctacgtgcaagcagattacggtgacgatc
ccgcagtggctctctatacaaagttgggcatacgggaagaagtgatgcactttgatatcgacccaagtaccgcca
cctaacaattcgttcaagccgagatcggcttcccggccgcggagttgttcggtaaattgtcaacgccgccaggt
ggcacttttcggggaaatgtgcgcgcccgcgttcctgctggcgctgggcctgtttctggcgctggacttcccgctgttc
cgtcagcagcttttcgcccacgccttgatgatcgcggcggccttggcctgcatatcccgattcaacggccccagg
gcgtccagaacgggcttcaggcgctcccgaaggt (SEQ ID NO:42)

Figure 153A tggcgaatgggacgcgccctgtagcggcgcattaagcgcggcgggtgtggtggttacgcgcagcgtgaccgctacacttg
ccagcgccctagcgcccgctcctttcgctttcttccttcctttctcgccacgttcgccggctttccccgtcaagctctaaatcgg
gggctcccttttaggggttccgatttagtgctttacggcacctcgaccccaaaaaacttgattagggtgatggttcacgtagtggg
ccatcgccctgatagacggttttcgccctttgacgttggagtccacgttctttaatagtggactcttgttccaaactggaacaac
actcaaccctatctcggtctattcttttgatttataagggattttgccgatttcggcctattggtaaaaaatgagctgatttaacaa
aaatttaacgcgaattttaacaaaatattaacgtttacaatttcaggtggcacttttcggggaaatgtgcgcggaaccccctattt
gtttattttctaaatacattcaaatatgtatccgctcatgaattaattcttagaaaaactcatcgagcatcaaatgaaactgcaat
ttattcatatcaggattatcaataccatatttttgaaaaagccgtttctgtaatgaaggagaaaactcaccgaggcagttccata
ggatggcaagatcctggtatcggtctgcgattccgactcgtccaacatcaatacaacctattaatttcccctcgtcaaaaata
aggttatcaagtgagaaatcaccatgagtgacgactgaatccggtgagaatggcaaaagtttatgcatttctttccagacttgt
tcaacaggccagccattacgctcgtcatcaaaatcactcgcatcaaccaaaccgttattcattcgtgattgcgcctgagcga
gacgaaatacgcgatcgctgttaaaaggacaattacaaacaggaatcgaatgcaaccggcgcaggaacactgccagc
gcatcaacaatattttcacctgaatcaggatattcttctaatacctggaatgctgtttccggggatcgcagtggtgagtaacc
atgcatcatcaggagtacggataaaatgcttgatggtcggaagaggcataaaattccgtcagccagtttagtctgaccatctc
atctgtaacatcattggcaacgctaccttgccatgtttcagaaacaactctggcgcatcgggcttcccatacaatcgatagat
tgtcgcacctgattgcccgacattatcgcgagcccatttataccatataaatcagcatccatgttggaatttaatcgcggccta
gagcaagacgtttcccgttgaatatggctcataacaccccttgtattactgtttatgtaagcagacagttttattgttcatgaccaa
aatcccttaacgtgagttttcgttccactgagcgtcagaccccgtagaaaagatcaaaggatcttcttgagatcctttttttctgc
gcgtaatctgctgcttgcaaacaaaaaaaccaccgctaccagcggtggtttgtttgccggatcaagagctaccaactctttt
ccgaaggtaactggcttcagcagagcgcagataccaaatactgtccttctagtgtagccgtagttaggccaccacttcaag
aactctgtagcaccgcctacatacctcgctctgctaatcctgttaccagtggctgctgccagtggcgataagtcgtgtcttacc
gggttggactcaagacgatagttaccggataaggcgcagcggtcgggctgaacggggggttcgtgcacacagcccagct
tggagcgaacgacctacaccgaactgagatacctacagcgtgagctatgagaaagcgccacgcttcccgaagggaga
aaggcggacaggtatccggtaagcggcagggtcggaacaggagagcgcacgagggagcttccaggggggaaacgcc
tggtatctttatagtcctgtcgggtttcgccacctctgacttgagcgtcgatttttgtgatgctcgtcaggggggcggagcctatgg
aaaaacgccagcaacgcggcctttttacggttcctggccttttgctggccttttgctcacatgttctttcctgcgttatcccctgatt
ctgtggataaccgtattaccgcctttgagtgagctgataccgctcgccgcagccgaacgaccgagcgcagcgagtcagtg
agcgaggaagcggaagagcgcctgatgcggtattttctccttacgcatctgtgcggtatttcacaccgcatatatggtgcact
ctcagtacaatctgctctgatgccgcatagttaagccagtatacactccgctatcgctacgtgactgggtcatggctgcgccc
cgacacccgccaacacccgctgacgcgccctgacgggcttgtctgctcccggcatccgcttacagacaagctgtgaccgt
ctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctg
ataaagcgggccatgttaagggcggttttttcctgtttggtcactgatgcctccgtgaagggggattctgttcatgggggtaat
gataccgatgaaacgagagaggatgctcacgatacgggttactgatgatgaacatgcccggttactggaacgttgtgagg
gtaaacaactggcggtatggatgcggcgggaccagagaaaaatcactcagggtcaatgccagcgcttcgttaatacaga
tgtaggtgttccacagggtagccagcagcatcctgcgatgcagatccggaacataatggtgcagggcgctgacttccgcgt
ttccagactttacgaaacacggaaaccgaagaccattcatgttgttgctcaggtcgcagacgttttgcagcagcagtcgcttc
acgttcgctcgcgtatcggtgattcattctgctaaccagtaaggcaaccccgccagcctagccgggtcctcaacgacagga
gcacgatcatgcgcacccgtggggccgccatgccggcgataatggcctgcttctcgccgaaacgtttggtggcgggacca
gtgacgaaggcttgagcgagggcgtgcaagattccgaataccgcaagcgacaggccgatcatcgtcgcgctccagcga
aagcggtcctcgccgaaaatgacccagagcgctgccggcacctgtcctacgagttgcatgataaagaagacagtcataa
gtgcggcgacgatagtcatgccccgcgcccaccggaaggagctgactgggttgaaggctctcaagggcatcggtcgag
atcccggtgcctaatgagtgagctaacttacattaattgcgttgcgctcactgcccgctttccagtcgggaaacctgtcgtgcc
agctgcattaatgaatcggccaacgcgcggggagaggcggtttgcgtattgggcgccagggtggtttttcttttcaccagtga
gacgggcaacagctgattgcccttcaccgcctggccctgagagagttgcagcaagcggtccacgctggtttgccccagca
ggcgaaaatcctgtttgatggtggttaacggcgggatataacatgagctgtcttcggtatcgtcgtatcccactaccgagatat
ccgcaccaacgcgcagcccggactcggtaatggcgcgcattgcgcccagcgccatctgatcgttggcaaccagcatcgc
agtgggaacgatgccctcattcagcatttgcatggtttgttgaaaaccggacatggcactccagtcgccttcccgttccgctat
cggctgaatttgattgcgagtgagatatttatgccag

Figure 153B ccagccagacgcagacgcgccgagacagaacttaatgggcccgctaacagcgcgatttgctggtgaccca
atgcgaccagatgctccacgcccagtcgcgtaccgtcttcatgggagaaaataatactgttgatgggtgtctgg
tcagagacatcaagaaataacgccggaacattagtgcaggcagcttccacagcaatggcatcctggtcatc
cagcggatagttaatgatcagcccactgacgcgttgcgcgagaagattgtgcaccgccgctttacaggcttcg
acgccgcttcgttctaccatcgacaccaccacgctggcacccagttgatcggcgcgagatttaatcgccgcga
caatttgcgacggcgcgtgcagggccagactggaggtggcaacgccaatcagcaacgactgtttgcccgcc
agttgttgtgccacgcggttgggaatgtaattcagctccgccatcgccgcttccacttttccgcgtttcgcaga
aacgtggctggcctggttcaccacgcgggaaacggtctgataagagacaccggcatactctgcgacatcgt
ataacgttactggtttcacattcaccaccctgaattgactctcttccgggcgctatcatgccataccgcgaaaggt
tttgcgccattcgatggtgtccgggatctcgacgctctcccttatgcgactcctgcattaggaagcagcccagta
gtaggttgaggccgttgagcaccgccgccgcaaggaatggtgcatgcaaggagatggcgcccaacagtcc
cccggccacggggcctgccaccatacccacgccgaaacaagcgctcatgagcccgaagtggcgagccc
gatcttccccatcggtgatgtcggcgatataggcgccagcaaccgcacctgtggcgccggtgatgccggcca
cgatgcgtccggcgtagaggatcgagatctcgatcccgcgaaattaatacgactcactatagggaattgtga
gcggataacaattcccctctagaaataattttgtttaactttaagaaggagatatacatatgcgttgtagcgtgtcc
accgaaaatgtgtcttcaccgaaactgaaaccgaagctcgtcgttctgcgaactacgaacctaacagctgg
gactatgattacctgctgtcctccgacacggacgagtccatcgaagtatacaaagacaaagcgaaaaagct
ggaagccgaagttcgtcgcgagattaataacgaaaaagcagaatttctgaccctgctggaactgattgacaa
cgtccagcgcctgggcctgggttaccgtttcgagtctgatatccgtggtgcgctggatcgcttcgtttcctccggc
ggcttcgatgcggtaaccaagacttccctgcacggtacggcactgtctttccgtctgctgcgtcaacacggttttg
aggtttctcaggaagcgttcagcggcttcaaagaccaaaacggcaacttcctggagaacctgaaggaagat
atcaaagctatcctgagcctgtacgaggccagcttcctggctctggaaggcgaaaacatcctggacgaggc
gaaggttttcgcaatctctcatctgaaagaactgtctgaagaaaagatcggtaaagagctggcagaacaggt
gaaccatgcactggaactgccactgcatcgccgtactcagcgtctggaagcagtatggtctatcgaggcctac
cgtaaaaaggaggacgcgaatcaggtctgctggagctggcaattctggattacaacatgatccagtctgtat
accagcgtgatctgcgtgaaacgtcccgttggtggcgtcgtgtgggtctggcgaccaaaactgcacttgctcgtg
accgcctgattgagagcttctactgggccgtgggtgtagcattcgaaccgcaatactccgactgccgtaactcc
gtcgcaaaaatgttttctttcgtaaccattatcgacgatatctacgatgtatacggcaccctggacgaactggag
ctgtttactgatgcagttgagcgttgggacgtaaacgccatcaacgacctgccggattacatgaaactgtgcttt
ctggctctgtataacactattaacgaaatcgcctacgacaacctgaaagataaaggtgagaacatcctgccgt
atctgaccaaagcctgggctgacctgtgcaacgctttcctgcaagaagccaagtggctgtacaacaaatctac
tccgaccttgacgactacttcggcaacgcatggaaatcctcttctggcccgctgcaactggtgttcgcttacttcg
ctgtcgtgcagaacattaaaaaggaagagatcgaaaacctgcaaaaataccatgacaccatctctcgtcctt
cccatatcttccgtctgtgcaatgacctggctagcgcgtctgcggaaattgcgcgtggtgaaaccgcaaatagc
gtttcttgttacatgcgcactaaaggtatctccgaagaactggctaccgaaagcgtgatgaatctgatcgatgaa
acctggaaaagatgaacaaggaaaaactgggtggtagcctgttcgcgaaaccgttcgtggaaaccgcga
tcaacctggcacgtcaatctcactgcacttatcataacggcgacgcgcatacctctccggatgagctgacccg
caaacgcgttctgtctgtaatcactgaaccgattctgccgtttgaacgctaaggatccgaattcgagctccgtcg
acaagcttgcggccgcactcgagcaccaccaccaccaccactgagatccggctgctaacaaagcccgaa
aggaagctgagttggctgctgccaccgctgagcaataactagcataacccctgggcctctaaacgggtctt
gagggttttttgctgaaaggaggaactatatccggat (SEQ ID NO:43)

Figure 156A 1-
gtttgacagcttatcatcgactgcacggtgcaccaatgcttctggcgtcaggcagccatcggaagctgtggtatggctgtgcag
gtcgtaaatcactgcataattcgtgtcgctcaaggcgcactcccgttctggataatgttttttgcgccgacatcataacggttctgg
caaatattctgaaatgagctgttgacaattaatcatccggctcgtataatgtgtggaattgtgagcggataacaatttcacacag
gaaacagcgccgctgagaaaaagcgaagcggcactgctctttaacaatttatcagacaatctgtgtgggcactcgaccgga
attatcgattaactttattattaaaaattaaagaggtatatattaatgtatcgattaaataaggaggaataaaccatgagatgtagc
gtgtccaccgaaaatgtgtctttcaccgaaactgaaaccgaagctcgtcgttctgcgaactacgaacctaacagctgggacta
tgattacctgctgtcctccgacacggacgagtccatcgaagtatacaaagacaaagcgaaaaagctggaagccgaagttc
gtcgcgagattaataacgaaaagcagaatttctgaccctgctggaactgattgacaacgtccagcgcctgggcctgggtta
ccgtttcgagtctgatatccgtggtgcgctggatcgcttcgtttcctccggcggcttcgatgcggtaaccaagacttccctgcacg
gtacggcactgtcttccgtctgctgcgtcaacacggttttgaggtttctcaggaagcgttcagcggcttcaaagaccaaaacgg
caacttcctggagaacctgaaggaagatatcaaagctatcctgagcctgtacgaggccagcttcctggctctggaaggcgaa
aacatcctggacgaggcgaaggttttcgcaatctctcatctgaaagaactgtctgaagaaaagatcggtaaagagctggcag
aacaggtgaaccatgcactggaactgccactgcatcgccgtactcagcgtctggaagcagtatggtctatcgaggcctaccg
taaaaaggaggacgcgaatcaggttctgctggagctggcaattctggattacaacatgatccagtctgtataccagcgtgatct
gcgtgaaacgtcccgttggtggcgtcgtgtgggtctggcgaccaaactgcactttgctcgtgaccgcctgattgagagcttctac
tgggccgtgggtgtagcattcgaaccgcaatactccgactgccgtaactccgtcgcaaaaatgttttctttcgtaaccattatcga
cgatatctacgatgtatacggcaccctggacgaactggagctgtttactgatgcagttgagcgttgggacgtaaacgccatca
acgacctgccggattacatgaaactgtgtcttctggctctgtataacactattaacgaaatcgcctacgacaacctgaaagata
aaggtgagaacatcctgccgtatctgaccaaagcctgggctgacctgtgcaacgctttcctgcaagaagccaagtggctgta
caacaaatctactccgacctttgacgactacttcggcaacgcatggaaatcctcttctggcccgctgcaactggtgttcgcttact
tcgctgtcgtgcagaacattaaaaaggaagagatcgaaaacctgcaaaaataccatgacaccatctctcgtccttcccatatc
ttccgtctgtgcaatgacctggctagcgcgtctgcggaaattcgcgcgtggtgaaaccgcaaatagcgtttcttgttacatgcgca
ctaaaggtatctccgaagaactggctaccgaaagcgtgatgaatctgatcgatgaaacctggaaaaagatgaacaaggaa
aaactgggtggtagcctgttcgcgaaaccgttcgtggaaaccgcgatcaacctggcacgtcaatctcactgcacttatcataa
cggcgacgcgcatacctctccggatgagctgacccgcaaacgcgttctgtctgtaatcactgaaccgattctgccgtttgaacg
ctaactgcagctggtaccatatgggaattcgaagctttctagaacaaaaactcatctcagaagaggatctgaatagcgccgtc
gaccatcatcatcatcatcattgagtttaaacggtctccagcttggctgttttggcggatgagagaagattttcagcctgatacag
attaaatcagaacgcagaagcggtctgataaaacagaatttgcctggcggcagtagcgcggtggtcccacctgaccccatg
ccgaactcagaagtgaaacgccgtagcgccgatggtagtgtggggtctccccatgcgagagtagggaactgccaggcatc
aaataaaacgaaaggctcagtcgaaagactgggcctttcgttttatctgttgtttgtcggtgaacgctctcctgagtaggacaaat
ccgccgggagcggatttgaacgttgcgaagcaacggcccggagggtggcgggcaggacgcccgccataaactgccagg
catcaaattaagcagaaggccatcctgacggatggcctttttgcgtttctacaaactcttttgtttatttttctaaatacattcaaatat
gtatccgctcatgagacaataaccctgataaatgcttcaataatattgaaaaaggaagagtatgagtattcaacatttccgtgtc
gcccttattcccttttttgcggcattttgccttcctgtttttgctcacccagaaacgctggtgaaagtaaaagatgctgaagatcagtt
gggtgcacgagtgggttacatcgaactggatctcaacagcggtaagatccttgagagttttcgccccgaagaacgttttccaat
gatgagcacttttaaagttctgctatgtggcgcggtattatcccgtgttgacgccgggcaagagcaactcggtcgccgcataca
ctattctcagaatgacttggttgagtactcaccagtcacagaaaagcatcttacggatggcatgacagtaagagaattatgcag
tgctgccataaccatgagtgataacactgcggccaacttacttctgacaacgatcggaggaccgaaggagctaaccgcttttt
gcacaacatggggatcatgtaactcgccttgatcgttgggaaccggagctgaatgaagccataccaaacgacgagcgtg
acaccacgatgcctgtagcaatggcaacaacgttgcgcaaactattaactggcgaactacttactctagcttcccggcaaca
attaatagactggatggaggcggataaagttgcaggaccacttctgcgctcggcccttccggctggctggttattgctgataaa
tctggagccggtgagcgtgggtctcgcggtatcattgcagcactggggccagatggtaagccctcccgtatcgtagttatctac
acgacggggagtcaggcaactatggatgaacgaaatagacagatcgctgagataggtgcctcactgattaagcattggtaa
ctgtcagaccaagtttactcatatatactttagattgatttaaaacttcatttttaatttaaaaggatctaggtgaagatcctttttgata
atctcatgaccaaaatcccttaacgtgagttttcgttccactgagcgtcagaccccgtagaaaagatcaaaggatcttcttgaga
tcctttttttctgcgcgtaatctgctgcttgcaaacaaaaaaaccaccgctaccagcggtggtttgttgccggatcaagagctac
caactctttttccgaaggtaactggcttcagcagagcgcagataccaaatactgtccttctagtgtagccgtagttaggccacca
cttcaagaactctgtagcaccgcctacatacctcgctctgctaatcctgttaccagtggctgc

Figure 156B tgccagtggcgataagtcgtgtcttaccgggttggactcaagacgatagttaccggataaggcgcagcggtcg
ggctgaacggggggttcgtgcacacagcccagcttggagcgaacgacctacaccgaactgagatacctac
agcgtgagctatgagaaagcgccacgcttcccgaagggagaaaggcggacaggtatccggtaagcggc
agggtcggaacaggagagcgcacgagggagcttcaggggggaaacgcctggtatctttatagtcctgtcgg
gtttcgccacctctgacttgagcgtcgattttttgtgatgctcgtcaggggggcggagcctatggaaaaacgcca
gcaacgcggcctttttacggttcctggcctttttgctggcctttttgctcacatgttctttcctgcgttatcccctgattcgt
ggataaccgtattaccgcctttgagtgagctgataccgctcgccgcagccgaacgaccgagcgcagcgagt
cagtgagcgaggaagcggaagagcgcctgatgcggtatttttctccttacgcatctgtgcggtatttcacaccgc
atatggtgcactctcagtacaatctgctctgatgccgcatagttaagccagtatacactccgctatcgctacgtga
ctgggtcatggctgcgccccgacacccgccaacacccgctgacgcgccctgacgggcttgtctgctcccggc
atccgcttacagacaagctgtgaccgtctccgggagctgcatgtgtcagaggttttcaccgtcatccgaaac
gcgcgaggcagcagatcaattcgcgcgcgaaggcgaagcggcatgcatttacgttgacaccatcgaatggt
gcaaaaccttcgcggtatggcatgatagcgcccggaagagagtcaattcagggtggtgaatgtgaaacca
gtaacgttatacgatgtcgcagagtatgccggtgtctcttatcagaccgtttcccgcgtggtgaaccaggccagc
cacgtttctgcgaaaacgcgggaaaaagtggaagcggcgatggcggagctgaattacattcccaaccgcgt
ggcacaacaactggcgggcaaacagtcgttgctgattggcgttgccacctccagtctggccctgcacgcgcc
gtcgcaaattgtcgcggcgattaaatctcgcgccgatcaactgggtgccagcgtggtggtgtcgatggtagaa
cgaagcggcgtcgaagcctgaaagcggcggtgcacaatcttctcgcgcaacgcgtcagtgggctgatcatt
aactatccgctggatgaccaggatgccattgctgtggaagctgcctgcactaatgttccggcgttatttcttgatgt
ctctgaccagacacccatcaacagtattattttctcccatgaagacggtacgcgactgggcgtggagcatctgg
tcgcattgggtcaccagcaaatcgcgctgttagcgggcccattaagttctgtctcggcgcgtctgcgtctggctg
gctggcataaatatctcactcgcaatcaaattcagccgatagcggaacgggaaggcgactggagtgccatgt
ccggttttcaacaaaccatgcaaatgctgaatgagggcatcgttcccactgcgatgctggttgccaacgatca
gatggcgctgggcgcaatgcgcgccattaccgagtccgggctgcgcgttggtgcggatatctcggtagtggg
atacgacgataccgaagacagctcatgttatatcccgcgtcaaccaccatcaaacaggattttcgcctgctg
gggcaaaccagcgtggaccgcttgctgcaactctctcagggccaggcggtgaagggcaatcagctgttgcc
cgtctcactggtgaaaagaaaaaccaccctggcgcccaatacgcaaaccgcctctccccgcgcgttggccg
attcattaatgcagctggcacgacaggtttcccgactggaaagcgggcagtgagcgcaacgcaattaatgtg
agttagcgcgaattgatctg (SEQ ID NO:44)

Figure 159A 1-
gtttgacagcttatcatcgactgcacggtgcaccaatgcttctggcgtcaggcagccatcggaagctgtggtatggctgtgcag
gtcgtaaatcactgcataattcgtgtcgctcaaggcgcactcccgttctggataatgttttttgcgccgacatcataacggttctgg
caaatattctgaaatgagctgttgacaattaatcatccggctcgtataatgtgtggaattgtgagcggataacaatttcacacag
gaaacagcgccgctgagaaaaagcgaagcggcactgctctttaacaatttatcagacaatctgtgtgggcactcgaccgga
attatcgattaactttattattaaaaattaaagaggtatatattaatgtatcgattaaataaggaggaataaaccatgagatgtag
cgtgtccaccgaaaatgtgtctttcaccgaaactgaaaccgaagctcgtcgttctgcgaactacgaacctaacagctgggact
atgattacctgctgtcctccgacacggacgagtccatcgaagtatacaaagacaaagcgaaaaagctggaagccgaagtt
cgtcgcgagattaataacgaaaaagcagaatttctgaccctgctggaactgattgacaacgtccagcgcctgggcctgggtt
accgtttcgagtctgatatccgtggtgcgctggatcgcttcgtttcctccggcggcttcgatgcggtaaccaagacttccctgcac
ggtacggcactgtcttccgtctgctgcgtcaacacggttttgaggtttctcaggaagcgttcagcggcttcaaagaccaaaac
ggcaacttcctggagaacctgaaggaagatatcaaagctatcctgagcctgtacgaggccagcttcctggctctggaaggc
gaaaacatcctggacgaggcgaaggttttcgcaatctctcatctgaaagaactgtctgaagaaaagatcggtaaagagctg
gcagaacaggtgaaccatgcactggaactgccactgcatcgccgtactcagcgtctggaagcagtatggtctatcgaggcc
taccgtaaaaaggaggacgcgaatcaggttctgctggagctggcaattctggattacaacatgatccagtctgtataccagc
gtgatctgcgtgaaacgtcccgttggtggcgtcgtgtgggtctggcgaccaaactgcactttgctcgtgaccgcctgattgaga
gcttctactgggccgtgggtgtagcattcgaaccgcaatactccgactgccgtaactccgtcgcaaaaatgttttctttcgtaacc
attatcgacgatatctacgatgtatacggcaccctggacgaactggagctgtttactgatgcagttgagcgttgggacgtaaac
gccatcaacgacctgccggattacatgaaactgtgctttctggctctgtataacactattaacgaaatcgcctacgacaacctg
aaagataaaggtgagaacatcctgccgtatctgaccaaagcctgggctgacctgtgcaacgctttcctgcaagaagccaag
tggctgtacaacaaatctactccgacctttgacgactacttcggcaacgcatggaaatcctcttctggcccgctgcaactggtgt
tcgcttacttcgctgtcgtgcagaacattaaaaaggaagagatcgaaaacctgcaaaaataccatgacaccatctctcgtcct
tcccatatcttccgtctgtgcaatgacctggctagcgcgtctgcggaaattgcgcgtggtgaaaccgcaaatagcgtttcttgtta
catgcgcactaaaggtatctccgaagaactggctaccgaaagcgtgatgaatctgatcgatgaaacctggaaaaagatga
acaaggaaaaactgggtggtagcctgttcgcgaaaccgttcgtggaaaccgcgatcaacctggcacgtcaatctcactgca
cttatcataacggcgacgcgcataccctccggatgagctgaccccgaaacgcgttctgtctgtaatcactgaaccgattctgc
cgtttgaacgctaactgcataaaggaggtaaaaaaacatggtatcctgttctgcgccgggtaagatttacctgttcggtgaaca
cgccgtagtttatggcgaaactgcaattgcgtgtgcggtggaactgcgtacccgtgttcgcgcgaactcaatgactctatcac
tattcagagccagatcggccgcaccggtctggatttcgaaaagcacccttatgtgtctgcggtaattgagaaaatgcgcaaat
ctattcctattaacggtgttttcttgaccgtcgattccgacatcccggtgggctccggtctggggtagcagcgcagccgttactatcg
cgtctattggtgcgctgaacgagctgttcggctttggcctcagcctgcaagaaatcgctaaactgggccacgaaatcgaaatt
aaagtacagggtgccgcgtccccaaccgatacgtatgttctaccttcggcggcgtggttaccatcccggaacgtcgcaaact
gaaaactccggactgcggcattgtgattggcgataccggcgttttctcctccaccaaagagttagtagctaacgtacgtcagct
gcgcgaaagctacccggatttgatcgaaccgctgatgacctctattggcaaaatctctcgtatcggcgaacaactggttctgtc
tggcgactacgcatccatcggccgcctgatgaacgtcaaccagggtctcctggacgccctgggcgttaacatcttagaactg
agccagctgatctattccgctcgtgcggcaggtgcgtttggcgctaaaatcacggggcgctggcggcggtggctgtatggttgc
gctgaccgctccggaaaaatgcaaccaagtggcagaagcggtagcaggcgctggcggtaaagtgactatcactaaaccg
accgagcaaggtctgaaagtagattaaagtctagttaaagtttaaacggtctccagcttggctgttttggcggatgagagaag
attttcagcctgatacagattaaatcagaacgcagaagcggtctgataaaacagaatttgcctggcggcagtagcgcggtgg
tcccacctgaccccatgccgaactcagaagtgaaacgccgtagcgccgatggtagtgtggggtctcccatgcgagagtag
ggaactgccaggcatcaaataaaacgaaaggctcagtcgaaagactgggcctttcgtttatctgtttgtcggtgaacgct
ctcctgagtaggacaaatccgcgggagcggatttgaacgttgcgaagcaacggcccggagggtggcgggcaggacgc
ccgccataaactgccaggcatcaaattaagcagaaggccatcctgacggatggccttttgcgtttctacaaactcttttgtttat
ttttctaaatacattcaaatatgtatccgctcatgagacaataacccctgataaatgcttcaataatattgaaaaaggaagagtatg
agtattcaacatttccgtgtcgcccttattcctttttgcggcattttgccttcctgtttttgctcacccagaaacgctggtgaaagtaa
aagatgctgaagatcagttgggtgcacgagtgggttacatcgaactggatctcaacagcggtaagatccttgagagttttcgc
cccgaagaacgttttccaatgatgagcacttttaaagttctgctatgtggcgcggtattatcccgtgttgacgccgggcaagagc
aactcggtcgccgcatacactattctcagaatgacttggttgagtactcaccagtcacagaaaagcatcttacggatggcatg
acagtaagagaattatgcagtgctgccataaccatgagtgataacactgcggccaacttacttctgacaacg

Figure 159B atcggaggaccgaaggagctaaccgctttttgcacaacatgggggatcatgtaactcgccttgatcgttgggaac
cggagctgaatgaagccataccaaacgacgagcgtgacaccacgatgcctgtagcaatggcaacaacgttgc
gcaaactattaactggcgaactacttactctagcttcccggcaacaattaatagactggatggaggcggataaagt
tgcaggaccacttctgcgctcggcccttccggctggctggtttattgctgataaatctggagccggtgagcgtgggtc
tcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcaga
ccaagtttactcatatatactttagattgatttaaaacttcattttaatttaaaaggatctaggtgaagatccttttgataa
tctcatgaccaaaatcccttaacgtgagttttcgttccactgagcgtcagaccccgtagaaaagatcaaaggatctt
cttgagatcctttttttctgcgcgtaatctgctgcttgcaaacaaaaaaaccaccgctaccagcggtggtttgtttgccg
gatcaagagctaccaactctttttccgaaggtaactggcttcagcagagcgcagataccaaatactgtcctctagt
gtagccgtagttaggccaccacttcaagaactctgtagcaccgcctacatacctcgctctgctaatcctgttaccagt
ggctgctgccagtggcgataagtcgtgtcttaccgggttggactcaagacgatagttaccggataaggcgcagcg
gtcgggctgaacggggggtcgtgcacacagcccagcttggagcgaacgacctacaccgaactgagatacct
acagcgtgagctatgagaaagcgccacgcttcccgaagggagaaaggcggacaggtatccggtaagcggca
gggtcggaacaggagagcgcacgagggagcttccaggggggaaacgcctggtatctttatagtcctgtcgggtttc
gccacctctgacttgagcgtcgatttttgtgatgctcgtcaggggggcggagcctatggaaaaacgccagcaacg
cggcctttttacggttcctggccttttgctggccttttgctcacatgttctttcctgcgttatcccctgattctgtggataaccg
tattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatggtgcactctc
agtacaatctgctctgatgccgcatagttaagccagtatacactccgctatcgctacgtgactgggtcatggctgcg
ccccgacacccgccaacacccgctgacgcgccctgacgggcttgtctgctcccggcatccgcttacagacaag
ctgtgaccgtctccgggagctgcatgtgtcagaggttttcaccgtcatcaccgaaacgcgcgaggcagcagatca
attcgcgcgcgaaggcgaagcggcatgcatttacgttgacaccatcgaatggtgcaaaacctttcgcggtatggc
atgatagcgcccggaagagagtcaattcagggtggtgaatgtgaaaccagtaacgttatacgatgtcgcagagt
atgccggtgtctcttatcagaccgtttcccgcgtggtgaaccaggccagccacgtttctgcgaaaacgcgggaaa
aagtggaagcggcgatggcggagctgaattacattcccaaccgcgtggcacaacaactggcgggcaaacagt
cgttgctgattggcgttgccacctccagtctggccctgcacgcgccgtcgcaaattgtcgcggcgattaaatctcgc
gccgatcaactgggtgccagcgtggtggtcgatggtagaacgaagcggcgtcgaagcctgtaaagcggcg
gtgcacaatcttctcgcgcaacgcgtcagtgggctgatcattaactatccgctggatgaccaggatgccattgctgt
ggaagctgcctgcactaatgttccggcgttatttcttgatgtctctgaccagacacccatcaacagtattattttctccc
atgaagacggtacgcgactgggcgtggagcatctggtcgcattgggtcaccagcaaatcgcgctgttagcgggc
ccattaagttctgtctcggcgcgtctgcgtctggctggctggcataaatatctcactcgcaatcaaattcagccgata
gcggaacgggaaggcgactggagtgccatgtccggttttcaacaaaccatgcaaatgctgaatgagggcatcgt
tcccactgcgatgctggttgccaacgatcagatggcgctgggcgcaatgcgcgccattaccgagtccgggctgc
gcgttggtgcggatatctcggtagtgggatacgacgataccgaagacagctcatgttatatcccgccgtcaacca
ccatcaaacaggattttcgcctgctggggcaaaccagcgtggaccgcttgctgcaactctctcagggccaggcg
gtgaagggcaatcagctgttgcccgtctcactggtgaaaagaaaaaccaccctggcgcccaatacgcaaaccg
cctctccccgcgcgttggccgattcattaatgcagctggcacgacaggtttcccgactggaaagcgggcagtgag
cgcaacgcaattaatgtgagttagcgcgaattgatctg (SEQ ID NO:45)

Figure 160B gcggccgcgcccttgacgatgccacatcctgagcaaataattcaaccactaattgtgagcggataacacaaggagga
aacagccatggtatcctgttctgcgccgggtaagatttacctgttcggtgaacacgccgtagtttatggcgaaactgcaatt
gcgtgtgcggtggaactgcgtacccgtgttcgcgcggaactcaatgactctatcactattcagagccagatcggccgcac
cggtctggatttcgaaaagcacccttatgtgtctgcggtaattgagaaaatgcgcaaatctattcctattaacggtgtttcttg
accgtcgattccgacatcccggtgggctccggtctgggtagcagcgcagccgttactatcgcgtctattggtgcgctgaac
gagctgttcggctttggcctcagcctgcaagaaatcgctaaactgggccacgaaatcgaaattaaagtacagggtgccg
cgtccccaaccgatacgtatgtttctaccttcggcggcgtggttaccatcccggaacgtcgcaaactgaaaactccggac
tgcggcattgtgattggcgataccggcgttttctcctccaccaaagagttagtagctaacgtacgtcagctgcgcgaaagc
tacccggatttgatcgaaccgctgatgacctctattggcaaaatctctcgtatcggcgaacaactggttctgtctggcgact
acgcatccatcggccgcctgatgaacgtcaaccagggtctcctggacgccctgggcgttaacatcttagaactgagcca
gctgatctattccgctcgtgcggcaggtgcgtttggcgctaaaatcacgggcgctggcggcggtggctgtatggttgcgct
gaccgctccggaaaaatgcaaccaagtggcagaagcggtagcaggcgctggcggtaaagtgactatcactaaaccg
accgagcaaggtctgaaagtagattaagccttgacttaatagctgcttatttcgcccttatggtacctagtaggaggaaaa
aaacatggaaatgcgtcaaccggctgtcgcaggtcaattctacccactgcgttgcgagaacctggaaaacgaactgaa
acgctgcttcgaaggcctggagatccgcgaacaagaagtgctgggcgcagtctgtccgcacgccggttatatgtactct
ggcaaagttgcggcgcacgtctatgccactctgccggaagctgataccctacgtaatcttcggcccgaaccacaccggct
acggtagccctgtctctgtgagccgtgaaacttggaagaccccgttgggcaatatcgatgttgacctggaactggcggac
ggcttcctggggttccatcgtagatgcggatgaactcggtcacaaatacgaacactctatcgaagttcagctgccgtttctgc
aataccgttttgaacgcgatttcaaaaattctgccaatctgcatgggtatgcaagacgaagaaaccgcggtcgaagtaggt
aacctgctggcggatctgatcagcgagtccggtaaacgtgctgtgatcatcgcaagctctgatttcacccactatgagac
ggctgaacgtgccaaagaaatcgattccgaagttattgattctatcctgaactttgacatctctggcatgtacgatcgcctgt
atcgccgtaacgcctctgtttgcggttacggcccgatcaccgctatgctgacggcaagcaaaaagctgggcggctctcgt
gcgactttgctgaaatacgcaaacagcggtgacgtgtccggtgataaagacgctgtggtgggctacgccgccatcatcg
ttgagtaagctgattaaaggttgaacagataggatttcgtcatggatcctacaaggaggaaaaaaacatgaatgcttcta
atgaaccggtgattctgaaactgggtggctctgctattaccgacaaaggtgcctacgaaggcgtagttaaggaagctgat
ttgctgcgcatcgcacaggaagttagcggtttccgtggcaagatgatcgtggttcatggtgctggtagcttcggccatacgt
acgcgaagaaatacggcctggaccgtaccttcgacccagagggcgcaattgttactcatgaatcgttaaaaagctcgc
ctccaaagttgtaggtgctctgaatagcttcggcgtgcgtgctatcgcggtgcatcctatggactgcgcagtatgccgtaac
ggtcgtatcgaaacgatgtatctggactccatcaagttaatgctggaaaaaggtctggtgccggttctgcacggcgacgtc
gcaatggatattgaactgggcacttgtatcctgtccggtgatcaaatcgttccttacctggccaaagaactgggtatctccc
gcctcggcctgggcagcgcagaggatggtgtgctggatatggagggcaaacctgtaccggaaatcaccccagaaact
ttcgaagagttccgccactgcatcggtggttctggttctactgatgtaaccggtggcatgctgggcaaagtgctggaacttct
ggaattgagcaaaaattcttccattactagctacattttcaacgctggtaaagcagacaacatctaccgcttctgaatggtg
agtccatcggcactcgcatcagcccggacaagcgtgtttaagctagttattaacctaaatgctctaaaccagttatgagct
ctacaaggaggaaaaaaacatgattaacactaccagccgccgcaaaattgaacacctgaaactctgcgcagaatcc
ccggttgaagcgcgtcaggtatctgccggctttgaagacgttactctgatccaccgcgctttaccggagctgaacatggat
gaactggacctcagcgttgatttcctgggtaaacgcatcaaagcgccgttcctgattgcgtctatcacgggtggtcaccca
gataccatcccggttaacgctgcgctggcagctgctgctgaggagctgggtgttggcatcggcgttggctctcagcgcgc
ggccattgatgatccgagccaggaagacagcttccgtgtagtgcgtgatgaagcccagatgcgtttgtttatggcaacgt
cggcgcagcacagatccgtcagtatggtgttgaaggtgttgaaaaactgatcgaaatgattgacgcagatgccttggca
atccacctgaactttctgcaagaagcggtccaaccggaaggtgaccgcgacgcgaccggttgcctggacatgattacc
gaaatttgctctcagattaaaactccggtaatcgtgaaagaaaccggtgcaggcattagccgtgaagatgcgattctgttc
cagaaagctggcgtgagcgcaatcgacgttggcggcgcgggcggcacctcctgggctggcgtcgaggtctaccgtgc
taaagaaagccgtgactctgttagcgagcgtttaggtgagctgtttgggatttcggcattccgacggtagcttctctgattga
atcccgcgtttccttgccgctgatcgcaaccggcggtatccgtaacggtctggacattgctaaaagcattgctctcggcgc
aagcgctgccagcgccgctctgccgttcgttggtccgtccctggagggcaaagaatccgttgtacgtgtgctgagctgcat
gctggaagaatttaaagcagcaatgttttgtgcggttgcggcaacatcaaaga

Figure 160C cctgcacaactctccagtagtggtaactggttggacccgcgaatacctggagcagcgcggttttaacgttaagga
cctctccctgccgggcaacgctctgtaagcttcaacgcgtctacaaataaaaaaggcacgtcagatgacgtgcct
tttttcttgtctaga
(SEQ ID NO:46)

MCM376 - MVK from M. mazei archeal Lower in pET200D
6647 bp

Figure 161B aagggcgagctcaacgatccggctgctaacaaagcccgaaaggaagctgagttggctgctgccaccgctgagcaata
actagcataaccccttggggcctctaaacgggtcttgaggagttttttgctgaaaggaggaactatatccggatatccgc
aagaggcccggcagtaccggcataaccaagcctatgcctacagcatccaggtgacggtgccgaggatgacgatga
gcgcattgttagatttcatacacggtgcctgactgcgttagcaatttaactgtgataaactaccgcattaaagcttatcgatga
taagctgtcaaacatgagaattaattcttgaagacgaaagggcctcgtgatacgcctattttataggttaatgtcatgataat
aatggtttcttagacgtcaggtggcacttttcggggaaatgtgcgcggaaccccctatttgtttattttctaaatacattcaaatat
gtatccgctcatgagacaataaccctgataaatgcttcaataatattgaaaaaggaagagtatgattgaacaagatggatt
gcacgcaggttctccggccgcttgggtggagaggctattcggctatgactgggcacaactgacaatcggctgctctgatg
ccgccgtgttccggctgtcagcgcaggggcgcccggttcttttgtcaagaccgacctgtccggtgccctgaatgaactgc
aggacgaggcagcgcggctatcgtggctggccacgacgggcgttcttgcgcagctgtgctcgacgttgtcactgaagc
gggaagggactggctgctattgggcgaagtgccggggcaggatctcctgtcatctcaccttgctcctgccgagaaagtat
ccatcatggctgatgcaatgcggcggctgcatacgcttgatccggctacctgcccattcgaccaccaagcgaaacatcg
catcgagcgggcacgtactcggatgaagccggtcttgtcgatcaggatgatctggacgaagagcatcaggggctcgc
gccagccgaactgttcgccaggctcaaggcgcgcatgcccgacggcgaggatctcgtcgtgacacatggcgatgcctg
cttgccgaatatcatggtggaaaatggccgcttttctggattcatcgactgtggccggctgggtgtggcggaccgctatcag
gacatagcgttggctacccgtgatattgctgaagagcttggcggcgaatgggctgaccgcttcctcgtgctttacggtatcg
ccgctcccgattcgcagcgcatcgccttctatcgccttcttgacgagttcttctgagcgggactctggggttcgaaatgaccg
accaagcgacgcctaactgtcagaccaagtttactcatatatactttagattgatttaaaacttcattttaatttaaaaggatct
aggtgaagatccttttttgataatctcatgaccaaaatcccttaacgtgagttttcgttccactgagcgtcagaccccgtagaa
aagatcaaaggatcttcttgagatccttttttctgcgcgtaatctgctgcttgcaaacaaaaaaaccaccgctaccagcggt
ggtttgtttgccggatcaagagctaccaactctttttccgaaggtaactggcttcagcagagcgcagataccaaatactgtc
cttctagtgtagccgtagttaggccaccacttcaagaactctgtagcaccgcctacatacctcgctctgctaatcctgttacc
agtggctgctgccagtggcgataagtcgtgtcttaccgggttggactcaagacgatagttaccggataaggcgcagcggt
cgggctgaacggggggttcgtgcacacagcccagcttggagcgaacgacctacaccgaactgagatacctacagcgt
gagctatgagaaagcgccacgcttcccgaagggagaaaggcggacaggtatccggtaagcggcagggtcggaaca
ggagagcgcacgagggagcttccaggggaaacgcctggtatctttatagtcctgtcgggtttcgccacctctgacttga
gcgtcgatttttgtgatgctcgtcaggggggcggagcctatggaaaaacgccagcaacgcggcctttttacggttcctggc
cttttgctggccttttgctcacatgttctttcctgcgttatccctgattctgtggataaccgtattaccgcctttgagtgagctgata
ccgctcgccgcagccgaacgaccgagcgcagcgagtcagtgagcgaggaagcggaagagcgcctgatgcggtattt
tctccttacgcatctgtgcggtatttcacaccgcaatggtgcactctcagtacaatctgctctgatgccgcatagttaagcca
gtatacactccgctatcgctacgtgactgggtcatggctgcgccccgacacccgccaacacccgctgacgcgccctgac
gggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcat
ccgcgtccagctcgttgagtttctccagaagcgttaatgtctggcttctgataaagcgggccatgttaagggcggttttttcct
gtttggtcactgatgcctccgtgtaaggggggatttctgttcatgggggtaatgataccgatgaaacgagagaggatgctca
cgatacgggttactgatgatgaacatgcccggttactggaacgttgtgagggtaaacaactggcggtatggatgcggcg
ggaccagagaaaaatcactcagggtcaatgccagcgcttcgttaatacagatgtaggtgttccacagggtagccagca
gcatcctgcgatgcagatccggaacataatggtgcagggcgctgacttccgcgtttccagactttacgaaacacggaaa
ccgaagaccattcatgttgttgctcaggtcgcagacgttttgcagcagcagtcgcttcacgttcgctcgcgtatcggtgattc
attctgctaaccagtaaggcaaccccgccagcctagccgggtcctcaacgacaggagcacgatcatgcgcacccgtg
gccaggacccaacgctgcccgagatgcgccgcgtgcggctgctggagatggcggacgcgatggatatgttctgccaa
gggttggtttgcgcattcacagttctccgcaagaattgattggctccaattcttggagtggtgaatccgttagcgaggtgccg
ccggcttccattcaggtcgaggtggcccggctccatgcaccgcgacgcaacgcggggaggcagacaaggtataggg
cggcgcctacaatccatgccaacccgttccatgtgctcgccgaggcggcataaatcgccgtgacgatcagcggtccaat
gatcgaagttaggctggtaagagccgcgagcgatccttgaagctgtcctgatggtcgtcatctacctgcctggacagcat
ggcctgcaacgcgggcatcccgatgccgccggaagcgagaagaatcataatggggaaggccatccagcctcgcgtc
gcgaacgccagcaagacgtagcccagcgcgt

Figure 161C cggccgccatgccggcgataatggcctgcttctcgccgaaacgtttggtggcgggaccagtgacgaaggcttgag
cgagggcgtgcaagattccgaataccgcaagcgacaggccgatcatcgtcgcgctccagcgaaagcggtcctc
gccgaaaatgacccagagcgctgccggcacctgtcctacgagttgcatgataaagaagacagtcataagtgcgg
cgacgatagtcatgccccgcgcccaccggaaggagctgactgggttgaaggctctcaagggcatcggtcgagat
cccggtgcctaatgagtgagctaacttacattaattgcgttgcgctcactgcccgctttccagtcgggaaacctgtcgt
gccagctgcattaatgaatcggccaacgcgcggggagaggcggtttgcgtattgggcgccagggtggttttcttttc
accagtgagacgggcaacagctgattgcccttcaccgcctggccctgagagagttgcagcaagcggtccacgct
ggtttgccccagcaggcgaaaatcctgtttgatggtggttaacggcgggataacatgagctgtcttcggtatcgtcg
tatccactaccgagatatccgcaccaacgcgcagcccggactcggtaatggcgcgcattgcgcccagcgccat
ctgatcgttggcaaccagcatcgcagtgggaacgatgccctcattcagcatttgcatggtttgttgaaaaccggacat
ggcactccagtcgccttcccgttccgctatcggctgaatttgattgcgagtgagatatttatgccagccagccagacg
cagacgcgccgagacagaacttaatgggcccgctaacagcgcgatttgctggtgacccaatgcgaccagatgct
ccacgcccagtcgcgtaccgtcttcatgggagaaaataatactgttgatgggtgtctggtcagagacatcaagaaat
aacgccggaacattagtgcaggcagcttccacagcaatggcatcctggtcatccagcggatagttaatgatcagcc
cactgacgcgttgcgcgagaagattgtgcaccgccgctttacaggcttcgacgccgcttcgttctaccatcgacacc
accacgctggcacccagttgatcggcgcgagatttaatcgccgcgacaatttgcgacggcgcgtgcagggccag
actggaggtggcaacgccaatcagcaacgactgtttgcccgccagttgttgtgccacgcggttgggaatgtaattca
gctccgccatcgccgcttccacttttttcccgcgttttcgcagaaacgtggctggcctggttcaccacgcgggaaacgg
tctgataagagacaccggcatactctgcgacatcgtataacgttactggtttcacattcaccaccctgaattgactctct
tccgggcgctatcatgccataccgcgaaaggtttgcgccattcgatggtgtccgggatctcgacgctctcccttatgc
gactcctgcattaggaagcagcccagtagtaggttgaggccgttgagcaccgccgccgcaaggaatggtgcatg
caaggagatggcgcccaacagtcccccggccacggggcctgccaccatacccacgccgaaacaagcgctcat
gagcccgaagtggcgagcccgatcttccccatcggtgatgtcggcgatataggcgccagcaaccgcacctgtgg
cgccggtgatgccggccacgatgcgtccggcgtagaggatcgagatctcgatcccgcgaaattaatacgactcac
tataggggaattgtgagcggataacaattcccctctagaaataattttgtttaactttaagaaggagatatacatatgc
ggggttctcatcatcatcatcatcatggtatggctagcatgactggtggacagcaaatgggtcgggatctgtacgacg
atgacgataaggatcatcccttcaccatggtatcctgttctgcgccgggtaagatttacctgttcggtgaacacgccgt
agtttatggcgaaactgcaattgcgtgtgcggtggaactgcgtacccgtgttcgcgcggaactcaatgactctatcac
tattcagagccagatcggccgcaccggtctggatttcgaaaagcacccttatgtgtctgcggtaattgagaaaatgc
gcaaatctattcctattaacggtgttttcttgaccgtcgattccgacatcccggtgggctccggtctgggtagcagcgca
gccgttactatcgcgtctattggtgcgctgaacgagctgttcggctttggcctcagcctgcaagaaatcgctaaactgg
gccacgaaatcgaaattaaagtacagggtgccgcgtccccaaccgatacgtatgtttctaccttcggcggcgtggtt
accatcccggaacgtcgcaaactgaaaactccggactgcggcattgtgattggcgataccggcgtttctcctccac
caaagagttagtagctaacgtacgtcagctgcgcgaaagctacccggatttgatcgaaccgctgatgacctctattg
gcaaaatctctcgtatcggcgaacaactggttctgtcggcgactacgcatccatcggccgcctgatgaacgtcaac
cagggtctcctggacgccctgggcgttaacatcttagaactgagccagctgatctattccgctcgtcggcaggtgc
gtttggcgctaaaatcacgggcgctggcggcggtgctgatggttgcgctgaccgctccggaaaaatgcaacca
agtggcagaagcggtagcaggcgctggcggtaaagtgactatcactaaaccgaccgagcaaggtctgaaagta
gattaa
(SEQ ID NO:47)

CDS 2: Gentamycin resistance gene; CDS: 1 *E. coli* replication protein

Figure 163A 1-
ctcgggccgtctcttgggcttgatcggccttcttgcgcatctcacgcgctcctgcggcggcctgtagggcaggctcatacccct
gccgaaccgcttttgtcagccggtcggccacggcttccggcgtctcaacgcgctttgagattcccagcttttcggccaatccct
gcggtgcataggcgcgtggctcgaccgcttgcgggctgatggtgacgtggcccactggtggccgctccagggcctcgtaga
acgcctgaatgcgcgtgtgacgtgccttgctgccctcgatgccccgttgcagccctagatcggccacagcggccgcaaacg
tggtctggtcgcgggtcatctgcgctttgttgccgatgaactccttggccgacagcctgccgtcctgcgtcagcggcaccacga
acgcggtcatgtgcgggctggtttcgtcacggtggatgctggccgtcacgatgcgatccgcccgtacttgtccgccagccac
ttgtgcgccttctcgaagaacgccgcctgctgttcttggctggccgacttccaccattccgggctggccgtcatgacgtactcga
ccgccaacacagcgtcctgcgccgcttctctggcagcaactcgcgcagtcggcccatcgcttcatcggtgctgctggccgc
ccagtgctcgttctctggcgtcctgctggcgtcagcgttgggcgtctcgcgctcgcggtaggcgtgcttgagactggccgccac
gttgcccattttcgccagcttcttgcatcgcatgatcgcgtatgccgccatgcctgcccctccctttggtgtccaaccggctcgac
gggggcagcgcaaggcggtgcctccggcgggccactcaatgcttgagtatactcactagactttgcttcgcaaagtcgtgac
cgcctacggcggctgcggcgccctacgggcttgctctccgggcttcgccctgcgcggtcgctgcgctccttgccagcccgt
ggatatgtggacgatggccgcgagcggccaccggctggctcgcttcgctcggcccgtggacaaccctgctggacaagctg
atggacaggctgcgcctgccacgagcttgaccacagggattgcccaccggctacccagccttcgaccacatacccaccg
gctccaactcgcgggcctgcggccttgccccatcaatttttttaattttctctggggaaaagcctccggcctgcggcctgcgcgc
ttcgcttgccggttggacaccaagtggaaggcgggtcaaggctcgcgcagcgaccgcgcagcggcttggccttgacgcgc
ctggaacgacccaagcctatgcgagtgggggcagtcgaaggcgaagcccgcccgcctgcccccgagcctcacggcg
gcgagtgcggggtgttccaaggggggcagcgccaccttgggcaaggccgaaggccgcgcagtcgatcaacaagccccgg
agggggccacttttgccggaggggggagccgcgccgaaggcgtgggggaaccccgcagggtgcccttctttgggcacca
aagaactagatataggcgaaatgcgaaagacttaaaaatcaacaacttaaaaaaggggggtacgcaacagctcattgc
ggcaccccccgcaatagctcattgcgtaggttaaagaaaatctgtaattgactgccacttttacgcaacgcataattgttgtcgc
gctgccgaaaagttgcagctgattgcgcatggtgccgcaaccgtgcggcaccctaccgcatggagataagcatggccacg
cagtccagagaaatcggcattcaagccaagaacaagcccggtcactgggtgcaaacggaacgcaaagcgcatgaggc
gtgggccgggcttattgcgaggaaaccacggcggcaatgctgctgcatcacctcgtggcgcagatgggccaccagaac
gccgtggtggtcagccagaagacactttccaagctcatcggacgttctttgcggacggtccaatacgcagtcaaggacttggt
ggccgagcgctggatctccgtcgtgaagctcaacgccccggcaccgtgtcggcctacgtggtcaatgaccgcgtggcgtg
gggccagccccgcgaccagttgcgcctgtcggtgttcagtgccgccgtggtggttgatcacgacgaccaggacgaatcgct
gttggggcatggcgacctgcgccgcatcccgaccctgtatccgggcgagcagcaactaccgaccggccccggcgagga
gccgcccagccagcccggcattccgggcatggaaccagacctgccagccttgaccgaaacggaggaatgggaacggc
gcgggcagcagcgcctgccgatgcccgatgagccgtgtttctggacgatggcgagccgttggagccgccgacacgggtc
acgctgccgcgccggtagcacttgggttgcgcagcaacccgtaagtgcgctgttccagactatcggctgtagccgcctcgcc
gccctataccttgtctgcctccccgcgttgcgtcgcggtgcatggagccgggccacctcgacctgaatggaagccggcggc
acctcgctaacggattcaccgtttttatcaggctctgggaggcagaataaatgatcatatcgtcaattattacctccacgggga
gagcctgagcaaactggcctcaggcatttgagaagcacacggtcacactgcttccggtagtcaataaaccggtaaaccag
caatagacataagcggctatttaacgaccctgccctgaaccgacgaccgggtcgaatttgctttcgaattctgccattcatcc
gcttattatcacttattcaggcgtagcaccaggcgtttaagggcaccaataactgccttaaaaaaattacgccccgccctgcc
actcatcgcagtcggcctattggttaaaaaatgagctgatttaacaaaaatttaacgcgaattttaacaaaatattaacgcttac
aatttccattcgccattcaggctgcgcaactgttgggaagggcgatcggtgcgggcctcttcgctattacgccagctggcgaa
agggggatgctgcaaggcgattaagttgggtaacgccaggggttttcccagtcacgacgttgtaaaacgacggccagtga
gcgcgcgtaatacgactcactataggcgaattggagctccaccgcggtggcggccgctctagaactagtggatccccg
ggctgcatgctcgagcggccgccagtgtgatggatatctgcagaattcgcccttcttgatatcttagtgtgcgttaaccaccacc
cacattggtccctgcccgaccgcatagcggcctttttcatgcagtagcccctgctcgccaacaatttcgtataccgagatgtggt
gagattttttgccccggcggcaatcagatacttgccgctgtgatcaacattgaagccgcgcggctgggtttccgttggctggaag
ccttctttactcaacacgctgccatcttccgaaacgctgaaaacggtaatcaggctggcggtacggtcgcaggcgtataaatg
gcgaccatccggggtgatatgaatatcagccgcccaacgggtgtcggagaagtttccggcatcatatccagcgtctggaca
cattcgatattaccgtgcggatctttcagttcccagacatccactgagctgtttaactcattgacgcaatacgcatattgtcgtttg
gatggaataccatatgacgcgggccggcccccttcaacggtggtcacttccgcagggtcctgcgccacgagatgaccatcat
cgctgaccgtaaacaggcaaatgcgatcctgctttaatgccggaacccacagcgtacggttgt

Figure 163B ccggtgagatattggcggaatggcaaccgtccagcccctcgaccacatcgacgacgcccactggcaggccatcttcca
gacgcgttacgctcacgttacccgcattgtaagaacctacaaagacaaactgccctggtgatcggtggaaatatgcgt
cggactacccggcagcgcagactctgcggcaaaggtcagtgcgccatcgtccggggcgatacgatacgccaggacg
cgaaactcagggcgaacaccaacatagagataacgtttgtccgggctgaccaccatcggctgcacctgccccggcac
atcgacaacctgtgtcagcgtcagtgcgccttcatgattcagattccagacgtgaatttgctggctctcagggctggcgata
taaactgtttgcttcatgaatgctcctttgggttacctccgggaaacgcggttgatttgtttagtggttgaattatttgctcaggat
gtggcatagtcaagggcgtgacggctcgctaatacaactcactatagggctcgaggaagttcctatactttctagagaat
aggaacttccgcgccgcacacaaaaaccaacacacagatcatgaaaataaagctctttattggtaccgaattcgcca
gggagctctcagacgtcgcttggtcggtctttattcgaaccccagagtcccgcttacgccccgccctgccactcatcgcag
tactgttgtaattcattaagcattctgccgacatggaagccatcacaaacggcatgatgaacctgaatcgccagcggcat
cagcaccttgtcgccttgcgtataatatttgcccatggtgaaaacgggggcgaagaagttgtccatattggccacgtttaaa
tcaaaactggtgaaactcacccagggattggctgagacgaaaaacatattctcaataaacccctttagggaaataggcc
aggttttcaccgtaacacgccacatcttgcgaatatatgtgtagaaactgccggaaatcgtcgtggtattcactccagagc
gatgaaaacgtttcagtttgctcatggaaaacggtgtaacaaggggtgaacactatcccatatcaccagctcaccgtctttc
attgccatacggaattccggatgagcattcatcaggcgggcaagaatgtgaataaaggccggataaaacttgtgcttattt
ttctttacggtctttaaaaaggccgtaatatccagctgaacggtctggttataggtacattgagcaactgactgaaatgcctc
aaaatgttcttacgatgccattgggatatatcaacggtggtatatccagtgatttttttctccatggtttagttcctcaccttgtcg
tattatactatgccgatatactatgccgatgattaattgtcaacacgtgctgctgcaggtcgaaaggcccggagatgagga
agaggagaacagcgcggcagacgtgcgcttttgaagcgtgcagaatgccgggcctccggaggaccttcgggcgccc
gccccgccctgagcccgccctgagcccgccccggacccacccttcccagcctctgagcccagaaagcgaagg
agcaaagctgctattggccgctgccccaaaggcctacccgcttccattgctcagcggtgctgtccatctgcacgagacta
gtgagacgtgctacttccatttgtcacgtcctgcacgacgcgagctgcggggcgggggaacttcctgactaggggag
gagtggaaggtggcgcgaaggggccaccaaagaacggagccggttggcgcctaccggtggatgtggaatgtgtgcg
aggccagaggccacttgtgtagcgccaagtgcccagcggggctgctaaagcgcatgctccagactgccttgggaaaa
gcgcctcccctacccggtagaatgaagttcctatactttctagagaataggaacttcgcggccgcccttagtgagggtta
attcaactgactgtaacagctaaaattagtcgcttttggcggtaagggcgaattccagcacactggcggccgttactagtg
gatccgagctcggtaccaagcttgatgcaggaattcgatatcaagcttatcgataccgtcgacctcgagggggggcccg
gtacccagcttttgttccctttagtgagggttaattgcgcgcttggcgtaatcatggtcatagctgtttcctgtgtgaaattgttat
ccgctcacaattccacacaacatacgagccggaagcataaagtgtaaagcctggggtgcctaatgagtgagctaactc
acattaattgcgttgcgctcactgcccgctttccagtcgggaaacctgtcgtgccagctgcattaatgaatcggccaacgc
gcggggagaggcggtttgcgtattggcgcatgcataaaaactgttgtaattcattaagcattctgccgacatggaagcc
atcacaaacggcatgatgaacctgaatcgccagcggcatcagcaccttgtcgccttgcgtataatatttgcccatggacg
cacaccgtggaaacggatgaaggcacgaacccagttgacataagcctgttcggttcgtaaactgtaatgcaagtagcgt
atgcgctcacgcaactggtccagaaccttgaccgaacgcagcggtggtaacggcgcagtggcggttttcatggcttgtta
tgactgtttttttgtacagtctatgcctcgggcatccaagcagcaagcgcgttacgccgtgggtcgatgtttgatgttatgag
cagcaacgatgttacgcagcagcaacgatgttacgcagcagggcagtcgccctaaaacaaagttaggtggctcaagt
atgggcatcattcgcacatgtaggctcggccctgaccaagtcaaatccatgcgggctgctcttgatcttttcggtcgtgagtt
cggagacgtagccacctactcccaacatcagccggactccgattacctcgggaacttgctccgtagtaagacattcatc
gcgcttgctgccttcgaccaagaagcggttgttggcgctctcgcggcttacgttctgcccaggtttgagcagccgcgtagtg
agatctatatctatgatctcgcagtctccggcgagcaccggaggcagggcattgccaccgcgctcatcaatctcctcaag
catgaggccaacgcgcttggtgcttatgtgatctacgtgcaagcagattacggtgacgatcccgcagtggctctctataca
aagttgggcatacgggaagaagtgatgcactttgatatcgacccaagtaccgccacctaacaattcgttcaagccgaga
tcggcttccggccgcgcgagttgttcggtaaattgtcacaacgccgccaggtggcacttttcggggaaatgtgcgcgccc
gcgttcctgctggcgctgggcctgtttctggcgctggacttcccgctgttccgtcagcagcttttcgcccacgccttgatgat
cgcggcggccttggcctgcatatcccgattcaacggcccagggcgtccagaacgggcttcaggcgctcccgaaggt
(SEQ ID NO:48)

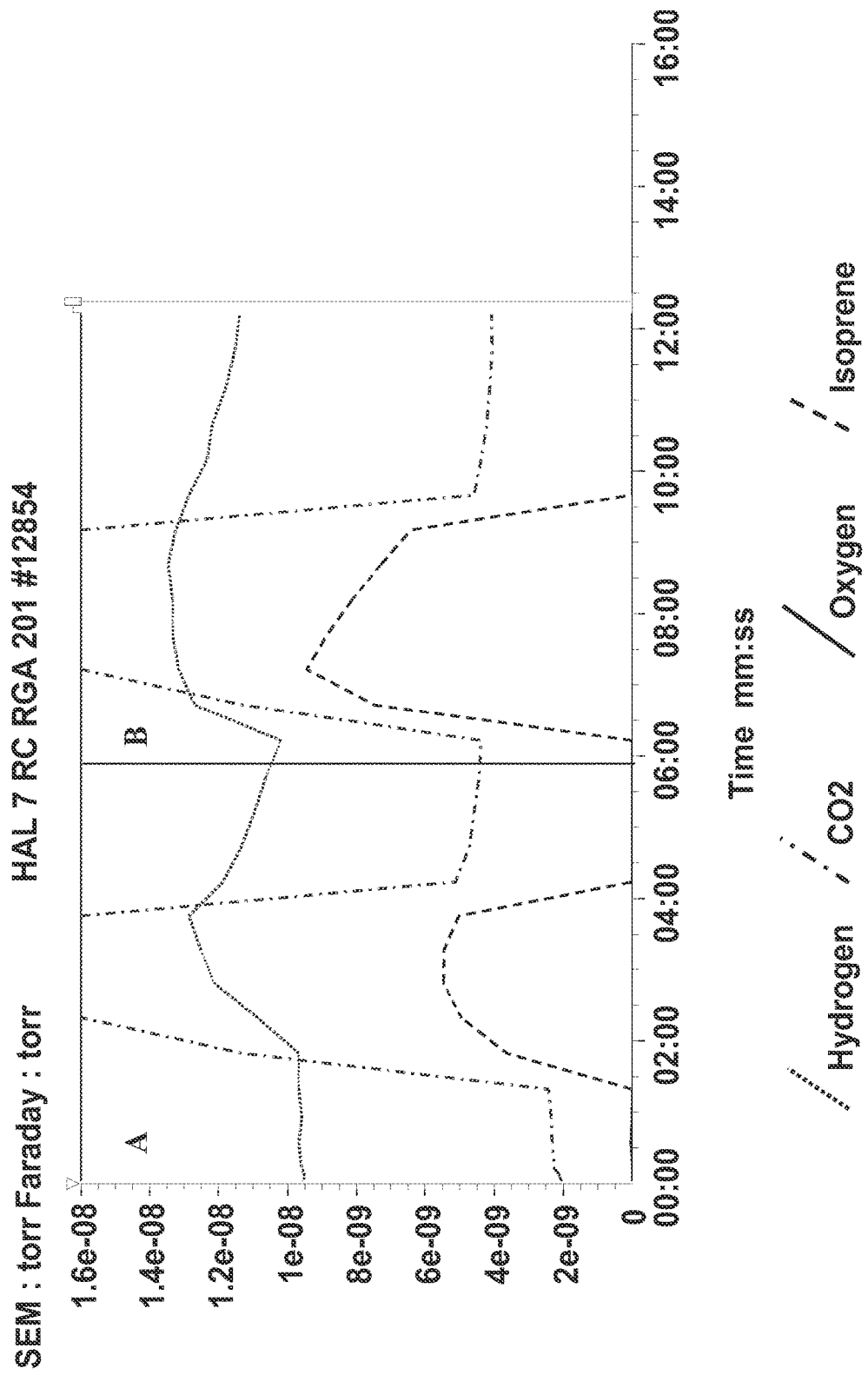
Figures 165A-B

Figures 166A-B
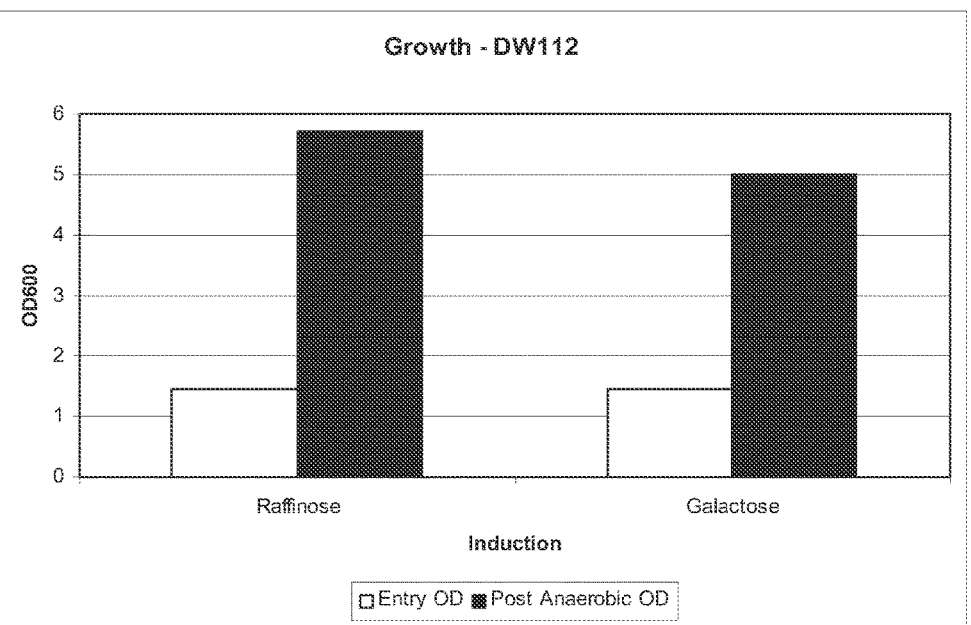
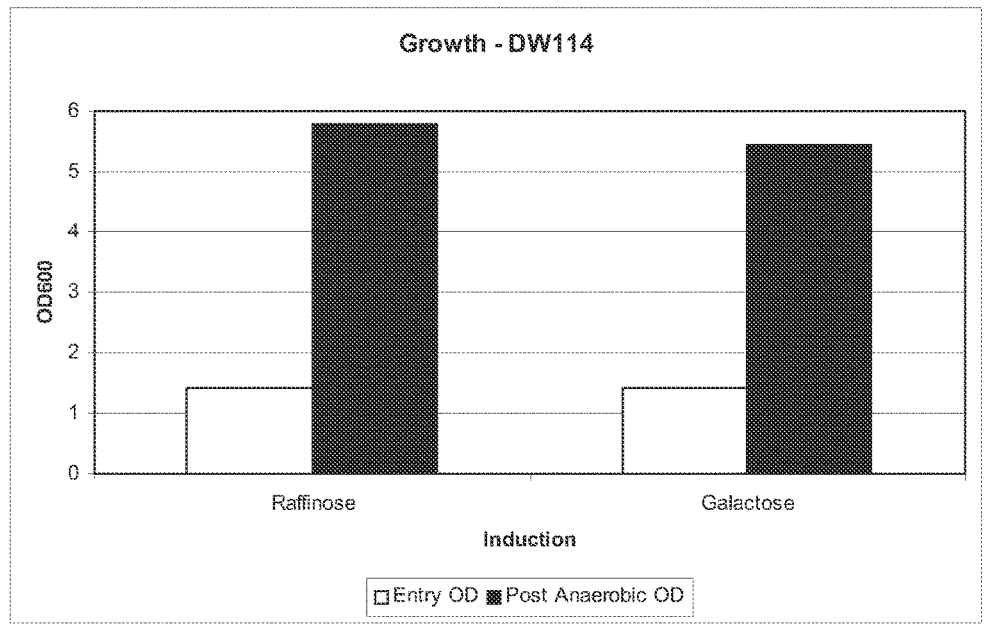

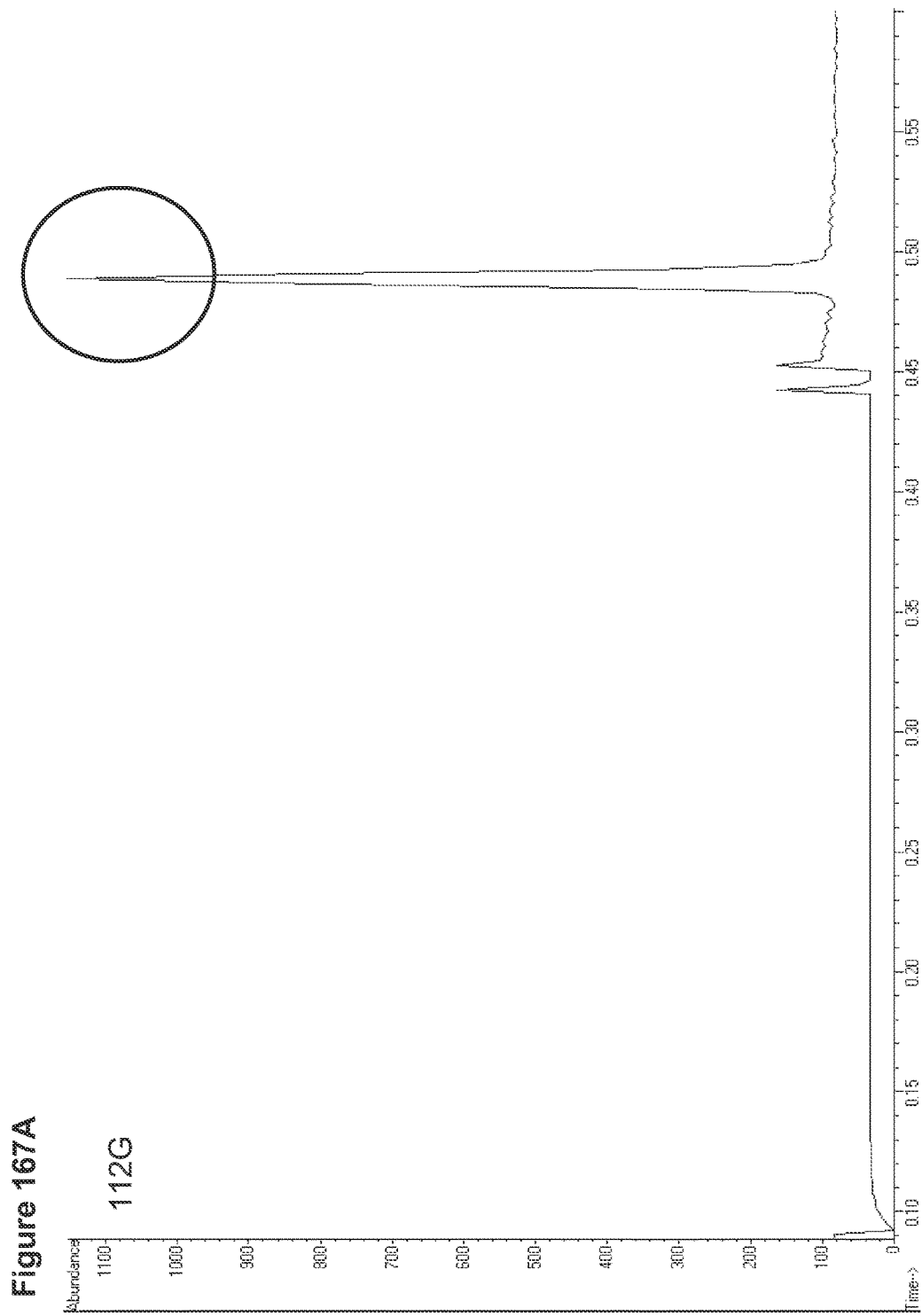

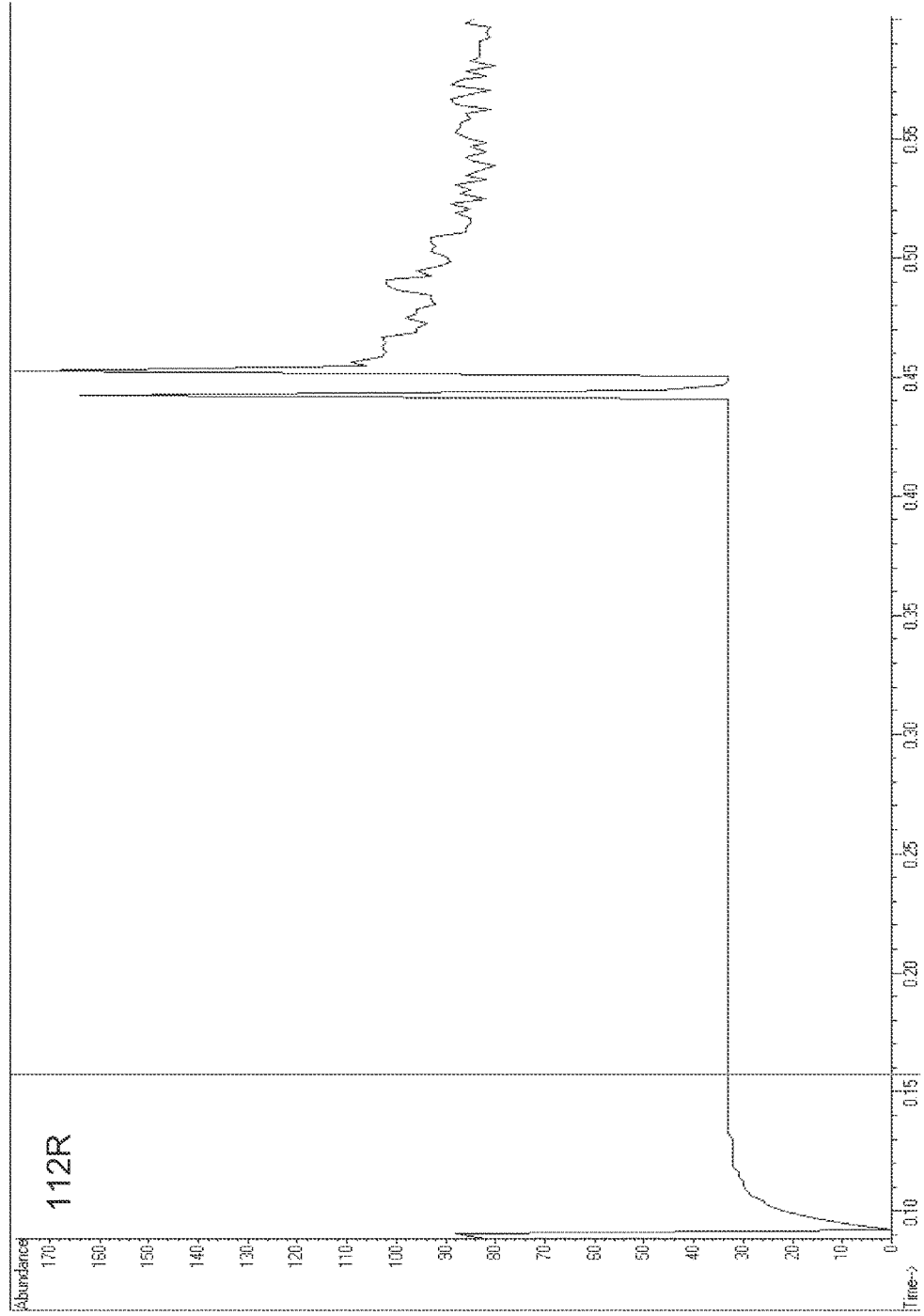

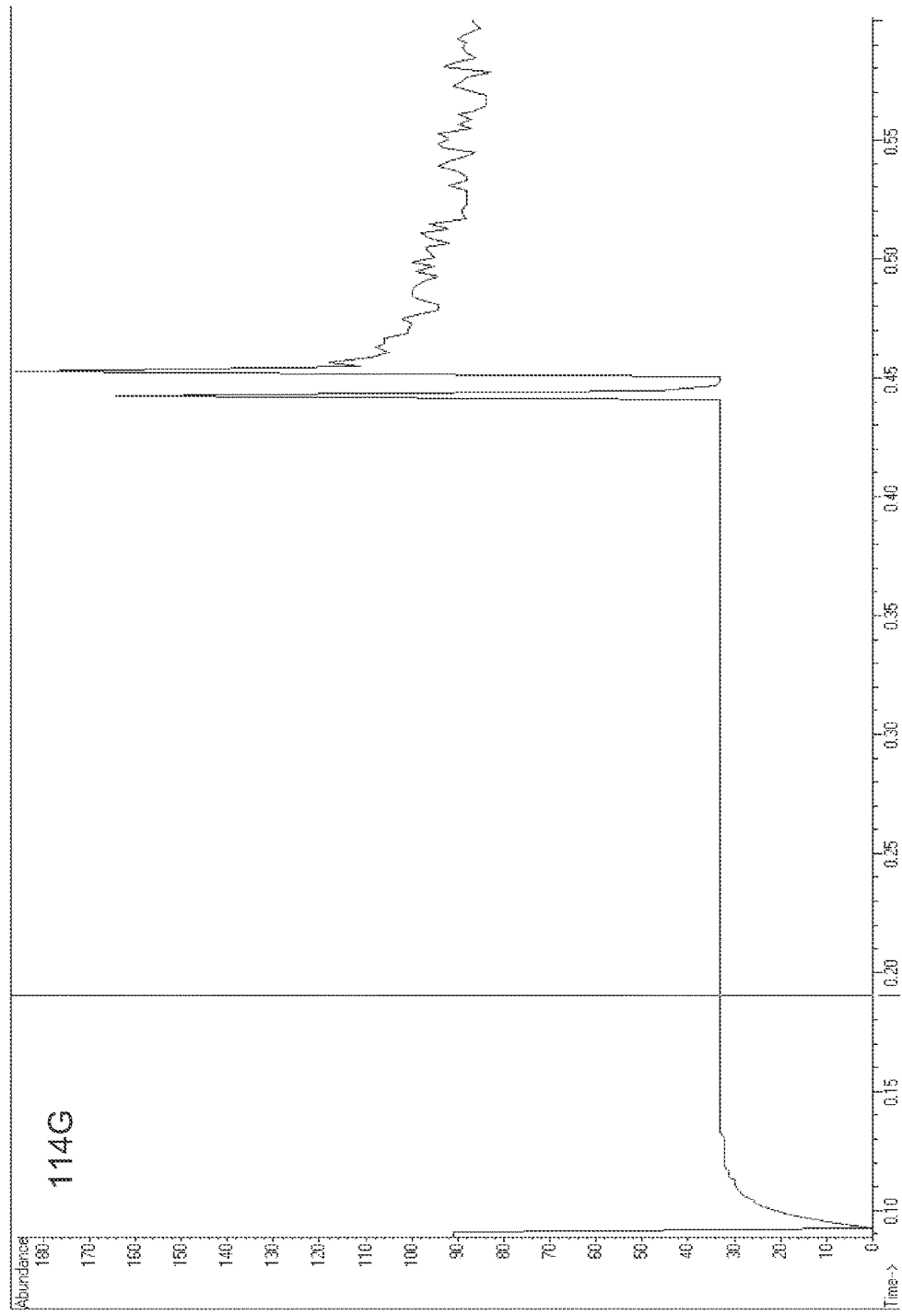

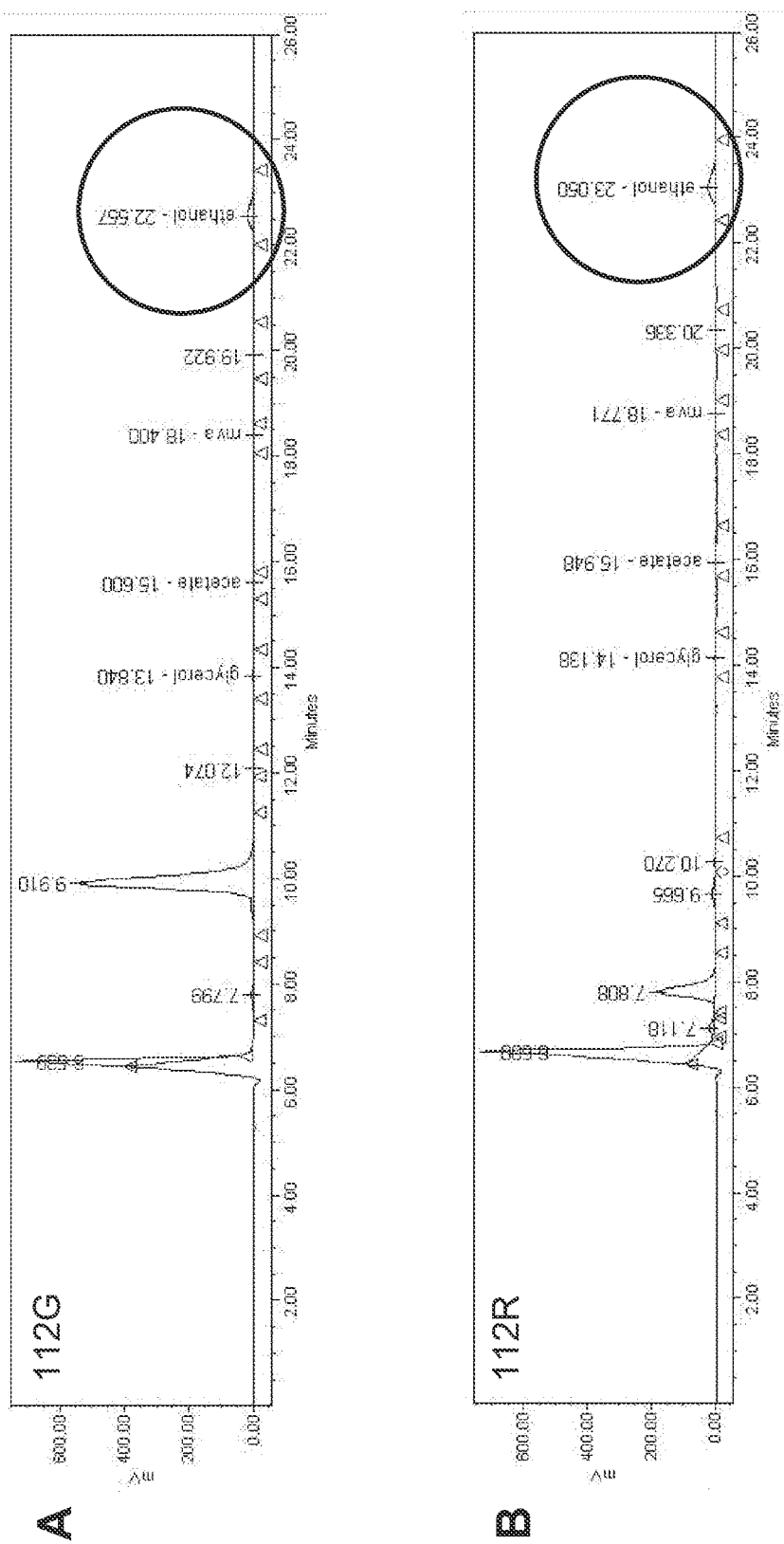
Figures 168A-B

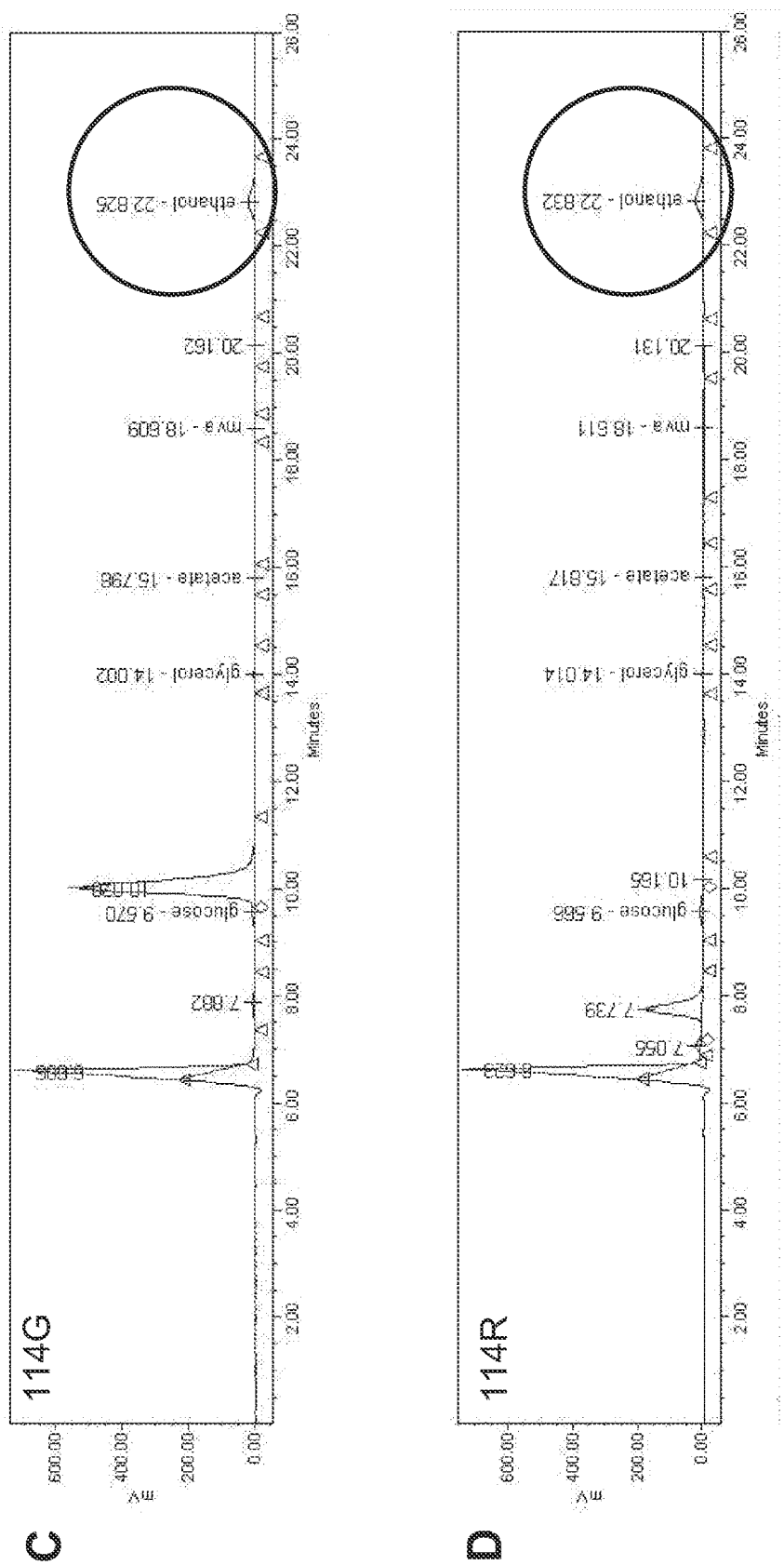
Figures 168C-D

Figure 171B ctcgggccgtctcttgggcttgatcggccttcttgcgcatctcacgcgctcctgcggcggcctgtagggcaggctcat
accccTgccgaaccgcttttgtcagccggtcggccacggcttccggcgtctcaacgcgctttgagattccagcttttc
ggccaatccctgcggtgcataggcgcgtggctcgaccgcttgcgggctgatggtgacgtggcccactggtggccgc
tccagggcctcgtagaacgcctgaatgcgcgtgtgacgtgccttgctgccctcgatgccccgttgcagccctagatc
ggccacagcggccgcaaacgtggtctggtcgcgggtcatctgcgctttgttgccgatgaactccttggccgacagcc
tgccgtcctgcgtcagcggcaccacgaacgcggtcatgtgcgggctggtttcgtcacggtggatgctggccgtcacg
atgcgatccgccccgtacttgtccgccagccacttgtgcgccttctcgaagaacgccgcctgctgttcttggctggcc
gacttccaccattccgggctggccgtcatgacgtactcgaccgccaacacagcgtccttgcgccgcttctctggcagc
aactcgcgcagtcggcccatcgcttcatcggtgctgctggccgcccagtgctcgttctctggcgtcctgctggcgtca
gcgttgggcgtctcgcgctcgcggtaggcgtgcttgagactggccgccacgttgcccattttcgccagcttcttgcatc
gcatgatcgcgtatgccgccatgcctgcccctcccttttggtgtccaaccggctcgacggggcagcgcaaggcggt
gcctccggcgggccactcaatgcttgagtatactcactagactttgcttcgcaaagtcgtgaccgcctacggcggctg
cggcgccctacgggcttgctctccgggcttcgccctgcgcggtcgctgcgctcccttgccagcccgtggatatgtgg
acgatggccgcgagcggccaccggctggctcgcttcgctcggcccgtggacaaccctgctggacaagctgatgga
caggctgcgcctgcccacgagcttgaccacagggattgcccaccggctacccagccttcgaccacatacccaccg
gctccaactgcgcggcctgcggccttgccccatcaatttttttaattttctctggggaaaagcctccggcctgcggcctg
cgcgcttcgcttgccggttggacaccaagtggaaggcgggtcaaggctcgcgcagcgaccgcgcagcggcttggc
cttgacgcgcctggaacgacccaagcctatgcgagtgggggcagtcgaaggcgaagcccgcccgcctgccccc
gagcctcacggcggcgagtgcggggttccaaggggcagcgccaccttgggcaaggccgaaggccgcgcagt
cgatcaacaagccccggaggggccacttttttgccggagggggagccgcgccgaaggcgtgggggaaccccgca
ggggtgcccttctttgggcaccaaagaactagatataggcgaaatgcgaaagacttaaaaatcaacaacttaaaaa
agggggtacgcaacagctcattgcggcaccccccgcaatagctcattgcgtaggttaaagaaaatctgtaattgact
gccacttttacgcaacgcataattgttgtcgcgctgccgaaaagttgcagctgattgcgcatggtgccgcaaccgtgc
ggcaccctaccgcatggagataagcatggccacgcagtccagagaaatcggcattcaagccaagaacaagcccg
gtcactgggtgcaaacggaacgcaaagcgcatgaggcgtgggccgggcttattgcgaggaaacccacggcggca
atgctgctgcatcacctcgtggcgcagatgggccaccagaacgccgtggtggtcagccagaagacactttccaagc
tcatcggacgttctttgcggacggtccaatacgcagtcaaggacttggtggccgagcgctggatctccgtcgtgaagc
tcaacggccccggcaccgtgtcggcctacgtggtcaatgaccgcgtggcgtggggccagccccgcgaccagttgc
gcctgtcggtgttcagtgccgccgtggtggttgatcacgacgaccaggacgaatcgctgttggggcatggcgacctg
cgccgcatcccgaccctgtatccgggcgagcagcaactaccgaccggccccggcgaggagccgcccagccagc
ccggcattccgggcatggaaccagacctgccagccttgaccgaaacggaggaatgggaacggcgcgggcagca
gcgcctgccgatgcccgatgagccgtgttttctggacgatggcgagccgttggagccgccgacacgggtcacgctg
ccgcgccggtagcacttgggttgcgcagcaacccgtaagtgcgctgttccagactatcggctgtagccgcctcgccg
ccctataccttgtctgcctccccgcgttgcgtcgcggtgcatggagccgggccacctcgacctgaatggaagccggc
ggcacctcgctaacggattcaccgttttttatcaggctctggaggcagaataaatgatcatatcgtcaattattacctcca
cggggagagcctgagcaaactggcctcaggcatttgagaagcacacggtcacactgcttccggtagtcaataaacc
ggtaaaccagcaatagacataagcggctatttaacgaccctgccctgaaccgacgaccgggtcgaatttgctttcgaa
tttctgccattcatccgcttattatcacttattcaggcgtagcaccaggcgtttaagggcaccaataactgccttaaaaaa
attacgccccgccctgccactcatcgcagtcggcctattggttaaaaatgagctgatttaacaaaaatttaacgcgaat
tttaacaaaatattaa

Figure 171C cgcttacaatttccattcgccattcaggctgcgcaactgttgggaagggcgatcggtgcgggcctcttcgctattacgccagctggc
gaaaggggatgtgctgcaaggcgattaagttgggtaacgccagggttttcccagtcacgacgttgtaaaacgacggccagtga
gcgcgcgtaatacgactcactatagggcgaattggagctccaccgcggtggcggccgctctagaactagtgttgacaattaatcat
ccggctcgtataatgtgtggaattgtgagcggataacaatttaggaggaaaaaaaaatgagttatactgtcggtacctatttagcgga
gcggcttgtccagattggtctcaagcatcacttcgcagtcgcgggcgactacaacctcgtccttcttgacaacctgcttttgaacaaa
aacatggagcaggtttattgctgtaacgaactgaactgcggtttcagtgcagaaggttatgctcgtgccaaaggcgcagcagcag
ccgtcgttacctacagcgtcggtgcgctttccgcatttgatgctatcggtggcgcctatgcagaaaaccttccggttatcctgatctcc
ggtgctccgaacaacaatgatcacgctgctggtcacgtgttgcatcacgctcttggcaaaaccgactatcactatcagttggaaatg
gccaagaacatcacggccgccgctgaagcgatttacaccccggaagaagctccggctaaaatcgatcacgtgattaaaactgct
cttcgtgagaagaagccggtttatctcgaaatcgcttgcaacattgcttccatgccctgcgccgctcctggaccggcaagcgcattg
ttcaatgacgaagccagcgacgaagcttctttgaatgcagcggttgaagaaaccctgaaattcatcgccaaccgcgacaaagttg
ccgtcctcgtcggcagcaagctgcgcgcagctggtgctgaagaagctgctgtcaaatttgctgatgctctcggtggcgcagttgct
accatggctgctgcaaaaagcttcttcccagaagaaaaaccgcattacatcggcacctcatgggtgaagtcagctatccgggcg
ttgaaaagacgatgaaagaagccgatgcggttatcgctctggctcctgtcttcaacgactactccaccactggttggacggatattc
ctgatcctaagaaactggttctcgctgaaccgcgttctgtcgtcgttaacggcattcgcttcccccagcgtccatctgaaagactatctg
acccgtttggctcagaaagtttccaagaaaaccggtgcattggacttcttcaaatccctcaatgcaggtgaactgaagaaagccgct
ccggctgatccgagtgctccgttggtcaacgcagaaatcgcccgtcaggtcgaagctcttctgaccccgaacacgacggttattg
ctgaaaccggtgactcttggttcaatgctcagcgcatgaagctcccgaacggtgctcgcgttgaatatgaaatgcagtggggtcac
attggttggtccgttcctgccgccttcggttatgccgtcggtgctccggaacgtcgcaacatcctcatggttggtgatggttccttcca
gctgacggctcaggaagtcgctcagatggttcgcctgaaactgccggttatcatcttcttgatcaataactatggttacaccatcgaa
gttatgatccatgatggtccgtacaacaacatcaagaactgggattatgccggtctgatggaagtgttcaacggtaacggtggttat
gacagcggtgctggtaaaggcctgaaggctaaaaccggtggcgaactggcagaagctatcaaggttgctctggcaaacaccga
cggcccaaccctgatcgaatgcttcatcggtcgtgaagactgcactgaagaattggtcaaatggggtaagcgcgttgctgccgcc
aacagccgtaagcctgttaacaagctcctctagtttttaaataaacctgcaggaattcgatatcaagcttatcgataccgtcgacctcg
agggggggcccggtacccagcttttgttccctttagtgagggttaattgcgcgcttggcgtaatcatggtcatagctgtttcctgtgtg
aaattgttatccgctcacaattccacacaacatacgagccggaagcataaagtgtaaagcctggggtgcctaatgagtgagctaac
tcacattaattgcgttgcgctcactgcccgctttccagtcgggaaacctgtcgtgccagctgcattaatgaatcggccaacgcgcgg
ggagaggcggtttgcgtattgggcgcatgcataaaaactgttgtaattcattaagcattctgccgacatggaagccatcacaaacg
gcatgatgaacctgaatcgccagcggcatcagcaccttgtcgccttgcgtataatatttgcccatggacgcacaccgtggaaacgg
atgaaggcacgaacccagttgacataagcctgttcggttcgtaaactgtaatgcaagtagcgtatgcgctcacgcaactggtccag
aaccttgaccgaacgcagcggtggtaacggcgcagtggcggttttcatggcttgttatgactgtttttttgtacagtctatgcctcggg
catccaagcagcaagcgcgttacgccgtgggtcgatgtttgatgttatggagcagcaacgatgttacgcagcagcaacgatgttac
gcagcagggcagtcgccctaaaacaaagttaggtggctcaagtatgggcatcattcgcacatgtaggctcggccctgaccaagtc
aaatccatgcgggctgctcttgatctttcggtcgtgagttcggagacgtagccacctactcccaacatcagccggactccgattac
ctcgggaacttgctccgtagtaagacattcatcgcgcttgctgccttcgaccaagaagcggttgttgcgctctcgcggcttacgttc
tgcccaggtttgagcagccgcgtagtgagatctatatctatgatctcgcagtctccggcgagcaccggaggcagggcattgccac
cgcgctcatcaatctcctcaagcatgaggccaacgcgcttggtgcttatgtgatctacgtgcaagcagattacggtgacgatcccg
cagtggctctctatacaaagttgggcatacgggaagaagtgatgcactttgatatcgacccaagtaccgccacctaacaattcgttc
aagccgagatcggcttccggccgcggagttgttcggtaaattgtcacaacgccgccaggtggcacttttcggggaaatgtgcgc
gcccgcgttcctgctggcgctgggcctgtttctggcgctggacttcccgctgttccgtcagcagcttttcgcccacggccttgatgat
cgcggcggccttggcctgcatatcccgattcaacggccccagggcgtccagaacgggcttcaggcgctcccgaaggt (SEQ ID NO:148)

Figure 172B tggcgaatgggacgcgccctgtagcggcgcattaagcgcggcgggtgtggtggttacgcgcagcgtgaccgctacacttg
ccagcgccctagcgcccgctcctttcgctttcttcccttcctttctcgccacgttcgccggctttccccgtcaagctctaaatcgg
gggctccctttaggggttccgatttagtgctttacggcacctcgaccccaaaaaacttgattagggtgatggttcacgtagtggg
ccatcgccctgatagacggtttttcgcccttttgacgttggagtccacgttctttaatagtggactcttgttccaaactggaacaac
actcaaccctatctcggtctattcttttgatttataagggattttgccgatttcggcctattggttaaaaaatgagctgatttaacaaa
aatttaacgcgaattttaacaaaatattaacgtttacaatttcaggtggcacttttcggggaaatgtgcgcggaaccctatttgtt
tatttttctaaatacattcaaatatgtatccgctcatgaattaattcttagaaaaactcatcgagcatcaaatgaaactgcaatttatt
catatcaggattatcaataccatattttgaaaaagccgtttctgtaatgaaggagaaaactcaccgaggcagttccataggatg
gcaagatcctggtatcggtctgcgattccgactcgtccaacatcaatacaacctattaatttcccctcgtcaaaaataaggttatc
aagtgagaaatcaccatgagtgacgactgaatccggtgagaatggcaaaagtttatgcatttctttccagacttgttcaacagg
ccagccattacgctcgtcatcaaaatcactcgcatcaaccaaaccgttattcattcgtgattgcgcctgagcgagacgaaatac
gcgatcgctgttaaaaggacaattacaaacaggaatcgaatgcaaccggcgcaggaacactgccagcgcatcaacaatatt
ttcacctgaatcaggatattcttctaatacctggaatgctgttttcccggggatcgcagtggtgagtaaccatgcatcatcagga
gtacggataaaatgcttgatggtcggaagaggcataaattccgtcagccagtttagtctgaccatctcatctgtaacatcattgg
caacgctacctttgccatgtttcagaaacaactctggcgcatcgggcttcccatacaatcgatagattgtcgcacctgattgccc
gacattatcgcgagcccatttatacccatataaatcagcatccatgttggaatttaatcgcggcctagagcaagacgtttcccgt
tgaatatggctcataacacccccttgtattactgtttatgtaagcagacagttttattgttcatgaccaaaatcccttaacgtgagtttt
cgttccactgagcgtcagaccccgtagaaaagatcaaaggatcttcttgagatcctttttttctgcgcgtaatctgctgcttgcaa
acaaaaaaaccaccgctaccagcggtggtttgtttgccggatcaagagctaccaactctttttccgaaggtaactggcttcagc
agagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttac
cggataaggcgcagcggtcgggctgaacggggggttcgtgcacacagcccagcttggagcgaacgacctacaccgaact
gagatacctacagcgtgagctatgagaaagcgccacgcttcccgaagggagaaaggcggacaggtatccggtaagcggc
agggtcggaacaggagagcgcacgagggagcttccaggggggaaacgcctggtatctttatagtcctgtcgggtttcgccac
ctctgacttgagcgtcgatttttgtgatgctcgtcaggggggcggagcctatggaaaaacgccagcaacgcggcctttttacg
gttcctggccttttgctggccttttgctcacatgttctttcctgcgttatcccctgattctgtggataaccgtattaccgcctttgagt
gagctgataccgctcgccgcagccgaacgaccgagcgcagcgagtcagtgagcgaggaagcggaagagcgcctgatgc
ggtattttctccttacgcatctgtgcggtatttcacaccgcatatatggtgcactctcagtacaatctgctctgatgccgcatagtt
aagccagtatacactccgctatcgctacgtgactgggtcatggctgcgccccgacacccgccaacacccgctgacgcgccc
tgacgggcttgtctgctcccggcatccgcttacagacaagctgtgaccgtctccgggagctgcatgtgtcagaggttttcacc
gtcatcaccgaaacgcgcgaggcagctgcggtaaagctcatcagcgtggtcgtgaagcgattcacagatgtctgcctgttca
tccgcgtccagctcgttgagtttctccagaagcgttaatgtctggcttctgataaagcgggccatgttaagggcggttttttcctg
tttggtcactgatgcctccgtgtaagggggatttctgttcatgggggtaatgataccgatgaaacgagagaggatgctcacgat
acgggttactgatgatgaacatgcccggttactggaacgttgtgagggtaaacaactggcggtatggatgcggcgggacca
gagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattc
atgttgttgctcaggtcgcagacgttttgcagcagcagtcgcttcacgttcgctcgcgtatcggtgattcattctgctaaccagt

Figure 172C aaggcaaccccgccagcctagccgggtcctcaacgacaggagcacgatcatgcgcacccgtggggccgccatgccggc
gataatggcctgcttctcgccgaaacgtttggtggcgggaccagtgacgaaggcttgagcgagggcgtgcaagattccgaa
taccgcaagcgacaggccgatcatcgtcgcgctccagcgaaagcggtcctcgccgaaaatgacccagagcgctgccggc
acctgtcctacgagttgcatgataaagaagacagtcataagtgcggcgacgatagtcatgccccgcgcccaccggaagga
gctgactggttgaaggctctcaagggcatcggtcgagatcccggtgcctaatgagtgagctaacttacattaattgcgttgc
gctcactgcccgctttccagtcgggaaacctgtcgtgccagctgcattaatgaatcggccaacgcgcggggagaggcggttt
gcgtattgggcgccagggtggttttctttcaccagtgagacgggcaacagctgattgcccttcaccgcctggccctgagag
agttgcagcaagcggtccacgctggtttgccccagcaggcgaaaatcctgtttgatggtggttaacggcgggatataacatg
agctgtcttcggtatcgtcgtatcccactaccgagatatccgcaccaacgcgcagcccggactcggtaatggcgcgcattgc
gcccagcgccatctgatcgttggcaaccagcatcgcagtgggaacgatgccctcattcagcatttgcatggtttgttgaaaac
cggacatggcactccagtcgccttcccgttccgctatcggctgaatttgattgcgagtgagatatttatgccagccagccagac
gcagacgcgccgagacagaacttaatgggcccgctaacagcgcgatttgctggtgacccaatgcgaccagatgctccacg
cccagtcgcgtaccgtcttcatgggagaaaataatactgttgatgggtgtctggtcagagacatcaagaaataacgccggaa
cattagtgcaggcagcttccacagcaatggcatcctggtcatccagcggatagttaatgatcagcccactgacgcgttgcgc
gagaagattgtgcaccgccgctttacaggcttcgacgccgcttcgttctaccatcgacaccaccacgctggcacccagttgat
cggcgcgagatttaatcgccgcgacaatttgcgacggcgcgtgcagggccagactggaggtggcaacgccaatcagcaa
cgactgtttgcccgccagttgttgtgccacgcggttgggaatgtaattcagctccgccatcgccgcttccacttttttcccgcgttt
tcgcagaaacgtggctggcctggttcaccacgcgggaaacggtctgataagagacaccggcatactctgcgacatcgtata
acgttactggtttcacattcaccaccctgaattgactctcttccgggcgctatcatgccataccgcgaaaggttttgcgccattcg
atggtgtccgggatctcgacgctctcccttatgcgactcctgcattaggaagcagcccagtagtaggttgaggccgttgagca
ccgccgccgcaaggaatggtgcatgcaaggagatggcgcccaacagtcccccggccacggggcctgccaccatacccca
cgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatac
gactcactataggggaattgtgagcggataacaattcccctctagaaataattttgtttaactttaagaaggagatatacatatgg
aagctcgtcgttctgcgaactacgaacctaacagctgggactatgattacctgctgtcctccgacacggacgagtccatcgaa
gtatacaaagacaaagcgaaaaagctggaagccgaagttcgtcgcgagattaataacgaaaaagcagaatttctgaccctg
ctggaactgattgacaacgtccagcgcctgggcctgggttaccgtttcgagtctgatatccgtggtgcgctggatcgcttcgttt
cctccggcggcttcgatgcggtaaccaagacttccctgcacggtacggcactgtcttccgtctgctgcgtcaacacggttttg
aggtttctcaggaagcgttcagcggcttcaaagaccaaaacggcaacttcctggagaacctgaaggaagatatcaaagctat
cctgagcctgtacgaggccagcttcctggctctggaaggcgaaaacatcctggacgaggcgaaggttttcgcaatctctcat
ctgaaagaactgtctgaagaaaagatcggtaaagagctggcagaacaggtgaaccatgcactggaactgccactgcatcgc
cgtactcagcgtctggaagcagtatggtctatcgaggcctaccgtaaaaaggaggacgcgaatcaggttctgctggagctg
gcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactc
cgactgccgtaactccgtcgcaaaaatgttttctttcgtaaccattatcgacgatatctacgatgtatacggcacccctggacgaa
ctggagctgtttactgatgcagttgagcgttgggacgtaaacgccatcaacgacctgccggattacatgaaactgtgctttctg
gctctgtataacactattaacgaaatcgcctacgacaacctgaaagataaaggtga

Figure 172D gaacatcctgccgtatctgaccaaagcctgggctgacctgtgcaacgctttcctgcaagaagccaagtggctgtacaacaaa
tctactccgacctttgacgactacttcggcaacgcatggaaatcctcttctggcccgctgcaactggtgttcgcttacttcgctgt
cgtgcagaacattaaaaaggaagagatcgaaaacctgcaaaaataccatgacaccatctctcgtccttcccatatcttccgtct
gtgcaatgacctggctagcgcgtctgcggaaattgcgcgtggtgaaaccgcaaatagcgtttcttgttacatgcgcactaaag
gtatctccgaagaactggctaccgaaagcgtgatgaatctgatcgatgaaacctggaaaaagatgaacaaggaaaaactgg
gtggtagcctgttcgcgaaaccgttcgtggaaaccgcgatcaacctggcacgtcaatctcactgcacttatcataacggcgac
gcgcatacctctccggatgagctgacccgcaaacgcgttctgtctgtaatcactgaaccgattctgccgtttgaacgctaagg
atccgaattcgagctccgtcgacaagcttgcggccgcactcgagcaccaccaccaccaccactgagatccggctgctaaca
aagcccgaaaggaagctgagttggctgctgccaccgctgagcaataactagcataaccccttggggcctctaaacgggtctt
gaggggttttttgctgaaaggaggaactatatccggat (SEQ ID NO: 151)

Figure 174B tggcgaatgggacgcgccctgtagcggcgcattaagcgcggcgggtgtggtggttacgcgcagcgtgaccgctacactt
gccagcgccctagcgcccgctcctttcgctttcttcccttccttttctcgccacgttcgccggctttccccgtcaagctctaaatc
gggggctcccttttagggttccgatttagtgctttacggcacctcgaccccaaaaaacttgattagggtgatggttcacgtagt
gggccatcgccctgatagacggttttttcgcccttttgacgttggagtccacgttctttaatagtggactcttgttccaaactggaa
caacactcaaccctatctcggtctattcttttgatttataagggattttgccgatttcggcctattggttaaaaaatgagctgattta
acaaaaatttaacgcgaatttttaacaaaatattaacgtttacaatttcaggtggcacttttcggggaaatgtgcgcggaacccc
tatttgtttattttttctaaatacattcaaatatgtatccgctcatgaattaattcttagaaaaactcatcgagcatcaaatgaaactg
caatttattcatatcaggattatcaataccatattttttgaaaaagccgtttctgtaatgaaggagaaaactcaccgaggcagttc
cataggatggcaagatcctggtatcggtctgcgattccgactcgtccaacatcaatacaacctattaatttcccctcgtcaaaa
ataaggttatcaagtgagaaatcaccatgagtgacgactgaatccggtgagaatggcaaaagtttatgcatttctttccagact
tgttcaacaggccagccattacgctcgtcatcaaaatcactcgcatcaaccaaaccgttattcattcgtgattgcgcctgagc
gagacgaaatacgcgatcgctgttaaaaggacaattacaaacaggaatcgaatgcaaccggcgcaggaacactgccagc
gcatcaacaatatttttcacctgaatcaggatattcttctaatacctggaatgctgttttcccggggatcgcagtggtgagtaacc
atgcatcatcaggagtacggataaaatgcttgatggtcggaagaggcataaattccgtcagccagtttagtctgaccatctca
tctgtaacatcattggcaacgctaccctttgccatgtttcagaaacaactctggcgcatcgggcttcccatacaatcgatagatt
gtcgcacctgattgcccgacattatcgcgagcccatttatacccatataaatcagcatccatgttggaatttaatcgcggccta
gagcaagacgtttcccgttgaatatggctcataacacccccttgtattactgtttatgtaagcagacagttttattgttcatgacca
aaatcccttaacgtgagttttcgttccactgagcgtcagaccccgtagaaaagatcaaaggatcttcttgagatcctttttttctg
cgcgtaatctgctgcttgcaaacaaaaaaaccaccgctaccagcggtggtttgtttgccggatcaagagctaccaactctttt
tccgaaggtaactggcttcagcagagcgcagataccaaatactgtccttctagtgtagccgtagttaggccaccacttcaag
aactctgtagcaccgcctacatacctcgctctgctaatcctgttaccagtggctgctgccagtggcgataagtcgtgtcttacc
gggttggactcaagacgatagttaccggataaggcgcagcggtcgggctgaacggggggttcgtgcacacagcccagct
tggagcgaacgacctacaccgaactgagatacctacagcgtgagctatgagaaagcgccacgcttcccgaagggagaa
aggcggacaggtatccggtaagcggcagggtcggaacaggagagcgcacgagggagcttccaggggggaaacgcctg
gtatctttatagtcctgtcgggtttcgccacctctgacttgagcgtcgatttttgtgatgctcgtcaggggggcggagcctatg
gaaaaacgccagcaacgcggcctttttacggttcctggccttttgctggccttttgctcacatgttctttcctgcgttatcccctg
attctgtggataaccgtattaccgcctttgagtgagctgataccgctcgccgcagccgaacgaccgagcgcagcgagtca
gtgagcgaggaagcggaagagcgcctgatgcggtattttctccttacgcatctgtgcggtatttcacaccgcatatatggtg
cactctcagtacaatctgctctgatgccgcatagttaagccagtatacactccgctatcgctacgtgactgggtcatggctgc
gccccgacacccgccaacacccgctgacgcgccctgacgggcttgtctgctcccggcatccgcttacagacaagctgtg
accgtctccgggagctgcatgtgtcagaggttttcaccgtcatcaccgaaacgcgcgaggcagctgcggtaaagctcatc
agcgtggtcgtgaagcgattcacagatgtctgcctgttcatccgcgtccagctcgttgagtttctccagaagcgttaatgtctg
gcttctgataaagcgggccatgttaagggcggttttttcctgtttggtcactgatgcctccgtgtaagggggatttctgttcatg
ggggtaatgataccgatgaaacgagagaggatgctcacgatacgggttactgatgatgaacatgcccggttactggaacg
ttgtgagggtaaacaactggcggtatggatgcggcgggaccagagaaaaatcactcagggtcaatgccagcgcttcgtta
atacagatgtaggtgttccacagggtagccagcagcatcctgcgatgcagatccggaacataatggtgcagggcgctgac
ttccgcgtttccagactttacgaaacacggaaaccgaagaccattcatgttgttgctcaggtcgcagacgttttgcagcagca
gtcgcttcacgttcgctcgcgtatcggtgattcattctgctaaccagtaaggcaaccccgccagcctagccgggtcctcaac
gacaggagcacgatcatgcgcacccgtggggccgccatgccggcgataatggcctgcttctcgccgaaacgtttggtgg
cgggaccagtgacgaaggcttgagcgagggcgtgcaagattccgaa

Figure 174C taccgcaagcgacaggccgatcatcgtcgcgctccagcgaaagcggtcctcgccgaaaatgacccagagcgctgccg
gcacctgtcctacgagttgcatgataaagaagacagtcataagtgcggcgacgatagtcatgccccgcgcccaccgga
aggagctgactgggttgaaggctctcaagggcatcggtcgagatcccggtgcctaatgagtgagctaacttacattaattg
cgttgcgctcactgcccgctttccagtcgggaaacctgtcgtgccagctgcattaatgaatcggccaacgcgcggggag
aggcggtttgcgtattgggcgccagggtggttttcttttcaccagtgagacgggcaacagctgattgcccttcaccgcctg
gccctgagagagttgcagcaagcggtccacgctggtttgccccagcaggcgaaaatcctgtttgatggtggttaacggc
gggatataacatgagctgtcttcggtatcgtcgtatcccactaccgagatatccgcaccaacgcgcagcccggactcggt
aatggcgcgcattgcgcccagcgccatctgatcgttggcaaccagcatcgcagtgggaacgatgccctcattcagcattt
gcatggtttgttgaaaaccggacatggcactccagtcgccttcccgttccgctatcggctgaatttgattgcgagtgagata
tttatgccagccagccagacgcagacgcgccgagacagaacttaatgggcccgctaacagcgcgatttgctggtgacc
caatgcgaccagatgctccacgcccagtcgcgtaccgtcttcatgggagaaaataatactgttgatgggtgtctggtcaga
gacatcaagaaataacgccggaacattagtgcaggcagcttccacagcaatggcatcctggtcatccagcggatagtta
atgatcagcccactgacgcgttgcgcgagaagattgtgcaccgccgctttacaggcttcgacgccgcttcgttctaccatc
gacaccaccacgctggcacccagttgatcggcgcgagatttaatcgccgcgacaatttgcgacggcgcgtgcagggcc
agactggaggtggcaacgccaatcagcaacgactgtttgcccgccagtgttgtgccacgcggttgggaatgtaattcag
ctccgccatcgccgcttccacttttcccgcgttttcgcagaaacgtggctggcctggttcaccacgcgggaaacggtctg
ataagagacaccggcatactctgcgacatcgtataacgttactggtttcacattcaccaccctgaattgactctcttccgggc
gctatcatgccataccgcgaaaggttttgcgccattcgatggtgtccgggatctcgacgctctcccttatgcgactcctgca
ttaggaagcagcccagtagtaggttgaggccgttgagcaccgccgccgcaaggaatggtgcatgcaaggagatggcg
cccaacagtccccggccacggggcctgccaccatacccacgccgaaacaagcgctcatgagcccgaagtggcgag
cccgatcttccccatcggtgatgtcggcgatataggcgccagcaaccgcacctgtggcgccggtgatgccggccacga
tgcgtccggcgtagaggatcgagatctcgatcccgcgaaattaatacgactcactatagggaattgtgagcggataaca
attcccctctagaaataattttgtttaactttaagaaggagatatacatatggaagctcgtcgttctgcgaactacgaacctaa
cagctgggactatgattacctgctgtcctccgacacggacgagtccatcgaagtatacaaagacaaagcgaaaaagctg
gaagccgaagttcgtcgcgagattaataacgaaaaagcagaattctgaccctgctggaactgattgacaacgtccagcg
cctgggcctgggttaccgtttcgagtctgatatccgtggtgcgctggatcgcttcgtttcctccggcggcttcgatgcggta
accaagacttccctgcacggtacggcactgtctttccgtctgctgcgtcaacacggttttgaggtttctcaggaagcgttca
gcggcttcaaagaccaaaacggcaacttcctggagaacctgaaggaagatatcaaagctatcctgagcctgtacgaggc
cagcttcctggctctggaaggcgaaaacatcctggacgaggcgaaggttttcgcaatctctcatctgaaagaactgtctga
agaaaagatcggtaaagagctggcagaacaggtgaaccatgcactggaactgccactgcatcgccgtactcagcgtct
ggaagcagtatggtctatcgaggcctaccgtaaaaaggaggacgcgaatcaggttctgctggagctggcaattctggatt
acaacatgatccagtctgtataccagcgtgatctgcgtgaaacgtcccgttggtggcgtcgtgtgggtctggcgaccaaa
ctgcactttgctcgtgaccgcctgattgagagcttctactgggccgtgggtgtagcattcgaaccgcaatactccgactgc
cgtaactccgtcgcaaaaatgttttctttcgtaaccattatcgacgatatctacgatgtatacggcacccctggacgaactgga
gctgtttactgatgcagttgagcgttgggacgtaaacgccatcaacgacctgccggattacatgaaactgtgctttctggct
ctgtataacactattaacgaaatcgcctacgacaacctgaaagataaaggtgagaacatcctgccgtatctgaccaaagc
ctgggctgacctgtgcaacgctttcctgcaagaagccaagtggctgtacaacaaatctactccgaccttgacgactacttc
ggcaacgcatggaaatcctcttctggcccgctgcaactggtgttcgcttacttcgctgtcgtgcagaacattaaaaaggaa
gagatcgaaaacctgcaaaaataccatgacaccatctctcgtccttcccatatcttccgtctgtgcaatgacctggctagcg
cgtctgcggaaattgcgcgtggtgaaaccgcaaatagcgtttcttgttacatgcgcactaaaggtatctccgaagaactgg
ctaccgaaagcgtgatg

Figure 174D aatctgatcgatgaaacctggaaaaagatgaacaaggaaaaactgggtggtagcctgttcgcgaaaccgttcgtggaaac
cgcgatcaacctggcacgtcaatctcactgcacttatcataacggcgacgcgcatacctctccggatgagctgacccgcaa
acgcgttctgtctgtaatcactgaaccgattctgccgtttgaacgctaaggatccattcgcccttaggaggtaaaaaaacatg
agttttgatattgccaaatacccgaccctggcactggtcgactccacccaggagttacgactgttgccgaaagagagtttac
cgaaactctgcgacgaactgcgccgctatttactcgacagcgtgagccgttccagcgggcacttcgcctccgggctgggc
acggtcgaactgaccgtggcgctgcactatgtctacaacaccccgtttgaccaattgatttgggatgtggggcatcaggctt
atccgcataaaattttgaccggacgccgcgacaaaatcggcaccatccgtcagaaaggcggtctgcacccgttcccgtgg
cgcggcgaaagcgaatatgacgtattaagcgtcgggcattcatcaacctccatcagtgccggaattggtattgcggttgctg
ccgaaaaagaaggcaaaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcgatttccgaaaatgtcggc
gcgctcaacaaccatctggcacagctgctttccggtaagctttactcttcactgcgcgaaggcgggaaaaaagttttctctgg
cgtgccgccaattaaagagctgctcaaacgcaccgaagaacatattaaaggcatggtagtgcctggcacgttgtttgaaga
gctgggctttaactacatcggcccggtggacggtcacgatgtgctggggcttatcaccacgctaaagaacatgcgcgacct
gaaaggcccgcagttcctgcatatcatgaccaaaaaaggtcgtggttatgaaccggcagaaaaagacccgatcactttcca
cgccgtgcctaaatttgatccctccagcggttgtttgccgaaaagtagcggcggtttgccgagctattcaaaaatctttggcg
actggttgtgcgaaacggcagcgaaagacaacaagctgatggcgattactccggcgatgcgtgaaggttccggcatggtc
gagttttcacgtaaattcccggatcgctacttcgacgtggcaattgccgagcaacacgcggtgacctttgctgcgggtctgg
cgattggtgggtacaaaccccattgtcgcgatttactccactttcctgcaacgcgcctatgatcaggtgctgcatgacgtggcg
attcaaaagcttccggtcctgttcgccatcgaccgcgcgggcattgttggtgctgacggtcaaacccatcagggtgcttttga
tctctcttacctgcgctgcataccggaaatggtcattatgaccccgagcgatgaaaacgaatgtcgccagatgctctataccg
gctatcactataacgatggcccgtcagcggtgcgctacccgcgtggcaacgcggtcggcgtggaactgacgccgctgga
aaaactaccaattggcaaaggcattgtgaagcgtcgtggcgagaaactggcgatccttaactttggtacgctgatgccaga
agcggcgaaagtcgccgaatcgctgaacgccacgctggtcgatatgcgttttgtgaaaccgcttgatgaagcgttaattctg
gaaatggccgccagccatgaagcgctggtcaccgtagaagaaaacgccattatgggcggcgcaggcagcggcgtgaa
cgaagtgctgatggcccatcgtaaaccagtacccgtgctgaacattggcctgccggacttctttattccgcaaggaactcag
gaagaaatgcgcgccgaactcggcctcgatgccgctggtatggaagccaaaatcaaggcctggctggcataactgcatc
gcccttaggaggtaaaaaaaaatgactgccgacaacaatagtatgccccatggtgcagtatctagttacgccaaattagtgc
aaaaccaaacacctgaagacattttggaagagtttcctgaaattattccattacaacaaagacctaatacccgatctagtgag
acgtcaaatgacgaaagcggagaaacatgttttctggtcatgatgaggagcaaattaagttaatgaatgaaaattgtattgttt
tggattgggacgataatgctattggtgccggtaccaagaaagtttgtcatttaatggaaaatattgaaaagggtttactacatc
gtgcattctccgtctttattttcaatgaacaaggtgaattacttttacaacaaagagccactgaaaaaataactttccctgatcttt
ggactaacacatgctgctctcatccactatgtattgatgacgaattaggtttgaagggtaagctagacgataagattaagggc
gctattactgcggcggtgagaaaactagatcatgaattaggtattccagaagatgaaactaagacaaggggtaagtttcactt
tttaaacagaatccattacatggcaccaagcaatgaaccatggggtgaacatgaaattgattacatcctatttataagatcaa
cgctaaagaaaacttgactgtcaacccaaacgtcaatgaagttagagacttcaaatgggtttcaccaaatgatttgaaaacta
tgtttgctgacccaagttacaagtttacgccttggtttaagattatttgcgagaattacttattcaactggtgggagcaattagat
gacctttctgaagtggaaaatgacaggcaaattcatagaatgctataacaacgcgtcctgcagctggcggccgcactcgag
caccaccaccaccaccactgagatccggctgctaacaaagcccgaaaggaagctgagttggctgctgccaccgctgagc
aataactagcataaccccttggggcctctaaacgggtcttgaggggttttttgctgaaaggaggaactatatccggat (SEQ ID NO:154)

Figures 176A-B
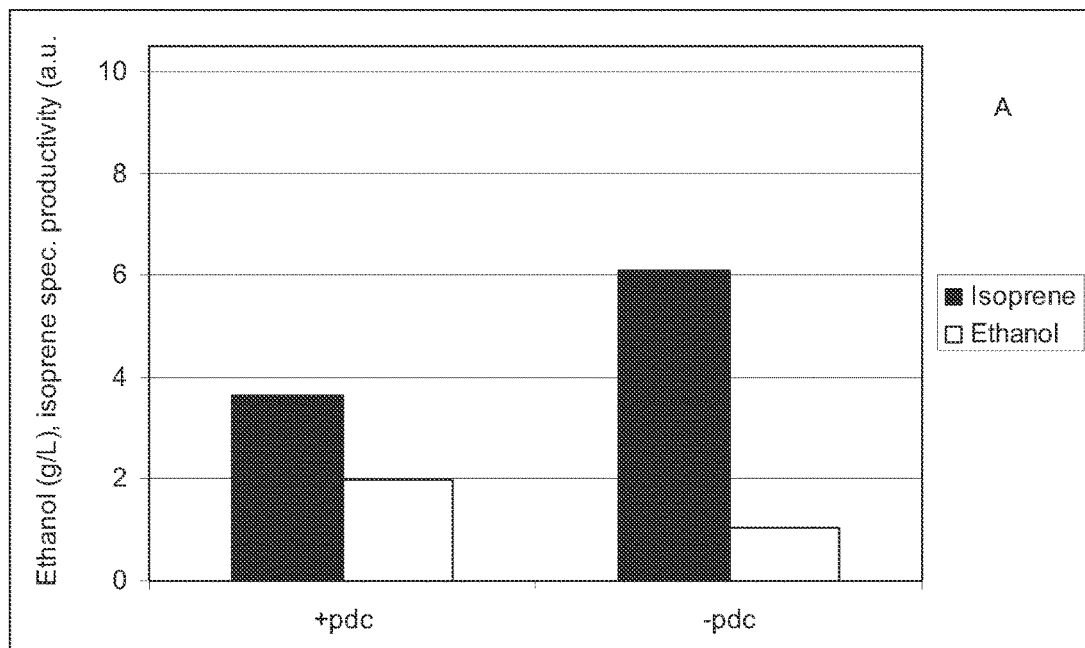
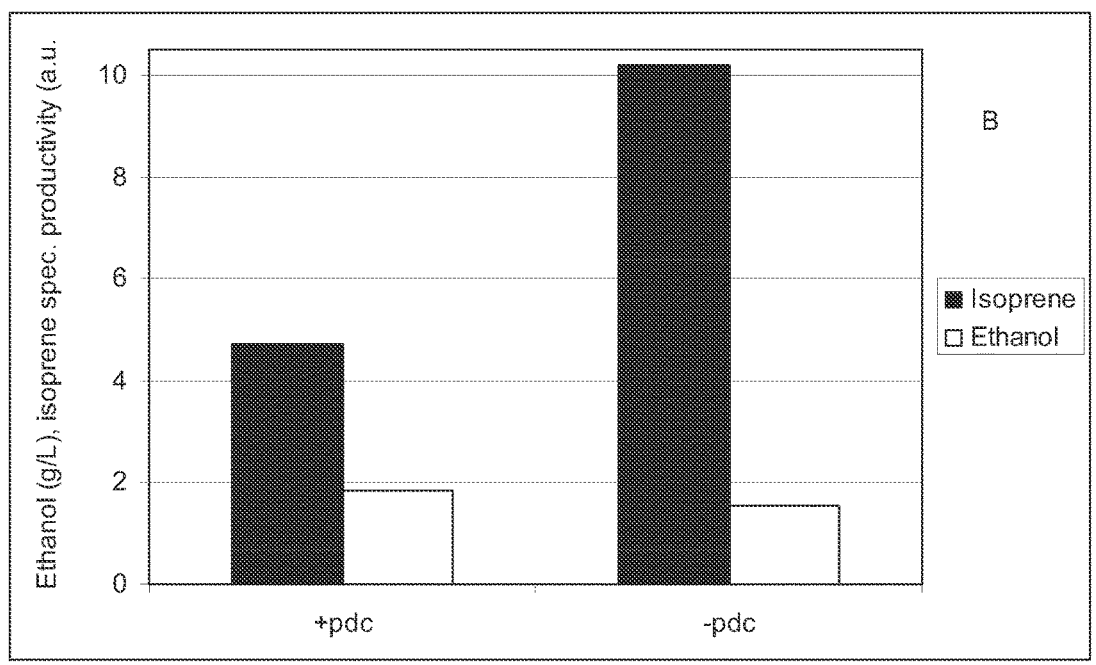

Figure 179A tggcgaatgggacgcgccctgtagcggcgcattaagcgcggcgggtgtggtggttacgcgcagcgtgaccgctacacttgccagc
gccctagcgcccgctcctttcgctttcttcccttccttctcgccacgttcgccggcttccccgtcaagctctaaatcgggggctcccttta
gggttccgatttagtgctttacggcacctcgaccccaaaaaacttgattagggtgatggttcacgtagtgggccatcgccctgatagacg
gttttcgcccttgacgttggagtccacgttctttaatagtggactcttgttccaaactggaacaacactcaaccctatctcggtctattctttt
gatttataagggattttgccgatttcggcctattggttaaaaaatgagctgatttaacaaaaatttaacgcgaattttaacaaaatattaacgtt
tacaatttcaggtggcacttttcggggaaatgtgcgcggaaccccctatttgtttattttctaaatacattcaaatatgtatccgctcatgaatt
aattcttagaaaaactcatcgagcatcaaatgaaactgcaatttattcatatcaggattatcaataccatattttgaaaaagccgttctgta
atgaaggagaaaactcaccgaggcagttccataggatggcaagatcctggtatcggtctgcgattccgactcgtccaacatcaataca
acctattaatttcccctcgtcaaaaataaggttatcaagtgagaaatcaccatgagtgacgactgaatccggtgagaatggcaaaagttt
atgcatttctttccagacttgttcaacaggccagccattacgctcgtcatcaaaatcactcgcatcaaccaaaccgttattcattcgtgattg
cgcctgagcgagacgaaatacgcgatcgctgttaaaaggacaattacaaacaggaatcgaatgcaaccggcgcaggaacactgcc
agcgcatcaacaatattttcacctgaatcaggatattcttctaatacctggaatgctgttttcccggggatcgcagtggtgagtaaccatgc
atcatcaggagtacggataaaatgcttgatggtcggaagaggcataaattccgtcagccagtttagtctgaccatctcatctgtaacatca
ttggcaacgctaccttgccatgtttcagaaacaactctggcgcatcgggcttcccatacaatcgatagattgtcgcacctgattgcccga
cattatcgcgagcccatttatacccatataaatcagcatccatgttggaatttaatcgcggcctagagcaagacgtttcccgttgaatatgg
ctcataacaccccttgtattactgtttatgtaagcagacagttttattgttcatgaccaaaatcccttaacgtgagttttcgttccactgagcgt
cagacccgctagaaaagatcaaaggatcttcttgagatcctttttttctgcgcgtaatctgctgcttgcaaacaaaaaaaccaccgctacc
agcggtggtttgtttgccggatcaagagctaccaactctttttccgaaggtaactggcttcagcagagcgcagataccaaatactgtccttt
ctagtgtagccgtagttaggccaccacttcaagaactctgtagcaccgcctacatacctcgctctgctaatcctgttaccagtggctgctg
ccagtggcgataagtcgtgtcttaccgggttggactcaagacgatagttaccggataaggcgcagcggtcgggctgaacggggggtt
cgtgcacacagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccaggggggaaac
gcctggtatctttatagtcctgtcgggtttcgccacctctgacttgagcgtcgatttttgtgatgctcgtcaggggggcggagcctatgga
aaaacgccagcaacgcggccttttttacggttcctggccttttgctggccttttgctcacatgttctttcctgcgttatcccctgattctgtgga
taaccgtattaccgcctttgagtgagctgataccgctcgccgcagccgaacgaccgagcgcagcgagtcagtgagcgaggaagcg
gaagagcgcctgatgcggtattttctccttacgcatctgtgcggtatttcacaccgcatatatggtgcactctcagtacaatctgctctgat
gccgcatagttaagccagtatacactccgctatcgctacgtgactgggtcatggctgcgccccgacacccgccaacacccgctgacg
cgccctgacgggcttgtctgctcccggcatccgcttacagacaagctgtgaccgtctccgggagctgcatgtgtcagaggttttcaccg
tcatcaccgaaacgcgcgaggcagctgcggtaaagctcatcagcgtggtcgtgaagcgattcacagatgtctgcctgttcatccgcgt
ccagctcgttgagtttctccagaagcgttaatgtctggcttctgataaagcgggccatgttaagggcggttttttcctgtttggtcactgatg
cctccgtgtaagggggatttctgttcatgggggtaatgataccgatgaaacgagagaggatgctcacgatacgggttactgatgatgaa
catgcccggttactggaacgttgtgagggtaaacaactggcggtatggatgcggcgggaccagagaaaaatcactcagggtcaatg
ccagcgcttcgttaatacagatgtaggtgttccacagggtagccagcagcatcctgcgatgcagatccggaacataatggtgcagggc
gctgacttccgcgtttccagactttacgaaacacggaaaccgaagaccattcatgttgttgctcaggtcgcagacgttttgcagcagcag
tcgcttcacgttcgctcgcgtatcggtgattcattctgctaaccagtaaggcaacccccgccagcctagccgggtcctcaacgacagga
gcacgatcatgcgcacccgtggggccgccatgccggcgataatggcctgcttctcgccgaaacgtttggtggcgggaccagtgacg
aaggcttgagcgagggcgtgcaagattccgaataccgcaagcgacaggccgatcatcgtcgcgctccagcgaaagcggtcctcgc
cgaaaatgacccagagcgctgccggcacctgtcctacgagttgcatgataaagaagacagtcataagtgcggcgacgatagtcatgc
cccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcgggga
gaggcggtttgcgtattgggcgccagggtggtttttcttttcaccagtgagacgggcaacagctgattgcccttcaccgcctggccct

Figure 179B

Cagagagttgcagcaagcggtccacgctggtttgccccagcaggcgaaaatcctgtttgatggtggttaacggcgggatataacat
gagctgtcttcggtatcgtcgtatcccactaccgagatatccgcaccaacgcgcagcccggactcggtaatggcgcgcattgcgcc
cagcgccatctgatcgttggcaaccagcatcgcagtgggaacgatgccctcattcagcatttgcatggtttgttgaaaaccggacatg
gcactccagtcgccttcccgttccgctatcggctgaatttgattgcgagtgagatatttatgccagccagccagacgcagacgcgcc
gagacagaacttaatgggcccgctaacagcgcgatttgctggtgacccaatgcgaccagatgctccacgcccagtcgcgtaccgtc
ttcatgggagaaaataatactgttgatgggtgtctggtcagagacatcaagaaataacgccggaacattagtgcaggcagcttccac
agcaatggcatcctggtcatccagcggatagttaatgatcagcccactgacgcgttgcgcgagaagattgtgcaccgccgctttaca
ggcttcgacgccgcttcgttctaccatcgacaccaccacgctggcacccagttgatcggcgcgagatttaatcgccgcgacaatttg
cgacggcgcgtgcagggccagactggaggtggcaacgccaatcagcaacgactgtttgcccgccagttgttgtgccacgcggttg
ggaatgtaattcagctccgccatcgccgcttccacttttcccgcgttttcgcagaaacgtggctggcctggttcaccacgcgggaaa
cggtctgataagagacaccggcatactctgcgacatcgtataacgttactggtttcacattcaccaccctgaattgactctcttccgggc
gctatcatgccataccgcgaaaggttttgcgccattcgatggtgtccgggatctcgacgctctccctatgcgactcctgcattaggaa
gcagcccagtagtaggttgaggccgttgagcaccgccgccgcaaggaatggtgcatgcaaggagatggcgcccaacagtcccc
cggccacggggcctgccaccatacccacgccgaaacaagcgctcatgagcccgaagtggcgagcccgatcttccccatcggtga
tgtcggcgatataggcgccagcaaccgcacctgtggcgccggtgatgccggccacgatgcgtccggcgtagaggatcgagatct
cgatcccgcgaaattaatacgactcactatagggaattgtgagcggataacaattcccctctagaaataattttgtttaactttaagaag
gagatatacatatgaccgaagctcgtcgttctgcgaactacgaacctaacagctgggactatgattacctgctgtcctccgacacgga
cgagtccatcgaagtatacaaagacaaagcgaaaaagctggaagccgaagttcgtcgcgagattaataacgaaaaagcagaatttc
tgaccctgctggaactgattgacaacgtccagcgcctgggcctgggttaccgtttcgagtctgatatccgtggtgcgctggatcgctt
cgtttcctccggcggcttcgatgcggtaaccaagacttccctgcacggtacggcactgtctttccgtctgctgcgtcaacacggttttg
aggtttctcaggaagcgttcagcggcttcaaagaccaaaacggcaacttcctggagaacctgaaggaagatatcaaagctatcctga
gcctgtacgaggccagcttcctggctctggaaggcgaaaacatcctggacgaggcgaaggttttcgcaatctctcatctgaaagaac
tgtctgaagaaaagatcggtaaagagctggcagaacaggtgaaccatgcactggaactgccactgcatcgccgtactcagcgtctg
gaagcagtatggtctatcgaggcctaccgtaaaaaggaggacgcgaatcaggttctgctggagctggcaattctggattacaacatg
atccagtctgtataccagcgtgatctgcgtgaaacgtccgttggtggcgtcgtgggtctggcgaccaaactgcactttgctcgtg
accgcctgattgagagcttctactgggccgtgggtgtagcattcgaaccgcaatactccgactgccgtaactccgtcgcaaaaatgtt
ttctttcgtaaccattatcgacgatatctacgatgtatacggcaccctggacgaactggagctgttactgatgcagttgagcgttggga
cgtaaacgccatcaacgacctgccggattacatgaaactgtgctttctggctctgtataacactattaacgaaatcgcctacgacaacc
tgaaagataaaggtgagaacatcctgccgtatctgaccaaagcctgggctgacctgtgcaacgctttcctgcaagaagccaagtgg
ctgtacaacaaatctactccgacctttgacgactacttcggcaacgcatggaaatcctcttctggcccgctgcaactggtgttcgcttac
ttcgctgtcgtgcagaacattaaaaaggaagagatcgaaaacctgcaaaaataccatgacaccatctctcgtccttcccatatcttccg
tctgtgcaatgacctggctagcgcgtctgcggaaattgcgcgtggtgaaaccgcaaatagcgtttcttgttacatgcgcactaaaggt
atctccgaagaactggctaccgaaagcgtgatgaatctgatcgatgaaacctggaaaaagatgaacaaggaaaaactgggtggta
gcctgttcgcgaaaccgttcgtggaaaccgcgatcaacctggcacgtcaatctcactgcacttatcataacggcgacgcgcatacct
ctccggatgagctgacccgcaaacgcgttctgtctgtaatcactgaaccgattctgccgtttgaacgctaaggatccgaattcgagct
ccgtcgacaagcttgcggccgcactcgagcaccaccaccaccaccactgagatccggctgctaacaaagcccgaaaggaagctg
agttggctgctgccaccgctgagcaataactagcataaccccttggggcctctaaacgggtcttgaggggttttttgctgaaaggagg
aactatatccggat (SEQ ID NO:159)

Figure 181A gccctcgatgccccgttgcagccctagatcggccacagcggccgcaaacgtggtctggtcgcgggtcatctgcgctttgttgc
cgatgaactccttggccgacagcctgccgtcctgcgtcagcggcaccacgaacgcggtcatgtgcgggctggtttcgtcacg
gtggatgctggccgtcacgatgcgatccgccccgtacttgtccgccagccacttgtgcgccttctcgaagaacgccgcctgct
gttcttggctggccgacttccaccattccgggctggccgtcatgacgtactcgaccgccaacacagcgtccttgcgccgcttct
ctggcagcaactcgcgcagtcggcccatcgcttcatcggtgctgctggccgcccagtgctcgttctctggcgtcctgctggcg
tcagcgttgggcgtctcgcgctcgcggtaggcgtgcttgagactggccgccacgttgcccattttcgccagcttcttgcatcgc
atgatcgcgtatgccgccatgcctgccccctcccttttggtgtccaaccggctcgacggggcagcgcaaggcggtgcctccg
gcgggccactcaatgcttgagtatactcactagactttgcttcgcaaagtcgtgaccgcctacggcggctgcggcgccctacg
ggcttgctctccgggcttcgccctgcgcggtcgctgcgctcccttgccagcccgtggatatgtggacgatggccgcgagcgg
ccaccggctggctcgcttcgctcggcccgtggacaaccctgctggacaagctgatggacaggctgcgcctgcccacgagct
tgaccacagggattgccaccggctacccagccttcgaccacatacccaccggctccaactgcgcggcctgcggccttgcc
ccatcaatttttttaattttctctggggaaaagcctccggcctgcggcctgcgcgcttcgcttgccggttggacaccaagtggaa
ggcgggtcaaggctcgcgcagcgaccgcgcagcggcttggccttgacgcgcctggaacgacccaagcctatgcgagtgg
gggcagtcgaaggcgaagcccgcccgcctgcccccgagcctcacggcggcgagtgcgggggttccaaggggggcagc
gccaccttgggcaaggccgaaggccgcgcagtcgatcaacaagcccggaggggccacttttttgccggaggggagccg
cgccgaaggcgtgggggaaccccgcagggtgcccttctttgggcaccaaagaactagatatagggcgaaatgcgaaaga
cttaaaaatcaacaacttaaaaaaggggggtacgcaacagctcattgcggcaccccccgcaatagctcattgcgtaggttaaa
gaaaatctgtaattgactgccactttacgcaacgcataattgttgtcgcgctgccgaaaagttgcagctgattgcgcatggtgcc
gcaaccgtgcggcaccctaccgcatggagataagcatggccacgcagtccagagaaatcggcattcaagccaagaacaag
cccggtcactgggtgcaaacggaacgcaaagcgcatgaggcgtgggccgggcttattgcgaggaaacccacggcggcaa
tgctgctgcatcacctcgtggcgcagatgggccaccagaacgccgtggtggtcagccagaagacactttccaagctcatcgg
acgttctttgcggacggtccaatacgcagtcaaggacttggtggccgagcgctggatctccgtcgtgaagctcaacggcccc
ggcaccgtgtcggcctacgtggtcaatgaccgcgtggcgtggggccagccccgcgaccagttgcgcctgtcggtgttcagt
gccgccgtggtggttgatcacgacgaccaggacgaatcgctgttggggcatggcgacctgcgccgcatcccgaccctgtat
ccgggcgagcagcaactaccgaccggccccggcgaggagccgcccagccagcccggcattccgggcatggaaccaga
cctgccagccttgaccgaaacggaggaatgggaacggcgcgggcagcagcgcctgccgatgcccgatgagccgtgtttc
tggacgatggcgagccgttggagccgccgacacgggtcacgctgccgcgccggtagcacttgggttgcgcagcaacccgt
aagtgcgctgttccagactatcggctgtagccgcctcgccgcccataccttgtctgcctccccgcgttgcgtcgcggtgcatg
gagccgggccacctcgacctgaatggaagccggcggcacctcgctaacggattcaccgttttatcaggctctggaggca
gaataaatgatcatatcgtcaattattacctccacggggagagcctgagcaaactggcctcaggcatttgagaagcacacggt
cacactgcttccggtagtcaataaaccggtaaaccagcaatagacataagcggctatttaacgaccctgccctgaaccgacga
ccgggtcgaatttgctttcgaatttctgccattcatccgcttattatcacttattcaggcgtagcaccaggcgtttaagggcaccaa
taactgccttaaaaaaattacgccccgccctgccactcatcgcagtcggcctattggttaaaaaatgagctgatttaacaaaaatt
taacgcgaattttaacaaaatattaacgcttacaatttccattcgccattcaggctgcgcaactgttgggaagggcgatcggtgc
gggcctcttcgctattacgccagctggcgaaaggggggatgtgctgcaaggcgattaagttgggtaacgccagggttttcccag
tcacgacgttgtaaaacgacggccagtgagcgcgcgtaatacgactcactatagggcgaattggagctccaccgcggtggc
ggccgctctagagctcatgatcgcggcatgttctgatattttcctaaaaaagataaaaagtctttcgcttcggcagaagagg
ttcatcatgaacaaaaattcggcatttttaaaaatgcctatagctaaatccggaacgacactttagaggtttctgggtcatcctgatt
cagacatagtgttttgaatatatggagtaagcaatgatgaccgaagctcgtcgttctgcgaactacgaacctaacagctgggac
tatgattacctgctgtcctccgacacggacgagtccatcgaagtatacaaagacaaagcgaaaaagctggaagccgaagttc
gtcgcgagattaataacgaaaaagcagaatttctgaccctgctggaactgattgacaacgtccagcgcctgggcctgggttac
cgtttcgagtctgatatccgtggtgcgctggatcgcttcgtttcctccggcggcttcgatgcggtaaccaagacttccctgcacg
gtacggcactgtctttccgtctgctgcgtcaacacggttttgaggtttctcaggaagcgttcag

Figure 181B cggcttcaaagaccaaaacggcaacttcctggagaacctgaaggaagatatcaaagctatcctgagcctgtacgaggcc
agcttcctggctctggaaggcgaaaacatcctggacgaggcgaaggttttcgcaatctctcatctgaaagaactgtctgaa
gaaaagatcggtaaagagctggcagaacaggtgaaccatgcactggaactgccactgcatcgccgtactcagcgtctgg
aagcagtatggtctatcgaggcctaccgtaaaaaggaggacgcgaatcaggttctgctggagctggcaattctggattaca
acatgatccagtctgtataccagcgtgatctgcgtgaaacgtcccgttggtggcgtcgtgtgggtctggcgaccaaactgc
actttgctcgtgaccgcctgattgagagcttctactgggccgtgggtgtagcattcgaaccgcaatactccgactgccgtaa
ctccgtcgcaaaaatgttttctttcgtaaccattatcgacgatatctacgatgtatacggcaccctggacgaactggagctgtt
tactgatgcagttgagcgttgggacgtaaacgccatcaacgacctgccggattacatgaaactgtgctttctggctctgtata
acactattaacgaaatcgcctacgacaacctgaaagataaaggtgagaacatcctgccgtatctgaccaaagcctgggct
gacctgtgcaacgctttcctgcaagaagccaagtggctgtacaacaaatctactccgacctttgacgactacttcggcaac
gcatggaaatcctcttctggcccgctgcaactggtgttcgcttacttcgctgtcgtgcagaacattaaaaaggaagagatcg
aaaacctgcaaaaataccatgacaccatctctcgtccttcccatatcttccgtctgtgcaatgacctggctagcgcgtctgcg
gaaattgcgcgtggtgaaaccgcaaatagcgtttcttgttacatgcgcactaaaggtatctccgaagaactggctaccgaa
agcgtgatgaatctgatcgatgaaacctggaaaaagatgaacaaggaaaaactgggtggtagcctgttcgcgaaaccgtt
cgtggaaaccgcgatcaacctggcacgtcaatctcactgcacttatcataacggcgacgcgcatacctctccggatgagc
tgacccgcaaacgcgttctgtctgtaatcactgaaccgattctgccgtttgaacgctaaggatccgaattcgagctccgtcg
acctgcaggaattcgatatcaagcttatcgataccgtcgacctcgagggggggcccggtacccagcttttgttccctttagt
gagggttaattgcgcgcttggcgtaatcatggtcatagctgtttcctgtgtgaaattgttatccgctcacaattccacacaaca
tacgagccggaagcataaagtgtaaagcctggggtgcctaatgagtgagctaactcacattaattgcgttgcgctcactgc
ccgctttccagtcgggaaacctgtcgtgccagctgcattaatgaatcggccaacgcgcggggagaggcggtttgcgtatt
gggcgcatgcataaaaactgttgtaattcattaagcattctgccgacatggaagccatcacaaacggcatgatgaacctga
atcgccagcggcatcagcaccttgtcgccttgcgtataatatttgcccatggtgaaaacgggggcgaagaagttgtccata
ttggccacgtttaaatcaaaactggtgaaactcacccagggattggctgagacgaaaaacatattctcaataaacccttag
ggaaataggccaggttttcaccgtaacacgccacatcttgcgaatatatgtgtagaaactgccggaaatcgtcgtggtattc
actccagagcgatgaaaacgtttcagtttgctcatggaaaacggtgtaacaagggtgaacactatcccatatcaccagctc
accgtctttcattgccatacggaattccggatgagcattcatcaggcgggcaagaatgtgaataaaggccggataaaactt
gtgcttattttctttacggtctttaaaaaggccgtaatatccagctgaacggtctggttataggtacattgagcaactgactga
aatgcctcaaaatgttctttacgatgccattgggatatatcaacggtggtatatccagtgatttttttctccatttttagcttccttag
ctcctgaaaatctcgataactcaaaaaatacgcccggtagtgatcttatttcattatggtgaaagttggaacctcttacgtgcc
gatcaacgtctcattttcgccaaaagttggcccagggcttcccggtatcaacagggacaccaggatttatttattctgcgaa
gtgatcttccgtcacaggtatttattcgaagacgaaagggcctcgtgatacgcctatttttataggttaatgtcatgataataat
ggtttcttagacgtcaggtggcacttttcggggaaatgtgcgcgcccgcgttcctgctggcgctgggcctgtttctggcgct
ggacttcccgctgttccgtcagcagcttttcgcccacggccttgatgatcgcggcggccttggcctgcatatcccgattcaa
cggccccagggcgtccagaacgggcttcaggcgctcccgaaggtctcgggccgtctcttgggcttgatcggccttcttgc
gcatctcacgcgctcctgcggcggcctgtagggcaggctcataccctgccgaaccgcttttgtcagccggtcggccac
ggcttccggcgtctcaacgcgctttgagattcccagcttttcggccaatccctgcggtgcataggcgcgtggctcgaccgc
ttgcgggctgatggtgacgtggcccactggtggccgctccagggcctcgtagaacgcctgaatgcgcgtgtgacgtgcct
tgct (SEQ ID NO:160)

Figure 183B accttcgggagcgcctgaagcccgttctggacgccctggggccgttgaatcgggatatgcaggccaaggccgccgcgat
catcaaggccgtgggcgaaaagctgctgacggaacagcgggaagtccagcgccagaaacaggcccagcgccagcag
gaacgcgggcgcgcacatttccccgaaaagtgccacctggcggcgttgtgacaatttaccgaacaactccgcggccggg
aagccgatctcggcttgaacgaattgttaggtggcggtacttgggtcgatatcaaagtgcatcacttcttcccgtatgcccaa
ctttgtatagagagccactgcgggatcgtcaccgtaatctgcttgcacgtagatcacataagcaccaagcgcgttggcctca
tgcttgaggagattgatgagcgcggtggcaatgccctgcctccggtgctcgccggagactgcgagatcatagatatagatc
tcactacgcggctgctcaaacctgggcagaacgtaagccgcgagagcgccaacaaccgcttcttggtcgaaggcagcaa
gcgcgatgaatgtcttactacggagcaagttcccgaggtaatcggagtccggctgatgttgggagtaggtggctacgtctc
cgaactcacgaccgaaaagatcaagagcagcccgcatggatttgacttggtcagggccgagcctacatgtgcgaatgatg
cccatacttgagccacctaactttgttttagggcgactgccctgctgcgtaacatcgttgctgctgcgtaacatcgttgctgctc
cataacatcaaacatcgacccacggcgtaacgcgcttgctgcttggatgcccgaggcatagactgtacaaaaaaacagtc
ataacaagccatgaaaaccgccactgcgccgttaccaccgctgcgttcggtcaaggttctggaccagttgcgtgagcgcat
acgctacttgcattacagtttacgaaccgaacaggcttatgtcaactgggttcgtgccttcatccgtttccacggtgtgcgtcc
atgggcaaatattatacgcaaggcgacaaggtgctgatgccgctggcgattcaggttcatcatgccgtttgtgatggcttcca
tgtcggcagaatgcttaatgaattacaacagttttatgcatgcgcccaatacgcaaaccgcctctccccgcgcgttggccga
ttcattaatgcagctggcacgacaggtttcccgactgaaagcgggcagtgagcgcaacgcaattaatgtgagttagctca
ctcattaggcaccccaggctttacactttatgcttccggctcgtatgttgtgtggaattgtgagcggataacaatttcacacagg
aaacagctatgaccatgattacgccaagcgcgcaattaaccctcactaaagggaacaaaagctgggtaccgggccccc
ctcgagctgttgacaattaatcatccggctcgtataatgtgtggaattgtgagcggataacaatttcacacaggaaacagcgc
cgctgagaaaaagcgaagcggcactgctctttaacaatttatcagacaatctgtgtgggcactcgaccggaattatcgatta
actttattattaaaaattaaagaggtatatattaatgtatcgattaaataaggaggaataaaccatggatccgagctcaggaggt
aaaaaaacatgaaaacagtagttattattgatgcattacgaacaccaattggaaaatataaaggcagcttaagtcaagtaagt
gccgtagacttaggaacacatgttacaacacaactttaaaaagacattccactatttctgaagaaattgatcaagtaatctttg
gaaatgttttacaagctggaaatggccaaaatcccgcacgacaaatagcaataaacagcggtttgtctcatgaaattcccgc
aatgacggttaatgaggtctgcggatcaggaatgaaggccgttatttggcgaaacaattgattcaattaggagaagcggaa
gttttaattgctggcgggattgagaatatgtcccaagcacctaaattacaacgttttaattacgaaacagaaagctacgatgcg
ccttttctagtatgatgtatgatggattaacggatgcctttagtggtcaggcaatgggcttaactgctgaaaatgtggccgaaa
agtatcatgtaactagagaagagcaagatcaattttctgtacattcacaattaaaagcagctcaagcacaagcagaagggat
attcgctgacgaaatagccccattagaagtatcaggaacgcttgtggagaaagatgaagggattcgccctaattcgagcgtt
gagaagctaggaacgcttaaaacagttttaaagaagacggtactgtaacagcagggaatgcatcaaccattaatgatggg
gcttctgctttgattattgcttcacaagaatatgccgaagcacacggtcttccttatttagctattattcgagacagtgtggaagt
cggtattgatccagcctatatgggaatttcgccgattaaagccattcaaaaactgttagcgcgcaatcaacttactacggaag
aaattgatctgtatgaaatcaacgaagcatttgcagcaacttcaatcgtggtccaaagagaactggctttaccagaggaaaa
ggtcaacatttatggtggcggtatt

Figure 183C tcattaggtcatgcgattggtgccacaggtgctcgtttattaacgagtttaagttatcaattaaatcaaaaagaaaagaaatat
ggagtggcttctttatgtatcggcggtggcttaggactcgctatgctactagagagacctcagcaaaaaaaaacagccg
attttatcaaatgagtcctgaggaacgcctggcttctcttcttaatgaaggccagatttctgctgatacaaaaaaagaatttga
aaatacggctttatcttcgcagattgccaatcatatgattgaaaatcaaatcagtgaaacagaagtgccgatgggcgttggc
ttacatttaacagtggacgaaactgattatttggtaccaatggcgacagaagagccctcagttattgcggctttgagtaatgg
tgcaaaaatagcacaaggatttaaaacagtgaatcaacaacgcttaatgcgtggacaaatcgttttttacgatgttgcagat
cccgagtcattgattgataaaactacaagtaagagaagcggaagttttttcaacaagcagagttaagttatccatctatcgttaa
acggggcggcggcttaagagatttgcaatatcgtacttttgatgaatcatttgtatctgtcgacttttagtagatgttaaggat
gcaatgggggcaaatatcgttaacgctatgttggaaggtgtggccgagttgttccgtgaatggtttgcggagcaaaagatt
ttattcagtattttaagtaattatgccacggagtcggttgttacgatgaaaacggctattccagtttcacgtttaagtaaggggga
gcaatggccgggaaattgctgaaaaaattgttttagcttcacgctatgcttcattagatccttatcgggcagtcacgcataac
aaaggaatcatgaatggcattgaagctgtagttttagctacaggaaatgatacacgcgctgttagcgcttcttgtcatgctttt
gcggtgaaggaaggtcgctaccaaggcttgactagttggacgctggatggcgaacaactaattggtgaaatttcagttcc
gcttgctttagccacggttggcggtgccacaaaagtcttacctaaatctcaagcagctgctgatttgttagcagtgacggat
gcaaaagaactaagtcgagtagtagcggctgttggtttggcacaaaatttagcggcgttacgggccttagtctctgaagga
attcaaaaaggacacatggctctacaagcacgttctttagcgatgacggtcggagctactggtaaagaagttgaggcagt
cgctcaacaattaaaacgtcaaaaaacgatgaaccaagaccgagccatggctatttttaaatgatttaagaaaacaataaag
gaggtaaaaaaacatgacaattggggattgataaaattagttttttttgtgccccccttattatattgatatgacggcactggctga
agccagaaatgtagaccctggaaaatttcatattggtattgggcaagaccaaatggcggtgaacccaatcagccaagata
ttgtgacatttgcagccaatgccgcagaagcgatcttgaccaaagaagataaagaggccattgatatggtgattgtcggg
actgagtccagtatcgatgagtcaaaagcggccgcagttgtcttacatcgtttaatggggattcaacctttcgctcgctctttc
gaaatcaaggaagcttgttacggagcaacagcaggcttacagttagctaagaatcacgtagccttacatccagataaaaa
agtcttggtcgtagcggcagatattgcaaaatatggcttaaattctggcggtgagcctacacaaggagctggggcggttg
caatgttagttgctagtgaaccgcgcatttttggctttaaaagaggataatgtgatgctgacgcaagatatctctatgacttttggc
gtccaacaggccacccgtatcctatggtcgatggtcctttgtcaaacgaaacctacatccaatcttttgcccaagtctggga
tgaacataaaaaacgaaccggtcttgattttgcagattatgatgctttagcgttccatattccttacacaaaaatgggcaaaa
aagccttattagcaaaaatctccgaccaaactgaagcagaacaggaacgaattttagcccgttatgaagaaagtatcgtct
atagtcgtcgcgtaggaaacttgtatacgggttcactttatctgggactcatttccccttttagaaaatgcaacgactttaaccg
caggcaatcaaattggtttattcagttatggttctggtgctgtcgctgaattttttcactggtgaattagtagctggttatcaaaat
catttacaaaaagaaactcatttagcactgctggataatcggacagaacttctatcgctgaatatgaagccatgtttgcaga
aactttagacacagacattgatcaaacgttagaagatgaattaaaatatagtatttctgctattaataataccgttcgttcttatc
gaaactaaagatctgcagctggtaccatatgggaattcgaagcttgggcccgaacaaaaactcatctcagaagaggatct
gaatagcgccgtcgaccatcatcatcatcatcattgagtttaaacggtctccagcttggctgttttggcggatgagagaaga
ttttcagcctgatacagattaaatcagaacgcagaagcggtctgataaaacagaatttgcctggcggcagtagcgcggtg
gtcccacctgacccccatgccgaactcagaagtgaaacgccgtagcgccgatggtagtgtggggtctccccatgcgaga
gtaggaactgccaggcatcaaataaaacgaaaggctcagtcgaaagactgggcctttctagagcggccgccaccgc
ggtggagctccaattcgccctatagtgagtcgtattacgcgcgctcactggccgtcgttttacaacgtcgtgactgggaaa
accctggcgttacccaacttaatcgccttgcagcacatccccctttcgccagctggcgtaatagcgaagaggcccgcacc
gatcgcccttcccaacagtt

Figure 183D gcgcagcctgaatggcgaatggaaattgtaagcgttaatattttgttaaaattcgcgttaaattttgttaaatcagctcatttttaa
ccaataggccgactgcgatgagtggcagggcggggcgtaattttttaaggcagttattggtgcccttaaacgcctggtgcta
cgcctgaataagtgataataagcggatgaatggcagaaattcgaaagcaaattcgacccggtcgtcggttcagggcagggt
cgttaaatagccgcttatgtctattgctggtttaccggtttattgactaccggaagcagtgtgaccgtgtgcttctcaaatgcctga
ggccagtttgctcaggctctccccgtggaggtaataattgacgatatgatcatttattctgcctcccagagcctgataaaaacgg
tgaatccgttagcgaggtgccgccggcttccattcaggtcgaggtggcccggctccatgcaccgcgacgcaacgcgggga
ggcagacaaggtataggcggcgaggcggctacagccgatagtctggaacagcgcacttacgggttgctgcgcaaccca
agtgctaccggcgcggcagcgtgacccgtgtcggcggctccaacggctcgccatcgtccagaaaacacggctcatcggg
catcggcaggcgctgctgcccgcgccgttccattcctccgtttcggtcaaggctggcaggtctggttccatgcccggaatg
ccgggctggctgggcggctcctcgccggggccggtcggtagttgctgctcgcccggatacagggtcgggatgcggcgca
ggtcgccatgccccaacagcgattcgtcctggtcgtcgtgatcaaccaccacggcggcactgaacaccgacaggcgcaac
tggtcgcggggctggccccacgccacgcggtcattgaccacgtaggccgacacggtgccggggccgttgagcttcacga
cggagatccagcgctcggccaccaagtccttgactgcgtattggaccgtccgcaaagaacgtccgatgagcttggaaagtg
tcttctggctgaccaccacggcgttctggtggcccatctgcgccacgaggtgatgcagcagcattgccgccgtgggtttcctc
gcaataagcccggcccacgcctcatgcgctttgcgttccgtttgcacccagtgaccgggcttgttcttggcttgaatgccgattt
ctctggactgcgtggccatgcttatctccatgcggtagggtgccgcacggttgcggcaccatgcgcaatcagctgcaacttt
cggcagcgcgacaacaattatgcgttgcgtaaaagtggcagtcaattacagattttctttaacctacgcaatgagctattgcgg
ggggtgccgcaatgagctgttgcgtaccccccttttttaagttgttgattttttaagtcttcgcatttcgccctatatctagttctttgg
tgcccaaagaagggcacccctgcggggttcccccacgccttcggcgcggctccccctccggcaaaaagtggcccctccg
gggcttgttgatcgactgcgcggccttcggccttgcccaaggtggcgctgccccttggaaccccgcactcgccgcgtg
aggctcgggggggcaggcgggcgggcttcgccttcgactgcccccactcgcataggcttgggtcgttccaggcgcgtcaag
gccaagccgctgcgcggtcgctgcgcgagccttgacccgccttccacttggtgtccaaccggcaagcgaagcgcgcagg
ccgcaggccggaggcttttccccagagaaaattaaaaaaattgatgggggcaaggccgcaggccgcgcagttggagccggt
gggtatgtggtcgaaggctgggtagccggtgggcaatccctgtggtcaagctcgtgggcaggcgcagcctgtccatcagct
tgtccagcagggttgtccacggggccgagcgaagcgagccagccggtggccgctcgcggccatcgtccacatatccacgg
gctggcaagggagcgcagcgaccgcgcagggcgaagcccggagagcaagcccgtagggcgccgcagccgccgtagg
cggtcacgactttgcgaagcaaagtctagtgagtatactcaagcattgagtggcccgccggaggcaccgccttgcgctgcc
cccgtcgagccggttggacaccaaaagggagggcaggcatggcggcatacgcgatcatgcgatgcaagaagctggcg
aaaatgggcaacgtggcggccagtctcaagcacgcctaccgcgagcgcgagacgcccaacgctgacgccagcaggacg
ccagagaacgagcactgggcggccagcagcaccgatgaagcgatgggccgactgcgcgagttgctgccagagaagcg
gcgcaaggacgctgtgttggcggtcgagtacgtcatgacggccagcccggaatggtggaagtcggccagccaagaacag
caggcggcgttcttcgagaaggcgcacaagtggctggcggacaagtacggggcggatcgcatcgtgacggccagcatcc
accgtgacgaaaccagcccgcacatgaccgcgttcgtggtgccgctgacgcaggacggcaggctgtcggccaaggagtt
catcggcaacaaagcgcagatgacccgcgaccagaccacgtttgcggccgctgtggccgatctagggctgcaacggggc
atcgagggcagcaaggcacgtcacacgcgcattcaggcgttctacgaggccctggagcggccaccagtggccacgtca
ccatcagcccgcaagcggtcgagccacgcgcctatgcaccgcagggattggccgaaaagctgggaatctcaaagcgcgtt
gagacgccggaagccgtggccgaccggctgacaaaagcggttcggcaggggtatgagcctgccctacaggccgccgca
ggagcgcgtgagatgcgcaagaaggccgatcaagcccaagagacggcccgag (SEQ ID NO:161)

Figure 184B ctagagtatacatttaaatggtaccctctagtcaaggccttaagtgagtcgtattacggactggccgtcgttttacaacgtcgt
gactgggaaaaccctggcgttacccaacttaatcgccttgcagcacatccccctttcgccagctggcgtaatagcgaaga
ggcccgcaccgatcgcccttcccaacagttgcgcagcctgaatggcgaatggcgcctgatgcggtattttctccttacgc
atctgtgcggtatttcacaccgcatatggtgcactctcagtacaatctgctctgatgccgcatagttaagccagccccgaca
cccgccaacacccgctgacgagcttagtaaagccctcgctagattttaatgcggatgttgcgattacttcgccaactattgc
gataacaagaaaaagccagcctttcatgatatatctcccaatttgtgtagggcttattatgcacgcttaaaaataataaaagc
agacttgacctgatagtttggctgtgagcaattatgtgcttagtgcatctaacgcttgagttaagccgcgccgcgaagcgg
cgtcggcttgaacgaattgttagacattatttgccgactaccttggtgatctcgcctttcacgtagtggacaaattcttccaact
gatctgcgcgcgaggccaagcgatcttcttcttgtccaagataagcctgtctagcttcaagtatgacgggctgatactggg
ccggcaggcgctccattgcccagtcggcagcgacatccttcggcgcgattttgccggttactgcgctgtaccaaatgcgg
gacaacgtaagcactacatttcgctcatcgccagcccagtcgggcggcgagttccatagcgttaaggtttcatttagcgcc
tcaaatagatcctgttcaggaaccggatcaaagagttcctccgccgctggacctaccaaggcaacgctatgttctcttgctt
ttgtcagcaagatagccagatcaatgtcgatcgtggctggctcgaagatacctgcaagaatgtcattgcgctgccattctcc
aaattgcagttcgcgcttagctggataacgccacggaatgatgtcgtcgtgcacaacaatggtgacttctacagcgcgga
gaatctcgctctctccaggggaagccgaagtttccaaaaggtcgttgatcaaagctcgccgcgttgtttcatcaagccttac
ggtcaccgtaaccagcaaatcaatatcactgtgtggcttcaggccgccatccactgcggagccgtacaaatgtacggcc
agcaacgtcggttcgagatggcgctcgatgacgccaactacctctgatagttgagtcgatacttcggcgatcaccgcttcc
ctcatgatgtttaactttgttttagggcgactgccctgctgcgtaacatcgttgctgctccataacatcaaacatcgacccacg
gcgtaacgcgcttgctgcttggatgcccgaggcatagactgtaccccaaaaaaacagtcataacaagccatgaaaaccg
ccactgcgccgttaccaccgctgcgttcggtcaaggttctggaccagttgcgtgagcgcatacgctacttgcattacagct
tacgaaccgaacaggcttatgtccactgggttcgtgccttcatccgtttccacggtgtgcgtcacccggcaaccttgggca
gcagcgaagtcgaggcatttctgtcctggctggcgaacgagcgcaaggtttcggtctccacgcatcgtcaggcattggc
ggccttgctgttcttctacggcaaggtgctgtgcacggatctgccctggcttcaggagatcggaagacctcggccgtcgc
ggcgcttgccggtggtgctgaccccggatgaagtggttcgcatcctcggttttctggaaggcgagcatcgtttgttcgccc
agcttctgtatggaacgggcatgcggatcagtgagggtttgcaactgcgggtcaaggatctggatttcgatcacggcacg
atcatcgtgcgggagggcaagggctccaaggatcgggccttgatgttacccgagagcttggcacccagcctgcgcgag
cagggggaattaattcccacgggttttgctgcccgcaaacgggctgttctggtgttgctagtttgttatcagaatcgcagatcc
ggcttcagccggtttgccggctgaaagcgctatttcttccagaattgccatgattttttccccacgggaggcgtcactggct
cccgtgttgtcggcagctttgattcgataagcagcatcgcctgtttcaggctgtctatgtgtgactgttgagctgtaacaagtt
gtctcaggtgttcaatttcatgttctagttgctttgttttactggtttcacctgttctattaggtgttacatgctgttcatctgttacat
tgtcgatctgttcatggtgaacagctttgaatgcaccaaaaactcgtaaaagctctgatgtatctatctttttacaccgttttca
tctgtgcatatggacagttttcccttttgatatgtaacggtgaacagttgttctactttgtttgttagtcttgatgcttcactgatag
atacaagagccataagaacctcagatccttccgtatttagccagtatgttctctagtgtggttcgttgttttttgcgtgagccatg
agaacgaaccattgagatcatacttactttgcatgtcactcaaaaattttgcctcaaaactggtgagctg

Figure 184C aattttttgcagttaaagcatcgtgtagtgtttttcttagtccgttatgtaggtaggaatctgatgtaatggttgttggtatttttgtc
accattcattttatctggttgttctcaagttcggttacgagatccatttgtctatctagttcaacttggaaaatcaacgtatcag
tcgggcggcctcgcttatcaaccaccaatttcatattgctgtaagtgtttaaatctttacttattggtttcaaaacccattggtt
aagcctttaaactcatggtagttattttcaagcattaacatgaacttaaattcatcaaggctaatctctatatttgccttgtga
gttttctttttgtgttagttcttttaataaccactcataaaatcctcatagagtatttgttttcaaaagacttaacatgttccagattat
atttatgaatttttttaactggaaaagataaggcaatatctcttcactaaaaactaattctaatttttcgcttgagaacttggca
tagtttgtccactggaaaatctcaaagcctttaaccaaaggattcctgatttccacagttctcgtcatcagctctctggttgct
ttagctaatacaccataagcatttccctactgatgttcatcatctgagcgtattggttataagtgaacgataccgtccgttct
ttccttgtagggttttcaatcgtgggggttgagtagtgccacacagcataaaattagcttggtttcatgctccgttaagtcata
gcgactaatcgctagttcatttgctttgaaaacaactaattcagacatacatctcaattggtctaggtgattttaatcactata
ccaattgagatgggctagtcaatgataattactagtcctttctctttgagttgtgggtatctgtaaattctgctagacctttgct
ggaaaacttgtaaattctgctagaccctctgtaaattccgctagacctttgtgtgttttttttgtttatattcaagtggttataattt
atagaataaagaaagaataaaaaaagataaaaagaatagatcccagccctgtgtataactcactactttagtcagttccg
cagtattacaaaaggatgtcgcaaacgctgtttgctcctctacaaaacagaccttaaaaccctaaaggcttaagtagcac
cctcgcaagctcgggcaaatcgctgaatattccttttgtctccgaccatcaggcacctgagtcgctgtcttttcgtgacatt
cagttcgctgcgctcacggctctggcagtgaatgggggtaaatggcactacaggcgccttttatggattcatgcaagga
aactaccataatacaagaaaagcccgtcacgggcttctcagggcgtttatggcgggtctgctatgtggtgctatctga
cttttgctgttcagcagttcctgccctctgatttccagtctgaccacttcggattatcccgtgacaggtcattcagactggc
taatgcacccagtaaggcagcggtatcatcaacaggcttaccgtcttactgtcgggaattcatttaaatagtcaaaagcc
tccgaccggaggcttttgactgctaggcgatctgtgctgtttgccacggtatgcagcaccagcgcgagattatgggctc
gcacgctcgactgtcggacgggggcactggaacgagaagtcaggcgagccgtcacgcccttgacaatgccacatcc
tgagcaaataattcaaccactaaacaaatcaaccgcgtttcccggaggtaaccaagcttgcgggagagaatgatgaac
aagagccaacaagttcagacaatcaccctggccgccgcccagcaaatggcggcggcggtgaaaaaaaagccact
gagatcaacgtggcggtggtgttttccgtagttgaccgcggaggcaacacgctgcttatccagcggatggacgaggcc
ttcgtctccagctgcgatatttccctgaataaagcctggagcgcctgcagcctgaagcaaggtacccatgaaattacgtc
agcggtccagccaggacaatctctgtacggtctgcagctaaccaaccaacagcgaattattattttttggcggcggcctg
ccagttatttttaatgagcaggtaattggcgccgtcggcgttagcggcggtacggtcgagcaggatcaattattagccca
gtgcgccctggattgttttccgcattataacctgaagcgagaaggtatattatgagctatcgtatgttccgccaggcattct
gagtgttaacgaggggaccgtcatgtcgctttcaccgccaggcgtacgcctgtttacgatccgcgcgggcaccatgc
cggcgccatcaatgagctgtgctgggggctggaggagcagggggtcccctgccagaccataacctatgacggaggc
ggtgacgccgctgcgctgggcgccctggcggccagaagctcgcccctgcgggtgggtatcgggctcagcgcgtcc
ggcgagatagccctcactcatgcccagctgccggcggacgcgccgctggctaccggacacgtcaccgatagcgacg
atcaactgcgtacgctcggcgccaacgccgggcagctggttaaagtcctgccgttaagtgagagaaactgaactggc
ctagcaaacacagaaaaaagcccgcacctgacagtgcgggcttttttttcctaggcgatctgtgctgtttgccacggtat
gcagcaccagcgcgagattatgggctcgcacgctcgactgtcggacgggggcactggaacgagaagtcaggcgag
ccgtcacgcccttgacaatgccacatcctgagcaaataattcaaccactaaacaaatcaaccgcgtttcccggaggtaa
ccaagcttcaccttttgagccgatgaacaatgaaaagatcaaaacgatttgcagtactggcccagcgccccgtcaatca
ggacgggctgattggcgagtggcctgaagaggggctgatcgccatg

Figure 184D gacagccccttttgacccggtctcttcagtaaaagtggacaacggtctgatcgtcgaactggacggcaaacgccgggacc
agtttgacatgatcgaccgatttatcgccgattacgcgatcaacgttgagcgcacagagcaggcaatgcgcctggaggc
ggtggaaatagcccgtatgctggtggatattcacgtcagccgggaggagatcattgccatcactaccgccatcacgccg
gccaaagcggtcgaggtgatggcgcagatgaacgtggtggagatgatgatggcgctgcagaagatgcgtgcccgccg
gaccccctccaaccagtgccacgtcaccaatctcaaagataatccggtgcagattgccgctgacgccgccgaggccgg
gatccgcggcttctcagaacaggagaccacggtcggtatcgcgcgctacgcgccgtttaacgccctggcgctgttggtc
ggttcgcagtgcggccgccccggcgtgttgacgcagtgctcggtggaagaggccaccgagctggagctgggcatgcg
tggcttaaccagctacgccgagacggtgtcggtctacggcaccgaagcggtatttaccgacggcgatgatacgccgtgg
tcaaaggcgttcctcgcctcggcctacgcctcccgcgggttgaaaatgcgctacacctccggcaccggatccgaagcg
ctgatgggctattcggagagcaagtcgatgctctacctcgaatcgcgctgcatcttcattactaaaggcgccggggttcag
ggactgcaaaacggcgcggtgagctgtatcggcatgaccggcgctgtgccgtcgggcattcgggcggtgctggcgga
aaacctgatcgcctctatgctcgacctcgaagtggcgtccgccaacgaccagactttctcccactcggatattcgccgcac
cgcgcgcaccctgatgcagatgctgccgggcaccgactttatttttctccggctacagcgcggtgccgaactacgacaac
atgttcgccggctcgaacttcgatgcggaagattttgatgattacaacatcctgcagcgtgacctgatggttgacggcggc
ctgcgtccggtgaccgaggcggaaaccattgccattcgccagaaagcggcgcgggcgatccaggcggttttccgcga
gctggggctgccgccaatcgccgacgaggaggtggaggccgccacctacgcgcacggcagcaacgagatgccgcc
gcgtaacgtggtggaggatctgagtgcggtggaagagatgatgaagcgcaacatcaccggcctcgatattgtcggcgc
gctgagccgcagcggctttgaggatatcgccagcaatattctcaatatgctgcgccagcgggtcaccggcgattacctgc
agacctcggccattctcgatcggcagttcgaggtggtgagtgcggtcaacgacatcaatgactatcaggggccgggcac
cggctatcgcatctctgccgaacgctgggcggagatcaaaaatattccgggcgtggttcagcccgacaccattgaataa
ggcggtattcctgtgcaacagacaacccaaattcagccctctttaccctgaaaacccgcgagggcggggtagcttctgc
cgatgaacgcgccgatgaagtggtgatcggcgtcggccctgccttcgataaacaccagcatcacactctgatcgatatgc
cccatggcgcgatcctcaaagagctgattgccggggtggaagaagaggggcttcacgcccgggtggtgcgcattctgc
gcacgtccgacgtctcctttatggcctgggatgcggccaacctgagcggctcggggatcggcatcggtatccagtcgaa
ggggaccacggtcatccatcagcgcgatctgctgccgctcagcaacctggagctgttctcccaggcgccgctgctgac
gctggagacctaccggcagattggcaaaaacgctgcgcgctatgcgcgcaaagagtcaccttcgccggtgccggtggt
gaacgatcagatggtgcggccgaaatttatggccaaagccgcgctatttcatatcaaagagaccaaacatgtggtgcag
gacgccgagcccgtcaccctgcacatcgacttagtaagggagtgaccatgagcgagaaaaccatgcgcgtgcaggatt
atccgttagccacccgctgcccggagcatatcctgacgcctaccggcaaaccattgaccgatattaccctcgagaaggtg
ctctctggcgaggtgggcccgcaggatgtgcggatctcccgccagacccttgagtaccaggcgcagattgccgagcag
atgcagcgccatgcggtggcgcgcaatttccgccgcgcggcggagcttatcgccattcctgacgagcgcattctggcta
tctataacgcgctgcgcccgttccgctcctcgcaggcggagctgctggcgatcgccgacgagctggagcacacctggc
atgcgacagtgaatgccgcctttgtccgggagtcggcggaagtgtatcagcagcggcataagctgcgtaaaggaagcta
agcggaggtcagcatgccgttaatagccgggattgatatcggcaacgccaccaccgaggtggcgctggcgtccgacta
cccgcaggcgagggcgtttgttgccagcgggatcgtcgcgacgacgggcatgaaagggacgcgggac

Figure 184E aatatcgccgggacccctcgccgcgctggagcaggccctggcgaaaacaccgtggtcgatgagcgatgtctctcgcat
ctatcttaacgaagccgcgccggtgattggcgatgtggcgatggagaccatcaccgagaccattatcaccgaatcgac
catgatcggtcataacccgcagacgccgggcggggtgggcgttggcgtggggacgactatcgccctcgggcggctg
gcgacgctgccggcggcgcagtatgccgaggggtggatcgtactgattgacgacgccgtcgatttccttgacgccgtg
tggtggctcaatgaggcgctcgaccggggatcaacgtggtggcggcgatcctcaaaaaggacgacggcgtgctgg
tgaacaaccgcctgcgtaaaaccctgccggtggtggatgaagtgacgctgctggagcaggtccccgaggggtaatg
gcggcggtggaagtggccgcgccgggccaggtggtgcggatcctgtcgaatccctacgggatcgccaccttcttcgg
gctaagcccggaagagacccaggccatcgtccccatcgcccgcgcccctgattggcaaccgttccgcggtggtgctca
agaccccgcaggggatgtgcagtcgcgggtgatcccggcgggcaacctctacattagcggcgaaaagcgccgcg
gagaggccgatgtcgccgagggcgcggaagccatcatgcaggcgatgagcgcctgcgctccggtacgcgacatcc
gcggcgaaccgggcacccacgccggcggcatgcttgagcgggtgcgcaaggtaatggcgtccctgaccggccatg
agatgagcgcgatatacatccaggatctgctggcggtggatacgtttattccgcgcaaggtgcagggcgggatggccg
gcgagtgcgccatggagaatgccgtcgggatggcggcgatggtgaaagcggatcgtctgcaaatgcaggttatcgcc
cgcgaactgagcgcccgactgcagaccgaggtggtggtgggcggcgtggaggccaacatggccatcgccggggc
gttaaccactcccggctgtgcggcgccgctggcgatcctcgacctcggcgccggctcgacggatgcggcgatcgtca
acgcggaggggcagataacggcggtccatctcgccggggcggggaatatggtcagcctgttgattaaaaccgagct
gggcctcgaggatctttcgctggcggaagcgataaaaaaaatacccgctggccaaagtggaaagcctgttcagtattcgt
cacgagaatggcgcggtggagttctttcgggaagccctcagcccggcggtgttcgccaaagtggtgtacatcaagga
gggcgaactggtgccgatcgataacgccagcccgctggaaaaaattcgtctcgtgcgccggcaggcgaaagagaaa
gtgtttgtcaccaactgcctgcgcgcgctgcgccaggtctcacccggcggttccattcgcgatatcgcctttgtggtgct
ggtgggcggctcatcgctggactttgagatcccgcagcttatcacggaagccttgtcgcactatggcgtggtcgccgg
gcagggcaatattcggggaacagaagggccgcgcaatgcggtcgccacccgggctgctactggccggtcaggcgaa
ttaaacgggcgctcgcgccagcctctaggtacaaataaaaaaggcacgtcagatgacgtgccttttttcttgtctagcgt
gcaccaatgcttctggcgtcaggcagccatcggaagctgtggtatggctgtgcaggtcgtaaatcactgcataattcgtg
tcgctcaaggcgcactcccgttctggataatgttttttgcgccgacatcataacggttctggcaaatattctgaaatgagct
gttgacaattaatcatccggctcgtataatgtgtggaattgtgagcggataacaatttcacacaggaaacagaccatgact
agtaaggaggacaattccatggctgctgctgctgatagattaaacttaacttccggccacttgaatgctggtagaaagag
aagttcctcttctgtttctttgaaggctgccgaaaagcctttcaaggttactgtgattggatctggtaactggggtactactat
tgccaaggtggttgccgaaaattgtaagggatacccagaagttttcgctccaatagtacaaatgtgggtgttcgaagaag
agatcaatggtgaaaaattgactgaaatcataaatactagacatcaaaacgtgaaatacttgcctggcatcactctacccg
acaatttggttgctaatccagacttgattgattcagtcaaggatgtcgacatcatcgttttcaacattccacatcaatttttgcc
ccgtatctgtagccaattgaaaggtcatgttgattcacacgtcagagctatctcctgtctaaagggttttgaagttggtgcta
aaggtgtccaattgctatcctcttacatcactgaggaactaggtattcaatgtggtgctctatctggtgctaacattgccacc
gaagtcgctcaagaacactggtctgaaacaacagttgcttaccacattccaaaggatttcagaggcgagggcaaggac
gtcgaccataaggttctaaagg

Figure 184F ccttgttccacagaccttacttccacgttagtgtcatcgaagatgttgctggtatctccatctgtggtgctttgaagaacgttgt
tgccttaggttgtggtttcgtcgaaggtctaggctggggtaacaacgcttctgctgccatccaaagagtcggtttgggtgag
atcatcagattcggtcaaatgttttcccagaatctagagaagaaacatactaccaagagtctgctggtgttgctgatttgatc
accacctgcgctggtggtagaaacgtcaaggttgctaggctaatggctacttctggtaaggacgcctgggaatgtgaaaa
ggagttgttgaatggccaatccgctcaaggtttaattacctgcaaagaagttcacgaatggttggaaacatgtggctctgtc
gaagacttcccattatttgaagccgtataccaaatcgtttacaacaactacccaatgaagaacctgccggacatgattgaag
aattagatctacatgaagattagatttattggatccaggaaacagactagaattatgggattgactactaaacctctatctttg
aaagttaacgccgctttgttcgacgtcgacggtaccattatcatctctcaaccagccattgctgcattctggagggatttcgg
taaggacaaaccttatttcgatgctgaacacgttatccaagtctcgcatggttggagaacgtttgatgccattgctaagttcg
ctccagactttgccaatgaagagtatgttaacaaattagaagctgaaattccggtcaagtacggtgaaaaatccattgaagt
cccaggtgcagttaagctgtgcaacgctttgaacgctctaccaaaagagaaatgggctgtggcaacttccggtacccgtg
atatggcacaaaaatggttcgagcatctgggaatcaggagaccaaagtacttcattaccgctaatgatgtcaaacagggta
agcctcatccagaaccatatctgaagggcaggaatggcttaggatatccgatcaatgagcaagacccttccaaatctaag
gtagtagtatttgaagacgctccagcaggtattgccgccggaaaagccgccggttgtaagatcattggtattgccactactt
tcgacttggacttcctaaaggaaaaaggctgtgacatcattgtcaaaaaccacgaatccatcagagttggcggctacaatg
ccgaaacagacgaagttgaattcatttttgacgactacttatatgctaaggacgatctgttgaaatggtaacccgggctgca
ggcatgcaagcttggctgttttggcggatgagagaagattttcagcctgatacagattaaatcagaacgcagaagcggtct
gataaaacagaatttgcctggcggcagtagcgcggtggtcccacctgaccccatgccgaactcagaagtgaaacgccg
tagcgccgatggtagtgtggggtctccccatgcgagagtagggaactgccaggcatcaaataaaacgaaaggctcagt
cgaaagactgggcctttcgttttatctgttgtttgtcggtgaacgctctcctgagtaggacaaatccgccgggagcggattt
gaacgttgcgaagcaacggcccggagggtggcgggcaggacgcccgccataaactgccaggcatcaaattaagcag
aaggccatcctgacggatggcctttttgcgtttctacaaactccagctggatcgggcg (SEQ ID NO:162)

Figure 185B ctagagtatacatttaaatggtaccctctagtcaaggccttaagtgagtcgtattacggactggccgtcgttttacaacgt
cgtgactgggaaaaccctggcgttacccaacttaatcgccttgcagcacatccccctttcgccagctggcgtaatagc
gaagaggcccgcaccgatcgcccttcccaacagttgcgcagcctgaatggcgaatggcgcctgatgcggtattttct
ccttacgcatctgtgcggtatttcacaccgcatatggtgcactctcagtacaatctgctctgatgccgcatagttaagcca
gccccgacacccgccaacacccgctgacgagcttagtaaagccctcgctagattttaatgcggatgttgcgattacttc
gccaactattgcgataacaagaaaaagccagcctttcatgatatatctcccaatttgtgtagggcttattatgcacgctta
aaaataataaaagcagacttgacctgatagtttggctgtgagcaattatgtgcttagtgcatctaacgcttgagttaagcc
gcgccgcgaagcggcgtcggcttgaacgaattgttagacattatttgccgactaccttggtgatctcgcctttcacgta
gtggacaaattcttccaactgatctgcgcgcgaggccaagcgatcttcttcttgtccaagataagcctgtctagcttcaa
gtatgacgggctgatactgggccggcaggcgctccattgcccagtcggcagcgacatccttcggcgcgattttgccg
gttactgcgctgtaccaaatgcgggacaacgtaagcactacatttcgctcatcgccagcccagtcgggcggcgagtt
ccatagcgttaaggtttcatttagcgcctcaaatagatcctgttcaggaaccggatcaaagagttcctccgccgctgga
cctaccaaggcaacgctatgttctcttgcttttgtcagcaagatagccagatcaatgtcgatcgtggctggctcgaagat
acctgcaagaatgtcattgcgctgccattctccaaattgcagttcgcgcttagctggataacgccacggaatgatgtcg
tcgtgcacaacaatggtgacttctacagcgcggagaatctcgctctctccaggggaagccgaagtttccaaaaggtc
gttgatcaaagctcgccgcgttgtttcatcaagccttacggtcaccgtaaccagcaaatcaatatcactgtgtggcttca
ggccgccatccactgcggagccgtacaaatgtacggccagcaacgtcggttcgagatggcgctcgatgacgccaa
ctacctctgatagttgagtcgatacttcggcgatcaccgcttccctcatgatgtttaactttgttttagggcgactgccctg
ctgcgtaacatcgttgctgctccataacatcaaacatcgacccacggcgtaacgcgcttgctgcttggatgcccgagg
catagactgtaccccaaaaaaacagtcataacaagccatgaaaaccgccactgcgccgttaccaccgctgcgttcgg
tcaaggttctggaccagttgcgtgagcgcatacgctacttgcattacagcttacgaaccgaacaggcttatgtccactg
ggttcgtgccttcatccgtttccacggtgtgcgtcacccggcaaccttgggcagcagcgaagtcgaggcatttctgtcc
tggctggcgaacgagcgcaaggtttcggtctccacgcatcgtcaggcattggcggccttgctgttcttctacggcaag
gtgctgtgcacggatctgccctggcttcaggagatcggaagacctcggccgtcgcggcgcttgccggtggtgctga
ccccggatgaagtggttcgcatcctcggttttctggaaggcgagcatcgtttgttcgcccagcttctgtatggaacggg
catgcggatcagtgagggtttgcaactgcgggtcaaggatctggatttcgatcacggcacgatcatcgtgcgggagg
gcaagggctccaaggatcgggccttgatgttacccgagagcttggcacccagcctgcgcgagcaggggaattaatt
cccacgggttttgctgccgcaaacgggctgttctggtgttgctagtttgttatcagaatcgcagatccggcttcagccg
gtttgccggctgaaagcgctatttcttccagaattgccatgattttttccccacgggaggcgtcactggctcccgtgttgt
cggcagctttgattcgataagcagcatcgcctgtttcaggctgtctatgtgtgactgttgagctgtaacaagttgtctcag
gtgttcaatttcatgttctagttgctttgttttactggttcacctgttctattaggtgttacatgctgttcatctgttacattgtcg
atctgttcatggtgaacagctttgaatgcaccaaaaactcgtaaaagctc

Figure 185C tgatgtatctatctttttacaccgttttcatctgtgcatatggacagttttcccttgatatgtaacggtgaacagttgttctac
ttttgtttgttagtcttgatgcttcactgatagatacaagagccataagaacctcagatccttccgtatttagccagtatgttc
tctagtgtggttcgttgttttgcgtgagccatgagaacgaaccattgagatcatacttactttgcatgtcactcaaaaattt
tgcctcaaaactggtgagctgaattttgcagttaaagcatcgtgtagtgttttcttagtccgttatgtaggtaggaatctg
atgtaatggttgttggtattttgtcaccattcattttatctggttgttctcaagttcggttacgagatccatttgtctatctagtt
caacttggaaaatcaacgtatcagtcgggcggcctcgcttatcaaccaccaatttcatattgctgtaagtgtttaaatcttt
acttattggtttcaaaacccattggttaagccttttaaactcatggtagttattttcaagcattaacatgaacttaaattcatca
aggctaatctctatatttgccttgtgagttttcttttgtgttagttcttttaataaccactcataaatcctcatagagtatttgtttt
caaaagacttaacatgttccagattatattttatgaattttttaactggaaaagataaggcaatatctcttcactaaaaacta
attctaattttcgcttgagaacttggcatagtttgtccactggaaaatctcaaagcctttaaccaaaggattcctgatttcc
acagttctcgtcatcagctctctggttgctttagctaatacaccataagcattttccctactgatgttcatcatctgagcgta
ttggttataagtgaacgataccgtccgttctttccttgtagggttttcaatcgtggggttgagtagtgccacacagcataa
aattagcttggtttcatgctccgttaagtcatagcgactaatcgctagttcatttgctttgaaaacaactaattcagacatac
atctcaattggtctaggtgatttaatcactataccaattgagatgggctagtcaatgataattactagtcccttttcctttgag
ttgtgggtatctgtaaattctgctagacctttgctggaaaacttgtaaattctgctagaccctctgtaaattccgctagacct
ttgtgtgttttttttgtttatattcaagtggttataatttatagaataaagaaagaataaaaaaagataaaaagaatagatccc
agccctgtgtataactcactactttagtcagttccgcagtattacaaaaggatgtcgcaaacgctgtttgctcctctacaa
aacagaccttaaaaccctaaaggcttaagtagcaccctcgcaagctcgggcaaatcgctgaatattcctttgtctccg
accatcaggcacctgagtcgctgtcttttcgtgacattcagttcgctgcgctcacggctctggcagtgaatgggggta
aatggcactacaggcgccttttatggattcatgcaaggaaactacccataatacaagaaaagcccgtcacgggcttct
cagggcgtttatggcgggtctgctatgtggtgctatctgactttttgctgttcagcagttcctgccctctgattttccagtct
gaccacttcggattatcccgtgacaggtcattcagactggctaatgcacccagtaaggcagcggtatcatcaacaggc
ttacccgtcttactgtcgggaattcatttaaatagtcaaaagcctccgaccggaggcttttgactgctaggcgatctgtgc
tgtttgccacggtatgcagcaccagcgcgagattatgggctcgcacgctcgactgtcggacgggggcactggaacg
agaagtcaggcgagccgtcacgcccttgacaatgccacatcctgagcaaataattcaaccactaaacaaatcaaccg
cgtttccggaggtaaccaagcttgcgggagagaatgatgaacaagagccaacaagttcagacaatcaccctggcc
gccgcccagcaaatggcggcggcggtggaaaaaaagccactgagatcaacgtggcggtggtgttttccgtagttg
accgcggaggcaacacgctgcttatccagcggatggacgaggccttcgtctccagctgcgatatttccctgaataaa
gcctggagcgcctgcagcctgaagcaaggtacccatgaaattacgtcagcggtccagccaggacaatctctgtacg
gtctgcagctaaccaaccaacagcgaattattattttttggcggcggcctgccagttattttaatgagcaggtaattggc
gccgtcggcgttagcggcggtacggtcgagcaggatcaattattagcccagtgcgccctggattgttttccgcattat
aacctgaagcgagaaggtatattatgagctatcgtatgttccgccaggcattctgagtgttaacgaggggaccgtcatg
tcgctttcaccgccaggcgtacgcctgttttacgatccgcgcgggcaccatgccggcgccatcaatgagctgtgctg
ggggctggaggagcaggggtcccctgccagaccataacctatgacggaggcggtgacgccgctgcgctgggc
gccctggcggccagaagctcgccccctgcgggtgggtatcgggctcagcgcgtccggcgagatagc

Figure 185D cctcactcatgcccagctgccggcggacgcgccgctggctaccggacacgtcaccgatagcgacgatcaactgc
gtacgctcggcgccaacgccgggcagctggttaaagtcctgccgttaagtgagagaaactgaactggcctagcaa
acacagaaaaagcccgcacctgacagtgcgggcttttttttttcctaggcgatctgtgctgtttgccacggtatgcag
caccagcgcgagattatgggctcgcacgctcgactgtcggacggggcactggaacgagaagtcaggcgagcc
gtcacgcccttgacaatgccacatcctgagcaaataattcaaccactaaacaaatcaaccgcgtttcccggaggtaa
ccaagcttcaccttttgagccgatgaacaatgaaaagatcaaaacgatttgcagtactggcccagcgcccgtcaat
caggacgggctgattggcgagtggcctgaagaggggctgatcgccatggacagcccctttgacccggtctcttca
gtaaaagtggacaacggtctgatcgtcgaactggacggcaaacgccgggaccagtttgacatgatcgaccgattta
tcgccgattacgcgatcaacgttgagcgcacagagcaggcaatgcgcctggaggcggtggaaatagcccgtatg
ctggtggatattcacgtcagccgggaggagatcattgccatcactaccgccatcacgccggccaaagcggtcgag
gtgatggcgcagatgaacgtggtggagatgatgatggcgctgcagaagatgcgtgcccgccggaccccctccaa
ccagtgccacgtcaccaatctcaaagataatccggtgcagattgccgctgacgccgccgaggccgggatccgcg
gcttctcagaacaggagaccacggtcggtatcgcgcgctacgcgccgtttaacgccctggcgctgttggtcggttc
gcagtgcggccgccccggcgtgttgacgcagtgctcggtggaagaggccaccgagctggagctgggcatgcgt
ggcttaaccagctacgccgagacggtgtcggtcacggcaccgaagcggtatttaccgacggcgatgatacgccg
tggtcaaaggcgttcctcgcctcggcctacgcctcccgcgggttgaaaatgcgctacacctccggcaccggatcc
gaagcgctgatggctattcggagagcaagtcgatgctctacctcgaatcgcgctgcatcttcattactaaaggcgc
cggggttcagggactgcaaaacggcgcggtgagctgtatcggcatgaccggcgctgtgccgtcgggcattcggg
cggtgctggcggaaaacctgatcgcctctatgctcgacctcgaagtggcgtccgccaacgaccagactttctccca
ctcggatattcgccgcaccgcgcgcaccctgatgcagatgctgccgggcaccgactttattttctccggctacagcg
cggtgccgaactacgacaacatgttcgccggctcgaacttcgatgcggaagattttgatgattacaacatcctgcag
cgtgacctgatggttgacggcggcctgcgtccggtgaccgaggcggaaaccattgccattcgccagaaagcggc
gcgggcgatccaggcggttttccgcgagctggggctgccgccaatcgccgacgaggaggtggaggccgccacc
tacgcgcacggcagcaacgagatgccgccgcgtaacgtggtggaggatctgagtgcggtggaagagatgatga
agcgcaacatcaccggcctcgatattgtcggcgcgctgagccgcagcggctttgaggatatcgccagcaatattct
caatatgctgcgccagcgggtcaccggcgattacctgcagacctcggccattttcgatcggcagttcgaggtggtg
agtgcggtcaacgacatcaatgactatcaggggccgggcaccggctatcgcatctctgccgaacgctgggcgga
gatcaaaaatattccgggcgtggttcagcccgacaccattgaacaaggcggtattcctgtgcaacagacaacccaa
attcagccctcttttaccctgaaaacccgcgagggcggggtagcttctgccgatgaacgcgccgatgaagtggtga
tcggcgtcggccctgccttcgataaacaccagcatcacactctgatcgatatgccccatggcgcgatcctcaaaga
gctgattgccggggtggaagaagaggggcttcacgcccgggtggtgcgcattctgcgcacgtccgacgtctcctt
atggcctgggatgcggccaacctgagcggctcggggatcggcatcggtatccagtcgaaggggaccacggtcat
ccatcagcgcgatctgctgccgctcagcaacctggagctgttctcccaggcgccgctgctgacgctggagaccta
ccggcagattggcaaaaacgctgcgcgctatgcgcgcaaagagtcaccttcgccggtgccggtggtgaacgatc
agatggtgcggccgaaatttatggccaaagccgcgctatttcatatcaaagagaccaaacatgtggtgcaggacgc
cgagcccgtcaccctgcacatcgacttagtaaggg

Figure 185E agtgaccatgagcgagaaaaccatgcgcgtgcaggattatccgttagccacccgctgcccggagcatatcctgacg
cctaccggcaaaccattgaccgatattaccctcgagaaggtgctctctggcgaggtgggcccgcaggatgtgcggat
ctcccgccagacccttgagtaccaggcgcagattgccgagcagatgcagcgccatgcggtggcgcgcaatttccgc
cgcgcggcggagcttatcgccattcctgacgagcgcattctggctatctataacgcgctgcgcccgttccgctcctcg
caggcggagctgctggcgatcgccgacgagctggagcacacctggcatgcgacagtgaatgccgcctttgtccgg
gagtcggcggaagtgtatcagcagcggcataagctgcgtaaaggaagctaagcggaggtcagcatgccgttaatag
ccgggattgatatcggcaacgccaccaccgaggtggcgctggcgtccgactacccgcaggcgagggcgtttgttgc
cagcgggatcgtcgcgacgacgggcatgaaagggacgcgggacaatatcgccgggaccctcgccgcgctggag
caggccctggcgaaaacaccgtggtcgatgagcgatgtctctcgcatctatcttaacgaagccgcgccggtgattgg
cgatgtggcgatggagaccatcaccgagaccattataccgaatcgaccatgatcggtcataacccgcagacgccg
ggcggggtgggcgttggcgtggggacgactatcgccctcgggcggctggcgacgctgccggcggcgcagtatgc
cgaggggtggatcgtactgattgacgacgccgtcgatttccttgacgccgtgtggtggctcaatgaggcgctcgacc
gggggatcaacgtggtggcggcgatcctcaaaaaggacgacggcgtgctggtgaacaaccgcctgcgtaaaaccc
tgccggtggtggatgaagtgacgctgctggagcaggtccccgagggggtaatggcggcggtggaagtggccgcg
ccgggccaggtggtgcggatcctgtcgaatccctacgggatcgccaccttcttcgggctaagcccggaagagaccc
aggccatcgtccccatcgcccgcgccctgattggcaaccgttccgcggtggtgctcaagaccccgcaggggatgt
gcagtcgcgggtgatcccggcgggcaacctctacattagcggcgaaaagcgccgcggagaggccgatgtcgccg
agggcgcggaagccatcatgcaggcgatgagcgcctgcgctccggtacgcgacatccgcggcgaaccgggcac
ccacgccggcggcatgcttgagcgggtgcgcaaggtaatggcgtccctgaccggccatgagatgagcgcgatata
catccaggatctgctggcggtggatacgttattccgcgcaaggtgcagggcgggatggccggcgagtgcgccatg
gagaatgccgtcgggatggcggcgatggtgaaagcggatcgtctgcaaatgcaggttatcgcccgcgaactgagc
gcccgactgcagaccgaggtggtggtgggcggcgtggaggccaacatggccatcgccggggcgttaaccactcc
cggctgtgcggcgccgctggcgatcctcgacctcggcgccggctcgacggatgcggcgatcgtcaacgcggagg
ggcagataacggcggtccatctcgccggggcggggaatatggtcagcctgttgattaaaaaccgagctgggcctcga
ggatctttcgctggcggaagcgataaaaaaatacccgctggccaaagtggaaagcctgttcagtattcgtcacgaga
atggcgcggtggagttctttcgggaagccctcagcccggcggtgttcgccaaagtggtgtacatcaaggagggcga
actggtgccgatcgataacgccagcccgctggaaaaaattcgtctcgtgcgccggcaggcgaaagagaaagtgttt
gtcaccaactgcctgcgcgcgctgcgccaggtctcacccggcggttccattcgcgatatcgcctttgtggtgctggtg
ggcggctcatcgctggactttgagatcccgcagcttatcacggaagccttgtcgcactatgcgtggtcgccgggca
gggcaatattcggggaacagaagggccgcgcaatgcggtcgccaccgggctgctactggccggtcaggcgaatta
aacgggcgctcgcgccagcctctaggtacaaataaaaaggcacgtcagatgacgtgccttttttcttgtctagcgtgc
accaatgcttctggcgtcaggcagccatcggaagctgtggtatggctgtgcaggtcgtaaatcactgcataattcgtgt
cgctcaaggcgcactcccgttctggataatgttttttgcgccgacatcataacggttctggcaaatattctgaaatgagct
gttgacaattaatcatccggctcgtataatgtgtggaattgtgagcggataacaatttc

Figure 185F acacaggaaacagaccatgactagtaaggaggacaattccatggctgctgctgctgatagattaaacttaacttccgg
ccacttgaatgctggtagaaagagaagttcctcttctgtttctttgaaggctgccgaaaagcctttcaaggttactgtgatt
ggatctggtaactggggtactactattgccaaggtggttgccgaaaattgtaagggatacccagaagttttcgctccaa
tagtacaaatgtgggtgttcgaagaagagatcaatggtgaaaaattgactgaaatcataaatactagacatcaaaacgt
gaaatacttgcctggcatcactctacccgacaatttggttgctaatccagacttgattgattcagtcaaggatgtcgacat
catcgttttcaacattccacatcaattttttgccccgtatctgtagccaattgaaaggtcatgttgattcacacgtcagagct
atctcctgtctaaagggttttgaagttggtgctaaaggtgtccaattgctatcctcttacatcactgaggaactaggtattc
aatgtggtgctctatctggtgctaacattgccaccgaagtcgctcaagaacactggtctgaaacaacagttgcttacca
cattccaaaggatttcagaggcgagggcaaggacgtcgaccataaggttctaaaggccttgttccacagaccttactt
ccacgttagtgtcatcgaagatgttgctggtatctccatctgtggtgctttgaagaacgttgttgccttaggttgtggtttcg
tcgaaggtctaggctggggtaacaacgcttctgctgccatccaaagagtcggtttgggtgagatcatcagattcggtc
aaatgtttttcccagaatctagagaagaaacatactaccaagagtctgctggtgttgctgatttgatcaccacctgcgct
ggtggtagaaacgtcaaggttgctaggctaatggctacttctggtaaggacgcctgggaatgtgaaaaggagttgttg
aatggccaatccgctcaaggtttaattacctgcaaagaagttcacgaatggttggaaacatgtggctctgtcgaagact
tcccattatttgaagccgtataccaaatcgtttacaacaactacccaatgaagaacctgccggacatgattgaagaatta
gatctacatgaagattagatttattggatccaggaaacagactagaattatgggattgactactaaacctctatctttgaa
agttaacgccgctttgttcgacgtcgacggtaccattatcatctctcaaccagccattgctgcattctggagggatttcgg
taaggacaaaccttatttcgatgctgaacacgttatccaagtctcgcatggttggagaacgtttgatgccattgctaagtt
cgctccagactttgccaatgaagagtatgttaacaaattagaagctgaaattccggtcaagtacggtgaaaaatccatt
gaagtcccaggtgcagttaagctgtgcaacgctttgaacgctctaccaaaagagaaatgggctgtggcaacttccggt
acccgtgatatggcacaaaaatggttcgagcatctgggaatcaggagaccaaagtacttcattaccgctaatgatgtc
aaacagggtaagcctcatccagaaccatatctgaagggcaggaatggcttaggatatccgatcaatgagcaagacc
cttccaaatctaaggtagtagtatttgaagacgctccagcaggtattgccgccggaaaagccgccggttgtaagatcat
tggtattgccactactttcgacttggacttcctaaaggaaaaaggctgtgacatcattgtcaaaaaccacgaatccatca
gagttggcggctacaatgccgaaacagacgaagttgaattcatttttgacgactacttatatgctaaggacgatctgttg
aaatggtaacccgggctgcaggcatgcaagcttggctgttttggcggatgagagaagattttcagcctgatacagatt
aaatcagaacgcagaagcggtctgataaaacagaatttgcctggcggcagtagcgcggtggtcccacctgaccccca
tgccgaactcagaagtgaaacgccgtagcgccgatggtagtgtggggtctccccatgcgagagtagggaactgcca
ggcatcaaataaaacgaaaggctcagtcgaaagactgggcctttcgttttatctgttgtttgtcggtgaacgctctcctg
agtaggacaaatccgccgggagcggatttgaacgttgcgaagcaacggcccggagggtggcgggcaggacgcc
cgccataaactgccaggcatcaaattaagcagaaggccatcctgacggatggcctttttgcgtttctacaaactccagc
tggatcgggcg (SEQ ID NO:163)

METHODS OF PRODUCING ISOPRENE AND A CO-PRODUCT

CROSS-REFERENCE TO RELATED APPLICATIONS

This application is a divisional of U.S. patent application Ser. No. 12/650,332, filed Dec. 30, 2009, now U.S. Pat. No. 8,895,288, which claims priority to U.S. Provisional Patent Application No. 61/141,652, filed Dec. 30, 2008, and to U.S. Provisional Patent Application No. 61/187,934, filed Jun. 17, 2009, the disclosures of which are incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 643842001310_Sequence_Listing.txt, date recorded: Jan. 3, 2014, size: 488,111 bytes.)

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway (FIGS. 19A and 19B). However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

BRIEF SUMMARY OF THE INVENTION

The invention provides cells capable of co-producing isoprene and a co-product under oxygen-limited conditions, cells in oxygen-limited culture that co-produce isoprene and a co-product, methods of producing isoprene and a co-product, and compositions comprising isoprene and a co-product. In one aspect, provided herein are cells capable of co-producing isoprene and a co-product selected from the group consisting of ethanol, 1,3-propanediol, and hydrogen under oxygen-limited conditions, comprising a heterologous nucleic acid encoding an isoprene synthase polypeptide, wherein the cells (i) have an average volumetric productivity of isoprene greater than about 0.1 mg/L$_{broth}$/hr and an average volumetric productivity of the co-product greater than about 0.1 mg/L$_{broth}$/hr; or (ii) produce isoprene at a rate between about 400 nmole/g$_{wcm}$/hr to about 2.0×10$^5$ nmole/g$_{wcm}$/hr and produce the co-product at a rate between about 0.01 mmol/L$_{broth}$/hr and about 200 mmol/L$_{broth}$/hr. In some embodiments, the cells are grown in oxygen limited culture. In some embodiments, the heterologous nucleic acid encoding an isoprene synthase polypeptide is operably linked to a promoter. In some embodiments, the isoprene synthase polypeptide is a plant isoprene synthase polypeptide. In some embodiments, the plant isoprene synthase polypeptide is from *Populus alba*. In some embodiments, the cells further comprise a heterologous nucleic acid encoding an MVA pathway polypeptide, a DXS polypeptide, or an IDI polypeptide.

In some embodiments, the MVA pathway polypeptide is an upper MVA pathway polypeptide. In some embodiments, the MVA pathway polypeptide is a lower MVA pathway polypeptide. In some embodiments, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some embodiments, the upper MVA pathway polypeptide is from the genus *Enterococcus*. In some embodiments, the upper MVA pathway polypeptide is from *Enterococcus faecalis*. In some embodiments, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some embodiments, the lower MVA pathway polypeptide is an MVK polypeptide. In some embodiments, the MVK polypeptide is from the genus *Methanosarcina*. In some embodiments, the MVK polypeptide is from *Methanosarcina mazei*.

In some embodiments, the co-product is ethanol. In some embodiments, the cells further comprise a heterologous nucleic acid encoding a polypeptide involved in ethanol fermentation. In some embodiments, the polypeptide involved in ethanol fermentation is an alcohol dehydrogenase B (adhB) polypeptide, an alcohol dehydrogenase E (adhE) polypeptide, or a pyruvate decarboxylase (pdc) polypeptide. In some embodiments, the co-product is 1,3-propanediol. In some embodiments, the cells further comprise a heterologous nucleic acid encoding a polypeptide involved in the glycerol pathway or the 1,3-propanediol pathway. In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, orfY, 1,3-propanediol oxidoreductase (dhaT), glycerol dehydrogenase (dhaD), or dihydroxyacetone kinase (dhaK). In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, and orfY. In some embodiments, the co-product is hydrogen. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide.

In another aspect, provided herein are methods of co-producing isoprene and a co-product, the method comprising: (a) culturing cells capable of co-producing isoprene and a co-product selected from the group consisting of ethanol, 1,3-propanediol, and hydrogen under conditions suitable for the co-production of isoprene and the co-product, wherein the cells comprise a heterologous nucleic acid encoding an isoprene synthase polypeptide; and (b) co-producing isoprene and the co-product, wherein the cells (i) have an average volumetric productivity of isoprene greater than about 0.1 mg/$L_{broth}$/hr and an average volumetric productivity of the co-product greater than about 0.1 mg/$L_{broth}$/hr; or (ii) produce isoprene at a rate between about 400 nmole/$g_{wcm}$/hr to about $2.0 \times 10^5$ nmole/$g_{wcm}$/hr and produce the co-product at a rate between about 0.01 mmol/$L_{broth}$/hr and about 200 mmol/$L_{broth}$/hr. In some embodiments, the cells are grown in oxygen-limited culture. In some embodiments, the heterologous nucleic acid encoding an isoprene synthase polypeptide is operably linked to a promoter. In some embodiments, the isoprene synthase polypeptide is a plant isoprene synthase polypeptide. In some embodiments, the plant isoprene synthase polypeptide is from *Populus alba*. In some embodiments, the cells further comprise a heterologous nucleic acid encoding an MVA pathway polypeptide, a DXS polypeptide, or an IDI polypeptide.

In some embodiments, the MVA pathway polypeptide is an upper MVA pathway polypeptide. In some embodiments, the MVA pathway polypeptide is a lower MVA pathway polypeptide. In some embodiments, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some embodiments, the upper MVA pathway polypeptide is from the genus *Enterococcus*. In some embodiments, the upper MVA pathway polypeptide is from *Enterococcus faecalis*. In some embodiments, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some embodiments, the lower MVA pathway polypeptide is an MVK polypeptide. In some embodiments, the MVK polypeptide is from the genus *Methanosarcina*. In some embodiments, the MVK polypeptide is from *Methanosarcina mazei*.

In some embodiments, the co-product is ethanol. In some embodiments, the cells further comprise a heterologous nucleic acid encoding a polypeptide involved in ethanol fermentation. In some embodiments, the polypeptide involved in ethanol fermentation is an alcohol dehydrogenase B (adhB) polypeptide, an alcohol dehydrogenase E (adhE) polypeptide, or a pyruvate decarboxylase (pdc) polypeptide. In some embodiments, the co-product is 1,3-propanediol. In some embodiments, the cells further comprise a heterologous nucleic acid encoding a polypeptide involved in the glycerol pathway or the 1,3-propanediol pathway. In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, orfY, 1,3-propanediol oxidoreductase (dhaT), glycerol dehydrogenase (dhaD), or dihydroxyacetone kinase (dhaK). In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, and orfY. In some embodiments, the co-product is hydrogen. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide.

In another aspect, provided herein are cells in oxygen-limited culture that co-produce isoprene and hydrogen. In some embodiments, the invention provides cells in oxygen-limited culture that produce isoprene at a rate greater than about 400 nmole of isoprene per gram of wet cell mass per hour (nmole/$g_{wcm}$/hr) and produce hydrogen at a rate greater than about 125 nmole of hydrogen per gram of wet cell mass per hour (nmole/$g_{wcm}$/hr). In some embodiments, the cells comprise a heterologous nucleic acid that (i) encodes an isoprene synthase polypeptide and (ii) is operably linked to a promoter. In some embodiments, the cells produce isoprene at a rate between about 400 nmole/$g_{wcm}$/hr and about $2.0 \times 10^5$ nmole/$g_{wcm}$/hr, and hydrogen at a rate between about 125 nmole/$g_{wcm}$/hr and about $1.25 \times 10^4$ nmole/$g_{wcm}$/hr. In some embodiments, the cells are capable of co-producing isoprene and hydrogen under oxygen-limited conditions. In some embodiments, the isoprene synthase polypeptide is a plant isoprene synthase polypeptide. In some embodiments, the cells further comprise a heterologous nucleic acid encoding a mevalonic acid (MVA) pathway polypeptide, a 1-deoxyxylulose-5-phosphate synthase (DXS) polypeptide, or an isopentenyl-diphosphate delta-isomerase (IDI) polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In another aspect, provided herein are cells in oxygen-limited culture that co-produce isoprene and hydrogen, wherein the cells have an average volumetric productivity of isoprene greater than about 0.1 mg/$L_{broth}$/hr and an average volumetric productivity of hydrogen greater than about 0.005 mg/$L_{broth}$/hr. In some embodiments, the invention provides cells in oxygen-limited culture that have a peak volumetric productivity of isoprene greater than about 0.5 mg/$L_{broth}$/hr and a peak volumetric productivity of hydrogen greater than about 5 mg/$L_{broth}$/hr. In some embodiments, the cells are capable of co-producing isoprene and hydrogen under oxygen-limited conditions. In some embodiments, the cells comprise a heterologous nucleic acid that (i) encodes an isoprene synthase polypeptide and (ii) is operably linked to a promoter. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In another aspect, provided herein are cells in oxygen-limited culture that co-produce isoprene and hydrogen, wherein the cells convert more than about 0.002 molar percent of the carbon in a cell culture medium into isoprene, and produce hydrogen in an amount equivalent to more than about 0.024 molar percent of the carbon that the cells consume from a cell culture medium. In some embodiments, the cells are capable of co-producing isoprene and hydrogen under oxygen-limited conditions. In some embodiments, the cells comprise a heterologous nucleic acid that (i) encodes an isoprene synthase polypeptide and (ii) is operably linked to a promoter. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In another aspect, provided herein are cells in oxygen-limited culture that co-produce isoprene and hydrogen, wherein the cells produce isoprene and hydrogen in a ratio ranging from at least one molar percent of isoprene for every three molar percent of hydrogen to at least one molar percent of isoprene for every four molar percent of hydrogen. In some embodiments, the cells are capable of co-producing isoprene and hydrogen under oxygen-limited conditions. In some embodiments, the cells comprise a heterologous nucleic acid that (i) encodes an isoprene synthase polypeptide and (ii) is operably linked to a promoter. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In another aspect, provided herein are cells in oxygen-limited culture that co-produce isoprene and hydrogen, wherein the cells produce isoprene at a volumetric pressure greater than about $3.6 \times 10^{-6}$ atmospheres (equivalent to 10 µg/$L_{offgas}$) and produce hydrogen at a volumetric pressure greater than about $0.55 \times 10^{-6}$ atmospheres. In some embodiments, the cells produce isoprene at a volumetric pressure between about $3.6 \times 10^{-6}$ atmospheres and about 0.45 atmospheres. In some embodiments, the cells produce hydrogen at a volumetric pressure between about $0.55 \times 10^{-6}$ atmospheres and about $1.0 \times 10^{-2}$ atmospheres. In some embodiments, the cells are capable of co-producing isoprene and hydrogen under oxygen-limited conditions. In some embodiments, the cells comprise a heterologous nucleic acid that (i) encodes an isoprene synthase polypeptide and (ii) is operably linked to a promoter. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In another aspect, provided herein are cells in oxygen-limited culture that coproduce isoprene and hydrogen, comprising a heterologous nucleic acid encoding an isoprene synthase polypeptide, wherein the cells: (i) produce isoprene at a rate greater than about 400 nmole/$g_{wcm}$/hr and produce hydrogen at a rate greater than about 125 nmole/$g_{wcm}$/hr; (ii) have an average volumetric productivity of isoprene greater than about 0.1 mg/$L_{broth}$/hr and an average volumetric productivity of hydrogen greater than about 0.05 mg/$L_{broth}$/hr; or (iii) convert more than about 0.002 molar percent of the carbon that the cells consume from a cell culture medium into isoprene, and produce hydrogen equivalent to more than about 0.024 molar percent of the carbon that the cells consume from a cell culture medium. In some embodiments, the cells are capable of co-producing isoprene and hydrogen under oxygen-limited conditions. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In another aspect, provided herein are cells in oxygen-limited culture that co-produce isoprene and hydrogen, comprising a heterologous nucleic acid encoding an isoprene synthase polypeptide, wherein the heterologous nucleic acid is operably linked to a promoter, wherein the cells produce isoprene and hydrogen in a ratio ranging from at least one molar percent of isoprene for every three molar percent of hydrogen to at least one molar percent of isoprene for every four molar percent of hydrogen. In some embodiments, the cells are capable of co-producing isoprene and hydrogen under oxygen-limited conditions. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In another aspect, provided herein are cells in oxygen-limited culture that co-produce isoprene and a 2-(C2) or 3-carbon (C3) alcohol or diol. In some embodiments, the C2- or C3-alcohol or diol is ethanol. Thus in one aspect, provided herein are cells in oxygen-limited culture that co-produce isoprene and ethanol, wherein the cells have an average volumetric productivity of isoprene greater than about 0.1 mg/$L_{broth}$/hr and an average volumetric productivity of ethanol greater than about 0.1 mg/$L_{broth}$/hr. In some embodiments, the invention provides cells in oxygen-limited culture that have a peak volumetric productivity of isoprene greater than about 0.5 mg/$L_{broth}$/hr and a peak volumetric productivity of ethanol greater than about 0.1 mg/$L_{broth}$/hr. In some embodiments, the cells are capable of co-producing isoprene and a 2-(C2) or 3-carbon (C3) alcohol or diol under oxygen-limited conditions. In some embodiments, the C2- or C3-alcohol or diol is ethanol. In some embodiments, the cells comprise a heterologous nucleic acid that (i) encodes an isoprene synthase polypeptide and (ii) is operably linked to a promoter. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding an ethanol fermentation-related polypeptide. In some embodiments, the ethanol fermentation-related polypeptide is an alcohol dehydrogenase polypeptide. In some embodiments, the ethanol fermentation-related polypeptide is a pyruvate decarboxylase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In some embodiments, the C2- or C3-alcohol or diol is 1,2-propanediol. Thus in another aspect, provided herein are cells in oxygen-limited culture that co-produce isoprene and 1,2-propanediol, wherein the cells have an average volumetric productivity of isoprene greater than about 0.1 mg/L$_{broth}$/hr and an average volumetric productivity of 1,2-propanediol greater than about 0.1 mg/L$_{broth}$/hr. In some embodiments, the invention provides cells in oxygen-limited culture that have a peak volumetric productivity of isoprene greater than about 0.5 mg/L$_{broth}$/hr and a peak volumetric productivity of 1,2-propanediol greater than about 0.1 mg/L$_{broth}$/hr. In some embodiments, the cells are capable of co-producing isoprene and a 2-(C2) or 3-carbon (C3) alcohol or diol under oxygen-limited conditions. In some embodiments, the C2- or C3-alcohol or diol is 1,2-propanediol. In some embodiments, the cells comprise a heterologous nucleic acid that (i) encodes an isoprene synthase polypeptide and (ii) is operably linked to a promoter. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding one or more polypeptides involved in the glycerol pathway or the 1,3-propanediol pathway. In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, orfY, 1,3-propanediol oxidoreductase (dhaT), glycerol dehydrogenase (dhaD), or dihydroxyacetone kinase (dhaK). In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, and orfY. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In some embodiments, the C2- or C3-alcohol or diol is 1,3-propanediol. Thus in another aspect, provided herein are cells in oxygen-limited culture that co-produce isoprene and 1,3-propanediol, wherein the cells have an average volumetric productivity of isoprene greater than about 0.1 mg/L$_{broth}$/hr and an average volumetric productivity of 1,3-propanediol greater than about 0.1 mg/L$_{broth}$/hr. In some embodiments, the invention provides cells in oxygen-limited culture that have a peak volumetric productivity of isoprene greater than about 0.5 mg/L$_{broth}$/hr and a peak volumetric productivity of 1,3-propanediol greater than about 0.1 mg/L$_{broth}$/hr. In some embodiments, the cells are capable of co-producing isoprene and a 2-(C2) or 3-carbon (C3) alcohol or diol under oxygen-limited conditions. In some embodiments, the C2- or C3-alcohol or diol is 1,3-propanediol. In some embodiments, the cells comprise a heterologous nucleic acid that (i) encodes an isoprene synthase polypeptide and (ii) is operably linked to a promoter. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding one or more polypeptides involved in the glycerol pathway or the 1,3-propanediol pathway. In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, orfY, 1,3-propanediol oxidoreductase (dhaT), glycerol dehydrogenase (dhaD), or dihydroxyacetone kinase (dhaK). In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, and orfY. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In another aspect, provided herein are methods of co-producing isoprene and hydrogen, the methods comprising (a) culturing cells under conditions suitable for the co-production of isoprene and hydrogen; and (b) co-producing isoprene and hydrogen, wherein the cells produce isoprene at a rate greater than about 400 nmole/$g_{wcm}$/hr and produce hydrogen at a rate greater than about 125 nmole/$g_{wcm}$/hr. In some embodiments, the cells are grown in oxygen-limited culture. In some embodiments, the cells comprise a heterologous nucleic acid that (i) encodes an isoprene synthase polypeptide and (ii) is operably linked to a promoter. In some embodiments, the cells produce isoprene at a rate between about 400 nmole/$g_{wcm}$/hr and about $2.0\times10^5$ nmole/$g_{wcm}$/hr, and hydrogen at a rate between about 125 nmole/$g_{wcm}$/hr and about $1.25\times10^4$ nmole/$g_{wcm}$/hr. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen. In some embodiments, the method also includes recovering isoprene and hydrogen produced by the cells. In some embodiments, the method includes purifying isoprene produced by the cells. In some embodiments, the method includes purifying hydrogen produced by the cells. In some embodiments, the method includes polymerizing the isoprene.

In another aspect, provided herein are methods of co-producing isoprene and hydrogen, the methods comprising (a) culturing cells under conditions suitable for the co-production of isoprene and hydrogen; and (b) co-producing isoprene and hydrogen, wherein the cells have an average volumetric productivity of isoprene greater than about 0.1 mg/$L_{broth}$/hr and an average volumetric productivity of hydrogen greater than about 0.05 mg/$L_{broth}$/hr. In some embodiments, the cells are grown in oxygen-limited culture. In some embodiments, the cells comprise a heterologous nucleic acid that (i) encodes an isoprene synthase polypeptide and (ii) is operably linked to a promoter. In some embodiments, the cells produce isoprene at a peak volumetric productivity of isoprene greater than about 0.5 mg/$L_{broth}$/hr, and hydrogen at a peak volumetric productivity of isoprene greater than about 5 mg/$L_{broth}$/hr. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen. In some embodiments, the method also includes recovering isoprene and hydrogen produced by the cells. In some embodiments, the method includes purifying isoprene produced by the cells. In some embodiments, the method includes purifying hydrogen produced by the cells. In some embodiments, the method includes polymerizing the isoprene.

In another aspect, provided herein are methods of co-producing isoprene and hydrogen, the methods comprising (a) culturing cells under conditions suitable for the co-production of isoprene and hydrogen; and (b) co-producing isoprene and hydrogen, wherein the cells convert more than about 0.002 molar percent of the carbon that the cells consume from a cell culture medium into isoprene, and produce hydrogen equivalent to more than about 0.024 molar percent of the carbon that the cells consume from the culture medium. In some embodiments, the cells are grown in oxygen-limited culture. In some embodiments, the cells comprise a heterologous nucleic acid that (i) encodes an isoprene synthase polypeptide and (ii) is operably linked to a promoter. In some embodiments, the cells produce isoprene at a rate between about 400 nmole/$g_{wcm}$/hr and about $2.0\times10^5$ nmole/$g_{wcm}$/hr, and hydrogen at a rate between about 125 nmole/$g_{wcm}$/hr and about $1.25\times10^4$ nmole/$g_{wcm}$/hr. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a hydrogenase polypeptide. In some embodiments, the hydrogenase polypeptide is a ferredoxin-dependent hydrogenase polypeptide, a NADPH-dependent hydrogenase polypeptide, or an oxygen-tolerant hydrogenase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen. In some embodiments, the method also includes recovering isoprene and hydrogen produced by the cells. In some embodiments, the method includes purifying isoprene produced by the cells. In some embodiments, the method includes purifying hydrogen produced by the cells. In some embodiments, the method includes polymerizing the isoprene.

In another aspect, provided herein are methods of co-producing isoprene and a 2-(C2) or 3-carbon (C3) alcohol or diol. In some embodiments, the C2- or C3-alcohol or diol is ethanol. Thus in one aspect, provided herein are methods of co-producing isoprene and ethanol, the methods comprising (a) culturing cells under conditions suitable for the co-production of isoprene and ethanol; and (b) co-producing isoprene and ethanol, wherein the cells have an average volumetric productivity of isoprene greater than about 0.1 mg/$L_{broth}$/hr and an average volumetric productivity of ethanol greater than about 0.1 mg/$L_{broth}$/hr. In some embodiments, the cells are grown in oxygen-limited culture. In some embodiments, the cells comprise a heterologous nucleic acid that (i) encodes an isoprene synthase polypeptide and (ii) is operably linked to a promoter. In some embodiments, the cells produce isoprene at a peak volumetric productivity of isoprene greater than about 0.5 mg/$L_{broth}$/hr, and ethanol at a peak volumetric productivity of isoprene greater than about 0.1 mg/$L_{broth}$/hr. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding an ethanol fermentation-related polypeptide. In some embodiments, the ethanol fermentation-related polypeptide is an alcohol dehydrogenase polypeptide. In some embodiments, the ethanol fermentation-related polypeptide is a pyruvate decarboxylase polypeptide. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen. In some embodiments, the method also includes recovering isoprene and ethanol produced by the cells. In some embodiments, the method includes purifying isoprene produced by the cells. In some embodiments, the method includes purifying ethanol produced by the cells. In some embodiments, the method includes polymerizing the isoprene.

In some embodiments, the C2- or C3-alcohol or diol is 1,2-propanediol. Thus in one aspect, provided herein are methods of co-producing isoprene and 1,2-propanediol, the methods comprising (a) culturing cells under conditions suitable for the co-production of isoprene and 1,2-propanediol; and (b) co-producing isoprene and 1,2-propanediol, wherein the cells have an average volumetric productivity of isoprene greater than about 0.1 mg/$L_{broth}$/hr and an average volumetric productivity of 1,2-propanediol greater than about 0.1 mg/$L_{broth}$/hr. In some embodiments, the cells are grown in oxygen-limited culture. In some embodiments, the cells comprise a heterologous nucleic acid that (i) encodes an isoprene synthase polypeptide and (ii) is operably linked to a promoter. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding one or more polypeptides involved in the glycerol pathway or the 1,3-propanediol pathway. In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, orfY, 1,3-propanediol oxidoreductase (dhaT), glycerol dehydrogenase (dhaD), or dihydroxyacetone kinase (dhaK). In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, and orfY. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In some embodiments, the C2- or C3-alcohol or diol is 1,3-propanediol. Thus in one aspect, provided herein are methods of co-producing isoprene and 1,3-propanediol, the methods comprising (a) culturing cells under conditions suitable for the co-production of isoprene and 1,3-propanediol; and (b) co-producing isoprene and 1,3-propanediol, wherein the cells have an average volumetric productivity of isoprene greater than about 0.1 mg/$L_{broth}$/hr and an average volumetric productivity of 1,3-propanediol greater than about 0.1 mg/$L_{broth}$/hr. In some embodiments, the cells are grown in oxygen-limited culture. In some embodiments, the cells comprise a heterologous nucleic acid that (i) encodes an isoprene synthase polypeptide and (ii) is operably linked to a promoter. In some embodiments, the isoprene synthase polypeptide is a plant isoprene synthase polypeptide. In some embodiments, the cells further comprise a heterologous nucleic acid encoding a mevalonic acid (MVA) pathway polypeptide, a DXS polypeptide, or an IDI polypeptide. In some embodiments, the cells further comprise a heterologous nucleic acid encoding a deoxyxylulose-5-phosphate (DXP) pathway polypeptide. In some embodiments, the cells further comprise a heterologous nucleic acid encoding one or more polypeptides involved in the glycerol pathway or the 1,3-propanediol pathway. In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, orfY, 1,3-propanediol oxidoreductase (dhaT), glycerol dehydrogenase (dhaD), or dihydroxyacetone kinase (dhaK). In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, and orfY. In some embodiments, the cells are cultured in a culture medium that includes one or more carbon sources, such as, but not limited to, a carbohydrate (e.g., xylose or glucose), acetate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source (e.g., a hydrolyzed biomass carbon source), polypeptide (e.g., a microbial or plant protein or peptide), yeast extract, or a component from a yeast extract. In some embodiments, the cells are grown in oxygen-limited culture. In some embodiments, the cells are cultured in the presence of oxygen under conditions where 0.5 moles of oxygen are taken up per mole of isoprene produced. In some embodiments, the cells are grown anaerobically, in the absence of oxygen.

In some embodiments of any of the various aspects described herein, the MVA pathway polypeptide is an upper MVA pathway polypeptide. In some embodiments, the MVA pathway polypeptide is a lower MVA pathway polypeptide. In some embodiments, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some embodiments, the upper MVA pathway polypeptide is from the genus Enterococcus. In some embodiments, the upper MVA pathway polypeptide is from Enterococcus faecalis. In some embodiments, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some embodiments, the lower MVA pathway polypeptide is an MVK polypeptide. In some embodiments, the MVK polypeptide is from the genus Methanosarcina. In some embodiments, the MVK polypeptide is from Methanosarcina mazei.

In another aspect, provided herein are compositions comprising isoprene and hydrogen. In some embodiments, the compositions comprise isoprene and hydrogen in ratios ranging from at least one molar percent of isoprene for every three molar percent of hydrogen to at least one molar percent of isoprene for every four molar percent of hydrogen. In some embodiments, the composition further comprises from 1 to 11 molar percent isoprene and from 4 to 44 molar percent hydrogen. In some embodiments, the composition further comprises oxygen, carbon dioxide, or nitrogen. In some embodiments, the composition further comprises from 0 to 21 molar percent oxygen, from 18 to 44 molar percent carbon dioxide, and from 0 to 78 molar percent nitrogen. In some embodiments, the composition further comprises 1.0× $10^{-4}$ molar percent or less of non-methane volatile impurities. In some embodiments, the non-methane volatile impurities comprise one or more of the following: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, 3-hexen-1-ol, 3-hexen-1-yl acetate, limonene, geraniol (trans-3,7-dimethyl-2,6-octadien-1-ol) and citronellol (3,7-dimethyl-6-octen-1-ol) or a linear isoprene polymer (such as a linear isoprene dimer or a linear isoprene trimer derived from the polymerization of multiple isoprene units). In some embodiments, the non-methane volatile impurities comprise one or more of the following: the isoprene composition includes one or more of the following: an alcohol, an aldehyde, an ester or a ketone (such as any of the alcohols, aldehydes, esters or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone. In some embodiments, the non-methane volatile impurities comprise one or more of the following: methanol, acetaldehyde, ethanol, methanethiol, 1-butanol, 3-methyl-1-propanol, acetone, acetic acid, 2-butanone, 2-methyl-1-butanol, or indole.

It is to be understood that one, some, or all of the properties of the various embodiments described herein may be combined to form other embodiments of the present invention.

BRIEF DESCRIPTION OF THE DRAWINGS

FIG. 1 is the nucleotide sequence of a kudzu isoprene synthase gene codon-optimized for expression in E. coli (SEQ ID NO:1). The atg start codon is in italics, the stop codon is in bold and the added PstI site is underlined.

FIGS. 3A-C are the nucleotide sequence of pTrcKudzu (SEQ ID NO:2). The RBS is underlined, the kudzu isoprene synthase start codon is in bold capitol letters and the stop codon is in bold, capital letters. The vector backbone is pTrcHis2B.

FIGS. 5A-C are the nucleotide sequence of pETNHisKudzu (SEQ ID NO:3).

FIGS. 7A-C are the nucleotide sequence of pCL-lac-Kudzu (SEQ ID NO:4).

FIGS. 12A-C are the nucleotide sequence of pBS Kudzu #2 (SEQ ID NO:5).

FIG. 13 is the nucleotide sequence of kudzu isoprene synthase codon-optimized for expression in *Yarrowia* (SEQ ID NO:6).

FIGS. 15A-C are the nucleotide sequence of vector pSPZ1(MAP29Spb) (SEQ ID NO:7).

FIG. 16 is the nucleotide sequence of the synthetic kudzu (*Pueraria montana*) isoprene gene codon-optimized for expression in *Yarrowia* (SEQ ID NO:8).

FIG. 17 is the nucleotide sequence of the synthetic hybrid poplar (*Populus alba×Populus tremula*) isoprene synthase gene (SEQ ID NO:9). The ATG start codon is in bold and the stop codon is underlined.

FIGS. 18A1-18A2 show a schematic outlining construction of vectors pYLA 1, pYL1 and pYL2 (primer YURA51=SEQ ID NO:79, primer YURA3=SEQ ID NO:73, primer Y18S5=SEQ ID NO:72, primer Y18S3=SEQ ID NO:71, primer XPRT5=SEQ ID NO:70, and primer XPRT3=SEQ ID NO: 69).

FIG. 18D shows a schematic outlining construction of the vector pYLI(KZ1) (primer ICL1 5=SEQ ID NO:66 and primer ICL1 3=SEQ ID NO: 65).

FIGS. 22A-D are the nucleotide sequence of pTrcKudzu yIDI DXS Kan (SEQ ID NO:10).

FIG. 23A is a graph showing production of isoprene from glucose in BL21/pTrcKudzukan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

FIGS. 25A-D are a nucleotide sequence of pTrcKKDyIkIS kan (SEQ ID NO:11).

FIGS. 27A-D are the nucleotide sequence of pCL PtrcUpper Pathway (SEQ ID NO:12).

FIGS. 29A-D are a nucleotide sequence of cassette containing the lower MVA pathway and yeast idi for integration into the *B. subtilis* chromosome at the nprE locus (SEQ ID NO:13).

FIGS. 31A-B are a nucleotide sequence of p9796-poplar (SEQ ID NO:14).

FIGS. 33A-C are a nucleotide sequence of pTrcPoplar (SEQ ID NO:15).

FIGS. 35A-C are a nucleotide sequence of pTrcKudzu yIDI Kan (SEQ ID NO:16).

FIGS. 37A-C are a nucleotide sequence of pTrcKudzuDXS Kan (SEQ ID NO:17).

FIGS. 39A-C are a nucleotide sequence of pCL PtrcKudzu (SEQ ID NO:18).

FIGS. 41A-C are a nucleotide sequence of pCL PtrcKudzu A3 (SEQ ID NO:19).

FIGS. 43A-C are a nucleotide sequence of pCL PtrcKudzu yIDI (SEQ ID NO:20).

FIGS. 45A-D are a nucleotide sequence of pCL PtrcKudzu DXS (SEQ ID NO:21).

FIGS. 51A-C are the nucleotide sequence of pJMupperpathway2 (SEQ ID NO:22).

FIG. 75A is a table of the conversion of the CAFT Model results from weight percent to volume percent for series A.

FIG. 75B is a graph of the flammability results from the CAFT model for Series A in FIG. 68 plotted as volume percent.

FIG. 76A is a table of the conversion of the CAFT Model results from weight percent to volume percent for series B.

FIG. 76B is a graph of the flammability results from the CAFT model for Series B in FIG. 69 plotted as volume percent.

FIG. 78A is a graph of the flammability Curve for Test Series 1: 0% Steam, 0 psig, and 40° C.

FIG. 78B is a table summarizing the explosion and non-explosion data points for Test Series 1.

FIG. 79A is a graph of the flammability curve for Test Series 2: 4% Steam, 0 psig, and 40° C.

FIG. 79B is a table summarizing the explosion and non-explosion data points for Test Series 2.

FIGS. 80A-B are a table of the detailed experimental conditions and results for Test Series 1.

FIG. 81 is a table of the detailed experimental conditions and results for Test Series 2.

FIG. 82 is a graph of the calculated adiabatic flame temperature plotted as a function of fuel concentration for various nitrogen/oxygen ratios at 3 atmospheres of pressure.

Figure 88A:
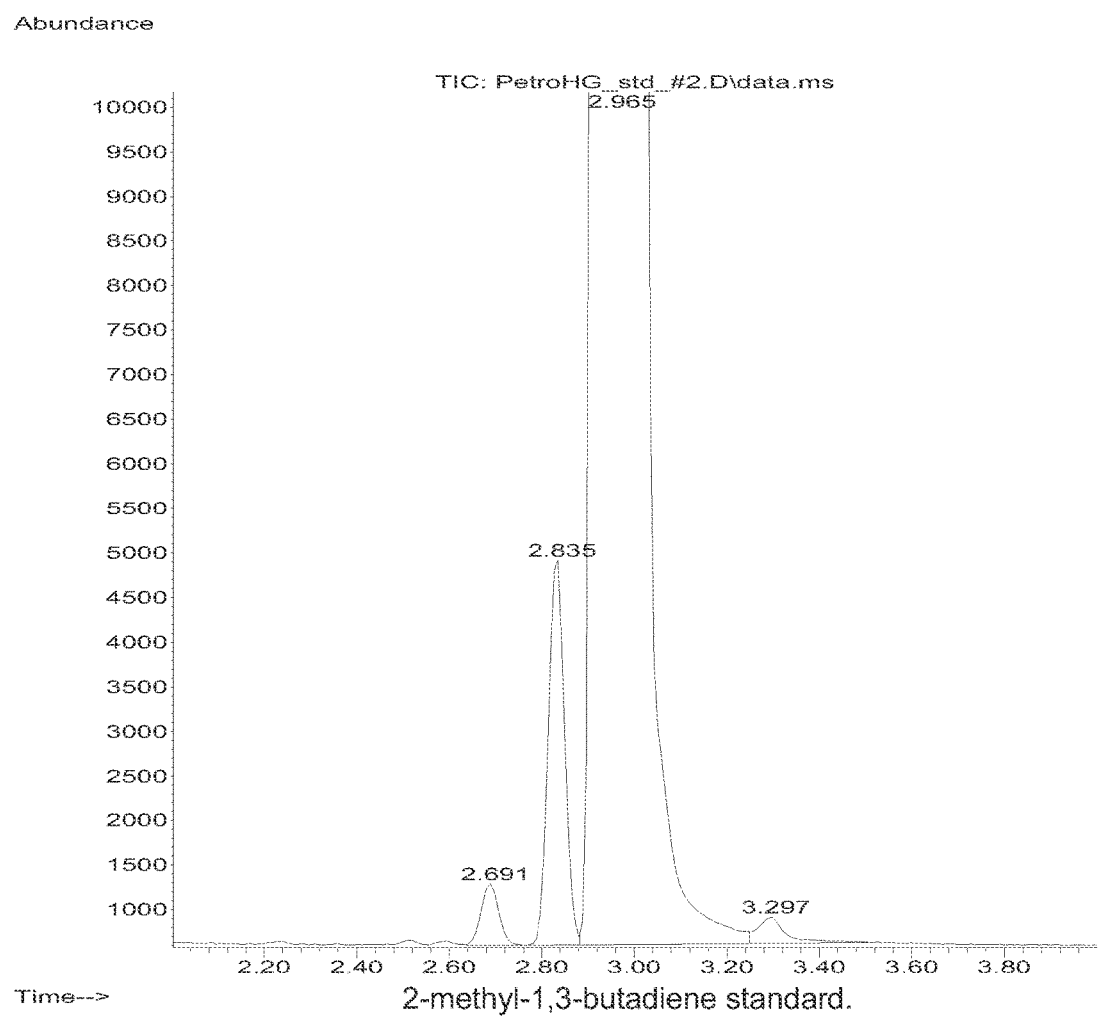
Figure 88B:
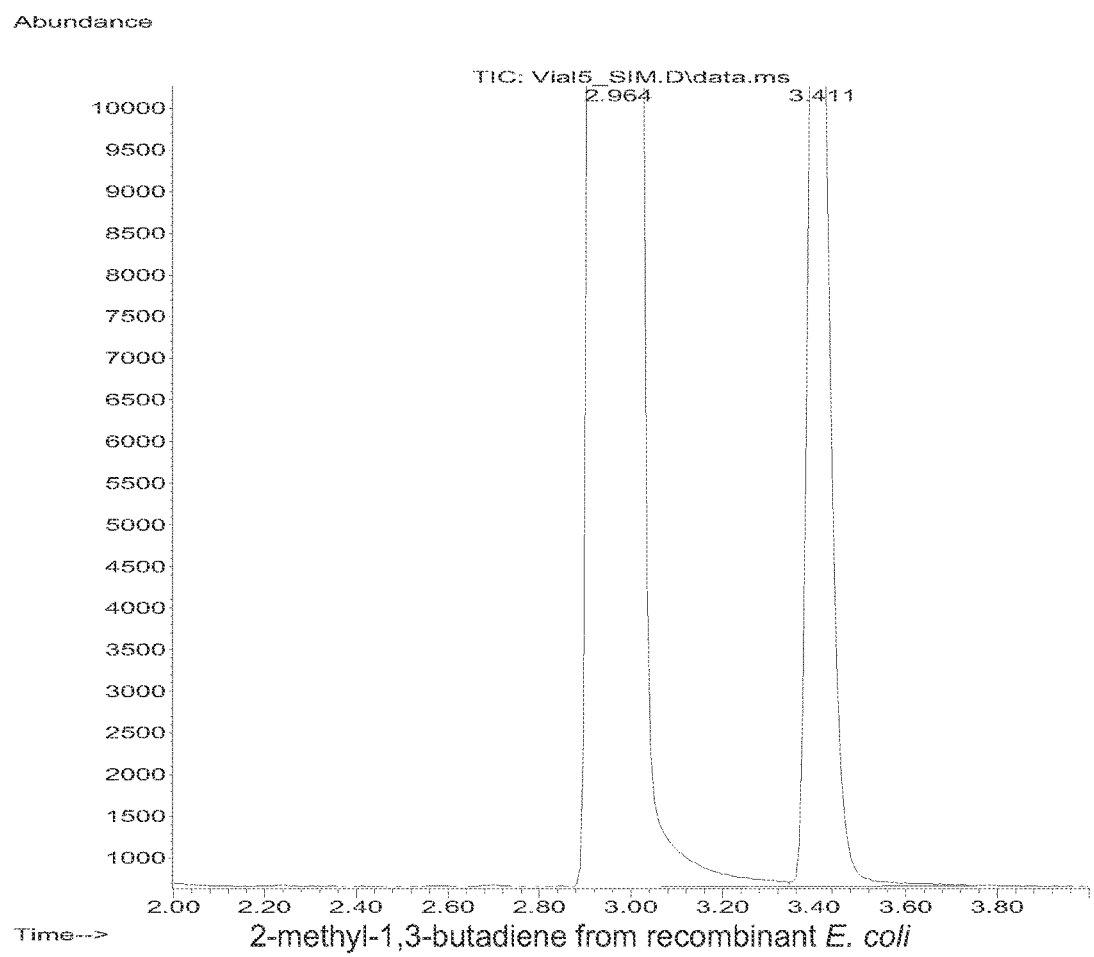

FIGS. 88A-B are GC/MS chromatogram comparing C5 hydrocarbons from petroleum-derived isoprene (FIG. 88A) and biologically produced isoprene (FIG. 88B). The standard contains three C5 hydrocarbon impurities eluting around the main isoprene peak (FIG. 88A). In contrast, biologically produced isoprene contains amounts of ethanol and acetone (run time of 3.41 minutes) (FIG. 88A).

Figure 89:
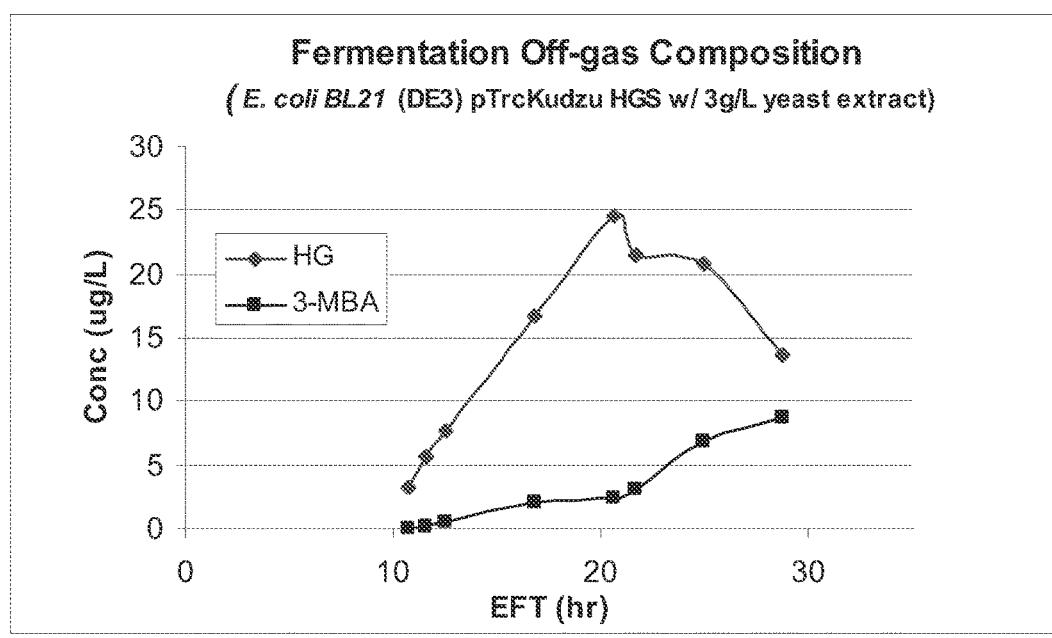

FIG. 89 is a graph of the analysis of fermentation off-gas of an *E. coli* BL21 (DE3) pTrcIS strain expressing a Kudzu isoprene synthase and fed glucose with 3 g/L yeast extract.

FIG. 90 shows the structures of several impurities that are structurally similar to isoprene and may also act as polymerization catalyst poisons.

Figure 91:
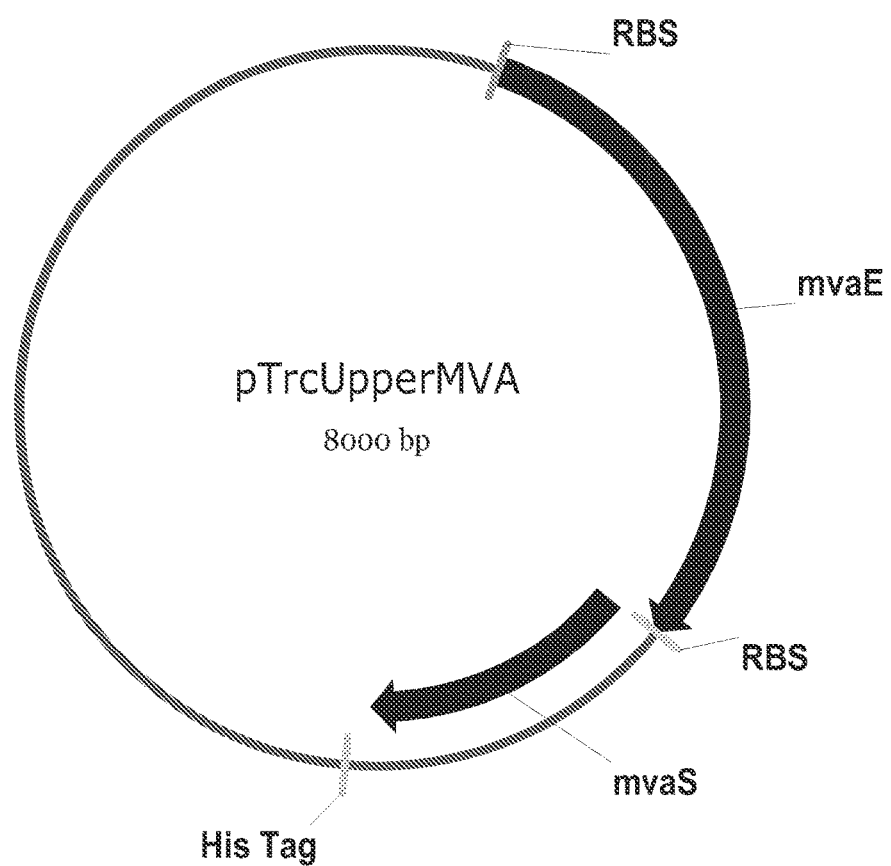

FIG. 91 is a map of pTrcHis2AUpperPathway (also called pTrcUpperMVA).

FIGS. 92A-92C are the nucleotide sequence of pTrcHis2AUpperPathway (also called pTrcUpperMVA) (SEQ ID NO:23).

Figure 93:
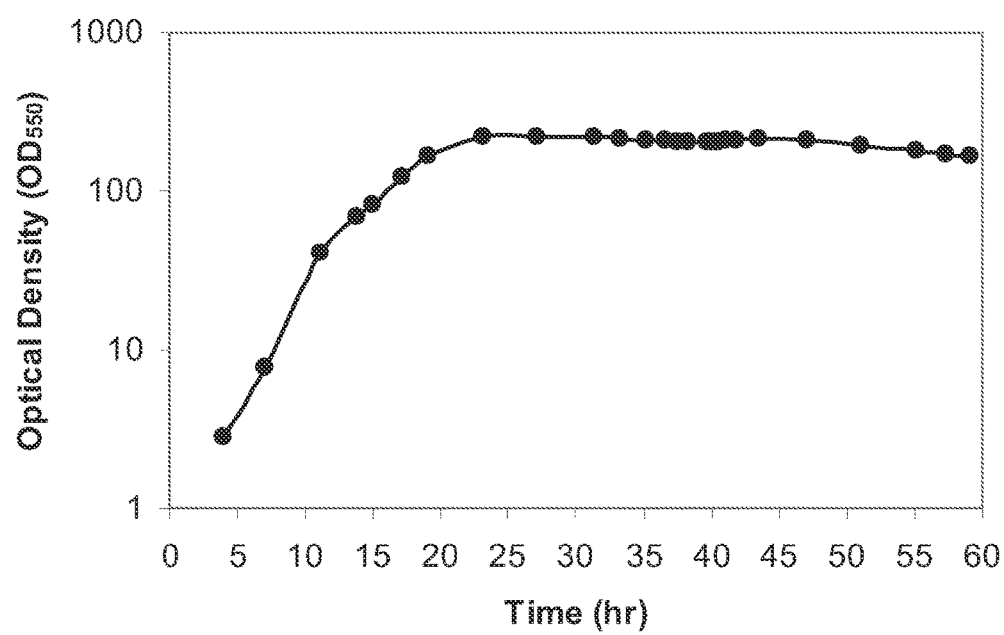

FIG. 93 is a time course of optical density within the 15-L bioreactor fed with glucose.

Figure 94:
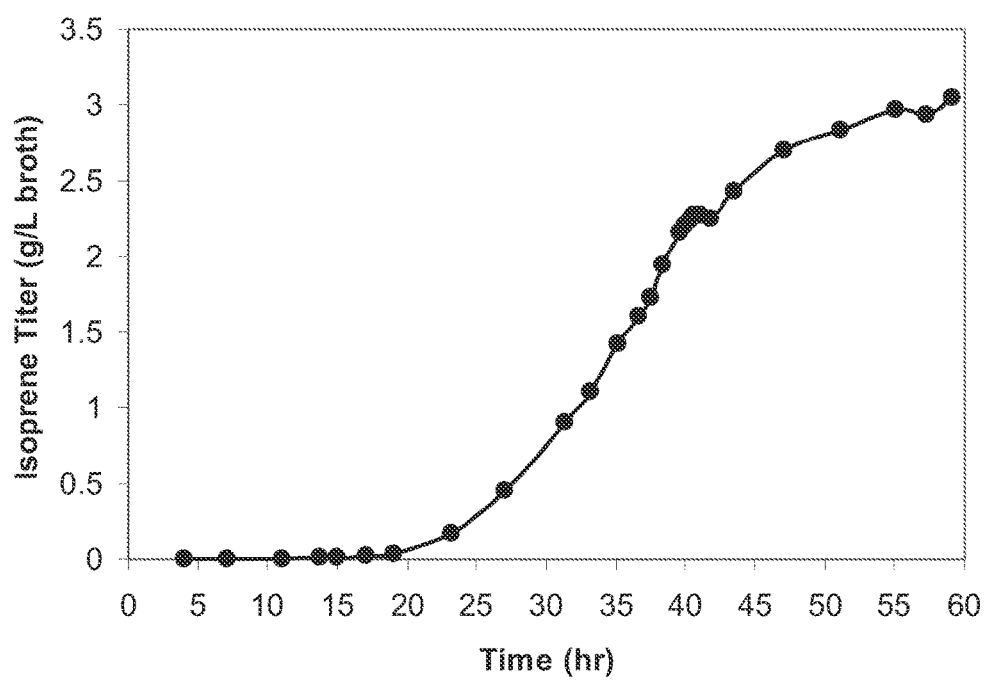

FIG. 94 is a time course of isoprene titer within the 15-L bioreactor fed with glucose. The titer is defined as the amount of isoprene produced per liter of fermentation broth.

Figure 95:
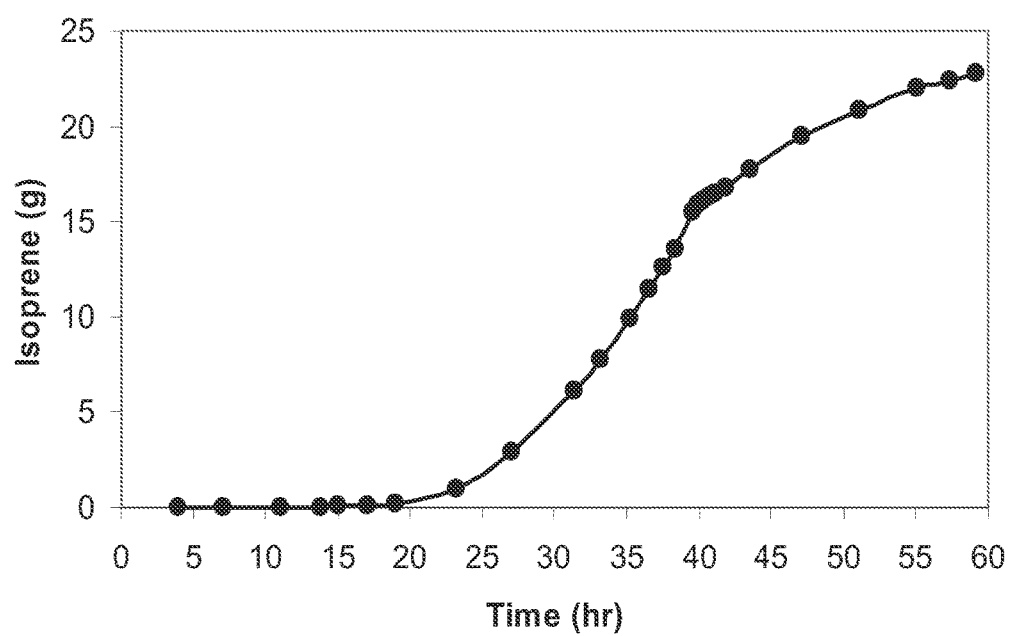

FIG. 95 is a time course of total isoprene produced from the 15-L bioreactor fed with glucose.

Figure 96:
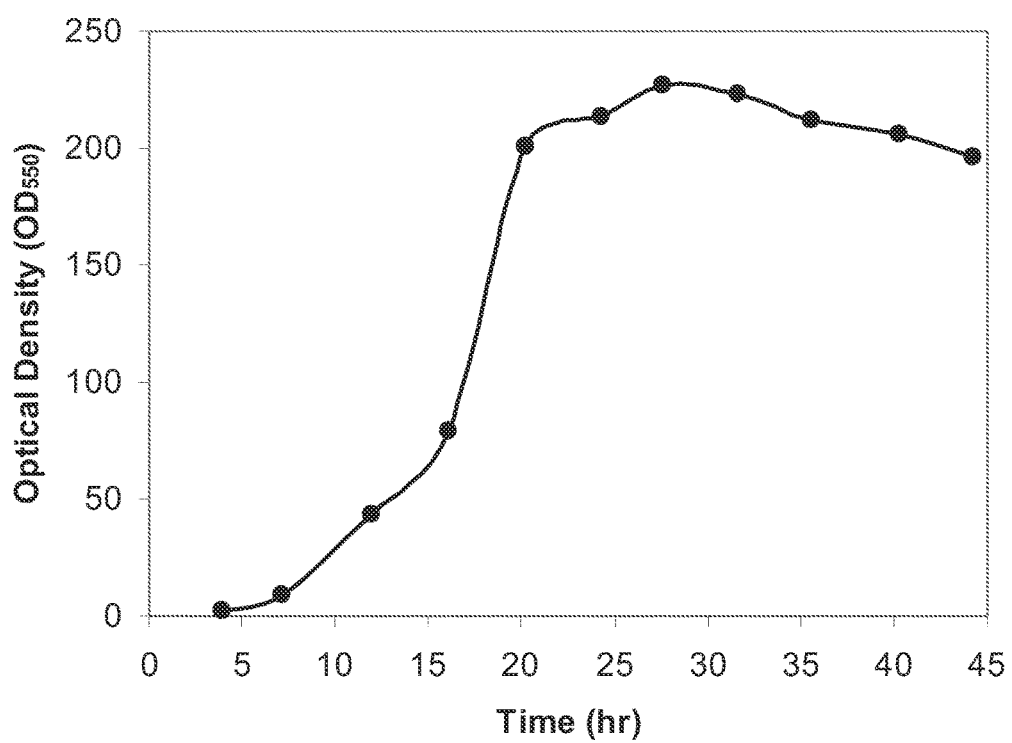

FIG. 96 is a time course of optical density within the 15-L bioreactor fed with invert sugar.

Figure 97:
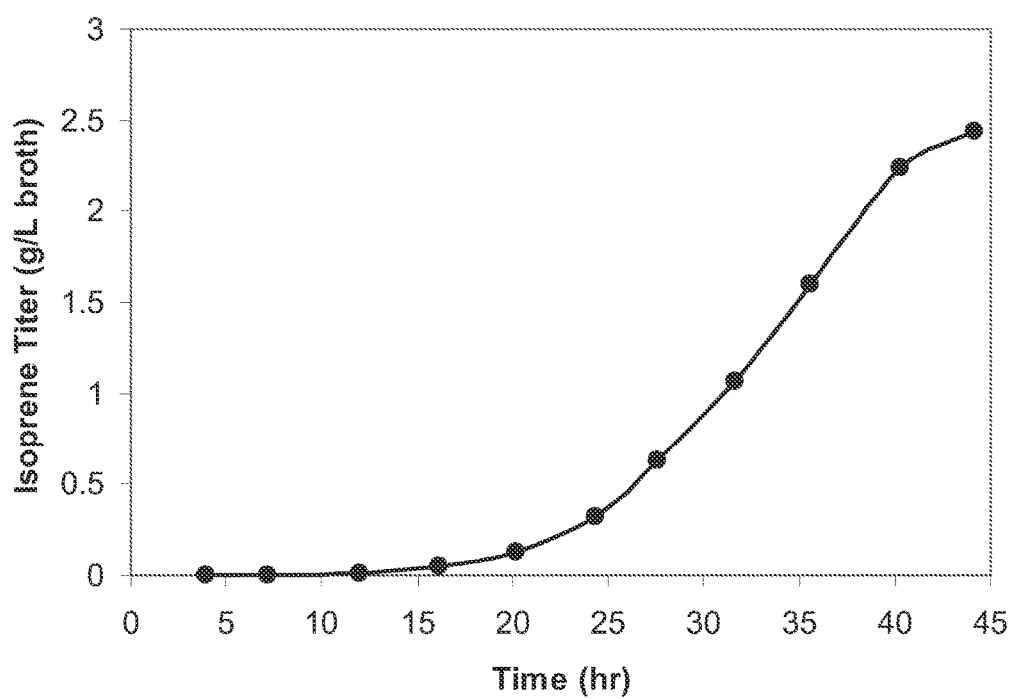

FIG. 97 is a time course of isoprene titer within the 15-L bioreactor fed with invert sugar. The titer is defined as the amount of isoprene produced per liter of fermentation broth.

Figure 98:
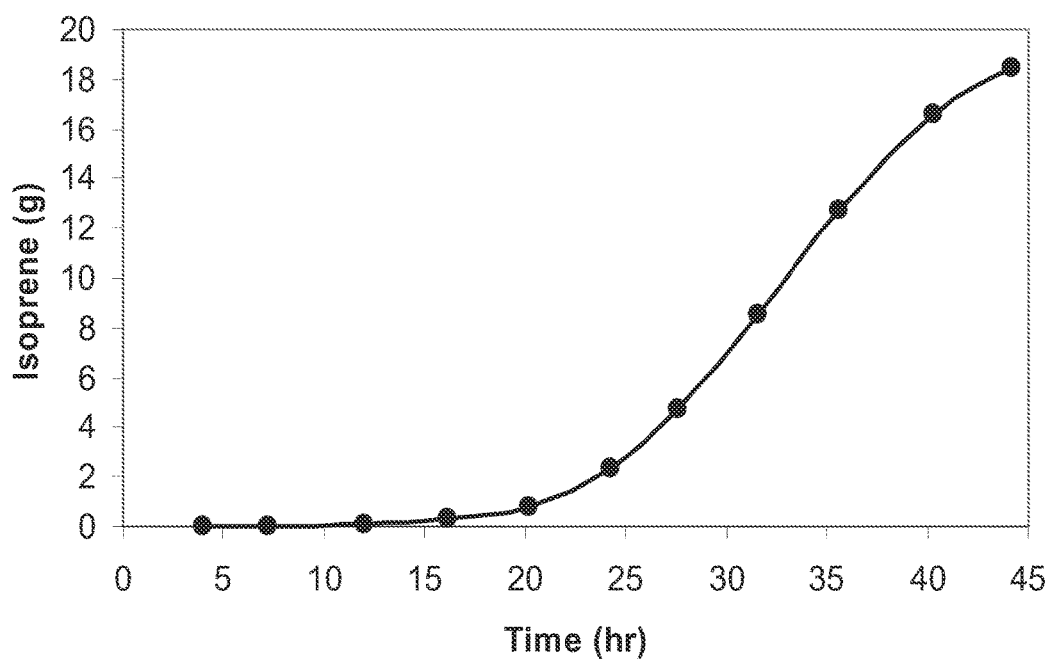

FIG. 98 is a time course of total isoprene produced from the 15-L bioreactor fed with invert sugar.

Figure 99:
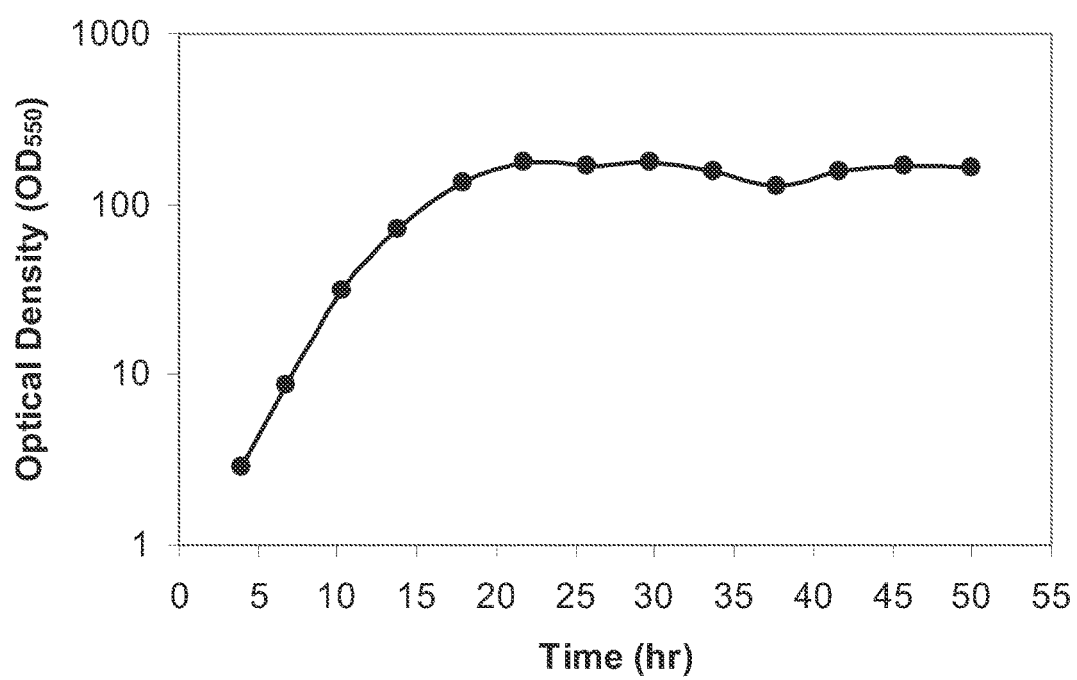

FIG. 99 is a time course of optical density within the 15-L bioreactor fed with glucose.

Figure 100:
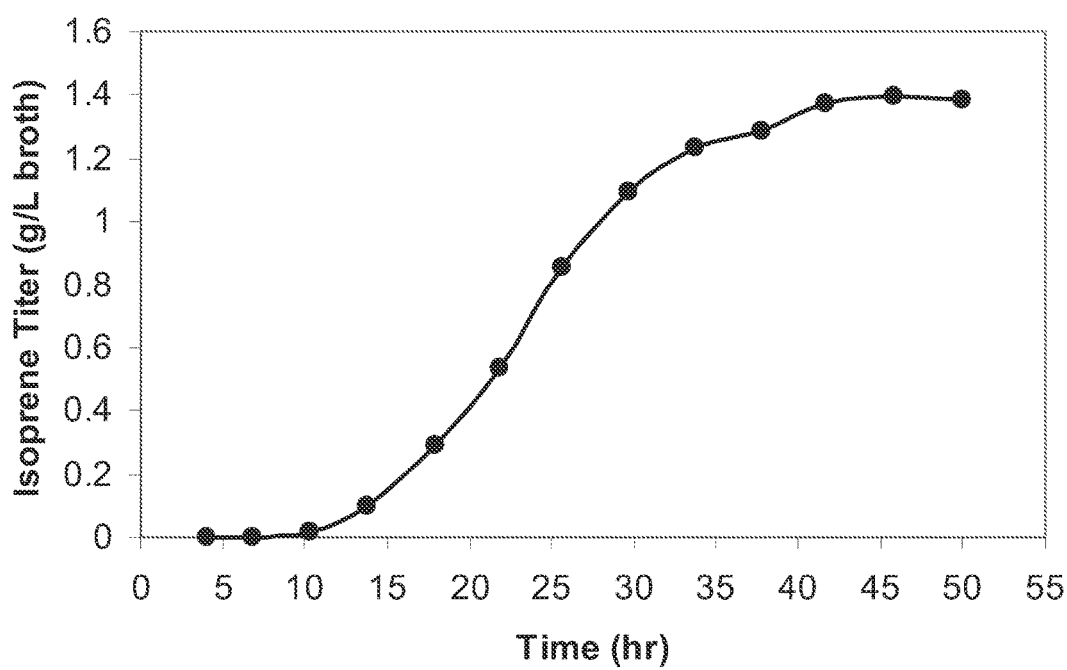

FIG. 100 is a time course of isoprene titer within the 15-L bioreactor fed with glucose. The titer is defined as the amount of isoprene produced per liter of fermentation broth.

Figure 101:
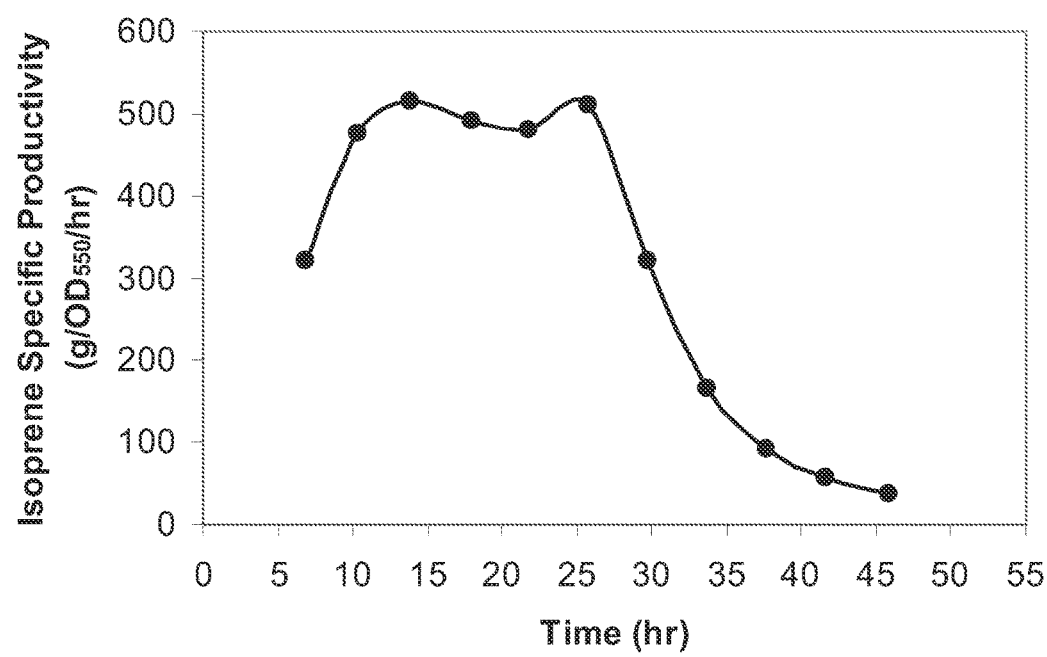

FIG. 101 is a time course of isoprene specific activity from the 15-L bioreactor fed with glucose.

Figure 102:
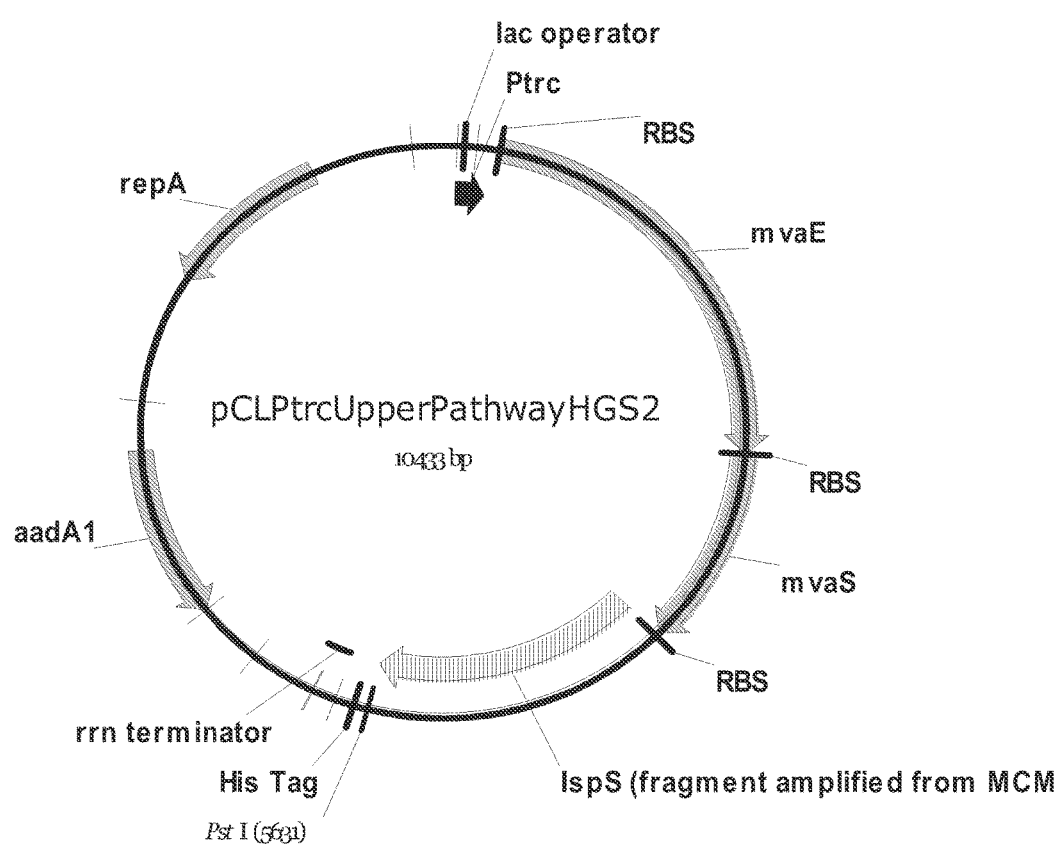

FIG. 102 is a map of pCLPtrcUpperPathwayHGS2.

FIGS. 103A-103C are the nucleotide sequence of pCLPtrcUpperPathwayHGS2 (SEQ ID NO:24).

Figure 104:
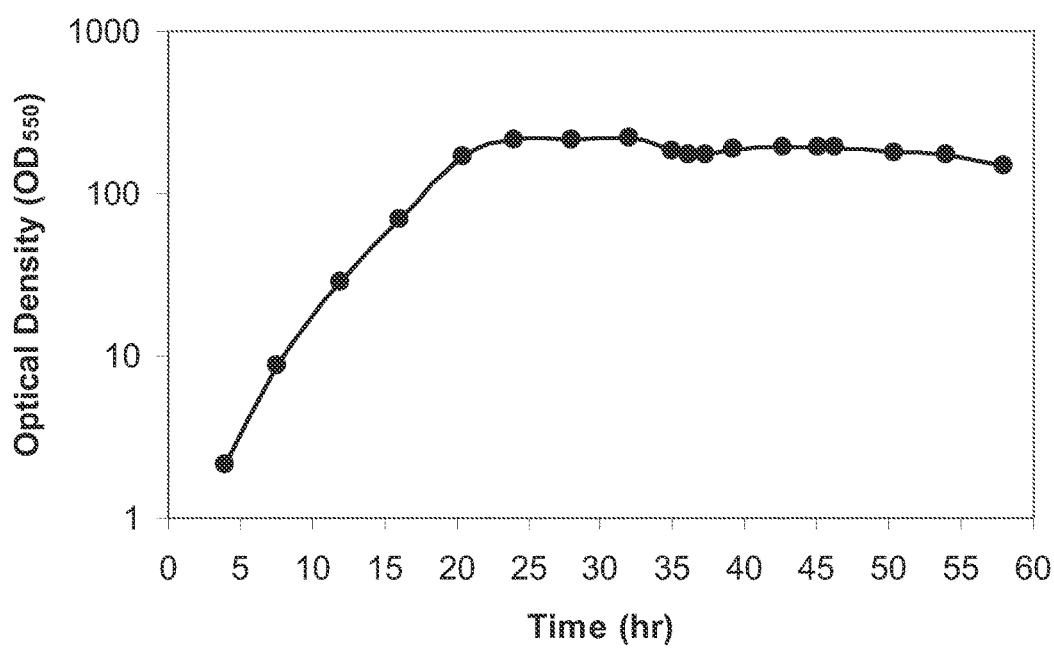

FIG. 104 is a time course of optical density within the 15-L bioreactor fed with glucose.

Figure 105:
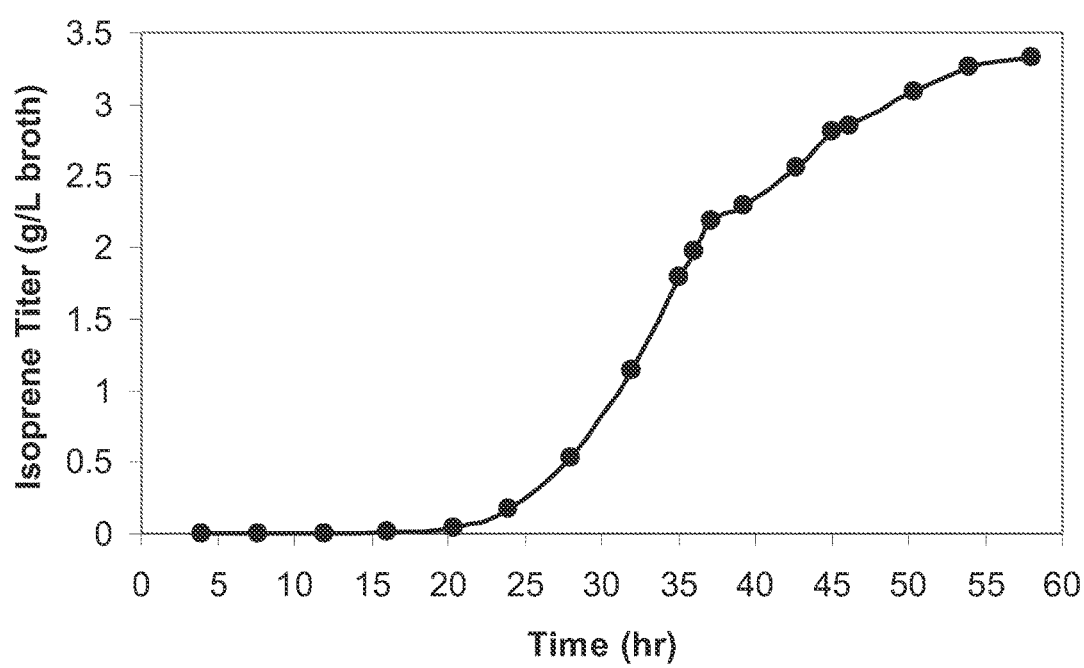

FIG. 105 is a time course of isoprene titer within the 15-L bioreactor fed with glucose. The titer is defined as the amount of isoprene produced per liter of fermentation broth.

Figure 106:
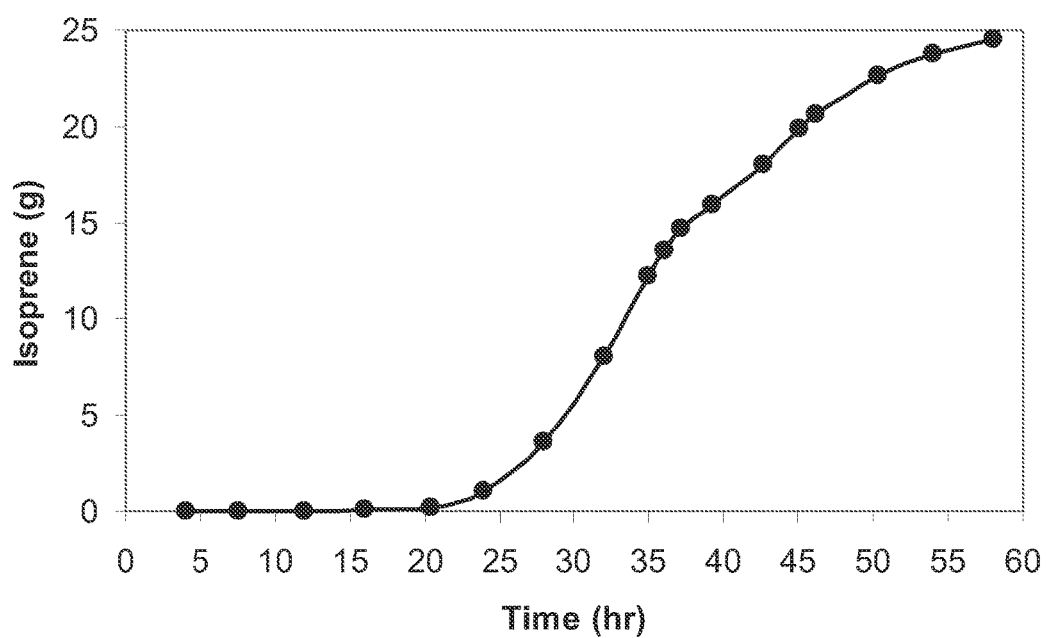

FIG. 106 is a time course of total isoprene produced from the 15-L bioreactor fed with glucose.

Figure 107:
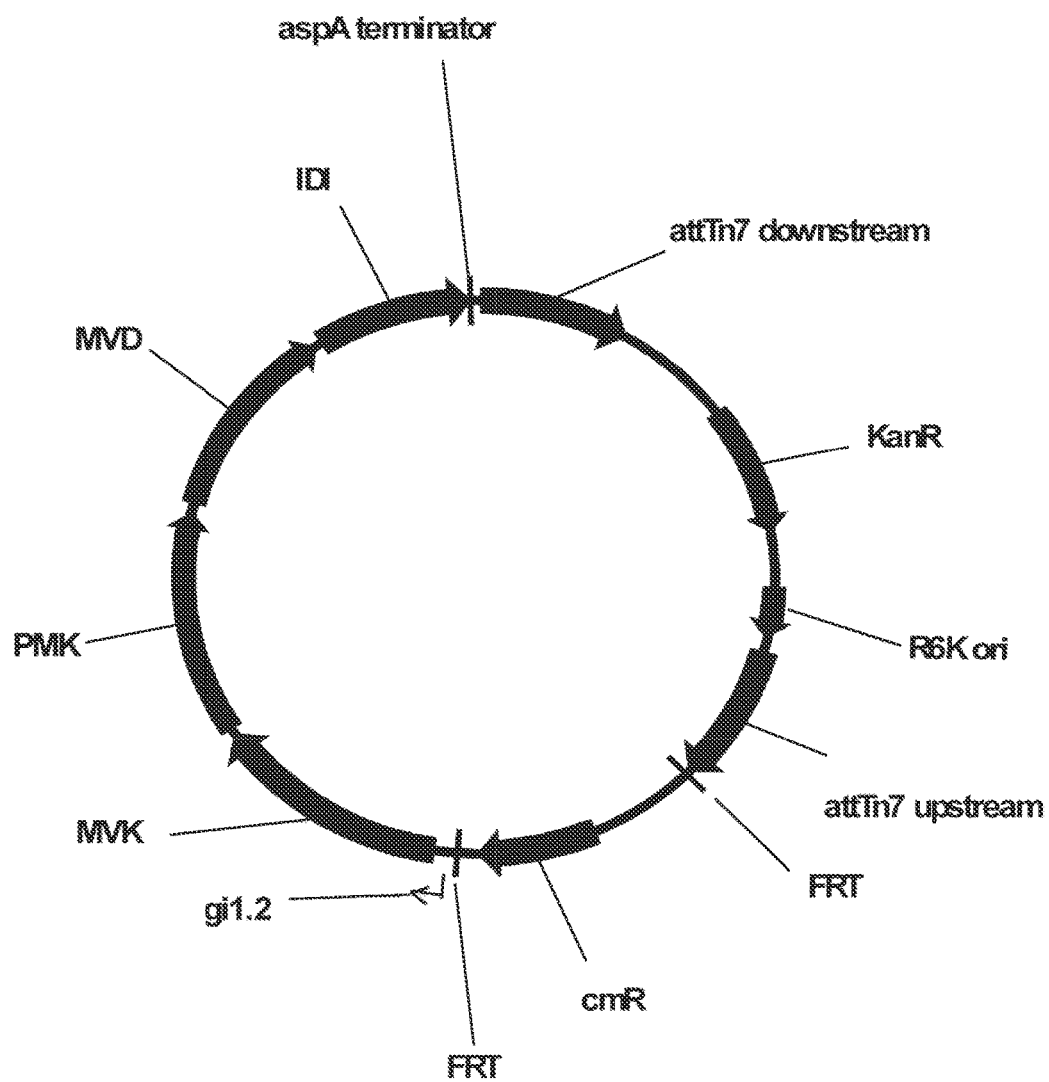

FIG. 107 is a map of plasmid MCM330 (FRT-cm-FRT-gi1.2-KKDy at attTn7).

FIGS. 108A-108C are the nucleotide sequence of plasmid MCM330 (SEQ ID NO:25).

Figure 109:
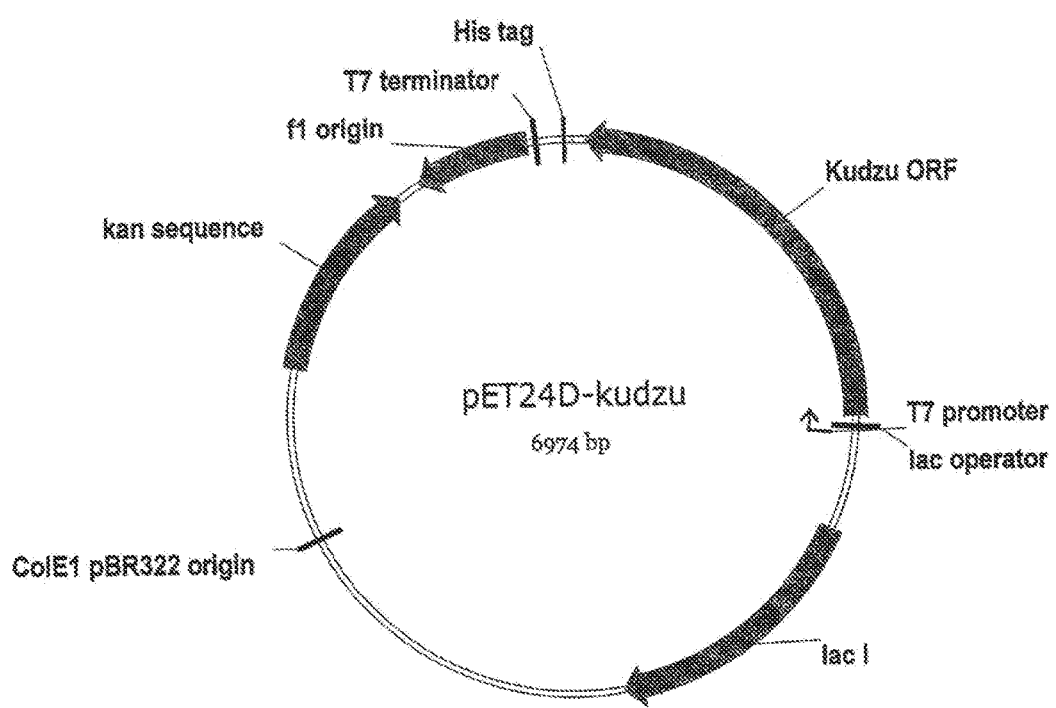

FIG. 109 is a map of pET24D-Kudzu.

FIGS. 110A-B are the nucleotide sequence of pET24D-Kudzu (SEQ ID NO:26).

Figure 111A:
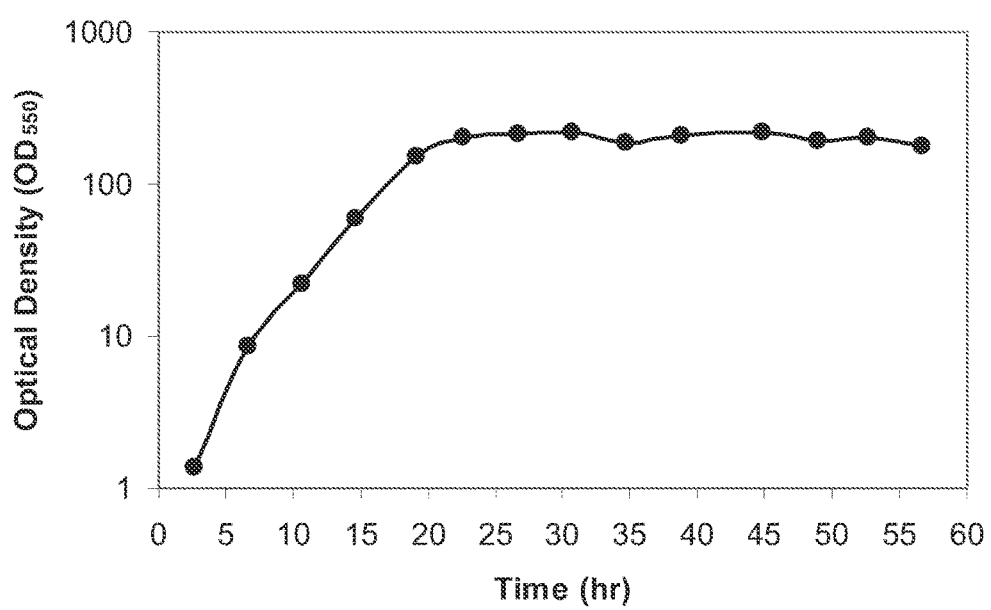

FIG. 111A is a time course of optical density within the 15-L bioreactor fed with glucose.

Figure 111B:
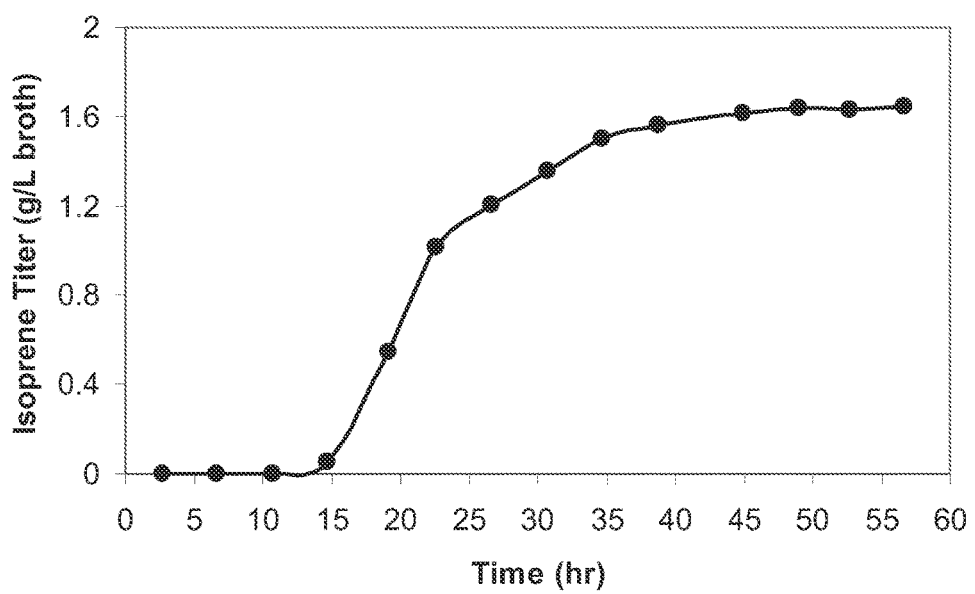

FIG. 111B is a time course of isoprene titer within the 15-L bioreactor fed with glucose. The titer is defined as the amount of isoprene produced per liter of fermentation broth.

Figure 111C:
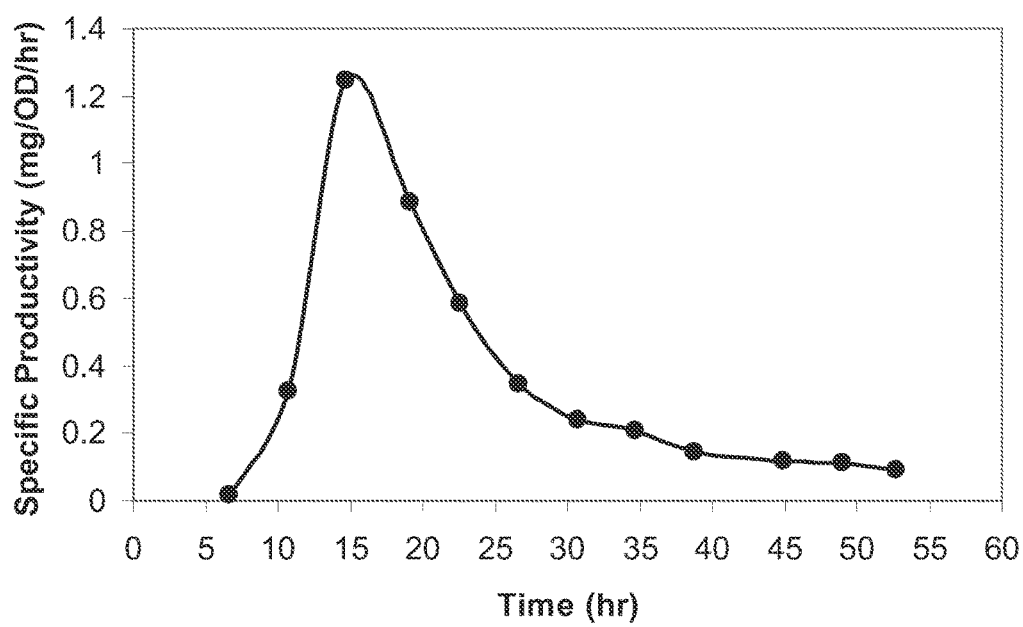

FIG. 111C is a time course of specific productivity of isoprene in the 15-L bioreactor fed with glucose.

Figure 112A:
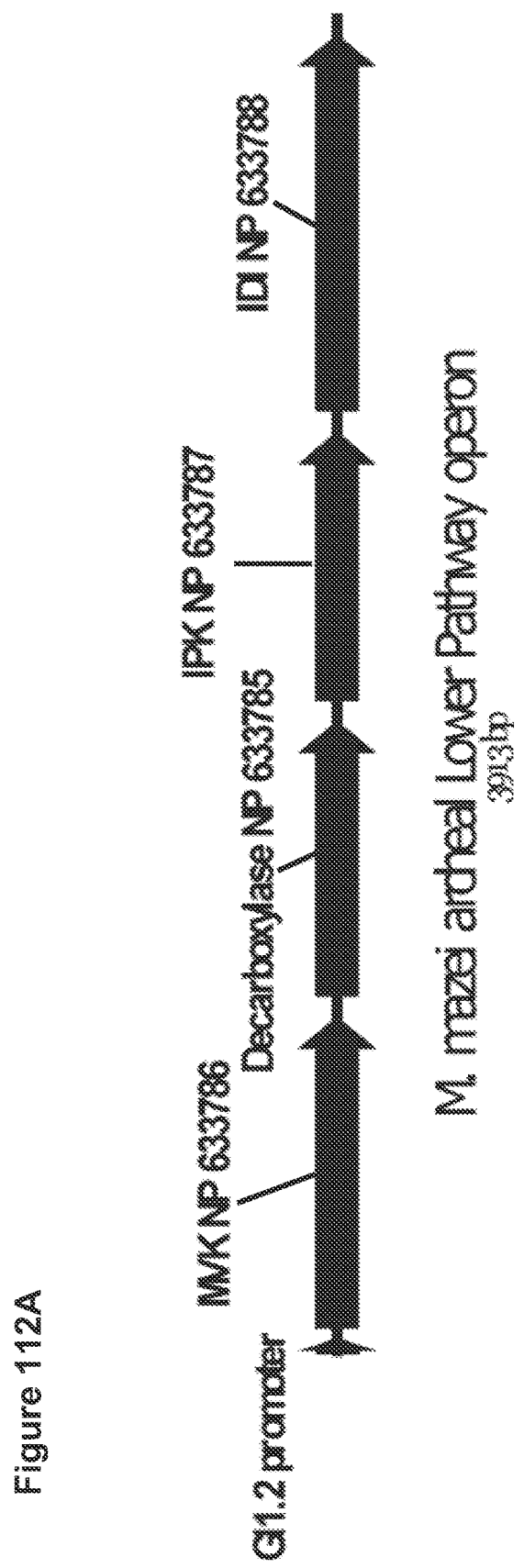

FIG. 112A is a map of the *M. mazei* archeal Lower Pathway operon.

FIGS. 112B-C are the nucleotide sequence of the *M. mazei* archeal lower Pathway operon (SEQ ID NO:27).

Figure 113A:
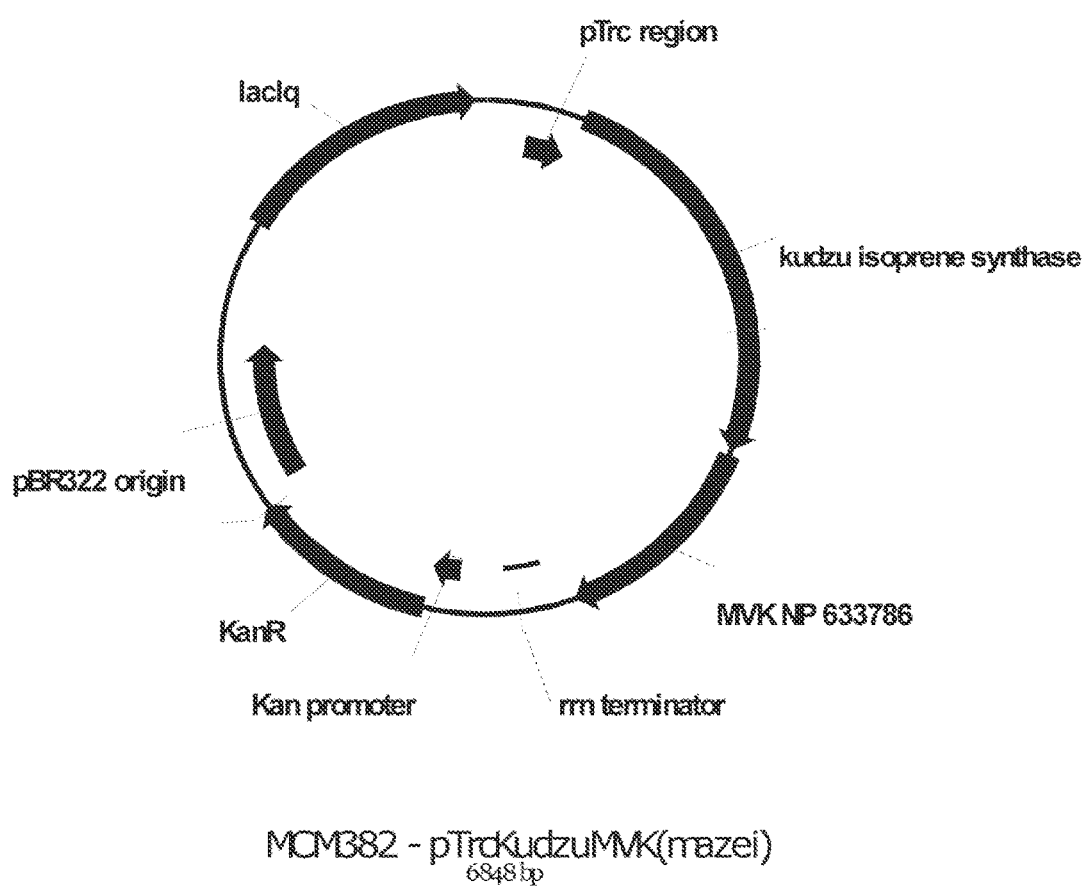

FIG. 113A is a map of MCM382-pTrcKudzuMVK (*mazei*).

FIGS. 113B-C are the nucleotide sequence of MCM382-pTrcKudzuMVK (*mazei*) (SEQ ID NO:28).

Figure 114A:
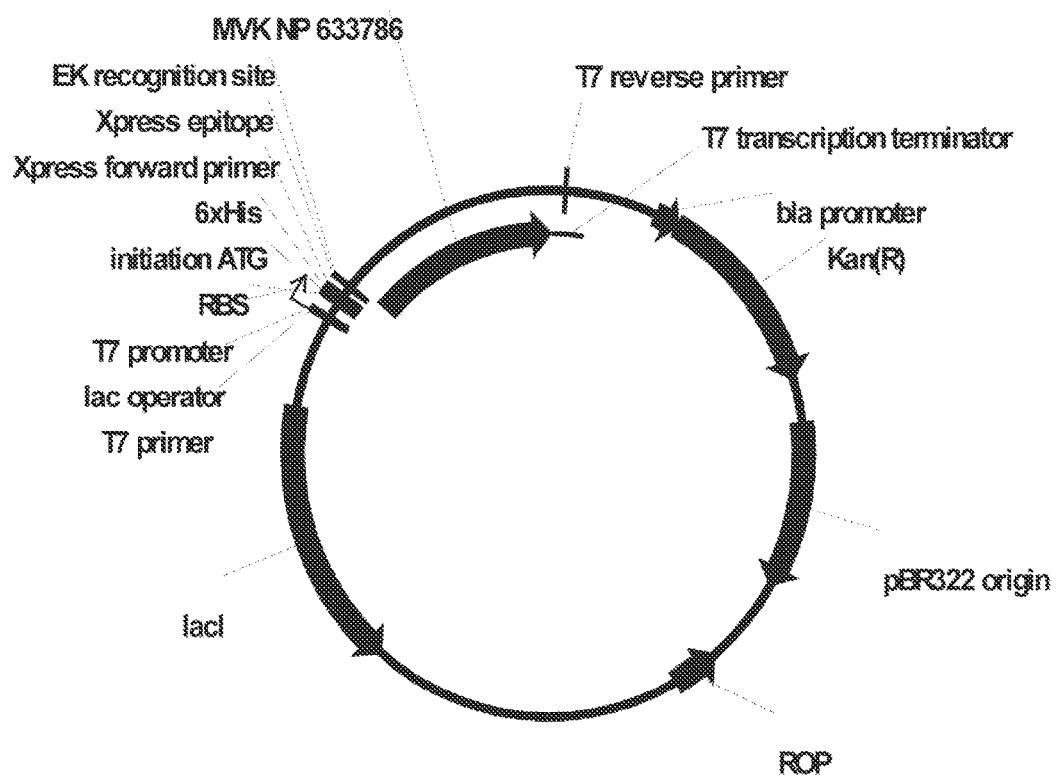

FIG. 114A is a map of MCM376-MVK from *M. mazei* archeal Lower in pET200D.

FIGS. 114B-C are the nucleotide sequence of MCM376-MVK from *M. mazei* archeal Lowerin pET200D (SEQ ID NO:29).

FIGS. 115A-115D demonstrate that over-expression of MVK and isoprene synthase results in increased isoprene production. Accumulated isoprene and $CO_2$ from MCM401 and MCM343 during growth on glucose in 100 mL bioreactors with 100 and 200 uM IPTG induction of isoprene production was measured over a 22 hour time course. FIG. 115A is a graph of the accumulated isoprene (%) from MCM343. FIG. 115B is a graph of the accumulated isoprene (%) from MCM401. FIG. 115C is a graph of the accumulated $CO_2$ (%) from MCM343. FIG. 115D is a graph of the accumulated $CO_2$ (%) from MCM401.

Figure 116:
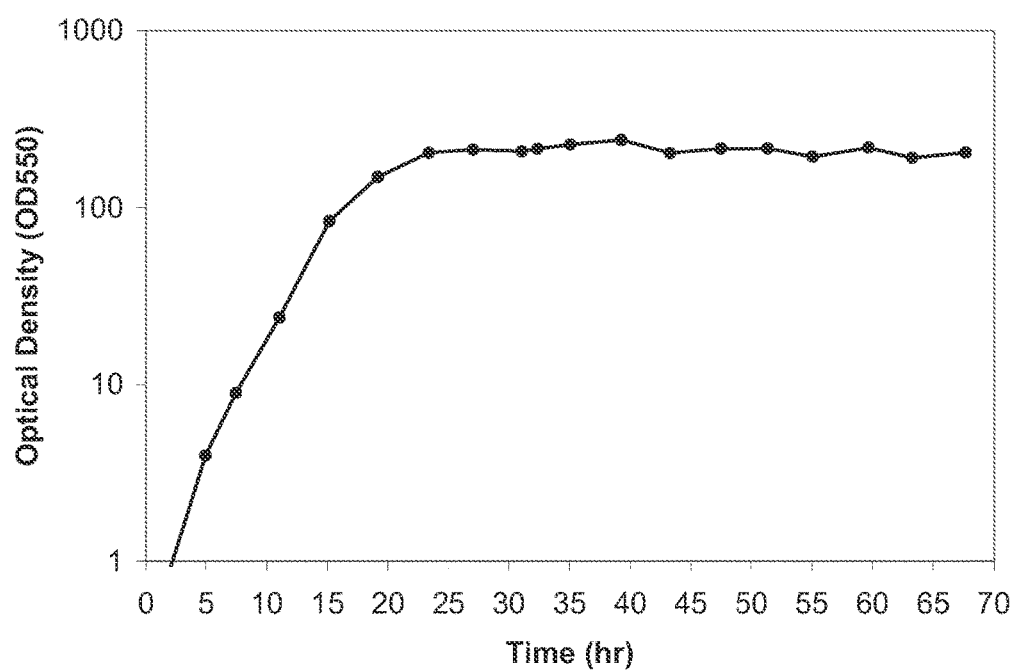

FIG. 116 is a time course of optical density within the 15-L bioreactor fed with glucose.

Figure 117:
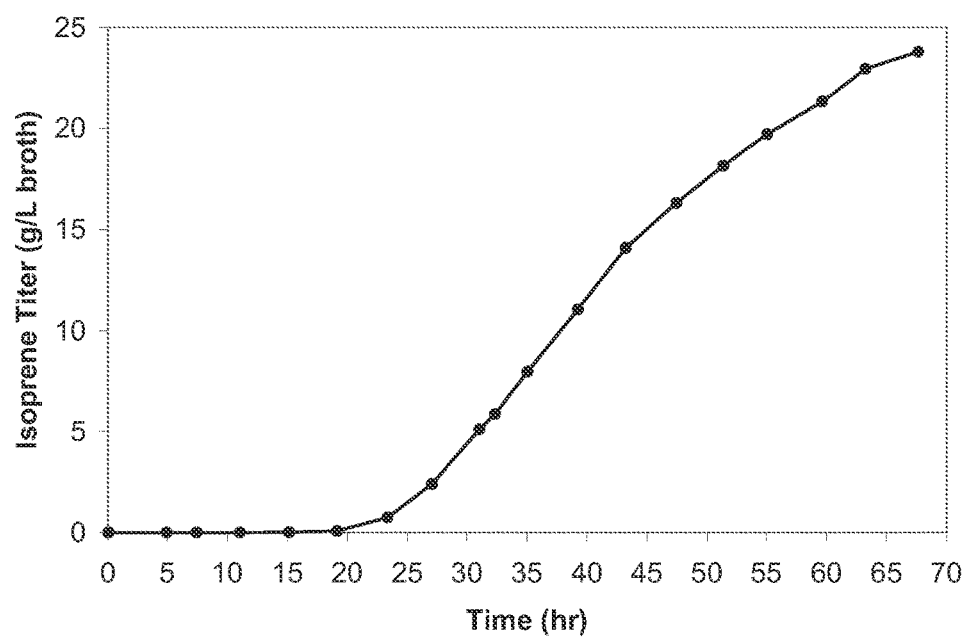

FIG. 117 is a time course of isoprene titer within the 15-L bioreactor fed with glucose. The titer is defined as the amount of isoprene produced per liter of fermentation broth.

Figure 118:
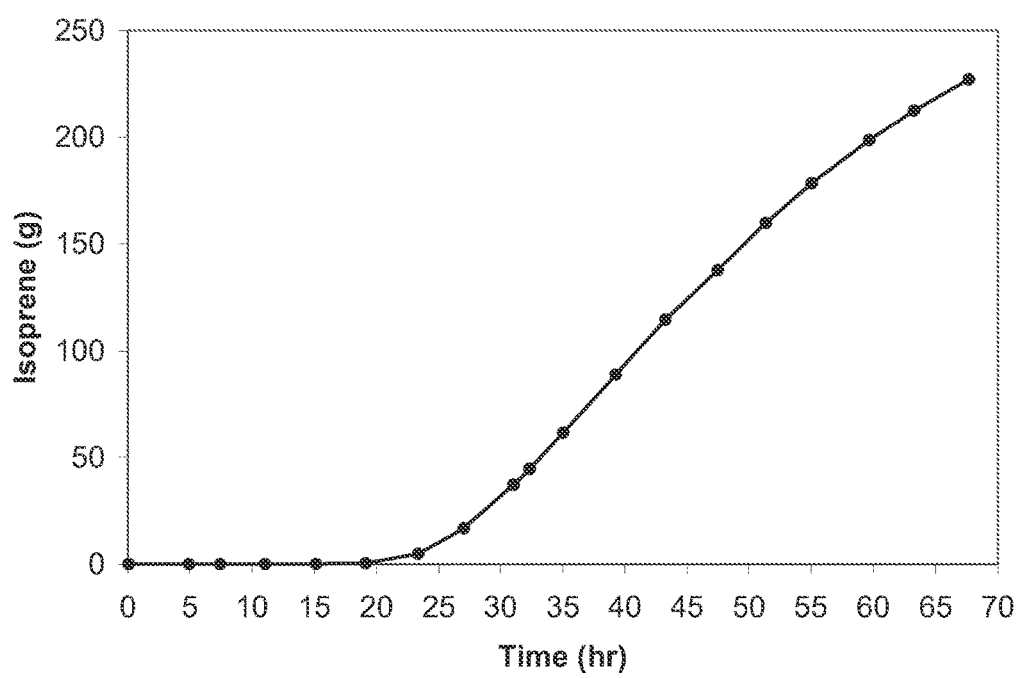

FIG. 118 is a time course of total isoprene produced from the 15-L bioreactor fed with glucose.

Figure 119:
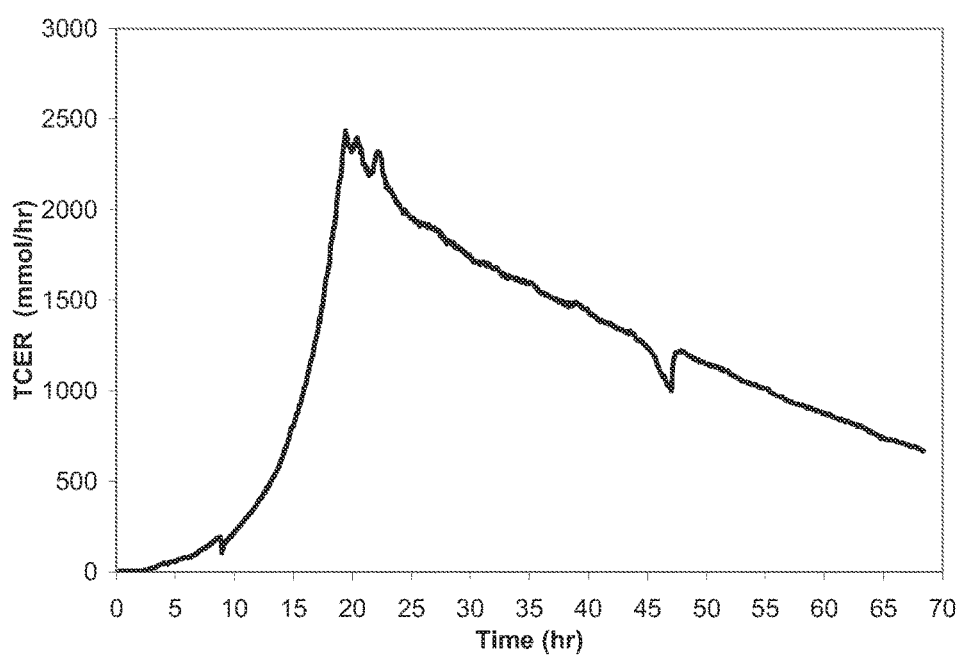

FIG. 119 is a graph of the total carbon dioxide evolution rate (TCER), or metabolic activity profile, within the 15-L bioreactor fed with glucose.

Figure 120:
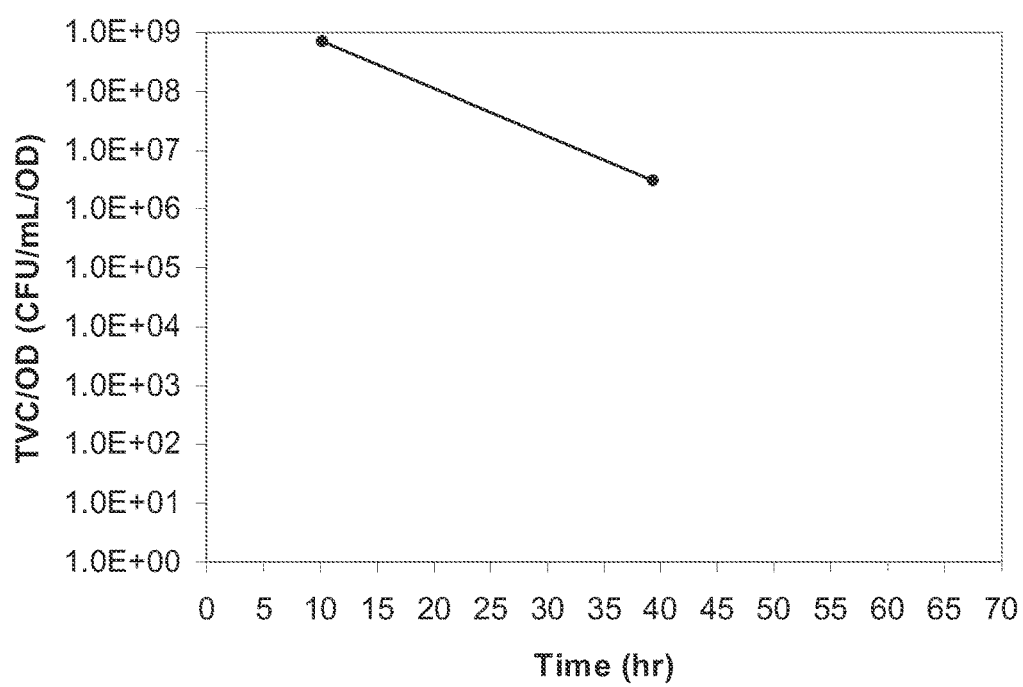

FIG. 120 is a graph of the cell viability during isoprene production within the 15-L bioreactor fed with glucose. TVC/OD is the total viable counts (colony forming units) in 1 mL of broth per optical density unit ($OD_{550}$).

Figure 121:
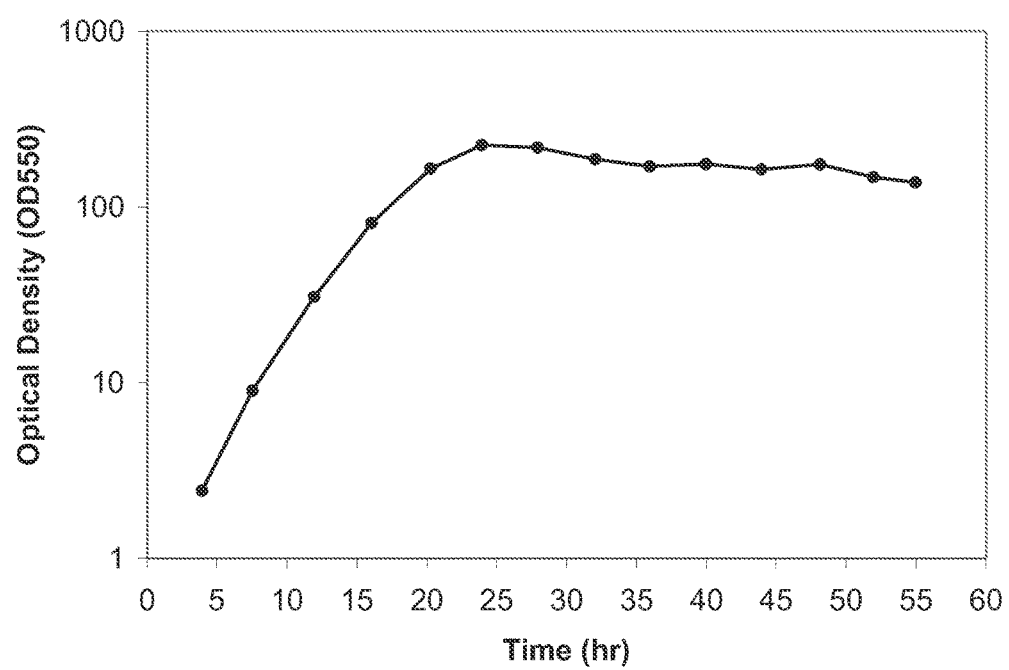

FIG. 121 is a time course of optical density within the 15-L bioreactor fed with glucose.

Figure 122:
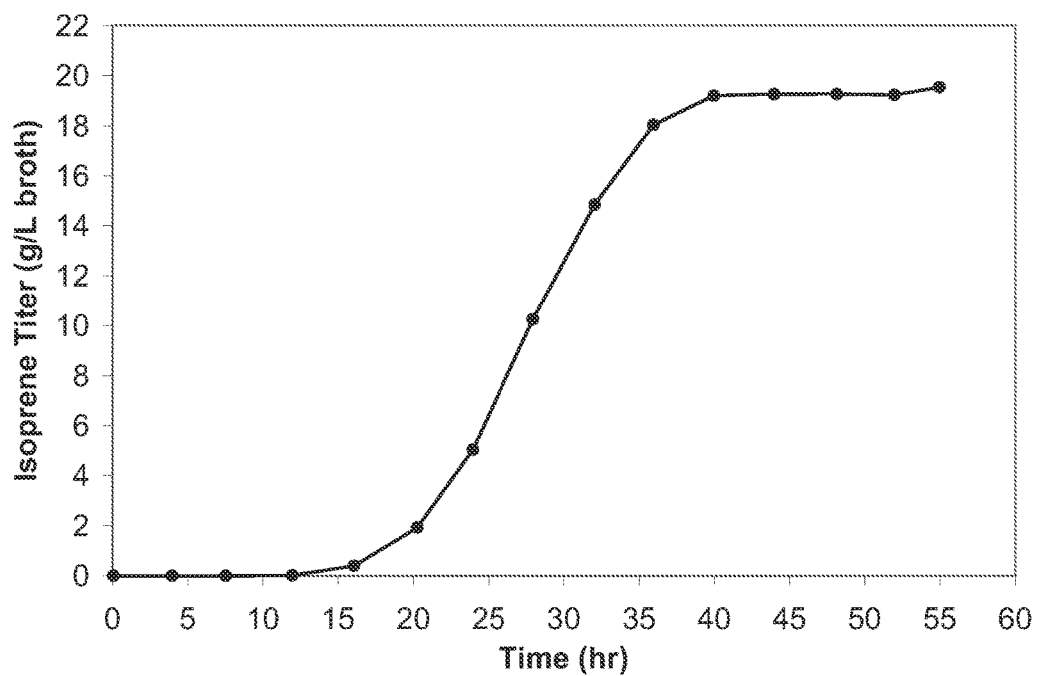

FIG. 122 is a time course of isoprene titer within the 15-L bioreactor fed with glucose. The titer is defined as the amount of isoprene produced per liter of fermentation broth.

Figure 123:
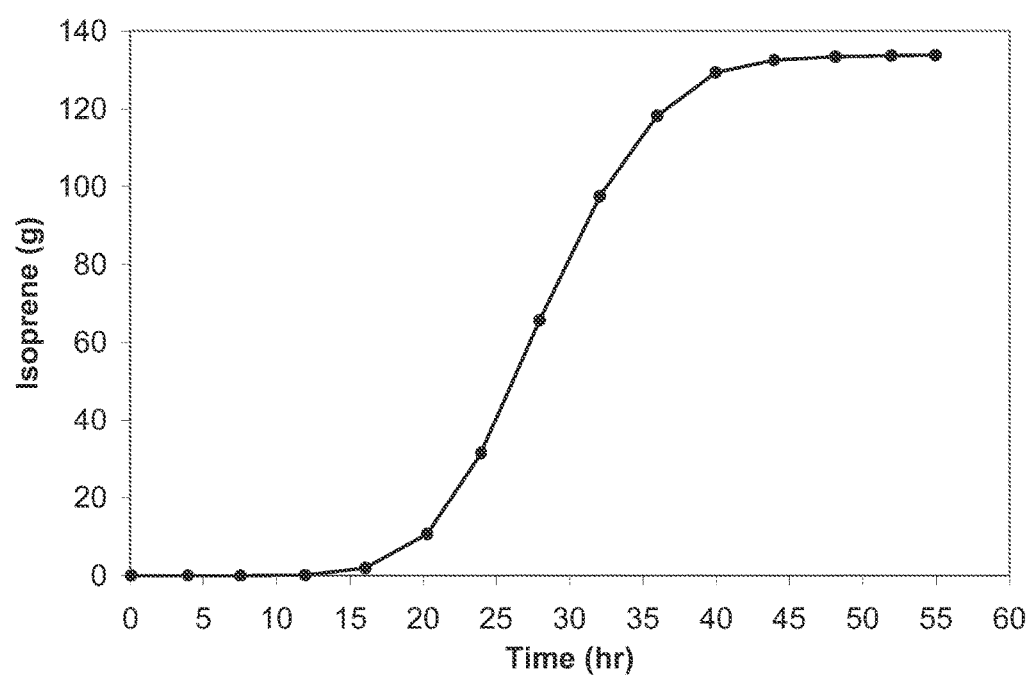

FIG. 123 is a time course of total isoprene produced from the 15-L bioreactor fed with glucose.

Figure 124:
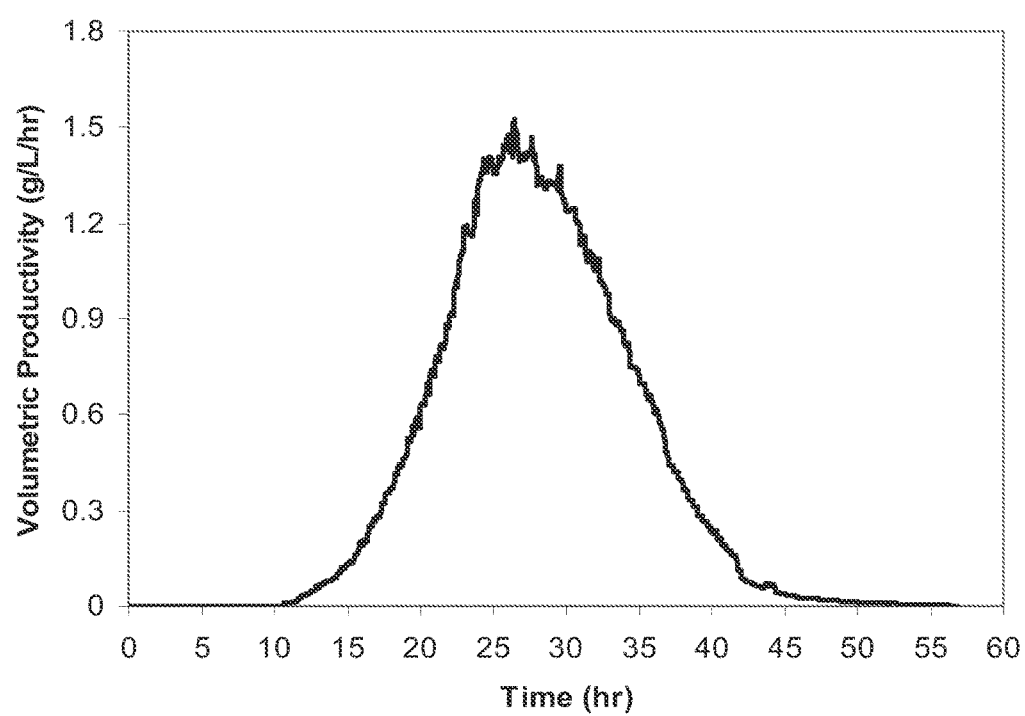

FIG. 124 is a time course of volumetric productivity within the 15-L bioreactor fed with glucose. The volumetric productivity is defined as the amount of isoprene produced per liter of broth per hour.

Figure 125:
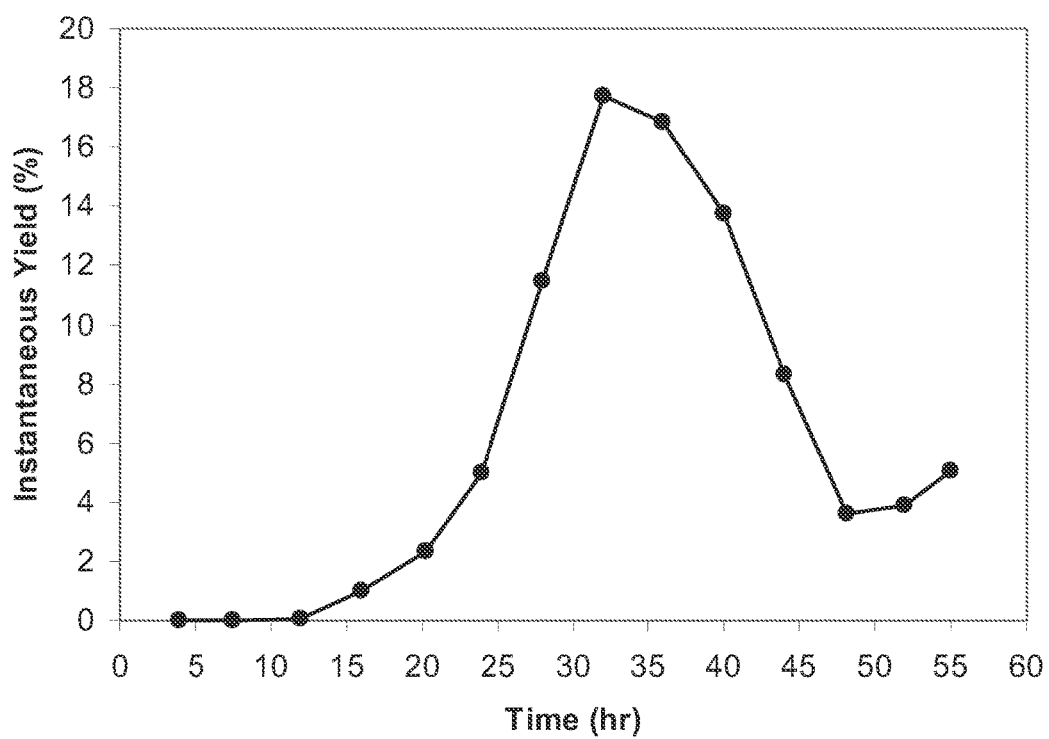

FIG. 125 is a time course of instantaneous yield within the 15-L bioreactor fed with glucose. The instantaneous yield is defined as the amount of isoprene (gram) produced per amount of glucose (gram) fed to the bioreactor (w/w) during the time interval between the data points.

Figure 126:
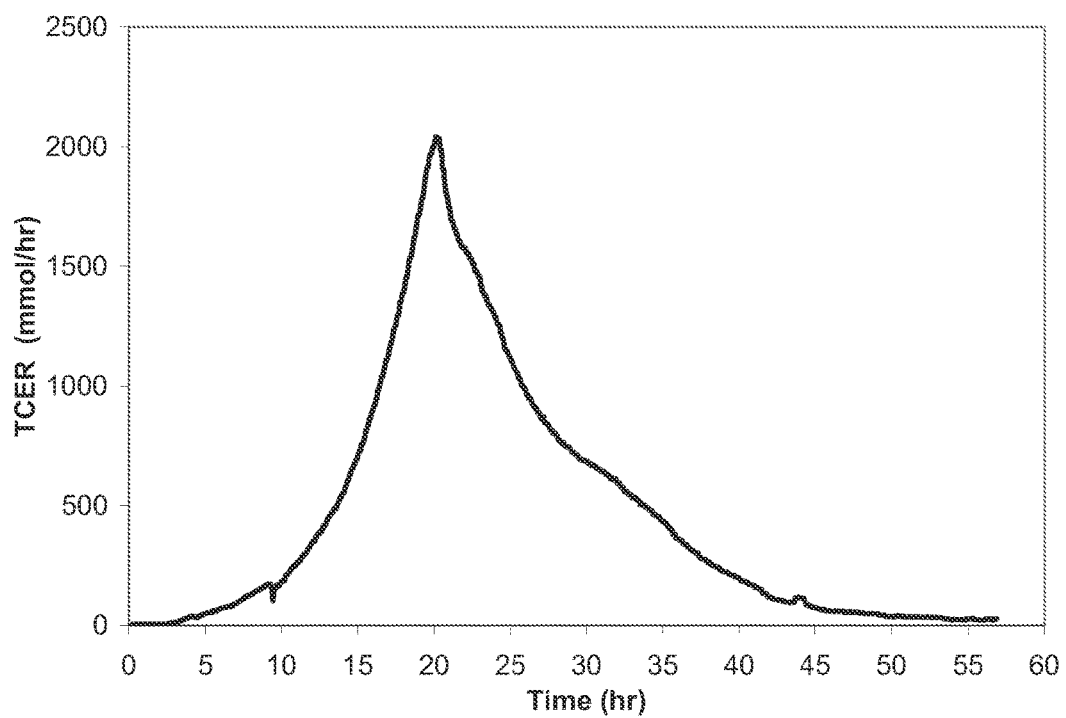

FIG. 126 is a graph of the total carbon dioxide evolution rate (TCER), or metabolic activity profile, within the 15-L bioreactor fed with glucose.

Figure 127:
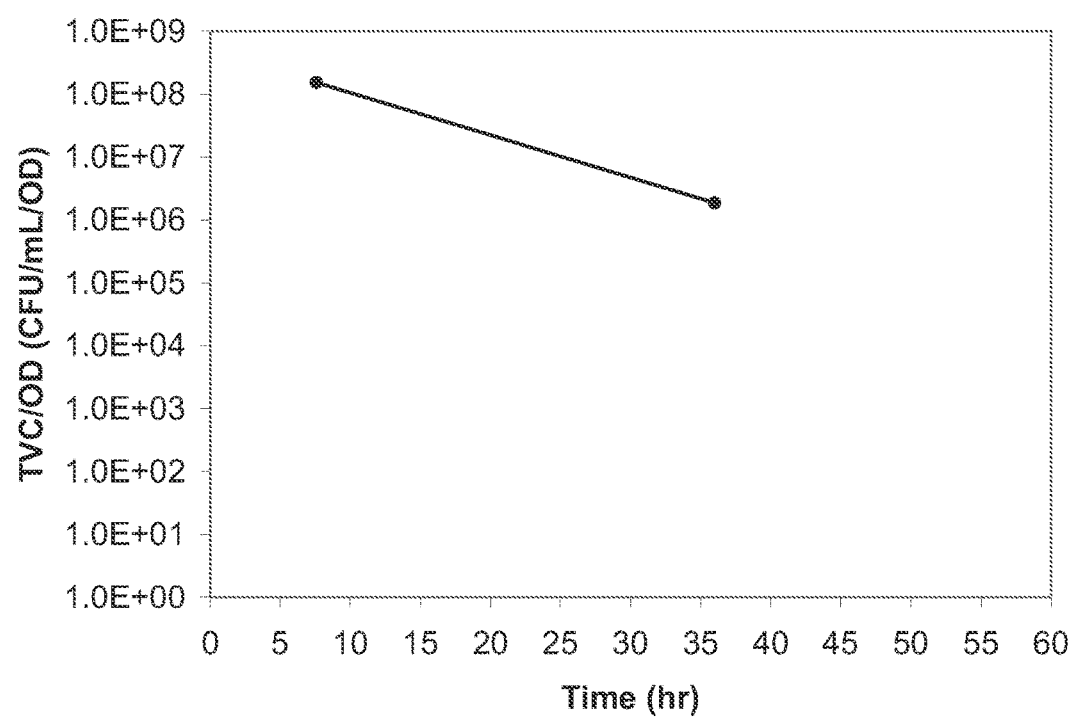

FIG. 127 is cell viability during isoprene production within the 15-L bioreactor fed with glucose. TVC/OD is the total viable counts (colony forming units) in 1 mL of broth per optical density unit ($OD_{550}$).

Figure 128:
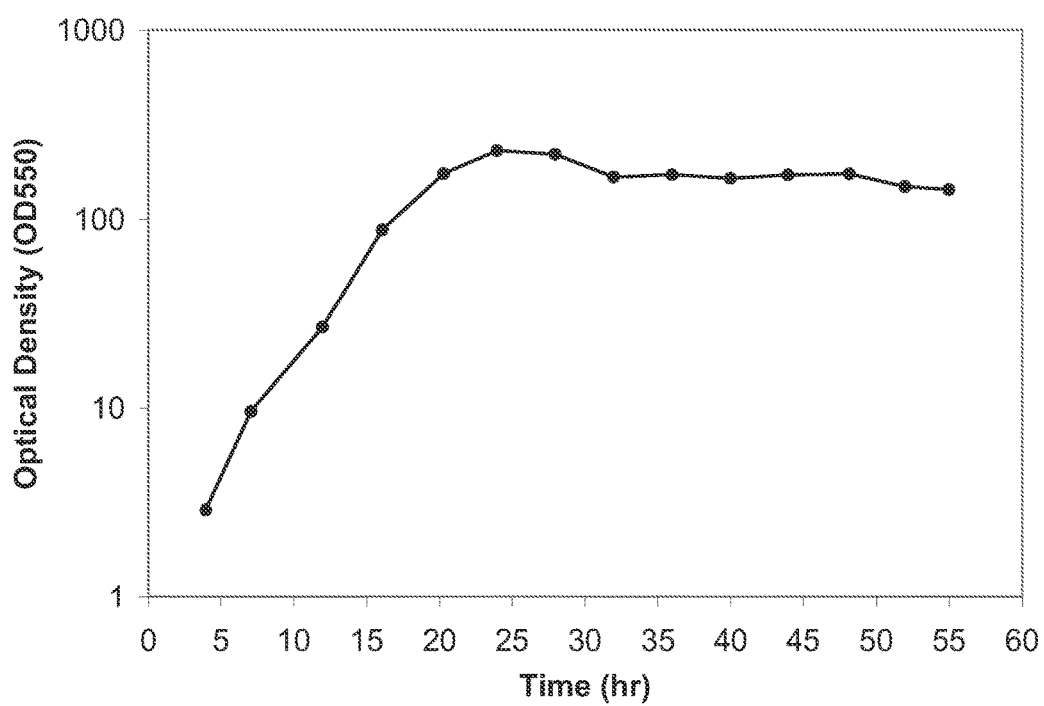

FIG. 128 is a time course of optical density within the 15-L bioreactor fed with glucose.

Figure 129:
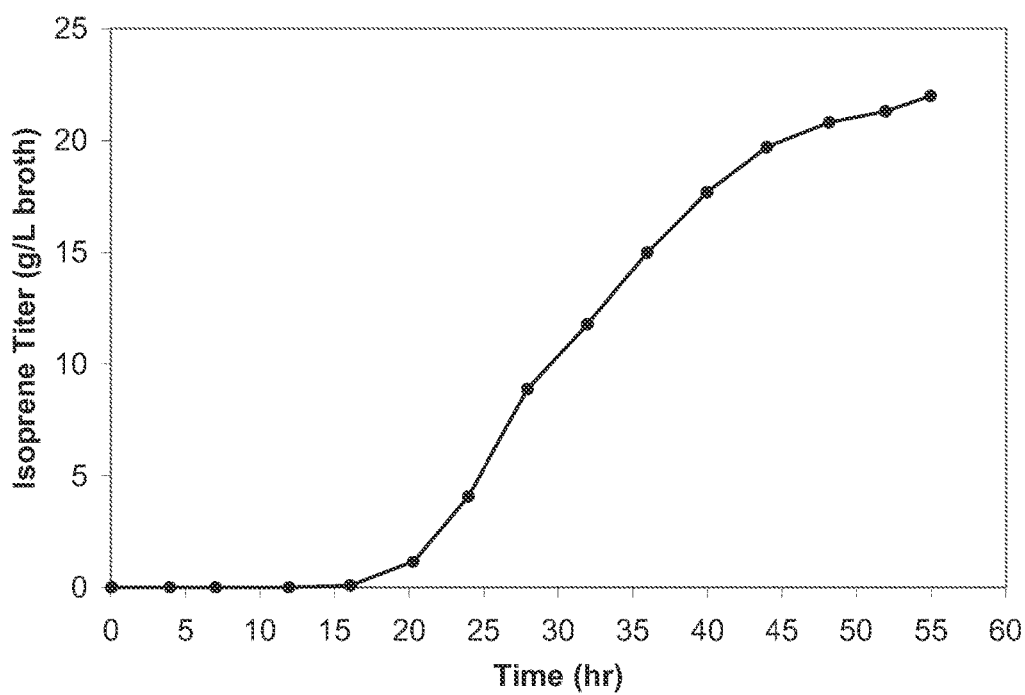

FIG. 129 is a time course of isoprene titer within the 15-L bioreactor fed with glucose. The titer is defined as the amount of isoprene produced per liter of fermentation broth.

Figure 130:
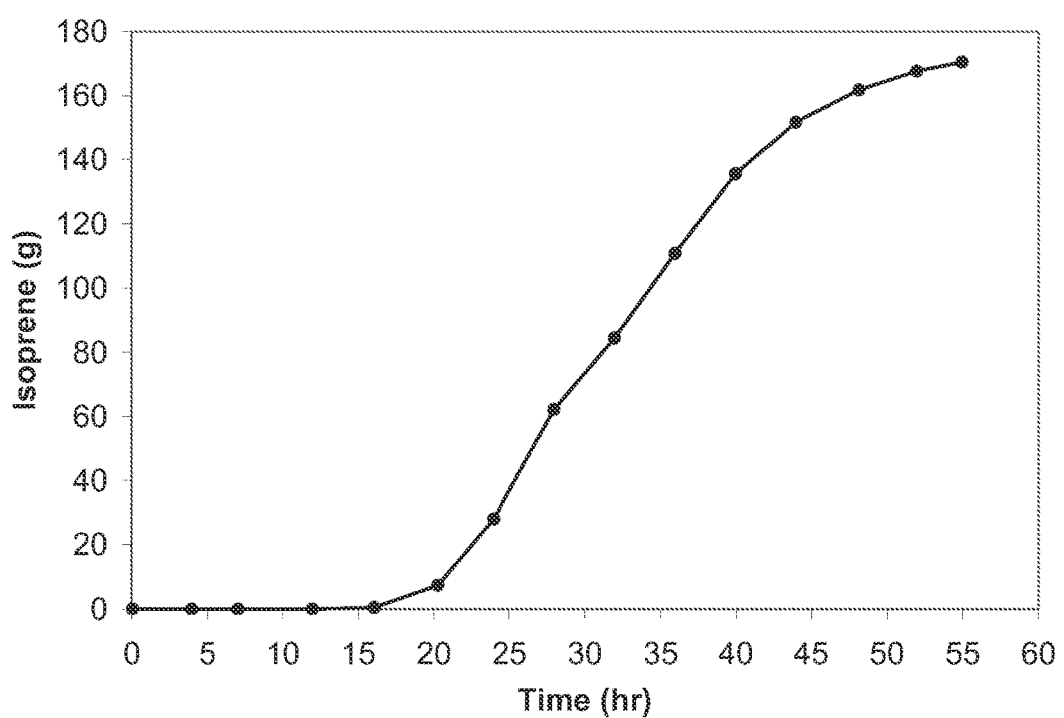

FIG. 130 is a time course of total isoprene produced from the 15-L bioreactor fed with glucose.

Figure 131:
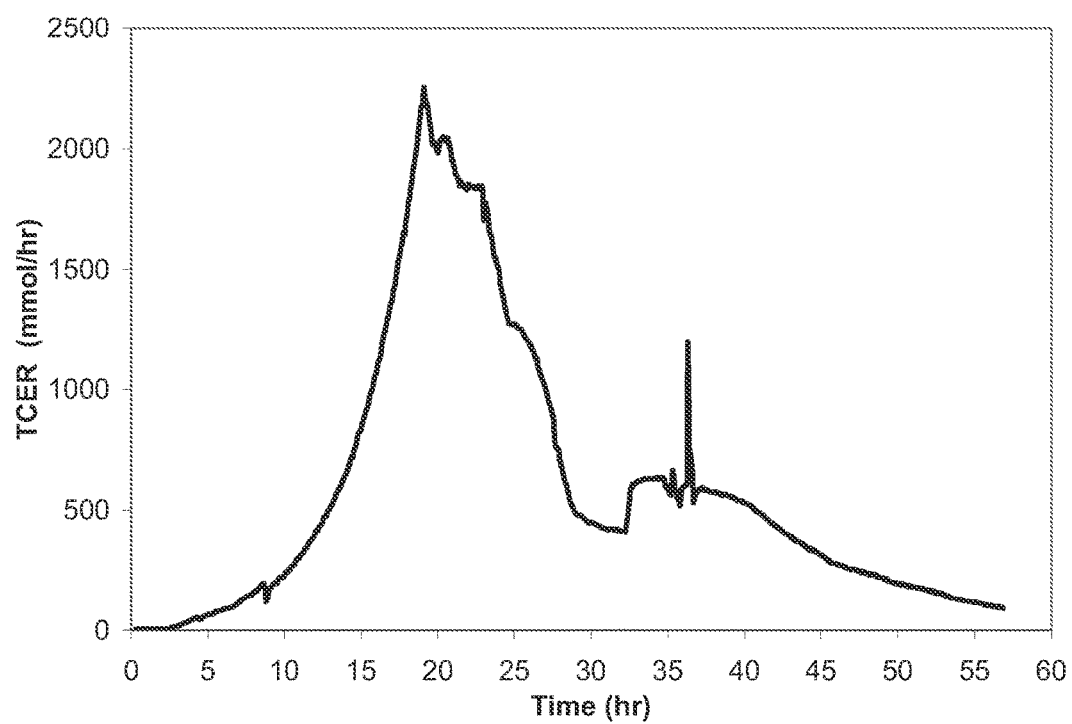

FIG. 131 is a graph of total carbon dioxide evolution rate (TCER), or metabolic activity profile, within the 15-L bioreactor fed with glucose.

Figure 132:
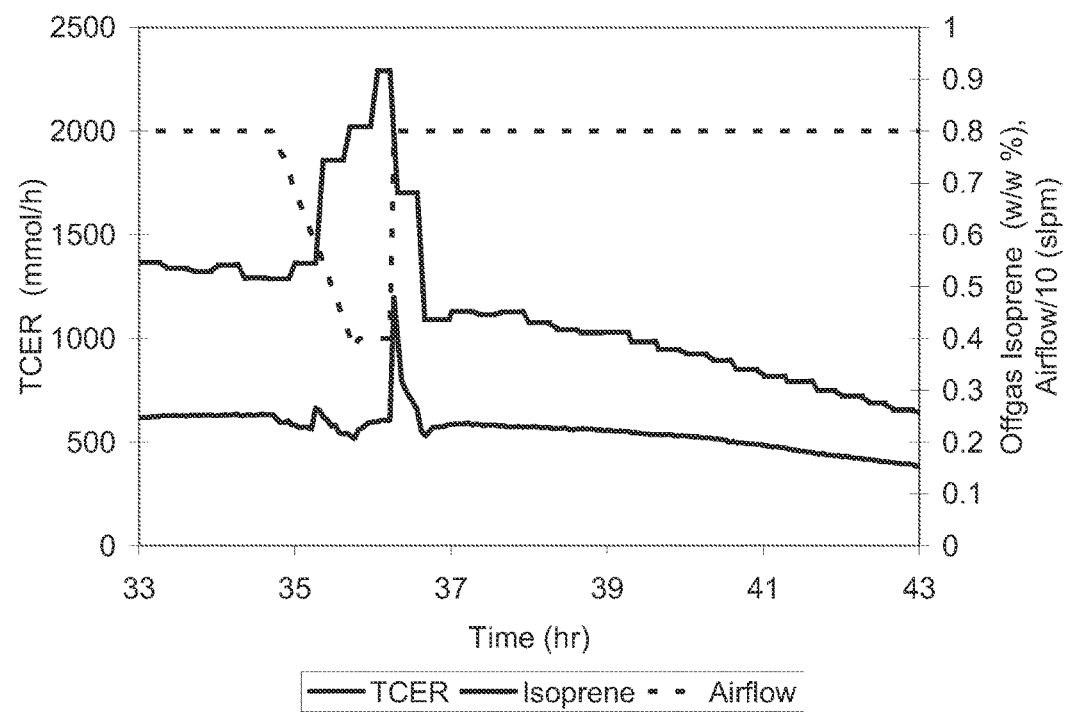

FIG. 132 is a graph showing that a transient decrease in the airflow to the bioreactor caused a spike in the concentration of isoprene in the offgas that did not cause a dramatic decrease in metabolic activity (TCER). TCER, or metabolic activity, is the total carbon dioxide evolution rate.

Figure 133:
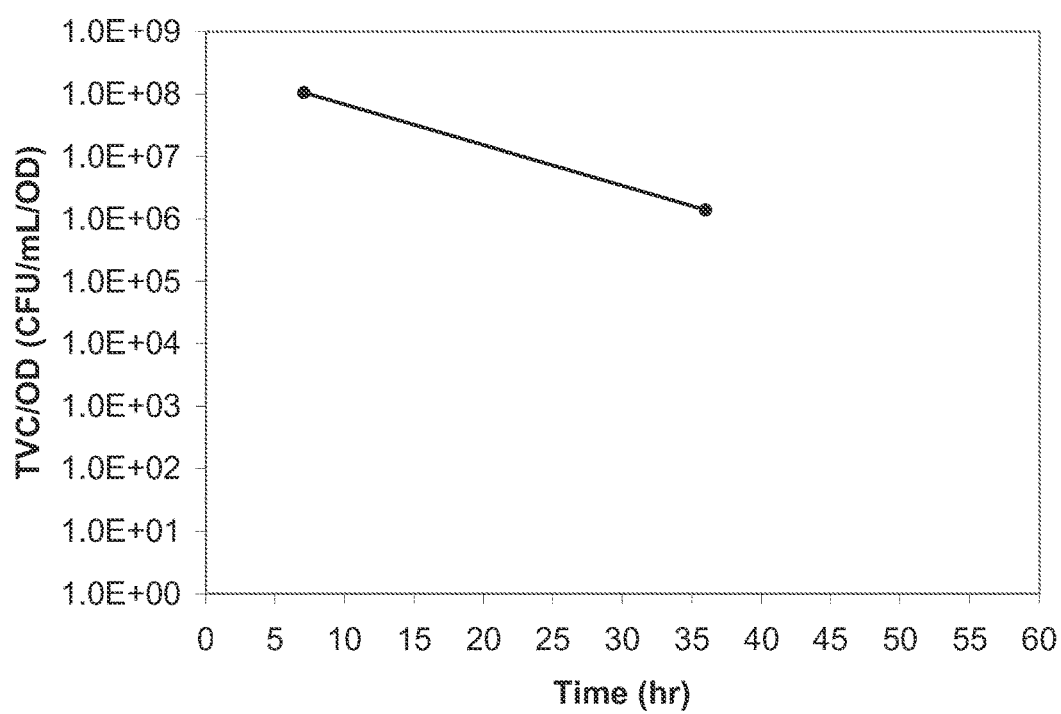

FIG. 133 is a graph of the cell viability during isoprene production within the 15-L bioreactor fed with glucose. TVC/OD is the total viable counts (colony forming units) in 1 mL of broth per optical density unit ($OD_{550}$).

Figure 134:
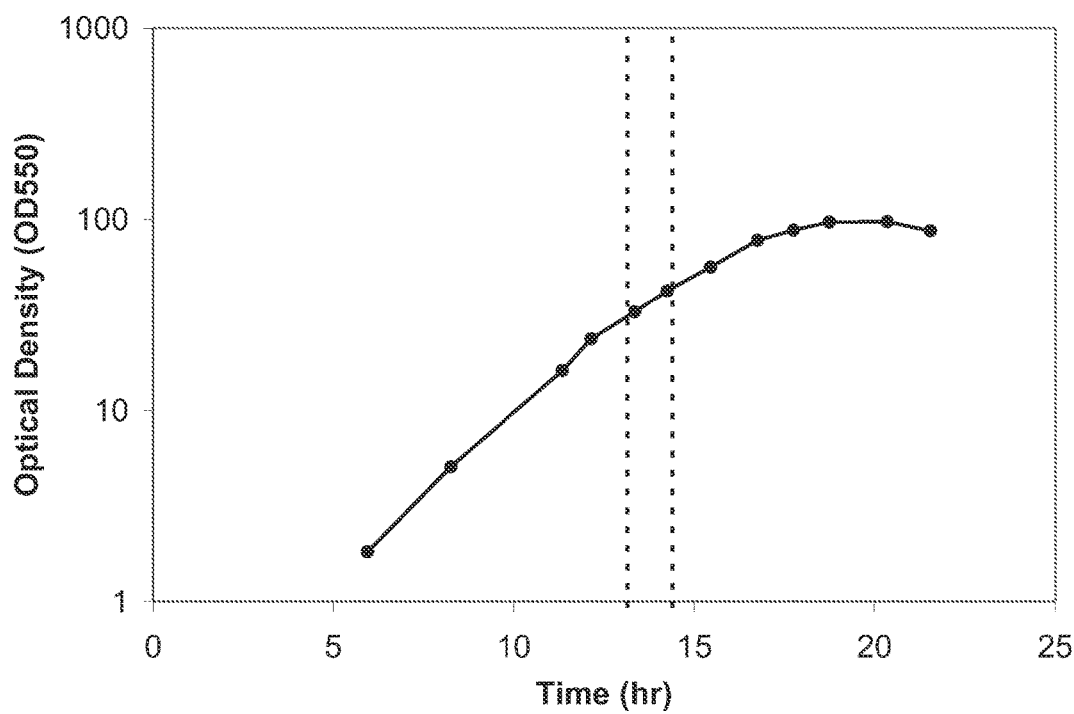

FIG. 134 is a time course of optical density within the 15-L bioreactor fed with glucose. Dotted vertical lines denote the time interval when isoprene was introduced into the bioreactor at a rate of 1 g/L/hr.

Figure 135:
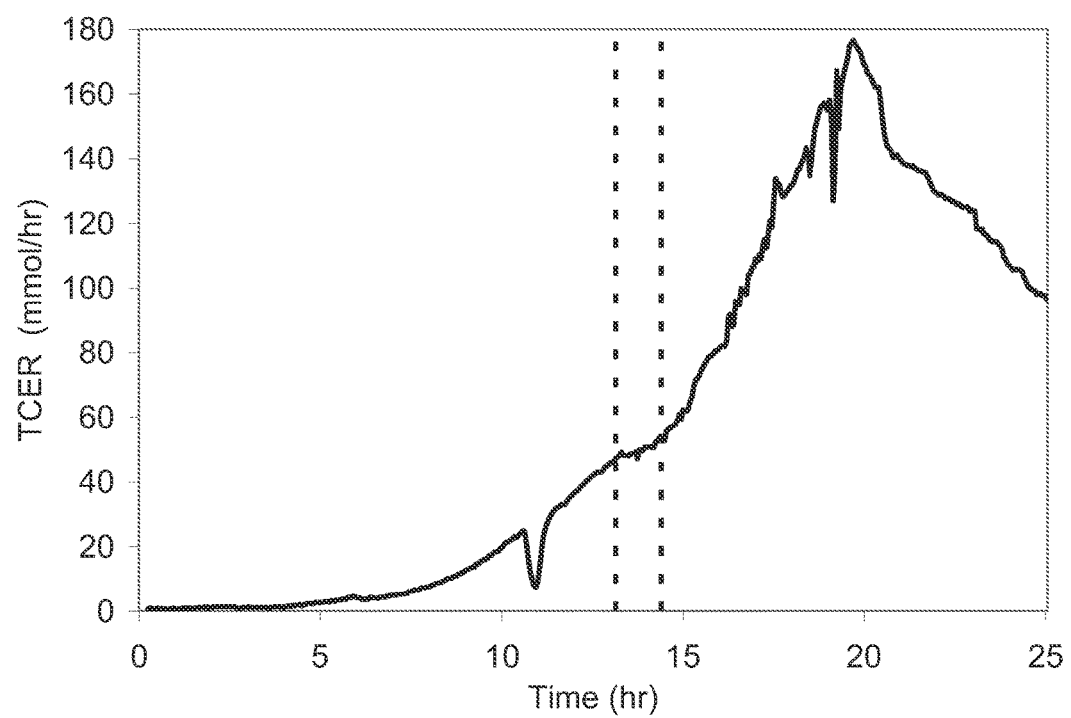

FIG. 135 is total carbon dioxide evolution rate (TCER), or metabolic activity profile, within the 15-L bioreactor fed with glucose. Dotted vertical lines denote the time interval when isoprene was introduced into the bioreactor at a rate of 1 g/L/hr.

Figure 136:
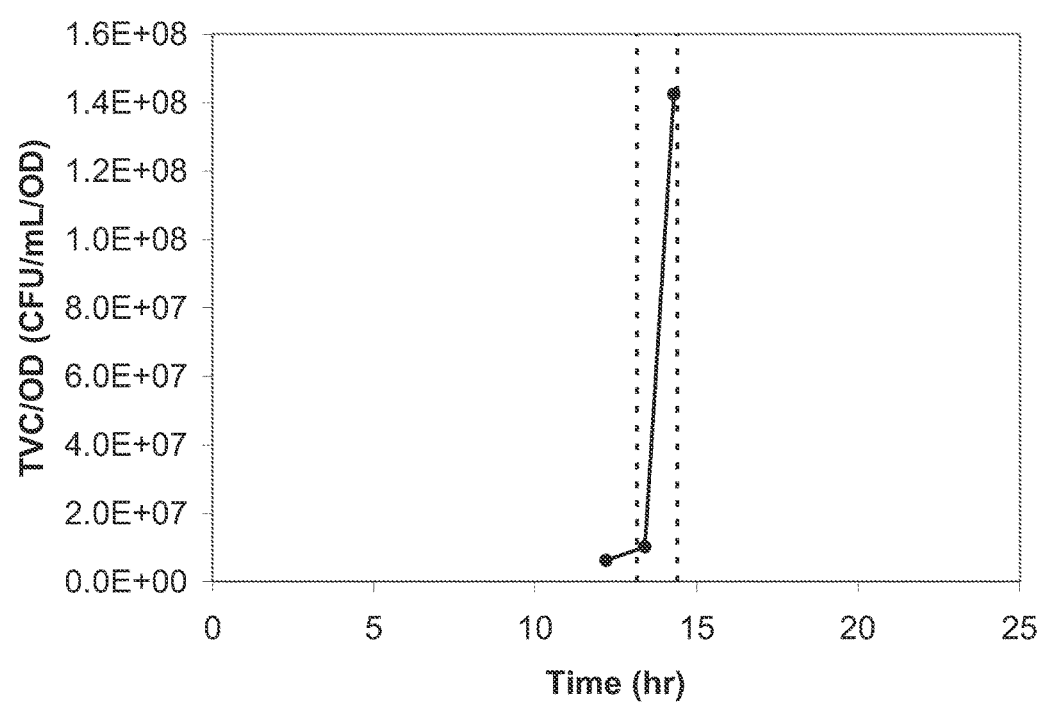

FIG. 136 is cell viability during isoprene production within the 15-L bioreactor fed with glucose. TVC/OD is the total viable counts (colony forming units) in 1 mL of broth per optical density unit ($OD_{550}$). Dotted vertical lines denote the time interval when isoprene was introduced into the bioreactor at a rate of 1 g/L/hr.

FIGS. 137A-B are the sequence of *Populus alba* pET24a: isoprene synthase gene highlighted in bold letters (SEQ ID NO:30).

FIGS. 137C-D are the sequence of *Populus nigra* pET24a: isoprene synthase gene highlighted in bold letters (SEQ ID NO:31).

FIGS. 137E-F are the sequence of *Populus tremuloides* pET24a (SEQ ID NO:32).

FIG. 137G is the amino acid sequence of *Populus tremuloides* isoprene synthase gene (SEQ ID NO:33).

FIGS. 137H-I are the sequence of *Populus trichocarpa* pET24a: isoprene synthase gene highlighted in bold letters (SEQ ID NO:34).

FIGS. 137J-K are the sequence of *Populus tremula×Populus alba* pET24a: isoprene synthase gene highlighted in bold letters (SEQ ID NO:35).

Figure 137L:
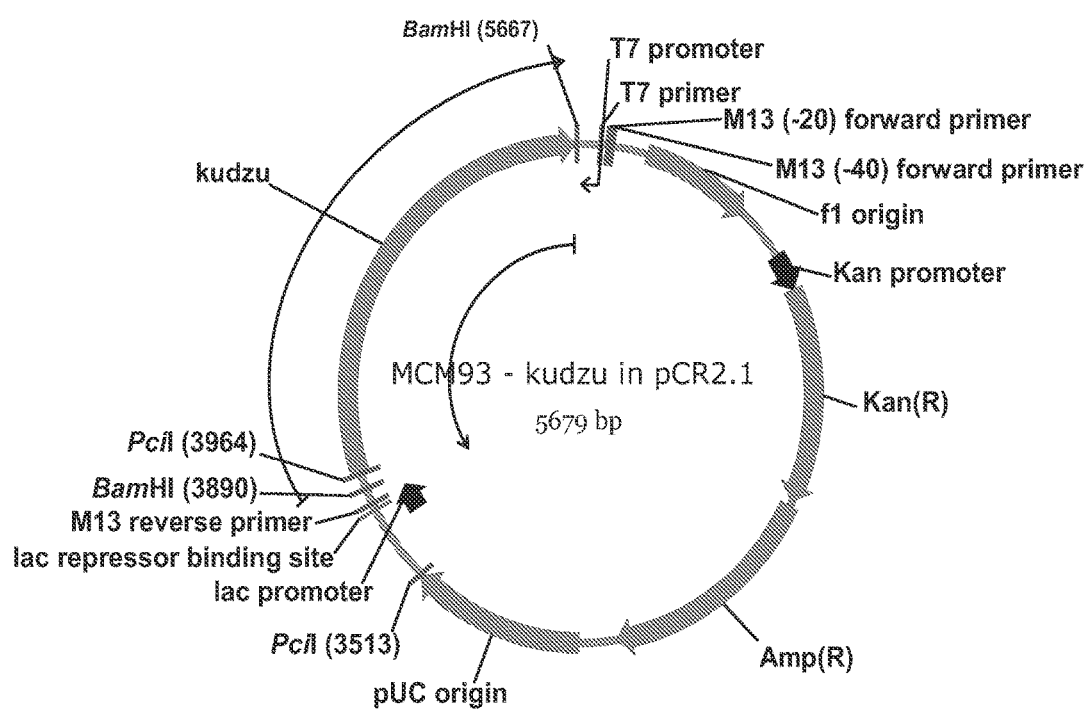

FIG. 137L is a map of MCM93 which contains the kudzu IspS coding sequence in a pCR2.1 backbone.

FIGS. 137M-N are the sequence of MCM93 (SEQ ID NO:36).

Figure 137O:
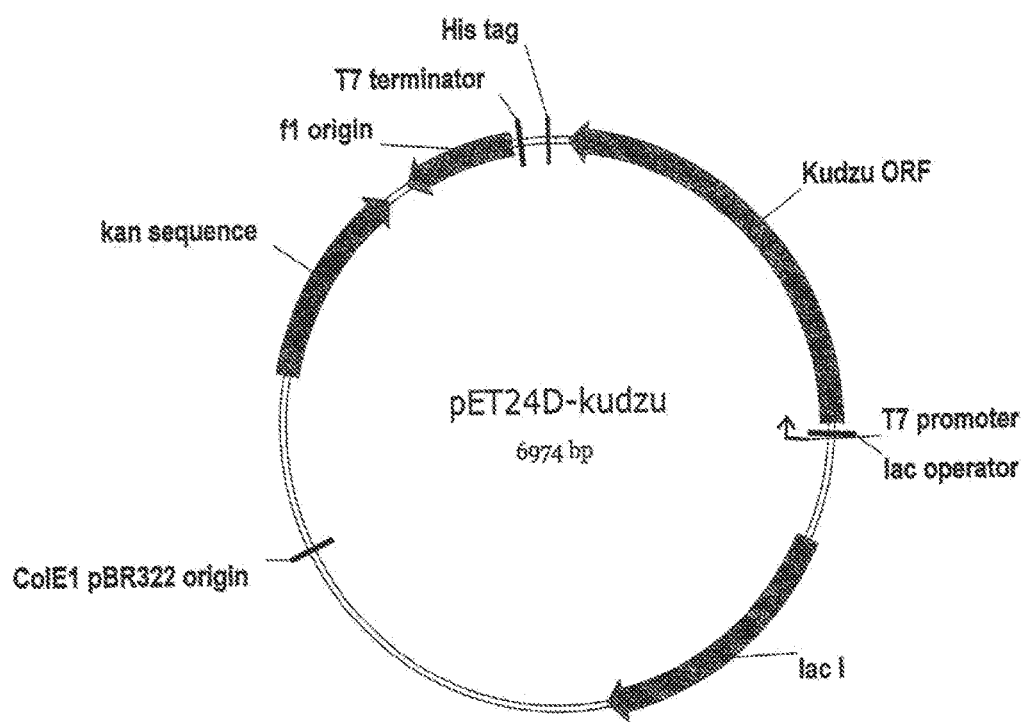

FIG. 137O is a map of pET24D-Kudzu.

FIGS. 137P-Q are the sequence of pET24D-Kudzu (SEQ ID NO:37).

Figure 138:
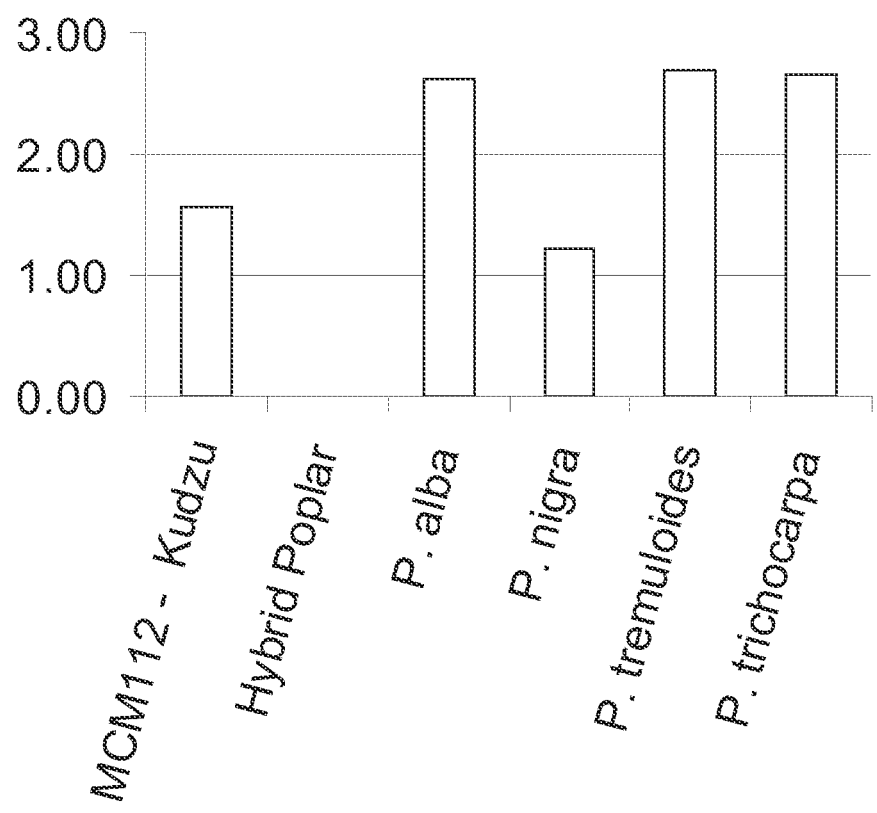

FIG. 138 is isoprene synthase expression data for various poplar species as measured in the whole cell head space assay. Y-axis is ug/L/OD of isoprene produced by 0.2 mL of a culture induced with IPTG.

Figure 139:
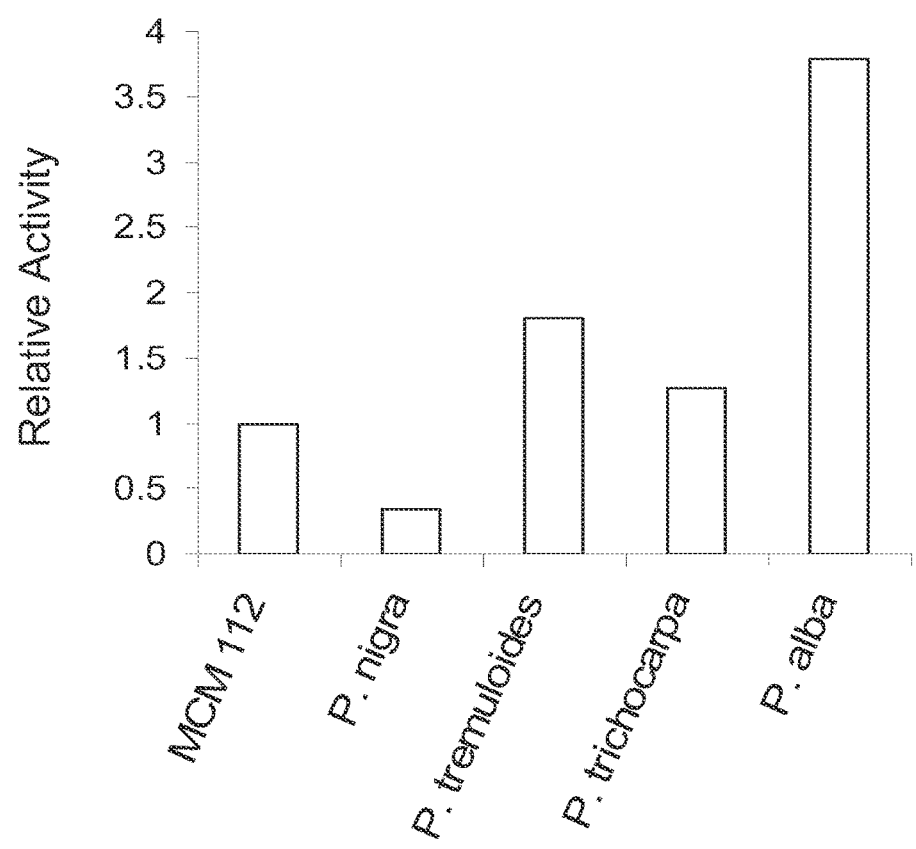

FIG. 139 is relative activity of Poplar isoprene synthase enzymes as measured by DMAPP assay. Poplar enzymes have significantly higher activity than the isoprene synthase from Kudzu. Poplar [*alba×tremula*] only had traces (<1%) of activity and is not shown in the plot.

Figure 140:
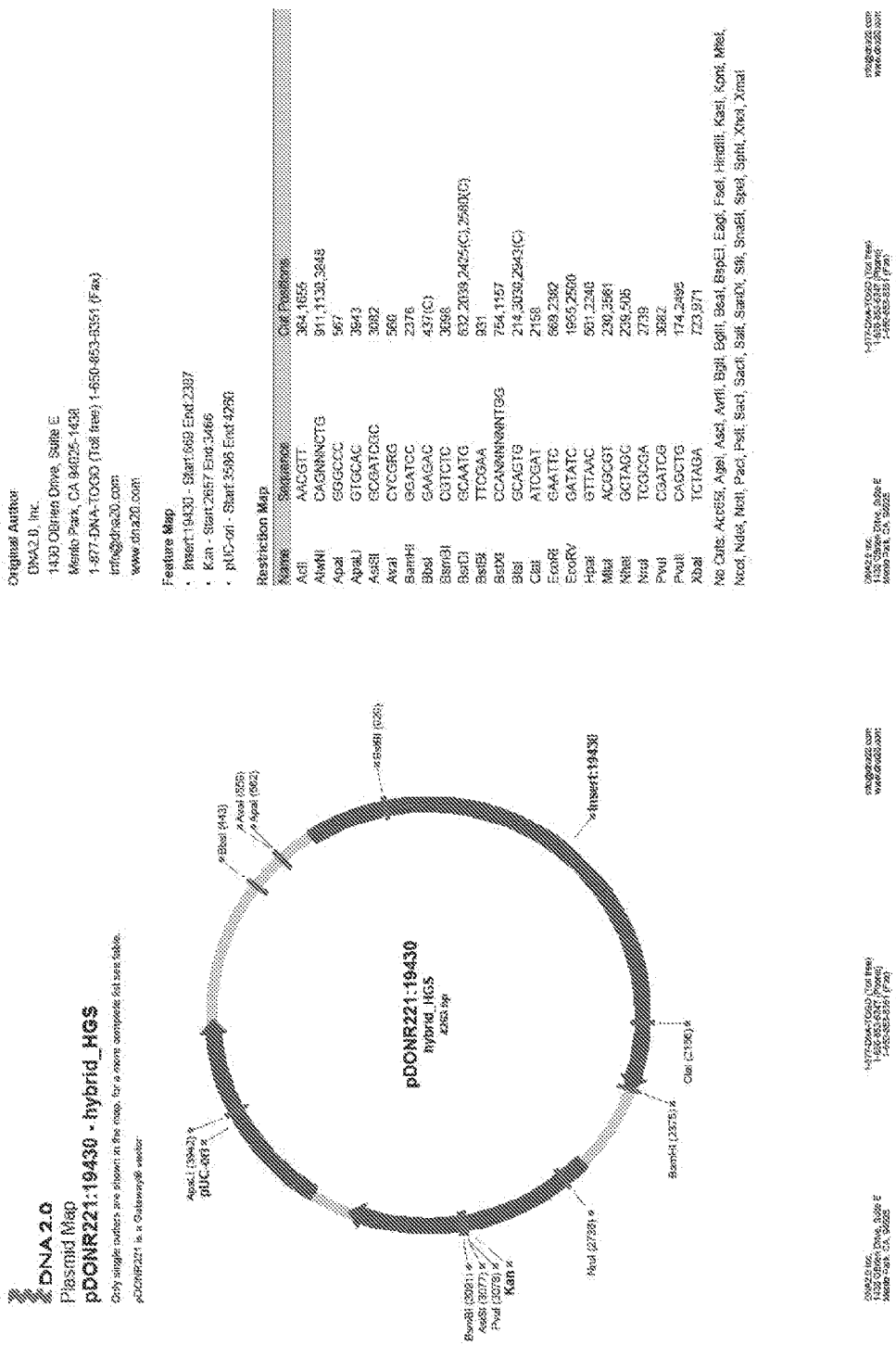

FIG. 140 is a map of pDONR221:19430-hybrid_HGS (BstXI restriction site) (SEQ ID NO:188).

FIG. 141 is the nucleotide sequence of pDONR221:19430-hybrid_HGS, the sequence of Kudzu isoprene synthase codon-optimized for yeast (SEQ ID NO:38).

Figure 142A:
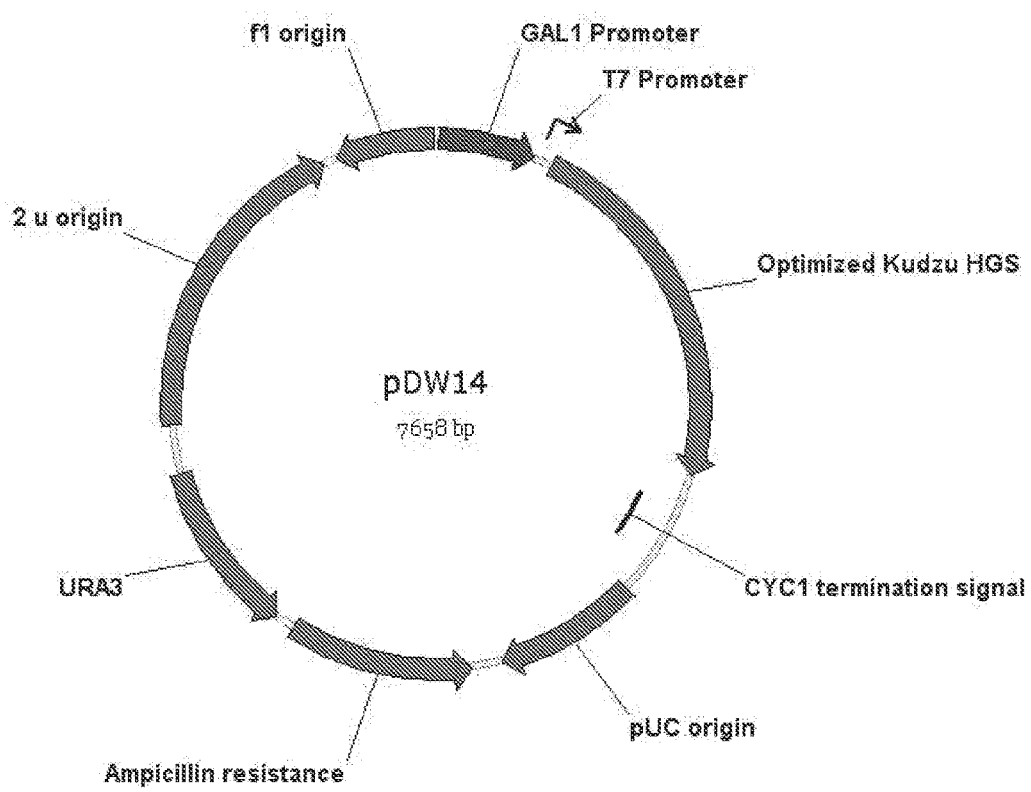

FIG. 142A is a map of pDW14.

FIGS. 142B-C are the complete nucleotide sequence of pDW14 (SEQ ID NO:39).

Figure 143:
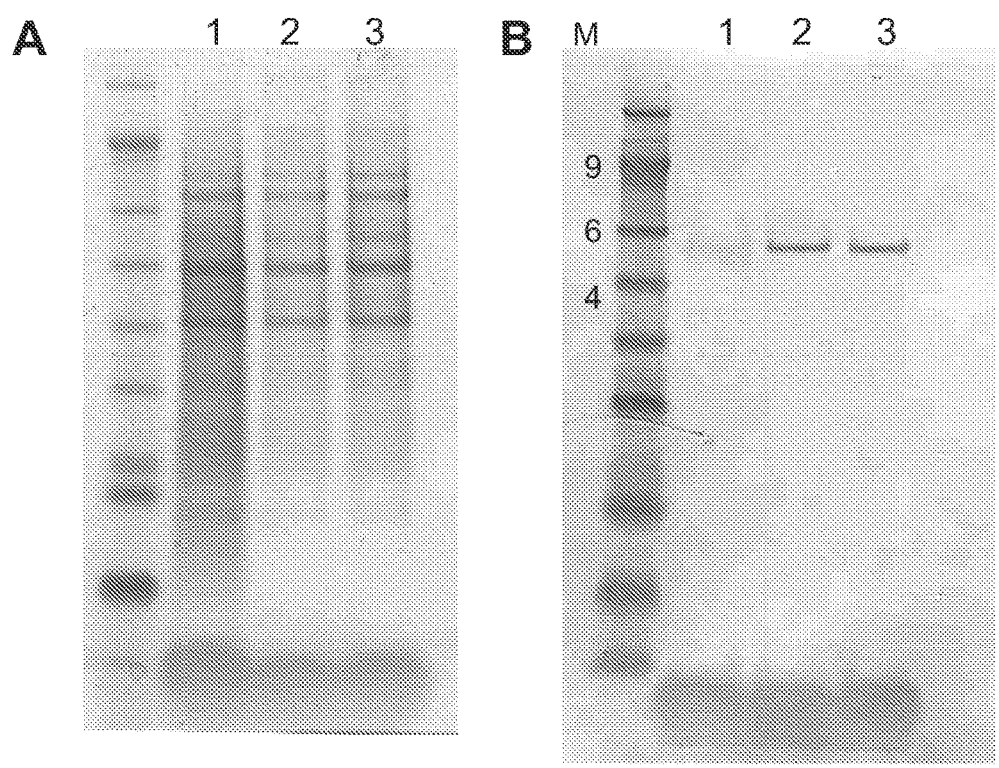

FIG. 143 shows induced INVSc-1 strains harboring pDW14 or pYES-DEST52. FIG. 143A. A 4-12% bis tris gel (Novex, Invitrogen) of lysates generated from INVSc-1 strains induced with galactose and stained with SimplylBlue SafeStain (Invitrogen). FIG. 143B. Western blot analysis of the same strains using the WesternBreeze kit (Invitrogen). Lanes are as follows: 1, INVSc-1+pYES-DEST52; 2, INVSc-1+pDW14 (isolate 1); 3, INVSc-1+pDW14 (isolate 2). MW (in kDa) is indicated (using the SeeBlue Plus2 molecular weight standard).

FIGS. 144A-B show induced INVSc-1 strains harboring pDW14 or pYES-DEST52. FIG. 144A. $OD_{600}$ of galactose-induced strains prior to lysis. The y-axis is $OD_{600}$. FIG. 144B. DMAPP assay of isoprene synthase headspace in control and isoprene synthase-harboring strains. Specific activity was calculated as g HG/L/OD. Samples are as follows: Control, INVSc-1+pYES-DEST52; HGS-1, INVSc-1+pDW14 (isolate 1); HGS-2, INVSc-1+pDW14 (isolate 2).

Figure 145A:
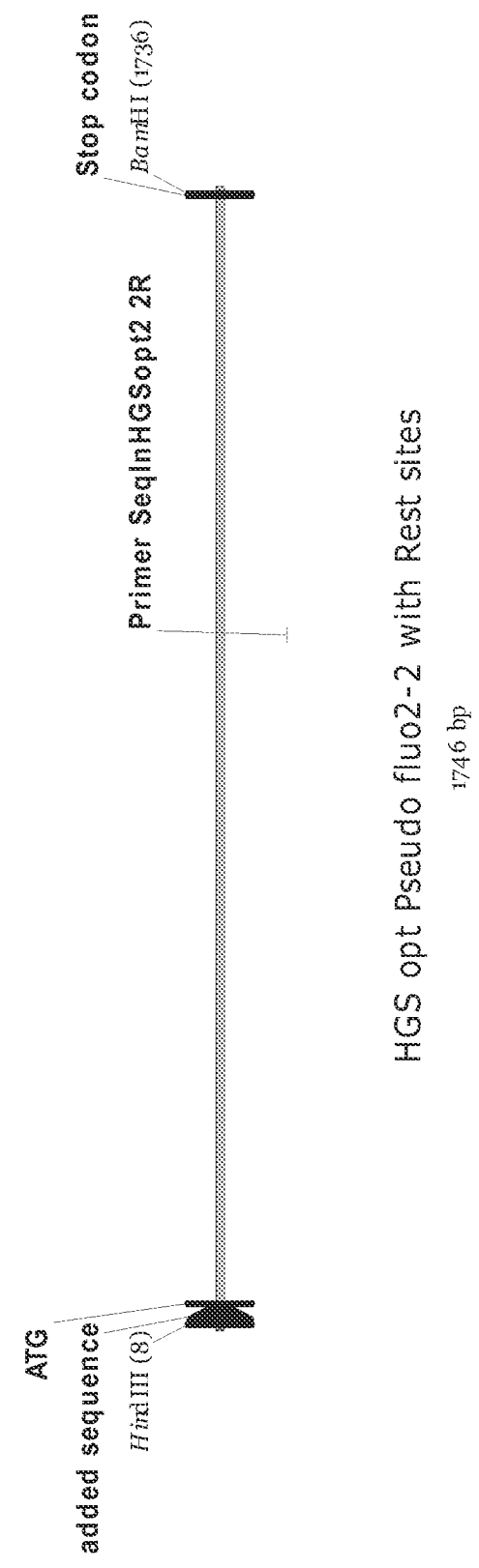

FIG. 145A is a map of codon optimized isoprene synthase fluo-opt2v2.

FIG. 145B is the nucleotide sequence of codon optimized isoprene synthase fluo-opt2v2 (SEQ ID NO:40).

Figure 146A:
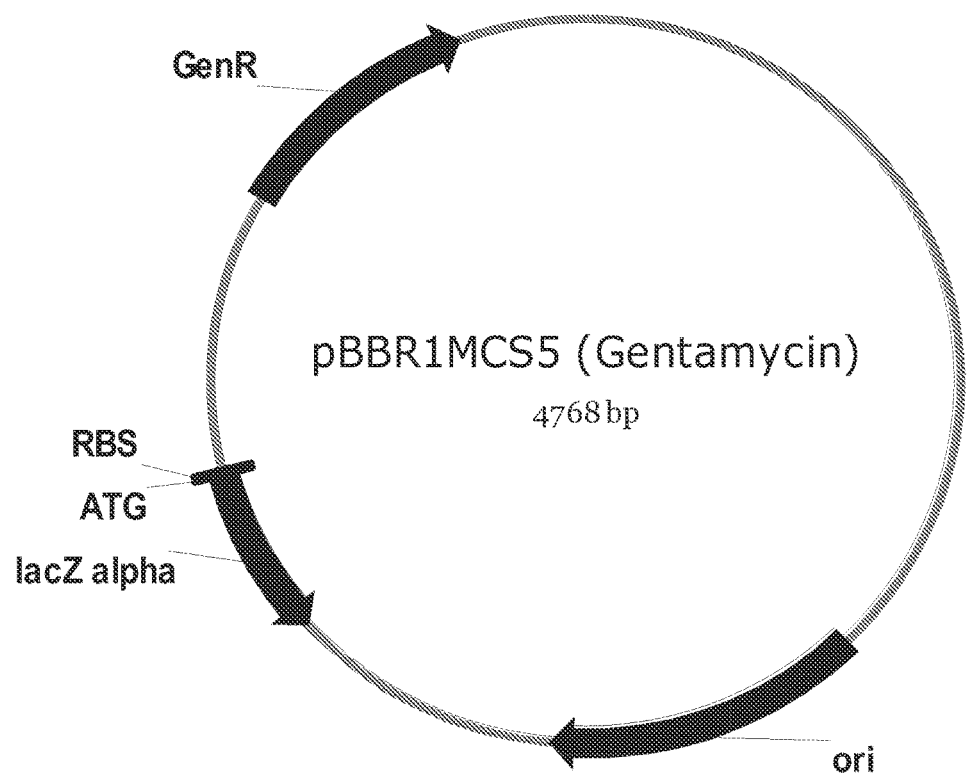

FIG. 146A is a map of pBBR1MCS5.

FIGS. 146B-C are the nucleotide sequence of pBBR1MCS5 (SEQ ID NO:41).

Figure 147A:
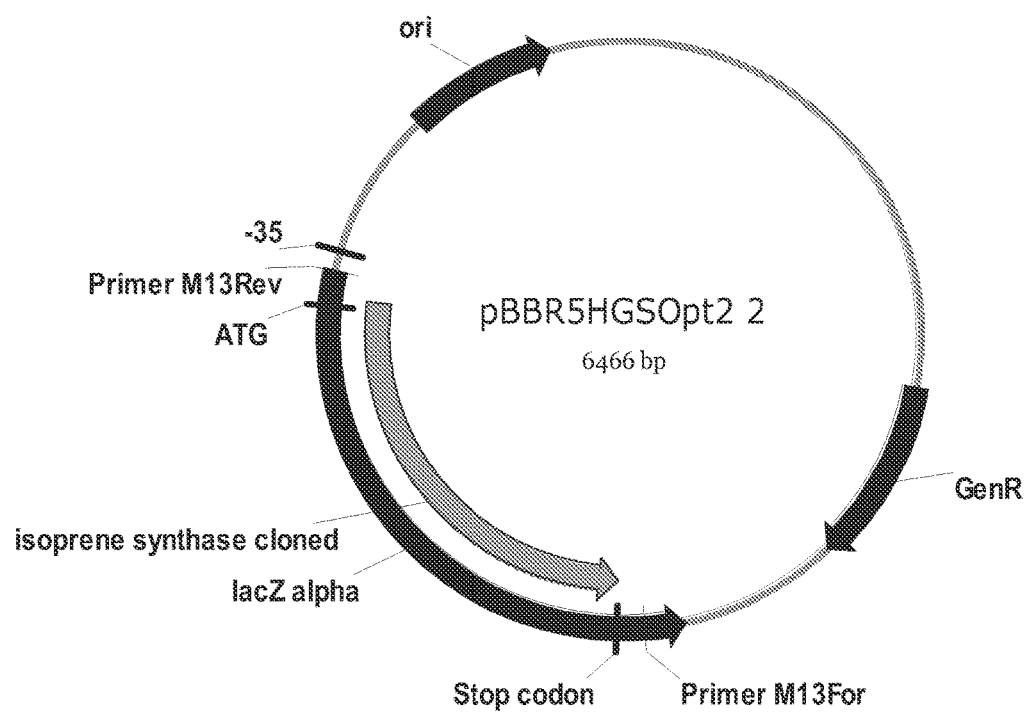

FIG. 147A is a map of pBBR5HGSOpt2_2.

FIGS. 147B-C are the nucleotide sequence of pBBR5HGSOpt2_2 (SEQ ID NO:42).

Figure 148:
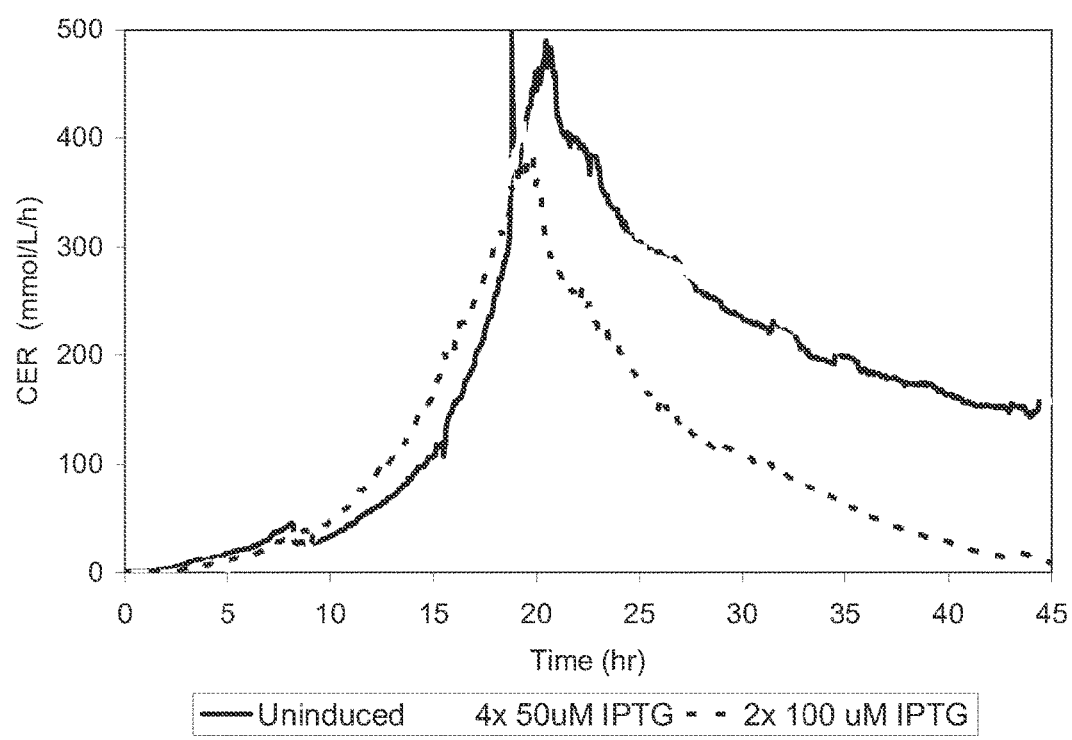

FIG. 148 is a graph of CER versus fermentation time for strain MCM401, uninduced, induced with IPTG (4×50 μmol) or IPTG (2×100 μmol).

Figure 149:
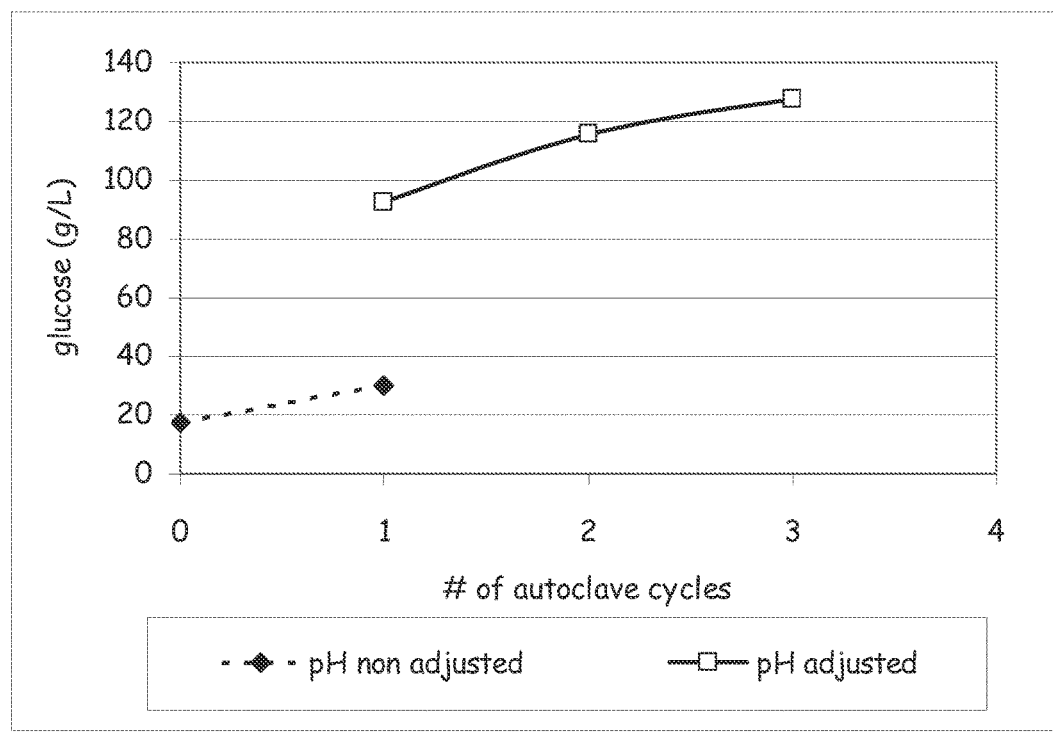

FIG. 149 shows concentration of glucose in sugar cane solutions, pH adjusted or not, as a function of the number of autoclaving cycles (one cycle=30 min).

Figure 150:
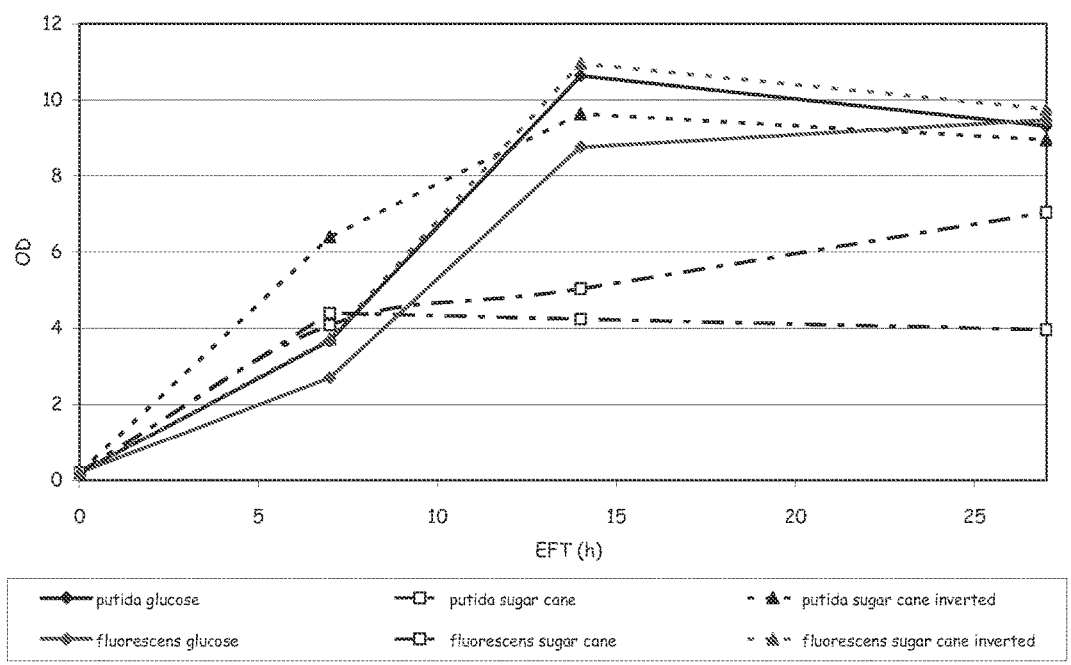

FIG. 150 shows growth curves ($OD_{600}$ as a function of time) of *Pseudomonas putida* F1 and *Pseudomonas fluorescens* ATCC13525 on glucose, sugar cane, and inverted sugar cane.

Figure 151:
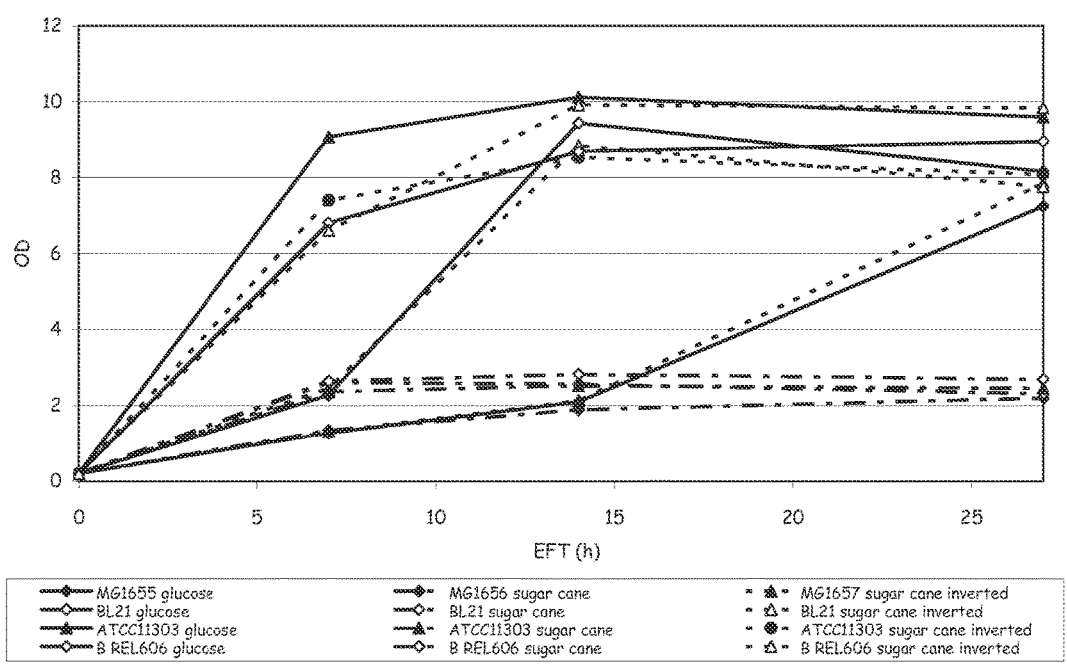

FIG. 151 shows growth curves ($OD_{600}$ as a function of time) of *E. coli* BL21(DE3), MG1655, ATCC11303 and B REL 606 on glucose, sugar cane, and inverted sugar cane.

Figure 152:
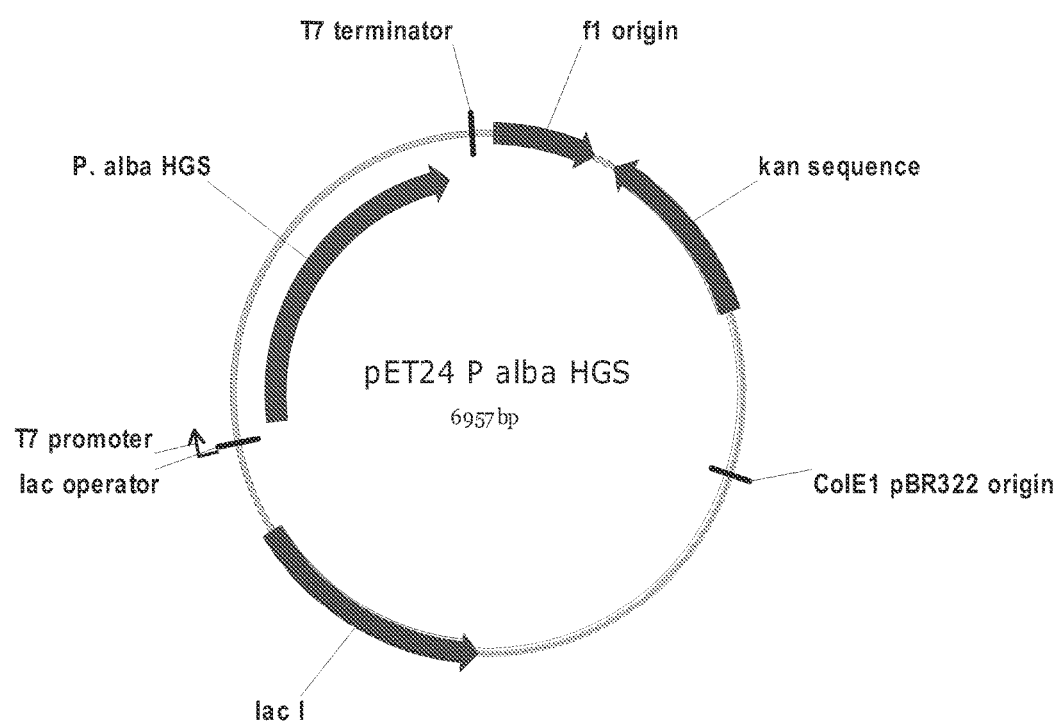

FIG. 152 is a map of plasmid pET24 *P. alba* HGS.

FIGS. 153A-B are the nucleotide sequence of plasmid pET24 *P. alba* HGS (SEQ ID NO:43).

Figure 154:
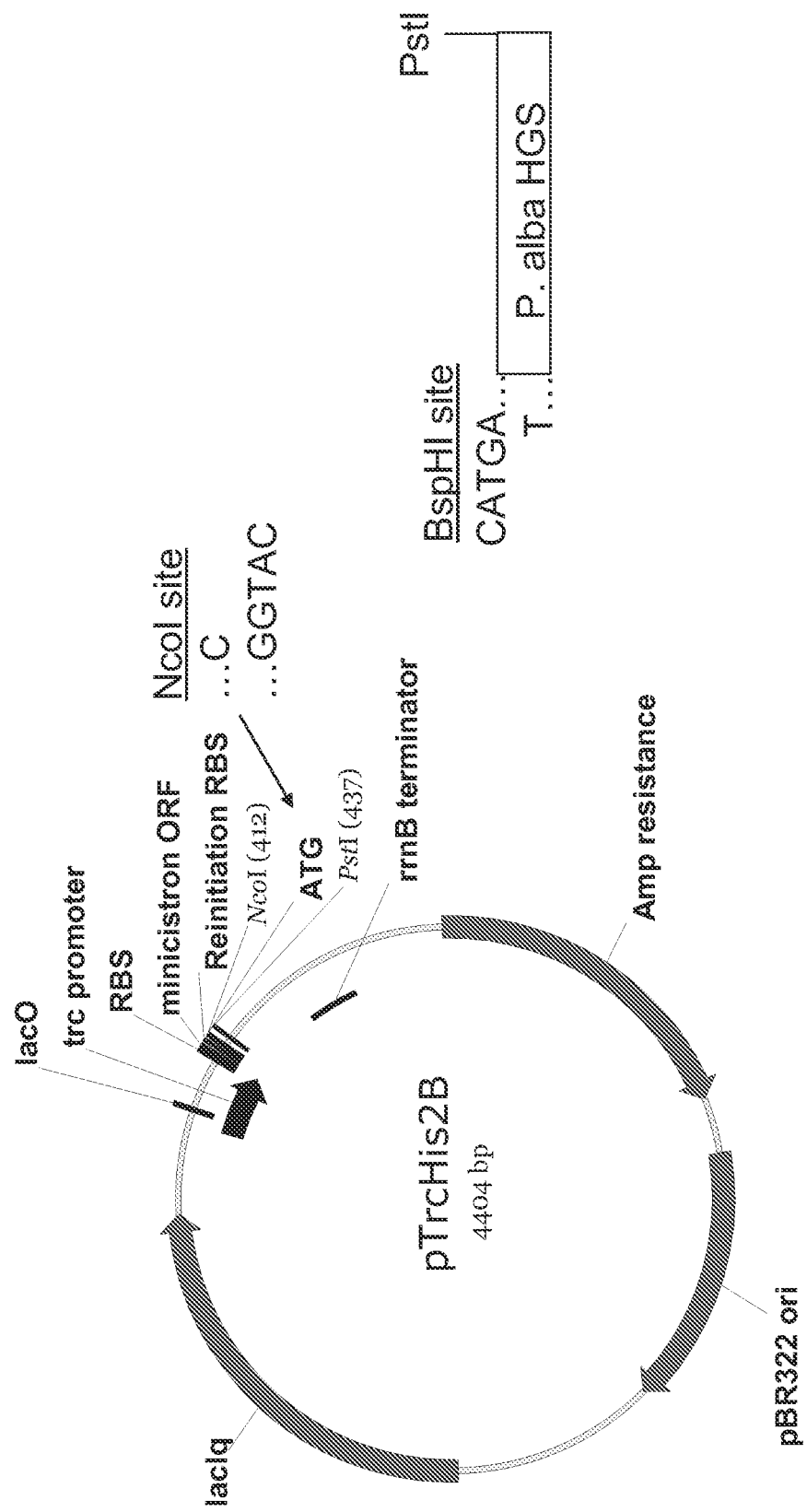

FIG. 154 is a schematic diagram showing restriction sites used for endonuclease digestion to construct plasmid EWL230 and compatible cohesive ends between BspHI and NcoI sites.

Figure 155:
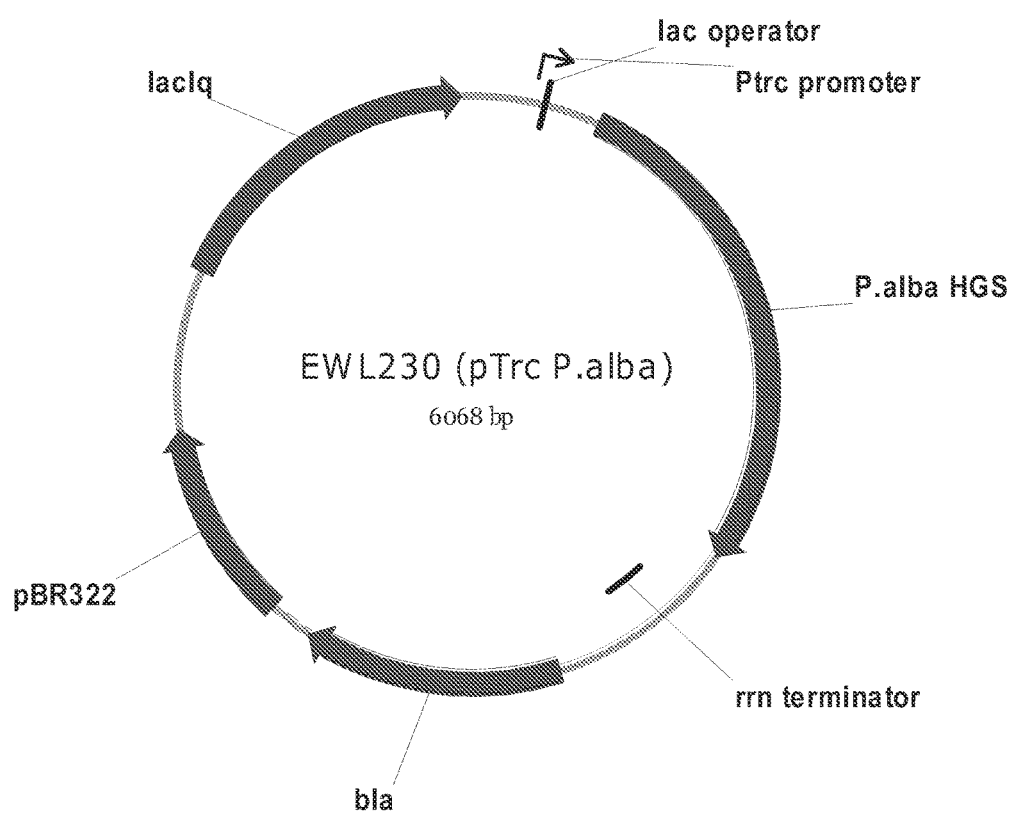

FIG. 155 is a map of plasmid EWL230.

FIGS. 156A-B are the nucleotide sequence of plasmid EWL230 (SEQ ID NO:44).

Figure 157:
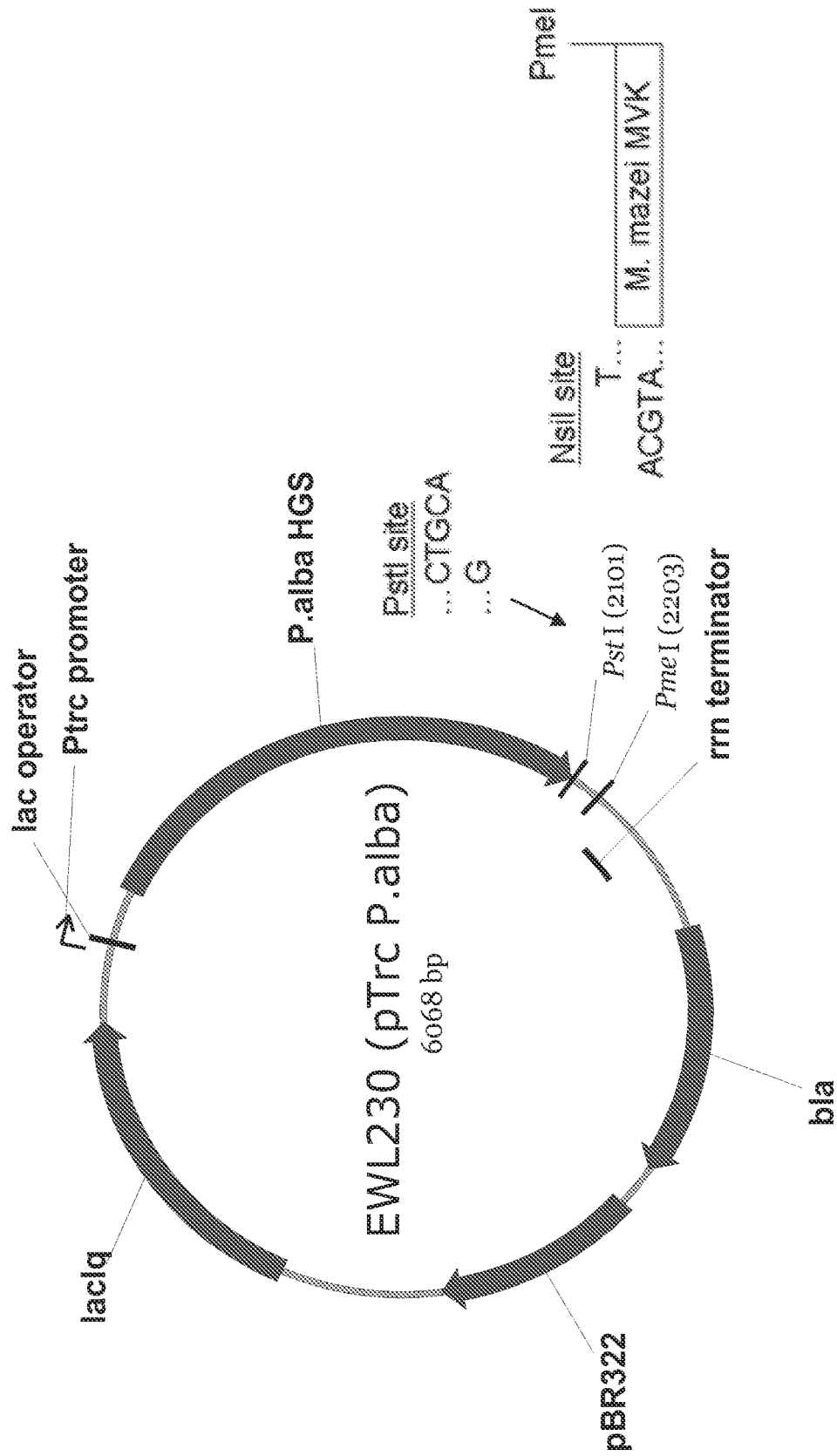

FIG. 157 is a schematic diagram showing restriction sites used for endonuclease digestion to construct plasmid EWL244 and compatible cohesive ends between NsiI and PstI sites.

Figure 158:
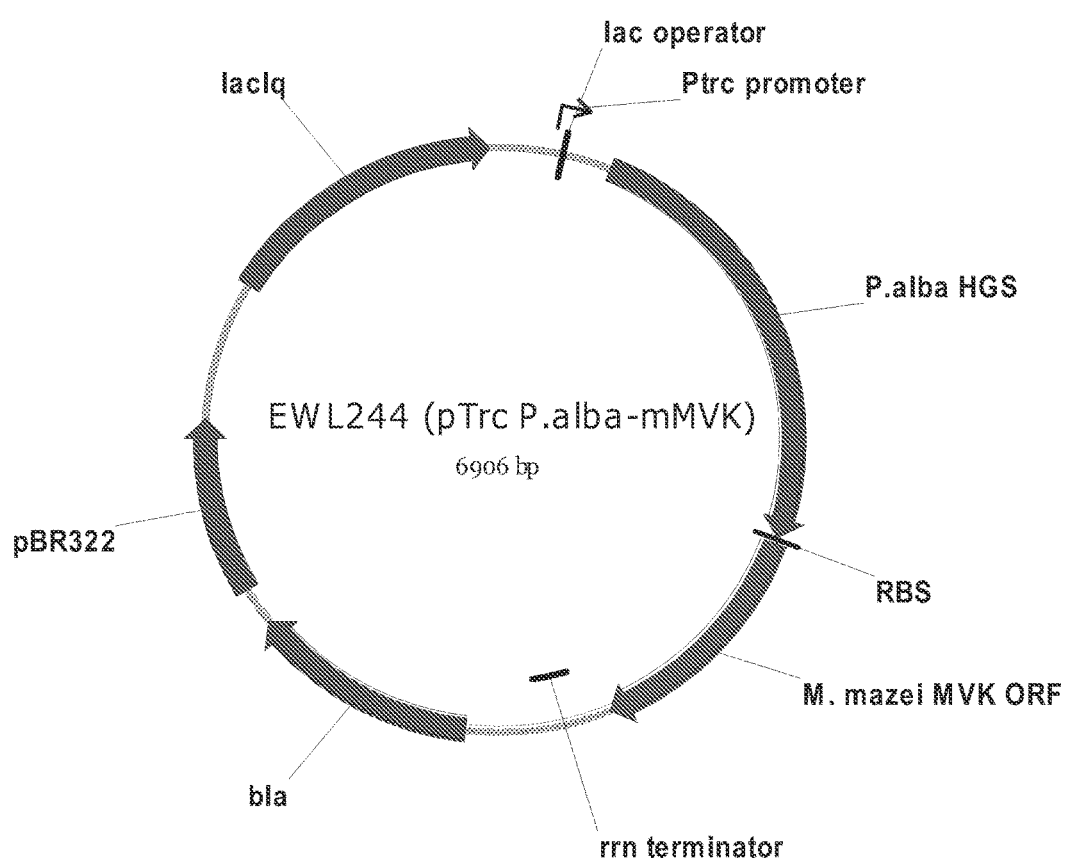

FIG. 158 is a map of plasmid EWL244.

FIGS. 159A-B are the nucleotide sequence of plasmid EWL244 (SEQ ID NO:45).

Figure 160A:
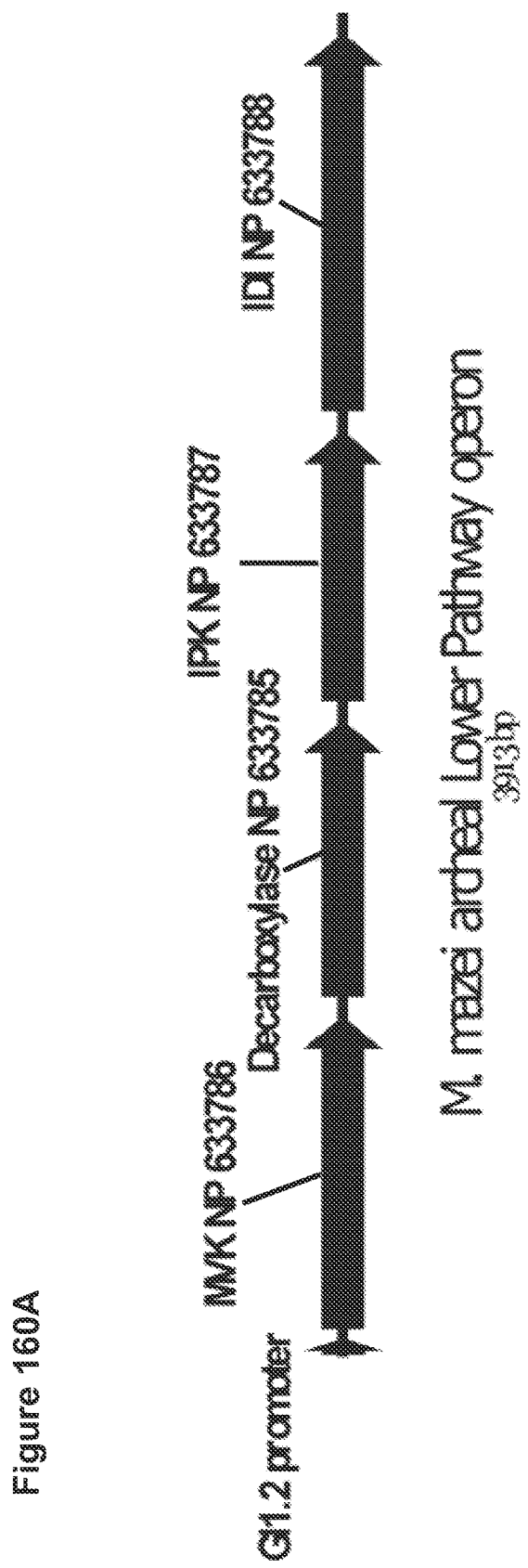

FIG. 160A is a map of the *M. mazei* Archaeal Lower Pathway operon.

FIGS. 160B-C are the nucleotide sequence of the *M. mazei* Archaeal Lower Pathway operon (SEQ ID NO:46).

Figure 161A:
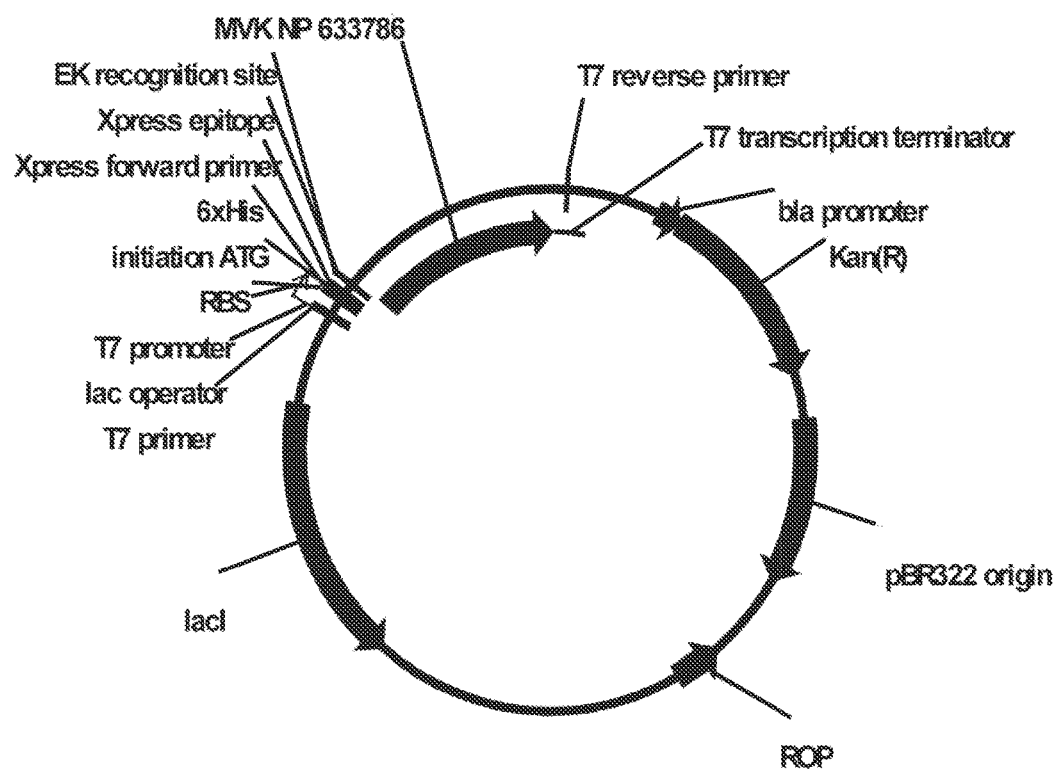

FIG. 161A is a map of MCM376-MVK from *M. mazei* Archaeal Lower in pET200D.

FIGS. 161B-C are the nucleotide sequence of MCM376-MVK from *M. mazei* Archaeal Lower in pET200D (SEQ ID NO:47).

Figure 162:
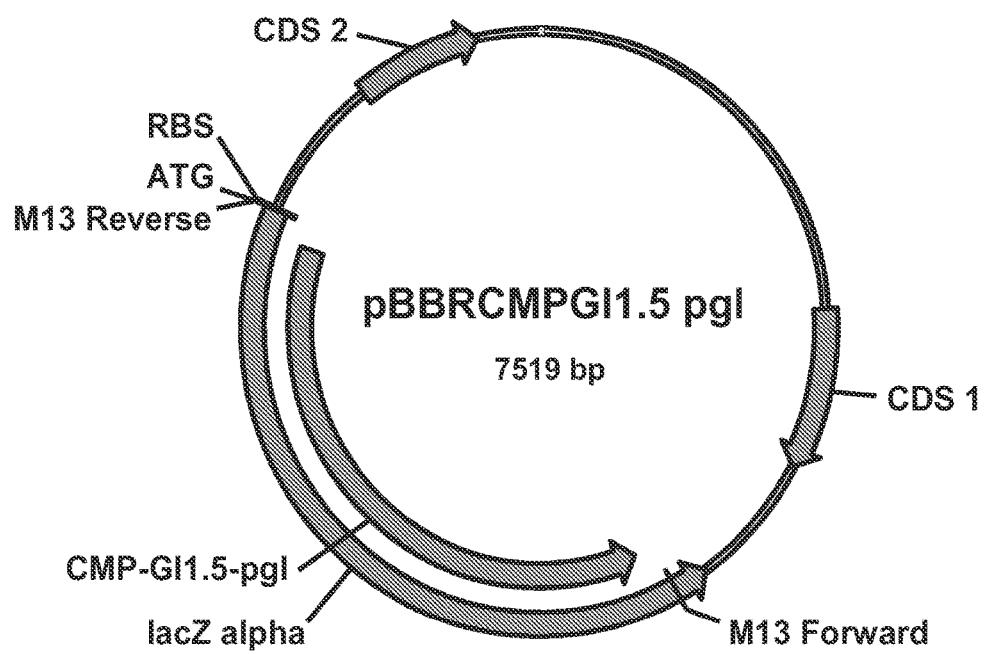

FIG. 162 is a map of plasmid pBBRCMPGI1.5-pgl.

FIGS. 163A-B are the nucleotide sequence of plasmid pBBRCMPGI1.5-pgl (SEQ ID NO:48).

Figure 164A:
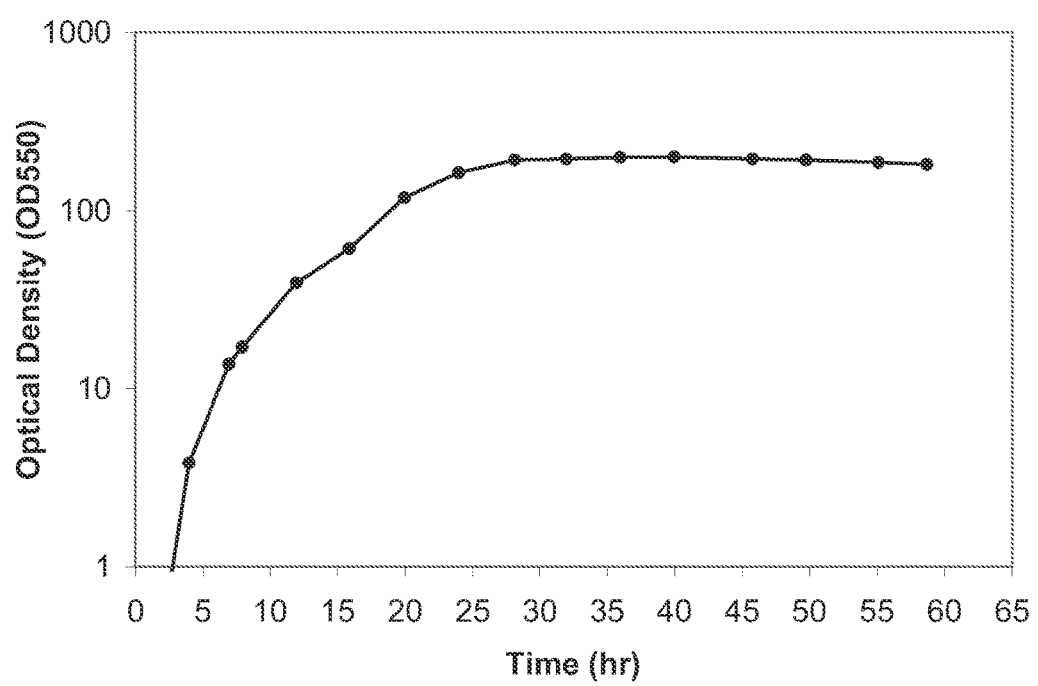
Figure 164B:
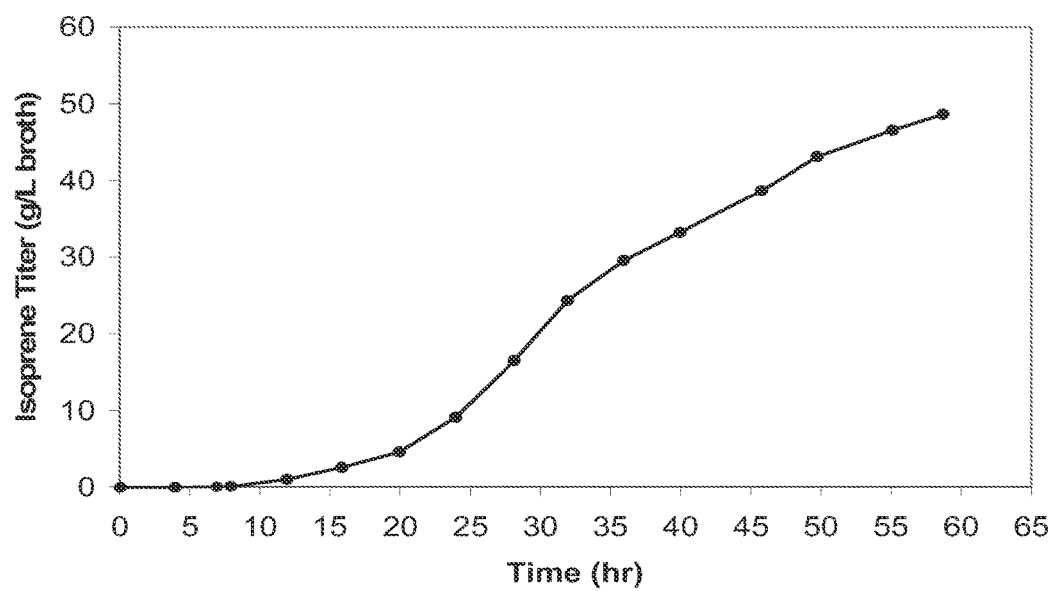
Figure 164C:
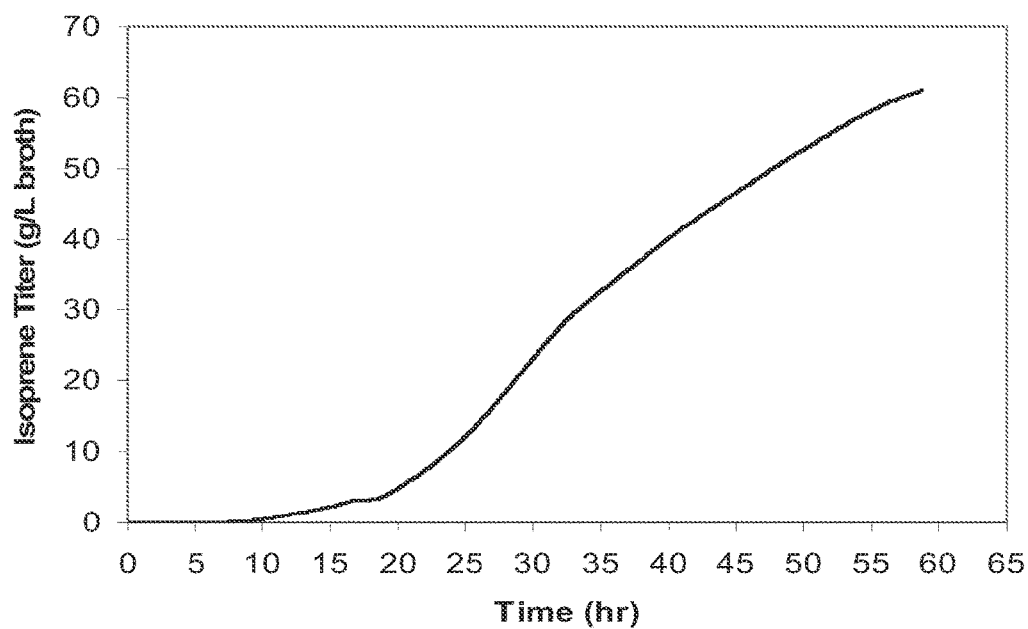
Figure 164D:
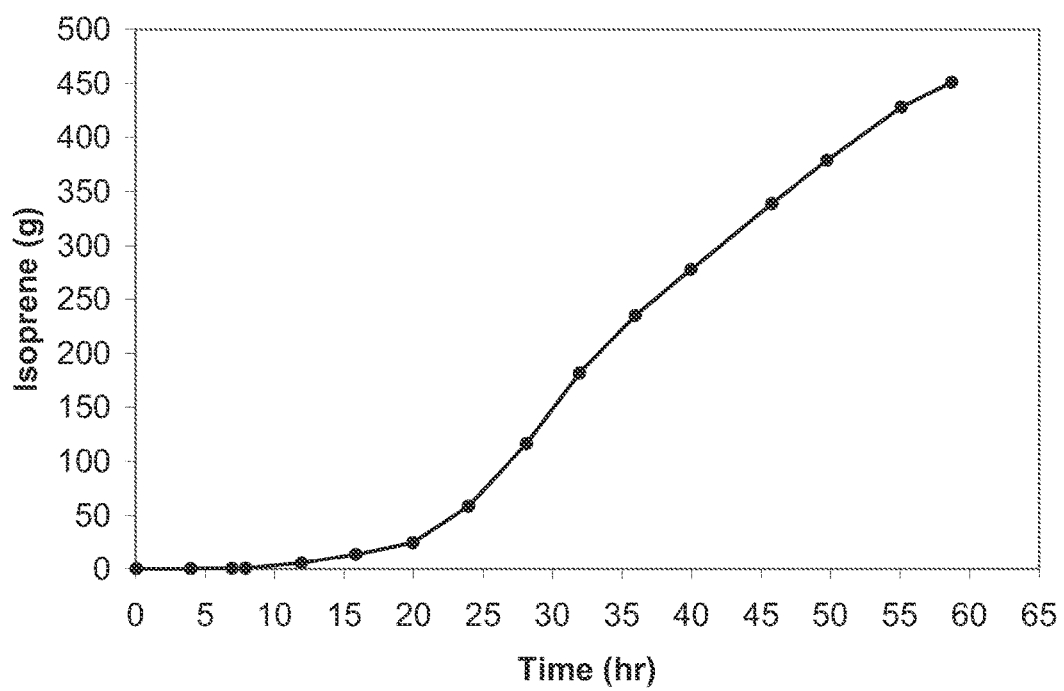
Figure 164E:
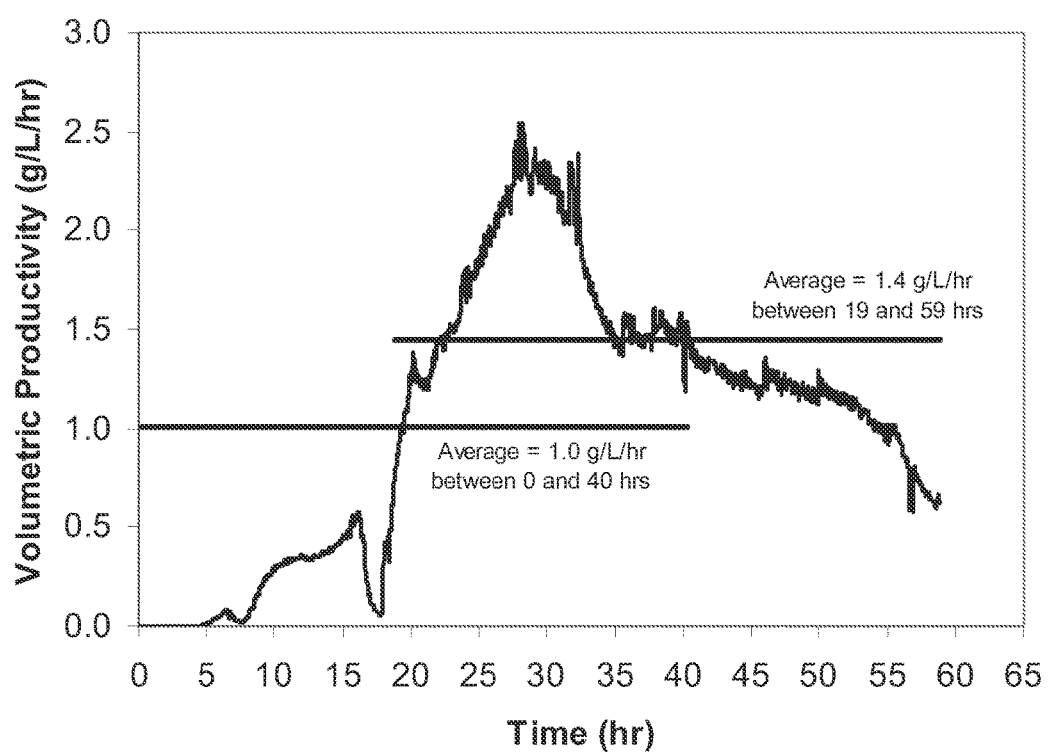
Figure 164F:
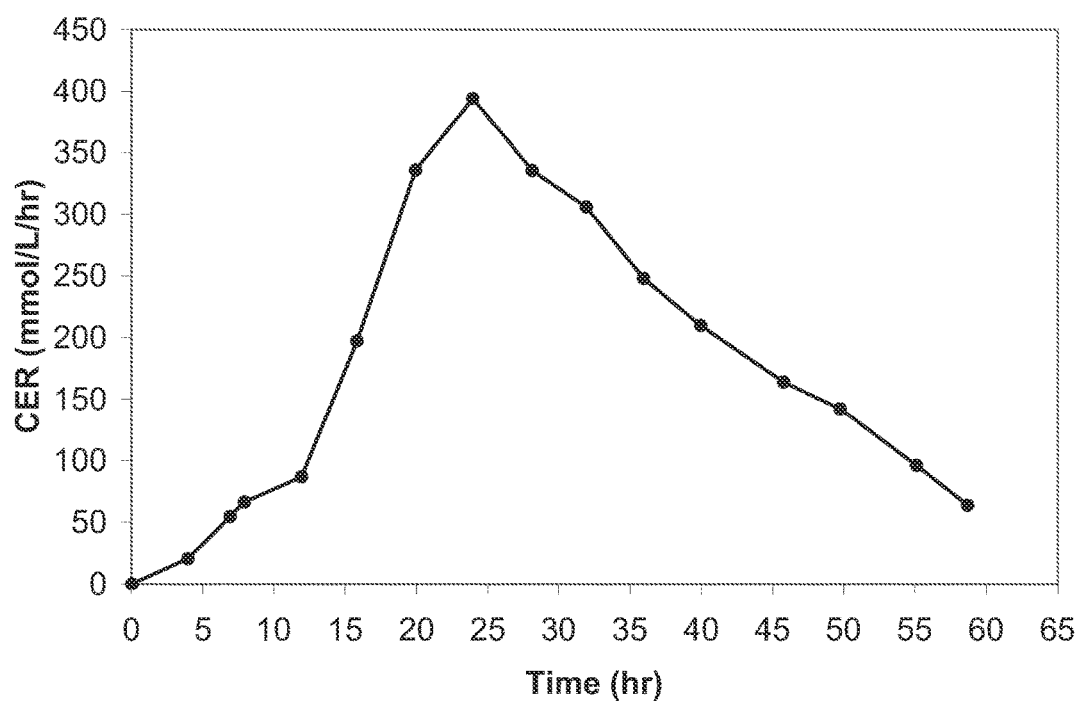
Figure 167D:
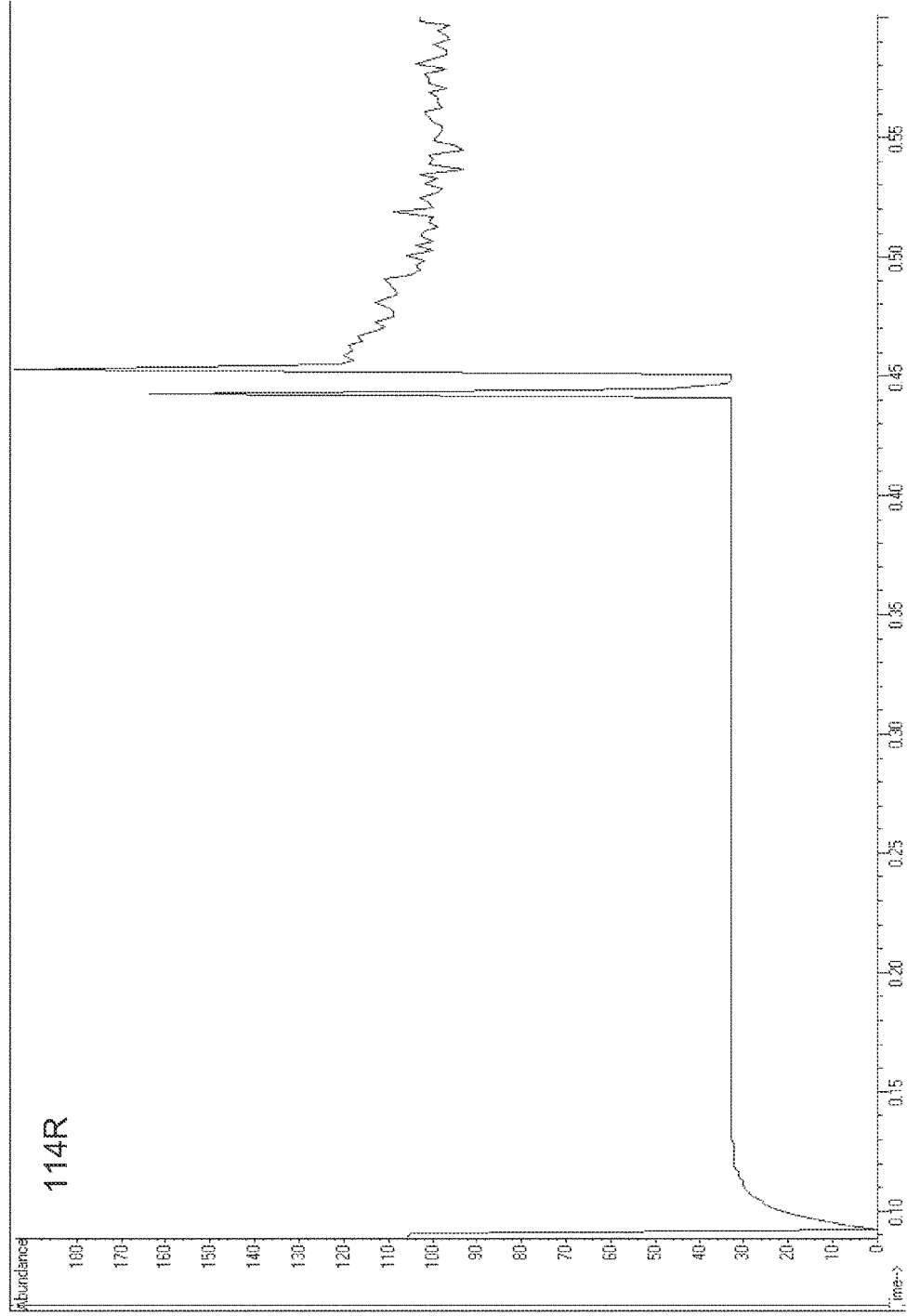

FIGS. 164A-F are graphs of isoprene production by *E. coli* strain expressing *M. mazei* mevalonate kinase, *P. alba* isoprene synthase, and pgl (RHM111608-2), and grown in fed-batch culture at the 15-L scale. FIG. 164A shows the time course of optical density within the 15-L bioreactor fed with glucose. FIG. 164B shows the time course of isoprene titer within the 15-L bioreactor fed with glucose. The titer is defined as the amount of isoprene produced per liter of fermentation broth. Method for calculating isoprene: cumulative isoprene produced in 59 hrs, g/Fermentor volume at 59 hrs, L [=] g/L broth. FIG. 164C also shows the time course of isoprene titer within the 15-L bioreactor fed with glucose. Method for calculating isoprene: ∫(Instantaneous isoprene production rate, g/L/hr)dt from t=0 to 59 hours [=] g/L broth. FIG. 164D shows the time course of total isoprene produced from the 15-L bioreactor fed with glucose. FIG. 164E shows volumetric productivity within the 15-L bioreactor fed with glucose. FIG. 164F shows carbon dioxide evolution rate (CER), or metabolic activity profile, within the 15-L bioreactor fed with glucose.

FIGS. 165A-B are graphs showing analysis of off-gas from fermentation in 15 L bioreactors. Sample A is strain RM111608-2 sampled at 64.8 hours. Sample B is strain EWL256 was *E. coli* BL21 (DE3), pCL upper, cmR-gi1.2-yKKDyI, pTrcAlba-mMVK sampled at 34.5 hours. Hydrogen is detected above the baseline ($0.95 \times 10^{-8}$ torr) for both samples.

FIGS. 166A-B show growth of a *S. cerevisiae* strain expressing codon-optimized Kudzu IspS (DW112) or a control strain expressing URA3 (DW114) measured by $OD_{600}$ before and after growth in sealed 20-ml GC vials in SC minimal medium with different carbon sources. Strains were grown aerobically in 0.5% glucose (Entry OD), and then grown anaerobically for 48 hours with an additional 1% raffinose or 2% galactose (Post Anaerobic OD). A. Growth of DW112, which harbors the galactose-inducible IspS. B. Growth of DW114, which harbors the vector control.

FIGS. 167A-D are raw GC traces of headspace gas produced by *S. cerevisiae* strains. A. 112G-DW112 (IspS-expressing) grown and induced in 0.5% glucose, 2% galactose. B. 112R-DW112 grown in 0.5% glucose, 1% raffinose. C. 114G-DW114 (control) grown and induced in 0.5% glucose, 2% galactose. D. 114R-DW114 grown in 0.5% glucose, 1% raffinose. The only detectable peak for isoprene, in sample 112G, is circled.

FIGS. 168A-D show raw HPLC traces of compounds produced by *S. cerevisiae* strains. A. 112G-DW112 (IspS-expressing) grown and induced in 0.5% glucose, 2% galactose. B. 112R-DW112 grown in 0.5% glucose, 1% raffinose. C. 114G-DW114 (control) grown and induced in 0.5% glucose, 2% galactose. D. 114R-DW114 grown in 0.5% glucose, 1% raffinose. Ethanol peaks are circled.

Figure 169:
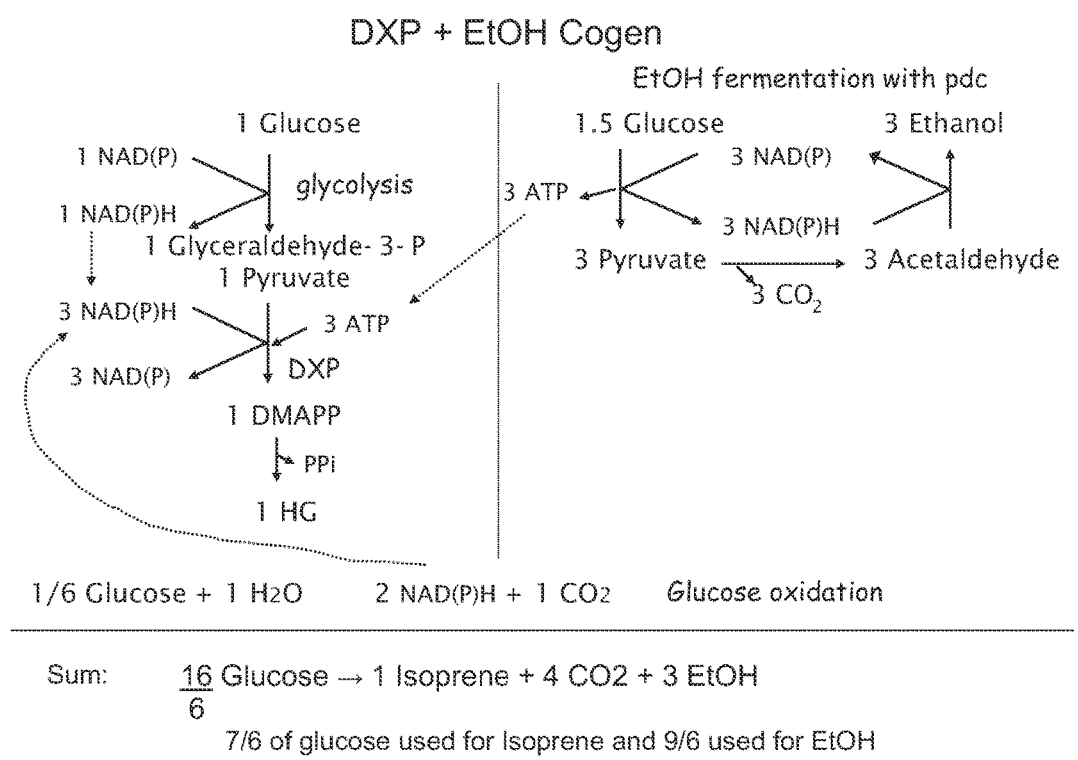

FIG. 169 shows a schematic of the DXP pathway and the pathway for ethanol fermentation with pyruvate decarboxylase.

Figure 170:
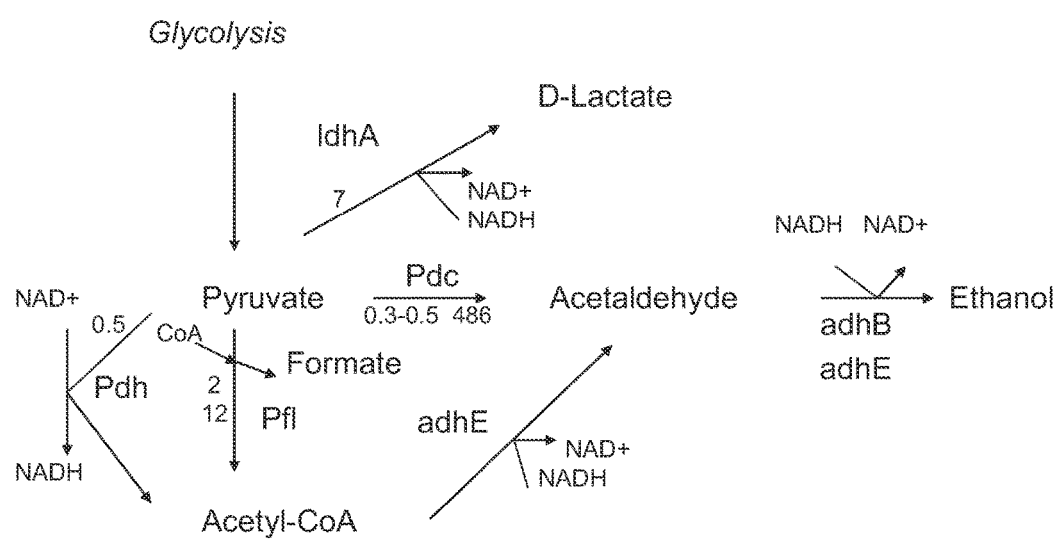

FIG. 170 shows a schematic of the reactions around pyruvate in *E. coli*. Enzymes endogenous to *E. coli* are shown in blue. Enzymes derived from *Zymomonas mobilis* are shown in red. Numbers listed on the arrows are the Michaelis-Menten constant ($K_m$) (mM) and the catalytic rate constant ($K_{cat}$)(1/s), in that order. Where only one number is listed, is the $K_m$ (mM).

Figure 171A:
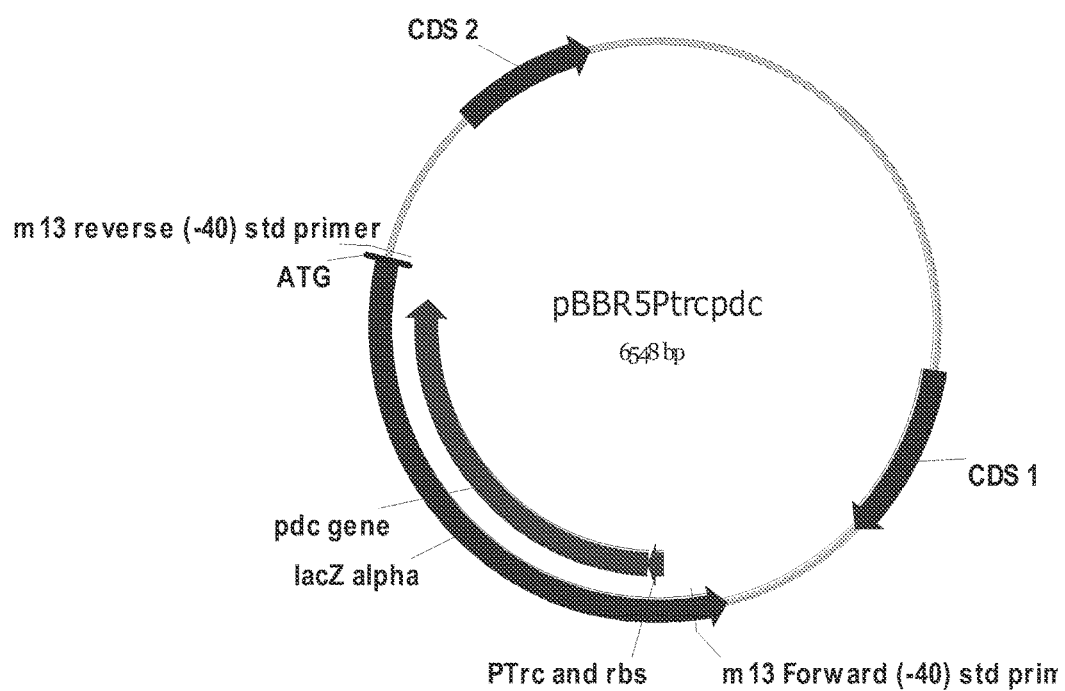

FIG. 171A is a map of plasmid pBBR5-Ptrcpdc; FIGS. 171B-C are the nucleotide sequence of plasmid pBBR5-Ptrcpdc (SEQ ID NO:148), encoding *Zymomonas mobilis* pyruvate decarboxylase under the control of the Trc promoter.

Figure 172A:
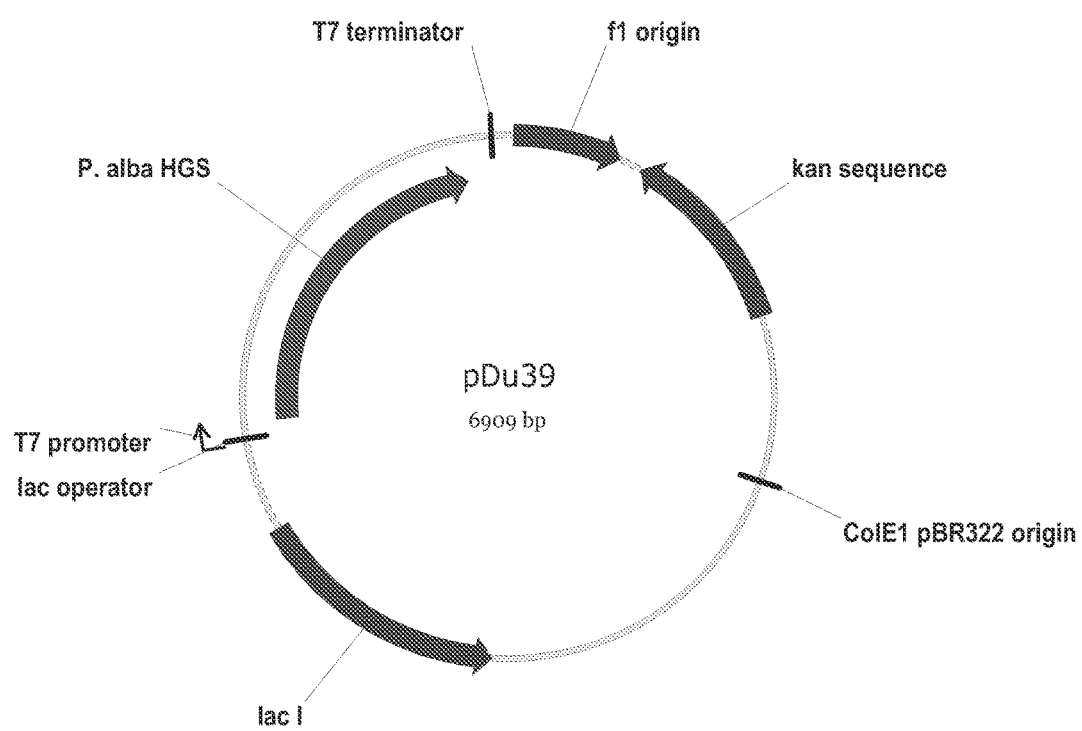

FIG. 172A is a map of plasmid pDu-39. FIGS. 172B-D are the nucleotide sequence of plasmid pDu-39 (SEQ ID NO:151).

Figure 173:
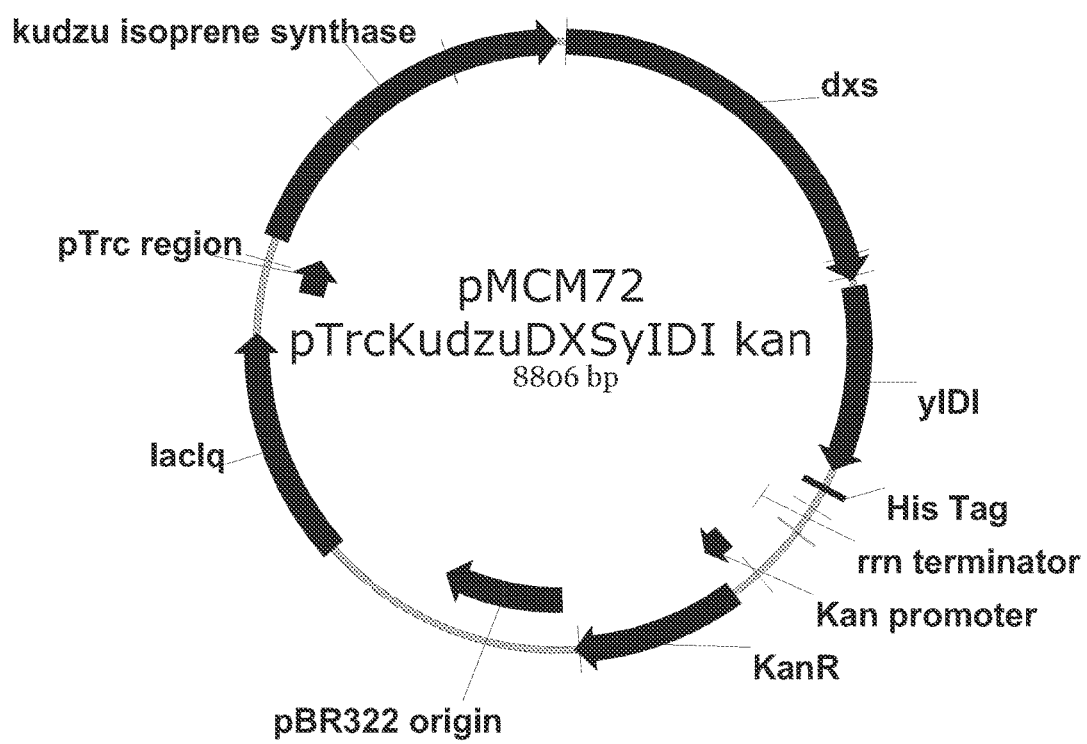

FIG. 173 is a map of plasmid pMCM72.

Figure 174A:
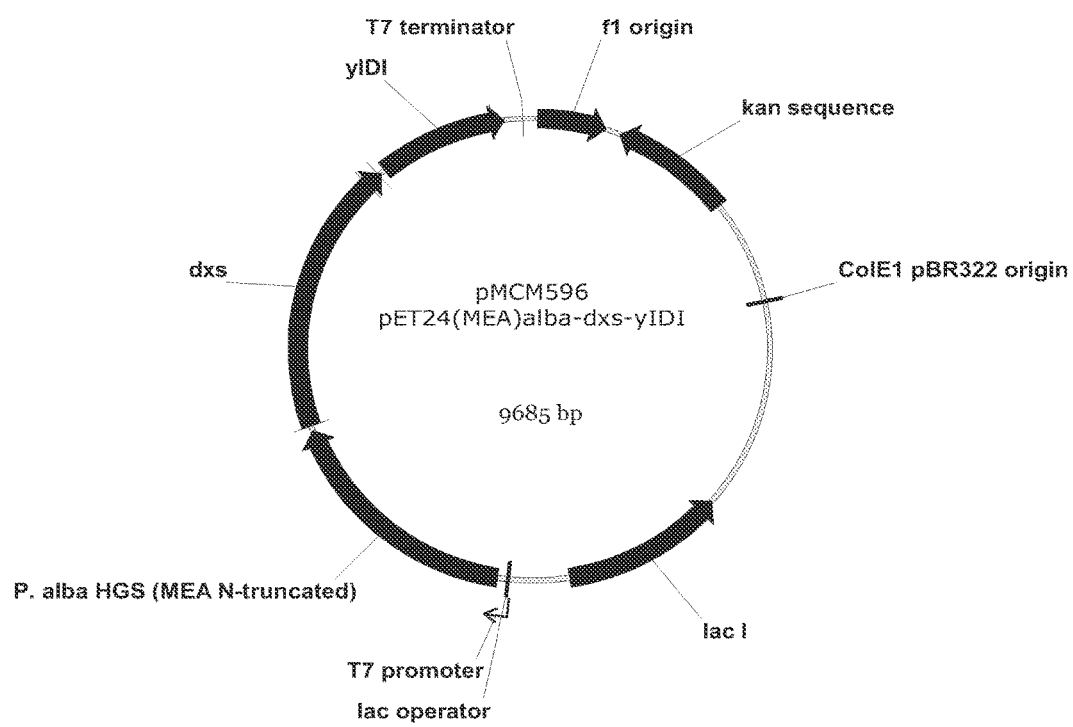

FIG. 174A is a map of plasmid pMCM596. FIGS. 174B-D are the nucleotide sequence of plasmid pMCM596 (SEQ ID NO:154).

Figure 175:
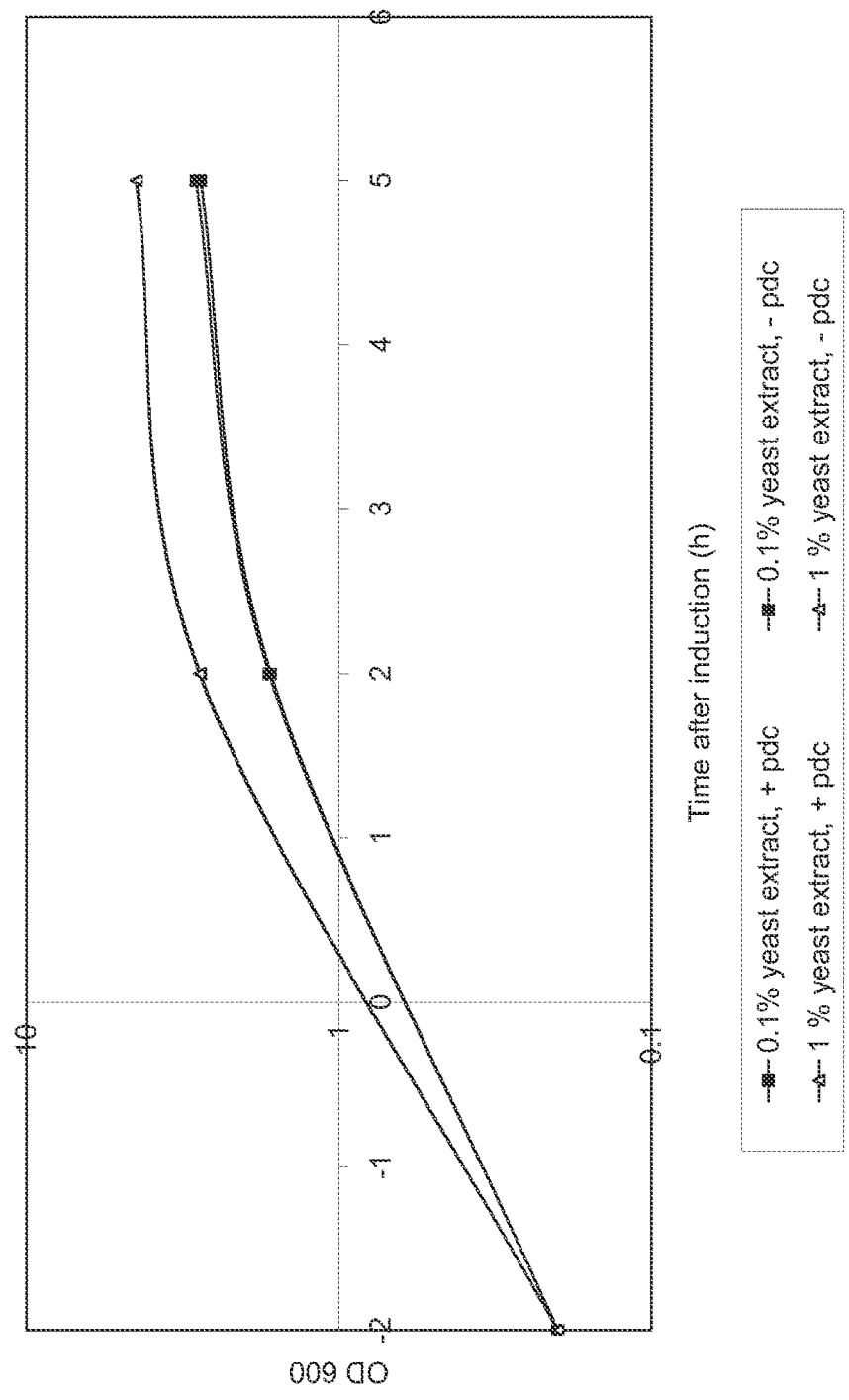

FIG. 175 is a growth curve of strain CMP182 and strain CMP183 in TM3+0.55 glucose+antibiotic, plus 0.1% (squares) or 1% (triangles) yeast extract.

FIGS. 176A-B show ethanol concentration and isoprene specific productivity (in arbitrary units) in the flasks containing 0.1% (A) (5 hours after induction) and 1% (B) (2 hours after induction) yeast extract. Both products are produced simultaneously.

Figure 177:
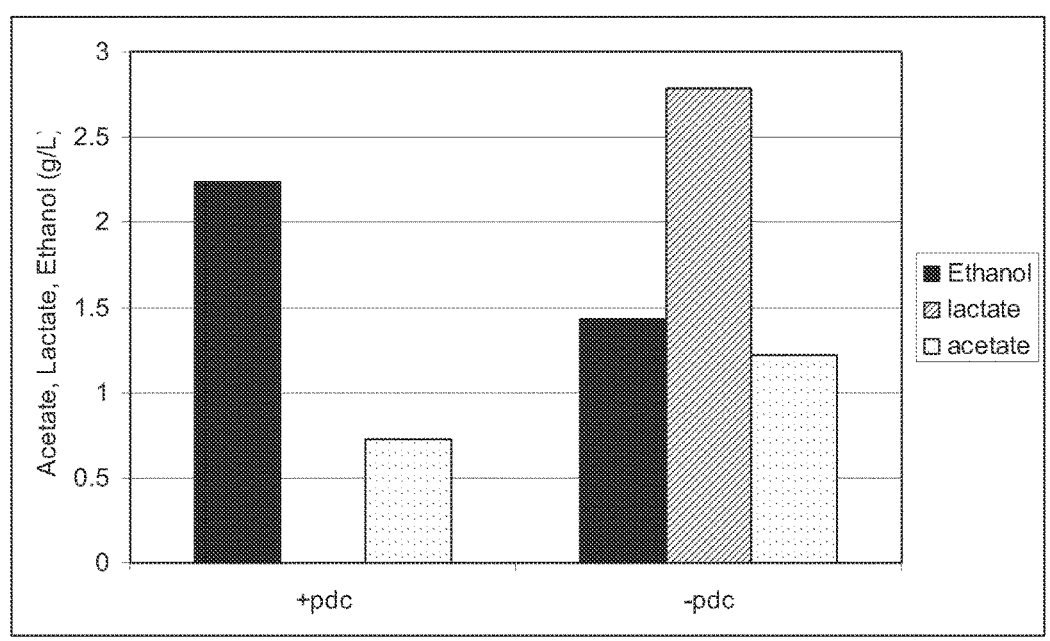

FIG. 177 shows fermentation products after 5 hours of induction in the 1% yeast extract flasks. The strain expressing pdc shows a higher concentration in ethanol, confirming the fact that pdc was expressed and active. As expected from comparing $K_m$s for ldhA and pdc, pyruvate flux to lactate is interrupted once pdc is expressed. Also, in the strain expressing pdc, more carbon is going towards acetaldehyde than towards acetyl-CoA, leading to a decrease of acetate.

Figure 178:
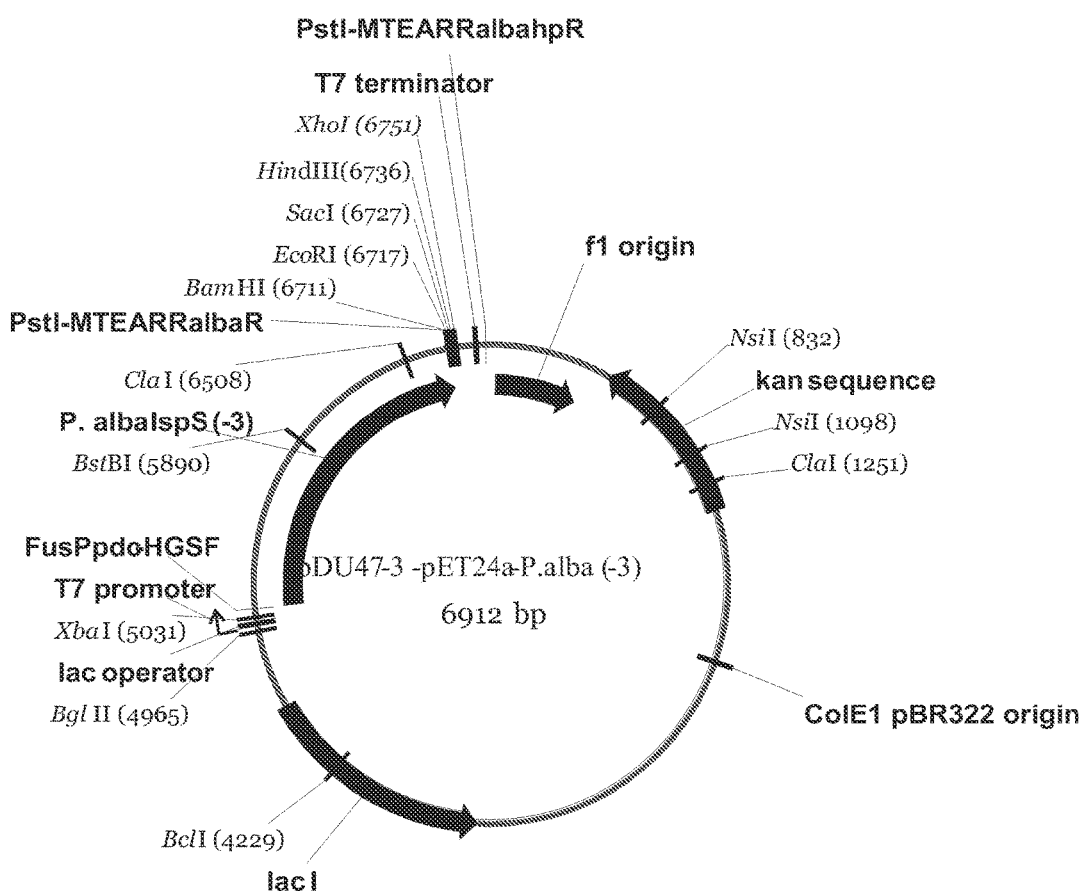

FIG. 178 is a map of plasmid pDU47-3-pET24a-*P. alba* (−3).

FIGS. 179A-B are the sequence of plasmid pDU47-3-pET24a-*P. alba* (−3) (SEQ ID NO:159).

Figure 180:
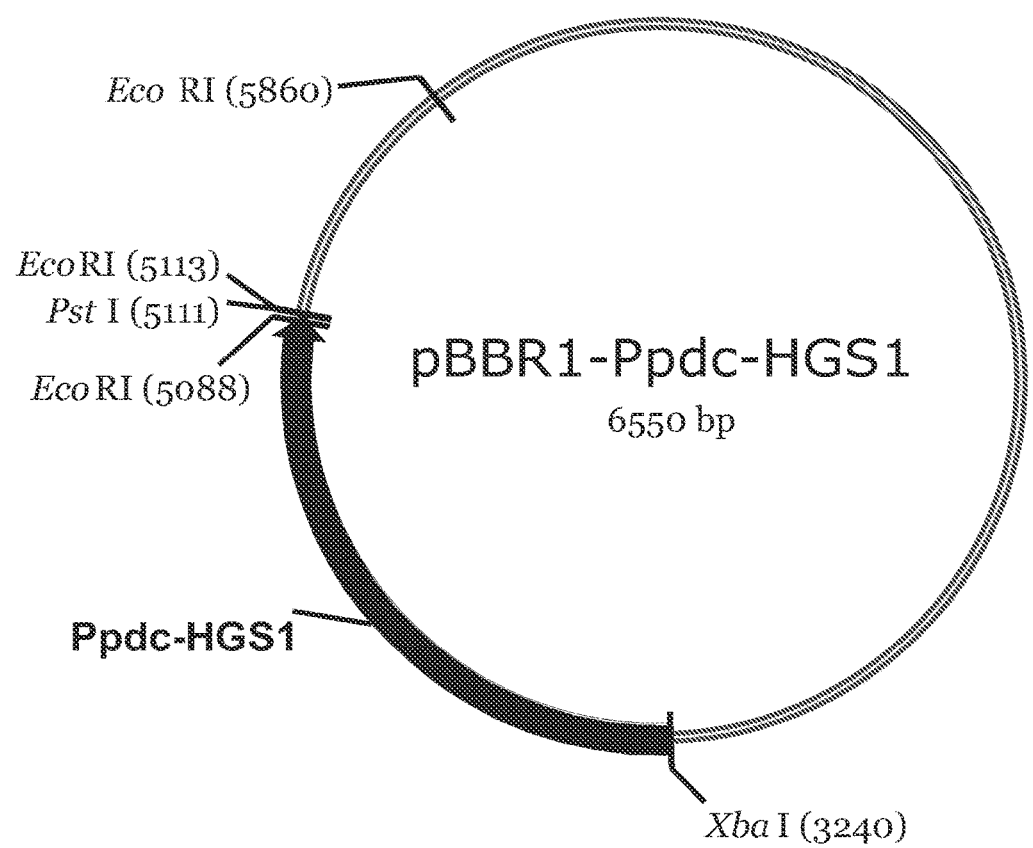

FIG. 180 is a map of plasmid pBBR-Ppdc-HGS1.

FIGS. 181A-B are the sequence of plasmid pBBR-Ppdc-HGS1 (SEQ ID NO:160).

Figure 182:
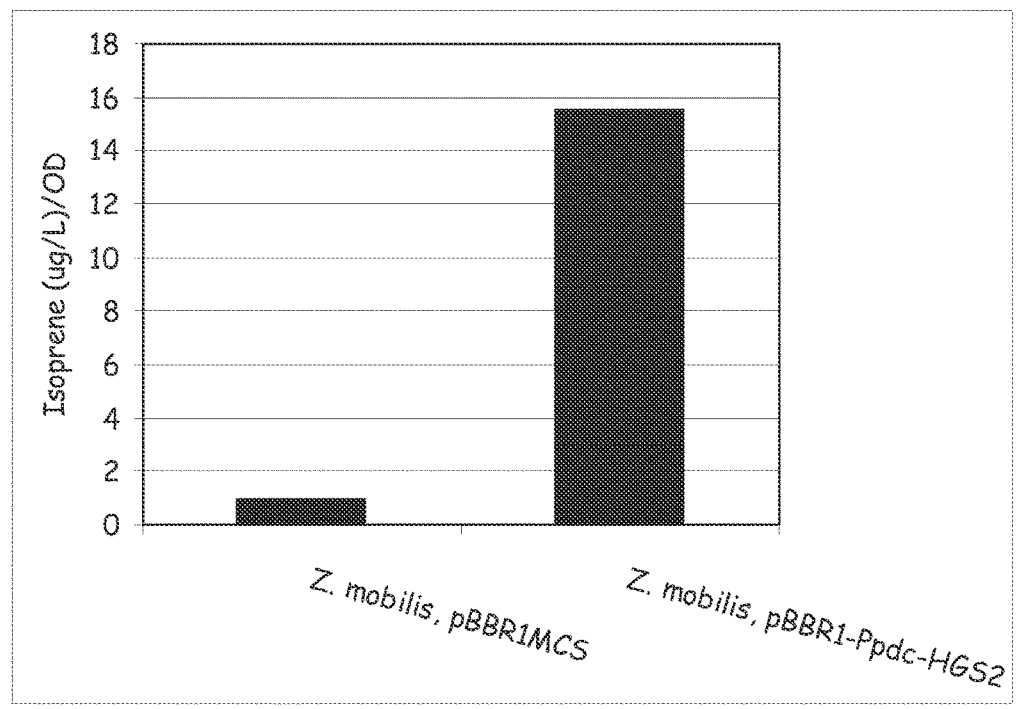

FIG. 182 shows production of isoprene by *Zymomonas mobilis* ZM4, pBBR1-MCS and *Zymomonas mobilis* ZM4, pBBR1-Ppdc-HGS1.

Figure 183A:
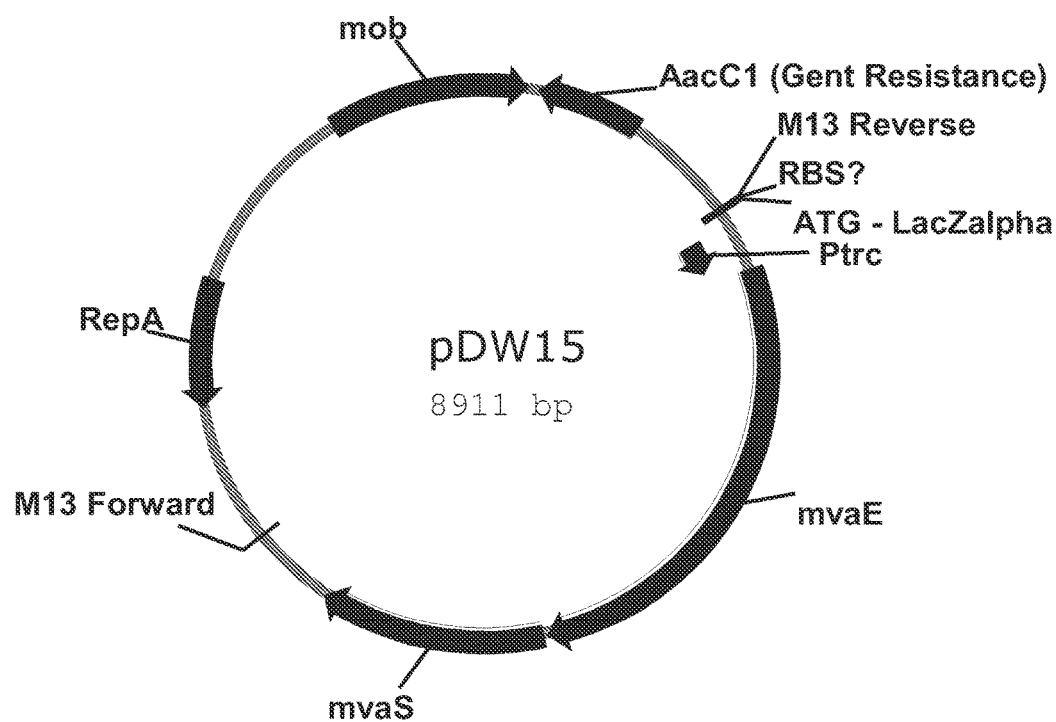

FIG. 183A shows a map of plasmid pDW15 (SEQ ID NO:161), expressing the upper MVA pathway polypeptides mvaE and mvaS from *Enterobacter faecalis*. FIGS. 183B-D are the sequence of pDW15.

Figure 184A:
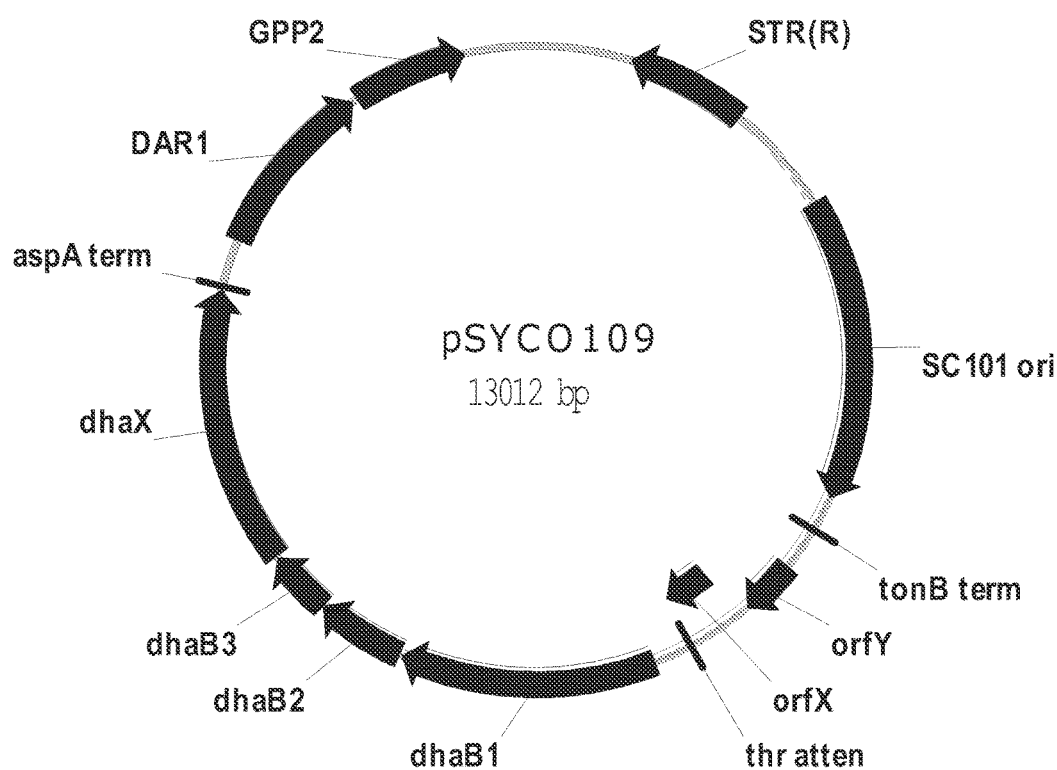

FIG. 184A shows a map of plasmid pSYCO109. FIGS. 184B-F are the sequence of pSYCO109 (SEQ ID NO:162).

Figure 185A:
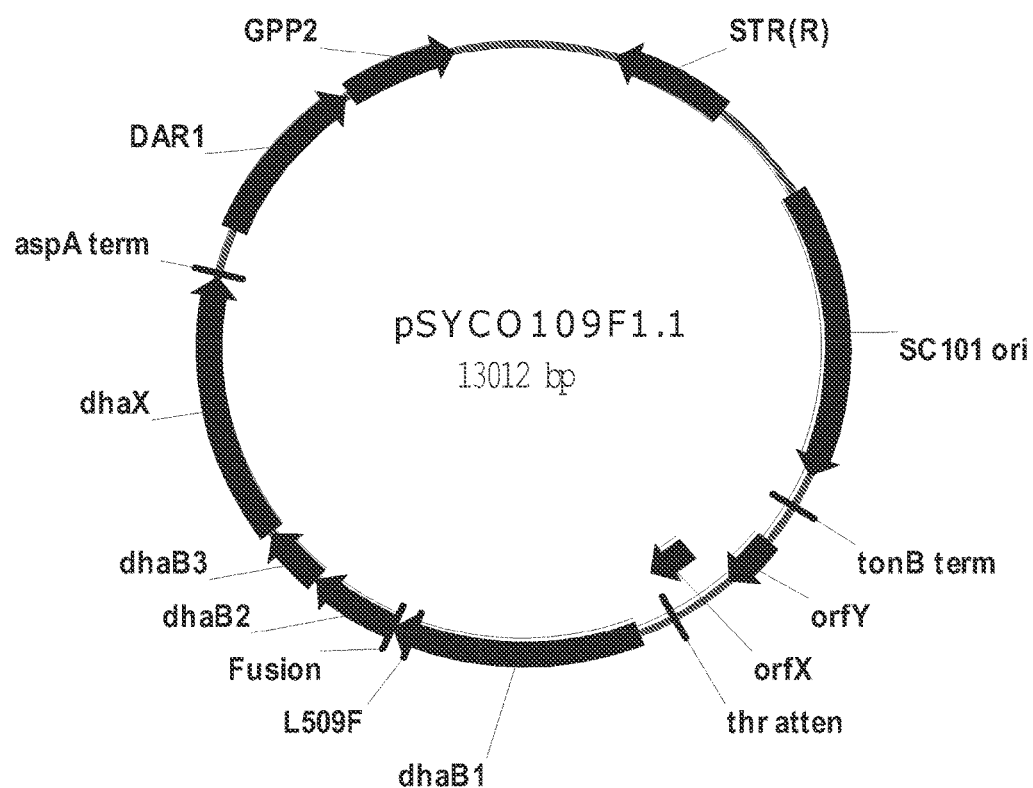

FIG. 185A shows a map of plasmid pSYCO109F1.1. FIGS. 185B-F are the sequence of pSYCO109F1.1 (SEQ ID NO:163).

Figure 186:
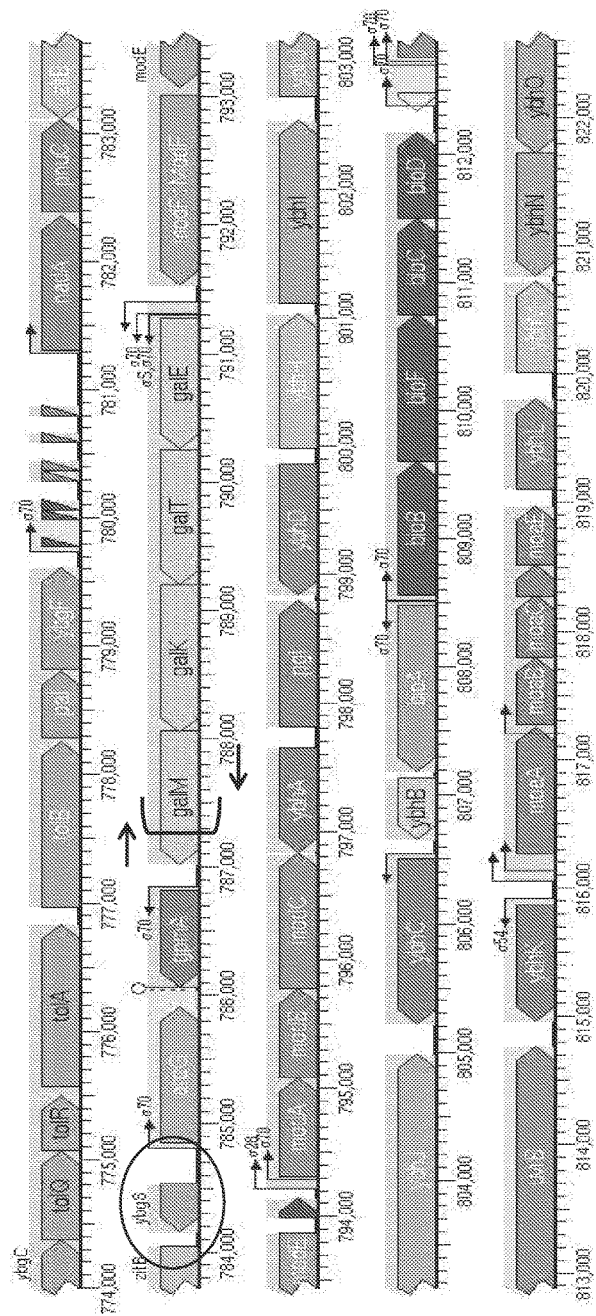

FIG. 186 shows the chromosomal organization of *E. coli* K12 MG1655 around the pgl gene. Brackets ([ ]) indicate the region deleted in *E. coli* BL21 compared to *E. coli* K12 MG1655, and restored in *E. coli* strain CMP241. The circled gene is ybgS. The forward arrow (→) indicates the annealing site of the galMR primer (SEQ ID NO:187). The reverse arrow (←) indicates the annealing site of the galMF primer (SEQ ID NO:186).

Figure 187A:
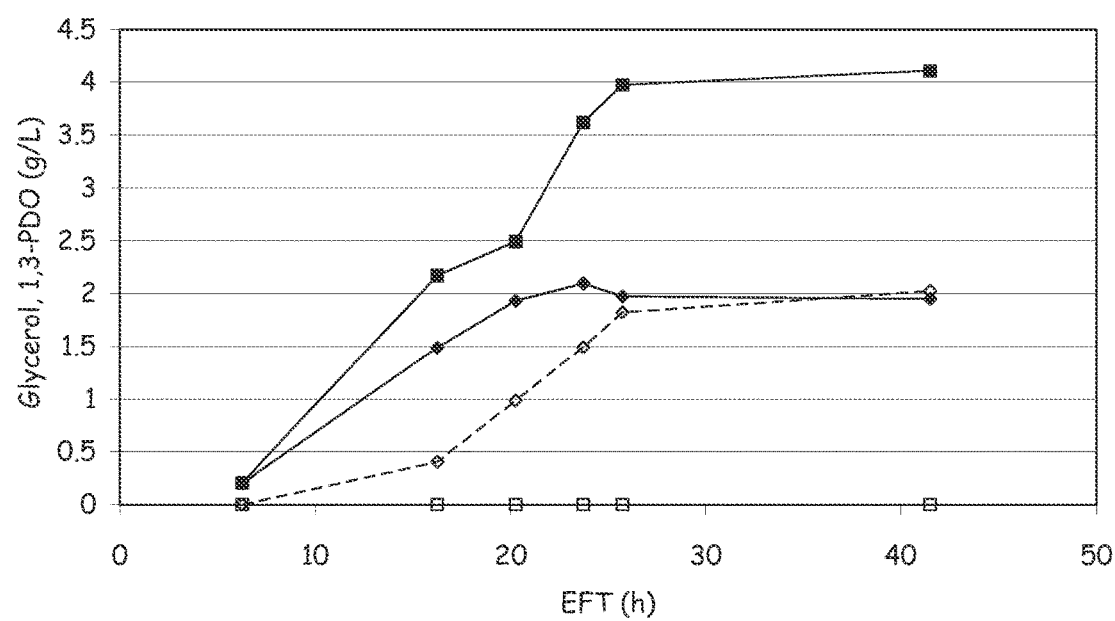

FIG. 187A shows the production of glycerol and/or 1,3-propanediol by *E. coli* strain CMP249 in the presence of 200 μM IPTG, plus or minus 125 mg/L vitamin B12. Closed symbols: glycerol, open symbols: 1,3-PDO. Grey: +B12, black: −B12. EFT: elapsed fermentation time.

Figure 187B:
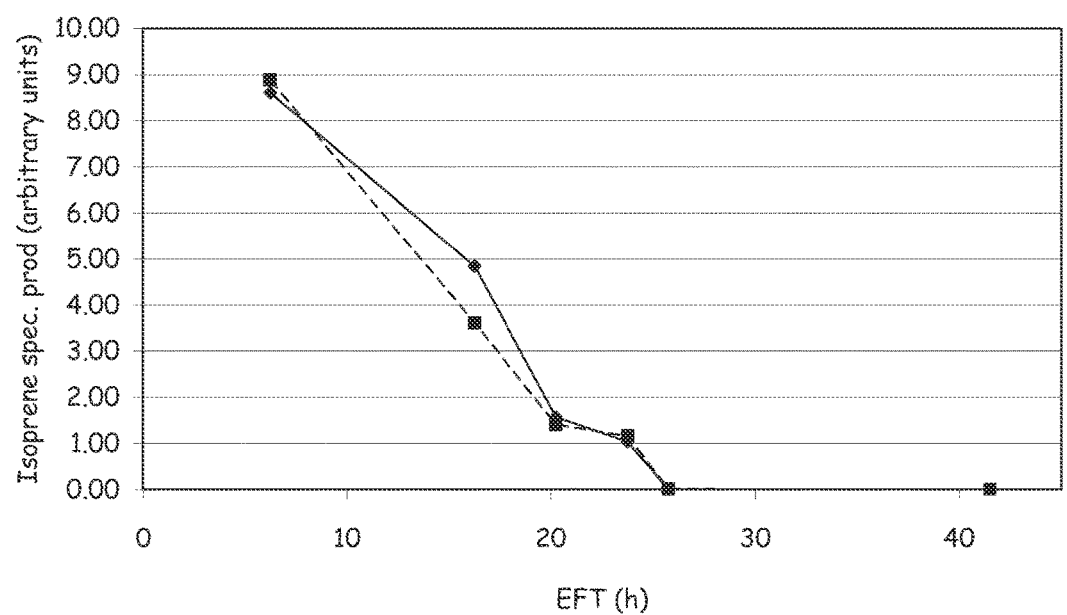
Figure 187C:
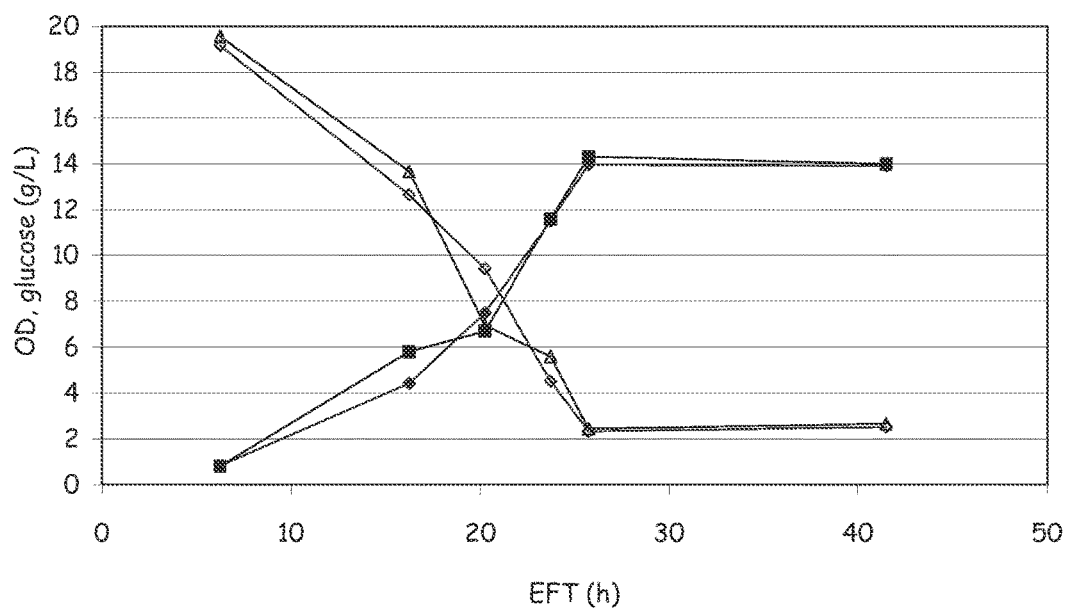
Figure 187D:
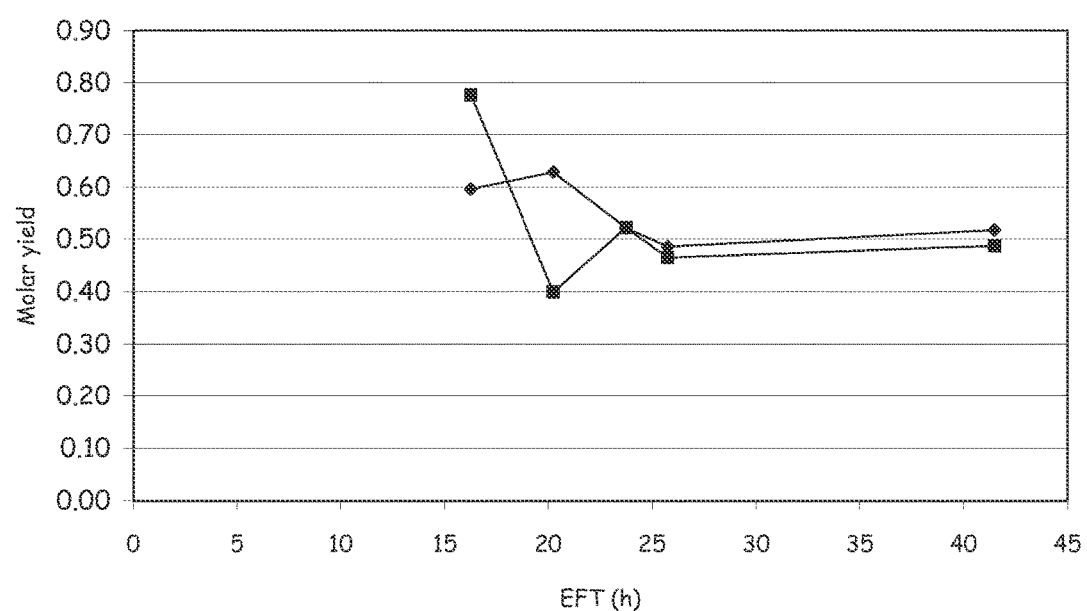

FIG. 187B shows production of isoprene by *E. coli* strain CMP249 in the presence of 200 μM IPTG, plus or minus 125 mg/L vitamin B12. Grey: +B12, black: −B12. EFT: elapsed fermentation time. FIG. 187C shows an OD profile and glucose consumption by *E. coli* strain CMP249 in the presence of 200 μM IPTG, plus or minus 125 mg/L vitamin B12. Closed symbols: glucose, open symbols: OD. Grey: +B12, black: −B12. EFT: elapsed fermentation time. FIG. 187D shows molar yield of 1,3-propanediol and glycerol in *E. coli* strain CMP249 grown in the presence of 200 μM IPTG, plus or minus 125 mg/L vitamin B12. Grey: +B12, black: −B12. EFT: elapsed fermentation time.

Figure 188:
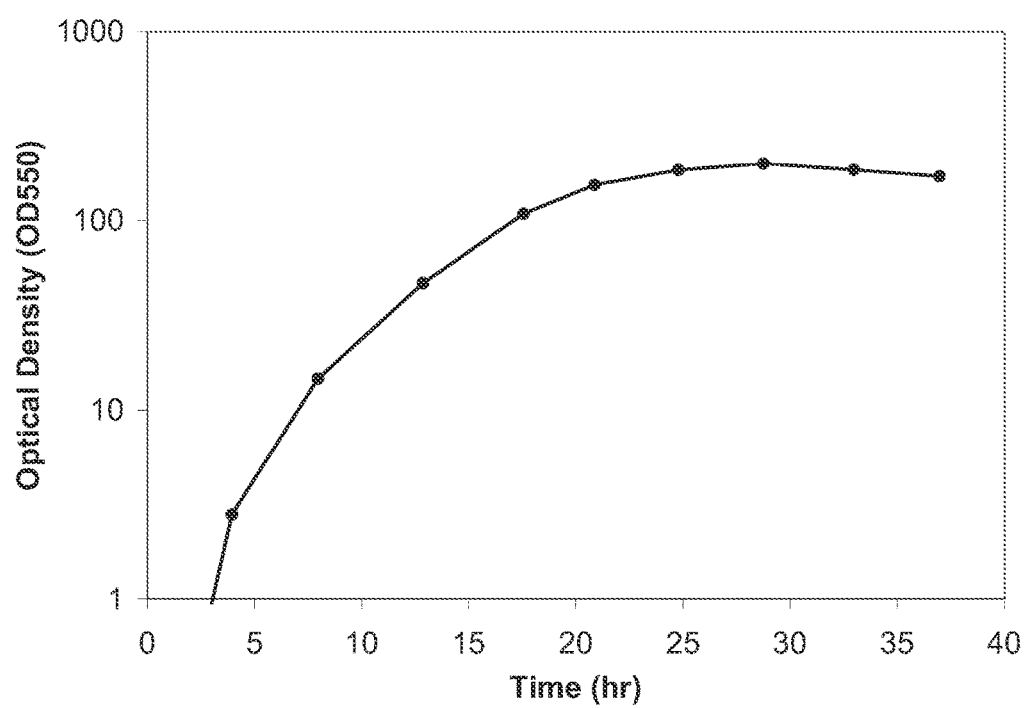

FIG. 188 shows the time course of optical density in a 15-L bioreactor containing *E. coli* strain CMP239 fed with glucose.

Figure 189:
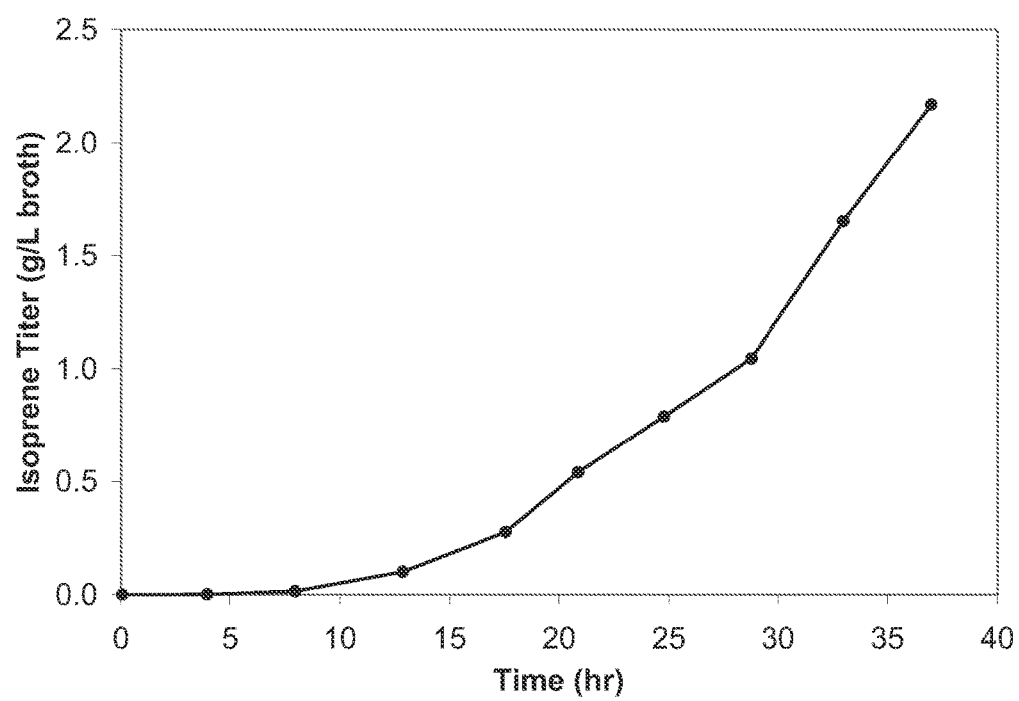

FIG. 189 shows the time course of isoprene titer in a 15-L bioreactor containing *E. coli* strain CMP239 fed with glucose. The isoprene titer is defined as the amount of isoprepe produced per liter of fermentation broth. Equation for calculating Isoprene Titer: ∫(Instantaneous isoprene production rate, g/L/hr)dt from t=0 to t hrs [=] g/L broth.

Figure 190:
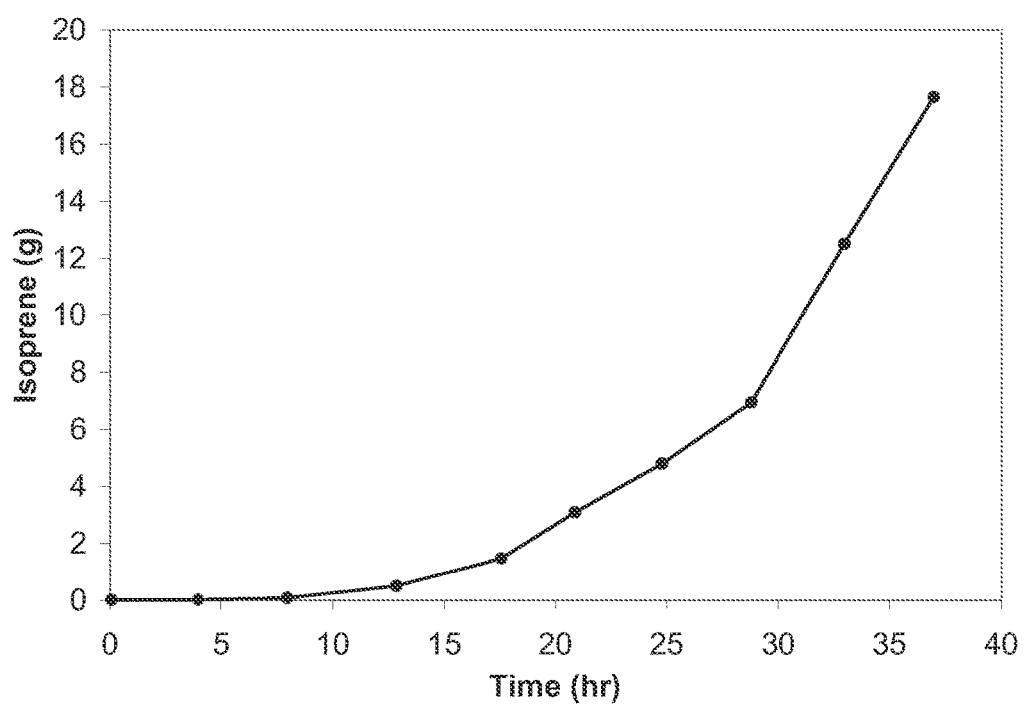

FIG. 190 shows the time course of total isoprene produced from the 15-L bioreactor containing *E. coli* strain CMP239 fed with glucose.

Figure 191:
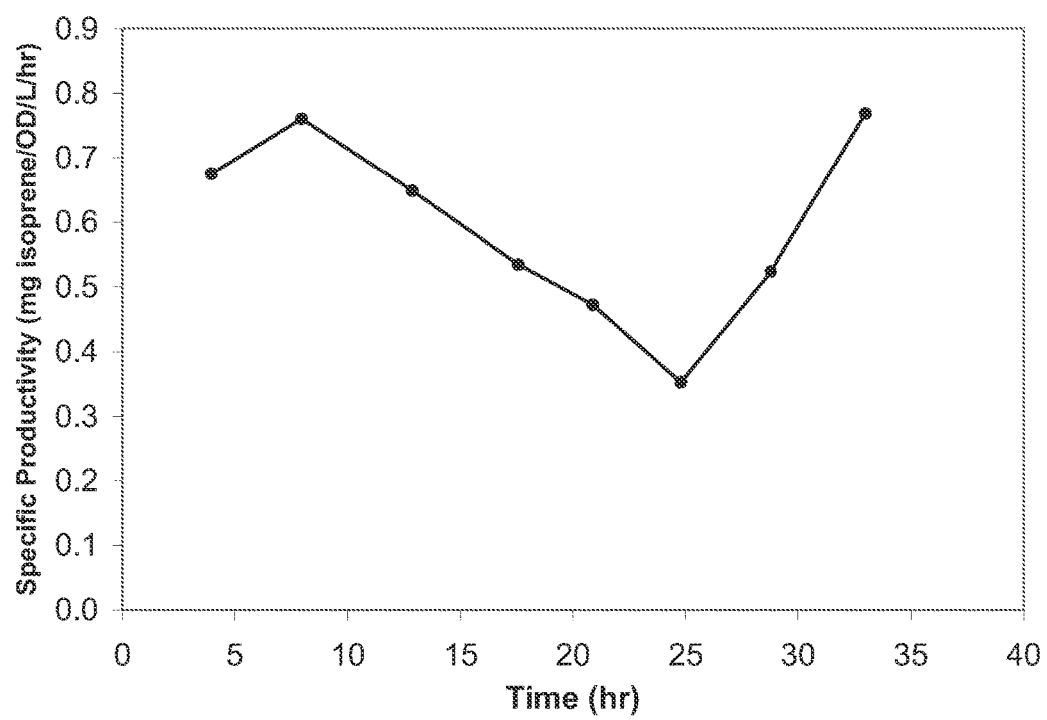

FIG. 191 shows the specific productivity of isoprene in the 15-L bioreactor containing *E. coli* strain CMP239 fed with glucose. Equation for calculating Specific Productivity levels: (mg isoprene$_t$−mg isoprene$_{to}$)/(OD550$_t$*L broth$_t$− OD550$_{to}$*L broth$_{to}$)/(t−t$_0$)[=] mg isoprene/OD/L/hr.

Figure 192:
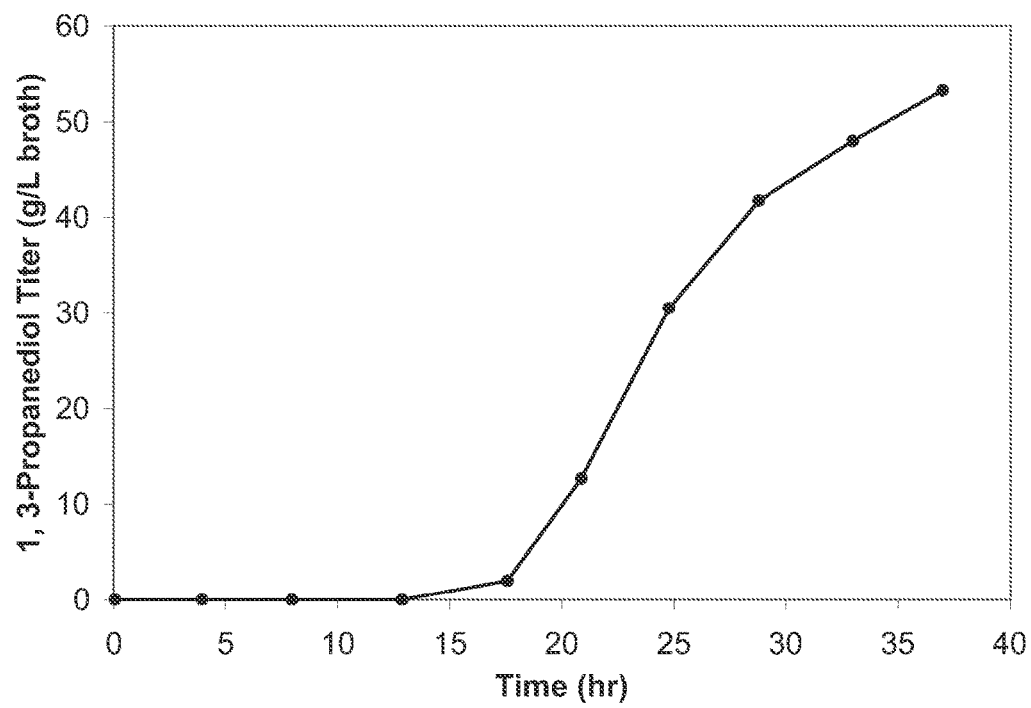

FIG. 192 shows the time course of 1,3-propanediol titer in the 15-L bioreactor containing *E. coli* strain CMP239 fed with glucose. The titer is defined as the amount of material produced per liter of fermentation broth. Equation for calculating 1,3-propanediol titer: Total material produced, g/volume fermentor broth, L [=] g/L broth.

Figure 193:
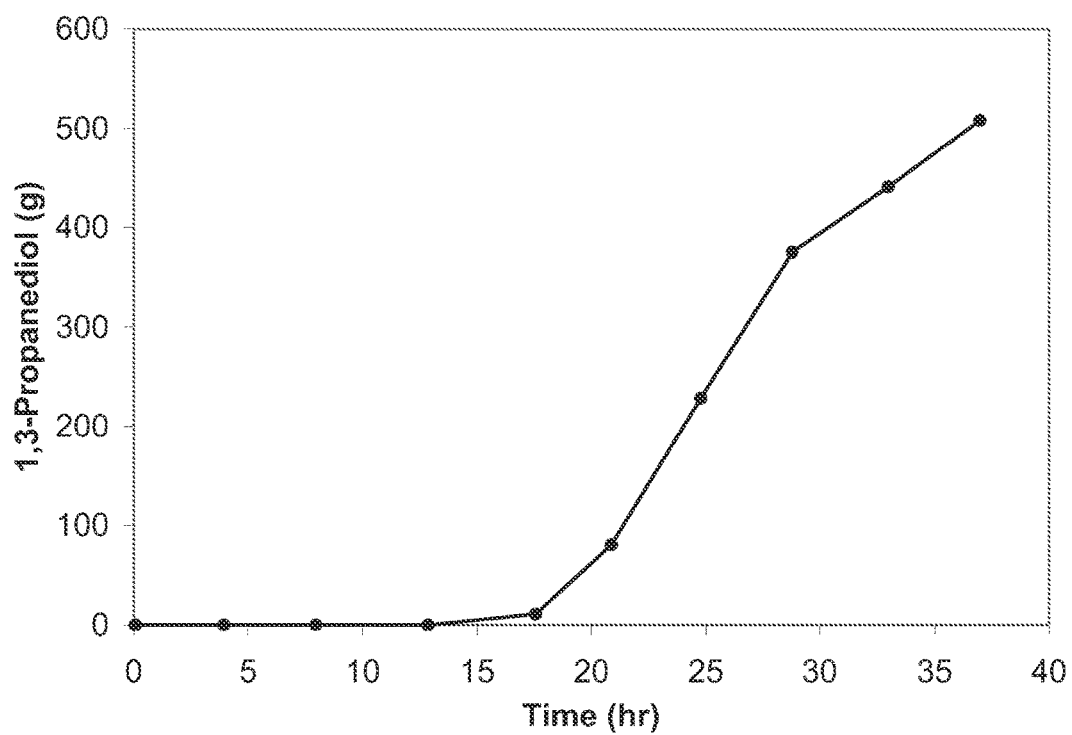

FIG. 193 shows the time course of total 1,3-propanediol produced from the 15-L bioreactor containing *E. coli* strain CMP239 fed with glucose.

Figure 194:
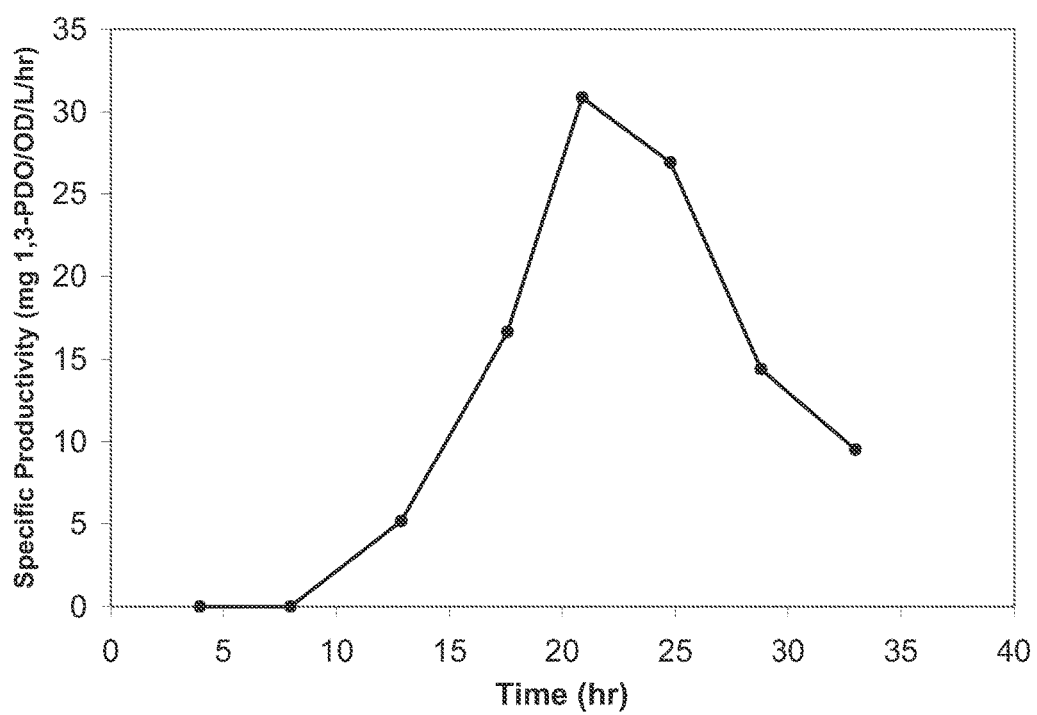

FIG. 194 shows the specific productivity of 1,3-PDO in the 15-L bioreactor containing *E. coli* strain CMP239 fed with glucose. Equation for calculating Specific Productivity levels: (mg 1,3-PDO$_t$−mg 1,3-PDO$_{to}$)/(OD550$_t$*L broth$_t$− OD550$_{to}$*L broth$_{to}$)/(t−t$_0$) [=] mg isoprene/OD/L/hr.

Figure 195:
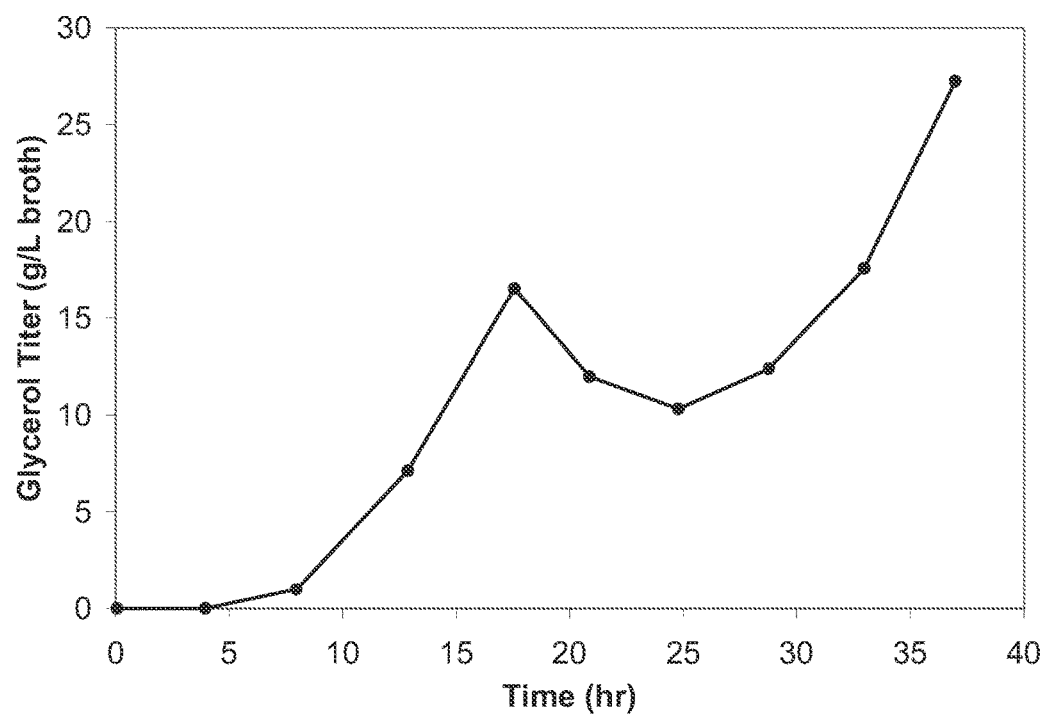

FIG. 195 shows the time course of glycerol titer hin the 15-L bioreactor containing *E. coli* strain CMP239 fed with glucose. The glycerol titer is defined as the amount of material produced per liter of fermentation broth. Equation for calculating glycerol titer: Total material produced, g/volume fermentor broth, L [=] g/L broth.

Figure 196:
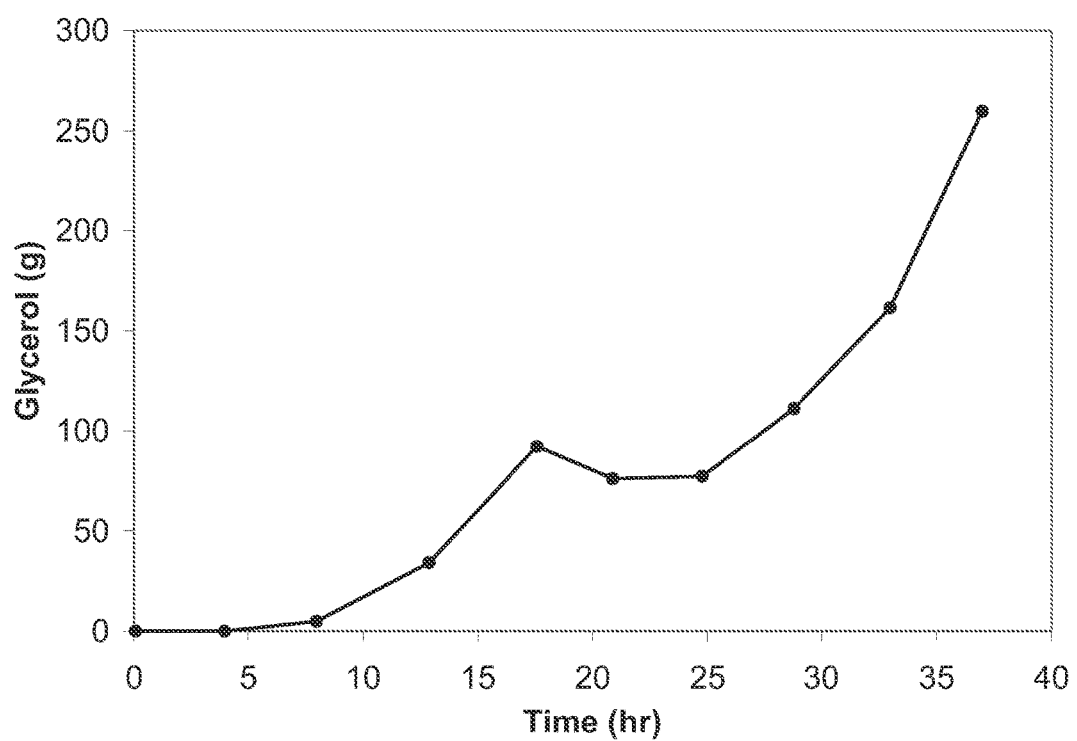

FIG. 196 shows the time course of total glycerol produced from the 15-L bioreactor containing *E. coli* strain CMP239 fed with glucose.

Figure 197:
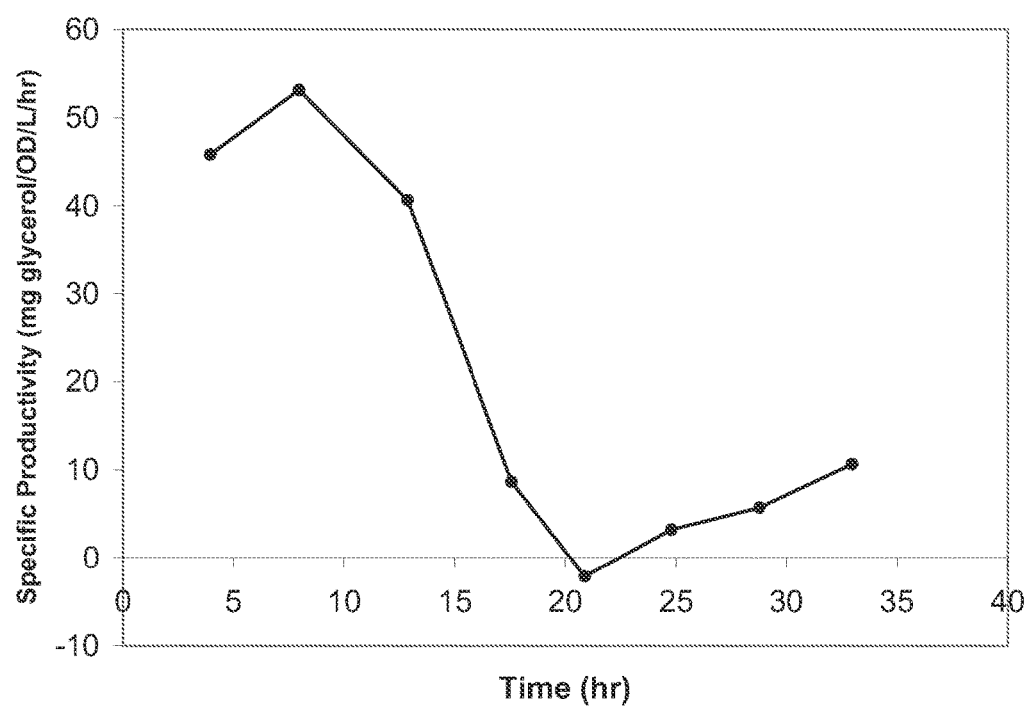

FIG. 197 shows the specific productivity of glycerol in the 15-L bioreactor containing *E. coli* strain CMP239 fed with glucose. Equation for calculating Specific Productivity levels: (mg glycerol$_t$−mg glycerol$_{to}$)/(OD550$_t$*L broth$_t$− OD550$_{to}$*L broth$_{to}$)/(t−t$_0$) [=] mg isoprene/OD/L/hr.

DETAILED DESCRIPTION

The invention provides, inter alia, compositions and methods for the production of isoprene and a co-product. In one aspect, the co-product is hydrogen. In another aspect, the co-product is a C2- or C3-alcohol or diol. In some embodiments, the C2- or C3-alcohol or diol is ethanol. In some embodiments, the C2- or C3-alcohol or diol is 1,2-propanediol. In some embodiments, the C2- or C3-alcohol or diol is 1,3-propanediol.

Provided herein are cells in oxygen-limited culture for co-production of isoprene and hydrogen, methods of co-producing isoprene and hydrogen by culturing such cells under conditions suitable for the co-production of isoprene and hydrogen, and compositions comprising isoprene and hydrogen. In some embodiments, the compositions further comprise oxygen, carbon dioxide, or nitrogen, and $1.0 \times 10^{-4}$ molar percent or less of non-methane volatile hydrocarbons. Both isoprene and hydrogen can be recovered and purified as necessary. Recovered isoprene can be polymerized to produce synthetic rubber. Recovered hydrogen can be used to power the fermentation process, thereby reducing the cost of isoprene production, reducing potential hazards associated with accumulation of high oxygen concentrations during conventional fermentation, and reducing the overall 'carbon footprint' of the process.

Existing aerobic systems for production of isoprene produce hydrogen gas via either the mevalonic acid ("MVA") pathway or the 1-deoxy-D-xylulose 5-phosphate ("DXP") pathway with molecular oxygen ($O_2$) as the primary electron acceptor. Both the DXP and MVA pathways start with glucose, require oxygen input, and evolve small amounts of hydrogen gas. At current peak isoprene productivity (e.g., ~6 g/L/hr), isoprene-producing aerobic cultures have an oxygen uptake rate ("OUR") of >200 mmol/L/hr. Conversion of glucose to hydrogen gas via the MVA pathway spills excess reducing equivalents that need to be disposed of, but releasing that excess to $O_2$ poses at least two problems: first, the combination of hydrogen gas and $O_2$ poses a safety hazard, and second, high OUR fermentations are capital and energy intensive. Because excess reducing equivalents represent potential energy, it would be useful to capture those excess reducing equivalents as $H_2$ instead of dumping them to $O_2$. Furthermore, the $H_2$ produced could be used to power the fermentation process, thereby directly reducing costs and indirectly reducing the overall 'carbon footprint' of the process. Hydrogen has been produced by both batch and continuous system fermentation using recombinant *E. coli* BL21. See, e.g., G. Chittibabu et al., "Feasibility studies on the fermentative hydrogen production by recombinant *Escherichia coli* BL-21," *Process Biochem.* 41(3):682-688 (2006), which is incorporated herein by reference, particularly with reference to production of hydrogen by fermentation with recombinant *E. coli* BL21.

There are at least three routes for getting excess reducing equivalents to hydrogenase in a bacterial system such as *E. coli*. First, using endogenous bacterial enzymes, such as the *E. coli* pyruvate formate lyase/formate dehydrogenase/formate hydrogen lyase/hydrogenase-3 system. See, e.g., Gerhard Gottschalk "Bacterial Metabolism," at pp. 194-196 (Springer Series in Microbiology, 1st ed. 1979). Second, by providing a heterologous electron capture system, such as glyceraldehyde-3-phosphate oxidoreductase ("GAPOR") and/or pyruvate oxidoreductase ("POR") with ferredoxin oxidoreductase, coupled with a heterologous hydrogenase activity, such as ferredoxin-dependent *Clostridium acetobutulicum* hydrogenase A (HydA). See, e.g., King et al., (2006), which is incorporated herein by reference in its entirety, particularly with respect to production of hydrogen by HydA and three HydA-associated maturation enzymes (HydE, HydG, and HydF). Third, by providing a heterologous electron transfer system, such as NAD(P)H to NADPH ferredoxin oxidoreductase (NFOR) (see, e.g., Viet et al., (2008)), which is incorporated herein by reference in its entirety, particularly with respect to production of hydrogen by NFOR; see also PCT Publication No. WO/2007/089901, which is incorporated herein by reference in its entirety, particularly with respect to optimization of *E. coli* strains for production of hydrogen) or *Clostridium kluyveri* NADH ferredoxin oxidoreductase (RnfCDGEAB) (Henning Seedorf et al., "The genome of *Clostridium kluyveri*, a strict anaerobe with unique metabolic features," *Proc. Nat'l Acad. Sci. U.S.A.* 105(6):2128-2133 (2008), which is incorporated herein by reference in its entirety, particularly with reference to NADH ferredoxin oxidoreductase, and with reference to components of the anaerobic ethanol-acetate fermentation pathway), coupled with a heterologous hydrogenase activity, such as ferredoxin-dependent *Clostridium acetobutulicum* hydrogenase A (HydA). See, e.g., King et al., (2006).

Thus, one strategy provided herein for capturing excess reducing equivalents as $H_2$ involves engineering a bacterial system to produce isoprene via anaerobic fermentation and to co-produce hydrogen by expression of an endogenous hydrogenase system. For example, isoprene-producing *E. coli* cells with functional $H_2$ flux can be engineered to express *E. coli* hydrogenase-3 (Hyd-3) polypeptides, *E. coli* pyruvate formate lyase ("PFL"), and the *E. coli* formate hydrogen lyase (FHL) complex, which produces hydrogen gas from formate and $CO_2$ under anaerobic conditions at acidic pH (see, e.g., Akihito Yoshida et al., "Efficient induction of formate hydrogen lyase of aerobically grown *Escherichia coli* in a three-step biohydrogen production process," *Appl. Microbiol. Biotechnol.* 74:754-760 (2007), which is incorporated herein by reference in its entirety, particularly with respect to the induction of expression of formate hydrogen lyase in *E. coli*).

A second strategy provided herein for capturing excess reducing equivalents as $H_2$ involves engineering a hybrid system for the co-production of isoprene and hydrogen under oxygen-limited conditions. Such a system would co-produce isoprene and hydrogen while utilizing less oxygen than current aerobic culture conditions. Most hydrogenases are oxygen-sensitive to some degree, however, but bacterial strains can be engineered to express an oxygen-tolerant or oxygen-insensitive hydrogenase, such as, for example, *Rubrivivax gelatinosus* hydrogenase (see, e.g., P. C. Maness et al., "Characterization of the oxygen tolerance of a hydrogenase linked to a carbon monoxide oxidation pathway in *Rubrivivax gelatinosus*," *Appl. Environ. Microbiol.* 68(6):2633-2636 (2002), which is incorporated herein by reference in its entirety, particularly with respect to *R. gelatinosus* hydrogenase), or *Ralstonia eutropha* hydrogenase (see, e.g., Burgdorf et al., (2005), which is incorporated herein by reference in its entirety, particularly with respect to *R. eutropha* hydrogenase polypeptides). Alternatively, heterologous nucleic acids encoding conventional oxygen-sensitive hydrogenase polypeptides can be mutagenized and screened to identify $O_2$-tolerant or $O_2$-insensitive hydrogenase mutants using standard methods and assays (see, e.g., L. E. Nagy et al., "Application of gene-shuffling for the rapid generation of novel [FeFe]-hydrogenase libraries," *Biotechnol. Letts.* 29(3)421-430 (2007), which is incorporated herein by reference, particularly with respect to mutagenesis and screening for oxygen tolerant hydrogenase polypeptides).

A third strategy provided herein for capturing excess reducing equivalents as $H_2$ involves engineering an obligate anaerobic bacterium to co-produce isoprene and hydrogen. Such a system would co-produce isoprene and hydrogen in anaerobic culture. For example, an obligate anaerobe can be engineered, for example, to express glyceraldehyde-3-phosphate oxidoreductase ("GAPOR") and/or pyruvate oxidoreductase ("POR"), ferredoxin oxidoreductase, NADPH ferredoxin oxidoreductase (NFOR) or *Clostridium kluyveri* NADH ferredoxin oxidoreductase (RnfCDGEAB), coupled with a heterologous hydrogenase activity, such as ferredoxin-dependent *Clostridium acetobutulicum* hydrogenase A (HydA) (see, e.g., King et al., (2006), which is incorporated herein by reference in its entirety, particularly with respect to production of hydrogen by HydA and three HydA-associated maturation enzymes (HydE, HydG, and HydF)) or NADPH-dependent *Pyrococcus furiosus* hydrogenase (see, e.g., J. Woodward et al., "Enzymatic production of biohydrogen," *Nature* 405(6790):1015-15 (2000), which is incorporated herein by reference in its entirety, particularly with respect to production of hydrogen by NADPH-dependent *P. furiosus* hydrogenase).

In any of the strategies described herein, hydrogen yields can be maximized by also blocking non-productive metabolic pathways, including those that produce fermentation side products such as lactate, acetate, pyruvate, ethanol, succinate, and glycerol or those involved in hydrogen reuptake, and by expressing an appropriate set of hydrogenase and/or other metabolic regulatory proteins, such as, for example, hydrogenase maturation proteins or transcription factors. See, e.g., Toshinori Maeda et al., "Enhanced hydrogen production from glucose by metabolically engineered *Escherichia coli*," *Appl. Microbiol. Biotechnol.* 77(4):879-890 (2007), which is incorporated by reference in its entirety, particularly with respect to production of *E. coli* strains with modified glucose metabolism.

In some embodiments, the C2- or C3-alcohol or diol is ethanol. Provided herein are cells in oxygen-limited culture for co-production of isoprene and ethanol, methods of co-producing isoprene and ethanol by culturing such cells under conditions suitable for the co-production of isoprene and ethanol, and compositions comprising isoprene, comprising ethanol or comprising isoprene and ethanol. In some embodiments, the compositions further comprise oxygen, carbon dioxide, or nitrogen, and $1.0 \times 10^{-4}$ molar percent or less of non-methane volatile hydrocarbons. Both isoprene and ethanol can be recovered and purified as necessary. Recovered isoprene can be polymerized to produce synthetic rubber. Recovered ethanol can be used to power the fermentation process, thereby reducing the cost of isoprene production, reducing potential hazards associated with accumulation of high ethanol concentrations during conventional fermentation, and reducing the overall 'carbon footprint' of the process.

Co-generation of isoprene and ethanol provides a way to increase the theoretical yield of isoprene from glucose by the DXP pathway, as the ATP generated in the production of ethanol can be utilized in the pathway to make isoprene. Moreover, the process would run anaerobically, decreasing capital investment for oxygen transfer. The process could even run in existing ethanol plants, in terms of tank stirring. Co-generation of isoprene and ethanol can be done in a variety of cell types, including yeast, such as *Saccharomyces cerevisiae*, and bacteria, such as *Escherichia coli* and *Zymomonas mobilis*. While *E. coli* can produce ethanol when it is grown anaerobically, using the enzyme adhE to go from acetyl-CoA to ethanol via acetaldehyde, ethanol production can be improved by expressing one or more enzymes associated with biochemical reactions around pyruvate in *E. coli* or other bacteria, such as *Zymomonas mobilis*. For example, ethanol production in *E. coli* can be greatly improved by co-expression of pyruvate decarboxylase (pdc) from *Zymomonas mobilis* (see Example 28).

In some embodiments, the C2- or C3-alcohol or diol is 1,2-propanediol. Provided herein are cells in oxygen-limited culture for co-production of isoprene and 1,2-propanediol, methods of co-producing isoprene and 1,2-propanediol by culturing such cells under conditions suitable for the co-production of isoprene and 1,2-propanediol, and compositions comprising isoprene, comprising 1,2-propanediol or comprising isoprene and 1,2-propanediol. In some embodiments, the compositions further comprise oxygen, carbon dioxide, or nitrogen, and $1.0 \times 10^{-4}$ molar percent or less of non-methane volatile hydrocarbons. Both isoprene and 1,2-propanediol can be recovered and purified as necessary. Recovered isoprene can be polymerized to produce synthetic rubber. Recovered 1,2-propanediol can be used to power the fermentation process, thereby reducing the cost of isoprene production, reducing potential hazards associated with accumulation of high 1,2-propanediol concentrations during conventional fermentation, and reducing the overall 'carbon footprint' of the process.

In some embodiments, the C2- or C3-alcohol or diol is 1,3-propanediol. Provided herein are cells in oxygen-limited culture for co-production of isoprene and 1,3-propanediol, methods of co-producing isoprene and 1,3-propanediol by culturing such cells under conditions suitable for the co-production of isoprene and 1,3-propanediol, and compositions comprising isoprene, comprising 1,3-propanediol or comprising isoprene and 1,3-propanediol. In some embodiments, the compositions further comprise oxygen, carbon dioxide, or nitrogen, and $1.0 \times 10^{-4}$ molar percent or less of non-methane volatile hydrocarbons. Both isoprene and 1,3-propanediol can be recovered and purified as necessary. Recovered isoprene can be polymerized to produce synthetic rubber. Recovered 1,3-propanediol can be used to power the fermentation process, thereby reducing the cost of isoprene production, reducing potential hazards associated with accumulation of high 1,3-propanediol concentrations during conventional fermentation, and reducing the overall 'carbon footprint' of the process.

DEFINITIONS

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

As used herein, the term "C2- or C3-alcohol or diol" includes, but is not limited to, ethanol (CAS No. 64-17-5), 1-propanol (CAS No. 71-23-8), 2-propanol (CAS No. 67-63-0), 1,2-propanediol (CAS No. 57-55-6), 1,3-propanediol (CAS No. 504-63-2), and glycerol (CAS No. 56-81-5). Unless otherwise indicated, the term "1,2-propanediol" refers to 1,2-(R)-propanediol, 1,2-(S)-propanediol, or a racemic mixture of 1,2-(RIS)-propanediol.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide whose amino acid sequence is not identical to that of another polypeptide naturally expressed in the same host cell. In particular, a heterologous polypeptide is not identical to a wild-type polypeptide that is found in the same host cell in nature.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

As used herein, a "nucleic acid" refers to two or more deoxyribonucleotides and/or ribonucleotides covalently joined together in either single or double-stranded form. It is to be understood that mutations, including single nucleotide mutations, can occur within a nucleic acid as defined herein.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. It is to be understood that mutations, including single nucleotide mutations, can occur within a nucleic acid as defined herein.

By "heterologous nucleic acid" is meant a nucleic acid whose nucleic acid sequence is not identical to that of another nucleic acid naturally found in the same host cell. In particular, a heterologous nucleic acid is not identical to a wild-type nucleic acid that is found in the same host cell in nature.

As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

The term "selective marker" or "selectable marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4.

Isoprene

As used herein, the term "isoprene" or "2-methyl-1,3-butadiene" (CAS#78-79-5) refers to the direct and final volatile C5 hydrocarbon product from the elimination of pyrophosphate from 3,3-dimethylallyl pyrophosphate (DMAPP), and does not involve the linking or polymerization of one or more isopentenyl diphosphate (IPP) molecules to one or more DMAPP molecules. The term "isoprene" is not generally intended to be limited to its method of production unless indicated otherwise herein.

The vast majority of isoprene is derived from petrochemical sources as an impure C5 hydrocarbon fraction which requires extensive purification before the material is suitable for polymerization. Several impurities are particularly problematic given their structural similarity to isoprene and the fact that they can act as polymerization catalyst poisons. Such compounds include 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, and cis-pent-3-ene-1-yne (FIG. 90). In some embodiments, the isoprene composition of the invention is substantially free of any contaminating unsaturated C5 hydrocarbons. As described further in Example 10, no detectable amount of unsaturated C5 hydrocarbons other than isoprene (such as 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) was found in isoprene compositions produced using the methods described herein. Some isoprene compositions produced using the methods described herein contain ethanol, acetone, and C5 prenyl alcohols as determined by GC/MS analysis. All of these components are far more readily removed from the isoprene stream than the isomeric C5 hydrocarbon fractions that are present in isoprene compositions derived from petrochemical sources. Accordingly, in some embodiments, the isoprene compositions of the invention require minimal treatment in order to be of polymerization grade.

In one aspect, compositions and methods of the invention increase the rate of isoprene production and increase the total amount of isoprene that is produced. For example, cell culture systems that generate $4.8 \times 10^4$ nmole/$g_{wcm}$/hr of isoprene have been produced (Table 1). The efficiency of these systems is demonstrated by the conversion of about 2.2% of the carbon that the cells consume from a cell culture medium into isoprene. As shown in the Examples and Table 2, approximately 3 g of isoprene per liter of broth was generated. If desired, even greater amounts of isoprene can be obtained using other conditions, such as those described herein. In some embodiments, a renewable carbon source is used for the production of isoprene. In some embodiments, the production of isoprene is decoupled from the growth of the cells. In some embodiments, the concentrations of isoprene and any oxidants are within the nonflammable ranges to reduce or eliminate the risk that a fire may occur during production or recovery of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further below, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) isoprene synthase polypeptide was expressed in a variety of host cells, such as *Escherichia coli, Panteoa citrea, Bacillus subtilis, Yarrowia lipolytica*, and *Trichoderma reesei*. All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 300 mg of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

TABLE 1

Exemplary yields of isoprene from a shake flask using the cell cultures and methods of the invention.

| Strain | Isoprene Production in a Headspace vial* | |
|---|---|---|
| | Headspace concentration μg/$L_{gas}$ | Specific Rate μg/$L_{broth}$/hr/OD (nmol/$g_{wcm}$/hr) |
| E. coli BL21/pTrcKudzu IS | 1.40 | 53.2 (781.2) |
| E. coli BL21/pCL DXS yidi Kudzu IS | 7.61 | 289.1 (4.25 × 10³) |
| E. coli BL21/MCM127 with kudzu IS and entire MVA pathway | 23.0 | 874.1 (12.8 × 10³) |
| E. coli BL21/pET N-HisKudzu IS | 1.49 | 56.6 (831.1) |
| Pantoea citrea/pTrcKudzu IS | 0.66 | 25.1 (368.6) |
| E. coli w/ Poplar IS [Miller (2001)] | — | 5.6 (82.2) |
| Bacillis licheniformis Fall US 5849970 | — | 4.2 (61.4) |
| Yarrowia lipolytica with kudzu isoprene synthase | ~0.05 μg/L | ~2 (~30) |
| Trichoderma reesei with kudzu isoprene synthase | ~0.05 μg/L | ~2 (~30) |
| E. coli BL21/pTrcKKD$_y$I$_k$IS with kudzu IS and lower MVA pathway | 85.9 | 3.2 × 10³ (4.8 × 10⁴) |

The assay for measuring isoprene production is described in Example I, part II. For this assay, a sample was removed at one or more time points from the shake flask and cultured for 30 minutes. The amount of isoprene produced in this sample was then measured. The headspace concentration and specific rate of isoprene production are listed in TABLE 1 and described further herein.
*Normalized to 1 mL of 1 OD$_{600}$, cultured for 1 hour in a sealed headspace vial with a liquid to headspace volume ratio of 1:19.

TABLE 2

Exemplary yields of isoprene in a fermentor using the cell cultures and methods of the invention.

| Strain | Isoprene Production in Fermentors | | |
|---|---|---|---|
| | Peak Headspace concentration** (μg/$L_{gas}$) | Titer (mg/$L_{broth}$) | Peak Specific rate μg/$L_{broth}$/hr/OD (nmol/$g_{wcm}$/hr) |
| E. coli BL21/pTrcKudzu with Kudzu IS | 52 | 41.2 | 37 (543.3) |
| E. coli FM5/pTrcKudzu IS | 3 | 3.5 | 21.4 (308.1) |
| E. coli BL21/triple strain (DXS, yidi, IS) | 285 | 300 | 240 (3.52 × 10³) |
| E. coli FM5/triple strain (DXS, yidi, IS) | 50.8 | 29 | 180.8 (2.65 × 10³) |
| E. coli/MCM127 with Kudzu IS and entire MVA pathway | 3815 | 3044 | 992.5 (1.46 × 10⁴) |
| E. coli BL21/pCLPtrc UpperPathway gi1.2 integrated lower pathway pTrcKudzu | 2418 | 1640 | 1248 (1.83 × 10⁴) |
| E. coli BL21/MCM401 with 4 × 50 μM IPTG | 13991 | 23805 | 3733 (5.49 × 10⁴) |
| E. coli BL21/MCM401 with 2 × 1000 μM IPTG | 22375 | 19541 | 5839.5 (8.59 × 10⁴) |
| E. coli BL21/pCLPtrc UpperPathwayHGS2-pTrcKKDyIkIS | 3500 | 3300 | 1088 (1.60 × 10⁴) |
| Bacillus subtilis wild-type | 1.5 | 2.5 | 0.8 (11.7) |
| Bacillus pBS Kudzu IS | 16.6 | ~30 (over 100 hrs) | 5 (73.4) |
| Bacillus Marburg 6051 [Wagner and Fall (1999)] | 2.04 | 0.61 | 24.5 (359.8) |
| Bacillus Marburg 6051 Fall U.S. Pat. No. 5,849,970 | 0.7 | 0.15 | 6.8 (100) |

The assay for measuring isoprene production is described in Example I, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in TABLE 2 and described further herein.
**Normalized to an off-gas flow rate of 1 vvm (1 volume off-gas per 1 $L_{broth}$ per minute).

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 19A:
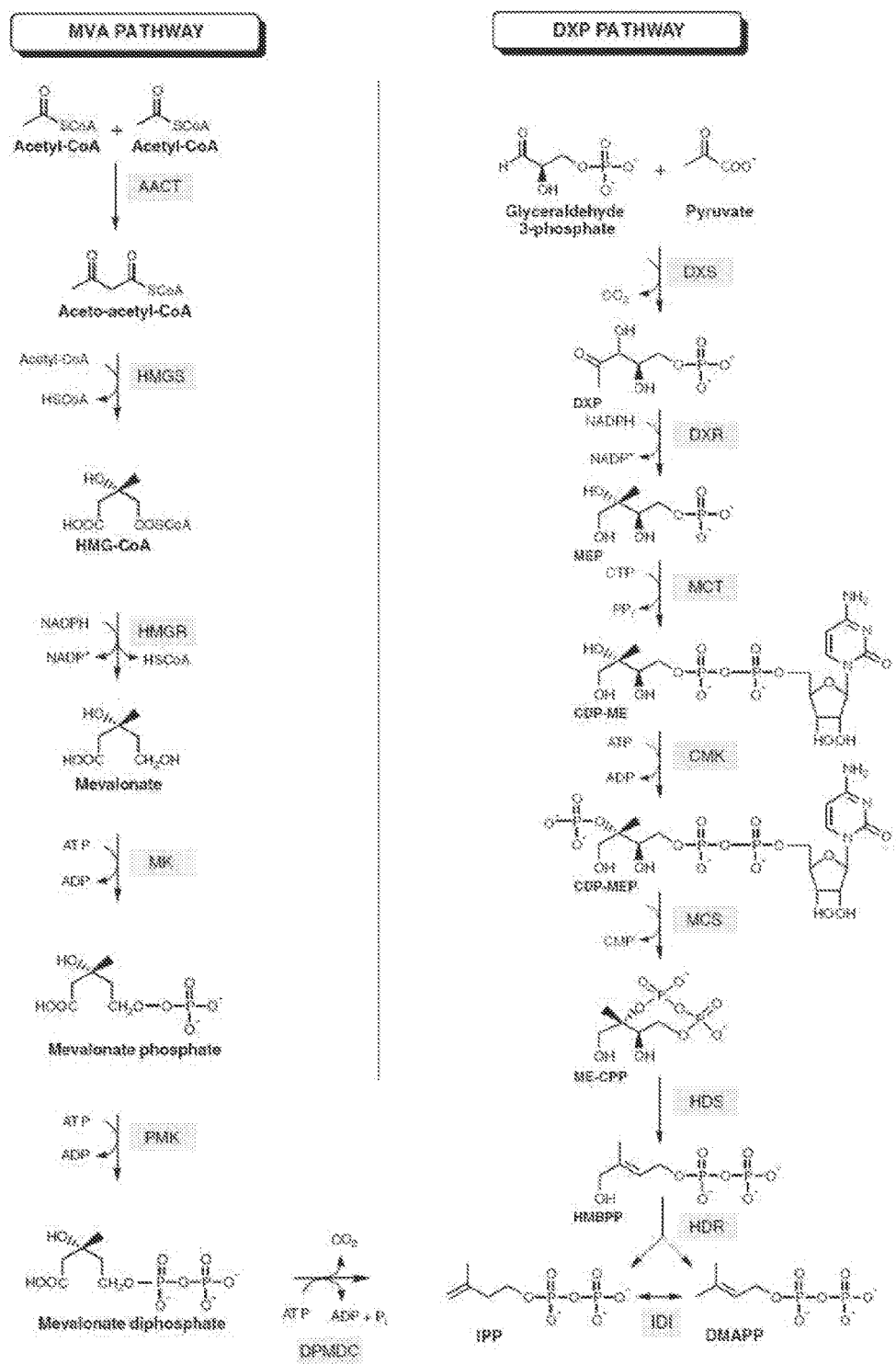
FIG. 19A shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERG8, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264: 19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

The encoded DXS and IDI polypeptides are part of the DXP pathway for the biosynthesis of isoprene (FIG. 19A). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount (and conversion rate) of IPP that is converted into DMAPP, which in turn is converted into isoprene.

For example, fermentation of E. coli cells with a kudzu isoprene synthase, S. cerevisia IDI, and E. coli DXS nucleic acids was used to produce isoprene. The levels of isoprene varied from 50 to 300 µg/L over a time period of 15 hours (Example 7, part VII).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by E. coli cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

Figure 19B:
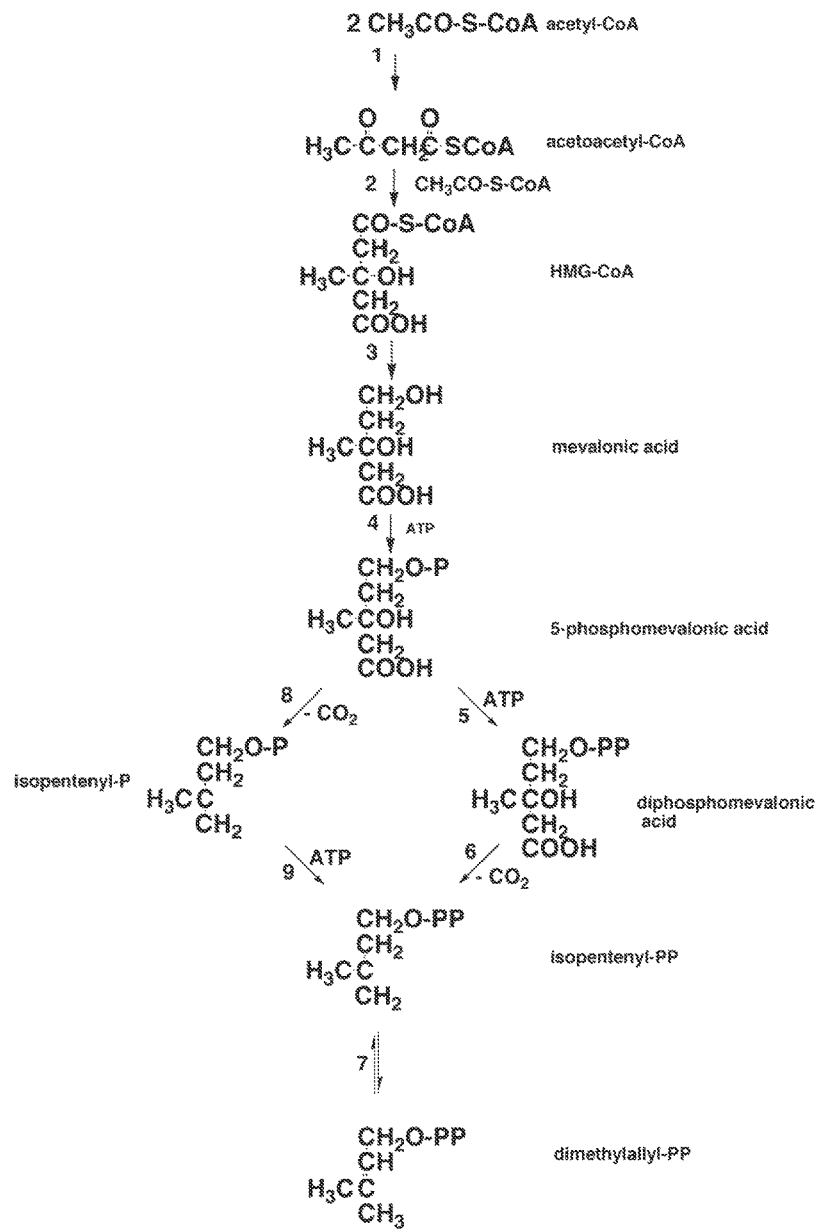
FIG. 19B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology. Reviews*, 71:97-120, 2007, which is incorporated by reference in its entirety, particular with respect to nucleic acids and polypeptides of the modified MVA pathway. The modified MVA pathway is present, for example, in some Archaeal organisms, such as *Methanosarcina mazei*.

In some embodiments, the production of isoprene by cells that contain a heterologous isoprene synthase nucleic acid is augmented by increasing the amount of a MVA polypeptide expressed by the cells (FIGS. 19A and 19B). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain an entire MVA pathway that includes AA-CoA thiolase, HMG-CoA synthase, HMG-CoA reductase, MVK, PMK, MVD, and IDI nucleic acids. In some embodiments, the cells contain an entire MVA pathway that includes AA-CoA thiolase, HMG-CoA synthase, HMG-CoA reductase, MVK, PMDC, IPK, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, E. coli cells containing a nucleic acid encoding a kudzu isoprene synthase polypeptide and nucleic acids encoding Saccharomyces cerevisiae MVK, PMK, MVD, and IDI polypeptides generated isoprene at a rate of $6.67 \times 10^{-4}$ mol/$L_{broth}$/$OD_{600}$/hr (see Example 8). Additionally, a 14 liter fermentation of E. coli cells with nucleic acids encoding Enterococcus faecalis AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in E. coli. E. coli cells that contain nucleic acids for both the upper MVA pathway and the lower MVA pathway as well as a kudzu isoprene synthase (strain MCM 127) produced significantly more isoprene (874 ug/L) compared to E. coli cells with nucleic acids for only the lower MVA pathway and the kudzu isoprene synthase (strain MCM 131) (see Table 3 and Example 8, part VIII).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Figure 48A:
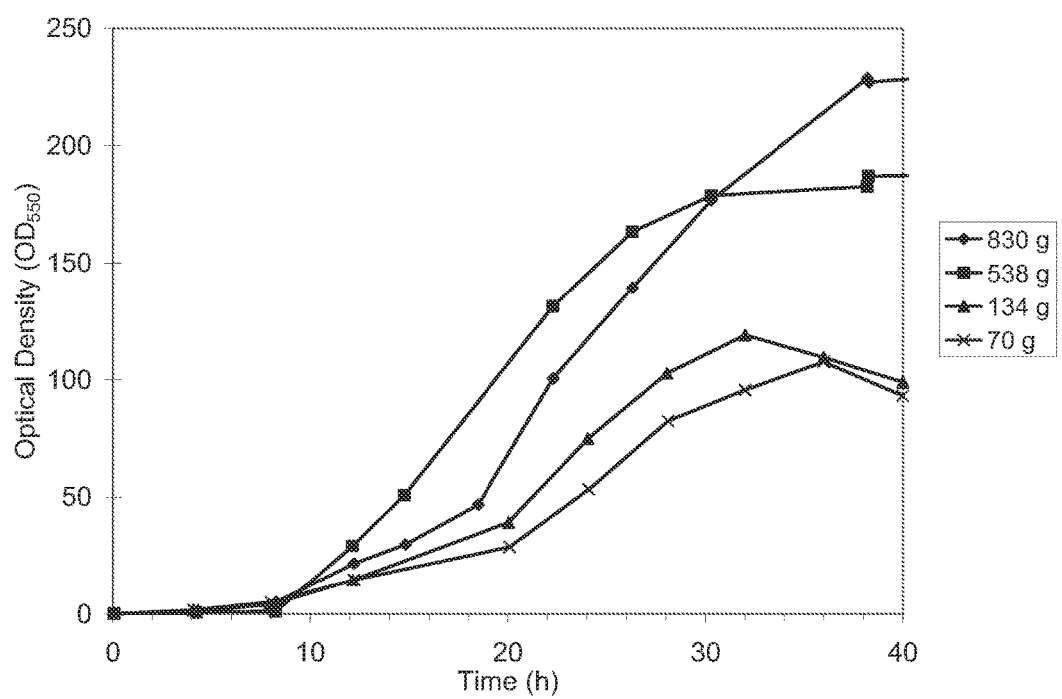
FIGS. 48A-C show graphs demonstrating the effect of yeast extract of isoprene production. Panel A shows the time course of optical density within fermentors fed with varying amounts of yeast extract. Panel B shows the time course of isoprene titer within fermentors fed with varying amounts of yeast extract. The titer is defined as the amount of isoprene produced per liter of fermentation broth. Panel C shows the effect of yeast extract on isoprene production in *E. coli* grown in fed-batch culture.
Figure 48B:
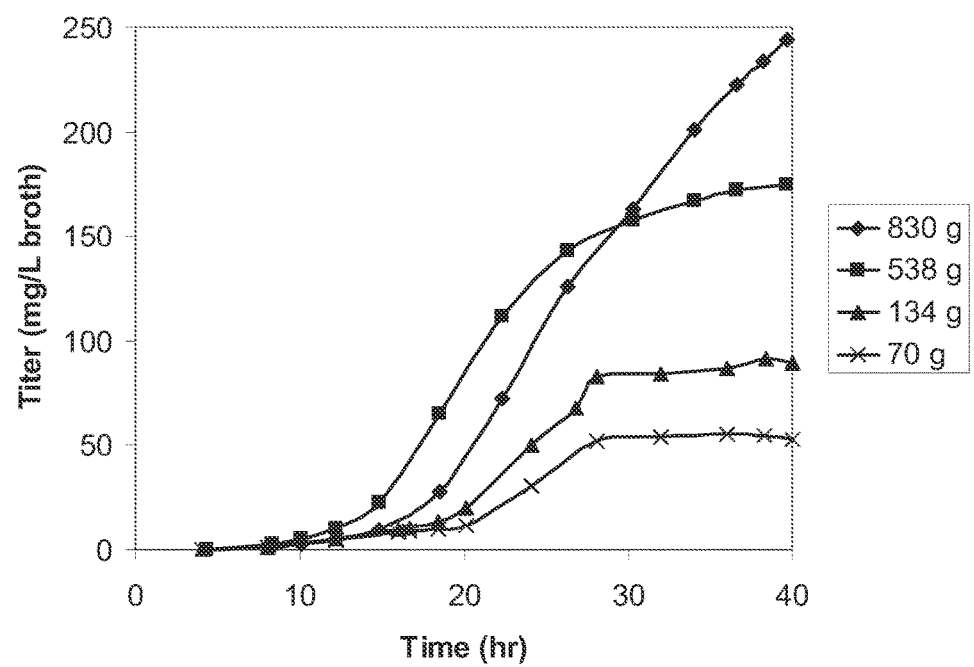
Figure 48C:
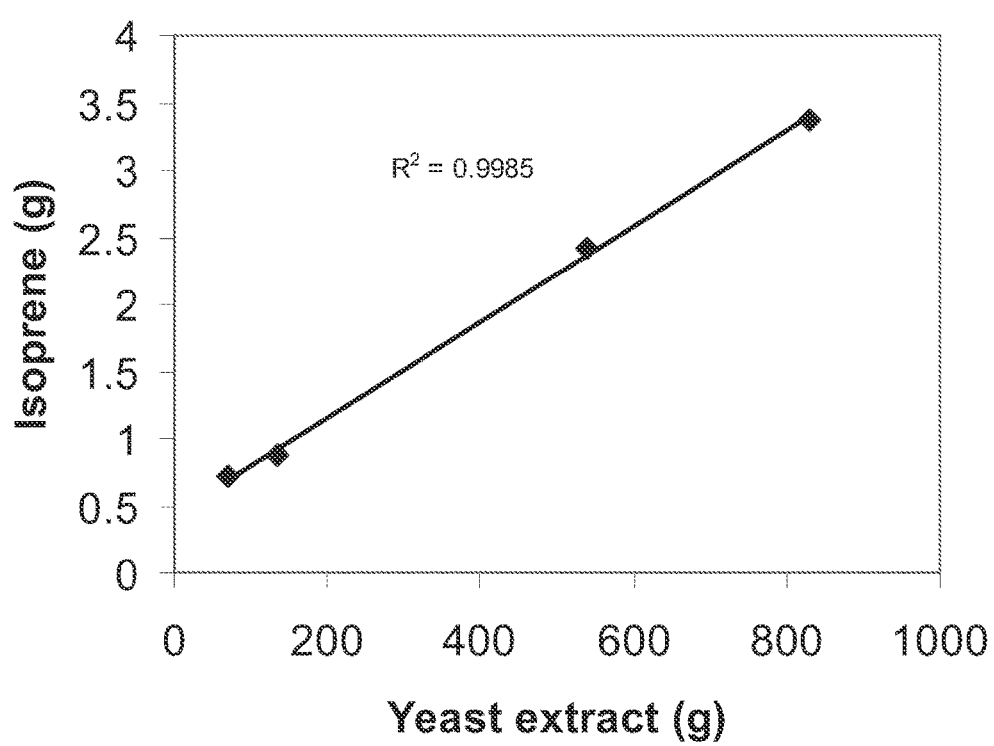

As indicated in Example 7, part VI, the amount of isoprene produced can be further increased by adding yeast extract to the cell culture medium. In this example, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 7, part VIII). Both of these experiments used E. coli cells with kudzu isoprene synthase, S. cerevisia IDI, and E. coli DXS nucleic acids to produce isoprene. Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Figure 46A:
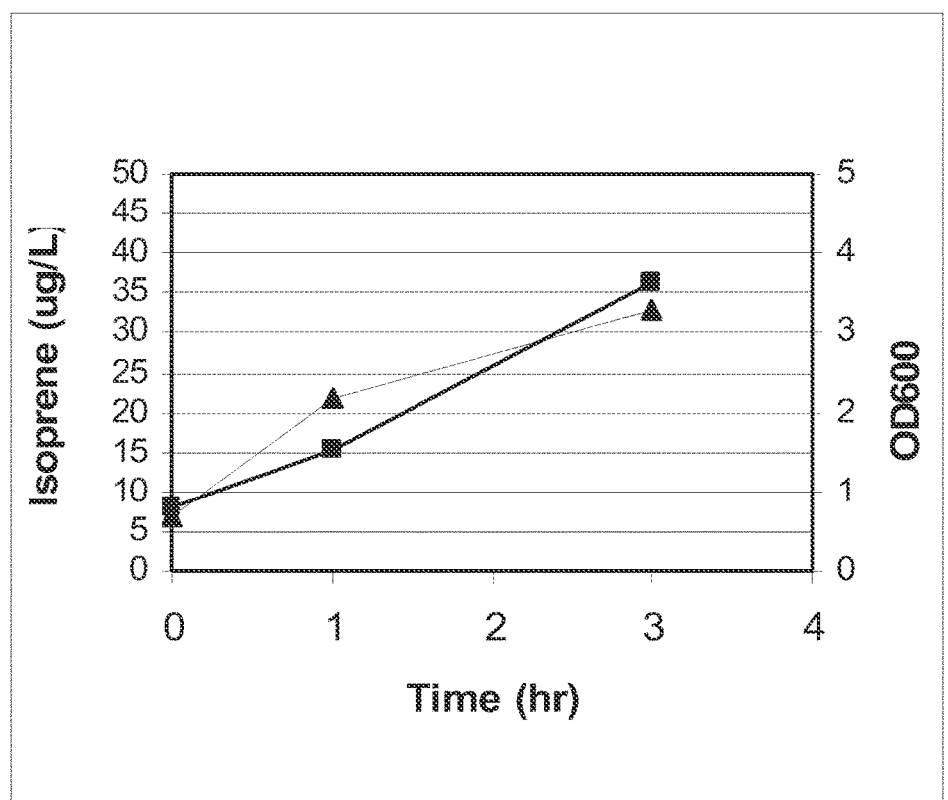
FIGS. 46A-E show graphs representing isoprene production from biomass feedstocks. Panel A shows isoprene production from corn stover, Panel B shows isoprene production from bagasse, Panel C shows isoprene production from softwood pulp, Panel D shows isoprene production from glucose, and Panel E shows isoprene production from cells with no additional feedstock. Grey squares represent $OD_{600}$ measurements of the cultures at the indicated times post-inoculation and black triangles represent isoprene production at the indicated times post-inoculation.
Figure 46B:
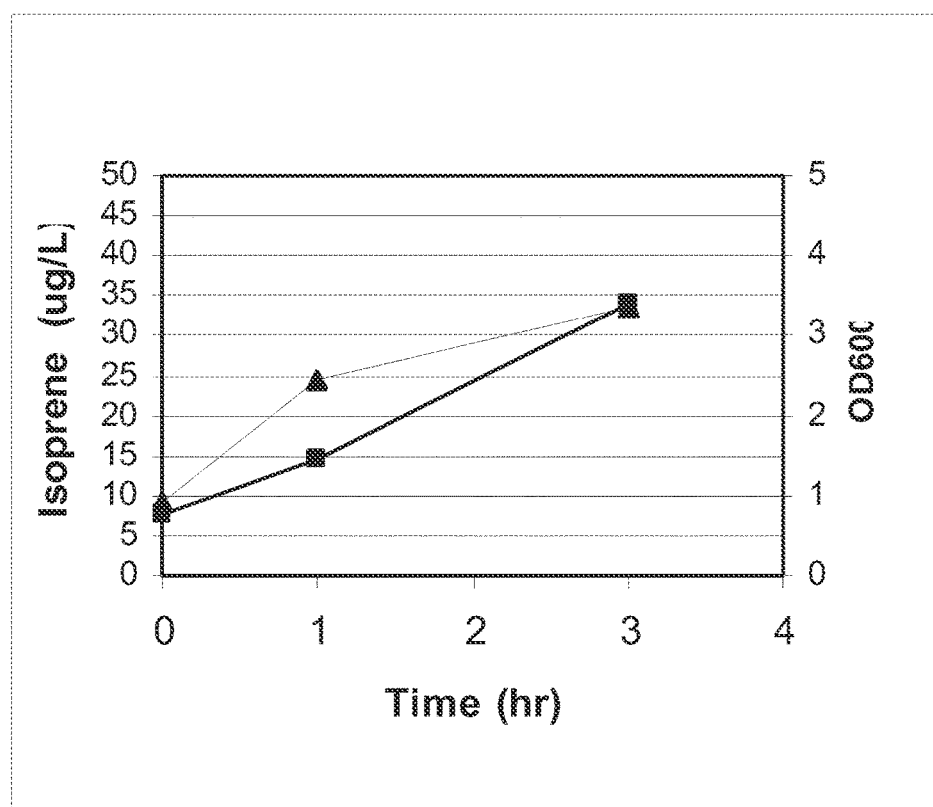
Figure 46C:
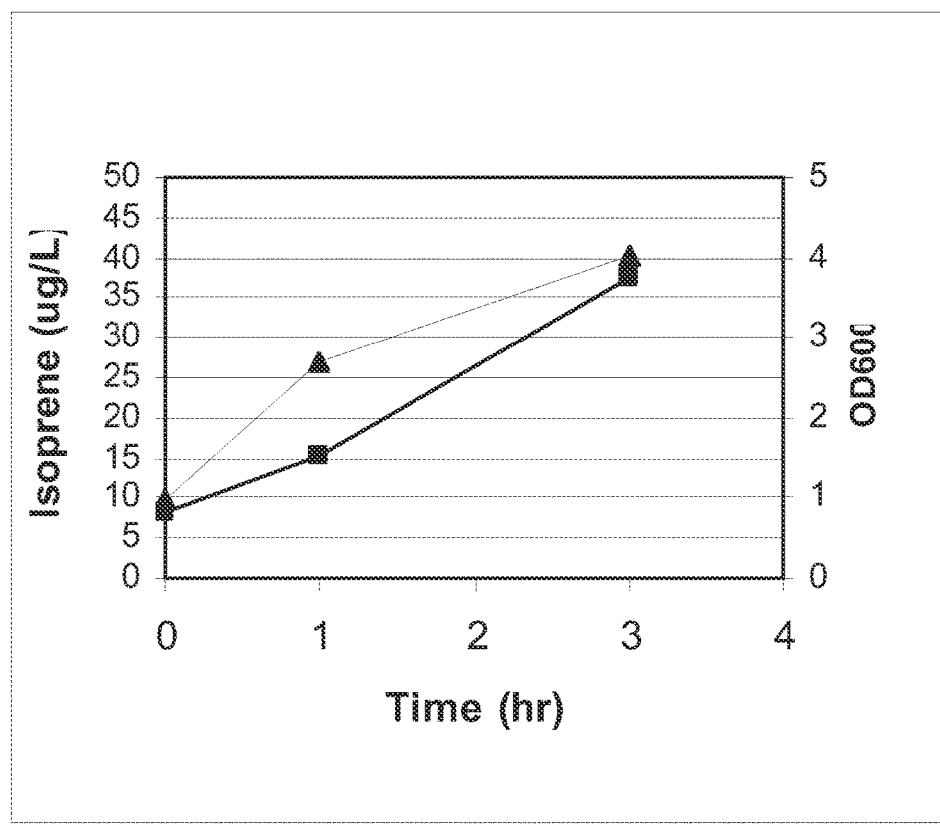
Figure 46D:
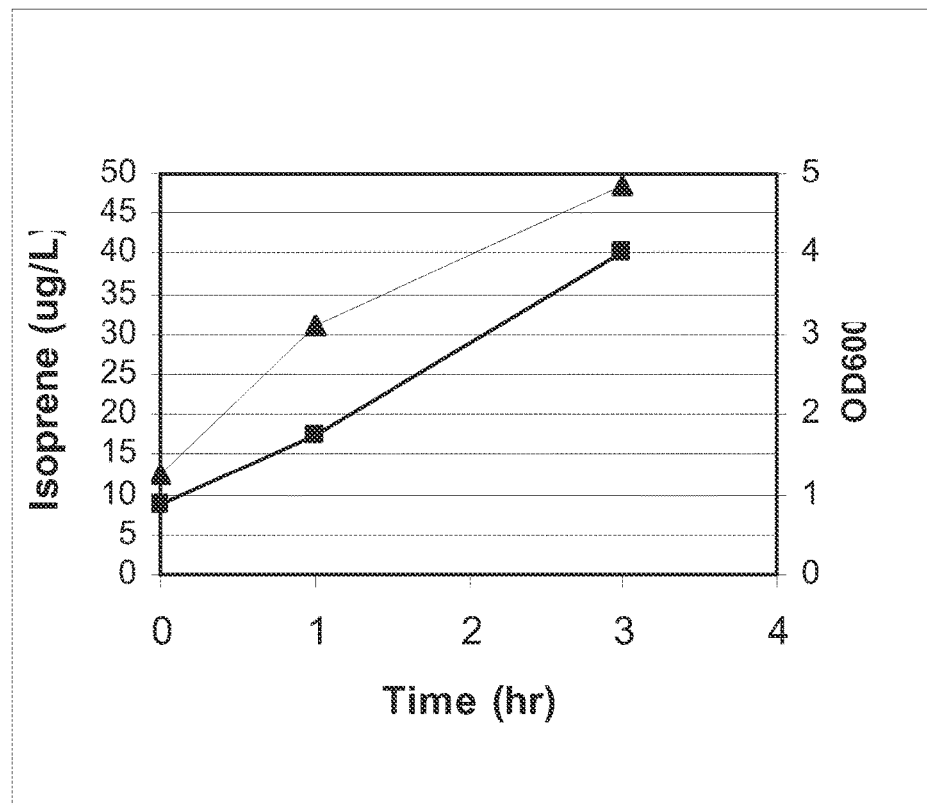
Figure 46E:
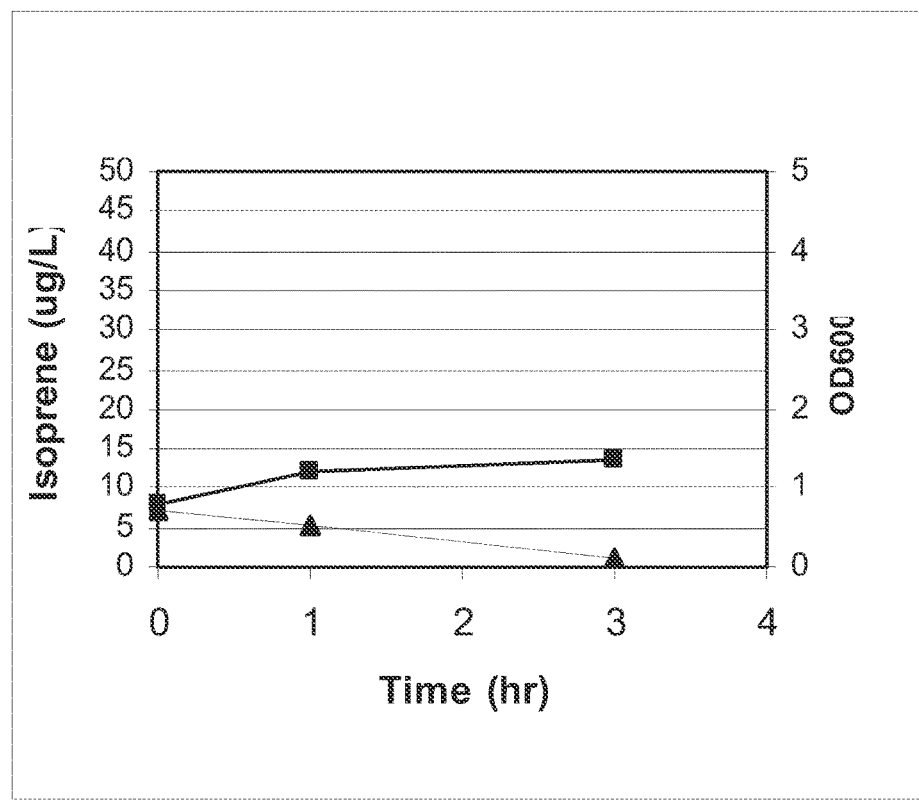
Figure 47A:
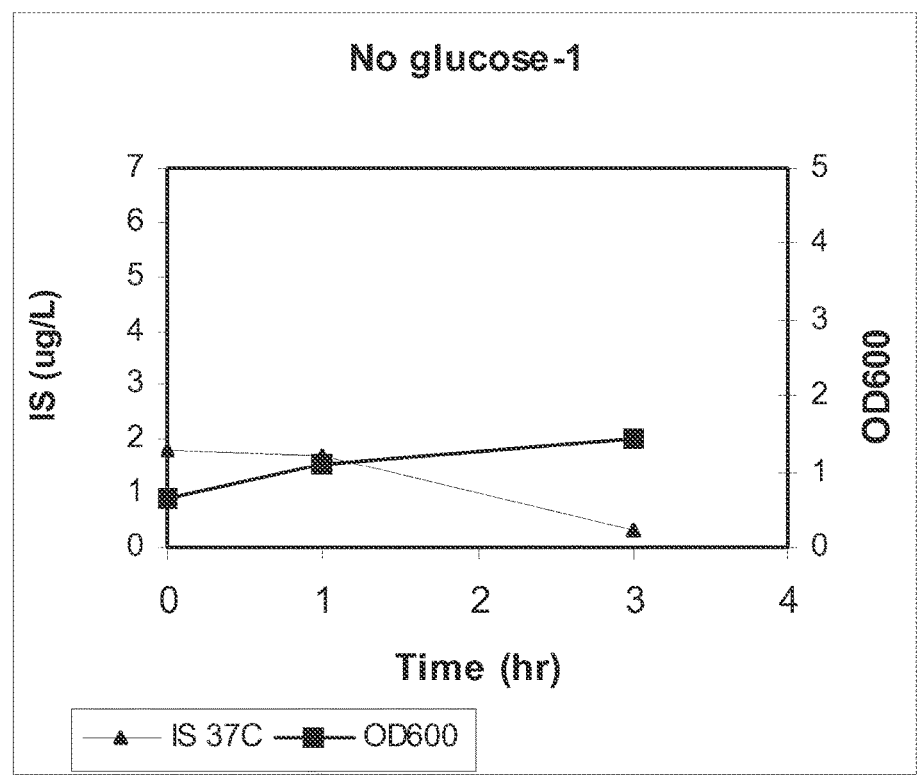
FIG. 47A shows a graph representing isoprene production by BL21 (λDE3) pTrcKudzu yIDI DXS (kan) in a culture with no glucose added. Squares represent $OD_{600}$, and triangles represent isoprene produced (μg/ml).
Figure 47B:
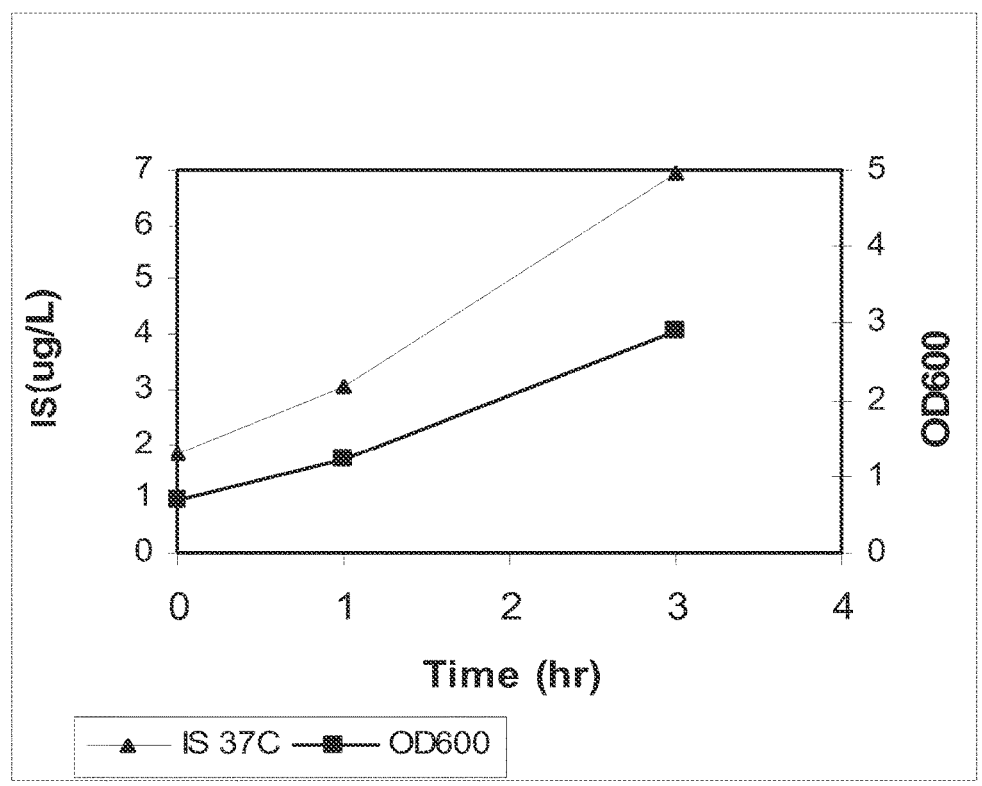
FIG. 47B shows a graph representing isoprene production from 1% glucose feedstock invert sugar by BL21 (λDE3) pTrcKudzu yIDI DXS (kan). Squares represent $OD_{600}$, and triangles represent isoprene produced (μg/ml).
Figure 47C:
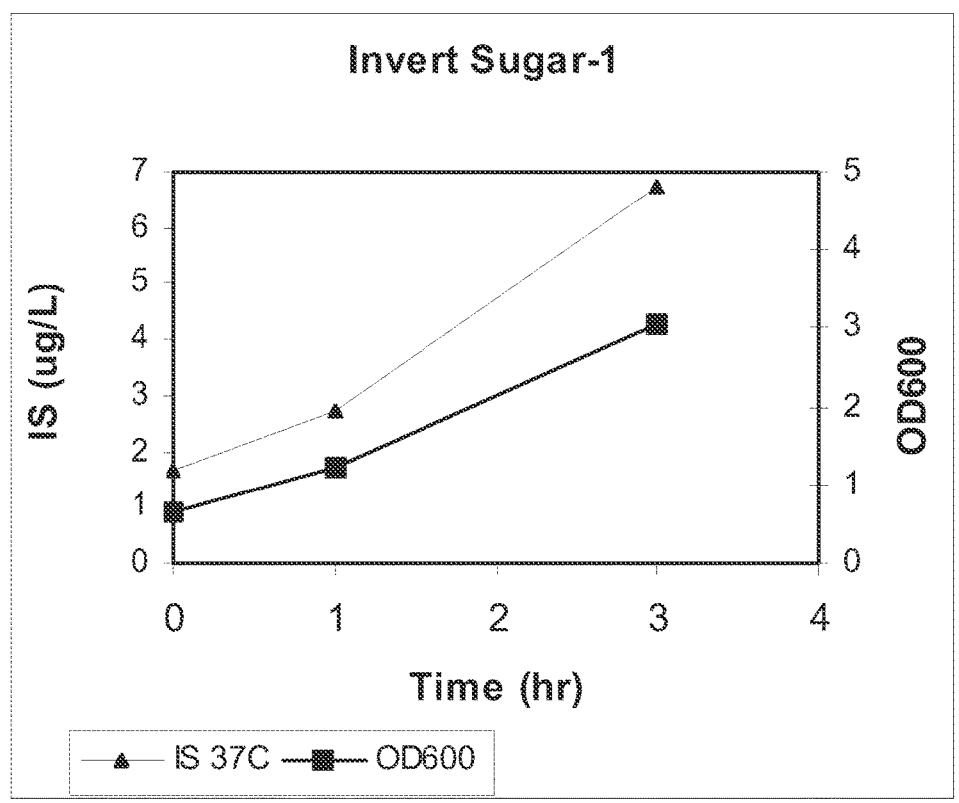
FIG. 47C shows a graph representing isoprene production from 1% invert sugar feedstock by BL21 (λDE3) pTrcKudzu yIDI DXS (kan). Squares represent $OD_{600}$, and triangles represent isoprene produced (μg/ml).
Figure 47D:
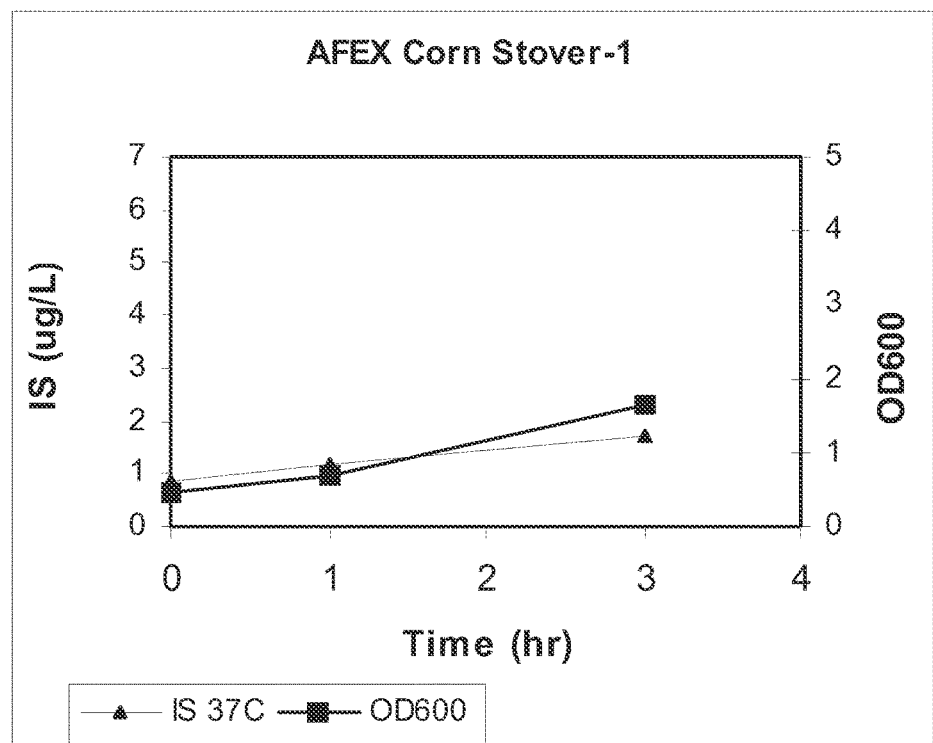
FIG. 47D shows a graph representing isoprene production from 1% AFEX corn stover feedstock by BL21 (λDE3) pTrcKudzu yIDI DXS (kan). Squares represent $OD_{600}$, and triangles represent isoprene produced (μg/ml).

Isoprene production was also demonstrated using three types of hydrolyzed biomass (bagasse, corn stover, and soft wood pulp) as the carbon source (FIGS. 46A-C). E. coli cells with kudzu isoprene synthase, S. cerevisia IDI, and E. coli DXS nucleic acids produced as much isoprene from these hydrolyzed biomass carbon sources as from the equivalent amount of glucose (e.g., 1% glucose, w/v). If desired, any other biomass carbon source can be used in the compositions and methods of the invention. Biomass carbon sources are desirable because they are cheaper than many conventional cell mediums, thereby facilitating the economical production of isoprene.

Additionally, invert sugar was shown to function as a carbon source for the generation of isoprene (FIGS. 47C and 96-98). For example, 2.4 g/L of isoprene was produced from cells expressing MVA pathway polypeptides and a Kudzu isoprene synthase (Example 8, part XV). Glycerol was as also used as a carbon source for the generation of 2.2 mg/L of isoprene from cells expressing a Kudzu isoprene synthase (Example 8, part XIV). Expressing a DXS nucleic acid, an IDI nucleic acid, and/or one or more MVA pathway nucleic acids (such as nucleic acids encoding the entire MVA pathway) in addition to an isoprene synthase nucleic acid may increase the production of isoprene from glycerol.

In some embodiments, an oil is included in the cell medium. For example, B. subtilis cells containing a kudzu isoprene synthase nucleic acid produced isoprene when cultured in a cell medium containing an oil and a source of glucose (Example 4, part III). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since much of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

One of the major hurdles to commercial production of small molecules such as isoprene in cells (e.g., bacteria) is the decoupling of production of the molecule from growth of the cells. In some embodiments for the commercially viable production of isoprene, a significant amount of the carbon from the feedstock is converted to isoprene, rather than to the growth and maintenance of the cells ("carbon efficiency"). In various embodiments, the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In particular embodiments, a significant portion of the carbon from the feedstock that is converted to downstream products is converted to isoprene. As described further in Example 11, E. coli cells expressing MVA pathway and kudzu isoprene synthase nucleic acids exhibited decoupling of the production of isoprene or the intermediate mevalonic acid from growth, resulting in high carbon efficiency. In particular, mevalonic acid was formed from cells expressing the upper MVA pathway from Enterococcus faecalis. Isoprene was formed from cells expressing the upper MVA pathway from Enterococcus faecalis, the lower MVA pathway from Saccharomyces cerevisiae, and the isoprene synthase from Pueraria montana (Kudzu). This decoupling of isoprene or mevalonic acid production from growth was demonstrated in four different strains of E. coli: BL21(LDE3), BL21 (LDE3) Tuner, FM5, and MG1655. The first two E. coli strains are B strains, and the latter two are K12 strains. Decoupling of production from growth was also demonstrated in a variant of MG1655 with ack and pta genes deleted. This variant also demonstrated less production of acetate.

Exemplary Polypeptides and Nucleic Acids

Various isoprene synthase, DXS, IDI, MVA pathway, hydrogenase, hydrogenase maturation or transcription factor polypeptides and nucleic acids can be used in the compositions and methods of the invention.

In some embodiments, the fusion polypeptide includes part or all of a first polypeptide (e.g., an isoprene synthase, DXS, IDI, MVA pathway, hydrogenase, hydrogenase maturation or transcription factor polypeptide or catalytically active fragment thereof) and may optionally include part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an Enterococcus faecalis mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring isoprene synthase, DXS, IDI, MVA pathway, hydrogenase, hydrogenase maturation or transcription factor polypeptide. In some embodiments, the polypeptide has one or more mutations compared to the sequence of a wild-type (i.e., a sequence occurring in nature) isoprene synthase, DXS, IDI, MVA pathway, hydrogenase, hydrogenase maturation or transcription factor polypeptide.

In some embodiments, the polypeptide is an isolated polypeptide. In some embodiments, the polypeptide is a heterologous polypeptide.

In some embodiments, the nucleic acid is a recombinant nucleic acid. In some embodiments, an isoprene synthase, DXS, IDI, MVA pathway, hydrogenase, hydrogenase maturation or transcription factor nucleic acid is operably linked to another nucleic acid encoding all or a portion of another polypeptide such that the recombinant nucleic acid encodes a fusion polypeptide that includes an isoprene synthase, DXS, IDI, MVA pathway, hydrogenase, hydrogenase maturation or transcription factor polypeptide and all or part of another polypeptide (e.g., a peptide that facilitates purification or detection of the fusion polypeptide, such as a His-tag). In some embodiments, part or all of a recombinant nucleic acid is chemically synthesized.

In some embodiments, the nucleic acid is a heterologous nucleic acid. In particular embodiments, the nucleic acid includes a segment of or the entire nucleic acid sequence of any naturally-occurring isoprene synthase, DXS, IDI, MVA pathway, hydrogenase, hydrogenase maturation or transcription factor nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, MVA pathway, hydrogenase, hydrogenase maturation or transcription factor nucleic acid. In some embodiments, the nucleic acid has one or more mutations compared to the sequence of a wild-type (i.e., a sequence occurring in nature) isoprene synthase, DXS, IDI, MVA pathway, hydrogenase, hydrogenase maturation or transcription factor nucleic acid. In some embodiments, the nucleic acid has one or more mutations (e.g., a silent mutation) that increase the transcription or translation of isoprene synthase, DXS, IDI, MVA pathway, hydrogenase, or transcription factor nucleic acid. In some embodiments, the nucleic acid is a degenerate variant of any nucleic acid encoding an isoprene synthase, DXS, IDI, MVA pathway, hydrogenase, hydrogenase maturation or transcription factor polypeptide.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the world-wide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007 or Sep. 14, 2008 such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 1. After induction is complete, approximately 10 mL of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 μL of 1M $MgCl_2$, 1 mM (250 μg/ml) DMAPP, 65 μL of Plant Extract Buffer (PEB) (50 mM Tris-HCl, pH 8.0, 20 mM $MgCl_2$, 5% glycerol, and 2 mM DTT) is added to 25 μL of cell extract in a 20 ml Headspace vial with a metal screw cap and teflon coated silicon septum (Agilent Technologies) and cultured at 37° C. for 15 minutes with shaking. The reaction is quenched by adding 200 μL of 250 mM EDTA and quantified by GC/MS as described in Example 1, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa*, or *Populus alba×tremula* (CAC35696) Miller et al., Planta 213: 483-487, 2001) aspen (such as *Populus tremuloides*) Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptides phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonte decarboxylase (MVD or DPMDC) polypeptides convert mevalonate-5-diphosphate into isopentenyl diphosphate (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Phosphomevalonate decarboxylase (PMDC) polypeptides convert mevalonate-5-phosphate into isopentenyl phosphate (IP). Standard methods (such as those described herein) can be used to determine whether a polypeptide has PMDC polypeptide activity by measuring the ability of the polypeptide to convert mevalonate-5-phosphate into IP in vitro, in a cell extract, or in vivo.

Isopentenyl phosphate kinase (IPK) polypeptides phosphorylate isopentyl phosphate (IP) to form isopentenyl diphosphate (IPP). Standard methods (such as those described herein) can be used to determine whether a polypeptide has IPK polypeptide activity by measuring the ability of the polypeptide to convert IP into IPP in vitro, in a cell extract, or in vivo.

Exemplary IDI polypeptides and nucleic acids are described above.

Exemplary Hydrogenase Polypeptides and Nucleic Acids

Hydrogenase polypeptides catalyze the reaction: $2H^+ + 2e^- \leftrightarrows H_2$. In vitro that reaction is reversible, but certain hydrogenases may work in only one direction in vivo, either oxidizing $H_2$ or reducing $H^+$. Hydrogenase polypeptides can be oxygen-sensitive, contain complex metal cofactors as part of their catalytic center and sometimes consist of multiple subunits, with hydrogenase gene expression sometimes involving additional accessory polypeptides, such as 'maturation' factors or transcription regulatory factors (i.e., activators or repressors). Hydrogenases are classified into at least three broad groups based upon the type of metal cofactor in their catalytic center: (1) nickel-iron ("NiFe") hydrogenases have a nickel/iron cofactor; (2) iron-iron hydrogenases ("FeFe") have an iron/iron cofactor; and (3) iron/sulfur-free ("Fe") hydrogenases, which lack the 4Fe4S clusters found in groups (1) and (2), have an iron cofactor and a methenyl-tetrahydromethanopterin electron carrier. See, e.g., Chung-Jung Chou et al., "Hydrogenesis in hyperthermophilic microorganisms: implications for biofuels," *Metabol. Eng.* 10:394-404 (2008), and Goniil Vardar-Schara et al., "Metabolically engineered bacteria for producing hydrogen via fermentation," *Microbial Biotechnol.* 1(2): 107-125 (2008), both of which are incorporated herein by reference in their entireties, particularly with respect to the various types and classes of hydrogenases. Although many organisms contain multiple hydrogenases, few contain genes for both NiFe and FeFe hydrogenases.

The catalytic center of NiFe hydrogenases consists of a nickel atom and an iron atom, each with two carbon monoxide (CO) and two cyanide ($CN^-$) ligands. The NiFe hydrogenases all comprise at least a second subunit containing multiple iron-sulfur (Fe–S) centers for the transfer of electrons to and from the catalytic center. The NiFe hydrogenases can be subdivided into four main classes: (1) respiratory enzymes, which are part of multienzyme systems that couple the oxidation of $H_2$ to reduction of terminal electron acceptors such as $SO_4^{2-}$ or $NO_3^-$ under anaerobic conditions, or to $O_2$ in aerobic microorganisms; (2) $H_2$ sensors, which activate expression of the metabolically active NiFe hyrogenases; (3) cytoplasmic hydrogenases, containing multiple subunits able to utilize $NADP^+$, which are readily reversible in vitro, but in vivo may only oxidize $H_2$; and (4) membrane-bound, energy-conserving multienzyme complexes also found in bacteria and Archaea. Chung-Jung Chou et al., "Hydrogenesis in hyperthermophilic microorganisms: implications for biofuels," *Metabol. Eng.* 10:394-404 (2008).

The catalytic center of FeFe hydrogenases contains a catalytic "H cluster" which coordinates a binuclear (FeFe) site bridged to a [4Fe-4S] center by a single protein (cysteine) ligand. The two iron atoms of the binuclear center each have two carbon monoxide (CO) and two cyanide (CN) ligands, and are also bridged by two sulfur atoms which are part of a small organic molecule. Most FeFe hydrogenases are monomeric enzymes of about 50 kilodaltons (kDa), and appear to function in vivo primarily to dispose of excess reducing equivalents by reducing protons to hydrogen gas. Chung-Jung Chou et al., "Hydrogenesis in hyperthermophilic microorganisms: implications for biofuels," *Metabol. Eng.* 10:394-404 (2008).

The catalytic center of Fe hydrogenases was originally thought to have an active site based on an organic cofactor with no metals involved, but was later shown to contain a mononuclear Fe atom. Despite the phylogenetic differences between the three types of hydrogenase, in addition to at least one iron atom, all three groups of hydrogenases also contain at least one carbon monoxide (CO) ligand to the iron atom in their active sites, which facilitates the catalytic oxidation of $H_2$ and the reduction of protons. Chung-Jung Chou et al., "Hydrogenesis in hyperthermophilic microorganisms: implications for biofuels," *Metabol. Eng.* 10:394-404 (2008).

Exemplary hydrogenase polypeptides include, but are not limited to, the *E. coli* hydrogenase-1 (Hyd-1) polypeptides, *E. coli* hydrogenase-2 (Hyd-2) polypeptides, *E. coli* hydrogenase-3 (Hyd-3) polypeptides, *E. coli* hydrogenase-4 (Hyd-4) polypeptides, *E. coli* formate hydrogen lyase (FHL) complex, which produces hydrogen gas from formate and $CO_2$ under anaerobic conditions at acidic pH (see, e.g., Akihito Yoshida et al., "Efficient induction of formate hydrogen lyase of aerobically grown *Escherichia coli* in a three-step biohydrogen production process," *Appl. Microbiol. Biotechnol.* 74:754-760 (2007), which is incorporated herein by reference in its entirety, particularly with respect to the induction of expression of formate hydrogen lyase in *E. coli*), *Ralstonia eutropha* H16 hydrogenase (*R. eutropha* HoxH) *Rhodococcus opacus* MR11 hydrogenase (*R. opacus* HoxH) polypeptides, *Synechosystis* sp. PCC 6803 hydrogenase (Syn. PCC 6803 HoxH) polypeptides, *Desulfovibrio gigas* hydrogenase (*D. gigas*) polypeptides, and *Desulfovibrio desulfuricans* ATCC 7757 hydrogenase (*D. desulfuricans*) polypeptides (see, e.g., Gönül Vardar-Schara et al., "Metabolically engineered bacteria for producing hydrogen via fermentation," *Microbial Biotechnol.* 1(2):107-125 (2008), which is incorporated herein by reference in its entirety, particularly with respect to the various types and classes of hydrogenases) and polypeptides (e.g., fusion polypeptides) having an activity of two or more hydrogenase polypeptides. In particular, hydrogenase polypeptides include polypeptides, fragments of polypeptides, peptides, and fusion polypeptides that have at least one activity of a hydrogenase polypeptide. Exemplary hydrogenase nucleic acids include nucleic acids that encode a polypeptide, fragment of a polypeptide, peptide, or fusion polypeptide that has at least one activity of a hydrogenase polypeptide, or at least one activity necessary for expression, processing, or maturation of a hydrogenase polypeptide. Exemplary hydrogenase polypeptides and nucleic acids include naturally-occurring polypeptides and nucleic acids from any of the source organisms described herein as well as mutant polypeptides and nucleic acids derived from any of the source organisms described herein.

*E. coli* Hyd-3, which is part of the anaerobic formate hydrogen lyase (FHL) complex, is encoded by the hyc operon (comprising the hycA, hycB, hycC, hycD, hycE, hycF, hycG, hycH, and hycI genes). *E. coli* Hyd-4 is encoded by the hyf operon (comprising the hyfA, hyfB, hyfC, hyfD, hyfE, hyfF, hyfG, hyfH, hyfI, hyfJ, and hyfR genes). *E. coli* FHL is encoded by six genes from the hyc operon (hycB, hycC, hycD, hycE, hycF and hycG) and the fdhF gene (encoding formate dehydrogenase H (Fdh-H)). Expression of the FHL complex can further involve expression of pyruvate formate lyase (pfl), FhlA, a transcription factor that activates transcription of fdhF and the hyc operon, or deletion/inactivation of HycA, a transcription factor encoded by the hycA gene that negatively regulates transcription of FHL. Co-production of isoprene and hydrogen can be improved by expression or inactivation/deletion of additional proteins involved in the regulation of gene expression for hydrogenases and other enzymes, such as, for example, iron-sulfur complex transcriptional regulator (iscR) (Kalim-Akhtar et al., "Deletion of iscR stimulates recombinant Clostridial Fe/Fe hydrogenase activity and $H_2$-accumulation in *Escherichia coli* BL21(DE3)," *Appl. Microbiol. Biotechnol.* 78:853-862 (2008), which is incorporated herein by reference in its entirety, particularly with reference to stimulation of Clostridial Fe/Fe hydrogenase activity and hydrogen accumulation in *E. coli* by deleting the iscR gene).

Exemplary ferredoxin-dependent hydrogenase polypeptides include, but are not limited to, *Clostridium acetobutylicum* hydrogenase A (HydA) (see, e.g., P. W. King et al., "Functional studies of [FeFe] hydrogenase maturation in an *Escherichia coli* biosynthetic system," *J. Bacteriol.* 188(6): 163-172 (2006), which is incorporated herein by reference in its entirety, particularly with respect to production of hydrogen by HydA and three HydA-associated maturation enzymes (HydE, HydG, and HydF), which may be expressed alone or in in conjunction with one or more of: (1) *Bacillus subtilis* NADPH ferredoxin oxidoreductase (NFOR) (see, e.g., Viet et al., (2008)), which is incorporated herein by reference in its entirety, particularly with respect to production of hydrogen by NFOR; see also PCT Publication No. WO/2007/089901, which is incorporated herein by reference in its entirety, particularly with respect to optimization of *E. coli* strains for production of hydrogen), *Clostridium kluyveri* NADH ferredoxin oxidoreductase (RnfCDGEAB) (Henning Seedorf et al., "The genome of *Clostridium kluyveri*, a strict anaerobe with unique metabolic features," *Proc. Nat'l Acad. Sci. U.S.A.* 105(6):2128-2133 (2008), which is incorporated herein by reference in its entirety, particular with reference to NADH ferredoxin oxidoreductase, and with reference to components of the anaerobic ethanol-acetate fermentation pathway), or *Clostridium pasteuranium* ferredoxin oxidoreductase (Fdx); (2) glyceraldehyde-6-phosphate ferredoxin oxidoreductase ("GAPOR"); or (3) pyruvate ferredoxin oxidoreductase ("POR"), and polypeptides (e.g., fusion polypeptides) having an activity of two or more hydrogenase polypeptides or of one or more hydrogenase polypeptides and an activity of one or more ferredoxin-dependent oxidoreductases. In particular, ferredoxin-dependent hydrogenase polypeptides include polypeptides, fragments of polypeptides, peptides, and fusion polypeptides that have at least one activity of a ferredoxin-dependent hydrogenase polypeptide.

Exemplary NADPH-dependent hydrogenase polypeptides include, but are not limited to thermophilic hydrogenase polypeptides such as *Pyrococcus furiosus* hydrogenase (see, e.g., J. Woodward et al., "Enzymatic production of biohydrogen," *Nature* 405(6790):1014-1015 (2000)), and polypeptides (e.g., fusion polypeptides) having an activity of two or more NADPH-dependent hydrogenase polypeptides. In particular, NADPH-dependent hydrogenase polypeptides include polypeptides, fragments of polypeptides, peptides, and fusion polypeptides that have at least one activity of a NADPH-dependent hydrogenase polypeptide.

Exemplary oxygen-tolerant or oxygen-insensitive hydrogenases include, but are not limited to, *Rubrivivax gelatinosus* hydrogenase (see, e.g., P. C. Maness et al., "Characterization of the oxygen tolerance of a hydrogenase linked to a carbon monoxide oxidation pathway in *Rubrivivax gelatinosus*," *Appl. Environ. Microbiol.* 68(6):2633-2636 (2002), which is incorporated herein by reference in its entirety, particularly with respect to *R. gelatinosus* hydrogenase), and *Ralstonia eutropha* hydrogenase polypeptides (see, e.g., T. Burgdorf et al., "[NiFe]-hydrogenases of *Ralstonia eutropha* H16: modular enzymes for oxygen-tolerant biological hydrogen oxidation," *J. Mol. Microbiol. Biotechnol.* 10(2-4):181-196 (2005), which is incorporated herein by reference in its entirety, particularly with respect to *R. eutropha* hydrogenase polypeptides). Alternatively, heterologous nucleic acids encoding hydrogenase polypeptides can be mutagenized and screened for $O_2$-tolerance or $O_2$-insensitivity using standard methods and assays (see, e.g., L. E. Nagy et al., "Application of gene-shuffling for the rapid generation of novel [FeFe]-hydrogenase libraries," *Biotechnol. Letts.* 29(3)421-430 (2007), which is incorporated herein by reference, particularly with respect to mutagenesis and screening for oxygen tolerant hydrogenase polypeptides).

Standard methods (such as those described herein) can be used to determine whether a polypeptide has hydrogenase activity by measuring the ability of the polypeptide to produce hydrogen gas in vitro, in a cell extract, or in vivo.

Exemplary Polypeptides and Nucleic Acids for Genes Related to Production of Fermentation Side Products In addition to expressing or over-expressing heterologous or native hydrogenases in *E. coli*, co-production of isoprene and hydrogen can be improved by inactivation of anaerobic biosynthetic pathways, thereby blocking the carbon flow to a variety of metabolites (i.e., fermentation side products) produced under oxygen-limited or anaerobic conditions, including, but not limited to, lactate, acetate, pyruvate, ethanol, succinate, and glycerol. Exemplary polypeptides involved in the production of fermentation side products include formate dehydrogenase N, alpha subunit (fdnG), formate dehydrogenase 0, large subunit (fdoG), nitrate reductase (narG), formate transporter A (focA), formate transporter B (focB), pyruvate oxidase (poxB), pyruvate dehydrogenase E1 component ackA/pta (aceE), alcohol dehydrogenase (adhE), fumarate reductase membrane protein (frdC), and lactate dehydrogenase (ldhA). See, e.g., Toshinori Maeda et al., "Enhanced hydrogen production from glucose by metabolically engineered *Escherichia coli*," *Appl. Microbiol. Biotechnol.* 77(4):879-890 (2007), which is incorporated by reference in its entirety, particularly with respect to production of *E. coli* strains with modified glucose metabolism. Exemplary polypeptides involved in the regulation or expression of genes involved in the production of fermentation side products that may also be inactivated to improve co-production of isoprene and hydrogen include, but are not limited to, repressor of formate hydrogen lyase (hycA), fumarate reductase regulator (fir), acetyl-coenzyme A synthetase (acs), and formate dehydrogenase regulatory protein (hycA), which regulates expression of the transcriptional regulator fhlA (formate hydrogen lyase transcriptional activator).

Exemplary Polypeptides and Nucleic Acids for Genes Related to Hydrogen Re-Uptake Exemplary polypeptides involved in hydrogen re-uptake that may also be inactivated to improve co-production of isoprene and hydrogen include, but are not limited to, *E. coli* hydrogenase-1 (Hyd-1) (hya operon) and *E. coli* hydrogenase-2 (Hyd-2) (hyb operon). *E. coli* Hyd-1 is encoded by the hya operon (comprising the hyaA, hyaB, hyaC, hyaD, hyaE, and hyaF genes). *E. coli* Hyd-2 is encoded by the hyb operon (comprising the hybA, hybB, hybC, hybD, hybE, hybF, hybG, and hybO genes).

Exemplary Polypeptides and Nucleic Acids for Genes Related to Ethanol Fermentation Exemplary polypeptides involved in ethanol fermentation include, but are not limited to, alcohol dehydrogenase B (adhB), alcohol dehydrogenase E (adhE) and pyruvate decarboxylase (pdc).

Alcohol dehydrogenases (adh) facilitate the interconversion between alcohols and aldehydes or ketones with the reduction of NAD+ to NADH. In humans and many other animals, they break down alcohols which could otherwise be toxic; in yeast and many bacteria, some alcohol dehydrogenases catalyze the opposite reaction as part of fermentation. In humans, adh exists in multiple forms as a dimer and is encoded by at least seven different genes. There are five classes (1-V) of alcohol dehydrogenase, but the primary hepatic form used in humans is class I. Class 1 consists of A, B, and C subunits that are encoded by the genes ADH1A, ADH1B, and ADH1C. Class I ADH is found in the lining of the stomach and in the liver, and catalyzes the oxidation of ethanol to acetaldehyde: $CH_3CH_2OH+NAD^+ \rightarrow CH_3CHO+NADH+H^+$ This allows the consumption of alcoholic beverages, but its evolutionary purpose is probably the breakdown of alcohols naturally contained in foods or produced by bacteria in the digestive tract.

Unlike humans, yeast and bacteria do not ferment glucose to lactate. Instead, they ferment it to ethanol and $CO_2$. In yeast and many bacteria, alcohol dehydrogenase plays an important part in fermentation: pyruvate resulting from glycolysis is converted to acetaldehyde and carbon dioxide, and the acetaldehyde is then reduced to ethanol by an alcohol dehydrogenase called adhE. The purpose of this latter step is the regeneration of NAD+, so that energy-generating glycolysis can continue. Pyruvate decarboxylase is a homotetrameric enzyme that catalyzes the decarboxylation of pyruvate to acetaldehyde and carbon dioxide. Under anaerobic conditions, this enzyme is part of the fermentation process that occurs in yeast, especially of the *Saccharomyces* genus, to produce ethanol by fermentation. Pyruvate decarboxylase is present in many bacteria as well, including *Excherichia* sp., such as *E. coli*, and *Zymomonas* sp., such as *Z. mobilis*.

Exemplary Glycerol Pathway or 1,3-Propanediol Pathway Polypeptides and Nucleic Acids Exemplary glycerol pathway polypeptides include, but are not limited to, DAR1 (dihydroxyacetone phosphate reductase), GPP2 (glycerol-phosphate phosphatase). Exemplary 1,3-propanediol pathway polypeptides include, but are not limited to dhaB1-3 (dhaB1, dhaB2, and dhaB3; glycerol dehydratase B1, B2, and B3), dhaX, orfX (protein X), and orfY (protein Y), as well as glycerol dehydratase variants with improved reaction kinetics, including variants of dhaB1, dhaB2, and dhaB3, such as those described in US Patent Publication No. 2008/0293119 A1, which is incorporated herein by reference in its entirety, particularly with respect to disclosure regarding variant glycerol dehydratase variants with improved reaction kinetics. The dha regulon enables organisms such as *Klebsiella pneumoniae* to grow anaerobically on glycerol and produce 1,3-propanediol (1,3-PD). *Escherichia coli* does not have a dha system, and thus is unable to grow anaerobically on glycerol without an exogenous electron acceptor and does not produce 1,3-propanediol. The dha regulon comprises at least four genes: glycerol dehydratase (dhaB), 1,3-propanediol oxidoreductase (dhaT), glycerol dehydrogenase (dhaD), and dihydroxyacetone kinase (dhaK). All four activities were inducible by the presence of glycerol.

Exemplary Methods for Isolating Nucleic Acids

Isoprene synthase, DXS, IDI, MVA pathway, ethanol fermentation-related, glycerol pathway, 1,3-propanediol pathway, hydrogenase, hydrogenase maturation and/or transcription factor nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, DXS, IDI, MVA pathway, ethanol fermentation-related, glycerol pathway, 1,3-propanediol pathway, hydrogenase, hydrogenase maturation and/or transcription factor nucleic acids (such as any isoprene synthase, DXS, IDI, MVA pathway, ethanol fermentation-related, glycerol pathway, 1,3-propanediol pathway, hydrogenase, hydrogenase maturation and/or transcription factor nucleic acids with a known nucleic acid sequence) can be chemically synthesized using standard methods.

Additional isoprene synthase, DXS, IDI, MVA pathway, ethanol fermentation-related, glycerol pathway, 1,3-propanediol pathway, hydrogenase, hydrogenase maturation and/or transcription factor polypeptides and nucleic acids which may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, $2^{nd}$ ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as *E. coli*. Once injected into the cell, the heterologous DNA circularizes under the influence of the cos sticky ends. In this manner, large segments of heterologous DNA can be introduced and expressed in host cells.

Additional methods for obtaining isoprene synthase, DXS, IDI, MVA pathway, ethanol fermentation-related, glycerol pathway, 1,3-propanediol pathway, hydrogenase, hydrogenase maturation and/or transcription factor nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, MVA pathway, ethanol fermentation-related, glycerol pathway, 1,3-propanediol pathway, hydrogenase, hydrogenase maturation and/or transcription factor polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., Applied. Microbiol. Biotechnol. 75: 1377-84, 2007; Withers et al., Appl Environ Microbiol. 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, MVA pathway, ethanol fermentation-related, glycerol pathway, 1,3-propanediol pathway, hydrogenase, hydrogenase maturation and/or transcription factor polypeptides and nucleic acids based on the similarity of their primary and/or predicted polypeptide secondary structure with that of known DXS, IDI, MVA pathway, ethanol fermentation-related, glycerol pathway, 1,3-propanediol pathway, hydrogenase, hydrogenase maturation and/or transcription factor polypeptides and nucleic acids. Standard databases such as the swissprot-trembl database (worldwide web at "expasy.org", Swiss Institute of Bioinformatics Swiss-Prot group CMU-1 rue Michel Servet CH-1211 Geneva 4, Switzerland) can also be used to identify isoprene synthase, DXS, IDI, MVA pathway, ethanol fermentation-related, glycerol pathway, 1,3-propanediol pathway, hydrogenase, hydrogenase maturation and/or transcription regulatory polypeptides and nucleic acids. The secondary and/or tertiary structure of an isoprene synthase, DXS, IDI, MVA pathway, ethanol fermentation-related, glycerol pathway, 1,3-propanediol pathway, hydrogenase, hydrogenase maturation and/or transcription factor polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, DXS, IDI, MVA pathway, ethanol fermentation-related, glycerol pathway, 1,3-propanediol pathway, hydrogenase, hydrogenase maturation and/or transcription factor polypeptide can be determined using standard methods. Additional isoprene synthase, DXS, IDI, MVA pathway, ethanol fermentation-related, glycerol pathway, 1,3-propanediol pathway, hydrogenase, hydrogenase maturation and/or transcription factor nucleic acids can also be identified by hybridization to probes generated from known isoprene synthase, DXS, IDI, MVA pathway, ethanol fermentation-related, glycerol pathway, 1,3-propanediol pathway, hydrogenase, hydrogenase maturation and/or transcription factor nucleic acids.

Exemplary Promoters and Vectors

Any of the isoprene synthase, DXS, IDI, MVA pathway, ethanol fermentation-related, glycerol pathway, 1,3-propanediol pathway, hydrogenase, hydrogenase maturation and/or transcription factor nucleic acids described herein can be included in one or more vectors. Accordingly, the invention also features vectors with one more nucleic acids encoding any of the isoprene synthase, DXS, IDI, MVA pathway, ethanol fermentation-related, glycerol pathway, 1,3-propanediol pathway, hydrogenase, hydrogenase maturation and/or transcription factor polypeptides that are described herein. In some embodiments, the vector contains a nucleic acid under the control of an expression control sequence.

In some embodiments, the vector contains a selective marker or selectable marker. Markers useful in vector systems for transformation of Trichoderma are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an A. nidulans amdS nucleic acid as a selective marker is described in Kelley et al., EMBO J. 4:475-479, 1985 and Penttila et al., Gene 61:155-164, 1987 (which are each hereby incorporated by reference in their entireties, particularly with respect to selective markers). In some embodiments, an isoprene synthase, DXS, IDI, MVA pathway, ethanol fermentation-related, glycerol pathway, 1,3-propanediol pathway, hydrogenase, hydrogenase maturation, or transcription regulatory nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, MVA pathway, ethanol fermentation-related, glycerol pathway, 1,3-propanediol pathway, hydrogenase, hydrogenase maturation and/or transcription factor nucleic acid in the host cell. Initiation control regions or promoters, which are useful to drive expression of isoprene synthase, DXS, IDI, MVA pathway, ethanol fermentation-related, glycerol pathway, 1,3-propanediol pathway, hydrogenase, hydrogenase maturation and/or transcription factor nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in Saccharomyces); AOX1 (useful for expression in Pichia); and lac, trp, ☒$P_L$, ☒$P_R$, T7, tac, and trc (useful for expression in E. coli).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132,527).

In various embodiments, an isoprene synthase, DXS, IDI, MVA pathway, ethanol fermentation-related, glycerol pathway, 1,3-propanediol pathway, hydrogenase, hydrogenase maturation and/or transcription factor nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, MVA pathway, ethanol fermentation-related, glycerol pathway, 1,3-propanediol pathway, hydrogenase, hydrogenase maturation and/or transcription factor nucleic acid is operably linked to a T7 promoter. In some embodiments, the heterologous or extra endogenous isoprene synthase, DXS, IDI, MVA pathway, ethanol fermentation-related, glycerol pathway, 1,3-propanediol pathway, hydrogenase, hydrogenase maturation and/or transcription factor nucleic acid operably linked to a T7 promoter is contained in a medium or high copy plasmid. In some embodiments, the heterologous or extra endogenous isoprene synthase, DXS, IDI, MVA pathway, ethanol fermentation-related, glycerol pathway, 1,3-propanediol pathway, hydrogenase, hydrogenase maturation and/or transcription factor nucleic acid is operably linked to a Trc promoter. In some embodiments, the heterologous or extra endogenous isoprene synthase, DXS, IDI, MVA pathway, ethanol fermentation-related, glycerol pathway, 1,3-propanediol pathway, hydrogenase, hydrogenase maturation and/or transcription factor nucleic acid operably linked to a Trc promoter is contained in a medium or high copy plasmid. In some embodiments, the heterologous or extra endogenous isoprene synthase, DXS, IDI, MVA pathway, ethanol fermentation-related, glycerol pathway, 1,3-propanediol pathway, hydrogenase, hydrogenase maturation and/or transcription factor nucleic acid is operably linked to a Lac promoter. In some embodiments, the heterologous or extra endogenous isoprene synthase, DXS, IDI, MVA pathway, ethanol fermentation-related, glycerol pathway, 1,3-propanediol pathway, hydrogenase, hydrogenase maturation and/or transcription factor nucleic acid operably linked to a Lac promoter is contained in a low copy plasmid. In some embodiments, the heterologous or extra endogenous isoprene synthase, DXS, IDI, MVA pathway, ethanol fermentation-related, glycerol pathway, 1,3-propanediol pathway, hydrogenase, hydrogenase maturation and/or transcription factor nucleic acid is operably linked to an endogenous promoter, such as an endogenous *Escherichia*, *Panteoa*, *Bacillus*, *Yarrowia*, *Streptomyces*, or *Trichoderma* promoter or an endogenous alkaline serine protease, isoprene synthase, DXS, IDI, MVA pathway, ethanol fermentation-related, glycerol pathway, 1,3-propanediol pathway, hydrogenase, hydrogenase maturation and/or transcription factor promoter. In some embodiments, the heterologous or extra endogenous isoprene synthase, DXS, IDI, MVA pathway, ethanol fermentation-related, glycerol pathway, 1,3-propanediol pathway, hydrogenase, hydrogenase maturation and/or transcription factor nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, $2^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, an isoprene synthase, DXS, IDI, MVA pathway, ethanol fermentation-related, glycerol pathway, 1,3-propanediol pathway, hydrogenase, hydrogenase maturation and/or transcription factor nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., *Mol. Cell. Biol.* 4:2306-2315, 1984 and Boel et al., *EMBO J.* 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei* cellobiohydrolase 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a *Trichoderma* strain (such as *T. reesei*). Other useful fungal terminators include the terminator from an *A. niger* or *A. awamori* glucoamylase nucleic acid (Nunberg et al., *Mol. Cell. Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, DXS, IDI, MVA pathway, ethanol fermentation-related, glycerol pathway, 1,3-propanediol pathway, hydrogenase, hydrogenase maturation and/or transcription factor nucleic acid to be expressed. In some embodiments, the coding region for an isoprene synthase, DXS, IDI, MVA pathway, ethanol fermentation-related, glycerol pathway, 1,3-propanediol pathway, hydrogenase, hydrogenase maturation and/or transcription factor nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, MVA pathway, ethanol fermentation-related, glycerol pathway, 1,3-propanediol pathway, hydrogenase, hydrogenase maturation and/or transcription factor nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, MVA pathway, ethanol fermentation-related, glycerol pathway, 1,3-propanediol pathway, hydrogenase, hydrogenase maturation and/or transcription factor nucleic acid), a promoter, a terminator, and other sequences and to insert them into a suitable vector are well known in the art. For example, restriction enzymes can be used to cleave the isoprene synthase, DXS, IDI, MVA pathway, ethanol fermentation-related, glycerol pathway, 1,3-propanediol pathway, hydrogenase, hydrogenase maturation and/or transcription factor nucleic acid and the vector. Then, the compatible ends of the cleaved isoprene synthase, DXS, IDI, MVA pathway, ethanol fermentation-related, glycerol pathway, 1,3-propanediol pathway, hydrogenase, hydrogenase maturation and/or transcription factor nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, MVA pathway, ethanol fermentation-related, glycerol pathway, 1,3-propanediol pathway, hydrogenase, hydrogenase maturation and/or transcription factor nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

In some embodiments, it may be desirable to under-express (e.g., mutate, inactivate, or delete) isoprene synthase, DXS, IDI, MVA pathway, ethanol fermentation-related, glycerol pathway, 1,3-propanediol pathway, hydrogenase, hydrogenase maturation, or transcription factor polypeptide-encoding nucleic acids at levels far below that those currently found in naturally-occurring cells. This result may be accomplished by the mutation or inactivation of transcriptional regulatory proteins required for expression of isoprene synthase, DXS, IDI, MVA pathway, ethanol fermentation-related, glycerol pathway, 1,3-propanediol pathway, hydrogenase, hydrogenase maturation and/or transcription factor nucleic acids, by deletion of the isoprene synthase, DXS, IDI, MVA pathway, ethanol fermentation-related, glycerol pathway, 1,3-propanediol pathway, hydrogenase, hydrogenase maturation and/or transcription factor nucleic acids, or by placing those nucleic acids under the control of a strong repressible promoter. Methods for mutating, inactivating, or deleting desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning and mutagenesis techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, MVA pathway, ethanol fermentation-related, glycerol pathway, 1,3-propanediol pathway, hydrogenase, hydrogenase maturation and/or transcription factor nucleic acids (and their encoded polypeptides) can be obtained from any organism that naturally contains isoprene synthase, DXS, IDI, MVA pathway, ethanol fermentation-related, glycerol pathway, 1,3-propanediol pathway, hydrogenase, hydrogenase maturation and/or transcription factor nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIGS. 19A and 19B). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways. Ethanol fermentation-related nucleic acids can be obtained, e.g., from any organism that naturally produces alcohol from glucose or other carbon source. Glycerol pathway and/or 1,3-propanediol pathway related nucleic acids can be obtained, e.g., from any organism that naturally as the ability to grow on glycerol as primary carbon source. Hydrogenase nucleic acids can be obtained, e.g., from any organism that oxidizes hydrogen or reduces hydrogen ions. Fermentation side product genes can be obtained or identified, e.g., from any organism that undergoes oxygen-limited or anaerobic respiration, such as glycolysis.

In some embodiments, the nucleic acid sequence of the isoprene synthase, DXS, IDI, MVA pathway, ethanol fermentation-related, glycerol pathway, 1,3-propanediol pathway, hydrogenase, hydrogenase maturation and/or transcription factor nucleic is identical to the sequence of a nucleic acid that is produced by any of the following organisms in nature. In some embodiments, the amino acid sequence of the isoprene synthase, DXS, IDI, MVA pathway, ethanol fermentation-related, glycerol pathway, 1,3-propanediol pathway, hydrogenase, hydrogenase maturation and/or transcription factor polypeptide is identical to the sequence of a polypeptide that is produced by any of the following organisms in nature. In some embodiments, the isoprene synthase, DXS, IDI, MVA pathway, ethanol fermentation-related, glycerol pathway, 1,3-propanediol pathway, hydrogenase, hydrogenase maturation and/or transcription factor nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens, H. lanuginose*, or *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans*, or *A. awamori*) (Ward et al., Appl. Microbiol. Biotechnol. 39: 7380743, 1993 and Goedegebuur et al., Genet. 41: 89-98, 2002), *Fusarium* sp., (e.g., *F. roseum, F. graminum F. cerealis, F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., *Sci.* 228: 21-26, 1985). The term "*Trichoderma*" or "*Trichoderma* sp." or "*Trichoderma* spp." refer to any fungal genus previously or currently classified as *Trichoderma*.

In some embodiments, the fungus is *A. nidulans, A. awamori, A. oryzae*, A. aculeatus, *A. niger, A. japonicus, T. reesei, T. viride, F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei*.

In some embodiments, the source organism is a yeast, such as *Saccharomyces* sp., *Schizosaccharomyces* sp., *Pichia* sp., or *Candida* sp. In some embodiments, the *Saccharomyces* sp. is *Saccharomyces cerevisiae*.

In some embodiments, the source organism is a bacterium, such as strains of *Bacillus* such as *B. licheniformis* or *B. subtilis*, strains of *Pantoea* such as *P. citrea*, strains of *Pseudomonas* such as *P. alcaligenes, P. putida*, or *P. fluorescens*, strains of *Streptomyces* such as *S. lividans* or *S. rubiginosus*, strains of *Corynebacterium* sp. such as *Corynebacterium glutamicum*, strains of *Rhodopseudomonas* sp. such as *Rhodopseudomonas palustris*, or strains of *Escherichia* such as *E. coli*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some embodiments, the source organism is a gram-positive bacterium. Non-limiting examples include strains of *Streptomyces* (e.g., *S. lividans, S. coelicolor*, or *S. griseus*) and *Bacillus*.

In some embodiments, the source organism is a gram-negative bacterium, such as *E. coli*., *Rhodopseudomonas* sp. such as *Rhodopseudomonas palustris*, or *Pseudomonas* sp., such as *P. alcaligenes, P. putida*, or *P. fluorescens, Zymonomas* sp., such as *Z. mobilis*.

In some embodiments, the source organism is a plant, such as a plant from the family Fabaceae, such as the Faboideae subfamily. In some embodiments, the source organism is kudzu, poplar (such as *Populus alba×tremula* CAC35696), aspen (such as *Populus tremuloides*), or *Quercus robur*.

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: *Chroococcales, Pleurocapsales, Oscillatoriales, Nostocales,* or *Stigonematales.*

Exemplary Host Cells

A variety of host cells can be used to express isoprene synthase, DXS, IDI, MVA pathway, ethanol fermentation-related, glycerol pathway, 1,3-propanediol pathway, hydrogenase, hydrogenase maturation and/or transcription factor polypeptides and to co-produce isoprene and hydrogen in the methods of the claimed invention. Exemplary host cells include cells from any of the organisms listed in the prior section under the heading "*Exemplary Source Organisms.*" The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

In some embodiments, the host cell naturally produces isoprene using both the DXP and MVA pathways, and one or more isoprene synthase, DXS, IDI, or MVA pathway nucleic acids are added to enhance production of isoprene by one or both of these pathways, one or more hydrogenase nucleic acids are added to enhance hydrogen production and one or more fermentation side product-producing genes are inactivated or deleted to limit production of fermentation side products. In some embodiments, the host cell naturally co-produces isoprene and hydrogen using both the DXP and MVA pathways and one or more isoprene synthase, DXS, IDI, or MVA pathway nucleic acids are added to enhance production of isoprene by one or both of these pathways, one or more hydrogenase nucleic acids are added to enhance hydrogen production, one or more fermentation side product-producing genes are inactivated or deleted to limit production of fermentation side products, and one or more hydrogen reuptake genes are inactivated or deleted to increase hydrogen production. In some embodiments, the host cell naturally co-produces isoprene and hydrogen using both the DXP and MVA pathways and a hydrogenase, and one or more isoprene synthase, DXS, IDI, or MVA pathway nucleic acids are added to enhance production of isoprene by one or both of these pathways, one or more hydrogenase nucleic acids are added to enhance hydrogen production, one or more hydrogenase maturation nucleic acids are added to enhance hydrogen production, one or more fermentation side product-producing genes are inactivated or deleted to limit production of fermentation side products, and one or more hydrogen reuptake genes are inactivated or deleted to increase hydrogen production. In some embodiments, the host cell naturally co-produces isoprene and hydrogen using both the DXP and MVA pathways and one or more isoprene synthase, DXS, IDI, or MVA pathway nucleic acids are added to enhance production of isoprene by one or both of these pathways, one or more hydrogenase nucleic acids are added to enhance hydrogen production, one or more hydrogenase maturation nucleic acids are added to enhance hydrogen production, one or more transcription factor nucleic acids are added or inactivated or deleted to enhance hydrogenase production, one or more fermentation side product-producing genes are inactivated or deleted to limit production of fermentation side products, and one or more hydrogen reuptake genes are inactivated or deleted to increase hydrogen production.

Exemplary Transformation Methods

Isoprene synthase, DXS, IDI, MVA pathway, ethanol fermentation-related, glycerol pathway, 1,3-propanediol pathway, hydrogenase, hydrogenase maturation and/or transcription factor nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, MVA pathway, ethanol fermentation-related, glycerol pathway, 1,3-propanediol pathway, hydrogenase, hydrogenase maturation and/or transcription factor polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. No. 6,022,725; U.S. Pat. No. 6,268,328; U.S. Pat. No. 7,262,041; WO 2005/001036; Harkki et al., *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes,*" in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (*Sci.* 9:991-1001, 2000; EP 238023; and Yelton et al., *Proceedings. Natl. Acad. Sci.* USA 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2 \times 10^6$/mL) are used in the transformation. A volume of 100 μL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that co-produce isoprene and hydrogen. By "cells in culture" is meant two or more cells in a solution (e.g., a cell growth medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

By "cells in oxygen-limited culture" is meant two or more cells in a solution (e.g., a cell growth medium) that allows the cell to under go one or more cell divisions, wherein the solution contains a limiting amount of oxygen. The term "oxygen-limited culture" means that the culture is either anoxic or contains less than the required amount of oxygen to support respiration via the biological transfer of reducing equivalents to oxygen, and also encompasses anaerobic cultures. Under oxygen-limited culture conditions, some electrons derived from carbon metabolism cannot be accepted because oxygen concentrations are too low, causing cells to switch to hydrogen production if they comprise the appropriate metabolic pathways for doing so. Oxygen-limited culture conditions occur when the oxygen transfer rate ("OTR") is less than the oxygen uptake rate ("OUR") indicated by dissolved oxygen concentrations of close to zero in culture medium.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharides), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as one or more carbon sources other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

In some embodiments, the cells are cultured under limited glucose conditions. By "limited glucose conditions" is meant that the amount of glucose that is added is less than or about 105% (such as about 100%) of the amount of glucose that is consumed by the cells. In particular embodiments, the amount of glucose that is added to the culture medium is approximately the same as the amount of glucose that is consumed by the cells during a specific period of time. In some embodiments, the rate of cell growth is controlled by limiting the amount of added glucose such that the cells grow at the rate that can be supported by the amount of glucose in the cell medium. In some embodiments, glucose does not accumulate during the time the cells are cultured. In various embodiments, the cells are cultured under limited glucose conditions for greater than or about 1, 2, 3, 5, 10, 15, 20, 25, 30, 35, 40, 50, 60, or 70 hours. In various embodiments, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions may allow more favorable regulation of the cells.

In some embodiments, the cells are cultured in the presence of an excess of glucose. In particular embodiments, the amount of glucose that is added is greater than about 105% (such as about or greater than 110, 120, 150, 175, 200, 250, 300, 400, or 500%) or more of the amount of glucose that is consumed by the cells during a specific period of time. In some embodiments, glucose accumulates during the time the cells are cultured.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitoleic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerides are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.*, 53(2) 541-543, 1989, which is hereby incorporated by reference in its entirety, particularly with respect to carbon sources) and in bacteria (Hunter et. al., *Biochemistry*, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl-Compd.*, [Int. Symp.], $7^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell medias). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20° C. to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until the desired amount of isoprene and hydrogen co-production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. In some embodiments, the cells are cultured under oxygen-limited conditions. In some embodiments, the cells are cultured in the presence of oxygen under conditions where 0.5 moles of oxygen are taken up per mole of isoprene produced. In some embodiments, the cells are cultured under anaerobic conditions. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, DXS, IDI, or MVA pathway nucleic acid(s) operably linked to the promoter. In some embodiments, a compound (such as IPTG) is added to induce expression of the isoprene synthase, DXS, IDI, or MVA pathway nucleic acid(s) operably linked to the promoter.

Exemplary Methods for Decoupling Isoprene Production from Cell Growth

Desirably, carbon from the feedstock is converted to isoprene rather than to the growth and maintenance of the cells. In some embodiments, the cells are grown to a low to medium $OD_{600}$, then production of isoprene is started or increased. This strategy permits a large portion of the carbon to be converted to isoprene.

In some embodiments, cells reach an optical density such that they no longer divide or divide extremely slowly, but continue to make isoprene for several hours (such as about 2, 4, 6, 8, 10, 15, 20, 25, 30, or more hours). For example, FIGS. 60A-67C illustrate that cells may continue to produce a substantial amount of mevalonic acid or isoprene after the cells reach an optical density such that they no longer divide or divide extremely slowly. In some cases, the optical density at 550 nm decreases over time (such as a decrease in the optical density after the cells are no longer in an exponential growth phase due to cell lysis), and the cells continue to produce a substantial amount of mevalonic acid or isoprene. In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour ($nmole/g_{wcm}/hr$) during this time period. In some embodiments, the amount of isoprene is between about 2 to about 5,000 $nmole/g_{wcm}/hr$, such as between about 2 to about 100 $nmole/g_{wcm}/hr$, about 100 to about 500 $nmole/g_{wcm}/hr$, about 150 to about 500 $nmole/g_{wcm}/hr$, about 500 to about 1,000 $nmole/g_{wcm}/hr$, about 1,000 to about 2,000 $nmole/g_{wcm}/hr$, or about 2,000 to about 5,000 $nmole/g_{wcm}/hr$. In some embodiments, the amount of isoprene is between about 20 to about 5,000 $nmole/g_{wcm}/hr$, about 100 to about 5,000 $nmole/g_{wcm}/hr$, about 200 to about 2,000 $nmole/g_{wcm}/hr$, about 200 to about 1,000 $nmole/g_{wcm}/hr$, about 300 to about 1,000 $nmole/g_{wcm}/hr$, or about 400 to about 1,000 $nmole/g_{wcm}/hr$.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth ($mg/L_{broth}$, wherein the volume of broth includes the volume of the cells and the cell medium) during this time period. In some embodiments, the amount of isoprene is between about 2 to about 5,000 $mg/L_{broth}$, such as between about 2 to about 100 $mg/L_{broth}$, about 100 to about 500 $mg/L_{broth}$, about 500 to about 1,000 $mg/L_{broth}$, about 1,000 to about 2,000 $mg/L_{broth}$, or about 2,000 to about 5,000 $mg/L_{broth}$. In some embodiments, the amount of isoprene is between about 20 to about 5,000 $mg/L_{broth}$, about 100 to about 5,000 $mg/L_{broth}$, about 200 to about 2,000 $mg/L_{broth}$, about 200 to about 1,000 $mg/L_{broth}$, about 300 to about 1,000 $mg/L_{broth}$, or about 400 to about 1,000 $mg/L_{broth}$.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene during this time period. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells are in stationary phase. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells divide slowly or not at all such that the optical density at 550 nm of the cells increases by less than or about 50% (such as by less than or about 40, 30, 20, 10, 5, or 0%). In some embodiments, isoprene is only produced in the growth phase.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

Production of Isoprene within Safe Operating Ranges

The production of isoprene within safe operating levels according to its flammability characteristics simplifies the design and construction of commercial facilities, vastly improves the ability to operate safely, and limits the potential for fires to occur. In particular, the optimal ranges for the production of isoprene are within the safe zone, i.e., the nonflammable range of isoprene concentrations. In one such aspect, the invention features a method for the production of isoprene within the nonflammable range of isoprene concentrations (outside the flammability envelope of isoprene).

Thus, computer modeling and experimental testing were used to determine the flammability limits of isoprene (such as isoprene in the presence of $O_2$, $N_2$, $CO_2$, or any combination of two or more of the foregoing gases) in order to ensure process safety. The flammability envelope is characterized by the lower flammability limit (LFL), the upper flammability limit (UFL), the limiting oxygen concentration (LOC), and the limiting temperature. For a system to be flammable, a minimum amount of fuel (such as isoprene) must be in the presence of a minimum amount of oxidant, typically oxygen. The LFL is the minimum amount of isoprene that must be present to sustain burning, while the UFL is the maximum amount of isoprene that can be present. Above this limit, the mixture is fuel rich and the fraction of oxygen is too low to have a flammable mixture. The LOC indicates the minimum fraction of oxygen that must also be present to have a flammable mixture. The limiting temperature is based on the flash point of isoprene and is that lowest temperature at which combustion of isoprene can propagate. These limits are specific to the concentration of isoprene, type and concentration of oxidant, inerts present in the system, temperature, and pressure of the system. Compositions that fall within the limits of the flammability envelope propagate combustion and require additional safety precautions in both the design and operation of process equipment.

The following conditions were tested using computer simulation and mathematical analysis and experimental testing. If desired, other conditions (such as other temperature, pressure, and permanent gas compositions) may be tested using the methods described herein to determine the LFL, UFL, and LOC concentrations.

(1) Computer Simulation and Mathematical Analysis
Test Suite 1:
isoprene: 0 wt %-14 wt %
$O_2$: 6 wt %-21 wt %
$N_2$: 79 wt %-94 wt %
Test Suite 2:
isoprene: 0 wt %-14 wt %
$O_2$: 6 wt %-21 wt %
$N_2$: 79 wt %-94 wt %
Saturated with $H_2O$
Test Suite 3:
isoprene: 0 wt %-14 wt %
$O_2$: 6 wt %-21 wt %
$N_2$: 79 wt %-94 wt %
$CO_2$: 5 wt %-30 wt %
(2) Experimental Testing for Final Determination of Flammability Limits
Test Suite 1:
isoprene: 0 wt %-14 wt %
$O_2$: 6 wt %-21 wt %
$N_2$: 79 wt %-94 wt %
Test Suite 2:
isoprene: 0 wt %-14 wt %
$O_2$: 6 wt %-21 wt %
$N_2$: 79 wt %-94 wt %
Saturated with $H_2O$ Simulation software was used to give an estimate of the flammability characteristics of the system for several different testing conditions. $CO_2$ showed no significant affect on the system's flammability limits. Test suites 1 and 2 were confirmed by experimental testing. The modeling results were in-line with the experimental test results. Only slight variations were found with the addition of water.

The LOC was determined to be 9.5 vol % for an isoprene, $O_2$, $N_2$, and $CO_2$ mixture at 40° C. and 1 atmosphere. The addition of up to 30% $CO_2$ did not significantly affect the flammability characteristics of an isoprene, $O_2$, and $N_2$ mixture. Only slight variations in flammability characteristics were shown between a dry and water saturated isoprene, $O_2$, and $N_2$ system. The limiting temperature is about −54° C. Temperatures below about −54° C. are too low to propagate combustion of isoprene.

In some embodiments, the LFL of isoprene ranges from about 1.5 vol. % to about 2.0 vol %, and the UFL of isoprene ranges from about 2.0 vol. % to about 12.0 vol. %, depending on the amount of oxygen in the system. In some embodiments, the LOC is about 9.5 vol % oxygen. In some embodiments, the LFL of isoprene is between about 1.5 vol. % to about 2.0 vol %, the UFL of isoprene is between about 2.0 vol. % to about 12.0 vol. %, and the LOC is about 9.5 vol % oxygen when the temperature is between about 25° C. to about 55° C. (such as about 40° C.) and the pressure is between about 1 atmosphere and 3 atmospheres.

In some embodiments, isoprene is produced in the presence of less than about 9.5 vol % oxygen (that is, below the LOC required to have a flammable mixture of isoprene). In some embodiments in which isoprene is produced in the presence of greater than or about 9.5 vol % oxygen, the isoprene concentration is below the LFL (such as below about 1.5 vol. %). For example, the amount of isoprene can be kept below the LFL by diluting the isoprene composition with an inert gas (e.g., by continuously or periodically adding an inert gas such as nitrogen to keep the isoprene composition below the LFL). In some embodiments in which isoprene is produced in the presence of greater than or about 9.5 vol % oxygen, the isoprene concentration is above the UFL (such as above about 12 vol. %). For example, the amount of isoprene can be kept above the UFL by using a system (such as any of the cell culture systems described herein) that produces isoprene at a concentration above the UFL. If desired, a relatively low level of oxygen can be used so that the UFL is also relatively low. In this case, a lower isoprene concentration is needed to remain above the UFL.

In some embodiments in which isoprene is produced in the presence of greater than or about 9.5 vol % oxygen, the isoprene concentration is within the flammability envelope (such as between the LFL and the UFL). In some embodiments when the isoprene concentration may fall within the flammability envelope, one or more steps are performed to reduce the probability of a fire or explosion. For example, one or more sources of ignition (such as any materials that may generate a spark) can be avoided. In some embodiments, one or more steps are performed to reduce the amount of time that the concentration of isoprene remains within the flammability envelope. In some embodiments, a sensor is used to detect when the concentration of isoprene is close to or within the flammability envelope. If desired, the concentration of isoprene can be measured at one or more time points during the culturing of cells, and the cell culture conditions and/or the amount of inert gas can be adjusted using standard methods if the concentration of isoprene is close to or within the flammability envelope. In particular embodiments, the cell culture conditions (such as fermentation conditions) are adjusted to either decrease the concentration of isoprene below the LFL or increase the concentration of isoprene above the UFL. In some embodiments, the amount of isoprene is kept below the LFL by diluting the isoprene composition with an inert gas (such as by continuously or periodically adding an inert gas to keep the isoprene composition below the LFL).

In some embodiments, the amount of flammable volatiles other than isoprene (such as one or more sugars) is at least about 2, 5, 10, 50, 75, or 100-fold less than the amount of isoprene produced. In some embodiments, the portion of the gas phase other than isoprene gas comprises between about 0% to about 100% (volume) oxygen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 100% (volume) oxygen. In some embodiments, the portion of the gas phase other than isoprene gas comprises between about 0% to about 99% (volume) nitrogen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 99% (volume) nitrogen.

In some embodiments, the portion of the gas phase other than isoprene gas comprises between about 1% to about 50% (volume) $CO_2$, such as between about 1% to about 10%, about 10% to about 20%, about 20% to about 30%, about 30% to about 40%, or about 40% to about 50% (volume) $CO_2$.

In some embodiments, an isoprene composition also contains ethanol. For example, ethanol may be used for extractive distillation of isoprene, resulting in compositions (such as intermediate product streams) that include both ethanol and isoprene. Desirably, the amount of ethanol is outside the flammability envelope for ethanol. The LOC of ethanol is about 8.7 vol %, and the LFL for ethanol is about 3.3 vol % at standard conditions, such as about 1 atmosphere and about 60° F. (NFPA 69 *Standard on Explosion Prevention Systems,* 2008 edition, which is hereby incorporated by reference in its entirety, particularly with respect to LOC, LFL, and UFL values). In some embodiments, compositions that include isoprene and ethanol are produced in the presence of less than the LOC required to have a flammable mixture of ethanol (such as less than about 8.7 vol %). In some embodiments in which compositions that include isoprene and ethanol are produced in the presence of greater than or about the LOC required to have a flammable mixture of ethanol, the ethanol concentration is below the LFL (such as less than about 3.3 vol. %).

In various embodiments, the amount of oxidant (such as oxygen) is below the LOC of any fuel in the system (such as isoprene or ethanol). In various embodiments, the amount of oxidant (such as oxygen) is less than about 60, 40, 30, 20, 10, or 5% of the LOC of isoprene or ethanol. In various embodiments, the amount of oxidant (such as oxygen) is less than the LOC of isoprene or ethanol by at least 2, 4, 5, or more absolute percentage points (vol %). In particular embodiments, the amount of oxygen is at least 2 absolute percentage points (vol %) less than the LOC of isoprene or ethanol (such as an oxygen concentration of less than 7.5 vol % when the LOC of isoprene is 9.5 vol %). In various embodiments, the amount of fuel (such as isoprene or ethanol) is less than or about 25, 20, 15, 10, or 5% of the LFL for that fuel.

High Efficiency Production and Recovery of Isoprene, a Volatile Hydrocarbon, by Fermentation Methods are provided herein of producing isoprene comprising a) culturing cells under suitable conditions for production of isoprene; and b) producing isoprene, wherein the liquid phase concentration of isoprene is less than about 200 mg/L. In some embodiments, the liquid phase concentration of isoprene in the culture is less than about any of 175 mg/L, 150 mg/L, 125 mg/L, 100 mg/L, 75 mg/L, 50 mg/L, 25 mg/L, 20 mg/L, 15 mg/L, 10 mg/L, 5 mg/L, or 2.5 mg/L. In some embodiments, the liquid phase concentration of isoprene in culture is between about any of 0.1 mg/L to 200 mg/L, 1 mg/L to 200 mg/L, 1 mg/L to 150 mg/L, 1 mg/L to 100 mg/L, 1 mg/L to 50 mg/L, 1 mg/L to 25 mg/L, 1 mg/L to 20 mg/L, or 10 mg/L to 20 mg/L. In some embodiments, the isoprene produced is any concentration or amount disclosed in the section entitled "Exemplary Production of Isoprene." In some embodiments, the liquid phase concentration is below the solubility limit of isoprene.

In some embodiments of the methods, the cells produce greater than about 400 nmole/$g_{wcm}$/hour of isoprene. In some embodiments, the amount of isoprene is between about any of 400 nmole/$g_{wcm}$/hour to 1 mole/$g_{wcm}$/hour, 400 nmole/$g_{wcm}$/hour to 1 mmole/$g_{wcm}$/hour, 400 nmole/$g_{wcm}$/hour to 40 mmole/$g_{wcm}$/hour, 400 nmole/$g_{wcm}$/hour to 4 mmole/$g_{wcm}$/hour, 1 mmole/$g_{wcm}$/hour to 1.5 mmole/$g_{wcm}$/hour, 1.5 mmole/$g_{wcm}$/hour to 3 mmole/$g_{wcm}$/hour, 3 mmole/$g_{wcm}$/hour to 5 mmole/$g_{wcm}$/hour, 5 mmole/$g_{wcm}$/hour to 25 mmole/$g_{wcm}$/hour, 25 mmole/$g_{wcm}$/hour to 100 mmole/$g_{wcm}$/hour, 100 mmole/$g_{wcm}$/hour to 500 mmole/$g_{wcm}$/hour, or 500 mmole/$g_{wcm}$/hour to 1000 mmole/$g_{wcm}$/hour. In some embodiments, the amount of isoprene is about any of 1 mmole/$g_{wcm}$/hour, 1.5 mmole/$g_{wcm}$/hour, 2 mmole/$g_{wcm}$/hour, 3 mmole/$g_{wcm}$/hour, 4 mmole/$g_{wcm}$/hour, or 5 mmole/$g_{wcm}$/hour.

The low value for Henry's coefficient means that isoprene can be recovered from fermentation broth by gas stripping at low sparging rates, for example 0.01 vvm to 2 vvm. In some embodiments, the gas sparging rate is between about any of 0.1 vvm to 1 vvm, 0.01 vvm to 0.5 vvm, 0.2 vvm to 1 vvm, or 0.5 vvm to 1 vvm. In some embodiments, the gas sparging rate is about any of 0.1 vvm, 0.25 vvm, 0.5 vvm, 0.75 vvm, 1 vvm, 1.25 vvm, 1.5 vvm, 1.75 vvm, or 2 vvm. In some embodiments, the low sparging rates are maintained for the entire course of the fermentation run, during growth phase, or during stationary phase. In some embodiments, the low sparging rates are maintained for between about any of 1 hour to 5 hours, 5 hours to 10 hours, 10 hours to 20 hours, 20 hours to 30 hours, 30 hours to 40 hours, 40 hours to 50 hours, or 50 hours to 60 hours. The lower desirable gas sparge limit is defined by the point at which the aqueous phase becomes saturated with isoprene and a liquid organic phase forms. This can only occur below the boiling point of isoprene (34.1° C. at 1 atm), above which a liquid isoprene phase will never form. At temperatures below the boiling point of isoprene, the formation of a liquid phase is determined by the aqueous solubility of isoprene, which is approximately 650 mg/L at 25° C. While it is highly desirable to avoid the formation of a liquid isoprene phase, it is not absolutely required provided that the cells can tolerate the presence of liquid isoprene without toxic effects.

In some embodiments, the oxygen, $CO_2$, and isoprene are any of the amounts or concentrations discussed in the section entitled "Production of Isoprene with Safe Operating Ranges." In some embodiments, all the oxygen is consumed by the cells while maintaining fully aerobic metabolism. In some embodiments, an excess of oxygen is used in order to satisfy the oxygen demands of the cells. Desirable ranges of oxygen in the off-gas are less than 20%, or less than 15% or less than 10% (v/v). Levels of oxygen below the limiting oxygen concentration required for combustion of isoprene (9.5% v/v at 1 atm) are particularly desirable. In some embodiments, oxygen-enriched air is utilized with the purpose of allowing minimal gas sweep rates while satisfying the cellular oxygen demand. In some embodiments, the portion of the gas phase of the gas sweep comprises between about 0.1% to about 10%, about 10% to about 20%, or about 20% to about 30% (volume) oxygen. In some embodiments, isoprene fermentations are performed under high pressure in order minimize the amount of excess oxygen required to maintain the required dissolved oxygen levels in the liquid phase.

In some embodiments, the reduction of the gas sweep rate through the fermentor is advantageous for an integrated isoprene production process in that such conditions enrich the off-gas isoprene levels up to about 30,000 ug/L (about 1% v/v) without adversely affecting the physiology of the cells.

In some embodiments, reduced gas-sparge rates do not significantly adversely affect the physiology of the cells. In some embodiments, the carbon dioxide evolution rate of cells in culture with reduced gas-sparge rates is between about any of $1 \times 10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour. In some embodiments, cell viability with reduced gas-sparge rates is reduced by less than about any of 1.75-fold, 1.5-fold, 1.25-fold, 1-fold, 0.75-fold, 0.5-fold, or 0.25-fold. In some embodiments, cell viability with reduced gas-sparge rates is reduced by about 2-fold. In some embodiments, cell viability with reduced gas-sparge rates of a cell expressing a MVA pathway and/or DXP pathway RNA and/or protein from one or more of a heterologous and/or duplicate copy of a MVA pathway and/or DXP pathway nucleic acid is compared to a control cell lacking one or more of a heterologous and/or duplicate copy of a MVA pathway and/or DXP pathway nucleic acid with reduced gas-sparge rates. In some embodiments, cell viability with reduced gas-sparge rates of a cell expressing a MVA pathway and/or DXP pathway RNA and/or protein from one or more of a heterologous and/or duplicate copy of a MVA pathway and/or DXP pathway nucleic acid under the control of an inducible promoter, wherein the promotor is induced, is compared to a control cell containing one or more of a heterologous and/or duplicate copy of a MVA pathway and/or DXP pathway nucleic acid under the control of an inducible promoter, wherein the promotor is not induced (uninduced) with reduced gas-sparge rates. In some embodiments, the inducible promoter is a beta-galactosidase promotor.

In some embodiments, the fermentation of a genetically modified host organism that converts at least 5% of the total carbon consumed by the organism into a volatile, unsaturated hydrocarbon. In some embodiments, the production of an unsaturated hydrocarbon at such a rate as to be present in the fermentation off-gas at a level of at least about any of 100 ug/L, 500 ug/L, 1000 ug/L, 2, 500 ug/L, 5,000 ug/L, 7,500 ug/L, or 10,000 ug/L.

In some embodiments, the unsaturated hydrocarbon is recovered from the off-gas stream in a manner that is suited to high-rates of production, which correspond to concentrations in the offgas of at least about any of 100 ug/L, 500 ug/L, 1000 ug/L, 2,500 ug/L, 5,000 ug/L, 7,500 ug/L, or 10,000 ug/L. In some embodiments, the continuous extraction and recovery of an unsaturated hydrocarbon from the fermentation off-gas in particular at low gas sweep rates such that the resulting off-gas is enriched in the volatile component of interest. In some embodiments, recovery of the volatile hydrocarbon by methods that depend on elevated concentrations of the volatile. For example, efficient capture of isoprene in fermentation off-gas through the use of compression/condensation or extractive distillation technologies. Also contemplated is the use of activated carbon cartridges in addition to silica gel adsorbants, desorption and concentration of isoprene from carbon cartridges, and/or construction and fermentation of host organisms such as E. coli strains that can convert about 5% or more of the glucose substrate to isoprene and result in off-gas concentrations of greater than about 15,000 ug/L isoprene. Recovery methods include any of the methods described herein.

Also provided herein are methods of producing a compound, wherein the compound has one or more characteristics selected from the group consisting of (a) a Henry's law coefficient of less than about 250 M/atm and (b) a solubility in water of less than about 100 g/L. In some embodiments, the method comprises: a) culturing cells under suitable conditions for production of the compound, wherein gas is added (such as the addition of gas to a system such as a fermentation system) at a gas sparging rate between about 0.01 vvm to about 2 vvm; and b) producing the compound.

In some embodiments, the amount of the compound that partitions into the cell mass is not included in the liquid phase solubility values. In some embodiments, the liquid phase concentration is below the solubility limit of compound.

In some embodiments, the compounds can be continuously recovered from fermentation broth by gas stripping at moderate to low gas sparging rates, in particular those compounds with Henry's law coefficients of about any of less than 250 M/atm, 200 M/atm, 150 M/atm, 100 M/atm, 75 M/atm, 50 M/atm, 25 M/atm, 10 M/atm, 5 M/atm, or 1 M/atm. Examples include aldehydes such as acetaldehyde (15 M/atm), ketones such as acetone (30 M/atm) or 2-butanone (20 M/atm), or alcohols including methanol (220 M/atm), ethanol (200 M/atm), 1-butanol (120 m/atm) or C5 alcohols including 3-methyl-3-buten-1-ol, and 3-methyl-2-buten-1-ol (50-100 M/atm). Esters of alcohols generally have lower Henry's constants than the respective alcohols, for example ethyl acetate (6-9 M/atm) or the acetyl esters of C5 alcohols (<5 M/atm). Compounds with Henry's law coefficients of less than 1M/atm are particularly desirable. Examples include hemiterpenes, monoterpenes, or sesquiterpenes, in addition to other hydrocarbons such as C1 to C5 hydrocarbons (e.g., methane, ethane, ethylene, or propylene). In some embodiments, the hydrocarbons such as C1 to C5 hydrocarbons are saturated, unsaturated, or branched.

In general, there is a correlation between Henry's law coefficient and water solubility in that compounds with very low coefficients are sparingly soluble in water (substantially water insoluble). Although volatiles with infinite solubilities in water (e.g. acetone or ethanol) can be removed by gas stripping, desirable solubility limits are less than about any of 100 g/L, 75 g/L, 50 g/L, 25 g/L, 10 g/L, 5 g/L, or 1 g/L.

In some embodiments of any of the methods of producing any of the compounds described above, the gas sparging rate is between about any of 0.1 vvm to 1 vvm, 0.2 vvm to 1 vvm, or 0.5 vvm to 1 vvm. In some embodiments, the gas sparging rate is about any of 0.1 vvm, 0.25 vvm, 0.5 vvm, 0.75 vvm, 1 vvm, 1.25 vvm, 1.5 vvm, 1.75 vvm, or 2 vvm. In some embodiments, the low sparging rates are maintained for the entire course of the fermentation run, during growth phase, or during stationary phase. In some embodiments, the low sparging rates are maintained for between about any of 1 hour to 5 hours, 5 hours to 10 hours, 10 hours to 20 hours, 20 hours to 30 hours, 30 hours to 40 hours, 40 hours to 50 hours, or 50 hours to 60 hours.

Any of the systems described herein can be used in the methods of producing a compound described above. Standard methods would be used to purify such as those described in the section entitled "Exemplary Purification Methods." Separation can be performed post-recovery for example, by distillation or selective adsorption techniques.

Exemplary Production of Isoprene

In some embodiments, the cells are cultured in a culture medium under conditions permitting the production of isoprene by the cells.

By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The peak specific productivity is determined by dividing the total productivity by the amount of cells, as determined by optical density at 600 nm ($OD_{600}$). In some embodiments, the isoprene amount is measured at the peak specific productivity time point. In some embodiments, the peak specific productivity for the cells is about any of the isoprene amounts per cell disclosed herein.

By "peak volumetric productivity" is meant the maximum amount of isoprene produced per volume of broth (including the volume of the cells and the cell medium) during the culturing of cells for a particular period of time (e.g., the culturing of cells during a particular fermentation run). By "peak specific volumetric productivity time point" is meant the time point during the culturing of cells for a particular period of time (e.g., the culturing of cells during a particular fermentation run) when the amount of isoprene produced per volume of broth is at a maximum. The peak specific volumetric productivity is determined by dividing the total productivity by the volume of broth and amount of time. In some embodiments, the isoprene amount is measured at the peak specific volumetric productivity time point. In some embodiments, the peak specific volumetric productivity for the cells is about any of the isoprene amounts per volume per time disclosed herein.

By "peak concentration" is meant the maximum amount of isoprene produced during the culturing of cells for a particular period of time (e.g., the culturing of cells during a particular fermentation run). By "peak concentration time point" is meant the time point during the culturing of cells for a particular period of time (e.g., the culturing of cells during a particular fermentation run) when the amount of isoprene produced per cell is at a maximum. In some embodiments, the isoprene amount is measured at the peak concentration time point. In some embodiments, the peak concentration for the cells is about any of the isoprene amounts disclosed herein.

By "average volumetric productivity" is meant the average amount of isoprene produced per volume of broth (including the volume of the cells and the cell medium) during the culturing of cells for a particular period of time (e.g., the culturing of cells during a particular fermentation run). The average volumetric productivity is determined by dividing the total productivity by the volume of broth and amount of time. In some embodiments, the average specific volumetric productivity for the cells is about any of the isoprene amounts per volume per time disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

By "relative detector response" refers to the ratio between the detector response (such as the GC/MS area) for one compound (such as isoprene) to the detector response (such as the GC/MS area) of one or more compounds (such as all C5 hydrocarbons). The detector response may be measured as described herein, such as the GC/MS analysis performed with an Agilent 6890 GC/MS system fitted with an Agilent HP-5MS GC/MS column (30 m×250 µm; 0.25 µm film thickness). If desired, the relative detector response can be converted to a weight percentage using the response factors for each of the compounds. This response factor is a measure of how much signal is generated for a given amount of a particular compound (that is, how sensitive the detector is to a particular compound). This response factor can be used as a correction factor to convert the relative detector response to a weight percentage when the detector has different sensitivities to the compounds being compared. Alternatively, the weight percentage can be approximated by assuming that the response factors are the same for the compounds being compared. Thus, the weight percentage can be assumed to be approximately the same as the relative detector response.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some embodiments, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example I, part II). If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

In some embodiments, the cells in culture have an average volumetric productivity of isoprene at greater than or about 0.1, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, or more mg of isoprene/L of broth/hr (mg/$L_{broth}$/hr, wherein the volume of broth includes the volume of the cells and the cell medium). In some embodiments, the average volumetric productivity of isoprene is between about 0.1 to about 3,500 mg/$L_{broth}$/hr, such as between about 0.1 to about 100 mg/$L_{broth}$/hr, about 100 to about 500 mg/$L_{broth}$/hr, about 500 to about 1,000 mg/$L_{broth}$/hr, about 1,000 to about 1,500 mg/$L_{broth}$/hr, about 1,500 to about 2,000 mg/$L_{broth}$/hr, about 2,000 to about 2,500 mg/$L_{broth}$/hr, about 2,500 to about 3,000 mg/$L_{broth}$/hr, or about 3,000 to about 3,500 mg/$L_{broth}$/hr. In some embodiments, the average volumetric productivity of isoprene is between about 10 to about 3,500 mg/$L_{broth}$/hr, about 100 to about 3,500 mg/$L_{broth}$/hr, about 200 to about 1,000 mg/$L_{broth}$/hr, about 200 to about 1,500 mg/$L_{broth}$/hr, about 1,000 to about 3,000 mg/$L_{broth}$/hr, or about 1,500 to about 3,000 mg/$L_{broth}$/hr.

In some embodiments, the cells in culture have a peak volumetric productivity of isoprene at greater than or about 0.5, 1.0, 10, 25, 50, 100, 150, 200, 250, 300, 400, 500, 600, 700, 800, 900, 1,000, 1100, 1200, 1300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 12,500, 15,000, or more mg of isoprene/L of broth/hr (mg/$L_{broth}$/hr, wherein the volume of broth includes the volume of the cells and the cell medium). In some embodiments, the peak volumetric productivity of isoprene is between about 0.5 to about 15,000 mg/$L_{broth}$/hr, such as between about 0.5 to about 10 mg/$L_{broth}$/hr, about 1.0 to about 100 mg/$L_{broth}$/hr, about 100 to about 500 mg/$L_{broth}$/hr, about 500 to about 1,000 mg/$L_{broth}$/hr, about 1,000 to about 1,500 mg/$L_{broth}$/hr, about 1,500 to about 2,000 mg/$L_{broth}$/hr, about 2,000 to about 2,500 mg/$L_{broth}$/hr, about 2,500 to about 3,000 mg/$L_{broth}$/hr, about 3,000 to about 3,500 mg/$L_{broth}$/hr, about 3,500 to about 5,000 mg/$L_{broth}$/hr, about 5,000 to about 7,500 mg/$L_{broth}$/hr, about 7,500 to about 10,000 mg/$L_{broth}$/hr, about 10,000 to about 12,500 mg/$L_{broth}$/h, or about 12,500 to about 15,000 mg/$L_{broth}$/hr. In some embodiments, the peak volumetric productivity of isoprene is between about 10 to about 15,000 mg/$L_{broth}$/hr, about 100 to about 2,500 mg/$L_{broth}$/hr, about 1,000 to about 5,000 mg/$L_{broth}$/hr, about 2,500 to about 7,500 mg/$L_{broth}$/hr, about 5,000 to about 10,000 mg/$L_{broth}$/hr, about 7,500 to about 12,500 mg/$L_{broth}$/hr, or about 10,000 to about 15,000 mg/$L_{broth}$/hr.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$) as described, for example, in Example I, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100    Equation 1

For this calculation, yeast extract can be assumed to contain 50% w/w carbon. As an example, for the 500 liter described in Example 7, part VIII, the percent conversion of carbon into isoprene can be calculated as shown in Equation 2.

% Carbon Yield=(39.1 g isoprene*1/68.1 mol/g*5 C/mol)/[(181221 g glucose*1/180 mol/g*6 C/mol)+(17780 g yeast extract*0.5*1/12 mol/g)]*100=0.042%    Equation 2

For the two 500 liter fermentations described herein (Example 7, parts VII and VIII), the percent conversion of carbon into isoprene was between 0.04-0.06%. A 0.11-0.16% carbon yield has been achieved using 14 liter systems as described herein. Example 11, part V describes the 1.53% conversion of carbon to isoprene using the methods described herein.

One skilled in the art can readily convert the rates of isoprene production or amount of isoprene produced into any other units. Exemplary equations are listed below for interconverting between units.

Units for Rate of Isoprene Production (Total and Specific)

1 g isoprene/$L_{broth}$/hr=14.7 mmol isoprene/$L_{broth}$/hr (total volumetric rate)    Equation 3

1 nmol isoprene/$g_{wcm}$/hr=1 nmol isoprene/$L_{broth}$/hr/$OD_{600}$(This conversion assumes that one liter of broth with an $OD_{600}$ value of 1 has a wet cell weight of 1 gram)    Equation 4

1 nmol isoprene/$g_{wcm}$/hr=68.1 ng isoprene/$g_{wcm}$/hr (given the molecular weight of isoprene)    Equation 5

1 nmol isoprene/$L_{gas}$ $O_2$/hr=90 nmol isoprene/$L_{broth}$/hr(at an $O_2$ flow rate of 90 L/hr per L of culture broth)    Equation 6

1 ug isoprene/$L_{gas}$ isoprene in off-gas=60 ug isoprene/$L_{broth}$/hr at a flow rate of 60 $L_{gas}$ per $L_{broth}$(1 vvm)    Equation 7

Units for Titer (Total and Specific)

1 nmol isoprene/mg cell protein=150 nmol isoprene/$L_{broth}$/$OD_{600}$(This conversion assumes that one liter of broth with an $OD_{600}$ value of 1 has a total cell protein of approximately 150 mg)(specific productivity)    Equation 8

1 g isoprene/$L_{broth}$=14.7 mmol isoprene/$L_{broth}$(total titer)    Equation 9

If desired, Equation 10 can be used to convert any of the units that include the wet weight of the cells into the corresponding units that include the dry weight of the cells.

Dry weight of cells=(wet weight of cells)/3.3    Equation 10

If desired, Equation 11 can be used to convert between units of ppm and µg/L. In particular, "ppm" means parts per million defined in terms of µg/g (w/w). Concentrations of gases can also be expressed on a volumetric basis using "ppmv" (parts per million by volume), defined in terms of µL/L (vol/vol). Conversion of µg/L to ppm (e.g., µg of analyte per g of gas) can be performed by determining the mass per L of off-gas (i.e., the density of the gas). For example, a liter of air at standard temperature and pressure (STP; 101.3 kPa (1 bar) and 273.15K). has a density of approximately 1.29 g/L. Thus, a concentration of 1 ppm (μg/g) equals 1.29 μg/L at STP (Equation 11). The conversion of ppm (μg/g) to μg/L is a function of both pressure, temperature, and overall composition of the off-gas.

> 1 ppm(ug/g) equals 1.29 μg/L at standard temperature and pressure(STP;101.3 kPa(1 bar) and 273.15K). Equation 11

Conversion of ug/L to ppmv (e.g., uL of analyte per L of gas) can be performed using the Universal Gas Law (equation 12). For example, an off-gas concentration of 1000 ug/$L_{gas}$ corresponds to 14.7 umol/$L_{gas}$. The universal gas constant is 0.082057 L·atm $K^{-1}$ $mol^{-1}$, so using equation 12, the volume occupied by 14.7 umol of HG at STP is equal to 0.329 mL. Therefore, the concentration of 1000 ug/L HG is equal to 329 ppmv or 0.0329% (v/v) at STP.

> $PV=nRT$, where "P" is pressure, "V" is volume, "n" is moles of gas, "R" is the Universal gas constant, and "T" is temperature in Kelvin. Equation 12

The amount of impurities in isoprene compositions are typically measured herein on a weight per volume (w/v) basis in units such as ug/L. If desired, measurements in units of ug/L can be converted to units of $mg/m^3$ using equation 13.

> 1 ug/L=1 $mg/m^3$ Equation 13

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

In some embodiments, the isoprene composition comprises greater than or about 99.90, 99.92, 99.94, 99.96, 99.98, or 100% isoprene by weight compared to the total weight of all C5 hydrocarbons in the composition. In some embodiments, the composition has a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the composition. In some embodiments, the isoprene composition comprises between about 99.90 to about 99.92, about 99.92 to about 99.94, about 99.94 to about 99.96, about 99.96 to about 99.98, about 99.98 to 100% isoprene by weight compared to the total weight of all C5 hydrocarbons in the composition.

In some embodiments, the isoprene composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne compared to the detector response for all C5 hydrocarbons in the composition. In some embodiments, the isoprene composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition.

In some embodiments, the isoprene composition comprises less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a compound that inhibits the polymerization of isoprene for any compound in the composition that inhibits the polymerization of isoprene. In some embodiments, the isoprene composition comprises less than or about 50, 40, 30, 20, 10, 5, 1, 0.5, 0.1, 0.05, 0.01, or 0.005 ug/L of a hydrocarbon other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne). In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a hydrocarbon other than isoprene. In some embodiments, the isoprene composition comprises less than or about 50, 40, 30, 20, 10, 5, 1, 0.5, 0.1, 0.05, 0.01, or 0.005 ug/L of a protein or fatty acid (such as a protein or fatty acid that is naturally associated with natural rubber).

In some embodiments, the isoprene composition comprises less than or about 10, 5, 1, 0.8, 0.5, 0.1, 0.05, 0.01, or 0.005 ppm of alpha acetylenes, piperylenes, acetonitrile, or 1,3-cyclopentadiene. In some embodiments, the isoprene composition comprises less than or about 5, 1, 0.5, 0.1, 0.05, 0.01, or 0.005 ppm of sulfur or allenes. In some embodiments, the isoprene composition comprises less than or about 30, 20, 15, 10, 5, 1, 0.5, 0.1, 0.05, 0.01, or 0.005 ppm of all acetylenes (such as 1-pentyne, 2-pentyne, 3-methyl-1-butyne, pent-4-ene-1-yne, trans-pent-3-ene-1-yne, cis-pent-3-ene-1-yne, pentyne-1, butyne-2, 2 MB1-3yne, and 1-pentyne-4-yne). In some embodiments, the isoprene composition comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimers (e.g., cyclic C10 compounds derived from the dimerization of two isoprene units).

In some embodiments, the isoprene composition includes ethanol, acetone, a C5 prenyl alcohol (such as 3-methyl-3-buten-1-ol or 3-methyl-2-buten-1-ol), or any two or more of the foregoing. In particular embodiments, the isoprene composition comprises greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In some embodiments, the isoprene composition comprises between about 0.005 to about 120, such as about 0.01 to about 80, about 0.01 to about 60, about 0.01 to about 40, about 0.01 to about 30, about 0.01 to about 20, about 0.01 to about 10, about 0.1 to about 80, about 0.1 to about 60, about 0.1 to about 40, about 5 to about 80, about 5 to about 60, or about 5 to about 40 ug/L of ethanol, acetone, a C5 prenyl alcohol, or any two or more of the foregoing.

In some embodiments, the isoprene composition includes one or more of the following components: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, or a linear isoprene polymer (such as a linear isoprene dimer or a linear isoprene trimer derived from the polymerization of multiple isoprene units). In various embodiments, the amount of one of these components relative to amount of isoprene in units of percentage by weight (i.e., weight of the component divided by the weight of isoprene times 100) is greater than or about 0.01, 0.02, 0.05, 0.1, 0.5, 1, 5, 10, 20, 30, 40, 50, 60, 70, 80, 90, 100, or 110% (w/w). In some embodiments, the relative detector response for the second compound compared to the detector response for isoprene is greater than or about 0.01, 0.02, 0.05, 0.1, 0.5, 1, 5, 10, 20, 30, 40, 50, 60, 70, 80, 90, 100, or 110%. In various embodiments, the amount of one of these components relative to amount of isoprene in units of percentage by weight (i.e., weight of the component divided by the weight of isoprene times 100) is between about 0.01 to about 105% (w/w), such as about 0.01 to about 90, about 0.01 to about 80, about 0.01 to about 50, about 0.01 to about 20, about 0.01 to about 10, about 0.02 to about 50, about 0.05 to about 50, about 0.1 to about 50, or 0.1 to about 20% (w/w).

In some embodiments, the isoprene composition includes one or more of the following: an alcohol, an aldehyde, an ester, or a ketone (such as any of the alcohols, aldehydes, esters, or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone.

In some embodiments, the isoprene composition contains one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the isoprene composition contains 1 ppm or more of one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the concentration of more of one or more of the following: methanol, acetaldehyde, ethanol, methanethiol, 1-butanol, 3-methyl-1-propanol, acetone, acetic acid, 2-butanone, 2-methyl-1-butanol, or indole, is between about 1 to about 10,000 ppm in an isoprene composition (such as off-gas before it is purified). In some embodiments, the isoprene composition (such as off-gas after it has undergone one or more purification steps) includes one or more of the following: methanol, acetaldehyde, ethanol, methanethiol, 1-butanol, 3-methyl-1-propanol, acetone, acetic acid, 2-butanone, 2-methyl-1-butanol, or indole, at a concentration between about 1 to about 100 ppm, such as about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, or about 90 to about 100 ppm. Volatile organic compounds from cell cultures (such as volatile organic compounds in the headspace of cell cultures) can be analyzed using standard methods such as those described herein or other standard methods such as proton transfer reaction-mass spectrometry (see, for example, Bunge et al., *Applied and Environmental Microbiology*, 74(7):2179-2186, 2008 which is hereby incorporated by reference in its entirety, particular with respect to the analysis of volatile organic compounds).

In some embodiments, the composition comprises greater than about 2 mg of isoprene, such as greater than or about 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene. In some embodiments, the amount of isoprene in the composition is between about 2 to about 5,000 mg, such as between about 2 to about 100 mg, about 100 to about 500 mg, about 500 to about 1,000 mg, about 1,000 to about 2,000 mg, or about 2,000 to about 5,000 mg. In some embodiments, the amount of isoprene in the composition is between about 20 to about 5,000 mg, about 100 to about 5,000 mg, about 200 to about 2,000 mg, about 200 to about 1,000 mg, about 300 to about 1,000 mg, or about 400 to about 1,000 mg. In some embodiments, greater than or about 20, 25, 30, 40, 50, 60, 70, 80, 90, or 95% by weight of the volatile organic fraction of the composition is isoprene.

In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments in which the composition includes ethanol, the composition also includes between about 4 to about 15% by weight of isoprene, such as between about 4 to about 8%, about 8 to about 12%, or about 12 to about 15% by weight of isoprene.

In some embodiments encompassed by the invention, a cell comprising one or more heterologous nucleic acids encoding an isoprene synthase polypeptide, DXS polypeptide, IDI polypeptide, and/or MVA pathway polypeptide produces an amount of an isoprenoid compound (such as a compound with 10 or more carbon atoms that is formed from the reaction of one or more IPP molecules with one or more DMAPP molecules) that is greater than or about 2-fold, 3-fold, 5-fold, 10-fold, 25-fold, 50-fold, 100-fold, 150-fold, 200-fold, 400-fold, or greater than the amount of the isoprenoid compound produced from a corresponding cell grown under essentially the same conditions without the one or more heterologous nucleic acids. In some embodiments encompassed by the invention, a cell comprising one or more heterologous nucleic acids encoding an isoprene synthase polypeptide, DXS polypeptide, IDI polypeptide, and/or MVA pathway polypeptide produces an amount of a C5 prenyl alcohol (such as 3-methyl-3-buten-1-ol or 3-methyl-2-buten-1-ol) that is greater than or about 2-fold, 3-fold, 5-fold, 10-fold, 25-fold, 50-fold, 100-fold, 150-fold, 200-fold, 400-fold, or greater than the amount of the C5 prenyl alcohol produced from a corresponding cell grown under essentially the same conditions without the one or more heterologous nucleic acids.

Exemplary Co-Production of Isoprene and Hydrogen

In some embodiments, any of the isoprene-producing cells described herein that comprise one or more heterologous nucleic acids encoding an isoprene synthase polypeptide, a DXS polypeptide, an IDI polypeptide, and/or an MVA pathway polypeptide operably linked to a promoter further comprise a heterologous nucleic acid also operably linked to a promoter encoding one or more hydrogenase polypeptides or one or more polypeptides involved in the regulation or expression of hydrogenase polypeptides (e.g., hydrogenase maturation proteins or transcription factors). In some embodiments, any of the isoprene-producing cells described herein that comprise one or more heterologous nucleic acids encoding an isoprene synthase polypeptide, a DXS polypeptide, an IDI polypeptide, an MVA pathway polypeptide, one or more hydrogenase polypeptides or one or more polypeptides involved in the regulation or expression of hydrogenase polypeptides operably linked to a promoter further comprise a mutation or deletion inactivating one or more polypeptides involved in the production of fermentation side products, one or more polypeptides involved in the regulation or expression of genes for the production of fermentation side products, or one or more polypeptides involved in hydrogen reuptake. Such cells can co-produce isoprene and hydrogen.

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans*, *Streptomyces coelicolor*, or *Streptomyces griseus* cells). In some embodiments of any of the aspects of the invention, the cells are gram-negative bacterial cells (e.g., *Escherichia* cells such as *Escherichia coli* cells, *Rhodopseudomonas* sp. such as *Rhodopseudomonas palustris* cells, *Pseudomonas* sp. such as *Pseudomonas fluorescens* cells or *Pseudomonas putida* cells, or *Pantoea* cells such as *Pantoea citrea* cells). In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells or *Sacchraomyces* cells such as *Saccaromyces cerevisiae*).

In some embodiments of any of the aspects of the invention, the isoprene synthase polypeptide is a polypeptide from a plant such as *Pueraria* (e.g., *Pueraria montana* or *Pueraria lobata*) or *Populus* (e.g., *Populus tremuloides, Populus alba, Populus nigra, Populus trichocarpa*, or the hybrid, *Populus alba×Populus tremula*).

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker or a selectable marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisia* or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic acid.

In some embodiments, the MVA pathway polypeptide is an upper MVA pathway polypeptide. In some embodiments, the MVA pathway polypeptide is a lower MVA pathway polypeptide. In some embodiments, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some embodiments, the upper MVA pathway polypeptide is from the genus *Enterococcus*. In some embodiments, the upper MVA pathway polypeptide is from *Enterococcus faecalis*. In some embodiments, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some embodiments, the lower MVA pathway polypeptide is an MVK polypeptide. In some embodiments, the MVK polypeptide is from the genus *Methanosarcina*. In some embodiments, the MVK polypeptide is from *Methanosarcina mazei*.

In some embodiments, the isoprene-producing cells described herein further comprise a heterologous nucleic acid encoding a hydrogenase polypeptide operably linked to a promoter. In some embodiments, the hydrogenase polypeptide comprises *E. coli* hydrogenase-1 (Hyd-1), *E. coli* hydrogenase-2 (Hyd-2), *E. coli* hydrogenase-3 (Hyd-3), *E. coli* hydrogenase-4 (Hyd-4), *E. coli* formate hydrogen lyase (FHL) complex, which produces hydrogen gas from formate and $CO_2$ under anaerobic conditions at acidic pH, *Rhodococcus opacus* MR11 hydrogenase (*R. opacus* HoxH), *Synechosystis* sp. PCC 6803 hydrogenase (Syn. PCC 6803 HoxH), *Desulfovibrio gigas* hydrogenase (*D. gigas*), and *Desulfovibrio desulfuricans* ATCC7757 hydrogenase (*D. desulfuricans*). In some embodiments, the isoprene-producing cells further comprising a heterologous nucleic acid encoding a hydrogenase polypeptide operably linked to a promoter further comprise *E. coli* hydrogenase-3 (Hyd-3),

*E. coli* pyruvate formate lyase (O), and *E. coli* formate hydrogen lyase (FHL) complex.

In some embodiments, the hydrogenase polypeptide encodes a ferredoxin-dependent hydrogenase polypeptide. In some embodiments, the ferredoxin-dependent hydrogenase polypeptide comprises *Clostridium acetobutulicum* hydrogenase A (HydA), which can be expressed in conjunction with one or more of: (1) *Bacillus subtilis* NADPH ferredoxin oxidoreductase (NFOR) or *Clostridium kluyveri* NADH ferredoxin oxidoreductase (RnfCDGEAB), *Clostridium* pasteuranium ferredoxin oxidoreductase (Fdx); (2) glyceraldehyde-6-phosphate ferredoxin oxidoreductase (GAPOR); or (3) pyruvate ferredoxin oxidoreductase (POR). In some embodiments, the ferredoxin-dependent hydrogenase polypeptide *Clostridium acetobutulicum* hydrogenase A (HydA) is expressed with three HydA-associated maturation enzymes (HydE, HydG, and HydF), and further in conjunction with one or more of: (1) *Bacillus subtilis* NADPH ferredoxin oxidoreductase (NFOR) or *Clostridium kluyveri* NADH ferredoxin oxidoreductase (RnfCDGEAB), *Clostridium pasteuranium* ferredoxin oxidoreductase (Fdx); (2) glyceraldehyde-6-phosphate ferredoxin oxidoreductase (GAPOR); or (3) pyruvate ferredoxin oxidoreductase (POR).

In some embodiments, the hydrogenase polypeptide encodes an NADPH-dependent hydrogenase polypeptide. In some embodiments, the NADPH-dependent hydrogenase polypeptide comprises *Pyrococcus furiosus* hydrogenase. In some embodiments, the hydrogenase polypeptide encodes an oxygen-tolerant hydrogenase. In some embodiments, the oxygen-tolerant hydrogenase comprises *Rubrivivax gelatinosus* hydrogenase, and *Ralstonia eutropha* hydrogenase.

In some embodiments, the isoprene-producing cells described herein further comprise a mutation or deletion inactivating a gene involved in regulation of hydrogenase activity, such as iron-sulfur complex transcriptional regulator (iscR) (Kalim-Akhtar et al., "Deletion of iscR stimulates recombinant Clostridial Fe/Fe hydrogenase activity and $H_2$-accumulation in *Escherichia coli* BL21(DE3)," *Appl. Microbiol. Biotechnol.* 78:853-862 (2008), which is incorporated herein by reference in its entirety, particularly with reference to stimulation of Clostridial Fe/Fe hydrogenase activity and hydrogen accumulation in *E. coli* by deleting the iscR gene).

In some embodiments, the isoprene-producing cells described herein further comprise a mutation or deletion inactivating a gene encoding one or more cellular polypeptides involved in production of fermentation side products, such as lactate, acetate, pyruvate, ethanol, succinate, and glycerol. In some embodiments, the inactivated polypeptides involved in production of fermentation side products comprise one or more polypeptides encoding formate dehydrogenase N, alpha subunit (fdnG), formate dehydrogenase 0, large subunit (fdoG), nitrate reductase (narG), formate transporter A (focA), formate transporter B (focB), pyruvate oxidase (poxB), pyruvate dehydrogenase E1 component ackA/pta (aceE), alcohol dehydrogenase (adhE), fumarate reductase membrane protein (frdC), or lactate dehydrogenase (ldhA).

In some embodiments, the isoprene-producing cells described herein further comprise a mutation or deletion inactivating a gene encoding one or more cellular polypeptides involved in the regulation or expression of genes involved in production of fermentation side products. In some embodiments, the inactivated polypeptides involved in the regulation or expression of genes involved in production of fermentation side products comprise repressor of formate hydrogen lyase (hycA), fumarate reductase regulator (fnr), acetyl-coenzyme A synthetase (acs), and formate dehydrogenase regulatory protein (hycA).

In some embodiments, the isoprene-producing cells described herein further comprise a mutation or deletion inactivating a gene encoding one or more cellular polypeptides involved in hydrogen re-uptake. In some embodiments, the inactivated polypeptides involved in hydrogen re-uptake comprise *E. coli* hydrogenase-1 (Hyd-1) (hya operon) and *E. coli* hydrogenase-2 (Hyd-2) (hyb operon).

In some embodiments of any of the aspects of the invention, the heterologous isoprene synthase, DXS polypeptide, IDI polypeptide, MVA pathway, hydrogenase, hydrogenase maturation or transcription factor polypeptide or nucleic acid is operably linked to a T7 promoter, such as a T7 promoter contained in a medium or high copy plasmid. In some embodiments of any of the aspects of the invention, the heterologous isoprene synthase, DXS polypeptide, IDI polypeptide, MVA pathway, hydrogenase, hydrogenase maturation or transcription factor nucleic acid is operably linked to a Trc promoter, such as a Trc promoter contained in a medium or high copy plasmid. In some embodiments of any of the aspects of the invention, the heterologous isoprene synthase, DXS polypeptide, IDI polypeptide, MVA pathway, hydrogenase, hydrogenase maturation or transcription factor nucleic acid is operably linked to a Lac promoter, such as a Lac promoter contained in a low copy plasmid. In some embodiments of any of the aspects of the invention, the heterologous isoprene synthase, DXS polypeptide, IDI polypeptide, MVA pathway, hydrogenase, hydrogenase maturation or transcription factor nucleic acid is operably linked to an endogenous promoter, such as an endogenous alkaline serine protease promoter. In some embodiments, the heterologous isoprene synthase, DXS polypeptide, IDI polypeptide, MVA pathway, hydrogenase, hydrogenase maturation or transcription factor nucleic acid integrates into a chromosome of the cells without a selective marker or without a selectable marker.

In some embodiments, one or more MVA pathway, IDI, DXS, isoprene synthase, hydrogenase, hydrogenase maturation or transcription factor nucleic acids are placed under the control of a promoter or factor that is more active in stationary phase than in the growth phase. For example, one or more MVA pathway, IDI, DXS, isoprene synthase, hydrogenase, hydrogenase maturation or transcription factor nucleic acids may be placed under control of a stationary phase sigma factor, such as RpoS. In some embodiments, one or more MVA pathway, IDI, DXS, isoprene synthase, hydrogenase, hydrogenase maturation or transcription factor nucleic acids are placed under control of a promoter inducible in stationary phase, such as a promoter inducible by a response regulator active in stationary phase.

In some embodiments of any of the aspects of the invention, at least a portion of the cells maintain the heterologous isoprene synthase, DXS polypeptide, IDI polypeptide, MVA pathway, hydrogenase, hydrogenase maturation or transcription factor nucleic acid for at least or about 5, 10, 20, 40, 50, 60, 65, or more cell divisions in a continuous culture (such as a continuous culture without dilution). In some embodiments of any of the aspects of the invention, the nucleic acid comprising the isoprene synthase, DXS polypeptide, IDI polypeptide, MVA pathway, hydrogenase, hydrogenase maturation or transcription factor nucleic acid also comprises a selective marker or a selectable marker, such as an antibiotic resistance nucleic acid.

In some embodiments of any of the aspects of the invention, cells that co-produce isoprene and hydrogen are cultured in any of the culture media described herein, under oxygen-limited conditions to facilitate the co-production of isoprene and hydrogen by the cells. In some embodiments, the cells are grown in oxygen-limited culture. In some embodiments, the cells are grown in the presence of 0.5 moles of oxygen per mole of isoprene. In some embodiments, the cells are grown anaerobically, in the absence of oxygen.

In some embodiments, any of the cells described herein are grown in oxygen-limited culture and co-produce isoprene and hydrogen. In some embodiments, the cells in oxygen-limited culture produce isoprene at a rate greater than about 400 nmole/$g_{wcm}$/hr, and produce hydrogen at a rate greater than about 125 nmole/$g_{wcm}$/hr. In some embodiments, the cells in oxygen-limited culture produce isoprene at a rate between about 400 nmole/$g_{wcm}$/hr to about $2.0\times10^5$ nmole/$g_{wcm}$/hr and hydrogen at a rate between about 125 nmole/$g_{wcm}$/hr to about $1.25\times10^4$ nmole/$g_{wcm}$/hr. In some embodiments, the cells in oxygen-limited culture produce isoprene at a rate between about 400 nmole/$g_{wcm}$/hr and about $2.0\times10^5$ nmole/$g_{wcm}$/hr, between about 500 nmole/$g_{wcm}$/hr and about $1.5\times10^5$ nmole/$g_{wcm}$/hr, between about 750 nmole/$g_{wcm}$/hr and about $1\times10^5$ nmole/$g_{wcm}$/hr, between about 1000 nmole/$g_{wcm}$/hr and about $1\times10^5$ nmole/$g_{wcm}$/hr, between about 2500 nmole/$g_{wcm}$/hr and about $1\times10^5$ nmole/$g_{wcm}$/hr, between about 5000 nmole/$g_{wcm}$/hr and about $1\times10^5$ nmole/$g_{wcm}$/hr, between about 7500 nmole/$g_{wcm}$/hr and about $1\times10^5$ nmole/$g_{wcm}$/hr, and between about $1\times10^4$ nmole/$g_{wcm}$/hr and about $1\times10^5$ nmole/$g_{wcm}$/hr. In some embodiments, the cells in oxygen-limited culture produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the cells in oxygen-limited culture produce hydrogen at a rate between about 125 nmole/$g_{wcm}$/hr to about $1.25\times10^4$ nmole/$g_{wcm}$/hr, between about 250 nmole/$g_{wcm}$/hr to about $1.25\times10^4$ nmole/$g_{wcm}$/hr, between about 500 nmole/$g_{wcm}$/hr to about $1.25\times10^4$ nmole/$g_{wcm}$/hr, between about 750 nmole/$g_{wcm}$/hr to about $1.25\times10^4$ nmole/$g_{wcm}$/hr, between about 1000 nmole/$g_{wcm}$/hr to about $1.25\times10^4$ nmole/$g_{wcm}$/hr, between about 1250 nmole/$g_{wcm}$/hr to about $1.25\times10^4$ nmole/$g_{wcm}$/hr, between about 2500 nmole/$g_{wcm}$/hr to about $1.25\times10^4$ nmole/$g_{wcm}$/hr, between about 5000 nmole/$g_{wcm}$/hr to about $1.25\times10^4$ nmole/$g_{wcm}$/hr, between about 7500 nmole/$g_{wcm}$/hr to about $1.25\times10^4$ nmole/$g_{wcm}$/hr, and between about $1.00\times10^4$ nmole/$g_{wcm}$/hr to about $1.25\times10^4$ nmole/$g_{wcm}$/hr. In some embodiments, the cells in oxygen-limited culture produce greater than about 125, 250, 500, 750, 1000, 1,250, 1,500, 1,750, 2,000, 2,500, 3,000, 4,000, 5,000, 7,500, 10,000, or more nmole/$g_{wcm}$/hr hydrogen.

In some embodiments, any of the cells described herein are grown in oxygen-limited culture and co-produce isoprene and hydrogen. In some embodiments, the cells in oxygen-limited culture have an average volumetric productivity of isoprene greater than about 0.1 mg/$L_{broth}$/hr and an average volumetric productivity of hydrogen greater than about 0.005 mg/$L_{broth}$/hr. In some embodiments, the cells in oxygen-limited culture have a peak volumetric productivity of isoprene greater than about 1000 mg/$L_{broth}$/hr and a peak volumetric productivity of hydrogen greater than about 5 mg/$L_{broth}$/hr. In some embodiments, the cells in oxygen-limited culture have a peak volumetric productivity of isoprene greater than about 3000 mg/$L_{broth}$/hr and a peak volumetric productivity of hydrogen greater than about 5 mg/$L_{broth}$/hr. In some embodiments, the cells in oxygen-limited culture have a peak volumetric productivity of isoprene greater than about 5000 mg/$L_{broth}$/hr and a peak volumetric productivity of hydrogen greater than about 5 mg/$L_{broth}$/hr. In some embodiments, the cells in oxygen-limited culture have an average volumetric productivity of isoprene between about 0.1 mg/$L_{broth}$/hr and about 5000 mg/$L_{broth}$/hr, and an average volumetric productivity of hydrogen between about 0.005 mg/$L_{broth}$/hr and about 5 mg/$L_{broth}$/hr. In some embodiments, the cells in oxygen-limited culture have an average volumetric productivity of isoprene between about 1 mg/$L_{broth}$/hr and about 5000 mg/$L_{broth}$/hr, between about 5 mg/$L_{broth}$/hr and about 5000 mg/$L_{broth}$/hr, between about 10 mg/$L_{broth}$/hr and about 5000 mg/$L_{broth}$/hr, between about 25 mg/$L_{broth}$/hr and about 5000 mg/$L_{broth}$/hr, between about 50 mg/$L_{broth}$/hr and about 5000 mg/$L_{broth}$/hr, between about 100 mg/$L_{broth}$/hr and about 5000 mg/$L_{broth}$/hr, between about 250 mg/$L_{broth}$/hr and about 5000 mg/$L_{broth}$/hr, between about 500 mg/$L_{broth}$/hr and about 5000 mg/$L_{broth}$/hr, between about 1000 mg/$L_{broth}$/hr and about 5000 mg/$L_{broth}$/hr, and between about 2500 mg/$L_{broth}$/hr and about 5000 mg/$L_{broth}$/hr, and an average volumetric productivity of hydrogen between about 0.01 mg/$L_{broth}$/hr and about 5 mg/$L_{broth}$/hr, between about 0.025 mg/$L_{broth}$/hr and about 5 mg/$L_{broth}$/hr, between about 0.05 mg/$L_{broth}$/hr and about 5 mg/$L_{broth}$/hr, between about 0.1 mg/$L_{broth}$/hr and about 5 mg/$L_{broth}$/hr, between about 0.25 mg/$L_{broth}$/hr and about 5 mg/$L_{broth}$/hr, between about 0.5 mg/$L_{broth}$/hr and about 5 mg/$L_{broth}$/hr, between about 1 mg/$L_{broth}$/hr and about 5 mg/$L_{broth}$/hr, and between about 2.5 mg/$L_{broth}$/hr and about 5 mg/$L_{broth}$/hr.

In some embodiments, any of the cells described herein are grown in oxygen-limited culture and co-produce isoprene and hydrogen. In some embodiments, the cells in oxygen-limited culture convert more than about 0.002 molar percent of the carbon that the cells consume from a cell culture medium into isoprene, and produce hydrogen equivalent to more than about 0.024 molar percent of the carbon that the cells consume from a cell culture medium. In some embodiments, the cells in oxygen-limited culture convert more than about 0.002 molar percent of the carbon that the cells consume from a cell culture medium into isoprene, and produce hydrogen equivalent to more than about 400 molar percent of the carbon that the cells consumer from a cell culture medium.

In some embodiments, any of the cells described herein that co-produce isoprene and hydrogen are grown in oxygen-limited culture. In some embodiments, the cells in oxygen-limited culture co-produce isoprene and hydrogen in a ratio ranging from at least one molar percent of isoprene for every three molar percent of hydrogen to at least one molar percent of isoprene for every four molar percent of hydrogen. In some embodiments, the cells in oxygen-limited culture produce from 1 to 11 molar percent isoprene and from 3 to 33 molar percent hydrogen. In some embodiments, the cells produce from 1 to 11 molar percent isoprene and from 4 to 44 molar percent hydrogen. In some embodiments, the cells in oxygen-limited culture also produce oxygen, carbon dioxide, or nitrogen. In some embodiments, the cells in oxygen limited culture produce from 0 to 21 molar percent oxygen, from 18 to 44 molar percent carbon dioxide, and from 0 to 78 molar percent nitrogen.

In another aspect, provided herein are cells in oxygen-limited culture that co-produce isoprene and hydrogen, comprising a heterologous nucleic acid encoding an isoprene synthase polypeptide, wherein the cells: (i) produce isoprene at a rate greater than about 400 nmole/$g_{wcm}$/hr and produce hydrogen at a rate greater than about 125 nmole/$g_{wcm}$/hr; (ii) have an average volumetric productivity of isoprene greater than about 0.1 mg/$L_{broth}$/hr and an average volumetric productivity of hydrogen greater than about 0.005 mg/$L_{broth}$/hr; or (iii) convert more than about 0.002 molar percent of the carbon that the cells consume from a cell culture medium into isoprene, and produce hydrogen equivalent to more than about 0.024 molar percent of the carbon that the cells consume from a cell culture medium. In some embodiments, the cells are capable of co-producing isoprene and hydrogen under oxygen-limited conditions.

In some embodiments, the cells in oxygen-limited culture comprise a heterologous nucleic acid encoding an isoprene synthase polypeptide, wherein the heterologous nucleic acid is operably linked to a promoter, and wherein the cells produce greater than about 400 nmole/$g_{wcm}$/hr of isoprene and greater than about 125 nmole/$g_{wcm}$/hr of hydrogen. In some embodiments, the cells in oxygen-limited culture comprise a heterologous nucleic acid encoding an isoprene synthase polypeptide, wherein the heterologous nucleic acid is operably linked to a promoter, and wherein the cells have an average volumetric productivity of isoprene greater than about 0.1 mg/$L_{broth}$/hr and an average volumetric productivity of hydrogen greater than about 0.005 mg/$L_{broth}$/hr. In some embodiments, the cells in oxygen-limited culture comprise a heterologous nucleic acid encoding an isoprene synthase polypeptide, wherein the heterologous nucleic acid is operably linked to a promoter, and wherein the cells convert more than about 0.002 molar percent of the carbon that the cells consume from a cell culture medium into isoprene, and more than about 0.024 molar percent of the carbon that the cells consume from a cell culture medium into hydrogen. In some embodiments, the isoprene synthase polypeptide is a plant isoprene synthase polypeptide.

In some embodiments, the cells in oxygen-limited culture comprising a heterologous nucleic acid encoding an isoprene synthase polypeptide produce isoprene at a rate between about 400 nmole/$g_{wcm}$/hr and about 2.0×10$^5$ nmole/$g_{wcm}$/hr, between about 500 nmole/$g_{wcm}$/hr and about 1.5× 10$^5$ nmole/$g_{wcm}$/hr, between about 750 nmole/$g_{wcm}$/hr and about 1×10$^5$ nmole/$g_{wcm}$/hr, between about 1000 nmole/$g_{wcm}$/hr and about 1×10$^5$ nmole/$g_{wcm}$/hr, between about 2500 nmole/$g_{wcm}$/hr and about 1×10$^5$ nmole/$g_{wcm}$/hr, between about 5000 nmole/$g_{wcm}$/hr and about 1×10$^5$ nmole/$g_{wcm}$/hr, between about 7500 nmole/$g_{wcm}$/hr and about 1×10$^5$ nmole/$g_{wcm}$/hr, and between about 1×10$^4$ nmole/$g_{wcm}$/hr and about 1×10$^5$ nmole/$g_{wcm}$/hr, and produce hydrogen at a rate between about 125 nmole/$g_{wcm}$/hr to about 1.25×10$^4$ nmole/$g_{wcm}$/hr, between about 250 nmole/$g_{wcm}$/hr to about 1.25×10$^4$ nmole/$g_{wcm}$/hr, between about 500 nmole/$g_{wcm}$/hr to about 1.25×10$^4$ nmole/$g_{wcm}$/hr, between about 750 nmole/$g_{wcm}$/hr to about 1.25×10$^4$ nmole/$g_{wcm}$/hr, between about 1000 nmole/$g_{wcm}$/hr to about 1.25×10$^4$ nmole/$g_{wcm}$/hr, between about 1250 nmole/$g_{wcm}$/hr to about 1.25×10$^4$ nmole/$g_{wcm}$/hr, between about 2500 nmole/$g_{wcm}$/hr to about 1.25×10$^4$ nmole/$g_{wcm}$/hr, between about 5000 nmole/$g_{wcm}$/hr to about 1.25×10$^4$ nmole/$g_{wcm}$/hr, between about 7500 nmole/$g_{wcm}$/hr to about 1.25×10$^4$ nmole/$g_{wcm}$/hr, and between about 1.00×10$^4$ nmole/$g_{wcm}$/hr to about 1.25×10$^4$ nmole/$g_{wcm}$/hr.

In some embodiments, provided herein are methods of co-producing isoprene and hydrogen, the methods comprising: (a) culturing cells under conditions suitable for the co-production of isoprene and hydrogen; and (b) co-producing isoprene and hydrogen, wherein the cells produce greater than about 400 nmole/$g_{wcm}$/hour of isoprene, and wherein the cells produce greater than about 125 nmole/$g_{wcm}$/hr of hydrogen. In some embodiments, the cells are grown in oxygen-limited culture.

In some embodiments, provided herein are methods of co-producing isoprene and hydrogen, the methods comprising: (a) culturing cells under conditions suitable for the co-production of isoprene and hydrogen; and (b) co-producing isoprene and hydrogen, wherein the cells have an average volumetric productivity of isoprene greater than about 0.1 mg/$L_{broth}$/hr and an average volumetric productivity of hydrogen greater than about 0.005 mg/$L_{broth}$/hr. In some embodiments, the cells are grown under oxygen-limited conditions.

In some embodiments, provided herein are methods of co-producing isoprene and hydrogen, the methods comprising: (a) culturing cells under conditions suitable for the co-production of isoprene and hydrogen; and (b) co-producing isoprene and hydrogen, wherein the cells convert more than about 0.002 molar percent of the carbon that the cells consume from a cell culture medium into isoprene, and produce hydrogen equivalent to more than about 0.024 molar percent of the carbon that the cells consume from a cell culture medium. In some embodiments, the cells are grown under oxygen-limited conditions.

In some embodiments, provided herein are compositions comprising isoprene and hydrogen in a ratio ranging from at least one molar percent of isoprene for every three molar percent of hydrogen to at least one molar percent of isoprene for every four molar percent of hydrogen, and 0.1 molar percent or less of volatile impurities. In some embodiments, the compositions further comprise from 1 to 11 molar percent isoprene and from 4 to 44 molar percent hydrogen. In some embodiments, the compositions further comprise oxygen, carbon dioxide, or nitrogen. In some embodiments, the compositions further comprise from 0 to 21 molar percent oxygen, from 18 to 44 molar percent carbon dioxide, and from 0 to 78 molar percent nitrogen. In some embodiments, the composition further comprises 1.0×10$^{-4}$ molar percent or less of non-methane volatile impurities. In some embodiments, the non-methane volatile impurities comprise one or more of the following: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, 3-hexen-1-ol, 3-hexen-1-yl acetate, limonene, geraniol (trans-3,7-dimethyl-2,6-octadien-1-ol) and citronellol (3,7-dimethyl-6-octen-1-ol) or a linear isoprene polymer (such as a linear isoprene dimer or a linear isoprene trimer derived from the polymerization of multiple isoprene units). In some embodiments, the non-methane volatile impurities comprise one or more of the following: the isoprene composition includes one or more of the following: an alcohol, an aldehyde, an ester, or a ketone (such as any of the alcohols, aldehydes, esters or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone. In some embodiments, the non-methane volatile impurities comprise one or more of the following: methanol, acetaldehyde, ethanol, methanethiol, 1-butanol, 3-methyl-1-propanol, acetone, acetic acid, 2-butanone, 2-methyl-1-butanol, or indole.

Also provided herein are methods of co-producing isoprene and hydrogen, the methods comprising: a) culturing cells under conditions suitable for the co-production of isoprene and hydrogen; and b) co-producing isoprene and hydrogen, wherein the peak concentration of the isoprene produced by the cells in oxygen-limited culture is greater than about 10 ng/$L_{broth}$ and the hydrogen evolution rate of the cells is greater than about 0.0025 mmol/$L_{broth}$/hour. In some embodiments, the cells are grown under oxygen-limited conditions. In some embodiments of any of these methods, the hydrogen evolution rate is between about any of 0.0025 mmol/$L_{broth}$/hr and about 10 mmol/$L_{broth}$/hr, between about 0.0025 mmol/$L_{broth}$/hr and about 5 mmol/$L_{broth}$/hr, between about 0.0025 mmol/$L_{broth}$/hr and about 2.5 mmol/$L_{broth}$/hr, between about 0.0025 mmol/$L_{broth}$/hr and about 1 mmol/$L_{broth}$/hr, between about 0.0025 mmol/$L_{broth}$/hr and about 0.5 mmol/$L_{broth}$/hr, between about 0.0025 mmol/$L_{broth}$/hr and about 0.25 mmol/$L_{broth}$/hr, between about 0.0025 mmol/$L_{broth}$/hr and about 0.025 mmol/$L_{broth}$/hr, between about 0.025 mmol/$L_{broth}$/hr and about 0.025 mmol/$L_{broth}$/hr, between about 0.025 mmol/$L_{broth}$/hr and about 0.5 mmol/$L_{broth}$/hr, between about 0.025 mmol/$L_{broth}$/hr and about 1 mmol/$L_{broth}$/hr, between about 0.025 mmol/$L_{broth}$/hr and about 2.5 mmol/$L_{broth}$/hr, between about 0.025 mmol/$L_{broth}$/hr and about 5 mmol/$L_{broth}$/hr, between about 0.025 mmol/$L_{broth}$/hr and about 10 mmol/$L_{broth}$/hr, between about 0.25 mmol/$L_{broth}$/hr and 1 mmol/$L_{broth}$/hr, between about 0.25 mmol/$L_{broth}$/hr and 2.5 mmol/$L_{broth}$/hr, between about 0.25 mmol/$L_{broth}$/hr and 2.5 mmol/$L_{broth}$/hr, between about 0.25 mmol/$L_{broth}$/hr and 10 mmol/$L_{broth}$/hr, between about 0.01 mmol/$L_{broth}$/hr and 10 mmol/$L_{broth}$/hr, between about 0.01 mmol/$L_{broth}$/hr and 50 mmol/$L_{broth}$/hr, between about 0.01 mmol/$L_{broth}$/hr and 100 mmol/$L_{broth}$/hr, and between about 0.01 mmol/$L_{broth}$/hr and 200 mmol/$L_{broth}$/hr.

Provided herein are also methods of co-producing isoprene and hydrogen comprising a) culturing cells under conditions suitable for the co-production of isoprene and hydrogen; and b) co-producing isoprene and hydrogen, wherein the liquid phase concentration of isoprene is less than about 200 mg/L, the cells produce greater than about 400 nmole/$g_{wcm}$/hour of isoprene, and the hydrogen evolution rate of the cells is greater than about 0.0025 mmol/L/hour. In some embodiments, the cells are grown under oxygen-limited conditions. In some embodiments, the liquid phase concentration of isoprene in the culture is less than about any of 175 mg/L, 150 mg/L, 125 mg/L, 100 mg/L, 75 mg/L, 50 mg/L, 25 mg/L, 20 mg/L, 15 mg/L, 10 mg/L, 5 mg/L, or 2.5 mg/L. In some embodiments, the liquid phase concentration of isoprene in culture is between about any of 0.1 mg/L to 200 mg/L, 1 mg/L to 200 mg/L, 1 mg/L to 150 mg/L, 1 mg/L to 100 mg/L, 1 mg/L to 50 mg/L, 1 mg/L to 25 mg/L, 1 mg/L to 20 mg/L, or 10 mg/L to 20 mg/L. In some embodiments of any of these methods, the hydrogen evolution rate is between about any of 0.0025 mmol/$L_{broth}$/hr and about 10 mmol/$L_{broth}$/hr, between about 0.0025 mmol/$L_{broth}$/hr and about 5 mmol/$L_{broth}$/hr, between about 0.0025 mmol/$L_{broth}$/hr and about 2.5 mmol/$L_{broth}$/hr, between about 0.0025 mmol/$L_{broth}$/hr and about 1 mmol/$L_{broth}$/hr, between about 0.0025 mmol/$L_{broth}$/hr and about 0.5 mmol/$L_{broth}$/hr, between about 0.0025 mmol/$L_{broth}$/hr and about 0.25 mmol/$L_{broth}$/hr, between about 0.0025 mmol/$L_{broth}$/hr and about 0.025 mmol/$L_{broth}$/hr, between about 0.025 mmol/$L_{broth}$/hr and about 0.5 mmol/$L_{broth}$/hr, between about 0.025 mmol/$L_{broth}$/hr and about 1 mmol/$L_{broth}$/hr, between about 0.025 mmol/$L_{broth}$/hr and about 2.5 mmol/$L_{broth}$/hr, between about 0.025 mmol/$L_{broth}$/hr and about 5 mmol/$L_{broth}$/hr, between about 0.025 mmol/$L_{broth}$/hr and about 10 mmol/$L_{broth}$/hr, between about 0.25 mmol/$L_{broth}$/hr and 1 mmol/$L_{broth}$/hr, between about 0.25 mmol/$L_{broth}$/hr and 2.5 mmol/$L_{broth}$/hr, between about 0.25 mmol/$L_{broth}$/hr and 2.5 mmol/$L_{broth}$/hr, and between about 0.25 mmol/$L_{broth}$/hr and 10 mmol/$L_{broth}$/hr.

In one aspect, provided herein are cells in oxygen-limited culture that co-produce isoprene and hydrogen. In some embodiments, the oxygen-limited culture is anaerobic. In some embodiments, the invention provides cells in oxygen-limited culture that produce greater than about 400 nmole/$g_{wcm}$/hr of isoprene and greater than about 125 nmole/$g_{wcm}$/hr of hydrogen. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions.

In some embodiments, provided herein are cells in oxygen-limited culture that convert more than about 0.002% of the carbon in a cell culture medium into isoprene and produce hydrogen equivalent to more than about 0.024 molar percent of the carbon in a cell culture medium. In some embodiments, the oxygen-limited culture is anaerobic. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions.

In some embodiments, provided herein are cells in oxygen-limited culture that comprise a heterologous nucleic acid encoding an isoprene synthase polypeptide. In some embodiments, the oxygen-limited culture is anaerobic. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions.

In one aspect, provided herein are methods of co-producing isoprene with another compound, such as methods of using any of the cells described herein to co-produce isoprene and hydrogen. In some embodiments, the method involves culturing cells under oxygen-limited conditions sufficient to produce greater than about 400 nmole/$g_{wcm}$/hr of isoprene and greater than about 125 nmole/$g_{wcm}$/hr of hydrogen. In some embodiments, the oxygen-limited culture is anaerobic. In some embodiments, the method also includes recovering the isoprene and hydrogen produced by the cells. In some embodiments, the method further includes purifying the isoprene and the hydrogen produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions. In various embodiments, the amount of isoprene produced (such as the total amount of isoprene produced or the amount of isoprene produced per liter of broth per hour per $OD_{600}$) during stationary phase is greater than or about 2 or more times the amount of isoprene produced during the growth phase for the same length of time.

In some embodiments, the method includes culturing cells under oxygen-limited conditions sufficient to convert more than about 0.002% of the carbon (mol/mol) in a cell culture medium into isoprene and to produce hydrogen equivalent to more than about 0.024 molar percent of the carbon in a cell culture medium. In some embodiments, the oxygen-limited culture is anaerobic. In some embodiments, the method also includes recovering isoprene and hydrogen produced by the cells. In some embodiments, the method further includes purifying isoprene and hydrogen produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract.

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In some embodiments, isoprene and hydrogen are only co-produced in stationary phase. In some embodiments, isoprene and hydrogen are co-produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time. In various embodiments, the amount of hydrogen produced (such as the total amount of hydrogen produced or the amount of hydrogen produced per liter of broth per hour per $OD_{600}$) during stationary phase is greater than or about 2, 3, 4, 5, 10, 20, 30, 40, 50, or more times the amount of hydrogen produced during the growth phase for the same length of time.

In some embodiments, the compositions provided herein comprise hydrogen and greater than or about 99.90, 99.92, 99.94, 99.96, 99.98, or 100% isoprene by weight compared to the total weight of all C5 hydrocarbons in the composition. In some embodiments, the composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition. In some embodiments, the composition has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne by weight compared to the total weight of all C5 hydrocarbons in the composition. In particular embodiments, the composition has greater than about 2 mg of isoprene and has greater than or about 99.90, 99.92, 99.94, 99.96, 99.98, or 100% isoprene by weight compared to the total weight of all C5 hydrocarbons in the composition. In some embodiments, the composition has less than or about 50, 40, 30, 20, 10, 5, 1, 0.5, 0.1, 0.05, 0.01, or 0.005 μg/L of a compound that inhibits the polymerization of isoprene for any compound in the composition that inhibits the polymerization of isoprene. In particular embodiments, the composition also comprises greater than about 2 mg of isoprene and greater than about 0.48 mg of hydrogen.

In some embodiments, the volatile organic fraction of the gas phase has less than or about 50, 40, 30, 20, 10, 5, 1, 0.5, 0.1, 0.05, 0.01, or 0.005 μg/L of a compound that inhibits the polymerization of isoprene for any compound in the volatile organic fraction of the gas phase that inhibits the polymerization of isoprene. In some embodiments, the volatile organic fraction of the gas phase also has greater than about 2 mg of isoprene and greater than about 0.48 mg of hydrogen.

In some embodiments, the invention also features systems that include any of the cells and/or compositions described herein. In some embodiments, the system includes a reactor that chamber comprises cells in oxygen-limited culture that produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene and greater than about 125, 250, 500, 750, 1000, 1,250, 1,500, 1,750, 2,000, 2,500, 3,000, 4,000, 5,000, 7,500, 10,000, or more nmole/$g_{wcm}$/hr hydrogen. In some embodiments, the system is not a closed system. In some embodiments, at least a portion of the isoprene is removed from the system. In some embodiments, the system includes a gas phase comprising isoprene and hydrogen. In various embodiments, the gas phase comprises any of the compositions described herein.

In one aspect, the invention provides a tire comprising polyisoprene. In some embodiments, the polyisoprene is produced by (i) polymerizing isoprene in any of the compositions described herein or (ii) polymerizing isoprene recovered from any of the compositions described herein. In some embodiments, the polyisoprene comprises cis-1,4-polyisoprene.

In one aspect, the invention features a product produced by any of the compositions or methods described herein.
Exemplary Co-Production of Isoprene and Ethanol The invention also provides compositions and methods for co-production of isoprene and a C2- or C3-alcohol or diol. In some embodiments, the C2- or C3-alcohol or diol is ethanol. In some embodiments, any of the isoprene-producing cells described herein that comprise one or more heterologous nucleic acids encoding an isoprene synthase polypeptide, a DXS polypeptide, an IDI polypeptide, and/or an MVA pathway polypeptide operably linked to a promoter further comprise a heterologous nucleic acid also operably linked to a promoter encoding one or more polypeptides involved in ethanol fermentation or one or more polypeptides involved in the regulation or expression of one or more polypeptides involved in ethanol fermentation (e.g., transcription factors and the like). In some embodiments, any of the isoprene-producing cells described herein that comprise one or more heterologous nucleic acids encoding an isoprene synthase polypeptide, a DXS polypeptide, an IDI polypeptide, an MVA pathway polypeptide, one or more polypeptides involved in ethanol fermentation or one or more polypeptides involved in the regulation or expression of one or more polypeptides involved in ethanol fermentation operably linked to a promoter further comprise a mutation or deletion inactivating one or more polypeptides involved in the production of fermentation side products, or one or more polypeptides involved in the regulation or expression of genes for the production of fermentation side products. Such cells can co-produce isoprene and ethanol.

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans, Streptomyces coelicolor*, or *Streptomyces griseus* cells). In some embodiments of any of the aspects of the invention, the cells are gram-negative bacterial cells (e.g., *Escherichia* cells such as *Escherichia coli* cells, *Rhodopseudomonas* sp. such as *Rhodopseudomonas palustris* cells, *Pseudomonas* sp. such as *Pseudomonas fluorescens* cells or *Pseudomonas putida* cells, *Pantoea* cells such as *Pantoea citrea* cells, or *Zymomonas* cells such as *Zymomonas mobilis* cells). In some embodiments of any of the aspects of the invention, the gram-negative bacterial cells are *E. coli*. In some embodiments of any of the aspects of the invention, the gram-negative bacterial cells are *Zymomonas mobilis*. In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells or *Saccharomyces* cells such as *Saccharomyces cerevisiae*). In some embodiments of any of the aspects of the invention, the yeast cells are *S. cerevisiae*.

In some embodiments of any of the aspects of the invention, the isoprene synthase polypeptide is a polypeptide from a plant such as *Pueraria* (e.g., *Pueraria montana* or *Pueraria lobata*) (also known as "Kudzu") or *Populus* (e.g., *Populus tremuloides, Populus alba, Populus nigra, Populus trichocarpa*, or the hybrid, *Populus alba×Populus tremula*).

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker or a selectable marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisia* or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic acid.

In some embodiments, the MVA pathway polypeptide is an upper MVA pathway polypeptide. In some embodiments, the MVA pathway polypeptide is a lower MVA pathway polypeptide. In some embodiments, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some embodiments, the upper MVA pathway polypeptide is from the genus *Enterococcus*. In some embodiments, the upper MVA pathway polypeptide is from *Enterococcus faecalis*. In some embodiments, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some embodiments, the lower MVA pathway polypeptide is an MVK polypeptide. In some embodiments, the MVK polypeptide is from the genus *Methanosarcina*. In some embodiments, the MVK polypeptide is from *Methanosarcina mazei*.

In some embodiments of any of the aspects of the invention, the cells further comprise a heterologous nucleic acid encoding one or more polypeptides involved in ethanol fermentation or one or more polypeptides involved in the regulation or expression of one or more polypeptides involved in ethanol fermentation (e.g., transcription factors and the like) operably linked to a promoter. In some embodiments of any of the aspects of the invention, the cells further comprise a heterologous nucleic acid encoding alcohol dehydrogenase B (adhB) from *Zymomonas mobilis* operably linked to a promoter. In some embodiments of any of the aspects of the invention, the cells further comprise a heterologous nucleic acid encoding alcohol dehydrogenase E (adhE) from *Zymomonas mobilis* operably linked to a promoter. In some embodiments of any of the aspects of the invention, the cells further comprise a heterologous nucleic acid encoding pyruvate decarboxylase (pdc) from *Zymomonas mobilis* operably linked to a promoter.

In some embodiments of any of the aspects of the invention, the heterologous isoprene synthase, DXS polypeptide, IDI polypeptide, MVA pathway, ethanol fermentation-related and/or transcription factor polypeptide or nucleic acid is operably linked to a T7 promoter, such as a T7 promoter contained in a medium or high copy plasmid. In some embodiments of any of the aspects of the invention, the heterologous isoprene synthase, DXS polypeptide, IDI polypeptide, MVA pathway, ethanol fermentation-related and/or transcription factor nucleic acid is operably linked to a Trc promoter, such as a Trc promoter contained in a medium or high copy plasmid. In some embodiments of any of the aspects of the invention, the heterologous isoprene synthase, DXS polypeptide, IDI polypeptide, MVA pathway, ethanol fermentation-related and/or transcription factor nucleic acid is operably linked to a Lac promoter, such as a Lac promoter contained in a low copy plasmid. In some embodiments of any of the aspects of the invention, the heterologous isoprene synthase, DXS polypeptide, IDI polypeptide, MVA pathway, ethanol fermentation-related polypeptide or transcription factor nucleic acid is operably linked to an endogenous promoter, such as an endogenous alkaline serine protease promoter. In some embodiments, the heterologous isoprene synthase, DXS polypeptide, IDI polypeptide, MVA pathway, ethanol fermentation-related and/or transcription factor nucleic acid integrates into a chromosome of the cells without a selective marker or without a selectable marker.

In some embodiments, one or more MVA pathway, IDI, DXS, isoprene synthase, ethanol fermentation-related and/or transcription factor nucleic acids are placed under the control of a promoter or factor that is more active in stationary phase than in the growth phase. For example, one or more MVA pathway, IDI, DXS, isoprene synthase, ethanol fermentation-related and/or transcription factor or transcription factor nucleic acids may be placed under control of a stationary phase sigma factor, such as RpoS. In some embodiments, one or more MVA pathway, IDI, DXS, isoprene synthase, ethanol fermentation-related and/or transcription factor or transcription factor nucleic acids are placed under control of a promoter inducible in stationary phase, such as a promoter inducible by a response regulator active in stationary phase.

In some embodiments of any of the aspects of the invention, at least a portion of the cells maintain the heterologous isoprene synthase, DXS polypeptide, IDI polypeptide, MVA pathway, ethanol fermentation-related and/or transcription factor nucleic acid for at least or about 5, 10, 20, 40, 50, 60, 65, or more cell divisions in a continuous culture (such as a continuous culture without dilution). In some embodiments of any of the aspects of the invention, the nucleic acid comprising the heterologous isoprene synthase, DXS polypeptide, IDI polypeptide, MVA pathway, ethanol fermentation-related and/or transcription factor nucleic acid also comprises a selective marker or a selectable marker, such as an antibiotic resistance nucleic acid.

In some embodiments of any of the aspects of the invention, cells that co-produce isoprene and ethanol are cultured in any of the culture media described herein, under oxygen-limited conditions to facilitate the co-production of isoprene and ethanol by the cells. In some embodiments, the cells are grown in oxygen-limited culture. In some embodiments, the cells are grown in the presence of 0.5 moles of oxygen per mole of isoprene. In some embodiments, the cells are grown anaerobically, in the absence of oxygen.

In some embodiments, any of the cells described herein are grown in oxygen-limited culture and co-produce isoprene and ethanol. In some embodiments, the cells in oxygen-limited culture have an average volumetric productivity of isoprene greater than about 0.1 mg/$L_{broth}$/hr and an average volumetric productivity of ethanol greater than about 0.1 mg/$L_{broth}$/hr. In some embodiments, the cells in oxygen-limited culture have a peak volumetric productivity of isoprene greater than about 1000 mg/$L_{broth}$/hr and a peak volumetric productivity of ethanol greater than about 1500 mg/$L_{broth}$/hr. In some embodiments, the cells in oxygen-limited culture have a peak volumetric productivity of isoprene greater than about 3000 mg/$L_{broth}$/hr and a peak volumetric productivity of ethanol greater than about 4500 mg/$L_{broth}$/hr. In some embodiments, the cells in oxygen-limited culture have a peak volumetric productivity of isoprene greater than about 5000 mg/$L_{broth}$/hr and a peak volumetric productivity of ethanol greater than about 7500 mg/$L_{broth}$/hr. In some embodiments, the cells in oxygen-limited culture have an average volumetric productivity of isoprene between about 0.1 mg/$L_{broth}$/hr and about 5000 mg/$L_{broth}$/hr, and an average volumetric productivity of ethanol between about 0.1 mg/$L_{broth}$/hr and about 7500 mg/$L_{broth}$/hr. In some embodiments, the cells in oxygen-limited culture have an average volumetric productivity of isoprene between about 1 mg/$L_{broth}$/hr and about 5000 mg/$L_{broth}$/hr, between about 5 mg/$L_{broth}$/hr and about 5000 mg/$L_{broth}$/hr, between about 10 mg/$L_{broth}$/hr and about 5000 mg/$L_{broth}$/hr, between about 25 mg/$L_{broth}$/hr and about 5000 mg/$L_{broth}$/hr, between about 50 mg/$L_{broth}$/hr and about 5000 mg/$L_{broth}$/hr, between about 100 mg/$L_{broth}$/hr and about 5000 mg/$L_{broth}$/hr, between about 250 mg/$L_{broth}$/hr and about 5000 mg/$L_{broth}$/hr, between about 500 mg/$L_{broth}$/hr and about 5000 mg/$L_{broth}$/hr, between about 1000 mg/$L_{broth}$/hr and about 5000 mg/$L_{broth}$/hr, and between about 2500 mg/$L_{broth}$/hr and about 5000 mg/$L_{broth}$/hr, and an average volumetric productivity of ethanol between about 0.1 mg/$L_{broth}$/hr and about 7500 mg/$L_{broth}$/hr, between about 1 mg/$L_{broth}$/hr and about 7500 mg/$L_{broth}$/hr, between about 10 mg/$L_{broth}$/hr and about 7500 mg/$L_{broth}$/hr, between about 100 mg/$L_{broth}$/hr and about 7500 mg/$L_{broth}$/hr, between about 500 mg/$L_{broth}$/hr and about 7500 mg/$L_{broth}$/hr, between about 1000 mg/$L_{broth}$/hr and about 7500 mg/$L_{broth}$/hr, between about 2500 mg/$L_{broth}$/hr and about 7500 mg/$L_{broth}$/hr, and between about 5000 mg/$L_{broth}$/hr and about 7500 mg/$L_{broth}$/hr.

In some embodiments, the cells in oxygen-limited culture comprise a heterologous nucleic acid encoding an isoprene synthase polypeptide, wherein the heterologous nucleic acid is operably linked to a promoter, and wherein the cells have an average volumetric productivity of isoprene greater than about 0.1 mg/$L_{broth}$/hr and an average volumetric productivity of ethanol greater than about 0.1 mg/$L_{broth}$/hr. In some embodiments, the isoprene synthase polypeptide is a plant isoprene synthase polypeptide.

In some embodiments, provided herein are methods of co-producing isoprene and ethanol, the methods comprising: (a) culturing cells under conditions suitable for the co-production of isoprene and ethanol; and (b) co-producing isoprene and ethanol, wherein the cells have an average volumetric productivity of isoprene greater than about 0.1 mg/$L_{broth}$/hr and an average volumetric productivity of ethanol greater than about 0.1 mg/$L_{broth}$/hr.

In some embodiments, provided herein are compositions comprising ethanol. In some embodiments, provided herein are compositions comprising isoprene. In some embodiments, the composition further comprises $1.0 \times 10^{-4}$ molar percent or less of non-methane volatile impurities. In some embodiments, the non-methane volatile impurities comprise one or more of the following: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, 3-hexen-1-ol, 3-hexen-1-yl acetate, limonene, geraniol (trans-3,7-dimethyl-2,6-octadien-1-ol) and citronellol (3,7-dimethyl-6-octen-1-ol) or a linear isoprene polymer (such as a linear isoprene dimer or a linear isoprene trimer derived from the polymerization of multiple isoprene units). In some embodiments, the non-methane volatile impurities comprise one or more of the following: the isoprene composition includes one or more of the following: an alcohol, an aldehyde, an ester or a ketone (such as any of the alcohols, aldehydes, esters or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone. In some embodiments, the non-methane volatile impurities comprise one or more of the following: methanol, acetaldehyde, ethanol, methanethiol, 1-butanol, 3-methyl-1-propanol, acetone, acetic acid, 2-butanone, 2-methyl-1-butanol, or indole.

Also provided herein are methods of co-producing isoprene and ethanol, the methods comprising: a) culturing cells under conditions suitable for the co-production of isoprene and ethanol; and b) co-producing isoprene and ethanol, wherein the peak concentration of the isoprene produced by the cells in oxygen-limited culture is greater than about 10 ng/$L_{broth}$ and the ethanol production rate of the cells is greater than about 0.002 mmol/$L_{broth}$/hour. In some embodiments of any of these methods, the ethanol production rate is between about any of 0.002 mmol/$L_{broth}$/hr and about 200 mmol/$L_{broth}$/hr, between about 0.01 mmol/$L_{broth}$/hr and about 200 mmol/$L_{broth}$/hr, between about 0.05 mmol/$L_{broth}$/hr and about 200 mmol/$L_{broth}$/hr, between about 0.1 mmol/$L_{broth}$/hr and about 200 mmol/$L_{broth}$/hr, between about 0.5 mmol/$L_{broth}$/hr and about 200 mmol/$L_{broth}$/hr, between about 1 mmol/$L_{broth}$/hr and about 200 mmol/$L_{broth}$/hr, between about 5 mmol/$L_{broth}$/hr and about 200 mmol/$L_{broth}$/hr, between about 10 mmol/$L_{broth}$/hr and about 200 mmol/$L_{broth}$/hr, between about 25 mmol/$L_{broth}$/hr and about 200 mmol/$L_{broth}$/hr, between about 50 mmol/$L_{broth}$/hr and about 200 mmol/$L_{broth}$/hr, between about 75 mmol/$L_{broth}$/hr and about 200 mmol/$L_{broth}$/hr, between about 100 mmol/$L_{broth}$/hr and about 200 mmol/$L_{broth}$/hr, and between about 150 mmol/$L_{broth}$/hr and about 200 mmol/$L_{broth}$/hr.

Provided herein are also methods of co-producing isoprene and ethanol comprising a) culturing cells under conditions suitable for the co-production of isoprene and ethanol; and b) co-producing isoprene and ethanol, wherein the liquid phase concentration of isoprene is less than about 200 mg/L, the cells produce greater than about 400 nmole/$g_{wcm}$/hour of isoprene, and the ethanol production rate of the cells is greater than about 0.01 mmol/$L_{broth}$/hour. In some embodiments, the cells are grown in oxygen-limited culture. In some embodiments, the liquid phase concentration of isoprene in the culture is less than about any of 175 mg/L, 150 mg/L, 125 mg/L, 100 mg/L, 75 mg/L, 50 mg/L, 25 mg/L, 20 mg/L, 15 mg/L, 10 mg/L, 5 mg/L, or 2.5 mg/L. In some embodiments, the liquid phase concentration of isoprene in culture is between about any of 0.1 mg/L to 200 mg/L, 1 mg/L to 200 mg/L, 1 mg/L to 150 mg/L, 1 mg/L to 100 mg/L, 1 mg/L to 50 mg/L, 1 mg/L to 25 mg/L, 1 mg/L to 20 mg/L, or 10 mg/L to 20 mg/L. In some embodiments of any of these methods, the cells in oxygen-limited culture produce isoprene at a rate between about 400 nmole/$g_{wcm}$/hr and about $2.0 \times 10^5$ nmole/$g_{wcm}$/hr, between about 500 nmole/$g_{wcm}$/hr and about $1.5 \times 10^5$ nmole/$g_{wcm}$/hr, between about 750 nmole/$g_{wcm}$/hr and about $1 \times 10^5$ nmole/$g_{wcm}$/hr, between about 1000 nmole/$g_{wcm}$/hr and about $1 \times 10^5$ nmole/$g_{wcm}$/hr, between about 2500 nmole/$g_{wcm}$/hr and about $1 \times 10^5$ nmole/$g_{wcm}$/hr, between about 5000 nmole/$g_{wcm}$/hr and about $1 \times 10^5$ nmole/$g_{wcm}$/hr, between about 7500 nmole/$g_{wcm}$/hr and about $1 \times 10^5$ nmole/$g_{wcm}$/hr, and between about $1 \times 10^4$ nmole/$g_{wcm}$/hr and about $1 \times 10^5$ nmole/$g_{wcm}$/hr, and produce ethanol at a rate between about any of 0.002 mmol/$L_{broth}$/hr and about 200 mmol/$L_{broth}$/hr, between about 0.01 mmol/$L_{broth}$/hr and about 200 mmol/$L_{broth}$/hr, between about 0.05 mmol/$L_{broth}$/hr and about 200 mmol/$L_{broth}$/hr, between about 0.1 mmol/$L_{broth}$/hr and about 200 mmol/$L_{broth}$/hr, between about 0.5 mmol/$L_{broth}$/hr and about 200 mmol/$L_{broth}$/hr, between about 1 mmol/$L_{broth}$/hr and about 200 mmol/$L_{broth}$/hr, between about 5 mmol/$L_{broth}$/hr and about 200 mmol/$L_{broth}$/hr, between about 10 mmol/$L_{broth}$/hr and about 200 mmol/$L_{broth}$/hr, between about 25 mmol/$L_{broth}$/hr and about 200 mmol/$L_{broth}$/hr, between about 50 mmol/$L_{broth}$/hr and about 200 mmol/$L_{broth}$/hr, between about 75 mmol/$L_{broth}$/hr and about 200 mmol/$L_{broth}$/hr, between about 100 mmol/$L_{broth}$/hr and about 200 mmol/$L_{broth}$/hr, and between about 150 mmol/$L_{broth}$/hr and about 200 mmol/$L_{broth}$/hr.

In one aspect, provided herein are cells in oxygen-limited culture that co-produce isoprene and ethanol. In some embodiments, the oxygen-limited culture is anaerobic. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions.

In some embodiments, provided herein are cells in oxygen-limited culture that comprise a heterologous nucleic acid encoding an isoprene synthase polypeptide. In some embodiments, the oxygen-limited culture is anaerobic. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions.

In one aspect, provided herein are methods of co-producing isoprene with another compound, such as methods of using any of the cells described herein to co-produce isoprene and ethanol. In some embodiments, the method involves culturing cells under oxygen-limited conditions. In some embodiments, the oxygen-limited culture is anaerobic. In some embodiments, the method also includes recovering the isoprene and ethanol produced by the cells. In some embodiments, the method further includes purifying the isoprene and the ethanol produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions. In various embodiments, the amount of isoprene produced (such as the total amount of isoprene produced or the amount of isoprene produced per liter of broth per hour per $OD_{600}$) during stationary phase is greater than or about 2 or more times the amount of isoprene produced during the growth phase for the same length of time.

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In some embodiments, isoprene and ethanol are only co-produced in stationary phase. In some embodiments, isoprene and ethanol are co-produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time. In various embodiments, the amount of ethanol produced (such as the total amount of ethanol produced or the amount of ethanol produced per liter of broth per hour per $OD_{600}$) during stationary phase is greater than or about 2, 3, 4, 5, 10, 20, 30, 40, 50, or more times the amount of ethanol produced during the growth phase for the same length of time.

In some embodiments, the compositions provided herein comprise ethanol and greater than or about 99.90, 99.92, 99.94, 99.96, 99.98, or 100% isoprene by weight compared to the total weight of all C5 hydrocarbons in the composition. In some embodiments, the composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition. In some embodiments, the composition has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne by weight compared to the total weight of all C5 hydrocarbons in the composition. In particular embodiments, the composition has greater than about 2 mg of isoprene and has greater than or about 99.90, 99.92, 99.94, 99.96, 99.98, or 100% isoprene by weight compared to the total weight of all C5 hydrocarbons in the composition. In some embodiments, the composition has less than or about 50, 40, 30, 20, 10, 5, 1, 0.5, 0.1, 0.05, 0.01, or 0.005 µg/L of a compound that inhibits the polymerization of isoprene for any compound in the composition that inhibits the polymerization of isoprene. In particular embodiments, the composition also comprises greater than about 2 mg of isoprene and greater than about 0.48 mg of ethanol.

In some embodiments, the volatile organic fraction of the gas phase has less than or about 50, 40, 30, 20, 10, 5, 1, 0.5, 0.1, 0.05, 0.01, or 0.005 µg/L of a compound that inhibits the polymerization of isoprene for any compound in the volatile organic fraction of the gas phase that inhibits the polymerization of isoprene. In some embodiments, the volatile organic fraction of the gas phase also has greater than about 2 mg of isoprene and greater than about 0.48 mg of ethanol.

In some embodiments, the invention also features systems that include any of the cells and/or compositions described herein. In some embodiments, the system includes a reactor that chamber comprises cells in oxygen-limited culture that produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene and greater than about 0.1, 0.25, 0.5, 1, 5, 10, 25, 50, 75, 100, 250, 500 or more mmol/$L_{broth}$/hr ethanol. In some embodiments, the system is not a closed system. In some embodiments, at least a portion of the isoprene is removed from the system. In some embodiments, the system includes a gas phase comprising isoprene and ethanol. In some embodiments, the system includes a gas phase comprising isoprene and a liquid phase comprising ethanol. In various embodiments, the gas phase comprises any of the compositions described herein. In various embodiments, the liquid phase comprises any of the compositions described herein.

In one aspect, the invention provides a tire comprising polyisoprene. In some embodiments, the polyisoprene is produced by (i) polymerizing isoprene in any of the compositions described herein or (ii) polymerizing isoprene recovered from any of the compositions described herein. In some embodiments, the polyisoprene comprises cis-1,4-polyisoprene.

In one aspect, the invention features a product produced by any of the compositions or methods described herein.

Exemplary Co-Production of Isoprene and 1,2-Propanediol or 1,3-Propanediol

In some embodiments, the C2- or C3-alcohol or diol is 1,2-propanediol. In some embodiments, the C2- or C3-alcohol or diol is 1,3-propanediol. In some embodiments, any of the isoprene-producing cells described herein that comprise one or more heterologous nucleic acids encoding an isoprene synthase polypeptide, a DXS polypeptide, an IDI polypeptide, and/or an MVA pathway polypeptide operably linked to a promoter further comprise a heterologous nucleic acid also operably linked to a promoter encoding one or more polypeptides in the glycerol pathway or the 1,3-propanediol pathway. Such cells can co-produce isoprene and 1,2-propanediol or 1,3-propanediol.

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans, Streptomyces coelicolor*, or *Streptomyces griseus* cells). In some embodiments of any of the aspects of the invention, the cells are gram-negative bacterial cells (e.g., *Escherichia* cells such as *Escherichia coli* cells, *Rhodopseudomonas* sp. such as *Rhodopseudomonas palustris* cells, *Pseudomonas* sp. such as *Pseudomonas fluorescens* cells or *Pseudomonas putida* cells, *Pantoea* cells such as *Pantoea citrea* cells, or *Zymomonas* cells such as *Zymomonas mobilis* cells). In some embodiments of any of the aspects of the invention, the gram-negative bacterial cells are *E. coli*. In some embodiments of any of the aspects of the invention, the gram-negative bacterial cells are *Zymomonas mobilis*. In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells or *Saccharomyces* cells such as *Saccharomyces cerevisiae*). In some embodiments of any of the aspects of the invention, the yeast cells are *S. cerevisiae*.

In some embodiments of any of the aspects of the invention, the isoprene synthase polypeptide is a polypeptide from a plant such as *Pueraria* (e.g., *Pueraria montana* or *Pueraria lobata*) (also known as "Kudzu") or *Populus* (e.g., *Populus tremuloides, Populus alba, Populus nigra, Populus trichocarpa*, or the hybrid, *Populus alba*×*Populus tremula*).

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker or a selectable marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisia* or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic acid.

In some embodiments, the MVA pathway polypeptide is an upper MVA pathway polypeptide. In some embodiments, the MVA pathway polypeptide is a lower MVA pathway polypeptide. In some embodiments, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some embodiments, the upper MVA pathway polypeptide is from the genus *Enterococcus*. In some embodiments, the upper MVA pathway polypeptide is from *Enterococcus faecalis*. In some embodiments, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some embodiments, the lower MVA pathway polypeptide is an MVK polypeptide. In some embodiments, the MVK polypeptide is from the genus *Methanosarcina*. In some embodiments, the MVK polypeptide is from *Methanosarcina mazei*.

In some embodiments of any of the aspects of the invention, the cells further comprise a heterologous nucleic acid encoding one or more polypeptides in the glycerol pathway or the 1,3-propanediol pathway operably linked to a promoter. In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, orfY, 1,3-propanediol oxidoreductase (dhaT), glycerol dehydrogenase (dhaD), or dihydroxyacetone kinase (dhaK) operably linked to a promoter. In some embodiments, the polypeptide involved in the glycerol pathway or the 1,3-propanediol pathway is dihydroxyacetone phosphate reductase (DAR1), glycerol-phosphate phosphatase (GPP2), glycerol dehydratase B1 (dhaB1), glycerol dehydratase B2 (dhaB2), glycerol dehydratase B3 (dhaB3), dhaX, orfX, and orfY operably linked to a promoter.

In some embodiments of any of the aspects of the invention, the heterologous isoprene synthase, DXS polypeptide, IDI polypeptide, MVA pathway, glycerol pathway or the 1,3-propanediol pathway polypeptide or nucleic acid is operably linked to a T7 promoter, such as a T7 promoter contained in a medium or high copy plasmid. In some embodiments of any of the aspects of the invention, the heterologous isoprene synthase, DXS polypeptide, IDI polypeptide, MVA pathway, glycerol pathway or the 1,3-propanediol pathway nucleic acid is operably linked to a Trc promoter, such as a Trc promoter contained in a medium or high copy plasmid. In some embodiments of any of the aspects of the invention, the heterologous isoprene synthase, DXS polypeptide, IDI polypeptide, MVA pathway, glycerol pathway or the 1,3-propanediol pathway nucleic acid is operably linked to a Lac promoter, such as a Lac promoter contained in a low copy plasmid. In some embodiments of any of the aspects of the invention, the heterologous isoprene synthase, DXS polypeptide, IDI polypeptide, MVA pathway, glycerol pathway or the 1,3-propanediol pathway nucleic acid is operably linked to an endogenous promoter, such as an endogenous alkaline serine protease promoter. In some embodiments, the heterologous isoprene synthase, DXS polypeptide, IDI polypeptide, MVA pathway, glycerol pathway or the 1,3-propanediol pathway nucleic acid integrates into a chromosome of the cells without a selective marker or without a selectable marker.

In some embodiments, one or more MVA pathway, IDI, DXS, isoprene synthase, glycerol pathway or the 1,3-propanediol pathway nucleic acids are placed under the control of a promoter or factor that is more active in stationary phase than in the growth phase. For example, one or more MVA pathway, IDI, DXS, isoprene synthase, glycerol pathway or the 1,3-propanediol pathway nucleic acids may be placed under control of a stationary phase sigma factor, such as RpoS. In some embodiments, one or more MVA pathway, IDI, DXS, isoprene synthase, glycerol pathway or the 1,3-propanediol pathway nucleic acids are placed under control of a promoter inducible in stationary phase, such as a promoter inducible by a response regulator active in stationary phase.

In some embodiments of any of the aspects of the invention, at least a portion of the cells maintain the heterologous isoprene synthase, DXS polypeptide, IDI polypeptide, MVA pathway, glycerol pathway or the 1,3-propanediol pathway nucleic acid for at least or about 5, 10, 20, 40, 50, 60, 65, or more cell divisions in a continuous culture (such as a continuous culture without dilution). In some embodiments of any of the aspects of the invention, the nucleic acid comprising the heterologous isoprene synthase, DXS polypeptide, IDI polypeptide, MVA pathway, glycerol pathway or the 1,3-propanediol pathway nucleic acid also comprises a selective marker or a selectable marker, such as an antibiotic resistance nucleic acid.

In some embodiments of any of the aspects of the invention, cells that co-produce isoprene and 1,2-propanediol are cultured in any of the culture media described herein, under oxygen-limited conditions to facilitate the co-production of isoprene and 1,2-propanediol by the cells. In some embodiments, the cells are grown in oxygen-limited culture. In some embodiments, the cells are grown in the presence of 0.5 moles of oxygen per mole of isoprene. In some embodiments, the cells are grown anaerobically, in the absence of oxygen.

In some embodiments, any of the cells described herein are grown in oxygen-limited culture and co-produce isoprene and 1,2-propanediol. In some embodiments, the cells in oxygen-limited culture have an average volumetric productivity of isoprene greater than about 0.1 mg/$L_{broth}$/hr and an average volumetric productivity of 1,2-propanediol greater than about 0.1 mg/$L_{broth}$/hr. In some embodiments, the cells in oxygen-limited culture have a peak volumetric productivity of isoprene greater than about 1000 mg/$L_{broth}$/hr and a peak volumetric productivity of 1,2-propanediol greater than about 1500 mg/$L_{broth}$/hr. In some embodiments, the cells in oxygen-limited culture have a peak volumetric productivity of isoprene greater than about 3000 mg/$L_{broth}$/hr and a peak volumetric productivity of 1,2-propanediol greater than about 4500 mg/$L_{broth}$/hr. In some embodiments, the cells in oxygen-limited culture have a peak volumetric productivity of isoprene greater than about 5000 mg/$L_{broth}$/hr and a peak volumetric productivity of 1,2-propanediol greater than about 7500 mg/$L_{broth}$/hr. In some embodiments, the cells in oxygen-limited culture have an average volumetric productivity of isoprene between about 0.1 mg/$L_{broth}$/hr and about 5000 mg/$L_{broth}$/hr, and an average volumetric productivity of 1,2-propanediol between about 0.1 mg/$L_{broth}$/hr and about 7500 mg/$L_{broth}$/hr. In some embodiments, the cells in oxygen-limited culture have an average volumetric productivity of isoprene between about 1 mg/$L_{broth}$/hr and about 5000 mg/$L_{broth}$/hr, between about 5 mg/$L_{broth}$/hr and about 5000 mg/$L_{broth}$/hr, between about 10 mg/$L_{broth}$/hr and about 5000 mg/$L_{broth}$/hr, between about 25 mg/$L_{broth}$/hr and about 5000 mg/$L_{broth}$/hr, between about 50 mg/$L_{broth}$/hr and about 5000 mg/$L_{broth}$/hr, between about 100 mg/$L_{broth}$/hr and about 5000 mg/$L_{broth}$/hr, between about 250 mg/$L_{broth}$/hr and about 5000 mg/$L_{broth}$/hr, between about 500 mg/$L_{broth}$/hr and about 5000 mg/$L_{broth}$/hr, between about 1000 mg/$L_{broth}$/hr and about 5000 mg/$L_{broth}$/hr, and between about 2500 mg/$L_{broth}$/hr and about 5000 mg/$L_{broth}$/hr, and an average volumetric productivity of 1,2-propanediol between about 0.1 mg/$L_{broth}$/hr and about 7500 mg/$L_{broth}$/hr, between about 1 mg/$L_{broth}$/hr and about 7500 mg/$L_{broth}$/hr, between about 10 mg/$L_{broth}$/hr and about 7500 mg/$L_{broth}$/hr, between about 100 mg/$L_{broth}$/hr and about 7500 mg/$L_{broth}$/hr, between about 500 mg/$L_{broth}$/hr and about 7500 mg/$L_{broth}$/hr, between about 1000 mg/$L_{broth}$/hr and about 7500 mg/$L_{broth}$/hr, between about 2500 mg/$L_{broth}$/hr and about 7500 mg/$L_{broth}$/hr, and between about 5000 mg/$L_{broth}$/hr and about 7500 mg/$L_{broth}$/hr.

In some embodiments, the cells in oxygen-limited culture comprise a heterologous nucleic acid encoding an isoprene synthase polypeptide, wherein the heterologous nucleic acid is operably linked to a promoter, and wherein the cells have an average volumetric productivity of isoprene greater than about 0.1 mg/$L_{broth}$/hr and an average volumetric productivity of 1,2-propanediol greater than about 0.1 mg/$L_{broth}$/hr. In some embodiments, the isoprene synthase polypeptide is a plant isoprene synthase polypeptide.

In some embodiments, provided herein are methods of co-producing isoprene and 1,2-propanediol, the methods comprising: (a) culturing cells under conditions suitable for the co-production of isoprene and 1,2-propanediol; and (b) co-producing isoprene and 1,2-propanediol, wherein the cells have an average volumetric productivity of isoprene greater than about 0.1 mg/$L_{broth}$/hr and an average volumetric productivity of 1,2-propanediol greater than about 0.1 mg/$L_{broth}$/hr.

In some embodiments, provided herein are compositions comprising 1,2-propanediol. In some embodiments, provided herein are compositions comprising isoprene. In some embodiments, the composition further comprises $1.0 \times 10^4$ molar percent or less of non-methane volatile impurities. In some embodiments, the non-methane volatile impurities comprise one or more of the following: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl- 3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, 3-hexen-1-ol, 3-hexen-1-yl acetate, limonene, geraniol (trans-3,7-dimethyl-2,6-octadien-1-ol) and citronellol (3,7-dimethyl-6-octen-1-ol) or a linear isoprene polymer (such as a linear isoprene dimer or a linear isoprene trimer derived from the polymerization of multiple isoprene units). In some embodiments, the non-methane volatile impurities comprise one or more of the following: the isoprene composition includes one or more of the following: an alcohol, an aldehyde, an ester or a ketone (such as any of the alcohols, aldehydes, esters or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone. In some embodiments, the non-methane volatile impurities comprise one or more of the following: methanol, acetaldehyde, ethanol, methanethiol, 1-butanol, 3-methyl-1-propanol, acetone, acetic acid, 2-butanone, 2-methyl-1-butanol, or indole.

Also provided herein are methods of co-producing isoprene and 1,2-propanediol, the methods comprising: a) culturing cells under conditions suitable for the co-production of isoprene and 1,2-propanediol; and b) co-producing isoprene and 1,2-propanediol, wherein the peak concentration of the isoprene produced by the cells in oxygen-limited culture is greater than about 10 ng/$L_{broth}$ and the 1,2-propanediol production rate of the cells is greater than about 0.002 mmol/$L_{broth}$/hour. In some embodiments of any of these methods, the 1,2-propanediol production rate is between about any of 0.002 mmol/$L_{broth}$/hr and about 200 mmol/$L_{broth}$/hr, between about 0.01 mmol/$L_{broth}$/hr and about 200 mmol/$L_{broth}$/hr, between about 0.05 mmol/$L_{broth}$/hr and about 200 mmol/$L_{broth}$/hr, between about 0.1 mmol/$L_{broth}$/hr and about 200 mmol/$L_{broth}$/hr, between about 0.5 mmol/$L_{broth}$/hr and about 200 mmol/$L_{broth}$/hr, between about 1 mmol/$L_{broth}$/hr and about 200 mmol/$L_{broth}$/hr, between about 5 mmol/$L_{broth}$/hr and about 200 mmol/$L_{broth}$/hr, between about 10 mmol/$L_{broth}$/hr and about 200 mmol/$L_{broth}$/hr, between about 25 mmol/$L_{broth}$/hr and about 200 mmol/$L_{broth}$/hr, between about 50 mmol/$L_{broth}$/hr and about 200 mmol/$L_{broth}$/hr, between about 75 mmol/$L_{broth}$/hr and about 200 mmol/$L_{broth}$/hr, between about 100 mmol/$L_{broth}$/hr and about 200 mmol/$L_{broth}$/hr, and between about 150 mmol/$L_{broth}$/hr and about 200 mmol/$L_{broth}$/hr.

In some embodiments of any of the aspects of the invention, cells that co-produce isoprene and 1,3-propanediol are cultured in any of the culture media described herein, under oxygen-limited conditions to facilitate the co-production of isoprene and 1,3-propanediol by the cells. In some embodiments, the cells are grown in oxygen-limited culture. In some embodiments, the cells are grown in the presence of 0.5 moles of oxygen per mole of isoprene. In some embodiments, the cells are grown anaerobically, in the absence of oxygen.

In some embodiments, any of the cells described herein are grown in oxygen-limited culture and co-produce isoprene and 1,3-propanediol. In some embodiments, the cells in oxygen-limited culture have an average volumetric productivity of isoprene greater than about 0.1 mg/$L_{broth}$/hr and an average volumetric productivity of 1,3-propanediol greater than about 0.1 mg/$L_{broth}$/hr. In some embodiments, the cells in oxygen-limited culture have a peak volumetric productivity of isoprene greater than about 1000 mg/$L_{broth}$/hr and a peak volumetric productivity of 1,3-propanediol greater than about 1500 mg/$L_{broth}$/hr. In some embodiments, the cells in oxygen-limited culture have a peak volumetric productivity of isoprene greater than about 3000 mg/$L_{broth}$/hr and a peak volumetric productivity of 1,3-propanediol greater than about 4500 mg/$L_{broth}$/hr. In some embodiments, the cells in oxygen-limited culture have a peak volumetric productivity of isoprene greater than about 5000 mg/$L_{broth}$/hr and a peak volumetric productivity of 1,3-propanediol greater than about 7500 mg/$L_{broth}$/hr. In some embodiments, the cells in oxygen-limited culture have an average volumetric productivity of isoprene between about 0.1 mg/$L_{broth}$/hr and about 5000 mg/$L_{broth}$/hr, and an average volumetric productivity of 1,3-propanediol between about 0.1 mg/$L_{broth}$/hr and about 7500 mg/1-broth/hr. In some embodiments, the cells in oxygen-limited culture have an average volumetric productivity of isoprene between about 1 mg/$L_{broth}$/hr and about 5000 mg/$L_{broth}$/hr, between about 5 mg/$L_{broth}$/hr and about 5000 mg/$L_{broth}$/hr, between about 10 mg/$L_{broth}$/hr and about 5000 mg/$L_{broth}$/hr, between about 25 mg/$L_{broth}$/hr and about 5000 mg/$L_{broth}$/hr, between about 50 mg/$L_{broth}$/hr and about 5000 mg/$L_{broth}$/hr, between about 100 mg/$L_{broth}$/hr and about 5000 mg/$L_{broth}$/hr, between about 250 mg/$L_{broth}$/hr and about 5000 mg/$L_{broth}$/hr, between about 500 mg/$L_{broth}$/hr and about 5000 mg/$L_{broth}$/hr, between about 1000 mg/$L_{broth}$/hr and about 5000 mg/$L_{broth}$/hr, and between about 2500 mg/$L_{broth}$/hr and about 5000 mg/$L_{broth}$/hr, and an average volumetric productivity of 1,3-propanediol between about 0.1 mg/$L_{broth}$/hr and about 7500 mg/$L_{broth}$/hr, between about 1 mg/$L_{broth}$/hr and about 7500 mg/$L_{broth}$/hr, between about 10 mg/$L_{broth}$/hr and about 7500 mg/$L_{broth}$/hr, between about 100 mg/$L_{broth}$/hr and about 7500 mg/$L_{broth}$/hr, between about 500 mg/$L_{broth}$/hr and about 7500 mg/$L_{broth}$/hr, between about 1000 mg/$L_{broth}$/hr and about 7500 mg/$L_{broth}$/hr, between about 2500 mg/$L_{broth}$/hr and about 7500 mg/$L_{broth}$/hr, and between about 5000 mg/$L_{broth}$/hr and about 7500 mg/$L_{broth}$/hr.

In some embodiments, the cells in oxygen-limited culture comprise a heterologous nucleic acid encoding an isoprene synthase polypeptide, wherein the heterologous nucleic acid is operably linked to a promoter, and wherein the cells have an average volumetric productivity of isoprene greater than about 0.1 mg/$L_{broth}$/hr and an average volumetric productivity of 1,3-propanediol greater than about 0.1 mg/$L_{broth}$/hr. In some embodiments, the isoprene synthase polypeptide is a plant isoprene synthase polypeptide.

In some embodiments, provided herein are methods of co-producing isoprene and 1,3-propanediol, the methods comprising: (a) culturing cells under conditions suitable for the co-production of isoprene and 1,3-propanediol; and (b) co-producing isoprene and 1,3-propanediol, wherein the cells have an average volumetric productivity of isoprene greater than about 0.1 mg/$L_{broth}$/hr and an average volumetric productivity of 1,3-propanediol greater than about 0.1 mg/$L_{broth}$/hr.

In some embodiments, provided herein are compositions comprising 1,3-propanediol. In some embodiments, provided herein are compositions comprising isoprene. In some embodiments, the composition further comprises $1.0 \times 10^4$ molar percent or less of non-methane volatile impurities. In some embodiments, the non-methane volatile impurities comprise one or more of the following: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl- 1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, 3-hexen-1-ol, 3-hexen-1-yl acetate, limonene, geraniol (trans-3,7-dimethyl-2,6-octadien-1-ol) and citronellol (3,7-dimethyl-6-octen-1-ol) or a linear isoprene polymer (such as a linear isoprene dimer or a linear isoprene trimer derived from the polymerization of multiple isoprene units). In some embodiments, the non-methane volatile impurities comprise one or more of the following: the isoprene composition includes one or more of the following: an alcohol, an aldehyde, an ester or a ketone (such as any of the alcohols, aldehydes, esters or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone. In some embodiments, the non-methane volatile impurities comprise one or more of the following: methanol, acetaldehyde, ethanol, methanethiol, 1-butanol, 3-methyl-1-propanol, acetone, acetic acid, 2-butanone, 2-methyl-1-butanol, or indole.

Also provided herein are methods of co-producing isoprene and 1,3-propanediol, the methods comprising: a) culturing cells under conditions suitable for the co-production of isoprene and 1,3-propanediol; and b) co-producing isoprene and 1,3-propanediol, wherein the peak concentration of the isoprene produced by the cells in oxygen-limited culture is greater than about 10 $ng/L_{broth}$ and the 1,3-propanediol production rate of the cells is greater than about 0.002 $mmol/L_{broth}$/hour. In some embodiments of any of these methods, the 1,3-propanediol production rate is between about any of 0.002 $mmol/L_{broth}$/hr and about 200 $mmol/L_{broth}$/hr, between about 0.01 $mmol/L_{broth}$/hr and about 200 $mmol/L_{broth}$/hr, between about 0.05 $mmol/L_{broth}$/hr and about 200 $mmol/L_{broth}$/hr, between about 0.1 $mmol/L_{broth}$/hr and about 200 $mmol/L_{broth}$/hr, between about 0.5 $mmol/L_{broth}$/hr and about 200 $mmol/L_{broth}$/hr, between about 1 $mmol/L_{broth}$/hr and about 200 $mmol/L_{broth}$/hr, between about 5 $mmol/L_{broth}$/hr and about 200 $mmol/L_{broth}$/hr, between about 10 $mmol/L_{broth}$/hr and about 200 $mmol/L_{broth}$/hr, between about 25 $mmol/L_{broth}$/hr and about 200 $mmol/L_{broth}$/hr, between about 50 $mmol/L_{broth}$/hr and about 200 $mmol/L_{broth}$/hr, between about 75 $mmol/L_{broth}$/hr and about 200 $mmol/L_{broth}$/hr, between about 100 $mmol/L_{broth}$/hr and about 200 $mmol/L_{broth}$/hr, and between about 150 $mmol/L_{broth}$/hr and about 200 $mmol/L_{broth}$/hr.

Provided herein are also methods of co-producing isoprene and 1,3-propanediol comprising a) culturing cells under conditions suitable for the co-production of isoprene and 1,3-propanediol; and b) co-producing isoprene and 1,3-propanediol, wherein the liquid phase concentration of isoprene is less than about 200 mg/L, the cells produce greater than about 400 $nmole/g_{wcm}$/hour of isoprene, and the 1,3-propanediol production rate of the cells is greater than about 0.01 $mmol/L_{broth}$/hour. In some embodiments, the cells are grown in oxygen-limited culture. In some embodiments, the liquid phase concentration of isoprene in the culture is less than about any of 175 mg/L, 150 mg/L, 125 mg/L, 100 mg/L, 75 mg/L, 50 mg/L, 25 mg/L, 20 mg/L, 15 mg/L, 10 mg/L, 5 mg/L, or 2.5 mg/L. In some embodiments, the liquid phase concentration of isoprene in culture is between about any of 0.1 mg/L to 200 mg/L, 1 mg/L to 200 mg/L, 1 mg/L to 150 mg/L, 1 mg/L to 100 mg/L, 1 mg/L to 50 mg/L, 1 mg/L to 25 mg/L, 1 mg/L to 20 mg/L, or 10 mg/L to 20 mg/L. In some embodiments of any of these methods, the cells in oxygen-limited culture produce isoprene at a rate between about 400 $nmole/g_{wcm}$/hr and about $2.0 \times 10^5$ $nmole/g_{wcm}$/hr, between about 500 $nmole/g_{wcm}$/hr and about $1.5 \times 10^5$ $nmole/g_{wcm}$/hr, between about 750 $nmole/g_{wcm}$/hr and about $1 \times 10^5$ $nmole/g_{wcm}$/hr, between about 1000 $nmole/g_{wcm}$/hr and about $1 \times 10^5$ $nmole/g_{wcm}$/hr, between about 2500 $nmole/g_{wcm}$/hr and about $1 \times 10^5$ $nmole/g_{wcm}$/hr, between about 5000 $nmole/g_{wcm}$/hr and about $1 \times 10^5$ $nmole/g_{wcm}$/hr, between about 7500 $nmole/g_{wcm}$/hr and about $1 \times 10^5$ $nmole/g_{wcm}$/hr, and between about $1 \times 10^4$ $nmole/g_{wcm}$/hr and about $1 \times 10^5$ $nmole/g_{wcm}$/hr, and produce 1,3-propanediol at a rate between about any of 0.002 $mmol/L_{broth}$/hr and about 200 $mmol/L_{broth}$/hr, between about 0.01 $mmol/L_{broth}$/hr and about 200 $mmol/L_{broth}$/hr, between about 0.05 $mmol/L_{broth}$/hr and about 200 $mmol/L_{broth}$/hr, between about 0.1 $mmol/L_{broth}$/hr and about 200 $mmol/L_{broth}$/hr, between about 0.5 $mmol/L_{broth}$/hr and about 200 $mmol/L_{broth}$/hr, between about 1 $mmol/L_{broth}$/hr and about 200 $mmol/L_{broth}$/hr, between about 5 $mmol/L_{broth}$/hr and about 200 $mmol/L_{broth}$/hr, between about 10 $mmol/L_{broth}$/hr and about 200 $mmol/L_{broth}$/hr, between about 25 $mmol/L_{broth}$/hr and about 200 $mmol/L_{broth}$/hr, between about 50 $mmol/L_{broth}$/hr and about 200 $mmol/L_{broth}$/hr, between about 75 $mmol/L_{broth}$/hr and about 200 $mmol/L_{broth}$/hr, between about 100 $mmol/L_{broth}$/hr and about 200 $mmol/L_{broth}$/hr, and between about 150 $mmol/L_{broth}$/hr and about 200 $mmol/L_{broth}$/hr.

Exemplary Purification Methods

In some embodiments, any of the methods described herein further include recovering the co-produced compounds. In some embodiments, any of the methods described herein further include recovering the isoprene. In some embodiments, any of the methods described herein further include recovering the hydrogen by cryogenic membrane, adsorption matrix-based separation methods. In some embodiments, any of the methods described herein further include recovering the ethanol. In some embodiments, any of the methods described herein further include recovering the 1,3-propanediol.

The isoprene and co-products, for example, hydrogen, ethanol, 1,2-propanediol or 1,3-propanediol, produced using the compositions and methods of the invention can be recovered using standard techniques. such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007, 4,570,029, and 4,740,222 ("Recovery and Purification of Hydrogen from Refinery and Petrochemical Off-gas Streams") which are each hereby incorporated by reference in their entireties, particularly with respect to isoprene recovery and purification methods ('007 and '029 patents) and with respect to hydrogen recovery and purification methods ('222 patent)). In particular embodiments, extractive distillation with an alcohol (such as ethanol, methanol, propanol, or a combination thereof) is used to recover the isoprene. In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some embodiments, membrane enrichment of a dilute isoprene vapor stream above the dew point of the vapor resulting in the condensation of liquid isoprene. In some embodiments, the isoprene is compressed and condensed.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

The recovery of hydrogen may involve one step or multiple steps. In some embodiments, the removal of hydrogen gas from the fermentation off-gas and the conversion of hydrogen to a liquid phase are performed simultaneously. In some embodiments, the removal of hydrogen gas from the fermentation off-gas and the conversion of hydrogen to a liquid phase are performed sequentially. For example, hydrogen may be adsorbed to a solid phase and then desorbed from the solid phase by a pressure swing.

The recovery of ethanol may involve one step or multiple steps. In some embodiments, the ethanol is recovered from the fermentation broth by distillation. In some embodiments, the fermentation broth is first cleared of cells and debri by centrifugation, filtration or similar method.

The recovery of 1,2-propanediol or 1,3-propanediol may involve one step or multiple steps. In some embodiments, the 1,2-propanediol or 1,3-propanediol is recovered from the fermentation broth by distillation. In some embodiments, the 1,2-propanediol or 1,3-propanediol is recovered from the fermentation broth by chromatography or other standard methods. In some embodiments, the fermentation broth is first cleared of cells and debri by centrifugation, filtration or similar method.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, any of the methods described herein further include purifying the hydrogen. For example, the hydrogen produced using the compositions and methods of the invention can be purified using standard techniques. Purification refers to a process through which hydrogen is separated from one or more components that are present when the hydrogen is produced. In some embodiments, the hydrogen is obtained as a substantially pure gas. In some embodiments, the hydrogen is obtained as a substantially pure liquid. Examples of purification methods include (i) cryogenic condensation and (ii) solid matrix adsorption. As used herein, "purified hydrogen" means hydrogen that has been separated from one or more components that are present when the hydrogen is produced. In some embodiments, the hydrogen is at least about 20%, by weight, free from other components that are present when the hydrogen is produced. In various embodiments, the hydrogen is at least or about 25%, 30%, 40%, 50%, 60%, 70%, 75%, 80%, 90%, 95%, or 99%, by weight, pure. Purity can be assayed by any appropriate method, e.g., by column chromatography or GC-MS analysis.

In some embodiments, at least a portion of the gas phase remaining after one or more recovery steps for the removal of isoprene is recycled by introducing the gas phase into a cell culture system (such as a fermentor) for the production of isoprene.

In some embodiments, any of the methods described herein further include polymerizing the isoprene. For example, standard methods can be used to polymerize the purified isoprene to form cis-polyisoprene or other down stream products using standard methods. Accordingly, the invention also features a tire comprising polyisoprene, such as cis-1,4-polyisoprene and/or trans-1,4-polyisoprene made from any of the isoprene compositions disclosed herein.

Cell Viability at High Isoprene Titer

Isoprene is a hydrophobic molecule secreted by many plants, animals, and microbes. Bacteria, such as *Bacillus*, produce isoprene at fairly low levels. While there is some evidence that plants secrete isoprene to help with thermoprotection, it has been hypothesized that isoprene may act antagonistically to cyanobacteria or fungi, or as an antimicrobial agent. See, e.g., Ladygina et al., *Process Biochemistry* 41:1001-1014 (2006), which is incorporated by reference in its entirety, particularly with respect to isoprene acting antagonistically. Since the very low production levels happening in nature are sufficient to be anti-microbial, it was of great concern that the titers and productivity levels of isoprene necessary for commercialization of isoprene would kill the host microbe.

We have found methods for producing titers and productivity levels of isoprene for commercialization of isoprene while maintaining cell viability and/or metabolic activity as indicated by carbon dioxide evolution rate or total carbon dioxide evolution rate.

Provided herein are methods of producing isoprene comprising: a) culturing cells under suitable conditions for production of isoprene; and b) producing isoprene, wherein cells produce greater than about 400 nmole/$g_{wcm}$/hour of isoprene, and the carbon dioxide evolution rate of the cells is greater than about $1 \times 10^{-18}$ mmol/L/hour. In some embodiments, the isoprene produced is any concentration or amount disclosed in the section entitled "Exemplary Production of Isoprene." In some embodiments, the amount of isoprene is between about any of 400 nmole/$g_{wcm}$/hour to 1 mole/$g_{wcm}$/hour, 400 nmole/$g_{wcm}$/hour to 1 mmole/$g_{wcm}$/hour, 400 nmole/$g_{wcm}$/hour to 40 mmole/$g_{wcm}$/hour, 400 nmole/$g_{wcm}$/hour to 4 mmole/$g_{wcm}$/hour, 1 mmole/$g_{wcm}$/hour to 1.5 mmole/$g_{wcm}$/hour, 1.5 mmole/$g_{wcm}$/hour to 3 mmole/$g_{wcm}$/hour, 3 mmole/$g_{wcm}$/hour to 5 mmole/$g_{wcm}$/hour, 5 mmole/$g_{wcm}$/hour to 25 mmole/$g_{wcm}$/hour, 25 mmole/$g_{wcm}$/hour to 100 mmole/$g_{wcm}$/hour, 100 mmole/$g_{wcm}$/hour to 500 mmole/$g_{wcm}$/hour, or 500 mmole/$g_{wcm}$/hour to 1000 mmole/$g_{wcm}$/hour. In some embodiments, the amount of isoprene is about any of 1 mmole/$g_{wcm}$/hour, 1.5 mmole/$g_{wcm}$/hour, 2 mmole/$g_{wcm}$/hour, 3 mmole/$g_{wcm}$/hour, 4 mmole/$g_{wcm}$/hour, or 5 mmole/$g_{wcm}$/hour. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

Provided herein are also methods of producing isoprene comprising: a) culturing cells under suitable conditions for production of isoprene; and b) producing isoprene, wherein cells produce greater than about 400 nmole/$g_{wcm}$/hour of isoprene, and cell viability is reduced by less than about two-fold. In some embodiments, the isoprene produced is any concentration or amount disclosed in the section entitled "Exemplary Production of Isoprene." In some embodiments, the amount of isoprene is between about any of 400 nmole/$g_{wcm}$/hour to 1 mmole/$g_{wcm}$/hour, 400 nmole/$g_{wcm}$/hour to 1 mmole/$g_{wcm}$/hour, 400 nmole/$g_{wcm}$/hour to 40 mmole/$g_{wcm}$/hour, 400 nmole/$g_{wcm}$/hour to 4 mmole/$g_{wcm}$/hour, 1 mmole/$g_{wcm}$/hour to 1.5 mmole/$g_{wcm}$/hour, 1.5 mmole/$g_{wcm}$/hour to 3 mmole/$g_{wcm}$/hour, 3 mmole/$g_{wcm}$/hour to 5 mmole/$g_{wcm}$/hour, 5 mmole/$g_{wcm}$/hour to 25 mmole/$g_{wcm}$/hour, 25 mmole/$g_{wcm}$/hour to 100 mmole/$g_{wcm}$/hour, 100 mmole/$g_{wcm}$/hour to 500 mmole/$g_{wcm}$/hour, or 500 mmole/$g_{wcm}$/hour to 1000 mmole/$g_{wcm}$/hour. In some embodiments, the amount of isoprene is about any of 1 mmole/$g_{wcm}$/hour, 1.5 mmole/$g_{wcm}$/hour, 2 mmole/$g_{wcm}$/hour, 3 mmole/$g_{wcm}$/hour, 4 mmole/$g_{wcm}$/hour, or 5 mmole/$g_{wcm}$/hour. In some embodiments, cell viability is reduced by less than about any of 1.75-fold, 1.5-fold, 1.25-fold, 1-fold, 0.75-fold, 0.5-fold, or 0.25-fold. In some embodiments, cell viability is reduced by about 2-fold.

Further provided herein are methods of producing isoprene comprising: a) culturing cells under suitable conditions for production of isoprene; and b) producing isoprene, wherein the cumulative total productivity of the isoprene produced by the cells in culture is greater than about 0.2 mg/$L_{broth}$/hour and the carbon dioxide evolution rate of the cells is greater than about $1\times10^{-18}$ mmol/L/hour. In some embodiments, the cumulative total productivity of isoprene is any concentration or amount disclosed in the section entitled "Exemplary Production of Isoprene." In some embodiments, the cumulative total productivity of the isoprene is between about any of 0.2 mg/$L_{broth}$/hour to 5 g/$L_{broth}$/hour, 0.2 mg/$L_{broth}$/hour to 1 g/$L_{broth}$/hour, 1 g/$L_{broth}$/hour to 2.5 g/$L_{broth}$/hour, 2.5 g/$L_{broth}$/hour to 5 g/$L_{broth}$/hour. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

Provided herein are methods of producing isoprene comprising: a) culturing cells under suitable conditions for production of isoprene; and b) producing isoprene, wherein the cumulative total productivity of the isoprene produced by the cells in culture is greater than about 0.2 mg/$L_{broth}$/hour and cell viability is reduced by less than about two-fold. In some embodiments, the cumulative total productivity of isoprene is any concentration or amount disclosed in the section entitled "Exemplary Production of Isoprene." In some embodiments, the cumulative total productivity of the isoprene is between about any of 0.2 mg/$L_{broth}$/hour to 5 g/$L_{broth}$/hour, 0.2 mg/$L_{broth}$/hour to 1 g/$L_{broth}$/hour, 1 g/$L_{broth}$/hour to 2.5 g/$L_{broth}$/hour, 2.5 g/$L_{broth}$/hour to 5 g/$L_{broth}$/hour. In some embodiments, cell viability is reduced by less than about any of 1.75-fold, 1.5-fold, 1.25-fold, 1-fold, 0.75-fold, 0.5-fold, or 0.25-fold.

Methods of producing isoprene are also provided herein comprising: a) culturing cells under suitable conditions for production of isoprene; and b) producing isoprene, wherein the peak concentration of the isoprene produced by the cells in culture is greater than about 10 ng/$L_{broth}$ and the carbon dioxide evolution rate of the cells is greater than about $1\times10^{-18}$ mmol/L/hour. In some embodiments, the peak concentration of isoprene is any concentration or amount disclosed in the section entitled "Exemplary Production of Isoprene." In some embodiments, the peak concentration of isoprene is between about any of 10 ng/$L_{broth}$ to 500 ng/$L_{broth}$, 500 ng/$L_{broth}$ to 1 µg/$L_{broth}$, 1 µg/$L_{broth}$ to 5 µg/$L_{broth}$, 5 µg/$L_{broth}$ to 50 µg/$L_{broth}$, 5 µg/$L_{broth}$ to 100 µg/$L_{broth}$, 5 µg/$L_{broth}$ to 250 µg/$L_{broth}$, 250 µg/$L_{broth}$ to 500 µg/$L_{broth}$, 500 µg/$L_{broth}$ to 1 mg/$L_{broth}$, 1 mg/$L_{broth}$ to 50 mg/$L_{broth}$, 1 mg/$L_{broth}$ to 100 mg/$L_{broth}$, 1 mg/$L_{broth}$ to 200 mg/$L_{broth}$, 10 ng/$L_{broth}$ to 200 mg/$L_{broth}$, 5 µg/$L_{broth}$ to 100 mg/$L_{broth}$, or 5 µg/$L_{broth}$ to 200 mg/$L_{broth}$. In some embodiments, the peak concentration is any of about 10 ng/$L_{broth}$, 100 ng/$L_{broth}$, 1 µg/$L_{broth}$, 5 µg/$L_{broth}$, 1 mg/$L_{broth}$, 30 mg/$L_{broth}$, 100 mg/$L_{broth}$, or 200 mg/$L_{broth}$. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

In addition, methods of producing isoprene are also provided herein comprising: a) culturing cells under suitable conditions for production of isoprene; and b) producing isoprene, wherein the peak concentration of the isoprene produced by the cells in culture is greater than about 10 ng/$L_{broth}$ and cell viability is reduced by less than about two-fold. In some embodiments, the peak concentration of isoprene is any concentration or amount disclosed in the section entitled "Exemplary Production of Isoprene." In some embodiments, the peak concentration of isoprene is between about any of 10 ng/$L_{broth}$ to 500 ng/$L_{broth}$, 500 ng/$L_{broth}$ to 1 µg/$L_{broth}$, 1 µg/$L_{broth}$ to 5 µg/$L_{broth}$, 5 µg/$L_{broth}$ to 50 µg/$L_{broth}$, 5 µg/$L_{broth}$ to 100 µg/$L_{broth}$, 5 µg/$L_{broth}$ to 250 µg/$L_{broth}$, 250 µg/$L_{broth}$ to 500 µg/$L_{broth}$, 500 µg/$L_{broth}$ to 1 mg/$L_{broth}$, 1 mg/$L_{broth}$ to 50 mg/$L_{broth}$, 1 mg/$L_{broth}$ to 100 mg/$L_{broth}$, 1 mg/$L_{broth}$ to 200 mg/$L_{broth}$, 10 ng/$L_{broth}$ to 200 mg/$L_{broth}$, 5 µg/$L_{broth}$ to 100 mg/$L_{broth}$, or 5 µg/$L_{broth}$ to 200 mg/$L_{broth}$. In some embodiments, the peak concentration is any of about 10 ng/$L_{broth}$, 100 ng/$L_{broth}$, 1 µg/$L_{broth}$, 5 µg/$L_{broth}$, 1 mg/$L_{broth}$, 30 mg/$L_{broth}$, 100 mg/$L_{broth}$, or 200 mg/$L_{broth}$. In some embodiments, cell viability is reduced by less than about any of 1.75-fold, 1.5-fold, 1.25-fold, 1-fold, 0.75-fold, 0.5-fold, or 0.25-fold. In some embodiments, cell viability is reduced by about 2-fold.

Cells in culture are also provided herein comprising a nucleic acid encoding an isoprene synthase polypeptide, wherein the cells produce greater than about 400 nmole/

$g_{wcm}$/hour of isoprene and carbon dioxide evolution rate of the cells is greater than about $1\times10^{-18}$ mmol/L/hour. In some embodiments, the isoprene produced is any concentration or amount disclosed in the section entitled "Exemplary Production of Isoprene." In some embodiments, the amount of isoprene is between about any of 400 nmole/$g_{wcm}$/hour to 1 mole/$g_{wcm}$/hour, 400 nmole/$g_{wcm}$/hour to 1 mmole/$g_{wcm}$/hour, 400 nmole/$g_{wcm}$/hour to 40 mmole/$g_{wcm}$/hour, 400 nmole/$g_{wcm}$/hour to 4 mmole/$g_{wcm}$/hour, 1 mmole/$g_{wcm}$/hour to 1.5 mmole/$g_{wcm}$/hour, 1.5 mmole/$g_{wcm}$/hour to 3 mmole/$g_{wcm}$/hour, 3 mmole/$g_{wcm}$/hour to 5 mmole/$g_{wcm}$/hour, 5 mmole/$g_{wcm}$/hour to 25 mmole/$g_{wcm}$/hour, 25 mmole/$g_{wcm}$/hour to 100 mmole/$g_{wcm}$/hour, 100 mmole/$g_{wcm}$/hour to 500 mmole/$g_{wcm}$/hour, or 500 mmole/$g_{wcm}$/hour to 1000 mmole/$g_{wcm}$/hour. In some embodiments, the amount of isoprene is about any of 1 mmole/$g_{wcm}$/hour, 1.5 mmole/$g_{wcm}$/hour, 2 mmole/$g_{wcm}$/hour, 3 mmole/$g_{wcm}$/hour, 4 mmole/$g_{wcm}$/hour, or 5 mmole/$g_{wcm}$/hour. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

Provided herein are also cells in culture comprising a nucleic acid encoding an isoprene synthase polypeptide, wherein cumulative total productivity of the isoprene produced by the cells in culture is greater than about 0.2 mg/$L_{broth}$/hour and carbon dioxide evolution rate of the cells is greater than about $1\times10^{-18}$ mmol/L/hour. In some embodiments, the cumulative total productivity of isoprene is any concentration or amount disclosed in the section entitled "Exemplary Production of Isoprene." In some embodiments, the cumulative total productivity of the isoprene is between about any of 0.2 mg/$L_{broth}$/hour to 5 g/$L_{broth}$/hour, 0.2 mg/$L_{broth}$/hour to 1 g/$L_{broth}$/hour, 1 g/$L_{broth}$/hour to 2.5 g/$L_{broth}$/hour, 2.5 g/$L_{broth}$/hour to 5 g/$L_{broth}$/hour. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

In addition, provided herein are cells in culture comprising a nucleic acid encoding an isoprene synthase polypeptide, wherein peak concentration of the isoprene produced by the cells in culture is greater than about 10 ng/$L_{broth}$ and carbon dioxide evolution rate of the cells is greater than about $1\times10^{-18}$ mmol/L/hour. In some embodiments, the peak concentration of isoprene is any concentration or amount disclosed in the section entitled "Exemplary Production of Isoprene." In some embodiments, the peak concentration of isoprene is between about any of 10 ng/$L_{broth}$ to 500 ng/$L_{broth}$, 500 ng/$L_{broth}$ to 1 µg/$L_{broth}$, 1 µg/$L_{broth}$ to 5 µg/$L_{broth}$, 5 µg/$L_{broth}$ to 50 µg/$L_{broth}$, 5 µg/$L_{broth}$ to 100 µg/$L_{broth}$, 5 µg/$L_{broth}$ to 250 µg/$L_{broth}$, 250 µg/$L_{broth}$ to 500 µg/$L_{broth}$, 500 µg/$L_{broth}$ to 1 mg/$L_{broth}$, 1 mg/$L_{broth}$ to 50 mg/$L_{broth}$, 1 mg/$L_{broth}$ to 100 mg/$L_{broth}$, 1 mg/$L_{broth}$ to 200 mg/$L_{broth}$, 10 ng/$L_{broth}$ to 200 mg/$L_{broth}$, 5 µg/$L_{broth}$ to 100 mg/$L_{broth}$, or 5 µg/$L_{broth}$ to 200 mg/$L_{broth}$. In some embodiments, the peak concentration is any of about 10 ng/$L_{broth}$, 100 ng/$L_{broth}$, 1 µg/$L_{broth}$, 5 µg/$L_{broth}$, 1 mg/$L_{broth}$, 30 mg/$L_{broth}$, 100 mg/$L_{broth}$, or 200 mg/$L_{broth}$. In some embodiments, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about any of 50 mmol/L/hour, 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, or 500 mmol/L/hour.

In some embodiments of any of the methods and cells described herein, carbon dioxide evolution rate and/or cell viability of a cell expressing a MVA pathway and/or DXP pathway RNA and/or protein from one or more of a heterologous and/or duplicate copy of a MVA pathway and/or DXP pathway nucleic acid is compared to a control cell lacking one or more of a heterologous and/or duplicate copy of a MVA pathway and/or DXP pathway nucleic acid. In some embodiments, carbon dioxide evolution rate and/or cell viability of a cell expressing a MVA pathway and/or DXP pathway RNA and/or protein from one or more of a heterologous and/or duplicate copy of a MVA pathway and/or DXP pathway nucleic acid under the control of an inducible promoter, wherein the promotor is induced, is compared to a control cell containing one or more of a heterologous and/or duplicate copy of a MVA pathway and/or DXP pathway nucleic acid under the control of an inducible promoter, wherein the promotor is not induced (uninduced). In some embodiments, the inducible promoter is a beta-galactosidase promoter.

The invention provides methods of producing isoprene comprising: a) culturing cells under suitable conditions for production of isoprene; and b) producing isoprene, wherein cells produce greater than about 400 nmole/$g_{wcm}$/hour of isoprene, and the carbon dioxide evolution rate of the cells is greater than about $1\times10^{-18}$ mmol/L/hour. Further provided herein are methods of producing isoprene comprising: a) culturing cells under suitable conditions for production of isoprene; and b) producing isoprene, wherein the cumulative total productivity of the isoprene produced by the cells in culture is greater than about 0.2 mg/$L_{broth}$/hour and the carbon dioxide evolution rate of the cells is greater than about $1\times10^{-18}$ mmol/L/hour. Methods of producing isoprene are also provided herein comprising: a) culturing cells under suitable conditions for production of isoprene; and b) producing isoprene, wherein the peak concentration of the isoprene produced by the cells in culture is greater than about 10 ng/$L_{broth}$ and the carbon dioxide evolution rate of the cells is greater than about $1\times10^{-18}$ mmol/L/hour. In some embodiments of any of these methods, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about 50 mmol/L/hour or about 500 mmol/L/hour.

Further provided herein are cells in culture comprising a nucleic acid encoding an isoprene synthase polypeptide, wherein the cells produce greater than about 400 nmole/$g_{wcm}$/hour of isoprene and carbon dioxide evolution rate of the cells is greater than about $1\times10^{-18}$ mmol/L/hour. Provided herein are also cells in culture comprising a nucleic acid encoding an isoprene synthase polypeptide, wherein cumulative total productivity of the isoprene produced by the cells in culture is greater than about 0.2 mg/$L_{broth}$/hour and carbon dioxide evolution rate of the cells is greater than about $1\times10^{-18}$ mmol/L/hour. In addition, provided herein are cells in culture comprising a nucleic acid encoding an isoprene synthase polypeptide, wherein peak concentration of the isoprene produced by the cells in culture is greater than about 10 ng/$L_{broth}$ and carbon dioxide evolution rate of the cells is greater than about $1\times10^{-18}$ mmol/L/hour. In some embodiments of any of these cells in culture, the carbon dioxide evolution rate is between about any of $1\times10^{-18}$ mmol/L/hour to about 1 mol/L/hour, 1 mmol/L/hour to 1 mol/L/hour, 25 mmol/L/hour to 750 mmol/L/hour, 25 mmol/L/hour to 75 mmol/L/hour, 250 mmol/L/hour to 750 mmol/L/hour, or 450 mmol/L/hour to 550 mmol/L/hour. In some embodiments, the carbon dioxide evolution rate is about 50 mmol/L/hour or about 500 mmol/L/hour.

Provided herein are also methods of producing isoprene comprising a) culturing cells under suitable conditions for production of isoprene; and b) producing isoprene, wherein the liquid phase concentration of isoprene is less than about 200 mg/L and the cells produce greater than about 400 nmole/$g_{wcm}$/hour of isoprene. In some embodiments, the liquid phase concentration of isoprene in the culture is less than about any of 175 mg/L, 150 mg/L, 125 mg/L, 100 mg/L, 75 mg/L, 50 mg/L, 25 mg/L, 20 mg/L, 15 mg/L, 10 mg/L, 5 mg/L, or 2.5 mg/L. In some embodiments, the liquid phase concentration of isoprene in culture is between about any of 0.1 mg/L to 200 mg/L, 1 mg/L to 200 mg/L, 1 mg/L to 150 mg/L, 1 mg/L to 100 mg/L, 1 mg/L to 50 mg/L, 1 mg/L to 25 mg/L, 1 mg/L to 20 mg/L, or 10 mg/L to 20 mg/L.

Also provided herein are methods of producing a compound, wherein the compound has one or more characteristics selected from the group consisting of (a) a Henry's law coefficient of less than about 250 M/atm and (b) a solubility in water of less than about 100 g/L. In some embodiments, the method comprises: a) culturing cells under suitable conditions for production of the compound, wherein gas is added (such as the addition of gas to a system such as a fermentation system) at a gas sparging rate between about 0.01 vvm to about 2 vvm; and b) producing the compound. In some embodiments, the Henry's law coefficient of the compound is less than about any of 200 M/atm, 150 M/atm, 100 M/atm, 75 M/atm, 50 M/atm, 25 M/atm, 10 M/atm, 5 M/atm, or 1 M/atm. In some embodiments, the solubility in water of the compound is less than about any of 75 g/L, 50 g/L, 25 g/L, 10 g/L, 5 g/L, or 1 g/L. In some embodiments, the compound is selected from a group consisting of isoprene, an aldehyde (e.g., acetaldehyde), a ketone (e.g., acetone or 2-butanone), an alcohol (e.g., methanol, ethanol, 1-butanol, or C5 alcohols such as 3-methyl-3-buten-1-ol or 3-methyl-2-buten-1-ol), an ester of an alcohol (e.g., ethyl acetate or acetyl esters of C5 alcohols), a hemiterpene, a monoterpene, a sesquiterpene, and C1 to C5 hydrocarbons (e.g., methane, ethane, ethylene, or propylene). In some embodiments, the C1 to C5 hydrocarbons are saturated, unsaturated, or branched. In particular embodiments, the compound is isoprene. In some embodiments of the methods of producing any of the compounds described above, the gas sparging rate is between about any of 0.1 vvm to 1 vvm, 0.2 vvm to 1 vvm, or 0.5 vvm to 1 vvm.

In one aspect, the invention features cells in culture that produce isoprene. In some embodiments, the invention provides cells in culture that produce greater than about 400 nmole of isoprene/gram of cells for the wet weight of the cells/hour (nmole/$g_{wcm}$/hr) of isoprene. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions.

In some embodiments, the invention provides cells in culture that convert more than about 0.002% of the carbon in a cell culture medium into isoprene. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions.

In some embodiments, the invention provides cells in culture that comprise a heterologous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions.

In one aspect, the invention features methods of producing isoprene, such as methods of using any of the cells described herein to produce isoprene. In some embodiments, the method involves culturing cells under conditions sufficient to produce greater than about 400 nmole/$g_{wcm}$/hr of isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions. In various embodiments, the amount of isoprene produced (such as the total amount of isoprene produced or the amount of isoprene produced per liter of broth per hour per $OD_{600}$) during stationary phase is greater than or about 2 or more times the amount of isoprene produced during the growth phase for the same length of time. In some embodiments, the gas phase comprises greater than or about 9.5% (volume) oxygen, and the concentration of isoprene in the gas phase is less than the lower flammability limit or greater than the upper flammability limit. In particular embodiments, (i) the concentration of isoprene in the gas phase is less than the lower flammability limit or greater than the upper flammability limit, and (ii) the cells produce greater than about 400 nmole/$g_{wcm}$/hr of isoprene.

In some embodiments, the method includes culturing cells under conditions sufficient to convert more than about 0.002% of the carbon (mol/mol) in a cell culture medium into isoprene. In some embodiments, the method also includes recovering isoprene produced by the cells. In some embodiments, the method includes purifying isoprene produced by the cells. In some embodiments, the method includes polymerizing the isoprene. In some embodiments, the cells have a heterologous nucleic acid that (i) encodes an isoprene synthase polypeptide and (ii) is operably linked to a promoter. In some embodiments, the cells are cultured in a culture medium that includes one or more carbon sources, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, or a component from a yeast extract. In some embodiments, the cells are cultured under limited glucose conditions.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time.

In one aspect, the invention features compositions and systems that comprise isoprene. In some embodiments, the composition comprises greater than or about 2, 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene (w/w) of the volatile organic fraction of the composition is isoprene.

In some embodiments, the composition comprises greater than or about 99.90, 99.92, 99.94, 99.96, 99.98, or 100% isoprene by weight compared to the total weight of all C5 hydrocarbons in the composition. In some embodiments, the composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition. In some embodiments, the composition has less than or about 0.12, 0.10, 0.08, 0.06, 0.04, 0.02, 0.01, 0.005, 0.001, 0.0005, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne by weight compared to the total weight of all C5 hydrocarbons in the composition. In particular embodiments, the composition has greater than about 2 mg of isoprene and has greater than or about 99.90, 99.92, 99.94, 99.96, 99.98, or 100% isoprene by weight compared to the total weight of all C5 hydrocarbons in the composition.

In some embodiments, the composition has less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In particular embodiments, the composition also has greater than about 2 mg of isoprene.

In some embodiments, the composition has one or more compounds selected from the group consisting of ethanol, acetone, C5 prenyl alcohols, and isoprenoid compounds with 10 or more carbon atoms. In some embodiments, the composition has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the composition has greater than about 2 mg of isoprene and has one or more compounds selected from the group consisting of ethanol, acetone, C5 prenyl alcohols, and isoprenoid compounds with 10 or more carbon atoms.

In some embodiments, the composition includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to the amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w).

In some embodiments, the composition comprises (i) a gas phase that comprises isoprene and (ii) cells in culture that produce greater than about 400 nmole/$g_{wcm}$/hr of isoprene. In some embodiments, the composition comprises a closed system, and the gas phase comprises greater than or about 5, 10, 20, 30, 40, 50, 60, 70, 80, 90, 100 ug/L of isoprene when normalized to 1 mL of 1 $OD_{600}$ cultured for 1 hour. In some embodiments, the composition comprises an open system, and the gas phase comprises greater than or about 5, 10, 20, 30, 40, 50, 60, 70, 80, 90, 100 ug/L of isoprene when sparged at a rate of 1 vvm. In some embodiments, the volatile organic fraction of the gas phase comprises greater than or about 99.90, 99.92, 99.94, 99.96, 99.98, or 100% isoprene by weight compared to the total weight of all C5 hydrocarbons in the volatile organic fraction. In some embodiments, the volatile organic fraction of the gas phase comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1- butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the volatile organic fraction. In some embodiments, the volatile organic fraction of the gas phase has less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne by weight compared to the total weight of all C5 hydrocarbons in the volatile organic fraction. In particular embodiments, the volatile organic fraction of the gas phase has greater than about 2 mg of isoprene and has greater than or about 99.90, 99.92, 99.94, 99.96, 99.98, or 100% isoprene by weight compared to the total weight of all C5 hydrocarbons in the volatile organic fraction.

In some embodiments, the volatile organic fraction of the gas phase has less than or about 50, 40, 30, 20, 10, 5, 1, 0.5, 0.1, 0.05, 0.01, or 0.005 ug/L of a compound that inhibits the polymerization of isoprene for any compound in the volatile organic fraction of the gas phase that inhibits the polymerization of isoprene. In particular embodiments, the volatile organic fraction of the gas phase also has greater than about 2 mg of isoprene.

In some embodiments, the volatile organic fraction of the gas phase has one or more compounds selected from the group consisting of ethanol, acetone, C5 prenyl alcohols, and isoprenoid compounds with 10 or more carbon atoms. In some embodiments, the volatile organic fraction of the gas phase has greater than or about 0.005, 0.01, 0.05, 0.1, 0.5, 1, 5, 10, 20, 30, 40, 60, 80, 100, or 120 ug/L of ethanol, acetone, a C5 prenyl alcohol (such as 3-methyl-3-buten-1-ol or 3-methyl-2-buten-1-ol), or any two or more of the foregoing. In particular embodiments, the volatile organic fraction of the gas phase has greater than about 2 mg of isoprene and has one or more compounds selected from the group consisting of ethanol, acetone, C5 prenyl alcohols, and isoprenoid compounds with 10 or more carbon atoms.

In some embodiments, the volatile organic fraction of the gas phase has includes isoprene and one or more second compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, and 2,3-cycloheptenolpyridine. In various embodiments, the amount of one of these second components relative to amount of isoprene in units of percentage by weight (i.e., weight of the component divided by the weight of isoprene times 100) is at greater than or about 0.01, 0.02, 0.05, 0.1, 0.5, 1, 5, 10, 20, 30, 40, 50, 60, 70, 80, 90, 100, or 110% (w/w) in the volatile organic fraction of the gas phase.

In some embodiments of any of the compositions of the invention, at least a portion of the isoprene is in a gas phase. In some embodiments, at least a portion of the isoprene is in a liquid phase (such as a condensate). In some embodiments, at least a portion of the isoprene is in a solid phase. In some embodiments, at least a portion of the isoprene is adsorbed to a solid support, such as a support that includes silica and/or activated carbon. In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments, the composition includes between about 4 to about 15% by weight of isoprene, such as between about 4 to about 8%, about 8 to about 12%, or about 12 to about 15% by weight of isoprene.

In some embodiments, the invention also features systems that include any of the cells and/or compositions described herein. In some embodiments, the system includes a reactor that chamber comprises cells in culture that produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the system is not a closed system. In some embodiments, at least a portion of the isoprene is removed from the system. In some embodiments, the system includes a gas phase comprising isoprene. In various embodiments, the gas phase comprises any of the compositions described herein.

In one aspect, the invention provides a tire comprising polyisoprene. In some embodiments, the polyisoprene is produced by (i) polymerizing isoprene in any of the compositions described herein or (ii) polymerizing isoprene recovered from any of the compositions described herein. In some embodiments, the polyisoprene comprises cis-1,4-polyisoprene.

In some embodiments of any of the compositions, systems, and methods of the invention, a nonflammable concentration of isoprene in the gas phase is produced. In some embodiments, the gas phase comprises less than about 9.5% (volume) oxygen. In some embodiments, the gas phase comprises greater than or about 9.5% (volume) oxygen, and the concentration of isoprene in the gas phase is less than the lower flammability limit or greater than the upper flammability limit. In some embodiments, the portion of the gas phase other than isoprene comprises between about 0% to about 100% (volume) oxygen, such as between about 10% to about 100% (volume) oxygen. In some embodiments, the portion of the gas phase other than isoprene comprises between about 0% to about 99% (volume) nitrogen. In some embodiments, the portion of the gas phase other than isoprene comprises between about 1% to about 50% (volume) $CO_2$.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6%, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a DXS polypeptide. In some embodiments of any of the aspects of the invention, the cells further comprise one or more nucleic acids encoding an IDI polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker, such as an antibiotic resistance nucleic acid.

In some embodiments of any of the aspects of the invention, the heterologous isoprene synthase nucleic acid is operably linked to a T7 promoter, such as a T7 promoter contained in a medium or high copy plasmid. In some embodiments of any of the aspects of the invention, the heterologous isoprene synthase nucleic acid is operably linked to a Trc promoter, such as a Trc promoter contained in a medium or high copy plasmid. In some embodiments of any of the aspects of the invention, the heterologous isoprene synthase nucleic acid is operably linked to a Lac promoter, such as a Lac promoter contained in a low copy plasmid. In some embodiments of any of the aspects of the invention, the heterologous isoprene synthase nucleic acid is operably linked to an endogenous promoter, such as an endogenous alkaline serine protease promoter. In some embodiments, the heterologous isoprene synthase nucleic acid integrates into a chromosome of the cells without a selective marker.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

In some embodiments of any of the aspects of the invention, at least a portion of the cells maintain the heterologous isoprene synthase nucleic acid for at least or about 5, 10, 20, 40, 50, 60, 65, or more cell divisions in a continuous culture (such as a continuous culture without dilution). In some embodiments of any of the aspects of the invention, the nucleic acid comprising the isoprene synthase, IDI, or DXS nucleic acid also comprises a selective marker, such as an antibiotic resistance nucleic acid.

In some embodiments of any of the aspects of the invention, the cells further comprise a heterologous nucleic acid encoding an MVA pathway polypeptide (such as an MVA pathway polypeptide from *Saccharomyces cerevisia* or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic (in addition to the IDI nucleic acid).

In some embodiments of any of the aspects of the invention, the isoprene synthase polypeptide is a polypeptide from a plant such as *Pueraria* (e.g., *Pueraria montana* or *Pueraria lobata*) or *Populus* (e.g., *Populus tremuloides*, *Populus alba*, *Populus nigra*, *Populus trichocarpa*, or the hybrid, *Populus alba×Populus tremula*).

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans*, *Streptomyces coelicolor*, or *Streptomyces griseus* cells). In some embodiments of any of the aspects of the invention, the cells are gram-negative bacterial cells (e.g., *Escherichia* cells such as *Escherichia coli* cells, *Rhodopseudomonas* sp. such as *Rhodopseudomonas palustris* cells, *Pseudomonas* sp. such as *Pseudomonas fluorescens* cells or *Pseudomonas putida* cells, or *Pantoea* cells such as *Pantoea citrea* cells). In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells or *Sacchraomyces* cells such as *Saccaromyces cerevisiae*).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention features a product produced by any of the compositions or methods of the invention.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation.

All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Production of Isoprene in *E. Coli* Expressing Recombinant Kudzu Isoprene Synthase I. Construction of Vectors for Expression of the Kudzu Isoprene Synthase in *E. Coli*.

Figure 2:
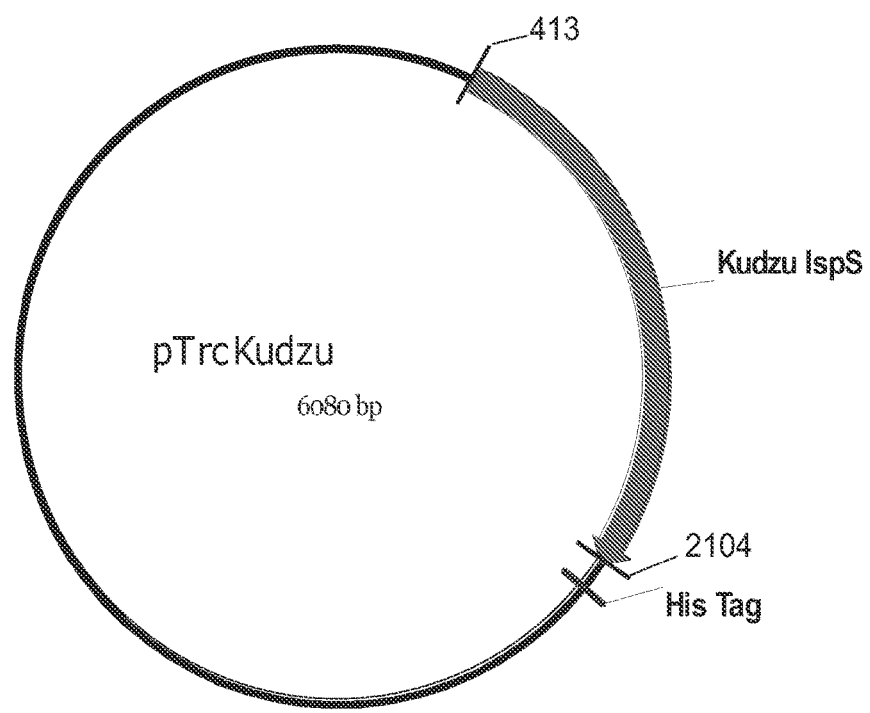
FIG. 2 is a map of pTrcKudzu.

The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (SEQ ID NO:1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3; SEQ ID NO:2).

Figure 4:
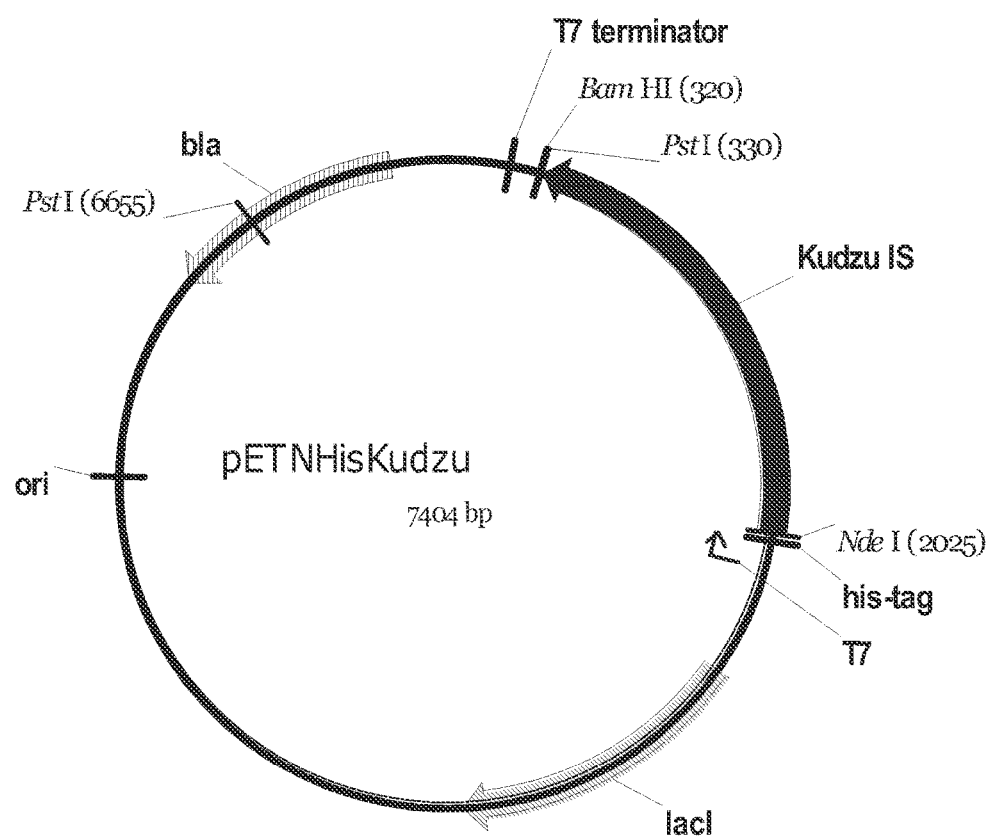
FIG. 4 is a map of pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGT-GAGATCATATGTGTGCGACCTCTTCTCAATTTAC (SEQ ID NO:49) and pET-His-Kudzu-R: 5'-CGGTCGACG-GATCCCTGCAGTTAGACATACATCAGCTG (SEQ ID NO:50). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 µl. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid, in which the kudzu isoprene synthase gene was expressed from the T7 promoter, was designated pETNHisKudzu (FIGS. 4 and 5; SEQ ID NO:3).

Figure 6:
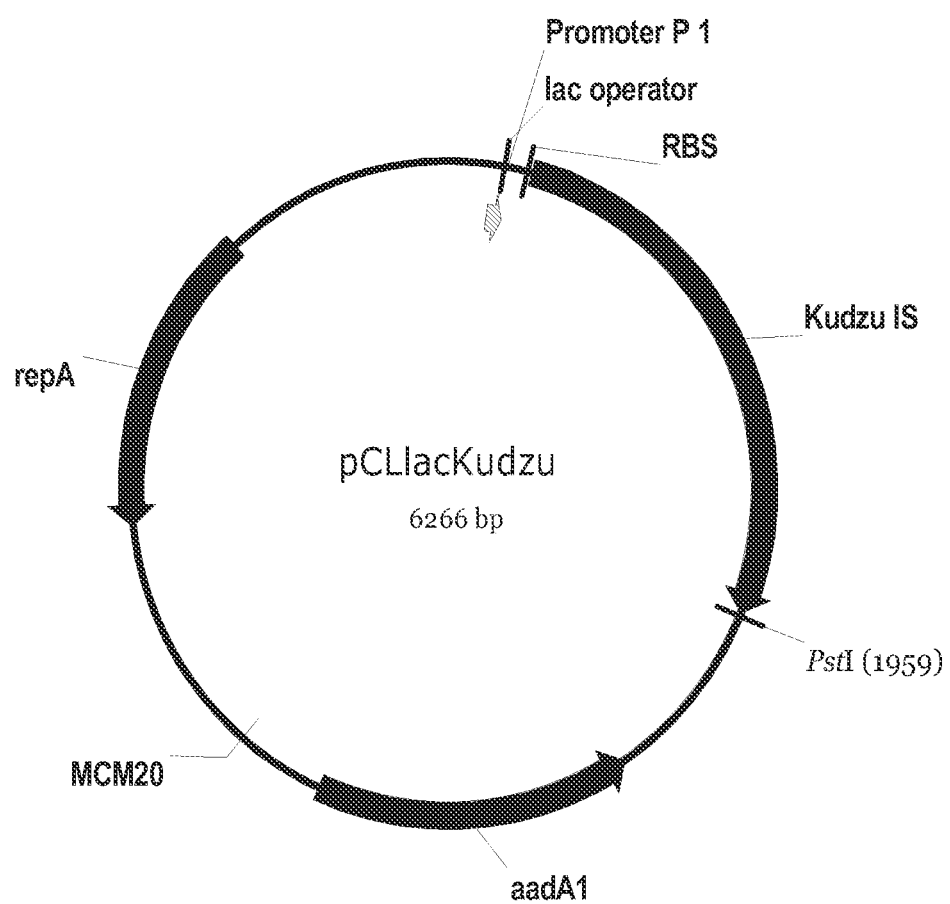
FIG. 6 is a map of pCL-lac-Kudzu.
Figure 8A:
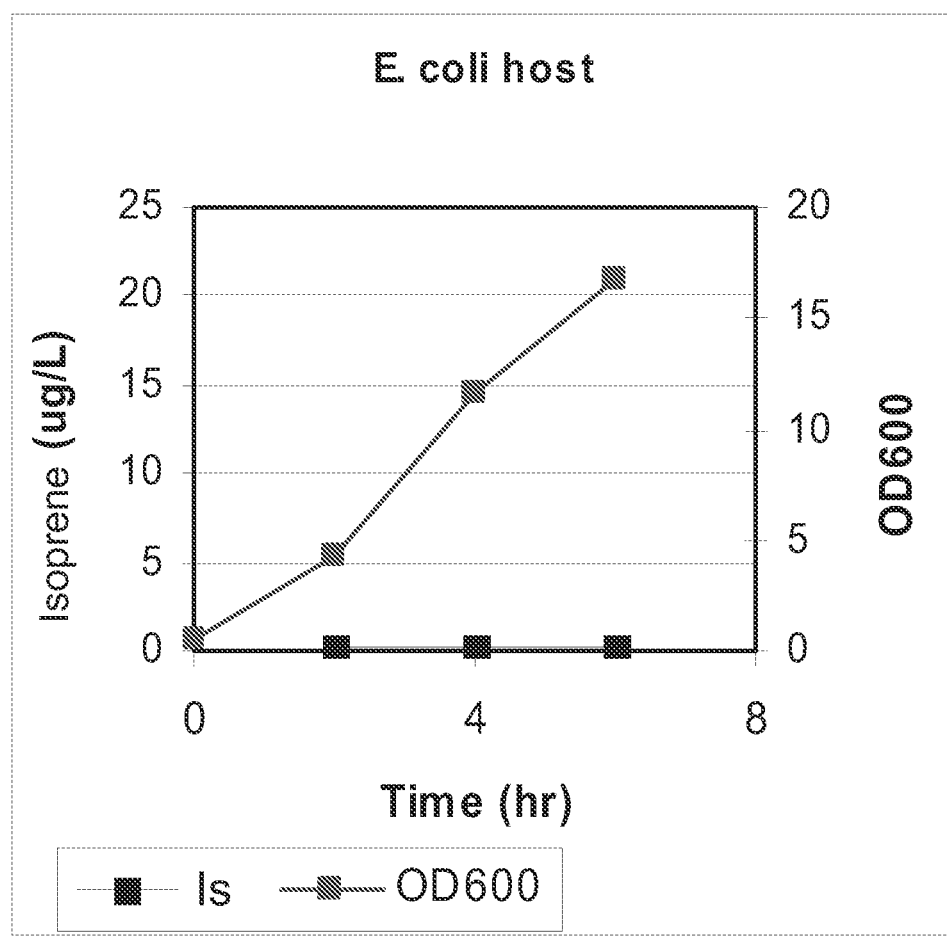
FIG. 8A is a graph showing the production of isoprene in E. coli BL21 cells with no vector.
Figure 8B:
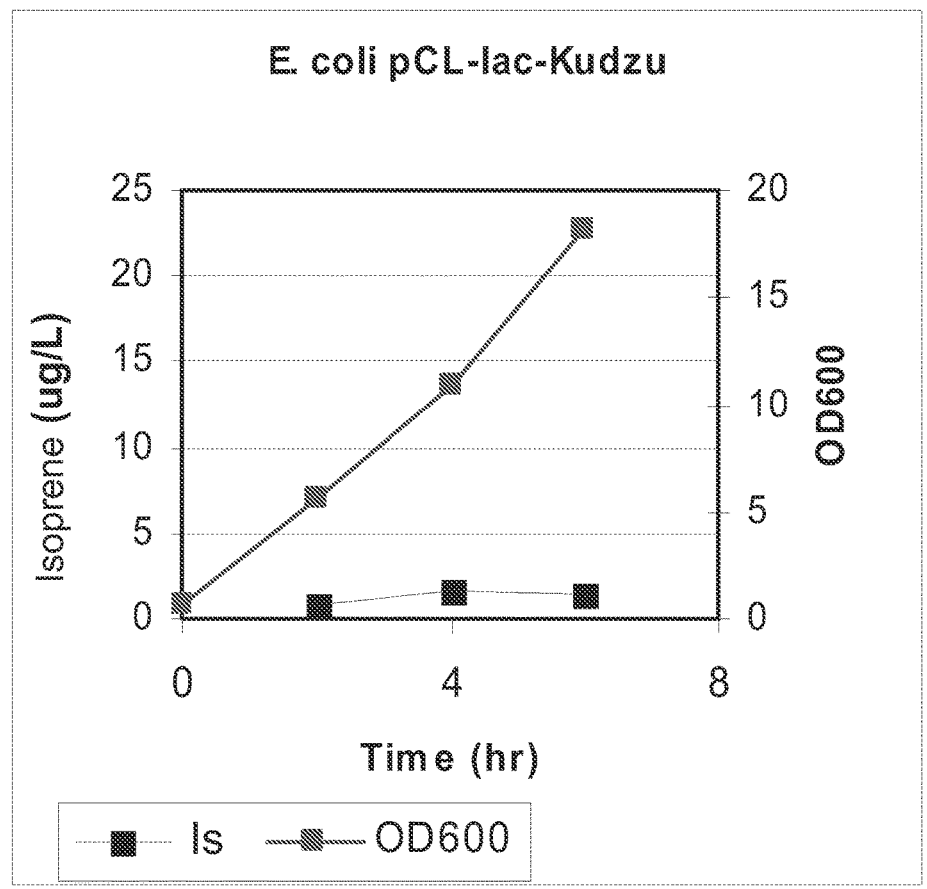
FIG. 8B is a graph showing the production of isoprene in E. coli BL21 cells with pCL-lac-Kudzu
Figure 8C:
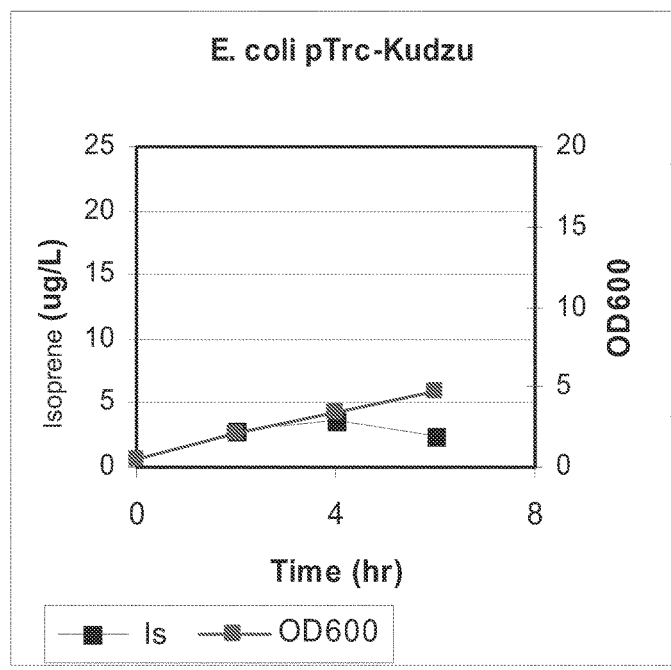
FIG. 8C is a graph showing the production of isoprene in E. coli BL21 cells with pTrcKudzu.
Figure 8D:
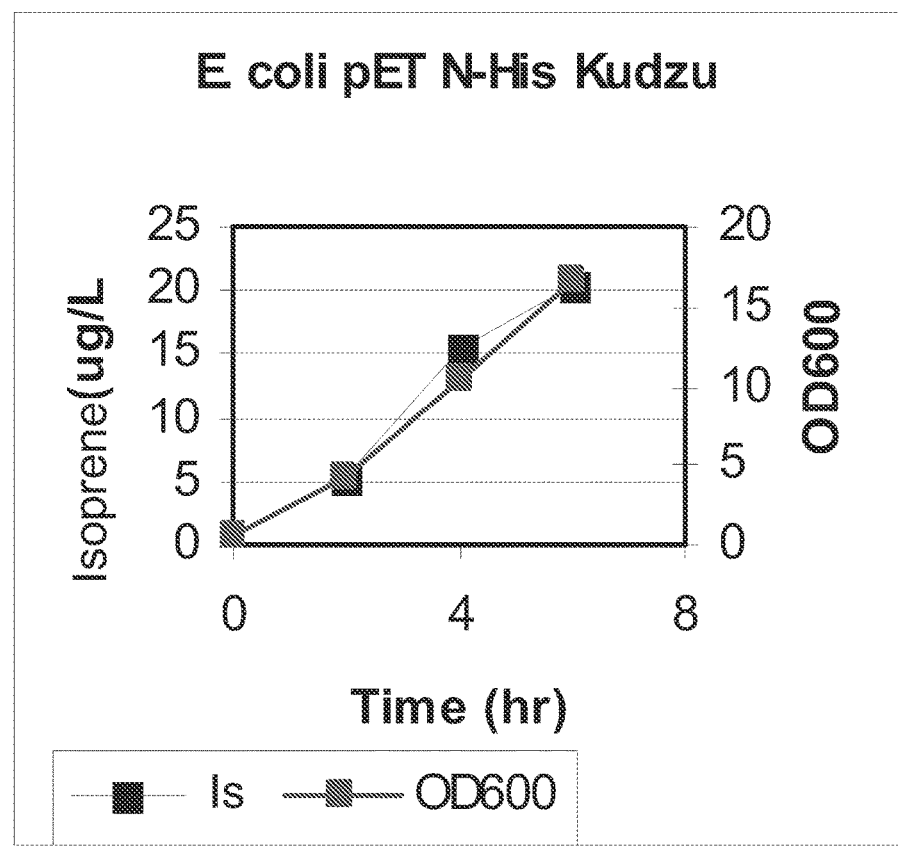
FIG. 8D is a graph showing the production of isoprene in E. coli BL21 cells with pETNHisKudzu.

The kudzu isoprene synthase gene was also cloned into the low copy number plasmid pCL1920. Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATAT-GAAAGCTTGTATCGATTAAATAAGGAG-GAATAAACC (SEQ ID NO:51) and BamH1-Kudzu R: 5'-CGGTCGACGGATCCCTGCAGTTAGACATA-CATCAGCTG (SEQ ID NO:50). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into *E. coli* Top10. Several transformants were checked by sequencing. The resulting plasmid was designated pCL-lac-Kudzu (FIGS. 6 and 7; SEQ ID NO:4).

II. Determination of Isoprene Production.

For the shake flask cultures, one ml of a culture was transferred from shake flasks to 20 ml CTC headspace vials (Agilent vial cat#5188 2753; cap cat#5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/min. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 2000 µg/L. The limit of detection was estimated to be 50 to 100 ng/L using this method.

III. Production of Isoprene in Shake Flasks Containing *E. Coli* Cells Expressing Recombinant Isoprene Synthase.

The vectors described above were introduced to *E. coli* strain BL21 (Novagen) to produce strains BL21/ptrcKudzu, BL21/pCL-lac-Kudzu and BL21/pETHisKudzu. The strains were spread for isolation onto LA (Luria agar)+carbenicillin (50 µg/ml) and incubated overnight at 37° C. Single colonies were inoculated into 250 ml baffled shake flasks containing 20 ml Luria Bertani broth (LB) and carbenicillin (100 µg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen)+carbenicillin (100 µg/ml) to an $OD_{600}$~0.05. The culture was incubated at 30° C. with shaking at 200 rpm. When the $OD_{600}$~0.5-0.8, 400 µM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIG. 8.

IV. Production of Isoprene from BL21/ptrcKudzu in 14 Liter Fermentation.

Large scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, $MgSO4*7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in diH$_2$O. The pH was adjusted to 6.8 with potassium hydroxide (KOH) and q.s. to volume. The final product was filter sterilized with 0.22 µA filter (only, do not autoclave). The recipe for 1000× Modified Trace Metal Solution was as follows: Citric Acids*H$_2$O 40 g, MnSO$_4$*H$_2$O 30 g, NaCl 10 g, FeSO$_4$*7H$_2$O 1 g, CoCl$_2$*6H$_2$O 1 g, ZnSO*7H$_2$O 1 g, CuSO$_4$*5H$_2$O 100 mg, H$_3$BO$_3$ 100 mg, NaMoO$_4$*2H$_2$O 100 mg. Each component was dissolved one at a time in diH$_2$O, pH to 3.0 with HCl/NaOH, then q.s. to volume and filter sterilized with a 0.22µ filter.

Figure 9A:
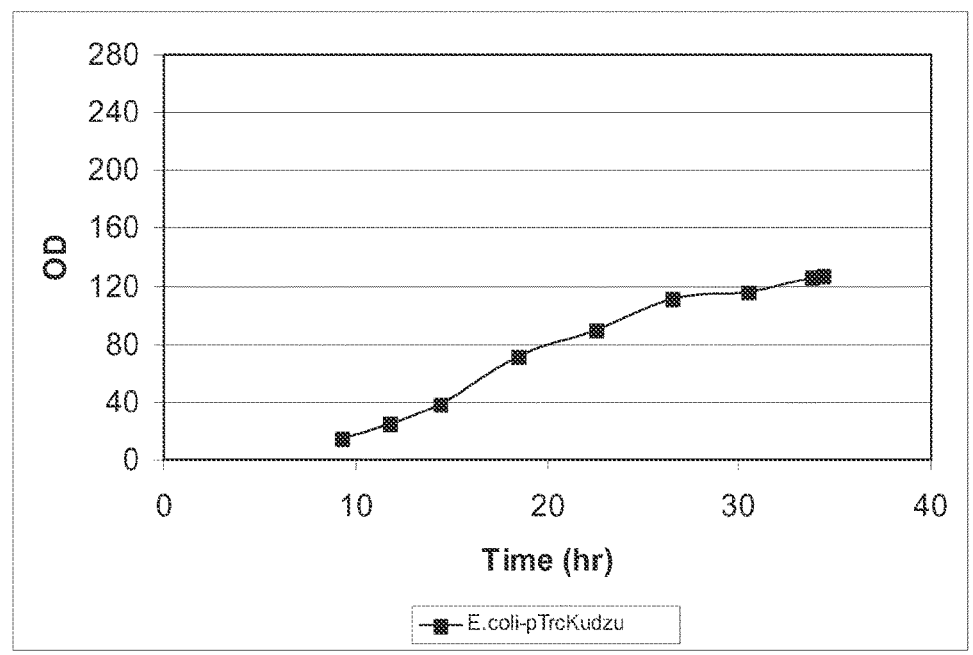
FIG. 9A is a graph showing OD over time of fermentation of E. coli BL21/pTrcKudzu in a 14 liter fed batch fermentation.
Figure 9B:
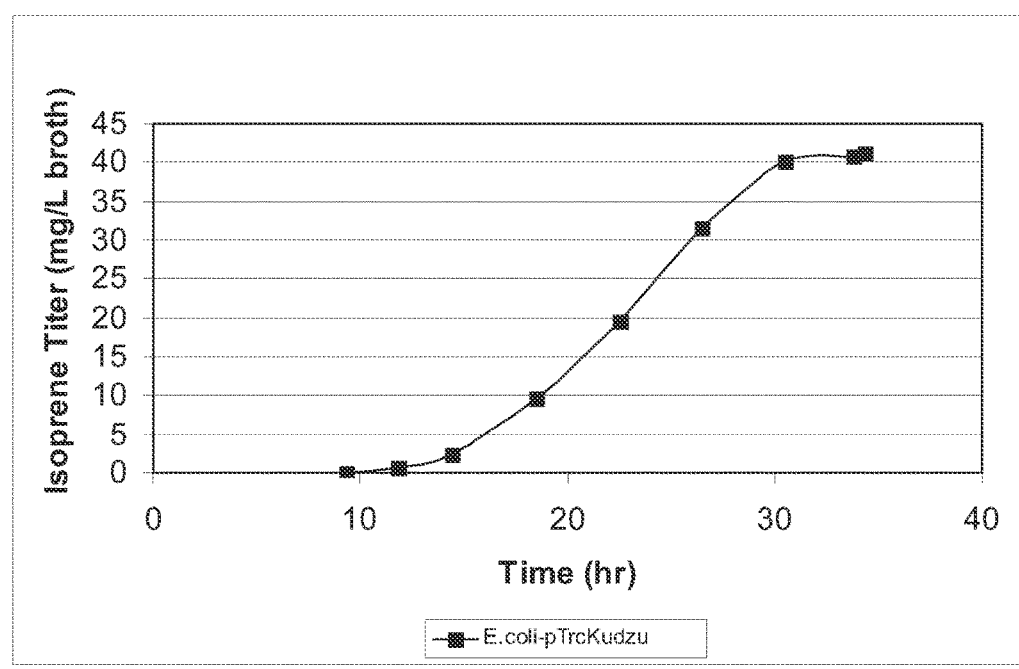
FIG. 9B is a graph showing isoprene production over time of fermentation of E. coli BL21/pTrcKudzu in a 14 liter fed batch fermentation.
Figure 10A:
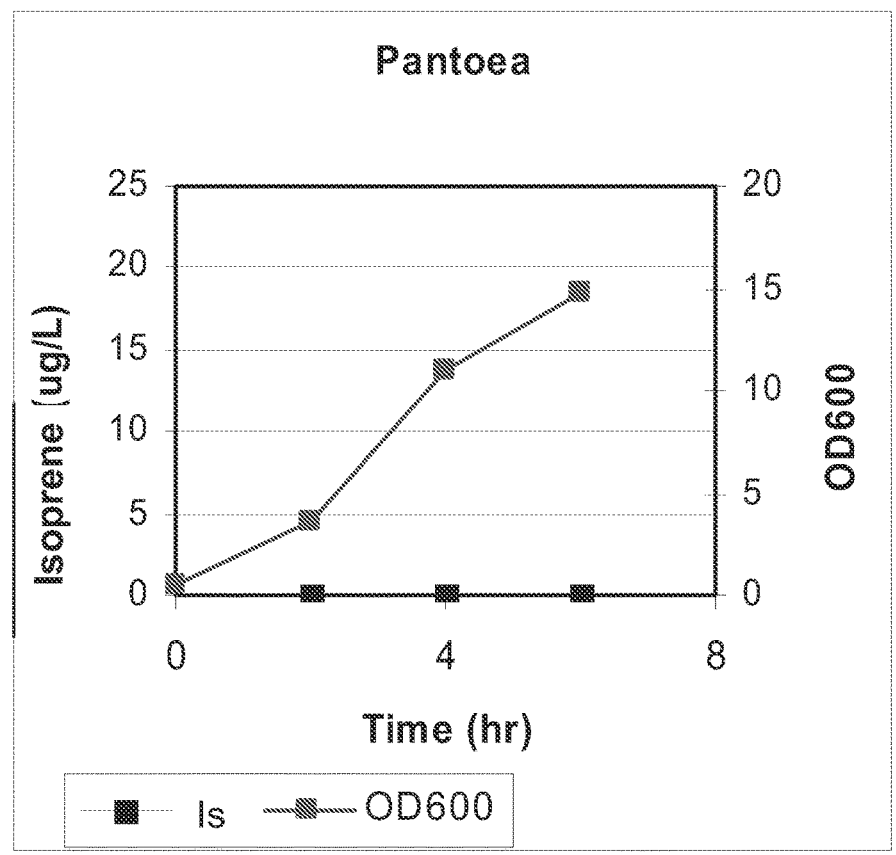
FIG. 10A is a graph showing the production of isoprene in *Panteoa citrea*. Control cells without recombinant kudzu isoprene synthase. Grey diamonds represent isoprene synthesis, black squares represent $OD_{600}$).
Figure 10B:
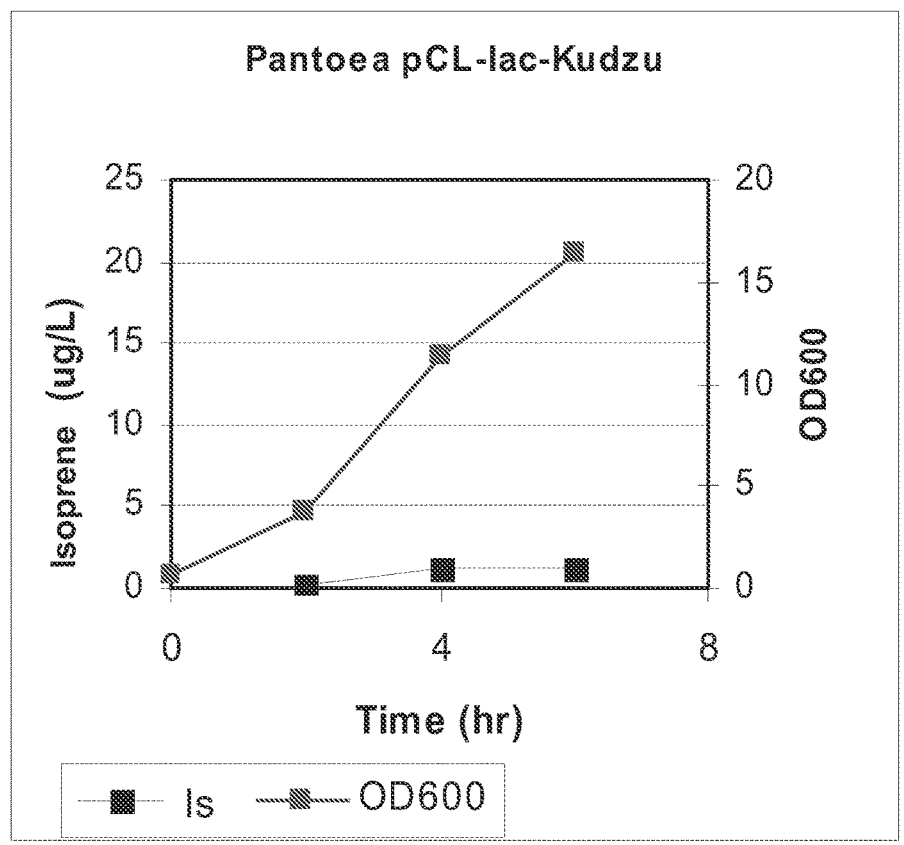
FIG. 10B is a graph showing the production of isoprene in *Panteoa citrea* expressing pCL-lac Kudzu. Grey diamonds represent isoprene synthesis, black squares represent $OD_{600}$.
Figure 10C:
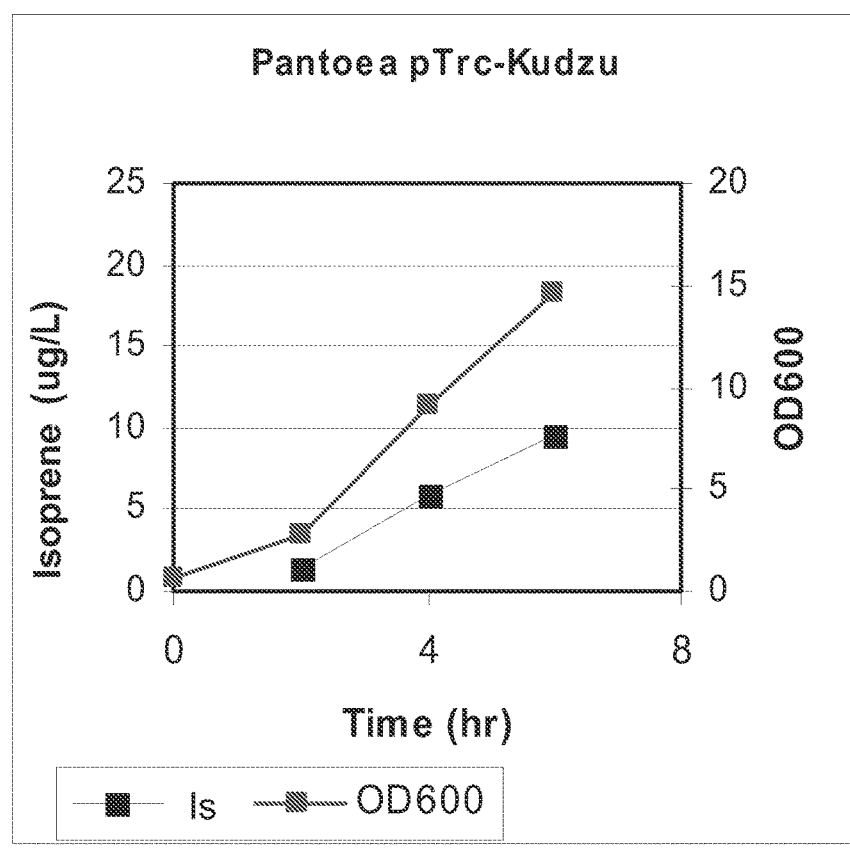
FIG. 10C is a graph showing the production of isoprene in *Panteoa citrea* expressing pTrcKudzu. Grey diamonds represent isoprene synthesis, black squares represent $OD_{600}$.

This experiment was carried out in 14 L bioreactor to monitor isoprene formation from glucose at the desired fermentation, pH 6.7 and temperature 34° C. An inoculum of E. coli strain BL21/ptrcKudzu taken from a frozen vial was prepared in soytone-yeast extract-glucose medium. After the inoculum grew to OD$_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIG. 9.

Example 2

Figure 30:
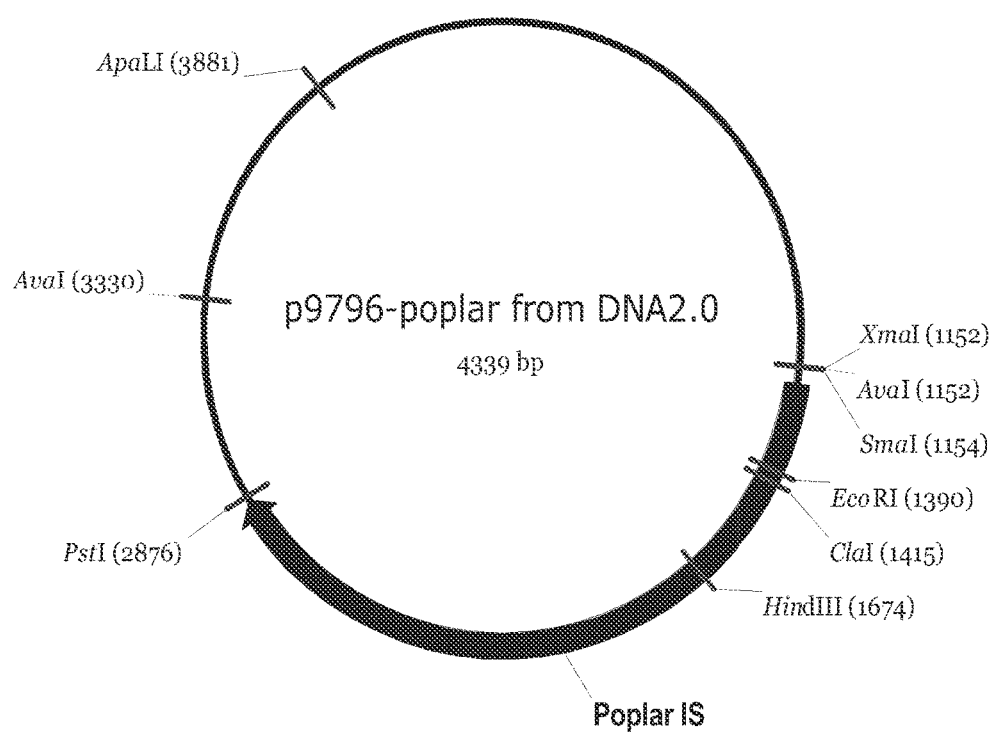
FIG. 30 is a map of p9796-poplar.
Figure 32:
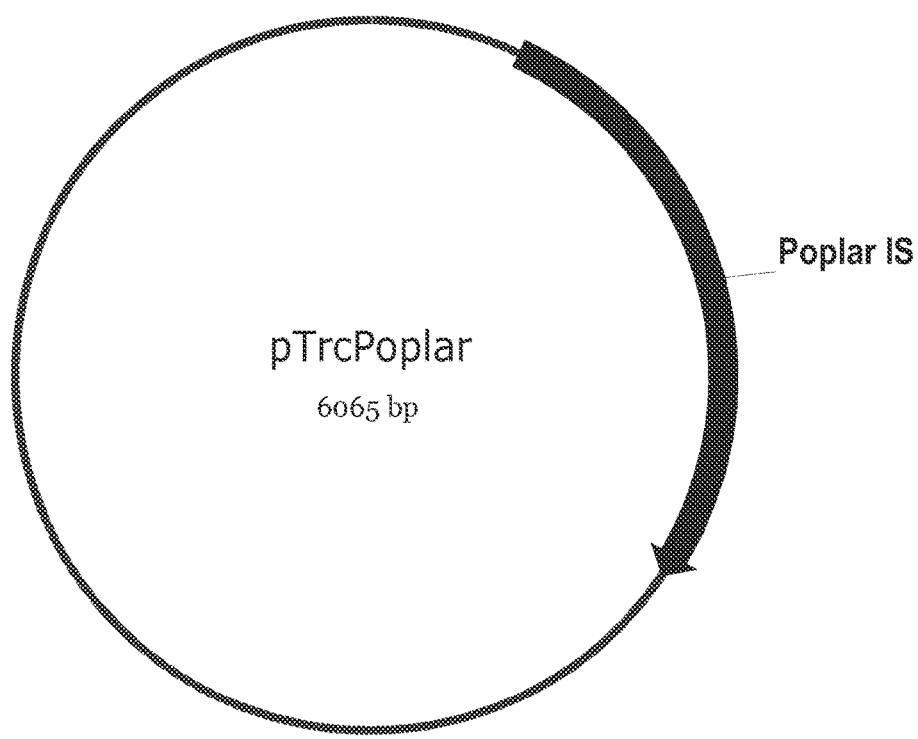
FIG. 32 is a map of pTrcPoplar.

Production of Isoprene in *E. Coli* Expressing Recombinant Poplar Isoprene Synthase The protein sequence for the poplar (*Populus alba*× *Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIGS. 30 and 31; SEQ ID NO:14). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 32 and 33; SEQ ID NO:15), was verified by sequencing.

Example 2B

Demonstration of Isoprene Synthase Activity from Several *Populus* Isoprene Synthases The following isoprene synthases were examined; *Populus alba* (Accession number BAD98243; FIGS. 137A and B; SEQ ID NO:30), *Populus nigra* (Accession number CAL69918; FIGS. 137C and D; SEQ ID NO:31), *Populus tremuloides* (Accession number AAQ16588; FIGS. 137 E, F, and G; SEQ ID NOs:32-33), *Populus trichocarpa* (Accession number ACD70404; FIGS. 137H and I; SEQ ID NO:34), *Populus alba*×*Populus tremula* (Accession number CAJ29303; FIGS. 137J and K; SEQ ID NO:35), and MCM112-Kudzu.

pET24Kudzu (also referred to as MCM112) was constructed as follows: the kudzu isoprene synthase gene was subcloned into the pET24d vector (Novagen) from the pCR2.1 vector (Invitrogen). The kudzu IspS gene was amplified from pTrcKudzu template DNA using primers MCM50 5'-GATCATGCAT TCGCCCTTAG GAGG-TAAAAAAACATGTGTGCGACCTCTTC TCAATT-TACT (SEQ ID NO:52); and MCM53 5'-CGGTCGACG-GATCCCTGCAG TTAGACATAC ATCAGCTG (SEQ ID NO:50). PCR reactions were carried out using Taq DNA Polymerase (Invitrogen), and the resulting PCR product was cloned into pCR2.1-TOPO TA cloning vector (Invitrogen), and transformed into *E. coli* Top10 chemically competent cells (Invitrogen). Transformants were plated on L-agar containing carbenicillin (50 µg/ml) and incubated overnight at 37° C. Five ml Luria Broth cultures containing carbenicillin 50 µg/ml were inoculated with single transformants and grown overnight at 37° C. Five colonies were screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu IspS coding sequence in a pCR2.1 backbone (FIG. 137L). The sequence of MCM93 (SEQ ID NO:36) is shown in FIGS. 137M and N.

The kudzu coding sequence was removed by restriction endonuclease digestion with PciI and BamH1 (Roche) and gel purified using the QIAquick Gel Extraction kit (Qiagen). The pET24d vector DNA was digested with NcoI and BamHI (Roche), treated with shrimp alkaline phosphatase (Roche), and purified using the QIAprep Spin Mini-prep Kit (Qiagen). The kudzu IspS fragment was ligated to the NcoI/BamH1 digested pET24d using the Rapid DNA Ligation Kit (Roche) at a 5:1 fragment to vector ratio in a total volume of 20 µl. A portion of the ligation mixture (5 µl) was transformed into *E. coli* Top 10 chemically competent cells and plated on L agar containing kanamycin (50 µg/ml). The correct transformant was confirmed by sequencing and transformed into chemically competent BL21(λDE3)pLysS cells (Novagen). A single colony was selected after overnight growth at 37° C. on L agar containing kanamycin (50 µg/ml). A map of the resulting plasmid designated as pET24D-Kudzu is shown in FIG. 137O. The sequence of pET24D-Kudzu (SEQ ID NO:37) is shown in FIGS. 137P and Q.

*Escherichia coli* optimized isoprene synthase genes cloned into the pET24a expression vector (Novagen) were purchased from DNA2.0 (Menlo Park, Calif.) for *Populus tremuloides*, *Populus alba*, *Populus nigra* and *Populus trichocarpa*. Genes were synthesized with the chloroplast transit peptide sequence removed, resulting in expression of mature proteins.

The construct for the Kudzu isoprene synthase was used as control in this example. The plasmids were transformed into the *E. coli* expression host BL21(DE3)plysS and transformants were grown in 0.6 ml TM3 medium. The recipe for TM3 medium is as follows: K$_2$HPO$_4$ (13.6 g/l) KH$_2$PO$_4$ (13.6 g/l), MgSO$_4$*7H$_2$O (2 g/L) Citric Acid Monohydrate (2 g/L) Ferric Ammonium Citrate (0.3 g/L) (NH$_4$)$_2$SO$_4$ (3.2 g/L) yeast extract (0.2 g/L) 1 ml of 1000× Trace Elements solution, pH adjusted to 6.8 with ammonium hydroxide qs to volume with sterile DIH$_2$O and filter sterilized with a 0.22 micron filter. The recipe for 1000× Trace Elements solution is as follows: Citric Acids*H$_2$O (40 g/L), MnSO$_4$*H$_2$O (30 g/L), NaCl (10 g/L), FeSO$_4$*7 H$_2$O (1 g/L), CoCl$_2$*6 H$_2$O (1 g/L), ZnSO$_4$*7 H$_2$O (1 g/L), CuSO$_4$*5 H$_2$O (100 mg/L), H$_3$BO$_3$ (100 mg/L), NaMoO$_4$*2 H$_2$O (100 mg/L). Each component was dissolved one at a time in DIH$_2$O, pH adjusted to 3.0 with HCl/NaOH, qs to volume and filter sterilized with a 0.22 micron filter.

The cultures were induced with 400 uM IPTG and growth was continued to OD$_{600}$ of about 5. Aliquots of culture were transferred to a deep well glass plate and wells were sealed with aluminum plate sealer. The plate was incubated at 25° C. for 30 minutes with shaking at 450 rpm. The reactions were heat inactivated by raising the temperature to 70° C. for 5 minutes. Whole cell head space was measured by the GCMS method as described in Example 1, Part II.

$K_m$ values were obtained from cultures grown in similar manner but cells were harvested and lysed by a freeze/thaw lysozyme protocol. A volume of 400 µL of culture was transferred into a new 96-well plate (Perkin Elmer, Catalog No. 6008290) and cells were harvested by centrifugation in a Beckman Coulter Allegra 6R centrifuge at 2500×g. The pellet was resuspended in 200 mL of hypotonic buffer (5 mM $MgCL_2$, 5 mM Tris HCl, 5 mM DTT pH 8.0) and the plate was frozen at −80° C. for a minimum time of 60 minutes. Cell lysate was prepared by thawing the plate and adding 32 mL of isoprene synthase DMAPP assay buffer (57 mM Tris HCl, 19 mM $MgCl_2$, 74 mg/mL DNase I (Sigma Catalog No. DN-25), 2.63×10$^5$ U/mL of ReadyLyse lysozyme solution (Epicentre Catalog No. R1802M), and 5 mg/mL of molecular biology grade BSA. The plate was incubated with shaking at 25° C. for 30 minutes and then placed on ice. DMAPP and lysate were added at desired concentration in a sealed deep well glass block for the whole cell head space assay described above. The reactions were allowed to proceed for 1 hour and then terminated by the heat step described above and head space activity was measured also as described.

In an alternate approach, the activity of the enzymes was measured from cells cultured in 25 mL volume and induced similarly as described above. Cells were harvested by centrifugation and the pellets were lysed by French pressing in buffer consisting of 50% glycerol mixed 1:1 with 20 mM Tris/HCl pH 7.4, 20 mM $MgCl_2$, 200 mM KCl, 1 mM DTT. A lysate volume of 25 uL was assayed for isoprene synthase activity in 2 mL screw cap vials containing 75 uL of assay buffer (66.6 mM Tris/HCl pH 8, 6.66 mM DMAPP, 43 mM, $MgCl_2$). The reaction was incubated for 15 minutes at 30° C. and was quenched by the addition of 100 uL of 250 mM EDTA through the septum of the vial. Isoprene was measured by GC/MS as described in Example 1, Part II.

All methods for the determination of activity showed that the poplar enzyme derived from the pure bred poplars were several-fold higher than the *Populus [alba×tremula]*. FIGS. 138 and 139 showed these results for the whole cell head space assay and the DMAPP assay, respectively, and surprisingly indicate that enzymes from *P. nigra*, *P. tremuloides*, *P. trichocarpa*, and *P. alba* all had significantly higher activity than hybrid [*P. alba×P. tremula*].

The DMAPP assay was performed as follows: a volume of 400 µL of culture was transferred into a new 96-well plate (Perkin Elmer, Catalog No. 6008290) and cells were harvested by centrifugation in a Beckman Coulter Allegra 6R centrifuge at 2500×g. The pellet was resuspended in 200 mL of hypotonic buffer (5 mM $MgCL_2$, 5 mM Tris HCl, 5 mM DTT pH 8.0) and the plate was frozen at −80° C. for a minimum time of 60 minutes. Cell lysate was prepared by thawing the plate and adding 32 mL of isoprene synthase DMAPP assay buffer (57 mM Tris HCl, 19 mM $MgCl_2$, 74 mg/mL DNase I (Sigma Catalog No. DN-25), 2.63×10$^5$ U/mL of ReadyLyse lysozyme solution (Epicentre Catalog No. R1802M), and 5 mg/mL of molecular biology grade BSA. The plate was incubated with shaking at 25° C. for 30 minutes and then placed on ice. For isoprene production an 80 mL aliquot of lysate was transferred to a 96-deep well glass plate (Zinsser Catalog No. 3600600) and 20 mL of a 10 mM DMAPP solution in 100 mM $K_2HPO_4$, pH 8.2 (Cayman Chemical Catalog No. 63180) was added. The plate was sealed with an aluminum plate seal (Beckman Coultor Catalog No. 538619) and incubated with shaking at 30° C. for 60 minutes. The enzymatic reactions were terminated by heating the glass block (70° C. for 5 minutes). The cell head space of each well was quantitatively analyzed as described in Example 1, Part II.

Notably, *P. alba*, *P. tremuloides*, *P. trichocarpa* had higher activity than the isoprene synthase from Kudzu. The enzyme from *P. alba* was expressed with the greatest activity of all enzymes tested. The higher activities observed with the cell lysate compared to the whole cell head space assay was likely due to limitations in DMAPP, the substrate for these enzymes, delivered by the endogenous deoxyxylulose 5-phosphate (DXP) pathway of the cell.

$K_m$ kinetic parameter was measured to be about 2 to 3 mM for all enzymes for which the value was determined.

Example 3

Production of Isoprene in *Panteoa Citrea* Expressing Recombinant Kudzu Isoprene Synthase The pTrcKudzu and pCL-lac Kudzu plasmids described in Example 1 were electroporated into *P. citrea* (U.S. Pat. No. 7,241,587). Trans b) Amplification of the Isoprene Synthase Gene The kudzu isoprene synthase gene was amplified from plasmid pTrcKudzu (SEQ ID NO:2). The gene had been codon optimized for *E. coli* and synthesized by DNA 2.0. The following primers were used:

CF 07-42 (+) Fuse the aprE promoter to kudzu isoprene synthase gene (GTG start codon)
(SEQ ID NO: 55)
5'- TAAAAGGAGAGGGTAAAGAGTGTGTGCGACCTCTTCTCAAT CF 07-45 (-) Fuse the 3' end of kudzu isoprene synthase gene to the terminator
(SEQ ID NO: 56)
5'- CCAAGGCCGGTTTTTTTTAGACATACATCAGCTGGTTAATC c) Amplification of the Transcription Terminator The terminator from the alkaline serine protease of *Bacillus amyliquefaciens* was amplified from a previously sequenced plasmid pJHPms382 using the following primers:

CF 07-44 (+) Fuse the 3' end of kudzu isoprene synthase to the terminator
(SEQ ID NO: 57)
5'- GATTAACCAGCTGATGTATGTCTAAAAAAAACCGGCCTTGG CF 07-46 (-) End of B. amyliquefaciens terminator (BamHI)
(SEQ ID NO: 58)
5'- GACATGACGGATCCGATTACGAATGCCGTCTC The kudzu fragment was fused to the terminator fragment using PCR with the following primers:

CF 07-42 (+) Fuse the aprE promoter to kudzu isoprene synthase gene (GTG start codon)
(SEQ ID NO: 55)
5'- TAAAAGGAGAGGGTAAAGAGTGTGTGCGACCTCTTCTCAAT CF 07-46 (-) End of B. amyliquefaciens terminator (BamHI)
(SEQ ID NO: 58)
5'- GACATGACGGATCCGATTACGAATGCCGTCTC The kudzu-terminator fragment was fused to the promoter fragment using PCR with the following primers:

CF 797 (+) Start aprE promoter MfeI
(SEQ ID NO: 53)
5'- GACATCAATTGCTCCATTTTCTTCTGCTATC CF 07-46 (-) End of B. amyliquefaciens terminator (BamHI)
(SEQ ID NO: 58)
5'- GACATGACGGATCCGATTACGAATGCCGTCTC The fusion PCR fragment was purified using a Qiagen kit and digested with the restriction enzymes MfeI and BamHI. This digested DNA fragment was gel purified using a Qiagen kit and ligated to a vector known as pBS19, which had been digested with EcoRI and BamHI and gel purified.

Figure 52:
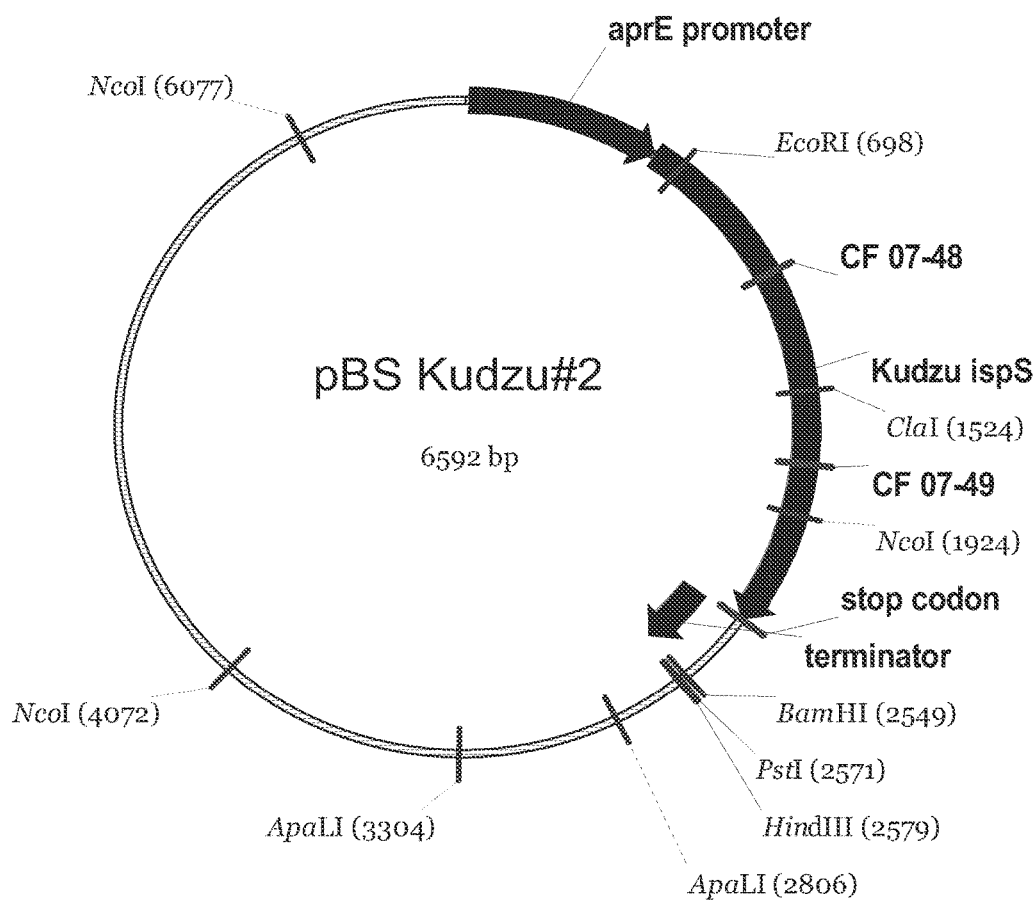
FIG. 52 is a map of pBS Kudzu #2.

The ligation mix was transformed into *E. coli* Top 10 cells and colonies were selected on LA+50 carbenicillin plates. A total of six colonies were chosen and grown overnight in LB+50 carbenicillin and then plasmids were isolated using a Qiagen kit. The plasmids were digested with EcoRI and BamHI to check for inserts and three of the correct plasmids were sent in for sequencing with the following primers:

CF 149 (+) EcoRI start of aprE promoter
(SEQ ID NO: 59)
5'- GACATGAATTCCTCCATTTTCTTCTGC CF 847 (+) Sequence in pXX 049 (end of aprE promoter)
(SEQ ID NO: 60)
5'- AGGAGAGGGTAAAGAGTGAG CF 07-45 (-) Fuse the 3' end of kudzu isoprene synthase to the terminator
(SEQ ID NO: 56)
5'- CCAAGGCCGGTTTTTTTTAGACATACATCAGCTGGTTAATC CF 07-48 (+) Sequencing primer for kudzu isoprene synthase
(SEQ ID NO: 61)
5'- CTTTTCCATCACCCACCTGAAG CF 07-49 (+) Sequencing in kudzu isoprene synthase
(SEQ ID NO: 62)
5'- GGCGAAATGGTCCAACAACAAAATTATC The plasmid designated pBS Kudzu #2 (FIGS. 52 and 12; SEQ ID NO:5) was correct by sequencing and was transformed into BG 3594 comK, a *Bacillus subtilis* host strain. Selection was done on LA+5 chloramphenicol plates. A transformant was chosen and struck to single colonies on LA+5 chloramphenicol, then grown in LB+5 chloramphenicol until it reached an $OD_{600}$ of 1.5. It was stored frozen in a vial at −80° C. in the presence of glycerol. The resulting strain was designated CF 443.

II. Production of Isoprene in Shake Flasks Containing *B. Subtilis* Cells Expressing Recombinant Isoprene Synthase.

Figure 11:
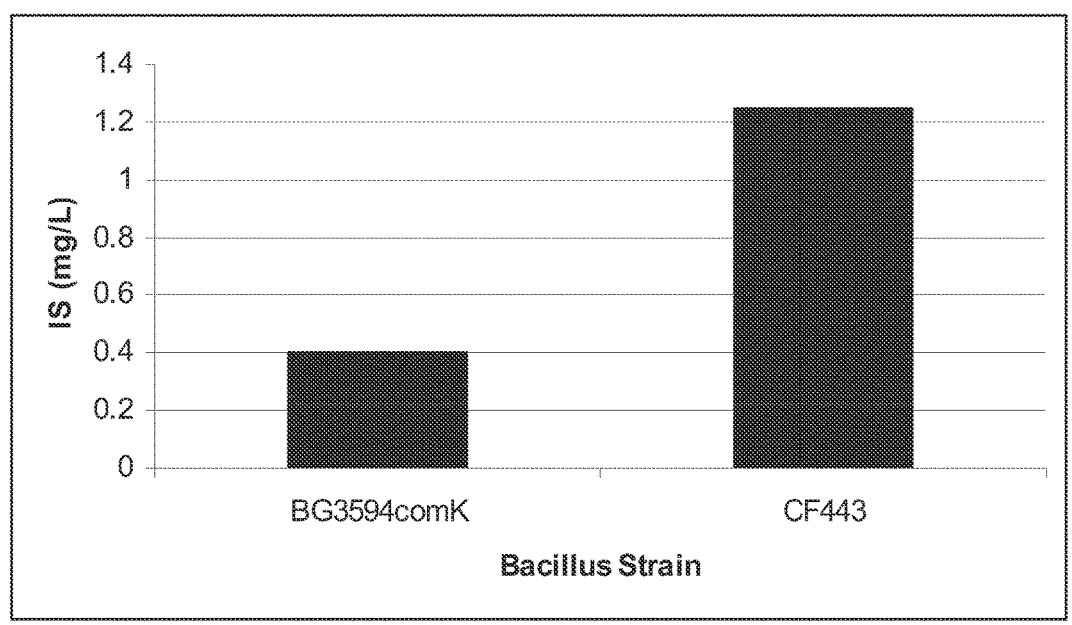
FIG. 11 is a graph showing the production of isoprene in *Bacillus subtilis* expressing recombinant isoprene synthase. BG3594comK is a *B. subtilis* strain without plasmid (native isoprene production). CF443 is *B. subtilis* strain BG3594comK with pBSKudzu (recombinant isoprene production). IS on the y-axis indicates isoprene.

Overnight cultures were inoculated with a single colony of CF 443 from a LA+Chlorphenicol (Cm, 25 µg/ml). Cultures were grown in LB+Cm at 37° C. with shaking at 200 rpm. These overnight cultures (1 ml) were used to inoculate 250 ml baffled shake flasks containing 25 ml Grants II media and chloramphenicol at a final concentration of 25 µg/ml. Grants II Media recipe was 10 g soytone, 3 ml 1M $K_2HPO_4$, 75 g glucose, 3.6 g urea, 100 ml 10×MOPS, q.s. to 1 L with $H_2O$, pH 7.2; 10×MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100× micronutrients recipe was 1.47 g $CaCl_2*2H_2O$, 0.4 g $FeSO_4*7H_2O$, 0.1 g $MnSO_4*H_2O$, 0.1 g $ZnSO_4*H_2O$, 0.05 g $CuCl_2*2H_2O$, 0.1 g $CoCl_2*6H_2O$, 0.1 g $Na_2MoO_4.2H_2O$, q.s. to 1 L with $H_2O$, Shake flasks were incubated at 37° C. and samples were taken at 18, 24, and 44 hours. At 18 hours the headspaces of $CF_{443}$ and the control strain were sampled. This represented 18 hours of accumulation of isoprene. The amount of isoprene was determined by gas chromatography as described in Example 1. Production of isoprene was enhanced significantly by expressing recombinant isoprene synthase (FIG. 11).

III. Production of Isoprene by CF443 in 14 L Fermentation.

Figure 53A:
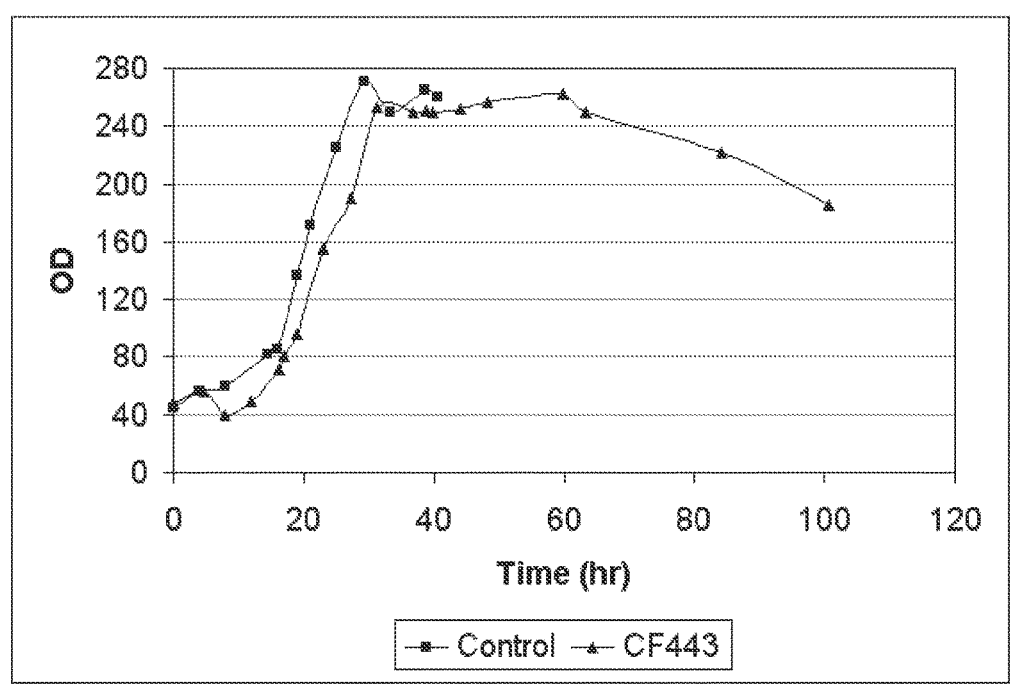
FIG. 53A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent CF443, *Bacillus* strain BG3594comK with pBSKudzu (recombinant isoprene production).
Figure 53B:
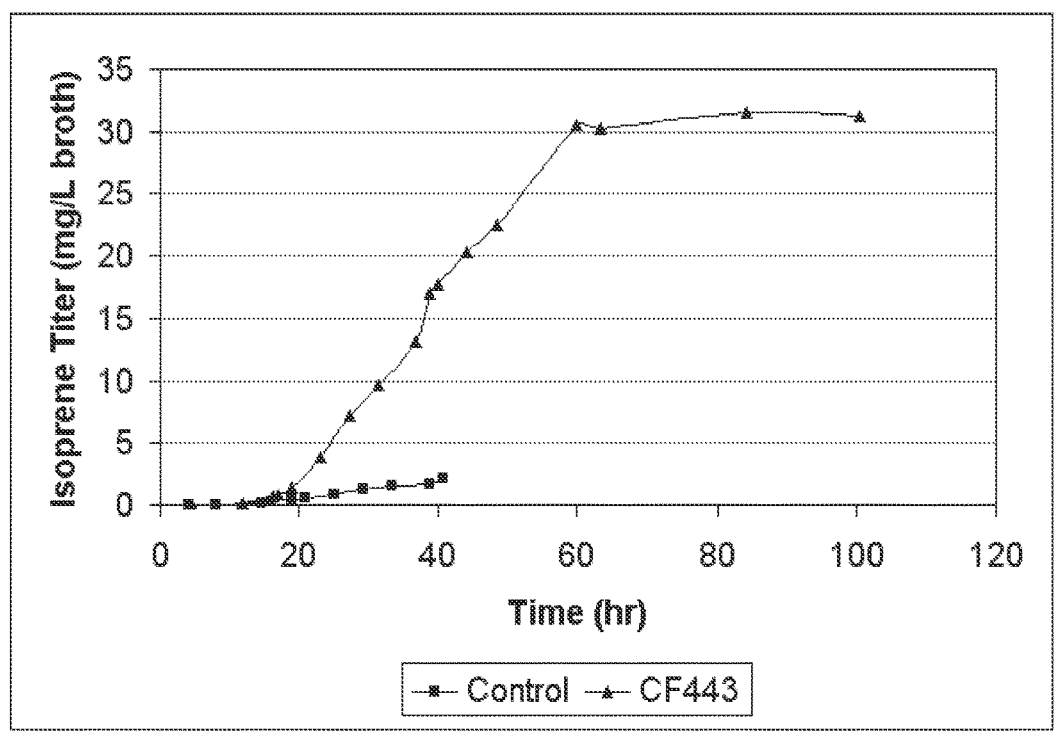
FIG. 53B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent CF443, *Bacillus* strain BG3594comK with pBSKudzu (recombinant isoprene production).

Large scale production of isoprene from *B. subtilis* containing the recombinant kudzu isoprene synthase gene on a replication plasmid was determined from a fed-batch culture. *Bacillus* strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, D0%, airflow, and pressure were monitored throughout the entire process. The DO % is maintained above 20. Samples were taken over the time course of 36 hours and analyzed for cell growth ($OD_{550}$) and isoprene production. Results of these experiments are presented in FIGS. 53A and 53B.

IV. Integration of the Kudzu Isoprene Synthase (ispS) in *B. Subtilis*.

The kudzu isoprene synthase gene was cloned in an integrating plasmid (pJH101-cmpR) under the control of the aprE promoter. Under the conditions tested, no isoprene was detected.

Example 5

Production of Isoprene in *Trichoderma*

I. Construction of Vectors for Expression of the Kudzu Isoprene Synthase in *Trichoderma Reesei*.

The *Yarrowia lipolytica* codon-optimized kudzu IS gene was synthesized by DNA 2.0 (SEQ ID NO:6) (FIG. 13). This plasmid served as the template for the following PCR amplification reaction: 1 µl plasmid template (20 ng/ul), 1 µl Primer EL-945 (10 uM) 5'-GCTTATGGATCCTCTAGAC-TATTACACGTACATCAATTGG (SEQ ID NO:63), 1 µl Primer EL-965 (10 uM) 5'-CACCATGTGTGCAACCTC-CTCCCAGTTTAC (SEQ ID NO:64), 1 µl dNTP (10 mM), 5 pJ 10×PfuUltra II Fusion HS DNA Polymerase Buffer, 1 pJ PfuUltra II Fusion HS DNA Polymerase, 40 pJ water in a total reaction volume of 50 µl. The forward primer contained an additional 4 nucleotides at the 5'-end that did not correspond to the *Y. lipolytica* codon-optimized kudzu isoprene synthase gene, but was required for cloning into the pENTR/D-TOPO vector. The reverse primer contained an additional 21 nucleotides at the 5'-end that did not correspond to the *Y. lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the *Y. lipolytica* codon-optimized kudzu isoprene synthase gene.

The PCR product was then cloned using the TOPO pENTR/D-TOPO Cloning Kit following manufacturer's protocol: 1 µl PCR reaction, 1 µl Salt solution, 1 µl TOPO pENTR/D-TOPO vector and 3 µl water in a total reaction volume of 6 µl. The reaction was incubated at room temperature for 5 minutes. One microliter of TOPO reaction was transformed into TOP10 chemically competent *E. coli* cells.

The transformants were selected on LA+50 µg/ml kanamycin plates. Several colonies were picked and each was inoculated into a 5 ml tube containing LB+50 µg/ml kanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid, encoding a *Y. lipolytica* codon-optimized kudzu isoprene synthase gene, was used for Gateway Cloning into a custom-made pTrex3g vector. Construction of pTrex3g is described in WO 2005/001036 A2. The reaction was performed following manufacturer's protocol for the Gateway LR Clonase II Enzyme Mix Kit (Invitrogen): 1 µl *Y. lipolytica* codon-optimized kudzu isoprene synthase gene pENTR/D-TOPO donor vector, 1 µl pTrex3g destination vector, 6 µl TE buffer, pH 8.0 in a total reaction volume of 8 µl. The reaction was incubated at room temperature for 1 hour and then 1 µl proteinase K solution was added and the incubation continued at 37° C. for 10 minutes. Then 1 µl of reaction was transformed into TOP10 chemically competent *E. coli* cells. The transformants were selected on LA+50 µg/ml carbenicillin plates. Several colonies were picked and each was inoculated into a 5 ml tube containing LB+50 µg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Figure 14:
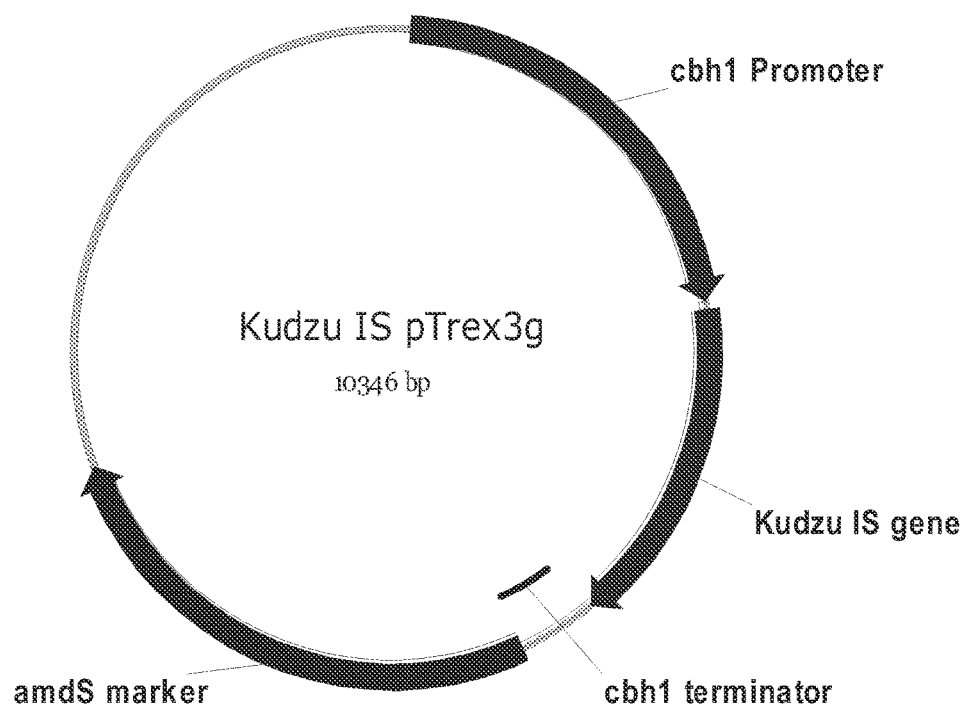
FIG. 14 is a map of pTrex3g comprising a kudzu isoprene synthase gene codon-optimized for expression in *Yarrowia*.

Biolistic transformation of *Y. lipolytica* codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2). Isolation of stable transformants and shake flask evaluation was performed using protocol listed in Example 11 of patent publication WO 2005/001036 A2.

II. Production of Isoprene in Recombinant Strains of *T. Reesei*.

One ml of 15 and 36 hour old cultures of isoprene synthase transformants described above were transferred to head space vials. The vials were sealed and incubated for 5 hours at 30° C. Head space gas was measured and isoprene was identified by the method described in Example 1. Two of the transformants showed traces of isoprene. The amount of isoprene could be increased by a 14 hour incubation. The two positive samples showed isoprene at levels of about 0.5 µg/L for the 14 hour incubation. The untransformed control showed no detectable levels of isoprene. This experiment shows that *T. reesei* is capable of producing isoprene from endogenous precursor when supplied with an exogenous isoprene synthase.

Example 6

Production of Isoprene in *Yarrowia*

I. Construction of Vectors for Expression of the Kudzu Isoprene Synthase in *Yarrowia Lipolytica*.

The starting point for the construction of vectors for the expression of the kudzu isoprene synthase gene in *Yarrowia lipolytica* was the vector pSPZ1(MAP29Spb). The complete sequence of this vector (SEQ ID NO:7) is shown in FIG. 15.

The following fragments were amplified by PCR using chromosomal DNA of a *Y. lipolytica* strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

ICL1 3
(SEQ ID NO: 65)
5'- GGTGAATTCAGTCTACTGGGGATTCCCAAATCTATATAC
TGCAGGTGAC

ICL1 5
(SEQ ID NO: 66)
5'- GCAGGTGGGAAACTATGCACTCC

XPR 3
(SEQ ID NO: 67)
5'- CCTGAATTCTGTTGGATTGGAGGATTGGATAGTGGG

XPR 5
(SEQ ID NO: 68)
5'- GGTGTCGACGTACGGTCGAGCTTATTGACC

XPRT3
(SEQ ID NO: 69)
5'- GGTGGGCCCGCATTTTGCCACCTACAAGCCAG

XPRT 5
(SEQ ID NO: 70)
5'- GGTGAATTCTAGAGGATCCCAACGCTGTTGCCTACAACGG

Y18S3
(SEQ ID NO: 71)
5'- GGTGCGGCCGCTGTCTGGACCTGGTGAGTTTCCCCG

Y18S 5
(SEQ ID NO: 72)
5'- GGTGGGCCCATTAAATCAGTTATCGTTTATTTGATAG

YURA3
(SEQ ID NO: 73)
5'- GGTGACCAGCAAGTCCATGGGTGGTTTGATCATGG

YURA 50
(SEQ ID NO: 74)
5'- GGTGCGGCCGCCTTTGGAGTACGACTCCAACTATG

YURA 51
(SEQ ID NO: 75)
5'- GCGGCCGCAGACTAAATTTATTTCAGTCTCC

For PCR amplification the PfuUltraII polymerase (Stratagene), supplier-provided buffer and dNTPs, 2.5 μM primers and the indicated template DNA were used as per the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Figure 18B:
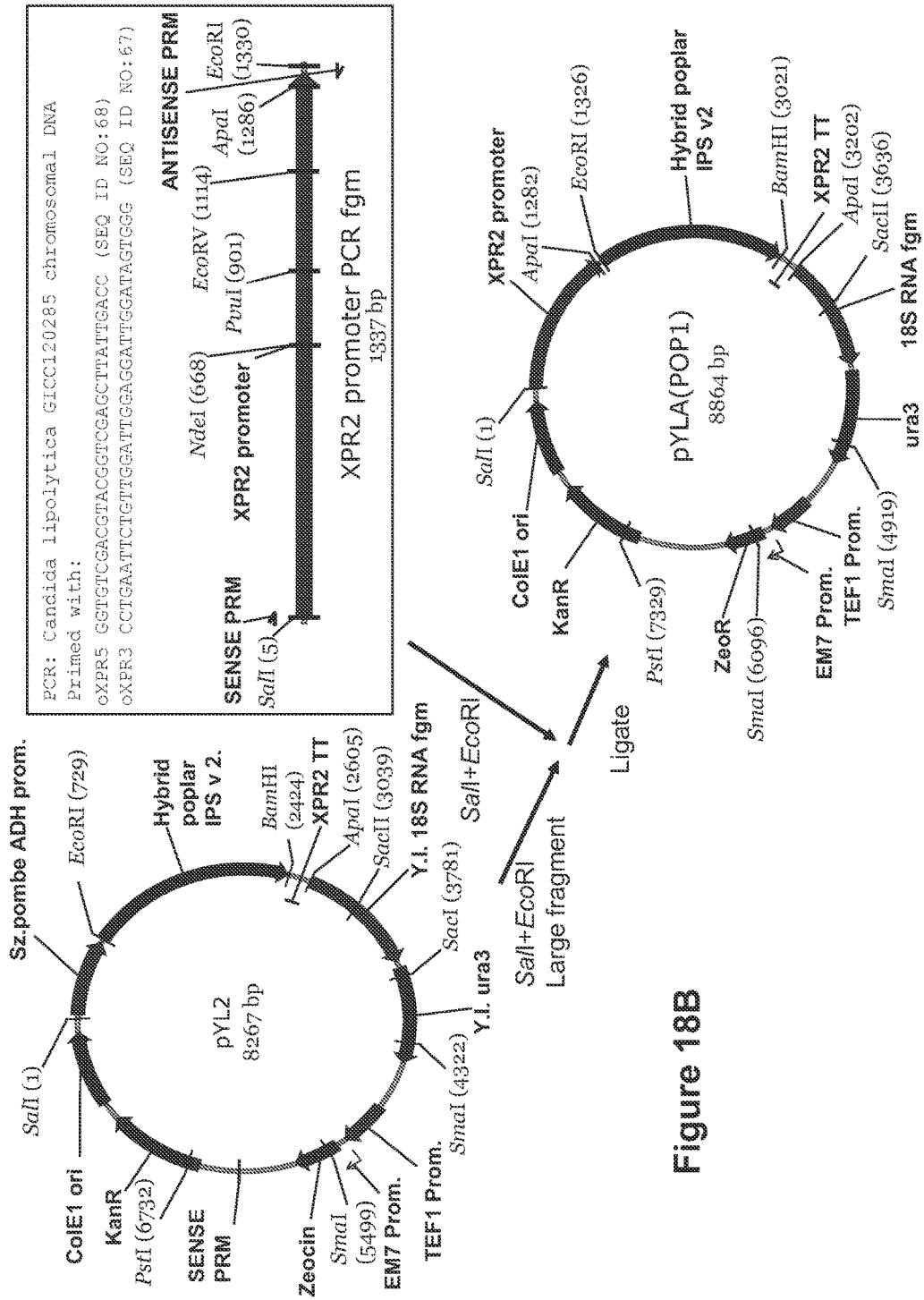
FIG. 18B shows a schematic outlining construction of the vector pYLA(POP1) (primer XPR5=SEQ ID NO:68 and primer XPR3=SEQ ID NO:67).
Figure 18C:
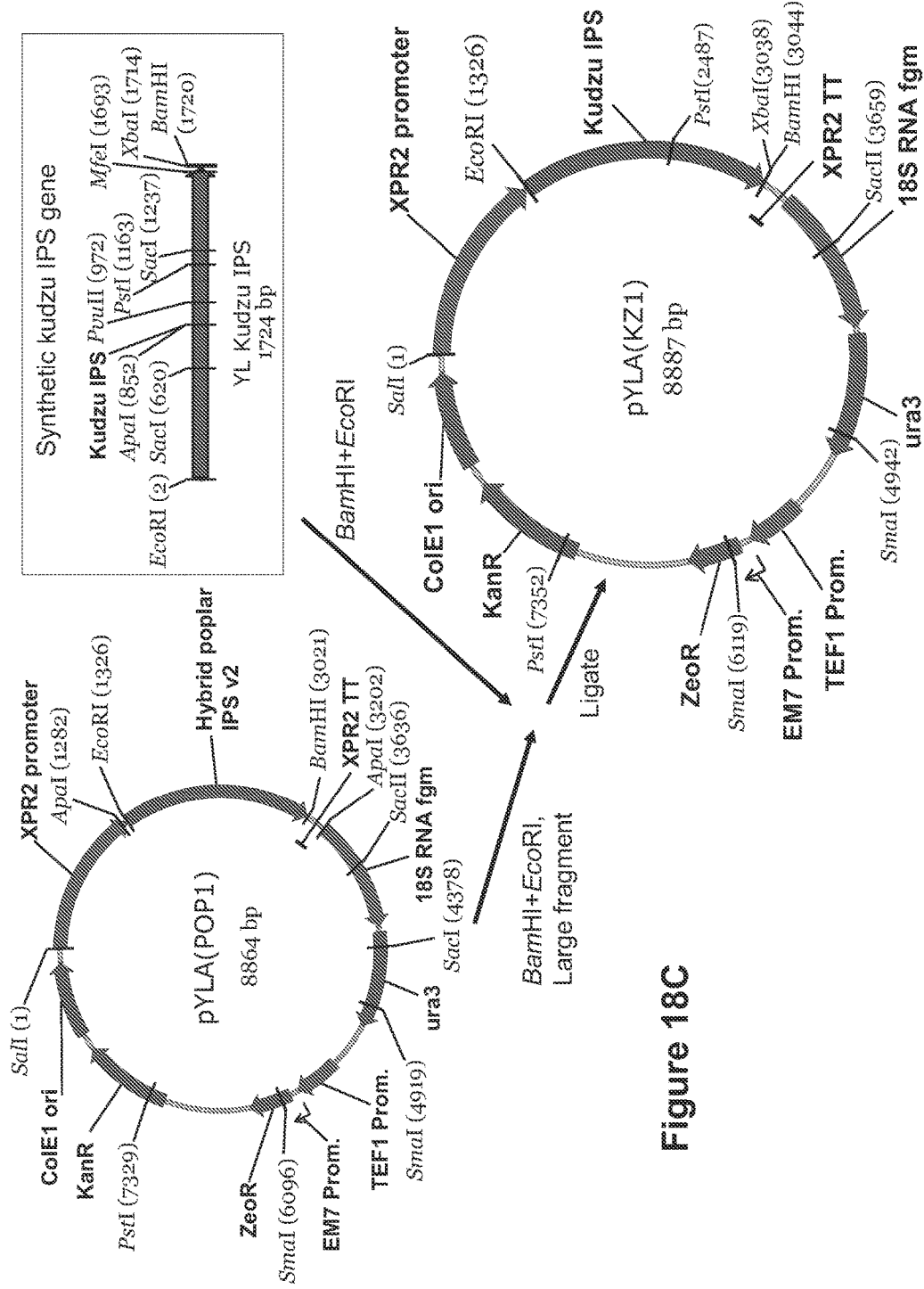
FIG. 18C shows a schematic outlining construction of the vector pYLA(KZ1)
Figure 18E:
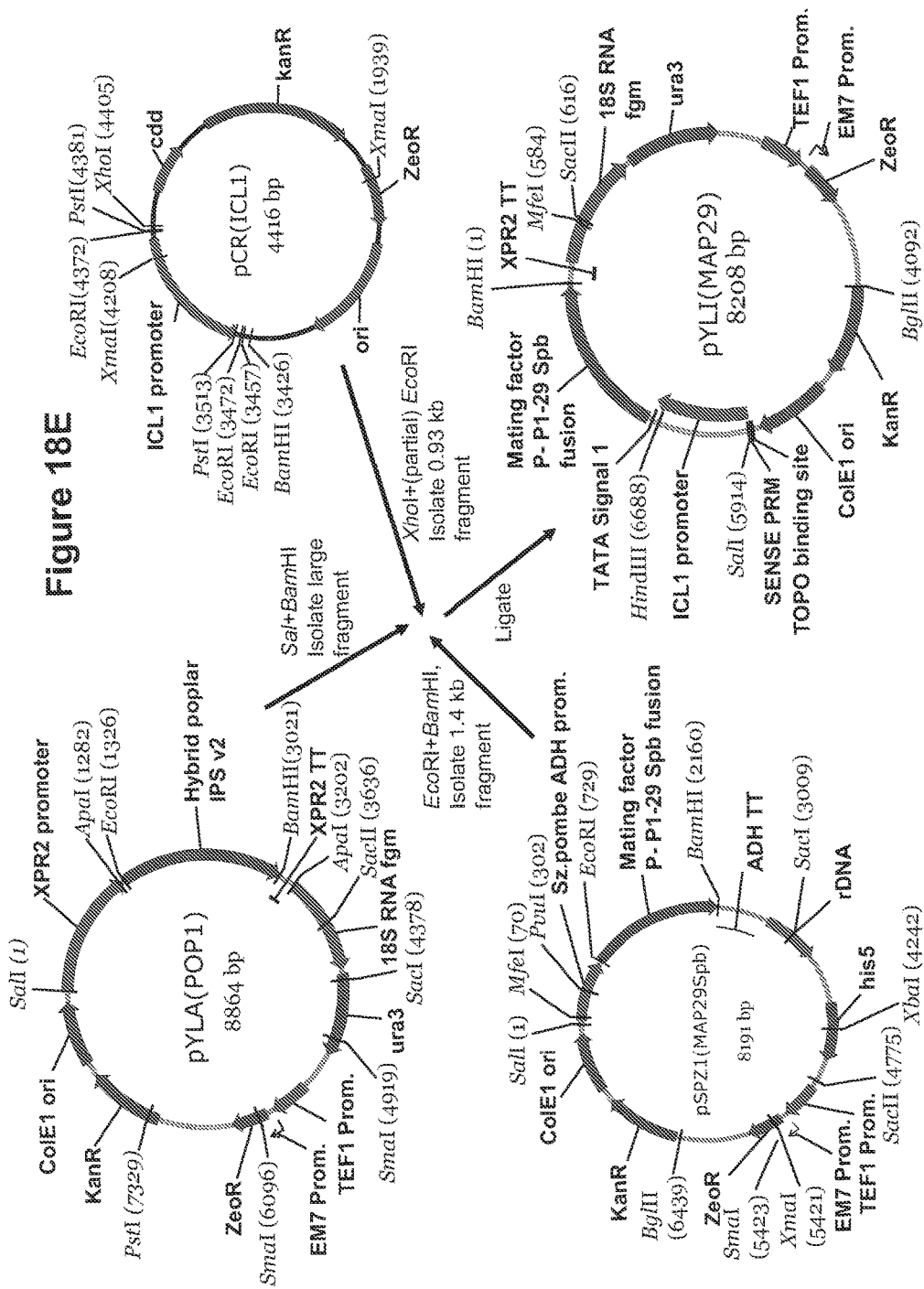
FIG. 18E shows a schematic outlining construction of the vector pYLI(MAP29)
Figure 18F:
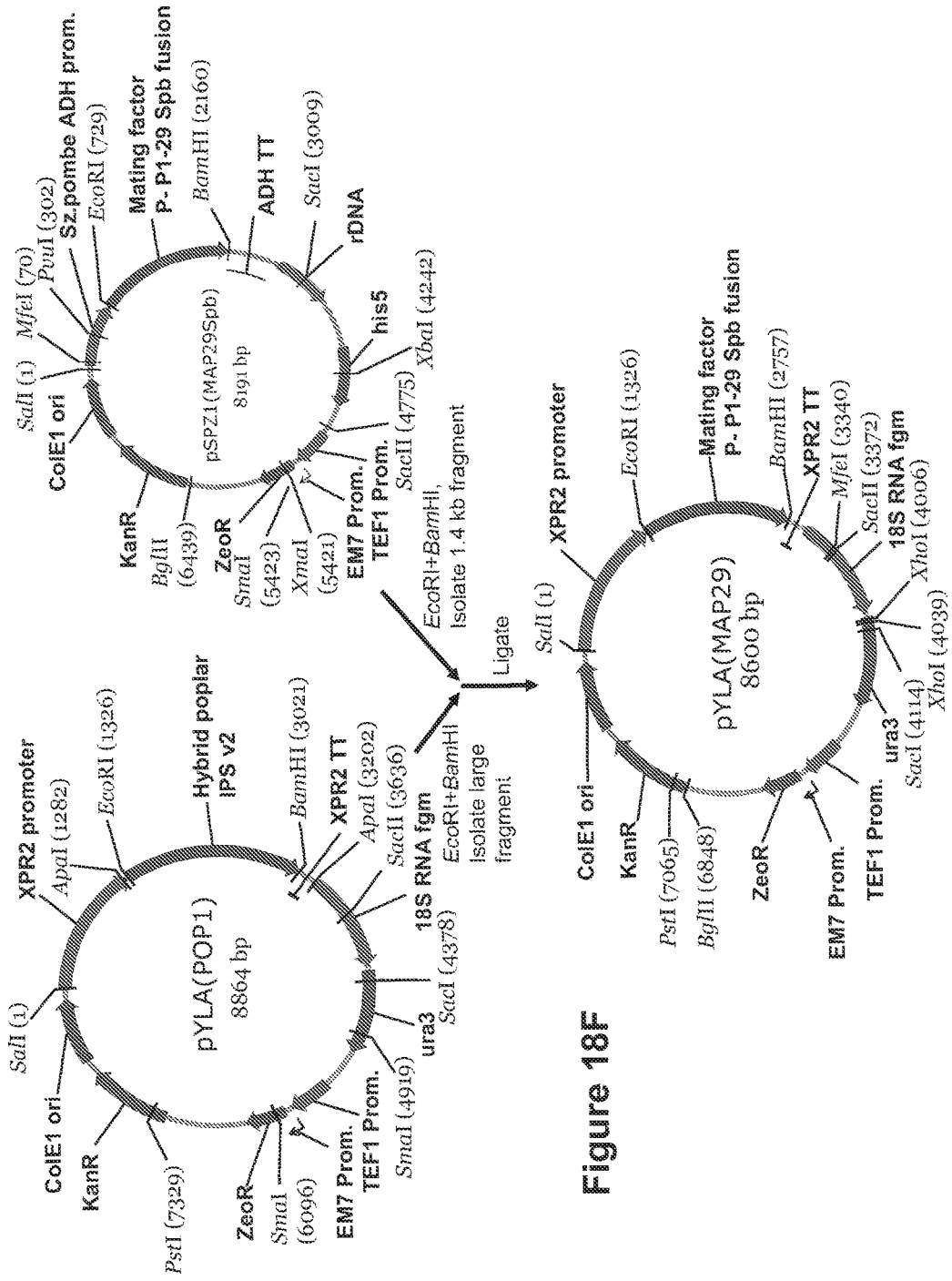
FIG. 18F shows a schematic outlining construction of the vector pYLA(MAP29)

Synthetic DNA molecules encoding the kudzu isoprene synthase gene, codon-optimized for expression in *Yarrowia*, was obtained from DNA 2.0 (FIG. 16; SEQ ID NO:8). Full detail of the construction scheme of the plasmids pYLA (KZ1) and pYLI(KZ1) carrying the synthetic kudzu isoprene synthase gene under control of XPR2 and ICL1 promoters respectively is presented in FIG. 18. Control plasmids in which a mating factor gene (MAP29) is inserted in place of an isoprene synthase gene were also constructed (FIGS. 18E and 18F).

A similar cloning procedure can be used to express a poplar (*Populus alba*×*Populus tremula*) isoprene synthase gene. The sequence of the poplar isoprene is described in Miller B. et al. (2001) *Planta* 213, 483-487 and shown in FIG. 17 (SEQ ID NO:9). A construction scheme for the generation of the plasmids pYLA(POP1) and pYLI(POP1) carrying synthetic poplar isoprene synthase gene under control of XPR2 and ICL1 promoters respectively is presented in FIGS. 18A and B.

II. Production of Isoprene by Recombinant Strains of *Y. Lipolytica*.

Vectors pYLA(KZ1), pYLI(KZ1), pYLA(MAP29) and pYLI(MAP29) were digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred μl aliquots of the cell suspension were mixed with linearized plasmid DNA solution (10-20 μg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Figure 20A:
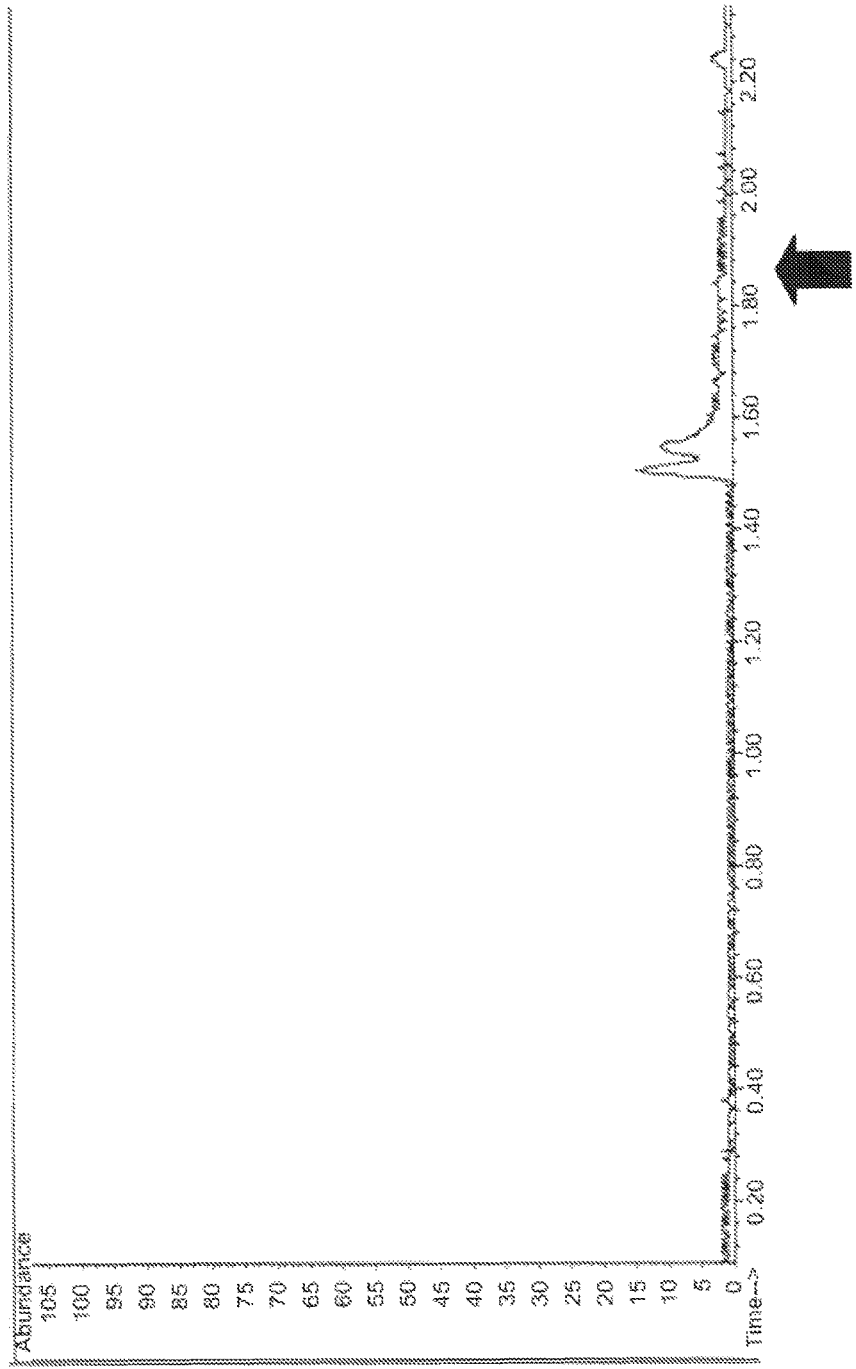
FIGS. 20A-B show graphs representing results of the GC-MS analysis of isoprene production by recombinant *Y. lipolytica* strains without (FIG. 20A) or with (FIG. 20B) a kudzu isoprene synthase gene. The arrows indicate the elution time of the authentic isoprene standard.
Figure 20B:
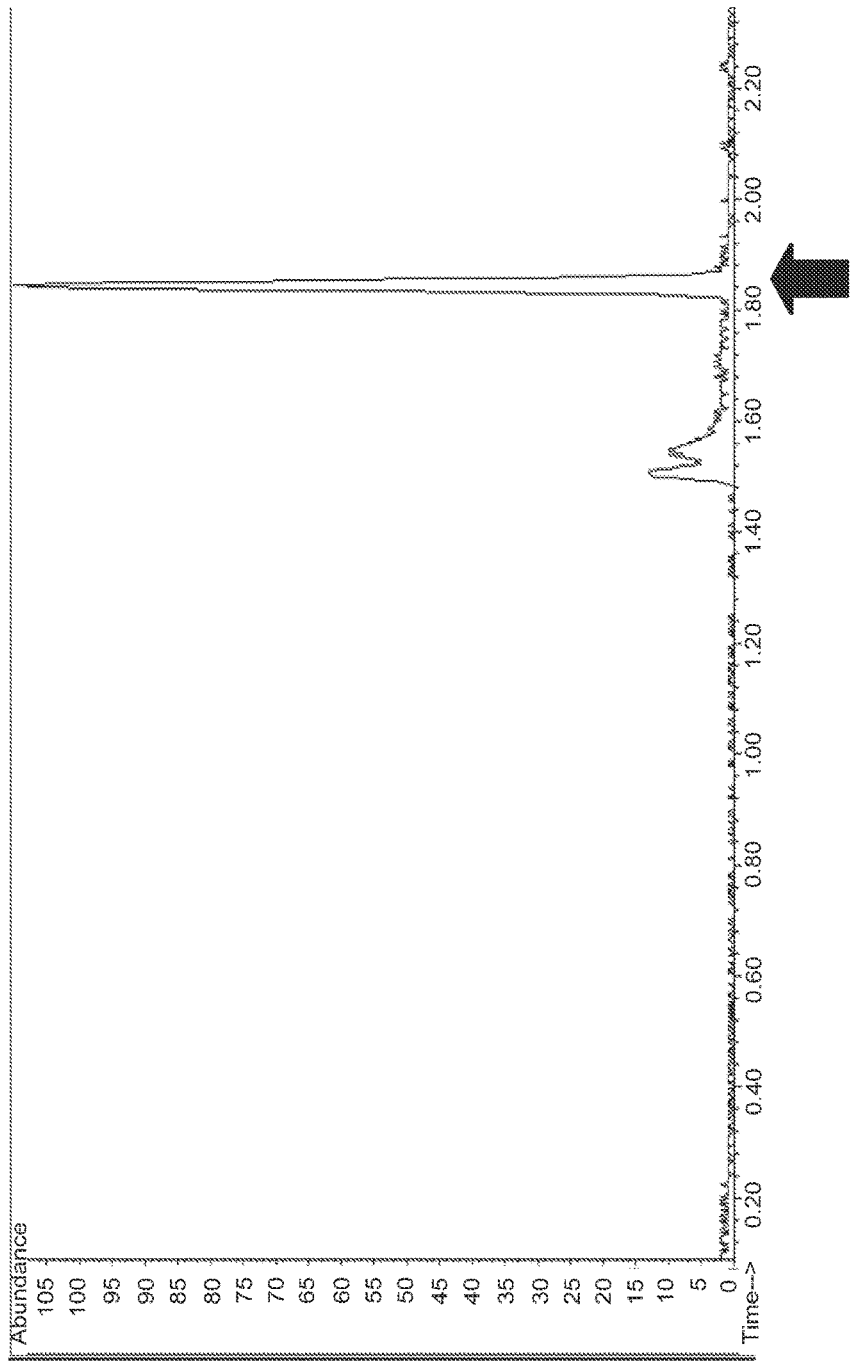

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 1. All transformants obtained with pYLA(KZ1) and pYLI(KZ1) produced readily detectable amounts of isoprene (0.5 μg/L to 1 μg/L, FIG. 20). No isoprene was detected in the headspace of the control strains carrying phytase gene instead of an isoprene synthase gene.

Example 7

Production of Isoprene in *E. Coli* Expressing Kudzu Isoprene Synthase and Idi, or dxs, or idi and dxs I. Construction of Vectors Encoding Kudzu Isoprene Synthase and idi, or dxs, or idi and dxs for the Production of Isoprene in *E. Coli*.

i) Construction of pTrcKudzuKan

Figure 34:
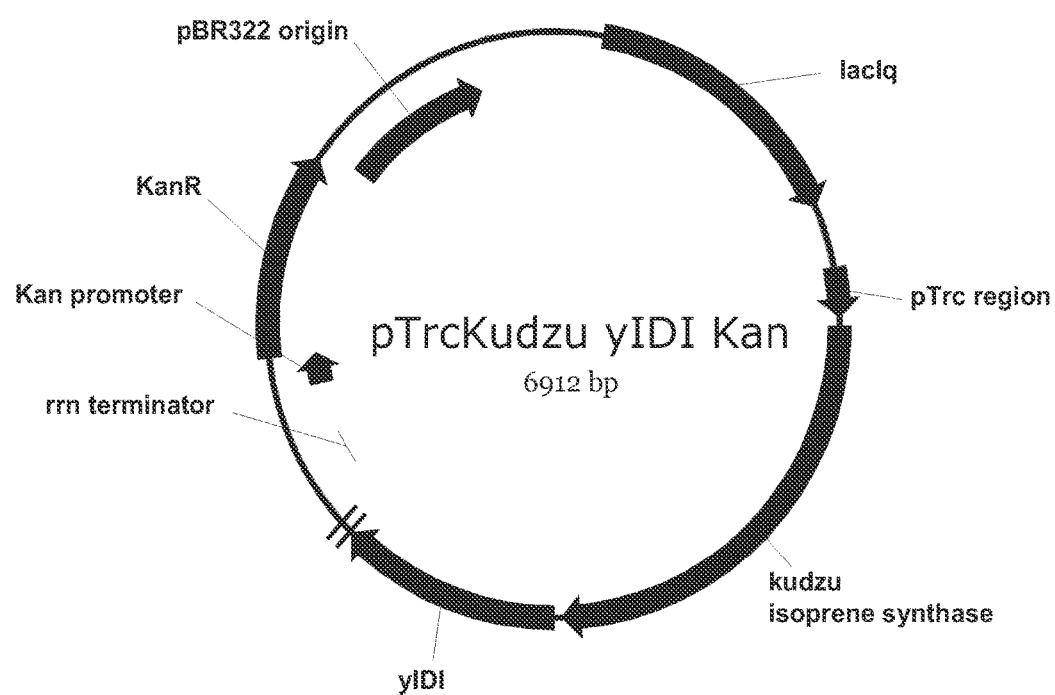
FIG. 34 is a map of pTrcKudzu yIDI Kan.

The bla gene of pTrcKudzu (described in Example 1) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the kan$^r$ gene which had been PCR amplified from pCR-Blunt-II-TOPO using primers MCM22 5'-GATCAAGCTTAACCGGAATTGCCAGCTG (SEQ ID NO:76) and MCM23 5'-GATCCGATCGTCAGAAGAACTCGTCAAGAAGGC (SEQ ID NO:77), digested with HindIII and PvuI, and end-filled. A transformant carrying a plasmid conferring kanamycin resistance (pTrcKudzuKan) was selected on LA containing kanamycin 50 μg/ml.

ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATG-CATCGCCCTTAGGAGGTAAAAAAAAATGAC (SEQ ID NO:78) and PstI-YIDI 1 R 5'-CCTTCTGCAG-GACGCGTTGTTATAGC (SEQ ID NO:79); and the template was *S. cerevisiae* genomic DNA. The PCR product was digested with NsiI and PstI and gel purified prior to ligation. The ligation mixture was transformed into chemically competent TOP10 cells and selected on LA containing 50 µg/ml kanamycin. Several transformants were isolated and sequenced and the resulting plasmid was called pTrcKudzu-yIDI(kan) (FIGS. 34 and 35; SEQ ID NO:16).

iii) Construction of pTrcKudzu DXS Kan

Figure 21:
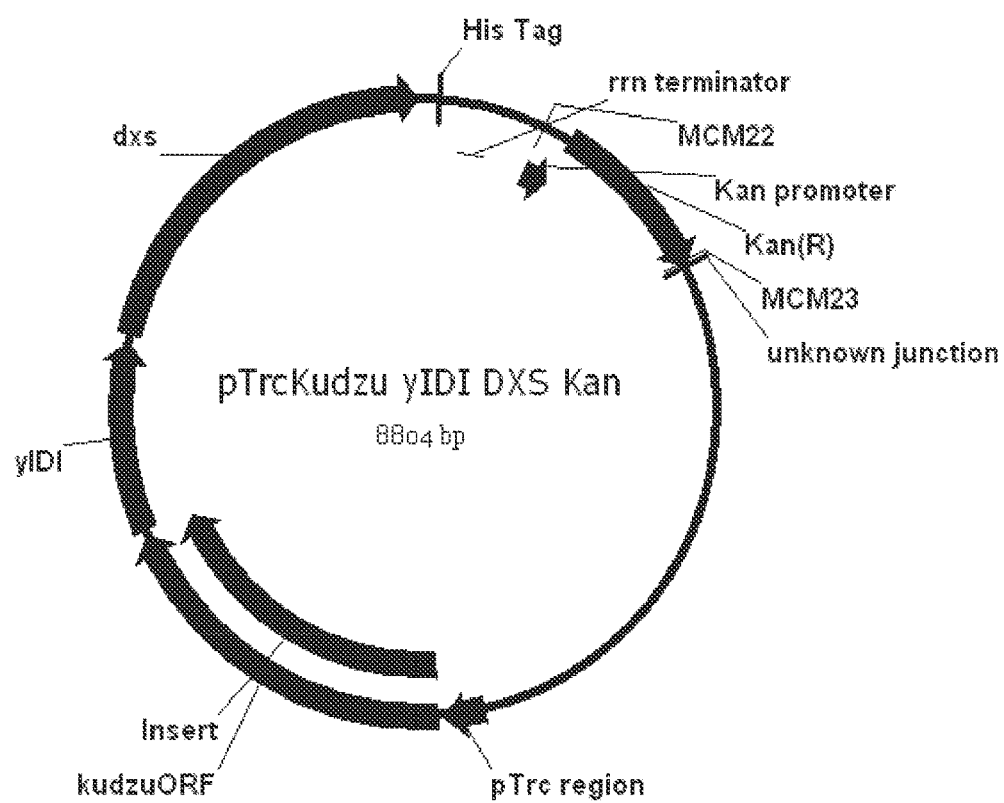
FIG. 21 is a map of pTrcKudzu yIDI DXS Kan.
Figure 36:
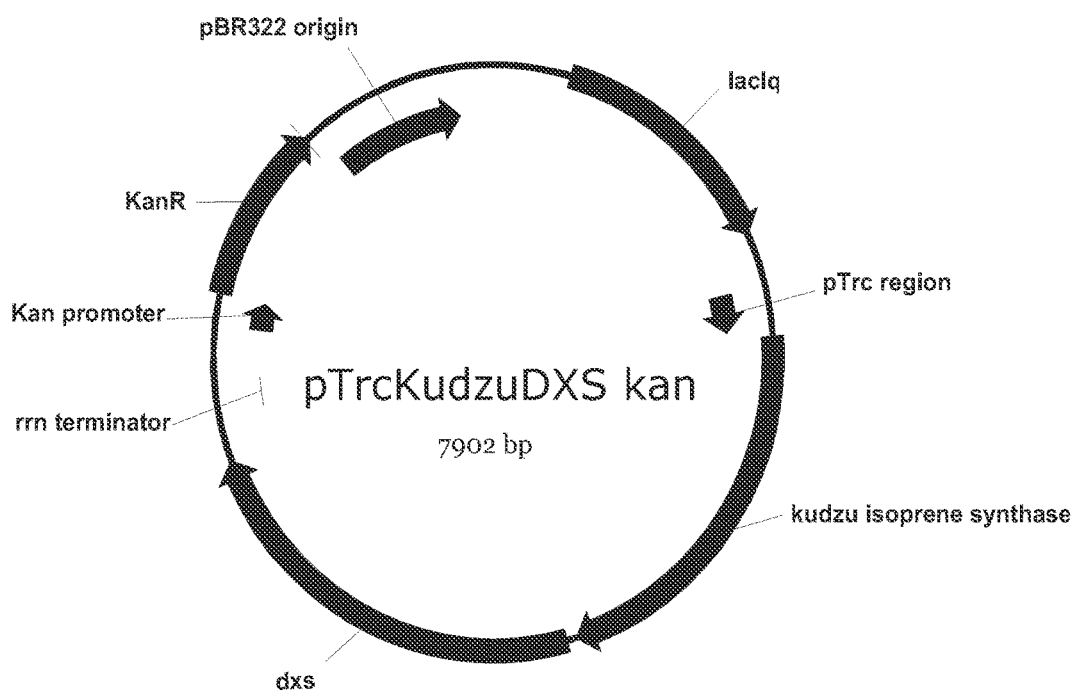
FIG. 36 is a map of pTrcKudzuDXS Kan.
Figure 38:
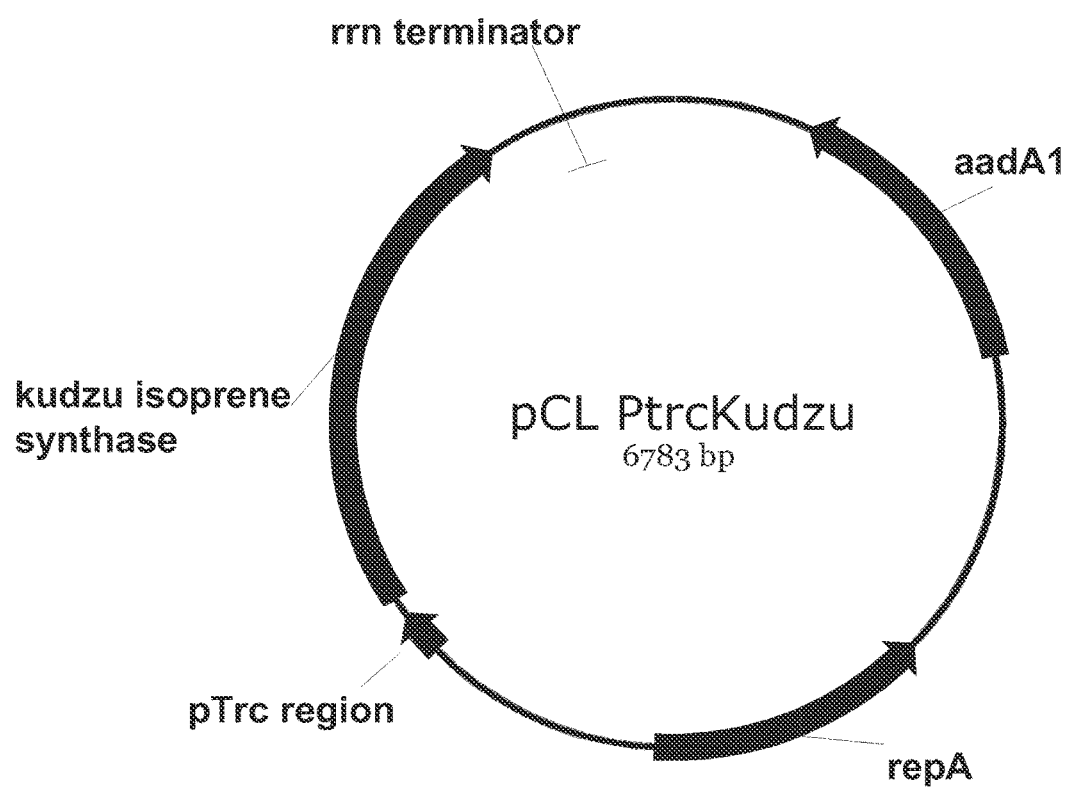
FIG. 38 is a map of pCL PtrcKudzu.
Figure 40:
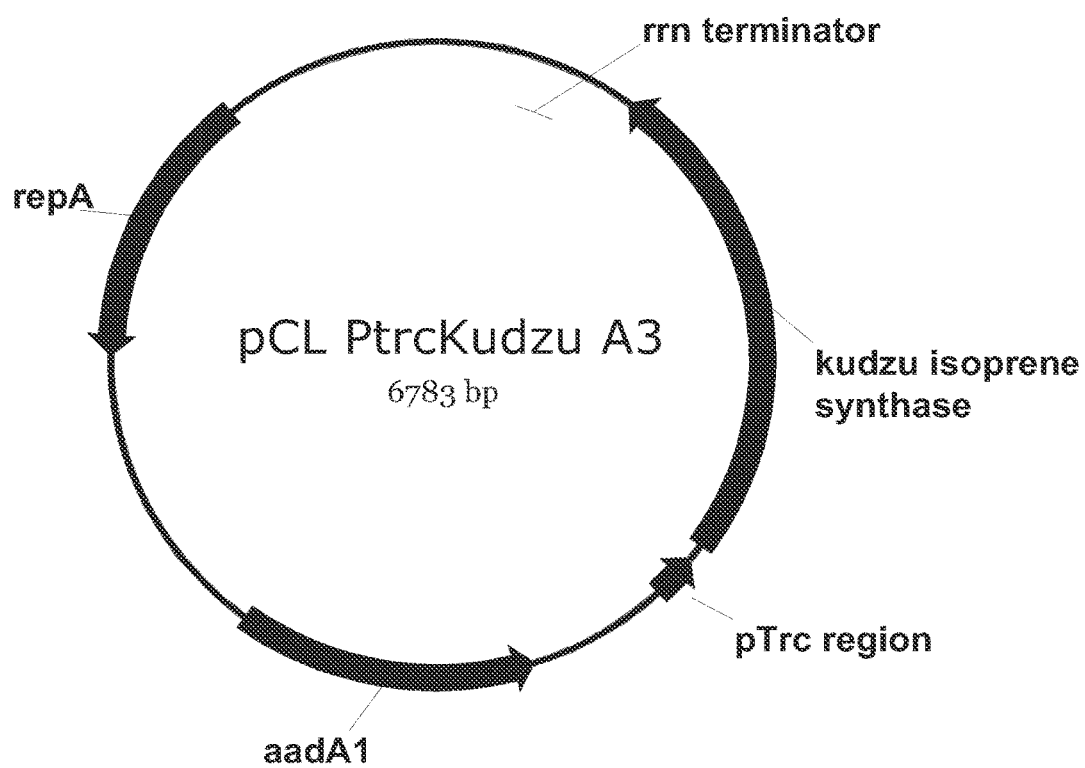
FIG. 40 is a map of pCL PtrcKudzu A3.

Plasmid pTrcKudzuKan was digested with PstI, treated with SAP, heat killed and gel purified. It was ligated to a PCR product encoding dxs from *E. coli* with a synthetic RBS. The primers for PCR were MCM 13 5'-GATCATG-CATTCGCCCTTAGGAGGTAAAAAAACATGAGTTTT-GATATTGCCAAATACCC G (SEQ ID NO:80) and MCM14 5'-CATGCTGCAGTTATGCCAGCCAGGCCTT-GAT (SEQ ID NO:81); and the template was *E. coli* genomic DNA. The PCR product was digested with NsiI and PstI and gel purified prior to ligation. The resulting transformation reaction was transformed into TOP10 cells and selected on LA with kanamycin 50 µg/ml. Several transformants were isolated and sequenced and the resulting plasmid was called pTrcKudzu-DXS(kan) (FIGS. 36 and 37; SEQ ID NO:17).

iv) Construction of pTrcKudzu-yIDI-dxs (kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAG-GTAAAAAAACATGAGTTTTGATATTGCCAAATACCC G (SEQ ID NO:80) and MCM14 5'-CATGCTGCAGTTAT-GCCAGCCAGGCCTTGAT (SEQ ID NO:81); template TOP10 cells) which had been digested with NsiI and PstI and gel purified. The final plasmid was called pTrcKudzu-yIDI-dxs (kan) (FIGS. 21 and 22; SEQ ID NO:10).

v) Construction of pCL PtrcKudzu

A fragment of DNA containing the promoter, structural gene and terminator from Example 1 above was digested from pTrcKudzu using SspI and gel purified. It was ligated to pCL1920 which had been digested with PvuII, treated with SAP and heat killed. The resulting ligation mixture was transformed into TOP10 cells and selected in LA containing spectinomycin 50 µg/ml. Several clones were isolated and sequenced and two were selected. pCL PtrcKudzu and pCL PtrcKudzu (A3) have the insert in opposite orientations (FIGS. 38-41; SEQ ID NOs:18-19).

vi) Construction of pCL PtrcKudzu yIDI

Figure 42:
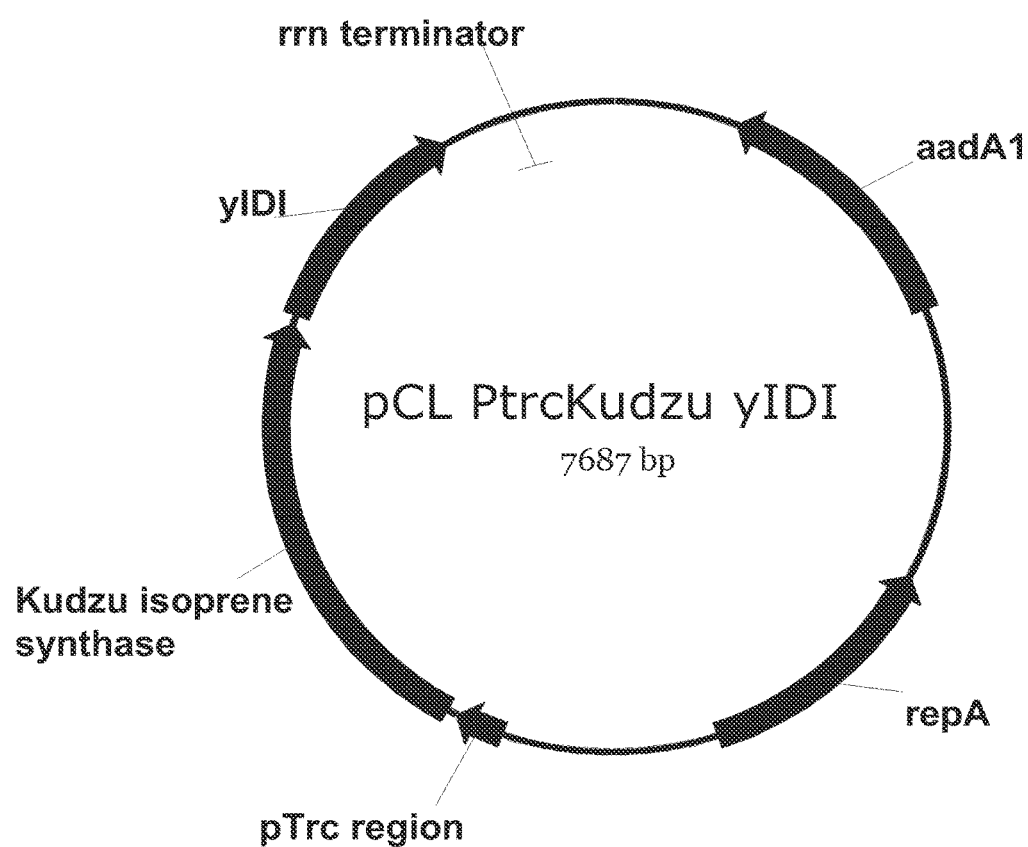
FIG. 42 is a map of pCL PtrcKudzu yIDI.

The NsiI-PstI digested, gel purified, IDI PCR amplicon from (ii) above was ligated into pCL PtrcKudzu which had been digested with PstI, treated with SAP, and heat killed. The ligation mixture was transformed into TOP10 cells and selected in LA containing spectinomycin 50 µg/ml. Several clones were isolated and sequenced and the resulting plasmid is called pCL PtrcKudzu yIDI (FIGS. 42 and 43; SEQ ID NO:20).

vii) Construction of pCL PtrcKudzu DXS

Figure 44:
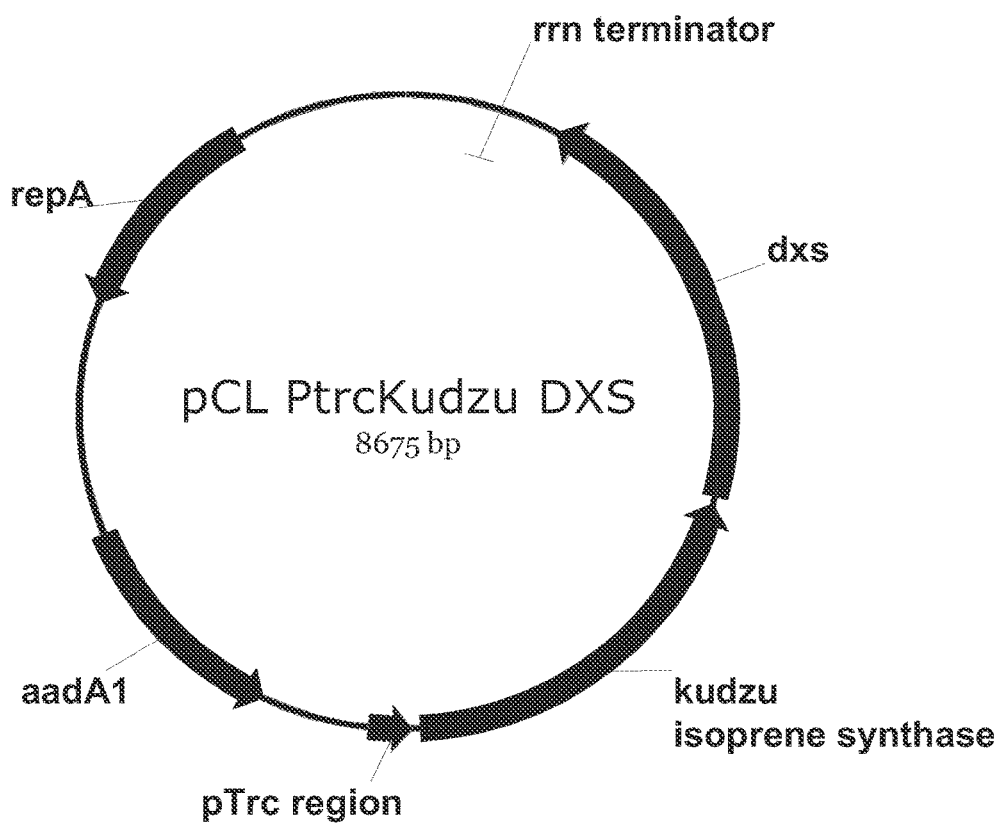
FIG. 44 is a map of pCL PtrcKudzu DXS.

The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP10 cells and selected in LA containing spectinomycin 50 µg/ml. Several clones were isolated and sequenced and the resulting plasmid is called pCL PtrcKudzu DXS (FIGS. 44 and 45; SEQ ID NO:21).

II. Measurement of Isoprene in Headspace from Cultures Expressing Kudzu Isoprene Synthase, idi, and/or dxs at Different Copy Numbers.

Cultures of *E. coli* BL21($\lambda$DE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 µg/mL. Cultures of pCL PtrcKudzu (E), pCL PtrcKudzu, pCL PtrcKudzu-yIDI (F) and pCL PtrcKudzu-DXS (G) were grown in LB spectinomycin 50 µg/mL. Cultures were induced with 400 µM IPTG at time 0 ($OD_{600}$ approximately 0.5) and samples taken for isoprene headspace measurement (see Example 1). Results are shown in FIG. 23A-23G.

Figure 23B:
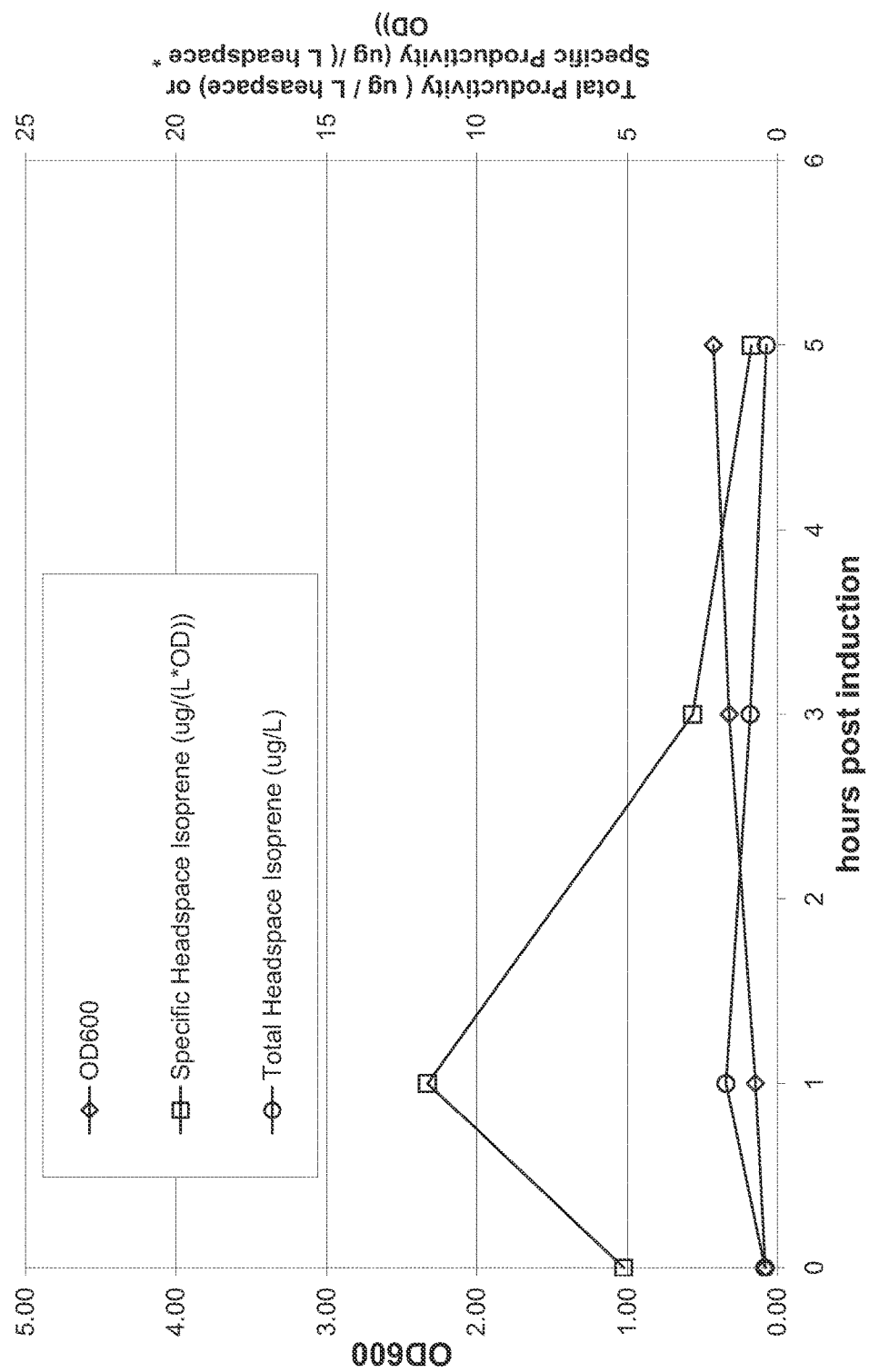
FIG. 23B is a graph showing production of isoprene from glucose in BL21/pTrcKudzu yIDI kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23C:
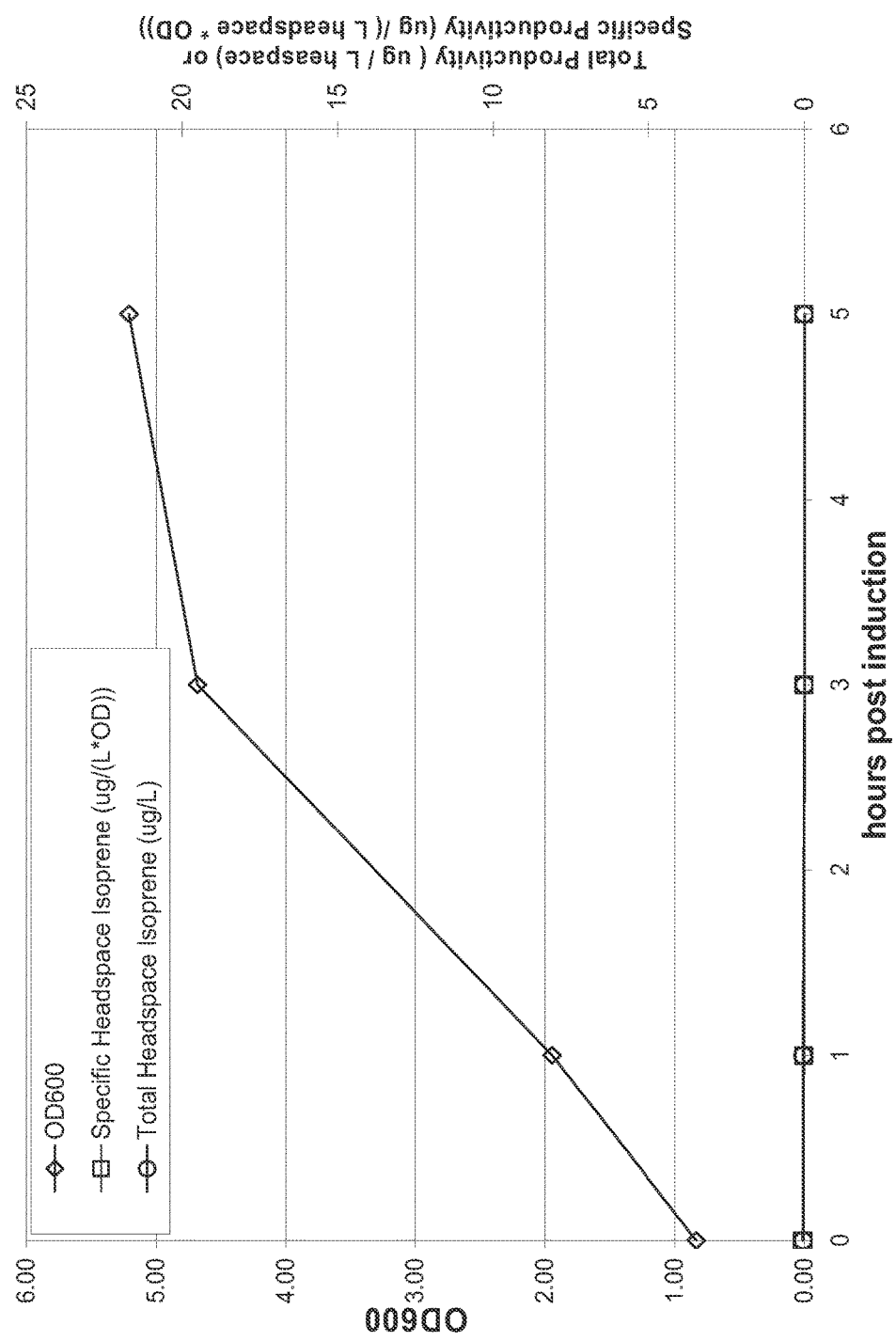
FIG. 23C is a graph showing production of isoprene from glucose in BL21/pTrcKudzu DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23D:
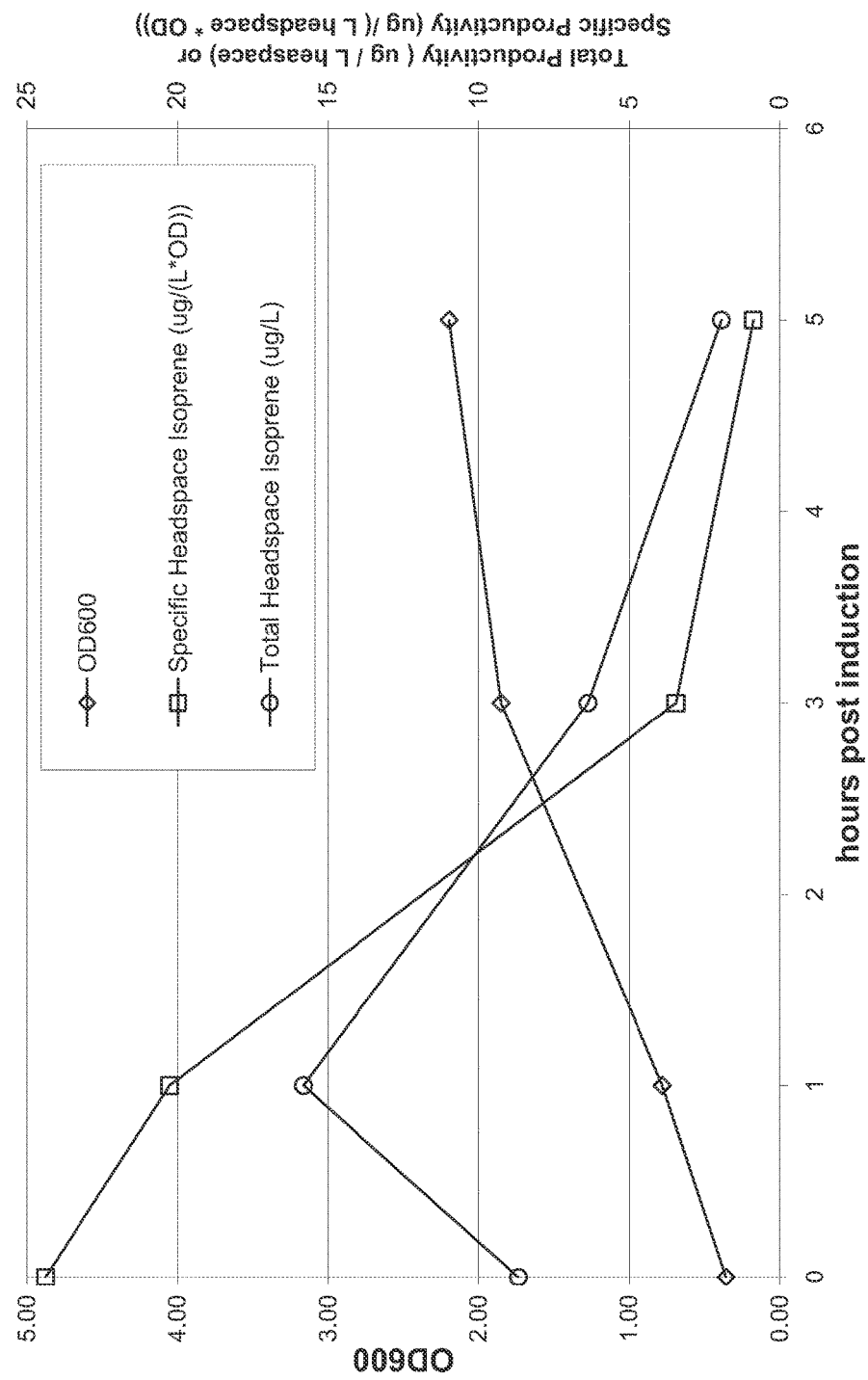
FIG. 23D is a graph showing production of isoprene from glucose in BL21/pTrcKudzu yIDI DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23E:
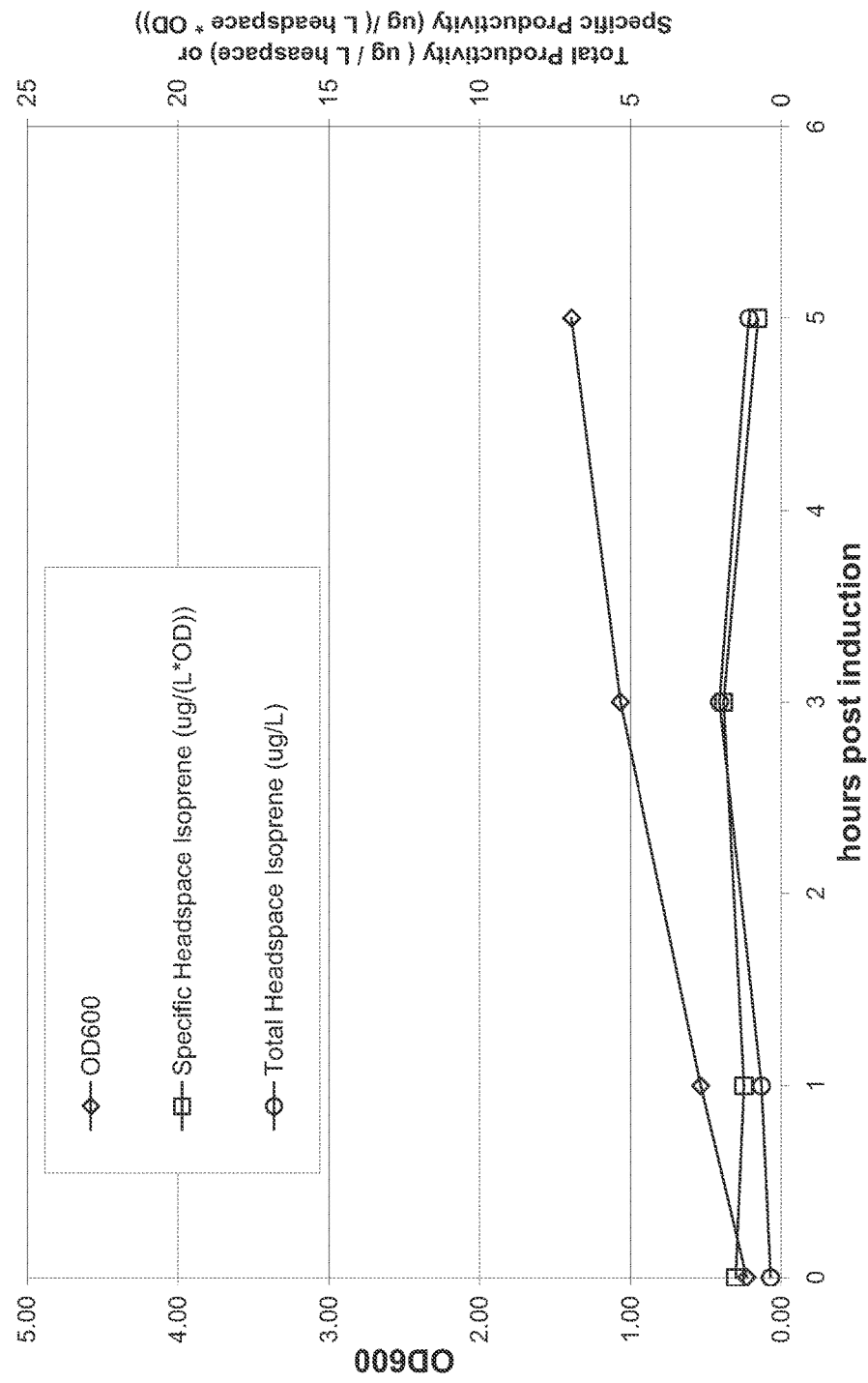
FIG. 23E is a graph showing production of isoprene from glucose in BL21/pCL PtrcKudzu. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23F:
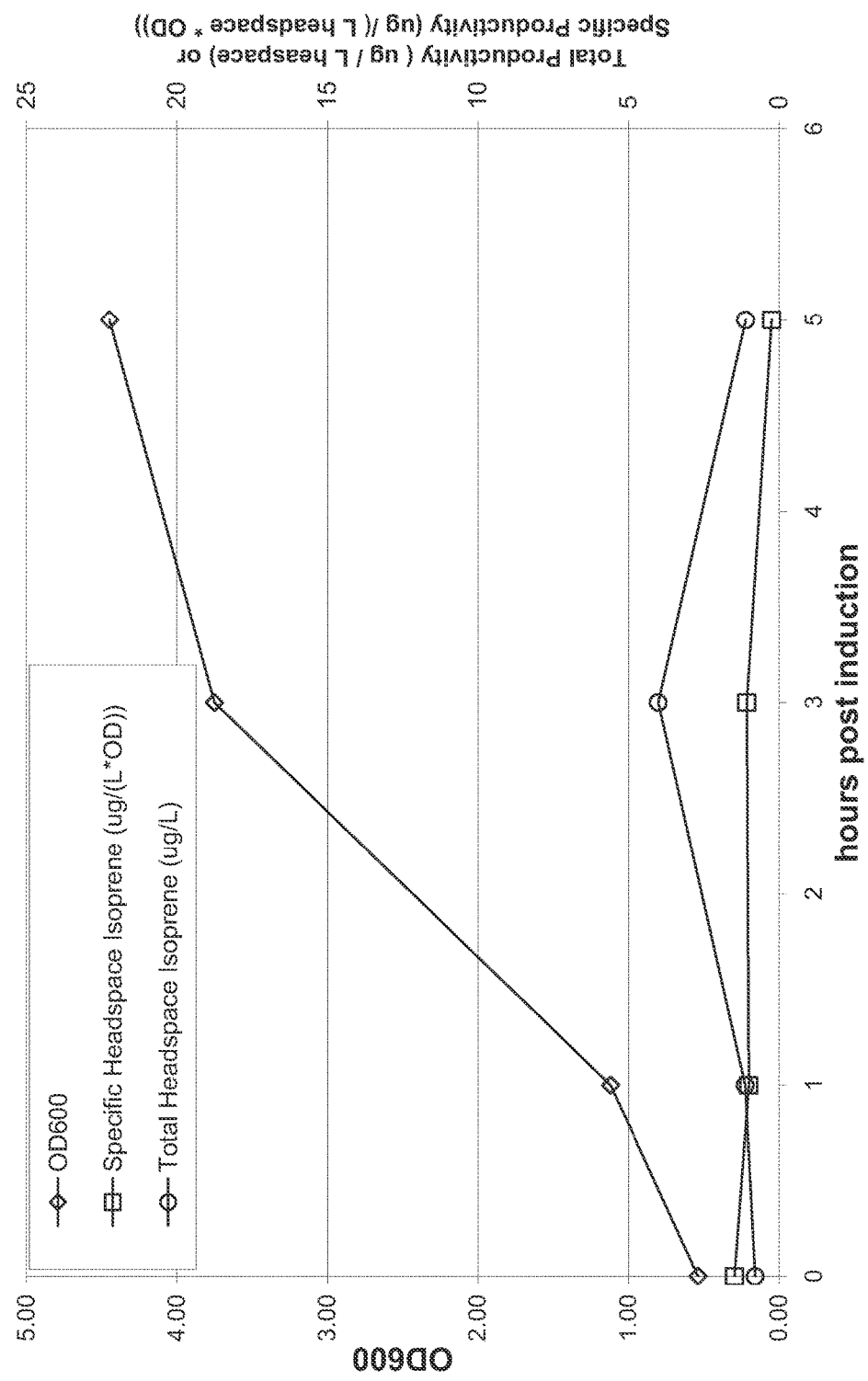
FIG. 23F is a graph showing production of isoprene from glucose in BL21/pCL PtrcKudzu yIDI. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23G:
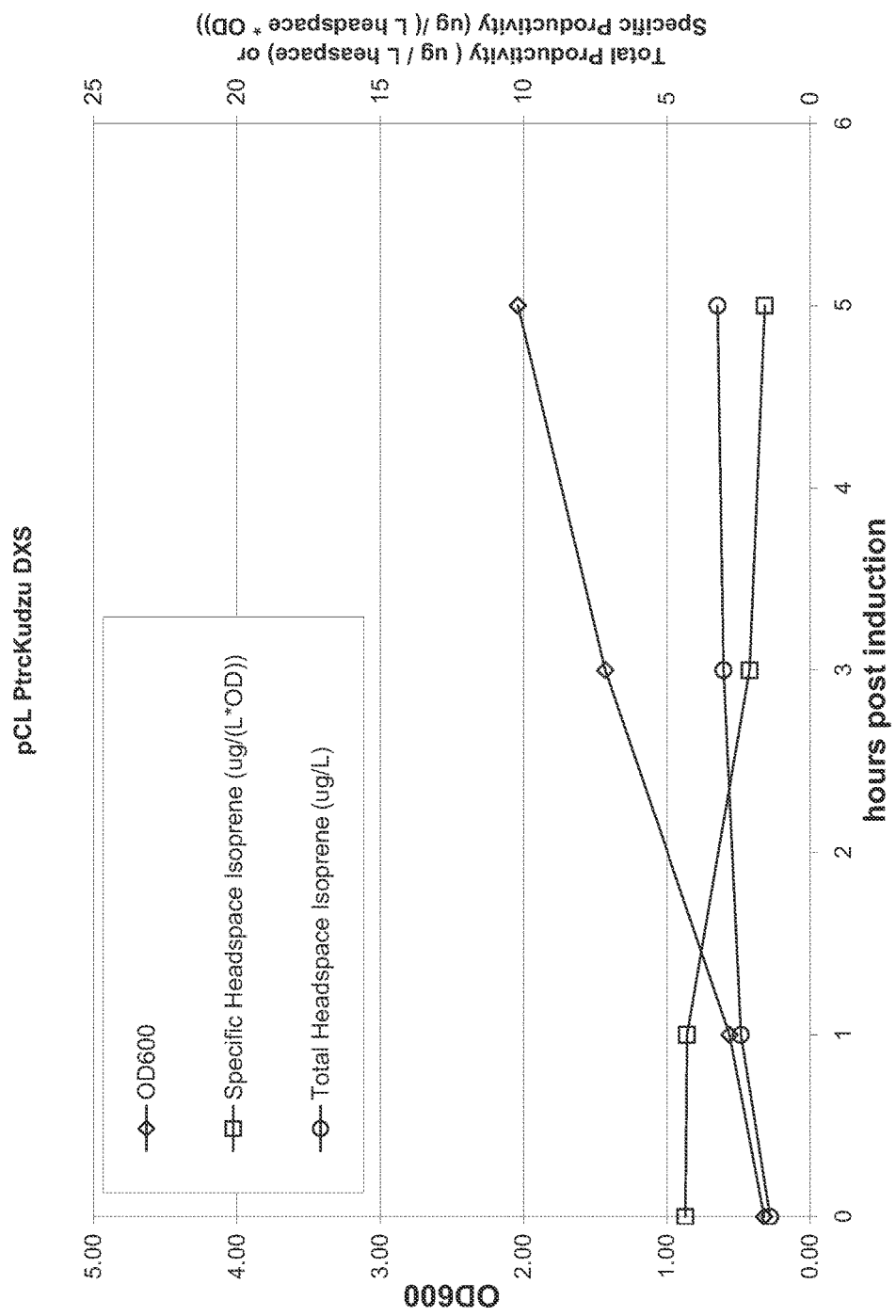
FIG. 23G is a graph showing production of isoprene from glucose in BL21/pCL PtrcKudzu DXS. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).
Figure 23H:
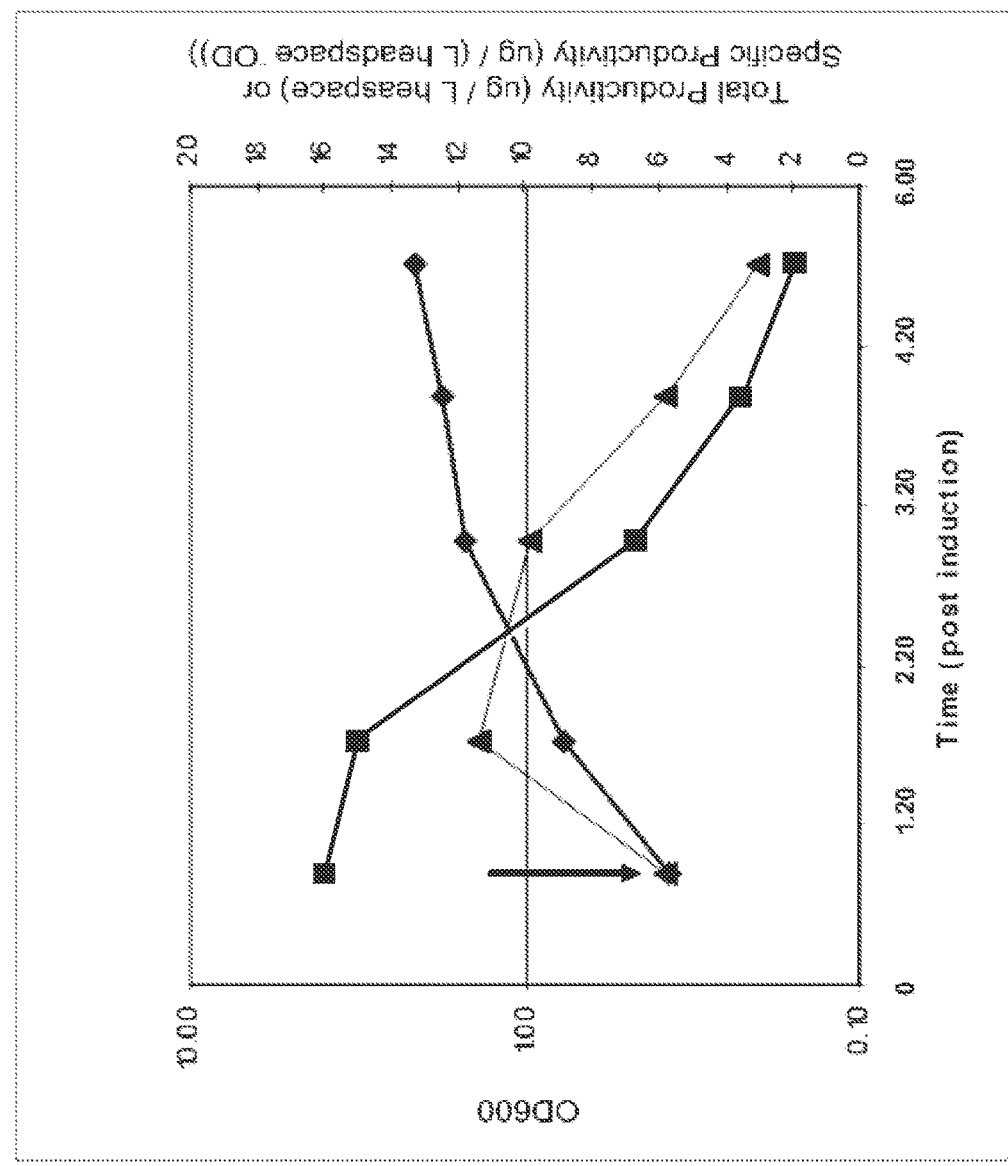
FIG. 23H is a graph showing production of isoprene from glucose in BL21/pTrcKudzuIDIDXSkan. The arrow indicates the time of induction with IPTG (400 μmol). The x-axis is time after induction; the y-axis is $OD_{600}$ and the y2-axis is total productivity of isoprene (μg/L headspace or specific productivity (μg/L headspace/OD). Black diamonds represent $OD_{600}$, black triangles represent isoprene productivity (μg/L) and white squares represent specific productivity of isoprene (μg/L/OD).

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 µg/ml) at 20° C. and used to inoculate shake flasks of TM3 (13.6 g $K_2PO_4$, 13.6 g $KH_2PO_4$, 2.0 g $MgSO_4.7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks were incubated at 30° C. until an $OD_{600}$ of 0.8 was reached, and then induced with 400 µM IPTG. Samples were taken at various times after induction and the amount of isoprene in the head space was measured as described in Example 1. Results are shown in FIG. 23H.

III. Production of Isoprene from Biomass in *E. Coli*/pTrcKudzu yIDI DXS.

The strain BL21 pTrcKudzuIDIDXS was tested for the ability to generate isoprene from three types of biomass; bagasse, corn stover and soft wood pulp with glucose as a control. Hydrolysates of the biomass were prepared by enzymatic hydrolysis (Brown, L. and Torget, R., 1996, NREL standard assay method Lap-009 "Enzymatic Saccharification of Lignocellulosic Biomass") and used at a dilution based upon glucose equivalents. In this example, glucose equivalents were equal to 1% glucose. A single colony from a plate freshly transformed cells of BL21 (DE3) pTrcKudzu yIDI DXS (kan) was used to inoculate 5 ml of LB plus kanamycin (50 µg/ml). The culture was incubated overnight at 25° C. with shaking. The following day the overnight culture was diluted to an $OD_{600}$ of 0.05 in 25 ml of TM3+0.2% YE+1% feedstock. The feedstock was corn stover, bagasse, or softwood pulp. Glucose was used as a positive control and no glucose was used as a negative control. Cultures were incubated at 30° C. with shaking at 180 rpm. The culture was monitored for $OD_{600}$ and when it reached an $OD_{600}$ of ~0.8, cultures were analyzed at 1 and 3 hours for isoprene production as described in Example 1. Cultures are not induced. All cultures containing added feedstock produce isoprene equivalent to those of the glucose positive control. Experiments were done in duplicate and are shown in FIG. 46.

IV. Production of Isoprene from Invert Sugar in *E. Coli*/pTrcKudzuIDIDXS.

A single colony from a plate freshly transformed cells of BL21 ($\lambda$DE3)/pTrcKudzu yIDI DXS (kan) was used to inoculate 5 mL of LB+kanamycin (50 µg/ml). The culture was incubated overnight at 25° C. with shaking. The following day the overnight culture was diluted to an $OD_{600}$ of 0.05 in 25 ml of TM3+0.2% YE+1% feedstock. Feedstock was glucose, inverted glucose or corn stover. The invert sugar feedstock (Danisco Invert Sugar) was prepared by enzymatically treating sucrose syrup. AFEX corn stover was prepared as described below (Part V). The cells were grown at 30° C. and the first sample was measured when the cultures reached an $OD_{600}$~0.8-1.0 (0 hour). The cultures were analyzed for growth as measured by $OD_{600}$ and for isoprene production as in Example 1 at 0, 1 and 3 hours. Results are shown in FIG. 47.

V. Preparation of Hydrolysate from AFEX Pretreated Corn Stover.

AFEX pretreated corn stover was obtained from Michigan Biotechnology Institute. The pretreatment conditions were 60% moisture, 1:1 ammonia loading, and 90° C. for 30 minutes, then air dried. The moisture content in the AFEX pretreated corn stover was 21.27%. The contents of glucan and xylan in the AFEX pretreated corn stover were 31.7% and 19.1% (dry basis), respectively. The saccharification process was as follows; 20 g of AFEX pretreated corn stover was added into a 500 ml flask with 5 ml of 1 M sodium citrate buffer pH 4.8, 2.25 ml of Accellerase 1000, 0.1 ml of Grindamyl H121 (Danisco xylanase product from *Aspergillus niger* for bread-making industry), and 72.65 ml of DI water. The flask was put in an orbital shaker and incubated at 50° C. for 96 hours. One sample was taken from the shaker and analyzed using HPLC. The hydrolysate contained 38.5 g/l of glucose, 21.8 g/l of xylose, and 10.3 g/l of oligomers of glucose and/or xylose.

VI. The Effect of Yeast Extract on Isoprene Production in *E. Coli* Grown in Fed-Batch Culture.

Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 48A). The isoprene level in the off-gas from the fermentor was determined as previously described. The isoprene titer increased over the course of the fermentation (FIG. 48B). The amount of isoprene produced was linearly proportional to the amount of fed yeast extract (FIG. 48C).

VII. Production of Isoprene in 500 L Fermentation of pTrcKudzu DXS yIDI.

A 500 liter fermentation of *E. coli* cells with a kudzu isoprene synthase, *S. cerevisiae* IDI, and *E. coli* DXS nucleic acids (*E. coli* BL21 (λDE3) pTrc Kudzu dxs yidi) was used to produce isoprene. The levels of isoprene varied from 50 to 300 µg/L over a time period of 15 hours. On the basis of the average isoprene concentrations, the average flow through the device and the extent of isoprene breakthrough, the amount of isoprene collected was calculated to be approximately 17 g.

VIII. Production of Isoprene in 500 L Fermentation of *E. Coli* Grown in Fed-Batch Culture.
Medium Recipe (Per Liter Fermentation Medium).

K$_2$HPO$_4$ 7.5 g, MgSO$_4$*7H$_2$O 2 g, citric acid monohydrate 2 g, ferric ammonium citrate 0.3 g, yeast extract 0.5 g, 1000× Modified Trace Metal Solution 1 ml. All of the components were added together and dissolved in diH$_2$O. This solution was autoclaved. The pH was adjusted to 7.0 with ammonia gas (NH$_3$) and q.s. to volume. Glucose 10 g, thiamine*HCl 0.1 g, and antibiotic were added after sterilization and pH adjustment.

1000× Modified Trace Metal Solution:

Citric Acids*H$_2$O 40 g, MnSO$_4$*H$_2$O 30 g, NaCl 10 g, FeSO$_4$*7H$_2$O 1 g, CoCl$_2$*6H$_2$O 1 g, ZnSO*7H$_2$O 1 g, CuSO$_4$*5H$_2$O 100 mg, H$_3$BO$_3$ 100 mg, NaMoO$_4$*2H$_2$O 100 mg. Each component is dissolved one at a time in DIH$_2$O, pH to 3.0 with HCl/NaOH, then q.s. to volume and filter sterilized with 0.22 micron filter.

Fermentation was performed in a 500-L bioreactor with *E. coli* cells containing the pTrcKudzu yIDI DXS plasmid. This experiment was carried out to monitor isoprene formation from glucose and yeast extract at the desired fermentation pH 7.0 and temperature 30° C. An inoculum of *E. coli* strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Figure 49A:
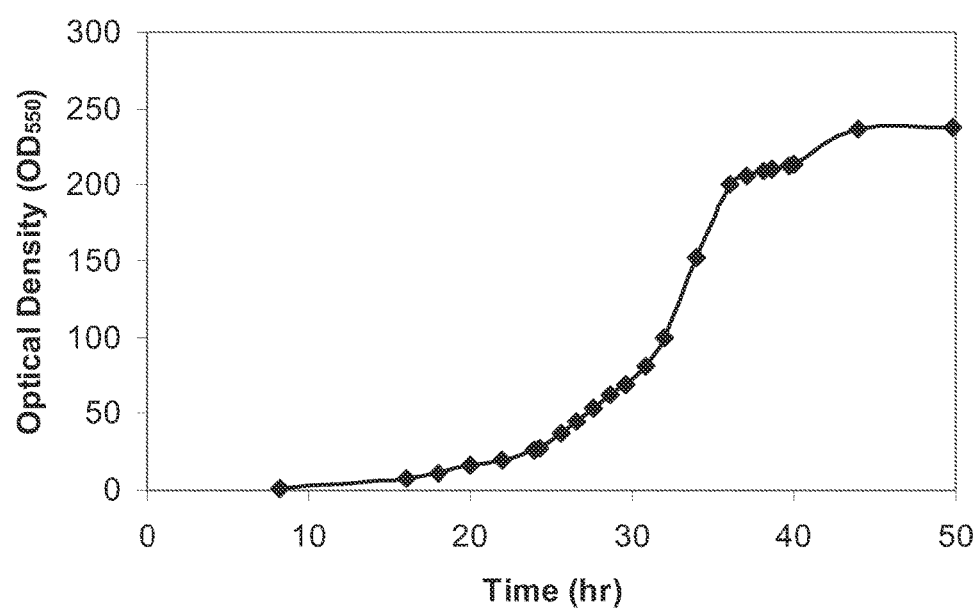
FIGS. 49A-C show graphs demonstrating isoprene production from a 500 L bioreactor with *E. coli* cells containing the pTrcKudzu+yIDI+DXS plasmid. Panel A shows the time course of optical density within the 500-L bioreactor fed with glucose and yeast extract. Panel B shows the time course of isoprene titer within the 500-L bioreactor fed with glucose and yeast extract. The titer is defined as the amount of isoprene produced per liter of fermentation broth. Panel C shows the time course of total isoprene produced from the 500-L bioreactor fed with glucose and yeast extract.
Figure 49B:
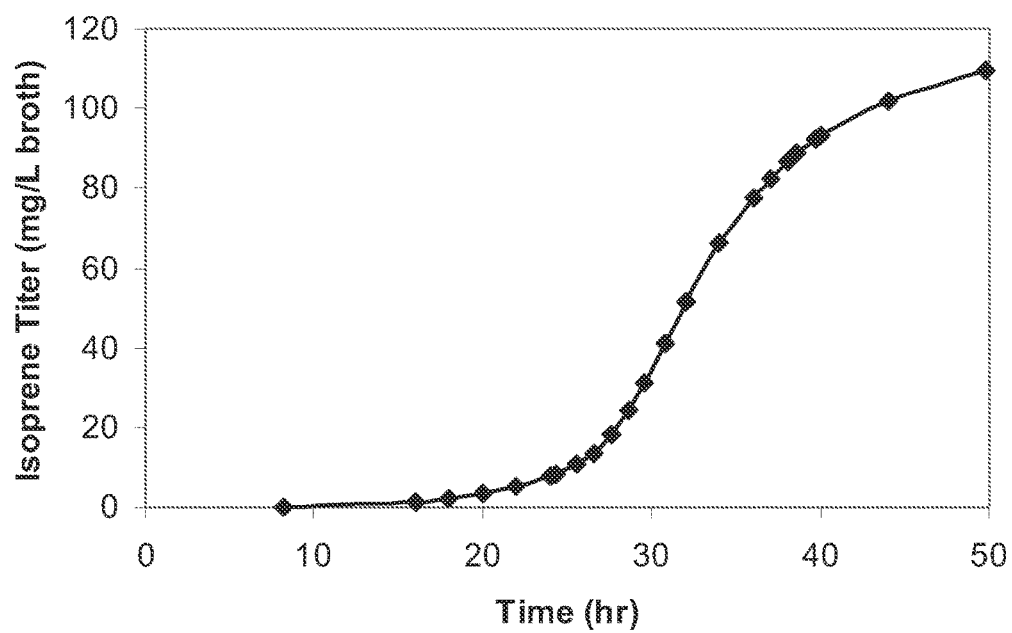
Figure 49C:
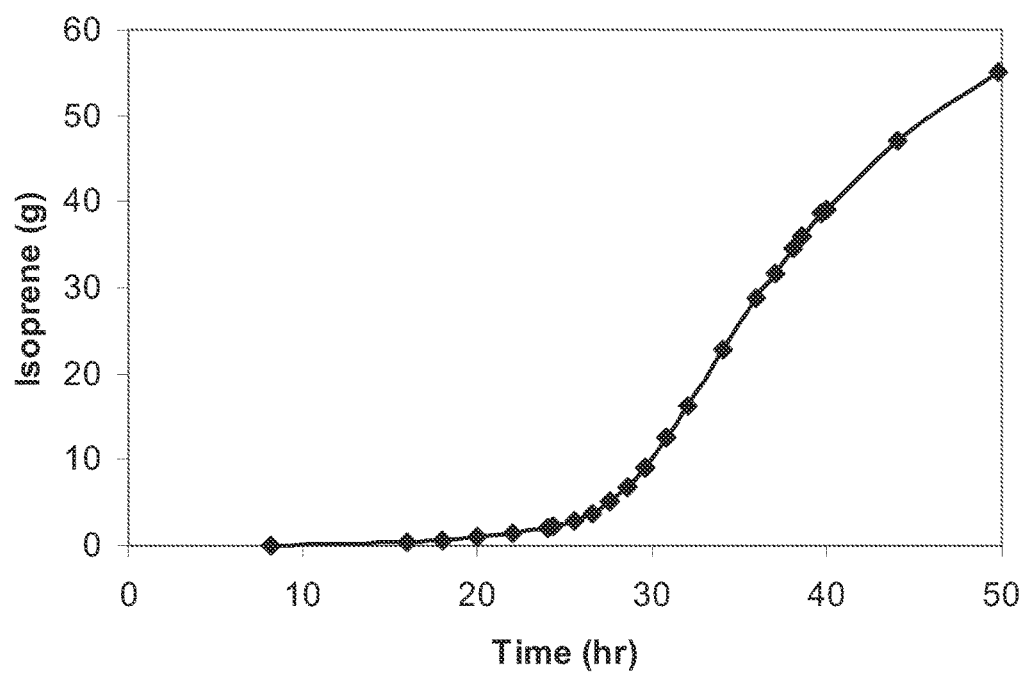

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 49A. The isoprene level in the off-gas from the bioreactor was determined as previously described. The isoprene titer increased over the course of the fermentation (FIG. 49B). The total amount of isoprene produced during the 50 hour fermentation was 55.1 g and the time course of production is shown in FIG. 49C.

Example 8

Production of Isoprene in *E. Coli* Expressing Kudzu Isoprene Synthase and Recombinant Mevalonic Acid Pathway Genes I. Cloning the Lower MVA Pathway.

The strategy for cloning the lower mevalonic pathway was as follows. Four genes of the mevalonic acid biosynthesis pathway; mevalonate kinase (MVK), phosphomevalonate kinase (PMK), diphosphomevalonte decarboxylase (MVD) and isopentenyl diphosphate isomerase genes were amplified by PCR from *S. cerevisiae* chromosomal DNA and cloned individually into the pCR BluntII TOPO plasmid (Invitrogen). In some cases, the idi gene was amplified from *E. coli* chromosomal DNA. The primers were designed such that an *E. coli* consensus RBS (AGGAGGT (SEQ ID NO:82) or AAGGAGG (SEQ ID NO:83)) was inserted at the 5' end, 8 bp upstream of the start codon and a PstI site was added at the 3' end. The genes were then cloned one by one into the pTrcHis2B vector until the entire pathway was assembled.

Chromosomal DNA from *S. cerevisiae* S288C was obtained from ATCC (ATCC 204508D). The MVK gene was amplified from the chromosome of *S. cerevisiae* using primers MVKF (5'-AGGAGGTAAAAAAACATGTCATTACCGTTCTTAACTTCTGC, SEQ ID NO:84) and MVK-PstI-R (5'-ATGGCTGCAGGCCTATCGCAAATTAGCT-TATGAAGTCCATGGTAAATTCGTG, SEQ ID NO:85) using PfuTurbo as per manufacturer's instructions. The correct sized PCR product (1370 bp) was identified by electrophoresis through a 1.2% E-gel (Invitrogen) and cloned into pZeroBLUNT TOPO. The resulting plasmid was designated pMVK1. The plasmid pMVK1 was digested with SacI and TaqI restriction endonucleases and the fragment was gel purified and ligated into pTrcHis2B digested with SacI and BstBI. The resulting plasmid was named pTrc-MVK1.

The second gene in the mevalonic acid biosynthesis pathway, PMK, was amplified by PCR using primers: PstI-PMK1 R (5'-GAATTCGCCCTTCTGCAGCTACC, SEQ ID NO:86) and BsiHKA I-PMK1 F (5'-CGACTGGTGCAC-CCTTAAGGAGGAAAAAAACATGTCAG, SEQ ID NO:87). The PCR reaction was performed using Pfu Turbo polymerase (Stratagene) as per manufacturer's instructions. The correct sized product (1387 bp) was digested with PstI and BsiHKI and ligated into pTrcMVK1 digested with PstI. The resulting plasmid was named pTrcKK. The MVD and the idi genes were cloned in the same manner. PCR was carried out using the primer pairs PstI-MVD 1 R (5'-GTGCTGGAATTCGCCCTTCTGCAGC, SEQ ID NO:88) and NsiI-MVD 1 F (5'-GTAGATGCATGCAGAATTCGC-CCTTAAGGAGG, SEQ ID NO:89) to amplify the MVD gene and PstI-YIDI 1 R (5'-CCTTCTGCAGGACGCGTT-GTTATAGC, SEQ ID NO:79) and NsiI-YIDI 1 F (5'-CATCAATGCATCGCCCTTAGGAGGTAAAAAAAAAT-GAC, SEQ ID NO:78) to amplify the yIDI gene. In some cases the IPP isomerase gene, idi from E. coli was used. To amplify idi from E. coli chromosomal DNA, the following primer set was used: PstI-CIDI 1 R (5'-GTGTGATGGA-TATCTGCAGAATTCG, SEQ ID NO:90) and NsiI-CIDI 1 F (5'-CATCAATGCATCGCCCTTAGGAGG-TAAAAAAACATG, SEQ ID NO:91). Template DNA was chromosomal DNA isolated by standard methods from E. coli FM5 (WO 96/35796 and WO 2004/033646, which are each hereby incorporated by reference in their entireties, particularly with respect to isolation of nucleic acids). The final plasmids were named pKKDIy for the construct encoding the yeast idi gene or pKKDIc for the construct encoding the E. coli idi gene. The plasmids were transformed into E. coli hosts BL21 for subsequent analysis. In some cases the isoprene synthase from kudzu was cloned into pKKDIy yielding plasmid pKKDIyIS.

The lower MVA pathway was also cloned into pTrc containing a kanamycin antibiotic resistance marker. The plasmid pTrcKKDIy was digested with restriction endonucleases ApaI and PstI, the 5930 bp fragment was separated on a 1.2% agarose E-gel and purified using the Qiagen Gel Purification kit according to the manufacturer's instructions. The plasmid pTrcKudzuKan, described in Example 7, was digested with restriction endonucleases ApaI and PstI, and the 3338 bp fragment containing the vector was purified from a 1.2% E-gel using the Qiagen Gel Purification kit. The 3338 bp vector fragment and the 5930 bp lower MVA pathway fragment were ligated using the Roche Quick Ligation kit. The ligation mix was transformed into E. coli TOP10 cells and tranformants were grown at 37° C. overnight with selection on LA containing kanamycin (50 µg/ml). The transformants were verified by restriction enzyme digestion and one was frozen as a stock. The plasmid was designated pTrcKanKKDIy.

II. Cloning a Kudzu Isoprene Synthase Gene into pTrcK-anKKDIy.

The kudzu isoprene synthase gene was amplified by PCR from pTrcKudzu, described in Example 1, using primers MCM50 5'-GATCATGCATTCGCCCTTAGGAGG-TAAAAAAACATGTGTGCGACCTCTTCTCAATTTAC T (SEQ ID NO:52) and MCM53 5'-CGGTCGACGGATC-CCTGCAGTTAGACATACATCAGCTG (SEQ ID NO:50). The resulting PCR fragment was cloned into pCR2.1 and transformed into E. coli TOP10. This fragment contains the coding sequence for kudzu isoprene synthase and an upstream region containing a RBS from E. coli. Transformants were incubated overnight at 37° C. with selection on LA containing carbenicillin (50 µg/ml). The correct insertion of the fragment was verified by sequencing and this strain was designated MCM93.

Figure 24:
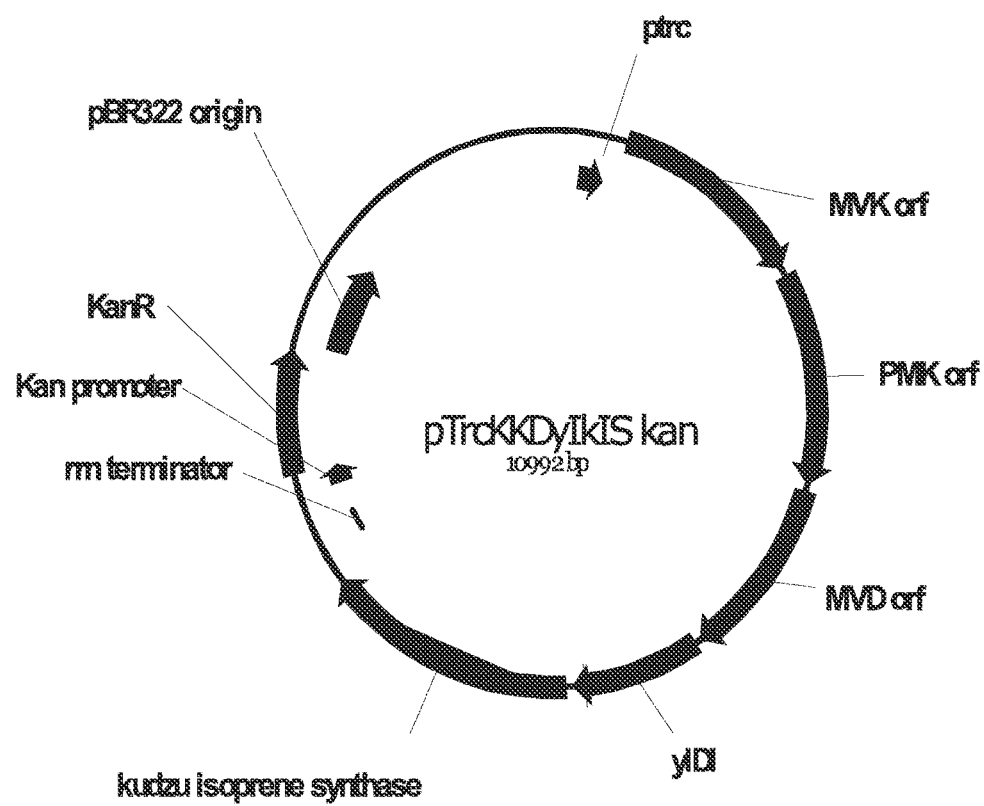
FIG. 24 is a map of pTrcKKDyIkIS kan.
Figure 26:
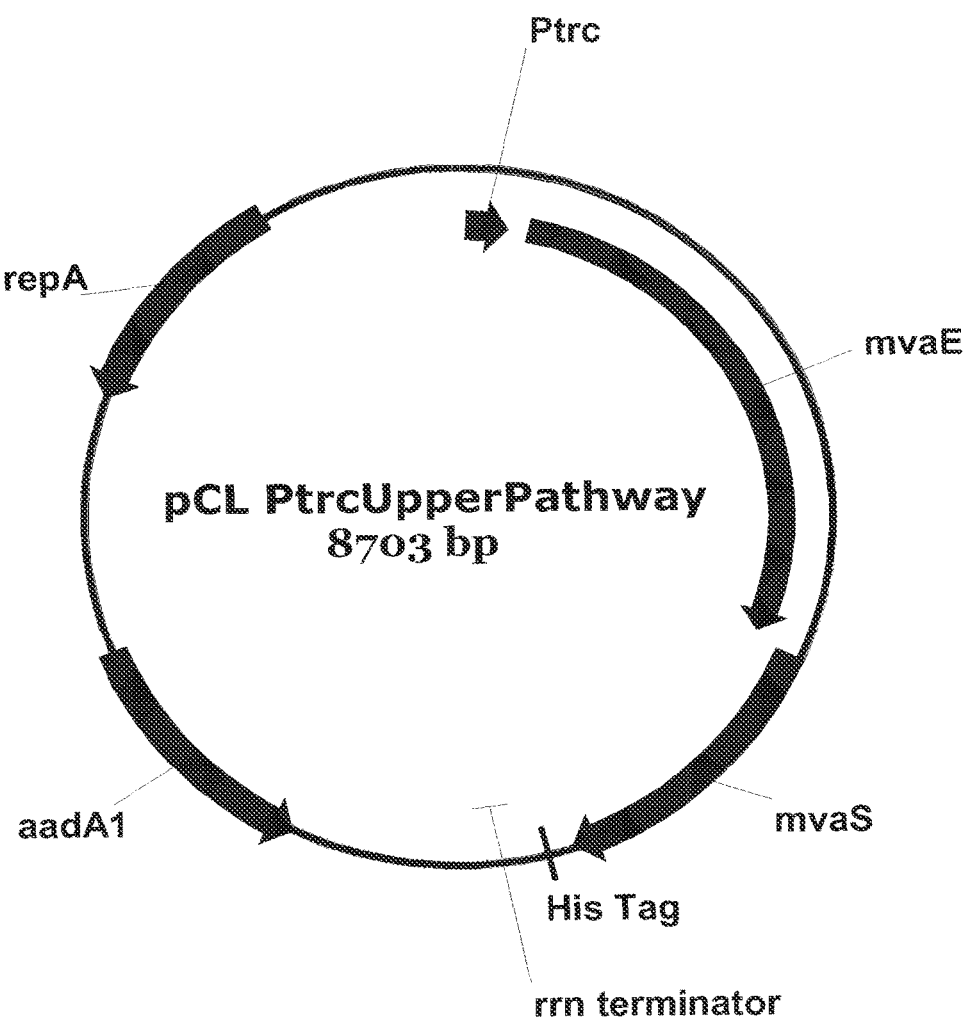
FIG. 26 is a map of pCL PtrcUpperPathway.

The plasmid from strain MCM93 was digested with restriction endonucleases NsiI and PstI to liberate a 1724 bp insert containing the RBS and kudzu isoprene synthase. The 1724 bp fragment was separated on a 1.2% agarose E-gel and purified using the Qiagen Gel Purification kit according to the manufacturer's instructions. Plasmid pTrcKanKKDIy was digested with the restriction endonuclease PstI, treated with SAP for 30 minutes at 37° C. and purified using the Qiagen PCR cleanup kit. The plasmid and kudzu isoprene synthase encoding DNA fragment were ligated using the Roche Quick Ligation kit. The ligation mix was transformed into E. coli TOP10 cells and transformants were grown overnight at 37° C. with selection on LA containing Kanamycin at 50 µg/ml. The correct transformant was verified by restriction digestion and the plasmid was designated pTrcKKDyIkISKan (FIGS. 24 and 25; SEQ ID NO:11). This plasmid was transformed into BL21(λDE3) cells (Invitrogen).

III. Isoprene Production from Mevalonate in E. Coli Expressing the Recombinant Lower Mevalonate Pathway and Isoprene Synthase from Kudzu.

Strain BL21/pTrcKKDyIkISKan was cultured in MOPS medium (Neidhardt et al., (1974) J. Bacteriology 119:736-747) adjusted to pH 7.1 and supplemented with 0.5% glucose and 0.5% mevalonic acid. A control culture was also set up using identical conditions but without the addition of 0.5% mevalonic acid. The culture was started from an overnight seed culture with a 1% inoculum and induced with 500 µM IPTG when the culture had reached an OD$_{600}$ of 0.3 to 0.5. The cultures were grown at 30° C. with shaking at 250 rpm. The production of isoprene was analyzed 3 hours after induction by using the head space assay described in Example 1. Maximum production of isoprene was 6.67× $10^{-4}$ mol/L$_{broth}$/OD$_{600}$/hr where L$_{broth}$ is the volume of broth and includes both the volume of the cell medium and the volume of the cells. The control culture not supplemented with mevalonic acid did not produce measurable isoprene.

IV. Cloning the Upper MVA Pathway.

The upper mevalonate biosynthetic pathway, comprising two genes encoding three enzymatic activities, was cloned from *Enterococcus faecalis*. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes second enzyme in the pathway, HMG-CoA synthase. The mvaE gene was amplified from *E. faecalis* genomic DNA (ATCC 700802D-5) with an E. coli ribosome binding site and a spacer in front using the following primers:

```
CF 07-60 (+) Start of mvaE w/RBS + ATG
start codon SacI
                                    (SEQ ID NO: 93)
5'- GAGACATGAGCTCAGGAGGTAAAAAAACATGAAAACAGTAG

TTATTATTG

CF 07-62 (-) Fuse mvaE to mvaS with RBS in
between
                                    (SEQ ID NO: 94)
5'- TTTATCAATCCCAATTGTCATGTTTTTTTACCTCCTTTATTG

TTTTCTTAAATC
```

The mvaS gene was amplified from *E. faecalis* genomic DNA (ATCC 700802D-5) with a RBS and spacer from *E. coli* in front using the following primers:

CF 07-61 (+) Fuse mvaE to mvaS with RBS in between
(SEQ ID NO: 95)
5' - GATTTAAGAAAACAATAAAGGAGGTAAAAAAACATGACAATTGGGATTGATAAA CF 07-102 (-) End of mvaS gene BglII
(SEQ ID NO: 96)
5' -GACATGACATAGATCTTTAGTTTCGATAAGAACGAACGGT The PCR fragments were fused together with PCR using the following primers:

```
CF 07-60 (+) Start of mvaE w/RBS +
ATG start codon SacI
                                    (SEQ ID NO: 93)
5' -GAGACATGAGCTCAGGAGGTAAAAAAACATGAAAACAGTAGTTAT

TATTG

CF 07-102 (-) End of mvaS gene BglII
                                    (SEQ ID NO: 96)
5' -GACATGACATAGATCTTTAGTTTCGATAAGAACGAACGGT
```

The fusion PCR fragment was purified using a Qiagen kit and digested with the restriction enzymes SacI and BglII. This digested DNA fragment was gel purified using a Qiagen kit and ligated into the commercially available vector pTrcHis2A, which had been digested with SacI and BglII and gel purified.

The ligation mix was transformed into E. coli Top 10 cells and colonies were selected on LA+50 µg/ml carbenicillin plates. A total of six colonies were chosen and grown overnight in LB+50 µg/ml carbenicillin and plasmids were isolated using a Qiagen kit. The plasmids were digested with SacI and BglII to check for inserts and one correct plasmid was sequenced with the following primers:

```
CF 07-58 (+) Start of mvaE gene
                                    (SEQ ID NO: 97)
5' - ATGAAAACAGTAGTTATTATTGATGC CF 07-59 (-) End of mvaE gene
                                    (SEQ ID NO: 98)
5' - ATGTTATTGTTTTCTTAAATCATTTAAAATAGC CF 07-82 (+) Start of mvaS gene
                                    (SEQ ID NO: 99)
5' - ATGACAATTGGGATTGATAAAATTAG CF 07-83 (-) End of mvaS gene
                                    (SEQ ID NO: 100)
5' - TTAGTTTCGATAAGAACGAACGGT CF 07-86 (+) Sequence in mvaE
                                    (SEQ ID NO: 101)
5' - GAAATAGCCCCATTAGAAGTATC CF 07-87 (+) Sequence in mvaE
                                    (SEQ ID NO: 102)
5' - TTGCCAATCATATGATTGAAAATC CF 07-88 (+) Sequence in mvaE
                                    (SEQ ID NO: 103)
5' - GCTATGCTTCATTAGATCCTTATCG CF 07-89 (+) Sequence mvaS
                                    (SEQ ID NO: 104)
5' - GAAACCTACATCCAATCTTTTGCCC
```

The plasmid called pTrcHis2AUpperPathway#1 was correct by sequencing and was transformed into the commercially available E. coli strain BL21. Selection was done on LA+50 µg/ml carbenicillin. Two transformants were chosen and grown in LB+50 µg/ml carbenicillin until they reached an $OD_{600}$ of 1.5. Both strains were frozen in a vial at −80° C. in the presence of glycerol. Strains were designated CF 449 for pTrcHis2AUpperPathway#1 in BL21, isolate #1 and CF 450 for pTrcHis2AUpperPathway#1 in BL21, isolate #2. Both clones were found to behave identically when analyzed.

V. Cloning of UpperMVA Pathway into pCL1920.

The plasmid pTrcHis2AUpperPathway was digested with the restriction endonuclease SspI to release a fragment containing pTrc-mvaE-mvaS-(His tag)-terminator. In this fragment, the his-tag was not translated. This blunt ended 4.5 kbp fragment was purified from a 1.2% E-gel using the Qiagen Gel Purification kit. A dephosphorylated, blunt ended 4.2 kbp fragment from pCL1920 was prepared by digesting the vector with the restriction endonuclease PvuII, treating with SAP and gel purifying from a 1.2% E-gel using the Qiagen Gel Purification kit. The two fragments were ligated using the Roche Quick Ligation Kit and transformed into TOP10 chemically competent cells. Transformants were selected on LA containing spectinomycin (50 µg/ml). A correct colony was identified by screening for the presence of the insert by PCR. The plasmid was designated pCL PtrcUpperPathway (FIGS. 26 and 27A-27D; SEQ ID NO:12).

VI. Strains Expressing the Combined Upper and Lower Mevalonic Acid Pathways.

To obtain a strain with a complete mevalonic acid pathway plus kudzu isoprene synthase, plasmids pTrcKKDyIkl-Skan and pCLpTrcUpperPathway were both transformed into BL21(λDE3) competent cells (Invitrogen) and transformants were selected on LA containing kanamycin (50 µg/ml) and Spectinomycin (50 µg/ml). The transformants were checked by plasmid prep to ensure that both plasmids were retained in the host. The strain was designated MCM127.

VII. Production of Mevalonic Acid from Glucose in E. Coli/pUpperpathway.

Single colonies of the BL21/pTrcHis2A-mvaE/mvaS or FM5/p pTrcHis2A-mvaE/mvaS are inoculated into LB+carbenicillin (100 µg/ml) and are grown overnight at 37° C. with shaking at 200 rpm. These cultures were diluted into 50 ml medium in 250 ml baffled flasks to an $OD_{600}$ of 0.1. The medium was TM3+1 or 2% glucose+carbenicillin (100 ug/ml) or TM3+1% glucose+hydrolyzed soy oil+carbenicillin (100 ug/ml) or TM3+biomass (prepared bagasse, corn stover or switchgrass). Cultures were grown at 30° C. with shaking at 200 rpm for approximately 2-3 hours until an $OD_{600}$ of 0.4 was reached. At this point the expression from the mvaE mvaS construct was induced by the addition of IPTG (400 µM). Cultures were incubated for a further 20 or 40 hours with samples taken at 2 hour intervals to 6 hour post induction and then at 24, 36 and 48 hours as needed. Sampling was done by removing 1 ml of culture, measuring the $OD_{600}$, pelleting the cells in a microfuge, removing the supernatant and analyzing it for mevalonic acid.

A 14 liter fermentation of E. coli cells with nucleic acids encoding Enterococcus faecalis AA-CoA thiolase, HMG-CoA synthase, and HMG-CoA reductase polypeptides produced 22 grams of mevalonic acid with TM3 medium and 2% glucose as the cell medium. A shake flask of these cells produced 2-4 grams of mevalonic acid per liter with LB medium and 1% glucose as the cell culture medium. The production of mevalonic acid in these strains indicated that the MVA pathway was functional in *E. coli*.

VIII. Production of Isoprene from *E. Coli* BL21 Containing the Upper and Lower MVA Pathway Plus Kudzu Isoprene Synthase.

The following strains were created by transforming in various combinations of plasmids containing the upper and lower MVA pathway and the kudzu isoprene synthase gene as described above and the plasmids containing the idi, dxs, and dxr and isoprene synthase genes described in Example 7. The host cells used were chemically competent BL21 (λDE3) and the transformations were done by standard methods. Transformants were selected on L agar containing kanamycin (50 µg/ml) or kanamycin plus spectinomycin (both at a concentration of 50 µg/ml). Plates were grown at 37° C. The resulting strains were designated as follows:
Grown on Kanamycin plus Spectinomycin (50 µg/ml each)
MCM127-pCL Upper MVA+pTrcKKDyIkIS (kan) in BL21 (λDE3)
MCM131-pCL1920+pTrcKKDyIkIS (kan) in BL21(λDE3)
MCM125-pCL Upper MVA+pTrcHis2B (kan) in BL21 (λDE3)
Grown on Kanamycin (50 µg/ml)
MCM64-pTrcKudzu yIDI DXS (kan) in BL21(λDE3)
MCM50-pTrcKudzu (kan) in BL21(λDE3)
MCM123-pTrcKudzu yIDI DXS DXR (kan) in BL21 (λDE3)

The above strains were streaked from freezer stocks to LA+appropriate antibiotic and grown overnight at 37° C. A single colony from each plate was used to inoculate shake flasks (25 ml LB+the appropriate antibiotic). The flasks were incubated at 22° C. overnight with shaking at 200 rpm. The next morning the flasks were transferred to a 37° C. incubator and grown for a further 4.5 hours with shaking at 200 rpm. The 25 ml cultures were centrifuged to pellet the cells and the cells were resuspended in 5 ml LB+the appropriate antibiotic. The cultures were then diluted into 25 ml LB+1% glucose+the appropriate antibiotic to an $OD_{600}$ of 0.1. Two flasks for each strain were set up, one set for induction with IPTG (800 µM) the second set was not induced. The cultures were incubated at 37° C. with shaking at 250 rpm. One set of the cultures were induced after 1.50 hours (immediately following sampling time point 1). At each sampling time point, the $OD_{600}$ was measured and the amount of isoprene determined as described in Example 1. Results are presented in Table 3. The amount of isoprene made is presented as the amount at the peak production for the particular strain.

TABLE 3

Production of isoprene in *E. coli* strains

| Strain | Isoprene (µg/liter/OD/hr) |
|---|---|
| MCM50 | 23.8 |
| MCM64 | 289 |
| MCM125 | ND |
| MCM131 | Trace |
| MCM127 | 874 |

ND: not detected
Trace: peak present but not integrable.

IX. Analysis of Mevalonic Acid.

Mevalonolactone (1.0 g, 7.7 mmol) (CAS#503-48-0) was supplied from Sigma-Aldrich (WI, USA) as a syrup that was dissolved in water (7.7 mL) and was treated with potassium hydroxide (7.7 mmol) in order to generate the potassium salt of mevalonic acid. The conversion to mevalonic acid was confirmed by $^1$H NMR analysis. Samples for HPLC analysis were prepared by centrifugation at 14,000 rpm for 5 minutes to remove cells, followed by the addition of a 300 µl aliquot of supernatant to 900 µl of $H_2O$. Perchloric acid (36 µl of a 70% solution) was then added followed by mixing and cooling on ice for 5 minutes. The samples were then centrifuged again (14,000 rpm for 5 min) and the supernatant transferred to HPLC. Mevalonic acid standards (20, 10, 5, 1 and 0.5 g/L) were prepared in the same fashion. Analysis of mevalonic acid (20 uL injection volume) was performed by HPLC using a BioRad Aminex 87-H+ column (300 mm by 7.0 mm) eluted with 5 mM sulfuric acid at 0.6 mL/min with refractive index (RI) detection. Under these conditions mevalonic acid eluted as the lactone form at 18.5 minutes.

X. Production of Isoprene from *E. Coli* BL21 Containing the Upper MVA Pathway Plus Kudzu Isoprene Synthase.

A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 2.2 g/L of isoprene.

Medium Recipe (Per Liter Fermentation Medium).

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component was dissolved one at a time in $diH_2O$, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpperPathway (FIG. 26) and pTrcKKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into soytone-yeast extract-glucose medium. After the inoculum grew to OD 1.0 when measured at 550 nm, 500 mL was used to inoculate a 5-L bioreactor.

Figure 54:
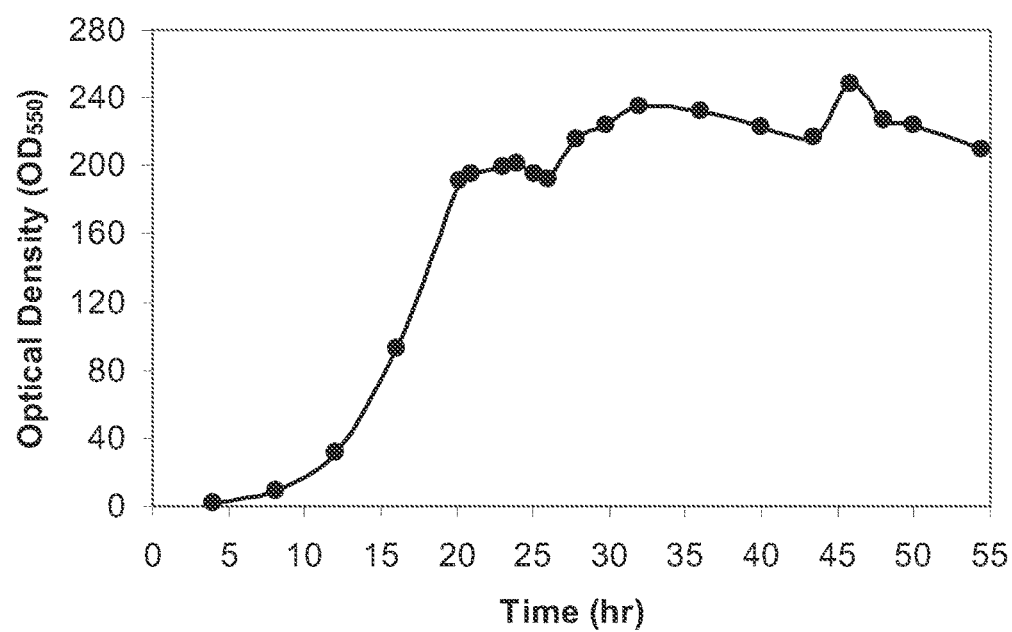
FIG. 54 is a time course of optical density within the 15-L bioreactor fed with glucose.
Figure 55:
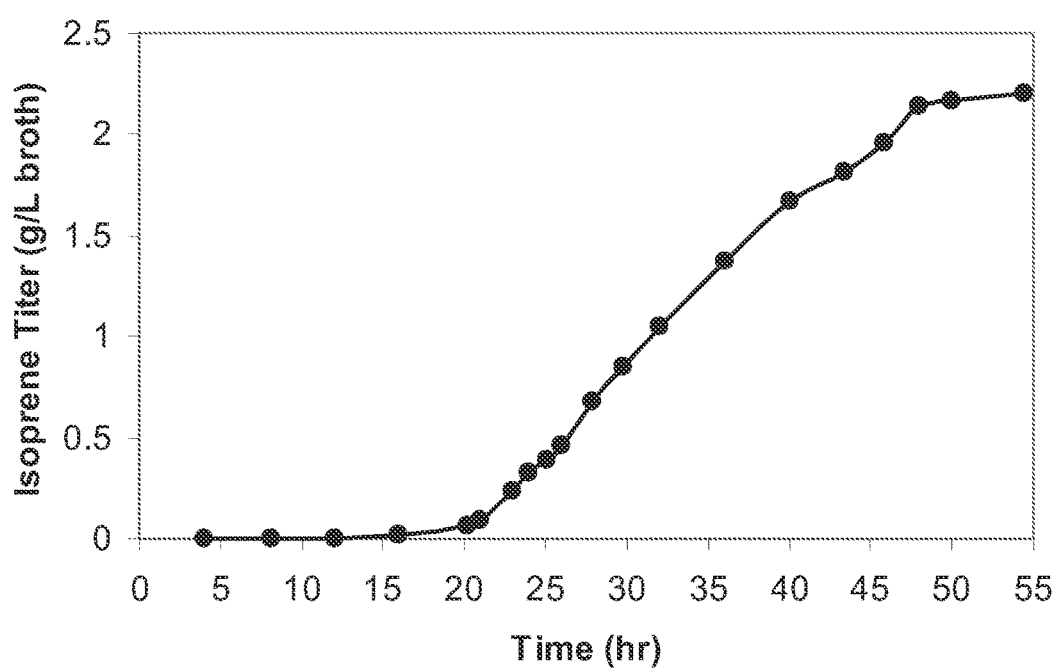
FIG. 55 is a time course of isoprene titer within the 15-L bioreactor fed with glucose. The titer is defined as the amount of isoprene produced per liter of fermentation broth.
Figure 56:
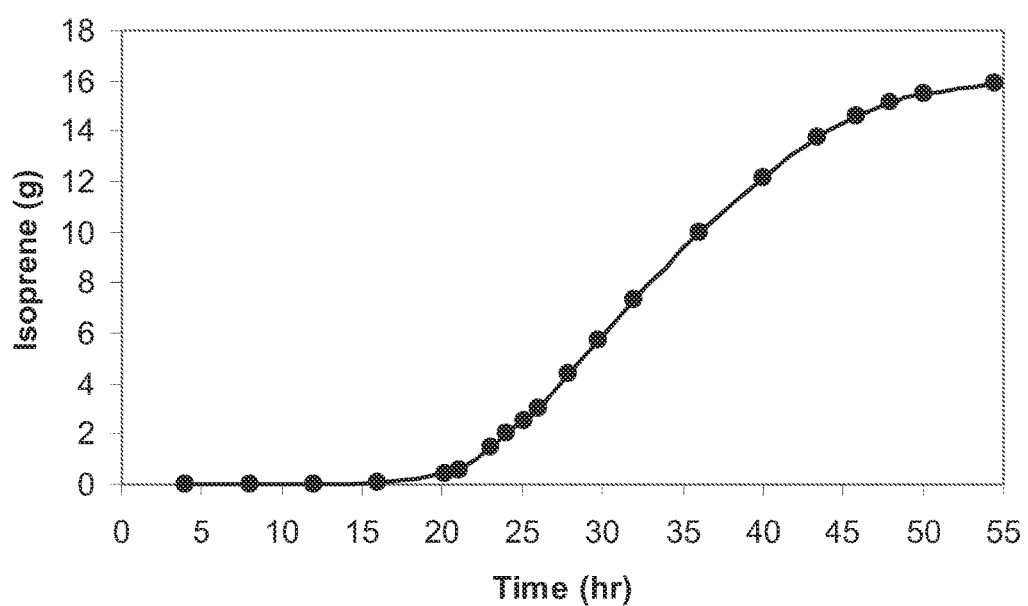
FIG. 56 is a time course of total isoprene produced from the 15-L bioreactor fed with glucose.

Glucose was fed at an exponential rate until cells reached the stationary phase. After this time the glucose feed was decreased to meet metabolic demands. The total amount of glucose delivered to the bioreactor during the 54 hour fermentation was 3.7 kg. Induction was achieved by adding isopropyl-beta-D-1-thiogalactopyranoside (IPTG). The IPTG concentration was brought to 25 uM when the optical density at 550 nm ($OD_{550}$) reached a value of 10. The IPTG concentration was raised to 50 uM when $OD_{550}$ reached 190. IPTG concentration was raised to 100 uM at 38 hours of fermentation. The $OD_{550}$ profile within the bioreactor over time is shown in FIG. 54. The isoprene level in the off gas from the bioreactor was determined as described herein. The isoprene titer increased over the course of the fermentation to a final value of 2.2 g/L (FIG. 55). The total amount of isoprene produced during the 54 hour fermentation was 15.9 g, and the time course of production is shown in FIG. 56.

XI. Isoprene Fermentation from *E. Coli* Expressing Genes from the Mevalonic Acid Pathway and Grown in Fed-Batch Culture at the 15-L Scale.

A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 3.0 g/L of isoprene.

Medium Recipe (Per Liter Fermentation Medium).

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component was dissolved one at a time in $diH_2O$, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpper-MVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time, the glucose feed was decreased to meet metabolic demands. The total amount of glucose delivered to the bioreactor during the 59 hour fermentation was 2.2 kg. Induction was achieved by adding IPTG. The IPTG concentration was brought to 25 uM when the optical density at 550 nm ($OD_{550}$) reached a value of 10. The IPTG concentration was raised to 50 uM when $OD_{550}$ reached 190. The $OD_{550}$ profile within the bioreactor over time is shown in FIG. 93. The isoprene level in the off gas from the bioreactor was determined as described herein. The isoprene titer increased over the course of the fermentation to a final value of 3.0 g/L (FIG. 94). The total amount of isoprene produced during the 59 hour fermentation was 22.8 g, and the time course of production is shown in FIG. 95. The molar yield of utilized carbon that went into producing isoprene during fermentation was 2.2%. The weight percent yield of isoprene from glucose was 1.0%.

XII. Isoprene Fermentation from *E. Coli* Expressing Genes from the Mevalonic Acid Pathway and Grown in Fed-Batch Culture at the 15-L Scale.

A 15-L scale fermentation of *E. coli* expressing mevalonic acid pathway polypeptides, *Pueraria lobata* isoprene synthase, and Kudzu isoprene synthase was used to produce isoprene from cells in fed-batch culture. This experiment demonstrates that growing cells under glucose limiting conditions resulted in the production of 3.3 g/L of isoprene.

i) Construction of pCLPtrcUpperPathwayHGS2

The gene encoding isoprene synthase from *Pueraria lobata* was PCR-amplified using primers NsiI-RBS-HGS F (CTTGATGCATCCTGCATTCGCCCTTAGGAGG, SEQ ID NO:105) and pTrcR (CCAGGCAAATTCTGTTT-TATCAG, SEQ ID NO:106), and pTrcKKDyIkIS as a template. The PCR product thus obtained was restriction-digested with NsiI and PstI and gel-purified. The plasmid pCL PtrcUpperPathway was restriction-digested with PstI and dephosphorylated using rAPid alkaline phosphatase (Roche) according to manufacturer's instructions.

These DNA fragments were ligated together and the ligation reaction was transformed into *E. coli* Top10 chemically competent cells (Invitrogen), plated on L agar containing spectinomycin (50 ug/ml) and incubated overnight at 370 C. Plasmid DNA was prepared from 6 clones using the Qiaquick Spin Mini-prep kit. The plasmid DNA was digested with restriction enzymes EcoRV and MluI to identify a clone in which the insert had the right orientation (i.e., the gene oriented in the same way as the pTrc promoter).

The resulting correct plasmid was designated pCLPtrcUpperPathwayHGS2. This plasmid was assayed using the headspace assay described herein and found to produce isoprene in *E. coli* Top10, thus validating the functionality of the gene. The plasmid was transformed into BL21(LDE3) containing pTrcKKDyIkIS to yield the strain BL21/pCLPtrcUpperPathwayHGS2-pTrcKKDyIkIS. This strain has an extra copy of the isoprene synthase compared to the BL21/pCL PtrcUpperMVA and pTrc KKDyIkIS strain (Example 8, part XI). This strain also had increased expression and activity of HMGS compared to the BL21/pCL PtrcUpperMVA and pTrc KKDyIkIS strain used in Example 8, part XI.

ii) Isoprene Fermentation from *E. Coli* Expressing pCLPtrcUpperPathwayHGS2-pTrcKKDyIkIS and Grown in Fed-Batch Culture at the 15-L Scale Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component is dissolved one at a time in $DiH_2O$, pH to 3.0 with HCl/NaOH, then q.s. to volume and filter sterilized with 0.22 micron filter.

Fermentation was performed in a 15-L bioreactor with BL21 (DE3) *E. coli* cells containing the pCLPtrcUpperPathwayHGS2 and pTrc KKDyIkIS plasmids. This experiment was carried out to monitor isoprene formation from glucose at the desired fermentation pH 7.0 and temperature 30° C. An inoculum of E. coli strain taken from a frozen vial was streaked onto an LB broth agar plate (with antibiotics) and incubated at 37° C. A single colony was inoculated into tryptone-yeast extract medium. After the inoculum grew to OD 1.0 measured at 550 nm, 500 mL was used to inoculate a 5-L bioreactor.

Glucose was fed at an exponential rate until cells reached the stationary phase. After this time the glucose feed was decreased to meet metabolic demands. The total amount of glucose delivered to the bioreactor during the 58 hour fermentation was 2.1 kg. Induction was achieved by adding IPTG. The IPTG concentration was brought to 25 uM when the optical density at 550 nm ($OD_{550}$) reached a value of 9. The IPTG concentration was raised to 50 uM when $OD_{550}$ reached 170. The $OD_{550}$ profile within the bioreactor over time is shown in FIG. 104. The isoprene level in the off gas from the bioreactor was determined as described herein. The isoprene titer increased over the course of the fermentation to a final value of 3.3 g/L (FIG. 105). The total amount of isoprene produced during the 58 hour fermentation was 24.5 g and the time course of production is shown in FIG. 106. The molar yield of utilized carbon that went into producing isoprene during fermentation was 2.5%. The weight percent yield of isoprene from glucose was 1.2%. Analysis showed that the activity of the isoprene synthase was increased by approximately 3-4 times that compared to BL21 expressing CL PtrcUpperMVA and pTrc KKDyIkIS plasmids (data not shown).

XIII. Chromosomal Integration of the Lower Mevalonate Pathway in E. Coli.

A synthetic operon containing mevalonate kinase, mevalonate phosphate kinase, mevalonate pyrophosphate decarboxylase, and the IPP isomerase was integrated into the chromosome of E. coli. If desired, expression may be altered by integrating different promoters 5' of the operon.

Table 4 lists primers used for this experiment.

i) Target Vector Construction

The attTn7 site was selected for integration. Regions of homology upstream (attTn7 up) (primers MCM78 and MCM79) and downstream (attTn7 down) (primers MCM88 and MCM89) were amplified by PCR from MG1655 cells. A 50 uL reaction with 1 uL 10 uM primers, 3 uL ddH2O, 45 uL Invitrogen Platinum PCR Supermix High Fidelity, and a scraped colony of MG1655 was denatured for 2:00 at 940 C, cycled 25 times (2:00 at 940 C, 0:30 at 500 C, and 1:00 at 680 C), extended for 7:00 at 720 C, and cooled to 40 C. This resulting DNA was cloned into pCR2.1 (Invitrogen) according to the manufacturer's instructions, resulting in plasmids MCM278 (attTn7 up) and MCM252 (attTn7 down). The 832 bp ApaI-PvuI fragment digested and gel purified from MCM252 was cloned into ApaI-PvuI digested and gel purified plasmid pR6K, creating plasmid MCM276. The 825 bp PstI-NotI fragment digested and gel purified from MCM278 was cloned into PstI-NotI digested and gel purified MCM276, creating plasmid MCM281.

ii) Cloning of Lower Pathway and Promoter

MVK-PMK-MVD-IDI genes were amplified from pTrcKKDyIkIS with primers MCM104 and MCM105 using Roche Expand Long PCR System according to the manufacturer's instructions. This product was digested with NotI and ApaI and cloned into MCM281 which had been digested with NotI and ApaI and gel purified. Primers MCM120 and MCM127 were used to amplify CMR cassette from the GeneBridges FRT-gb2-Cm-FRT template DNA using Stratagene Pfu Ultra II. A PCR program of denaturing at 95° C. for 4:00, 5 cycles of 95° C. for 0:20, 55° C. for 0:20, 72° C. for 2:00, 25 cycles of 95° C. for 0:20, 58° C. for 0:20, 72° C. for 2:00, 72° C. for 10:00, and then cooling to 4° C. was used with four 50 μL PCR reactions containing 1 uL~10 ng/μL template, 1 μL each primer, 1.25 μL 10 mM dNTPs, 5 μL 10× buffer, 1 μL enzyme, and 39.75 μL ddH20. Reactions were pooled, purified on a Qiagen PCR cleanup column, and used to electroporate water-washed Pir1 cells containing plasmid MCM296. Electroporation was carried out in 2 mM cuvettes at 2.5V and 200 ohms. Electroporation reactions

TABLE 4

| | Primers | |
|---|---|---|
| MCM78 | attTn7 up rev for integration construct | gcatgctcgagcggccgcTTTTAATCAAACATCCTGCCAACTC (SEQ ID NO: 107) |
| MCM79 | attTn7 down rev for integration construct | gatcgaagggcgatcgTGTCACAGTCTGGCGAAACCG (SEQ ID NO: 108) |
| MCM88 | attTn7 up forw for integration construct | ctgaattctgcagatatcTGTTTTTCCACTCTTCGTTCACTTT (SEQ ID NO: 109) |
| MCM89 | attTn7 down forw for integration construct | tctagagggcccAAGAAAAATGCCCCGCTTACG (SEQ ID NO: 110) |
| MCM104 | GI1.2 promoter-MVK | Gatcgcggccgcgcccttgacgatgccacatcctgagcaaataattcaaccactaattgtgagc ggataacacaaggaggaaacagctatgtcattaccgttcttaacttc (SEQ ID NO: 111) |
| MCM105 | aspA terminator-yIDI | Gatcgggccccaagaaaaaaggcacgtcatctgacgtgcctttttatttgtagacgcgttgttata gcattcta (SEQ ID NO: 112) |
| MCM120 | Forward of attTn7: attTn7 homology, GB marker homology | aaagtagccgaagatgacggtttgtcacatggagttggcaggatgtttgattaaaagcAATTA ACCCTCACTAAAGGGCGG (SEQ ID NO: 113) |
| MCM127 | Rev complement of 1.2 GI: GB marker homology(extra long), promoter, RBS, ATG | AGAGTGTTCACCAAAAATAATAACCTTTCCCGGTGCAgaagtt aagaacggtaatgacatagctgtttcctccttgtgttatccgctcacaattagtggttgaattatttgct caggatgtggcatcgtcaagggcTAATACGACTCACTATAGGGCTCG (SEQ ID NO: 114) | were recovered in LB for 3 hr at 30° C. Transformant MCM330 was selected on LA with CMP5, Kan50 (FIGS. 107 and 108A-108C; SEQ ID NO:25).

iii) Integration into E. Coli Chromosome

Miniprepped DNA (Qiaquick Spin kit) from MCM330 was digested with SnaBI and used to electroporate BL21 (DE3) (Novagen) or MG1655 containing GeneBridges plasmid pRedET Carb. Cells were grown at 30° C. to ~OD1 then induced with 0.4% L-arabinose at 37° C. for 1.5 hours. These cells were washed three times in 4° C. ddH2O before electroporation with 2 μL of DNA. Integrants were selected on L agar with containing chloramphenicol (5 μg/ml) and subsequently confirmed to not grow on L agar+Kanamycin (50 ug/ml). BL21 integrant MCM331 and MG1655 integrant MCM333 were frozen.

iv) Construction of pET24D-Kudzu Encoding Kudzu Isoprene Synthase

The kudzu isoprene synthase gene was subcloned into the pET24d vector (Novagen) from the pCR2.1 vector (Invitrogen). In particular, the kudzu isoprene synthase gene was amplified from the pTrcKudzu template DNA using primers MCM50 5'-GATCATGCAT TCGCCCTTAG GAGGTAAAAA AACATGTGTG CGACCTCTTC TCAATTTACT (SEQ ID NO:52) and MCM53 5'-CGGTCACGG ATCCCTGCAG TTAGACATAC ATCAGCTG (SEQ ID NO:50). PCR reactions were carried out using Taq DNA Polymerase (Invitrogen), and the resulting PCR product was cloned into pCR2.1-TOPO TA cloning vector (Invitrogen), and transformed into E. coli Top10 chemically competent cells (Invitrogen). Transformants were plated on L agar containing carbenicillin (50 μg/ml) and incubated overnight at 37° C. Five ml Luria Broth cultures containing carbenicillin 50 μg/ml were inoculated with single transformants and grown overnight at 37° C. Five colonies were screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu isoprene synthase coding sequence in a pCR2.1 backbone.

The kudzu coding sequence was removed by restriction endonuclease digestion with PciI and BamH1 (Roche) and gel purified using the QIAquick Gel Extraction kit (Qiagen). The pET24d vector DNA was digested with NcoI and BamHI (Roche), treated with shrimp alkaline phosphatase (Roche), and purified using the QIAprep Spin Mini-prep Kit (Qiagen). The kudzu isoprene synthase fragment was ligated to the NcoI/BamH1 digested pET24d using the Rapid DNA Ligation Kit (Roche) at a 5:1 fragment to vector ratio in a total volume of 20 μl. A portion of the ligation mixture (5 μl) was transformed into E. coli Top 10 chemically competent cells and plated on L agar containing kanamycin (50 μg/ml). The correct transformant was confirmed by sequencing and transformed into chemically competent BL21(λDE3)pLysS cells (Novagen). A single colony was selected after overnight growth at 37° C. on L agar containing kanamycin (50 μg/ml). A map of the resulting plasmid designated as pET24D-Kudzu is shown in FIG. 109. The sequence of pET24D-Kudzu (SEQ ID NO:26) is shown in FIGS. 110A and 110B. Isoprene synthase activity was confirmed using a headspace assay.

v) Production Strains

Strains MCM331 and MCM333 were cotransformed with plasmids pCLPtrcupperpathway and either pTrcKudzu or pETKudzu, resulting in the strains shown in Table 5.

TABLE 5

Production Strains

| Background | Integrated Lower | Upper MVA plasmid | Isoprene synthase plasmid | Production Stain |
|---|---|---|---|---|
| BL21(DE3) | MCM331 | pCLPtrcUpper Pathway | pTrcKudzu | MCM343 |
| BL21(DE3) | MCM331 | pCLPtrcUpper Pathway | pET24D-Kudzu | MCM335 |
| MG1655 | MCM333 | pCLPtrcUpper Pathway | pTrcKudzu | MCM345 | vi) Isoprene Fermentation from E. Coli Expressing Genes from the Mevalonic Acid Pathway and Grown in Fed-Batch Culture at the 15-L Scale.

Medium Recipe (Per Liter Fermentation Medium).

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component is dissolved one at a time in $DiH_2O$, pH to 3.0 with HCl/NaOH, then q.s. to volume and filter sterilized with a 0.22 micron filter.

Fermentation was performed in a 15-L bioreactor with BL21 (DE3) E. coli cells containing the gi1.2 integrated lower MVA pathway described above and the pCL PtrcUpperMVA and pTrcKudzu plasmids. This experiment was carried out to monitor isoprene formation from glucose at the desired fermentation pH 7.0 and temperature 30° C. An inoculum of E. coli strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time, the glucose feed was decreased to meet metabolic demands. The total amount of glucose delivered to the bioreactor during the 57 hour fermentation was 3.9 kg. Induction was achieved by adding IPTG. The IPTG concentration was brought to 100 uM when the carbon dioxide evolution rate reached 100 mmol/L/hr. The $OD_{550}$ profile within the bioreactor over time is shown in FIG. 111A. The isoprene level in the off gas from the bioreactor was determined as described herein. The isoprene titer increased over the course of the fermentation to a final value of 1.6 g/L (FIG. 111B). The specific productivity of isoprene over the course of the fermentation is shown in FIG. 111C and peaked at 1.2 mg/OD/hr. The total amount of isoprene produced during the 57 hour fermentation was 16.2 g. The molar yield of utilized carbon that went into producing isoprene during fermentation was 0.9%. The weight percent yield of isoprene from glucose was 0.4%.

XIV. Production of Isoprene from E. Coli BL21 Containing the Kudzu Isoprene Synthase Using Glycerol as a Carbon Source.

A 15-L scale fermentation of E. coli expressing Kudzu isoprene synthase was used to produce isoprene from cells fed glycerol in fed-batch culture. This experiment demonstrates that growing cells in the presence of glycerol (without glucose) resulted in the production of 2.2 mg/L of isoprene.

Medium Recipe (Per Liter Fermentation Medium).

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glycerol 5.1 g, thiamine*HCl 0.1 g, and antibiotics were added after sterilization and pH adjustment.

1000× Modified Trace Metal Solution:

The medium was generated using the following components per liter fermentation medium: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component was dissolved one at a time in $diH_2O$, pH to 3.0 with HCl/NaOH, then q.s. to volume and filter sterilized with a 0.22 micron filter.

Fermentation was performed in a 15-L bioreactor with BL21 (DE3) E. coli cells containing the pTrcKudzu plasmid. This experiment was carried out to monitor isoprene formation from glycerol at the desired fermentation pH 7.0 and temperature 35° C. An inoculum of E. coli strain taken from a frozen vial was streaked onto an LA broth agar plate (with antibiotics) and incubated at 37° C. A single colony was inoculated into soytone-yeast extract-glucose medium and grown at 35° C. After the inoculum grew to OD 1.0, measured at 550 nm, 600 mL was used to inoculate a 7.5-L bioreactor.

Figure 57:
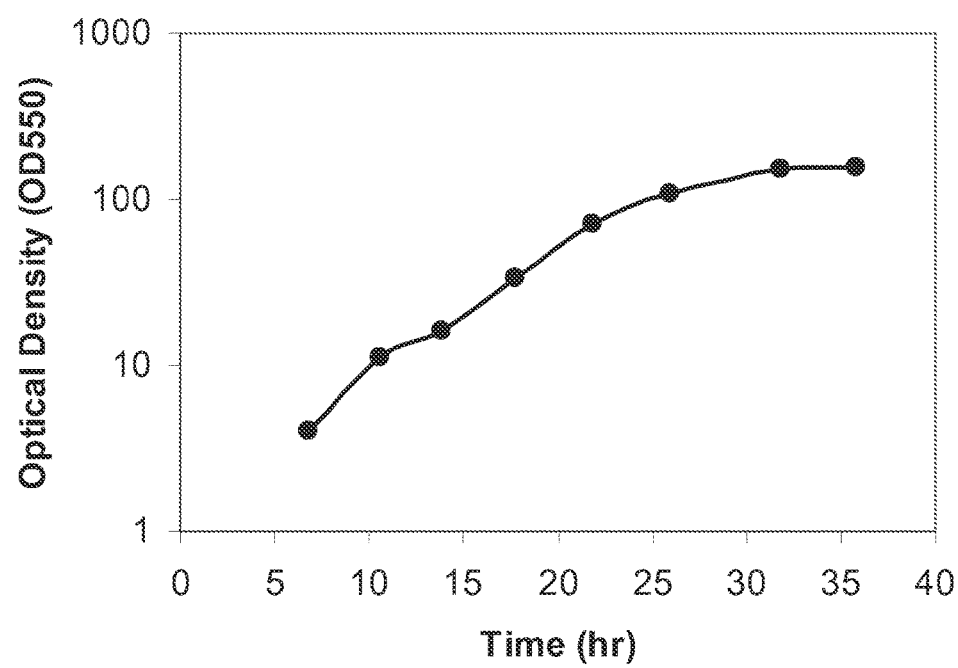
FIG. 57 is a time course of optical density within the 15-L bioreactor fed with glycerol.
Figure 58:
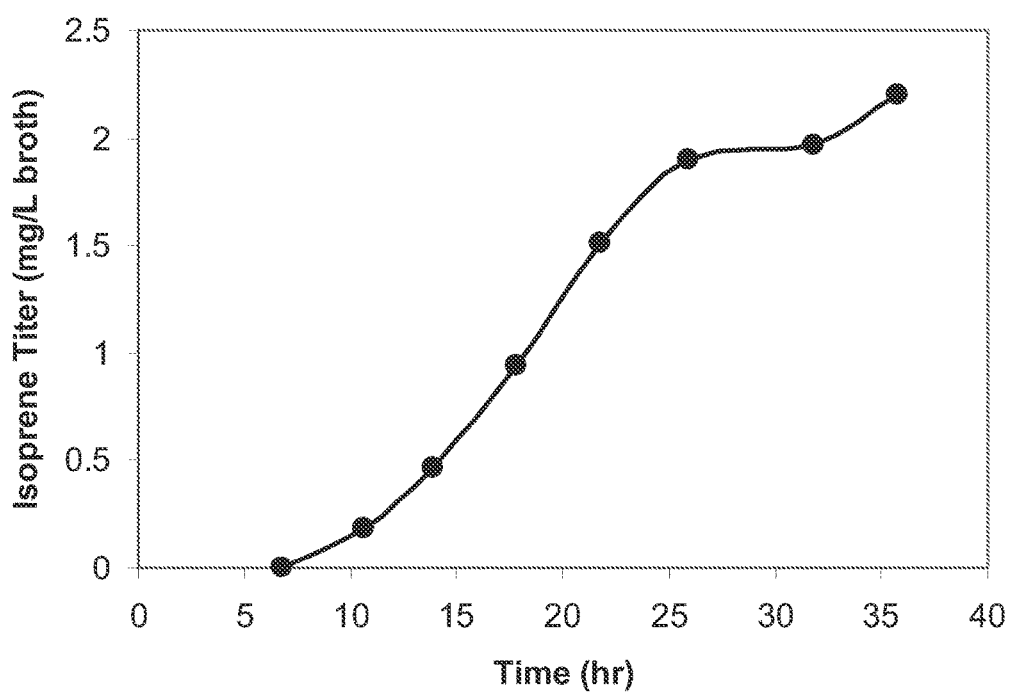
FIG. 58 is a time course of isoprene titer within the 15-L bioreactor fed with glycerol. The titer is defined as the amount of isoprene produced per liter of fermentation broth.
Figure 59:
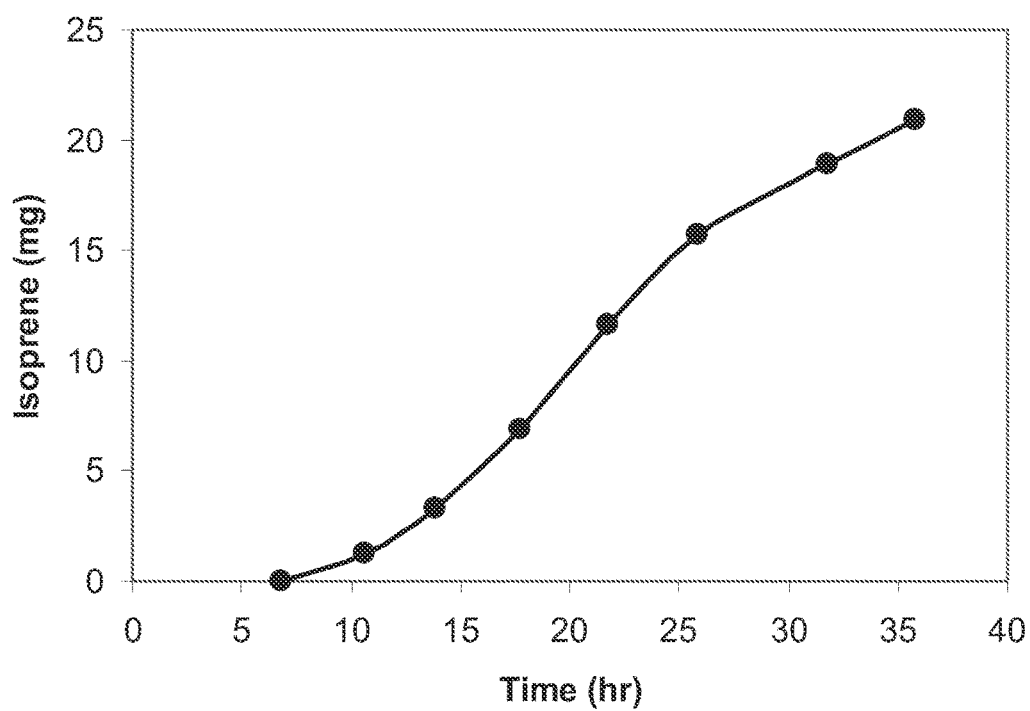
FIG. 59 is a time course of total isoprene produced from the 15-L bioreactor fed with glycerol.

Glycerol was fed at an exponential rate until cells reached an optical density at 550 nm ($OD_{550}$) of 153. The total amount of glycerol delivered to the bioreactor during the 36 hour fermentation was 1.7 kg. Other than the glucose in the inoculum, no glucose was added to the bioreactor. Induction was achieved by adding IPTG. The IPTG concentration was brought to 20 uM when the $OD_{550}$ reached a value of 50. The $OD_{550}$ profile within the bioreactor over time is shown in FIG. 57. The isoprene level in the off gas from the bioreactor was determined as described herein. The isoprene titer increased over the course of the fermentation to a final value of 2.2 mg/L (FIG. 58). The total amount of isoprene produced during the 54 hour fermentation was 20.9 mg, and the time course of production is shown in FIG. 59.

XV. Isoprene Fermentation from E. coli Expressing Genes from the Mevalonic Acid Pathway and Grown in Fed-Batch Culture at the 15-L Scale Using Invert Sugar as a Carbon Source.

A 15-L scale fermentation of E. coli expressing mevalonic acid pathway polypeptides and Kudzu isoprene synthase was used to produce isoprene from cells fed invert sugar in fed-batch culture. This experiment demonstrates that growing cells in the presence of invert sugar resulted in the production of 2.4 g/L of isoprene.

Medium Recipe (Per Liter Fermentation Medium).

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Invert sugar 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component is dissolved one at a time in DiH2O, pH to 3.0 with HCl/NaOH, then q.s. to volume and filter sterilized with 0.22 micron filter.

Fermentation was performed in a 15-L bioreactor with BL21 (DE3) E. coli cells containing the pCL PtrcUpperMVA and pTrc KKDyIkIS plasmids. This experiment was carried out to monitor isoprene formation from invert sugar at the desired fermentation pH 7.0 and temperature 30° C. An inoculum of E. coli strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Invert sugar was fed at an exponential rate until cells reached the stationary phase. After this time the invert sugar feed was decreased to meet metabolic demands. The total amount of invert sugar delivered to the bioreactor during the 44 hour fermentation was 2.4 kg. Induction was achieved by adding IPTG. The IPTG concentration was brought to 25 uM when the optical density at 550 nm ($OD_{550}$) reached a value of 9. The IPTG concentration was raised to 50 uM when $OD_{550}$ reached 200. The $OD_{550}$ profile within the bioreactor over time is shown in FIG. 96. The isoprene level in the off gas from the bioreactor was determined as described herein. The isoprene titer increased over the course of the fermentation to a final value of 2.4 g/L (FIG. 97). The total amount of isoprene produced during the 44 hour fermentation was 18.4 g and the time course of production is shown in FIG. 98. The molar yield of utilized carbon that went into producing isoprene during fermentation was 1.7%. The weight percent yield of isoprene from glucose was 0.8%.

Example 9

Construction of the Upper and Lower MVA Pathway for Integration into Bacillus Subtilis I. Construction of the Upper MVA Pathway in Bacillus Subtilis.

The upper pathway from Enterococcus faecalis is integrated into B. subtilis under control of the aprE promoter. The upper pathway consists of two genes; mvaE, which encodes for AACT and HMGR, and mvaS, which encodes for HMGS. The two genes are fused together with a stop codon in between, an RBS site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allowed them to be fused together by a PCR reaction. PCR amplifications are carried out using Herculase polymerase according to manufacturer's instructions.

1. PaprE
CF 07-134 (+) Start of aprE promoter PstI
(SEQ ID NO: 115)
5'- GACATCTGCAGCTCCATTTTCTTCTGC CF 07-94 (-) Fuse PaprE to mvaE
(SEQ ID NO: 116)
5'- CAATAATAACTACTGTTTTCACTCTTTACCCTCTCCTTTTAA
Template: Bacillus subtilis chromosomal DNA 2. mvaE
CF 07-93 (+) fuse mvaE to the aprE promoter (GTG start codon)
(SEQ ID NO: 117)
5'- TTAAAAGGAGAGGGTAAAGAGTGAAAACAGTAGTTATTATTG CF 07-62 (-) Fuse mvaE to mvaS with RBS in between
(SEQ ID NO: 94)
5'- TTTATCAATCCCAATTGTCATGTTTTTTTACCTCCTTTATTGTTTTCTTAAATC
Template: Enterococcus faecalis chromosomal DNA (from ATCC)

3. mvaS
CF 07-61 (+) Fuse mvaE to mvaS with RBS in between
(SEQ ID NO: 95)
5'- GATTTAAGAAAACAATAAAGGAGGTAAAAAAACATGACAATTGGGATTGATAAA CF 07-124 (-) Fuse the end of mvaS to the terminator
(SEQ ID NO: 118)
5'- CGGGGCCAAGGCCGGTTTTTTTTAGTTTCGATAAGAACGAACGGT
Template: Enterococcus faecalis chromosomal DNA 4. B. amyliquefaciens alkaline serine protease terminator
CF 07-123 (+) Fuse the end of mvaS to the terminator
(SEQ ID NO: 119)
5'- ACCGTTCGTTCTTATCGAAACTAAAAAAAACCGGCCTTGGCCCCG CF 07-46 (-) End of B. amyliquefaciens terminator BamHI
(SEQ ID NO: 58)
5'- GACATGACGGATCCGATTACGAATGCCGTCTC
Template: Bacillus amyliquefaciens chromosomal DNA PCR Fusion Reactions 5. Fuse mvaE to mvaS
CF 07-93 (+) fuse mvaE to the aprE promoter (GTG start codon)
(SEQ ID NO: 117)
5'- TTAAAAGGAGAGGGTAAAGAGTGAAAACAGTAGTTATTATTG CF 07-124 (-) Fuse the end of mvaS to the terminator
(SEQ ID NO: 118)
5'- CGGGGCCAAGGCCGGTTTTTTTTAGTTTCGATAAGAACGAACGGT
Template: #2 and 3 from above 6. Fuse mvaE-mvaS to aprE promoter
CF 07-134 (+) Start of aprE promoter PstI
(SEQ ID NO: 115)
5'- GACATCTGCAGCTCCATTTTCTTCTGC CF 07-124 (-) Fuse the end of mvaS to the terminator
(SEQ ID NO: 118)
5'- CGGGGCCAAGGCCGGTTTTTTTTAGTTTCGATAAGAACGAACGGT
Template #1 and #4 from above 7. Fuse PaprE-mvaE-mvaS to terminator
CF 07-134 (+) Start of aprE promoter PstI
(SEQ ID NO: 115)
5'- GACATCTGCAGCTCCATTTTCTTCTGC CF 07-46 (-) End of B. amyliquefaciens terminator BamHI
(SEQ ID NO: 58)
5'- GACATGACGGATCCGATTACGAATGCCGTCTC
Template: #4 and #6

Figure 50:
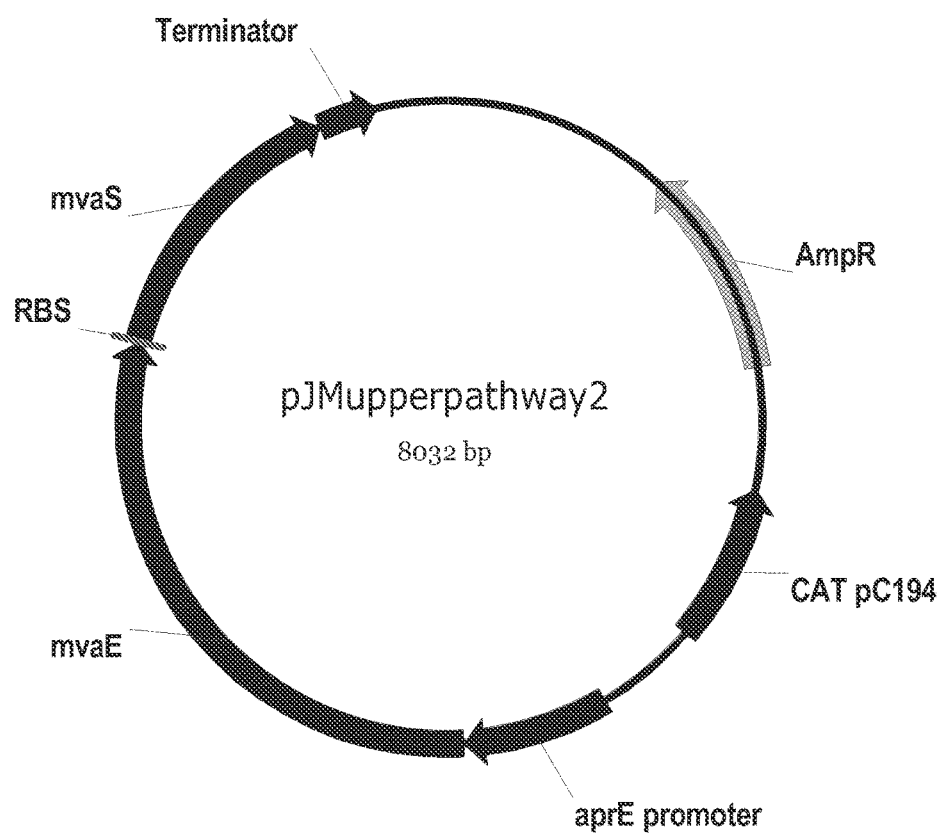
FIG. 50 is a map of pJMupperpathway2.

The product is digested with restriction endonucleases PstI/BamHI and ligated to pJM102 (Perego, M. 1993. Integrational vectors for genetic manipulation in Bacillus subtilis, p. 615-624. In A. L. Sonenshein, J. A. Hoch, and R. Losick (ed.), Bacillus subtilis and other gram-positive bacteria: biochemistry, physiology, and molecular genetics. American Society for Microbiology, Washington, D.C.) which is digested with PstI/BamHI. The ligation is transformed into E. coli TOP 10 chemically competent cells and transformants are selected on LA containing carbenicillin (50 μg/ml). The correct plasmid is identified by sequencing and is designated pJMUpperpathway2 (FIGS. 50 and 51;

SEQ ID NO:22). Purified plasmid DNA is transformed into Bacillus subtilis aprEnprE Pxyl-comK and transformants are selected on L agar containing chloramphenicol (5 μg/ml). A correct colony is selected and is plated sequentially on L agar containing chloramphenicol 10, 15 and 25 μg/ml to amplify the number of copies of the cassette containing the upper pathway.

The resulting strain is tested for mevalonic acid production by growing in LB containing 1% glucose and 1%. Cultures are analyzed by GC for the production of mevalonic acid.

This strain is used subsequently as a host for the integration of the lower mevalonic acid pathway.

The following primers are used to sequence the various constructs above.
Sequencing Primers:

```
CF 07-134 (+) Start of aprE promoter PstI
                                    (SEQ ID NO: 115)
5'- GACATCTGCAGCTCCATTTTCTTCTGC CF 07-58 (+) Start of mvaE gene
                                    (SEQ ID NO: 97)
5'- ATGAAAACAGTAGTTATTATTGATGC CF 07-59 (-) End of mvaE gene
                                    (SEQ ID NO: 98)
5'- ATGTTATTGTTTTCTTAAATCATTTAAAATAGC CF 07-82 (+) Start of mvaS gene
                                    (SEQ ID NO: 99)
5'- ATGACAATTGGGATTGATAAAATTAG CF 07-83 (-) End of mvaS gene
                                    (SEQ ID NO: 100)
5'- TTAGTTTCGATAAGAACGAACGGT CF 07-86 (+) Sequence in mvaE
                                    (SEQ ID NO: 101)
5'- GAAATAGCCCCATTAGAAGTATC CF 07-87 (+) Sequence in mvaE
                                    (SEQ ID NO: 102)
5'- TTGCCAATCATATGATTGAAAATC CF 07-88 (+) Sequence in mvaE
                                    (SEQ ID NO: 103)
5'- GCTATGCTTCATTAGATCCTTATCG CF 07-89 (+) Sequence mvaS
                                    (SEQ ID NO: 104)
5'- GAAACCTACATCCAATCTTTTGCCC
```

Transformants are selected on LA containing chloramphenicol at a concentration of 5 μg/ml. One colony is confirmed to have the correct integration by sequencing and is plated on LA containing increasing concentrations of chloramphenicol over several days, to a final level of 25 μg/ml. This results in amplification of the cassette containing the genes of interest. The resulting strain is designated CF 455: pJMupperpathway#1× Bacillus subtilis aprEnprE Pxyl comK (amplified to grow on LA containing chloramphenicol 25 μg/ml).

II. Construction of the Lower MVA Pathway in Bacillus Subtilis.

Figure 28:
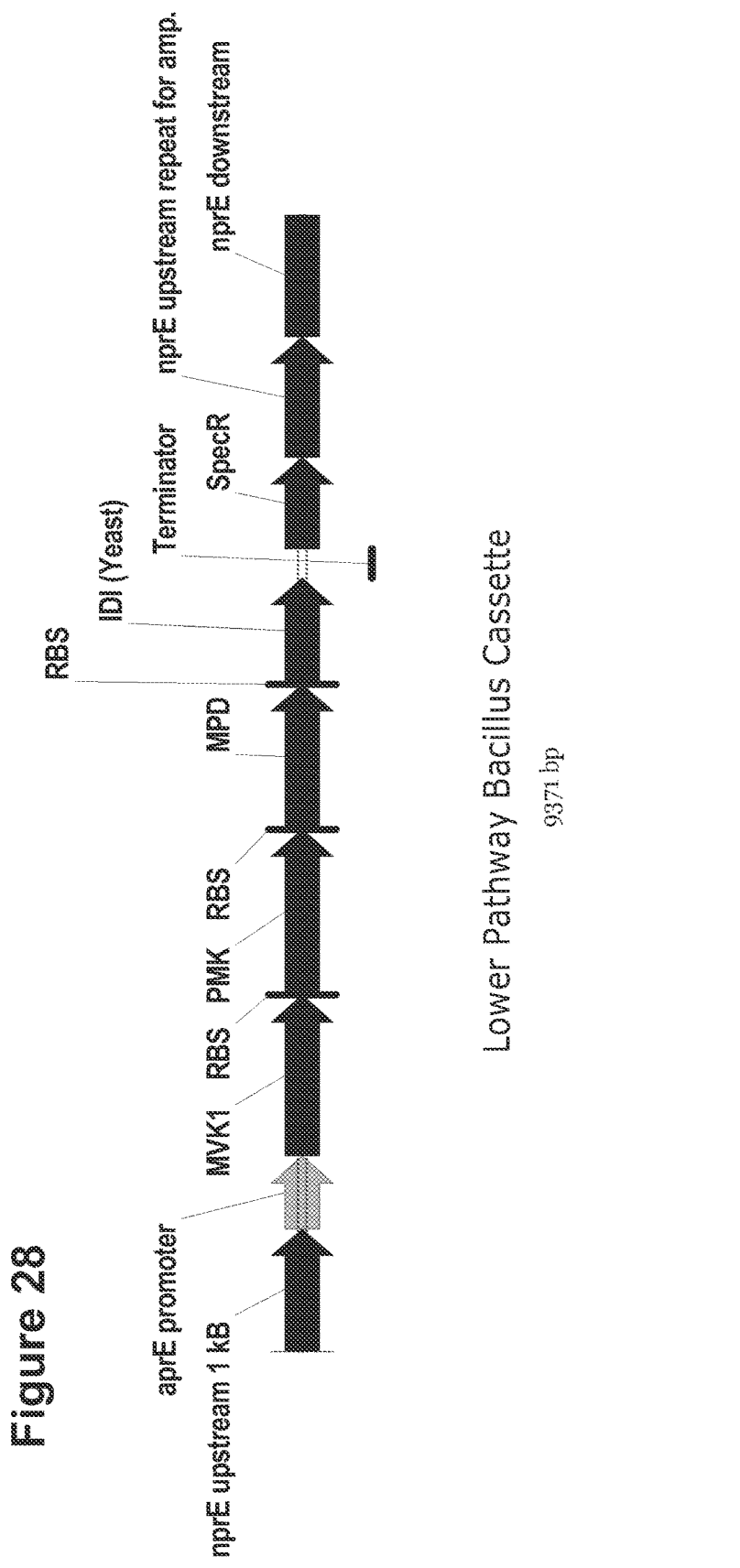
FIG. 28 shows a map of the cassette containing the lower MVA pathway and yeast idi for integration into the *B. subtilis* chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonte kinase gene with a *Bacillus* RBS upstream of the start site. RBS-MPD indicates the yeast diphosphomevalonate decarboxylase gene with a *Bacillus* RBS upstream of the start site. RBS-IDI indicates the yeast idi gene with a *Bacillus* RBS upstream of the start site. Terminator indicates the terminator alkaline serine protease transcription terminator from *B. amyliquefaciens*. SpecR indicates the spectinomycin resistance marker. "nprE upstream repeat for amp." indicates a direct repeat of the upstream region used for amplification.

The lower MVA pathway, consisting of the genes mvkl, pmk, mpd and idi are combined in a cassette consisting of flanking DNA regions from the nprE region of the B. subtilis chromosome (site of integration), the aprE promoter, and the spectinomycin resistance marker (see FIGS. 28 and 29; SEQ ID NO:13). This cassette is synthesized by DNA2.0 and is integrated into the chromosome of B. subtilis containing the upper MVA pathway integrated at the aprE locus. The kudzu isoprene synthase gene is expressed from the replicating plasmid described in Example 4 and is transformed into the strain with both upper and lower pathways integrated.

Example 10

Exemplary Isoprene Compositions and Methods of Making them

I. Compositional Analysis of Fermentation Off-Gas Containing Isoprene.

A 14 L scale fermentation was performed with a recombinant E. coli BL21 (DE3) strain containing two plasmids (pCL upperMev; pTrcKKDyIkIS) encoding the full mevalonate pathway for isoprenoid precursor biosynthesis, an isoprenyl pyrophosphate isomerase from yeast, and an isoprene synthase from Kudzu. Fermentation off-gas from the 14 L tank was collected into 20 mL headspace vials at around the time of peak isoprene productivity (27.9 hours elapsed fermentation time, "EFT") and analyzed by headspace GC/MS for volatile components.

Headspace analysis was performed with an Agilent 6890 GC/MS system fitted with an Agilent HP-5MS GC/MS column (30 m×250 μm; 0.25 μm film thickness). A combi-PAL autoinjector was used for sampling 500 uL aliquots from 20 mL headspace vials. The GC/MS method utilized helium as the carrier gas at a flow of 1 mL/min. The injection port was held at 250° C. with a split ratio of 50:1. The oven temperature was held at 37° C. for an initial 2 minute period, followed an increase to 237° C. at a rate of 25° C./min for a total method time of 10 minutes. The Agilent 5793N mass selective detector scanned from m/z 29 to m/z 300. The limit of detection of this system is approximately 0.1 ug/$L_{gas}$ or approximately 0.1 ppm. If desired, more sensitive equipment with a lower limit of detection may be used.

Figure 86A:
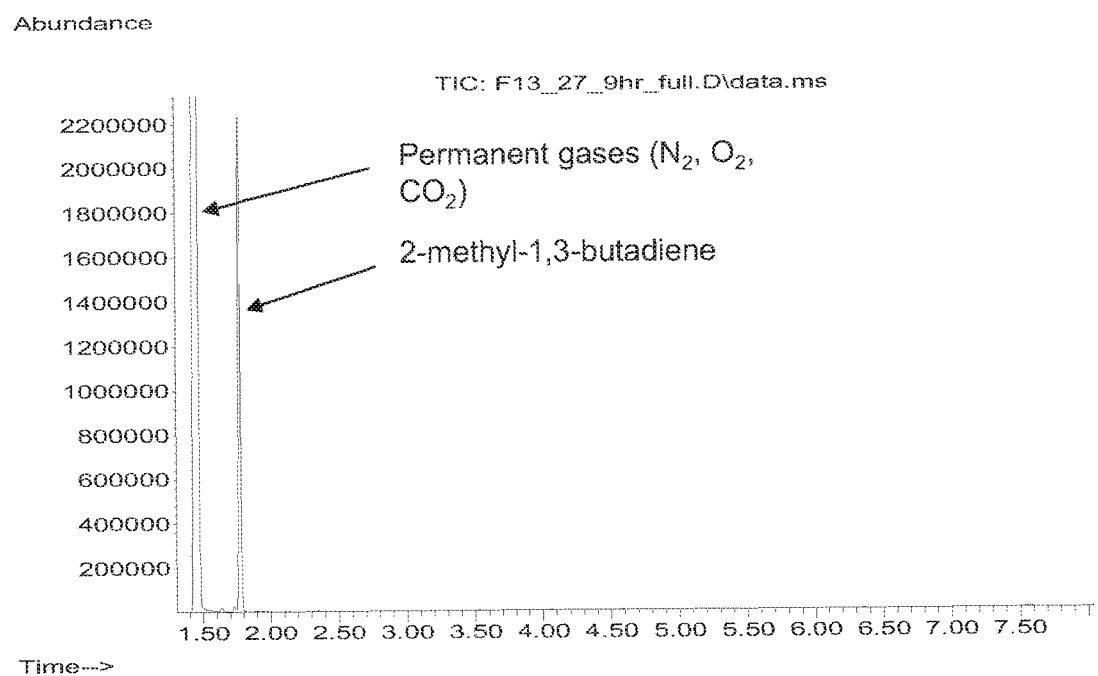
FIG. 86A is a GC/MS chromatogram of fermentation off-gas.
Figure 86B:
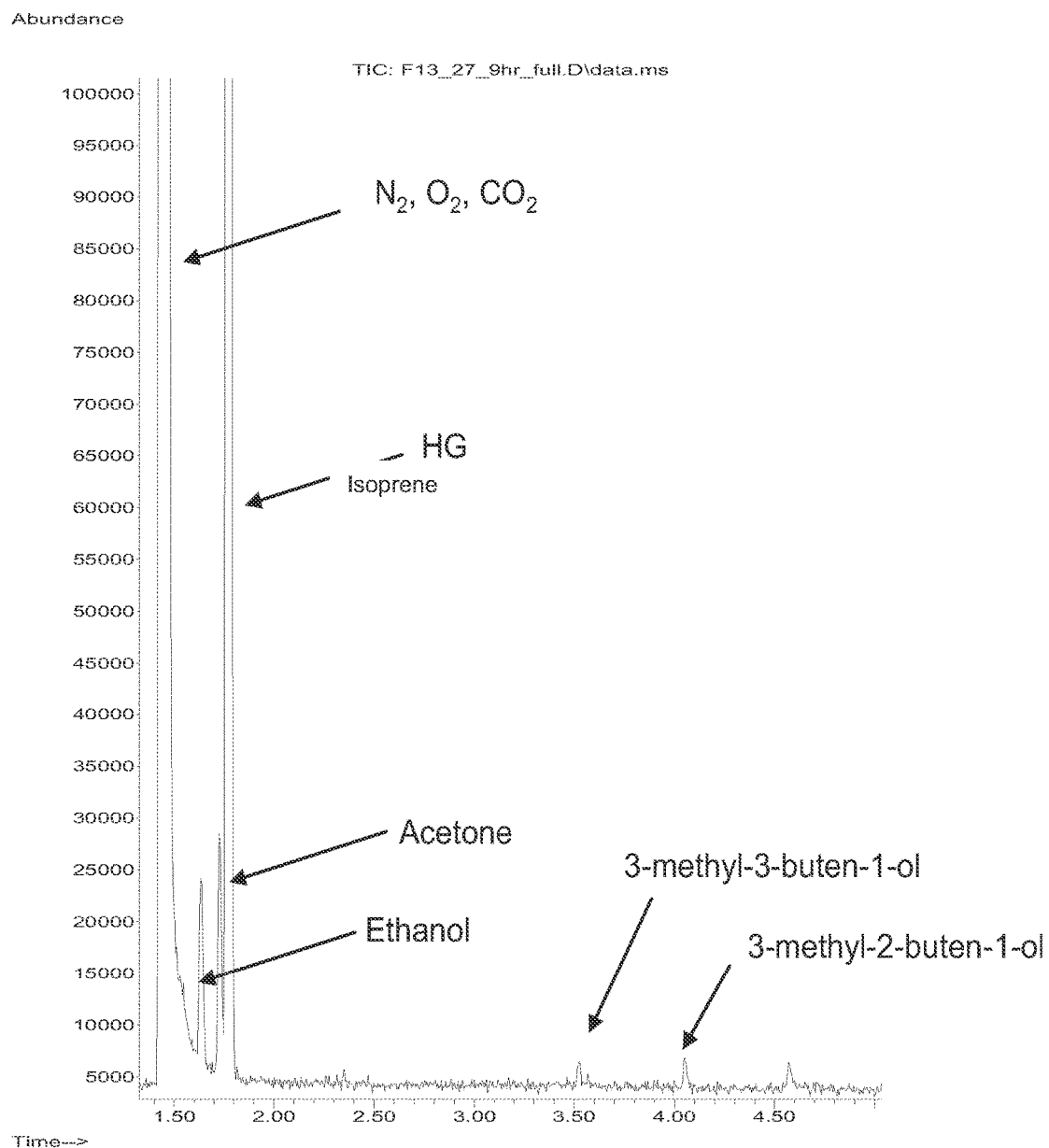
FIG. 86B is an expansion of FIG. 86A to show minor volatiles present in fermentation off-gas.
Figure 87A:
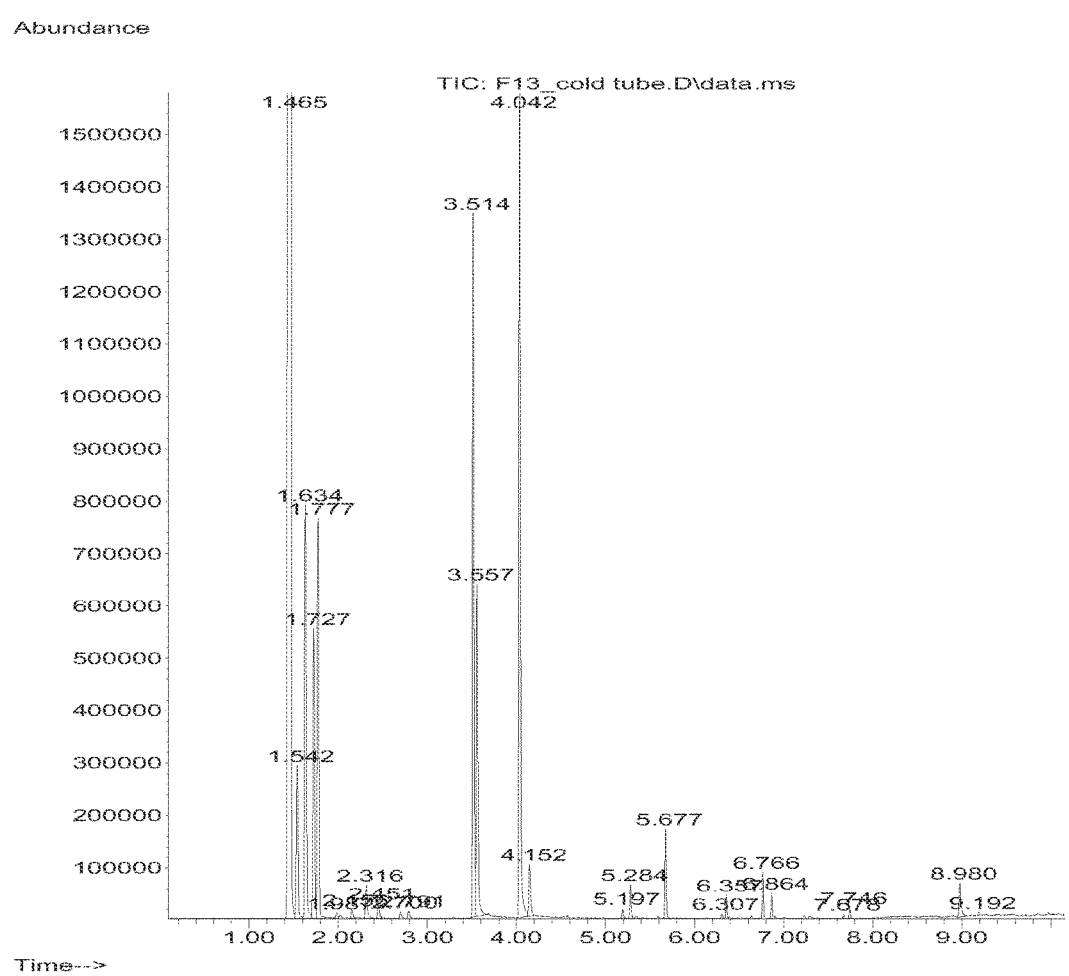
FIG. 87A is a GC/MS chromatogram of trace volatiles present in off-gas following cryo-trapping at −78° C.
Figure 87B:
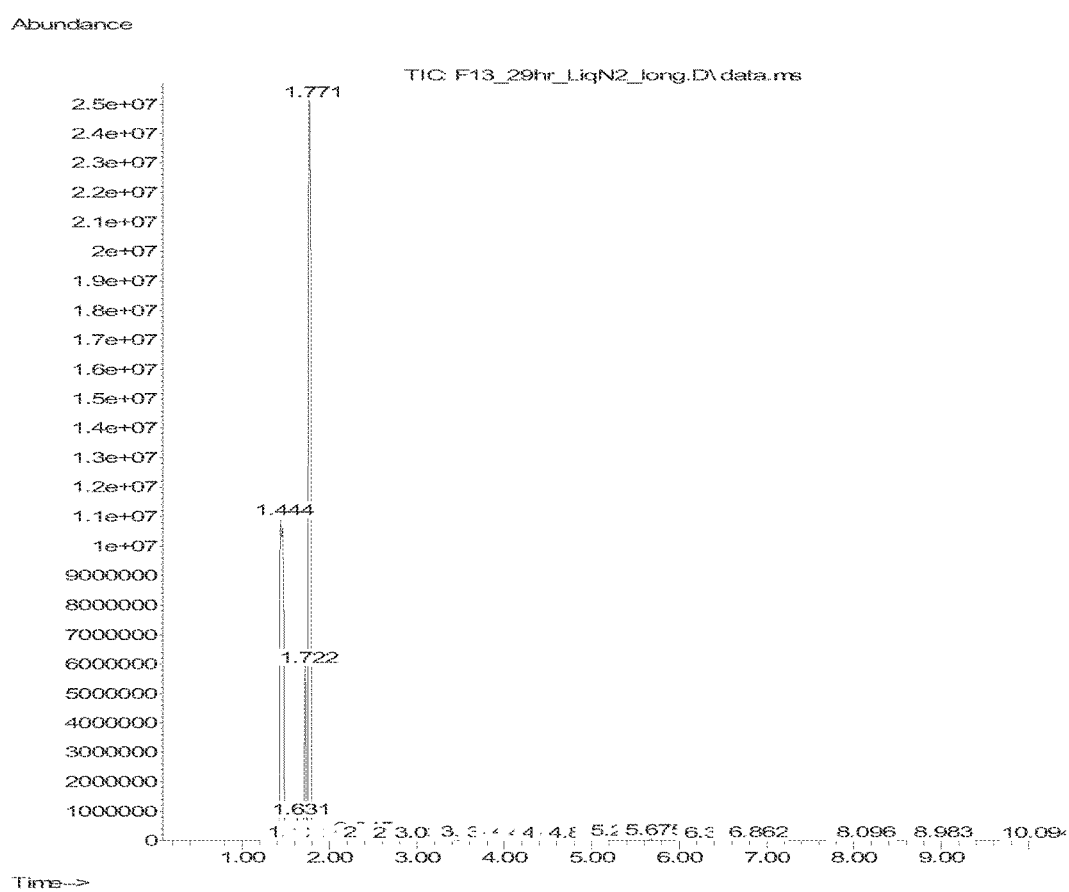
FIG. 87B is a GC/MS chromatogram of trace volatiles present in off-gas following cryo-trapping at −196° C.
Figure 87C:
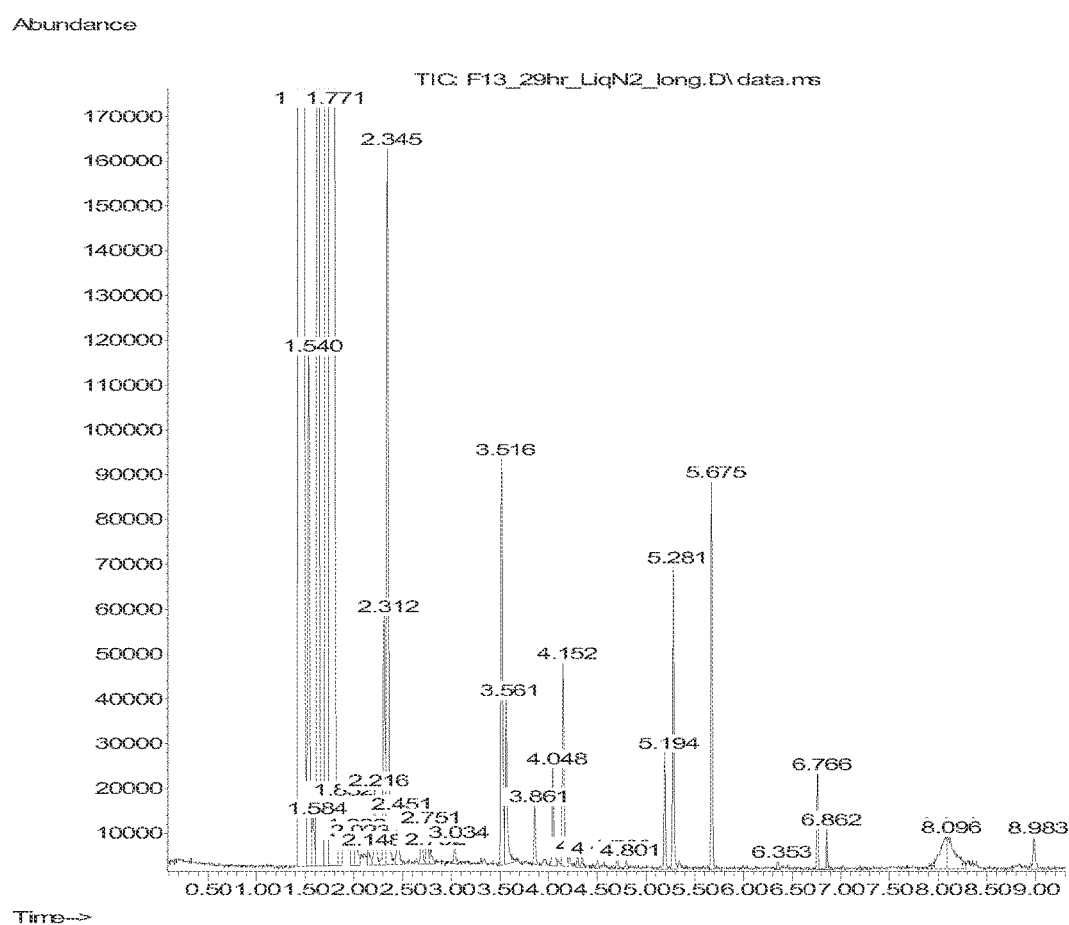
FIG. 87C is an expansion of FIG. 87B.
Figure 87D:
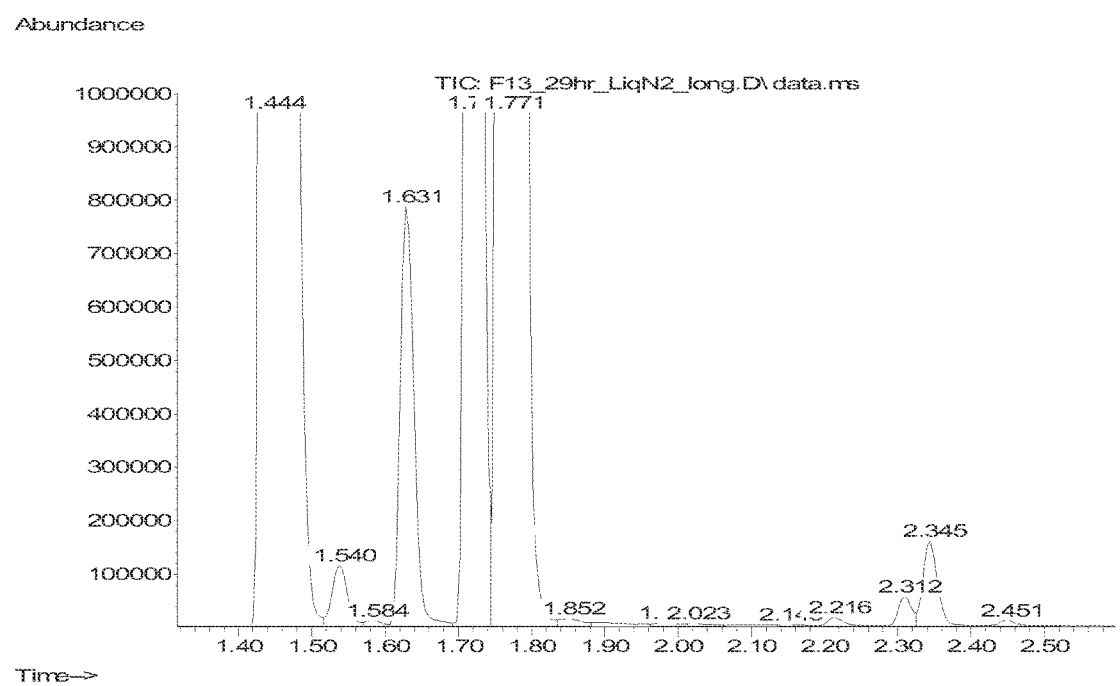
FIG. 87D is an expansion of FIG. 87C.

The off-gas consisted of 99.925% (v/v) permanent gases ($N_2$, $CO_2$ and $O_2$), approximately 0.075% isoprene (2-methyl-1,3-butadiene) (~750 ppmv, 2100 μg/L) and minor amounts (<50 ppmv) of ethanol, acetone, and two C5 prenyl alcohols. The amount of water vapor was not determined but was estimated to be equal to the equilibrium vapor pressure at 0° C. The composition of the volatile organic fraction was determined by integration of the area under the peaks in the GC/MS chromatogram (FIGS. 86A and 86B) and is listed in Table 6. Calibration curves for ethanol and acetone standards enabled the conversion of GC area to gas phase concentration in units of ug/L using standard methods.

TABLE 6

Composition of volatile organic components in fermentation off-gas.

| Compound | RT (min) | GC area | Area % | Conc. (ug/L) |
|---|---|---|---|---|
| Ethanol | 1.669 | 239005 | 0.84 | 62 +/− 6 |
| Acetone | 1.703 | 288352 | 1.02 | 42 +/− 4 |
| Isoprene (2-methyl-1,3-butadiene) | 1.829 | 27764544 | 97.81 | 2000 +/− 200 |
| 3-methyl-3-buten-1-ol | 3.493 | 35060 | 0.12 | <10 |
| 3-methyl-2-buten-1-ol | 4.116 | 58153 | 0.20 | <10 |

The off-gas was analyzed at the 27.9 hour time point of a fermentation using an E. coli BL21 (DE3) strain expressing a heterologous mevalonate pathway, an isoprenyl pyrophosphate isomerase from yeast, and an isoprene synthase from Kudzu.

II. Measurement of Trace Volatile Organic Compounds (VOCs) Co-Produced with Isoprene During Fermentation of a Recombinant E. Coli Strain.

A 14 L scale fermentation was performed with a recombinant E. coli BL21 (DE3) strain containing two plasmids (pCL upperMev; pTrcKKDyIkIS) encoding the full mevalonate pathway for isoprenoid precursor biosynthesis, an isoprenyl pyrophosphate isomerase from yeast, and an isoprene synthase from Kudzu.

Fermentation off-gas was passed through cooled headspace vials in order to concentrate and identify trace volatile organic components. The off-gas from this fermentation was sampled at a rate of 1 L/min for 10 minutes through a 20 mL headspace vial packed with quartz wool (2 g) and cooled to −78° C. with dry ice. The vial was recapped with a fresh vial cap and analyzed by headspace GC/MS for trapped VOCs using the conditions described in Example 10, part I. The ratios of compounds observed in FIGS. 87A-87D are a combination of overall level in the fermentation off-gas, the relative vapor pressure at −78° C., and the detector response of the mass spectrometer. For example, the low level of isoprene relative to oxygenated volatiles (e.g., acetone and ethanol) is a function of the high volatility of this material such that it does not accumulate in the headspace vial at −78° C.

The presence of many of these compounds is unique to isoprene compositions derived from biological sources. The results are depicted in FIGS. 87A-87D and summarized in Tables 7A and 7B.

TABLE 7A

Trace volatiles present in off-gas produced by *E. coli* BL21 (DE3) (pCL upperMev; pTrcKKDyIkIS) following cryo-trapping at −78° C.

| Compound | RT (min) | GC Area 1 | Area % 2 | Ratio % 3 |
|---|---|---|---|---|
| Acetaldehyde | 1.542 | 4019861 | 4.841 | 40.14 |
| Ethanol | 1.634 | 10553620 | 12.708 | 105.39 |
| Acetone | 1.727 | 7236323 | 8.714 | 72.26 |
| 2-methyl-1,3-butadiene | 1.777 | 10013714 | 12.058 | 100.00 |
| 1-propanol | 1.987 | 163574 | 0.197 | 1.63 |
| Diacetyl | 2.156 | 221078 | 0.266 | 2.21 |
| 2-methyl-3-buten-2-ol | 2.316 | 902735 | 1.087 | 9.01 |
| 2-methyl-1-propanol | 2.451 | 446387 | 0.538 | 4.46 |
| 3-methyl-1-butanal | 2.7 | 165162 | 0.199 | 1.65 |
| 1-butanol | 2.791 | 231738 | 0.279 | 2.31 |
| 3-methyl-3-buten-1-ol | 3.514 | 14851860 | 17.884 | 148.32 |
| 3-methyl-1-butanol | 3.557 | 8458483 | 10.185 | 84.47 |
| 3-methyl-2-buten-1-ol | 4.042 | 18201341 | 21.917 | 181.76 |
| 3-methyl-2-butenal | 4.153 | 1837273 | 2.212 | 18.35 |
| 3-methylbutyl acetate | 5.197 | 196136 | 0.236 | 1.96 |
| 3-methyl-3-buten-1-yl acetate | 5.284 | 652132 | 0.785 | 6.51 |
| 2-heptanone | 5.348 | 67224 | 0.081 | 0.67 |
| 2,5-dimethylpyrazine | 5.591 | 58029 | 0.070 | 0.58 |
| 3-methyl-2-buten-1-yl acetate | 5.676 | 1686507 | 2.031 | 16.84 |
| 6-methyl-5-hepten-2-one | 6.307 | 101797 | 0.123 | 1.02 |
| 2,4,5-trimethylpyridine | 6.39 | 68477 | 0.082 | 0.68 |
| 2,3,5-trimethylpyrazine | 6.485 | 30420 | 0.037 | 0.30 |
| (E)-3,7-dimethyl-1,3,6-octatriene | 6.766 | 848928 | 1.022 | 8.48 |
| (Z)-3,7-dimethyl-1,3,6-octatriene | 6.864 | 448810 | 0.540 | 4.48 |
| 3-methyl-2-but-1-enyl butyrate | 7.294 | 105356 | 0.127 | 1.05 |
| Citronellal | 7.756 | 208092 | 0.251 | 2.08 |
| 2,3-cycloheptenolpyridine | 8.98 | 1119947 | 1.349 | 11.18 |

1 GC area is the uncorrected area under the peak corresponding to the listed compound.
2 Area % is the peak area expressed as a % relative to the total peak area of all compounds.
3 Ratio % is the peak area expressed as a % relative to the peak area of 2-methyl-1,3-butadiene.

TABLE 7B

Trace volatiles present in off-gas produced by *E. coli* BL21 (DE3) (pCL upperMev; pTrcKKDyIkIS) following cryo-trapping at −196° C.

| Compound | RT (min) | GC Area 1 | Area % 2 | Ratio % 3 |
|---|---|---|---|---|
| Acetaldehyde | 1.54 | 1655710 | 0.276 | 0.33 |
| Methanethiol | 1.584 | 173620 | 0.029 | 0.03 |
| Ethanol | 1.631 | 10259680 | 1.707 | 2.03 |
| Acetone | 1.722 | 73089100 | 12.164 | 14.43 |
| 2-methyl-1,3-butadiene | 1.771 | 506349429 | 84.269 | 100.00 |
| methyl acetate | 1.852 | 320112 | 0.053 | 0.06 |
| 1-propanol | 1.983 | 156752 | 0.026 | 0.03 |
| Diacetyl | 2.148 | 67635 | 0.011 | 0.01 |
| 2-butanone | 2.216 | 254364 | 0.042 | 0.05 |
| 2-methyl-3-buten-2-ol | 2.312 | 684708 | 0.114 | 0.14 |
| ethyl acetate | 2.345 | 2226391 | 0.371 | 0.44 |
| 2-methyl-1-propanol | 2.451 | 187719 | 0.031 | 0.04 |
| 3-methyl-1-butanal | 2.696 | 115723 | 0.019 | 0.02 |
| 3-methyl-2-butanone | 2.751 | 116861 | 0.019 | 0.02 |
| 1-butanol | 2.792 | 54555 | 0.009 | 0.01 |
| 2-pentanone | 3.034 | 66520 | 0.011 | 0.01 |
| 3-methyl-3-buten-1-ol | 3.516 | 1123520 | 0.187 | 0.22 |
| 3-methyl-1-butanol | 3.561 | 572836 | 0.095 | 0.11 |
| ethyl isobutyrate | 3.861 | 142056 | 0.024 | 0.03 |
| 3-methyl-2-buten-1-ol | 4.048 | 302558 | 0.050 | 0.06 |
| 3-methyl-2-butenal | 4.152 | 585690 | 0.097 | 0.12 |
| butyl acetate | 4.502 | 29665 | 0.005 | 0.01 |
| 3-methylbutyl acetate | 5.194 | 271797 | 0.045 | 0.05 |
| 3-methyl-3-buten-1-yl acetate | 5.281 | 705366 | 0.117 | 0.14 |
| 3-methyl-2-buten-1-yl acetate | 5.675 | 815186 | 0.136 | 0.16 |
| (E)-3,7-dimethyl-1,3,6-octatriene | 6.766 | 207061 | 0.034 | 0.04 |
| (Z)-3,7-dimethyl-1,3,6-octatriene | 6.863 | 94294 | 0.016 | 0.02 |
| 2,3-cycloheptenolpyridine | 8.983 | 135104 | 0.022 | 0.03 |

1 GC area is the uncorrected area under the peak corresponding to the listed compound.
2 Area % is the peak area expressed as a % relative to the total peak area of all compounds.
3 Ratio % is the peak area expressed as a % relative to the peak area of 2-methyl-1,3-butadiene.

III. Absence of C5 Hydrocarbon Isomers in Isoprene Derived from Fermentation.

Cryo-trapping of isoprene present in fermentation off-gas was performed using a 2 mL headspace vial cooled in liquid nitrogen. The off-gas (1 L/min) was first passed through a 20 mL vial containing sodium hydroxide pellets in order to minimize the accumulation of ice and solid $CO_2$ in the 2 mL vial (−196° C.). Approximately 10 L of off-gas was passed through the vial, after which it was allowed to warm to −78° C. with venting, followed by resealing with a fresh vial cap and analysis by GC/MS.

GC/MS headspace analysis was performed with an Agilent 6890 GC/MS system using a 100 uL gas tight syringe in headspace mode. A Zebron ZB-624 GC/MS column (30 m×250 μm; 1.40 μm film thickness) was used for separation of analytes. The GC autoinjector was fitted with a gas-tight 100 uL syringe, and the needle height was adjusted to allow the injection of a 50 uL headspace sample from a 2 mL GC vial. The GC/MS method utilized helium as the carrier gas at a flow of 1 mL/min. The injection port was held at 200° C. with a split ratio of 20:1. The oven temperature was held at 37° C. for the 5 minute duration of the analysis. The Agilent 5793N mass selective detector was run in single ion monitoring (SIM) mode on m/z 55, 66, 67 and 70. Under these conditions, isoprene was observed to elute at 2.966 minutes (FIG. 88B). A standard of petroleum derived isoprene (Sigma-Aldrich) was also analyzed using this method and was found to contain additional C5 hydrocarbon isomers, which eluted shortly before or after the main peak and were quantified based on corrected GC area (FIG. 88A).

TABLE 8A

GC/MS analysis of petroleum-derived isoprene

| Compound | RT (min) | GC area | Area % of total C5 hydrocarbons |
|---|---|---|---|
| 2-methyl-1-butene | 2.689 | 18.2 × 103 | 0.017% |
| (Z)-2-pentene | 2.835 | 10.6 × 104 | 0.101% |
| Isoprene | 2.966 | 10.4 × 107 | 99.869% |
| 1,3-cyclopentadiene (CPD) | 3.297 | 12.8 × 103 | 0.012% |

TABLE 8B

GC/MS analysis of fermentation-derived isoprene
(% total C5 hydrocarbons)

| Compound | RT (min) | Corrected GC Area | % of total C5 hydrocarbons |
|---|---|---|---|
| Isoprene | 2.966 | 8.1 × 107 | 100% |

In a separate experiment, a standard mixture of C5 hydrocarbons was analyzed to determine if the detector response was the same for each of the compounds. The compounds were 2-methyl-1-butene, 2-methyl-1,3-butadiene, (E)-2-pentene, (Z)-2-pentene and (E)-1,3-pentadiene. In this case, the analysis was performed on an Agilent DB-Petro column (100 m×0.25 mm, 0.50 um film thickness) held at 50° C. for 15 minutes. The GC/MS method utilized helium as the carrier gas at a flow of 1 mL/min. The injection port was held at 200° C. with a split ratio of 50:1. The Agilent 5793N mass selective detector was run in full scan mode from m/z 19 to m/z 250. Under these conditions, a 100 ug/L concentration of each standard produced the same detector response within experimental error.

IV. Compositions Comprising Isoprene Adsorbed to a Solid Phase.

Biologically-produced isoprene was adsorbed to activated carbon resulting in a solid phase containing 50 to 99.9% carbon, 0.1% to 50% isoprene, 0.01% to 5% water, and minor amounts (<0.1%) of other volatile organic components.

Fermentation off-gas was run through a copper condensation coil held at 0° C., followed by a granulated silica desiccant filter in order to remove water vapor. The dehumidified off-gas was then run through carbon containing filters (Koby Jr, Koby Filters, Mass.) to the point at which breakthrough of isoprene was detected in the filter exhaust by GC/MS. The amount of isoprene adsorbed to the cartridge can be determined indirectly by calculating the concentration in the off-gas, the overall flow rate and the percent breakthrough over the collection period. Alternately the adsorbed isoprene can be recovered from the filters by thermal, vacuum, or solvent-mediated desorption.

V. Collection and Analysis of Condensed Isoprene.

Fermentation off-gas is dehumidified, and the $CO_2$ removed by filtration through a suitable adsorbent (e.g., ascarite). The resulting off-gas stream is then run through a liquid nitrogen-cooled condenser in order to condense the VOCs in the stream. The collection vessel contains t-butyl catechol to inhibit the resulting isoprene condensate. The condensate is analyzed by GC/MS and NMR in order to determine purity using standard methods, such as those described herein.

VI. Production of Prenyl Alcohols by Fermentation.

Analysis of off-gas from an *E. coli* BL21 (DE3) strain expressing a Kudzu isoprene synthase revealed the presence of both isoprene and 3-methyl-3-buten-1-ol (isoprenol). The levels of the two compounds in the fermentation off-gas over the fermentation are shown in FIG. 89 as determined by headspace GC/MS. Levels of isoprenol (3-methyl-3-buten-1-ol, 3-MBA) attained was nearly 10 ug/$L_{offgas}$ in this experiment. Additional experiments produced levels of approximately 20 ug/$L_{offgas}$ in the fermentation off-gas.

Example 11

The Decoupling of Growth and Production of Isoprene in *E. Coli* Expressing Genes from the Mevalonic Acid Pathway and Fermented in a Fed-Batch Culture Example 11 illustrates the decoupling of cell growth from mevalonic acid and isoprene production.

I. Fermentation Conditions

Medium Recipe (Per Liter Fermentation Medium).

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component was dissolved one at a time in Di$H_2O$, pH to 3.0 with HCl/NaOH, then q.s. to volume, and filter sterilized with a 0.22 micron filter.

Fermentation was performed with *E. coli* cells containing the pTrcHis2AUpperPathway (also called pTrcUpperMVA, FIGS. 91 and 92A-92C; SEQ ID NO:23) (50 µg/ml carbenicillin) or the pCL PtrcUpperMVA (also called pCL PtrcUpperPathway (FIG. 26)) (50 µg/ml spectinomycin) plasmids. For experiments in which isoprene was produced, the *E. coli* cells also contained the pTrc KKDyIkIS (50 µg/ml kanamycin) plasmid. These experiments were carried out to monitor mevalonic acid or isoprene formation from glucose at the desired fermentation pH 7.0 and temperature 30° C. An inoculum of an *E. coli* strain taken from a frozen vial was streaked onto an LA broth agar plate (with antibiotics) and incubated at 37° C. A single colony was inoculated into tryptone-yeast extract medium. After the inoculum grew to optical density 1.0 when measured at 550 nm, it was used to inoculate the bioreactor.

Glucose was fed at an exponential rate until cells reached the stationary phase. After this time the glucose feed was decreased to meet metabolic demands. Induction was achieved by adding IPTG. The mevalonic acid concentration in fermentation broth was determined by applying perchloric acid (Sigma-Aldrich #244252) treated samples (0.3 M incubated at 4° C. for 5 minutes) to an organic acids HPLC column (BioRad #125-0140). The concentration was determined by comparing the broth mevalonic acid peak size to a calibration curve generated from mevalonolacetone (Sigma-Aldrich #M4667) treated with perchloric acid to form D,L-mevalonate. The isoprene level in the off gas from the bioreactor was determined as described herein. The isoprene titer is defined as the amount of isoprene produced per liter of fermentation broth.

Figure 60A:
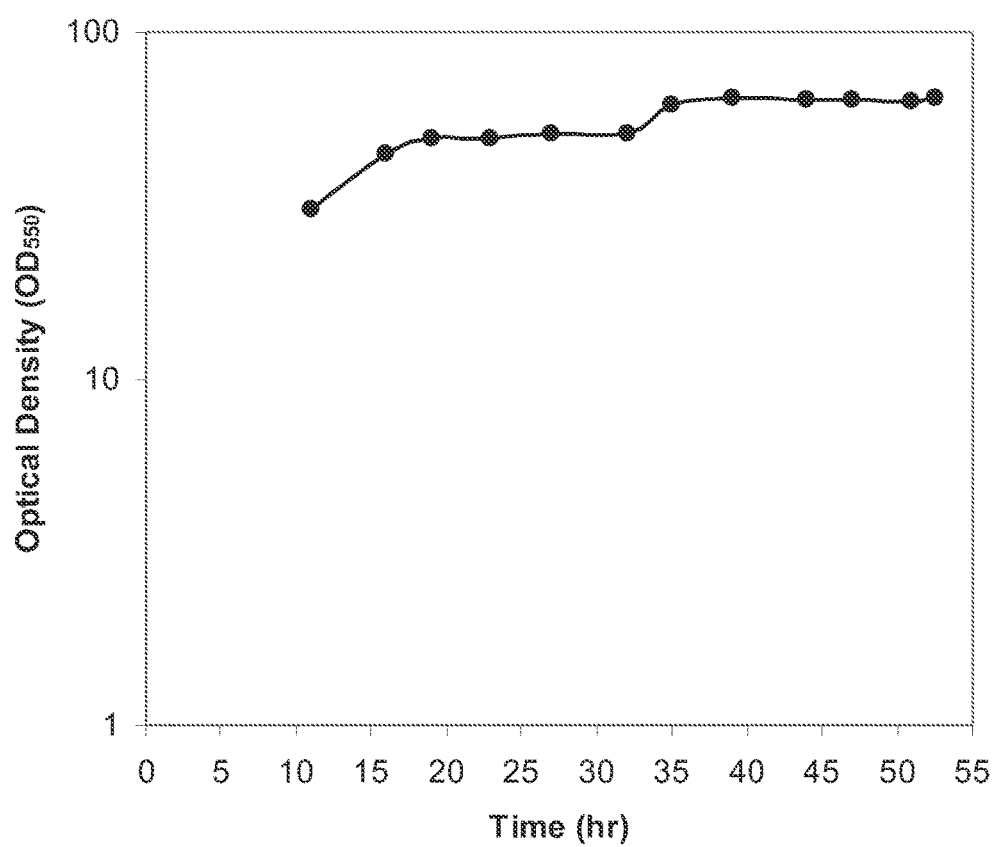
FIGS. 60A-60C are the time courses of optical density, mevalonic acid titer, and specific productivity within the 150-L bioreactor fed with glucose.
Figure 60B:
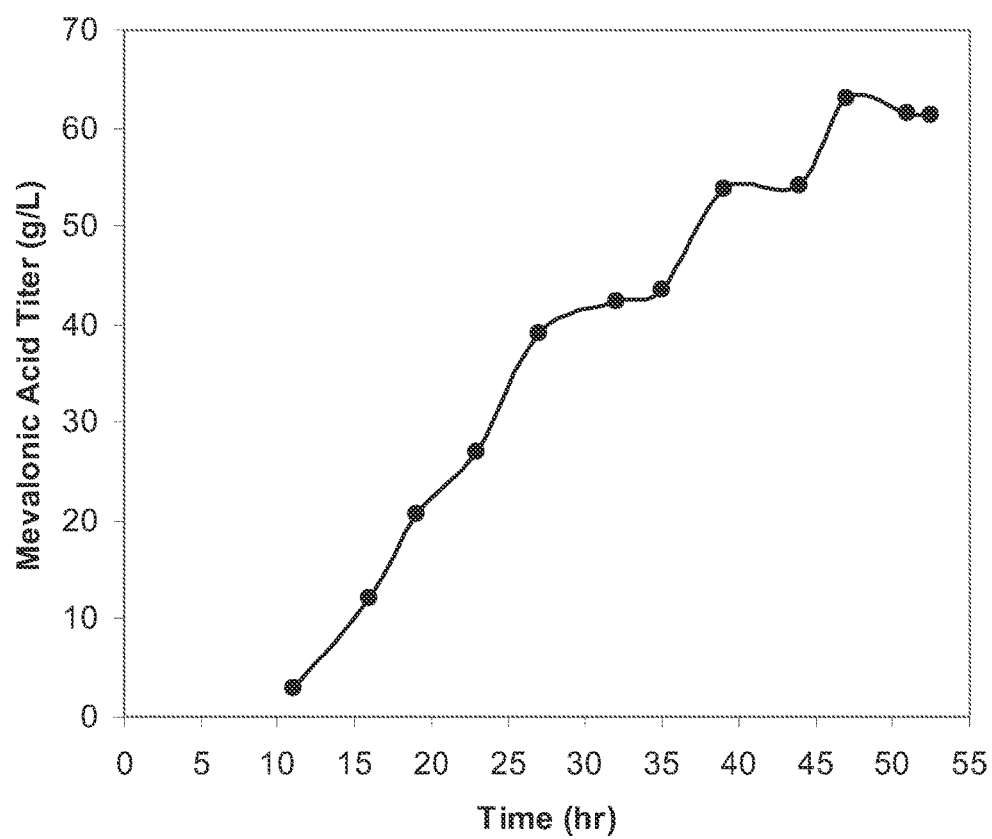
Figure 60C:
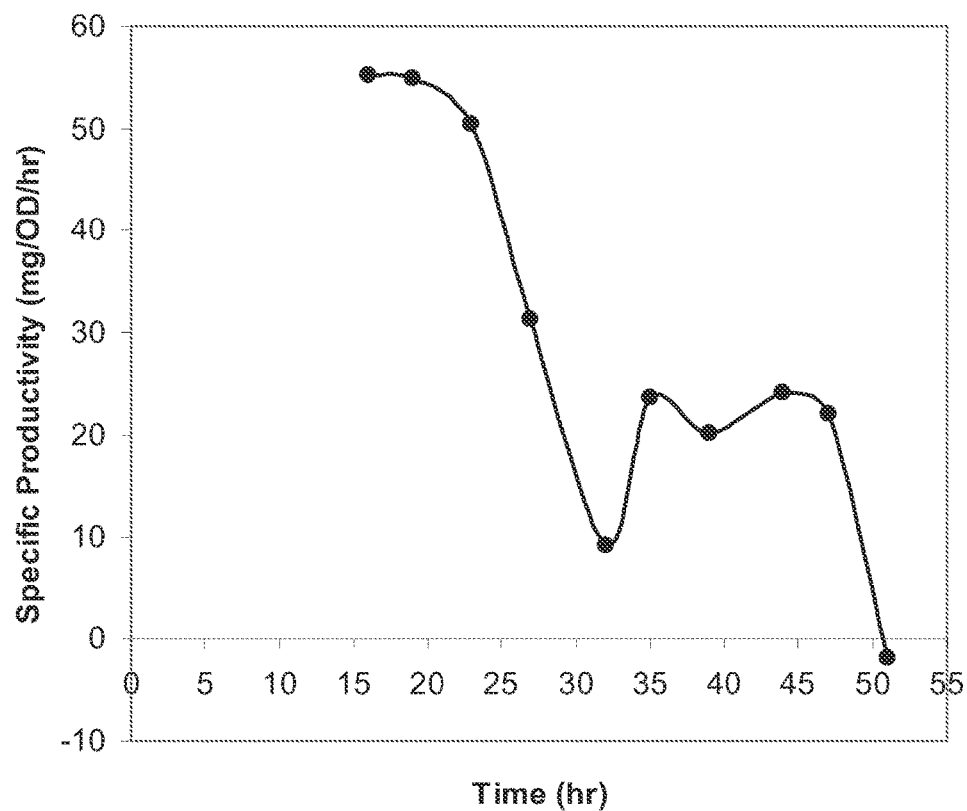

II. Mevalonic Acid Production from *E. Coli* BL21 (DE3) Cells Expressing the pTrcUpperMVA Plasmid at a 150-L Scale BL21 (DE3) cells that were grown on a plate as explained above in Example 11, part I were inoculated into a flask containing 45 mL of tryptone-yeast extract medium and incubated at 30° C. with shaking at 170 rpm for 5 hours. This solution was transferred to a 5-L bioreactor of tryptone-yeast extract medium, and the cells were grown at 30° C. and 27.5 rpm until the culture reached an $OD_{550}$ of 1.0. The 5 L of inoculum was seeded into a 150-L bioreactor containing 45-kg of medium. The IPTG concentration was brought to 1.1 mM when the $OD_{550}$ reached a value of 10. The $OD_{550}$ profile within the bioreactor over time is shown in FIG. 60A. The mevalonic acid titer increased over the course of the fermentation to a final value of 61.3 g/L (FIG. 60B). The specific productivity profile throughout the fermentation is shown in FIG. 60C and a comparison to FIG. 60A illustrates the decoupling of growth and mevalonic acid production. The total amount of mevalonic acid produced during the 52.5 hour fermentation was 4.0 kg from 14.1 kg of utilized glucose. The molar yield of utilized carbon that went into producing mevalonic acid during fermentation was 34.2%.

Figure 61A:
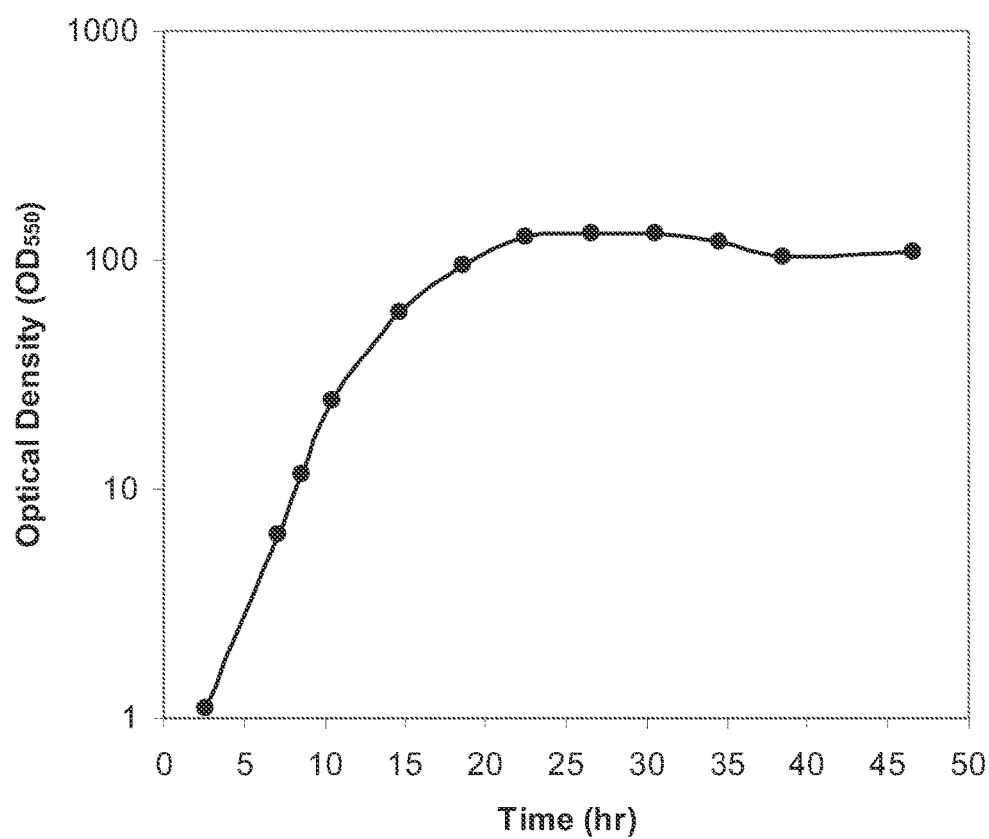
FIGS. 61A-61C are the time courses of optical density, mevalonic acid titer, and specific productivity within the 15-L bioreactor fed with glucose.
Figure 61B:
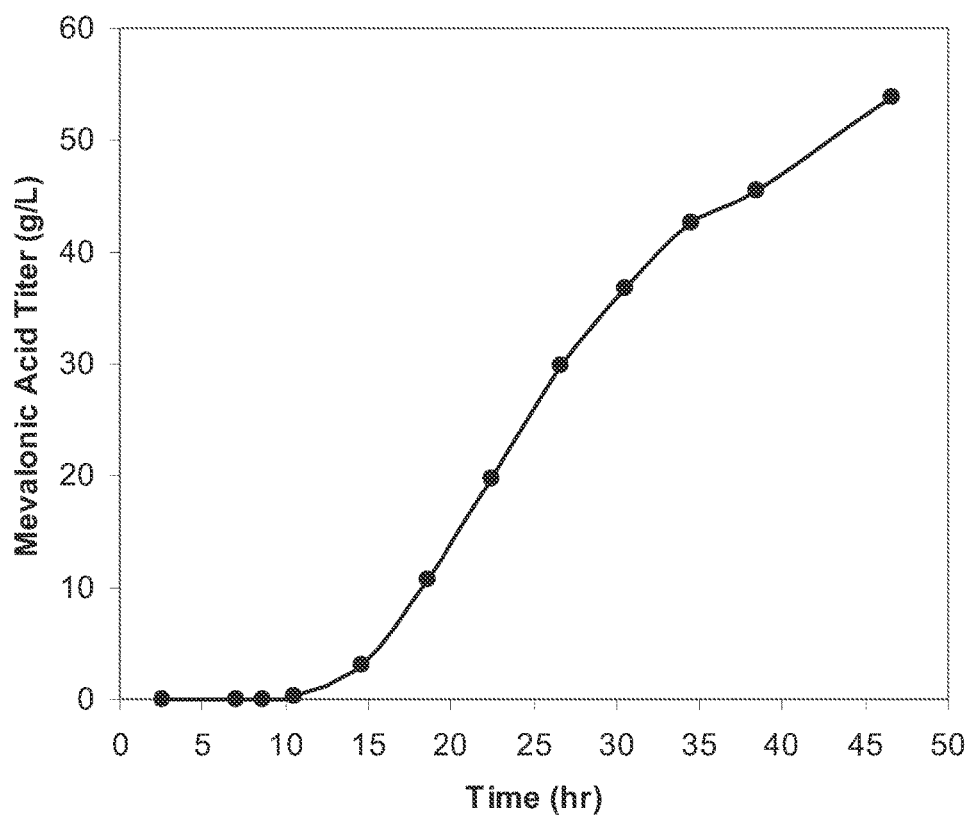
Figure 61C:
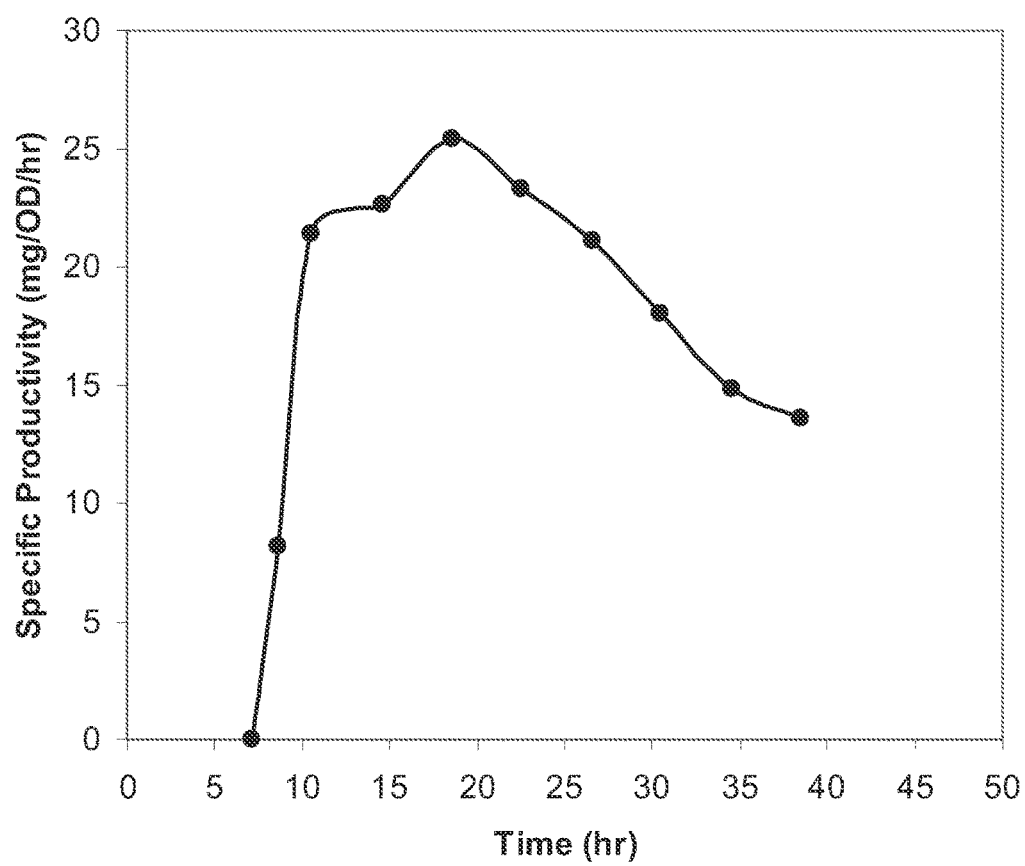

III. Mevalonic Acid Production from *E. Coli* BL21 (DE3) Cells Expressing the pTrcUpperMVA Plasmid at a 15-L Scale BL21 (DE3) cells that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 10. The $OD_{550}$ profile within the bioreactor over time is shown in FIG. 61A. The mevalonic acid titer increased over the course of the fermentation to a final value of 53.9 g/L (FIG. 61B). The specific productivity profile throughout the fermentation is shown in FIG. 61C and a comparison to FIG. 61A illustrates the decoupling of growth and mevalonic acid production. The total amount of mevalonic acid produced during the 46.6 hour fermentation was 491 g from 2.1 kg of utilized glucose. The molar yield of utilized carbon that went into producing mevalonic acid during fermentation was 28.8%.

Figure 62A:
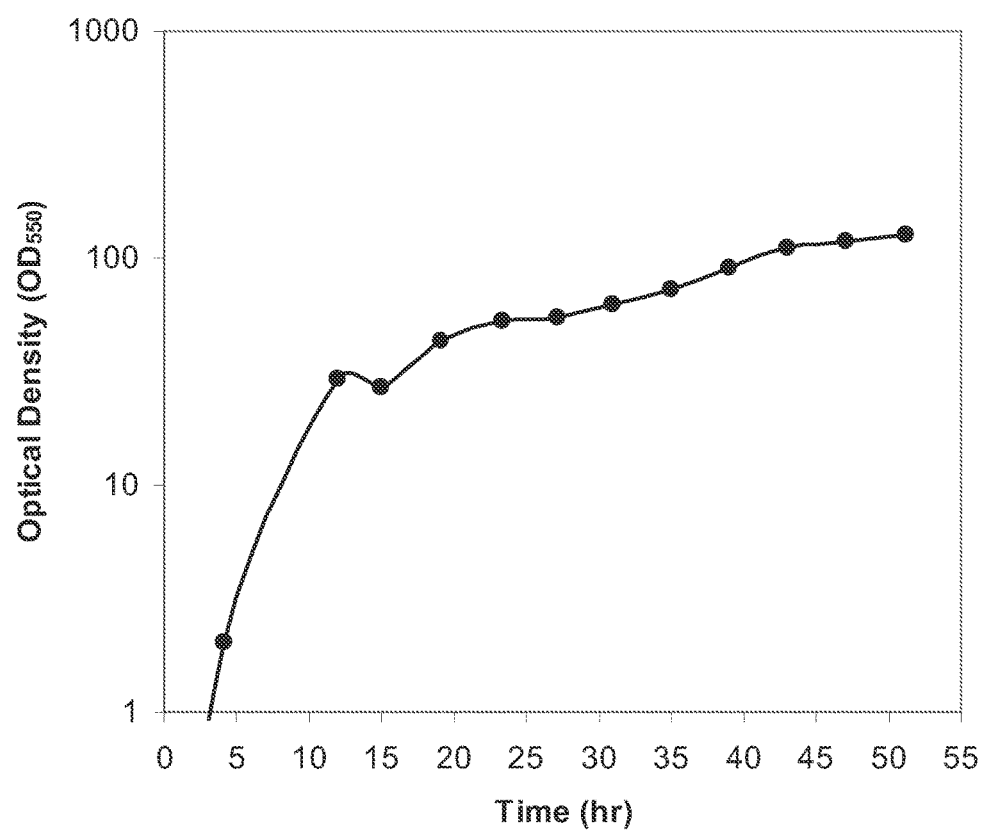
FIGS. 62A-62C are the time courses of optical density, mevalonic acid titer, and specific productivity within the 15-L bioreactor fed with glucose.
Figure 62B:
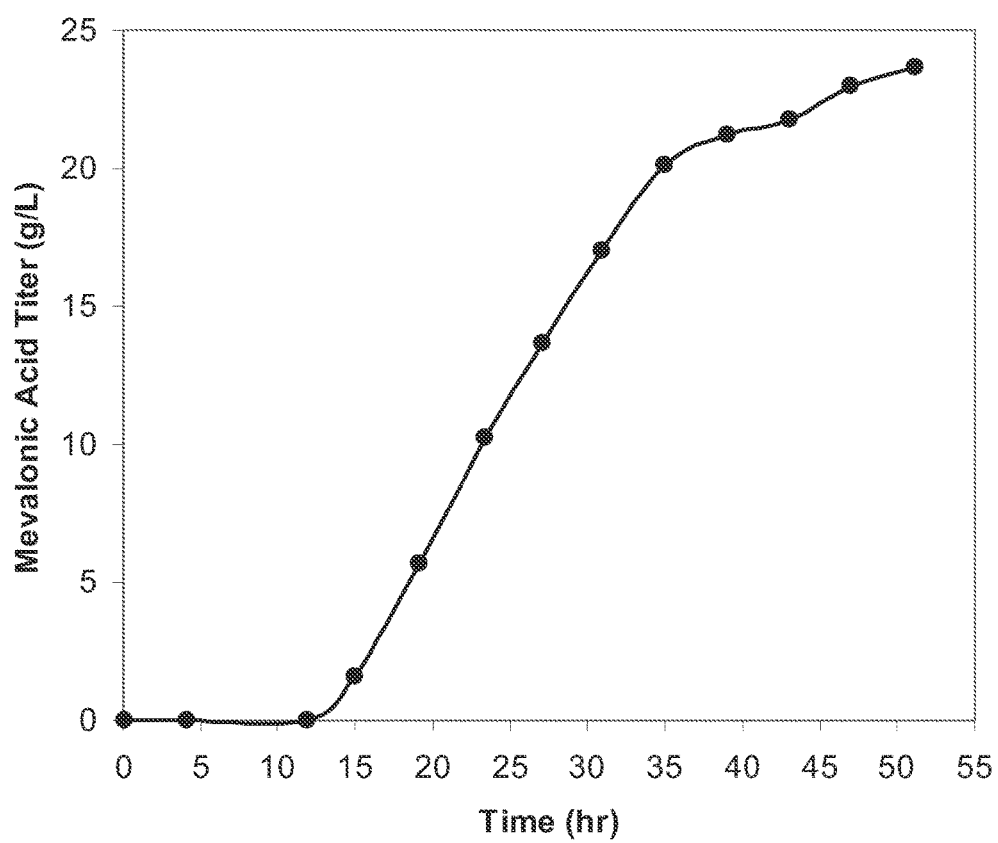
Figure 62C:
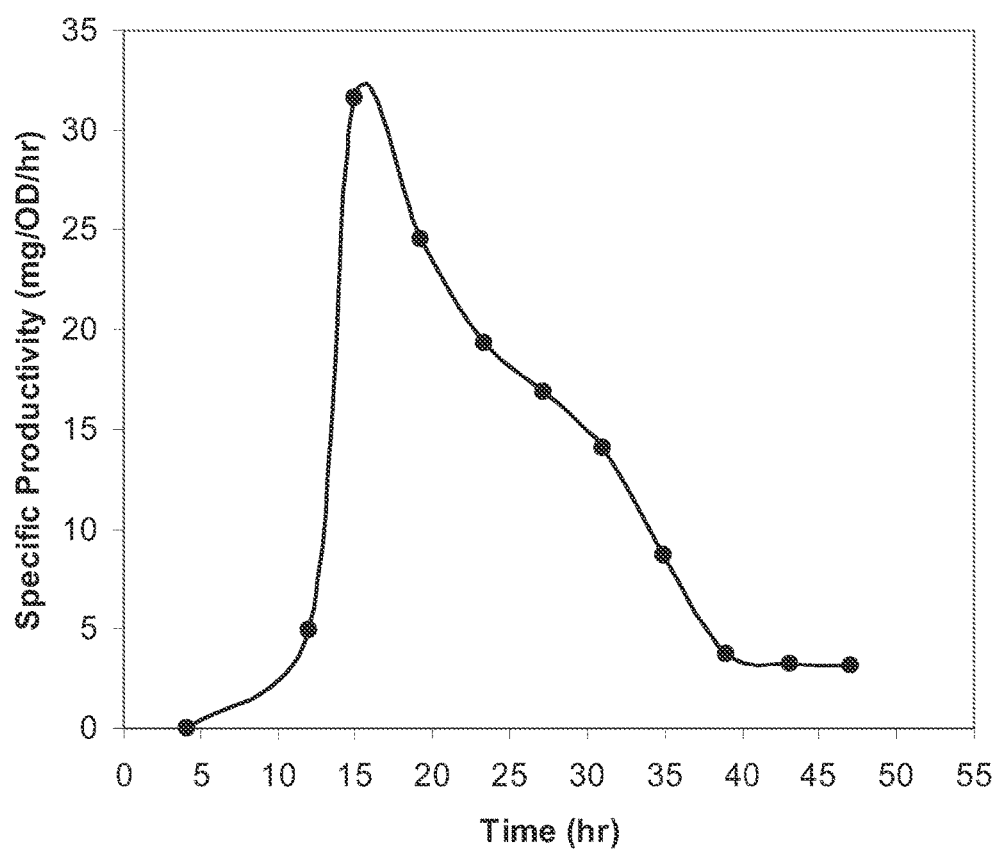

IV. Mevalonic Acid Production from *E. Coli* FM5 Cells Expressing the pTrcUpperMVA Plasmid at a 15-L Scale FM5 cells that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 30. The $OD_{550}$ profile within the bioreactor over time is shown in FIG. 62A. The mevalonic acid titer increased over the course of the fermentation to a final value of 23.7 g/L (FIG. 62B). The specific productivity profile throughout the fermentation is shown in FIG. 62C and a comparison to FIG. 62A illustrates the decoupling of growth and mevalonic acid production. The total amount of mevalonic acid produced during the 51.2 hour fermentation was 140 g from 1.1 kg of utilized glucose. The molar yield of utilized carbon that went into producing mevalonic acid during fermentation was 15.2%.

Figure 63A:
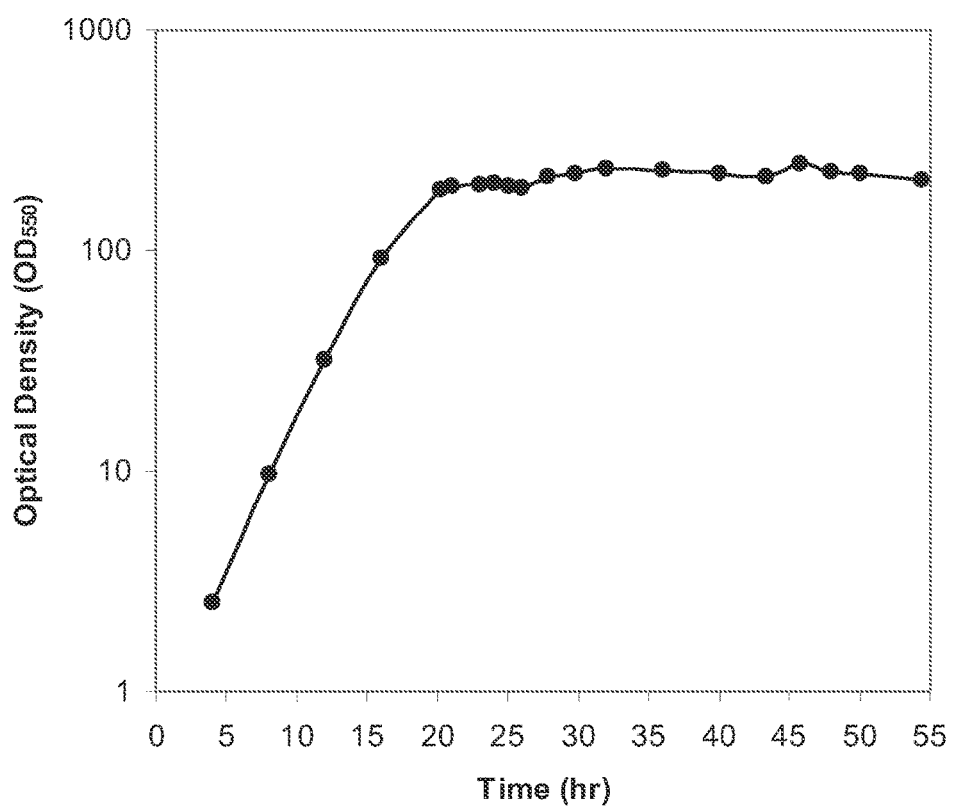
FIGS. 63A-63C are the time courses of optical density, isoprene titer, and specific productivity within the 15-L bioreactor fed with glucose.
Figure 63B:
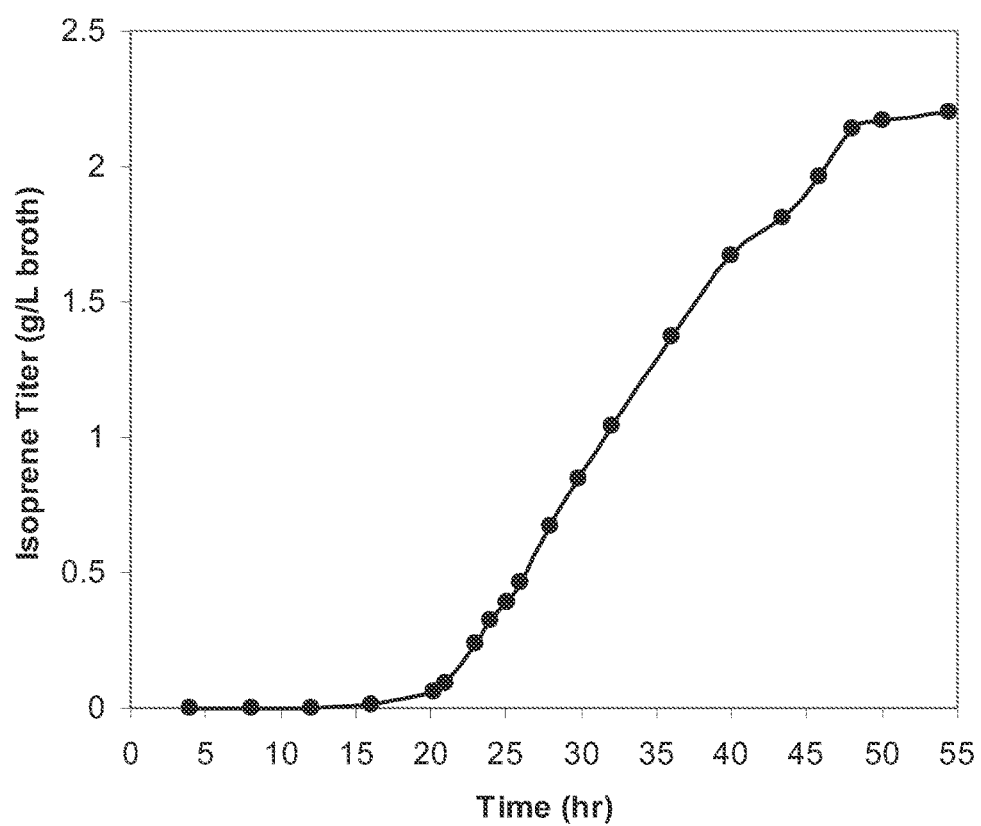
Figure 63C:
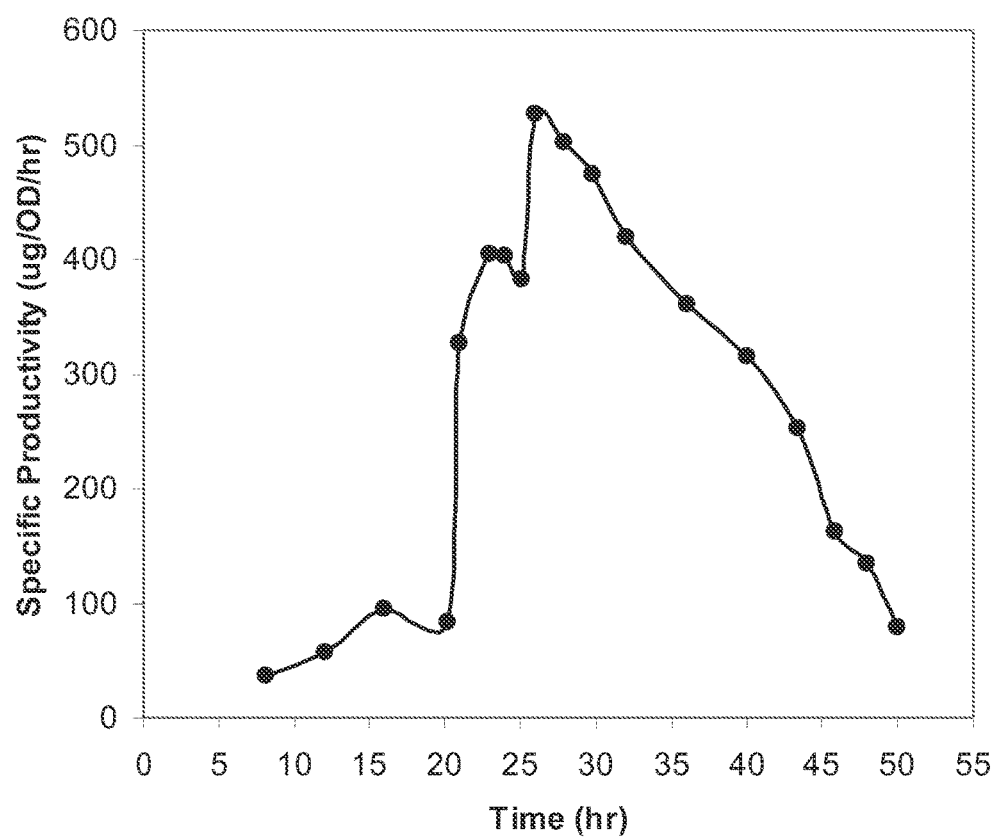

V. Isoprene Production from *E. Coli* BL21 (DE3) Cells Expressing the pCL PtrcUpperMVA and pTrc KKDyIkIS Plasmids at a 15-L Scale BL21 (DE3) cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 25 µM when the $OD_{550}$ reached a value of 10. The IPTG concentration was raised to 50 uM when $OD_{550}$ reached 190. The IPTG concentration was raised to 100 uM at 38 hours of fermentation. The $OD_{550}$ profile within the bioreactor over time is shown in FIG. 63A. The isoprene titer increased over the course of the fermentation to a final value of 2.2 g/L broth (FIG. 63B). The specific productivity profile throughout the fermentation is shown in FIG. 63C and a comparison to FIG. 63A illustrates the decoupling of growth and isoprene production. The total amount of isoprene produced during the 54.4 hour fermentation was 15.9 g from 2.3 kg of utilized glucose. The molar yield of utilized carbon that went into producing isoprene during fermentation was 1.53%.

Figure 64A:
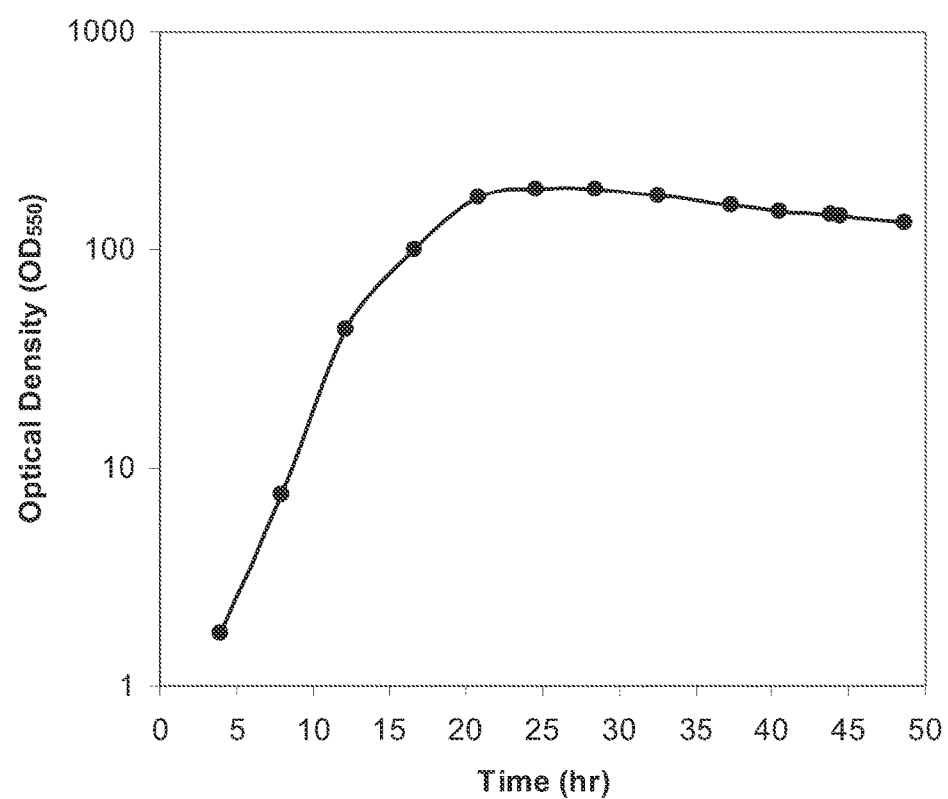
FIGS. 64A-64C are the time courses of optical density, isoprene titer, and specific productivity within the 15-L bioreactor fed with glucose.
Figure 64B:
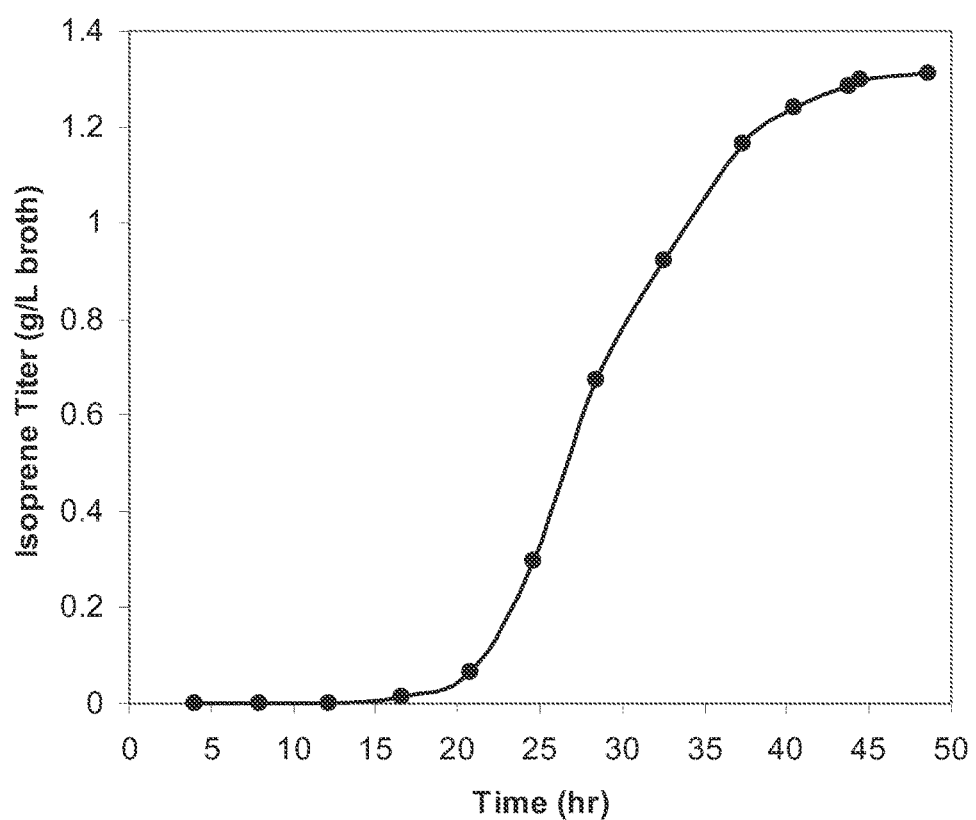
Figure 64C:
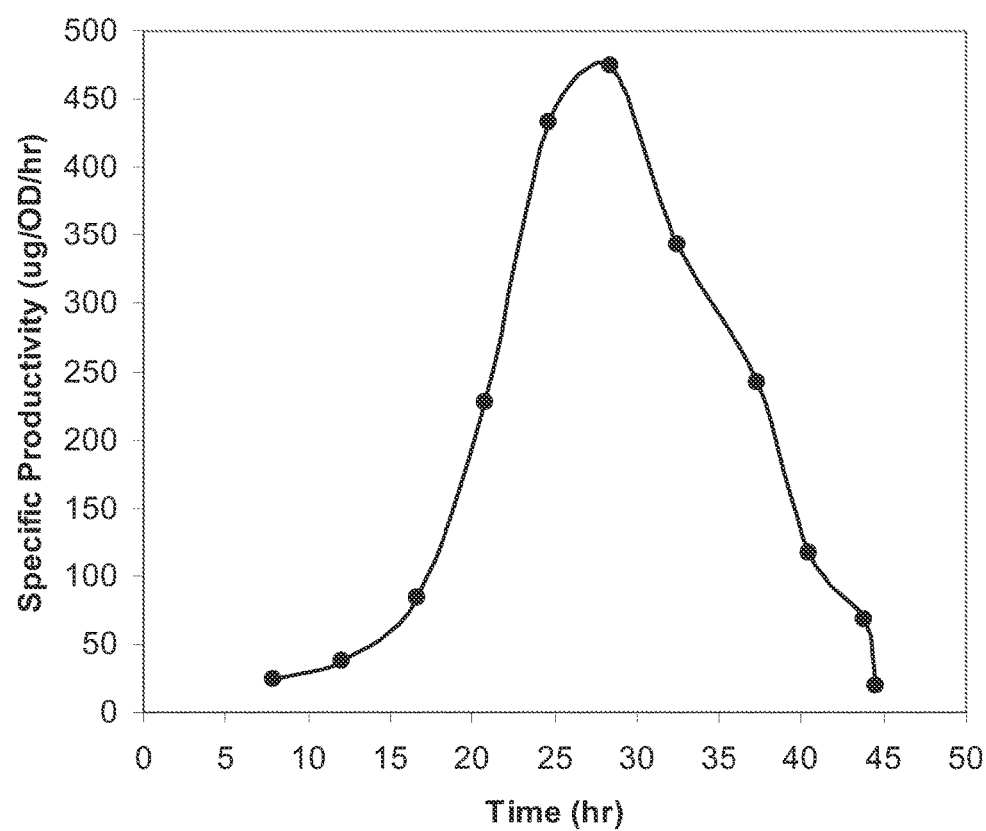

VI. Isoprene Production from *E. Coli* BL21 (DE3) Tuner Cells Expressing the pCL PtrcUpperMVA and pTrc KKDyIkIS Plasmids at a 15-L Scale BL21 (DE3) tuner cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 26 µM when the $OD_{550}$ reached a value of 10. The IPTG concentration was raised to 50 uM when $OD_{550}$ reached 175. The $OD_{550}$ profile within the bioreactor over time is shown in FIG. 64A. The isoprene titer increased over the course of the fermentation to a final value of 1.3 g/L broth (FIG. 64B). The specific productivity profile throughout the fermentation is shown in FIG. 64C and a comparison to FIG. 64A illustrates the decoupling of growth and isoprene production. The total amount of isoprene produced during the 48.6 hour fermentation was 9.9 g from 1.6 kg of utilized glucose. The molar yield of utilized carbon that went into producing isoprene during fermentation was 1.34%.

Figure 65A:
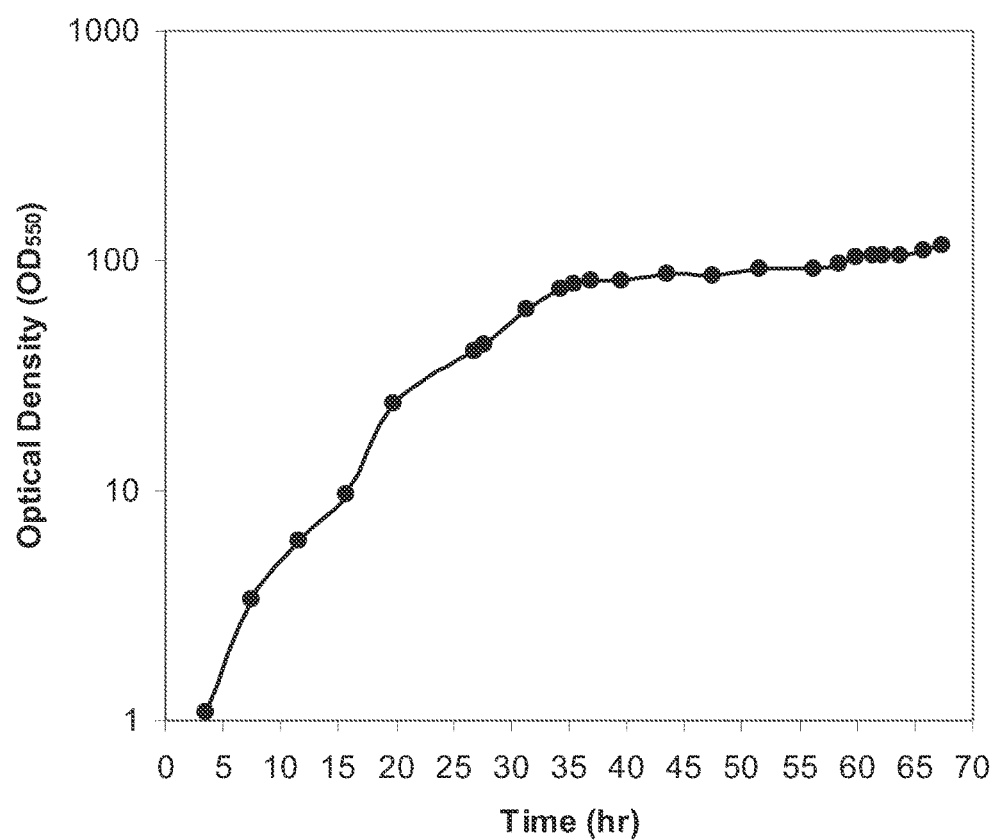
FIGS. 65A-65C are the time courses of optical density, isoprene titer, and specific productivity within the 15-L bioreactor fed with glucose.
Figure 65B:
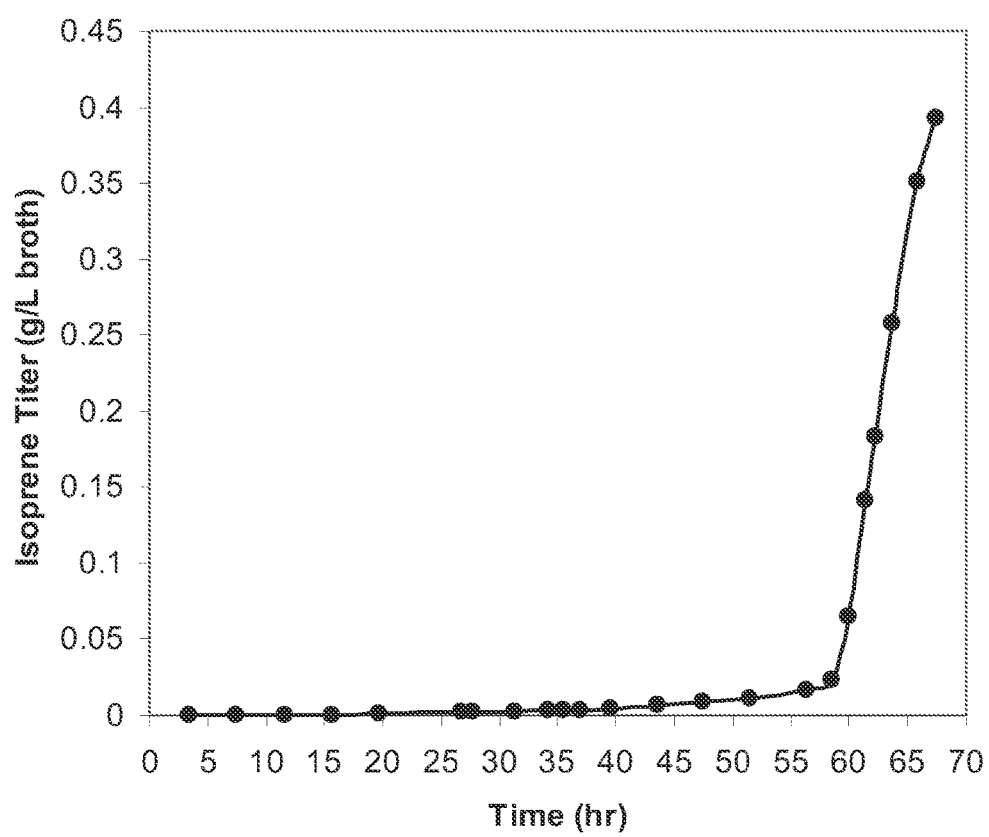
Figure 65C:
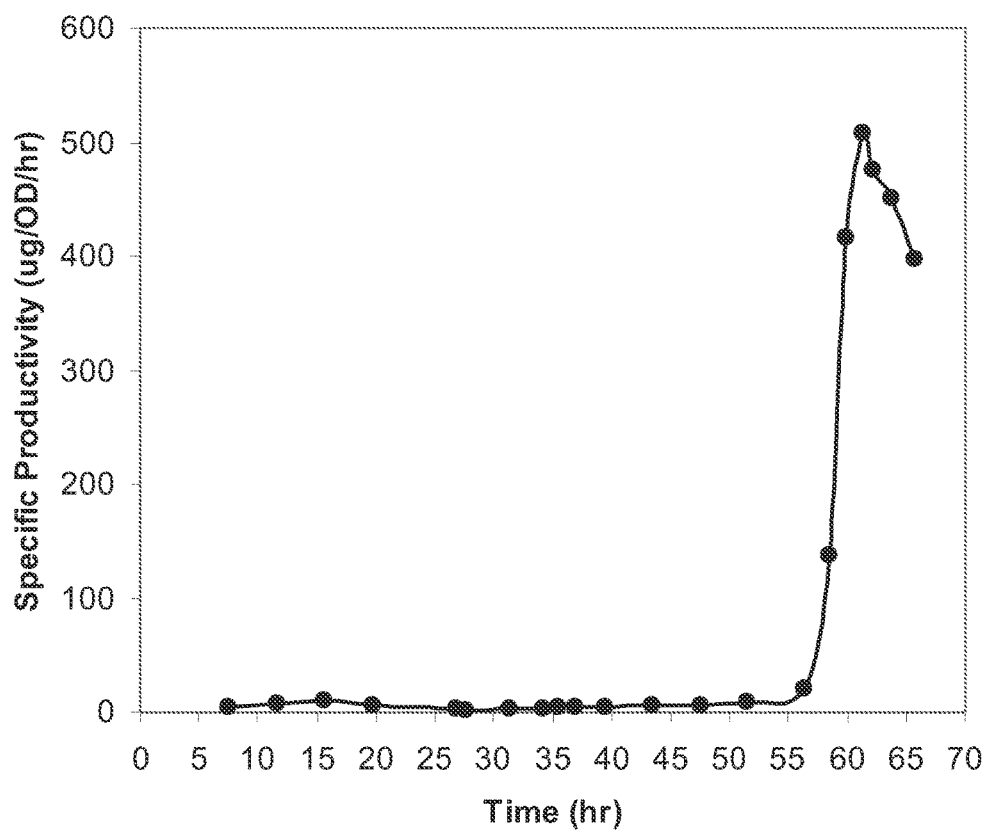

VII. Isoprene Production from *E. Coli* MG1655 Cells Expressing the pCL PtrcUpperMVA and pTrc KKDyIkIS Plasmids at a 15-L Scale MG1655 cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 24 µM when the $OD_{550}$ reached a value of 45. The $OD_{550}$ profile within the bioreactor over time is shown in FIG. 65A. The isoprene titer increased over the course of the fermentation to a final value of 393 mg/L broth (FIG. 65B). The specific productivity profile throughout the fermentation is shown in FIG. 65C and a comparison to FIG. 65A illustrates the decoupling of growth and isoprene production. The total amount of isoprene produced during the 67.4 hour fermentation was 2.2 g from 520 g of utilized glucose. The molar yield of utilized carbon that went into producing isoprene during fermentation was 0.92%.

Figure 66A:
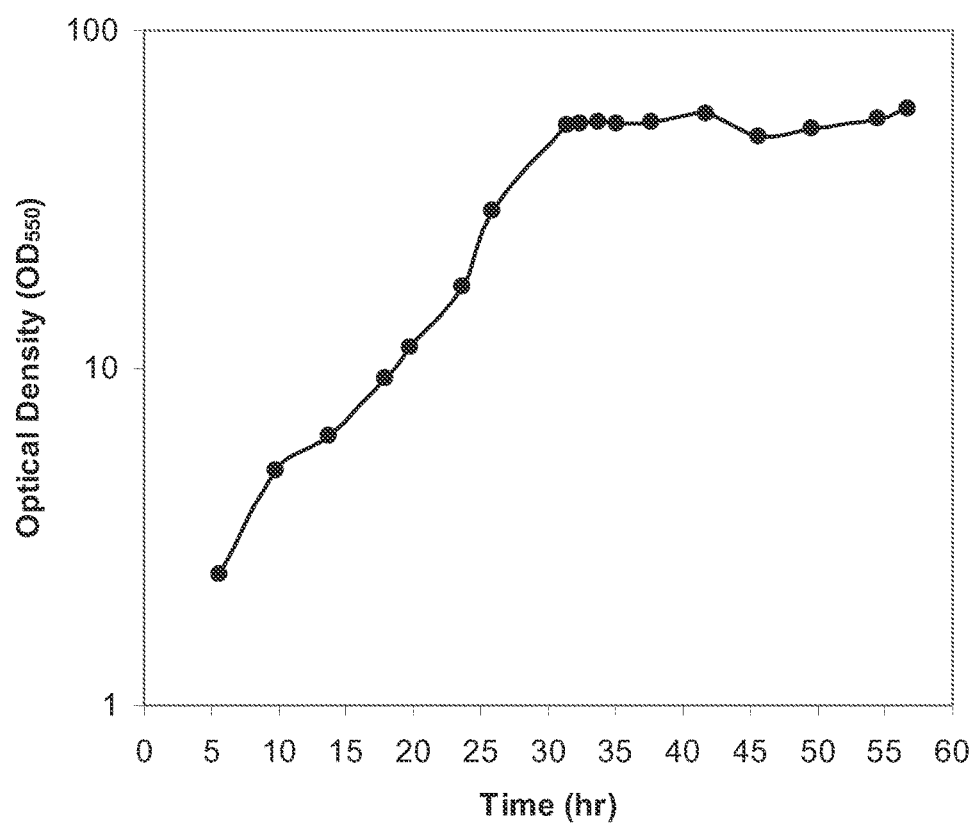
FIGS. 66A-66C are the time courses of optical density, isoprene titer, and specific productivity within the 15-L bioreactor fed with glucose.
Figure 66B:
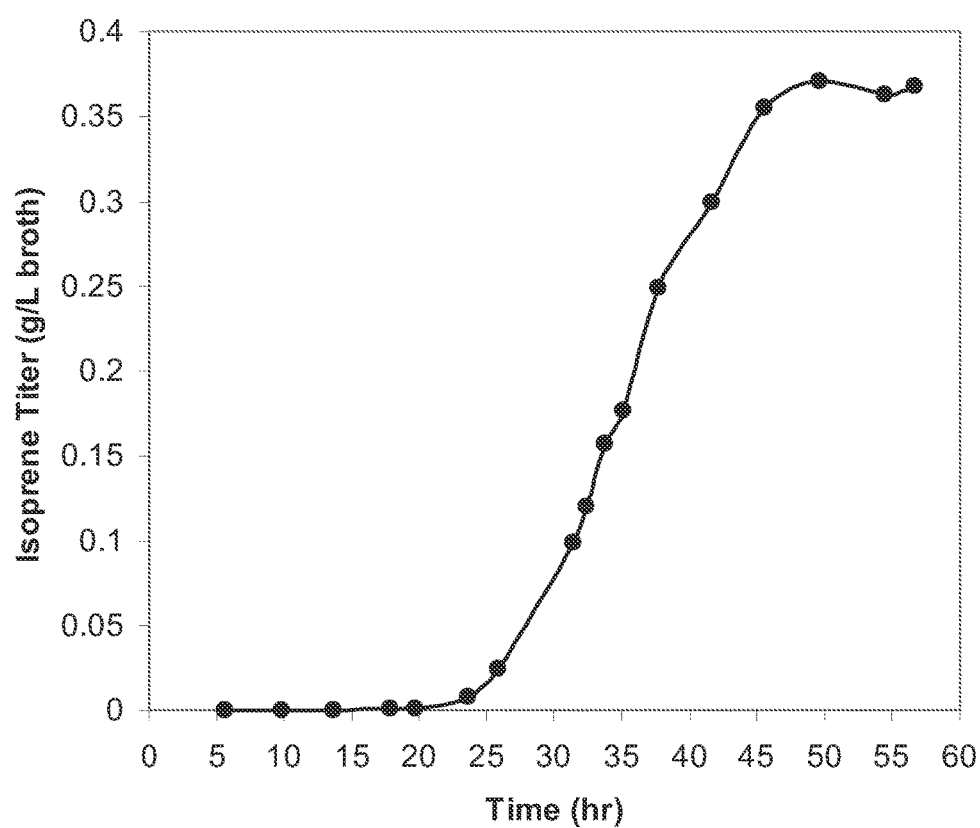
Figure 66C:
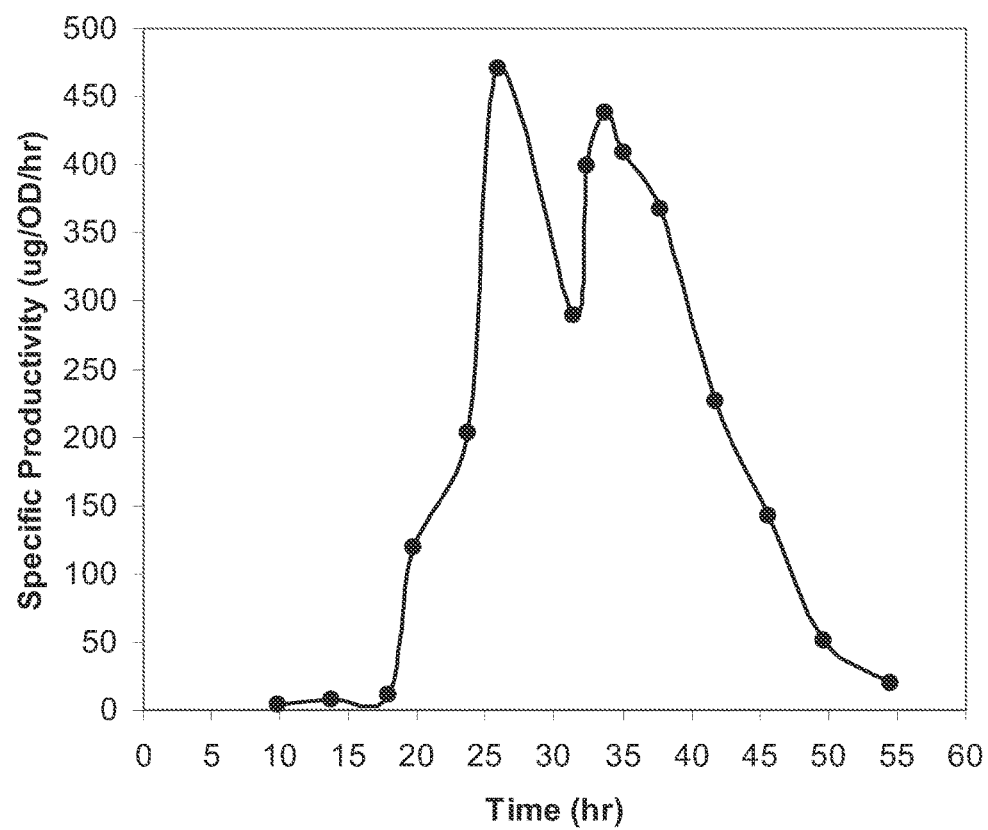

VIII. Isoprene Production from *E. Coli* MG1655ack-pta Cells Expressing the pCL PtrcUpperMVA and pTrc KKDyIkIS Plasmids at a 15-L Scale MG1655ack-pta cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 30 µM when the $OD_{550}$ reached a value of 10. The $OD_{550}$ profile within the bioreactor over time is shown in FIG. 66A. The isoprene titer increased over the course of the fermentation to a final value of 368 mg/L broth (FIG. 66B). The specific productivity profile throughout the fermentation is shown in FIG. 66C and a comparison to FIG. 66A illustrates the decoupling of growth and isoprene production. The total amount of isoprene produced during the 56.7 hour fermentation was 1.8 g from 531 g of utilized glucose. The molar yield of utilized carbon that went into producing isoprene during fermentation was 0.73%.

Figure 67A:
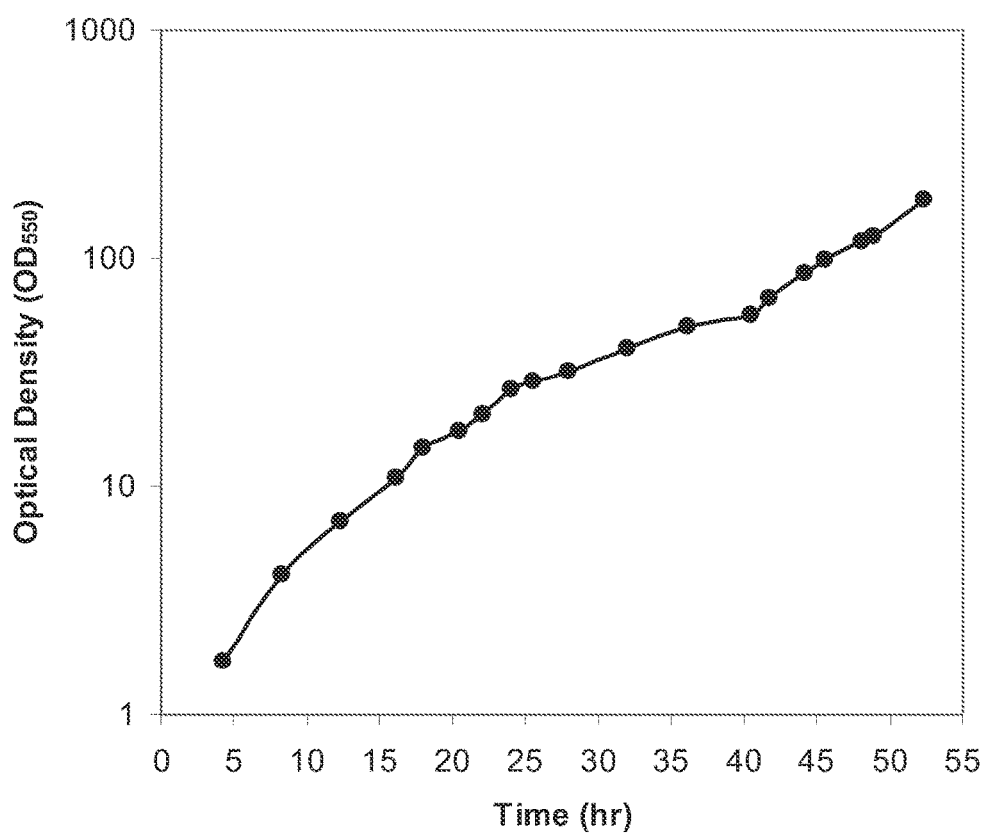
FIG. 67A-67C are the time courses of optical density, isoprene titer, and specific productivity within the 15-L bioreactor fed with glucose.
Figure 67B:
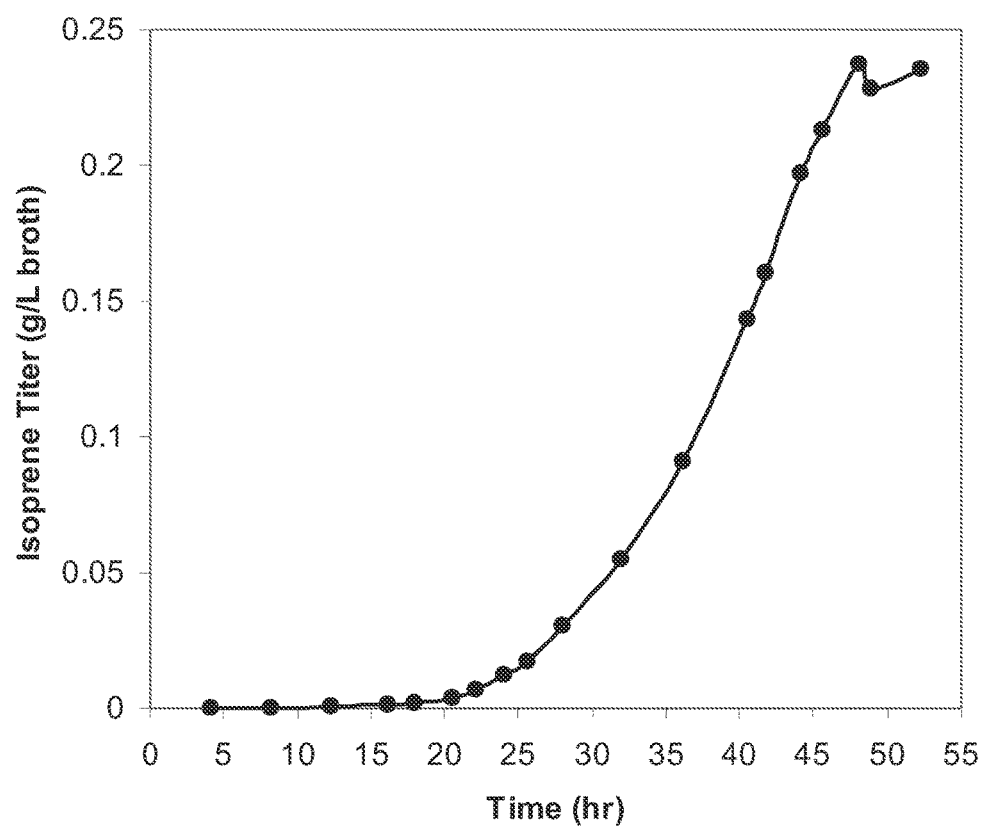
Figure 67C:
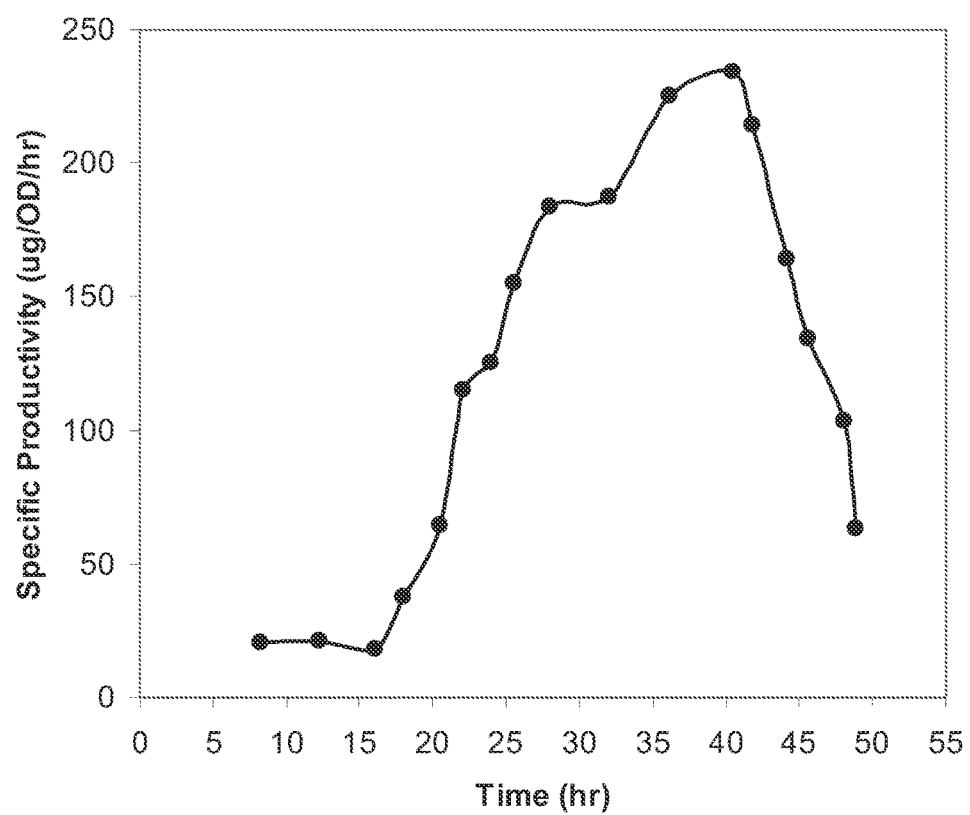

IX. Isoprene Production from *E. Coli* FM5 Cells Expressing the pCL PtrcUpperMVA and pTrc KKDyIkIS Plasmids at a 15-L Scale FM5 cells expressing the pCL PtrcUpperMVA and pTrc KKDyIkIS plasmids that were grown on a plate as explained above in Example 11, part I were inoculated into a flask containing 500 mL of tryptone-yeast extract medium and grown at 30° C. at 160 rpm to $OD_{550}$ 1.0. This material was seeded into a 15-L bioreactor containing 45-kg of medium. The IPTG concentration was brought to 27 µM when the $OD_{550}$ reached a value of 15. The $OD_{550}$ profile within the bioreactor over time is shown in FIG. 67A. The isoprene titer increased over the course of the fermentation to a final value of 235 mg/L broth (FIG. 67B). The specific productivity profile throughout the fermentation is shown in FIG. 67C and a comparison to FIG. 67A illustrates the decoupling of growth and isoprene production. The total amount of isoprene produced during the 52.3 hour fermentation was 1.4 g from 948 g of utilized glucose. The molar yield of utilized carbon that went into producing isoprene during fermentation was 0.32%.

Example 12

Production of Isoprene During the Exponential Growth Phase of *E. Coli* Expressing Genes from the Mevalonic Acid Pathway and Fermented in a Fed-Batch Culture Example 12 illustrates the production of isoprene during the exponential growth phase of cells.

Medium Recipe (Per Liter Fermentation Medium).

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, and $NaMoO_4*2H_2O$ 100 mg. Each component is dissolved one at a time in DiH2O, pH to 3.0 with HCl/NaOH, then q.s. to volume and filter sterilized with 0.22 micron filter.

Fermentation was performed in a 15-L bioreactor with ATCC11303 *E. coli* cells containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time the glucose feed was decreased to meet metabolic demands. The total amount of glucose delivered to the bioreactor during the 50 hour fermentation was 2.0 kg. Induction was achieved by adding IPTG. The IPTG concentration was brought to 25 uM when the optical density at 550 nm ($OD_{550}$) reached a value of 10. The IPTG concentration was raised to 50 uM when $OD_{550}$ reached 190. The $OD_{550}$ profile within the bioreactor over time is shown in FIG. 99. The isoprene level in the off gas from the bioreactor was determined as described herein. The isoprene titer increased over the course of the fermentation to a final value of 1.4 g/L (FIG. 100). The total amount of isoprene produced during the 50 hour fermentation was 10.0 g. The profile of the isoprene specific productivity over time within the bioreactor is shown in FIG. 101. The molar yield of utilized carbon that contributed to producing isoprene during fermentation was 1.1%. The weight percent yield of isoprene from glucose was 0.5%.

Example 13

Flammability Modeling and Testing of Isoprene

I. Summary of Flammability Modeling and Testing of Isoprene

Flammability modeling and experiments were performed for various hydrocarbon/oxygen/nitrogen/water/carbon dioxide mixtures. This modeling and experimental tested was aimed at defining isoprene and oxygen/nitrogen flammability curves under specified steam and carbon monoxide concentrations at a fixed pressure and temperature. A matrix of the model conditions is shown in Table 9, and a matrix of the experiments performed is shown in Table 5.

TABLE 9

Summary of Modeled Isoprene Flammability

| Series | Temperature (° C.) | Pressure (psig) | Steam Concentration (wt %) | Carbon Dioxide Concentration (wt. %) | Isoprene Concentration (vol. %) | Oxygen Concentration (vol. %) |
|---|---|---|---|---|---|---|
| A | 40 | 0 | 0 | 0 | Varying | Varying |
| B | 40 | 0 | 4 | 0 | Varying | Varying |
| C | 40 | 0 | 0 | 5 | Varying | Varying |
| D | 40 | 0 | 0 | 10 | Varying | Varying |
| E | 40 | 0 | 0 | 15 | Varying | Varying |
| F | 40 | 0 | 0 | 20 | Varying | Varying |
| G | 40 | 0 | 0 | 30 | Varying | Varying |

TABLE 10

Summary of Isoprene Flammability Tests

| Series Number | Temperature (° C.) | Pressure (psig) | Steam Concentration (vol. %) | Isoprene Concentration (vol. %) | Oxygen Concentration (vol. %) |
| --- | --- | --- | --- | --- | --- |
| 1 | 40 | 0 | 0 | Varying | Varying |
| 2 | 40 | 0 | 4 | Varying | Varying |

II. Description of Calculated Adiabatic Flame Temperature (CAFT) Model

Calculated adiabatic flame temperatures (CAFT) along with a selected limit flame temperature for combustion propagation were used to determine the flammability envelope for isoprene. The computer program used in this study to calculate the flame temperatures is the NASA Glenn Research Center CEA (Chemical Equilibrium with Applications) software.

There are five steps involved in determining the flammability envelope using an adiabatic flame temperature model for a homogeneous combustion mechanism (where both the fuel and oxidant are in the gaseous state): selection of the desired reactants, selection of the test condition, selection of the limit flame temperature, modification of the reactants, and construction of a flammability envelope from calculations.

In this first step, selection of desired reactants, a decision must be made as to the reactant species that will be present in the system and the quantities of each. In many cases the computer programs used for the calculations have a list of reactant and product species. If any of the data for the species to be studied are not found in the program, they may be obtained from other sources such as the JANAF tables or from the internet. In this current model data for water, nitrogen, oxygen and carbon dioxide were present in the program database. The program database did not have isoprene as a species; therefore the thermodynamic properties were incorporated manually.

The next step is to decide whether the initial pressure and temperature conditions that the combustion process is taking place in. In this model the pressure was 1 atmosphere (absolute) and the temperature was 40° C., the boiling point of isoprene.

The limit flame temperature for combustion can be either selected based on theoretical principles or determined experimentally. Each method has its own limitations.

Based on prior studies, the limit flame temperatures of hydrocarbons fall in the range of 1000 K to 1500 K. For this model, the value of 1500 K was selected. This is the temperature at which the reaction of carbon monoxide to carbon dioxide (a highly exothermic reaction and constitutes a significant proportion of the flame energy) becomes self sustaining.

Once the limit flame temperature has been decided upon, model calculations are performed on the given reactant mixture (species concentrations) and the adiabatic flame temperature is determined. Flame propagation is considered to have occurred only if the temperature is greater than the limit flame temperature. The reactant mixture composition is then modified to create data sets for propagation and non-propagation mixtures.

This type of model shows good agreement with the experimentally determined flammability limits. Regions outside the derived envelope are nonflammable and regions within it are flammable. The shape of the envelope forms a nose. The nose of the envelope is related to the limiting oxygen concentration (LOC) for gaseous fuels.

III. Results from Calculated Adiabatic Flame Temperature (CAFT) Model

Plotted in FIGS. 68 through 74 are the CAFT model results for Series A to G, respectively. The figures plot the calculated adiabatic flame temperature (using the NASA CEA program) as a function of fuel concentration (by weight) for several oxygen/nitrogen ratios (by weight). The parts of the curve that are above 1500 K, the selected limit flame temperature, contain fuel levels sufficient for flame propagation. The results may be difficult to interpret in the form presented in FIGS. 68 through 74. Additionally, the current form is not conducive to comparison with experimental data which is generally presented in terms of volume percent.

Figure 68:
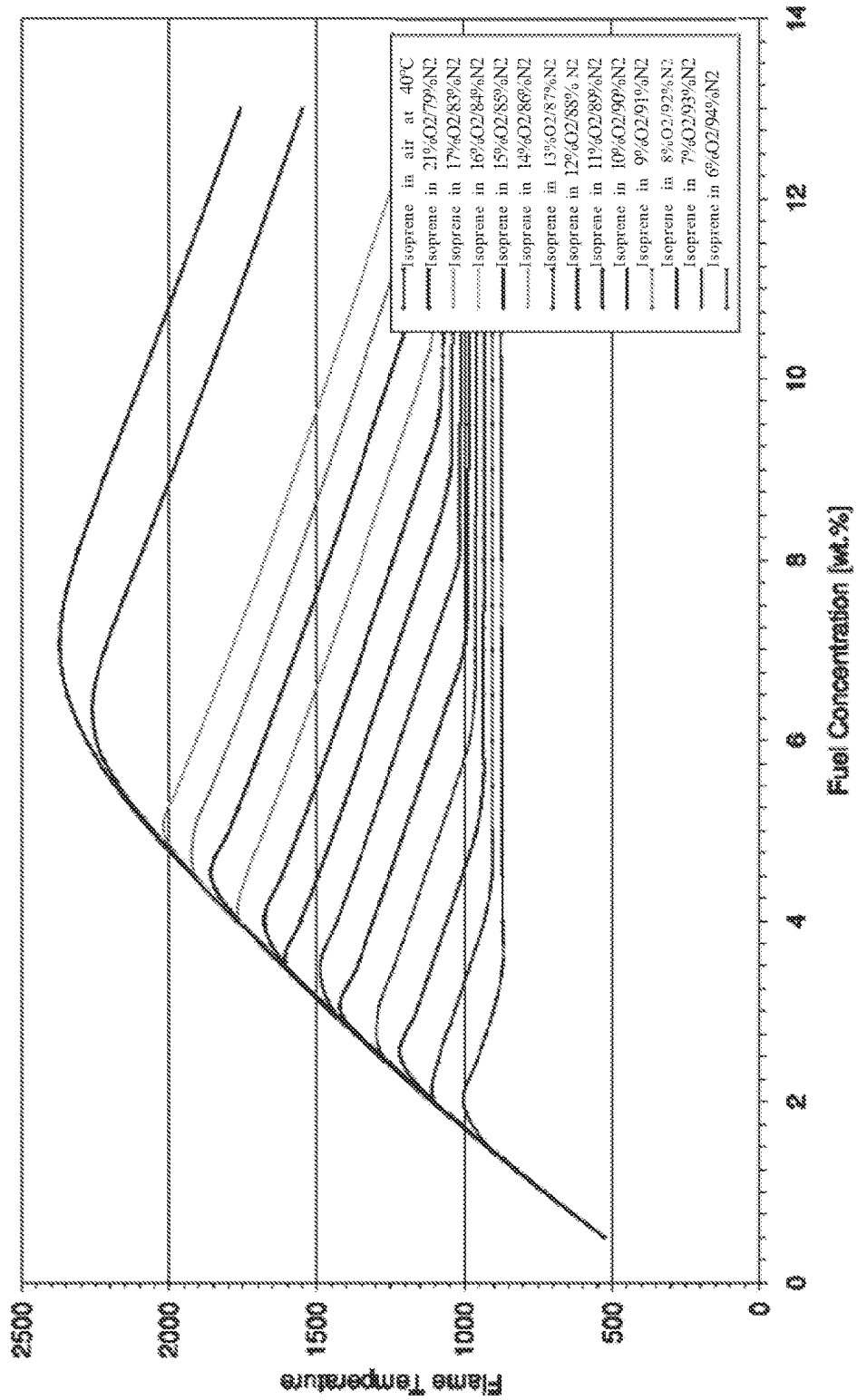
FIG. 68 is a graph of the calculated adiabatic flame temperatures for Series A as a function of fuel concentration for various oxygen levels. The figure legend lists the curves in the order in which they appear in the graph. For example, the first entry in the figure legend (isoprene in air at 40° C.) corresponds to the highest curve in the graph.
Figure 69:
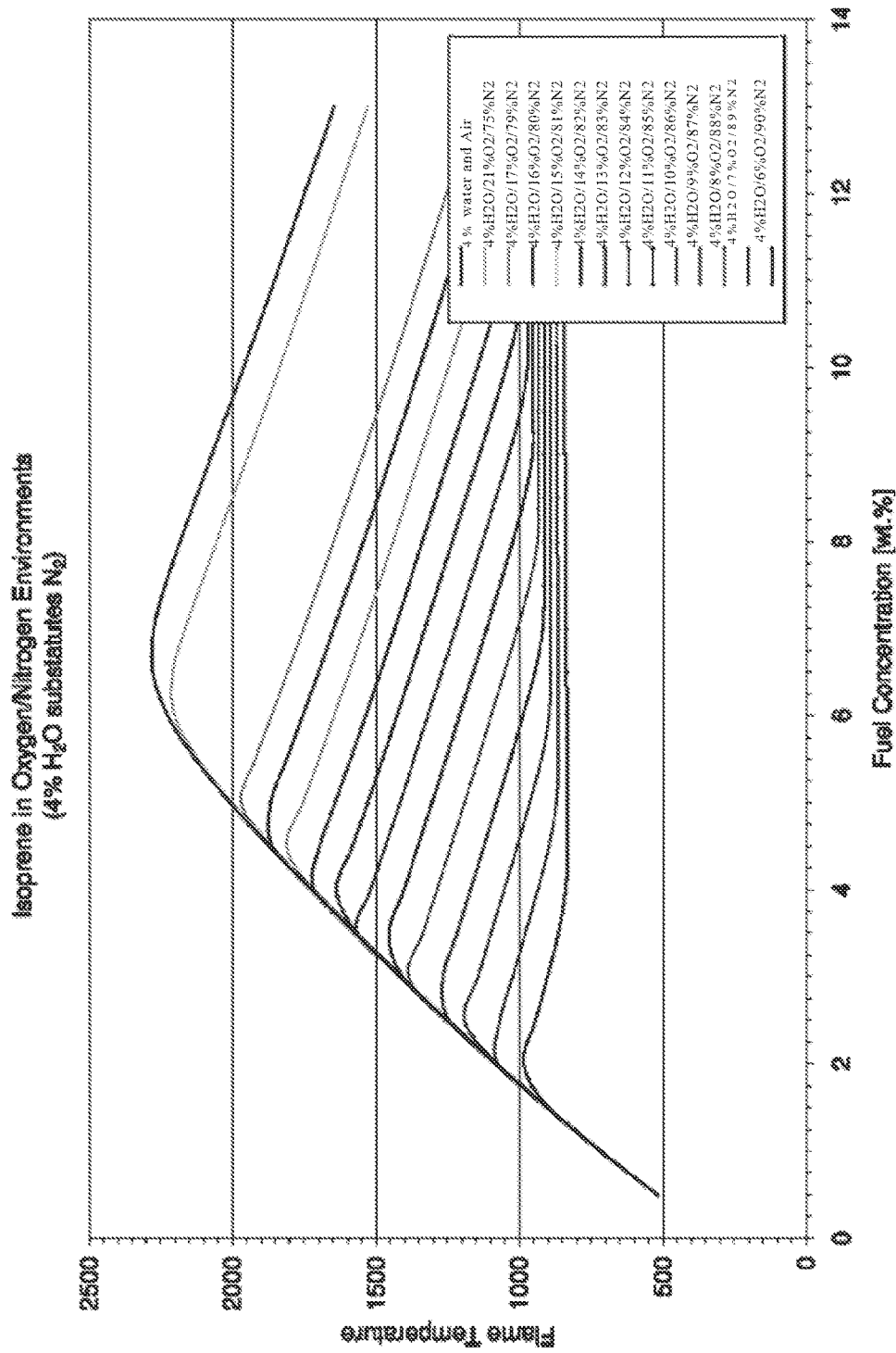
FIG. 69 is a graph of the calculated adiabatic flame temperatures for Series B as a function of fuel concentration for various oxygen levels with 4% water. The figure legend lists the curves in the order in which they appear in the graph.
Figure 70:
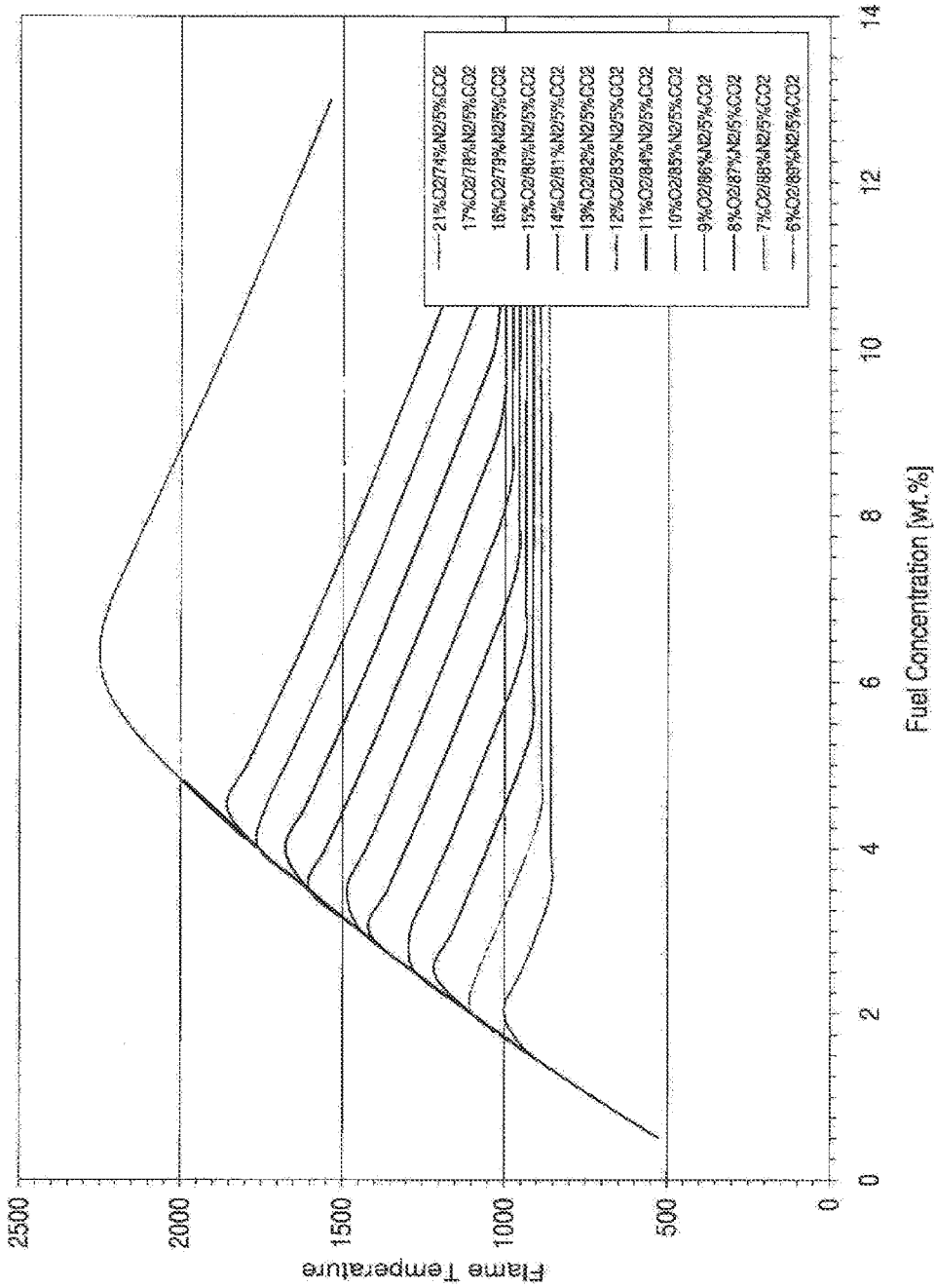
FIG. 70 is a graph of the calculated adiabatic flame temperatures for Series C as a function of fuel concentration for various oxygen levels with 5% $CO_2$. The figure legend lists the curves in the order in which they appear in the graph.
Figure 71:
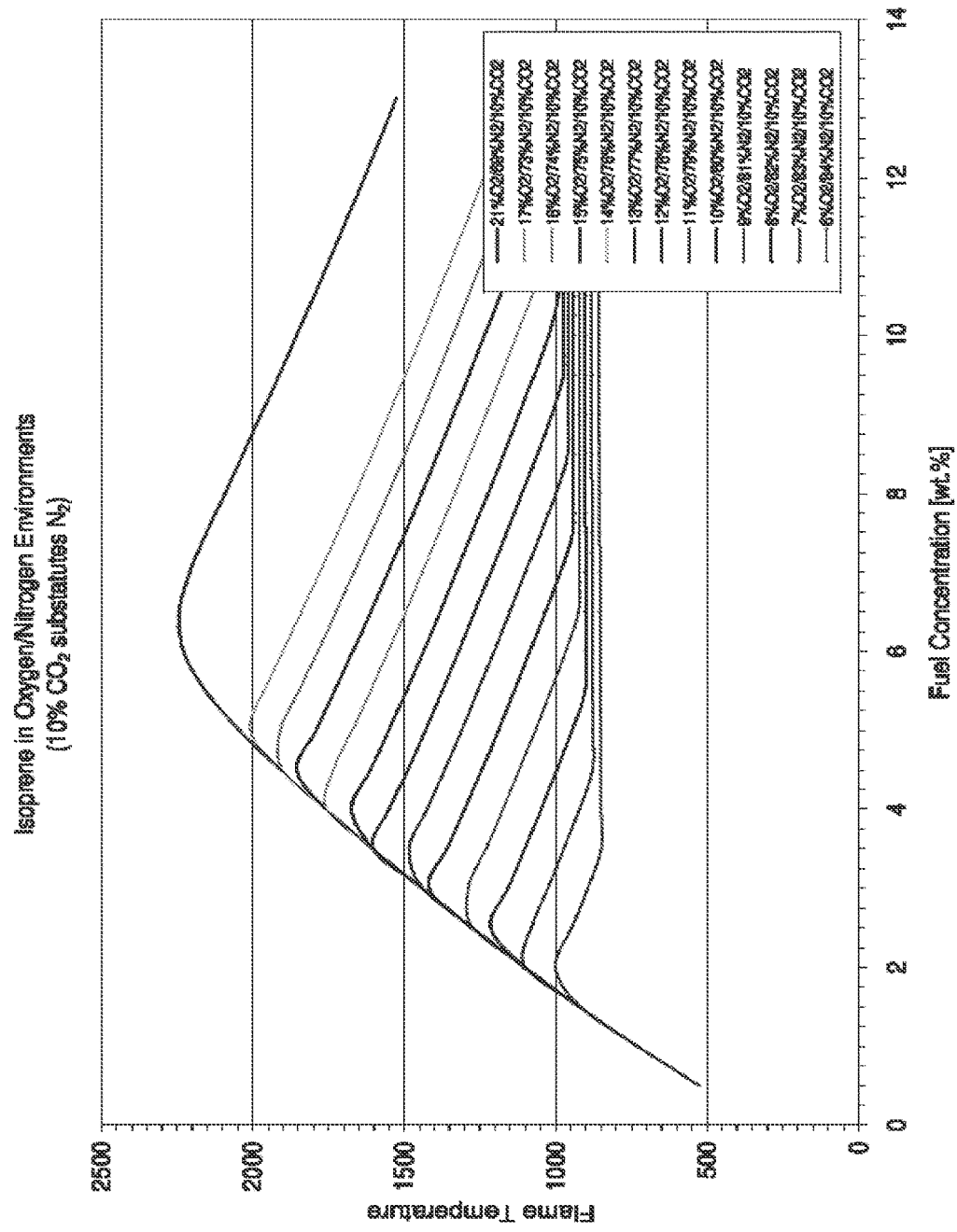
FIG. 71 is a graph of the calculated adiabatic flame temperatures for Series D as a function of fuel concentration for various oxygen levels with 10% $CO_2$. The figure legend lists the curves in the order in which they appear in the graph.
Figure 72:
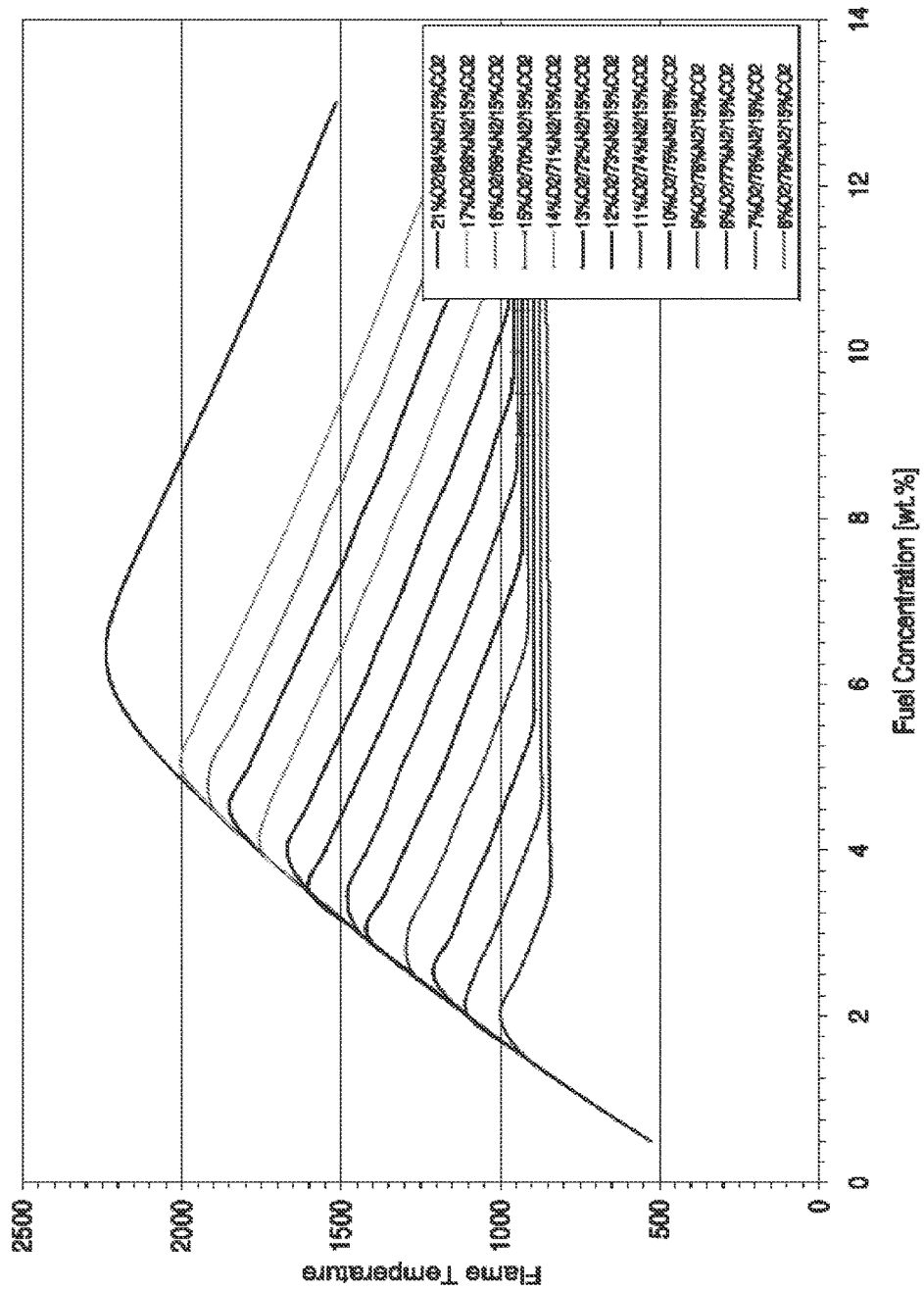
FIG. 72 is a graph of the calculated adiabatic flame temperatures for Series E as a function of fuel concentration for various oxygen levels with 15% $CO_2$. The figure legend lists the curves in the order in which they appear in the graph.
Figure 73:
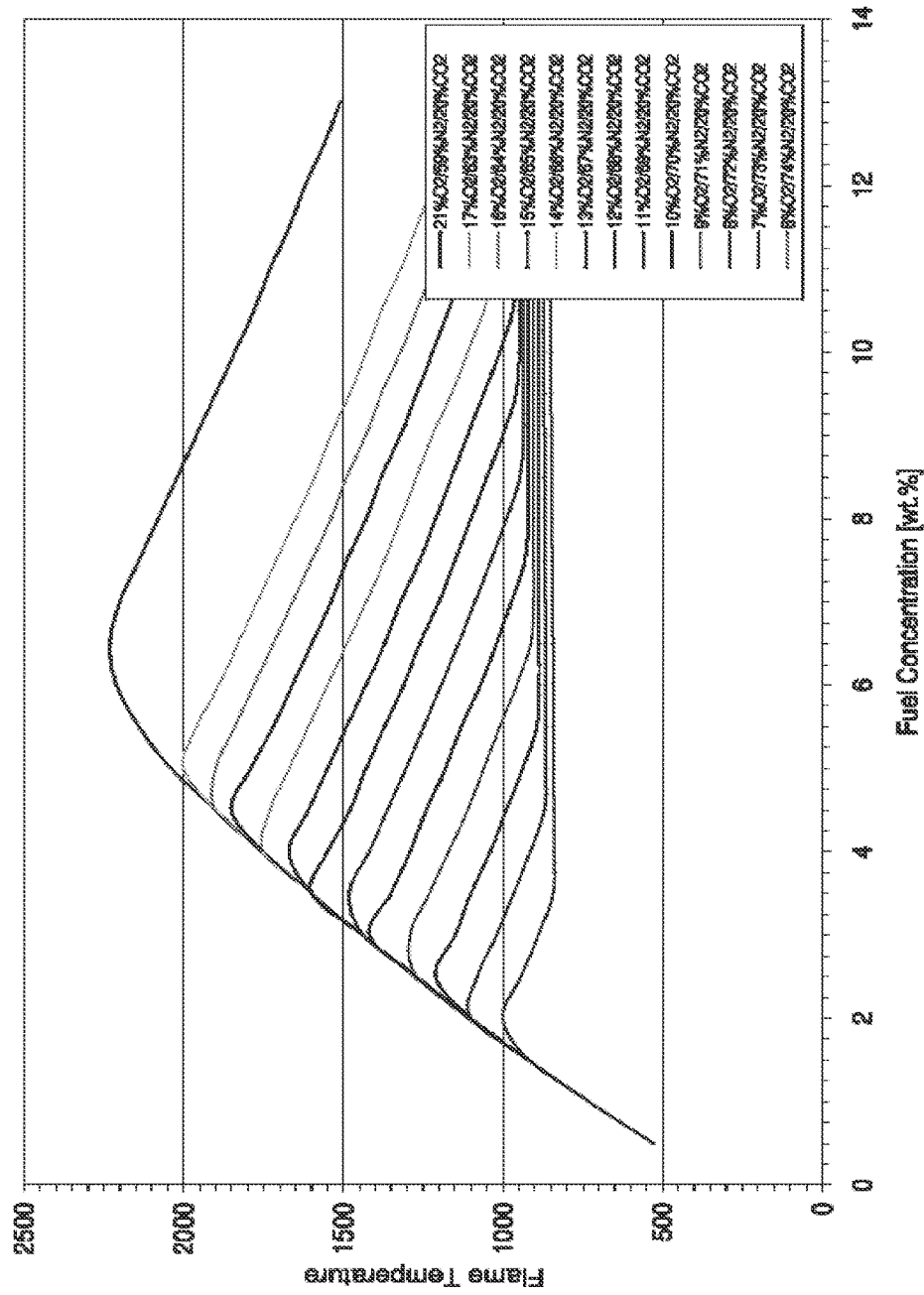
FIG. 73 is a graph of the calculated adiabatic flame temperatures for Series F as a function of fuel concentration for various oxygen levels with 20% $CO_2$. The figure legend lists the curves in the order in which they appear in the graph.
Figure 74:
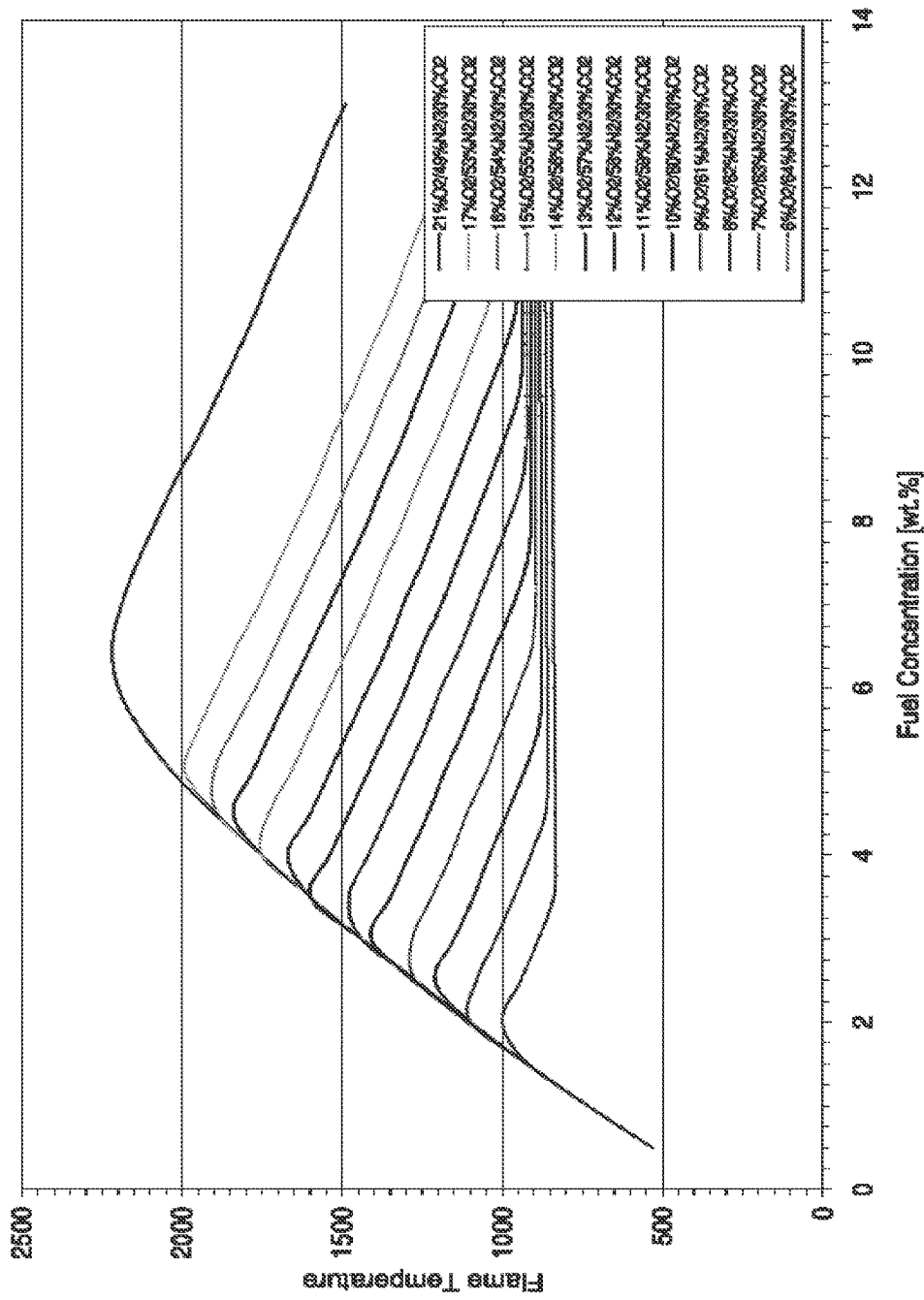
FIG. 74 is a graph of the calculated adiabatic flame temperatures for Series G as a function of fuel concentration for various oxygen levels with 30% $CO_2$. The figure legend lists the curves in the order in which they appear in the graph.

Using Series A as an example the data in FIG. 68 can be plotted in the form of a traditional flammability envelope. Using FIG. 68 and reading across the 1500 K temperature line on the ordinate one can determine the fuel concentration for this limit flame temperature by dropping a tangent to the abscissa for each curve (oxygen to nitrogen ratio) that it intersects. These values can then be tabulated as weight percent of fuel for a given weight percent of oxidizer (FIG. 75A). Then knowing the composition of the fuel (100 wt. % isoprene) and the composition of the oxidizer (relative content of water, oxygen and nitrogen) molar quantities can be established.

From these molar quantities percentage volume concentrations can be calculated. The concentrations in terms of volume percent can then be plotted to generate a flammability envelope (FIG. 75B). The area bounded by the envelope is the explosible range and the area excluded is the non-explosible range. The "nose" of the envelope is the limiting oxygen concentration. FIGS. 76A and 76B contain the calculated volume concentrations for the flammability envelope for Series B generated from data presented in FIG. 69. A similar approach can be used on data presented in FIGS. 70-74.

IV. Flammability Testing Experimental Equipment and Procedure

Figure 77:
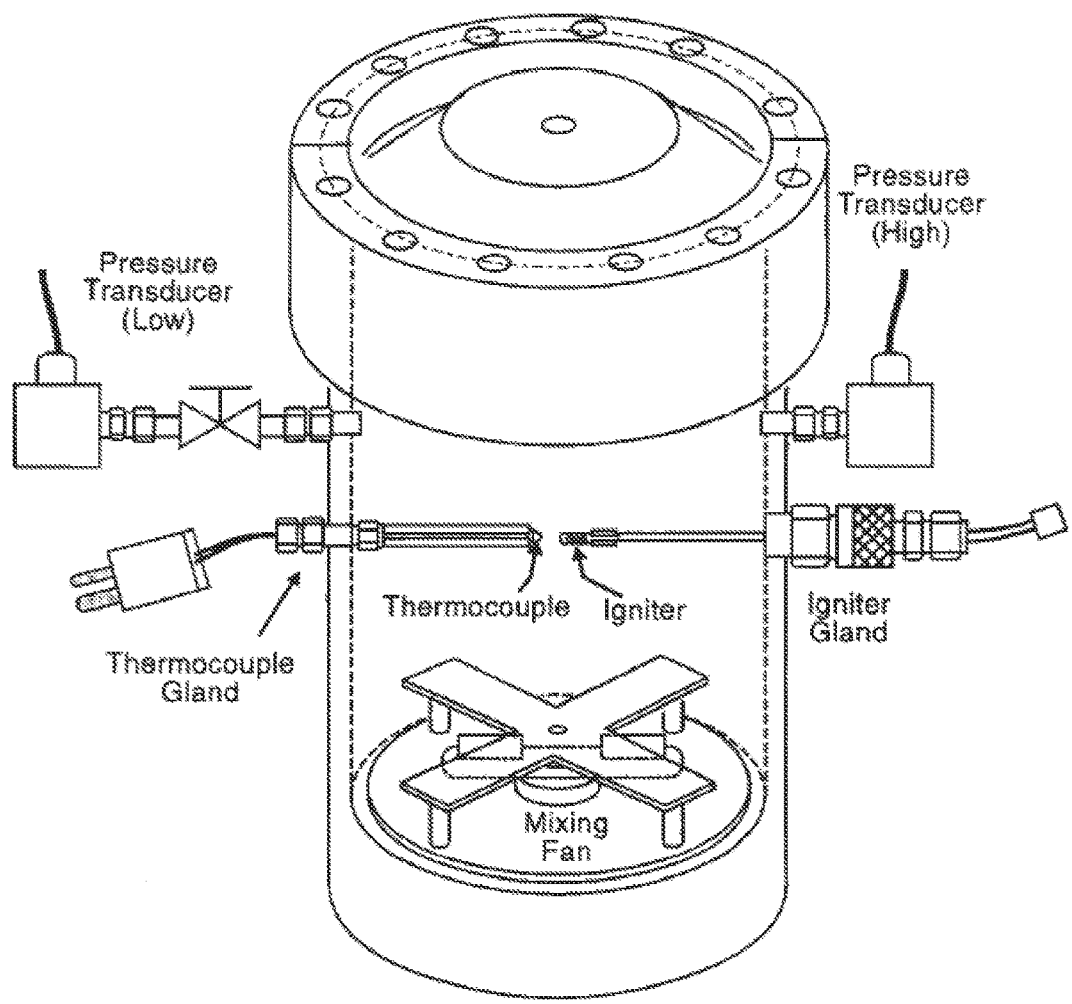
FIG. 77 is a figure depicting the flammability test vessel.

Flammability testing was conducted in a 4 liter high pressure vessel. The vessel was cylindrical in shape with an inner diameter of 6" and an internal height of 8.625". The temperature of the vessel (and the gases inside) was maintained using external heaters that were controlled by a PID controller. To prevent heat losses, ceramic wool and reflective insulation were wrapped around the pressure vessel. Type K thermocouples were used the measure the temperature of the gas space as well as the temperature of the vessel itself. FIG. 77 illustrates the test vessel.

Before a test was run, the vessel was evacuated and purged with nitrogen to ensure that any gases from previous tests were removed. A vacuum was then pulled on the vessel. The pressure after this had been done was typically around 0.06 bar(a). Due to the nitrogen purging, the gas responsible for this initial pressure was assumed to be nitrogen. Using partial pressures, water, isoprene, nitrogen, and oxygen were then added in the appropriate amounts to achieve the test conditions in question. A magnetically driven mixing fan within the vessel ensured mixing of the gaseous contents. The gases were allowed to mix for about 2 minutes with the fan being turned off approximately 1 minute prior to ignition.

The igniter was comprised of a 1.5 ohm nicrome coil and an AC voltage source on a timer circuit. Using an oscilloscope, it was determined that 34.4 VAC were delivered to the igniter for 3.2 seconds. A maximum current of 3.8 amps occurred approximately halfway into the ignition cycle. Thus, the maximum power was 131 W and the total energy provided over the ignition cycle was approximately 210 J.

Deflagration data was acquired using a variable reluctance Validyne DP215 pressure transducer connected to a data acquisition system. A gas mixture was considered to have deflagrated if the pressure rise was greater than or equal to 5%.

V. Results of Flammability Testing

The first experimental series (Series 1) was run at 40° C. and 0 psig with no steam. Running tests at varying concentrations of isoprene and oxygen produced the flammability curve shown in FIG. 78A. The data points shown in this curve are only those that border the curve. A detailed list of all the data points taken for this series is shown in FIGS. 80A and 80B.

Figure 78C:
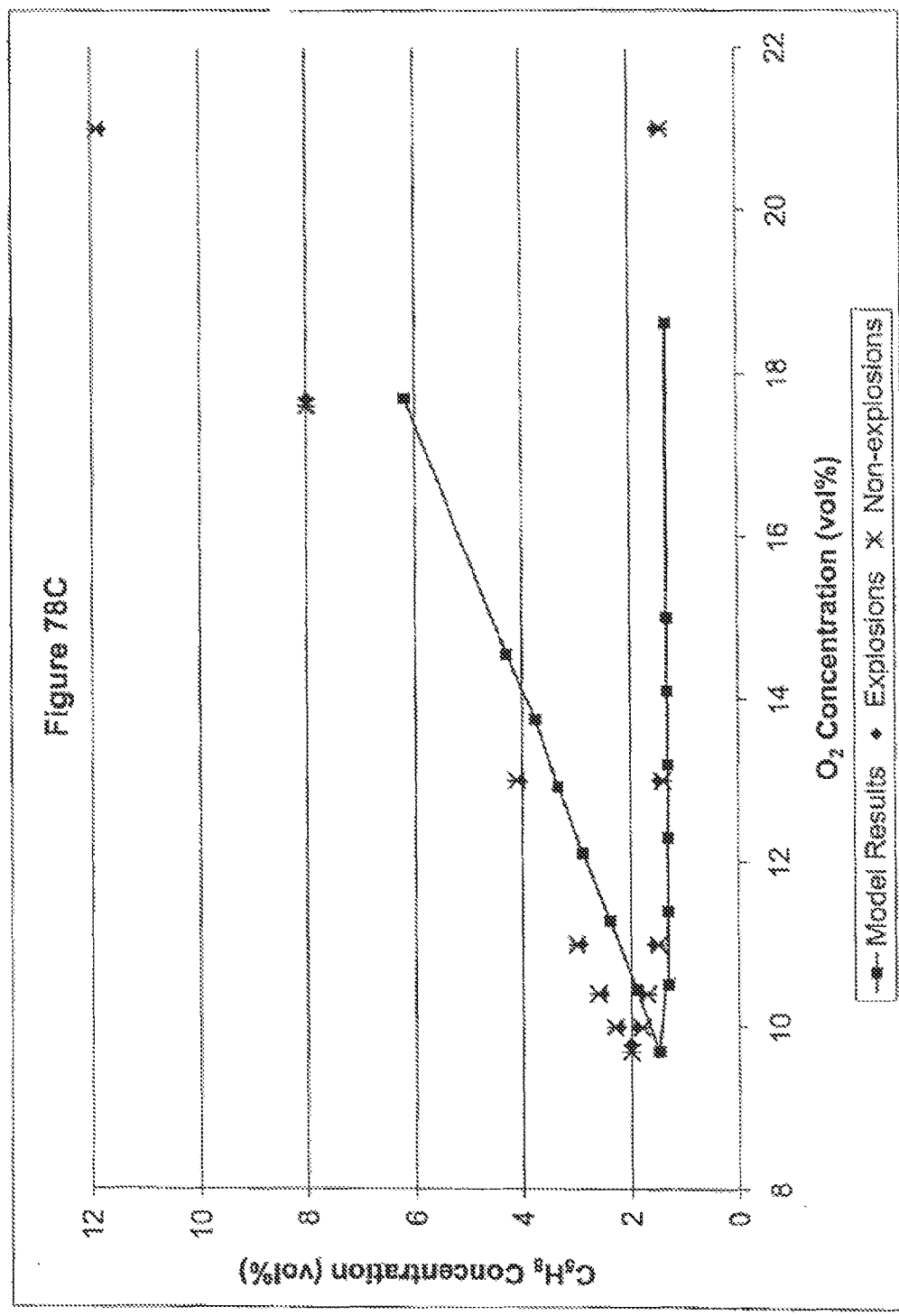
FIG. 78C is a graph of the flammability curve for Test Series 1 compared with the CAFT Model.

FIG. 78B summarizes the explosibility data points shown in FIG. 78A. FIG. 78C is a comparison of the experimental data with the CAFT model predicted flammability envelope. The model agrees very well with the experimental data. Discrepancies may be due to the non-adiabatic nature of the test chamber and limitations of the model. The model looks at an infinite time horizon for the oxidation reaction and does not take into consideration any reaction kinetic limitation.

Additionally, the model is limited by the number of equilibrium chemical species that are in its database and thus may not properly predict pyrolytic species. Also, the flammability envelope developed by the model uses one value for a limit flame temperature (1500K). The limit flame temperature can be a range of values from 1,000K to 1,500K depending on the reacting chemical species. The complex nature of pyrolytic chemical species formed at fuel concentrations above the stoichiometric fuel/oxidizer level is one reason why the model may not accurately predict the upper flammable limit for this system.

The second experimental series (Series 2) was run at 40° C. and 0 psig with a fixed steam concentration of 4%. Running tests at varying concentrations of isoprene and oxygen produced the flammability curve shown in FIG. 79A. The data points shown in this curve are only those that border the curve. A detailed list of all the data points taken for this series is shown in FIG. 81. Due to the similarity between the data in Series 1 only the key points of lower flammable limit, limiting oxygen concentration, and upper flammable limits were tested. The addition of 4% steam to the test mixture did not significantly change the key limits of the flammability envelope. It should be noted that higher concentrations of steam/water and or other inertants may influence the flammability envelope.

Figure 79C:
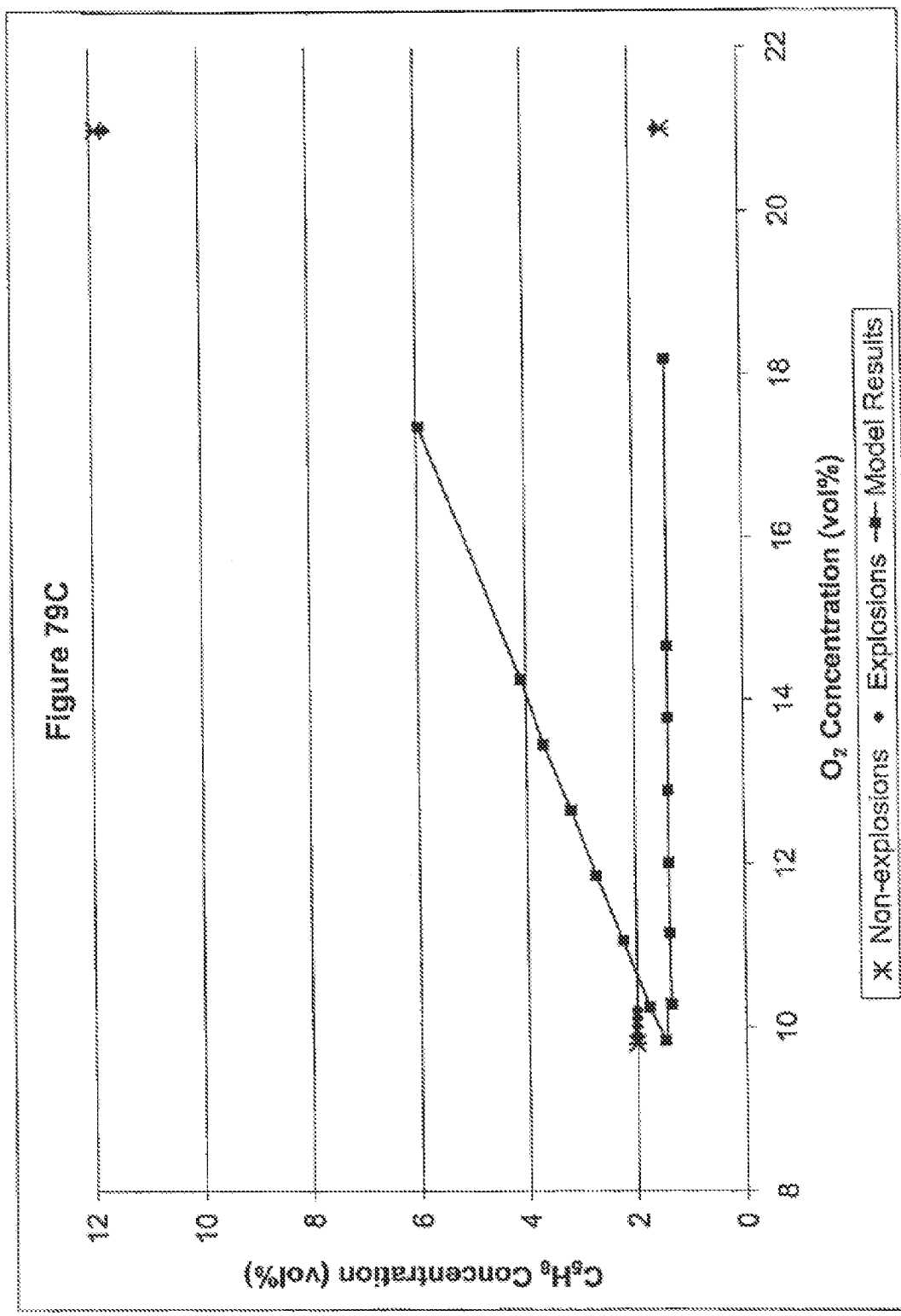
FIG. 79C is a graph of the flammability curve for Test Series 2 compared with the CAFT Model.

FIG. 79B summarizes the explosibility data points shown in FIG. 79A. FIG. 79C is a comparison of the experimental data with the CAFT model predicted flammability envelope. The model agrees very well with the experimental data. Discrepancies may be due to the same factors described in Series 1

V. Calculation of Flammability Limits of Isoprene in Air at 3 Atmospheres of Pressure The methods described in Example 13, parts I to IV were also used to calculate the flammability limits of isoprene at an absolute system pressure of 3 atmospheres and 40° C. These results were compared to those of Example 13, parts I to IV at an absolute system pressure of 1 atmosphere and 40° C. This higher pressure was tested because the flammability envelope expands or grows larger as the initial system pressure is increased. The upper flammability limit is affected the most, followed by the limiting oxygen composition. The lower flammability limit is the least affected (see, for example, "Bulletin 627—Flammability Characteristics of Combustible Gases and Vapors" written by Michael G. Zabetakis and published by the former US Bureau of Mines (1965), which is hereby incorporated by reference in its entirety, particular with respect to the calculation of flammability limits).

Figure 83:
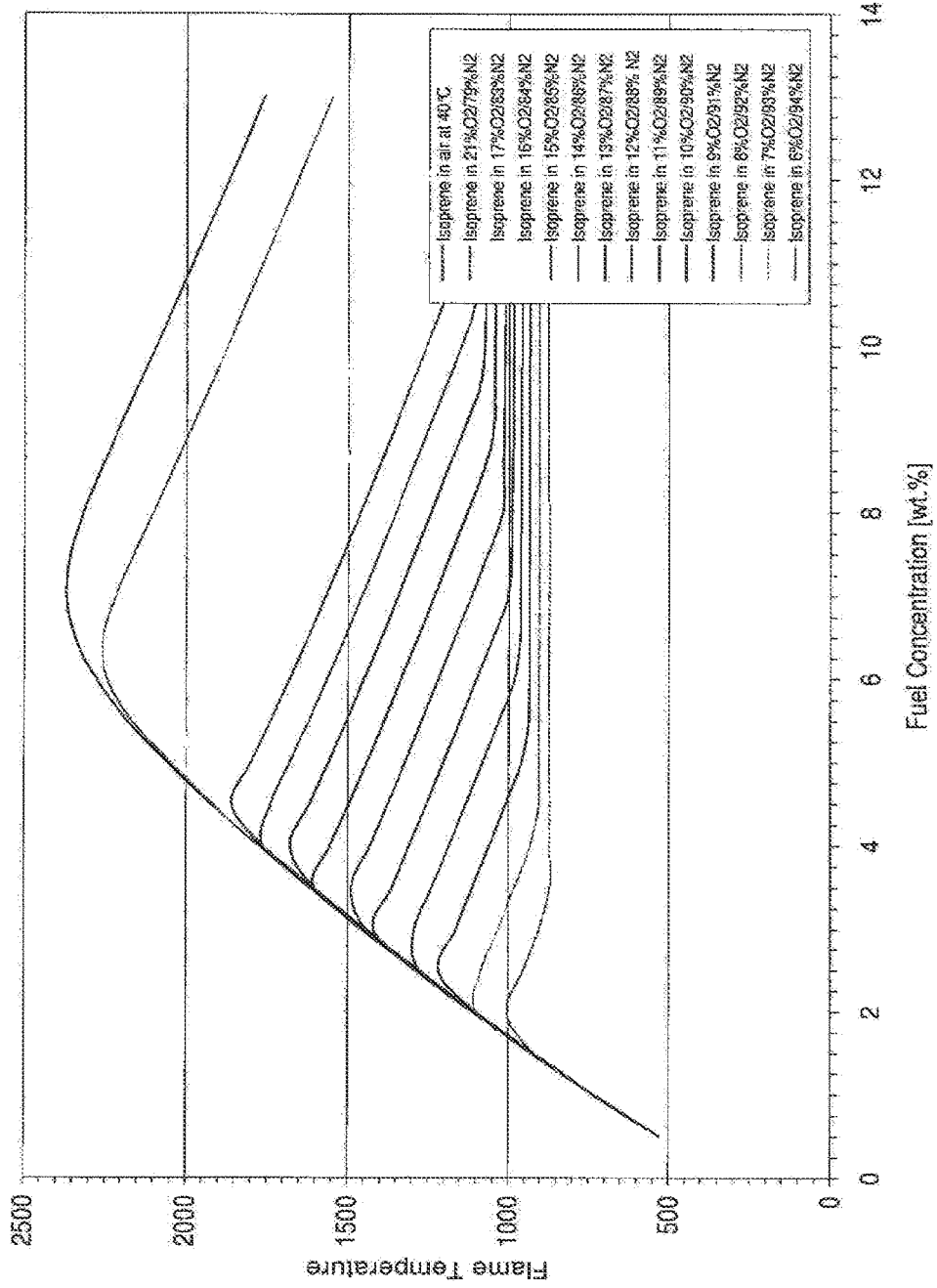
FIG. 83 is a graph of the calculated adiabatic flame temperature plotted as a function of fuel concentration for various nitrogen/oxygen ratios at 1 atmosphere of pressure.
Figure 84:
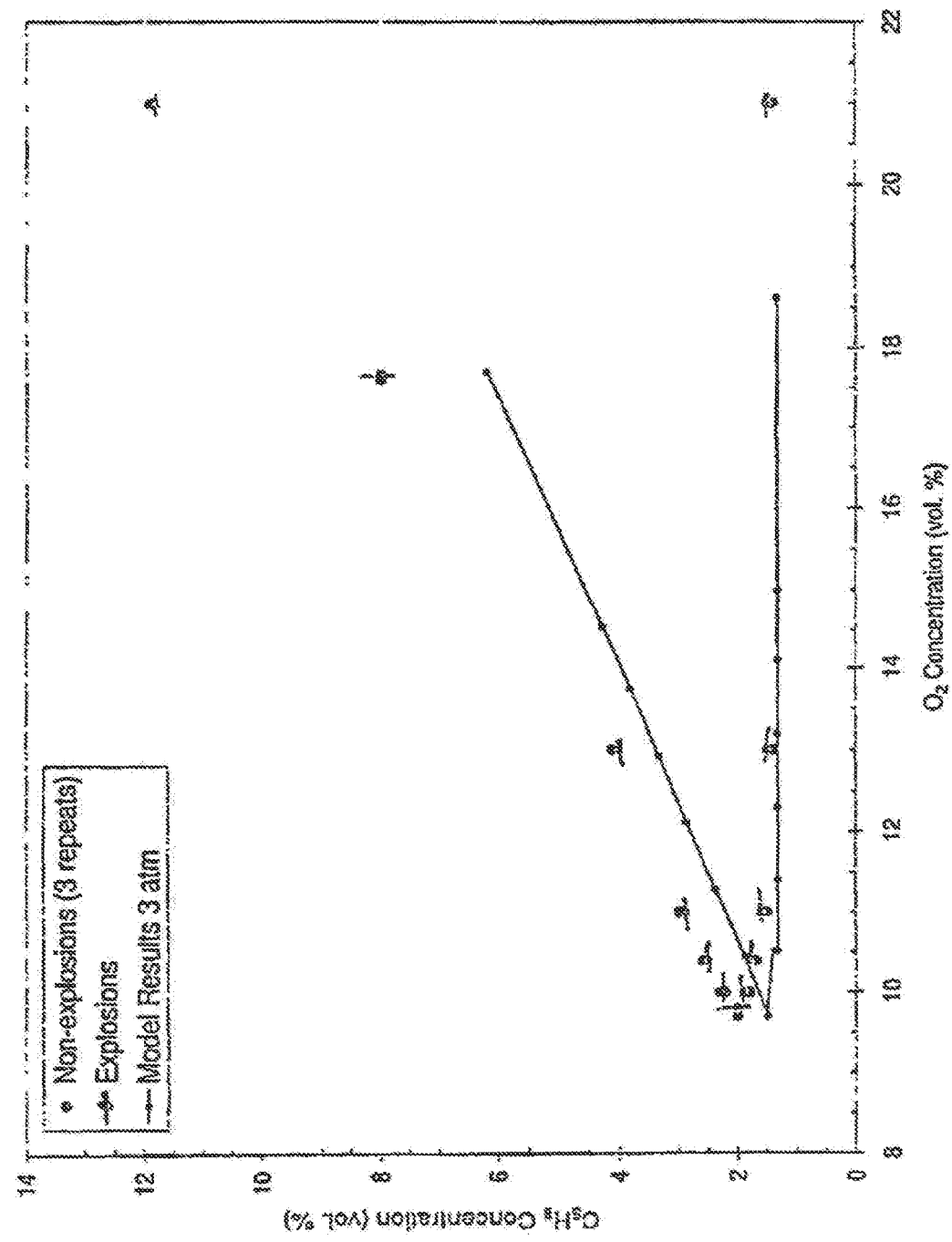
FIG. 84 is a graph of the flammability envelope constructed using data from FIG. 82 and following the methodology described in Example 13. The experimental data points (circles) are from tests described herein that were conducted at 1 atmosphere initial system pressure.
Figure 85:
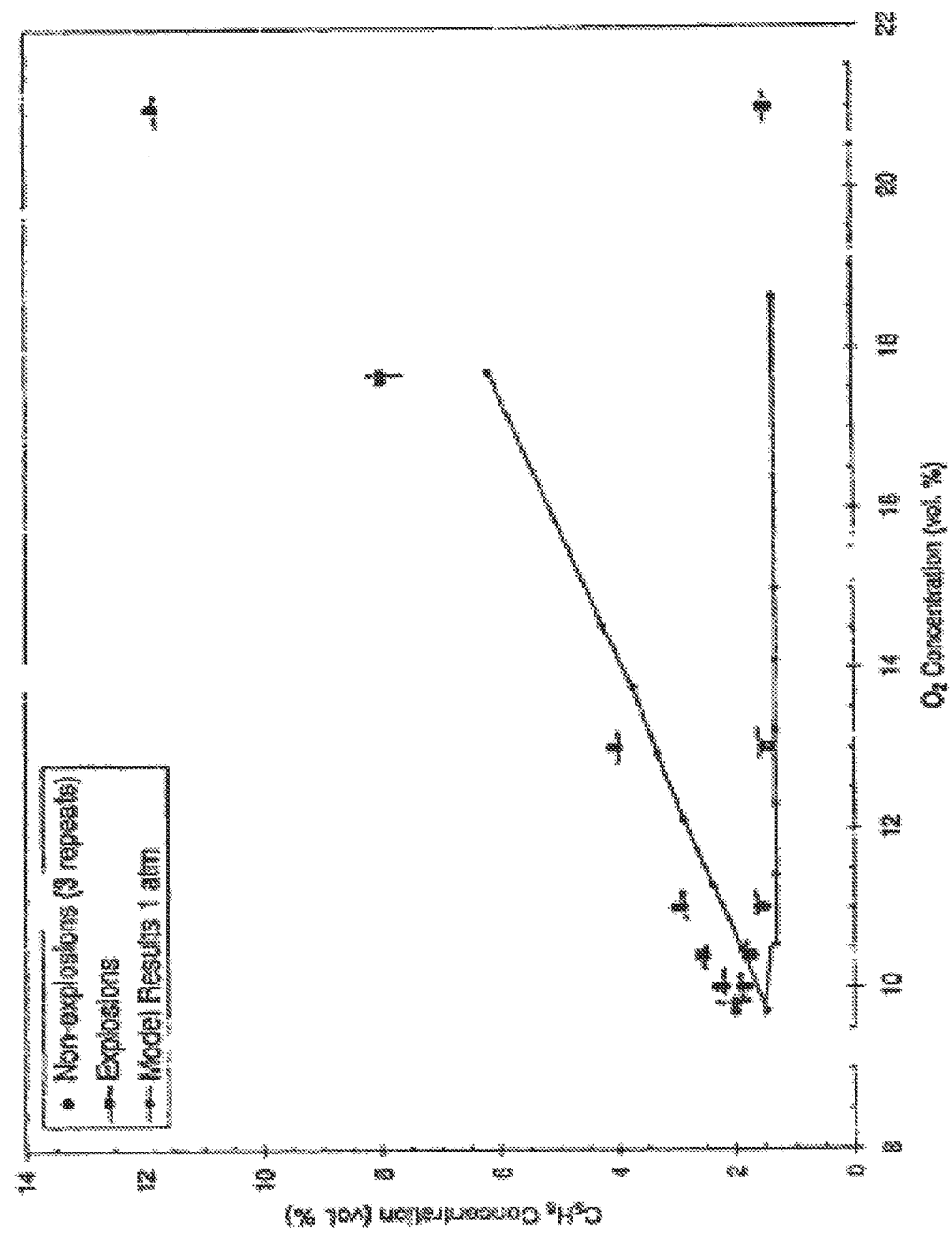
FIG. 85 is a graph of the flammability envelope constructed using data from FIG. 83 and following the methodology described in Example 13. The experimental data points (circles) are from tests described herein that were conducted at 1 atmosphere initial system pressure.

In FIG. 82, the calculated adiabatic flame temperature is plotted as a function of isoprene (fuel) concentration, expressed in weight percent of the total fuel/nitrogen/oxygen, where the system pressure was initially 3 atmospheres. The calculated flame temperatures are very similar to those determined initially in the 1 atmosphere system (FIG. 83). As a result, when flammability envelopes are generated using the calculated adiabatic flammability data, the curves are very similar (see FIGS. 84 and 85). Therefore, based on these theoretical calculations, a system pressure increase from 1 atmosphere to 3 atmosphere does not result in a significant increase/broadening of the flammability envelope. If desired, these model results may be validated using experimental testing (such as the experimental testing described herein at a pressure of 1 atmosphere).

VII. Summary of Flammability Studies

A calculated adiabatic temperature model was developed for the flammability envelope of the isoprene/oxygen/nitrogen/water/carbon dioxide system at 40° C. and 0 psig. The CAFT model that was developed agreed well with the experimental data generated by the tests conducted in this work. The experimental results from Series 1 and 2 validated the model results from Series A and B.

Example 14

Expression Constructs and Strains

I. Construction of Plasmids Encoding Mevalonate Kinase.

A construct encoding the *Methanosarcina mazei* lower MVA pathway (Accession numbers NC_003901.1, NC_003901.1, NC_003901.1, and NC_003901.1, which are each hereby incorporated by reference in their entireties) was synthesized with codon optimization for expression in *E. coli*. This construct is named *M. mazei* archeal Lower Pathway operon (FIGS. 112A-112C; SEQ ID NO:27) and encodes *M. mazei* MVK, a putative decarboxylase, IPK, and IDI enzymes. The gene encoding MVK (Accession number NC_003901.1) was PCR amplified using primers MCM165 and MCM177 (Table 11) using the Strategene Herculase II Fusion kit according to the manufacturer's protocol using 30 cycles with an annealing temperature of 550 C and extension time of 60 seconds. This amplicon was purified using a Qiagen PCR column and then digested at 370 C in a 10 µL reaction with PmeI (in the presence of NEB buffer 4 and BSA). After one hour, NsiI and Roche buffer H were added for an additional hour at 370 C. The digested DNA was purified over a Qiagen PCR column and ligated to a similarly digested and purified plasmid MCM29 (MCM29 is *E. coli* TOP10 (Invitrogen) transformed with pTrcKudzu encoding Kudzu isoprene synthase) in an 11 uL reaction 5 uL Roche Quick Ligase buffer 1, 1 uL buffer 2, 1 uL plasmid, 3 uL amplicon, and 1 uL ligase (1 hour at room temperature). MCM 29 is pTrcKudzuKan. The ligation reaction was introduced into Invitrogen TOP10 cells and transformants selected on LA/kan50 plates incubated at 370 C overnight. The MVK insert in the resulting plasmid MCM382 was sequenced (FIGS. 113A-113C; SEQ ID NO: 28).

TABLE 11

Oligonucleotides.

| | |
|---|---|
| MCM161 *M. mazei* MVK for | CACCATGGTATCCTGTTCTGCG (SEQ ID NO: 120) |
| MCM162 *M. mazei* MVK rev | TTAATCTACTTTCAGACCTTGC (SEQ ID NO: 121) |
| MCM165 *M. mazei* MVK for w/ RBS | gcgaacgATGCATaaaggaggtaaaaaaacATGGTATCCTGTTCTG CGCCGGGTAAGATTTACCTG (SEQ ID NO: 122) |
| MCM177 *M. mazei* MVK rev Pst | gggcccgtttaaactttaactagactTTAATCTACTTTCAGACCTTGC (SEQ ID NO: 123) |

II. Creation of Strains Overexpressing Mevalonate Kinase and Isoprene Synthase.

Plasmid MCM382 was transformed into MCM331 cells (which contains chromosomal construct gi1.2KKDyI encoding *S. cerevisiae* mevalonate kinase, mevalonate phosphate kinase, mevalonate pyrophosphate decarboxylase, and IPP isomerase) that had been grown to midlog in LB medium and washed three times in iced, sterile water. One µL of DNA was added to 50 µL of cell suspension, and this mixture was electroporated in a 2 mm cuvette at 2.5 volts, 25 uFd followed immediately by recovery in 500 µL LB medium for one hour at 370 C. Transformant was selected on LA/kan50 and named MCM391. Plasmid MCM82 was introduced into this strain by the same electroporation protocol followed by selection on LA/kan50/spec50. The resulting strain MCM401 contains a cmp-marked chromosomal construct gi1.2KKDyI, kan-marked plasmid MCM382, and spec-marked plasmid MCM82 (which is pCL PtrcUpperPathway encoding *E. faecalis* mvaE and mvaS). See Table 12.

TABLE 12

Strains overexpressing mevalonate kinase and isoprene synthase.

| | |
|---|---|
| MCM382 | *E. coli* BL21 (lambdaDE3) pTrcKudzuMVK(*M. mazei*)GI1.2KKDyI |
| MCM391 | MCM331 pTrcKudzuMVK(*M. mazei*) |
| MCM401 | MCM331pTrcKudzuMVK(*M. mazei*)pCLPtrcUpperpathway |
| MCM396 | MCM333pTrcKudzuMVK(*M. mazei*) |
| MCM406 | MCM333pTrcKudzuMVK(*M. mazei*)pCLPtrcUpperpathway |

III. Construction of Plasmid MCM376-MVK from *M. Mazei* Archeal Lower in pET200D.

The MVK ORF from the *M. mazei* archeal Lower Pathway operon (FIGS. 112A-112C; SEQ ID NO:27) was PCR amplified using primers MCM161 and MCM162 (Table 11) using the Invitrogen Platinum HiFi PCR mix. 45 uL of PCR mix was combined with 1 uL template, 1 uL of each primer at 10 uM, and 2 uL water. The reaction was cycled as follows: 940 C for 2:00; 30 cycles of 940 C for 0:30, 550 C for 0:30, and 680 C for 1:15; and then 720 C for 7:00, and 40 C until cool. 3 uL of this PCR reaction was ligated to Invitrogen pET200D plasmid according to the manufacturer's protocol. 3 uL of this ligation was introduced into Invitrogen TOP10 cells, and transformants were selected on LA/kan50. A plasmid from a transformant was isolated and the insert sequenced, resulting in MCM376 (FIGS. 114A-114C; SEQ ID NO:29).

V. Creation of Expression Strain MCM378.

Plasmid MCM376 was transformed into Invitrogen BL21 (DE3) pLysS cells according to the manufacturer's protocol. Transformant MCM378 was selected on LA/kan50.

Example 15

Production of Isoprene by *E. Coli* Expressing the Upper Mevalonic Acid (MVA) Pathway, the Integrated Lower MVA Pathway (Gi1.2KKDyI), Mevalonate Kinase from *M. Mazei*, and Isoprene Synthase from Kudzu and Grown in Fed-Batch Culture at the 20 mL Batch Scale Medium Recipe (Per Liter Fermentation Medium).

Each liter of fermentation medium contained $K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 1 g, and 1000× Trace Metal Solution 1 ml. All of the components were added together and dissolved in $diH_2O$. The pH was adjusted to 6.8 with ammonium hydroxide (30%) and brought to volume. Media was filter sterilized with a 0.22 micron filter. Glucose (2.5 g) and antibiotics were added after sterilization and pH adjustment. 1000× Trace Metal Solution:

1000× Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in $diH_2O$, pH to 3.0 with HCl/NaOH, then brought to volume and filter sterilized with a 0.22 micron filter.

Strains:

MCM343 cells are BL21 (DE3) *E. coli* cells containing the upper mevalonic acid (MVA) pathway (pCL Upper), the integrated lower MVA pathway (gi1.2KKDyI), and isoprene synthase from Kudzu (pTrcKudzu).

MCM401 cells are BL21 (DE3) *E. coli* cells containing the upper mevalonic acid (MVA) pathway (pCL PtrcUpperPathway), the integrated lower MVA pathway (gi1.2KKDyI), and high expression of mevalonate kinase from *M. mazei* and isoprene synthase from Kudzu (pTrcKudzuMVK (*M. mazei*)).

Isoprene production was analyzed by growing the strains in 100 mL bioreactors with a 20 mL working volume at a temperature of 30° C. An inoculum of *E. coli* strain taken from a frozen vial was streaked onto an LB broth agar plate (with antibiotics) and incubated at 30° C. A single colony was inoculated into media and grown overnight. The bacteria were diluted into 20 mL of media to reach an optical density of 0.05 measured at 550 nm. The 100 mL bioreactors were sealed, and air was pumped through at a rate of 8 mL/min. Adequate agitation of the media was obtained by stirring at 600 rpm using magnetic stir bars. The off-gas from the bioreactors was analyzed using an on-line Hiden HPR-20 mass spectrometer. Masses corresponding to isoprene, $CO_2$, and other gasses naturally occurring in air were monitored. Accumulated isoprene and $CO_2$ production were calculated by summing the concentration (in percent) of the respective gasses over time. Atmospheric $CO_2$ was subtracted from the total in order to estimate the $CO_2$ released due to metabolic activity.

Isoprene production from a strain expressing the full mevalonic acid pathway and Kudzu isoprene synthase (MCM343) was compared to a strain that in addition over-expressed MVK from *M. mazei* and Kudzu isoprene synthase (MCM401) in 100 mL bioreactors. The bacteria were grown under identical conditions in defined media with glucose as carbon source. Induction of isoprene production was achieved by adding isopropyl-beta-D-1-thiogalactopyranoside (IPTG) to a final concentration of either 100 uM or 200 uM. Off-gas measurements revealed that the strain over-expressing both MVK and isoprene synthase (MCM401) produced significantly more isoprene compared to the strain expressing only the mevalonic acid pathway and Kudzu isoprene synthase (MCM343) as shown in FIGS. 115A-115D. At 100 uM induction, the MCM401 strain produced 2-fold more isoprene compared to the MCM343 strain. At 200 uM IPTG induction, the MCM401 strain produced 3.4-fold more isoprene when compared to the MCM343 strain. Analysis of $CO_2$ in the off-gas from the bioreactors, which is a measure of metabolic activity, indicates that metabolic activity was independent from IPTG induction and isoprene production.

Example 16

Production of Isoprene by *E. Coli* Expressing the Upper Mevalonic Acid (MVA) Pathway, the Integrated Lower MVA Pathway (Gi1.2KKDyI), Mevalonate Kinase from *M. Mazei*, and Isoprene Synthase from Kudzu and Grown in Fed-Batch Culture at the 15-L Scale Medium Recipe (Per Liter Fermentation Medium).

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $DIH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in $DIH_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK (*M. mazei*)). This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate 5-L of medium in a 15-L bioreactor.

Glucose was fed at an exponential rate until cells reached the stationary phase. After this time the glucose feed was decreased to meet metabolic demands. The total amount of glucose delivered to the bioreactor during the 68 hour fermentation was 3.8 kg. Induction was achieved by adding isopropyl-beta-D-1-thiogalactopyranoside (IPTG). The IPTG concentration was brought to 51 uM when the optical density at 550 nm ($OD_{550}$) reached a value of 9. The IPTG concentration was raised to 88 uM when $OD_{550}$ reached 149. Additional IPTG additions raised the concentration to 119 uM at $OD_{550}$=195 and 152 uM at $OD_{550}$=210. The $OD_{550}$ profile within the bioreactor over time is shown in FIG. 116. The isoprene level in the off gas from the bioreactor was determined using a Hiden mass spectrometer. The isoprene titer increased over the course of the fermentation to a final value of 23.8 g/L (FIG. 117). The total amount of isoprene produced during the 68 hour fermentation was 227.2 g and the time course of production is shown in FIG. 118. The metabolic activity profile, as measured by TCER, is shown in FIG. 119. The total viable count (total colony forming units) decreased by two orders of magnitude between 10 and 39 hours of fermentation (FIG. 120). The molar yield of utilized carbon that went into producing isoprene during fermentation was 13.0%. The weight percent yield of isoprene from glucose was 6.3%.

Example 17

Production of Isoprene by *E. Coli* Expressing the Upper Mevalonic Acid (MVA) Pathway, the Integrated Lower MVA Pathway (Gi1.2KKDyI), Mevalonate Kinase from *M. Mazei*, and Isoprene Synthase from Kudzu and Grown in Fed-Batch Culture at the 15-L Scale (2×100 μM IPTG induction)

Medium Recipe (Per Liter Fermentation Medium).

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $DIH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in $DIH_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK (*M. mazei*)). This experiment was carried out to monitor isoprene formation from glucose at the desired fermentation pH 7.0 and temperature 30° C. An inoculum of E. coli strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate 5-L medium in a 15-L bioreactor.

Glucose was fed at an exponential rate until cells reached the stationary phase. After this time the glucose feed was decreased to meet metabolic demands. The total amount of glucose delivered to the bioreactor during the 55 hour fermentation was 1.9 kg. Induction was achieved by adding isopropyl-beta-D-1-thiogalactopyranoside (IPTG). The IPTG concentration was brought to 111 uM when the optical density at 550 nm ($OD_{550}$) reached a value of 9. The IPTG concentration was raised to 193 uM when $OD_{550}$ reached 155. The $OD_{550}$ profile within the bioreactor over time is shown in FIG. 121. The isoprene level in the off gas from the bioreactor was determined using a Hiden mass spectrometer. The isoprene titer increased over the course of the fermentation to a final value of 19.5 g/L (FIG. 122). The total amount of isoprene produced during the 55 hour fermentation was 133.8 g and the time course of production is shown in FIG. 123. Instantaneous volumetric productivity levels reached values as high as 1.5 g isoprene/L broth/hr (FIG. 124). Instantaneous yield levels reached as high as 17.7% w/w (FIG. 125). The metabolic activity profile, as measured by TCER, is shown in FIG. 126. The total viable count (total colony forming units) decreased by two orders of magnitude between 8 and 36 hours of fermentation (FIG. 127). The molar yield of utilized carbon that went into producing isoprene during fermentation was 15.8%. The weight percent yield of isoprene from glucose over the entire fermentation was 7.4%.

In addition, as a control, fermentation was performed in a 15-L bioreactor with BL21 (DE3) E. coli cells containing the upper mevalonic acid (MVA) pathway (pCL PtrcUpperPathway encoding E. faecalis mvaE and mvaS), the integrated lower MVA pathway (gi1.2KKDyI encoding S. cerevisiae mevalonate kinase, mevalonate phosphate kinase, mevalonate pyrophosphate decarboxylase, and IPP isomerase), and high expression of mevalonate kinase from M. mazei and isoprene synthase from Kudzu (pTrcKudzuMVK (M. mazei)). This experiment was carried out to monitor uninduced cell metabolic activity as measured by CER from glucose at the desired fermentation pH 7.0 and temperature 30° C. An inoculum of E. coli strain (MCM401 described above) taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate 5-L medium in a 15-L bioreactor. Glucose was fed at an exponential rate until cells reached the stationary phase. After this time the glucose feed was decreased to meet metabolic demands.

FIG. 148 compares the CER profiles for the uninduced cells described above and the cells induced by adding isopropyl-beta-D-1-thiogalactopyranoside (IPTG) in Examples 16 and 17.

Example 18

Production of Isoprene by E. Coli Expressing the Upper Mevalonic Acid (MVA) Pathway, the Integrated Lower MVA Pathway (Gi1.2KKDyI), Mevalonate Kinase from M. Mazei, and Isoprene Synthase from Kudzu and Grown in Fed-Batch Culture at the 15-L Scale (1×50 µM IPTG+150 µM IPTG Fed Induction)

Medium Recipe (Per Liter Fermentation Medium).

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in $DIH_2O$, pH to 3.0 with HCl/NaOH, then q.s. to volume and filter sterilized with a 0.22 micron filter.

Fermentation was performed in a 15-L bioreactor with BL21 (DE3) E. coli cells containing the upper mevalonic acid (MVA) pathway (pCL PtrcUpperPathway encoding E. faecalis mvaE and mvaS), the integrated lower MVA pathway (gi1.2KKDyI encoding S. cerevisiae mevalonate kinase, mevalonate phosphate kinase, mevalonate pyrophosphate decarboxylase, and IPP isomerase), and high expression of mevalonate kinase from M. mazei and isoprene synthase from Kudzu (pTrcKudzuMVK (M. mazei)). This experiment was carried out to monitor isoprene formation from glucose at the desired fermentation pH 7.0 and temperature 30° C. An inoculum of E. coli strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate 5-L medium in a 15-L bioreactor.

Glucose was fed at an exponential rate until cells reached the stationary phase. After this time the glucose feed was decreased to meet metabolic demands. The total amount of glucose delivered to the bioreactor during the 55 hour fermentation was 2.2 kg. Induction was achieved by adding isopropyl-beta-D-1-thiogalactopyranoside (IPTG). The IPTG concentration was brought to 51 uM when the optical density at 550 nm ($OD_{550}$) reached a value of 10. In addition to the IPTG spike, at $OD_{550}$=10 a constant feed began and delivered 164 mg of IPTG over 18 hours. The $OD_{550}$ profile within the bioreactor over time is shown in FIG. 128. The isoprene level in the off gas from the bioreactor was determined using a Hiden mass spectrometer. The isoprene titer increased over the course of the fermentation to a final value of 22.0 g/L (FIG. 129). The total amount of isoprene produced during the 55 hour fermentation was 170.5 g and the time course of production is shown in FIG. 130. The metabolic activity profile, as measured by TCER, is shown in FIG. 131. When the airflow to the bioreactor was decreased from 8 slpm to 4 slpm for a period of about 1.7 hours, the concentration of isoprene in the offgas increased from 0.51 to 0.92 w/w % (FIG. 132). These elevated levels of isoprene did not appear to have any negative impact on cell metabolic activity as measured by the total carbon dioxide evolution rate (TCER), since TCER declined only 7% between 37.2 and 39.3 hours (FIG. 132). The total viable count (total colony forming units) decreased by two orders of magnitude between 7 and 36 hours of fermentation (FIG. 133). The molar yield of utilized carbon that went into producing isoprene during fermentation was 16.6%. The weight percent yield of isoprene from glucose over the entire fermentation was 7.7%.

Example 19

The Effect of Externally Applied Isoprene on a Wild-Type E. Coli Grown in Fed-Batch Culture at the 1-L Scale Medium Recipe (Per Liter Fermentation Medium).

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in $DIH_2O$, pH to 3.0 with HCl/NaOH, then q.s. to volume and filter sterilized with a 0.22 micron filter.

Fermentation was performed in a 1-L bioreactor with BL21 (DE3) E. coli cells. This experiment was carried out to monitor the effects of isoprene on cell viability and metabolic activity in a glucose fed-batch bioreactor at the desired fermentation pH 7.0 and temperature 30° C. An inoculum of E. coli strain from a frozen vial was inoculated into tryptone-yeast extract medium. After the inoculum grew to OD 1.0, measured at 550 nm, 50 mL was used to inoculate 0.5-L medium in a 1-L bioreactor.

Glucose was fed at an exponential rate until cells reached the stationary phase. After this time the glucose feed was fed to meet metabolic demands. Isoprene was fed into the bioreactor using nitrogen gas as a carrier. The rate of isoprene feeding was 1 g/L/hr during mid-growth phase ($OD_{550}$=31-44) and lasted for a total of 75 minutes (13.2 to 14.4 hours). The $OD_{550}$ profile within the bioreactor over time is shown in FIG. 134. The metabolic activity profile, as measured by TCER, is shown in FIG. 135. The total viable count (total colony forming units) increased by 14-fold during the period when isoprene was introduced into the bioreactor (FIG. 136).

Example 20

Production of Isoprene and Expression of Isoprene Synthase by Saccharomyces Cerevisiae The Kudzu isoprene synthase enzyme was optimized for expression according to a hybrid Saccharomyces cerevisiae/Pichia pastoris codon usage table, synthesized, and cloned into pDONR221:19430 (by DNA 2.0, FIG. 140 for map and FIG. 141 for sequence (SEQ ID NO:38)). A Gateway® Cloning (Invitrogen) reaction was performed according to the manufacturer's protocol: Since pDONR221:19430 was an "entry" vector, the LR Clonase II enzyme (the LR Reaction) was used to introduce the codon-optimized isoprene synthase into the "destination" vector pYES-DEST52 (Invitrogen).

The LR Reaction was then transformed into Top10 chemically competent cells (Invitrogen) according to the manufacturer's protocol, and bacteria harboring pYES-DEST52 plasmids with the isoprene synthase ORF were selected for on LA plates containing 50 µg/ml carbenicillin. Individual positive transformants were tested by colony PCR (see below for primer concentrations and thermocycling parameters) using illustra PuReTaq Ready-To-Go™ PCR Beads (GE Healthcare) with the T7 forward primer and the Yeast isoprene synthase-Rev2 primer (See Table 13).

TABLE 13

Primer sequences for amplifying isoprene synthase.

| Primer Name | Sequence (5' to 3') | Purpose |
| --- | --- | --- |
| Yeast HGS -For2 | CACCAAAGACTTCATAGACT (SEQ ID NO: 124) | Forward primer for yeast optimized isoprene synthase |
| Yeast HGS -Rev2 | AGAGATATCTTCCTGCTGCT (SEQ ID NO: 125) | Reverse primer for yeast optimized isoprene synthase |
| T7 Forward | TAATACGACTCACTATAGGG (SEQ ID NO: 126) | PCR and sequencing primer |

Plasmids that yielded a PCR fragment of the correct size (1354 bp) were purified by miniprep (Qiagen) and sent for sequencing (Quintara Biosciences, Berkeley, Calif.) with the T7 Forward and Yeast isoprene synthase—For 2 primers (See Table 13). Results from sequencing runs were compared to the known sequence of pDONR221:19430 (using Vector NTI software, Invitrogen), and a single plasmid, pDW14, was selected for further study (FIG. 142A for map and FIGS. 142B and C for the complete sequence (SEQ ID NO:39)). The sequence of pDW14 diverged from that of pDONR221:19430 by a single nucleotide (marked in bold in FIG. 142B). The single nucleotide change (G to A) did not result in a change in the ORF, since it was in the third position of a lysine-encoding codon. It is unknown whether this base change was introduced in the LR cloning reaction, or was an error in the original sequence that was synthesized by DNA 2.0. All sequenced plasmids contained this base change.

Purified pDW14 was transformed into Saccharomyces cerevisiae strain INVSc-1 using the protocol described in the S. c. EasyComp Transformation kit (Invitrogen). INVSc-1 strains harboring pDW14 or pYES-DEST52 (which contains an intact URA3 gene) were selected for and maintained on SC Minimal Medium with 2% glucose without uracil, as described in the pYES-DEST52 Gateway Vector manual (Invitrogen). Two independent isolates of INVSc-1 containing pDW14 and a single control strain with pYES-DEST52 were chosen for further analysis.

To induce isoprene synthase expression, cultures were grown overnight in liquid SC Minimal Medium. The cultures were then diluted to an $OD_{600}$ of approximately 0.2 and grown for 2-3 hours. Cultures were spun by centrifugation, washed once, resuspended in an equal volume (10 ml) of SC minimal medium with 1% raffinose, 2% galactose without uracil, and grown overnight to induce the expression of isoprene synthase. The $OD_{600}$ of the strains was determined (FIG. 144A), and strains were harvested by centrifugation and resuspended in 2 ml of lysis buffer (a 1:1 mix of 50% glycerol and PEB pH 7.4: Tris Base 2.423 g/L, $MgCl_2$ (Anhydrous) 1.904 g/L, KCl 14.910 g/L, DTT 0.154 g/L, Glycerol 50 mL/L).

The lysis mixtures were passed through a french press three times, and lysates were analyzed by SDS-PAGE. For Coomassie gel analysis (FIG. 143A), samples were diluted 1:1 with 2×SDS loading buffer with reducing agent, loaded (20 μl total volume) onto a 4-12% bis-tris gel, run in MES buffer, and stained using SimplyBlue SafeStain according to the manufacturer's protocol (the Invitrogen Novex system).

The WesternBreeze kit (Invitrogen) was used for transfer and chromogenic detection of isoprene synthase on a nitrocellulose membrane. The primary antibody was 1799A 10 week diluted 1:1000 in Invitrogen antibody diluent. Primary antibody binding was followed by development with a secondary antibody labeled with Alexa Fluor 488 (Invitrogen Catalog No. A-11008) to permit quantitative signal determination. The western blot procedure was carried out as described by Invitrogen. The fluorescence signal was recorded with a Molecular Dynamics Storm instrument using the blue filter setting and quantitatively analyzed with the Molecular Dynamics ImageQuant image analysis software package. Specific activity of the library members was calculated from the ratio of the amount of isoprene produced divided by either the A600 of the induction cultures or the isoprene synthase protein concentration determined by western blot. FIG. 143B shows that isoprene synthase was present in the induced INVSc-1 strains harboring pDW14 (lanes 2 and 3) in comparison to the control harboring pYES-DEST52 (lane 1).

The DMAPP assay for isoprene synthase headspace was performed on 25 μL of the lysate from each strain to which 5 μL 1 M $MgCl_2$, 5 μL 100 mM DMAPP, and 65 μL 50 mM Tris pH 8 were added. The reaction was performed at 30° C. for 15 minutes in a gas tight 1.8 mL GC tube. Reactions were terminated by addition of 100 uL 250 mM EDTA pH 8. FIG. 144B showed the specific activity values (inpg HG/L/OD) of the induced strains harboring pDW14 in comparison to the control. Induced strains harboring pDW14 displayed approximately 20× higher activity than the control lacking isoprene synthase.

PCR Cycling Parameters

Illustra PuReTaq Ready-To-Go™ PCR Beads (GE Healthcare) were used with oligonucleotide primer pairs at a concentration of 0.4 μM each in 25 μl total volume/reaction. For analysis of plasmids resulting from the LR Clonase reaction (Invitrogen), a small amount of bacteria from individual colonies on a selective plate was added to each tube containing the PCR mix described above. The reaction cycle was as follows: 1) 95° C. for 4 minutes; 2) 95° C. for 20 seconds; 3) 52° C. for 20 seconds; 4) 72° C. for 30 seconds; 5 cycles of steps 2 through 4; 5) 95° C. for 20 seconds; 6) 55° C. for 20 seconds; 7) 72° C. for 30 seconds; 25 cycles of steps 5 through 7, 72° C. for 10 minutes, and 4° C. until cool.

Example 21

Production of Isoprene in *Pseudomonas* and Other Gram Negative Bacteria Construction of pBBR5HGSOpt2_2, Conjugation in *Pseudomonas* and Measurement of Isoprene Synthase Activity A gene encoding isoprene synthase from *Pueraria lobata* (Kudzu plant) was codon-optimized for different microbial species of interest (Table 14; fluo-opt2v2 was the sequence chosen) and was synthesized by DNA2.0, Menlo Park, Calif. The map and sequence of fluo-opt2v2 can be found in FIGS. 145A and 145B (SEQ ID NO:40). HindIII and BamHI restriction sites were added to the synthesized sequence for easier cloning, and a RBS was added in front of the ATG to enhance transcription.

Number of rare codons, as a function of the microbial species, in different versions of codon-optimized isoprene synthase from *Pueraria lobata*. Several rounds of optimization led to a gene with no rare codons in the all the species of interest.

TABLE 14

Number of rare codons.

| Organism | fluo-opt1 (quote) | fluo-opt2 | fluo-opt3 | E. coli opt | fluo-opt2v2 |
|---|---|---|---|---|---|
| *Pseudomonas fluorescens* Pf-5 | 19 | X | X | 57 | 0 |
| *Phodopseudomonas palustris* CGA009 | 37 | 13 | 3 | 74 | 0 |
| *Pseudomonas putida* F1 | 0 | 0 | 0 | 29 | 0 |
| *Corynebacterium glutamicum* (ATCC) | 4 (Ser) | 0 | 0 | 0 | 0 |
| *Pseudomonas fluorescens* PfO-1 | 1 (Val) | 0 | 0 | 57 | 0 |

The gene was provided by DNA2.0 in a cloning vector. The vector was digested with HindIII/BamHI, the band corresponding to the insert of interest was gel-purified, and relegated with HindIII/BamHI-digested pBBR1MCS5 (Kovach et al, Gene 166:175-176, 1995, which is incorporated by reference in its entirety, particularly with respect to pBBR1MCS5), FIG. 146A for map and FIGS. 146B and C for sequence (SEQ ID NO:41). This resulted in plasmid pBBR5HGSOpt2_2 (FIG. 147A for map and FIGS. 147B and C for sequence (SEQ ID NO:42)) in which isoprene synthase was expressed from the lac promoter presented in pBBR1MCS5.

The vector was transformed in *E. coli* S17-1 and mated with *Pseudomonas putida* F1 ATCC700007 and *Pseudomonas fluorescens* ATCC 13525. After conjugation on LB, selection for plasmid-harboring *Pseudomonas* strains was on M9+16 mM sodium citrate+Gentamicin 50 ug/ml. Presence of the plasmid in the strains thus generated was checked by plasmid preparation using the Qiagen kit (Valencia, Calif.).

Isoprene synthase activities of the recombinant strains *P. putida*, pBBR5HGSOpt2_2 and *P. fluorescens*, pBBR5HGSOpt2_2 were assayed by growing the strains in TM3 medium (as described in Example 1 Part II)+10 g/L glucose, harvesting the biomass in mid-log phase, breaking the cells by French Press and proceeding with the DMAPP assay. Results of the assay were presented in Table 15. The presence of activity measured by the DMAPP assay confirmed that isoprene synthase was expressed in *Pseudomonas*.

Isoprene synthase activity was examined in *Pseudomonas putida* and *Pseudomonas fluorescens* expressing isoprene synthase from the lac promoter, using plasmid pBBR5HGSOpt2_2

TABLE 15

Isoprene synthase activity in Pseudomonas putida and Pseudomonas fluorescens.

| Strain | OD | Isoprene synthase activity mg isoprene/(L.h.OD) |
|---|---|---|
| P. fluorescens, pBBR5HGSOpt2_2 | 1.46 | 0.96 |
| P. putida, pBBR5HGSOpt2_2 | 3.44 | 0.65 |
| Control (P. putida w/o plasmid) | 8.32 | To be determined |

Example 22

Growth of E. Coli and Pseudomonas Strains on Sugar Cane Compared to Glucose, and Expression of Isoprene Synthase Using Both Substrates I. Preparation of Liquid Sugar Cane.

Crystallized raw cane sugar was dissolved in water in the following way: 750 g $H_2O$ was added to 250 g sugar. The solution was stirred and gently heated until dissolution. Some material was not soluble. The weight of the solution was adjusted to 1 kg after dissolution to replenish the evaporated water. The volume of the solution was measured to be 940 mL. Hence the concentration of the solution was 265 g/L. The product label claimed 14 g of carbohydrate for 15 g of raw sugar cane. Hence the carbohydrate concentration of the solution was 248 g/L. Dry solids were measured to be 24.03%, close enough of the expected 250 g/kg. pH of the solution was 5.49. Glucose concentration was measured using an enzymatic/spectrophotometric assay, with glucose oxidase. The glucose concentration was 17.4 g/L.

As a majority of microorganisms do not use sucrose, but can use glucose and fructose, the solution was split in two. One half was autoclaved once for 30 minutes (sugar cane as is). Some inversion resulted, as the glucose content increased to 29.75 g/L (See FIG. 149). The other half of the solution was adjusted to pH 4.0 using phosphoric acid, then the solution was inverted by autoclaving (inverted sugar cane). Three cycles of 30 min were sufficient to obtain complete inversion, as shown on FIG. 149. Both solutions were used for the growth curves described below.

II. Growth Curves of Different Strains of E. Coli and Pseudomonas on Sugar Cane Compared to Glucose.

One colony of each of the strains presented in Table 16 was inoculated in 25 ml TM3+10 g/L glucose, and was grown overnight at 30° C. and 200 rpm. TM3 is described in Example 7, Section II. The morning after, 1 ml of each culture was used to inoculate flasks containing 25 mL TM3 and 10 g/L glucose, 10 g/L sugar cane as is, or 10 g/L inverted sugar cane (sugar cane solutions described above). The flasks were incubated at 30° C. and 200 rpm and samples were taken regularly to measure OD600. FIGS. 150 and 151 show that growth rate and biomass yield were comparable for glucose and inverted sugar cane, both for Pseudomonas and E. coli strains. P. fluorescens showed some signs of being able to use sugar cane which has not been inverted too.

TABLE 16

Strains used in this study.

| | Strain |
|---|---|
| Escherichia coli | BL21 |
| | MG1655 |
| | ATCC11303 |
| | B REL 606 |

TABLE 16-continued

Strains used in this study.

| | Strain |
|---|---|
| Pseudomonas | putida F1 (ATCC700007) |
| | Fluorescens (ATCC13525) |

III. Comparison of Isoprene Production from E. Coli Expressing Isoprene Synthase when Grown on Glucose or Sugar Cane.

E. coli MCM401 (BL21(DE3)) containing the full MVA pathway, mevalonate kinase from M. mazei and isoprene synthase from Pueraria lobata, as described in Example 14, Section II was grown in TM3+either 10 g/L glucose or 10 g/L inverted sugar cane (based on carbohydrate concentration of the syrup). Flasks were inoculated from an overnight culture on TM3+10 g/L glucose at an $OD_{600}$=0.2. Antibiotics were added where needed. After two hours, the E. coli cultures were induced with 400 μM IPTG. After 6 hours of growth, isoprene production and isoprene synthase activities, using the DMAPP assay as described in Example 2B, were measured. Results are presented in Table 17 and illustrate clearly that inverted sugar cane is equivalent to glucose in terms of isoprene and isoprene synthase production on a per cell basis.

TABLE 17

| Strain | Carbon Source | OD | Isoprene synthase activity mg isoprene/ (L.h.OD) | Isoprene production mg isoprene/ (L.h.OD) |
|---|---|---|---|---|
| MCM401 | Glucose | 2.20 | 21.06 | 8.98 |
| MCM401 | Sugar cane inverted | 2.32 | 20.20 | 9.23 |

Example 23

Construction of E. Coli Strains Expressing the S. Cerevisiae Gi1.2KKDyI Operon, P. Alba Isoprene Synthase, M. Mazei Mevalonate Kinase, pCL Upper MVA (E. Faecalis mvaE and mvaS) and ybhE (pgl)

(i) Construction of Strain EWL201 (BL21, Cm-GI1.2-KKDyI)

E. coli BL21 (Novagen brand, EMD Biosciences, Inc.) was a recipient strain, transduced with MCM331 P1 lysate (lysate prepared according to the method described in Ausubel, et al., Current Protocols in Molecular Biology. John Wiley and Sons, Inc.). MCM331 cells contain chromosomal construct gi1.2KKDyI encoding S. cerevisiae mevalonate kinase, mevalonate phosphate kinase, mevalonate pyrophosphate decarboxylase, and IPP isomerase (i.e., the gi1.2-KKDyI operon from S. cerevisiae). Transductants were selected for by spreading cells onto L Agar and 20 μg/μl chloramphenicol. The plates were incubated overnight at 30° C. Analysis of transductants showed no colonies on control plates (water+cells control plate for reversion and water and P1 lysate control plate for lysate contamination.

Four transductants were picked and used to inoculate 5 mL L Broth and 20 μg/μl chloramphenicol. The cultures were grown overnight at 30° C. with shaking at 200 rpm. To make genomic DNA preps of each transductant for PCR analysis, 1.5 mL of overnight cell culture were centrifuged. The cell pellet was resuspended with 400 µl Resuspension Buffer (20 mM Tris, 1 mM EDTA, 50 mM NaCl, pH 7.5) and 4 µl RNase, DNase-free (Roche) was added. The tubes were incubated at 37° C. for 30 minutes followed by the addition of 4 µl 10% SDS and 4 µl of 10 mg/ml Proteinase K stock solution (Sigma-Aldrich). The tubes were incubated at 37° C. for 1 hour. The cell lysate was transferred into 2 ml Phase Lock Light Gel tubes (Eppendorf) and 200 µl each of saturated phenol pH7.9 (Ambion Inc.) and chloroform were added. The tubes were mixed well and microcentrifuged for 5 minutes. A second extraction was done with 400 µl chloroform and the aqueous layer was transferred to a new eppendorf tube. The genomic DNA was precipitated by the addition of 1 ml of 100% ethanol and centrifugation for 5 minutes. The genomic DNA pellet was washed with 1 ml 70% ethanol. The ethanol was removed and the genomic DNA pellet was allowed to air dry briefly. The genomic DNA pellet was resuspended with 200 µl TE.

Using Pfu Ultra II DNA polymerase (Stratagene) and 200 ng/µl of genomic DNA as template, 2 different sets of PCR reaction tubes were prepared according to manufacturer's protocol. For set 1, primers MCM130 and GB Cm-Rev (Table 18) were used to ensure transductants were successfully integrated into the attTn7 locus. PCR parameters for set 1 were 95° C. for 2 minutes (first cycle only), 95° C. for 25 seconds, 55° C. for 25 seconds, 72° C. for 25 seconds (repeat steps 2-4 for 28 cycles), 72° C. for 1 minute. For set 2, primers MVD For and MVD Rev (Table 18) were used to ensure that the gi1.2-KKDyI operon integrated properly. PCR parameters for set 2 were 95° C. for 2 minutes (first cycle only), 95° C. for 25 seconds, 55° C. for 25 seconds, 72° C. for 10 seconds (repeat steps 2-4 for 28 cycles), 72° C. for 1 minute. Analysis of PCR amplicons on a 1.2% E-gel (Invitrogen Corp.) showed that all 4 transductant clones were correct. One was picked and designated as strain EWL201.

(ii) Construction of Strain EWL204 (BL21, Loopout-GI1.2-KKDyI)

The chloramphenicol marker was looped out of strain EWL201 using plasmid pCP20 as described by Datsenko and Wanner (2000) (Datsenko et al., *Proc Natl. Acad. Sci. USA* 97:6640-6645, 2000). One-step inactivation of chromosomal genes in *Escherichia coli* K-12 using PCR products. (Datsenko et al., *PNAS*, 97: 6640-6645, 2000). EWL201 cells were grown in L Broth to midlog phase and then washed three times in ice-cold, sterile water. An aliquot of 50 µl of cell suspension was mixed with 1 µl of pCP20 and the cell suspension mixture was electroporated in a 2 mm cuvette (Invitrogen Corp.) at 2.5 Volts and 25 uFd using a Gene Pulser Electroporator (Bio-Rad Inc.). 1 ml of LB was immediately added to the cells, then transferred to a 14 ml polypropylene tube (Sarstedt) with a metal cap. Cells were allowed to recover by growing for 1 hour at 30° C. Transformants were selected on L Agar and 20 µg/µl chloramphenicol and 50 µg/µl carbenicillin and incubated at 30° C. overnight. The next day, a single clone was grown in 10 ml L Broth and 50 µg/µl carbenicillin at 30° C. until early log phase. The temperature of the growing culture was then shifted to 42° C. for 2 hours. Serial dilutions were made, the cells were then spread onto LA plates (no antibiotic selection), and incubated overnight at 30° C. The next day, 20 colonies were picked and patched onto L Agar (no antibiotics) and LA and 20 µg/µl chloramphenicol plates. Plates were then incubated overnight at 30° C. Cells able to grow on LA plates, but not LA and 20 µg/µl chloramphenicol plates, were deemed to have the chloramphenicol marker looped out (picked one and designated as strain EWL204).

(iii) Construction of Plasmid pEWL230 (pTrc *P. alba*)

Generation of a synthetic gene encoding *Populus alba* isoprene synthase (*P. alba* HGS) was outsourced to DNA2.0 Inc. (Menlo Park, Calif.) based on their codon optimization method for *E. coli* expression. The synthetic gene was custom cloned into plasmid pET24a (Novagen brand, EMD Biosciences, Inc.) and delivered lyophilized (FIGS. 152, 153A-B; SEQ ID NO:43).

A PCR reaction was performed to amplify the *P. alba* isoprene synthase (*P. alba* HGS) gene using pET24a *P. alba* HGS as the template, primers MCM182 and MCM192, and Herculase II Fusion DNA polymerase (Stratagene) according to manufacturer's protocol. PCR conditions were as follows: 95° C. for 2 minutes (first cycle only), 95° C. for 25 seconds, 55° C. for 20 seconds, 72° C. for 1 minute, repeat for 25 cycles, with final extension at 72° C. for 3 minutes. The *P. alba* isoprene synthase PCR product was purified using QIAquick PCR Purification Kit (Qiagen Inc.).

*P. alba* isoprene synthase PCR product was then digested in a 20 µl reaction containing 1 µl BspHI endonuclease (New England Biolabs) with 2 µl 10×NEB Buffer 4. The reaction was incubated for 2 hours at 37° C. The digested PCR fragment was then purified using the QIAquick PCR Purification Kit. A secondary restriction digest was performed in a 20 µl reaction containing 1 µl PstI endonuclease (Roche) with 2 µl 10× Buffer H. The reaction was incubated for 2 hours at 37° C. The digested PCR fragment was then purified using the QIAquick PCR Purification Kit. Plasmid pTrcHis2B (Invitrogen Corp.) was digested in a 20 µl reaction containing 1 µl NcoI endonuclease (Roche), 1 µl PstI endonuclease, and 2 µl 10× Buffer H. The reaction was incubated for 2 hours at 37° C. The digested pTrcHis2B vector was gel purified using a 1.2% E-gel (Invitrogen Corp.) and extracted using the QIAquick Gel Extraction Kit (Qiagen) (FIG. 154). Using the compatible cohesive ends of BspHI and NcoI sites, a 20 µl ligation reaction was prepared containing 5 µl *P. alba* isoprene synthase insert, 2 µl pTrc vector, 1 µl T4 DNA ligase (New England Biolabs), 2 µl 10× ligase buffer, and 10 µl ddH₂O. The ligation mixture was incubated at room temperature for 40 minutes. The ligation mixture was desalted by floating a 0.025 µm nitrocellulose membrane filter (Millipore) in a petri dish of ddH₂O and applying the ligation mixture gently on top of the nitrocellulose membrane filter for 30 minutes at room temperature. MCM446 cells (see Section II) were grown in LB to midlog phase and then washed three times in ice-cold, sterile water. An aliquot of 50 µl of cell suspension was mixed with 5 µl of desalted pTrc *P. alba* HGS ligation mix. The cell suspension mixture was electroporated in a 2 mm cuvette at 2.5 Volts and 25 uFd using a Gene Pulser Electroporator. 1 ml of LB is immediately added to the cells, then transferred to a 14 ml polypropylene tube (Sarstedt) with a metal cap. Cells were allowed to recover by growing for 2 hour at 30° C. Transformants were selected on L Agar and 50 µg/µl carbenicillin and 10 mM mevalonic acid and incubated at 30° C. The next day, 6 transformants were picked and grown in 5 ml L Broth and 50 µg/µl carbenicillin tubes overnight at 30° C. Plasmid preps were performed on the overnight cultures using QIAquick Spin Miniprep Kit (Qiagen). Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. All 6 plasmids were the correct size and shipped to Quintara Biosciences (Berkeley, Calif.) for sequencing with primers MCM65, MCM66, EL1000 (Table 18). DNA sequencing results showed all 6 plasmids were correct. One plasmid was picked designated as plasmid EWL230 (FIGS. 155, 156A-B; SEQ ID NO:44).

(iv) Construction of Plasmid pEWL244 (pTrc P. alba-mMVK)

A PCR reaction was performed to amplify the Methanosarcina mazei (M. mazei) MVK gene using MCM376 as the template (see section (v) below), primers MCM165 and MCM177 (see Table 18), and Pfu Ultra II Fusion DNA polymerase (Stratagene) according to manufacturer's protocol. PCR conditions were as follows: 95° C. for 2 minutes (first cycle only), 95° C. for 25 seconds, 55° C. for 25 seconds, 72° C. for 18 seconds, repeat for 28 cycles, with final extension at 72° C. for 1 minute. The M. mazei MVK PCR product was purified using QIAquick PCR Purification Kit (Qiagen Inc.).

The M. mazei MVK PCR product was then digested in a 40 µl reaction containing 8 µl PCR product, 2 µl PmeI endonuclease (New England Biolabs), 4 µl 10×NEB Buffer 4, 4 µl 10×NEB BSA, and 22 µl of ddH$_2$O. The reaction was incubated for 3 hours at 37° C. The digested PCR fragment was then purified using the QIAquick PCR Purification Kit. A secondary restriction digest was performed in a 47 µl reaction containing 2µ NsiI endonuclease (Roche), 4.7 µl 10× Buffer H, and 40 µl of PmeI digested M. mazei MVK fragment. The reaction was incubated for 3 hours at 37° C. The digested PCR fragment was then gel purified using a 1.2% E-gel and extracted using the QIAquick Gel Extraction Kit. Plasmid EWL230 was digested in a 40 µl reaction containing 10 µl plasmid, 2 µl PmeI endonuclease, 4.7 µl 10×NEB Buffer 4, 4 µl 10×NEB BSA, and 20 µl of ddH$_2$O. The reaction was incubated for 3 hours at 37° C. The digested PCR fragment was then purified using the QIAquick PCR Purification Kit. A secondary restriction digest was performed in a 47 µl reaction containing 2 µl PstI endonuclease, 4.7 µl Buffer H, and 40 µl of PmeI digested EWL230 linear fragment. The reaction was incubated for 3 hours at 37° C. The digested PCR fragment was then gel purified using a 1.2% E-gel and extracted using the QIAquick Gel Extraction Kit (FIG. 157). Using the compatible cohesive ends of NsiI and PstI sites, a 20 µl ligation reaction was prepared containing 8 µl M. mazei MVK insert, 3 µl EWL230 plasmid, 1 µl T4 DNA ligase, 2 µl 10× ligase buffer, and 6 µl ddH$_2$O. The ligation mixture was incubated overnight at 16° C. The next day, the ligation mixture was desalted by floating a 0.025 µm nitrocellulose membrane filter in a petri dish of ddH$_2$O and applying the ligation mixture gently on top of the nitrocellulose membrane filter for 30 minutes at room temperature. MCM446 cells were grown in LB to midlog phase and then washed three times in ice-cold, sterile water. An aliquot of 50 µl of cell suspension was mixed with 5 µl of desalted pTrc P. alba-mMVK ligation mix. The cell suspension mixture was electroporated in a 2 mm cuvette at 2.5 Volts and 25 uFd using a Gene Pulser Electroporator. 1 ml of LB is immediately added to the cells, then the cells are transferred to a 14 ml polypropylene tube with a metal cap. Cells were allowed to recover by growing for 2 hour at 30° C. Transformants were selected on LA and 50 µl/µl carbenicillin and 5 mM mevalonic acid plates and incubated at 30° C. The next day, 6 transformants were picked and grown in 5 ml LB and 50 µl/µl carbenicillin tubes overnight at 30° C. Plasmid preps were performed on the overnight cultures using QIAquick Spin Miniprep Kit. Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 µl reaction to ensure the correct sized linear fragment. Three of the 6 plasmids were the correct size and shipped to Quintara Biosciences for sequencing with primers MCM65, MCM66, EL1000, EL1003, and EL1006 (Table 18). DNA sequencing results showed all 3 plasmids were correct. One was picked and designated as plasmid EWL244 (FIGS. 158 and 159A-B; SEQ ID NO:45).

(v) Construction of Plasmid MCM376-MVK from M. Mazei Archaeal Lower in pET200D.

The MVK ORF from the M. mazei archaeal Lower Pathway operon (FIGS. 160A-C; SEQ ID NO:46) was PCR amplified using primers MCM161 and MCM162 (Table 18) using the Invitrogen Platinum HiFi PCR mix. 45 uL of PCR mix was combined with 1 uL template, 1 uL of each primer at 10 uM, and 2 uL water. The reaction was cycled as follows: 94° C. for 2:00 minutes; 30 cycles of 94° C. for 0:30 minutes, 55° C. for 0:30 minutes and 68° C. for 1:15 minutes; and then 72° C. for 7:00 minutes, and 4° C. until cool. 3 uL of this PCR reaction was ligated to Invitrogen pET200D plasmid according to the manufacturer's protocol. 3 uL of this ligation was introduced into Invitrogen TOP10 cells, and transformants were selected on LA/kan50. A plasmid from a transformant was isolated and the insert sequenced, resulting in MCM376 (FIGS. 161A-C; SEQ ID NO:47).

(vi) Construction of strain EWL251 (BL21(DE3), Cm-GI1.2-KKDyI, pTrc P. alba-mMVK)

MCM331 cells (which contain chromosomal construct gi1.2KKDyI encoding S. cerevisiae mevalonate kinase, mevalonate phosphate kinase, mevalonate pyrophosphate decarboxylase, and IPP isomerase) were grown in LB to midlog phase and then washed three times in ice-cold, sterile water. Mixed 50 µl of cell suspension with 1 µl of plasmid EWL244. The cell suspension mixture was electroporated in a 2 mm cuvette at 2.5 Volts and 25 uFd using a Gene Pulser Electroporator. 1 ml of LB is immediately added to the cells, and then the cells were transferred to a 14 ml polypropylene tube with a metal cap. Cells were allowed to recover by growing for 2 hours at 30° C. Transformants were selected on LA and 50 µg/µl carbenicillin and 5 mM mevalonic acid plates and incubated at 37° C. One colony was selected and designated as strain EWL251.

(Vii) Construction of Strain EWL256 (BL21(DE3), Cm-GI1.2-KKDyI, pTrc P. Alba-mMVK, pCL Upper MVA)

EWL251 cells were grown in LB to midlog phase and then washed three times in ice-cold, sterile water. Mixed 50 µl of cell suspension with 1 µl of plasmid MCM82 (comprising pCL PtrcUpperPathway (also known as "pCL Upper MVA"), encoding E. faecalis mvaE and mvaS). Plasmid pCL Ptrc Upper Pathway was constructed as described in Example 8 above. The cell suspension mixture was electroporated in a 2 mm cuvette at 2.5 Volts and 25 gd using a Gene Pulser Electroporator. 1 ml of LB was immediately added to the cells. Cells were then transferred to a 14 ml polypropylene tube with a metal cap. Cells were allowed to recover by growing for 2 hours at 30° C. Transformants were selected on LA and 50 µg/µl carbenicillin and 50 µg/µl spectinomycin plates and incubated at 37° C. One colony was picked and designated as strain EWL256.

TABLE 18

Primer Sequences

| Primer name | Primer sequence |
|---|---|
| MCM130 | ACCAATTGCACCCGGCAGA (SEQ ID NO: 127) |
| GB Cm Rev | GCTAAAGCGCATGCTCCAGAC (SEQ ID NO: 128) |
| MVD For | GACTGGCCTCAGATGAAAGC (SEQ ID NO: 129) |
| MVD Rev | CAAACATGTGGCATGGAAAG (SEQ ID NO: 130) |
| MCM182 | GGGCCCGTTTAAACTTTAACTAGACTCTGCAGTTAGCGTTCAAACGGCAGAA (SEQ ID NO: 131) |
| MCM192 | CGCATGCATGTCATGAGATGTAGCGTGTCCACCGAAAA (SEQ ID NO: 132) |
| MCM65 | ACAATTTCACACAGGAAACAGC (SEQ ID NO: 133) |
| MCM66 | CCAGGCAAATTCTGTTTTATCAG (SEQ ID NO: 106) |
| EL1000 | GCACTGTCTTTCCGTCTGCTGC (SEQ ID NO: 134) |
| MCM165 | GCGAACGATGCATAAAGGAGGTAAAAAAACATGGTATCCTGTTCTGCGCCGGG TAAGATTTACCTG (SEQ ID NO: 122) |
| MCM177 | GGGCCCGTTTAAACTTTAACTAGACTTTAATCTACTTTCAGACCTTGC (SEQ ID NO: 123) |
| EL1003 | GATAGTAACGGCTGCGCTGCTACC (SEQ ID NO: 137) |
| EL1006 | GACAGCTTATCATCGACTGCACG (SEQ ID NO: 138) |
| MCM161 | CACCATGGTATCCTGTTCTGCG (SEQ ID NO: 120) |
| MCM162 | TTAATCTACTTTCAGACCTTGC (SEQ ID NO: 121) |

(viii) Construction of Strain RM111608-2 (Cm-GI1.2-KKDyI, pTrc P. alba-mMVK, pCL Upper MVA, pBBRC-MPGI1.5-pgl)

The BL21 strain of E. coli producing isoprene (EWL256) was constructed with constitutive expression of the ybhE gene (encoding E. coli 6-phosphogluconolactonase) on a replicating plasmid pBBR1MCS5(Gentamycin) (obtained from Dr. K. Peterson, Louisiana State University).

FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers Pg1-F (SEQ ID NO:139) and Pg1GI1.5-R (SEQ ID NO:140) were used to amplify the resistance cassette from the FRT-gb2-Cm-FRT template using Stratagene Herculase II Fusion kit according to the manufacturer's protocol. The PCR reaction (50 uL final volume) contained: 5 uL buffer, 1 uL template DNA (FRT-gb2-Cm-F from Gene Bridges), 10 pmols of each primer, and 1.5 uL 25 mM dNTP mix, made to 50 uL with dH$_2$O. The reaction was cycled as follows: 1×2 minutes, 95° C. then 30 cycles of (30 seconds at 95° C.; 30 seconds at 63° C.; 3 minutes at 72° C.).

The resulting PCR product was purified using the QiaQick PCR purification kit (Qiagen) and electroporated into electrocompetent MG1655 cells harboring the pRed-ET recombinase-containing plasmid as follows. Cells were prepared by growing in 5 mLs of L broth to and OD600-0.6 at 30° C. The cells were induced for recombinase expression by the addition of 4% arabinose and allowed to grow for 30 minutes at 30° C. followed by 30 minutes of growth at 37° C. An aliquot of 1.5 mLs of the cells was washed 3-4 times in ice cold dH$_2$O. The final cell pellet was resuspended in 40 uL of ice cold dH$_2$O and 2-5 uL of the PCR product was added. The electroporation was carried out in 1-mm gap cuvettes, at 1.3 kV in a Gene Pulser Electroporator (Bio-Rad Inc.). Cells were recovered for 1-2 hours at 30° C. and plated on L agar containing chloramphenicol (5 ug/mL). Five transformants were analyzed by PCR and sequencing using primers flanking the integration site (2 primer sets: pgl and 49 rev and 3' EcoRV-pglstop; Bottom Pgb2 and Top GB's CMP (946)). A correct transformant was selected and this strain was designated MG1655 GI1.5-pgl::CMP.

The chromosomal DNA of MG1655 GI1.5-pgl::CMP was used as template to generate a PCR fragment containing the FRT-CMP-FRT-GI1.5-ybhE construct. This construct was cloned into pBBR1MCS5(Gentamycin) as follows. The fragment, here on referred to as CMP-GI1.5-pgl, was amplified using the 5' primer Pglconfirm-F (SEQ ID NO:141) and 3' primer 3' EcoRV-pglstop (SEQ ID NO:142). The resulting fragment was cloned using the Invitrogen TOPO-Blunt cloning kit into the plasmid vector pCR-Blunt II-TOPO as suggested from the manufacturer. The NsiI fragment harboring the CMP-GI1.5-pgl fragment was cloned into the PstI site of pBBR1MCS5 (Gentamycin). A 20 µl ligation reaction was prepared containing 5 µl CMP-GI1.5-pgl insert, 2 µl pBBR1MCS5 (Gentamycin) vector, 1 µl T4 DNA ligase (New England Biolabs), 2 µl 10× ligase buffer, and 10 µl ddH$_2$O. The ligation mixture was incubated at room temperature for 40 minutes then 2-4 uL were electroporated into electrocompetent Top10 cells (Invitrogen) using the parameters disclosed above. Transformants were selected on L agar containing 10 ug/ml chloramphenicol and 5 ug/ml Gentamycin. The sequence of the selected clone was determined using a number of the primers described above as well as with the in-house T3 and Reverse primers provided by Sequetech, Calif. This plasmid was designated pBBRC-MPGI1.5-pgl (FIGS. 162, 163A-B and SEQ ID NO:48).

Plasmid pBBRCMPGI1.5-pgl was electroporated into EWL256, as described herein and transformants were plated on L agar containing Chloramphenicol (10 ug/mL), Gentamycin (5 ug/mL), spectinomycin (50 ug/mL), and carbenicillin (50 ug/mL). One transformant was selected and designated strain RM111608-2.

Primers:

```
Pgl-F                                        (SEQ ID NO: 139)
5'-
ACCGCCAAAAGCGACTAATTTTAGCTGTTACAGTCAGTTGAATTAACCCTCACTAAAGG
GCGGCCGC-3'

PglGI1.5-R                                   (SEQ ID NO: 140)
5'-
GCTGGCGATATAAACTGTTTGCTTCATGAATGCTCCTTTGGGTTACCTCCGGGAAACGC
GGTTGATTTGTTTAGTGGTTGAATTATTTGCTCAGGATGTGGCATAGTCAAGGGCGTGA
CGGCTCGCTAATACGACTCACTATAGGGCTCGAG-3'

3'EcoRV-pglstop:                             (SEQ ID NO: 142)
5'-CTT GAT ATC TTA GTG TGC GTT AAC CAC CAC pgl +49 rev:                                 (SEQ ID NO: 143)
CGTGAATTTGCTGGCTCTCAG Bottom Pgb2:                                 (SEQ ID NO: 144)
GGTTTAGTTCCTCACCTTGTC Top GB's CMP (946):                          (SEQ ID NO: 145)
ACTGAAACGTTTTCATCGCTC Pglconfirm-F                                 (SEQ ID NO: 141)
5'-ACCGCCAAAAGCGACTAATTTTAGCT-3'
```

Example 24

Improvement of Isoprene Production by Constitutive Expression of ybhE (pgl) in E. Coli This example shows production of isoprene in a strain constitutively expressing E. coli ybhE (pgl) compared to a control strain expressing ybhE at wild-type levels (i.e., EWL256). The gene ybhE (pgl) encodes E. coli 6-phosphogluconolactonase that suppresses posttranslational gluconylation of heterologously expressed proteins and improves product solubility and yield while also improving biomass yield and flux through the pentose phosphate pathway (Aon et al., Applied and Environmental Microbiology, 74(4): 950-958, 2008).

Small Scale Analysis

Media Recipe (Per Liter Fermentation Media):
$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 1 g, 1000× Trace Metals Solution 1 ml. All of the components were added together and dissolved in $diH_2O$. The pH was adjusted to 6.8 with ammonium hydroxide (30%) and brought to volume. Media was filter-sterilized with a 0.22 micron filter. Glucose 5.0 g and antibiotics were added after sterilization and pH adjustment.

1000× Trace Metal Solution (Per Liter Fermentation Media):

Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(a) Experimental Procedure

Isoprene production was analyzed by growing the strains in a Cellerator™ from MicroReactor Technologies, Inc. The working volume in each of the 24 wells was 4.5 mL. The temperature was maintained at 30° C., the pH setpoint was 7.0, the oxygen flow setpoint was 20 sccm and the agitation rate was 800 rpm. An inoculum of E. coli strain taken from a frozen vial was streaked onto an LB broth agar plate (with antibiotics) and incubated at 30° C. A single colony was inoculated into media with antibiotics and grown overnight. The bacteria were diluted into 4.5 mL of media with antibiotics to reach an optical density of 0.05 measured at 550 nm.

Off-gas analysis of isoprene was performed using a gas chromatograph-mass spectrometer (GC-MS) (Agilent) headspace assay. Sample preparation was as follows: 100 µL of whole broth was placed in a sealed GC vial and incubated at 30° C. for a fixed time of 30 minutes. Following a heat kill step, consisting of incubation at 70° C. for 5 minutes, the sample was loaded on the GC.

Optical density (OD) at a wavelength of 550 nm was obtained using a microplate reader (Spectramax) during the course of the run. Specific productivity was obtained by dividing the isoprene concentration (μg/L) by the OD reading and the time (hour).

The two strains EWL256 and RM11608-2 were assessed at 200 and 400 uM IPTG induction levels. Samples were analyzed for isoprene production and cell growth (OD550) at 1, 2.5, 4.75, and 8 hours post-induction. Samples were done in duplicate.

(b) Results

The experiment demonstrated that at 2 different concentrations of IPTG the strain expressing the ybhE (pgl) had a dramatic 2-3 fold increase in specific productivity of isoprene compared to the control strain.

Isoprene fermentation from *E. coli* expressing Cm-GI1.2-KKDyI, *M. mazei* mevalonate kinase, *P. alba* isoprene synthase, and ybhE (pgl) (RM111608-2) and grown in fed-batch culture at the 15-L scale Medium Recipe (per Liter Fermentation Medium):

$K_2HPO_4$ 7.5 g, $MgSO_4$*$7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component is dissolved one at a time in $DiH_2O$, pH to 3.0 with HCl/NaOH, then q. s. to volume and filter sterilized with a 0.22 micron filter Fermentation was performed in a 15-L bioreactor with BL21 (DE3) *E. coli* cells containing the upper mevalonic acid (MVA) pathway (pCL Upper), the integrated lower MVA pathway (gi1.2KKDyI), high expression of mevalonate kinase from *M. mazei* and isoprene synthase from *P. alba* (pTrcAlba-mMVK), and high expression of *E. coli* pgl (pBBR-pgl). This experiment was carried out to monitor isoprene formation from glucose at the desired fermentation pH 7.0 and temperature 34° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

Glucose was fed at an exponential rate until cells reached the stationary phase. After this time the glucose feed was decreased to meet metabolic demands. The total amount of glucose delivered to the bioreactor during the 40 hour (59 hour) fermentation was 3.1 kg (4.2 kg at 59 hour). Induction was achieved by adding IPTG. The IPTG concentration was brought to 110 uM when the optical density at 550 nm ($OD_{550}$) reached a value of 4. The IPTG concentration was raised to 192 uM when $OD_{550}$ reached 150. The $OD_{550}$ profile within the bioreactor over time is shown in FIG. 164A. The isoprene level in the off gas from the bioreactor was determined using a Hiden mass spectrometer. The isoprene titer increased over the course of the fermentation to a maximum value of 33.2 g/L at 40 hours (48.6 g/L at 59 hours) (FIG. 164B). The isoprene titer increased over the course of the fermentation to a maximum value of 40.0 g/L at 40 hours (60.5 g/L at 59 hours) (FIG. 164C). The total amount of isoprene produced during the 40-hour (59-hour) fermentation was 281.3 g (451.0 g at 59 hours) and the time course of production is shown in FIG. 164D. The time course of volumetric productivity is shown in FIG. 164E and shows that an average rate of 1.0 g/L/hr was maintained between 0 and 40 hours (1.4 g/L/hour between 19 and 59 hour). The metabolic activity profile, as measured by CER, is shown in FIG. 164F. The molar yield of utilized carbon that went into producing isoprene during fermentation was 19.6% at 40 hours (23.6% at 59 hours). The weight percent yield of isoprene from glucose was 8.9% at 40 hours (10.7% at 59 hours).

Example 25

Co-Production of Isoprene and Hydrogen in *E. Coli* Strains Expressing *M. Mazei* Mevalonate Kinase, *P. Alba* Isoprene Synthase, pCL Upper MVA (*E. Faecalis* mvaE and mvaS) and ybhE (pgl)

Collection and Analysis of Fermentation Off-Gas for Hydrogen and Isoprene Levels Fermentations were performed using strains RM111608-2 (*E. coli* BL21 (DE3), pCL Upper MVA, cmR-gi1.2-yK-KDyI, pTrcAlba-mMVK, pBBR cmR-gi1.5-pgl) and EWL 256 (*E. coli* BL21 (DE3), pCL Upper MVA, cmR-gi1.2-yKKDyI, pTrcAlba-mMVK). Construction of bacterial strains is described in Example 23 above.

Large scale production of isoprene from *E. coli* was determined from a fed-batch culture of *E. coli* strains EWL256 and RM111608-2 expressing *M. mazei* mevalonate kinase, *P. alba* isoprene synthase, pCL Upper MVA (*E. faecalis* mvaE and mvaS) and either constitutively expressing ybhE (pgl) (RM111608-2) or normally expressing ybhE (pgl) (EWL256). This experiment demonstrates that growing cells in the presence of glucose resulted in the co-production of isoprene and hydrogen.

The recipe for the fermentation medium (TM2) per liter of TM2 fermentation medium was as follows: $K_2HPO_4$ 13.6 g, $KH_2PO_4$ 13.6 g, $MgSO_4$*$7H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. 1000× Modified Trace Metal Solution: Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. For the 1000× Modified Trace Metal Solution, each component is dissolved one at a time in $DiH_2O$, pH to 3.0 with HCl/NaOH, then brought to final volume in distilled water and filter sterilized with a 0.22 micron (μm) filter (this solution is not autoclaved). For the TM2 fermentation medium, all of the components were added together, dissolved in $diH_2O$, the pH was adjusted to 6.8 with potassium hydroxide (KOH), q.s. to volume, and the medium was filter sterilized with a 0.22 micron (μm) filter. Glucose was sourced from Cargill as 99DE (dextrose equivalent), 71% DS (dry solids) syrup.

Fermentations were performed in 15-L bioreactors with *E. coli* strains EWL256 or RM111608-2, containing the upper mevalonic acid (MVA) pathway (pCL Upper MVA), the integrated lower MVA pathway (cmR-gi1.2-yKKDyI), mevalonate kinase from *M. mazei* and isoprene synthase from *P. alba* (pTrcAlba-mMVK), and constitutively expressing ybhE (pgl) (RM111608-2) or normally expressing ybhE (pgl) (EWL256). This experiment was carried out to monitor isoprene formation from glucose at the desired fermentation conditions (pH 7.0 and temperature 34° C.).

An inoculum of the appropriate E. coli strain taken from a frozen vial was prepared in peptone-yeast extract medium. After the inoculum grew to $OD_{550}$=0.6, 600 mL was used to inoculate a 15-L bioreactor containing TM2 medium. Glucose was fed at an exponential rate until cells reached the stationary phase. After this time the glucose feed was decreased to meet metabolic demands. The total amount of glucose delivered to the bioreactor during the 67 hour fermentation was 3.9 kg. Induction was achieved by adding isopropyl-beta-D-1-thiogalactopyranoside (IPTG). The IPTG concentration was brought to 102 uM when the optical density at 550 nm ($OD_{550}$) reached a value of 9. The IPTG concentration was raised to 192 uM when $OD_{550}$ reached 140. At various times after inoculation, samples were removed and the amount of isoprene produced was determined as described below. Levels of hydrogen, nitrogen, oxygen, carbon dioxide, and isoprene in the off gas from the bioreactor were determined using a Hiden HPR-20 mass spectrometer as discussed below.

Samples of fermentation off-gas from 15-L bioreactors were collected into 20 mL glass headspace vials by sparging the vials at 1 $L_{offgas}$/min for 10 seconds and sealed with metal screw caps fitted with teflon-coated septa (Agilent, CA). The vials were analyzed within 30 minutes of collection.

Analysis of the two samples was performed by infusion into a Hiden HPR-20 mass spectrometer (Hiden Analytics, U.K.) at a rate of 4 scc/min (4 mL/min) by placing the inlet tube of the mass spectrometer into the uncapped headspace vials for 1-2 minutes. The HPR-20 instrument was configured to scan masses corresponding to hydrogen (m/z 2), nitrogen (m/z 28), oxygen (m/z 32), carbon dioxide (m/z 44) and isoprene (m/z 67). The Faraday detector was used for masses 28, 32, 44 and 67. The SEM detector was used for hydrogen (m/z 2). Detector response was measured in arbitrary units of pressure (Torr). Absolute hydrogen levels were estimated by comparison to an authentic hydrogen gas standard. Results were recorded using MASsoft V 6.21.0.51 software (Hiden Analytics, United Kingdom).

Results

Off-gas samples were taken from two fermentation runs and analyzed as described above:

A) Strain RM111608-2 (E. coli BL21 (DE3), pCL upper, cmR-gi1.2-yKKDyI, pTrcAlba-mMVK, pBBR cmR-gi1.5-pgl). Sample was taken at 64.8 hours into the run during which time the fermentation was being run anaerobically with a nitrogen sparge at 1 vvm.

B) Strain EWL256 (E. coli BL21 (DE3), pCL upper, cmR-gi1.2-yKKDyI, pTrcAlba-mMVK). Sample was taken at 34.5 hours into the run during which time the fermentation was being run aerobically with an air sparge at 1 vvm.

The results are depicted in FIGS. 165A-B. In both cases low levels of hydrogen were detected, in addition to isoprene, oxygen and carbon dioxide. The baseline reading for hydrogen was $0.95 \times 10^{-8}$ Torr. Both Sample A and B gave reading of around $1.3 \times 10^{-8}$ Torr. Based on a comparison to a hydrogen standard, the amount of hydrogen present in the off-gas for samples A and B was estimated to be less than 10 ppmv (parts per million volume) but above the baseline. As shown in FIGS. 165A-B, both samples A and B also contained significant amounts of isoprene and carbon dioxide.

Example 26

Co-Production of Isoprene and Hydrogen in E. Coli Strains Expressing M. Mazei Mevalonate Kinase, P. Alba Isoprene Synthase, pCL Upper MVA (E. Faecalis mvaE and mvaS) and ybhE (pgl)

Collection and Analysis of Fermentation Off-Gas for Hydrogen and Isoprene Levels The objective of this experiment is to co-produce hydrogen and isoprene in an engineered strain of E. coli. For this purpose, a portion of the hyc operon encoding E. coli hydrogenase-3 will be expressed in strain EWL256 [BL21 (DE3), pCL upper, cmR-gi1.2-yKKDyI, pTrcAlba-mMVK], prepared as described herein, although any of the bacterial strains described herein, such as RM111608-2, can be similarly modified. An expression construct comprising hyc operon genes hycB (gi|16130631), hycC (gi|16130630), hycD (gi|16130629), hycE (gi|16130628), hycF (gi|16130627), and hycG (gi|16130626) is prepared by standard cloning methods known in the art based upon publicly available gene sequences, and introduced into strain EWL256 to produce new strain EWL256+Hyd-3.

The impact of additional mutations on co-production of hydrogen and isoprene is assessed alone or in combination in EWL256+Hyd-3, by introducing genes involved in the maturation or regulation of hydrogenase-3 (e.g., hycH (gi|16130625) and hycI (gi|16130624)), by inactivating or deleting genes involved in hydrogen uptake or transport (e.g., E. coli hydrogenase-1 (hya operon) and hydrogenase-2 (hyb operon)) or related proteins (e.g., formate dehydrogenase (fdhF (gi|16130624)), repressor of formate lyase (hycA (gi|16130632)), formate dehydrogenase N, alpha subunit (fdnG (gi|16129433)), formate dehydrogenase O, large subunit (fdoG (gi|16131734)), nitrate reductase (narG (gi|16129187)), fumarate reductase regulator (Pr (gi|16129295)), and acetyl-coenzyme A synthetase (acs (gi|16131895))), by activating genes involved in upregulation of hydrogenases (e.g., activator of formate hydrogen lyase (fhlA (gi|16130638)), by inactivating or deleting genes involved in the production of fermentation side products (e.g., lactate dehydrogenase (ldhA (gi|16129341)), fumarate reductase membrane protein (frdC (gi|16131977)), alcohol dehydrogenase (adhE (gi|16129202)), pyruvate oxidase (poxB (gi|16128839)), pyruvate dehydrogenase E1 component ackAlpta (aceE (gi|16128107)), formate dehydrogenase regulatory protein (hycA (gi|16130632)), and formate transporters A and B (FocA (gi|16128871) and FocB (gi|16130417)), or by expression of heterologous genes involved in hydrogen metabolism (e.g., glyceraldehyde-3-phosphate dehydrogenase from Clostridium acetobutylicum (gapC (gi|15893997)).

Fermentations are performed using engineered variants of strain EWL 256+Hyd-3 (BL21 (DE3), pCL upper, cmR-gi1.2-yKKDyI, pTrcAlba-mMVK and hycB-F), modified to comprise one or more additional mutations as described herein, either alone or in combination, essentially as described in Example 25 above. Co-production of hydrogen and isoprene is assessed by analysis of off-gas samples essentially as described above. Strains are selected for further analysis based upon the rate of isoprene and hydrogen co-production.

Example 27

Co-Production of Ethanol and Isoprene by Saccharomyces Cerevisiae

To determine the feasibility of co-production of isoprene and ethanol in a Saccharomyces cerevisiae strain, IspS (Isoprene Synthase)-expressing *S. cerevisiae* was grown anaerobically under inducing conditions for 48 hours, and the production of isoprene and ethanol was measured.

Strains Used in this Example.

(1) DW112: *S. cerevisiae* (InvSC1)+pDW14 encoding codon-optimized IspS (Kudzu) on 2-micron plasmid (ura); and (2) DW114: *S. cerevisiae* (InvSC1)+pYES-DEST52—empty vector control (ura). Abbreviations used in this Example. (1) 112G (112gal): strain DW112 induced (0.5% glucose, 2% galactose); (2) 112R (112raf): strain DW112 uninduced (0.5% glucose, 1% raffinose); (3) 114G (114gal): strain DW114 induced (0.5% glucose, 2% galactose); and (4) 114R (114raf): strain DW114 uninduced (0.5% glucose, 1% raffinose).

Growth and Induction Conditions.

INVSc-1 strains harboring pDW14 (strain DW112) or pYES-DEST52 (strain DW114) (see Example 20 for details on vector construction) were selected for on SC Minimal Medium with 2% glucose without uracil, as described in the pYES-DEST52 Gateway Vector manual (Invitrogen). SC Minimal Medium without uracil contains: 0.67% yeast nitrogen base (without amino acids; with ammonium sulfate); 2% carbon source (e.g., glucose for propagation or galactose for induction); 0.01% (adenine, arginine, cysteine, leucine, lysine, threonine, tryptophan); 0.005% (aspartic acid, histidine, isoleucine, methionine, phenylalanine, proline, serine, tyrosine, valine); and optionally 2% agar (for plates). FIG. 141 shows the sequence of the codon-optimized IspS from Kudzu; FIG. 142A shows a map of the replicating vector for galactose-inducible expression in yeast; and FIGS. 142B-C show the complete nucleotide sequence of the expression vector for galactose-inducible expression of Kudzu IspS in *S. cerevisiae* (SEQ ID NO:39).

For propagation, strains were grown aerobically at 30° C. in either solid or liquid SC minimal medium without uracil with 2% glucose. After overnight incubation, strains were diluted to an $OD_{600}$ of 1.0 in 20 ml of SC minimal medium without uracil with 0.5% glucose, and grown for an additional 2 hours. At an $OD_{600}$ of approximately 1.4 (see FIG. 166), 10 ml of each strain were transferred to sealed 20 ml gas chromatography (GC) vials and either raffinose or galactose was added to a final concentration of 1% or 2%, respectively. This resulted in both uninduced (R, for raffinose) and induced (G, for galactose) growth of both DW112 and DW114. The GC vials were sealed and incubated for 48 hours at 30° C.

Detection of Isoprene by GC-MS.

After 48 hours of incubation in sealed GC vials, strains were assayed for isoprene production via GC-MS (see below for method). Control samples (112R, 114G, and 114R) displayed no isoprene production, whereas the strain containing Kudzu IspS, grown in the presence of 2% galactose (112G), produced a detectable level of isoprene (see Table 19 and FIG. 167). For the controls, there was no detectable peak at the retention time for isoprene (0.49 min), so it was not possible to generate an integrated value for isoprene (see FIG. 167). Using a calibration factor of 888/µg, the peak area for 112G corresponds to a concentration of isoprene in the headspace gas of 4.97 µg/L.

TABLE 19

GC-MS data

| Sample | Retention time (min) | Peak height | Corrected area | Calibration factor | Concentration (area/cal. factor) |
|---|---|---|---|---|---|
| 112G | 0.49 | 1025 | 4413 | 888/µg | 4.97 µg/L |

GC-MS Method for Isoprene Detection.

The analysis was performed using an Agilent 6890 GC/MS system interfaced with a CTC Analytics (Switzerland) CombiPAL autosampler operating in headspace mode. An Agilent HP-5MS GC/MS column (15 m×0.25 mm; 0.25 µm film thickness) was used for separation of analytes. The sampler was set up to inject 100 µL of headspace gas. The GC/MS method used helium as the carrier gas at a flow rate of 2 mL/minute. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 0.01 to 0.45 minutes to allow the elution of permanent gases. Under these conditions isoprene (2-methyl-1,3-butadiene) was observed to elute at 0.49 minutes. A calibration table was used to quantify the absolute amount of isoprene and was found to be linear from 1 µg/L to 20000 µg/L. The limit of detection was estimated to be 50 to 100 ng/L using this method.

Detection of Ethanol by HPLC.

After detection of isoprene by GC-MS, vials were opened and the $OD_{600}$ of each culture was measured. $OD_{600}$ values were between 5.0 and 5.7, indicating that for all strains, growth occurred during the 48 hour incubation (see FIG. 166). Production of ethanol in all samples was then measured by HPLC (see below). All four cultures produced ethanol. FIG. 168 shows peaks and integrated values (g/L) for ethanol, and Table 20 shows all data from the HPLC protocol.

Organic Acids HPLC Method.

This method was developed to separate and quantify typical organic acids from fermentation processes. Running Buffer was 0.01 $NH_2SO_4$ buffer (equivalent to 5 mM). Running buffer was prepared as follows: using a 4 L graduated cylinder, add 17.75 ml of the 10% $H_2SO_4$ stock solution to 4.0 L deionized water. This solution will be used to refill the HPLC buffer bottle. Detector. A Knauer K2301 RI detector was used to quantify the peaks as they came off the column.

Preparation of Broth Samples for HPLC.

Broth samples were prepared for HPLC as follows: (1) Broth was poured into a labeled Eppendorf tube (~1.8 mL); (2) Tubes were centrifuged at 14,000 rpm for 5 minutes to pellet cells; (3) 300 µL of supernatant was transferred to a fresh Eppendorf tube; (4) 900 µL of $H_2O$ was added to the supernatant. One can dilute the sample less if one wants to see low concentration analytes, however, this will dirty the column more. The samples should be limited to those diluted less than 4×; (5) 36 µL of 70% perchloric acid (Sigma, Catalog No. 244252) was added and the tube inverted several times to mix; (6) Tubes were incubated on ice for 5 min to precipitate proteins, and then centrifuged at 14,000 rpm for 5 minutes. At this point, the supernatant was ready to be analyzed.

The supernatant was then poured into a plastic, conical bottom HPLC vial. The cap was screwed onto the vial, the vial was tapped on a hard surface to remove bubbles from the bottom (otherwise, the HPLC injection needle would remove only air), and the samples were run on the HPLC loaded with an Aminex HPX-87H Ion Exclusion Column 300 mm×7.8 mm (Catalog #125-0140; Bio Rad, Hercules, Calif.), run at 50° C., equipped with a Microguard Cation H refill 30 mm×4.6 mm guard column (Catalog #125-0129; Bio Rad, Herculues, Calif.), using 0.01 $NH_2SO_4$ as running buffer, at a flow rate of 0.6 ml/minute, at an approximate running pressure of ~950 psi, with an injection volume of 20 microliters. Run time was about 26 to 36 minutes; for example, the void came off at about 6 minutes; glucose came off at 8.5 minutes; acetic acid came off at 14 minutes, and ethanol came off at 21 minutes. When the column and guard column are not in use, they are stored in 0.01N $H_2SO_4$.

TABLE 20

HPLC data

| Sample Name | Name | Amount (g/L) | Retention Time | Area | % Area | Height |
|---|---|---|---|---|---|---|
| 112G | | | 6.539274 | 3038675 | 21.90461 | 499230.5 |
| 112G | | | 7.799441 | 242845.5 | 1.750578 | 9319.017 |
| 112G | glucose | | 9.194 | | | |
| 112G | | | 9.910056 | 9733369 | 70.16403 | 548067.4 |
| 112G | | | 12.07399 | 6070 | 0.043756 | 397.731 |
| 112G | lactic | | 13.044 | | | |
| 112G | glycerol | 0.258157 | 13.84041 | 107065 | 0.771789 | 5342.111 |
| 112G | acetate | 0.045332 | 15.59951 | 11295 | 0.081421 | 704.9043 |
| 112G | mva | 0.022844 | 18.39964 | 10628 | 0.076613 | 588.5367 |
| 112G | | | 19.92238 | 71118 | 0.512662 | 2513.014 |
| 112G | ethanol | 3.056254 | 22.55683 | 651241.5 | 4.694544 | 21362 |
| 112R | | | 6.679975 | 6760286 | 62.07404 | 673489.1 |
| 112R | | | 7.11816 | 157055.5 | 1.442109 | 14593.57 |
| 112R | | | 7.808459 | 2616853 | 24.02837 | 179605.7 |
| 112R | glucose | | 9.194 | | | |
| 112R | | | 9.664757 | 304552.7 | 2.796452 | 10171.72 |
| 112R | | | 10.26993 | 104312.8 | 0.957817 | 5681.594 |
| 112R | lactic | | 13.044 | | | |
| 112R | glycerol | 0.241637 | 14.13761 | 100214 | 0.920181 | 4987.541 |
| 112R | acetate | 0.055357 | 15.94772 | 13793 | 0.12665 | 683.0312 |
| 112R | mva | 0.022971 | 18.77139 | 10687 | 0.09813 | 580.4755 |
| 112R | | | 20.33575 | 33230.5 | 0.305128 | 1384.247 |
| 112R | ethanol | 3.706021 | 23.0497 | 789697 | 7.251126 | 25052.53 |
| 114G | | | 6.605895 | 4805009 | 30.84022 | 599783.9 |
| 114G | | | 7.882295 | 241598 | 1.55066 | 9176.059 |
| 114G | glucose | 0.37193 | 9.569593 | 188423.8 | 1.20937 | 10212.97 |
| 114G | | | 10.02025 | 9492665 | 60.92723 | 535906.8 |
| 114G | lactic | | 13.044 | | | |
| 114G | glycerol | 0.257023 | 14.00157 | 106595 | 0.684164 | 5186.41 |
| 114G | acetate | 0.051408 | 15.79813 | 12809 | 0.082213 | 704.3561 |
| 114G | mva | 0.023238 | 18.60869 | 10811.5 | 0.069392 | 579.3297 |
| 114G | | | 20.16202 | 52365 | 0.336097 | 1935.451 |
| 114G | ethanol | 3.144548 | 22.82513 | 670055.5 | 4.30065 | 21595.97 |
| 114R | | | 6.622579 | 5297638 | 56.41625 | 627059 |
| 114R | | | 7.055373 | 157610.6 | 1.678446 | 15390.13 |
| 114R | | | 7.738859 | 2558683 | 27.24824 | 175422.1 |
| 114R | glucose | 0.607738 | 9.565885 | 307886.2 | 3.278779 | 10379.93 |
| 114R | | | 10.16476 | 71425.78 | 0.760636 | 4133.971 |
| 114R | lactic | | 13.044 | | | |
| 114R | glycerol | 0.245692 | 14.01421 | 101895.5 | 1.085118 | 4966.784 |
| 114R | acetate | 0.049779 | 15.81667 | 12403 | 0.132084 | 599.6038 |
| 114R | mva | 0.105887 | 18.61106 | 49263 | 0.524618 | 1138.927 |
| 114R | | | 20.13147 | 46185 | 0.491839 | 1616.316 |
| 114R | ethanol | 3.694678 | 22.83235 | 787280 | 8.383998 | 25084.6 |
| 114R-2 | | | 6.614597 | 5118040 | 55.89791 | 606469.3 |
| 114R-2 | | | 7.053017 | 176053.7 | 1.922813 | 16687.26 |
| 114R-2 | | | 7.734239 | 2544066 | 27.78563 | 172083.4 |
| 114R-2 | glucose | 0.60747 | 9.553156 | 307750.8 | 3.361175 | 10424.68 |
| 114R-2 | | | 10.15617 | 61748.18 | 0.674398 | 3441.637 |
| 114R-2 | lactic | | 13.044 | | | |
| 114R-2 | glycerol | 0.242708 | 14.00365 | 100658 | 1.099361 | 4942.726 |
| 114R-2 | acetate | 0.056583 | 15.77043 | 14098.5 | 0.15398 | 628.3414 |
| 114R-2 | mva | 0.029084 | 18.60404 | 13531 | 0.147782 | 658.1601 |
| 114R-2 | | | 20.15232 | 38940 | 0.425293 | 1504.547 |
| 114R-2 | ethanol | 3.665969 | 22.81841 | 781162.5 | 8.531655 | 25133.2 |

Example 28

Co-Generation of Isoprene Via the DXP Pathway and Ethanol in *E. Coli*

As shown in FIG. 169, cogeneration of isoprene and ethanol is a way of increasing the theoretical yield of isoprene from glucose by the DXP pathway, as the ATP generated in the production of ethanol can be utilized in the pathway to make isoprene. Maximum theoretical mass yield (without counting carbon used for building biomass) is then 32.3%. Assuming a CPI (cell productivity index) of 5, mass yield would be 29% in comparison to 27% for the DXP pathway only. Thus, when the process runs anaerobically, the capital investment decreases for oxygen transfer. The process could run in existing ethanol plants, in terms of tank stirring.

Although *E. coli* can produce ethanol when it is grown anaerobically, using the enzyme adhE to go from acetyl-CoA to ethanol via acetaldehyde, ethanol production is greatly improved by expressing pyruvate decarboxylase (pdc) from *Zymomonas*. As shown on FIG. 170, pdc uses pyruvate as a substrate, has a low Km, and production of ethanol through pdc and adhE (*E. coli*) or adhB (*Zymomo*-

*nas*) requires less reducing equivalents than through pfl and adhE. Although pdc expression alone already significantly increases the amount of ethanol produced by *E. coli*, adding adhB from *Zymomonas* has been shown to increase the concentration of ethanol produced more than 20 times (Ingram et al. 1987).

Cloning of *Zymomonas Mobilis* Pyruvate Decarboxylase (pdc) Behind a Trc Promoter in pBBR1-MCS5.

Pyruvate decarboxylase (pdc) was amplified from *Zymomonas mobilis* ZM4 genomic DNA (ATCC31821) using primers SpeI-PTrc-rbs-pdcF (5'-gttactACTAGTGTT-GACAATTAATCATCCGGCTCGTATAATGTGTGGAAT-TGTGAGCGGAT AACAATTTaggaggaaaaaaaaATGAGT-TATACTGTCGGTACCTATTTAG-3'; SEQ ID NO:146) and PstI-pdcR (5'-gttagatCTGCAGgtttatttaaaaactagag-gagcttg-3'; SEQ ID NO:147). The resulting PCR product was purified, digested with SpeI/PstI and religated with SpeI/PstI-digested pBBR1-MCS5 (Kovach et al., *Biotechniques* (1994) 5:800-802). The plasmid was extracted from a white colony selected on LB+Gentamicin (5 ppm)+Xgal and was found to be correct by sequencing. This plasmid clone was named pBBR5-Ptrcpdc (FIG. 171A shows a map of pBBR5-Ptrcpdc; FIGS. 171B-C show the sequence of pBBR5-Ptrcpdc; SEQ ID NO:148).

Construction of an *E. Coli* Strain Co-Expressing Pdc and the DXP Pathway.

Construction of strain MCM597 (BL21(DE3), pET24 (MEA)alba+DXS+yIDI). Construction of pDU-39. Primer sequences: (1) Alba TRC(MEA)-NdeI-F: 5'-gaaactgaaac-cCATATGgaagctcgtcgttctgc-3' (SEQ ID NO:149); (2) Alba FLTRC (−) TER-R: 5'-cccgcgcttaCTCGAGgcgttcaaacggca-gaatcggttcagtg-3' (SEQ ID NO:150). A truncated version of the *Populus alba* isoprene synthase was created by amplifying the gene using the primer set Alba TRC(MEA)-NdeI-F/Alba FLTRC(−) TER-R and the template pET24a *P. alba* HGS (see, e.g., Example 23(iii), SEQ ID NO:43, and FIGS. 152, 153A, and 153B). The PCR reaction was set up as follows: 1 (pET24a-*P. alba*); 5 μl 10×PfuUltraII Fusion buffer; 1 μl 10 mM dNTPs; 1 primer (50 μM) Set #1 forward; 1 μl primer (50 μM) Set #1 reverse; 41 μl ddiH2O; +1 μl of PfuUltra II Fusion DNA Polymerase from Stratagene. Cycling parameters were 95° C./1 minute, followed by 29 cycles of 95° C./30 seconds, 55° C./20 seconds, 72° C./25 seconds, followed by 72° C./3 minutes. The reactions were then held at 4° C. until cool (Eppendorf Mastercycler).

The PCR products were digested with NdeI-XhoI restriction endonucleases (Roche) and gel purified using the QIAquick Gel Extraction Kit (Qiagen) according to the manufacturer's instructions. An aliquot of 3 μl of the purified product was ligated using T4 ligase (New England BioLabs) to pET-24a vector (Invitrogen) that was previously digested with NdeI-XhoI, gel purified and treated with Shrimp Alkaline Phosphatase (SAP, Roche). The ligation was carried out overnight at 16° C.

An aliquot of 5 uL of the overnight ligation mixture was transformed into TOP10 cells (Invitrogen) and transformants were selected on L agar containing kanamycin (50 μg/ml) at 37° C. overnight. Plasmids were isolated from a few of the transformants using the QiaQuick Spin Kit (Qiagen) according to the manufacturer's instructions. The insert was verified by NdeI-XhoI restriction endonuclease digestion and the clones were sequenced with the commercially available T7 promoter and T7 terminator primers (Quintara Bio Sequencing Service, Berkeley, Calif.). The correct plasmid was designated pDu-39 (FIG. 172; SEQ ID NO:151)

Construction of MCM597.

Primer Sequences: (1) MCM270 5'-GATCGGATCCAT-TCGCCCTTAGGAGGTAAA-3' (SEQ ID NO:152); and (2) MCM271 5'-GATCGCGGCCGCCAGCTGCAG-GACGCGTTGTTATAGCATT-3' (SEQ ID NO:153).

The DXS-yIDI genes were amplified by PCR using primers MCM270/MCM271 and the template pMCM72 (FIG. 173 is a map of pMCM72). Two identical PCR reactions were set up according to the manufacturer's protocol for Herculase II Fusion (Stratagene): 35 μL water, 10 μL buffer, 1.25 μL each primer, 0.5 μL dNTPs, 1 μL polymerase. Reactions were cycled: 95° C./2:00, followed by thirty cycles of 95° C./15 seconds, 55° C./15 seconds, 72° C./1 minute, 45 seconds, followed by 72° C./3 minutes. The reactions were then kept at 4° C. until cold.

The resulting PCR fragment was digested with BamHI and NotI (Roche), and then ligated with Roche Rapid Ligation Kit into pDu39 that had been digested with the same restriction endonucleases. The ligation reaction was set up in 10 μL containing 5 μL Buffer 1, 1 μL vector, 3 μL insert and 1 μL ligase, then incubated for 1 hour at room temperature. An aliquot of 5 μL was transformed into *E. coli* Top10 chemically competent cells (Invitrogen). Transformants were selected on L agar containing kanamycin (50 μg/ml) at 37° C. overnight. Plasmids were purified from a few transformants and screened for the presence of insert by PCR using Herculase II Fusion (Stratagene): 17.5 μL water, 5 μL buffer, 0.625 μL each primer, 0.25 μL dNTPs, 0.5 μL polymerase. Reactions were cycled as follows: 95° C./2 minutes, followed by 30 cycles of 95° C./15 seconds, 52° C./15 seconds, 72° C./45 seconds, then held at 72° C./3 minutes. The reactions were then held at 4° C. until cold. Clones with a PCR product near 1.5 kbp in length were sequenced (Quintara Biosciences, Berkeley Calif.). A correct plasmid was designated pMCM596 (FIG. 174A is a map of pMCM596; FIGS. 174B-D are the sequence of pMCM596 (SEQ ID NO: 154)). The plasmid was then transformed into electrocompetent BL21(DE3)pLysS cells (Invitrogen) and transformants were selected on L agar containing kanamycin (50 μg/ml) and chloramphenicol (35 μg/mL). One colony was selected and designated MCM597.

MCM597 (BL21(DE3), pET24(MEA)alba+DXS+yIDI) was transformed with pBBR5-Ptrcpdc and pBBR1-MCS5 as a control. Colonies were selected on LB+Kanamycin 50 ppm, Chloramphenicol (35 ppm), Gentamycin (5 ppm). One colony of each was selected and named strain CMP182 and strain CMP183 respectively.

Co-Production of Isoprene and Ethanol in *E. Coli*.

One colony each of strains CMP182 and CMP183 was incubated overnight in TM3 medium with 1% glucose and 1% yeast extract, and appropriate antibiotics, at 30° C. and 170 rpm. The morning after, cultures were diluted in the 20 mL of the same medium, containing 0.5% glucose, and 0.11% or 1% yeast extract, to an OD=1 and incubated at 30° C. and 170 rpm. The 1% yeast extracts flasks were done in duplicate. Duplicates were highly similar so results from only one set of flasks were presented. After 2 h, 200 uM IPTG was added and agitation was reduced to 40 rpm. Samples were taken 2 hours and 5 hours after induction, and analyzed for OD, organic acids by HPLC (Ion exclusion column Aminex HPX-87H, 300 mm×7.8 mm) and specific productivity of isoprene. Isoprene concentration was measured in the offgas by GC/MS as described herein. The specific productivity of each strain is reported as μg/L per OD per hour. Note the ratio of 1900 μl headspace:100 μl broth in assay vials for 30 minutes incubation results in the following conversion of isoprene μg/L of culture to specific productivity: (isoprene/L determined by GC-MS)×(38)/(OD 600 nm of the culture). With 1% yeast extract, glucose was depleted at 5 hours after induction.

FIG. 175 shows that growth was not affected by the expression of pdc. Cultures containing 1% yeast extract grew to a higher OD.

FIG. 176 shows ethanol concentration and isoprene specific productivity (in arbitrary units) in the flasks containing 0.1% (A) (5 hours after induction) and 1% (B) (2 hours after induction) yeast extract. It can be seen that the strains are directing carbon both towards isoprene and ethanol. As expected from a functional pdc, more ethanol is produced in the strain harboring pdc. Specific productivity of isoprene is lower in the strain harboring pdc, since more carbon flux is going to ethanol, but it is still significant, showing that dxs (using pyruvate and glyceraldehyde as substrates) can take carbon flux from pdc.

FIG. 177 shows fermentation products after 5 hours of induction in the 1% yeast extract flasks. The strain expressing pdc shows a higher concentration in ethanol, confirming the fact that pdc was expressed and active. As expected from comparing $K_m$s for ldhA and pdc, pyruvate flux to lactate is interrupted once pdc is expressed. Also, in the strain expressing pdc, more carbon is going towards acetaldehyde than towards acetyl-CoA, leading to a decrease of acetate.

Example 29

Coproduction Of Isoprene and Ethanol in Zymomonas Mobilis

Construction of a Plasmid for Production of Isoprene in *Zymomonas Mobilis*.

*Zymomonas mobilis* ZM4 (ATCC31821) was obtained from ATCC (Manassas, Va.). It was routinely grown in 10 ml tubes containing RM medium (20 g/L glucose, yeast extract 10 g/L, $KH_2PO_4$ 2 g/L, adjusted to pH 6.0), at 30° C. without shaking. *Zymomonas mobilis* is well-known for its capacity to produce ethanol. J. Swings et al. (1977) *Bacteriol. Rev.* 41:1-46.

A PCR product containing the *Z. mobilis* pdc promoter in front of a gene coding for a truncated isoprene synthase from *Populus alba* was generated by PCR SOEing (Polymerase Chain Reaction—Splicing by Overlapping Extension) using primer XbaI-PpdcF (5'-ctaaacTCTAGAGC TCA TGA TCG CGG CAT GTT CTG-3'; SEQ ID NO:155) and primer FusPpdc-HGSR (5'-gcagaacgacgagcttcggtcattgcttactccatat-attcaaaacactatg-3'; SEQ ID NO:156) for amplifying the pdc promoter, and using primer PstI-MTEARRalbahpR (5'-ctac-gaCTGCAGCCGGATATAGTTCCTCCTTTCAGC-3'; SEQ ID NO:157) and FusPpdc-HGSF (5'-catagtgtttt-gaatatatggagtaagcaAtgaccgaagctcgtcgttctgc-3'; SEQ ID NO:158) for amplifying the isoprene synthase gene, followed by a PCR reaction on a mixture of the two products obtained in step 1, with primers XbaI-PpdcF (SEQ ID NO:155) and PstI-MTEARRalbahpR (SEQ ID NO:157). Template for the pdc promoter was genomic DNA of *Z. mobilis* ZM4 and the truncated isoprene synthase was amplified from plasmid pDU47 (a map of pDU47 is shown in FIG. 178; the sequence of plasmid pDU47 (SEQ ID NO:159) is shown in FIG. 179). The codon bias for that gene has been optimized for *E. coli*.

The PCR product obtained was digested with XbaI/PstI and religated with XbaI/PstI-digested pBBR1-MCS (Kovach et al., *Biotechniques* (1994) 5:800-802). pBBR1-MCS is a broad-host range plasmid shown to be stably replicating in *Zymomonas* (Jeon et al., *FEMS Microbiol. Letters* (2005) 244:85-92). The plasmid obtained was named pBBR-Ppdc-HGS1 (a map of plasmid pBBR-Ppdc-HGS1 is shown in FIG. 180; the sequence of plasmid pBBR-Ppdc-HGS1 (SEQ ID NO:160) is shown in FIG. 181).

Transformation of *Z. Mobilis* ZM4 with pBBR1-MCS or pBBR1-Ppdc-HGS1.

Plasmids pBBR1-MCS and pBBR1-Ppdc-HGS1 were transformed into *Z. mobilis* ZM4 by biparental mating (via *E. coli* 517-1) according to Conway et al. (Conway et al., *Appl. Environ. Microbiol.* (1987) 53:235-241), or electroporation according to Jeon et al. (Jeon et al., *FEMS Microbiol. Letters* (2005) 244:85-92). Transformants were selected on RM+chloramphenicol 100 µg/ml following electroporation and appeared after 48 h at 30° C. in anaerobic conditions. Cultures for conjugation were incubated on RM overnight then restreaked on YPG (yeast extract, 10 g/L, peptone, 10 g/L, glucose, 70 g/L, pH 6.0)+40 µg/ml nalidixic acid+chloramphenicol 100 µg/ml.

Both methods yielded an abundance of colonies on RM+chloramphenicol 100 µg/ml or YPG+40 µg/mlnalidixic acid+chloramphenicol 100 µg/ml. Plasmid was extracted from the *Zymomonas* cells using a Qiagen mini-prep kit (Qiagen, Valencia, Calif.) and shown to be present by gel electrophoresis.

Production of Isoprene and Coproduction of Isoprene and Ethanol by *Z. Mobilis* ZM4, pBBR1-Ppdc-HGS1.

One colony each of *Zymomonas mobilis* ZM4, pBBR1-MCS and *Zymomonas mobilis* ZM4, pBBR1-Ppdc-HGS1 were inoculated in 10 ml RM+chloramphenicol 100 µg/ml in a 20 ml headspace vial sealed and incubated overnight standing at 30° C. After 16 hours, a vial was removed and analyzed for isoprene concentration in the headspace, OD and organic acids or alcohols. Isoprene production in that same vial was measured using a headspace assay as follows. The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 µM film thickness) was used for separation of analytes. The sampler was set up to inject 500 µL of headspace gas. The GC/MS method used helium as the carrier gas at a flow rate of 1 ml/minute. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene, which was found to be linear from 1 µg/L to 200 µg/L. The limit of detection was estimated to be 50 to 100 ng/L using this method.

Organic acids and alcohols were analyzed by HPLC (Ion exclusion column Aminex HPX-87H, 300 mm×7.8 mm, 0.005 M $H_2SO_4$, 0.6 mL/min as the mobile phase). Cells of *Zymomonas mobilis* ZM4 transformed with pBBR1-MCS were growing faster than cells of *Zymomonas mobilis* ZM4 transformed with pBBR1-Ppdc-HGS1 (data not shown). At the end of the culture, cells were harvested, lysed by two passages through a French press, and extracts were analyzed by a Western blot probed with a monoclonal antibody against purified *Populus alba* isoprene synthase. The protein was detected in cells of *Zymomonas mobilis* ZM4 transformed with pBBR1-Ppdc-HGS1 but not in cells of *Zymomonas mobilis* ZM4 transformed with pBBR1-MCS.

FIG. 182 shows the amount of isoprene detected divided by OD. $OD_{600}$ was 1.9 and 2.1 for *Zymomonas mobilis* ZM4, pBBR1-MCS and *Zymomonas mobilis* ZM4, pBBR1-Ppdc-HGS1 respectively (not significantly different). *Zymomonas mobilis* ZM4, pBBR1-Ppdc-HGS1 produced 16× more isoprene/OD than *Zymomonas mobilis* ZM4, pBBR1-MCS. Table 21 presents relative OD and relative ethanol production from *Zymomonas mobilis* ZM4, pBBR1-Ppdc-HGS1 compared to *Zymomonas mobilis* ZM4, pBBR1-MCS. Lactate was not detected in those cultures, and acetate levels were less than 0.1 g/L. Ethanol (more than 9 g/L) was produced at equal concentrations for both *Zymomonas mobilis* ZM4, pBBR1-MCS and *Zymomonas mobilis* ZM4, pBBR1-Ppdc-HGS1.

TABLE 21

Relative OD and relative ethanol production of *Zymomonas mobilis* ZM4, pBBR1-MCS compared to *Zymomonas mobilis* ZM4, pBBR1-Ppdc-HGS1

| Relative OD of *Zymomonas mobilis* ZM4, pBBR1-MCS compared to *Zymomonas mobilis* ZM4, pBBR1-Ppdc-HGS1 | Relative EtOH production of *Zymomonas mobilis* ZM4, pBBR1-MCS compared to *Zymomonas mobilis* ZM4, pBBR1-Ppdc-HGS1 |
|---|---|
| 0.89 | 1.03 |

It has been found that an increased amount of isoprene per OD can be obtained in the same setting if the inoculum consists of a growing culture (data not shown).

Example 30

Coproduction of Isoprene and 1,3-propanediol

Other two-(C2) and three-carbon (C3) alcohols and diols such as, for example, 1,2-propane diol or 1,3-propanediol (1,3-PDO), are co-produced with isoprene in a variety of organisms, including yeasts, such as *S. cerevisiae*, and bacteria, such as *Escherichia* sp. (e.g., *E. coli*) and *Zymomonas* sp. (e.g., *Z. mobilis*). Yield of isoprene and 1,3-PDO is estimated from the following equations:

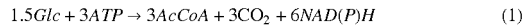
$1.5 Glc + 3 ATP \rightarrow 3 AcCoA + 3 CO_2 + 6 NAD(P)H$ (1)

$3 AcCoA + 2 NAD(P)H \rightarrow MVA$ (2)

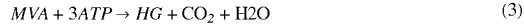
$MVA + 3 ATP \rightarrow HG + CO_2 + H2O$ (3)

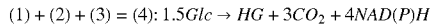
$(1) + (2) + (3) = (4): 1.5 Glc \rightarrow HG + 3 CO_2 + 4 NAD(P)H$

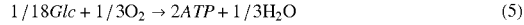
$1/18 Glc + 1/3 O_2 \rightarrow 2 ATP + 1/3 H_2O$ (5)

$0.5 Glc + ATP + 2 NAD(P)H \rightarrow PDO$ (6)

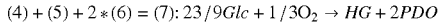
$(4) + (5) + 2*(6) = (7): 23/9 Glc + 1/3 O_2 \rightarrow HG + 2 PDO$

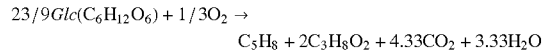
$23/9 Glc (C_6H_{12}O_6) + 1/3 O_2 \rightarrow$
$\qquad C_5H_8 + 2 C_3H_8O_2 + 4.33 CO_2 + 3.33 H_2O$ At a CPI (cell productivity index) of 6, isoprene yield on sugar=13%; PDO yield on sugar=30%.

Construction of CMP250, an *E. Coli* Strain Expressing the Pathways for Isoprene Production Via the MVA Pathway and 1,3-Propanediol Production.

Construction of pDW15. Plasmid pBBr1-MCS5 (Kovach et al, *Gene* 166:175-176, 1995) was digested with XhoI/XbaI and religated with a Ptrc Upper MVA piece amplified from pTrcUpperPathway (FIGS. 26 and 27A-27D; SEQ ID NO:12). The resulting plasmid was named pDW15 (SEQ ID NO:161; see FIG. 183A for a plasmid map, and FIGS. 183B-D for the plasmid sequence). Plasmid pDW15 expressed the upper mevalonic acid pathway polypeptides mvaE and mvaS from *Enterobacter* faecalis.

Construction of *E. Coli* Strain CMP250.

Strain EWL204 was electroporated (protocol described in Example 23) with pEWL244 and pDW15 (see Example 23 for information regarding the construction of strain EWL204 and plasmid pEWL244, as well as for the electroporation protocol). Transformants were selected on LB+Carbenicillin (50 µg/mL)+Gentamycin (5 µg/mL). The resulting strain was then electroporated with plasmid pSYCO109 (see U.S. Pat. No. 7,371,558, which is incorporated herein by reference, particularly with respect to construction of the plasmids designated pSYCO101 et seq., including pSYCO109) (SEQ ID NO:162; see FIG. 184A for a plasmid map and FIGS. 184B-F for the sequence). The plasmid pSYCO109 encodes (1) DAR1 (dihydroxyacetone phosphate reductase) and GPP2 (glycerol-phosphate phosphatase), both genes from the glycerol pathway; (2) dhaB1-3, dhaX, orfX, and orfY, all genes from the 1,3-propanediol pathway. The plasmid pSYCO109 also includes an *E. coli* threonine operator attenuator (Thr atten), an *E. coli* TonB terminator (TonB term), a trc promoter (trc), and an aspartate ammonia lyase gene terminator (AspA term). Transformants were selected on LB+Carbenicillin (50 µg/mL)+Gentamycin (5 µg/mL)+Spectinomycin 50 µg/mL. The resulting strain was designated CMP250.

Alternatively, a cassette containing, in this order, the *E. coli* MG1655 native pgl promoter, *E. coli* MG1655 native pgl gene (ybhE, not present in BL21), and an FRT-Chloramphenicol-FRT cassette (GeneBridges, Heidelberg, Germany) was recombined in the chromosome of EWL204 by Red/ET recombination (GeneBridges, Heidelberg, Germany). The chosen site of integration was between ybhJ and ybhC. The marker was looped out using 706-Flp (GeneBridges, Heidelberg, Germany) and the strain thus generated was named CMP251. Strain CMP251 was electroporated with plasmids pEWL244, pDW15 and pSYCO109 in the order described in the paragraph above, to produce strain CMP252.

Additional strains are constructed with deletions in a variety of genes involved with metabolic pathways relating to the production of C2- or C3-alcohols or diols, such as 1,3-propanediol, including: (1) a strain in which the glpK and gldA genes are deleted; (2) a strain in which the tpiA gene is deleted; or (3) a strain in which ptsHlcrr is deleted, and in which the galP and glk genes are constitutively expressed (see, e.g., US Patent Publication No. 2009/0142843-A1, entitled "Glucose Transport Mutants For Production Of Biomaterial," which is hereby incorporated by reference, in particular with respect to construction of various bacterial strains). Other strains are constructed with one or more useful mutations, including, for example, deletions of edd, ndh, arcA, mgsA, qor, ackA-pta, poxB, ldhA, or mutations that result in the downregulation of gapA or upregulation of ppc. These and other deletions are constructed by commonly-used methods, such as making lysates from the Keio mutant having the deletion of interest (Baba et al., *Mol. Syst. Biol.* 2:2006.0008 (published online February 2006) and transducing the mutation of interest into the desired bacterial strain, such as, for example, CMP250 or CMP252.

Coproduction of Isoprene and 1,3-Propanediol.

Strains CMP250, CMP252, or other strains derived from strains CMP250 and CMP252 but incorporating one or more of the additional mutations described above, are grown anaerobically in HM1 medium and expression of the various plasmids incorporating MVA pathway polypeptides and/or other heterologous polypeptides as described elsewhere herein is induced. Isoprene concentrations in the offgas are measured by GC/MS as described elsewhere herein, and 1,3-propanediol concentrations in the fermentation broth are measured by HPLC as described elsewhere herein, or by other suitable method known to one skilled in the art. The various bacterial strains are shown to have a high productivity of both isoprene and 1,3-propanediol, produced in a mass ratio of approximately 13:30.

Example 31

Construction of E. Coli Strain CMP249 for Co-Production of Isoprene and 1,3-propanediol Yield calculations for co-production of isoprene and 1,3-PDO, based on the following equations:

$$1.5 Glc + 3 ATP \rightarrow 3 AcCoA + 3 CO_2 + 6 NAD(P)H \quad (1)$$

$$3 AcCoA + 2 NAD(P)H \rightarrow MVA \quad (2)$$

$$MVA + 3 ATP \rightarrow HG + CO_2 + H_2O \quad (3)$$
$$(1) + (2) + (3) = (4): 1.5 Glc \rightarrow HG + 4 CO_2 + 4 NAD(P)H$$

$$1/18 Glc + 1/3 O_2 \rightarrow 2 ATP + 1/3 H_2O \quad (5)$$

$$0.5 Glc + ATP + 2 NAD(P)H \rightarrow PDO \quad (6)$$
$$(4) + (5) + 2*(6) =$$
$$(7): 23/9 Glc + 1/3 O_2 \rightarrow HG + 2 PDO + 4.33 CO_2 + 3.33 H_2O$$
$$23/9 C_6H_{12}O_6 + 1/3 O_2 \rightarrow C_5H_8 + 2 C_3H_8O_2 + 4.33 CO_2 + 3.33 H_2O$$

At a cell productivity index (CPI) of 6, the isoprene yield on sugar=13%, with a maximum of 14.8%; the 1,3-propanediol yield on sugar=30%, with a maximum of 33%. The peak oxygen uptake rate (OUR)~17 was 3 g/L/hr.

Construction of Co-Production Strain CMP249 (BL21 PL.2 mKKDyIgldAglpK::Kan tpgI, pDW15, pEWL244, pSYCO109).

Plasmids pEWL244, pSYCO109 and pDW15. The plasmid pSYCO109 (SEQ ID NO:162; FIG. 184A for a plasmid map; FIGS. 184B-F for the sequence) contains all of the necessary pathway genes to convert dihydroxyacetone-phosphate into 1,3-propanediol via glycerol, and is described in U.S. Pat. No. 7,371,558. pSYCO109F1.1 (SEQ ID NO:163; see FIG. 185A for a plasmid map and FIGS. 185B-F for the plasmid sequence) contains a fusion of two subunits of the glycerol dehydratase enzyme with an amino acid change. The plasmid EWL244 (pTrcAlba-mMVK) contains the genes encoding P. alba isoprene synthase and Methanosarcina mazei mevalonate kinase (mMVK) transcribed from the trc promoter, constructed as described in Example 23 herein (SEQ ID NO:45; see FIG. 158 for a map of plasmid EWL244 and FIGS. 159A-B for the plasmid sequence).

Construction of pDW15 (Ptrc-Upper MVA Pathway on pBBR1MCS-5).

To insert the upper MVA pathway onto the pBBR1MCS-5 vector, the entire expression cassette containing pTrc, mvaE, mvaS, and the rrn terminator was amplified by PCR from plasmid MCM82 (described in Example 23 herein) using the primers Upper5'XhoI (SEQ ID NO:164) and Upper3'XbaI (SEQ ID NO:165). The PCR reaction contained 1 µl MCM82 (approx. 30 ng), 10 µl 5× Herculase® Buffer (Stratagene, La Jolla, Calif.), 0.5 µl dNTPs (100 mM), 1 µl Upper5'XhoI (SEQ ID NO:164) (20 uM), 1 µl Upper3'XbaI (SEQ ID NO:165) (20 uM), 35.5 µl diH$_2$O, and 1 µl Herculase DNA Polymerase (Stratagene). The reactions were cycled as follows: 95° C./4 minutes; 5 cycles of 95° C./20 minutes, 52° C. 20 seconds, 72° C. 4 minutes; 25 cycles of 95° C./20 minutes, 55° C. 20 seconds, 72° C./4 minutes; 72° C./10 minutes, then cooled to 4° C.

The size of the approximately 4.2 kb PCR product was confirmed by gel electrophoresis (E-Gel, Invitrogen, Carlsbad, Calif.) and then purified using QiaQuick purification columns (Qiagen, La Jolla, Calif.) according to the manufacturer's recommended protocol. Purified PCR product and the pBBR1MCS-5 vector were then treated with XbaI and XhoI restriction endonucleases overnight at 37° C. Digestions were performed as follows: 6 µl diH$_2$O, 2 µl 10× Buffer H (Roche), 10 µl DNA (pBBR1MCS-5 or PCR insert), 1 µl XhoI (Roche), and 1 µl XbaI (Roche) were incubated overnight at 37° C. The restriction enzymes were then heat inactivated for 20 minutes at 65° C., before ligation.

Ligation reactions were carried out at 4° C. overnight as follows: 2 µl diH20, 1 µl 10× ligase buffer (New England Biolabs), 1 µl T4 DNA ligase (NEB), 2 µl vector (pBBR1MCS-5), and 4 µl insert (upper MVA expression cassette). The reaction mixture was then microdialyzed (Millipore, Billerica, Mass.). Approximately 5 µl of the ligation reactions was transformed into chemically competent E. coli TOP10 cells (Invitrogen, Carlsbad, Calif.) according to the manufacturer's recommended protocol, recovered at 37° C. in LB for 1 hour, and then plated onto LB plates containing X-gal and Gentamicin at 10 µg/ml. Colonies displaying no β-galactosidase activity were selected for further analysis by PCR using primers M13 Reverse and MCM163 to confirm the presence of the insert. The plasmid from one of these colonies was purified (Qiagen) and completely sequenced (Quintara Biosciences, see Table 1 for primer sequences) to verify that it contained the complete upper MVA pathway expression cassette in the correct orientation. FIG. 183A shows a map of plasmid pDW15 (SEQ ID NO:161), expressing the upper MVA pathway polypeptides mvaE and mvaS from Enterobacter faecalis. FIGS. 183B-D show the sequence of pDW15.

TABLE 22

| PCR and Sequencing Primers | |
|---|---|
| Upper5'XhoI | atgctcgagctgttgacaattaatcatccggctc (SEQ ID NO: 164) |
| Upper3'XbaI | cgatctagaaaggcccagtctttcgactgagcc (SEQ ID NO: 165) |
| MCM163 | GGATTTTGGCCATTTCCAGCTT (SEQ ID NO: 166) |
| CF07-58 | atgaaaacagtagttattattgatgc (SEQ ID NO: 97) |

TABLE 22-continued

PCR and Sequencing Primers

| | | |
|---|---|---|
| CF07-59 | cttaaatcatttaaaatagc | (SEQ ID NO: 168) |
| CF07-82 | atgacaattgggattgataaaattag | (SEQ ID NO: 99) |
| CF07-86 | gaaatagccccattagaagtatc | (SEQ ID NO: 101) |
| CF07-87 | ttgccaatcatatgattgaaaatc | (SEQ ID NO: 102) |
| CF07-88 | gctatgcttcattagatccttatcg | (SEQ ID NO: 103) |
| CF07-89 | gaaacctacatccaatcttttgccc | (SEQ ID NO: 104) |

Construction of Strains MCM518-521 and 528-531: Lambda Promoters Driving integrated mKKDyI.

Primers MCM120 and MCM224 were used to amplify the resistance cassette from the GeneBridges FRT-gb2-Cm-FRT template using Stratagene Herculase II Fusion kit according to the manufacturer's protocol. Four 50 µL PCR reactions were cycled as follows: 95° C./2 minutes; 30 cycles of 95° C./20 seconds, 55° C./20 seconds, 72° C./1 minute; 72° C./3 minutes; and cooled to 4° C. The four reactions were pooled and purified on a Qiagen PCR column according to the manufacturer's protocol and eluted with 60 µL Elution Buffer at 55° C.

Plasmid pRedET-carb (GeneBridges) was electroporated into MCM446 (*E. coli* BL21 cmR-gi1.6mKKDyI A1-3 (A), constructed as described in International Publication No. WO 2009/076676 A2, which is incorporated herein by reference) as described elsewhere herein. Transformants were recovered by shaking for one hour in SOC medium (Invitrogen) at 30° C. and then selected on L agar containing carbenicillin (50 ug/mL) plates at 30° C. overnight. A carbenicillin resistant colony was frozen as MCM508.

Strain MCM508 was grown from a fresh streak in 5 mL L Broth containing carbenicillin (50 µg/mL) at 30° C. to an OD600 of ~0.5. 40 mM L-arabinose was added and culture was incubated at 37° C. for 1.5 hours. Cells were harvested and electroporated with 3 µL of purified amplicons as previously, and then recovered in 500 µL SOC at 37° C. for 1.5-3 hours. Transformants were selected on L agar plates containing 10 µg/ml kanamycin at 37° C.

Recombination of the amplicon at the target locus was confirmed by PCR with primers GB-DW (SEQ ID NO:177) and MCM208 (SEQ ID NO:175). The resulting amplicons were sequenced to identify four clones with the sequences below. Carbenicillin-sensitive clones were frozen as strains MCM518-521.

MCM518-521 were restreaked on L agar containing 10 µg/ml kanamycin and grown overnight at 37° C.

Strains MCM518-521 were cultured in L Broth containing kanamycin (10 µg/mL) at 37° C. and then electrotransformed with plasmid pCP20. Cells were recovered in 500 µL SOC, shaking at 30° C. for 1 hour. Transformants were selected on L agar containing carbenicillin (50 µg/mL) plates at 30° C. overnight. The following morning a colony from each transformation was grown at 30° C. in liquid LB/carbenicillin (50 µg/mL) until visibly turbid. The culture was then shifted to 37° C. for at least 3 hours. Cells were streaked from this culture onto L agar plates and grown overnight at 37° C.

The following day colonies were patched to L agar, L agar containing carbenicillin (50 µg/mL), and L agar containing kanamycin (10 µg/ml). Clones that grew on neither carbenicillin (50 µg/mL) nor kanamycin (10 µg/ml) were cultured in liquid LB from the patch on L agar and frozen as MCM528-531.

Strain Genotypes

| Strain | Description | Parent |
|---|---|---|
| MCM508 | BL21 gi1.6-mKKDyI + predet.-carb | MCM446 |
| MCM518 | BL21 neo-PL.6-mKKDyI, clone10 | MCM508 |
| MCM519 | BL21 neo-PL.0-mKKDyI, clone11 | MCM508 |
| MCM520 | BL21 neo-PL.0-mKKDyI (bad RBS in front of mMVK), clone13 | MCM508 |
| MCM521 | BL21 neo-PL.2-mKKDyI, clone15 | MCM508 |
| MCM528 | BL21 PL.6-mKKDyI, loopedout | MCM518 |
| MCM529 | BL21 PL.0-mKKDyI, loopedout | MCM519 |
| MCM530 | BL21 PL.0-mKKDyl (bad RBS in front of mMVK), loopedout | MCM520 |
| MCM531 | BL21 PL.2-mKKDyI, loopedout | MCM521 |

Primers

MCM120 (SEQ ID NO: 113)

aaagtagccgaagatgacggtttgtcacatggagttggcaggatgtttgattaaaagcAATTAACCCTCACTAAAGGGCGG

MCM208 (SEQ ID NO: 175)

GCTCTGAATAGTGATAGAGTCA

MCM224 (SEQ ID NO 176)

taaatcttacccggcgcagaacaggataccatgtttttttacctcctttgcaccttcatggtggtcagtgcgtcctgctgatgtgctcagtatcac cgccagtggtatttaNgtcaacaccgccagagataatttatcaccgcagatggttatctgtatgttttttatatgaatttaatacgactcactatag

```
ggctcg

GB-DW
                                                                    (SEQ ID NO: 177)
Aaagaccgaccaagcgacgtctga
```

These assemblies include the new promoters inserted on the chromosome in strains MCM518-521, as well as the very beginning of the mMVK ORF. Upstream of these assemblies is sequence from the GeneBridges FRT-gb2-Cm-FRT cassette. Downstream is the remainder of the mMVK ORF and then the rest of the lower MVA pathway integron from strain MCM508.

```
MCM518:
                                                                    (SEQ ID NO: 178)
aaagaccgaccaagcgacgtctgagagctccctggcgaattcggtaccaataaaagagctttattttcatgatctgtgtgttggtttttgtgtgcggc gcggaagttcctattctctagaaagtataggaacttcctcgagccctatagtgagtcgtattaaattcatataaaaaacatacagataaccatctgcg gtgataaattatctctggcggtgttgacataaataccactggcggtgatactgagcacatcagcaggacgcactgaccaccatgaaggtgcaaag gaggtaaaaaaacatggtatcctgttctgcgccgggtaagatttacctgttcggtgaacacgccgtagtttatggcgaaactgcaattgcgtgtgc ggtggaactgcgtacccgtgttcgcgcggaactcaatgactctatcactattcagagc.

MCM519:
                                                                    (SEQ ID NO: 179)
aaagaccgaccaagcgacgtctgagagctccctggcgaattcggtaccaataaaagagctttattttcatgatctgtgtgttggtttttgtgtgcggc gcggaagttcctattctctagaaagtataggaacttcctcgagccctatagtgagtcgtattaaattcatataaaaaacatacagataaccatctgcg gtgataaattatctctggcggtgttgacctaaataccactggcggtgatactgagcacatcagcaggacgcactgaccaccatgaaggtgcaaag gaggtaaaaaaacatggtatcctgttctgcgccgggtaagatttacctgttcggtgaacacgccgtagtttatggcgaaactgcaattgcgtgtgc ggtggaactgcgtacccgtgttcgcgcggaactcaatgactctatcactattcagagc.

MCM520:
                                                                    (SEQ ID NO: 180)
aaagaccgaccaagcgacgtctgagagctccctggcgaattcggtaccaataaaagagctttattttcatgatctgtgtgttggtttttgtgtgcggc gcggaagttcctattctctagaaagtataggaacttcctcgagccctatagtgagtcgtattaaattcatataaaaaacatacagataaccatctgcg gtgataaattatctctggcggtgttgacctaaataccactggcggtgatactgagcacatcagcaggacgcactgaccaccatgaaggtgcaaag gtaaaaaaacatggtatcctgttctgcgccgggtaagatttacctgttcggtgaacacgccgtagtttatggcgaaactgcaattgcgtgtgcggtg gaactgcgtacccgtgttcgcgcggaactcaatgactctatcactattcagagc.

MCM521:
                                                                    (SEQ ID NO: 181)
aaagaccgaccaagcgacgtctgagagctccctggcgaattcggtaccaataaaagagctttattttcatgatctgtgtgttggtttttgtgtgcggc gcggaagttcctattctctagaaagtataggaacttcctcgagccctatagtgagtcgtattaaattcatataaaaaacatacagataaccatctgcg gtgataaattatctctggcggtgttgacgtaaataccactggcggtgatactgagcacatcagcaggacgcactgaccaccatgaaggtgcaaa ggaggtaaaaaaacatggtatcctgttctgcgccgggtaagatttacctgttcggtgaacacgccgtagtttatggcgaaactgcaattgcgtgtg cggtggaactgcgtacccgtgttcgcgcggaactcaatgactctatcactattcagagc.
```

Deletion of glpK and gldA in MCM531.

A P1 lysate was made of strain JW3897 (glpK::Kan) or JW5556 (gldA::Kan) from the Keio collection (Baba et al. 2006). The gldA:Kan P1 lysate was used to transduce MCM531 and transductants were selected on L agar containing kanamycin (10 µg/mL). 3 colonies were screened by PCR using primers CMP5 (SEQ ID NO:184) and CMP6 (SEQ ID NO:185) to confirm the deletion of gldA. One correct colony was selected and designated CMP212 (MCM531gldA::Kan). The Kan antibiotic resistance marker was looped out by transforming CMP212 with pCP20, selecting transformants at 30° C. on LB+carbenicillin 50 µg/L, streaking two transformants on LB at 42° C. overnight, and, from that, selecting a colony sensitive to kanamycin and carbenicillin. The resultant strain was designated CMP219 (MCM531 gldA ML). The glpK: Kan P1 lysate was used to transduce strain CMP219 and transductants were selected on L agar containing kanamycin (10 µg/mL). Three colonies were screened by PCR using primers CMP1 (SEQ ID NO:182) and CMP3 (SEQ ID NO:183) to confirm the deletion of glpK. One correct colony was selected and designated CMP229 (CMP219 glpK::Kan).

Primers

```
                                                                    (SEQ ID NO: 182)
CMP1  GCTATTCTGATGGGGCTGATCC (SEQ ID NO: 183)
CMP3  GCCTTTATCGCCTACTGCCAGC
```

CMP5 CGTAGCGCATCAGGCAATTTTGCG (SEQ ID NO: 184)

CMP6 GTGACTTCCGAAGGTCTGGCAGC (SEQ ID NO: 185)

Construction of CMP239.

E. coli strain CMP239 is derived from E. coli BL21 harboring the pathway for the production of isoprene and the pathway for production of 1,3-propanediol. Strain CMP229 (constructed as described above) was electroporated with pEWL244 (SEQ ID NO:45 and FIGS. 158-159) and pDW15 (SEQ ID NO:161 and FIG. 183). Transformants were selected on L agar containing Carbenicillin (50 µg/mL) and Gentamycin (5 µg/mL). The resulting strain was electroporated with plasmid pSYCO109F1.1 (SEQ ID NO:163 and FIG. 185; see also US Patent Publication No. US 2008/0293119 A1, which is incorporated herein by reference, particularly with respect to disclosure relating to plasmid pSYCO109F1.1) and transformants were selected on L agar containing carbenicillin (50 µg/mL), gentamycin (5 µg/mL) and spectinomycin (50 µg/mL). The strain thus generated was named CMP239.

Restoration of pgl in CMP229.

This example describes the construction of *Escherichia coli* strains derived from BL21 transduced with P1 phage containing *E. coli* MG1655 genomic DNA and selected for recombination of a 17,257 bp piece present in MG1655 but absent in BL21 and BL21(DE3).

A P1 lysate was made of *E. coli* strain MG1655. The lysate was used to infect strain CMP229. Transductants were selected for by plating the cells on M9 medium supplemented with 0.5% (w/v) galactose (the galactose utilization operon is adjacent to the pgl gene). Each liter of M9 medium contains 200 ml of M9 salts, 2 ml of sterile 1 M MgSO$_4$, and 100 µl of sterile 1 M CaCl$_2$. The volume is adjusted to 1000 ml with distilled H$_2$O, and the solution is filter sterilized. Each liter of M9 salts contains 64 g Na$_2$HPO$_4$.7H$_2$O, 15 g KH$_2$PO$_4$, 2.5 g NaCl, and 5.0 g NH$_4$Cl. The solution is stirred until the salts dissolve. Volume is then adjusted to 1000 ml with distilled H$_2$O and the solution is sterilized by autoclaving. Integration of the 17,257 bp fragment in colonies which grew on the M9+galactose was confirmed by PCR with the galMF primer (5'-GAC GCT TTC GCC AAG TCA GG; SEQ ID NO:186) and the galMR primer (5'-GTCAGGCTGGAATACTCTTCG; SEQ ID NO:187), which anneal to the galM gene as shown on FIG. 186, using the protocol. One colony was stirred in 30 µL H$_2$O and heated to 95° C. for 5 minutes. The resulting solution was spun down and 2 µL of the supernatant were used as the template in the following PCR reaction: 2 µl colony in H$_2$O, 5 µl Herculase® Buffer, 1 µl 100 mM dNTPs, 1 µl 10 µM Forward primer, 1 µl 10 µM Reverse primer, 39.5 µL H$_2$O+0.5 µL of Herculase® Enhanced DNA Polymerase from Stratagene (La Jolla, Calif.). The reactions were cycled as follows: 95° C./2 minutes; 30 cycles of 95° C./30 seconds, 52° C. (3° C. lower than lower T$^m$ of primers)/30 seconds, 72° C./60 seconds (~60 seconds/kbp); 72° C./7 minutes; then cooled to 4° C. (PCRExpress Thermocycler from ThermoHybaid). A PCR using those primers does not give a product if the template is chromosomal DNA of BL21, which lacks the 17,257 bp fragment obtained from *E. coli* strain MG1655 (see FIG. 186).

The size of the resulting PCR fragments was determined on a 0.8% E-gel (Invitrogen), using DNA Molecular Weight X (Roche) as a ladder. A correct colony was selected and designated CMP241 (BL21 PL.2 mKKDyI (MCM531) t gldAML t glpK::Kan t pgl+4).

Construction of *E. Coli* Strain CMP249.

This experiment describes the construction of a strain derived from BL21 harboring the pathway for the production of isoprene and the pathway for production of 1,3-propanediol. This strain also contain a 17,257 bp piece present in *E. coli* K12 strain MG1655 but absent in BL21 and BL21(DE3). Strain CMP241 (constructed as described above) was electroporated with pEWL244 (SEQ ID NO:45 and FIGS. 158-159) and pDW15 (SEQ ID NO:161 and FIG. 183). Transformants were selected on L agar containing Carbenicillin (50 µg/mL) and Gentamycin (5 µg/mL). The resulting strain was electroporated with plasmid pSYCO109F1.1 and transformants were selected on L agar containing carbenicillin (50 µg/mL), gentamycin (5 µg/mL) and spectinomycin (50 µg/mL). The strain thus generated was named CMP249.

Co-Production of Isoprene and 1,3-Propanediol (1,3-PDO) by *E. Coli* Strain CMP249.

CMP249 was tested in shake flasks for the production of both isoprene and 1,3-PDO.

Culture Conditions.

Shake flask experiments were done in 250 ml Erlenmeyer flasks containing 25 mL TM3 medium (per liter: 13.6 g K$_2$PO$_4$, 13.6 g KH$_2$PO$_4$, 2.0 g MgSO$_4$*7H$_2$O, 2.0 g citric acid monohydrate, 0.3 g ferric ammonium citrate, 3.2 g (NH$_4$)$_2$SO$_4$, 0.2 g yeast extract, 1.0 ml 1000× Modified Trace Metal Solution, adjusted to pH 6.8, brought to final volume with H$_2$O, and filter sterilized) containing 2% glucose, 200 µM IPTG and extra yeast extract to reach a total of 1 g/L. Shake flasks were run with and without vitamin B12. Each liter of 1000× Modified Trace Metal Solution contains: citric acid*H$_2$O (4.0 g/L), MnSO$_4$*H$_2$O (3.0 g/L), NaCl (1.0 g/L), FeSO$_4$*7H$_2$O (0.10 g/L), CoCl$_2$*6H$_2$O (0.10 g/L), ZnSO$_4$*7H$_2$O (0.10 g/L), CuSO$_4$*5H$_2$O (0.010 g/L), H$_3$BO$_3$ (0.010 g/L), and Na$_2$MoO$_4$.2H$_2$O (0.010 g/L). Cultures were grown at 30° C. with shaking at 250 rpm in an Infors Multitron shaker. The production of glycerol from pSYCO109 was driven by an IPTG-inducible Trc promoter (inducible in the presence of the product of the lad gene), while the production of 1,3-PDO was induced by the addition of vitamin B$_{12}$ (at concentrations ranging from 5-125 mg/mL). The production of isoprene was induced by the addition of IPTG (for example, at 200 µM). The growth of the culture was followed by monitoring optical density (OD) at a wavelength of 600 nM.

Detection of Glycerol and 1,3-PDO.

The methods used are described in US Patent Publication No. US 2008/0176302 A1, which is incorporated herein by reference, particular with respect to methods of detecting production of 1,3-PDO by HPLC. Briefly, the conversion of glucose to 1,3-propanediol was monitored by HPLC. Analyses were performed using standard chromatography. One suitable method utilized a Waters Alliance HPLC system using R1 detection. Samples were injected onto an Aminex HPX87H column (7.8 mm×300 mm, Biorad, Hercules, Calif.) equipped with a Cation H Refill Cartridge precolumn (4.6 mm×30 mm, Biorad, Hercules, Calif.), temperature controlled at 50° C., using 5 mM H$_2$SO$_4$ as mobile phase at a flow rate of 0.4 mL/minute. The system was calibrated weekly against standards of known concentration. Typically, the retention times of glucose, glycerol, 1,3-propanediol, and acetic acid were 12.7 min, 19.0 min, 25.2 min, and 21.5 min, respectively.

Headspace Analysis for the Detection of Isoprene.

The headspace analysis was performed as described in International Patent Publication No. WO 2009/076676 A2, which is incorporated herein by reference, particularly with respect to methods of headspace analysis to detect isoprene. Briefly, one ml of a shake flask culture was transferred from to a 20 ml CTC headspace vial (Agilent vial cat#5188 2753; cap cat#5188 2759). The cap was screwed on tightly and the vial was incubated at the equivalent temperature with shaking at 250 rpm. After 30 minutes, the vials were removed from the incubator and analyzed as follows. The analysis was performed using an Agilent 6890 GC/MS system interfaced with a CTC Analytics (Switzerland) CombiPAL autosampler operating in headspace mode, An Agilent HP-5MS GC/MS column (30 m×0.25 mm; 0.25 µm film thickness) was used for separation of analytes. The sampler was set up to inject 500 µL of headspace gas. The GUMS method utilized helium as the carrier gas at a flow of 1 ml/minutes. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 200 µg/L. The limit of detection was estimated to be 50 to 100 ng/L using this method.

Shake Flask Experiments.

Shake flask experiments were run with strain CMP249. Different concentrations of vitamin B12 were tested (data not shown), with 125 mg/L and above showing the same amount of 1,3-propanediol (lower concentrations resulted in production of less 1,3-propanediol). The simultaneous production of isoprene and glycerol or 1,3-propanediol was measured. FIGS. 187A-D present data from the same set of shake flasks. FIG. 187A shows production of glycerol and 1,3-propanediol by $E.\ coli$ strain CMP249 in the presence of 200 µM IPTG. FIG. 187B shows production of isoprene by $E.\ coli$ strain CMP249 in the presence of 200 µM IPTG, plus or minus 125 mg/L vitamin B12. FIG. 187C shows an OD profile and glucose consumption by $E.\ coli$ strain CMP249 in the presence of 200 µM IPTG, plus or minus 125 mg/L vitamin B12. FIG. 187D shows molar yield of 1,3-propanediol and glycerol from strain CMP249 in the presence of 200 µM IPTG, plus or minus 125 mg/L vitamin B12. Glycerol/1,3-propanediol molar yield is calculated as follows: Molar yield=(glycerol produced (g/L)/92+1,3-propanediol produced (g/L)/76)/(glucose consumed (g/L)/180).

Example 32

Co-Production of Isoprene and 1,3-Propanediol in
$E.\ Coli$ BL21 Grown in Fed-Batch Culture at the
15-L Scale Medium Recipe (Per Liter Fermentation Medium):

7.5 g $K_2HPO_4$, 2 g $MgSO_4*7H_2O$, 2 g citric acid monohydrate, 0.3 g ferric ammonium citrate, 0.5 g yeast extract, 1 ml 1000× Modified Trace Metal Solution. All of the components were added together and dissolved in $diH_2O$. The solution was heat sterilized at 121° C. for 20 minutes, then the pH was adjusted to 7.0 with 28% ammonium hydroxide and brought to final volume. Ten g of glucose, 8 mL of Mercury Vitamin Solution, and appropriate antibiotics were added after sterilization and pH adjustment.

1000× Modified Trace Metal Solution (Per Liter):

40 g Citric Acid*$H_2O$, 30 g $MnSO_4*H_2O$, 10 g NaCl, 1 g $FeSO_4.7H_2O$, 1 g $CoCl_2*6H_2O$, 1 g $ZnSO_4.7H_2O$, 100 mg $CuSO_4.5H_2O$, 100 mg $H_3BO_3$, 100 mg $NaMoO_4.2H_2O$. Each component was dissolved one at a time in $diH_2O$, the pH was adjusted to 3.0 with HCl/NaOH, the solution was brought to final volume, and then filter sterilized with a 0.22 micron filter.

Mercury Vitamin Solution (Per Liter):

1.0 g Thiamine hydrochloride, 1.0 g D-(+)-biotin, 1.0 g nicotinic acid, 4.8 g D-pantothenic acid, 4.0 g pyridoxine hydrochloride. Each component was dissolved one at a time in diH2O, the pH was adjusted to 3.0 with HCl/NaOH, the solution was brought to final volume and filter sterilized with a 0.22 micron filter.

Feed Solution (Per Kilogram):

0.57 kg Glucose, 0.38 kg $diH_2O$, 7.5 g $K_2HPO_4$, and 10 g 100% Foamblast. All components were mixed together and autoclaved. 5.6 mL Macro Salt Solution, 0.8 mL 1000× Modified Trace Metal Solution, and 6.7 mL Mercury Vitamin Solution were added after the solution had cooled to 25° C.

Macro Salt Solution (Per Liter):

296 g $MgSO_4*7H_2O$, 296 g citric acid monohydrate, and 49.6 g ferric ammonium citrate were dissolved in water, brought to final volume and filter sterilized with a 0.22 micron filter.

This experiment monitors isoprene and 1,3-propanediol formation from glucose at the desired fermentation pH (7.0) and temperature (34° C.). Fermentation was performed in a 15-L bioreactor with $E.\ coli$ BL21 cells of strain CMP239 (prepared as described above). Strain CMP239 expresses the upper mevalonic acid (MVA) pathway (pDW15; see Example 30 above), the integrated lower MVA pathway (PL.2 mKKDyI), mevalonate kinase from $M.\ mazei$ and truncated isoprene synthase from $P.\ alba$ (pTrcAlba(MEA) mMVK (pDW34)), and the genes required for 1,3-propanediol production (pSYCO109F1.1), without restoration of the pgl gene. A frozen vial of $E.\ coli$ strain CMP239 was thawed and inoculated into tryptone-yeast extract medium. After the inoculum grew to optical density 1.0, measured at 550 nm ($OD_{550}$), 500 mL was used to inoculate a 15-L bioreactor and bring the initial tank volume to 5-L.

The feed solution was fed at an exponential rate until a top feed rate of 5.8 g/minute was reached. After this time, the glucose feed was adjusted to meet metabolic demands at rates less than or equal to 5.8 g/min. The total amount of glucose delivered to the bioreactor was 4.2 kg over 37 hours of fermentation. Induction was achieved by adding isopropyl-beta-D-1-thiogalactopyranoside (IPTG) in a stepwise fashion shown in Table 23.

Two shots of 208 mg of vitamin B12 were administered at 12.8 and 35.8 hours. The $OD_{550}$ profile within the bioreactor over time is shown in FIG. 188. The isoprene level in the off gas from the bioreactor was determined using a Hiden mass spectrometer. The isoprene titer increased over the course of the fermentation to a maximum value of 2.2 g/L at 37 hrs (FIG. 189). The total amount of isoprene produced during the 37 hour fermentation was 17.7 g and the time course of production is shown in FIG. 190. The time course of isoprene specific productivity is shown in FIG. 191. The 1,3-propanediol titer increased over the course of the fermentation to a maximum value of 53.3 g/L at 37 hrs (FIG. 192). The total amount of 1,3-propanediol produced during the 37 hour fermentation was 507.9 g and the time course of production is shown in FIG. 193. The time course of 1,3-propanediol specific productivity is shown in FIG. 194. The glycerol titer increased over the course of the fermentation to a maximum value of 27.3 g/L at 37 hours (FIG. 195). The total amount of glycerol produced during the 37 hour fermentation was 259.8 g and the time course of production is shown in FIG. 196. The time course of glycerol specific productivity is shown in FIG. 197. Final product yields are shown in Table 24.

TABLE 23

IPTG additions during the fermentation.

| Time (hr) | Optical Density (550 nm) | IPTG concentration (uM) |
|---|---|---|
| 5.3 | 25.0 | 51.1 |
| 17.8 | 110.0 | 95.9 |
| 18.4 | 122.0 | 138.4 |
| 24.3 | 182.0 | 207.0 |
| 31.1 | 195.0 | 261.0 |

TABLE 24

Product yields after 37 hours of fermentation.

|  | Isoprene | 1,3-Propanediol | Glycerol |
|---|---|---|---|
| Mole carbon %, product C/total C * 100 | 1.0 | 14.9 | 7.2 |
| Weight %, g product/g glucose * 100 | 0.4 | 12.7 | 6.5 |

APPENDIX 1

Exemplary 1-deoxy-D-xylulose-5-phosphate Synthase Nucleic Acids and Polypeptides ATH: AT3G21500(DXPS1)
AT4G15560(CLA1) AT5G11380(DXPS3)
OSA: 4338768 4340090 4342614
CME: CMF089C
PFA: MAL13P1.186
TAN: TA20470
TPV: TP01_0516
ECO: b0420(dxs)
ECJ: JW0410(dxs)
ECE: Z0523(dxs)
ECS: ECs0474
ECC: c0531(dxs)
ECI: UTI89_C0443(dxs)
ECP: ECP_0479
ECV: APECO1_1590(dxs)
ECW: EcE24377A_0451(dxs)
ECX: EcHS_A0491
STY: STY0461(dxs)
STT: t2441(dxs)
SPT: SPA2301(dxs)
SEC: SC0463(dxs)
STM: STM0422(dxs)
YPE: YPO3177(dxs)
YPK: y1008(dxs)
YPM: YP_0754(dxs)
YPA: YPA_2671
MSU: MS1059(dxs)
APL: APL_0207(dxs)
XFA: XF2249
XFT: PD1293(dxs)
XCC: XCC2434(dxs)
XCB: XC_1678
XCV: XCV2764(dxs)
XAC: XAC2565(dxs)
XOO: XOO2017(dxs)
XOM: XOO_1900(XOO1900)
VCH: VC0889
VVU: VV1_0315
VVY: VV0868
VPA: VP0686
VFI: VF0711
PPR: PBPRA0805
PAE: PA4044(dxs)
PAU: PA14_11550(dxs)
PAP: PSPA7_1057(dxs)
PPU: PP_0527(dxs)
PST: PSPTO_0698(dxs)
PSB: Psyr_0604
PSP: PSPPH_0599(dxs)
PFL: PFL_5510(dxs)
PFO: Pfl_5007
PEN: PSEEN0600(dxs)
PMY: Pmen_3844
PAR: Psyc_0221(dxs)
YPN: YPN_0911
YPP: YPDSF_2812
YPS: YPTB0939(dxs)
YPI: YpsIP31758_3112(dxs)
SFL: SF0357(dxs)
SFX: S0365(dxs)
SFV: SFV_0385(dxs)
SSN: SSON_0397(dxs)
SBO: SBO_0314(dxs)
SDY: SDY_0310(dxs)
ECA: ECA1131(dxs)
PLU: plu3887(dxs)
BUC: BU464(dxs)
BAS: BUsg448(dxs)
WBR: WGLp144(dxs)
SGL: SG0656
KPN: KPN_00372(dxs)
BFL: Bfl238(dxs)
BPN: BPEN_244(dxs)
HIN: HI1439(dxs)
HIT: NTHI1691(dxs)
HIP: CGSHiEE_04795
HIQ: CGSHiGG_01080
HDU: HD0441(dxs)
HSO: HS_0905(dxs)
PMU: PM0532(dxs)
ACI: ACIAD3247(dxs)
SON: SO_1525(dxs)
SDN: Sden_2571
SFR: Sfri_2790
SAZ: Sama_2436
SBL: Sbal_1357
SLO: Shew_2771
SHE: Shewmr4_2731
SHM: Shewmr7_2804
SHN: Shewana3_2901
SHW: Sputw3181_2831
ILO: IL2138(dxs)
CPS: CPS_1088(dxs)
PHA: PSHAa2366(dxs)
PAT: Patl_1319
SDE: Sde_3381
PIN: Ping_2240
MAQ: Maqu_2438
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
NOC: Noc_1743
AEH: Mlg_1381

-continued

PCR: Pcryo_0245
CSA: Csal_0099
ABO: ABO_2166(dxs)
AHA: AHA_3321(dxs)
BCI: BCI_0275(dxs)
RMA: Rmag_0386
VOK: COSY_0360(dxs)
NME: NMB1867
NMA: NMA0589(dxs)
NMC: NMC0352(dxs)
NGO: NGO0036
CVI: CV_2692(dxs)
RSO: RSc2221(dxs)
REU: Reut_A0882
REH: H16_A2732(dxs)
RME: Rmet_2615
BMA: BMAA0330(dxs)
BMV: BMASAVP1_1512(dxs)
BML: BMA10299_1706(dxs)
BMN: BMA10247_A0364(dxs)
BXE: Bxe_B2827
BUR: Bcep18194_B2211
BCN: Bcen_4486
BCH: Bcen2424_3879
BAM: Bamb_3250
BPS: BPSS1762(dxs)
BPM: BURPS1710b_A0842(dxs)
BPL: BURPS1106A_A2392(dxs)
BPD: BURPS668_A2534(dxs)
BTE: BTH_II0614(dxs)
CJD: JJD26997_1642(dxs)
CFF: CFF8240_0264(dxs)
CCV: CCV52592_1671(dxs)
CCV52592_1722
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
PCA: Pcar_1667
PPD: Ppro_1191 Ppro_2403
DVU: DVU1350(dxs)
DVL: Dvul_1718
DDE: Dde_2200
LIP: LI0408(dsx)
DPS: DP2700
ADE: Adeh_1097
MXA: MXAN_4643(dxs)
SAT: SYN_02456
SFU: Sfum_1418
PUB: SAR11_0611(dxs)
MLO: mlr7474
MES: Meso_0735
SME: SMc00972(dxs)
ATU: Atu0745(dxs)
ATC: AGR_C_1351
RET: RHE_CH00913(dxs)
SAL: Sala_2354
ELI: ELI_12520
GOX: GOX0252
GBE: GbCGDNIH1_0221
GbCGDNIH1_2404
RRU: Rru_A0054 Rru_A2619
MAG: amb2904
MGM: Mmc1_1048
SUS: Acid_1783
BSU: BG11715(dxs)
BHA: BH2779
BAN: BA4400(dxs)
BAR: GBAA4400(dxs)
BAA: BA_4853
BAT: BAS4081
BCE: BC4176(dxs)
BCA: BCE_4249(dxs)
BCZ: BCZK3930(dxs)
BTK: BT9727_3919(dxs)
BTL: BALH_3785(dxs)
HCH: HCH_05866(dxs)
BPE: BP2798(dxs)
BPA: BPP2464(dxs)
BBR: BB1912(dxs)
RFR: Rfer_2875
POL: Bpro_1747
PNA: Pnap_1501
AJS: Ajs_1038
MPT: Mpe_A2631
HAR: HEAR0279(dxs)
MMS: mma_0331
NEU: NE1161(dxs)
NET: Neut_1501
NMU: Nmul_A0236
EBA: ebA4439(dxs)
AZO: azo1198(dxs)
DAR: Daro_3061
TBD: Tbd_0879
MFA: Mfla_2133
HPY: HP0354(dxs)
HPJ: jhp0328(dxs)
HPA: HPAG1_0349
HHE: HH0608(dxs)
HAC: Hac_0968(dxs)
WSU: WS1996
TDN: Tmden_0475
CJE: Cj0321(dxs)
CJR: CJE0366(dxs)
CJJ: CJJ81176_0343(dxs)
CJU: C8J_0298(dxs)
RLE: RL0973(dxs)
BME: BMEI1498
BMF: BAB1_0462(dxs)
BMS: BR0436(dxs)
BMB: BruAb1_0458(dxs)
BOV: BOV_0443(dxs)
BJA: bll2651(dxs)
BRA: BRADO2161(dxs)
BBT: BBta_2479(dxs)
RPA: RPA0952(dxs)
RPB: RPB_4460
RPC: RPC_1149
RPD: RPD_4305
RPE: RPE_1067
NWI: Nwi_0633
NHA: Nham_0778
BHE: BH04350(dxs)
BQU: BQ03540(dxs)
BBK: BARBAKC583_0400(dxs)
CCR: CC_2068
SIL: SPO0247(dxs)
SIT: TM1040_2920
RSP: RSP_0254(dxsA) RSP_1134(dxs)
JAN: Jann_0088 Jann_0170
RDE: RD1_0101(dxs) RD1_0548(dxs)
MMR: Mmar10_0849
HNE: HNE_1838(dxs)
ZMO: ZMO1234(dxs) ZMO1598(dxs)
NAR: Saro_0161
LIN: lin1402(tktB)
LWE: lwe1380(tktB)
LLA: L108911(dxsA) L123365(dxsB)
LLC: LACR_1572 LACR_1843
LLM: llmg_0749(dxsB)
SAK: SAK_0263
LPL: lp_2610(dxs)
LJO: LJ0406
LAC: LBA0356
LSL: LSL_0209(dxs)
LGA: LGAS_0350
STH: STH1842
CAC: CAC2077 CA_P0106(dxs)
CPE: CPE1819
CPF: CPF_2073(dxs)
CPR: CPR_1787(dxs)
CTC: CTC01575
CNO: NT01CX_1983
CTH: Cthe_0828
CDF: CD1207(dxs)

| | |
|---|---|
| BLI: BL01523(dxs) | CBO: CBO1881(dxs) |
| BLD: BLi02598(dxs) | CBA: CLB_1818(dxs) |
| BCL: ABC2462(dxs) | CBH: CLC_1825(dxs) |
| BAY: RBAM_022600 | CBF: CLI_1945(dxs) |
| BPU: BPUM_2159 | CKL: CKL_1231(dxs) |
| GKA: GK2392 | CHY: CHY_1985(dxs) |
| GTN: GTNG_2322 | DSY: DSY2348 |
| LMO: lmo1365(tktB) | DRM: Dred_1078 |
| LMF: LMOf2365_1382(dxs) | PTH: PTH_1196(dxs) |
| SWO: Swol_0582 | PAC: PPA1062 |
| CSC: Csac_1853 | TFU: Tfu_1917 |
| TTE: TTE1298(dxs) | FRA: Francci3_1326 |
| MTA: Moth_1511 | FAL: FRAAL2088(dxs) |
| MPE: MYPE730 | ACE: Acel_1393 |
| MGA: MGA_1268(dxs) | SEN: SACE_1815(dxs) SACE_4351 |
| MTU: Rv2682c(dxs1) Rv3379c(dxs2) | BLO: BL1132(dxs) |
| MTC: MT2756(dxs) | BAD: BAD_0513(dxs) |
| MBO: Mb2701c(dxs1) Mb3413c(dxs2) | FNU: FN1208 FN1464 |
| MLE: ML1038(dxs) | RBA: RB2143(dxs) |
| MPA: MAP2803c(dxs) | CTR: CT331(dxs) |
| MAV: MAV_3577(dxs) | CTA: CTA_0359(dxs) |
| MSM: MSMEG_2776(dxs) | CMU: TC0608 |
| MMC: Mmcs_2208 | CPN: CPn1060(tktB_2) |
| CGL: NCgl1827(cgl1902) | CPA: CP0790 |
| CGB: cg2083(dxs) | CPJ: CPj1060(tktB_2) |
| CEF: CE1796 | CPT: CpB1102 |
| CDI: DIP1397(dxs) | CCA: CCA00304(dxs) |
| CJK: jk1078(dxs) | CAB: CAB301(dxs) |
| NFA: nfa37410(dxs) | CFE: CF0699(dxs) |
| RHA: RHA1_ro06843 | PCU: pc0619(dxs) |
| SCO: SCO6013(SC1C3.01) | TPA: TP0824 |
| SCO6768(SC6A5.17) | TDE: TDE1910(dxs) |
| SMA: SAV1646(dxs1) SAV2244(dxs2) | LIL: LA3285(dxs) |
| TWH: TWT484 | LIC: LIC10863(dxs) |
| TWS: TW280(Dxs) | LBJ: LBJ_0917(dxs) |
| LXX: Lxx10450(dxs) | LBL: LBL_0932(dxs) |
| CMI: CMM_1660(dxsA) | SYN: sll1945(dxs) |
| AAU: AAur_1790(dxs) | SYW: SYNW1292(Dxs) |
| SYC: syc1087_c(dxs) | PGI: PG2217(dxs) |
| SYF: Synpcc7942_0430 | CHU: CHU_3643(dxs) |
| SYD: Syncc9605_1430 | GFO: GFO_3470(dxs) |
| SYE: Syncc9902_1069 | FPS: FP0279(dxs) |
| SYG: sync_1410(dxs) | CTE: CT0337(dxs) |
| SYR: SynRCC307_1390(dxs) | CPH: Cpha266_0671 |
| SYX: SynWH7803_1223(dxs) | PVI: Cvib_0498 |
| CYA: CYA_1701(dxs) | PLT: Plut_0450 |
| CYB: CYB_1983(dxs) | DET: DET0745(dxs) |
| TEL: tll0623 | DEH: cbdb_A720(dxs) |
| GVI: gll0194 | DRA: DR_1475 |
| ANA: alr0599 | DGE: Dgeo_0994 |
| AVA: Ava_4532 | TTH: TTC1614 |
| PMA: Pro0928(dxs) | TTJ: TTHA0006 |
| PMM: PMM0907(Dxs) | AAE: aq_881 |
| PMT: PMT0685(dxs) | TMA: TM1770 |
| PMN: PMN2A_0300 | PMO: Pmob_1001 |
| PMI: PMT9312_0893 | |
| PMB: A9601_09541(dxs) | |
| PMC: P9515_09901(dxs) | |
| PMF: P9303_15371(dxs) | |
| PMG: P9301_09521(dxs) | |
| PMH: P9215_09851 | |
| PMJ: P9211_08521 | |
| PME: NATL1_09721(dxs) | |
| TER: Tery_3042 | |
| BTH: BT_1403 BT_4099 | |
| BFR: BF0873 BF4306 | |
| BFS: BF0796(dxs) BF4114 | |

Exemplary acetyl-CoA-acetyltransferase Nucleic Acids and Polypeptides

| | |
|---|---|
| HSA: 38(ACAT1) 39(ACAT2) | AFM: AFUA_6G14200 AFUA_8G04000 |
| PTR: 451528(ACAT1) | AOR: AO090103000012 AO090103000406 |
| MCC: 707653(ACAT1) 708750(ACAT2) | CNE: CNC05280 |
| MMU: 110446(Acat1) 110460(Acat2) | UMA: UM03571.1 |
| RNO: 25014(Acat1) | DDI: DDB_0231621 |

-continued

| | |
|---|---|
| CFA: 484063(ACAT2) 489421(ACAT1) | PFA: PF14_0484 |
| GGA: 418968(ACAT1) | TET: TTHERM_00091590 |
| 421587(RCJMB04_34i5) | TTHERM_00277470 TTHERM_00926980 |
| XLA: 379569(MGC69098) | TCR: 511003.60 |
| 414622(MGC81403) 414639(MGC81256) | ECO: b2224(atoB) |
| 444457(MGC83664) | ECJ: JW2218(atoB) JW5453(yqeF) |
| XTR: 394562(acat2) | ECE: Z4164(yqeF) |
| DRE: 30643(acat2) | ECS: ECs3701 |
| SPU: 759502(LOC759502) | ECC: c2767(atoB) c3441(yqeF) |
| DME: Dmel_CG10932 Dmel_CG9149 | ECI: UTI89_C2506(atoB) |
| CEL: T02G5.4 T02G5.7 T02G5.8(kat-1) | UTI89_C3247(yqeF) |
| ATH: AT5G48230(ACAT2/EMB1276) | ECP: ECP_2268 ECP_2857 |
| OSA: 4326136 4346520 | ECV: APECO1_3662(yqeF) |
| CME: CMA042C CME087C | APECO1_4335(atoB) |
| SCE: YPL028W(ERG10) | APECO1_43352(atoB) |
| AGO: AGOS_ADR165C | ECX: EcHS_A2365 |
| PIC: PICST_31707(ERG10) | STY: STY3164(yqeF) |
| CAL: CaO19.1591(erg10) | STT: t2929(yqeF) |
| CGR: CAGL0L12364g | SPT: SPA2886(yqeF) |
| SPO: SPBC215.09c | SEC: SC2958(yqeF) |
| MGR: MGG_01755 MGG_13499 | STM: STM3019(yqeF) |
| ANI: AN1409.2 | SFL: SF2854(yqeF) |
| SFX: S3052(yqeF) | PSB: Psyr_0824 Psyr_3031 |
| SFV: SFV_2922(yqeF) | PSP: PSPPH_0850(phbA1) |
| SSN: SSON_2283(atoB) SSON_3004(yqeF) | PSPPH_2209(phbA2) |
| SBO: SBO_2736(yqeF) | PFL: PFL_1478(atoB-2) PFL_2321 |
| ECA: ECA1282(atoB) | PFL_3066 PFL_4330(atoB-2) PFL_5283 |
| ENT: Ent638_3299 | PFO: Pfl_1269 Pfl_1739 Pfl_2074 Pfl_2868 |
| SPE: Spro_0592 | PEN: PSEEN3197 PSEEN3547(fadAx) |
| HIT: NTHI0932(atoB) | PSEEN4635(phbA) |
| XCC: XCC1297(atoB) | PMY: Pmen_1138 Pmen_2036 Pmen_3597 |
| XCB: XC_2943 | Pmen_3662 Pmen_3820 |
| XCV: XCV1401(thlA) | PAR: Psyc_0252 Psyc_1169 |
| XAC: XAC1348(atoB) | PCR: Pcryo_0278 Pcryo_1236 Pcryo_1260 |
| XOO: XOO1881(atoB) | PRW: PsycPRwf_2011 |
| XOM: XOO_1778(XOO1778) | ACI: ACIAD0694 ACIAD1612 |
| VCH: VCA0690 | ACIAD2516(atoB) |
| VCO: VC0395_0630 | SON: SO_1677(atoB) |
| VVU: VV2_0494 VV2_0741 | SDN: Sden_1943 |
| VVY: VVA1043 VVA1210 | SFR: Sfri_1338 Sfri_2063 |
| VPA: VPA0620 VPA1123 VPA1204 | SAZ: Sama_1375 |
| PPR: PBPRB1112 PBPRB1840 | SBL: Sbal_1495 |
| PAE: PA2001(atoB) PA2553 PA3454 | SBM: Shew185_1489 |
| PA3589 PA3925 | SBN: Sbal195_1525 |
| PAU: PA14_38630(atoB) | SLO: Shew_1667 Shew_2858 |
| PPU: PP_2051(atoB) PP_2215(fadAx) | SPC: Sputcn32_1397 |
| PP_3754 PP_4636 | SSE: Ssed_1473 Ssed_3533 |
| PPF: Pput_2009 Pput_2403 Pput_3523 | SPL: Spea_2783 |
| Pput_4498 | SHE: Shewmr4_2597 |
| PST: PSPTO_0957(phbA-1) | SHM: Shewmr7_2664 |
| PSPTO_3164(phbA-2) | SHN: Shewana3_2771 |
| SHW: Sputw3181_2704 | REU: Reut_A0138 Reut_A1348 Reut_A1353 |
| ILO: IL0872 | Reut_B4561 Reut_B4738 Reut_B5587 |
| CPS: CPS_1605 CPS_2626 | Reut_C5943 Reut_C6062 |
| PHA: PSHAa0908 PSHAa1454(atoB) | REH: H16_A0170 H16_A0867 H16_A0868 |
| PSHAa1586(atoB) | H16_A0872 H16_A1297 |
| PAT: Patl_2923 | H16_A1438(phaA) H16_A1445(bktB) |
| SDE: Sde_3149 | H16_A1528 H16_A1713 H16_A1720 |
| PIN: Ping_0659 Ping_2401 | H16_A1887 H16_A2148 H16_B0380 |
| MAQ: Maqu_2117 Maqu_2489 Maqu_2696 | H16_B0381 H16_B0406 H16_B0662 |
| Maqu_3162 | H16_B0668 H16_B0759 H16_B1369 |
| CBU: CBU_0974 | H16_B1771 |
| LPN: lpg1825(atoB) | RME: Rmet_0106 Rmet_1357 Rmet_1362 |
| LPF: lpl1789 | Rmet_5156 |
| LPP: lpp1788 | BMA: BMA1316 BMA1321(phbA) |
| NOC: Noc_1891 | BMA1436 |
| AEH: Mlg_0688 Mlg_2706 | BMV: BMASAVP1_A1805(bktB) |
| HHA: Hhal_1685 | BMASAVP1_A1810(phbA) |
| HCH: HCH_05299 | BML: BMA10299_A0086(phbA) |
| CSA: Csal_0301 Csal_3068 | BMA10299_A0091 |
| ABO: ABO_0648(fadAx) | BMN: BMA10247_1076(bktB) |
| MMW: Mmwyl1_0073 Mmwyl1_3021 | BMA10247_1081(phbA) |
| Mmwyl1_3053 Mmwyl1_3097 | BXE: Bxe_A2273 Bxe_A2335 Bxe_A2342 |
| Mmwyl1_4182 | Bxe_A4255 Bxe_B0377 Bxe_B0739 |
| AHA: AHA_2143(atoB) | Bxe_C0332 Bxe_C0574 Bxe_C0915 |
| CVI: CV_2088(atoB) CV_2790(phaA) | BVI: Bcep1808_0519 Bcep1808_1717 |
| RSO: RSc0276(atoB) RSc1632(phbA) | Bcep1808_2877 Bcep1808_3594 |
| RSc1637(bktB) RSc1761(RS02948) | Bcep1808_4015 Bcep1808_5507 |
| | Bcep1808_5644 |

-continued

BUR: Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332
BCN: Bcen_1553 Bcen_1599 Bcen_2158 Bcen_2563 Bcen_2998 Bcen_6289
BCH: Bcen2424_0542 Bcen2424_1790 Bcen2424_2772 Bcen2424_5368 Bcen2424_6232 Bcen2424_6276
BAM: Bamb_0447 Bamb_1728 Bamb_2824 Bamb_4717 Bamb_5771 Bamb_5969
BPS: BPSL1426 BPSL1535(phbA) BPSL1540
BPM: BURPS1710b_2325(bktB) BURPS1710b_2330(phbA) BURPS1710b_2453(atoB-2)
BPL: BURPS1106A_2197(bktB) BURPS1106A_2202(phbA)
BPD: BURPS668_2160(bktB) BURPS668_2165(phbA)
BTE: BTH_I2144 BTH_I2256 BTH_I2261
PNU: Pnuc_0927
BPE: BP0447 BP0668 BP2059
BPA: BPP0608 BPP1744 BPP3805 BPP4216 BPP4361
BBR: BB0614 BB3364 BB4250 BB4804 BB4947
BBA: Bd0404(atoB) Bd2095
DOL: Dole_0671 Dole_1778 Dole_2160 Dole_2187
ADE: Adeh_0062 Adeh_2365
AFW: Anae109_0064 Anae109_1504
MXA: MXAN_3791
SAT: SYN_02642
SFU: Sfum_2280 Sfum_3582
RPR: RP737
RCO: RC1134 RC1135
RFE: RF_0163(paaJ)
RBE: RBE_0139(paaJ)
RAK: A1C_05820
RBO: A1I_07215
RCM: A1E_04760
PUB: SAR11_0428(thlA)
MLO: mlr3847
MES: Meso_3374
PLA: Plav_1573 Plav_2783
SME: SMa1450 SMc03879(phbA)
SMD: Smed_0499 Smed_3117 Smed_5094 Smed_5096
ATU: Atu2769(atoB) Atu3475
ATC: AGR_C_5022(phbA) AGR_L_2713
RET: RHE_CH04018(phbAch) RHE_PC00068(ypc00040) RHE_PF00014(phbAf)
RLE: RL4621(phaA) pRL100301 pRL120369
BME: BMEI0274 BMEII0817
SIL: SPO0142(bktB) SPO0326(phbA) SPO0773 SPO3408
SIT: TM1040_0067 TM1040_2790 TM1040_3026 TM1040_3735
RSP: RSP_0745 RSP_1354 RSP_3184
RSH: Rsph17029_0022 Rsph17029_2401 Rsph17029_3179 Rsph17029_3921
RSQ: Rsph17025_0012 Rsph17025_2466 Rsph17025_2833
JAN: Jann_0262 Jann_0493 Jann_4050
RDE: RD1_0025 RD1_0201(bktB) RD1_3394(phbA)
PDE: Pden_2026 Pden_2663 Pden_2870 Pden_2907 Pden_4811 Pden_5022
DSH: Dshi_0074 Dshi_3066 Dshi_3331
MMR: Mmar10_0697
HNE: HNE_2706 HNE_3065 HNE_3133
NAR: Saro_0809 Saro_1069 Saro_1222 Saro_2306 Saro_2349
SAL: Sala_0781 Sala_1244 Sala_2896 Sala_3158
RFR: Rfer_0272 Rfer_1000 Rfer_1871 Rfer_2273 Rfer_2561 Rfer_2594 Rfer_3839
POL: Bpro_1577 Bpro_2140 Bpro_3113 Bpro_4187
PNA: Pnap_0060 Pnap_0458 Pnap_0867 Pnap_1159 Pnap_2136 Pnap_2804
AAV: Aave_0031 Aave_2478 Aave_3944 Aave_4368
AJS: Ajs_0014 Ajs_0124 Ajs_1931 Ajs_2073 Ajs_2317 Ajs_3548 Ajs_3738 Ajs_3776
VEI: Veis_1331 Veis_3818 Veis_4193
DAC: Daci_0025 Daci_0192 Daci_3601 Daci_5988
MPT: Mpe_A1536 Mpe_A1776 Mpe_A1869 Mpe_A3367
HAR: HEAR0577(phbA)
MMS: mma_0555
NEU: NE2262(bktB)
NET: Neut_0610
EBA: ebA5202 p2A409(tioL)
AZO: azo0464(fadA1) azo0469(fadA2) azo2172(thlA)
DAR: Daro_0098 Daro_3022
HPA: HPAG1_0675
HAC: Hac_0958(atoB)
GME: Gmet_1719 Gmet_2074 Gmet_2213 Gmet_2268 Gmet_3302
GUR: Gura_3043
BMF: BAB1_1783(phbA-1) BAB2_0790(phbA-2)
BMS: BR1772(phbA-1) BRA0448(phbA-2)
BMB: BruAb1_1756(phbA-1) BruAb2_0774(phbA-2)
BOV: BOV_1707(phbA-1)
OAN: Oant_1130 Oant_3107 Oant_3718 Oant_4020
BJA: bll0226(atoB) bll3949 bll7400 bll7819 blr3724(phbA)
BRA: BRADO0562(phbA) BRADO0983(pimB) BRADO3110 BRADO3134(atoB)
BBT: BBta_3558 BBta_3575(atoB) BBta_5147(pimB) BBta_7072(pimB) BBta_7614(phbA)
RPA: RPA0513(pcaF) RPA0531 RPA3715(pimB)
RPB: RPB_0509 RPB_0525 RPB_1748
RPC: RPC_0504 RPC_0636 RPC_0641 RPC_0832 RPC_1050 RPC_2005 RPC_2194 RPC_2228
RPD: RPD_0306 RPD_0320 RPD_3105 RPD_3306
RPE: RPE_0168 RPE_0248 RPE_3827
NWI: Nwi_3060
XAU: Xaut_3108 Xaut_4665
CCR: CC_0510 CC_0894 CC_3462

MAG: amb0842
MGM: Mmc1_1165
ABA: Acid345_3239
BSU: BG11319(mmgA) BG13063(yhfS)
BHA: BH1997 BH2029 BH3801(mmgA)
BAN: BA3687 BA4240 BA5589
BAR: GBAA3687 GBAA4240 GBAA5589
BAA: BA_0445 BA_4172 BA_4700
BAT: BAS3418 BAS3932 BAS5193
BCE: BC3627 BC4023 BC5344
BCA: BCE_3646 BCE_4076 BCE_5475
BCZ: BCZK3329(mmgA) BCZK3780(thl) BCZK5044(atoB)
BCY: Bcer98_2722 Bcer98_3865
BTK: BT9727_3379(mmgA)
BT9727_3765(thl) BT9727_5028(atoB)
BTL: BALH_3262(mmgA) BALH_3642(fadA) BALH_4843(atoB)
BLI: BL03925(mmgA)
BLD: BLi03968(mmgA)
BCL: ABC0345 ABC2989 ABC3617

SWI: Swit_0632 Swit_0752 Swit_2893
Swit_3602 Swit_4887 Swit_5019
Swit_5309
ELI: ELI_01475 ELI_06705 ELI_12035
GBE: GbCGDNIH1_0447
ACR: Acry_1847 Acry_2256
RRU: Rru_A0274 Rru_A1380 Rru_A1469
Rru_A1946 Rru_A3387
SAM: MW0330 MW0531(vraB)
SAR: SAR0351(thl) SAR0581
SAS: SAS0330 SAS0534
SAC: SACOL0426 SACOL0622(atoB)
SAB: SAB0304(th1) SAB0526
SAA: SAUSA300_0355
SAUSA300_0560(vraB)
SAO: SAOUHSC_00336 SAOUHSC_00558
SAJ: SaurJH9_0402
SAH: SaurJH1_0412
SEP: SE0346 SE2384
SER: SERP0032 SERP0220
SHA: SH0510(mvaC) SH2417
SSP: SSP0325 SSP2145
LMO: lmo1414
LMF: LMOf2365_1433
LIN: lin1453
LWE: lwe1431
LLA: L11745(thiL) L25946(fadA)
LLC: LACR_1665 LACR_1956
LLM: llmg_0930(thiL)
SPY: SPy_0140 SPy_1637(atoB)
SPZ: M5005_Spy_0119 M5005_Spy_0432
M5005_Spy_1344(atoB)
SPM: spyM18_0136 spyM18_1645(atoB)
SPG: SpyM3_0108 SpyM3_1378(atoB)
SPS: SPs0110 SPs0484

STH: STH2913 STH725 STH804
CAC: CAC2873 CA_P0078(thiL)
CPE: CPE2195(atoB)
CPF: CPF_2460
CPR: CPR_2170
CTC: CTC00312
CNO: NT01CX_0538 NT01CX_0603
CDF: CD1059(thlA1) CD2676(thlA2)
CBO: CBO3200(thl)
CBE: Cbei_0411 Cbei_3630
CKL: CKL_3696(thlA1) CKL_3697(thlA2)
CKL_3698(thlA3)
AMT: Amet_4630
AOE: Clos_0084 Clos_0258
CHY: CHY_1288 CHY_1355(atoB)
CHY_1604 CHY_1738
DSY: DSY0632 DSY0639 DSY1567
DSY1710 DSY2402 DSY3302
DRM: Dred_0400 Dred_1491 Dred_1784
Dred_1892
SWO: Swol_0308 Swol_0675 Swol_0789
Swol_1486 Swol_1934 Swol_2051
TTE: TTE0549(paaJ)
MTA: Moth_1260
MTU: Rv1135A Rv1323(fadA4)
Rv3546(fadA5)
MTC: MT1365(phbA)
MBO: Mb1167 Mb1358(fadA4)
Mb3576(fadA5) Mb3586c(fadA6)
NFA: nfa10750(fadA4)
RHA: RHA1_ro01455 RHA1_ro01623
RHA1_ro01876 RHA1_ro02517(catF)
RHA1_ro03022 RHA1_ro03024
RHA1_ro03391 RHA1_ro03892
RHA1_ro04599 RHA1_ro05257
RHA1_ro08871
SCO: SCO5399(SC8F4.03)
SMA: SAV1384(fadA5) SAV2856(fadA1)
ART: Arth_1160 Arth_2986 Arth_3268
Arth_4073
NCA: Noca_1371 Noca_1797 Noca_1828
Noca_2764 Noca_4142

ABC3891(mmgA)
BAY: RBAM_022450
BPU: BPUM_2374(yhfS) BPUM_2941
BPUM_3373
OIH: OB0676 OB0689 OB2632 OB3013
GKA: GK1658 GK3397
SAU: SA0342 SA0534(vraB)
SAV: SAV0354 SAV0576(vraB)
SPH: MGAS10270_Spy0121
MGAS10270_Spy0433
MGAS10270_Spy1461(atoB)
SPI: MGAS10750_Spy0124
MGAS10750_Spy0452
MGAS10750_Spy1453(atoB)
SPJ: MGAS2096_Spy0123
MGAS2096_Spy0451
MGAS2096_Spy1365(atoB)
SPK: MGAS9429_Spy0121
MGAS9429_Spy0431
MGAS9429_Spy1339(atoB)
SPF: SpyM50447(atoB2)
SPA: M6_Spy0166 M6_Spy0466
M6_Spy1390
SPB: M28_Spy0117 M28_Spy0420
M28_Spy1385(atoB)
SAK: SAK_0568
LJO: LJ1609
LAC: LBA0626(thiL)
LSA: LSA1486
LDB: Ldb0879
LBU: LBUL_0804
LBR: LVIS_2218
LCA: LSEI_1787
LGA: LGAS_1374
LRE: Lreu_0052
EFA: EF1364
OOE: OEOE_0529
MBB: BCG_1197 BCG_1385(fadA4)
BCG_3610(fadA5) BCG_3620c(fadA6)
MLE: ML1158(fadA4)
MPA: MAP2407c(fadA3) MAP2436c(fadA4)
MAV: MAV_1544 MAV_1573 MAV_1863
MAV_5081
MSM: MSMEG_2224 MSMEG_4920
MUL: MUL_0357
MVA: Mvan_1976 Mvan_1988 Mvan_4305
Mvan_4677 Mvan_4891
MGI: Mflv_1347 Mflv_1484 Mflv_2040
Mflv_2340 Mflv_4356 Mflv_4368
MMC: Mmcs_1758 Mmcs_1769 Mmcs_3796
Mmcs_3864
MKM: Mkms_0251 Mkms_1540
Mkms_1805 Mkms_1816 Mkms_2836
Mkms_3159 Mkms_3286 Mkms_3869
Mkms_3938 Mkms_4227 Mkms_4411
Mkms_4580 Mkms_4724 Mkms_4764
Mkms_4776
MJL: Mjls_0231 Mjls_1739 Mjls_1750
Mjls_2819 Mjls_3119 Mjls_3235
Mjls_3800 Mjls_3850 Mjls_4110
Mjls_4383 Mjls_4705 Mjls_4876
Mjls_5018 Mjls_5063 Mjls_5075
CGL: NCgl2309(cgl2392)
CGB: cg2625(pcaF)
CEF: CE0731 CE2295
CJK: jk1543(fadA3)
BGA: BG0110(fadA)
BAF: BAPKO_0110(fadA)
LIL: LA0457(thiL1) LA0828(thiL2)
LA4139(fadA)
LIC: LIC10396(phbA)
LBJ: LBJ_2862(paaJ-4)
LBL: LBL_0209(paaJ-4)
SYN: slr1993(phaA)
SRU: SRU_1211(atoB) SRU_1547
CHU: CHU_1910(atoB)
GFO: GFO_1507(atoB)
FJO: Fjoh_4612
FPS: FP0770 FP1586 FP1725

-continued

TFU: Tfu_1520 Tfu_2394
FRA: Francci3_3687
FRE: Franean1_1044 Franean1_2711 Franean1_2726 Franean1_3929 Franean1_4037 Franean1_4577
FAL: FRAAL2514 FRAAL2618 FRAAL5910(atoB)
ACE: Acel_0626 Acel_0672
SEN: SACE_1192(mmgA) SACE_2736(fadA6) SACE_4011(catF) SACE_6236(fadA4)
STP: Strop_3610
SAQ: Sare_1316 Sare_3991
RXY: Rxyl_1582 Rxyl_1842 Rxyl_2389 Rxyl_2530
FNU: FN0495
TVO: TVN0649
PTO: PTO1505
APE: APE_2108
SSO: SSO2377(acaB-4)
STO: ST0514
SAI: Saci_0963 Saci_1361(acaB1)
MSE: Msed_0656
PAI: PAE1220
PIS: Pisl_0029 Pisl_1301
PCL: Pcal_0781
PAS: Pars_0309 Pars_1071
CMA: Cmaq_1941

RRS: RoseRS_3911 RoseRS_4348
RCA: Rcas_0702 Rcas_3206
HAU: Haur_0522
DRA: DR_1072 DR_1428 DR_1960 DR_2480 DR_A0053
DGE: Dgeo_0755 Dgeo_1305 Dgeo_1441 Dgeo_1883
TTH: TTC0191 TTC0330
TTJ: TTHA0559
TME: Tmel_1134
FNO: Fnod_0314
PMO: Pmob_0515
HMA: rrnAC0896(acaB3) rrnAC2815(aca2) rrnAC3497(yqeF) rrnB0240(aca1) rrnB0242(acaB2) rrnB0309(acaB1)
TAC: Ta0582

Exemplary HMG-CoA Synthase Nucleic Acids and Polypeptides

HSA: 3157(HMGCS1) 3158(HMGCS2)
PTR: 457169(HMGCS2) 461892(HMGCS1)
MCC: 702553(HMGCS1) 713541(HMGCS2)
MMU: 15360(Hmgcs2) 208715(Hmgcs1)
RNO: 24450(Hmgcs2) 29637(Hmgcs1)
CFA: 479344(HMGCS1) 607923(HMGCS2)
BTA: 407767(HMGCS1)
SSC: 397673(CH242-38B5.1)
GGA: 396379(HMGCS1)
XLA: 380091(hmgcs1) 447204(MGC80816)
DRE: 394060(hmgcs1)
SPU: 578259(LOC578259)
DME: Dmel_CG4311(Hmgs)
CEL: F25B4.6
ATH: AT4G11820(BAP1)
OSA: 4331418 4347614
CME: CMM189C
SCE: YML126C(ERG13)
AGO: AGOS_ADL356C
PIC: PICST_83020
CAL: CaO19_7312(CaO19.7312)
CGR: CAGL0H04081g
SPO: SPAC4F8.14c(hcs)
MGR: MGG_01026
ANI: AN4923.2
AFM: AFUA_3G10660 AFUA_8G07210
AOR: AO090003000611 AO090010000487
SAU: SA2334(mvaS)
SAV: SAV2546(mvaS)
SAM: MW2467(mvaS)
SAR: SAR2626(mvaS)
SAS: SAS2432
SAC: SACOL2561
SAB: SAB2420(mvaS)
SAA: SAUSA300_2484
SAO: SAOUHSC_02860
SAJ: SaurJH9_2569
SAH: SaurJH1_2622
SEP: SE2110
SER: SERP2122
SHA: SH0508(mvaS)
SSP: SSP0324
LMO: lmo1415
LMF: LMOf2365_1434(mvaS)

CNE: CNC05080 CNG02670
UMA: UM05362.1
ECU: ECU10_0510
DDI: DDBDRAFT_0217522
DDB_0219924(hgsA)
TET: TTHERM_00691190
TBR: Tb927.8.6110
YPE: YPO1457
YPK: y2712(pksG)
YPM: YP_1349(pksG)
YPA: YPA_0750
YPN: YPN_2521
YPP: YPDSF_1517
YPS: YPTB1475
CBD: COXBU7E912_1931
TCX: Tcr_1719
DNO: DNO_0799
BMA: BMAA1212
BPS: BPSS1002
BPM: BURPS1710b_A2613
BPL: BURPS1106A_A1384
BPD: BURPS668_A1470
BTE: BTH_II1670
MXA: MXAN_3948(tac) MXAN_4267(mvaS)
BSU: BG10926(pksG)
OIH: OB2248
SPJ: MGAS2096_Spy0759(mvaS1)
SPK: MGAS9429_Spy0743(mvaS1)
SPF: SpyM51121(mvaS)
SPA: M6_Spy0704
SPB: M28_Spy0667(mvaS.1)
SPN: SP_1727
SPR: spr1571(mvaS)
SPD: SPD_1537(mvaS)
SAG: SAG1316
SAN: gbs1386
SAK: SAK_1347
SMU: SMU.943c
STC: str0577(mvaS)
STL: stu0577(mvaS)
STE: STER_0621
SSA: SSA_0338(mvaS)
SSU: SSU05_1641

LIN: lin1454
LWE: lwe1432(mvaS)
LLA: L13187(hmcM)
LLC: LACR_1666
LLM: llmg_0929(hmcM)
SPY: SPy_0881(mvaS.2)
SPZ: M5005_Spy_0687(mvaS.1)
SPM: spyM18_0942(mvaS2)
SPG: SpyM3_0600(mvaS.2)
SPS: SPs1253
SPH: MGAS10270_Spy0745(mvaS1)
SPI: MGAS10750_Spy0779(mvaS1)
LRE: Lreu_0676
PPE: PEPE_0868
EFA: EF1363
OOE: OEOE_0968
LME: LEUM_1184
NFA: nfa22120
SEN: SACE_4570(pksG)
BBU: BB0683
BGA: BG0706
BAF: BAPKO_0727
FJO: Fjoh_0678
HAL: VNG1615G(mvaB)
HMA: rrnAC1740(mvaS)
HWA: HQ2868A(mvaB)
NPH: NP2608A(mvaB_1)
NP4836A(mvaB_2)
SSV: SSU98_1652
SGO: SGO_0244
LPL: lp_2067(mvaS)
LJO: LJ1607
LAC: LBA0628(hmcS)
LSA: LSA1484(mvaS)
LSL: LSL_0526
LDB: Ldb0881(mvaS)
LBU: LBUL_0806
LBR: LVIS_1363
LCA: LSEI_1785
LGA: LGAS_1372

Exemplary Hydroxymethylglutaryl-CoA Reductase Nucleic Acids and Polypeptides

HSA: 3156(HMGCR)
PTR: 471516(HMGCR)
MCC: 705479(HMGCR)
MMU: 15357(Hmgcr)
RNO: 25675(Hmgcr)
CFA: 479182(HMGCR)
BTA: 407159(HMGCR)
GGA: 395145(RCJMB04_14m24)
SPU: 373355(LOC373355)
DME: Dmel_CG10367(Hmgcr)
CEL: F08F8.2
OSA: 4347443
SCE: YLR450W(HMG2) YML075C(HMG1)
AGO: AGOS_AER152W
CGR: CAGL0L11506g
SPO: SPCC162.09c(hmg1)
ANI: AN3817.2
AFM: AFUA_1G11230 AFUA_2G03700
AOR: AO090103000311 AO090120000217
CNE: CNF04830
UMA: UM03014.1
ECU: ECU10_1720
DDI: DDB_0191125(hmgA)
DDB_0215357(hmgB)
TBR: Tb927.6.4540
TCR: 506831.40 509167.20
LMA: LmjF30.3190
SPH: MGAS10270_Spy0744
SPI: MGAS10750_Spy0778
SPJ: MGAS2096_Spy0758
SPK: MGAS9429_Spy0742
SPA: M6_Spy0703
SPN: SP_1726
SAG: SAG1317
SAN: gbs1387
STC: str0576(mvaA)
STL: stu0576(mvaA)
STE: STER_0620
SSA: SSA_0337(mvaA)
LPL: lp_0447(mvaA)
LJO: LJ1608
LSL: LSL_0224
LBR: LVIS_0450
LGA: LGAS_1373
VCH: VCA0723
VCO: VC0395_0662
VVU: VV2_0117
VVY: VVA0625
VPA: VPA0968
VFI: VFA0841
PAT: Patl_0427
CBU: CBU_0030 CBU_0610
CBD: COXBU7E912_0151
COXBU7E912_0622(hmgA)
TCX: Tcr_1717
DNO: DNO_0797
CVI: CV_1806
SUS: Acid_5728 Acid_6132
SAU: SA2333(mvaA)
SAV: SAV2545(mvaA)
SAM: MW2466(mvaA)
SAB: SAB2419c(mvaA)
SEP: SE2109
LWE: lwe0819(mvaA)
LLA: L10433(mvaA)
LLC: LACR_1664
LLM: llmg_0931(mvaA)
SPY: SPy_0880(mvaS.1)
SPM: spyM18_0941(mvaS1)
SPG: SpyM3_0599(mvaS.1)
SPS: SPs1254
MEM: Memar_2365
MBN: Mboo_0137
MTH: MTH562
MST: Msp_0584(hmgA)
MSI: Msm_0227
MKA: MK0355(HMG1)
AFU: AF1736(mvaA)
HAL: VNG1875G(mvaA)
HMA: rrnAC3412(mvaA)
HWA: HQ3215A(hmgR)
NPH: NP0368A(mvaA_2)
NP2422A(mvaA_1)
TAC: Ta0406m
TVO: TVN1168
PTO: PTO1143
PAB: PAB2106(mvaA)
PFU: PF1848

EFA: EF1364
NFA: nfa22110
BGA: BG0708(mvaA)
SRU: SRU_2422
FPS: FP2341
MMP: MMP0087(hmgA)
MMQ: MmarC5_1589
MAC: MA3073(hmgA)
MBA: Mbar_A1972
MMA: MM_0335
MBU: Mbur_1098
MHU: Mhun_3004

TKO: TK0914
RCI: RCIX1027(hmgA) RCIX376(hmgA)
APE: APE_1869
IHO: Igni_0476
HBU: Hbut_1531
SSO: SSO0531
STO: ST1352
SAI: Saci_1359
PAI: PAE2182
PIS: Pisl_0814
PCL: Pcal_1085
PAS: Pars_0796

Exemplary mevalonate kinase nucleic acids and polypeptides

HSA: 4598(MVK)
MCC: 707645(MVK)
MMU: 17855(Mvk)
RNO: 81727(Mvk)
CFA: 486309(MVK)
BTA: 505792(MVK)
GGA: 768555(MVK)
DRE: 492477(zgc:103473)
SPU: 585785(LOC585785)
DME: Dmel_CG33671
OSA: 4348331
SCE: YMR208W(ERG12)
AGO: AGOS_AER335W
PIC: PICST_40742(ERG12)
CGR: CAGL0F03861g
SPO: SPAC13G6.11c
MGR: MGG_06946
ANI: AN3869.2
AFM: AFUA_4G07780
AOR: AO090023000793
CNE: CNK01740
ECU: ECU09_1780
DDI: DDBDRAFT_0168621
TET: TTHERM_00637680
TBR: Tb927.4.4070
TCR: 436521.9 509237.10
LMA: LmjF31.0560
LLM: llmg_0425(mvk)
SPY: SPy_0876(mvaK1)
SPZ: M5005_Spy_0682(mvaK1)
SPM: spyM18_0937(mvaK1)
SPG: SpyM3_0595(mvaK1)
SPS: SPs1258
SPH: MGAS10270_Spy0740(mvaK1)
SPI: MGAS10750_Spy0774(mvaK1)
SPJ: MGAS2096_Spy0753(mvaK1)
SPK: MGAS9429_Spy0737(mvaK1)
SPF: SpyM51126(mvaK1)
SPA: M6_Spy0699
SPB: M28_Spy0662(mvaK1)
SPN: SP_0381
SPR: spr0338(mvk)
SPD: SPD_0346(mvk)
SAG: SAG1326
SAN: gbs1396
SAK: SAK_1357(mvk)
SMU: SMU.181
STC: str0559(mvaK1)
STL: stu0559(mvaK1)
STE: STER_0598
SSA: SSA_0333(mvaK1)
SSU: SSU05_0289
SSV: SSU98_0285
SGO: SGO_0239(mvk)
LPL: lp_1735(mvaK1)
LJO: LJ1205
HAL: VNG1145G(mvk)
HMA: rrnAC0077(mvk)

CBU: CBU_0608 CBU_0609
CBD: COXBU7E912_0620(mvk)
LPN: lpg2039
LPF: lpl2017
LPP: lpp2022
BBA: Bd1027(lmbP) Bd1630(mvk)
MXA: MXAN_5019(mvk)
OIH: OB0225
SAU: SA0547(mvaK1)
SAV: SAV0590(mvaK1)
SAM: MW0545(mvaK1)
SAR: SAR0596(mvaK1)
SAS: SAS0549
SAC: SACOL0636(mvk)
SAB: SAB0540(mvaK1)
SAA: SAUSA300_0572(mvk)
SAO: SAOUHSC_00577
SEP: SE0361
SER: SERP0238(mvk)
SHA: SH2402(mvaK1)
SSP: SSP2122
LMO: lmo0010
LMF: LMOf2365_0011
LIN: lin0010
LWE: lwe0011(mvk)
LLA: L7866(yeaG)
LLC: LACR_0454
LAC: LBA1167(mvaK)
LSA: LSA0908(mvaK1)
LSL: LSL_0685(eRG)
LDB: Ldb0999(mvk)
LBU: LBUL_0906
LBR: LVIS_0858
LCA: LSEI_1491
LGA: LGAS_1033
LRE: Lreu_0915
PPE: PEPE_0927
EFA: EF0904(mvk)
OOE: OEOE_1100
LME: LEUM_1385
NFA: nfa22070
BGA: BG0711
BAF: BAPKO_0732
FPS: FP0313
MMP: MMP1335
MAE: Maeo_0775
MAC: MA0602(mvk)
MBA: Mbar_A1421
MMA: MM_1762
MBU: Mbur_2395
MHU: Mhun_2890
MEM: Memar_1812
MBN: Mboo_2213
MST: Msp_0858(mvk)
MSI: Msm_1439
MKA: MK0993(ERG12)

HWA: HQ2925A(mvk)
NPH: NP2850A(mvk)
PTO: PTO1352
PHO: PH1625
PAB: PAB0372(mvk)
PFU: PF1637(mvk)
TKO: TK1474
RCI: LRC399(mvk)
APE: APE_2439
HBU: Hbut_0877
SSO: SSO0383
STO: ST2185
SAI: Saci_2365(mvk)
MSE: Msed_1602
PAI: PAE3108
PIS: Pisl_0467
PCL: Pcal_1835

Exemplary Phosphomevalonate Kinase Nucleic Acids and Polypeptides

HSA: 10654(PMVK)
PTR: 457350(PMVK)
MCC: 717014(PMVK)
MMU: 68603(Pmvk)
CFA: 612251(PMVK)
BTA: 513533(PMVK)
DME: Dmel_CG10268
ATH: AT1G31910
OSA: 4332275
SCE: YMR220W(ERG8)
AGO: AGOS_AER354W
PIC: PICST_52257(ERG8)
CGR: CAGL0F03993g
SPO: SPAC343.01c
MGR: MGG_05812
ANI: AN2311.2
AFM: AFUA_5G10680
AOR: AO090010000471
CNE: CNM00100
UMA: UM00760.1
DDI: DDBDRAFT_0184512
TBR: Tb09.160.3690
TCR: 507913.20 508277.140
LMA: LmjF15.1460
MXA: MXAN_5017
OIH: OB0227
SAU: SA0549(mvaK2)
SPJ: MGAS2096_Spy0755(mvaK2)
SPK: MGAS9429_Spy0739(mvaK2)
SPF: SpyM51124(mvaK2)
SPA: M6_Spy0701
SPB: M28_Spy0664(mvaK2)
SPN: SP_0383
SPR: spr0340(mvaK2)
SPD: SPD_0348(mvaK2)
SAG: SAG1324

SAV: SAV0592(mvaK2)
SAM: MW0547(mvaK2)
SAR: SAR0598(mvaK2)
SAS: SAS0551
SAC: SACOL0638
SAB: SAB0542(mvaK2)
SAA: SAUSA300_0574
SAO: SAOUHSC_00579
SAJ: SaurJH9_0615
SEP: SE0363
SER: SERP0240
SHA: SH2400(mvaK2)
SSP: SSP2120
LMO: lmo0012
LMF: LMOf2365_0013
LIN: lin0012
LWE: lwe0013
LLA: L10014(yebA)
LLC: LACR_0456
LLM: llmg_0427
SPY: SPy_0878(mvaK2)
SPZ: M5005_Spy_0684(mvaK2)
SPM: spyM18_0939
SPG: SpyM3_0597(mvaK2)
SPS: SPs1256
SPH: MGAS10270_Spy0742(mvaK2)
SPI: MGAS10750_Spy0776(mvaK2)
LRE: Lreu_0913
PPE: PEPE_0925
EFA: EF0902
NFA: nfa22090
BGA: BG0710
BAF: BAPKO_0731
NPH: NP2852A
SSO: SSO2988
STO: ST0978

SAN: gbs1394
SAK: SAK_1355
SMU: SMU.938
STC: str0561(mvaK2)
STL: stu0561(mvaK2)
STE: STER_0600
SSA: SSA_0335(mvaK2)
SSU: SSU05_0291
SSV: SSU98_0287
SGO: SGO_0241
LPL: lp_1733(mvaK2)
LJO: LJ1207
LAC: LBA1169
LSA: LSA0906(mvaK2)
LSL: LSL_0683
LDB: Ldb0997(mvaK)
LBU: LBUL_0904
LBR: LVIS_0860
LCA: LSEI_1092
LGA: LGAS_1035
SAI: Saci_1244

Exemplary Diphosphomevalonate Decarboxylase Nucleic Acids and Polypeptides

HSA: 4597(MVD)
PTR: 468069(MVD)
MCC: 696865(MVD)
MMU: 192156(Mvd)
RNO: 81726(Mvd)
CFA: 489663(MVD)
GGA: 425359(MVD)
DME: Dmel_CG8239
SCE: YNR043W(MVD1)
AGO: AGOS_AGL232C
PIC: PICST_90752
CGR: CAGL0C03630g
SPO: SPAC24C9.03
MGR: MGG_09750
ANI: AN4414.2
AFM: AFUA_4G07130
AOR: AO090023000862
CNE: CNL04950
UMA: UM05179.1
DDI: DDBDRAFT_0218058
TET: TTHERM_00849200
TBR: Tb10.05.0010 Tb10.61.2745
TCR: 507993.330 511281.40
LMA: LmjF18.0020
CBU: CBU_0607(mvaD)
LPF: lpl2018
LPP: lpp2023
TCX: Tcr_1734
DNO: DNO_0504(mvaD)
BBA: Bd1629
MXA: MXAN_5018(mvaD)
OIH: OB0226
SAU: SA0548(mvaD)
SAV: SAV0591(mvaD)
SAM: MW0546(mvaD)
SAR: SAR0597(mvaD)
SAS: SAS0550
SAC: SACOL0637(mvaD)
SAB: SAB0541(mvaD)
SAA: SAUSA300_0573(mvaD)
SAO: SAOUHSC_00578
SAJ: SaurJH9_0614
SAH: SaurJH1_0629
SEP: SE0362
SER: SERP0239(mvaD)
SHA: SH2401(mvaD)
SSP: SSP2121
LMO: lmo0011
LMF: LMOf2365_0012(mvaD)
LIN: lin0011

CBD: COXBU7E912_0619(mvaD)
LPN: lpg2040
LLC: LACR_0455
LLM: llmg_0426(mvaD)
SPY: SPy_0877(mvaD)
SPZ: M5005_Spy_0683(mvaD)
SPM: spyM18_0938(mvd)
SPG: SpyM3_0596(mvaD)
SPS: SPs1257
SPH: MGAS10270_Spy0741(mvaD)
SPI: MGAS10750_Spy0775(mvaD)
SPJ: MGAS2096_Spy0754(mvaD)
SPK: MGAS9429_Spy0738(mvaD)
SPF: SpyM51125(mvaD)
SPA: M6_Spy0700
SPB: M28_Spy0663(mvaD)
SPN: SP_0382
SPR: spr0339(mvd1)
SPD: SPD_0347(mvaD)
SAG: SAG1325(mvaD)
SAN: gbs1395
SAK: SAK_1356(mvaD)
SMU: SMU.937
STC: str0560(mvaD)
STL: stu0560(mvaD)
STE: STER_0599
SSA: SSA_0334(mvaD)
SSU: SSU05_0290
SSV: SSU98_0286
SGO: SGO_0240(mvaD)
LPL: lp_1734(mvaD)
LWE: lwe0012(mvaD)
LLA: L9089(yeaH)
LJO: LJ1206
LAC: LBA1168(mvaD)
LSA: LSA0907(mvaD)
LSL: LSL_0684
LDB: Ldb0998(mvaD)
LBU: LBUL_0905
LBR: LVIS_0859
LCA: LSEI_1492
LGA: LGAS_1034
LRE: Lreu_0914
PPE: PEPE_0926
EFA: EF0903(mvaD)
LME: LEUM_1386
NFA: nfa22080
BBU: BB0686
BGA: BG0709
BAF: BAPKO_0730
GFO: GFO_3632
FPS: FP0310(mvaD)
HAU: Haur_1612
HAL: VNG0593G(dmd)
HMA: rrnAC1489(dmd)
HWA: HQ1525A(mvaD)
NPH: NP1580A(mvaD)
PTO: PTO0478 PTO1356
SSO: SSO2989
STO: ST0977
SAI: Saci_1245(mvd)
MSE: Msed_1576

Exemplary Isopentenyl Phosphate Kinases (IPK) Nucleic Acids and Polypeptides

| *Methanobacterium thermoautotrophicum* gi|2621082 | *Picrophilus torridus* DSM9790 (IG-57) gi|48477569 |
| --- | --- |
| *Methanococcus jannaschii* DSM 2661 gi|1590842; | *Pyrococcus abyssi* gi|14520758 |
| *Methanocaldococcus jannaschii* gi|1590842 | *Pyrococcus horikoshii* OT3 gi|3258052 |
| *Methanothermobacter thermautotrophicus* gi|2621082 | *Archaeoglobus fulgidus* DSM4304 gi|2648231 |

Exemplary Isopentenyl-Diphosphate Delta-Isomerase (IDI) Nucleic Acids and Polypeptides HSA: 3422(IDI1) 91734(IDI2)
PTR: 450262(IDI2) 450263(IDI1)
MCC: 710052(LOC710052) 721730(LOC721730)
MMU: 319554(Idi1)
RNO: 89784(Idi1)
GGA: 420459(IDI1)
XLA: 494671(LOC494671)
XTR: 496783(idi2)
SPU: 586184(LOC586184)
CEL: K06H7.9(idi-1)
ATH: AT3G02780(IPP2)
OSA: 4338791 4343523
CME: CMB062C
SCE: YPL117C(IDI1)
AGO: AGOS_ADL268C
PIC: PICST_68990(IDI1)
CGR: CAGL0J06952g
SPO: SPBC106.15(idi1)
ANI: AN0579.2
AFM: AFUA_6G11160
AOR: AO090023000500
CNE: CNA02550
UMA: UM04838.1
TET: TTHERM_00237280
TTHERM_00438860
TBR: Tb09.211.0700
TCR: 408799.19 510431.10
LMA: LmjF35.5330
EHI: 46.t00025
ECO: b2889(idi)
ECJ: JW2857(idi)
ECE: Z4227
ECS: ECs3761
ECC: c3467
ECI: UTI89_C3274
ECP: ECP_2882
ECV: APECO1_3638
ECW: EcE24377A_3215(idi)
ECX: EcHS_A3048
STY: STY3195
STT: t2957
SPT: SPA2907(idi)
SEC: SC2979(idi)
STM: STM3039(idi)
SFL: SF2875(idi)
SFX: S3074
SFV: SFV_2937

-continued

ECU: ECU02_0230
DDI: DDB_0191342(ipi)

ECA: ECA2789
PLU: plu3987
ENT: Ent638_3307
SPE: Spro_2201
VPA: VPA0278
VFI: VF0403
PPR: PBPRA0469(mvaD)
PEN: PSEEN4850
CBU: CBU_0607(mvaD)
CBD: COXBU7E912_0619(mvaD)
LPN: lpg2051
LPF: lpl2029
LPP: lpp2034
TCX: Tcr_1718
HHA: Hhal_1623
DNO: DNO_0798
EBA: ebA5678 p2A143
DVU: DVU1679(idi)
DDE: Dde_1991
LIP: LI1134
BBA: Bd1626
AFW: Anae109_4082
MXA: MXAN_5021(fni)
RPR: RP452
RTY: RT0439(idi)
RCO: RC0744
RFE: RF_0785(fni)
RBE: RBE_0731(fni)
RAK: A1C_04190
OIH: OB0537
SAU: SA2136(fni)
SAV: SAV2346(fni)
SAM: MW2267(fni)
SAR: SAR2431(fni)
SAS: SAS2237
SAC: SACOL2341(fni)
SAB: SAB2225c(fni)
SAA: SAUSA300_2292(fni)
SAO: SAOUHSC_02623
SEP: SE1925
SER: SERP1937(fni-2)
SHA: SH0712(fni)
SSP: SSP0556
LMO: lmo1383
LMF: LMOf2365_1402(fni)
LIN: lin1420
LWE: lwe1399(fni)
LLA: L11083(yebB)
LLC: LACR_0457
LLM: llmg_0428(fni)
SPY: SPy_0879
SPZ: M5005_Spy_0685
SPM: spyM18_0940
SPG: SpyM3_0598
SPS: SPs1255
SPH: MGAS10270_Spy0743
SPI: MGAS10750_Spy0777
SPJ: MGAS2096_Spy0756
STH: STH1674
CBE: Cbei_3081
DRM: Dred_0474
SWO: Swol_1341
MTA: Moth_1328
MTU: Rv1745c(idi)
MTC: MT1787(idi)
MBO: Mb1774c(idi)
MBB: BCG_1784c(idi)
MPA: MAP3079c
MAV: MAV_3894(fni)
MSM: MSMEG_1057(fni)
MSMEG_2337(fni)
MUL: MUL_0380(idi2)
MVA: Mvan_1582 Mvan_2176
MGI: Mflv_1842 Mflv_4187
MMC: Mmcs_1954
MKM: Mkms_2000

SSN: SSON_3042 SSON_3489(yhfK)
SBO: SBO_3103
SDY: SDY_3193
RBO: A1I_04755
RCM: A1E_02555
RRI: A1G_04195
MLO: mlr6371
RET: RHE_PD00245(ypd00046)
XAU: Xaut_4134
SIL: SPO0131
SIT: TM1040_3442
RSP: RSP_0276
RSH: Rsph17029_1919
RSQ: Rsph17025_1019
JAN: Jann_0168
RDE: RD1_0147(idi)
DSH: Dshi_3527
BSU: BG11440(ypgA)
BAN: BA1520
BAR: GBAA1520
BAA: BA_2041
BAT: BAS1409
BCE: BC1499
BCA: BCE_1626
BCZ: BCZK1380(fni)
BCY: Bcer98_1222
BTK: BT9727_1381(fni)
BTL: BALH_1354
BLI: BL02217(fni)
BLD: BLi02426
BAY: RBAM_021020(fni)
BPU: BPUM_2020(fni)
SPK: MGAS9429_Spy0740
SPF: SpyM51123(fni)
SPA: M6_Spy0702
SPB: M28_Spy0665
SPN: SP_0384
SPR: spr0341(fni)
SPD: SPD_0349(fni)
SAG: SAG1323
SAN: gbs1393
SAK: SAK_1354(fni)
SMU: SMU.939
STC: str0562(idi)
STL: stu0562(idi)
STE: STER_0601
SSA: SSA_0336
SGO: SGO_0242
LPL: lp_1732(idi1)
LJO: LJ1208
LAC: LBA1171
LSA: LSA0905(idi)
LSL: LSL_0682
LDB: Ldb0996(fni)
LBU: LBUL_0903
LBR: LVIS_0861
LCA: LSEI_1493
LGA: LGAS_1036
LRE: Lreu_0912
EFA: EF0901
OOE: OEOE_1103
AAU: AAur_0321(idi)
PAC: PPA2115
FRA: Francci3_4188
FRE: Franean1_5570
FAL: FRAAL6504(idi)
KRA: Krad_3991
SEN: SACE_2627(idiB_2) SACE_5210(idi)
STP: Strop_4438
SAQ: Sare_4564 Sare_4928
RXY: Rxyl_0400
BBU: BB0684
BGA: BG0707
SYN: sll1556
SYC: syc2161_c
SYF: Synpcc7942_1933
CYA: CYA_2395(fni)
CYB: CYB_2691(fni)
TEL: tll1403

| | |
|---|---|
| MJL: Mjls_1934 | ANA: all4591 |
| CGL: NCgl2223(cgl2305) | AVA: Ava_2461 Ava_B0346 |
| CGB: cg2531(idi) | TER: Tery_1589 |
| CEF: CE2207 | SRU: SRU_1900(idi) |
| CDI: DIP1730(idi) | CHU: CHU_0674(idi) |
| NFA: nfa19790 nfa22100 | GFO: GFO_2363(idi) |
| RHA: RHA1_ro00239 | FJO: Fjoh_0269 |
| SCO: SCO6750(SC5F2A.33c) | FPS: FP1792(idi) |
| SMA: SAV1663(idi) | CTE: CT0257 |
| LXX: Lxx23810(idi) | CCH: Cag_1445 |
| CMI: CMM_2889(idiA) | CPH: Cpha266_0385 |
| PVI: Cvib_1545 | AFU: AF2287 |
| PLT: Plut_1764 | HAL: VNG1818G(idi) VNG6081G(crt_1) |
| RRS: RoseRS_2437 | VNG6445G(crt_2) VNG7060 VNG7149 |
| RCA: Rcas_2215 | HMA: rrnAC3484(idi) |
| HAU: Haur_4687 | HWA: HQ2772A(idiA) HQ2847A(idiB) |
| DRA: DR_1087 | NPH: NP0360A(idiB_1) NP4826A(idiA) |
| DGE: Dgeo_1381 | NP5124A(idiB_2) |
| TTH: TT_P0067 | TAC: Ta0102 |
| TTJ: TTHB110 | TVO: TVN0179 |
| MJA: MJ0862 | PTO: PTO0496 |
| MMP: MMP0043 | PHO: PH1202 |
| MMQ: MmarC5_1637 | PAB: PAB1662 |
| MMX: MmarC6_0906 | PFU: PF0856 |
| MMZ: MmarC7_1040 | TKO: TK1470 |
| MAE: Maeo_1184 | RCI: LRC397(fni) |
| MVN: Mevan_1058 | APE: APE_1765.1 |
| MAC: MA0604(idi) | SMR: Smar_0822 |
| MBA: Mbar_A1419 | IHO: Igni_0804 |
| MMA: MM_1764 | HBU: Hbut_0539 |
| MBU: Mbur_2397 | SSO: SSO0063 |
| MTP: Mthe_0474 | STO: ST2059 |
| MHU: Mhun_2888 | SAI: Saci_0091 |
| MLA: Mlab_1665 | MSE: Msed_2136 |
| MEM: Memar_1814 | PAI: PAE0801 |
| MBN: Mboo_2211 | PIS: Pisl_1093 |
| MTH: MTH48 | PCL: Pcal_0017 |
| MST: Msp_0856(fni) | PAS: Pars_0051 |
| MSI: Msm_1441 | TPE: Tpen_0272 |
| MKA: MK0776(lldD) | |

Exemplary Isoprene Synthase Nucleic Acids and Polypeptides
Genbank Accession Nos.
AY341431
AY316691
AY279379
AJ457070
AY182241

We claim:

1. Recombinant host cells comprising (a) a heterologous nucleic acid encoding an isoprene synthase polypeptide, (b) a nucleic acid encoding an isopentenyl-diphosphate delta-isomerase (IDI) polypeptide, (c) nucleic acid(s) encoding a 1-Deoxyxylulose-5-phosphate synthase (DXS) polypeptide and/or one or more mevalonate (MVA) pathway polypeptides and (d) heterologous nucleic acid(s) encoding (i) one or more polypeptide involved in ethanol fermentation, wherein the polypeptide involved in ethanol fermentation is an alcohol dehydrogenase from yeast or bacteria, or (ii) a pyruvate decarboxylase (pdc) polypeptide, wherein said cells co-produce isoprene and ethanol under oxygen-limited culture conditions, wherein the oxygen transfer rate (OTR) is less than the oxygen uptake rate (OUR).

2. The cells of claim 1, wherein the heterologous nucleic acid encoding an isoprene synthase polypeptide is operably linked to a promoter.

3. The cells of claim 2, wherein the isoprene synthase polypeptide is a plant isoprene synthase polypeptide.

4. The cells of claim 3, wherein the plant isoprene synthase polypeptide is from *Populus alba*.

5. The cells of claim 1, wherein the cells further comprise one or more heterologous nucleic acid encoding a deoxyxylulose-5-phosphate (DXP) pathway polypeptide.

6. The cells of claim 1, wherein the cells comprise a DXP pathway polypeptide and a MVA pathway polypeptide.

7. The cells of claim 1, wherein the cells comprise one or more MVA pathway polypeptides selected from the group consisting of: (i) an acetoacetyl-Coenzyme A synthase (thiolase) polypeptide; (ii) a 3-hydroxy-3-methylglutaryl-Coenzyme A synthase polypeptide (iii) a 3-hydroxy-3-methylglutaryl-Coenzyme A reductase polypeptide, (iv) mevalonate kinase (MVK); (v) phosphomevalonate kinase (PMK); and (vi) diphosphomevalonate decarboxylase (MVD).

8. The cells of claim 1, wherein the cells are fungal cells.

9. The cells of claim 8, wherein the fungal cells are yeast cells.

10. The cells of claim 9, wherein the yeast cells are *Saccharomyces* sp., *Schizosaccharomyces* sp., *Pichia* sp., or *Candida* sp.

11. The cells of claim 10, wherein the yeast cells are *Saccharomyces cerevisiae*.

12. The cells of claim 1, wherein the cells are bacterial cells.

13. The cells of claim 12, wherein the bacterial cells are *Bacillus* sp., *Streptomyces* sp., *Escherichia* sp., *Rhodopseudomonas* sp., *Pseudomonas* sp., *Pantoea* sp., or *Zymomonas* sp.

14. The cells of claim 13, wherein the cells are *E. coli* cells.

15. The cells of claim 1, wherein the oxygen-limited conditions are anaerobic conditions.

16. The recombinant host cells of claim 1, wherein the alcohol dehydrogenase is an alcohol dehydrogenase E (adhE) from *E. coli* or *Zymomonas*.

17. The recombinant host cells of claim 1, wherein the alcohol dehydrogenase is an alcohol dehydrogenase B (adhB) from *Zymomonas*.

18. A method of co-producing isoprene and ethanol, the method comprising: (a) culturing recombinant host cells capable of co-producing isoprene and ethanol under oxygen limited culture conditions wherein, the oxygen transfer rate (OTR) is less than the oxygen uptake rate (OUR), and wherein the cells comprise (a) a heterologous nucleic acid encoding an isoprene synthase polypeptide (b) a nucleic acid encoding an isopentenyl-diphosphate delta-isomerase (IDI) polypeptide, (c) nucleic acid(s) encoding a 1-Deoxyxylulose-5-phosphate synthase (DXS) polypeptide and/or one or more mevalonate (MVA) pathway polypeptides and (d) heterologous nucleic acid(s) encoding (i) one or more polypeptide involved in ethanol fermentation, wherein the polypeptide involved in ethanol fermentation is an alcohol dehydrogenase from yeast or bacteria, or (ii) a pyruvate decarboxylase (pdc) polypeptide; and (b) co-producing isoprene and ethanol.

19. The method of claim 18, wherein the heterologous nucleic acid encoding an isoprene synthase polypeptide is operably linked to a promoter.

20. The method of claim 19, wherein the isoprene synthase polypeptide is a plant isoprene synthase polypeptide.

21. The method of claim 20, wherein the plant isoprene synthase polypeptide is from *Populus alba*.

22. The method of claim 18, wherein the cells further comprise one or more heterologous nucleic acid encoding a deoxyxylulose-5-phosphate (DXP) pathway polypeptide.

23. The method of claim 18, wherein the cells comprise a DXP pathway polypeptide and a MVA pathway polypeptide.

24. The method of claim 18, wherein the cells comprise one or more MVA pathway polypeptides selected from the group consisting of: (i) an acetoacetyl-Coenzyme A synthase (thiolase) polypeptide; (ii) a 3-hydroxy-3-methylglutaryl-Coenzyme A synthase polypeptide (iii) a 3-hydroxy-3-methylglutaryl-Coenzyme A reductase polypeptide, (iv) mevalonate kinase (MVK); (v) phosphomevalonate kinase (PMK); and (vi) diphosphomevalonate decarboxylase (MVD).

25. The method of claim 18, wherein the cells are fungal cells.

26. The method of claim 25, wherein the fungal cells are yeast cells.

27. The method of claim 26, wherein the yeast cells are *Saccharomyces* sp., *Schizosaccharomyces* sp., *Pichia* sp., or *Candida* sp.

28. The method of claim 27, wherein the yeast cells are *Saccharomyces cerevisiae*.

29. The method of claim 18, wherein the cells are bacterial cells.

30. The method of claim 29, wherein the bacterial cells are *Bacillus* sp., *Streptomyces* sp., *Escherichia* sp., *Rhodopseudomonas* sp., *Pseudomonas* sp., *Pantoea* sp., or *Zymomonas* sp.

31. The method of claim 30, wherein the cells are *E. coli* cells.

32. The method of claim 18, wherein the oxygen-limited conditions are anaerobic conditions.

\* \* \* \* \*

```
                         SEQUENCE LISTING

<160> NUMBER OF SEQ ID NOS: 188

<210> SEQ ID NO 1
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 1
atgtgtgcga cctcttctca atttactcag attaccgagc ataattcccg tcgttccgca      60
aactatcagc caaacctgtg gaatttcgaa ttcctgcaat ccctggagaa cgacctgaaa     120
gtggaaaagc tggaggagaa agcgaccaaa ctggaggaag aagttcgctg catgatcaac     180
cgtgtagaca cccagccgct gtccctgctg gagctgatcg acgatgtgca gcgcctgggt     240
ctgacctaca aatttgaaaa agacatcatt aaagccctgg aaaacatcgt actgctggac     300
gaaaacaaaa agaacaaatc tgacctgcac gcaaccgctc tgtctttccg tctgctgcgt     360
cagcacggtt tcgaggtttc tcaggatgtt tttgagcgtt tcaaggataa agaaggtggt     420
```

```
ttcagcggtg aactgaaagg tgacgtccaa ggcctgctga gcctgtatga agcgtcttac    480
ctgggtttcg agggtgagaa cctgctggag gaggcgcgta cctttccat cacccacctg    540 aagaacaacc tgaaagaagg cattaatacc aaggttgcag aacaagtgag ccacgccctg    600
gaactgccat atcaccagcg tctgcaccgt ctggaggcac gttggttcct ggataaatac    660
gaaccgaaag aaccgcatca ccagctgctg ctggagctgg cgaagctgga ttttaacatg    720
gtacagaccc tgcaccagaa agagctgcaa gatctgtccc gctggtggac cgagatgggc    780
ctggctagca aactggattt tgtacgcgac cgcctgatgg aagtttattt ctgggcactg    840
ggtatggcgc cagacccgca gtttggtgaa tgtcgcaaag ctgttactaa aatgtttggt    900
ctggtgacga tcatcgatga cgtgtatgac gtttatggca ctctggacga actgcaactg    960
ttcaccgatg ctgtagagcg ctgggacgtt aacgctatta acaccctgcc ggactatatg    1020
aaactgtgtt tcctggcact gtacaacacc gttaacgaca cgtcctattc tattctgaaa    1080
gagaaaggtc ataacaacct gtcctatctg acgaaaagct ggcgtgaact gtgcaaagcc    1140
tttctgcaag aggcgaaatg gtccaacaac aaaattatcc cggctttctc caagtacctg    1200
gaaaacgcca gcgtttcctc ctccggtgta gcgctgctgg cgccgtctta cttttccgta    1260
tgccagcagc aggaagacat ctccgaccac gcgctgcgtt ccctgaccga cttccatggt    1320
ctggtgcgtt ctagctgcgt tatcttccgc ctgtgcaacg atctggccac ctctgcggcg    1380
gagctggaac gtgcgagac taccaattct atcattagct acatgcacga aaacgatggt    1440
accagcgagg aacaggcccg cgaagaactg cgtaaactga tcgacgccga atggaaaaag    1500
atgaatcgtg aacgcgttag cgactccacc ctgctgccta aagcgttcat ggaaatcgca    1560
gttaacatgg cacgtgtttc ccactgcacc taccagtatg gcgatggtct gggtcgccca    1620
gactacgcga ctgaaaaccg catcaaactg ctgctgattg ccccttttcccc gattaaccag    1680 ctgatgtatg tctaactgca g    1701
```

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgtgtgc    420
gacctcttct caatttactc agattaccga gcataattcc cgtcgttccg caaactatca    480
gccaaacctg tggaatttcg aattcctgca atccctggag aacgacctga agtggaaaaa    540
gctggaggag aaagcgacca aactggagga agaagttcgc tgcatgatca ccgtgtaga     600 cacccagccg ctgtccctgc tggagctgat cgacgatgtg cagcgcctgg gtctgaccta    660
caaatttgaa aaagacatca ttaaagccct ggaaaacatc gtactgctgg acgaaaacaa    720 aagaacaaa tctgacctgc acgcaaccgc tctgtctttc cgtctgctgc gtcagcacgg    780
```

```
tttcgaggtt tctcaggatg tttttgagcg tttcaaggat aaagaaggtg gtttcagcgg    840
tgaactgaaa ggtgacgtcc aaggcctgct gagcctgtat gaagcgtctt acctgggttt    900
cgagggtgag aacctgctgg aggaggcgcg tacctttccc atcacccacc tgaagaacaa    960
cctgaaagaa ggcattaata ccaaggttgc agaacaagtg agccacgccc tggaactgcc   1020
atatcaccag cgtctgcacc gtctggaggc acgttggttc ctggataaat acgaaccgaa   1080
agaaccgcat caccagctgc tgctggagct ggcgaagctg gattttaaca tggtacagac   1140
cctgcaccag aaagagctgc aagatctgtc ccgctggtgg accgagatgg gcctggctag   1200
caaactggat tttgtacgcg accgcctgat ggaagtttat ttctgggcac tgggtatggc   1260
gccagacccg cagtttggtg aatgtcgcaa agctgttact aaaatgtttg gtctggtgac   1320
gatcatcgat gacgtgtatg acgtttatgg cactctggac gaactgcaac tgttcaccga   1380
tgctgtagag cgctgggacg ttaacgctat taacaccctg ccggactata tgaaactgtg   1440
tttcctggca ctgtacaaca ccgttaacga cacgtcctat tctattctga agagaaaagg   1500
tcataacaac ctgtcctatc tgacgaaaag ctggcgtgaa ctgtgcaaag cctttctgca   1560
agaggcgaaa tggtccaaca acaaaattat cccggctttc tccaagtacc tggaaaacgc   1620
cagcgtttcc tcctccggtg tagcgctgct ggcgccgtct acttttccg tatgccagca    1680 gcaggaagac atctccgacc acgcgctgcg ttccctgacc gacttccatg gtctggtgcg   1740
ttctagctgc gttatcttcc gcctgtgcaa cgatctggcc acctctgcgg cggagctgga   1800
acgtggcgag actaccaatt ctatcattag ctacatgcac gaaaacgatg gtaccagcga   1860
ggaacaggcc cgcgaagaac tgcgtaaact gatcgacgcc gaatggaaaa agatgaatcg   1920
tgaacgcgtt agcgactcca ccctgctgcc taaagcgttc atggaaatcg cagttaacat   1980
ggcacgtgtt tcccactgca cctaccagta tggcgatggt ctgggtcgcc agactacgc    2040 gactgaaaac cgcatcaaac tgctgctgat tgaccctttc ccgattaacc agctgatgta   2100
tgtctaactg cagctggtac catatgggaa ttcgaagctt tctagaacaa aaactcatct   2160
cagaagagga tctgaatagc gccgtcgacc atcatcatca tcatcattga gtttaaacgg   2220
tctccagctt ggctgttttg gcggatgaga gaagattttc agcctgatac agattaaatc   2280
agaacgcaga agcggtctga taaaacagaa tttgcctggc ggcagtagcg cggtggtccc   2340
acctgacccc atgccgaact cagaagtgaa acgccgtagc gccgatggta gtgtgggtc    2400 tccccatgcg agagtaggga actgccaggc atcaaataaa acgaaaggct cagtcgaaag   2460
actgggcctt tcgttttatc tgttgtttgt cggtgaacgc tctcctgagt aggacaaatc   2520
cgccgggagc ggatttgaac gttgcgaagc aacggcccgg agggtggcgg caggacgcc    2580 cgccataaac tgccaggcat caaattaagc agaaggccat cctgacggat ggcctttttg   2640
cgtttctaca aactctttt gtttatttt ctaaatacat tcaaatatgt atccgctcat     2700
gagacaataa ccctgataaa tgcttcaata atattgaaaa aggaagagta tgagtattca   2760
acatttccgt gtcgccctta ttccctttt tgcggcattt tgccttcctg tttttgctca    2820
cccagaaacg ctggtgaaag taaaagatgc tgaagatcag ttgggtgcac gagtgggtta   2880
catcgaactg gatctcaaca gcggtaagat ccttgagagt tttcgccccg aagaacgttt   2940
tccaatgatg agcactttta aagttctgct atgtggcgcg gtattatccc gtgttgacgc   3000
cgggcaagag caactcggtc gccgcataca ctattctcag aatgacttgg ttgagtactc   3060
accagtcaca gaaaagcatc ttacggatgg catgacagta agagaattat gcagtgctgc   3120
```

```
cataaccatg agtgataaca ctgcggccaa cttacttctg acaacgatcg gaggaccgaa    3180
ggagctaacc gctttttttgc acaacatggg ggatcatgta actcgccttg atcgttggga    3240
accggagctg aatgaagcca taccaaacga cgagcgtgac accacgatgc ctgtagcaat    3300
ggcaacaacg ttgcgcaaac tattaactgg cgaactactt actctagctt cccggcaaca    3360
attaatagac tggatggagg cggataaagt tgcaggacca cttctgcgct cggcccttcc    3420
ggctggctgg tttattgctg ataaatctgg agccggtgag cgtgggtctc gcggtatcat    3480
tgcagcactg gggccagatg gtaagccctc ccgtatcgta gttatctaca cgacggggag    3540
tcaggcaact atggatgaac gaaatagaca gatcgctgag ataggtgcct cactgattaa    3600
gcattggtaa ctgtcagacc aagtttactc atatatactt tagattgatt taaaacttca    3660
tttttaattt aaaaggatct aggtgaagat cctttttgat aatctcatga ccaaaatccc    3720
ttaacgtgag ttttcgttcc actgagcgtc agaccccgta gaaaagatca aaggatcttc    3780
ttgagatcct ttttttctgc gcgtaatctg ctgcttgcaa acaaaaaaac caccgctacc    3840
agcggtggtt tgtttgccgg atcaagagct accaactctt tttccgaagg taactggctt    3900
cagcagagcg cagataccaa atactgtcct tctagtgtag ccgtagttag gccaccactt    3960
caagaactct gtagcaccgc ctacatacct cgctctgcta atcctgttac cagtggctgc    4020
tgccagtggc gataagtcgt gtcttaccgg gttggactca agacgatagt taccggataa    4080
ggcgcagcgg tcgggctgaa cggggggttc gtgcacacag cccagcttgg agcgaacgac    4140
ctacaccgaa ctgagatacc tacagcgtga gctatgagaa agcgccacgc ttcccgaagg    4200
gagaaaggcg gacaggtatc cggtaagcgg cagggtcgga acaggagagc gcacgaggga    4260
gcttccaggg ggaaacgcct ggtatcttta tagtcctgtc gggtttcgcc acctctgact    4320
tgagcgtcga tttttgtgat gctcgtcagg gggcggagc ctatggaaaa acgccagcaa    4380
cgcggccttt ttacggttcc tggccttttg ctggccttttt gctcacatgt tctttcctgc    4440
gttatcccct gattctgtgg ataaccgtat taccgccttt gagtgagctg ataccgctcg    4500
ccgcagccga acgaccgagc gcagcgagtc agtgagcgag gaagcggaag agcgcctgat    4560
gcggtatttt ctccttacgc atctgtgcgg tatttcacac cgcatatggt gcactctcag    4620
tacaatctgc tctgatgccg catagttaag ccagtataca ctccgctatc gctacgtgac    4680
tgggtcatgg ctgcgccccg acacccgcca cacccgctg acgcgccctg acgggcttgt    4740
ctgctcccgg catccgctta cagacaagct gtgaccgtct ccgggagctg catgtgtcag    4800
aggttttcac cgtcatcacc gaaacgcgcg aggcagcaga tcaattcgcg cgcgaaggcg    4860
aagcggcatg catttacgtt gacaccatcg aatggtgcaa aacctttcgc ggtatggcat    4920
gatagcgccc ggaagagagt caattcaggg tggtgaatgt gaaaccagta acgttatacg    4980
atgtcgcaga gtatgccggt gtctcttatc agaccgtttc ccgcgtggtg aaccaggcca    5040
gccacgtttc tgcgaaaacg cgggaaaaag tggaagcggc gatggcggag ctgaattaca    5100
ttcccaaccg cgtggcacaa caactggcgg gcaaacagtc gttgctgatt ggcgttgcca    5160
cctccagtct ggccctgcac gcgccgtcgc aaattgtcgc ggcgattaaa tctcgcgccg    5220
atcaactggg tgccagcgtg gtggtgtcga tggtagaacg aagcggcgtc gaagcctgta    5280
aagcggcggt gcacaatctt ctcgcgcaac gcgtcagtgg gctgatcatt aactatccgc    5340
tggatgacca ggatgccatt gctgtggaag ctgcctgcac taatgttccg gcgttatttc    5400
ttgatgtctc tgaccagaca cccatcaaca gtattatttt ctcccatgaa gacggtacgc    5460
gactgggcgt ggagcatctg gtcgcattgg gtcaccagca aatcgcgctg ttagcgggcc    5520
```

| | |
|---|---|
| cattaagttc tgtctcggcg cgtctgcgtc tggctggctg gcataaatat ctcactcgca | 5580 |
| atcaaattca gccgatagcg gaacgggaag gcgactggag tgccatgtcc ggttttcaac | 5640 |
| aaaccatgca aatgctgaat gagggcatcg ttcccactgc gatgctggtt gccaacgatc | 5700 |
| agatggcgct gggcgcaatg cgcgccatta ccgagtccgg gctgcgcgtt ggtgcggata | 5760 |
| tctcggtagt gggatacgac gataccgaag acagctcatg ttatatcccg ccgtcaacca | 5820 |
| ccatcaaaca ggattttcgc ctgctggggc aaaccagcgt ggaccgcttg ctgcaactct | 5880 |
| ctcagggcca ggcggtgaag gcaatcagc tgttgcccgt ctcactggtg aaaagaaaaa | 5940 |
| ccaccctggc gcccaatacg caaaccgcct ctccccgcgc gttggccgat tcattaatgc | 6000 |
| agctggcacg acaggtttcc cgactggaaa gcgggcagtg agcgcaacgc aattaatgtg | 6060 |
| agttagcgcg aattgatctg | 6080 |

<210> SEQ ID NO 3
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 3

| | |
|---|---|
| ttctcatgtt tgacagctta tcatcgataa gctttaatgc ggtagtttat cacagttaaa | 60 |
| ttgctaacgc agtcaggcac cgtgtatgaa atctaacaat gcgctcatcg tcatcctcgg | 120 |
| caccgtcacc ctggatgctg taggcatagg cttggttatg ccggtactgc cgggcctctt | 180 |
| gcgggatatc cggatatagt tcctcctttc agcaaaaaac ccctcaagac ccgtttagag | 240 |
| gccccaaggg gttatgctag ttattgctca gcggtggcag cagccaactc agcttccttt | 300 |
| cgggctttgt tagcagccgg atccctgcag ttagacatac atcagctggt taatcgggaa | 360 |
| agggtcaatc agcagcagtt tgatgcggtt ttcagtcgcg tagtctgggc gacccagacc | 420 |
| atcgccatac tggtaggtgc agtgggaaac acgtgccatg ttaactgcga tttccatgaa | 480 |
| cgctttaggc agcagggtgg agtcgctaac gcgttcacga ttcatctttt tccattcggc | 540 |
| gtcgatcagt ttacgcagtt cttcgcgggc ctgttcctcg ctggtaccat cgttttcgtg | 600 |
| catgtagcta atgatagaat tggtagtctc gccacgttcc agctccgccg cagaggtggc | 660 |
| cagatcgttg cacaggcgga agataacgca gctagaacgc accagaccat ggaagtcggt | 720 |
| cagggaacgc agcgcgtggt cggagatgtc ttcctgctgc tggcatacgg aaaagtaaga | 780 |
| cggcgccagc agcgctacac cggaggagga aacgctggac ttttccaggt acttggagaa | 840 |
| agccgggata attttgttgt tggaccattt cgcctcttgc agaaaggctt gcacagttc | 900 |
| acgccagctt tcgtcagat aggacaggtt gttatgacct ttctctttca gaatagaata | 960 |
| ggacgtgtcg ttaacggtgt tgtacagtgc caggaaacac agtttcatat agtccggcag | 1020 |
| ggtgttaata gcgttaacgt cccagcgctc tacagcatcg tgaacagtt gcagttcgtc | 1080 |
| cagagtgcca taaacgtcat acacgtcatc gatgatcgtc accagaccaa acatttagt | 1140 |
| aacagctttg cgacattcac caaactgcgg gtctggcgcc ataccagtg cccagaaata | 1200 |
| aacttccatc aggcggtcgc gtacaaaatc cagtttgcta gccaggccca tctcggtcca | 1260 |
| ccagcgggac agatcttgca gctctttctg gtgcagggtc tgtaccatgt taaaatccag | 1320 |
| cttcgccagc tccagcagca gctggtgatg cggttctttc ggttcgtatt tatccaggaa | 1380 |
| ccaacgtgcc tccagacggt gcagacgctg gtgatatggc agttccaggg cgtggctcac | 1440 |

```
ttgttctgca accttggtat taatgccttc tttcaggttg ttcttcaggt gggtgatgga    1500
aaaggtacgc gcctcctcca gcaggttctc accctcgaaa cccaggtaag acgcttcata    1560
caggctcagc aggccttgga cgtcaccttt cagttcaccg ctgaaaccac cttctttatc    1620
cttgaaacgc tcaaaaacat cctgagaaac ctcgaaaccg tgctgacgca gcagacggaa    1680
agacagagcg gttgcgtgca ggtcagattt gttcttttg ttttcgtcca gcagtacgat    1740
gttttccagg gctttaatga tgtcttttc aaatttgtag gtcagaccca ggcgctgcac    1800
atcgtcgatc agctccagca gggacagcgg ctgggtgtct acacggttga tcatgcagcg    1860
aacttcttcc tccagtttgg tcgctttctc ctccagcttt tccactttca ggtcgttctc    1920
cagggattgc aggaattcga aattccacag gtttggctga tagtttgcgg aacgacggga    1980
attatgctcg gtaatctgag taaattgaga agaggtcgca cacatatgac gaccttcgat    2040
atggccgctg ctgtgatgat gatgatgatg atgatgatga tggcccatgg tatatctcct    2100
tcttaaagtt aaacaaaatt atttctagag gggaattgtt atccgctcac aattccccta    2160
tagtgagtcg tattaatttc gcgggatcga gatctcgatc ctctacgccg gacgcatcgt    2220
ggccggcatc accggcgcca caggtgcggt tgctggcgcc tatatcgccg acatcaccga    2280
tgggggaagat cgggctcgcc acttcgggct catgagcgct tgtttcggcg tgggtatggt    2340
ggcaggcccc gtggccgggg gactgttggg cgccatctcc ttgcatgcac cattccttgc    2400
ggcggcggtg ctcaacggcc tcaacctact actgggctgc ttcctaatgc aggagtcgca    2460
taagggagag cgtcgagatc ccggacacca tcgaatggcg caaaacctt cgcggtatgg    2520
catgatagcg cccggaagag agtcaattca gggtggtgaa tgtgaaacca gtaacgttat    2580
acgatgtcgc agagtatgcc ggtgtctctt atcagaccgt ttcccgcgtg gtgaaccagg    2640
ccagccacgt ttctgcgaaa acgcgggaaa aagtggaagc ggcgatggcg gagctgaatt    2700
acattcccaa ccgcgtggca caacaactgg cgggcaaaca gtcgttgctg attggcgttg    2760
ccacctccag tctggccctg cacgcgccgt cgcaaattgt cgcggcgatt aaatctcgcg    2820
ccgatcaact gggtgccagc gtggtggtgt cgatggtaga acgaagcggc gtcgaagcct    2880
gtaaagcggc ggtgcacaat cttctcgcgc aacgcgtcag tgggctgatc attaactatc    2940
cgctggatga ccaggatgcc attgctgtgg aagctgcctg cactaatgtt ccggcgttat    3000
ttcttgatgt ctctgaccag acacccatca acagtattat tttctcccat gaagacggta    3060
cgcgactggg cgtggagcat ctggtcgcat tgggtcacca gcaaatcgcg ctgttagcgg    3120
gcccattaag ttctgtctcg gcgcgtctgc gtctggctgg ctggcataaa tatctcactc    3180
gcaatcaaat tcagccgata gcggaacggg aaggcgactg gagtgccatg tccggttttc    3240
aacaaaccat gcaaatgctg aatgagggca tcgttcccac tgcgatgctg gttgccaacg    3300
atcagatggc gctgggcgca atgcgcgcca ttaccgagtc cgggctgcgc gttggtgcgg    3360
atatctcggt agtgggatac gacgataccg aagacagctc atgttatatc ccgccgttaa    3420
ccaccatcaa acaggatttt cgcctgctgg ggcaaaccag cgtggaccgc ttgctgcaac    3480
tctctcaggg ccaggcggtg aagggcaatc agctgttgcc cgtctcactg gtgaaaagaa    3540
aaaccaccct ggcgcccaat acgcaaaccg cctctccccg cgcgttggcc gattcattaa    3600
tgcagctggc acgacaggtt tcccgactgg aaagcgggca gtgagcgcaa cgcaattaat    3660
gtaagttagc tcactcatta ggcaccggga tctcgaccga tgcccttgag agccttcaac    3720
ccagtcagct ccttccggtg ggcgcggggc atgactatcg tcgccgcact tatgactgtc    3780
ttctttatca tgcaactcgt aggacaggtg ccggcagcgc tctgggtcat tttcggcgag    3840
```

```
gaccgctttc gctggagcgc gacgatgatc ggcctgtcgc ttgcggtatt cggaatcttg    3900
cacgccctcg ctcaagcctt cgtcactggt cccgccacca aacgtttcgg cgagaagcag    3960
gccattatcg ccggcatggc ggccgacgcg ctgggctacg tcttgctggc gttcgcgacg    4020
cgaggctgga tggccttccc cattatgatt cttctcgctt ccggcggcat cgggatgccc    4080
gcgttgcagg ccatgctgtc caggcaggta gatgacgacc atcagggaca gcttcaagga    4140
tcgctcgcgg ctcttaccag cctaacttcg atcactggac cgctgatcgt cacggcgatt    4200
tatgccgcct cggcgagcac atggaacggg ttggcatgga ttgtaggcgc cgccctatac    4260
cttgtctgcc tccccgcgtt gcgtcgcggt gcatggagcc gggccacctc gacctgaatg    4320
gaagccggcg gcacctcgct aacggattca ccactccaag aattggagcc aatcaattct    4380
tgcggagaac tgtgaatgcg caaaccaacc cttggcagaa catatccatc gcgtccgcca    4440
tctccagcag ccgcacgcgg cgcatctcgg gcagcgttgg gtcctggcca cgggtgcgca    4500
tgatcgtgct cctgtcgttg aggacccggc taggctggcg gggttgcctt actggttagc    4560
agaatgaatc accgatacgc gagcgaacgt gaagcgactg ctgctgcaaa acgtctgcga    4620
cctgagcaac aacatgaatg gtcttcggtt tccgtgtttc gtaaagtctg gaaacgcgga    4680
agtcagcgcc ctgcaccatt atgttccgga tctgcatcgc aggatgctgc tggctaccct    4740
gtggaacacc tacatctgta ttaacgaagc gctggcattg accctgagtg atttttctct    4800
ggtcccgccg catccatacc gccagttgtt taccctcaca acgttccagt aaccgggcat    4860
gttcatcatc agtaacccgt atcgtgagca tcctctctcg tttcatcggt atcattaccc    4920
ccatgaacag aaatccccct tacacggagg catcagtgac caaacaggaa aaaaccgccc    4980
ttaacatggc ccgctttatc agaagccaga cattaacgct tctggagaaa ctcaacgagc    5040
tggacgcgga tgaacaggca gacatctgtg aatcgcttca cgaccacgct gatgagcttt    5100
accgcagctg cctcgcgcgt ttcggtgatg acggtgaaaa cctctgacac atgcagctcc    5160
cggagacggt cacagcttgt ctgtaagcgg atgccgggag cagacaagcc cgtcagggcg    5220
cgtcagcggg tgttggcggg tgtcggggcg cagccatgac ccagtcacgt agcgatagcg    5280
gagtgtatac tggcttaact atgcggcatc agagcagatt gtactgagag tgcaccatat    5340
atgcggtgtg aaataccgca cagatgcgta aggagaaaat accgcatcag gcgctcttcc    5400
gcttcctcgc tcactgactc gctgcgctcg gtcgttcggc tgcggcgagc ggtatcagct    5460
cactcaaagg cggtaatacg gttatccaca gaatcagggg ataacgcagg aaagaacatg    5520
tgagcaaaag gccagcaaaa ggccaggaac cgtaaaaagg ccgcgttgct ggcgtttttc    5580
cataggctcc gcccccctga cgagcatcac aaaaatcgac gctcaagtca gaggtggcga    5640
aacccgacag gactataaag ataccaggcg tttccccctg gaagctccct cgtgcgctct    5700
cctgttccga ccctgccgct taccggatac ctgtccgcct ttctcccttc gggaagcgtg    5760
gcgctttctc atagctcacg ctgtaggtat ctcagttcgg tgtaggtcgt tcgctccaag    5820
ctgggctgtg tgcacgaacc ccccgttcag cccgaccgct gcgccttatc cggtaactat    5880
cgtcttgagt ccaacccggt aagacacgac ttatcgccac tggcagcagc cactggtaac    5940
aggattagca gagcgaggta tgtaggcggt gctacagagt tcttgaagtg gtggcctaac    6000
tacggctaca ctagaaggac agtatttggt atctgcgctc tgctgaagcc agttaccttc    6060
ggaaaaagag ttggtagctc ttgatccggc aaacaaacca ccgctggtag cggtggtttt    6120
tttgtttgca agcagcagat tacgcgcaga aaaaaaggat ctcaagaaga tcctttgatc    6180
```

| | |
|---|---|
| ttttctacgg ggtctgacgc tcagtggaac gaaaactcac gttaagggat tttggtcatg | 6240 |
| agattatcaa aaaggatctt cacctagatc cttttaaatt aaaaatgaag ttttaaatca | 6300 |
| atctaaagta tatatgagta aacttggtct gacagttacc aatgcttaat cagtgaggca | 6360 |
| cctatctcag cgatctgtct atttcgttca tccatagttg cctgactccc cgtcgtgtag | 6420 |
| ataactacga tacgggaggg cttaccatct ggccccagtg ctgcaatgat accgcgagac | 6480 |
| ccacgctcac cggctccaga tttatcagca ataaaccagc cagccggaag ggccgagcgc | 6540 |
| agaagtggtc ctgcaacttt atccgcctcc atccagtcta ttaattgttg ccgggaagct | 6600 |
| agagtaagta gttcgccagt taatagtttg cgcaacgttg ttgccattgc tgcaggcatc | 6660 |
| gtggtgtcac gctcgtcgtt tggtatggct tcattcagct ccggttccca acgatcaagg | 6720 |
| cgagttacat gatcccccat gttgtgcaaa aaagcggtta gctccttcgg tcctccgatc | 6780 |
| gttgtcagaa gtaagttggc cgcagtgtta tcactcatgg ttatggcagc actgcataat | 6840 |
| tctcttactg tcatgccatc cgtaagatgc ttttctgtga ctggtgagta ctcaaccaag | 6900 |
| tcattctgag aatagtgtat gcggcgaccg agttgctctt gcccggcgtc aacacgggat | 6960 |
| aataccgcgc cacatagcag aactttaaaa gtgctcatca ttggaaaacg ttcttcgggg | 7020 |
| cgaaaactct caaggatctt accgctgttg agatccagtt cgatgtaacc cactcgtgca | 7080 |
| cccaactgat cttcagcatc ttttactttc accagcgttt ctgggtgagc aaaaacagga | 7140 |
| aggcaaaatg ccgcaaaaaa gggaataagg gcgacacgga aatgttgaat actcatactc | 7200 |
| ttcctttttc aatattattg aagcatttat cagggttatt gtctcatgag cggatacata | 7260 |
| tttgaatgta tttagaaaaa taaacaaata ggggttccgc gcacatttcc ccgaaaagtg | 7320 |
| ccacctgacg tctaagaaac cattattatc atgacattaa cctataaaaa taggcgtatc | 7380 |
| acgaggccct ttcgtcttca agaa | 7404 |

<210> SEQ ID NO 4
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 4

| | |
|---|---|
| cccgtcttac tgtcgggaat tcgcgttggc cgattcatta atgcagctgg cacgacaggt | 60 |
| ttcccgactg gaaagcgggc agtgagcgca acgcaattaa tgtgagttag ctcactcatt | 120 |
| aggcacccca ggctttacac tttatgcttc cggctcgtat gttgtgtgga attgtgagcg | 180 |
| gataacaatt tcacacagga aacagctatg accatgatta cgccaagctt gtatcgatta | 240 |
| aataaggagg aataaaccat gtgtgcgacc tcttctcaat ttactcagat taccgagcat | 300 |
| aattcccgtc gttccgcaaa ctatcagcca aacctgtgga atttcgaatt cctgcaatcc | 360 |
| ctggagaacg acctgaaagt ggaaaagctg gaggagaaag cgaccaaact ggaggaagaa | 420 |
| gttcgctgca tgatcaaccg tgtagacacc cagccgctgt ccctgctgga gctgatcgac | 480 |
| gatgtgcagc gcctgggtct gacctacaaa tttgaaaaag acatcattaa agccctggaa | 540 |
| aacatcgtac tgctggacga aaacaaaaag aacaaatctg acctgcacgc aaccgctctg | 600 |
| tctttccgtc tgctgcgtca gcacggtttc gaggtttctc aggatgtttt tgagcgtttc | 660 |
| aaggataaag aaggtggttt cagcggtgaa ctgaaaggtg acgtccaagg cctgctgagc | 720 |
| ctgtatgaag cgtcttacct gggtttcgag ggtgagaacc tgctggagga ggcgcgtacc | 780 |
| ttttccatca cccacctgaa gaacaacctg aaagaaggca ttaataccaa ggttgcagaa | 840 |

```
caagtgagcc acgccctgga actgccatat caccagcgtc tgcaccgtct ggaggcacgt    900
tggttcctgg ataaatacga accgaaagaa ccgcatcacc agctgctgct ggagctggcg    960
aagctggatt taacatggt acagaccctg caccagaaag agctgcaaga tctgtcccgc   1020
tggtggaccg agatgggcct ggctagcaaa ctggattttg tacgcgaccg cctgatggaa   1080
gtttatttct gggcactggg tatggcgcca gacccgcagt ttggtgaatg tcgcaaagct   1140
gttactaaaa tgtttggtct ggtgacgatc atcgatgacg tgtatgacgt ttatggcact   1200
ctggacgaac tgcaactgtt caccgatgct gtagagcgct gggacgttaa cgctattaac   1260
accctgccgg actatatgaa actgtgtttc ctggcactgt acaacaccgt taacgacacg   1320
tcctattcta ttctgaaaga gaaaggtcat aacaacctgt cctatctgac gaaaagctgg   1380
cgtgaactgt gcaaagcctt tctgcaagag gcgaaatggt ccaacaacaa aattatcccg   1440
gctttctcca gtacctgga aaacgccagc gtttcctcct ccggtgtagc gctgctggcg   1500
ccgtcttact tttccgtatg ccagcagcag gaagacatct ccgaccacgc gctgcgttcc   1560
ctgaccgact ccatggtct ggtgcgttct agctgcgtta tcttccgcct gtgcaacgat   1620
ctggccacct ctgcggcgga gctggaacgt ggcgagacta ccaattctat cattagctac   1680
atgcacgaaa acgatggtac cagcgaggaa caggcccgcg aagaactgcg taaactgatc   1740
gacgccgaat ggaaaaagat gaatcgtgaa cgcgttagcg actccaccct gctgcctaaa   1800
gcgttcatgg aaatcgcagt taacatggca cgtgtttccc actgcaccta ccagtatggc   1860
gatggtctgg tcgcccaga ctacgcgact gaaaaccgca tcaaactgct gctgattgac   1920
cctttcccga ttaaccagct gatgtatgtc taactgcagg tcgactctag aggatccccg   1980
ggtaccgagc tcgaattcac tggccgtcgt tttacaacgt cgtgactggg aaaaccctgg   2040
cgttacccaa cttaatcgcc ttgcagcaca tccccctttc gccagctggc gtaatagcga   2100
agaggcccgc accgatcgcc cttcccaaca gttgcgcagc ctgaatggcg aatggcgcct   2160
gatgcggtat tttctcctta cgcatctgtg cggtatttca caccgcatat ggtgcactct   2220
cagtacaatc tgctctgatg ccgcatagtt aagccagccc cgacacccgc caacacccgc   2280
tgacgagctt agtaaagccc tcgctagatt ttaatgcgga tgttgcgatt acttcgccaa   2340
ctattgcgat aacaagaaaa agccagcctt tcatgatata tctcccaatt tgtgtagggc   2400
ttattatgca cgcttaaaaa taataaaagc agacttgacc tgatagtttg gctgtgagca   2460
attatgtgct tagtgcatct aacgcttgag ttaagccgcg ccgcgaagcg cgtcggctt   2520
gaacgaattg ttagacatta tttgccgact accttggtga tctcgccttt cacgtagtgg   2580
acaaattctt ccaactgatc tgcgcgcgag gccaagcgat cttcttcttg tccaagataa   2640
gcctgtctag cttcaagtat gacgggctga tactgggccg gcaggcgctc cattgcccag   2700
tcggcagcga catccttcgg cgcgattttg ccggttactg cgctgtacca aatgcgggac   2760
aacgtaagca ctacatttcg ctcatcgcca gcccagtcgg gcggcgagtt ccatagcgtt   2820
aaggtttcat ttagcgcctc aaatagatcc tgttcaggaa ccggatcaaa gagttcctcc   2880
gccgctggac ctaccaaggc aacgctatgt tctcttgctt ttgtcagcaa gatagccaga   2940
tcaatgtcga tcgtggctgg ctcgaagata cctgcaagaa tgtcattgcg ctgccattct   3000
ccaaattgca gttcgcgctt agctggataa cgccacggaa tgatgtcgtc gtgcacaaca   3060
atggtgactt ctacagcgcg gagaatctcg ctctctccag gggaagccga agtttccaaa   3120
aggtcgttga tcaaagctcg ccgcgttgtt tcatcaagcc ttacggtcac cgtaaccagc   3180
```

```
aaatcaatat cactgtgtgg cttcaggccg ccatccactg cggagccgta caaatgtacg    3240
gccagcaacg tcggttcgag atggcgctcg atgacgccaa ctacctctga tagttgagtc    3300
gatacttcgg cgatcaccgc ttccctcatg atgtttaact ttgttttagg gcgactgccc    3360
tgctgcgtaa catcgttgct gctccataac atcaaacatc gacccacggc gtaacgcgct    3420
tgctgcttgg atgcccgagg catagactgt accccaaaaa aacagtcata acaagccatg    3480
aaaaccgcca ctgcgccgtt accaccgctg cgttcggtca aggttctgga ccagttgcgt    3540
gagcgcatac gctacttgca ttacagctta cgaaccgaac aggcttatgt ccactgggtt    3600
cgtgccttca tccgtttcca cggtgtgcgt cacccggcaa ccttgggcag cagcgaagtc    3660
gaggcatttc tgtcctggct ggcgaacgag cgcaaggttt cggtctccac gcatcgtcag    3720
gcattggcgg ccttgctgtt cttctacggc aaggtgctgt gcacggatct gccctggctt    3780
caggagatcg gaagacctcg gccgtcgcgg cgcttgccgg tggtgctgac cccggatgaa    3840
gtggttcgca tcctcggttt tctggaaggc gagcatcgtt tgttcgccca gcttctgtat    3900
ggaacgggca tgcggatcag tgagggtttg caactgcggg tcaaggatct ggatttcgat    3960
cacggcacga tcatcgtgcg ggagggcaag ggctccaagg atcgggcctt gatgttaccc    4020
gagagcttgg cacccagcct gcgcgagcag gggaattaat tcccacgggt tttgctgccc    4080
gcaaacgggc tgttctggtg ttgctagttt gttatcagaa tcgcagatcc ggcttcagcc    4140
ggtttgccgg ctgaaagcgc tatttcttcc agaattgcca tgattttttc cccacgggag    4200
gcgtcactgg ctcccgtgtt gtcggcagct ttgattcgat aagcagcatc gcctgtttca    4260
ggctgtctat gtgtgactgt tgagctgtaa caagttgtct caggtgttca atttcatgtt    4320
ctagttgctt tgttttactg gtttcacctg ttctattagg tgttacatgc tgttcatctg    4380
ttacattgtc gatctgttca tggtgaacag ctttgaatgc accaaaaact cgtaaaagct    4440
ctgatgtatc tatcttttt acaccgtttt catctgtgca tatggacagt tttcccttg     4500 atatgtaacg gtgaacagtt gttctacttt tgtttgttag tcttgatgct tcactgatag    4560
atacaagagc cataagaacc tcagatcctt ccgtatttag ccagtatgtt ctctagtgtg    4620
gttcgttgtt tttgcgtgag ccatgagaac gaaccattga gatcatactt actttgcatg    4680
tcactcaaaa attttgcctc aaaactggtg agctgaattt ttgcagttaa agcatcgtgt    4740 agtgttttc ttagtccgtt atgtaggtag gaatctgatg taatggttgt tggtatttg     4800 tcaccattca tttttatctg gttgttctca agttcggtta cgagatccat ttgtctatct    4860
agttcaactt ggaaaatcaa cgtatcagtc gggcggcctc gcttatcaac caccaatttc    4920
atattgctgt aagtgtttaa atctttactt attggtttca aaacccattg gttaagcctt    4980
ttaaactcat ggtagttatt ttcaagcatt aacatgaact taaattcatc aaggctaatc    5040
tctatatttg ccttgtgagt tttcttttgt gttagttctt ttaataacca ctcataaatc    5100
ctcatagagt atttgttttc aaaagactta acatgttcca gattatattt tatgaatttt    5160
tttaactgga aaagataagg caatatctct tcactaaaaa ctaattctaa tttttcgctt    5220
gagaacttgg catagtttgt ccactggaaa atctcaaagc ctttaaccaa aggattcctg    5280
atttccacag ttctcgtcat cagctctctg gttgctttag ctaatacacc ataagcattt    5340
tccctactga tgttcatcat ctgagcgtat tggttataag tgaacgatac cgtccgttct    5400
ttccttgtag ggttttcaat cgtgggttg agtagtgcca cacagcataa aattagcttg     5460
gtttcatgct ccgttaagtc atagcgacta atcgctagtt catttgcttt gaaacaact    5520 aattcagaca tacatctcaa ttggtctagg tgattttaat cactatacca attgagatgg    5580
```

```
gctagtcaat gataattact agtccttttc ctttgagttg tgggtatctg taaattctgc    5640
tagacctttg ctggaaaact tgtaaattct gctagaccct ctgtaaattc cgctagacct    5700
ttgtgtgttt tttttgttta tattcaagtg gttataattt atagaataaa gaaagaataa    5760
aaaaagataa aaagaataga tcccagccct gtgtataact cactacttta gtcagttccg    5820
cagtattaca aaaggatgtc gcaaacgctg tttgctcctc tacaaacag accttaaaac    5880 cctaaaggct taagtagcac cctcgcaagc tcgggcaaat cgctgaatat tccttttgtc    5940
tccgaccatc aggcacctga gtcgctgtct ttttcgtgac attcagttcg ctgcgctcac    6000
ggctctggca gtgaatgggg gtaaatggca ctacaggcgc cttttatgga ttcatgcaag    6060
gaaactaccc ataatacaag aaaagcccgt cacgggcttc tcagggcgtt tatggcggg    6120 tctgctatgt ggtgctatct gacttttgc tgttcagcag ttcctgccct ctgattttcc    6180
agtctgacca cttcggatta tcccgtgaca ggtcattcag actggctaat gcacccagta    6240
aggcagcggt atcatcaaca ggctta                                          6266

<210> SEQ ID NO 5
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 5
gaattgctcc attttcttct gctatcaaaa taacagactc gtgatttttcc aaacgagctt      60 tcaaaaaagc ctctgcccct tgcaaatcgg atgcctgtct ataaaattcc cgatattggt     120
taaacagcgg cgcaatggcg gccgcatctg atgtctttgc ttggcgaatg ttcatcttat     180
ttcttcctcc ctctcaataa tttttttcatt ctatcccttt tctgtaaagt ttatttttca    240 gaatacttt atcatcatgc tttgaaaaaa tatcacgata atatccattg ttctcacgga    300
agcacacgca ggtcatttga acgaattttt tcgacaggaa tttgccggga ctcaggagca    360
tttaacctaa aaaagcatga catttcagca taatgaacat ttactcatgt ctattttcgt    420 tctttttctgt atgaaaatag ttatttcgag tctctacgga aatagcgaga gatgatatac    480
ctaaatagag ataaaatcat ctcaaaaaaa tgggtctact aaaatattat tccatctatt    540
acaataaatt cacagaatag tctttttaagt aagtctactc tgaattttt taaaaggaga    600 gggtaaagag tgtgtgcgac ctcttctcaa tttactcaga ttaccgagca taattcccgt    660
cgttccgcaa actatcagcc aaacctgtgg aatttcgaat tcctgcaatc cctggagaac    720
gacctgaaag tggaaaagct ggaggagaaa gcgaccaaac tggaggaaga agttcgctgc    780
atgatcaacc gtgtagacac ccagccgctg tccctgctgg agctgatcga cgatgtgcag    840
cgcctgggtc tgacctacaa atttgaaaaa gacatcatta agccctgga aacatcgta    900 ctgctggacaaaaacaaaaa gaacaaatct gacctgcacg caaccgctct gtcttttcgt    960
ctgctgcgtc agcacggttt cgaggtttct caggatgttt ttgagcgttt caaggataaa   1020
gaaggtggtt tcagcggtga actgaaaggt gacgtccaag gcctgctgag cctgtatgaa   1080
gcgtcttacc tgggtttcga gggtgagaac ctgctggagg aggcgcgtac cttttccatc   1140
acccacctga gaacaacct gaaagaaggc attaatacca aggttgcaga acaagtgagc   1200
cacgccctgg aactgccata tcaccagcgt ctgcaccgtc tggaggcacg ttggttcctg   1260
gataaatacg aaccgaaaga accgcatcac cagctgctgc tggagctggc gaagctggat   1320
```

```
tttaacatgg tacagaccct gcaccagaaa gagctgcaag atctgtcccg ctggtggacc    1380
gagatgggcc tggctagcaa actggatttt gtacgcgacc gcctgatgga agtttatttc    1440
tgggcactgg gtatggcgcc agacccgcag tttggtgaat gtcgcaaagc tgttactaaa    1500
atgtttggtc tggtgacgat catcgatgac gtgtatgacg tttatggcac tctggacgaa    1560
ctgcaactgt tcaccgatgc tgtagagcgc tgggacgtta acgctattaa caccctgccg    1620
gactatatga actgtgtttt cctggcactg tacaacaccg ttaacgacac gtcctattct    1680
attctgaaag agaaaggtca taacaacctg tcctatctga cgaaaagctg gcgtgaactg    1740
tgcaaagcct ttctgcaaga ggcgaaatgg tccaacaaca aaattatccc ggctttctcc    1800
aagtacctgg aaaacgccag cgtttcctcc tccggtgtag cgctgctggc gccgtcttac    1860
ttttccgtat gccagcagca ggaagacatc tccgaccacg cgctgcgttc cctgaccgac    1920
ttccatggtc tggtgcgttc tagctgcgtt atcttccgcc tgtgcaacga tctggccacc    1980
tctgcggcgg agctggaacg tggcgagact accaattcta tcattagcta catgcacgaa    2040
aacgatggta ccagcgagga acaggcccgc gaagaactgc gtaaactgat cgacgccgaa    2100
tggaaaaaga tgaatcgtga acgcgttagc gactccaccc tgctgcctaa agcgttcatg    2160
gaaatcgcag ttaacatggc acgtgtttcc cactgcacct accagtatgg cgatggtctg    2220
ggtcgcccag actacgcgac tgaaaaccgc atcaaactgc tgctgattga ccctttcccg    2280
attaaccagc tgatgtatgt ctaaaaaaaa ccggccttgg ccccgccggt tttttattat    2340
ttttcttcct ccgcatgttc aatccgctcc ataatcgacg gatggctccc tctgaaaatt    2400
ttaacgagaa acgcgggtt gacccggctc agtcccgtaa cggccaagtc ctgaaacgtc    2460
tcaatcgccg cttccggtt tccggtcagc tcaatgccgt aacggtcggc ggcgttttcc    2520
tgataccggg agacggcatt cgtaatcgga tcctctagag tcgacctgca ggcatgcaag    2580
cttttgcctcg cgcgtttcgg tgatgacggt gaaaacctct gacacatgca gctcccggag    2640
acggtcacag cttgtctgta agcggatgcc gggagcagac aagcccgtca gggcgcgtca    2700
gcgggtgttg gcgggtgtcg ggcgcagcc atgacccagt cacgtagcga tagcggagtg    2760
tatactggct taactatgcg gcatcagagc agattgtact gagagtgcac catatgcggt    2820
gtgaaatacc gcacagatgc gtaaggagaa ataccgcat caggcgctct ccgcttcct    2880
cgctcactga ctcgctgcgc tcggtcgttc ggctgcggcg agcggtatca gctcactcaa    2940
aggcggtaat acggttatcc acagaatcag gggataacgc aggaaagaac atgtgagcaa    3000
aaggccagca aaaggccagg aaccgtaaaa aggccgcgtt gctggcgttt ttccataggc    3060
tccgcccccc tgacgagcat cacaaaaatc gacgctcaag tcagaggtgg cgaaacccga    3120
caggactata aagataccag gcgtttcccc ctggaagctc cctcgtgcgc tctcctgttc    3180
cgaccctgcc gcttaccgga tacctgtccg cctttctccc ttcgggaagc gtggcgcttt    3240
ctcaatgctc acgctgtagg tatctcagtt cggtgtaggt cgttcgctcc aagctgggct    3300
gtgtgcacga accccccgtt cagcccgacc gctgcgcctt atccggtaac tatcgtcttg    3360
agtccaaccc ggtaagacac gacttatcgc cactggcagc agccactggt aacaggatta    3420
gcagagcgag gtatgtaggc ggtgctacag agttcttgaa gtggtggcct aactacggct    3480
acactagaag gacagtattt ggtatctgcg ctctgctgaa gccagttacc ttcggaaaaa    3540
gagttggtag ctcttgatcc ggcaaacaaa ccaccgctgg tagcggtggt ttttttgttt    3600
gcaagcagca gattacgcgc agaaaaaaag gatctcaaga agatcctttg atcttttcta    3660
cggggtctga cgctcagtgg aacgaaaact cacgttaagg gattttggtc atgagattat    3720
```

```
caaaaaggat cgaagtcggt tcagaaaaag aaggatatgg atctggagct gtaatataaa   3780
aaccttcttc aactaacggg gcaggttagt gacattagaa aaccgactgt aaaaagtaca   3840
gtcggcatta tctcatatta taaaagccag tcattaggcc tatctgacaa ttcctgaata   3900
gagttcataa acaatcctgc atgataacca tcacaaacag aatgatgtac ctgtaaagat   3960
agcggtaaat atattgaatt acctttatta atgaattttc ctgctgtaat aatgggtaga   4020
aggtaattac tattattatt gatatttaag ttaaacccag taaatgaagt ccatggaata   4080
atagaaagag aaaaagcatt ttcaggtata ggtgttttgg gaaacaattt aaaagaacca   4140
ttatatttct ctacatcaga aaggtataaa tcataaaact ctttgaagtc attctttaca   4200
ggagtccaaa taccagagaa tgttttagat acaccatcaa aaattgtata aagtggctct   4260
aacttatccc aataacctaa ctctccgtcg ctattgtaac cagttctaaa agctgtattt   4320
gagtttatca cccttgtcac taagaaaata aatgcagggt aaaatttata tccttcttgt   4380
tttatgtttc ggtataaaac actaatcatca atttctgtgg ttatactaaa agtcgtttgt   4440
tggttcaaat aatgattaaa tatctctttt ctcttccaat tgtctaaatc aattttatta   4500
aagttcattt gatatgcctc ctaaatttttt atctaaagtg aatttaggag cttacttgt    4560
ctgctttctt cattagaatc aatccttttt taaagtcaat attactgtaa cataaatata   4620
tattttaaaa atatcccact ttatccaatt ttcgtttgtt gaactaatgg gtgctttagt   4680
tgaagaataa agaccacatt aaaaaatgtg gtcttttgtg ttttttttaaa ggatttgagc  4740
gtacgcgaaa aatccttttc tttctttctt atcttgataa taagggtaac tattgccggt   4800
tgtccattca tggctgaact ctgcttcctc tgttgacatg acacacatca tctcaatatc   4860
cgaatagggc ccatcagtct gacgaccaag agagccataa acaccaatag ccttaacatc   4920
atccccatat ttatccaata ttcgttcctt aatttcatga acaatcttca ttctttcttc   4980
tctagtcatt attattggtc cattcactat tctcattccc ttttcagata attttagatt   5040
tgctttttcta aataagaata tttggagagc accgttctta ttcagctatt aataactcgt   5100
cttcctaagc atccttcaat cctttttaata acaattatag catctaatct tcaacaaact  5160
ggcccgtttg ttgaactact cttttaataaa ataatttttc cgttcccaat tccacattgc  5220
aataatagaa aatccatctt catcggcttt ttcgtcatca tctgtatgaa tcaaatcgcc   5280
ttcttctgtg tcatcaaggt ttaatttttt atgtatttct tttaacaaac caccatagga   5340
gattaacctt ttacggtgta aaccttcctc caaatcagac aaacgtttca aattcttttc   5400
ttcatcatcg gtcataaaat ccgtatcctt tacaggatat tttgcagttt cgtcaattgc   5460
cgattgtata tccgatttat atttattttt cggtcgaatc atttgaactt ttacatttgg   5520
atcatagtct aatttcattg ccttttttcca aaattgaatc cattgttttt gattcacgta   5580
gttttctgtt attctaaaat aagttggttc cacacatacc attacatgca tgtgctgatt   5640
ataagaatta tctttattat ttattgtcac atccgttgca cgcataaaac caacaagatt   5700
tttattaatt tttttatatt gcatcattcg gcgaaatcct tgagccatat ctgtcaaact   5760
cttatttaat tcttcgccat cataaacatt tttaactgtt aatgtgagaa acaaccaacg   5820
aactgttggc ttttgtttaa taacttcagc aacaacctttt tgtgactgaa tgccatgttt   5880
cattgctctc ctccagttgc acattggaca aagcctggat ttgcaaaacc acactcgata   5940
ccactttctt tcgcctgttt cacgattttg tttatactct aatatttcag cacaatcttt   6000
tactctttca gcctttttaa attcaagaat atgcagaagt tcaaagtaat caacattagc   6060
```

| | |
|---|---|
| gattttctttt tctctccatg gtctcacttt tccactttttt gtcttgtcca ctaaaaccct | 6120 |
| tgattttttca tctgaataaa tgctactatt aggacacata atattaaaag aaaccccccat | 6180 |
| ctatttagtt atttgtttag tcacttataa ctttaacaga tggggttttt ctgtgcaacc | 6240 |
| aattttaagg gttttcaata ctttaaaaca catacatacc aacacttcaa cgcacctttc | 6300 |
| agcaactaaa ataaaaatga cgttatttct atatgtatca agataagaaa gaacaagttc | 6360 |
| aaaaccatca aaaaaagaca ccttttcagg tgctttttttt attttataaa ctcattccct | 6420 |
| gatctcgact tcgttctttt tttacctctc ggttatgagt tagttcaaat tcgttctttt | 6480 |
| taggttctaa atcgtgtttt tcttggaatt gtgctgtttt atcctttacc ttgtctacaa | 6540 |
| accccttaaa aacgttttta aaggctttta agccgtctgt acgttcctta ag | 6592 |

<210> SEQ ID NO 6
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 6

| | |
|---|---|
| atgtgtgcaa cctcctccca gtttactcag attaccgagc ataattctcg acgatctgct | 60 |
| aactaccagc cgaaccttttg gaactttgag tttctccagt ctctcgaaaa tgacctgaag | 120 |
| gtggaaaagc tcgaggagaa ggcgaccaaa ctcgaggagg aggtgcgatg tatgatcaac | 180 |
| agagttgaca cccaacccct gtctttgctg gagctgatcg acgatgtgca gcggttgggt | 240 |
| tgacttata aattcgagaa ggacattatc aaggcactgg agaacattgt gctcctcgac | 300 |
| gagaacaaga gaacaagtc tgatcttcac gctaccgctc tctctttccg acttcttcga | 360 |
| caacacggct tcgaggtgtc gcaggacgtc ttcgagagat ttaaggacaa ggagggagga | 420 |
| tttagcggcg agctgaaggg agacgttcag ggtcttctct ccttgtacga ggcgtcctac | 480 |
| ctgggattcg agggagagaa cctcctggag gaagctcgta cattttccat cactcacctt | 540 |
| aagaataacc ttaaggaggg aattaacacc aaggtggccg agcaggtttc tcacgccctg | 600 |
| gagctcccct accaccaacg gctccataga ctggaggctc gttggttcct ggacaaaatat | 660 |
| gagccaaagg agcctcatca tcagttgctg ttggagttgg ccaagctgga cttcaatatg | 720 |
| gttcagacgc tgcaccaaaa ggagttgcag gacctgtctc gatggtggac cgagatggga | 780 |
| ttggcctcga agctggattt tgtccgtgac cgacttatgg aggtctattt tggggccctt | 840 |
| ggaatggcgc ctgaccccca gttcggagag tgccggaagg cggtgacgaa gatgttcggt | 900 |
| cttgtgacta tcatcgacga cgtctacgat gtctacggca cactcgacga gttgcagctg | 960 |
| ttcactgacg ccgtcgagcg atgggatgtg aacgccatta atactctccc tgactatatg | 1020 |
| aagctgtgct tcctggctct gtacaacact gtcaacgata cctcgtactc tatcctcaag | 1080 |
| gagaagggac acaacaatct ctcctacttg accaaatcct ggcgagaact gtgcaaggct | 1140 |
| tttctgcagg aggctaaatg gtccaataac aagatcattc tgctttttc taaatacctg | 1200 |
| gaaaatgcct cggtgtcgag ctctggcgtc gcccttctgg ccccttccta cttctccgtc | 1260 |
| tgccagcagc aggaggatat ttccgatcat gctcttagat cgctgaccga ttttcacggc | 1320 |
| ctcgtgcgat cttcctgcgt gatttttcgg ttgtgtaatg accttgcgac ctctgctgct | 1380 |
| gagctggaac gaggcgagac tacaaattcc attatttctt acatgcacga aaacgatgga | 1440 |
| acatctgaag aacaggctag agaggaactg cgaaagttga tcgacgccga gtggaagaag | 1500 |
| atgaacagag agcgggtgtc cgactctacc ctgcttccca aggccttcat ggagatcgcc | 1560 |

```
gtgaacatgg ctcgagtttc ccattgtact taccagtacg gtgacggcct gggtcgtccg   1620
gactacgcta cagagaaccg aatcaagctg ctgctcatcg acccttccc tatcaaccaa    1680 ttgatgtacg tgtaa                                                    1695

<210> SEQ ID NO 7
<211> LENGTH: 8191
<212> TYPE: DNA
<213> ORGANISM: Artificial Sequence
<220> FEATURE:
<223> OTHER INFORMATION: Synthetic Construct

<400> SEQUENCE: 7
tcgaccggtg agaagaacag catcgggaca agggaaggaa gaacaaagac aaagaaaaca     60
aaagaaagca attgaaaaca aaacaaaaca attttcattc cttctcttat cattcctttt    120
cttttctttt ctctcattca acgcactcca tcgtatccgt attcctctta ttttttctct    180
ttctctatat ccatttcttt ctctctaggt gtgtcctctc tctctcttca atttctctac    240
tccgcattcc aacgcatcct tcccccaacc tcccatttcc tccttacggc ccgatagcga    300
tcgtctttcc ctcgctatca ctcgctaccg gcccctcctc tgcaccgtaa cctcctacgt    360
atttaccata tcataaagtt ttttccgacg cttatcgctg acccctgtc gccctcctat     420 tggcttccgg attatcttct tgtccataag gtgatccatg cttcctgaag attcccgaaa    480
tgtgtccact ttggcgggga atcattccat ccacttcttt ctctctcgct ttcctcattc    540
ggcgctcccc ttccgcgtct cattggtctt ccgctccgtt tttgctttgc cgatgttact    600
tggggagagg tgcgataatc ctttcgcaaa aactcggttt gacgcctccc atggtataaa    660
tagtgggtgg tggacaggtg ccttcgcttt tctttaagca agagaatccc attgtcttga    720
ctatcacgaa ttcacataca ttatgaagat caccgctgtc attgcccttt tattctcact    780
tgctgctgcc tcacctattc cagttgccga tcctggtgtg gtttcagtta gcaagtcata    840
tgctgatttc cttcgtgttt accaaagttg gaacactttt gctaatcctg atagacccaa    900
ccttaagaag agaaatgata cacctgcaag tggatatcaa gttgaaaaag tcgtaatttt    960
gtcacgtcac ggtgttaggg cccctacaaa aatgactcaa accatgcgtg atgtcactcc   1020
taatacatgg ccagaatggc ccgttaaatt aggatatatt acaccaagag gtgaacactt   1080
gatatcactt atgggcggtt tttaccgtca aaaattccag caacaaggaa tcctttctca   1140
gggctcctgt cctactccta actccatata tgtctgggct gacgtcgatc agcgtacttt   1200
aaaaactggt gaagcattcc ttgctggttt ggcaccacaa tgtggcttga caattcatca   1260
ccaacaaaat cttgagaaag ctgatcctct tttttcatccc gttaaagctg aacctgctc   1320 tatggataaa actcaagttc aacaagctgt tgagaaggag gcacaaactc ctatagaaa    1380 tttgaatcaa cattacatcc ccttttttagc tttaatgaat acaacattaa attttagtac   1440
ttctgcctgg tgccaaaaac actctgctga taaatcctgt gacctaggtt tatccatgcc   1500
ttctaaattg tccataaaag ataatggtaa caaggtcgca ttggatggag ctattggtct   1560
atcctctact ttggccgaga ttttttcttct tgaatatgct caaggcatgc ctcaagctgc   1620
ttggggtaac atccactcag agcaagagtg ggcttccttg ctaaagttgc ataatgttca   1680
attcgatttg atggcccgaa cacttatat tgctcgacat aacggtactc ctttattgca   1740
agctatatca aatgcccta atcccaacgc cactgaatca aaacttccag atatttcacc   1800
tgataacaaa atattgttca ttgcaggtca tgacacaaat attgctaata tagccggcat   1860
```

```
gttaaatatg cgttggacat taccaggtca accagataat actcctccag gtggtgccct    1920
agtatttgaa cgtcttgctg ataaaagtgg aaaacaatat gtttctgtat ctatggttta    1980
tcaaacacta gaacaacttc gatcacagac tcccctttct ctaaatcagc ctgccggatc    2040
tgttcaactt aaaattccag gttgcaatga tcaaacagcc gagggttact gtcctctttc    2100
cacttttaca agagttgttt cccaatctgt tgaacctgga tgccaacttc aataatgagg    2160
atccaagtaa gggaatgaga atgtgatcca cttttaattc ctaatgaata catgcctata    2220
gttcttttct tttgttcttt atgtcgtttt tcgatggtac ggccgttgtc aatctcagtt    2280
tgtgtgcttg gttgcagctt ggtttcaaat ctgttcatct catgaatctt ttaccatttc    2340
accacacgtt tataccattc tctcatagaa tcttcatcaa accatctcgg ggttagagtg    2400
gaaagaaagt cttgttcttt tatttccttt tttccatctt caaggctttt cttttcttcc    2460
tcctcctcgt tcatcttgag gtttgacgtg tctgtttaga attttgagct gttgcagcat    2520
cttatttttt gttttgcgaa aacgaagcgc tttactctct tcatcagttg gacgattgta    2580
cctttgaaaa ccaactactt tgcatgtttt tgtatagaaa tcaatgatat tagaatccca    2640
tcctttaatt tctttcaaag tagttgagct atagttaagt gtaagggccc tactgcgaaa    2700
gcatttgcca aggatgtttt cattaatcaa gaacgaaagt taggggatcg aagacgatca    2760
gataccgtcg tagtcttaac cataaactat gccgactagg gatcgggcaa tgtttcattt    2820
atcgacttgc tcggcaccct acgagaaatc aaagtctttg ggttccgggg ggagtatggt    2880
cgcaaggctg aaacttaaag gaattgacgg aagggcacca caatggagtg gagcctgcgg    2940
cttaatttga ctcaacacgg ggaaactcac caggtccaga catagtaagg attgacagat    3000
tgagagctct ttcttgattc tatgggtggt ggtgcatggc cgttcttagt tggtggagtg    3060
atttgtctgc ttaattgcga taacgaacga gaccttaacc tgctaaatag ctggatcagc    3120
cattttggct gatcattagc ttcttagagg gactattggc ataaagccaa tggaagtttg    3180
aggcaataac aggtctgtga tgcccttaga tgttctgggc cgcacgcgcg ctacactgac    3240
ggagccaacg agttgaaaaa aatcttttga ttttttatcc ttggccggaa ggtctgggta    3300
atcttgttaa actccgtcgt gctggggata gagcattgca attattgcgg ccgctcctca    3360
attcgatgtt gcagatttta caagttttta aaatgtattt cattattact ttttatatgc    3420
ctaataaaaa agccatagtt taatctatag ataacttttt ttccagtgca ctaacggacg    3480
ttacattccc atacaaaact gcgtagttaa agctaaggaa aagttaatat catgttaatt    3540
aaatacgcta tttacaataa gacattgaac tcatttatat cgttgaatat gaataaccaa    3600
tttcagcgaa tttttaacaa acatcgttca cctcgtttaa ggatatcttg tgtatggggt    3660
gttgacttgc tttatcgaat aattaccgta cctgtaattg gcttgctgga tatagcggta    3720
gtctaatatc tagcaaaaat cttttgggtg aaaaggcttg caatttcacg acaccgaact    3780
atttgtcatt ttttaataag gaagttttcc ataaattcct gtaattctcg gttgatctaa    3840
ttgaaaagag tagttttgca tcacgatgag gagggctttt gtagaaagaa atacgaacga    3900
aacgaaaatc agcgttgcca tcgctttgga caaagctccc ttacctgaag agtcgaattt    3960
tattgatgaa cttataactt ccaagcatgc aaaccaaaag ggagaacaag taatccaagt    4020
agacacggga attggattct tggatcacat gtatcatgca ctggctaaac atgcaggctg    4080
gagcttacga ctttactcaa gaggtgattt aatcatcgat gatcatcaca ctgcagaaga    4140
tactgctatt gcacttggta ttgcattcaa gcaggctatg ggtaactttg ccggcgttaa    4200
aagatttgga catgcttatt gtccacttga cgaagctctt tctagaagcg tagttgactt    4260
```

```
gtcgggacgg ccctatgctg ttatcgattt gggattaaag cgtgaaaagg ttggggaatt    4320
gtcctgtgaa atgatccctc acttactata ttccttttcg gtagcagctg gaattacttt    4380
gcatgttacc tgcttatatg gtagtaatga ccatcatcgt gctgaaagcg cttttaaatc    4440
tctggctgtt gccatgcgcg cggctactag tcttactgga agttctgaag tcccaagcac    4500
gaagggagtg ttgtaaagat gaattggatt atgtcaggaa aagaacgaca attttgcatc    4560
caaattgtct aaattttaga gttgcttgaa acaatagaa ccttacttgc tttataatta    4620
cgttaattag aagcgttatc tcgtgaagga atatagtacg tagccgtata aattgaattg    4680
aatgttcagc ttatagaata gagacacttt gctgttcaat cgtcgtcac ttaccatact    4740 cactttatta tacgacttta agtataaact ccgcggttat ggtaaaatta atgatgcaca    4800
aacgtccgat tccatatggg tacactacaa ttaaatactt ttaagctgat cccccacaca    4860
ccatagcttc aaaatgtttc tactcctttt ttactcttcc agattttctc ggactccgcg    4920
catcgccgta ccacttcaaa acacccaagc acagcatact aaattttccc tctttcttcc    4980
tctagggtgt cgttaattac ccgtactaaa ggtttggaaa agaaaaaga gaccgcctcg    5040 tttcttttc ttcgtcgaaa aaggcaataa aaatttttat cacgtttctt tttcttgaaa    5100
tttttttttt tagttttttt ctctttcagt gacctccatt gatatttaag ttaataaacg    5160
gtcttcaatt tctcaagttt cagtttcatt tttcttgttc tattcaaact ttttttactt    5220
cttgttcatt agaaagaaag catagcaatc taatctaagg gcggtgttga caattaatca    5280
tcggcatagt atatcggcat agtataatac gacaaggtga ggaactaaac catggccaag    5340
ttgaccagtg ccgttccggt gctcaccgcg cgcgacgtcg ccggagcggt cgagttctgg    5400
accgaccggc tcgggttctc ccgggacttc gtggaggacg acttcgccgg tgtggtccgg    5460
gacgacgtga ccctgttcat cagcgcggtc caggaccagg tggtgccgga caacaccctg    5520
gcctgggtgt gggtgcgcgg cctggacgag ctgtacgccg agtggtcgga ggtcgtgtcc    5580
acgaacttcc gggacgcctc cgggccggcc atgaccgaga tcggcgagca gccgtggggg    5640
cgggagttcg ccctgcgcga cccggccggc aactgcgtgc acttcgtggc cgaggagcag    5700
gactgacacg tccgacggcg gcccacgggt cccaggcctc ggagatccgt cccccttttc    5760
ctttgtcgat atcatgtaat tagttatgtc acgcttacat tcacgccctc ccccacatc    5820 cgctctaacc gaaaaggaag gagttagaca acctgaagtc taggtcccta tttatttttt    5880
tatagttatg ttagtattaa gaacgttatt tatatttcaa attttctttt tttttctgta    5940
cagacgcgag cttcccagta aatgtgccat ctcgtaggca gaaaacggtt ccccgtagg    6000 gtctctctct tggcctcctt tctaggtcgg gctgattgct cttgaagctc tctgggggg    6060 ctcacaccat aggcagataa cgttccccac cggctcgcct cgtaagcgca caaggactgc    6120
tcccaaagat cctaggcggg attttgccga tttcggccta aggaaccgg aacacgtaga    6180 aagccagtcc gcagaaacgg tgctgacccc ggatgaatgt cagctactgg gctatctgga    6240
caagggaaaa cgcaagcgca aagagaaagc aggtagcttg cagtgggctt acatggcgat    6300
agctagactg ggcggtttta tggacagcaa gcgaaccgga attgccagct ggggcgccct    6360
ctggtaaggt tgggaagccc tgcaaagtaa actggatggc tttcttgccg ccaaggatct    6420
gatggcgcag gggatcaaga tctgatcaag agacaggatg aggatcgttt cgcatgattg    6480
aacaagatgg attgcacgca ggttctccgg ccgcttgggt ggagaggcta ttcggctatg    6540
actgggcaca acagacaatc ggctgctctg atgccgccgt gttccggctg tcagcgcagg    6600
```

```
ggcgcccggt tctttttgtc aagaccgacc tgtccggtgc cctgaatgaa ctgcaggacg    6660
aggcagcgcg gctatcgtgg ctggccacga cgggcgttcc ttgcgcagct gtgctcgacg    6720
ttgtcactga agcgggaagg gactggctgc tattgggcga agtgccgggg caggatctcc    6780
tgtcatctcg ccttgctcct gccgagaaag tatccatcat ggctgatgca atgcggcggc    6840
tgcatacgct tgatccggct acctgcccat tcgaccacca agcgaaacat cgcatcgagc    6900
gagcacgtac tcggatggaa gccggtcttg tcgatcagga tgatctggac gaagagcatc    6960
aggggctcgc gccagccgaa ctgttcgcca ggctcaaggc gcgcatgccc gacggcgagg    7020
atctcgtcgt gatccatggc gatgcctgct tgccgaatat catggtggaa aatggccgct    7080
tttctggatt caacgactgt ggccggctgg gtgtggcgga ccgctatcag gacatagcgt    7140
tggatacccg tgatattgct gaagagcttg gcggcgaatg ggctgaccgc ttcctcgtgc    7200
tttacggtat cgccgctccc gattcgcagc gcatcgcctt ctatcgcctt cttgacgagt    7260
tcttctgaat tgaaaaggt accaagttta ctcatatata ctttagattg atttaaaact    7320
tcatttttaa tttaaaagga tctaggtgaa gatcctttt gataatctca tgaccaaaat    7380
cccttaacgt gagttttcgt tccactgagc gtcagacccc gtagaaaaga tcaaaggatc    7440
ttcttgagat cctttttttc tgcgcgtaat ctgctgcttg caaacaaaaa aaccaccgct    7500
accagcggtg gtttgtttgc cggatcaaga gctaccaact cttttccga aggtaactgg    7560 cttcagcaga gcgcagatac caaatactgt ccttctagtg tagccgtagt taggccacca    7620
cttcaagaac tctgtagcac cgcctacata cctcgctctg ctaatcctgt taccagtggc    7680
tgctgccagt ggcgataagt cgtgtcttac cgggttggac tcaagacgat agttaccgga    7740
taaggcgcag cggtcgggct gaacgggggg ttcgtgcaca cagcccagct tggagcgaac    7800
gacctacacc gaactgagat acctacagcg tgagcattga aaagcgcca cgcttcccga    7860 agggagaaag gcggacaggt atccggtaag cggcagggtc ggaacaggag agcgcacgag    7920
ggagcttcca gggggaaacg cctggtatct ttatagtcct gtcgggttc gccacctctg    7980 acttgagcgt cgatttttgt gatgctcgtc agggggcgg agcctatgga aaaacgccag    8040
caacgcggcc ttttacggtt cctggccctt tgctggcctt ttgctcaca tgttctttcc    8100 tgcgttatcc cctgattctg tggataaccg tattaccgcc tttgagtgag ctgataccgc    8160
tcgccgcagc cgaacgaccg agcgcagcga g                                  8191

<210> SEQ ID NO 8
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 8
gaattcaaaa caaatgtgt gcaacctcct cccagtttac tcagattacc gagcataatt      60
ctcgacgatc tgctaactac cagccgaacc tttggaactt tgagtttctc cagtctctcg     120
aaaatgacct gaaggtggaa aagctcgagg agaaggcgac caaactcgag gaggaggtgc     180
gatgtatgat caacagagtt gacacccaac ccctgtcttt gctggagctg atcgacgatg     240
tgcagcggtt gggtttgact tataaattcg agaaggacat tatcaaggca ctggagaaca     300
ttgtgctcct cgacgagaac aagaagaaca agtctgatct tcacgctacc gctctctctt     360
tccgacttct tcgacaacac ggcttcgagg tgtcgcagga cgtcttcgag agatttaagg     420
acaaggaggg aggatttagc ggcgagctga agggagacgt tcagggtctt ctctccttgt     480
```

```
acgagcgtc ctacctggga ttcgagggag agaacctcct ggaggaagct cgtacatttt    540
ccatcactca ccttaagaat aaccttaagg agggaattaa caccaaggtg gccgagcagg    600
tttctcacgc cctggagctc ccctaccacc aacggctcca tagactggag gctcgttggt    660
tcctggacaa atatgagcca aaggagcctc atcatcagtt gctgttggag ttggccaagc    720
tggacttcaa tatggttcag acgctgcacc aaaaggagtt gcaggacctg tctcgatggt    780
ggaccgagat gggattggcc tcgaagctgg attttgtccg tgaccgactt atggaggtct    840
attttttggc ccttggaatg gcgcctgacc cccagttcgg agagtgccgg aaggcggtga    900
cgaagatgtt cggtcttgtg actatcatcg acgacgtcta cgatgtctac ggcacactcg    960
acgagttgca gctgttcact gacgccgtcg agcgatggga tgtgaacgcc attaatactc   1020
tccctgacta tatgaagctg tgcttcctgg ctctgtacaa cactgtcaac gatacctcgt   1080
actctatcct caaggagaag ggacacaaca atctctccta cttgaccaaa tcctggcgag   1140
aactgtgcaa ggcttttctg caggaggcta aatggtccaa taacaagatc attcctgctt   1200
tttctaaata cctggaaaat gcctcggtgt cgagctctgg cgtcgccctt ctggcccctt   1260
cctacttctc cgtctgccag cagcaggagg atatttccga tcatgctctt agatcgctga   1320
ccgattttca cggcctcgtg cgatcttcct gcgtgatttt tcggttgtgt aatgaccttg   1380
cgacctctgc tgctgagctg gaacgaggcg agactacaaa ttccattatt tcttacatgc   1440
acgaaaacga tggaacatct gaagaacagg ctagagagga actgcgaaag ttgatcgacg   1500
ccgagtggaa gaagatgaac agagagcggg tgtccgactc taccctgctt cccaaggcct   1560
tcatggagat cgccgtgaac atggctcgag tttcccattg tacttaccag tacggtgacg   1620
gcctgggtcg tccggactac gctacagaga accgaatcaa gctgctgctc atcgacccct   1680
tccctatcaa ccaattgatg tacgtgtaat agtctagagg atcc                    1724
```

<210> SEQ ID NO 9
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 9

```
gaattcaaca aaatgtgct ctgtttccac tgagaacgtg tcctttactg agactgagac     60
tgaagcacgt agaagcgcca actacgaacc caactcctgg gattatgact ttctgctgtc    120
ttctgacacc gacgagtcga tcgaggttta aaggataag gccaagaaac ttgaggccga    180
ggtcagacga gagattaaca acgagaaggc cgagttcctg acccttcttg agctgatcga    240
caacgttcaa cgacttggtc ttggttaccg tttcgaatcc gatatccgac gtgcattgga    300
tcgatttgtc tcgtccggag gtttcgatgg tgtgactaag acgtcgctgc acgccacagc    360
tctttccttc agactgttgc ggcagcatgg atttgaggtt tcccaggaag cctttttctgg    420 tttcaaggat cagaacggaa acttttttgga gaatctcaag gaggacacca aggccatcct    480
gtcgttgtat gaggcctcgt tcctggctct tgagggcgag aatattctgg atgaggctcg    540
ggttttcgct atttcgcacc tgaaggagtt gtcggaggaa aagatcggaa aggaactggc    600
cgagcaggtc aaccatgcac ttgaacttcc cctgcatcga cgtacccagc gactggaggc    660 cgtgtgggagc atcgaggcgt acagaaaaaa ggaggatgct aatcaggttc tgctcgaact    720
cgctatcctc gactataaca tgattcagag cgtgtaccag cgtgacttgc gagagacaag    780
```

| | |
|---|---|
| ccggtggtgg cgacgggtgg gactggccac gaagctccac tttgctaaag atcgattgat | 840 |
| tgagtcgttc tactgggcag tgggtgtggc ctttgagcct cagtactccg actgccgaaa | 900 |
| ctccgttgca aagatgtttt cttttgtcac tatcatcgac gacatctacg atgtttacgg | 960 |
| cactctcgat gaactcgaac tcttcacgga cgctgtcgag cgatgggatg tgaatgccat | 1020 |
| taatgatctg ccagattata tgaagttgtg tttcttggcg ctctacaaca caattaatga | 1080 |
| aattgcctac gacaacctca aggacaaggg agagaacatt ctgccctacc ttactaaagc | 1140 |
| ctgggccgac ctgtgtaacg cctttttgca ggaagccaag tggctctata caaatctac | 1200 |
| tcctacattt gatgactact tcggcaacgc ttggaagtct tccagcggcc ctctccagtt | 1260 |
| gatcttcgct tactttgcag tggtccagaa catcaagaaa gaggagattg agaacctcca | 1320 |
| gaagtatcac gacatcatct cccgaccttc gcacatcttt cgactgtgca atgaccttgc | 1380 |
| ctccgcatcc gctgagattg cccgaggaga aacagccaat tctgtgtcgt gttacatgcg | 1440 |
| tacaaagggc atctccgagg agctggctac cgagtctgtg atgaacctga tcgatgaaac | 1500 |
| ctgtaagaag atgaacaaag agaaactggg cggttctctg ttcgccaaac catttgttga | 1560 |
| aaccgcgatc aatctggctc gtcagtctca ttgtacttac cataacggtg acgcgcacac | 1620 |
| ttcgccggac gaattgaccc gtaagcgtgt gctttcggtg attaccgagc cgatcctgcc | 1680 |
| gttcgaaaga taataggatc c | 1701 |

<210> SEQ ID NO 10
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 10

| | |
|---|---|
| gctggtacca tatgggaatt cgaagctttc tagaacaaaa actcatctca gaagaggatc | 60 |
| tgaatagcgc cgtcgaccat catcatcatc atcattgagt ttaaacggtc tccagcttgg | 120 |
| ctgttttggc ggatgagaga agattttcag cctgatacag attaaatcag aacgcagaag | 180 |
| cggtctgata aaacagaatt tgcctggcgg cagtagcgcg gtggtcccac ctgaccccat | 240 |
| gccgaactca gaagtgaaac gccgtagcgc cgatggtagt gtggggtctc cccatgcgag | 300 |
| agtagggaac tgccaggcat caaataaaac gaaaggctca gtcgaaagac tgggcctttc | 360 |
| gttttatctg ttgtttgtcg gtgaacgctc tcctgagtag gacaaatccg ccgggagcgg | 420 |
| atttgaacgt tgcgaagcaa cggcccggag ggtggcgggc aggacgcccg ccataaactg | 480 |
| ccaggcatca aattaagcag aaggccatcc tgacggatgg cctttttgcg tttctacaaa | 540 |
| ctcttttgt ttatttttct aaatacattc aaatatgtat ccgcttaacc ggaattgcca | 600 |
| gctggggcgc cctctggtaa ggttgggaag ccctgcaaag taaactggat gctttctcg | 660 |
| ccgccaagga tctgatggcg caggggatca agctctgatc aagagacagg atgaggatcg | 720 |
| tttcgcatga ttgaacaaga tggattgcac gcaggttctc cggccgcttg ggtggagagg | 780 |
| ctattcggct atgactgggc acaacagaca atcggctgct ctgatgccgc cgtgttccgg | 840 |
| ctgtcagcgc aggggcgccc ggttcttttt gtcaagaccg acctgtccgg tgccctgaat | 900 |
| gaactgcaag acgaggcagc gcggctatcg tggctggcca cgacgggcgt tccttgcgca | 960 |
| gctgtgctcg acgttgtcac tgaagcggga agggactggc tgctattggg cgaagtgccg | 1020 |
| gggcaggatc tcctgtcatc tcaccttgct cctgccgaga agtatccat catggctgat | 1080 |
| gcaatgcggc ggctgcatac gcttgatccg gctacctgcc cattcgacca ccaagcgaaa | 1140 |

-continued

```
catcgcatcg agcgagcacg tactcggatg gaagccggtc ttgtcgatca ggatgatctg    1200
gacgaagagc atcaggggct cgcgccagcc gaactgttcg ccaggctcaa ggcgagcatg    1260
cccgacggcg aggatctcgt cgtgacccat ggcgatgcct gcttgccgaa tatcatggtg    1320
gaaaatggcc gcttttctgg attcatcgac tgtggccggc tgggtgtggc ggaccgctat    1380
caggacatag cgttggctac ccgtgatatt gctgaagagc ttggcggcga atgggctgac    1440
cgcttcctcg tgctttacgg tatcgccgct cccgattcgc agcgcatcgc cttctatcgc    1500
cttcttgacg agttcttctg acatgaccaa aatcccttaa cgtgagtttt cgttccactg    1560
agcgtcagac cccgtagaaa agatcaaagg atcttcttga tcctttttt ttctgcgcgt    1620 aatctgctgc ttgcaaacaa aaaaaccacc gctaccagcg gtggtttgtt tgccggatca    1680
agagctacca actctttttc cgaaggtaac tggcttcagc agagcgcaga taccaaatac    1740
tgtccttcta gtgtagccgt agttaggcca ccacttcaag aactctgtag caccgcctac    1800
atacctcgct ctgctaatcc tgttaccagt ggctgctgcc agtggcgata agtcgtgtct    1860
taccgggttg gactcaagac gatagttacc ggataaggcg cagcggtcgg gctgaacggg    1920
gggttcgtgc acacagccca gcttggagcg aacgacctac accgaactga gatacctaca    1980
gcgtgagcta tgagaaagcg ccacgcttcc cgaagggaga aaggcggaca ggtatccggt    2040
aagcggcagg gtcggaacag gagagcgcac gagggagctt ccagggggaa acgcctggta    2100
tctttatagt cctgtcgggt ttcgccacct ctgacttgag cgtcgatttt tgtgatgctc    2160 gtcaggggg cggagcctat ggaaaaacgc cagcaacgcg gccttttac ggttcctggc    2220 cttttgctgg cctttgctc acatgttctt tcctgcgtta tcccctgatt ctgtggataa    2280
ccgtattacc gcctttgagt gagctgatac cgctcgccgc agccaacga ccgagcgcag    2340 cgagtcagtg agcgaggaag cggaagagcg cctgatgcgg tatttctcc ttacgcatct    2400 gtgcggtatt tcacaccgca tatggtgcac tctcagtaca atctgctctg atgccgcata    2460
gttaagccag tatacactcc gctatcgcta cgtgactggg tcatggctgc gccccgacac    2520
ccgccaacac ccgctgacgc gccctgacgg gcttgtctgc tcccggcatc cgcttacaga    2580
caagctgtga ccgtctccgg gagctgcatg tgtcagaggt tttcaccgtc atcaccgaaa    2640
cgcgcgaggc agcagatcaa ttcgcgcgcg aaggcgaagc ggcatgcatt tacgttgaca    2700
ccatcgaatg gtgcaaaacc tttcgcggta tggcatgata gcgcccggaa gagagtcaat    2760
tcagggtggt gaatgtgaaa ccagtaacgt tatacgatgt cgcagagtat gccggtgtct    2820
cttatcagac cgtttcccgc gtggtgaacc aggccagcca cgtttctgcg aaaacgcggg    2880
aaaaagtgga agcggcgatg gcggagctga attacattcc caaccgcgtg gcacaacaac    2940
tggcgggcaa acagtcgttg ctgattggcg ttgccacctc cagtctggcc ctgcacgcgc    3000
cgtcgcaaat tgtcgcggcg attaaatctc gcgccgatca actgggtgcc agcgtggtgg    3060
tgtcgatggt agaacgaagc ggcgtcgaag cctgtaaagc ggcggtgcac aatcttctcg    3120
cgcaacgcgt cagtgggctg atcattaact atccgctgga tgaccaggat gccattgctg    3180
tggaagctgc ctgcactaat gttccggcgt tatttcttga tgtctctgac cagacaccca    3240
tcaacagtat tattttctcc catgaagacg gtacgcgact gggcgtggag catctggtcg    3300
cattgggtca ccagcaaatc gcgctgttag cgggcccatt aagttctgtc tcggcgcgtc    3360
tgcgtctggt ggctggcat aaatatctca ctcgcaatca aattcagccg atagcggaac    3420
gggaaggcga ctggagtgcc atgtccggtt ttcaacaaac catgcaaatg ctgaatgagg    3480
```

```
gcatcgttcc cactgcgatg ctggttgcca acgatcagat ggcgctgggc gcaatgcgcg    3540
ccattaccga gtccgggctg cgcgttggtg cggatatctc ggtagtggga tacgacgata    3600
ccgaagacag ctcatgttat atcccgccgt caaccaccat caaacaggat tttcgcctgc    3660
tggggcaaac cagcgtggac cgcttgctgc aactctctca gggccaggcg gtgaagggca    3720
atcagctgtt gcccgtctca ctggtgaaaa gaaaaaccac cctggcgccc aatacgcaaa    3780
ccgcctctcc ccgcgcgttg gccgattcat taatgcagct ggcacgacag gtttcccgac    3840
tggaaagcgg gcagtgagcg caacgcaatt aatgtgagtt agcgcgaatt gatctggttt    3900
gacagcttat catcgactgc acggtgcacc aatgcttctg cgtcaggca gccatcggaa    3960 gctgtggtat ggctgtgcag gtcgtaaatc actgcataat tcgtgtcgct caaggcgcac    4020
tcccgttctg gataatgttt tttgcgccga catcataacg gttctggcaa atattctgaa    4080
atgagctgtt gacaattaat catccggctc gtataatgtg tggaattgtg agcggataac    4140
aatttcacac aggaaacagc gccgctgaga aaaagcgaag cggcactgct ctttaacaat    4200
ttatcagaca atctgtgtgg gcactcgacc ggaattatcg attaactta ttattaaaaa    4260 ttaaagaggt atatattaat gtatcgatta aataaggagg aataaaccat gtgtgcgacc    4320
tcttctcaat ttactcagat taccgagcat aattcccgtc gttccgcaaa ctatcagcca    4380
aacctgtgga atttcgaatt cctgcaatcc ctggagaacg acctgaaagt ggaaaagctg    4440
gaggagaaag cgaccaaact ggaggaagaa gttcgctgca tgatcaaccg tgtagacacc    4500
cagccgctgt ccctgctgga gctgatcgac gatgtgcagc gcctgggtct gacctacaaa    4560
tttgaaaaag acatcattaa agccctggaa aacatcgtac tgctggacga aaacaaaaag    4620
aacaaatctg acctgcacgc aaccgctctg tctttccgtc tgctgcgtca gcacggtttc    4680
gaggtttctc aggatgtttt tgagcgtttc aaggataaag aaggtggttt cagcggtgaa    4740
ctgaaaggtg acgtccaagg cctgctgagc ctgtatgaag cgtcttacct gggtttcgag    4800
ggtgagaacc tgctgagga ggcgcgtacc ttttccatca cccacctgaa gaacaacctg    4860
aaagaaggca ttaataccaa ggttgcagaa caagtgagcc acgccctgga actgccatat    4920
caccagcgtc tgcaccgtct ggaggcacgt tggttcctgg ataaatacga accgaaagaa    4980
ccgcatcacc agctgctgct ggagctggcg aagctggatt ttaacatggt acagaccctg    5040
caccagaaag agctgcaaga tctgtcccgc tggtggaccg agatgggcct ggctagcaaa    5100
ctggattttg tacgcgaccg cctgatggaa gtttatttct gggcactggg tatggcgcca    5160
gacccgcagt ttggtgaatg tcgcaaagct gttactaaaa tgtttggtct ggtgacgatc    5220
atcgatgacg tgtatgacgt ttatggcact ctggacgaac tgcaactgtt caccgatgct    5280
gtagagcgct gggacgttaa cgctattaac accctgccgg actatatgaa actgtgtttc    5340
ctggcactgt acaacaccgt taacgacacg tcctattcta ttctgaaaga gaaaggtcat    5400
aacaacctgt cctatctgac gaaaagctgg cgtgaactgt gcaaagcctt tctgcaagag    5460
gcgaaatggt ccaacaacaa aattatcccg gctttctcca gtacctgga aaacgccagc    5520 gtttcctcct ccggtgtagc gctgctggcg ccgtcttact tttccgtatg ccagcagcag    5580
gaagacatct ccgaccacgc gctgcgttcc ctgaccgact ccatggtct ggtgcgttct    5640 agctgcgtta tcttccgcct gtgcaacgat ctggccacct ctgcggcgga gctggaacgt    5700
ggcgagacta ccaattctat cattagctac atgcacgaaa acgatggtac cagcgaggaa    5760 cagggcccgcg aagaactgcg taaactgatc gacgccgaat ggaaaaagat gaatcgtgaa    5820
cgcgttagcg actccaccct gctgcctaaa gcgttcatgg aaatcgcagt taacatggca    5880
```

```
cgtgtttccc actgcaccta ccagtatggc gatggtctgg gtcgcccaga ctacgcgact    5940
gaaaaccgca tcaaactgct gctgattgac cctttcccga ttaaccagct gatgtatgtc    6000
taactgcatc gcccttagga ggtaaaaaaa aatgactgcc gacaacaata gtatgcccca    6060
tggtgcagta tctagttacg ccaaattagt gcaaaaccaa acacctgaag acattttgga    6120
agagtttcct gaaattattc cattacaaca aagacctaat acccgatcta gtgagacgtc    6180
aaatgacgaa agcggagaaa catgtttttc tggtcatgat gaggagcaaa ttaagttaat    6240
gaatgaaaat tgtattgttt tggattggga cgataatgct attggtgccg gtaccaagaa    6300
agtttgtcat ttaatggaaa atattgaaaa gggtttacta catcgtgcat tctccgtctt    6360
tattttcaat gaacaaggtg aattacttttt acaacaaaga gccactgaaa aataaacttt    6420
ccctgatctt tggactaaca catgctgctc tcatccacta tgtattgatg acgaattagg    6480
tttgaagggt aagctagacg ataagattaa gggcgctatt actgcggcgg tgagaaaact    6540
agatcatgaa ttaggtattc cagaagatga aactaagaca aggggtaagt ttcactttt    6600 aaacagaatc cattacatgg caccaagcaa tgaaccatgg ggtgaacatg aaattgatta    6660
catcctattt tataagatca acgctaaaga aaacttgact gtcaacccaa acgtcaatga    6720
agttagagac ttcaaatggg tttcaccaaa tgatttgaaa actatgtttg ctgacccaag    6780
ttacaagttt acgccttggt ttaagattat ttgcgagaat tacttattca actggtggga    6840
gcaattagat gacctttctg aagtggaaaa tgacaggcaa attcatagaa tgctataaca    6900
acgcgtcctg cattcgccct taggaggtaa aaaacatga gttttgatat tgccaaatac    6960
ccgaccctgg cactggtcga ctccacccag gagttacgac tgttgccgaa agagagttta    7020
ccgaaactct gcgacgaact gcgccgctat ttactgaca gcgtgagccg ttccagcggg    7080
cacttcgcct ccgggctggg cacggtcgaa ctgaccgtgg cgctgcacta tgtctacaac    7140
accccgtttg accaattgat ttgggatgtg gggcatcagg cttatccgca taaaattttg    7200
accggacgcc gcgacaaaat cggcaccatc cgtcagaaag gcggtctgca cccgttcccg    7260
tggcgcggcg aaagcgaata tgacgtatta agcgtcgggc attcatcaac ctccatcagt    7320
gccggaattg gtattgcggt tgctgccgaa aaagaaggca aaaatcgccg caccgtctgt    7380
gtcattggcg atggcgcgat taccgcaggc atggcgtttg aagcgatgaa tcacgcgggc    7440
gatatccgtc ctgatatgct ggtgattctc aacgacaatg aaatgtcgat ttccgaaaat    7500
gtcggcgcgc tcaacaacca tctggcacag ctgctttccg gtaagcttta ctcttcactg    7560
cgcgaaggcg ggaaaaaagt tttctctggc gtgccgccaa ttaaagagct gctcaaacgc    7620
accgaagaac atattaaagg catggtagtg cctggcacgt tgtttgaaga gctgggcttt    7680
aactacatcg gccggtgga cggtcacgat gtgctgggc ttatcaccac gctaaagaac    7740
atgcgcgacc tgaaaggccc gcagttcctg catatcatga ccaaaaaagg tcgtggttat    7800
gaaccggcag aaaaagaccc gatcactttc cacgccgtgc ctaaatttga tcctccagc    7860 ggttgtttgc cgaaaagtag cggcggtttg ccgagctatt caaaaatctt tggcgactgg    7920
ttgtgcgaaa cggcagcgaa agacaacaag ctgatggcga ttactccggc gatgcgtgaa    7980
ggttccggca tggtcgagtt ttcacgtaaa ttcccggatc gctacttcga cgtggcaatt    8040
gccgagcaac acgcggtgac ctttgctgcg gtctggcga ttggtgggta caaacccatt    8100
gtcgcgattt actccacttt cctgcaacgc gcctatgatc aggtgctgca tgacgtggcg    8160
attcaaaagc ttccggtcct gttcgccatc gaccgcgcgg gcattgttgg tgctgacggt    8220
```

| | | |
|---|---|---|
| caaacccatc agggtgcttt tgatctctct tacctgcgct gcataccgga aatggtcatt | 8280 | |
| atgaccccga gcgatgaaaa cgaatgtcgc cagatgctct ataccggcta tcactataac | 8340 | |
| gatggcccgt cagcggtgcg ctacccgcgt ggcaacgcgg tcggcgtgga actgacgccg | 8400 | |
| ctggaaaaac taccaattgg caaaggcatt gtgaagcgtc gtggcgagaa actggcgatc | 8460 | |
| cttaactttg gtacgctgat gccagaagcg gcgaaagtcg ccgaatcgct gaacgccacg | 8520 | |
| ctggtcgata tgcgttttgt gaaaccgctt gatgaagcgt taattctgga aatggccgcc | 8580 | |
| agccatgaag cgctggtcac cgtagaagaa acgccatta tgggcggcgc aggcagcggc | 8640 | |
| gtgaacgaag tgctgatggc ccatcgtaaa ccagtacccg tgctgaacat tggcctgccg | 8700 | |
| gacttcttta ttccgcaagg aactcaggaa gaaatgcgcg ccgaactcgg cctcgatgcc | 8760 | |
| gctggtatgg aagccaaaat caaggcctgg ctggcataac tgca | 8804 | |

<210> SEQ ID NO 11
<211> LENGTH: 10992
<212> TYPE: DNA
<213> ORGANISM: Artificial Sequence
<220> FEATURE:
<223> OTHER INFORMATION: Synthetic Construct

<400> SEQUENCE: 11

| | | |
|---|---|---|
| gtttgacagc ttatcatcga ctgcacggtg caccaatgct tctggcgtca ggcagccatc | 60 | |
| ggaagctgtg gtatggctgt gcaggtcgta aatcactgca taattcgtgt cgctcaaggc | 120 | |
| gcactcccgt tctggataat gttttttgcg ccgacatcat aacggttctg gcaaatattc | 180 | |
| tgaaatgagc tgttgacaat taatcatccg gctcgtataa tgtgtggaat tgtgagcgga | 240 | |
| taacaatttc acacaggaaa cagcgccgct gagaaaaagc gaagcggcac tgctctttaa | 300 | |
| caatttatca gacaatctgt gtgggcactc gaccggaatt atcgattaac tttattatta | 360 | |
| aaaattaaag aggtatatat taatgtatcg attaaataag gaggaataaa ccatggatcc | 420 | |
| gagctcggat ccactagtaa cggccgccag tgtgctggaa ttcgcccta ggaggtaaaa | 480 | |
| aaacatgtca ttaccgttct taacttctgc accgggaaag gttattattt tggtgaaca | 540 | |
| ctctgctgtg tacaacaagc ctgccgtcgc tgctagtgtg tctgcgttga gaacctacct | 600 | |
| gctaataagc gagtcatctg caccagatac tattgaattg gacttcccgg acattagctt | 660 | |
| taatcataag tggtccatca atgatttcaa tgccatcacc gaggatcaag taaactccca | 720 | |
| aaaattggcc aaggctcaac aagccaccga tggcttgtct caggaactcg ttagtctttt | 780 | |
| ggatccgttg ttagctcaac tatccgaatc cttccactac catgcagcgt tttgtttcct | 840 | |
| gtatatgttt gtttgcctat gcccccatgc caagaatatt aagttttctt taaagtctac | 900 | |
| tttacccatc ggtgctgggt tgggctcaag cgcctctatt tctgtatcac tggccttagc | 960 | |
| tatggcctac ttgggggggt taataggatc taatgacttg gaaaagctgt cagaaaacga | 1020 | |
| taagcatata gtgaatcaat gggccttcat aggtgaaaag tgtattcacg gtacccttc | 1080 | |
| aggaatagat aacgctgtgg ccacttatgg taatgccctg ctatttgaaa aagactcaca | 1140 | |
| taatggaaca ataaacacaa acaattttaa gttcttagat gatttcccag ccattccaat | 1200 | |
| gatcctaacc tatactagaa ttccaaggtc tacaaaagat cttgttgctc gcgttcgtgt | 1260 | |
| gttggtcacc gagaaatttc ctgaagttat gaagccaatt ctagatgcca tgggtgaatg | 1320 | |
| tgccctacaa ggcttagaga tcatgactaa gttaagtaaa tgtaaaggca ccgatgacga | 1380 | |
| ggctgtagaa actaataatg aactgtatga acaactattg gaattgataa gaataaatca | 1440 | |
| tggactgctt gtctcaatcg gtgtttctca tcctggatta gaacttatta aaaatctgag | 1500 | |

```
cgatgatttg agaattggct ccacaaaact taccggtgct ggtggcggcg gttgctcttt    1560
gactttgtta cgaagagaca ttactcaaga gcaaattgac agcttcaaaa agaaattgca    1620
agatgatttt agttacgaga catttgaaac agacttgggt gggactggct gctgtttgtt    1680
aagcgcaaaa aatttgaata aagatcttaa atcaaatcc ctagtattcc aattatttga     1740
aaataaaact accacaaagc aacaaattga cgatctatta ttgccaggaa acacgaattt    1800
accatggact tcataagcta atttgcgata ggcctgcacc cttaaggagg aaaaaaacat    1860
gtcagagttg agagccttca gtgccccagg gaaagcgtta ctagctggtg gatatttagt    1920
tttagataca aaatatgaag catttgtagt cggattatcg gcaagaatgc atgctgtagc    1980
ccatccttac ggttcattgc aagggtctga taagtttgaa gtgcgtgtga aaagtaaaca    2040
atttaaagat ggggagtggc tgtaccatat aagtcctaaa agtggcttca ttcctgtttc    2100
gataggcgga tctaagaacc ctttcattga aaaagttatc gctaacgtat ttagctactt    2160
taaacctaac atggacgact actgcaatag aaacttgttc gttattgata ttttctctga    2220
tgatgcctac cattctcagg aggatagcgt taccgaacat cgtggcaaca gaagattgag    2280
ttttcattcg cacagaattg aagaagttcc caaaacaggg ctgggctcct cggcaggttt    2340
agtcacagtt ttaactacag ctttggcctc cttttttgta tcggacctgg aaaataatgt    2400
agacaaatat agagaagtta ttcataattt agcacaagtt gctcattgtc aagctcaggg    2460
taaaattgga agcgggtttg atgtagcggc ggcagcatat ggatctatca gatatagaag    2520
attcccaccc gcattaatct ctaatttgcc agatattgga agtgctactt acggcagtaa    2580
actggcgcat ttggttgatg aagaagactg gaatattacg attaaaagta accatttacc    2640
ttcgggatta actttatgga tgggcgatat taagaatggt tcagaaacag taaaactggt    2700
ccagaaggta aaaaattggt atgattcgca tatgccagaa agcttgaaaa tatatacaga    2760
actcgatcat gcaaattcta gatttatgga tggactatct aaactagatc gcttacacga    2820
gactcatgac gattacagcg atcagatatt tgagtctctt gagaggaatg actgtacctg    2880
tcaaaagtat cctgaaatca cagaagttag agatgcagtt gccacaatta gacgttcctt    2940
tagaaaaata actaaagaat ctggtgccga tatcgaacct cccgtacaaa ctagcttatt    3000
ggatgattgc cagaccttaa aaggagttct tacttgctta atacctggtg ctggtggtta    3060
tgacgccatt gcagtgatta ctaagcaaga tgttgatctt agggctcaaa ccgctaatga    3120
caaaagattt tctaaggttc aatggctgga tgtaactcag gctgactggg gtgttaggaa    3180
agaaaaagat ccggaaactt atcttgataa ataacttaag gtagctgcat gcagaattcg    3240
cccttaagga ggaaaaaaaa atgaccgttt acacagcatc cgttaccgca cccgtcaaca    3300
tcgcaaccct taagtattgg gggaaaaggg acacgaagtt gaatctgccc accaattcgt    3360
ccatatcagt gactttatcg caagatgacc tcagaacgtt gacctctgcg gctactgcac    3420
ctgagtttga acgcgacact ttgtggttaa atggagaacc acacagcatc gacaatgaaa    3480
gaactcaaaa ttgtctgcgc gacctacgcc aattaagaaa ggaaatggaa tcgaaggacg    3540
cctcattgcc cacattatct caatggaaac tccacattgt ctccgaaaat aactttccta    3600
cagcagctgg tttagcttcc tccgctgctg gctttgctgc attggtctct gcaattgcta    3660 agttataccda attaccacag tcaacttcag aaatatctag aatagcaaga aagggtctg    3720 gttcagcttg tagatcgttg tttggcgat acgtggcctg ggaaatggga aaagctgaag    3780
atggtcatga ttccatggca gtacaaatcg cagacagctc tgactggcct cagatgaaag    3840
```

```
cttgtgtcct agttgtcagc gatattaaaa aggatgtgag ttccactcag ggtatgcaat    3900
tgaccgtggc aacctccgaa ctatttaaag aaagaattga acatgtcgta ccaaagagat    3960
ttgaagtcat gcgtaaagcc attgttgaaa agatttcgc cacctttgca aaggaaacaa     4020
tgatggattc caactctttc catgccacat gtttggactc tttccctcca atattctaca    4080
tgaatgacac ttccaagcgt atcatcagtt ggtgccacac cattaatcag ttttacggag    4140
aaacaatcgt tgcatacacg tttgatgcag gtccaaatgc tgtgttgtac tacttagctg    4200
aaaatgagtc gaaactcttt gcatttatct ataaattgtt tggctctgtt cctggatggg    4260
acaagaaatt tactactgag cagcttgagg ctttcaacca tcaatttgaa tcatctaact    4320
ttactgcacg tgaattggat cttgagttgc aaaaggatgt tgccagagtg attttaactc    4380
aagtcggttc aggcccacaa gaaacaaacg aatctttgat tgacgcaaag actggtctac    4440
caaaggaata agatcaattc gctgcatcgc ccttaggagg taaaaaaaaa tgactgccga    4500
caacaatagt atgccccatg gtgcagtatc tagttacgcc aaattagtgc aaaaccaaac    4560
acctgaagac attttggaag agtttcctga aattattcca ttacaacaaa gacctaatac    4620
ccgatctagt gagacgtcaa atgacgaaag cggagaaaca tgttttttctg gtcatgatga    4680 ggagcaaatt aagttaatga atgaaaattg tattgttttg gattgggacg ataatgctat    4740
tggtgccggt accagaaaag tttgtcattt aatggaaaat attgaaaagg tttactaca    4800 tcgtgcattc tccgtctttta ttttcaatga acaaggtgaa ttacttttac aacaaagagc    4860
cactgaaaaa ataactttcc ctgatctttg gactaacaca tgctgctctc atccactatg    4920
tattgatgac gaattaggtt tgaagggtaa gctagcgat aagattaagg gcgctattac     4980
tgcggcggtg agaaaactag atcatgaatt aggtattcca gaagatgaaa ctaagacaag    5040
gggtaagttt cacttttttaa acagaatcca ttacatggca ccaagcaatg aaccatgggg    5100
tgaacatgaa attgattaca tcctatttta taagatcaac gctaaagaaa acttgactgt    5160
caacccaaac gtcaatgaag ttagagactt caaatgggtt tcaccaaatg atttgaaaac    5220
tatgtttgct gacccaagtt acaagtttac gccttggttt aagattattt gcgagaatta    5280
cttattcaac tggtgggagc aattagatga ccttttctgaa gtggaaaatg acaggcaaat    5340
tcatagaatg ctataacaac gcgtcctgca ttcgcccctta ggaggtaaaa aaacatgtgt    5400
gcgacctctt ctcaatttac tcagattacc gagcataatt cccgtcgttc cgcaaactat    5460
cagccaaacc tgtggaattt cgaattcctg caatccctgg agaacgacct gaaagtggaa    5520
aagctggagg agaaagcgac caaactggag gaagaagttc gctgcatgat caaccgtgta    5580
gacacccagc cgctgtccct gctggagctg atcgacgatg tgcagcgcct gggtctgacc    5640
tacaaatttg aaaagacat cattaaagcc ctggaaaaca tcgtactgct ggacgaaaac    5700
aaaaagaaca atctgacct gcacgcaacc gctctgtctt ccgtctgct gcgtcagcac    5760 ggtttcgagg tttctcagga tgttttttgag cgtttcaagg ataaagaagg tggtttcagc    5820
ggtgaactga aggtgacgt ccaaggcctg ctgagcctgt atgaagcgtc ttacctgggt    5880
ttcgagggtg agaacctgct ggaggaggcg cgtacctttt ccatcaccca cctgaagaac    5940
aacctgaaag aaggcattaa taccaaggtt gcagaacaag tgagccacgc cctgaactg     6000 ccatatcacc agcgtctgca ccgtctggag gcacgttggt tcctggataa atacgaaccg    6060
aaagaaccgc atcaccagct gctgctggag ctggcgaagc tggatttaa catggtacag    6120 accctgcacc agaaagagct gcaagatctg tcccgctggt ggaccgagat gggcctggct    6180
agcaaactgg attttgtacg cgaccgcctg atggaagttt atttctgggc actgggtatg    6240
```

```
gcgccagacc cgcagtttgg tgaatgtcgc aaagctgtta ctaaaatgtt tggtctggtg    6300
acgatcatcg atgacgtgta tgacgtttat ggcactctgg acgaactgca actgttcacc    6360
gatgctgtag agcgctggga cgttaacgct attaacaccc tgccggacta tatgaaactg    6420
tgtttcctgg cactgtacaa caccgttaac gacacgtcct attctattct gaaagagaaa    6480
ggtcataaca acctgtccta tctgacgaaa agctggcgtg aactgtgcaa agcctttctg    6540
caagaggcga aatggtccaa caacaaaatt atcccggctt tctccaagta cctggaaaac    6600
gccagcgttt cctcctccgg tgtagcgctg ctggcgccgt cttactttc cgtatgccag    6660 cagcaggaag acatctccga ccacgcgctg cgttccctga ccgacttcca tggtctggtg    6720
cgttctagct gcgttatctt ccgcctgtgc aacgatctgg ccacctctgc ggcggagctg    6780
gaacgtggcg agactaccaa ttctatcatt agctacatgc acgaaaacga tggtaccagc    6840
gaggaacagg cccgcgaaga actgcgtaaa ctgatcgacg ccgaatggaa aaagatgaat    6900
cgtgaacgcg ttagcgactc caccctgctg cctaaagcgt tcatggaaat cgcagttaac    6960
atggcacgtg tttcccactg cacctaccag tatggcgatg gtctgggtcg cccagactac    7020
gcgactgaaa accgcatcaa actgctgctg attgacccct tcccgattaa ccagctgatg    7080
tatgtctaac tgcagctggt accatatggg aattcgaagc tttctagaac aaaaactcat    7140
ctcagaagag gatctgaata gcgccgtcga ccatcatcat catcatcatt gagtttaaac    7200
ggtctccagc ttggctgttt tggcggatga gagaagattt tcagcctgat acagattaaa    7260
tcagaacgca gaagcggtct gataaaacag aatttgcctg gcggcagtag cgcggtggtc    7320
ccacctgacc ccatgccgaa ctcagaagtg aaacgccgta gcgccgatgg tagtgtgggg    7380
tctccccatg cgagagtagg gaactgccag gcatcaaata aaacgaaagg ctcagtcgaa    7440
agactgggcc tttcgtttta tctgttgttt gtcggtgaac gctctcctga gtaggacaaa    7500
tccgccggga gcggatttga acgttgcgaa gcaacggccc ggagggtggc gggcaggacg    7560
cccgccataa actgccaggc atcaaattaa gcagaaggcc atcctgacgg atggcctttt    7620
tgcgtttcta caaactcttt ttgtttattt ttctaaatac attcaaatat gtatccgctt    7680
aaccggaatt gccagctggg gcgccctctg gtaaggttgg gaagccctgc aaagtaaact    7740
ggatggcttt ctcgccgcca aggatctgat ggcgcagggg atcaagctct gatcaagaga    7800
caggatgagg atcgtttcgc atgattgaac aagatggatt gcacgcaggt tctccggccg    7860
cttgggtgga gaggctattc ggctatgact gggcacaaca gacaatcggc tgctctgatg    7920
ccgccgtgtt ccggctgtca gcgcaggggc gcccggttct ttttgtcaag accgacctgt    7980
ccggtgccct gaatgaactg caagacgagg cagcgcggct atcgtggctg gccacgacgg    8040
gcgttccttg cgcagctgtg ctcgacgttg tcactgaagc gggaagggac tggctgctat    8100
tgggcgaagt gccggggcag gatctcctgt catctcacct tgctcctgcc gagaaagtat    8160
ccatcatggc tgatgcaatg cggcggctgc atacgcttga tccggctacc tgcccattcg    8220
accaccaagc gaaacatcgc atcgagcgag cacgtactcg gatggaagcc ggtcttgtcg    8280
atcaggatga tctggacgaa gagcatcagg ggctcgcgcc agccgaactg ttcgccaggc    8340
tcaaggcgag catgcccgac ggcgaggatc tcgtcgtgac ccatggcgat gcctgcttgc    8400
cgaatatcat ggtggaaaat ggccgctttt ctggattcat cgactgtggc cggctgggtg    8460
tggcggaccg ctatcaggac atagcgttgg ctacccgtga tattgctgaa gagcttggcg    8520
gcgaatgggc tgaccgcttc ctcgtgcttt acggtatcgc cgctcccgat tcgcagcgca    8580
```

```
tcgccttcta tcgccttctt gacgagttct tctgacgcat gaccaaaatc ccttaacgtg   8640
agttttcgtt ccactgagcg tcagaccccg tagaaaagat caaaggatct tcttgagatc   8700 cttttttct  gcgcgtaatc tgctgcttgc aaacaaaaaa accaccgcta ccagcggtgg   8760
tttgtttgcc ggatcaagag ctaccaactc tttttccgaa ggtaactggc ttcagcagag   8820
cgcagatacc aaatactgtc cttctagtgt agccgtagtt aggccaccac ttcaagaact   8880
ctgtagcacc gcctacatac ctcgctctgc taatcctgtt accagtggct gctgccagtg   8940
gcgataagtc gtgtcttacc gggttggact caagacgata gttaccggat aaggcgcagc   9000
ggtcgggctg aacggggggt tcgtgcacac agcccagctt ggagcgaacg acctacaccg   9060
aactgagata cctacagcgt gagctatgag aaagcgccac gcttcccgaa gggagaaagg   9120
cggacaggta tccggtaagc ggcagggtcg gaacaggaga gcgcacgagg gagcttccag   9180
ggggaaacgc ctggtatctt tatagtcctg tcgggtttcg ccacctctga cttgagcgtc   9240
gatttttgtg atgctcgtca gggggcggag cctatggaaa aacgccagc aacgcggcct    9300 ttttacggtt cctggccttt tgctggcctt ttgctcacat gttctttcct gcgttatccc   9360
ctgattctgt ggataaccgt attaccgcct ttgagtgagc tgataccgct cgccgcagcc   9420
gaacgaccga gcgcagcgag tcagtgagcg aggaagcgga gagcgcctg atgcggtatt    9480 ttctccttac gcatctgtgc ggtatttcac accgcatatg gtgcactctc agtacaatct   9540
gctctgatgc cgcatagtta agccagtata cactccgcta tcgctacgtg actgggtcat   9600
ggctgcgccc cgacacccgc caacacccgc tgacgcgccc tgacgggctt gtctgctccc   9660
ggcatccgct tacagacaag ctgtgaccgt ctccgggagc tgcatgtgtc agaggttttc   9720
accgtcatca ccgaaacgcg cgaggcagca gatcaattcg cgcgcgaagg cgaagcggca   9780
tgcatttacg ttgacaccat cgaatggtgc aaaacctttc gcggtatggc atgatagcgc   9840
ccggaagaga gtcaattcag ggtggtgaat gtgaaaccag taacgttata cgatgtcgca   9900
gagtatgccg gtgtctctta tcagaccgtt tcccgcgtgg tgaaccaggc cagccacgtt   9960
tctgcgaaaa cgcgggaaaa agtggaagcg gcgatggcgg agctgaatta cattcccaac  10020
cgcgtggcac aacaactggc gggcaaacag tcgttgctga ttggcgttgc cacctccagt  10080
ctggccctgc acgcgccgtc gcaaattgtc gcggcgatta atctcgcgc cgatcaactg   10140 ggtgccagcg tggtggtgtc gatggtagaa cgaagcggcg tcgaagcctg taaagcggcg  10200
gtgcacaatc ttctcgcgca acgcgtcagt gggctgatca ttaactatcc gctggatgac  10260
caggatgcca ttgctgtgga agctgcctgc actaatgttc cggcgttatt tcttgatgtc  10320
tctgaccaga cacccatcaa cagtattatt ttctcccatg aagacggtac gcgactgggc  10380
gtggagcatc tggtcgcatt gggtcaccag caaatcgcgc tgttagcggg cccattaagt  10440
tctgtctcgg cgcgtctgcg tctggctggc tggcataaat atctcactcg caatcaaatt  10500
cagccgatag cggaacggga aggcgactgg agtgccatgt ccggttttca acaaaccatg  10560
caaatgctga atgagggcat cgttcccact gcgatgctgg ttgccaacga tcagatggcg  10620
ctgggcgcaa tgcgcgccat taccgagtcc gggctgcgcg ttggtgcgga tatctcggta  10680
gtgggatacg acgataccga agacagctca tgttatatcc cgccgtcaac caccatcaaa  10740
caggattttc gcctgctggg gcaaaccagc gtggaccgct tgctgcaact ctctcagggc  10800
caggcggtga agggcaatca gctgttgccc gtctcactgg tgaaaagaaa aaccaccctg  10860
gcgcccaata cgcaaaccgc ctctccccgc gcgttggccg attcattaat gcagctggca  10920
cgacaggttt cccgactgga aagcgggcag tgagcgcaac gcaattaatg tgagttagcg  10980
```
cgaattgatc tg                                                                       10992

<210> SEQ ID NO 12
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 12

```
cccgtcttac tgtcgggaat tcgcgttggc cgattcatta atgcagattc tgaaatgagc     60
tgttgacaat taatcatccg gctcgtataa tgtgtggaat tgtgagcgga taacaatttc    120
acacaggaaa cagcgccgct gagaaaaagc gaagcggcac tgctctttaa caatttatca    180
gacaatctgt gtgggcactc gaccggaatt atcgattaac tttattatta aaattaaag    240
aggtatatat taatgtatcg attaaataag gaggaataaa ccatggatcc gagctcagga    300
ggtaaaaaaa catgaaaaca gtagttatta ttgatgcatt acgaaccaca attggaaaat    360
ataaaggcag cttaagtcaa gtaagtgccg tagacttagg aacacatgtt acaacacaac    420
ttttaaaaag acattccact atttctgaag aaattgatca agtaatcttt ggaaatgttt    480
tacaagctgg aaatggccaa atcccgcac gacaaatagc aataaacagc ggtttgtctc    540
atgaaattcc cgcaatgacg gttaatgagg tctgcggatc aggaatgaag gccgttattt    600
tggcgaaaca attgattcaa ttaggagaag cggaagtttt aattgctggc gggattgaga    660
atatgtccca agcacctaaa ttacaacgtt ttaattacga acagaaagc tacgatgcgc    720
cttttttctag tatgatgtat gatggattaa cggatgcctt tagtggtcag gcaatgggct    780
taactgctga aaatgtggcc gaaaagtatc atgtaactag agaagagcaa gatcaatttt    840
ctgtacattc acaattaaaa gcagctcaag cacaagcaga agggatattc gctgacgaaa    900
tagccccatt agaagtatca ggaacgcttg tggagaaaga tgaaggatt cgccctaatt    960
cgagcgttga gaagctagga acgcttaaaa cagttttta agaagacggt actgtaacag   1020
cagggaatgc atcaaccatt aatgatgggg cttctgcttt gattattgct tcacaagaat   1080
atgccgaagc acacggtctt ccttattag ctattattcg agacagtgtg gaagtcggta   1140
ttgatccagc ctatatggga atttcgccga ttaaagccat tcaaaaactg ttagcgcgca   1200
atcaacttac tacggaagaa attgatctgt atgaaatcaa cgaagcattt gcagcaactt   1260
caatcgtggt ccaaagagaa ctggctttac cagaggaaaa ggtcaacatt tatggtggcg   1320
gtatttcatt aggtcatgcg attggtgcca caggtgctcg tttattaacg agtttaagtt   1380
atcaattaaa tcaaaagaa aagaaatatg gagtggcttc tttatgtatc ggcggtggct   1440
taggactcgc tatgctacta gagagacctc agcaaaaaaa aaacagccga ttttatcaaa   1500
tgagtcctga ggaacgcctg gcttctcttc ttaatgaagg ccagatttct gctgatacaa   1560
aaaaagaatt tgaaaatacg gctttatctt cgcagattgc caatcatatg attgaaaatc   1620
aaatcagtga acagaagtg ccgatgggcg ttggcttaca tttaacagtg gacgaaactg   1680
attatttggt accaatggcg acagaagagc cctcagttat tgcggctttg agtaatggtg   1740
caaaaatagc acaaggattt aaaacagtga atcaacaacg cttaatgcgt ggacaaatcg   1800
ttttttacga tgttgcagat cccgagtcat tgattgataa actacaagta agagaagcgg   1860
aagttttttca acaagcagag ttaagttatc catctatcgt taaacgggc ggcggcttaa   1920
gagatttgca atatcgtact tttgatgaat catttgtatc tgtcgacttt ttagtagatg   1980
```

| | |
|---|---|
| ttaaggatgc aatgggggca aatatcgtta acgctatgtt ggaaggtgtg gccgagttgt | 2040 |
| tccgtgaatg gtttgcggag caaaagattt tattcagtat tttaagtaat tatgccacgg | 2100 |
| agtcggttgt tacgatgaaa acggctattc cagtttcacg tttaagtaag gggagcaatg | 2160 |
| gccgggaaat tgctgaaaaa attgttttag cttcacgcta tgcttcatta gatccttatc | 2220 |
| gggcagtcac gcataacaaa ggaatcatga atggcattga agctgtagtt ttagctacag | 2280 |
| gaaatgatac acgcgctgtt agcgcttctt gtcatgcttt tgcggtgaag gaaggtcgct | 2340 |
| accaaggctt gactagttgg acgctggatg gcgaacaact aattggtgaa atttcagttc | 2400 |
| cgcttgcttt agccacggtt ggcggtgcca caaagtcttt acctaaatct caagcagctg | 2460 |
| ctgatttgtt agcagtgacg gatgcaaaag aactaagtcg agtagtagcg gctgttggtt | 2520 |
| tggcacaaaa tttagcggcg ttacgggcct tagtctctga aggaattcaa aaggacaca | 2580 |
| tggctctaca agcacgttct ttagcgatga cggtcggagc tactggtaaa gaagttgagg | 2640 |
| cagtcgctca acaattaaaa cgtcaaaaaa cgatgaacca agaccgagcc atggctattt | 2700 |
| taaatgattt aagaaaacaa taaggaggt aaaaaaacat gacaattggg attgataaaa | 2760 |
| ttagtttttt tgtgcccct tattatattg atatgacggc actggctgaa gccagaaatg | 2820 |
| tagaccctgg aaaatttcat attggtattg ggcaagacca aatggcggtg aacccaatca | 2880 |
| gccaagatat tgtgacattt gcagccaatg ccgcagaagc gatcttgacc aaagaagata | 2940 |
| aagaggccat tgatatggtg attgtcggga ctgagtccag tatcgatgag tcaaaagcgg | 3000 |
| ccgcagttgt cttacatcgt ttaatgggga ttcaacctt cgctcgctct ttcgaaatca | 3060 |
| aggaagcttg ttacggagca acagcaggct tacagttagc taagaatcac gtagccttac | 3120 |
| atccagataa aaaagtcttg gtcgtagcgg cagatattgc aaaatatggc ttaaattctg | 3180 |
| gcggtgagcc tacacaagga gctggggcgg ttgcaatgtt agttgctagt gaaccgcgca | 3240 |
| ttttggcttt aaaagaggat aatgtgatgc tgacgcaaga tatctatgac ttttggcgtc | 3300 |
| caacaggcca cccgtatcct atggtcgatg gtcctttgtc aaacgaaacc tacatccaat | 3360 |
| cttttgccca agtctgggat gaacataaaa aacgaaccgg tcttgatttt gcagattatg | 3420 |
| atgctttagc gttccatatt ccttacacaa aaatgggcaa aaaagcctta ttagcaaaaa | 3480 |
| tctccgacca aactgaagca gaacaggaac gaattttagc ccgttatgaa gaaagtatcg | 3540 |
| tctatagtcg tcgcgtagga aacttgtata cgggttcact ttatctggga ctcatttccc | 3600 |
| ttttagaaaa tgcaacgact ttaaccgcag gcaatcaaat tggtttattc agttatggtt | 3660 |
| ctggtgctgt cgctgaattt ttcactggtg aattagtagc tggttatcaa aatcatttac | 3720 |
| aaaaagaaac tcatttagca ctgctggata tcggacaga actttctatc gctgaatatg | 3780 |
| aagccatgtt tgcagaaact ttagacacag acattgatca aacgttagaa gatgaattaa | 3840 |
| aatatagtat ttctgctatt aataataccg ttcgttctta tcgaaactaa gagatctgca | 3900 |
| gctggtacca tatgggaatt cgaagcttgg gcccgaacaa aaactcatct cagaagagga | 3960 |
| tctgaatagc gccgtcgacc atcatcatca tcatcattga gtttaaacgg tctccagctt | 4020 |
| ggctgttttg gcggatgaga gaagattttc agcctgatac agattaaatc agaacgcaga | 4080 |
| agcggtctga taaaacagaa tttgcctggc ggcagtagcg cggtggtccc acctgacccc | 4140 |
| atgccgaact cagaagtgaa acgccgtagc gccgatggta gtgtggggtc tccccatgcg | 4200 |
| agagtaggga actgccaggc atcaaataaa acgaaaggct cagtcgaaag actgggcctt | 4260 |
| tcgttttatc tgttgtttgt cggtgaacgc tctcctgagt aggacaaatc cgccgggagc | 4320 |
| ggatttgaac gttgcgaagc aacggcccgg agggtggcgg gcaggacgcc gccataaac | 4380 |

```
tgccaggcat caaattaagc agaaggccat cctgacggat ggccttttttg cgtttctaca   4440
aactctttt  gtttatttt  ctaaatacat tcaaatatgt atccgctcat gagacaataa   4500
ccctgataaa tgcttcaata atctggcgta atagcgaaga ggcccgcacc gatcgccctt   4560
cccaacagtt gcgcagcctg aatggcgaat ggcgcctgat gcggtatttt ctccttacgc   4620
atctgtgcgg tatttcacac cgcatatggt gcactctcag tacaatctgc tctgatgccg   4680
catagttaag ccagccccga cacccgccaa cacccgctga cgagcttagt aaagccctcg   4740
ctagattta  atgcggatgt tgcgattact tcgccaacta ttgcgataac aagaaaaagc   4800
cagccttca  tgatatatct cccaatttgt gtagggctta ttatgcacgc ttaaaaataa   4860
taaaagcaga cttgacctga tagtttggct gtgagcaatt atgtgcttag tgcatctaac   4920
gcttgagtta agccgcgccg cgaagcggcg tcggcttgaa cgaattgtta gacattattt   4980
gccgactacc ttggtgatct cgcctttcac gtagtggaca aattcttcca actgatctgc   5040
gcgcgaggcc aagcgatctt cttcttgtcc aagataagcc tgtctagctt caagtatgac   5100
gggctgatac tgggccggca ggcgctccat tgcccagtcg gcagcgacat ccttcggcgc   5160
gattttgccg gttactgcgc tgtaccaaat gcgggacaac gtaagcacta catttcgctc   5220
atcgccagcc cagtcgggcg gcgagttcca tagcgttaag gtttcattta gcgcctcaaa   5280
tagatcctgt tcaggaaccg gatcaaagag ttcctccgcc gctggaccta ccaaggcaac   5340
gctatgttct cttgcttttg tcagcaagat agccagatca atgtcgatcg tggctggctc   5400
gaagatacct gcaagaatgt cattgcgctg ccattctcca aattgcagtt cgcgcttagc   5460
tggataacgc cacggaatga tgtcgtcgtg cacaacaatg gtgacttcta cagcgcggag   5520
aatctcgctc tctccagggg aagccgaagt ttccaaaagg tcgttgatca aagctcgccg   5580
cgttgtttca tcaagcctta cggtcaccgt aaccagcaaa tcaatatcac tgtgtggctt   5640
caggccgcca tccactgcgg agccgtacaa atgtacggcc agcaacgtcg gttcgagatg   5700
gcgctcgatg acgccaacta cctctgatag ttgagtcgat acttcggcga tcaccgcttc   5760
cctcatgatg tttaactttg ttttagggcg actgccctgc tgcgtaacat cgttgctgct   5820
ccataacatc aaacatcgac ccacggcgta acgcgcttgc tgcttggatg cccgaggcat   5880
agactgtacc ccaaaaaaac agtcataaca agccatgaaa accgccactg cgccgttacc   5940
accgctgcgt tcggtcaagg ttctggacca gttgcgtgag cgcatacgct acttgcatta   6000
cagcttacga accgaacagg cttatgtcca ctgggttcgt gccttcatcc gtttccacgg   6060
tgtgcgtcac ccggcaacct tgggcagcag cgaagtcgag gcatttctgt cctggctggc   6120
gaacgagcgc aaggtttcgg tctccacgca tcgtcaggca ttggcggcct tgctgttctt   6180
ctacggcaag gtgctgtgca cggatctgcc ctggcttcag gagatcggaa gacctcggcc   6240
gtcgcggcgc ttgccggtgg tgctgacccc ggatgaagtg gttcgcatcc tcggttttct   6300
ggaaggcgag catcgtttgt tcgcccagct tctgtatgga acgggcatgc ggatcagtga   6360
gggtttgcaa ctgcgggtca aggatctgga tttcgatcac ggcacgatca tcgtgcggga   6420
gggcaagggc tccaaggatc gggccttgat gttacccgag agcttggcac ccagcctgcg   6480
cgagcagggg aattaattcc cacgggtttt gctgcccgca acgggctgtt ctggtgttg    6540
ctagtttgtt atcagaatcg cagatccggc ttcagccggt tgccggctg  aaagcgctat   6600
ttcttccaga attgccatga tttttttcccc acgggaggcg tcactggctc ccgtgttgtc   6660
ggcagctttg attcgataag cagcatcgcc tgtttcaggc tgtctatgtg tgactgttga   6720
```

```
gctgtaacaa gttgtctcag gtgttcaatt tcatgttcta gttgctttgt tttactggtt    6780
tcacctgttc tattaggtgt tacatgctgt tcatctgtta cattgtcgat ctgttcatgg    6840
tgaacagctt tgaatgcacc aaaaactcgt aaaagctctg atgtatctat cttttttaca    6900
ccgttttcat ctgtgcatat ggacagtttt ccctttgata tgtaacggtg aacagttgtt    6960
ctacttttgt ttgttagtct tgatgcttca ctgatagata caagagccat aagaacctca    7020
gatccttccg tatttagcca gtatgttctc tagtgtggtt cgttgttttt gcgtgagcca    7080
tgagaacgaa ccattgagat catacttact ttgcatgtca ctcaaaaatt ttgcctcaaa    7140
actggtgagc tgaatttttg cagttaaagc atcgtgtagt gttttcttta gtccgttatg    7200
taggtaggaa tctgatgtaa tggttgttgg tattttgtca ccattcattt ttatctggtt    7260
gttctcaagt tcggttacga gatccatttg tctatctagt tcaacttgga aaatcaacgt    7320
atcagtcggg cggcctcgct tatcaaccac caatttcata ttgctgtaag tgtttaaatc    7380
tttacttatt ggtttcaaaa cccattggtt aagcctttta aactcatggt agttattttc    7440
aagcattaac atgaacttaa attcatcaag gctaatctct atatttgcct tgtgagtttt    7500
cttttgtgtt agttctttta ataaccactc ataaatcctc atagagtatt tgttttcaaa    7560
agacttaaca tgttccagat tatattttat gaattttttt aactggaaaa gataaggcaa    7620
tatctcttca ctaaaaacta attctaattt ttcgcttgag aacttggcat agtttgtcca    7680
ctggaaaatc tcaaagcctt taaccaaagg attcctgatt tccacagttc tcgtcatcag    7740
ctctctggtt gctttagcta atacaccata agcattttcc ctactgatgt tcatcatctg    7800
agcgtattgg ttataagtga acgataccgt ccgttcttte cttgtagggt tttcaatcgt    7860
ggggttgagt agtgccacac agcataaaat tagcttggtt tcatgctccg ttaagtcata    7920
gcgactaatc gctagttcat ttgctttgaa aacaactaat tcagacatac atctcaattg    7980
gtctaggtga ttttaatcac tataccaatt gagatgggct agtcaatgat aattactagt    8040 cctttttcctt tgagttgtgg gtatctgtaa attctgctag acctttgctg gaaaacttgt    8100
aaattctgct agaccctctg taaattccgc tagacctttg tgtgtttttt tgtttatat    8160 tcaagtggtt ataatttata gaataaagaa agaataaaaa aagataaaaa gaatagatcc    8220
cagccctgtg tataactcac tactttagtc agttccgcag tattacaaaa ggatgtcgca    8280
aacgctgttt gctcctctac aaaacagacc ttaaaaccct aaaggcttaa gtagcaccct    8340
cgcaagctcg ggcaaatcgc tgaatattcc ttttgtctcc gaccatcagg cacctgagtc    8400
gctgtctttt tcgtgacatt cagttcgctg cgctcacggc tctggcagtg aatgggggta    8460
aatggcacta caggcgcctt ttatggattc atgcaaggaa actacccata atacaagaaa    8520
agcccgtcac gggcttctca gggcgtttta tggcgggtct gctatgtggt gctatctgac    8580 ttttgctgt tcagcagttc ctgccctctg attttccagt ctgaccactt cggattatcc    8640
cgtgacaggt cattcagact ggctaatgca cccagtaagg cagcggtatc atcaacaggc    8700
tta                                                                 8703
```

<210> SEQ ID NO 13
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 13

```
tgtaaccttt gctttcaaat gagtagaaat aatgcacatc catgtttgta tcgtgcaaat      60
```

-continued

```
aaagtgtttc atccgtagga aaaaatgact ttagtatctg ttccgctttt tctgatgaaa    120
tgtgctcccc gacaaaattg aatgaatcat ggacatttgc tggctttgat acagcgaaag    180
cagccgttcc tatgttatat atcggattta acagcaggac aaaaaacacc atgacagcca    240
tcgtcaccca cttattcaca cgcacataaa cctttcctga cttttggaac agatgatagc    300
tcatcaaaaa tcccgccatt gccaaataaa tcgtatatgg cattactgca ccataatctt    360
ttgagatttg attgggatat ggcgcaagca gcaagacaag cagtccgata atcagcgtat    420
aaaataagcc tagtaagatc ttatccgttc tccaatacag cttgaaaaac actacattca    480
acgcaatggg aagagtgatg atgaaaaaca gaaacacgaa tgcaatcggc tccatcccat    540
ccgggtattc cttccaatac gaaaagaaac taaaaatcat ttgtacgatc ggcaaactga    600
caacagcaag gtcgaacgta taaaacttac cctttccgcc atgatcacgc ggcatcagca    660
tatagtgaaa agccgtcagc agcacatatc cgtataacaa aaaatgcagc agcggcagca    720
gttcttttcc gtcctctctt aagtaagcgc tggtgaagtt tgttgattgc acctggtgaa    780
taagttcaac agacactccc gccagcagca caatccgcaa tataacaccc gccaagaaca    840
ttgtgcgctg ccggtttatt ttgggatgat gcaccaaaag atataagccc gccagaacaa    900
caattgacca ttgaatcagc agggtgcttt gtctgcttaa tataaaataa cgttcgaaat    960
gcaatacata atgactgaat aactccaaca cgaacaacaa ctccattttc ttctgctatc   1020
aaaataacag actcgtgatt ttccaaacga gctttcaaaa aagcctctgc cccttgcaaa   1080
tcggatgcct gtctataaaa ttcccgatat tggttaaaca gcggcgcaat ggcggccgca   1140
tctgatgtct ttgcttggcg aatgttcatc ttatttcttc ctccctctca ataattttt    1200 cattctatcc cttttctgta aagtttattt ttcagaatac ttttatcatc atgctttgaa   1260
aaaatatcac gataatatcc attgttctca cggaagcaca cgcaggtcat ttgaacgaat   1320
tttttcgaca ggaatttgcc gggactcagg agcatttaac ctaaaaaagc atgacatttc   1380
agcataatga acatttactc atgtctattt tcgttctttt ctgtatgaaa atagttattt   1440
cgagtctcta cggaaatagc gagagatgat atacctaaat agagataaaa tcatctcaaa   1500
aaaatgggtc tactaaaata ttattccatc tattacaata aattcacaga atagtctttt   1560
aagtaagtct actctgaatt tttttaaaag gagagggtaa agagtgtcat taccgttctt   1620
aacttctgca ccgggaaagg ttattatttt tggtgaacac tctgctgtgt acaacaagcc   1680
tgccgtcgct gctagtgtgt ctgcgttgag aacctacctg ctaataagcg agtcatctgc   1740
accagatact attgaattgg acttcccgga cattagcttt aatcataagt ggtccatcaa   1800
tgatttcaat gccatcaccg aggatcaagt aaactcccaa aaattggcca aggctcaaca   1860
agccaccgat ggcttgtctc aggaactcgt tagtcttttg gatccgttgt tagctcaact   1920
atccgaatcc ttccactacc atgcagcgtt ttgtttcctg tatatgtttg tttgcctatg   1980
cccccatgcc aagaatatta agttttcttt aaagtctact ttacccatcg gtgctgggtt   2040
gggctcaagc gcctctattt ctgtatcact ggccttagct atggcctact tgggggggtt   2100
aataggatct aatgacttgg aaaagctgtc agaaaacgat aagcatatag tgaatcaatg   2160
ggccttcata ggtgaaaagt gtattcacgg taccccttca ggaatagata acgctgtggc   2220
cacttatggt aatgccctgc tatttgaaaa agactcacat aatggaacaa taaacacaaa   2280
caattttaag ttcttagatg atttcccagc cattccaatg atcctaacct atactagaat   2340
tccaaggtct acaaaagatc ttgttgctcg cgttcgtgtg ttggtcaccg agaaatttcc   2400
```

```
tgaagttatg aagccaattc tagatgccat gggtgaatgt gccctacaag gcttagagat      2460
catgactaag ttaagtaaat gtaaaggcac cgatgacgag gctgtagaaa ctaataatga      2520
actgtatgaa caactattgg aattgataag aataaatcat ggactgcttg tctcaatcgg      2580
tgtttctcat cctggattag aacttattaa aaatctgagc gatgatttga gaattggctc      2640
cacaaaactt accggtgctg gtggcggcgg ttgctctttg actttgttac gaagagacat      2700
tactcaagag caaattgaca gcttcaaaaa gaaattgcaa gatgatttta gttacgagac      2760
atttgaaaca gacttgggtg ggactggctg ctgtttgtta agcgcaaaaa atttgaataa      2820
agatcttaaa atcaaatccc tagtattcca attatttgaa aataaaacta ccacaaagca      2880
acaaattgac gatctattat tgccaggaaa cacgaattta ccatggactt cataaaagga      2940
gagggtgtca gagttgagag ccttcagtgc cccagggaaa gcgttactag ctggtggata      3000
tttagtttta gatacaaaat atgaagcatt tgtagtcgga ttatcggcaa gaatgcatgc      3060
tgtagcccat ccttacggtt cattgcaagg gtctgataag tttgaagtgc gtgtgaaaag      3120
taaacaattt aaagatgggg agtggctgta ccatataagt cctaaaagtg gcttcattcc      3180
tgtttcgata ggcggatcta agaacccttt cattgaaaaa gttatcgcta acgtatttag      3240
ctactttaaa cctaacatgg acgactactg caatagaaac ttgttcgtta ttgatatttt      3300
ctctgatgat gcctaccatt ctcaggagga tagcgttacc gaacatcgtg gcaacgaaag      3360
attgagtttt cattcgcaca gaattgaaga agttcccaaa acagggctgg gctcctcggc      3420
aggtttagtc acagttttaa ctacagcttt ggcctccttt tttgtatcgg acctggaaaa      3480
taatgtagac aaatatagag aagttattca taatttagca caagttgctc attgtcaagc      3540
tcagggtaaa attggaagcg ggtttgatgt agcggcggca gcatatggat ctatcagata      3600
tagaagattc ccacccgcat taatctctaa tttgccagat attggaagtg ctacttacgg      3660
cagtaaactg gcgcatttgg ttgatgaaga agactggaat attacgatta aaagtaacca      3720
tttaccttcg ggattaactt tatggatggg cgatattaag aatggttcag aaacagtaaa      3780
actggtccag aaggtaaaaa attggtatga ttcgcatatg ccagaaagct tgaaaatata      3840
tacagaactc gatcatgcaa attctagatt tatggatgga ctatctaaac tagatcgctt      3900
acacgagact catgacgatt acagcgatca gatatttgag tctcttgaga ggaatgactg      3960
tacctgtcaa aagtatcctg aaatcacaga agttagagat gcagttgcca caattagacg      4020
ttcctttaga aaaataacta agaatctggg tgccgatatc gaacctcccg tacaaactag      4080
cttattggat gattgccaga ccttaaaagg agttcttact tgcttaatac ctggtgctgg      4140
tggttatgac gccattgcag tgattactaa gcaagatgtt gatcttaggg ctcaaaccgc      4200
taatgacaaa agattttcta aggttcaatg gctggatgta actcaggctg actgggtgt       4260 taggaaagaa aaagatccgg aaacttatct tgataaataa aaggagaggg tgaccgttta      4320
cacagcatcc gttaccgcac ccgtcaacat cgcaacccTt aagtattggg ggaaagggga     4380
cacgaagttg aatctgccca ccaattcgtc catatcagtg actttatcgc aagatgacct      4440
cagaacgttg acctctgcgg ctactgcacc tgagtttgaa cgcgacactt tgtggttaaa      4500
tggagaacca cacagcatcg acaatgaaag aactcaaaat tgtctgcgcg acctacgcca      4560
attaagaaag gaaatggaat cgaaggacgc ctcattgccc acattatctc aatggaaact      4620
ccacattgtc tccgaaaata actttcctac agcagctggt ttagcttcct ccgctgctgg      4680
ctttgctgca ttggtctctg caattgctaa gttataccaa ttccacagt caacttcaga       4740 aatatctaga atagcaagaa aggggtctgg ttcagcttgt agatcgttgt ttggcggata      4800
```

```
cgtggcctgg gaaatgggaa aagctgaaga tggtcatgat tccatggcag tacaaatcgc   4860
agacagctct gactggcctc agatgaaagc ttgtgtccta gttgtcagcg atattaaaaa   4920
ggatgtgagt tccactcagg gtatgcaatt gaccgtggca acctccgaac tatttaaaga   4980
aagaattgaa catgtcgtac caaagagatt tgaagtcatg cgtaaagcca ttgttgaaaa   5040
agatttcgcc acctttgcaa aggaaacaat gatggattcc aactctttcc atgccacatg   5100
tttggactct ttccctccaa tattctacat gaatgacact tccaagcgta tcatcagttg   5160
gtgccacacc attaatcagt tttacggaga acaatcgtt gcatacacgt ttgatgcagg   5220
tccaaatgct gtgttgtact acttagctga aaatgagtcg aaactctttg catttatcta   5280
taaattgttt ggctctgttc ctggatggga caagaaattt actactgagc agcttgaggc   5340
tttcaaccat caatttgaat catctaactt tactgcacgt gaattggatc ttgagttgca   5400
aaaggatgtt gccagagtga ttttaactca agtcggttca ggcccacaag aaacaaacga   5460
atctttgatt gacgcaaaga ctggtctacc aaaggaataa aaggagaggg tgactgccga   5520
caacaatagt atgccccatg gtgcagtatc tagttacgcc aaattagtgc aaaaccaaac   5580
acctgaagac attttggaag agtttcctga aattattcca ttacaacaaa gacctaatac   5640
ccgatctagt gagacgtcaa atgacgaaag cggagaaaca tgttttctg gtcatgatga    5700 ggagcaaatt aagttaatga atgaaaattg tattgttttg gattgggacg ataatgctat   5760
tggtgccggt accaagaaag tttgtcattt aatggaaaat attgaaaagg gtttactaca   5820
tcgtgcattc tccgtcttta ttttcaatga acaaggtgaa ttacttttac aacaaagagc   5880
cactgaaaaa ataactttcc ctgatctttg gactaacaca tgctgctctc atccactatg   5940
tattgatgac gaattaggtt tgaagggtaa gctagacgat aagattaagg gcgctattac   6000
tgcggcggtg agaaaactag atcatgaatt aggtattcca gaagatgaaa ctaagacaag   6060
gggtaagttt cacttttaa acagaatcca ttcatggca ccaagcaatg aaccatgggg    6120
tgaacatgaa attgattaca tcctattta taagatcaac gctaagaaa acttgactgt    6180 caacccaaac gtcaatgaag ttagagactt caaatgggtt tcaccaaatg atttgaaaac   6240
tatgtttgct gacccaagtt acaagtttac gccttggttt aagattattt gcgagaatta   6300
cttattcaac tggtgggagc aattagatga cctttctgaa gtggaaaatg acaggcaaat   6360
tcatagaatg ctataaaaaa aaccggcctt ggccccgccg ttttttatt attttcttc    6420 ctccgcatgt tcaatccgct ccataatcga cggatggctc cctctgaaaa ttttaacgag   6480
aaacggcggg ttgacccgc tcagtcccgt aacggccaag tcctgaaacg tctcaatcgc    6540
cgcttcccgg tttccggtca gctcaatgcc gtaacggtcg gcggcgtttt cctgataccg   6600
ggagacggca ttcgtaattt gaatacatac gaacaaatta ataagtgaa aaaatactt     6660 cggaaacatt taaaaataa ccttattggt acttacatgt ttggatcagg agttgagagt    6720
ggactaaaac caaatagtga tcttgacttt ttagtcgtcg tatctgaacc attgacagat   6780
caaagtaaag aaatacttat acaaaaaatt agacctattt caaaaaaat aggagataaa     6840 agcaacttac gatatattga attaacaatt attattcagc aagaaatggt accgtggaat   6900
catcctccca acaagaatt tatttatgga gaatggttac aagagcttta tgaacaagga    6960
tacattcctc agaaggaatt aaattcagat ttaaccataa tgctttacca agcaaaacga   7020
aaaaataaaa gaatatacgg aaattatgac ttagaggaat tactacctga tattccattt   7080
tctgatgtga gaagagccat tatggattcg tcagaggaat aatagataa ttatcaggat    7140
```

-continued

```
gatgaaacca actctatatt aactttatgc cgtatgattt taactatgga cacgggtaaa    7200
atcataccaa aagatattgc gggaaatgca gtggctgaat cttctccatt agaacatagg    7260
gagagaattt tgttagcagt tcgtagttat cttggagaga atattgaatg gactaatgaa    7320
aatgtaaatt taactataaa ctatttaaat aacagattaa aaaaattata atgtaacctt    7380
tgctttcaaa tgagtagaaa taatgcacat ccatgtttgt atcgtgcaaa taaagtgttt    7440
catccgtagg aaaaaatgac tttagtatct gttccgcttt ttctgatgaa atgtgctccc    7500
cgacaaaatt gaatgaatca tggacatttg ctggctttga tacagcgaaa gcagccgttc    7560
ctatgttata tatcggattt aacagcagga caaaaaacac catgacagcc atcgtcaccc    7620
acttattcac acgcacataa accttcctg acttttggaa cagatgatag ctcatcaaaa    7680
atcccgccat tgccaaataa atcgtatatg gcattactgc accataatct tttgagattt    7740
gattgggata tggcgcaagc agcaagacaa gcagtccgat aatcagcgta taaaataagc    7800
ctagtaagat cttatccgtt ctccaataca gcttgaaaaa cactcattc aacgcaatgg     7860 gaagagtgat gatgaaaaac agaaacacga atgcaatcgg ctccatccca tccgggtatt    7920
ccttccaata cgaaaagaaa ctaaaaatca tttgtacgat cggcaaactg acaacagcaa    7980
ggtcgaacgt ataaaactta cccttccgc catgatcacg cggcatcagc atatagtgaa     8040
aagccgtcag cagcacatat ccgtataaca aaaatgcag cagcggcagc agttctttc     8100 cgtcctctct taagtaagcg ctggtgaagt ttgttgattg cacctggtga ataagttcaa    8160
cagacactcc cgccagcagc acaatccgca atataacacc cgccaagaac attgtgcgct    8220
gccggtttat tttgggatga tgcaccaaaa gatataagcc cgccagaaca caattgacc     8280 attgaatcag cagggtgctt tgtctgctta atataaaata acgttcgaaa tgcaatacat    8340
aatgactgaa taactccaac acgaacaaca aaagtgcgca ttttataaaa gctaatgatt    8400
cagtccacat aattgataga cgaattctgc tacaggtcac gtggctatgt gaaggatcgc    8460
gcgtccagtt aagagcaaaa acattgacaa aaaaatttat ttatgctaaa atttactatt    8520
aatatatttg tatgtataat aagattctcc tggccagggg aatcttattt tttgtggagg    8580
atcatttcat gaggaaaaat gagtccagct taacgtctct aatttcagct tttgcccgtg    8640
catatcacag ccgatatgac acacctctta tttttgatga ttttatcgca aaagatctca    8700
ttaacgaaaa agagtttatc gacatcagta aaaatatgat tcaagaaata tcgttttca    8760 acaaagagat cgccgaacgt cttcaaaatg atcctgaaaa aatattaaaa tgggttgcac    8820
aaatccagct gtctccaacg cccctagcac gtgcttctta ttgtgaaaaa gtcttgcaca    8880
acgaattaat cctgggggca aaacagtatg tcattcttgg agcgggactg gatactttct    8940
gctttcggca tccagaatta gaaaacagct tacaggtttt cgaggttgat catccggcca    9000
cacagcaatt gaaaaaaaat aagctgaagg atgcaaatct gacaattccg ggtcatcttc    9060
attttgttcc tatggatttc accaaaaacgt tttcgtatga tcctctctta gatgaaggat    9120
ttaaaaacac aaaaacattc ttcagccttc tcggagtgtc ttattatgta acacgggaag    9180
aaaatgcaag cttgatcagc aatttatttt ctcatgtccc gcctggaagc tctattgttt    9240
ttgattatgc ggacgaaaca cttttttacag caaaagggac gtcgaatcga gttgaacata    9300
tggtgaagat ggctgccgca agcggggaac cgatgaaatc atgtttcact tatcaagaga    9360
ttgaacatct g                                                         9371
```

<210> SEQ ID NO 14
<211> LENGTH: 4339

```
<212> TYPE: DNA
<213> ORGANISM: Artificial Sequence
<220> FEATURE:
<223> OTHER INFORMATION: Synthetic Construct

<400> SEQUENCE: 14
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa aataaggtta tcaagtgaga aatcaccatg agtgacgact     240
gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgtttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt ttcaatatta ttgaagcatt     840
tatcagggtt attgtctcat gagcggatac atatttgaat gtatttagaa aaataaacaa     900
atagggttca gtgttacaac caattaacca attctgaaca ttatcgcgag cccatttata     960
cctgaatatg gctcataaca ccccttgttt gcctggcggc agtagcgcgg tggtcccacc    1020
tgaccccatg ccgaactcag aagtgaaacg ccgtagcgcc gatggtagtg tggggactcc    1080
ccatgcgaga gtagggaact gccaggcatc aaataaaacg aaaggctcag tcgaaagact    1140
gggcctttcg cccgggctaa ttagggggtg tcgcccttta gtcgctgaac atgtgctctg    1200
tttctaccga gaacgtttcc ttcactgaga cggaaaccga ggcacgtcgt agcgcgaact    1260
acgagccgaa tagctgggac tacgatttcc tgctgtcttc cgatactgac gaatctattg    1320
aggtgtacaa agacaaagca aagaaactgg aggctgaagt gcgccgcgaa attaacaacg    1380
agaaagctga attcctgact ctgctggagc tgatcgataa cgtacagcgc ctgggtctgg    1440
gttaccgctt cgaatctgat atccgtcgcg cactggatcg tttcgtaagc agcggcggtt    1500
tcgatggcgt gaccaaaacg agcctgcacg ctaccgcgct gtccttccgt ctgctgcgtc    1560
agcacggctt cgaagtttct caggaagcat tctccggttt caaagatcaa acggtaact    1620 tcctggaaaa cctgaaagaa gacactaagg cgatcctgag cctgtatgag gcaagctttc    1680
tggccctgga gggtgagaac atcctggatg aggcgcgcgt attcgccatc tcccatctga    1740
aagagctgtc tgaagagaaa tcggtaagg aactggcaga gcaggttaat cacgcactgg    1800
aactgccgct gcatcgtcgt acccagcgtc tggaggcggt ttggtccatc gaagcgtacc    1860
gcaaaaagga ggatgctaac caggttctgc tggaactggc catcctggac tacaacatga    1920
tccagtccgt ttaccagcgt gatctgcgtg aaacctcccg ttggtggcgc cgtgtgggcc    1980
tggcgaccaa actgcacttc gctaaggacc gcctgattga gtcttttttac tgggcagtcg    2040 gcgttgcgtt cgaaccctcag tattctgact gccgtaacag cgttgcgaaa atgttcagct    2100
tcgttactat tatcgacgac atctacgacg tttacggtac tctggacgag ctggaactgt    2160
```

```
ttaccgacgc tgtcgaacgt tgggatgtta acgccatcaa cgatctgcct gactacatga    2220
aactgtgctt cctggcactg tataacacga tcaacgaaat tgcatacgac aacctgaaag    2280
acaaaggtga aaacatcctg ccgtacctga ctaaagcgtg gcggatctg tgtaacgctt     2340 ttctgcaaga agcgaaatgg ctgtataaca aatccactcc gacctttgac gattatttcg    2400
gcaatgcctg gaaatccagc tctggcccgc tgcaactgat cttcgcttat tttgcggttg    2460
tccaaaacat caaaaggag gaaattgaaa acctgcaaaa ataccacgat atcattagcc      2520
gtccttctca tatctttcgc ctgtgcaacg acctggcaag cgcgtccgca gagatcgcac    2580
gtggcgaaac cgctaactct gtttcctgct acatgcgcac caagggcatt tccgaagagc    2640
tggcaaccga gagcgtaatg aatctgatcg acgaaacctg taagaaaatg aacaaagaaa    2700
aactgggtgg ctccctgttc gctaaaccgt tcgtagagac tgctattaac ctggcacgtc    2760
agagccactg cacctaccac aatggtgacg cacatactag cccggatgaa ctgactcgta    2820
aacgtgtact gtctgttatc accgaaccga ttctgccgtt cgaacgttaa ctgcagcgtc    2880
aatcgaaagg gcgacacaaa atttattcta aatgcataat aaatactgat aacatcttat    2940
agtttgtatt atattttgta ttatcgttga catgtataat tttgatatca aaaactgatt    3000 ttcccttat tattttcgag atttatttc ttaattctct ttaacaaact agaaatattg       3060
tatatacaaa aaatcataaa taatagatga atagtttaat tataggtgtt catcaatcga    3120
aaaagcaacg tatcttattt aaagtgcgtt gctttttct catttataag gttaaataat    3180
tctcatatat caagcaaagt gacaggcgcc cttaaatatt ctgacaaatg ctctttccct    3240
aaactccccc cataaaaaaa cccgccgaag cgggttttta cgttatttgc ggattaacga    3300
ttactcgtta tcagaaccgc ccaggggggcc cgagcttaag actggccgtc gttttacaac    3360
acagaaagag tttgtagaaa cgcaaaaagg ccatccgtca ggggccttct gcttagtttg    3420
atgcctggca gttccctact ctcgccttcc gcttcctcgc tcactgactc gctgcgctcg    3480
gtcgttcggc tgcggcgagc ggtatcagct cactcaaagg cggtaatacg ttatccaca    3540 gaatcagggg ataacgcagg aaagaacatg tgagcaaaag gccagcaaaa ggccaggaac    3600
cgtaaaaagg ccgcgttgct ggcgtttttc cataggctcc gcccccctga cgagcatcac    3660
aaaaatcgac gctcaagtca gaggtggcga aacccgacag gactataaag ataccaggcg    3720
tttccccctg gaagctccct cgtgcgctct cctgttccga ccctgccgct taccggatac    3780
ctgtccgcct ttctcccttc gggaagcgtg gcgctttctc atagctcacg ctgtaggtat    3840
ctcagttcgg tgtaggtcgt tcgctccaag ctgggctgtg tgcacgaacc cccgttcag    3900 cccgaccgct gcgccttatc cggtaactat cgtcttgagt ccaacccggt aagacacgac    3960
ttatcgccac tggcagcagc cactggtaac aggattagca gagcgaggta tgtaggcggt    4020
gctacagagt tcttgaagtg gtgggctaac tacggctaca ctagaagaac agtatttggt    4080
atctgcgctc tgctgaagcc agttaccttc ggaaaaagag ttggtagctc ttgatccggc    4140
aaacaaacca ccgctggtag cggtggtttt tttgtttgca agcagcagat tacgcgcaga    4200
aaaaaaggat ctcaagaaga tccttgatc ttttctacgg ggtctgacgc tcagtggaac     4260
gacgcgcgcg taactcacgt taagggattt tggtcatgag cttgcgccgt cccgtcaagt    4320
cagcgtaatg ctctgctttt                                                4339
```

<210> SEQ ID NO 15
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 15

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgtgctc     420
tgtttctacc gagaacgttt ccttcactga gacggaaacc gaggcacgtc gtagcgcgaa     480
ctacgagccg aatagctggg actacgattt cctgctgtct tccgatactg acgaatctat     540
tgaggtgtac aaagacaaag caaagaaact ggaggctgaa gtgcgccgcg aaattaacaa     600
cgagaaagct gaattcctga ctctgctgga gctgatcgat aacgtacagc gcctgggtct     660
gggttaccgc ttcgaatctg atatccgtcg cgcactggat cgtttcgtaa gcagcggcgg     720
tttcgatggc gtgaccaaaa cgagcctgca cgctaccgcg ctgtccttcc gtctgctgcg     780
tcagcacggc ttcgaagttt ctcaggaagc attctccggt ttcaaagatc aaaacgttaa     840
cttcctggaa aacctgaaag aagacactaa ggcgatcctg agcctgtatg aggcaagctt     900
tctggccctg gagggtgaga acatcctgga tgaggcgcgc gtattcgcca tctcccatct     960
gaaagagctg tctgaagaga aaatcggtaa ggaactggca gagcaggtta atcacgcact    1020
ggaactgccg ctgcatcgtc gtacccagcg tctggaggcg gtttggtcca tcgaagcgta    1080
ccgcaaaaag gaggatgcta accaggttct gctggaactg gccatcctgg actacaacat    1140
gatccagtcc gtttaccagc gtgatctgcg tgaaacctcc cgttggtggc gccgtgtggg    1200
cctggcgacc aaaactgcact cgctaaggaa ccgcctgatt gagtcttttt actgggcagt    1260
cggcgttgcg ttcgaacctc agtattctga ctgccgtaac agcgttgcga aaatgttcag    1320
cttcgttact attatcgacg acatctacga cgtttacggt actctggacg agctggaact    1380
gtttaccgac gctgtcgaac gttgggatgt taacgccatc aacgatctgc ctgactacat    1440
gaaactgtgc ttcctggcac tgtataacac gatcaacgaa attgcatacg acaacctgaa    1500
agacaaaggt gaaaacatcc tgccgtacct gactaaagcg tgggcggatc tgtgtaacgc    1560
ttttctgcaa gaagcgaaat ggctgtataa caaatccact ccgacctttg acgattattt    1620
cggcaatgcc tggaaatcca gctctggccc gctgcaactg atcttcgctt attttgcggt    1680
tgtccaaaac atcaaaaagg aggaaattga aaacctgcaa aaataccacg atatcattag    1740
ccgtccttct catatctttc gcctgtgcaa cgacctggca agcgcgtccg cagagatcgc    1800
acgtggcgaa accgctaact ctgtttcctg ctacatgcgc accaagggca tttccgaaga    1860
gctggcaacc gagagcgtaa tgaatctgat cgacgaaacc tgtaagaaaa tgaacaaaga    1920
aaaactgggt ggctccctgt tcgctaaacc gttcgtagag actgctatta acctggcacg    1980
tcagagccac tgcacctacc acaatggtga cgcacatact agcccggatg aactgactcg    2040
taaacgtgta ctgtctgtta tcaccgaacc gattctgccg ttcgaacgtt aactgcagct    2100
ggtaccatat gggaattcga agctttctag aacaaaaact catctcagaa gaggatctga    2160
atagcgccgt cgaccatcat catcatcatc attgagttta acggtctcc agcttggctg    2220
```

```
ttttggcgga tgagagaaga ttttcagcct gatacagatt aaatcagaac gcagaagcgg     2280
tctgataaaa cagaatttgc ctggcggcag tagcgcggtg gtcccacctg accccatgcc     2340
gaactcagaa gtgaaacgcc gtagcgccga tggtagtgtg gggtctcccc atgcgagagt     2400
agggaactgc caggcatcaa ataaaacgaa aggctcagtc gaaagactgg gcctttcgtt     2460
ttatctgttg tttgtcggtg aacgctctcc tgagtaggac aaatccgccg ggagcggatt     2520
tgaacgttgc gaagcaacgg cccggagggt ggcgggcagg acgccgcca taaactgcca      2580 ggcatcaaat taagcagaag gccatcctga cggatggcct ttttgcgttt ctacaaactc     2640
tttttgttta tttttctaaa tacattcaaa tatgtatccg ctcatgagac aataaccctg     2700
ataaatgctt caataatatt gaaaaaggaa gagtatgagt attcaacatt tccgtgtcgc     2760
ccttattccc ttttttgcgg cattttgcct tcctgttttt gctcacccag aaacgctggt     2820
gaaagtaaaa gatgctgaag atcagttggg tgcacgagtg ggttacatcg aactggatct     2880
caacagcggt aagatccttg agagttttcg ccccgaagaa cgttttccaa tgatgagcac     2940
ttttaaagtt ctgctatgtg gcgcggtatt atcccgtgtt gacgccgggc aagagcaact     3000
cggtcgccgc atacactatt ctcagaatga cttggttgag tactcaccag tcacagaaaa     3060
gcatcttacg gatggcatga cagtaagaga attatgcagt gctgccataa ccatgagtga     3120
taacactgcg gccaacttac ttctgacaac gatcggagga ccgaaggagc taaccgcttt     3180
tttgcacaac atgggggatc atgtaactcg ccttgatcgt tgggaaccgg agctgaatga     3240
agccatacca aacgacgagc gtgacaccac gatgcctgta gcaatggcaa caacgttgcg     3300
caaactatta actggcgaac tacttactct agcttcccgg caacaattaa tagactggat     3360
ggaggcggat aaagttgcag gaccacttct gcgctcggcc cttccggctg gctggtttat     3420
tgctgataaa tctggagccg gtgagcgtgg gtctcgcggt atcattgcag cactggggcc     3480
agatggtaag ccctcccgta tcgtagttat ctacacgacg gggagtcagg caactatgga     3540
tgaacgaaat agacagatcg ctgagatagg tgcctcactg attaagcatt ggtaactgtc     3600
agaccaagtt tactcatata ctttagat tgatttaaaa cttcattttt aatttaaaag      3660
gatctaggtg aagatccttt ttgataatct catgaccaaa atcccttaac gtgagttttc     3720
gttccactga gcgtcagacc ccgtagaaaa gatcaaagga tcttcttgag atccttttttt    3780 tctgcgcgta atctgctgct tgcaaacaaa aaaaccaccg ctaccagcgg tggtttgttt     3840
gccggatcaa gagctaccaa ctctttttcc gaaggtaact ggcttcagca gagcgcagat     3900
accaaatact gtccttctag tgtagccgta gttaggccac cacttcaaga actctgtagc     3960
accgcctaca tacctcgctc tgctaatcct gttaccagtg gctgctgcca gtggcgataa     4020
gtcgtgtctt accgggttgg actcaagacg atagttaccg gataaggcgc agcggtcggg     4080
ctgaacgggg ggttcgtgca cacagcccag cttggagcga acgacctaca ccgaactgag     4140
atacctacag cgtgagctat gagaaagcgc cacgcttccc gaaggagaa aggcggacag      4200 gtatccggta agcggcaggg tcggaacagg agagcgcacg agggagcttc cagggggaaa     4260
cgcctggtat ctttatagtc ctgtcgggtt tcgccacctc tgacttgagc gtcgattttt     4320
gtgatgctcg tcaggggggc ggagcctatg gaaaaacgcc agcaacgcgg ccttttttacg    4380 gttcctggcc ttttgctggc cttttgctca catgttcttt cctgcgttat cccctgattc     4440
tgtggataac cgtattaccg cctttgagtg agctgatacc gctcgccgca gccgaacgac     4500
cgagcgcagc gagtcagtga gcgaggaagc ggaagagcgc ctgatgcggt attttctcct    4560
tacgcatctg tgcggtattt cacaccgcat atggtgcact ctcagtacaa tctgctctga    4620
```

```
tgccgcatag ttaagccagt atacactccg ctatcgctac gtgactgggt catggctgcg    4680
ccccgacacc cgccaacacc cgctgacgcg ccctgacggg cttgtctgct cccggcatcc    4740
gcttacagac aagctgtgac cgtctccggg agctgcatgt gtcagaggtt ttcaccgtca    4800
tcaccgaaac gcgcgaggca gcagatcaat tcgcgcgcga aggcgaagcg gcatgcattt    4860
acgttgacac catcgaatgg tgcaaaacct ttcgcggtat ggcatgatag cgcccggaag    4920
agagtcaatt caggggtggtg aatgtgaaac cagtaacgtt atacgatgtc gcagagtatg    4980
ccggtgtctc ttatcagacc gtttcccgcg tggtgaacca ggccagccac gtttctgcga    5040
aaacgcggga aaaagtggaa gcggcgatgg cggagctgaa ttacattccc aaccgcgtgg    5100
cacaacaact ggcgggcaaa cagtcgttgc tgattggcgt tgccacctcc agtctggccc    5160
tgcacgcgcc gtcgcaaatt gtcgcggcga ttaaatctcg cgccgatcaa ctgggtgcca    5220
gcgtggtggt gtcgatggta gaacgaagcg gcgtcgaagc ctgtaaagcg gcggtgcaca    5280
atcttctcgc gcaacgcgtc agtgggctga tcattaacta tccgctggat gaccaggatg    5340
ccattgctgt ggaagctgcc tgcactaatg ttccggcgtt atttcttgat gtctctgacc    5400
agacacccat caacagtatt attttctccc atgaagacgg tacgcgactg ggcgtggagc    5460
atctggtcgc attgggtcac cagcaaatcg cgctgttagc gggcccatta agttctgtct    5520
cggcgcgtct gcgtctggct ggctggcata aatatctcac tcgcaatcaa attcagccga    5580
tagcggaacg ggaaggcgac tggagtgcca tgtccggttt tcaacaaacc atgcaaatgc    5640
tgaatgaggg catcgttccc actgcgatgc tggttgccaa cgatcagatg gcgctgggcg    5700
caatgcgcgc cattaccgag tccgggctgc gcgttggtgc ggatatctcg gtagtgggat    5760
acgacgatac cgaagacagc tcatgttata cccgccgtc aaccaccatc aaacaggatt    5820
ttcgcctgct ggggcaaacc agcgtggacc gcttgctgca actctctcag gccaggcgg    5880 tgaagggcaa tcagctgttg cccgtctcac tggtgaaaag aaaaaccacc ctggcgccca    5940
atacgcaaac cgcctctccc cgcgcgttgg ccgattcatt aatgcagctg gcacgacagg    6000
tttcccgact ggaaagcggg cagtgagcgc aacgcaatta atgtgagtta gcgcgaattg    6060
atctg                                                                6065
```

<210> SEQ ID NO 16
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 16

```
ttgtctgctc ccggcatccg cttacagaca agctgtgacc gtctccggga gctgcatgtg     60
tcagaggttt tcaccgtcat caccgaaacg cgcgaggcag cagatcaatt cgcgcgcgaa    120
ggcgaagcgg catgcattta cgttgacacc atcgaatggt gcaaaacctt tcgcggtatg    180
gcatgatagc gcccggaaga gagtcaattc agggtggtga atgtgaaacc agtaacgtta    240
tacgatgtcg cagagtatgc cggtgtctct tatcagaccg tttcccgcgt ggtgaaccag    300
gccagccacg tttctgcgaa aacgcgggaa aaagtggaag cggcgatggc ggagctgaat    360
tacattccca accgcgtggc acaacaactg gcgggcaaac agtcgttgct gattggcgtt    420
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
```

```
tgtaaagcgg cggtgcacaa tcttctcgcg caacgcgtca gtgggctgat cattaactat    600
ccgctggatg accaggatgc cattgctgtg aagctgcct gcactaatgt tccggcgtta    660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg   1020
gatatctcgg tagtgggata cgacgatacc gaagacagct catgttatat cccgccgtca   1080
accaccatca acaggattt tcgcctgctg ggcaaacca gcgtggaccg cttgctgcaa    1140
ctctctcagg gccaggcggt gaagggcaat cagctgttgc ccgtctcact ggtgaaaaga   1200
aaaaccaccc tggcgcccaa tacgcaaacc gcctctcccc gcgcgttggc cgattcatta   1260
atgcagctgg cacgacaggt ttcccgactg gaaagcgggc agtgagcgca acgcaattaa   1320
tgtgagttag cgcgaattga tctggtttga cagcttatca tcgactgcac ggtgcaccaa   1380
tgcttctggc gtcaggcagc catcggaagc tgtggtatgg ctgtgcaggt cgtaaatcac   1440
tgcataattc gtgtcgctca aggcgcactc ccgttctgga taatgttttt tgcgccgaca   1500
tcataacggt tctggcaaat attctgaaat gagctgttga caattaatca tccggctcgt   1560
ataatgtgtg gaattgtgag cggataacaa tttcacacag gaaacagcgc cgctgagaaa   1620
aagcgaagcg gcactgctct ttaacaattt atcagacaat ctgtgtgggc actcgaccgg   1680
aattatcgat taactttatt attaaaaatt aagaggtat atattaatgt atcgattaaa   1740
taaggaggaa taaaccatgt gtgcgacctc ttctcaattt actcagatta ccagcataa   1800
ttcccgtcgt tccgcaaact atcagccaaa cctgtggaat ttcgaattcc tgcaatccct   1860
ggagaacgac ctgaaagtgg aaaagctgga ggagaaagcg accaaactgg aggaagaagt   1920
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgttttg agcgtttcaa   2160
ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga caacctgaa agaaggcatt aataccaagg ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagccttc tgcaagaggc gaaatggtcc aacaacaaaa ttatcccggc   2940
```

```
tttctccaag tacctggaaa acgccagcgt ttcctcctcc ggtgtagcgc tgctggcgcc    3000
gtcttacttt tccgtatgcc agcagcagga agacatctcc gaccacgcgc tgcgttccct    3060
gaccgacttc catggtctgg tgcgttctag ctgcgttatc ttccgcctgt gcaacgatct    3120
ggccacctct gcggcggagc tggaacgtgg cgagactacc aattctatca ttagctacat    3180
gcacgaaaac gatggtacca gcgaggaaca ggcccgcgaa gaactgcgta aactgatcga    3240
cgccgaatgg aaaaagatga atcgtgaacg cgttagcgac tccaccctgc tgcctaaagc    3300
gttcatggaa atcgcagtta acatggcacg tgtttcccac tgcacctacc agtatggcga    3360
tggtctgggt cgcccagact acgcgactga aaaccgcatc aaactgctgc tgattgaccc    3420
tttcccgatt aaccagctga tgtatgtcta actgcatcgc ccttaggagg taaaaaaaaa    3480
tgactgccga caacaatagt atgccccatg gtgcagtatc tagttacgcc aaattagtgc    3540
aaaaccaaac acctgaagac atttttggaag agtttcctga aattattcca ttacaacaaa    3600
gacctaatac ccgatctagt gagacgtcaa atgacgaaag cggagaaaca tgttttctg    3660
gtcatgatga ggagcaaatt aagttaatga atgaaaattg tattgttttg gattgggacg    3720
ataatgctat tggtgccggt accaagaaag tttgtcattt aatggaaaat attgaaaagg    3780
gtttactaca tcgtgcattc tccgtctta ttttcaatga acaaggtgaa ttacttttac    3840
aacaaagagc cactgaaaaa ataacttttcc ctgatctttg gactaacaca tgctgctctc    3900
atccactatg tattgatgac gaattaggtt tgaagggtaa gctagacgat aagattaagg    3960
gcgctattac tgcggcggtg agaaaactag atcatgaatt aggtattcca gaagatgaaa    4020
ctaagacaag gggtaagttt cacttttttaa acagaatcca ttacatggca ccaagcaatg    4080
aaccatgggg tgaacatgaa attgattaca tcctattta taagatcaac gctaaagaaa    4140
acttgactgt caacccaaac gtcaatgaag ttagagactt caaatgggtt tcaccaaatg    4200
atttgaaaac tatgtttgct gacccaagtt acaagtttac gccttggttt aagattattt    4260
gcgagaatta cttattcaac tggtgggagc aattagatga cctttctgaa gtggaaaatg    4320
acaggcaaat tcatagaatg ctataacaac gcgtcctgca gctggtacca tatgggaatt    4380
cgaagctttc tagaacaaaa actcatctca gaagaggatc tgaatagcgc cgtcgaccat    4440
catcatcatc atcattgagt ttaaacggtc tccagcttgg ctgttttggc ggatgagaga    4500
agattttcag cctgatacag attaaatcag aacgcagaag cggtctgata aaacagaatt    4560
tgcctggcgg cagtagcgcg gtggtcccac ctgaccccat gccgaactca gaagtgaaac    4620
gccgtagcgc cgatggtagt gtggggtctc cccatgcgag agtagggaac tgccaggcat    4680
caaataaaac gaaaggctca gtcgaaagac tgggcctttc gttttatctg ttgtttgtcg    4740
gtgaacgctc tcctgagtag acaaatccg ccggagcgg atttgaacgt tgcgaagcaa    4800
cggcccggag ggtggcgggc aggacgcccg ccataaactg ccaggcatca aattaagcag    4860
aaggccatcc tgacgatgg ccttttttgcg tttctacaaa ctcttttttgt ttatttttct    4920
aaatacattc aaatatgtat ccgcttaacc ggaattgcca gctgggcgc cctctggtaa    4980
ggttgggaag ccctgcaaag taaactggat ggctttctcg ccgccaagga tctgatggcg    5040
caggggatca agctctgatc aagagacagg atgaggatc tttcgcatga ttgaacaaga    5100
tggattgcac gcaggttctc cggccgcttg ggtggagagg ctattcggct atgactgggc    5160
acaacagaca atcggctgct ctgatgccgc cgtgttccgg ctgtcagcgc agggggcgccc    5220
ggttcttttt gtcaagaccg acctgtccgg tgccctgaat gaactgcaag acgaggcagc    5280
```

| | |
|---|---|
| gcggctatcg tggctggcca cgacgggcgt tccttgcgca gctgtgctcg acgttgtcac | 5340 |
| tgaagcggga agggactggc tgctattggg cgaagtgccg gggcaggatc tcctgtcatc | 5400 |
| tcaccttgct cctgccgaga agtatccat catggctgat gcaatgcggc ggctgcatac | 5460 |
| gcttgatccg gctacctgcc cattcgacca ccaagcgaaa catcgcatcg agcgagcacg | 5520 |
| tactcggatg gaagccggtc ttgtcgatca ggatgatctg gacgaagagc atcagggct | 5580 |
| cgcgccagcc gaactgttcg ccaggctcaa ggcgagcatg cccgacggcg aggatctcgt | 5640 |
| cgtgacccat ggcgatgcct gcttgccgaa tatcatggtg gaaaatggcc gcttttctgg | 5700 |
| attcatcgac tgtggccggc tgggtgtggc ggaccgctat caggacatag cgttggctac | 5760 |
| ccgtgatatt gctgaagagc ttggcggcga atgggctgac cgcttcctcg tgctttacgg | 5820 |
| tatcgccgct cccgattcgc agcgcatcgc cttctatcgc cttcttgacg agttcttctg | 5880 |
| acatgaccaa atcccttaa cgtgagtttt cgttccactg agcgtcagac cccgtagaaa | 5940 |
| agatcaaagg atcttcttga gatcctttt ttctgcgcgt aatctgctgc ttgcaaacaa | 6000 |
| aaaaaccacc gctaccagcg gtggtttgtt tgccggatca agagctacca actctttttc | 6060 |
| cgaaggtaac tggcttcagc agagcgcaga taccaaatac tgtccttcta gtgtagccgt | 6120 |
| agttaggcca ccacttcaag aactctgtag caccgcctac atacctcgct ctgctaatcc | 6180 |
| tgttaccagt ggctgctgcc agtggcgata agtcgtgtct taccggttg gactcaagac | 6240 |
| gatagttacc ggataaggcg cagcggtcgg gctgaacggg gggttcgtgc acacagccca | 6300 |
| gcttggagcg aacgacctac accgaactga gatacctaca gcgtgagcta tgagaaagcg | 6360 |
| ccacgcttcc cgaagggaga aaggcggaca ggtatccggt aagcggcagg tcggaacag | 6420 |
| gagagcgcac gagggagctt ccaggggaa acgcctggta tctttatagt cctgtcgggt | 6480 |
| ttcgccacct ctgacttgag cgtcgatttt tgtgatgctc gtcaggggg cggagcctat | 6540 |
| ggaaaaacgc cagcaacgcg gcctttttac ggttcctggc cttttgctgg ccttttgctc | 6600 |
| acatgttctt tcctgcgtta tcccctgatt ctgtggataa ccgtattacc gcctttgagt | 6660 |
| gagctgatac cgctcgccgc agccgaacga ccgagcgcag cgagtcagtg agcgaggaag | 6720 |
| cggaagagcg cctgatgcgg tattttctcc ttacgcatct gtgcggtatt tcacaccgca | 6780 |
| tatggtgcac tctcagtaca atctgctctg atgccgcata gttaagccag tatacactcc | 6840 |
| gctatcgcta cgtgactggg tcatggctgc gccccgacac ccgccaacac ccgctgacgc | 6900 |
| gccctgacgg gc | 6912 |

<210> SEQ ID NO 17
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 17

| | |
|---|---|
| ttgtctgctc ccggcatccg cttacagaca agctgtgacc gtctccggga gctgcatgtg | 60 |
| tcagaggttt tcaccgtcat caccgaaacg cgcgaggcag cagatcaatt cgcgcgcgaa | 120 |
| ggcgaagcgg catgcattta cgttgacacc atcgaatggt gcaaaacctt tcgcggtatg | 180 |
| gcatgatagc gcccggaaga gagtcaattc agggtggtga atgtgaaacc agtaacgtta | 240 |
| tacgatgtcg cagagtatgc cggtgtctct tatcagaccg tttcccgcgt ggtgaaccag | 300 |
| gccagccacg tttctgcgaa aacgcgggaa aaagtggaag cggcgatggc ggagctgaat | 360 |
| tacattccca accgcgtggc acaacaactg gcgggcaaac agtcgttgct gattggcgtt | 420 |

```
gccacctcca gtctggccct gcacgcgccg tcgcaaattg tcgcggcgat taaatctcgc    480
gccgatcaac tgggtgccag cgtggtggtg tcgatggtag aacgaagcgg cgtcgaagcc    540
tgtaaagcgg cggtgcacaa tcttctcgcg caacgcgtca gtgggctgat cattaactat    600
ccgctggatg accaggatgc cattgctgtg gaagctgcct gcactaatgt tccggcgtta    660
tttcttgatg tctctgacca gacacccatc aacagtatta ttttctccca tgaagacggt    720
acgcgactgg gcgtggagca tctggtcgca ttgggtcacc agcaaatcgc gctgttagcg    780
ggcccattaa gttctgtctc ggcgcgtctg cgtctggctg gctggcataa atatctcact    840
cgcaatcaaa ttcagccgat agcggaacgg gaaggcgact ggagtgccat gtccggtttt    900
caacaaacca tgcaaatgct gaatgagggc atcgttccca ctgcgatgct ggttgccaac    960
gatcagatgg cgctgggcgc aatgcgcgcc attaccgagt ccgggctgcg cgttggtgcg    1020
gatatctcgg tagtgggata cgacgatacc gaagacagct catgttatat cccgccgtca    1080
accaccatca acaggattt tcgcctgctg gggcaaacca gcgtggaccg cttgctgcaa    1140
ctctctcagg gccaggcggt gaagggcaat cagctgttgc ccgtctcact ggtgaaaaga    1200
aaaaccaccc tggcgcccaa tacgcaaacc gcctctcccc gcgcgttggc cgattcatta    1260
atgcagctgg cacgacaggt ttcccgactg gaaagcgggc agtgagcgca acgcaattaa    1320
tgtgagttag cgcgaattga tctggtttga cagcttatca tcgactgcac ggtgcaccaa    1380
tgcttctggc gtcaggcagc catcggaagc tgtggtatgg ctgtgcaggt cgtaaatcac    1440
tgcataattc gtgtcgctca aggcgcactc ccgttctgga taatgttttt tgcgccgaca    1500
tcataacggt tctggcaaat attctgaaat gagctgttga caattaatca tccggctcgt    1560
ataatgtgtg gaattgtgag cggataacaa tttcacacag gaaacagcgc cgctgagaaa    1620
aagcgaagcg gcactgctct ttaacaattt atcagacaat ctgtgtgggc actcgaccgg    1680
aattatcgat taactttatt attaaaaatt aagaggtat atattaatgt atcgattaaa    1740
taaggaggaa taaaccatgt gtgcgacctc ttctcaattt actcagatta ccgagcataa    1800
ttcccgtcgt tccgcaaact atcagccaaa cctgtggaat ttcgaattcc tgcaatccct    1860
ggagaacgac ctgaaagtgg aaaagctgga ggagaaagcg accaaactgg aggaagaagt    1920
tcgctgcatg atcaaccgtg tagacaccca gccgctgtcc ctgctggagc tgatcgacga    1980
tgtgcagcgc ctgggtctga cctacaaatt tgaaaaagac atcattaaag ccctggaaaa    2040
catcgtactg ctggacgaaa acaaaaagaa caaatctgac ctgcacgcaa ccgctctgtc    2100
tttccgtctg ctgcgtcagc acggtttcga ggtttctcag gatgttttg agcgtttcaa    2160 ggataaagaa ggtggtttca gcggtgaact gaaaggtgac gtccaaggcc tgctgagcct    2220
gtatgaagcg tcttacctgg gtttcgaggg tgagaacctg ctggaggagg cgcgtacctt    2280
ttccatcacc cacctgaaga caacctgaa agaaggcatt aataccaagg ttgcagaaca    2340
agtgagccac gccctggaac tgccatatca ccagcgtctg caccgtctgg aggcacgttg    2400
gttcctggat aaatacgaac gaaagaacc gcatcaccag ctgctgctgg agctggcgaa    2460
gctggatttt aacatggtac agaccctgca ccagaaagag ctgcaagatc tgtcccgctg    2520
gtggaccgag atgggcctgg ctagcaaact ggattttgta cgcgaccgcc tgatggaagt    2580
ttatttctgg gcactgggta tggcgccaga cccgcagttt ggtgaatgtc gcaaagctgt    2640
tactaaaatg tttggtctgg tgacgatcat cgatgacgtg tatgacgttt atggcactct    2700
ggacgaactg caactgttca ccgatgctgt agagcgctgg gacgttaacg ctattaacac    2760
```

```
cctgccggac tatatgaaac tgtgtttcct ggcactgtac aacaccgtta acgacacgtc    2820
ctattctatt ctgaaagaga aaggtcataa caacctgtcc tatctgacga aaagctggcg    2880
tgaactgtgc aaagcctttc tgcaagaggc gaaatggtcc aacaacaaaa ttatcccggc    2940
tttctccaag tacctggaaa acgccagcgt ttcctcctcc ggtgtagcgc tgctggcgcc    3000
gtcttacttt tccgtatgcc agcagcagga agacatctcc gaccacgcgc tgcgttccct    3060
gaccgacttc catggtctgg tgcgttctag ctgcgttatc ttccgcctgt gcaacgatct    3120
ggccacctct gcggcggagc tggaacgtgg cgagactacc aattctatca ttagctacat    3180
gcacgaaaac gatggtacca gcgaggaaca ggcccgcgaa gaactgcgta aactgatcga    3240
cgccgaatgg aaaaagatga atcgtgaacg cgttagcgac tccaccctgc tgcctaaagc    3300
gttcatggaa atcgcagtta acatggcacg tgtttcccac tgcacctacc agtatgcgca    3360
tggtctgggt cgcccagact acgcgactga aaaccgcatc aaactgctgc tgattgaccc    3420
tttcccgatt aaccagctga tgtatgtcta actgcattcg cccttaggag gtaaaaaaac    3480
atgagttttg atattgccaa ataccccgacc ctggcactgg tcgactccac ccaggagtta    3540
cgactgttgc cgaaagagag tttaccgaaa ctctgcgacg aactgcgccg ctatttactc    3600
gacagcgtga gccgttccag cgggcacttc gcctccgggc tgggcacggt cgaactgacc    3660
gtggcgctgc actatgtcta caacaccccg tttgaccaat tgatttggga tgtggggcat    3720
caggcttatc cgcataaaat tttgaccgga cgccgcgaca aaatcggcac catccgtcag    3780
aaaggcggtc tgcacccgtt cccgtggcgc ggcgaaagcg aatatgacgt attaagcgtc    3840
gggcattcat caacctccat cagtgccgga attggtattg cggttgctgc cgaaaaagaa    3900
ggcaaaaatc gccgcaccgt ctgtgtcatt ggcgatggcg cgattaccgc aggcatggcg    3960
tttgaagcga tgaatcacgc gggcgatatc cgtcctgata tgctggtgat tctcaacgac    4020
aatgaaatgt cgatttccga aaatgtcggc gcgctcaaca accatctggc acagctgctt    4080
tccggtaagc tttactcttc actgcgcgaa ggcgggaaaa aagttttctc tggcgtgccg    4140
ccaattaaag agctgctcaa acgcaccgaa gaacatatta aaggcatggt agtgcctggc    4200
acgttgtttg aagagctggg ctttaactac atcggcccgg tggacggtca cgatgtgctg    4260
gggcttatca ccacgctaaa gaacatgcgc gacctgaaag gcccgcagtt cctgcatatc    4320
atgaccaaaa aaggtcgtgg ttatgaaccg gcagaaaaag acccgatcac tttccacgcc    4380
gtgcctaaat ttgatccctc cagcggttgt ttgccgaaaa gtagcggcgg tttgccgagc    4440
tattcaaaaa tctttggcga ctggttgtgc gaaacggcag cgaaagacaa caagctgatg    4500
gcgattactc cggcgatgcg tgaaggttcc ggcatggtcg agttttcacg taaattcccg    4560
gatcgctact tcgacgtggc aattgccgag caacacgcgg tgacctttgc tgcgggtctg    4620
gcgattggtg ggtacaaacc cattgtcgcg atttactcca ctttcctgca acgcgcctat    4680
gatcaggtgc tgcatgacgt ggcgattcaa aagcttccgg tcctgttcgc catcgaccgc    4740
gcgggcattg ttggtgctga cggtcaaacc catcaggggtg ctttttgatct ctcttacctg    4800 cgctgcatac cggaaatggt cattatgacc ccgagcgatg aaaacgaatg tcgccagatg    4860
ctctataccg gctatcacta taacgatggc ccgtcagcgg tgcgctaccc gcgtggcaac    4920
gcggtcggcg tggaactgac gccgctggaa aaactaccaa ttggcaaagg cattgtgaag    4980
cgtcgtggcg agaaactggc gatccttaac tttggtacgc tgatgccaga agcggcgaaa    5040
gtcgccgaat cgctgaacgc cacgctggtc gatatgcgtt ttgtgaaacc gcttgatgaa    5100
gcgttaattc tggaaatggc cgccagccat gaagcgctgg tcaccgtaga agaaaacgcc    5160
```

```
attatgggcg gcgcaggcag cggcgtgaac gaagtgctga tggcccatcg taaaccagta   5220
cccgtgctga acattggcct gccggacttc tttattccgc aaggaactca ggaagaaatg   5280
cgcgccgaac tcggcctcga tgccgctggt atggaagcca aaatcaaggc ctggctggca   5340
taactgcagc tggtaccata tgggaattcg aagctttcta gaacaaaaac tcatctcaga   5400
agaggatctg aatagcgccg tcgaccatca tcatcatcat cattgagttt aaacggtctc   5460
cagcttggct gttttggcgg atgagagaag attttcagcc tgatacagat taaatcagaa   5520
cgcagaagcg gtctgataaa acagaatttg cctggcggca gtagcgcggt ggtcccacct   5580
gaccccatgc cgaactcaga agtgaaacgc cgtagcgccg atggtagtgt ggggtctccc   5640
catgcgagag tagggaactg ccaggcatca aataaaacga aggctcagt cgaaagactg   5700
ggcctttcgt tttatctgtt gtttgtcggt gaacgctctc ctgagtagga caaatccgcc   5760
gggagcggat ttgaacgttg cgaagcaacg gcccggaggg tggcgggcag gacgcccgcc   5820
ataaactgcc aggcatcaaa ttaagcagaa ggccatcctg acggatggcc tttttgcgtt   5880
tctacaaact cttttgttt attttctaa atacattcaa atatgtatcc gcttaaccgg   5940
aattgccagc tggggcgccc tctggtaagg ttgggaagcc ctgcaaagta aactggatgg   6000
ctttctcgcc gccaaggatc tgatggcgca ggggatcaag ctctgatcaa gagacaggat   6060
gaggatcgtt tcgcatgatt gaacaagatg gattgcacgc aggttctccg gccgcttggg   6120
tggagaggct attcggctat gactgggcac aacagacaat cggctgctct gatgccgccg   6180
tgttccggct gtcagcgcag gggcgcccgg ttcttttttgt caagaccgac ctgtccggtg   6240
ccctgaatga actgcaagac gaggcagcgc ggctatcgtg gctggccacg acgggcgttc   6300
cttgcgcagc tgtgctcgac gttgtcactg aagcgggaag ggactggctg ctattgggcg   6360
aagtgccggg gcaggatctc ctgtcatctc accttgctcc tgccgagaaa gtatccatca   6420
tggctgatgc aatgcggcgg ctgcatacgc ttgatccggc tacctgccca ttcgaccacc   6480
aagcgaaaca tcgcatcgag cgagcacgta ctcggatgga gccggtctt gtcgatcagg   6540
atgatctgga cgaagagcat caggggctcg cgccagccga actgttcgcc aggctcaagg   6600
cgagcatgcc cgacggcgag gatctcgtcg tgacccatgg cgatgcctgc ttgccgaata   6660
tcatggtgga aaatggccgc ttttctggat tcatcgactg tggccggctg ggtgtggcgg   6720
accgctatca ggacatagcg ttggctaccc gtgatattgc tgaagagctt ggcggcgaat   6780
gggctgaccg cttcctcgtg ctttacggta tcgccgctcc cgattcgcag cgcatcgcct   6840
tctatcgcct tcttgacgag ttcttctgac gcatgaccaa aatcccttaa cgtgagtttt   6900
cgttccactg agcgtcagac cccgtagaaa agatcaaagg atcttcttga tccttttt   6960
ttctgcgcgt aatctgctgc ttgcaaacaa aaaaccacc gctaccagcg gtggtttgtt   7020
tgccggatca agagctacca actcttttc cgaaggtaac tggcttcagc agagcgcaga   7080
taccaaatac tgtccttcta gtgtagccgt agttaggcca ccacttcaag aactctgtag   7140
caccgcctac atacctcgct ctgctaatcc tgttaccagt ggctgctgcc agtggcgata   7200
agtcgtgtct taccgggttg gactcaagac gatagttacc ggataaggcg cagcggtcgg   7260
gctgaacggg gggttcgtgc acacagccca gcttggagcg aacgacctac accgaactga   7320
gatacctaca gcgtgagcta tgagaaagcg ccacgcttcc cgaagggaga aggcggaca   7380
ggtatccggt aagcggcagg gtcggaacag gagagcgcac gagggagctt ccaggggggaa   7440
acgcctggta tctttatagt cctgtcgggt ttcgccacct ctgacttgag cgtcgatttt   7500
```

-continued

| | |
|---|---|
| tgtgatgctc gtcagggggg cggagcctat ggaaaaacgc cagcaacgcg gccttttac | 7560 |
| ggttcctggc cttttgctgg cctttgctc acatgttctt tcctgcgtta tccctgatt | 7620 |
| ctgtggataa ccgtattacc gcctttgagt gagctgatac cgctcgccgc agccgaacga | 7680 |
| ccgagcgcag cgagtcagtg agcgaggaag cggaagagcg cctgatgcgg tattttctcc | 7740 |
| ttacgcatct gtgcggtatt tcacaccgca tatggtgcac tctcagtaca atctgctctg | 7800 |
| atgccgcata gttaagccag tatacactcc gctatcgcta cgtgactggg tcatggctgc | 7860 |
| gccccgacac ccgccaacac ccgctgacgc gccctgacgg gc | 7902 |

<210> SEQ ID NO 18
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| ctggcgtaat agcgaagagg cccgcaccga tcgcccttcc caacagttgc gcagcctgaa | 60 |
| tggcgaatgg cgcctgatgc ggtatttct ccttacgcat ctgtgcggta tttcacaccg | 120 |
| catatggtgc actctcagta caatctgctc tgatgccgca tagttaagcc agccccgaca | 180 |
| cccgccaaca cccgctgacg agcttagtaa agccctcgct agattttaat gcggatgttg | 240 |
| cgattacttc gccaactatt gcgataacaa gaaaaagcca gcctttcatg atatatctcc | 300 |
| caatttgtgt agggcttatt atgcacgctt aaaataata aaagcagact tgacctgata | 360 |
| gtttggctgt gagcaattat gtgcttagtg catctaacgc ttgagttaag ccgcgccgcg | 420 |
| aagcggcgtc ggcttgaacg aattgttaga cattatttgc cgactacctt ggtgatctcg | 480 |
| cctttcacgt agtggacaaa ttcttccaac tgatctgcgc gcgaggccaa gcgatcttct | 540 |
| tcttgtccaa gataagcctg tctagcttca gtatgacgg gctgatactg gccggcagg | 600 |
| cgctccattg cccagtcggc agcgacatcc ttcggcgcga ttttgccggt tactgcgctg | 660 |
| taccaaatgc gggacaacgt aagcactaca tttcgctcat cgccagccca gtcgggcggc | 720 |
| gagttccata cgttaaggt tcatttagc gcctcaaata gatcctgttc aggaaccgga | 780 |
| tcaaagagtt cctccgccgc tggacctacc aaggcaacgc tatgttctct gcttttgtc | 840 |
| agcaagatag ccagatcaat gtcgatcgtg gctggctcga agatacctgc aagaatgtca | 900 |
| ttgcgctgcc attctccaaa ttgcagttcg cgcttagctg ataacgcca cggaatgatg | 960 |
| tcgtcgtgca caacaatggt gacttctaca gcgcggagaa tctcgctctc tccagggaa | 1020 |
| gccgaagttt ccaaaggtc gttgatcaaa gctcgccgcg ttgtttcatc aagccttacg | 1080 |
| gtcaccgtaa ccagcaaatc aatatcactg tgtggcttca ggccgccatc cactgcggag | 1140 |
| ccgtacaaat gtacggccag caacgtcggt tcgagatggc gctcgatgac gccaactacc | 1200 |
| tctgatagtt gagtcgatac ttcggcgatc accgcttccc tcatgatgtt taactttgtt | 1260 |
| ttagggcgac tgccctgctg cgtaacatcg ttgctgctcc ataacatcaa acatcgaccc | 1320 |
| acggcgtaac gcgcttgctg cttggatgcc cgaggcatag actgtacccc aaaaaaacag | 1380 |
| tcataacaag ccatgaaaac cgccactgcg ccgttaccac cgctgcgttc ggtcaaggtt | 1440 |
| ctggaccagt tgcgtgagcg catacgctac ttgcattaca gcttacgaac cgaacaggct | 1500 |
| tatgtccact gggttcgtgc cttcatccgt ttccacggtg tcgtcaccc ggcaaccttg | 1560 |
| ggcagcagcg aagtcgaggc atttctgtcc tggctggcga acgagcgcaa ggtttcggtc | 1620 |
| tccacgcatc gtcaggcatt ggcggccttg ctgttcttct acggcaaggt gctgtgcacg | 1680 |

```
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt acccgagag cttggcaccc agcctgcgcg agcaggggaa ttaattccca    1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgttttttgc gtgagccatg agaacgaacc attgagatca   2580
tacttacttt gcatgtcact caaaaatttt gcctcaaaac tggtgagctg aattttttgca  2640 gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttattttcaa gcattaacat gaacttaaat   2940
tcatcaaggc taatctctat atttgccttg tgagttttct tttgtgttag ttctttttaat  3000 aaccactcat aaatcctcat agagtatttg ttttcaaaag acttaacatg ttccagatta   3060
tattttatga attttttaa ctggaaaaga taaggcaata tctcttcact aaaaactaat    3120 tctaatttt cgcttgagaa cttggcatag tttgtccact ggaaaatctc aaagccttta    3180
accaaaggat tcctgatttc cacagttctc gtcatcagct ctctggttgc tttagctaat   3240
acaccataag catttttccct actgatgttc atcatctgag cgtattggtt ataagtgaac   3300
gataccgtcc gttctttcct tgtagggttt tcaatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac ctttgctgga aaacttgtaa attctgctag accctctgta   3600
aattccgcta gacctttgtg tgttttttt gtttatattc aagtggttat aatttatga    3660 ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtcttttc gtgacattca    3900 gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
```

```
gcgttttatg gcgggtctgc tatgtggtgc tatctgactt tttgctgttc agcagttcct    4080
gccctctgat tttccagtct gaccacttcg gattatcccg tgacaggtca ttcagactgg    4140
ctaatgcacc cagtaaggca gcggtatcat caacaggctt acccgtctta ctgtcgggaa    4200
ttcgcgttgg ccgattcatt aatgcagatt ctgaaatgag ctgttgacaa ttaatcatcc    4260
ggctcgtata atgtgtggaa ttgtgagcgg ataacaattt cacacaggaa acagcgccgc    4320
tgagaaaaag cgaagcggca ctgctcttta acaatttatc agacaatctg tgtgggcact    4380
cgaccggaat tatcgattaa ctttattatt aaaaattaaa gaggtatata ttaatgtatc    4440
gattaaataa ggaggaataa accatgtgtg cgacctcttc tcaatttact cagattaccg    4500
agcataattc ccgtcgttcc gcaaactatc agccaaacct gtggaatttc gaattcctgc    4560
aatccctgga gaacgacctg aaagtggaaa agctggagga gaaagcgacc aaactggagg    4620
aagaagttcg ctgcatgatc aaccgtgtag acacccagcc gctgtccctg ctggagctga    4680
tcgacgatgt gcagcgcctg ggtctgacct acaaatttga aaagacatc attaaagccc    4740 tggaaaacat cgtactgctg gacgaaaaca aaagaacaa atctgacctg cacgcaaccg    4800
ctctgtcttt ccgtctgctg cgtcagcacg gtttcgaggt ttctcaggat gttttttgagc    4860 gtttcaagga taaagaaggt ggtttcagcg gtgaactgaa aggtgacgtc caaggcctgc    4920
tgagcctgta tgaagcgtct tacctgggtt tcgagggtga gaacctgctg gaggaggcgc    4980
gtaccttttc catcacccac ctgaagaaca acctgaaaga aggcattaat accaaggttg    5040
cagaacaagt gagccacgcc ctggaactgc catatcacca gcgtctgcac cgtctggagg    5100
cacgttggtt cctggataaa tacgaaccga agaaccgca tcaccagctg ctgctggagc    5160
tggcgaagct ggattttaac atggtacaga ccctgcacca gaaagagctg caagatctgt    5220
cccgctggtg gaccgagatg ggcctggcta gcaaactgga ttttgtacgc gaccgcctga    5280
tggaagttta tttctgggca ctgggtatgg cgccagaccc gcagtttggt gaatgtcgca    5340
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460
ttaacaccct gccggactat atgaaactgt gttttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaaacg ccagcgtttc ctcctccggt gtagcgctgc    5700
tggcgccgtc ttactttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
tgatcgacgc cgaatggaaa agatgaatc gtgaacgcgt tagcgactcc accctgctgc    6000
ctaaagcgtt catggaaatc gcagttaaca tggcacgtgt ttcccactgc acctaccagt    6060
atggcgatgg tctgggtcgc ccagactacg cgactgaaaa ccgcatcaaa ctgctgctga    6120 ttgaccctttt cccgattaac cagctgatgt atgtctaact gcagctggta ccatatggga    6180
attcgaagct ttctagaaca aaaactcatc tcagaagagg atctgaatag cgccgtcgac    6240
catcatcatc atcatcattg agtttaaacg gtctccagct tggctgtttt ggcggatgag    6300
agaagatttt cagcctgata cagattaaat cagaacgcag aagcggtctg ataaaacaga    6360
atttgcctgg cggcagtagc gcggtggtcc cacctgaccc catgccgaac tcagaagtga    6420
```

```
aacgccgtag cgccgatggt agtgtggggt ctccccatgc gagagtaggg aactgccagg    6480
catcaaataa aacgaaaggc tcagtcgaaa gactgggcct ttcgttttat ctgttgtttg    6540
tcggtgaacg ctctcctgag taggacaaat ccgccgggag cggatttgaa cgttgcgaag    6600
caacggcccg gagggtggcg ggcaggacgc ccgccataaa ctgccaggca tcaaattaag    6660
cagaaggcca tcctgacgga tggccttttt gcgtttctac aaactctttt tgtttatttt    6720
tctaaataca ttcaaatatg tatccgctca tgagacaata accctgataa atgcttcaat    6780
aat                                                                  6783
```

<210> SEQ ID NO 19
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 19

```
cccgtcttac tgtcgggaat tcgcgttggc cgattcatta atgcagatta ttgaagcatt      60
tatcagggtt attgtctcat gagcggatac atatttgaat gtatttagaa aaataaacaa     120
aaagagtttg tagaaacgca aaaaggccat ccgtcaggat ggccttctgc ttaatttgat     180
gcctggcagt ttatggcggg cgtcctgccc gccaccctcc gggccgttgc ttcgcaacgt     240
tcaaatccgc tcccggcgga tttgtcctac tcaggagagc gttcaccgac aaacaacaga     300
taaaacgaaa ggcccagtct ttcgactgag cctttcgttt tatttgatgc ctggcagttc     360
cctactctcg catggggaga ccccacacta ccatcggcgc tacggcgttt cacttctgag     420
ttcggcatgg ggtcaggtgg gaccaccgcg ctactgccgc caggcaaatt ctgttttatc     480
agaccgcttc tgcgttctga tttaatctgt atcaggctga aaatcttctc tcatccgcca     540
aaacagccaa gctggagacc gtttaaactc aatgatgatg atgatgatgg tcgacggcgc     600
tattcagatc ctcttctgag atgagttttt gttctagaaa gcttcgaatt cccatatggt     660
accagctgca gttagacata catcagctgg ttaatcggga aagggtcaat cagcagcagt     720
ttgatgcggt tttcagtcgc gtagtctggg cgacccagac catcgccata ctggtaggtg     780
cagtgggaaa cacgtgccat gttaactgcg atttccatga acgctttagg cagcagggtg     840
gagtcgctaa cgcgttcacg attcatcttt ttccattcgg cgtcgatcag tttacgcagt     900
tcttcgcggg cctgttcctc gctggtacca tcgttttcgt gcatgtagct aatgatagaa     960
ttggtagtct cgccacgttc cagctccgcc gcagaggtgg ccagatcgtt gcacaggcgg    1020
aagataacgc agctagaacg caccagacca tggaagtcgg tcagggaacg cagcgcgtgg    1080
tcggagatgt cttcctgctg ctggcatacg gaaaagtaag acggcgccag cagcgctaca    1140
ccggaggagg aaacgctggc gttttccagg tacttggaga agccgggat aattttgttg     1200 ttggaccatt tcgcctcttg cagaaaggct ttgcacagtt cacgccagct tttcgtcaga    1260
taggacaggt tgttatgacc tttctctttc agaatagaat aggacgtgtc gttaacggtg    1320
ttgtacagtg ccaggaaaca cagtttcata tagtccggca gggtgttaat agcgttaacg    1380
tcccagcgct ctacagcatc ggtgaacagt tgcagttcgt ccagagtgcc ataaacgtca    1440
tacacgtcat cgatgatcgt caccagacca aacatttag taacagcttt gcgacattca    1500
ccaaactgcg ggtctggcgc catacccagt gcccagaaat aaacttccat caggcggtcg    1560
cgtacaaaat ccagtttgct agccaggccc atctcggtcc accagcggga cagatcttgc    1620
```

-continued

```
agctctttct ggtgcagggt ctgtaccatg ttaaaatcca gcttcgccag ctccagcagc   1680
agctggtgat gcggttcttt cggttcgtat ttatccagga accaacgtgc ctccagacgg   1740
tgcagacgct ggtgatatgg cagttccagg gcgtggctca cttgttctgc aaccttggta   1800
ttaatgcctt ctttcaggtt gttcttcagg tgggtgatgg aaaaggtacg cgcctcctcc   1860
agcaggttct caccctcgaa acccaggtaa gacgcttcat acaggctcag caggccttgg   1920
acgtcacctt tcagttcacc gctgaaacca ccttctttat ccttgaaacg ctcaaaaaca   1980
tcctgagaaa cctcgaaacc gtgctgacgc agcagacgga agacagagc ggttgcgtgc   2040 aggtcagatt tgttcttttt gttttcgtcc agcagtacga tgttttccag ggctttaatg   2100
atgtcttttt caaatttgta ggtcagaccc aggcgctgca catcgtcgat cagctccagc   2160
agggacagcg gctgggtgtc tacacggttg atcatgcagc gaacttcttc ctccagtttg   2220
gtcgctttct cctccagctt ttccactttc aggtcgttct ccaggattg caggaattcg   2280 aaattccaca ggtttggctg atagtttgcg gaacgacggg aattatgctc ggtaatctga   2340
gtaaattgag aagaggtcgc acacatggtt tattcctcct tatttaatcg atacattaat   2400
atatacctct ttaattttta ataataaagt taatcgataa ttccggtcga gtgcccacac   2460
agattgtctg ataaattgtt aaagagcagt gccgcttcgc ttttctcag cggcgctgtt   2520 tcctgtgtga aattgttatc cgctcacaat tccacacatt atacgagccg atgattaat   2580 tgtcaacagc tcatttcaga atctggcgta atagcgaaga ggcccgcacc gatcgccctt   2640
cccaacagtt gcgcagcctg aatggcgaat ggcgcctgat gcggtatttt ctccttacgc   2700
atctgtgcgg tatttcacac cgcatatggt gcactctcag tacaatctgc tctgatgccg   2760
catagttaag ccagccccga cacccgccaa cacccgctga cgagcttagt aaagccctcg   2820
ctagatttta atgcggatgt tgcgattact tcgccaacta ttgcgataac aagaaaaagc   2880
cagcctttca tgatatatct cccaatttgt gtagggctta ttatgcacgc ttaaaaataa   2940
taaaagcaga cttgacctga tagtttggct gtgagcaatt atgtgcttag tgcatctaac   3000
gcttgagtta agccgcgccg cgaagcggcg tcggcttgaa cgaattgtta gacattattt   3060
gccgactacc ttggtgatct cgcctttcac gtagtggaca aattcttcca actgatctgc   3120
gcgcgaggcc aagcgatctt cttcttgtcc aagataagcc tgtctagctt caagtatgac   3180
gggctgatac tgggccggca ggcgctccat tgcccagtcg gcagcgacat ccttcggcgc   3240
gattttgccg gttactgcgc tgtaccaaat gcgggacaac gtaagcacta catttcgctc   3300
atcgccagcc cagtcgggcg gcgagttcca tagcgttaag gtttcattta gcgcctcaaa   3360
tagatcctgt tcaggaaccg gatcaaagag ttcctccgcc gctggaccta ccaaggcaac   3420
gctatgttct cttgcttttg tcagcaagat agccagatca atgtcgatcg tggctggctc   3480
gaagatacct gcaagaatgt cattgcgctg ccattctcca aattgcagtt cgcgcttagc   3540
tggataacgc cacggaatga tgtcgtcgtg cacaacaatg gtgacttcta cagcgcggag   3600
aatctcgctc tctccagggg aagccgaagt ttccaaaagg tcgttgatca aagctcgccg   3660
cgttgtttca tcaagcctta cggtcaccgt aaccagcaaa tcaatatcac tgtgtggctt   3720
caggccgcca tccactgcgg agccgtacaa atgtacggcc agcaacgtcg gttcgagatg   3780
gcgctcgatg acgccaacta cctctgatag ttgagtcgat acttcggcga tcaccgcttc   3840
cctcatgatg tttaactttg ttttagggcg actgccctgc tgcgtaacat cgttgctgct   3900
ccataacatc aaacatcgac ccacggcgta acgcgcttgc tgcttggatg cccgaggcat   3960
agactgtacc ccaaaaaaac agtcataaca agccatgaaa accgccactg cgccgttacc   4020
```

```
accgctgcgt tcggtcaagg ttctggacca gttgcgtgag cgcatacgct acttgcatta    4080
cagcttacga accgaacagg cttatgtcca ctgggttcgt gccttcatcc gtttccacgg    4140
tgtgcgtcac ccggcaacct tgggcagcag cgaagtcgag gcatttctgt cctggctggc    4200
gaacgagcgc aaggtttcgg tctccacgca tcgtcaggca ttggcggcct tgctgttctt    4260
ctacggcaag gtgctgtgca cggatctgcc ctggcttcag gagatcggaa gacctcggcc    4320
gtcgcggcgc ttgccggtgg tgctgacccc ggatgaagtg gttcgcatcc tcggttttct    4380
ggaaggcgag catcgtttgt tcgcccagct tctgtatgga acgggcatgc ggatcagtga    4440
gggtttgcaa ctgcgggtca aggatctgga tttcgatcac ggcacgatca tcgtgcggga    4500
gggcaagggc tccaaggatc gggccttgat gttacccgag agcttggcac ccagcctgcg    4560
cgagcagggg aattaattcc cacgggtttt gctgcccgca aacgggctgt tctggtgttg    4620
ctagtttgtt atcagaatcg cagatccggc ttcagccggt ttgccggctg aaagcgctat    4680
ttcttccaga attgccatga tttttttcccc acgggaggcg tcactggctc ccgtgttgtc    4740
ggcagctttg attcgataag cagcatcgcc tgtttcaggc tgtctatgtg tgactgttga    4800
gctgtaacaa gttgtctcag gtgttcaatt tcatgttcta gttgctttgt tttactggtt    4860
tcacctgttc tattaggtgt tacatgctgt tcatctgtta cattgtcgat ctgttcatgg    4920
tgaacagctt tgaatgcacc aaaaactcgt aaaagctctg atgtatctat cttttttaca    4980
ccgttttcat ctgtgcatat ggacagtttt cccttttgata tgtaacggtg aacagttgtt    5040
ctactttttgt ttgttagtct tgatgcttca ctgatagata caagagccat aagaacctca    5100
gatccttccg tatttagcca gtatgttctc tagtgtggtt cgttgttttt gcgtgagcca    5160
tgagaacgaa ccattgagat catacttact ttgcatgtca ctcaaaaatt ttgcctcaaa    5220
actggtgagc tgaattttg cagttaaagc atcgtgtagt gttttttctta gtccgttatg    5280
taggtaggaa tctgatgtaa tggttgttgg tattttgtca ccattcatttt ttatctggtt    5340
gttctcaagt tcggttacga gatccatttg tctatctagt tcaacttgga aaatcaacgt    5400
atcagtcggg cggcctcgct tatcaaccac caatttcata ttgctgtaag tgtttaaatc    5460
tttacttatt ggtttcaaaa cccattggtt aagccttttta aactcatggt agttattttc    5520
aagcattaac atgaacttaa attcatcaag gctaatctct atatttgcct tgtgagtttt    5580
cttttgtgtt agttctttta ataaccactc ataaatcctc atagagtatt tgttttcaaa    5640
agacttaaca tgttccagat tatattttat gaattttttt aactggaaaa gataaggcaa    5700
tatctcttca ctaaaaacta attctaattt ttcgcttgag aacttggcat agtttgtcca    5760
ctggaaaatc tcaaagcctt taaccaaagg attcctgatt tccacagttc tcgtcatcag    5820
ctctctggtt gctttagcta atacaccata agcatttttcc ctactgatgt tcatcatctg    5880
agcgtattgg ttataagtga acgataccgt ccgttctttc cttgtagggt tttcaatcgt    5940
ggggttgagt agtgccacac agcataaaat tagcttggtt tcatgctccg ttaagtcata    6000
gcgactaatc gctagttcat ttgctttgaa aacaactaat tcagacatac atctcaattg    6060
gtctaggtga ttttaatcac tataccaatt gagatgggct agtcaatgat aattactagt    6120
ccttttcctt tgagttgtgg gtatctgtaa attctgctag acctttgctg gaaaacttgt    6180
aaattctgct agaccctctg taaattccgc tagaccttttg tgtgtttttt ttgtttatat    6240
tcaagtggtt ataatttata gaataaagaa agaataaaaa aagataaaaa gaatagatcc    6300
cagccctgtg tataactcac tactttagtc agttccgcag tattacaaaa ggatgtcgca    6360
```

```
aacgctgttt gctcctctac aaaacagacc ttaaaaccct aaaggcttaa gtagcaccct      6420
cgcaagctcg ggcaaatcgc tgaatattcc ttttgtctcc gaccatcagg cacctgagtc      6480
gctgtctttt tcgtgacatt cagttcgctg cgctcacggc tctggcagtg aatgggggta      6540
aatggcacta caggcgcctt ttatggattc atgcaaggaa actacccata atacaagaaa      6600
agcccgtcac gggcttctca gggcgtttta tggcgggtct gctatgtggt gctatctgac      6660 ttttgctgt tcagcagttc ctgccctctg attttccagt ctgaccactt cggattatcc       6720
cgtgacaggt cattcagact ggctaatgca cccagtaagg cagcggtatc atcaacaggc     6780
tta                                                                    6783

<210> SEQ ID NO 20
<211> LENGTH: 7687
<212> TYPE: DNA
<213> ORGANISM: Artificial Sequence
<220> FEATURE:
<223> OTHER INFORMATION: Synthetic Construct

<400> SEQUENCE: 20
ctggcgtaat agcgaagagg cccgcaccga tcgcccttcc caacagttgc gcagcctgaa        60
tggcgaatgg cgcctgatgc ggtatttttct ccttacgcat ctgtgcggta tttcacaccg      120
catatggtgc actctcagta caatctgctc tgatgccgca tagttaagcc agccccgaca       180
cccgccaaca cccgctgacg agcttagtaa agccctcgct agattttaat gcggatgttg       240
cgattacttc gccaactatt gcgataacaa gaaaaagcca gcctttcatg atatatctcc       300
caatttgtgt agggcttatt atgcacgctt aaaaataata aaagcagact tgacctgata       360
gtttggctgt gagcaattat gtgcttagtg catctaacgc ttgagttaag ccgcgccgcg       420
aagcggcgtc ggcttgaacg aattgttaga cattatttgc cgactacctt ggtgatctcg       480
cctttcacgt agtggacaaa ttcttccaac tgatctgcgc gcgaggccaa gcgatcttct       540
tcttgtccaa gataagcctg tctagcttca agtatgacgg gctgatactg ggccggcagg       600
cgctccattg cccagtcggc agcgacatcc ttcggcgcga ttttgccggt tactgcgctg       660
taccaaatgc gggacaacgt aagcactaca tttcgctcat cgccagccca gtcgggcggc       720
gagttccata gcgttaaggt ttcatttagc gcctcaaata gatcctgttc aggaaccgga       780
tcaaagagtt cctccgccgc tggacctacc aaggcaacgc tatgttctct tgcttttgtc       840
agcaagatag ccagatcaat gtcgatcgtg gctggctcga agatacctgc aagaatgtca       900
ttgcgctgcc attctccaaa ttgcagttcg cgcttagctg gataacgcca cggaatgatg       960
tcgtcgtgca caacaatggt gacttctaca gcgcggagaa tctcgctctc tccaggggaa      1020
gccgaagttt ccaaaaggtc gttgatcaaa gctcgccgcg ttgtttcatc aagccttacg      1080
gtcaccgtaa ccagcaaatc aatatcactg tgtggcttca ggccgccatc cactgcggag      1140
ccgtacaaat gtacggccag caacgtcggt tcgagatggc gctcgatgac gccaactacc      1200
tctgatagtt gagtcgatac ttcggcgatc accgcttccc tcatgatgtt taactttgtt     1260
ttagggcgac tgccctgctg cgtaacatcg ttgctgctcc ataacatcaa acatcgaccc     1320
acggcgtaac gcgcttgctg cttggatgcc cgaggcatag actgtacccc aaaaaaacag     1380
tcataacaag ccatgaaaac cgccactgcg ccgttaccac cgctgcgttc ggtcaaggtt     1440
ctggaccagt tgcgcgagcg catacgctac ttgcattaca gcttacgaac cgaacaggct     1500
tatgtccact gggttcgtgc cttcatccgt ttccacggtg tgcgtcaccc ggcaaccttg     1560
ggcagcagcg aagtcgaggc atttctgtcc tggctggcga acgagcgcaa ggtttcggtc     1620
```

```
tccacgcatc gtcaggcatt ggcggccttg ctgttcttct acggcaaggt gctgtgcacg    1680
gatctgccct ggcttcagga gatcggaaga cctcggccgt cgcggcgctt gccggtggtg    1740
ctgaccccgg atgaagtggt tcgcatcctc ggttttctgg aaggcgagca tcgtttgttc    1800
gcccagcttc tgtatggaac gggcatgcgg atcagtgagg gtttgcaact gcgggtcaag    1860
gatctggatt tcgatcacgg cacgatcatc gtgcgggagg caagggctc caaggatcgg     1920 gccttgatgt tacccgagag cttggcaccc agcctgcgcg agcaggggaa ttaattccca    1980
cgggttttgc tgcccgcaaa cgggctgttc tggtgttgct agtttgttat cagaatcgca    2040
gatccggctt cagccggttt gccggctgaa agcgctattt cttccagaat tgccatgatt    2100
ttttccccac gggaggcgtc actggctccc gtgttgtcgg cagctttgat tcgataagca    2160
gcatcgcctt tttcaggctg tctatgtgtg actgttgagc tgtaacaagt tgtctcaggt    2220
gttcaatttc atgttctagt tgctttgttt tactggtttc acctgttcta ttaggtgtta    2280
catgctgttc atctgttaca ttgtcgatct gttcatggtg aacagctttg aatgcaccaa    2340
aaactcgtaa aagctctgat gtatctatct tttttacacc gttttcatct gtgcatatgg    2400
acagttttcc ctttgatatg taacggtgaa cagttgttct acttttgttt gttagtcttg    2460
atgcttcact gatagataca agagccataa gaacctcaga tccttccgta tttagccagt    2520
atgttctcta gtgtggttcg ttgttttttgc gtgagccatg agaacgaacc attgagatca    2580
tacttacttt gcatgtcact caaaaatttt gcctcaaaac tggtgagctg aattttttgca   2640 gttaaagcat cgtgtagtgt ttttcttagt ccgttatgta ggtaggaatc tgatgtaatg    2700
gttgttggta ttttgtcacc attcattttt atctggttgt tctcaagttc ggttacgaga    2760
tccatttgtc tatctagttc aacttggaaa atcaacgtat cagtcgggcg gcctcgctta    2820
tcaaccacca atttcatatt gctgtaagtg tttaaatctt tacttattgg tttcaaaacc    2880
cattggttaa gccttttaaa ctcatggtag ttattttcaa gcattaacat gaacttaaat    2940
tcatcaaggc taatctctat atttgccttg tgagttttct tttgtgttag ttcttttaat    3000
aaccactcat aaatcctcat agagtatttg ttttcaaaag acttaacatg ttccagatta    3060
tattttatga atttttttaa ctggaaaaga taaggcaata tctcttcact aaaaactaat    3120
tctaattttt cgcttgagaa cttggcatag tttgtccact ggaaaatctc aaagccttta    3180
accaaaggat tcctgatttc cacagttctc gtcatcagct ctctggttgc tttagctaat    3240
acaccataag cattttccct actgatgttc atcatctgag cgtattggtt ataagtgaac    3300
gataccgtcc gttctttcct tgtagggttt tcaatcgtgg ggttgagtag tgccacacag    3360
cataaaatta gcttggtttc atgctccgtt aagtcatagc gactaatcgc tagttcattt    3420
gctttgaaaa caactaattc agacatacat ctcaattggt ctaggtgatt ttaatcacta    3480
taccaattga gatgggctag tcaatgataa ttactagtcc ttttccttttg agttgtgggt   3540 atctgtaaat tctgctagac ctttgctgga aaacttgtaa attctgctag accctctgta    3600
aattccgcta gacctttgtg tgttttttttt gtttatattc aagtggttat aatttataga    3660
ataaagaaag aataaaaaaa gataaaaaga atagatccca gccctgtgta taactcacta    3720
ctttagtcag ttccgcagta ttacaaaagg atgtcgcaaa cgctgtttgc tcctctacaa    3780
aacagacctt aaaacccctaa aggcttaagt agcaccctcg caagctcggg caaatcgctg    3840
aatattcctt ttgtctccga ccatcaggca cctgagtcgc tgtctttttc gtgacattca    3900
gttcgctgcg ctcacggctc tggcagtgaa tgggggtaaa tggcactaca ggcgcctttt    3960
```

```
atggattcat gcaaggaaac tacccataat acaagaaaag cccgtcacgg gcttctcagg    4020
gcgttttatg gcgggtctgc tatgtggtgc tatctgactt tttgctgttc agcagttcct    4080
gccctctgat tttccagtct gaccacttcg gattatcccg tgacaggtca ttcagactgg    4140
ctaatgcacc cagtaaggca gcggtatcat caacaggctt acccgtctta ctgtcgggaa    4200
ttcgcgttgg ccgattcatt aatgcagatt ctgaaatgag ctgttgacaa ttaatcatcc    4260
ggctcgtata atgtgtggaa ttgtgagcgg ataacaattt cacacaggaa acagcgccgc    4320
tgagaaaaag cgaagcggca ctgctcttta acaatttatc agacaatctg tgtgggcact    4380
cgaccggaat tatcgattaa ctttattatt aaaaattaaa gaggtatata ttaatgtatc    4440
gattaaataa ggaggaataa accatgtgtg cgacctcttc tcaatttact cagattaccg    4500
agcataattc ccgtcgttcc gcaaactatc agccaaacct gtggaatttc gaattcctgc    4560
aatccctgga gaacgacctg aaagtggaaa agctggagga gaaagcgacc aaactggagg    4620
aagaagttcg ctgcatgatc aaccgtgtag cacccagcc gctgtccctg ctggagctga    4680
tcgacgatgt gcagcgcctg ggtctgacct acaaatttga aaaagacatc attaaagccc    4740
tggaaaacat cgtactgctg gacgaaaaca aaaagaacaa atctgacctg cacgcaaccg    4800
ctctgtcttt ccgtctgctg cgtcagcacg gtttcgaggt ttctcaggat gttttttgagc    4860 gtttcaagga taaagaaggt ggtttcagcg gtgaactgaa aggtgacgtc caaggcctgc    4920
tgagcctgta tgaagcgtct tacctgggtt tcgagggtga gaacctgctg gaggaggcgc    4980
gtaccttttc catcacccac ctgaagaaca acctgaaaga aggcattaat accaaggttg    5040
cagaacaagt gagccacgcc ctggaactgc catatcacca gcgtctgcac cgtctctgagg    5100 cacgttggtt cctggataaa tacgaaccga agaaccgca tcaccagctg ctgctggagc    5160
tggcgaagct ggatttttaac atggtacaga ccctgcacca gaaagagctg caagatctgt    5220
cccgctggtg gaccgagatg ggcctggcta gcaaactgga ttttgtacgc gaccgcctga    5280
tggaagttta tttctgggca ctgggtatgg cgccagaccc gcagtttggt gaatgtcgca    5340
aagctgttac taaaatgttt ggtctggtga cgatcatcga tgacgtgtat gacgtttatg    5400
gcactctgga cgaactgcaa ctgttcaccg atgctgtaga gcgctgggac gttaacgcta    5460
ttaacaccct gccggactat atgaaactgt gtttcctggc actgtacaac accgttaacg    5520
acacgtccta ttctattctg aaagagaaag gtcataacaa cctgtcctat ctgacgaaaa    5580
gctggcgtga actgtgcaaa gcctttctgc aagaggcgaa atggtccaac aacaaaatta    5640
tcccggcttt ctccaagtac ctggaaaacg ccagcgtttc ctcctccggt gtagcgctgc    5700
tggcgccgtc ttacttttcc gtatgccagc agcaggaaga catctccgac cacgcgctgc    5760
gttccctgac cgacttccat ggtctggtgc gttctagctg cgttatcttc cgcctgtgca    5820
acgatctggc cacctctgcg gcggagctgg aacgtggcga gactaccaat tctatcatta    5880
gctacatgca cgaaaacgat ggtaccagcg aggaacaggc ccgcgaagaa ctgcgtaaac    5940
tgatcgacgc cgaatggaaa aagatgaatc gtgaacgcgt tagcgactcc accctgctgc    6000
ctaaagcgtt catggaaatc gcagttaaca tggcacgtgt tcccactgc acctaccagt    6060 atggcgatgt tctgggtcgc ccagactacg cgactgaaaa ccgcatcaaa ctgctgctga    6120
ttgacccttt cccgattaac cagctgatgt atgtctaact gcatcgccct aggaggtaa    6180 aaaaaaatga ctgccgacaa caatagtatg ccccatggtg cagtatctag ttacgccaaa    6240
ttagtgcaaa accaaacacc tgaagacatt ttggaagagt tcctgaaat tattccatta    6300 caacaaagac ctaatacccg atctagtgag acgtcaaatg acgaaagcgg agaaacatgt    6360
```

-continued

```
ttttctggtc atgatgagga gcaaattaag ttaatgaatg aaaattgtat tgttttggat    6420
tgggacgata atgctattgg tgccggtacc aagaaagttt gtcatttaat ggaaaatatt    6480
gaaaagggtt tactacatcg tgcattctcc gtctttattt tcaatgaaca aggtgaatta    6540
cttttacaac aaagagccac tgaaaaaata actttccctg atctttggac taacacatgc    6600
tgctctcatc cactatgtat tgatgacgaa ttaggtttga agggtaagct agacgataag    6660
attaagggcg ctattactgc ggcggtgaga aaactagatc atgaattagg tattccagaa    6720
gatgaaacta agacaagggg taagtttcac ttttttaaaca gaatccatta catggcacca    6780
agcaatgaac catggggtga acatgaaatt gattacatcc tattttataa gatcaacgct    6840
aaagaaaact tgactgtcaa cccaaacgtc aatgaagtta gagacttcaa atgggtttca    6900
ccaaatgatt tgaaaactat gtttgctgac ccaagttaca agtttacgcc ttggtttaag    6960
attatttgcg agaattactt attcaactgg tgggagcaat tagatgacct ttctgaagtg    7020
gaaaatgaca ggcaaattca tagaatgcta aacgacgcg tcctgcagct ggtaccatat    7080
gggaattcga agctttctag aacgaaaact catctcagaa gaggatctga atagcgccgt    7140
cgaccatcat catcatcatc attgagttta acggtctcc agcttggctg ttttggcgga    7200
tgagagaaga ttttcagcct gatacagatt aaatcagaac gcagaagcgg tctgataaaa    7260
cagaatttgc ctggcggcag tagcgcggtg gtcccacctg accccatgcc gaactcagaa    7320
gtgaaacgcc gtagcgccga tggtagtgtg gggtctcccc atgcgagagt agggaactgc    7380
caggcatcaa ataaaacgaa aggctcagtc gaaagactgg gcctttcgtt ttatctgttg    7440
tttgtcggtg aacgctctcc tgagtaggac aaatccgccg ggagcggatt tgaacgttgc    7500
gaagcaacgg cccggagggt ggcgggcagg acgcccgcca taaactgcca ggcatcaaat    7560
taagcagaag gccatcctga cggatggcct ttttgcgttt ctacaaactc ttttttgttta    7620 tttttctaaa tacattcaaa tatgtatccg ctcatgagac aataaccctg ataaatgctt    7680
caataat                                                              7687
```

<210> SEQ ID NO 21
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 21

```
cccgtcttac tgtcgggaat tcgcgttggc cgattcatta atgcagatta ttgaagcatt     60
tatcagggtt attgtctcat gagcggatac atatttgaat gtatttagaa aaataaacaa    120
aaagagtttg tagaaacgca aaaaggccat ccgtcaggat ggccttctgc ttaatttgat    180
gcctggcagt ttatggcggg cgtcctgccc gccaccctcc gggccgttgc ttcgcaacgt    240
tcaaatccgc tcccggcgga tttgtcctac tcaggagagc gttcaccgac aaacaacaga    300
taaaacgaaa ggcccagtct ttcgactgag cctttcgttt tatttgatgc ctggcagttc    360
cctactctcg catggggaga ccccacacta ccatcggcgc tacggcgttt cacttctgag    420
ttcggcatgg ggtcaggtgg gaccaccgcg ctactgccgc caggcaaatt ctgttttatc    480
agaccgcttc tgcgttctga tttaatctgt atcaggctga aaatcttctc tcatccgcca    540
aaacagccaa gctggagacc gtttaaactc aatgatgatg atgatgatgg tcgacggcgc    600
tattcagatc ctcttctgag atgagttttt gttctagaaa gcttcgaatt cccatatggt    660
```

```
accagctgca gttatgccag ccaggccttg attttggctt ccataccagc ggcatcgagg    720
ccgagttcgg cgcgcatttc ttcctgagtt ccttgcggaa taaagaagtc cggcaggcca    780
atgttcagca cgggtactgg tttacgatgg ccatcagca  cttcgttcac gccgctgcct    840
gcgccgccca taatggcgtt ttcttctacg gtgaccagcg cttcatggct ggcggccatt    900
tccagaatta acgcttcatc aagcggtttc acaaaacgca tatcgaccag cgtggcgttc    960
agcgattcgg cgactttcgc cgcttctggc atcagcgtac caaagttaag gatcgccagt   1020
ttctcgccac gacgcttcac aatgcctttg ccaattggta gttttttccag cggcgtcagt  1080
tccacgccga ccgcgttgcc acgcgggtag cgcaccgctg acgggccatc gttatagtga   1140
tagccggtat agagcatctg gcgacattcg ttttcatcgc tcggggtcat aatgaccatt   1200
tccggtatgc agcgcaggta agagagatca aaagcaccct gatgggtttg accgtcagca   1260
ccaacaatgc ccgcgcggtc gatggcgaac aggaccggaa gcttttgaat cgccacgtca   1320
tgcagcacct gatcataggc gcgttgcagg aaagtggagt aaatcgcgac aatgggtttg   1380
tacccaccaa tcgccagacc cgcagcaaag gtcaccgcgt gttgctcggc aattgccacg   1440
tcgaagtagc gatccgggaa tttacgtgaa aactcgacca tgccggaacc ttcacgcatc   1500
gccgagtaa  tcgccatcag cttgttgtct ttcgctgccg tttcgcacaa ccagtcgcca   1560
aagattttg  aatagctcgg caaaccgccg ctacttttcg gcaaacaacc gctggaggga   1620
tcaaatttag gcacgcgtg  gaaagtgatc gggtctttt  ctgccggttc ataaccacga   1680
ccttttttgg tcatgatatg caggaactgc gggcctttca ggtcgcgcat gttctttagc   1740
gtggtgataa gccccagcac atcgtgaccg tccaccgggc cgatgtagtt aaagcccagc   1800
tcttcaaaca acgtgccagg cactaccatg cctttaatat gttcttcggt gcgtttgagc   1860
agctctttaa ttggcggcac gccagagaaa actttttttcc cgccttcgcg cagtgaagag  1920
taaagcttac cggaaagcag ctgtgccaga tggttgttga gcgcgccgac attttcggaa   1980
atcgacattt cattgtcgtt gagaatcacc agcatatcag gacggatatc gcccgcgtga   2040
ttcatcgctt caaacgccat gcctgcggta atcgcgccat cgccaatgac acagacggtg   2100
cggcgatttt tgccttcttt ttcggcagca accgcaatac caattccggc actgatggag   2160
gttgatgaat gcccgacgct taatacgtca tattcgcttt cgccgcgcca cgggaacggg   2220
tgcagaccgc ctttctgacg gatggtgccg attttgtcgc ggcgtccggt caaaattta    2280
tgcggataag cctgatgccc cacatcccaa atcaattggt caaacggggt gttgtagaca   2340
tagtgcagcg ccacggtcag ttcgaccgtg cccagcccgg aggcgaagtg cccgctggaa   2400
cggctcacgc tgtcgagtaa atagcggcgc agttcgtcgc agagtttcgg taaactctct   2460
ttcggcaaca gtcgtaactc ctgggtggag tcgaccagtg ccagggtcgg gtatttggca   2520
atatcaaaac tcatgttttt ttacctccta agggcgaatg cagttagaca tacatcagct   2580
ggttaatcgg gaaagggtca atcagcagca gtttgatgcg gttttcagtc gcgtagtctg   2640
ggcgacccag accatcgcca tactggtagg tgcagtggga aacacgtgcc atgttaactg   2700
cgatttccat gaacgcttta ggcagcaggg tggagtcgct aacgcgttca cgattcatct   2760
ttttccattc ggcgtcgatc agtttacgca gttcttcgcg ggcctgttcc tcgctggtac   2820
catcgttttc gtgcatgtag ctaatgatag aattggtagt ctcgccacgt tccagctccg   2880
ccgcagaggt ggccagatcg ttgcacaggc ggaagataac gcagctagaa cgcaccagac   2940
catggaagtc ggtcagggaa cgcagcgcgt ggtcggagat gtcttcctgc tgctggcata   3000
cggaaaagta agacggcgcc agcagcgcta caccggagga ggaaacgctg gcgttttcca   3060
```

```
ggtacttgga gaaagccggg ataattttgt tgttggacca tttcgcctct tgcagaaagg    3120 cttttgcacag ttcacgccag cttttcgtca gataggacag gttgttatga cctttctctt   3180
tcagaataga ataggacgtg tcgttaacgg tgttgtacag tgccaggaaa cacagtttca    3240
tatagtccgg cagggtgtta atagcgttaa cgtcccagcg ctctacagca tcggtgaaca    3300
gttgcagttc gtccagagtg ccataaacgt catacacgtc atcgatgatc gtcaccagac    3360
caaacatttt agtaacagct tgcgacatt  caccaaactg cgggtctggc gccatacccag   3420 gtgcccagaa ataaacttcc atcaggcggt cgcgtacaaa atccagtttg ctagccaggc    3480
ccatctcggt ccaccagcgg gacagatctt gcagctcttt ctggtgcagg gtctgtacca    3540
tgttaaaatc cagcttcgcc agctccagca gcagctggtg atgcggttct ttcggttcgt    3600
atttatccag gaaccaacgt gcctccgac  ggtgcagacg ctggtgatat ggcagttcca    3660
gggcgtggct cacttgttct gcaaccttgg tattaatgcc ttctttcagg ttgttcttca    3720
ggtgggtgat ggaaaaggta cgcgcctcct ccagcaggt  ctcaccctcg aaacccaggt    3780
aagacgcttc ataggctc  agcaggcctt ggacgtcacc tttcagttca ccgctgaaac    3840
caccttcttt atccttgaaa cgctcaaaaa catcctgaga aacctcgaaa ccgtgctgac    3900
gcagcagacg gaaagacaga gcggttgcgt gcaggtcaga tttgttcttt ttgttttcgt    3960
ccagcagtac gatgttttcc agggctttaa tgatgtcttt ttcaaatttg taggtcagac    4020
ccaggcgctg cacatcgtcg atcagctcca gcagggacag cggctgggtg tctacacggt    4080
tgatcatgca gcgaacttct tcctccagtt tggtcgcttt ctcctccagc ttttccactt    4140
tcaggtcgtt ctccagggat tgcaggaatt cgaaattcca caggtttggc tgatagtttg    4200
cggaacgacg ggaattatgc tcggtaatct gagtaaattg agaagaggtc gcacacatgg    4260
tttattcctc cttatttaat cgatacatta atatatacct ctttaatttt taataataaa    4320
gttaatcgat aattccggtc gagtgcccac acagattgtc tgataaattg ttaaagagca    4380
gtgccgcttc gcttttctc  agcggcgctg tttcctgtgt gaaattgtta ccgctcaca    4440 attccacaca ttatacgagc cggatgatta attgtcaaca gctcatttca gaatctggcg    4500
taatagcgaa gaggcccgca ccgatcgccc ttcccaacag ttgcgcagcc tgaatggcga    4560
atggcgcctg atgcggtatt ttctccttac gcatctgtgc ggtatttcac accgcatatg    4620
gtgcactctc agtacaatct gctctgatgc cgcatagtta agccagcccc gacacccgcc    4680
aacacccgct gacgagctta gtaaagccct cgctagattt taatgcggat gttgcgatta    4740
cttcgccaac tattgcgata acaagaaaaa gccagccttt catgatatat ctcccaattt    4800
gtgtagggct tattatgcac gcttaaaaat aataaaagca gacttgacct gatagtttgg    4860
ctgtgagcaa ttatgtgctt agtgcatcta acgcttgagt taagccgcgc cgcgaagcgg    4920
cgtcggcttg aacgaattgt tagacattat ttgccgacta ccttggtgat ctcgcctttc    4980
acgtagtgga caaattcttc caactgatct gcgcgcgagg ccaagcgatc ttcttcttgt    5040
ccaagataag cctgtctagc ttcaagtatg acgggctgat actgggccgg caggcgctcc    5100
attgcccagt cggcagcgac atccttcggc gcgattttgc cggttactgc gctgtaccaa    5160
atgcgggaca acgtaagcac tacatttcgc tcatcgccag cccagtcggg cggcgagttc    5220
catagcgtta aggtttcatt tagcgcctca aatagatcct gttcaggaac cggatcaaag    5280
agttcctccg ccgctggacc taccaaggca acgctatgtt ctcttgcttt tgtcagcaag    5340
atagccagat caatgtcgat cgtggctggc tcgaagatac ctgcaagaat gtcattgcgc    5400
```

```
tgccattctc caaattgcag ttcgcgctta gctggataac gccacggaat gatgtcgtcg    5460
tgcacaacaa tggtgacttc tacagcgcgg agaatctcgc tctctccagg ggaagccgaa    5520
gtttccaaaa ggtcgttgat caaagctcgc cgcgttgttt catcaagcct tacggtcacc    5580
gtaaccagca aatcaatatc actgtgtggc ttcaggccgc catccactgc ggagccgtac    5640
aaatgtacgg ccagcaacgt cggttcgaga tggcgctcga tgacgccaac tacctctgat    5700
agttgagtcg atacttcggc gatcaccgct ccctcatga tgtttaactt tgttttaggg     5760
cgactgccct gctgcgtaac atcgttgctg ctccataaca tcaaacatcg acccacggcg    5820
taacgcgctt gctgcttgga tgcccgaggc atagactgta ccccaaaaaa acagtcataa    5880
caagccatga aaaccgccac tgcgccgtta ccaccgctgc gttcggtcaa ggttctggac    5940
cagttgcgtg agcgcatacg ctacttgcat tacagcttac gaaccgaaca ggcttatgtc    6000
cactgggttc gtgccttcat ccgtttccac ggtgtgcgtc acccggcaac cttgggcagc    6060
agcgaagtcg aggcatttct gtcctggctg gcgaacgagc gcaaggtttc ggtctccacg    6120
catcgtcagg cattggcggc cttgctgttc ttctacggca aggtgctgtg cacggatctg    6180
ccctggcttc aggagatcgg aagacctcgg ccgtcgcggc gcttgccggt ggtgctgacc    6240
ccggatgaag tggttcgcat cctcggtttt ctggaaggcg agcatcgttt gttcgcccag    6300
cttctgtatg gaacgggcat gcggatcagt gagggtttgc aactgcgggt caaggatctg    6360
gatttcgatc acggcacgat catcgtgcgg gagggcaagg gctccaagga tcgggccttg    6420
atgttacccg agagcttggc acccagcctg cgcgagcagg ggaattaatt cccacgggtt    6480
ttgctgcccg caaacgggct gttctggtgt tgctagtttg ttatcagaat cgcagatccg    6540
gcttcagccg gtttgccggc tgaaagcgct atttcttcca gaattgccat gattttttcc    6600
ccacgggagg cgtcactggc tcccgtgttg tcggcagctt tgattcgata agcagcatcg    6660
cctgtttcag gctgtctatg tgtgactgtt gagctgtaac aagttgtctc aggtgttcaa    6720
tttcatgttc tagttgcttt gttttactgg tttcacctgt tctattaggt gttacatgct    6780
gttcatctgt tacattgtcg atctgttcat ggtgaacagc tttgaatgca ccaaaaactc    6840
gtaaaagctc tgatgtatct atcttttttta caccgttttc atctgtgcat atggacagtt    6900 ttcccttga tatgtaacgg tgaacagttg ttctactttt gtttgttagt cttgatgctt     6960
cactgataga tacaagagcc ataagaacct cagatccttc cgtatttagc cagtatgttc    7020
tctagtgtgg ttcgttgttt ttgcgtgagc catgagaacg aaccattgag atcatactta    7080
ctttgcatgt cactcaaaaa ttttgcctca aaactggtga gctgaatttt tgcagttaaa    7140
gcatcgtgta gtgtttttct tagtccgtta tgtaggtagg aatctgatgt aatggttgtt    7200
ggtattttgt caccattcat ttttatctgg ttgttctcaa gttcggttac gagatccatt    7260
tgtctatcta gttcaacttg gaaaatcaac gtatcagtcg ggcggcctcg cttatcaacc    7320
accaatttca tattgctgta agtgtttaaa tctttactta ttggtttcaa aacccattgg    7380
ttaagccttt taaactcatg gtagttattt tcaagcatta acatgaactt aaattcatca    7440
aggctaatct ctatatttgc cttgtgagtt ttcttttgtg ttagttcttt taataaccac    7500
tcataaatcc tcatagagta tttgtttttca aagacttaa catgttccag attatatttt    7560
atgaattttt ttaactggaa aagataaggc aatatctctt cactaaaaac taattctaat    7620
ttttcgcttg agaacttggc atagtttgtc cactggaaaa tctcaaagcc tttaaccaaa    7680
ggattcctga tttccacagt tctcgtcatc agctctctgg ttgctttagc taatacacca    7740
taagcatttt ccctactgat gttcatcatc tgagcgtatt ggttataagt gaacgatacc    7800
```

```
gtccgttctt tccttgtagg gttttcaatc gtggggttga gtagtgccac acagcataaa    7860
attagcttgg tttcatgctc cgttaagtca tagcgactaa tcgctagttc atttgctttg    7920
aaaacaacta attcagacat acatctcaat tggtctaggt gattttaatc actataccaa    7980
ttgagatggg ctagtcaatg ataattacta gtccttttcc tttgagttgt gggtatctgt    8040
aaattctgct agacctttgc tggaaaactt gtaaattctg ctagaccctc tgtaaattcc    8100
gctagacctt tgtgtgtttt ttttgtttat attcaagtgg ttataattta tagaataaag    8160
aaagaataaa aaagataaa aagaatagat cccagccctg tgtataactc actactttag    8220
tcagttccgc agtattacaa aaggatgtcg caaacgctgt ttgctcctct acaaaacaga    8280
ccttaaaacc ctaaaggctt aagtagcacc ctcgcaagct cgggcaaatc gctgaatatt    8340
ccttttgtct ccgaccatca ggcacctgag tcgctgtctt tttcgtgaca ttcagttcgc    8400
tgcgctcacg gctctggcag tgaatggggg taaatggcac tacaggcgcc ttttatggat    8460
tcatgcaagg aaactaccca taatacaaga aaagcccgtc acgggcttct cagggcgttt    8520 tatgcgggt ctgctatgtg gtgctatctg acttttgct gttcagcagt cctgccctc    8580 tgattttcca gtctgaccac ttcggattat cccgtgacag gtcattcaga ctggctaatg    8640
cacccagtaa ggcagcggta tcatcaacag gctta                              8675
```

<210> SEQ ID NO 22
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 22

```
tcgctgcgct cggtcgttcg gctgcggcga gcggtatcag ctcactcaaa ggcggtaata      60
cggttatcca cagaatcagg ggataacgca ggaaagaaca tgtgagcaaa aggccagcaa     120
aaggccagga accgtaaaaa ggccgcgttg ctggcgtttt tccataggct ccgcccccct     180
gacgagcatc acaaaaatcg acgctcaagt cagaggtggc gaaacccgac aggactataa     240
agataccagg cgtttccccc tggaagctcc ctcgtgcgct ctcctgttcc gaccctgccg     300
cttaccggat acctgtccgc ctttctccct tcgggaagcg tggcgctttc tcatagctca     360
cgctgtaggt atctcagttc ggtgtaggtc gttcgctcca agctgggctg tgtgcacgaa     420
ccccccgttc agcccgaccg ctgcgcctta tccggtaact atcgtcttga gtccaacccg     480
gtaagacacg acttatcgcc actggcagca gccactggta acaggattag cagagcgagg     540
tatgtaggcg gtgctacaga gttcttgaag tggtggccta actacggcta cactagaaga     600
acagtatttg gtatctgcgc tctgctgaag ccagttacct tcggaaaaag agttggtagc     660
tcttgatccg gcaaacaaac caccgctggt agcggtggtt tttttgtttg caagcagcag     720
attacgcgca gaaaaaaagg atctcaagaa gatcctttga tcttttctac ggggtctgac     780
gctcagtgga acgaaaactc acgttaaggg attttggtca tgagattatc aaaaaggatc     840
ttcacctaga tccttttaaa ttaaaaatga agttttaaat caatctaaag tatatatgag     900
taaacttggt ctgacagtta ccaatgctta atcagtgagg cacctatctc agcgatctgt     960
ctatttcgtt catccatagt tgcctgactc cccgtcgtgt agataactac gatacgggag    1020
ggcttaccat ctggccccag tgctgcaatg ataccgcgag acccacgctc accggctcca    1080
gatttatcag caataaacca gccagccgga agggccgagc gcagaagtgg tcctgcaact    1140
```

```
ttatccgcct ccatccagtc tattaattgt tgccgggaag ctagagtaag tagttcgcca   1200
gttaatagtt tgcgcaacgt tgttgccatt gctacaggca tcgtggtgtc acgctcgtcg   1260
tttggtatgg cttcattcag ctccggttcc caacgatcaa ggcgagttac atgatccccc   1320
atgttgtgca aaaagcggt tagctccttc ggtcctccga tcgttgtcag aagtaagttg   1380
gccgcagtgt tatcactcat ggttatggca gcactgcata attctcttac tgtcatgcca   1440
tccgtaagat gcttttctgt gactggtgag tactcaacca agtcattctg agaatagtgt   1500
atgcggcgac cgagttgctc ttgcccggcg tcaatacggg ataataccgc gccacatagc   1560
agaactttaa aagtgctcat cattggaaaa cgttcttcgg ggcgaaaact ctcaaggatc   1620
ttaccgctgt tgagatccag ttcgatgtaa cccactcgtg cacccaactg atcttcagca   1680
tcttttactt tcaccagcgt ttctgggtga gcaaaaacag gaaggcaaaa tgccgcaaaa   1740
aagggaataa gggcgacacg gaaatgttga atactcatac tcttcctttt tcaatattat   1800
tgaagcattt atcagggtta ttgtctcatg agcggataca tatttgaatg tatttagaaa   1860
aataaacaaa taggggttcc gcgcacattt ccccgaaaag tgccacctga cgtctaagaa   1920
accattatta tcatgacatt aacctataaa aataggcgta tcacgaggcc ctttcgtctc   1980
gcgcgtttcg gtgatgacgg tgaaaacctc tgacacatgc agctcccgga gacggtcaca   2040
gcttgtctgt aagcggatgc cgggagcaga caagcccgtc agggcgcgtc agcgggtgtt   2100
ggcgggtgtc ggggctggct taactatgcg gcatcagagc agattgtact gagagtgcac   2160
catagatctg gagctgtaat ataaaaacct tcttcaacta acggggcagg ttagtgacat   2220
tagaaaaccg actgtaaaaa gtacagtcgg cattatctca tattataaaa gccagtcatt   2280
aggcctatct gacaattcct gaatagagtt cataaacaat cctgcatgat aaccatcaca   2340
aacagaatga tgtacctgta aagatagcgg taaatatatt gaattacctt tattaatgaa   2400
ttttcctgct gtaataatgg gtagaaggta attactatta ttattgatat ttaagttaaa   2460
cccagtaaat gaagtccatg gaataataga aagagaaaaa gcattttcag gtataggtgt   2520
tttgggaaac aatttccccg aaccattata tttctctaca tcagaaaggt ataaatcata   2580
aaactctttg aagtcattct ttacaggagt ccaaatacca gagaatgttt tagatacacc   2640
atcaaaaatt gtataaagtg gctctaactt atcccaataa cctaactctc cgtcgctatt   2700
gtaaccagtt ctaaaagctg tatttgagtt tatcacccct gtcactaaga aaataaatgc   2760
agggtaaaat ttatatcctt cttgttttat gtttcggtat aaaacactaa tatcaatttc   2820
tgtggttata ctaaaagtcg tttgttggtt caaataatga ttaaatatct cttttctctt   2880
ccaattgtct aaatcaattt tattaaagtt catttgatat gcctcctaaa tttttatcta   2940
aagtgaattt aggaggctta cttgtctgct ttcttcatta gaatcaatcc tttttttaaaa   3000 gtcaatatta ctgtaacata aatatatatt ttaaaaatat cccactttat ccaattttcg   3060
tttgttgaac taatgggtgc tttagttgaa gaataaaaga cctatgcggt gtgaaatacc   3120
gcacagatgc gtaaggagaa ataccgcat caggcgccat tcgccattca ggctgcgcaa   3180
ctgttgggaa gggcgatcgg tgcgggcctc ttcgctatta cgccagctgg cgaaaggggg   3240
atgtgctgca aggcgattaa gttgggtaac gccagggttt tcccagtcac gacgttgtaa   3300
aacgacggcc agtgccaagc ttgcatgcct gcactccatt ttcttctgct atcaaaataa   3360
cagactcgtg attttccaaa cgagctttca aaaaagcctc tgccccttgc aaatcggatg   3420
cctgtctata aaattcccga tattggttaa acagcggcgc aatggcggcc gcatctgatg   3480
tctttgcttg gcgaatgttc atcttatttc ttcctccctc tcaataattt tttcattcta   3540
```

```
tccctttttct gtaaagttta tttttcagaa tacttttatc atcatgcttt gaaaaaatat   3600
cacgataata tccattgttc tcacggaagc acacgcaggt catttgaacg aattttttcg   3660
acaggaattt gccgggactc aggagcattt aacctaaaaa agcatgacat ttcagcataa   3720
tgaacattta ctcatgtcta ttttcgttct tttctgtatg aaaatagtta tttcgagtct   3780
ctacggaaat agcgagagat gatataccta aatagagata aaatcatctc aaaaaaatgg   3840
gtctactaaa atattattcc atctattaca ataaattcac agaatagtct tttaagtaag   3900
tctactctga atttttttaa aaggagaggg taaagagtga aaacagtagt tattattgat   3960
gcattacgaa caccaattgg aaaatataaa ggcagcttaa gtcaagtaag tgccgtagac   4020
ttaggaacac atgttacaac acaacttttta aaaagacatt ccactatttc tgaagaaatt   4080
gatcaagtaa tctttggaaa tgttttacaa gctggaaatg ccaaaatcc cgcacgacaa   4140 atagcaataa acagcggttt gtctcatgaa attcccgcaa tgacggttaa tgaggtctgc   4200
ggatcaggaa tgaaggccgt tattttggcg aaacaattga ttcaattagg agaagcggaa   4260
gttttaattg ctggcgggat tgagaatatg tcccaagcac ctaaattaca acgttttaat   4320
tacgaaacag aaagctacga tgcgcctttt tctagtatga tgtatgatgg attaacggat   4380
gcctttagtg gtcaggcaat gggcttaact gctgaaaatg tggccgaaaa gtatcatgta   4440
actagagaag agcaagatca attttctgta cattcacaat taaaagcagc tcaagcacaa   4500
gcagaaggga tattcgctga cgaaatagcc ccattagaag tatcaggaac gcttgtggag   4560
aaagatgaag ggattcgccc taattcgagc gttgagaagc taggaacgct taaaacagtt   4620 tttaagaag acggtactgt aacagcaggg aatgcatcaa ccattaatga tggggcttct   4680
gctttgatta ttgcttcaca agaatatgcc gaagcacacg gtcttcctta tttagctatt   4740
attcgagaca gtgtggaagt cggtattgat ccagcctata tgggaatttc gccgattaaa   4800
gccattcaaa aactgttagc gcgcaatcaa cttactacgg aagaaattga tctgtatgaa   4860
atcaacgaag catttgcagc aacttcaatc gtggtccaaa gagaactggc tttaccagag   4920
gaaaaggtca acatttatgg tggcggtatt tcattaggtc atgcgattgg tgccacaggt   4980
gctcgtttat taacgagttt aagttatcaa ttaaatcaaa agaaaagaa atatggagtg   5040 gcttctttat gtatcggcgg tggcttagga ctcgctatgc tactagagag acctcagcaa   5100
aaaaaaaaca gccgatttta tcaaatgagt cctgaggaac gcctggcttc tcttcttaat   5160
gaaggccaga tttctgctga tacaaaaaaa gaatttgaaa atacggcttt atcttcgcag   5220
attgccaatc atatgattga aaatcaaatc agtgaaacag aagtgccgat gggcgttggc   5280
ttacatttaa cagtggacga aactgattat ttggtaccaa tggcgacaga agagccctca   5340
gttattgcgg ctttgagtaa tggtgcaaaa atagcacaag gatttaaaac agtgaatcaa   5400
caacgcttaa tgcgtggaca aatcgttttt tacgatgttg cagatcccga gtcattgatt   5460
gataaactac aagtaagaga agcggaagtt tttcaacaag cagagttaag ttatccatct   5520
atcgttaaac ggggcggcgg cttaagagat ttgcaatatc gtacttttga tgaatcattt   5580
gtatctgtcg acttttttagt agatgttaag gatgcaatgg gggcaaatat cgttaacgct   5640
atgttggaag gtgtggccga gttgttccgt gaatggtttg cggagcaaaa gattttattc   5700
agtattttaa gtaattatgc cacggagtcg gttgttacga tgaaaacggc tattccagtt   5760
tcacgtttaa gtaaggggag caatggccgg gaaattgctg aaaaaattgt tttagcttca   5820
cgctatgctt cattagatcc ttatcgggca gtcacgcata acaaaggaat catgaatggc   5880
```

```
attgaagctg tagttttagc tacaggaaat gatacacgcg ctgttagcgc ttcttgtcat    5940
gcttttgcgg tgaaggaagg tcgctaccaa ggcttgacta gttggacgct ggatggcgaa    6000
caactaattg gtgaaatttc agttccgctt gctttagcca cggttggcgg tgccacaaaa    6060
gtcttaccta atctcaagc agctgctgat ttgttagcag tgacggatgc aaaagaacta     6120
agtcgagtag tagcggctgt tggtttggca caaaatttag cggcgttacg ggccttagtc    6180
tctgaaggaa ttcaaaaagg acacatggct ctacaagcac gttctttagc gatgacggtc    6240
ggagctactg gtaaagaagt tgaggcagtc gctcaacaat taaaacgtca aaaaacgatg    6300
aaccaagacc gagccatggc tatttttaaat gatttaagaa acaataaaa ggagagggtg    6360
acaattggga ttgataaaat tagtttttttt gtgcccccctt attatattga tatgacggca   6420
ctggctgaag ccagaaatgt agaccctgga aaatttcata ttggtattgg gcaagaccaa    6480
atggcggtga acccaatcag ccaagatatt gtgacatttg cagccaatgc cgcagaagcg    6540
atcttgacca agaagataa agaggccatt gatatggtga ttgtcgggac tgagtccagt    6600
atcgatgagt caaaagcggc cgcagttgtc ttacatcgtt taatgggat tcaacctttc    6660
gctcgctctt tcgaaatcaa ggaagcttgt tacggagcaa cagcaggctt acagttagct    6720
aagaatcacg tagccttaca tccagataaa aaagtcttgg tcgtagcggc agatattgca   6780
aaatatggct taaattctgg cggtgagcct acacaaggag ctggggcggt tgcaatgtta    6840
gttgctagtg aaccgcgcat tttggcttta aagaggata atgtgatgct gacgcaagat    6900
atctatgact tttggcgtcc aacaggccac ccgtatccta tggtcgatgg tcctttgtca   6960
aacgaaacct acatccaatc tttttgcccaa gtctgggatg aacataaaaa acgaaccggt    7020
cttgattttg cagattatga tgctttagcg ttccatattc cttacacaaa aatgggcaaa    7080
aaagccttat tagcaaaaaat ctccgaccaa actgaagcag aacaggaacg aattttagcc   7140
cgttatgaag aaagtatcgt ctatagtcgt cgcgtaggaa acttgtatac gggttcactt    7200
tatctgggac tcatttccct tttagaaaat gcaacgactt taaccgcagg caatcaaatt    7260
ggtttattca gttatggttc tggtgctgtc gctgaatttt tcactggtga attagtagct    7320
ggttatcaaa atcatttaca aaagaaact catttagcac tgctggataa tcggacagaa    7380
ctttctatcg ctgaatatga agccatgttt gcagaaactt tagacacaga cattgatcaa    7440
acgttagaag atgaattaaa atatagtatt tctgctatta ataataccgt tcgttcttat   7500
cgaaactaaa aaaaccggc cttggccccg ccggtttttt attattttttc ttcctccgca    7560
tgttcaatcc gctccataat cgacggatgg ctccctctga aaattttaac gagaaacggc    7620
gggttgaccc ggctcagtcc cgtaacggcc aagtcctgaa acgtctcaat cgccgcttcc    7680
cggtttccgg tcagctcaat gccgtaacgg tcggcggcgt tttcctgata ccgggagacg    7740
gcattcgtaa tcgggatccc cgggtaccga gctcgaattc gtaatcatgt catagctgtt   7800
tcctgtgtga aattgttatc cgctcacaat tccacacaac atacgagccg gaagcataaa    7860
gtgtaaagcc tggggtgcct aatgagtgag ctaactcaca ttaattgcgt tgcgctcact    7920
gcccgctttc cagtcgggaa acctgtcgtg ccagctgcat taatgaatcg gccaacgcgc    7980
ggggagaggc ggtttgcgta ttgggcgctc ttccgcttcc tcgctcactg ac             8032
```

```
<210> SEQ ID NO 23
<211> LENGTH: 8000
<212> TYPE: DNA
<213> ORGANISM: Artificial Sequence
<220> FEATURE:
<223> OTHER INFORMATION: Synthetic Construct
```

<400> SEQUENCE: 23

```
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatggatcc   420
gagctcagga ggtaaaaaaa catgaaaaca gtagttatta ttgatgcatt acgaacacca   480
attggaaaat ataaaggcag cttaagtcaa gtaagtgccg tagacttagg aacacatgtt   540
acaacacaac ttttaaaaag acattccact atttctgaag aaattgatca gtaatctttt   600
ggaaatgttt tacaagctgg aaatggccaa atcccgcac acaaatagc aataaacagc   660
ggtttgtctc atgaaattcc cgcaatgacg gttaatgagg tctgcggatc aggaatgaag   720
gccgttattt tggcgaaaca attgattcaa ttaggagaag cggaagtttt aattgctggc   780
gggattgaga atatgtccca agcacctaaa ttacaacgtt ttaattacga aacagaaagc   840
tacgatgcgc cttttttctag tatgatgtat gatggattaa cggatgcctt tagtggtcag   900
gcaatgggct taactgctga aaatgtggcc gaaaagtatc atgtaactag agaagagcaa   960
gatcaatttt ctgtacattc acaattaaaa gcagctcaag cacaagcaga agggatattc  1020
gctgacgaaa tagccccatt agaagtatca ggaacgcttg tggagaaaga tgaagggatt  1080
cgccctaatt cgagcgttga gaagctagga acgcttaaaa cagttttaa agaagacggt  1140
actgtaacag cagggaatgc atcaaccatt aatgatgggg cttctgcttt gattattgct  1200
tcacaagaat atgccgaagc acacggtctt ccttatttag ctattattcg agacagtgtg  1260
gaagtcggta ttgatccagc ctatatggga atttcgccga ttaaagccat tcaaaaactg  1320
ttagcgcgca atcaacttac tacggaagaa attgatctgt atgaaatcaa cgaagcattt  1380
gcagcaactt caatcgtggt ccaaagagaa ctggctttac cagaggaaaa ggtcaacatt  1440
tatggtggcg gtatttcatt aggtcatgcg attggtgcca caggtgctcg tttattaacg  1500
agtttaagtt atcaattaaa tcaaaaagaa agaatatg gagtggcttc tttatgtatc  1560
ggcggtggct taggactcgc tatgctacta gagagacctc agcaaaaaaa aaacagccga  1620
ttttatcaaa tgagtcctga ggaacgcctg gcttctcttc ttaatgaagg ccagatttct  1680
gctgatacaa aaaagaatt tgaaaatacg gctttatctt cgcagattgc caatcatatg  1740
attgaaaatc aaatcagtga acagaagtg ccgatgggcg ttggcttaca tttaacagtg  1800
gacgaaactg attatttggt accaatggcg acagaagagc cctcagttat gcggctttg  1860
agtaatggtc aaaaatagc acaaggattt aaaacagtga atcaacaacg cttaatgcgt  1920
ggacaaatcg ttttttacga tgttgcagat cccgagtcat tgattgataa actacaagta  1980
agagaagcgg aagttttca acaagcagag ttaagttatc catctatcgt taaacgggc   2040
ggcggcttaa gagatttgca atatcgtact tttgatgaat catttgtatc tgtcgacttt  2100
ttagtagatg ttaaggatgc aatgggggca aatatcgtta acgctatgtt ggaaggtgtg  2160
gccgagttgt tccgtgaatg gtttgcggag caaaagattt tattcagtat tttaagtaat  2220
tatgccacgg agtcggttgt tacgatgaaa acggctattc cagtttcacg tttaagtaag  2280
```

```
gggagcaatg gccgggaaat tgctgaaaaa attgttttag cttcacgcta tgcttcatta    2340
gatccttatc gggcagtcac gcataacaaa ggaatcatga atggcattga agctgtagtt    2400
ttagctacag gaaatgatac acgcgctgtt agcgcttctt gtcatgcttt tgcggtgaag    2460
gaaggtcgct accaaggctt gactagttgg acgctggatg gcgaacaact aattggtgaa    2520
atttcagttc cgcttgcttt agccacggtt ggcggtgcca caaaagtctt acctaaatct    2580
caagcagctc tgatttgtt agcagtgacg gatgcaaaag aactaagtcg agtagtagcg    2640
gctgttggtt tggcacaaaa tttagcggcg ttacgggcct tagtctctga aggaattcaa    2700
aaaggacaca tggctctaca agcacgttct ttagcgatga cggtcggagc tactggtaaa    2760
gaagttgagg cagtcgctca acaattaaaa cgtcaaaaaa cgatgaacca agaccgagcc    2820
atggctattt taaatgattt aagaaaacaa taaaggaggt aaaaaaacat gacaattggg    2880
attgataaaa ttagtttttt tgtgcccccct tattatattg atatgacggc actggctgaa    2940
gccagaaatg tagaccctgg aaaatttcat attggtattg ggcaagacca aatggcggtg    3000
aacccaatca gccaagatat tgtgacattt gcagccaatg ccgcagaagc gatcttgacc    3060
aaagaagata aagaggccat tgatatggtg attgtcggga ctgagtccag tatcgatgag    3120
tcaaaagcgg ccgcagttgt cttacatcgt ttaatgggga ttcaaccttt cgctcgctct    3180
ttcgaaatca aggaagcttg ttacggagca acagcaggct tacagttagc taagaatcac    3240
gtagccttac atccagataa aaaagtcttg gtcgtagcgg cagatattgc aaaatatggc    3300
ttaaattctg gcggtgagcc tacacaagga gctgggcgg ttgcaatgtt agttgctagt    3360
gaaccgcgca ttttggcttt aaaagaggat aatgtgatgc tgacgcaaga tatctatgac    3420
ttttggcgtc caacaggcca cccgtatcct atggtcgatg gtccttttgtc aaacgaaacc    3480 tacatccaat ctttttgccca agtctgggat gaacataaaa aacgaaccgg tcttgatttt    3540
gcagattatg atgctttagc gttccatatt ccttacacaa aaatgggcaa aaaagcctta    3600
ttagcaaaaa tctccgacca aactgaagca gaacaggaac gaattttagc ccgttatgaa    3660
gaaagtatcg tctatagtcg tcgcgtagga aacttgtata cgggttcact ttatctggga    3720
ctcatttccc ttttagaaaa tgcaacgact ttaaccgcag gcaatcaaat tggtttattc    3780
agttatggtt ctggtgctgt cgctgaattt ttcactggtg aattagtagc tggttatcaa    3840
aatcatttac aaaaagaaac tcatttagca ctgctggata tcggacaga actttctatc    3900 gctgaatatg aagccatgtt tgcagaaact ttagacacag acattgatca aacgttagaa    3960
gatgaattaa aatatagtat ttctgctatt aataataccg ttcgttctta tcgaaactaa    4020
gagatctgca gctggtacca tatgggaatt cgaagcttgg gcccgaacaa aaactcatct    4080
cagaagagga tctgaatagc gccgtcgacc atcatcatca tcatcattga gtttaaacgg    4140
tctccagctt ggctgttttg gcggatgaga agagattttc agcctgatac agattaaatc    4200
agaacgcaga gcggtctga taaaacagaa tttgcctggc ggcagtagcg cggtggtccc    4260
acctgacccc atgccgaact cagaagtgaa acgccgtagc gccgatggta gtgtggggtc    4320
tccccatgcg agagtaggga actgccaggc atcaaataaa acgaaaggct cagtcgaaag    4380
actgggcctt tcgttttatc tgttgtttgt cggtgaacgc tctcctgagt aggacaaatc    4440
cgccgggagc ggatttgaac gttgcgaagc aacggcccgg agggtggcgg gcaggacgcc    4500
cgccataaac tgccaggcat caaattaagc agaaggccat cctgacggat ggcctttttg    4560
cgtttctaca aactcttttt gtttattttt ctaaatacat tcaaatatgt atccgctcat    4620
gagacaataa ccctgataaa tgcttcaata atattgaaaa aggaagagta tgagtattca    4680
```

| | |
|---|---|
| acatttccgt gtcgcccttacttccttttttgcggcatttt gccttcctg tttttgctca | 4740 |
| cccagaaacg ctggtgaaag taaaagatgc tgaagatcag ttgggtgcac gagtgggtta | 4800 |
| catcgaactg gatctcaaca gcggtaagat ccttgagagt tttcgccccg aagaacgttt | 4860 |
| tccaatgatg agcacttta aagttctgct atgtggcgcg gtattatccc gtgttgacgc | 4920 |
| cgggcaagag caactcggtc gccgcataca ctattctcag aatgacttgg ttgagtactc | 4980 |
| accagtcaca gaaaagcatc ttacggatgg catgacagta agagaattat gcagtgctgc | 5040 |
| cataaccatg agtgataaca ctgcggccaa cttacttctg acaacgatcg gaggaccgaa | 5100 |
| ggagctaacc gcttttttgc acaacatggg ggatcatgta actcgccttg atcgttggga | 5160 |
| accggagctg aatgaagcca taccaaacga cgagcgtgac accacgatgc ctgtagcaat | 5220 |
| ggcaacaacg ttgcgcaaac tattaactgg cgaactactt actctagctt cccggcaaca | 5280 |
| attaatagac tggatggagg cggataaagt tgcaggacca cttctgcgct cggcccttcc | 5340 |
| ggctggctgg tttattgctg ataaatctgg agccggtgag cgtgggtctc gcggtatcat | 5400 |
| tgcagcactg gggccagatg gtaagccctc ccgtatcgta gttatctaca cgacggggag | 5460 |
| tcaggcaact atggatgaac gaaatagaca gatcgctgag ataggtgcct cactgattaa | 5520 |
| gcattggtaa ctgtcagacc aagtttactc atatatactt tagattgatt taaaacttca | 5580 |
| tttttaattt aaaaggatct aggtgaagat cctttttgat aatctcatga ccaaaatccc | 5640 |
| ttaacgtgag ttttcgttcc actgagcgtc agaccccgta gaaaagatca aggatcttc | 5700 |
| ttgagatcct ttttttctgc gcgtaatctg ctgcttgcaa acaaaaaaac caccgctacc | 5760 |
| agcggtggtt tgtttgccgg atcaagagct accaactctt tttccgaagg taactggctt | 5820 |
| cagcagagcg cagataccaa atactgtcct tctagtgtag ccgtagttag gccaccactt | 5880 |
| caagaactct gtagcaccgc ctacatacct cgctctgcta atcctgttac cagtggctgc | 5940 |
| tgccagtggc gataagtcgt gtcttaccgg gttggactca agacgatagt taccggataa | 6000 |
| ggcgcagcgg tcgggctgaa cggggggttc gtgcacacag cccagcttgg agcgaacgac | 6060 |
| ctacaccgaa ctgagatacc tacagcgtga gctatgagaa agcgccacgc ttcccgaagg | 6120 |
| gagaaaggcg gacaggtatc cggtaagcgg cagggtcgga acaggagagc gcacgaggga | 6180 |
| gcttccaggg ggaaacgcct ggtatcttta tagtcctgtc gggtttcgcc acctctgact | 6240 |
| tgagcgtcga ttttttgtgat gctcgtcagg ggggcggagc ctatggaaaa acgccagcaa | 6300 |
| cgcggccttt ttacggttcc tggccttttg ctggcctttt gctcacatgt tctttcctgc | 6360 |
| gttatcccct gattctgtgg ataaccgtat taccgccttt gagtgagctg ataccgctcg | 6420 |
| ccgcagccga cgaccgagc gcagcgagtc agtgagcgag gaagcggaag agcgcctgat | 6480 |
| gcggtatttt ctccttacgc atctgtgcgg tatttcacac cgcatatggt gcactctcag | 6540 |
| tacaatctgc tctgatgccg catagttaag ccagtataca ctccgctatc gctacgtgac | 6600 |
| tgggtcatgg ctgcgccccg acacccgcca cacccgctg acgcgccctg acgggcttgt | 6660 |
| ctgctcccgg catccgctta cagacaagct gtgaccgtct ccgggagctg catgtgtcag | 6720 |
| aggttttcac cgtcatcacc gaaacgcgcg aggcagcaga tcaattcgcg cgcgaaggcg | 6780 |
| aagcggcatg catttacgtt gacaccatcg aatggtgcaa aaccttcgc ggtatggcat | 6840 |
| gatagcgccc ggaagagagt caattcaggg tggtgaatgt gaaaccagta acgttatacg | 6900 |
| atgtcgcaga gtatgccggt gtctcttatc agaccgtttc ccgcgtggtg aaccaggcca | 6960 |
| gccacgtttc tgcgaaaacg cgggaaaaag tggaagcggc gatggcggag ctgaattaca | 7020 |

| | | |
|---|---|---|
| ttcccaaccg | cgtggcacaa caactggcgg gcaaacagtc gttgctgatt ggcgttgcca | 7080 |
| cctccagtct | ggccctgcac gcgccgtcgc aaattgtcgc ggcgattaaa tctcgcgccg | 7140 |
| atcaactggg | tgccagcgtg gtggtgtcga tggtagaacg aagcggcgtc gaagcctgta | 7200 |
| aagcggcggt | gcacaatctt ctcgcgcaac gcgtcagtgg gctgatcatt aactatccgc | 7260 |
| tggatgacca | ggatgccatt gctgtggaag ctgcctgcac taatgttccg gcgttatttc | 7320 |
| ttgatgtctc | tgaccagaca cccatcaaca gtattatttt ctcccatgaa gacggtacgc | 7380 |
| gactgggcgt | ggagcatctg gtcgcattgg gtcaccagca aatcgcgctg ttagcgggcc | 7440 |
| cattaagttc | tgtctcggcg cgtctgcgtc tggctggctg gcataaatat ctcactcgca | 7500 |
| atcaaattca | gccgatagcg gaacgggaag gcgactggag tgccatgtcc ggttttcaac | 7560 |
| aaaccatgca | aatgctgaat gagggcatcg ttcccactgc gatgctggtt gccaacgatc | 7620 |
| agatggcgct | gggcgcaatg cgcgccatta ccgagtccgg gctgcgcgtt ggtgcggata | 7680 |
| tctcggtagt | gggatacgac gataccgaag acagctcatg ttatatcccg ccgtcaacca | 7740 |
| ccatcaaaca | ggattttcgc ctgctggggc aaaccagcgt ggaccgcttg ctgcaactct | 7800 |
| ctcagggcca | ggcggtgaag ggcaatcagc tgttgcccgt ctcactggtg aaaagaaaaa | 7860 |
| ccaccctggc | gcccaatacg caaaccgcct ctccccgcgc gttggccgat tcattaatgc | 7920 |
| agctggcacg | acaggtttcc cgactggaaa gcgggcagtg agcgcaacgc aattaatgtg | 7980 |
| agttagcgcg | aattgatctg | 8000 |

<210> SEQ ID NO 24
<211> LENGTH: 10433
<212> TYPE: DNA
<213> ORGANISM: Artificial Sequence
<220> FEATURE:
<223> OTHER INFORMATION: Synthetic Construct

<400> SEQUENCE: 24

| | | |
|---|---|---|
| cccgtcttac | tgtcgggaat tcgcgttggc cgattcatta atgcagattc tgaaatgagc | 60 |
| tgttgacaat | taatcatccg gctcgtataa tgtgtggaat tgtgagcgga taacaatttc | 120 |
| acacaggaaa | cagcgccgct gagaaaaagc gaagcggcac tgctctttaa caatttatca | 180 |
| gacaatctgt | gtgggcactc gaccggaatt atcgattaac tttattatta aaaattaaag | 240 |
| aggtatatat | taatgtatcg attaaataag gaggaataaa ccatggatcc gagctcagga | 300 |
| ggtaaaaaaa | catgaaaaca gtagttatta ttgatgcatt acgaacacca attggaaaat | 360 |
| ataaaggcag | cttaagtcaa gtaagtgccg tagacttagg aacacatgtt acaacacaac | 420 |
| ttttaaaaag | acattccact atttctgaag aaattgatca agtaatcttt ggaaatgttt | 480 |
| tacaagctgg | aaatggccaa atcccgcac gacaaatagc aataaacagc ggtttgtctc | 540 |
| atgaaattcc | cgcaatgacg gttaatgagg tctgcggatc aggaatgaag gccgttattt | 600 |
| tggcgaaaca | attgattcaa ttaggagaag cggaagtttt aattgctggc gggattgaga | 660 |
| atatgtccca | agcacctaaa ttacaacgtt ttaattacga aacagaaagc tacgatgcgc | 720 |
| cttttttctag | tatgatgtat gatggattaa cggatgcctt tagtggtcag gcaatgggct | 780 |
| taactgctga | aaatgtggcc gaaaagtatc atgtaactag agaagagcaa gatcaatttt | 840 |
| ctgtacattc | acaattaaaa gcagctcaag cacaagcaga agggatattc gctgacgaaa | 900 |
| tagcccccatt | agaagtatca ggaacgcttg tggagaaaga tgaagggatt cgccctaatt | 960 |
| cgagcgttga | gaagctagga acgcttaaaa cagtttttaa agaagacggt actgtaacag | 1020 |
| cagggaatgc | atcaaccatt aatgatgggg cttctgcttt gattattgct tcacaagaat | 1080 |

```
atgccgaagc acacggtctt ccttatttag ctattattcg agacagtgtg gaagtcggta    1140
ttgatccagc ctatatggga atttcgccga ttaaagccat tcaaaaactg ttagcgcgca    1200
atcaacttac tacggaagaa attgatctgt atgaaatcaa cgaagcattt gcagcaactt    1260
caatcgtggt ccaaagagaa ctggctttac cagaggaaaa ggtcaacatt tatggtggcg    1320
gtatttcatt aggtcatgcg attggtgcca caggtgctcg tttattaacg agtttaagtt    1380
atcaattaaa tcaaaagaa aagaaatatg gagtggcttc tttatgtatc ggcggtggct    1440
taggactcgc tatgctacta gagagacctc agcaaaaaaa aaacagccga ttttatcaaa    1500
tgagtcctga ggaacgcctg gcttctcttc ttaatgaagg ccagatttct gctgatacaa    1560
aaaagaatt tgaaaatacg gctttatctt cgcagattgc caatcatatg attgaaaatc    1620
aaatcagtga acagaagtg ccgatgggcg ttggcttaca tttaacagtg gacgaaactg    1680
attatttggt accaatggcg acagaagagc cctcagttat tgcggctttg agtaatggtg    1740
caaaaatagc acaaggattt aaaacagtga atcaacaacg cttaatgcgt ggacaaatcg    1800
ttttttacga tgttgcagat cccgagtcat tgattgataa actacaagta agagaagcgg    1860
aagttttca acaagcagag ttaagttatc catctatcgt taaacggggc ggcggcttaa    1920
gagatttgca atatcgtact tttgatgaat catttgtatc tgtcgacttt ttagtagatg    1980
ttaaggatgc aatgggggca aatatcgtta acgctatgtt ggaaggtgtg gccgagttgt    2040
tccgtgaatg gtttgcggag caaaagattt tattcagtat tttaagtaat tatgccacgg    2100
agtcggttgt tacgatgaaa acggctattc cagtttcacg tttaagtaag gggagcaatg    2160
gccgggaaat tgctgaaaaa attgttttag cttcacgcta tgcttcatta gatccttatc    2220
gggcagtcac gcataacaaa ggaatcatga atggcattga agctgtagtt ttagctacag    2280
gaaatgatac acgcgctgtt agcgcttctt gtcatgcttt tgcggtgaag gaaggtcgct    2340
accaaggctt gactagttgg acgctggatg gcgaacaact aattggtgaa atttcagttc    2400
cgcttgcttt agccacggtt ggcggtgcca caaaagtctt acctaaatct caagcagctg    2460
ctgatttgtt agcagtgacg gatgcaaaag aactaagtcg agtagtagcg gctgttggtt    2520
tggcacaaaa tttagcggcg ttacgggcct tagtctctga aggaattcaa aaaggacaca    2580
tggctctaca agcacgttct ttagcgatga cggtcggagc tactggtaaa gaagttgagg    2640
cagtcgctca acaattaaaa cgtcaaaaaa cgatgaacca agaccgagcc atggctattt    2700
taaatgattt aagaaaacaa taaggaggt aaaaaaacat gacaattggg attgataaaa    2760
ttagttttt tgtgccccct tattatattg atatgacggc actggctgaa gccagaaatg    2820
tagaccctgg aaaatttcat attggtattg ggcaagacca aatggcggtg aacccaatca    2880
gccaagatat tgtgacattt gcagccaatg ccgcagaagc gatcttgacc aaagaagata    2940
agaggccat tgatatggtg attgtcggga ctgagtccag tatcgatgag tcaaaagcgg    3000
ccgcagttgt cttacatcgt ttaatgggga ttcaaccttt cgctcgctct ttcgaaatca    3060
aggaagcttg ttacggagca acagcaggct tacagttagc taagaatcac gtagccttac    3120
atccagataa aaaagtcttg gtcgtagcgg cagatattgc aaaatatggc ttaaattctg    3180
gcggtgagcc tacacaagga gctggggcgg ttgcaatgtt agttgctagt gaaccgcgca    3240
ttttggcttt aaaagaggat aatgtgatgc tgacgcaaga tatctatgac ttttggcgtc    3300
caacaggcca cccgtatcct atggtcgatg gtccttttgc aaacgaaacc tacatccaat    3360
cttttgccca agtctgggat gaacataaaa acgaaccgg tcttgatttt gcagattatg    3420
```

```
atgctttagc gttccatatt ccttacacaa aaatgggcaa aaaagcctta ttagcaaaaa    3480
tctccgacca aactgaagca gaacaggaac gaattttagc ccgttatgaa gaaagtatcg    3540
tctatagtcg tcgcgtagga aacttgtata cgggttcact ttatctggga ctcatttccc    3600
ttttagaaaa tgcaacgact ttaaccgcag gcaatcaaat tggtttattc agttatggtt    3660
ctggtgctgt cgctgaattt ttcactggtg aattagtagc tggttatcaa aatcatttac    3720
aaaaagaaac tcatttagca ctgctggata tcggacaga actttctatc gctgaatatg    3780
aagccatgtt tgcagaaact ttagacacag acattgatca aacgttagaa gatgaattaa    3840
aatatagtat ttctgctatt aataataccg ttcgttctta tcgaaactaa agatctgcat    3900
cctgcattcg cccttaggag gtaaaaaaac atgtgtgcga cctcttctca atttactcag    3960
attaccgagc ataattcccg tcgttccgca aactatcagc caaacctgtg gaatttcgaa    4020
ttcctgcaat ccctggagaa cgacctgaaa gtggaaaagc tggaggagaa agcgaccaaa    4080
ctggaggaag aagttcgctg catgatcaac cgtgtagaca cccagccgct gtccctgctg    4140
gagctgatcg acgatgtgca gcgcctgggt ctgacctaca aatttgaaaa agacatcatt    4200
aaagccctgg aaaacatcgt actgctggac gaaaacaaaa agaacaaatc tgacctgcac    4260
gcaaccgctc tgtcttttccg tctgctgcgt cagcacggtt tcgaggtttc tcaggatgtt    4320
tttgagcgtt tcaaggataa agaaggtggt ttcagcggtg aactgaaagg tgacgtccaa    4380
ggcctgctga gctgtatga gcgtcttac ctgggtttcg agggtgagaa cctgctggag    4440
gaggcgcgta ccttttccat cacccacctg aagaacaacc tgaaagaagg cattaatacc    4500
aaggttgcag aacaagtgag ccacgccctg gaactgccat atcaccagcg tctgcaccgt    4560
ctggaggcac gttggttcct ggataaatac gaaccgaaag aaccgcatca ccagctgctg    4620
ctggagctgg cgaagctgga ttttaacatg gtacagaccc tgcaccagaa agagctgcaa    4680
gatctgtccc gctggtggac cgagatgggc ctggctagca aactggattt tgtacgcgac    4740
cgcctgatga agtttattt ctgggcactg gtatggcgc cagacccgca gtttggtgaa    4800
tgtcgcaaag ctgttactaa aatgtttggt ctggtgacga tcatcgatga cgtgtatgac    4860
gtttatggca ctctggacga actgcaactg ttcaccgatg ctgtagagcg ctgggacgtt    4920
aacgctatta acaccctgcc ggactatatg aaactgtgtt tcctggcact gtacaacacc    4980
gttaacgaca cgtcctattc tattctgaaa gagaaaggtc ataacaacct gtcctatctg    5040
acgaaaagct ggcgtgaact gtgcaaagcc tttctgcaag aggcgaaatg gtccaacaac    5100
aaaattatcc cggctttctc caagtacctg gaaaacgcca cgtttcctc ctccggtgta    5160
gcgctgctgg cgccgtctta cttttccgta tgccagcagc aggaagacat ctccgaccac    5220
gcgctgcgtt ccctgaccga cttccatggt ctggtgcgtt ctagctgcgt tatcttccgc    5280
ctgtgcaacg atctggccac ctctgcggcg gagctggaac gtggcgagac taccaattct    5340
atcattagct acatgcacga aaacgatggt accagcgagg aacaggcccg cgaagaactg    5400
cgtaaactga tcgacgccga atggaaaaag atgaatcgtg aacgcgttag cgactccacc    5460
ctgctgccta agcgttcat ggaaatcgca gttaacatgg cacgtgtttc ccactgcacc    5520
taccagtatg cgatggtct gggtcgccca gactacgcga ctgaaaaccg catcaaactg    5580
ctgctgattg accctttccc gattaaccag ctgatgtatg tctaactgca gctggtacca    5640
tatgggaatt cgaagcttgg gcccgaacaa aaactcatct cagaagagga tctgaatagc    5700
gccgtcgacc atcatcatca tcatcattga gtttaaacgg tctccagctt ggctgttttg    5760
gcggatgaga gaagattttc agcctgatac agattaaatc agaacgcaga agcggtctga    5820
```

-continued

| | | | | | |
|---|---|---|---|---|---|
| taaaacagaa | tttgcctggc | ggcagtagcg | cggtggtccc | acctgacccc | atgccgaact | 5880 |
| cagaagtgaa | acgccgtagc | gccgatggta | gtgtggggtc | tccccatgcg | agagtaggga | 5940 |
| actgccaggc | atcaaataaa | acgaaaggct | cagtcgaaag | actgggcctt | tcgttttatc | 6000 |
| tgttgtttgt | cggtgaacgc | tctcctgagt | aggacaaatc | cgccgggagc | ggatttgaac | 6060 |
| gttgcgaagc | aacggcccgg | agggtggcgg | gcaggacgcc | cgccataaac | tgccaggcat | 6120 |
| caaattaagc | agaaggccat | cctgacggat | ggccttttg | cgtttctaca | aactcttttt | 6180 |
| gtttatttt | ctaaatacat | tcaaatatgt | atccgctcat | gagacaataa | ccctgataaa | 6240 |
| tgcttcaata | atctggcgta | atagcgaaga | ggcccgcacc | gatcgccctt | cccaacagtt | 6300 |
| gcgcagcctg | aatggcgaat | ggcgcctgat | gcggtatttt | ctccttacgc | atctgtgcgg | 6360 |
| tatttcacac | cgcatatggt | gcactctcag | tacaatctgc | tctgatgccg | catagttaag | 6420 |
| ccagccccga | cacccgccaa | cacccgctga | cgagcttagt | aaagccctcg | ctagatttta | 6480 |
| atgcggatgt | tgcgattact | tcgccaacta | ttgcgataac | aagaaaaagc | cagccttca | 6540 |
| tgatatatct | cccaatttgt | gtagggctta | ttatgcacgc | ttaaaaataa | taaaagcaga | 6600 |
| cttgacctga | tagtttggct | gtgagcaatt | atgtgcttag | tgcatctaac | gcttgagtta | 6660 |
| agccgcgccg | cgaagcggcg | tcggcttgaa | cgaattgtta | gacattattt | gccgactacc | 6720 |
| ttggtgatct | cgcctttcac | gtagtggaca | aattcttcca | actgatctgc | gcgcgaggcc | 6780 |
| aagcgatctt | cttcttgtcc | aagataagcc | tgtctagctt | caagtatgac | gggctgatac | 6840 |
| tgggccggca | ggcgctccat | tgcccagtcg | gcagcgacat | ccttcggcgc | gattttgccg | 6900 |
| gttactgcgc | tgtaccaaat | gcgggacaac | gtaagcacta | catttcgctc | atcgccagcc | 6960 |
| cagtcgggcg | gcgagttcca | tagcgttaag | gtttcattta | gcgcctcaaa | tagatcctgt | 7020 |
| tcaggaaccg | gatcaaagag | ttcctccgcc | gctggaccta | ccaaggcaac | gctatgttct | 7080 |
| cttgcttttg | tcagcaagat | agccagatca | atgtcgatcg | tggctggctc | gaagatacct | 7140 |
| gcaagaatgt | cattgcgctg | ccattctcca | aattgcagtt | cgcgcttagc | tggataacgc | 7200 |
| cacggaatga | tgtcgtcgtg | cacaacaatg | gtgacttcta | cagcgcggag | aatctcgctc | 7260 |
| tctccagggg | aagccgaagt | ttccaaaagg | tcgttgatca | aagctcgccg | cgttgtttca | 7320 |
| tcaagcctta | cggtcaccgt | aaccagcaaa | tcaatatcac | tgtgtggctt | caggccgcca | 7380 |
| tccactgcgg | agccgtacaa | atgtacggcc | agcaacgtcg | gttcgagatg | gcgctcgatg | 7440 |
| acgccaacta | cctctgatag | ttgagtcgat | acttcggcga | tcaccgcttc | cctcatgatg | 7500 |
| tttaactttg | ttttagggcg | actgccctgc | tgcgtaacat | cgttgctgct | ccataacatc | 7560 |
| aaacatcgac | ccacggcgta | acgcgcttgc | tgcttggatg | cccgaggcat | agactgtacc | 7620 |
| ccaaaaaaac | agtcataaca | agccatgaaa | accgccactg | cgccgttacc | accgctgcgt | 7680 |
| tcggtcaagg | ttctggacca | gttgcgtgag | cgcatacgct | acttgcatta | cagcttacga | 7740 |
| accgaacagg | cttatgtcca | ctgggttcgt | gccttcatcc | gtttccacgg | tgtgcgtcac | 7800 |
| ccggcaacct | gggcagcag | cgaagtcgag | gcatttctgt | cctggctggc | gaacgagcgc | 7860 |
| aaggtttcgg | tctccacgca | tcgtcaggca | ttggcggcct | tgctgttctt | ctacggcaag | 7920 |
| gtgctgtgca | cggatctgcc | ctggcttcag | gagatcggaa | gacctcggcc | gtcgcggcgc | 7980 |
| ttgccggtgg | tgctgacccc | ggatgaagtg | gttcgcatcc | tcggttttct | ggaaggcgag | 8040 |
| catcgtttgt | tcgcccagct | tctgtatgga | acgggcatgc | ggatcagtga | gggtttgcaa | 8100 |
| ctgcgggtca | aggatctgga | tttcgatcac | ggcacgatca | tcgtgcggga | gggcaagggc | 8160 |

```
tccaaggatc gggccttgat gttacccgag agcttggcac ccagcctgcg cgagcagggg    8220
aattaattcc cacgggtttt gctgcccgca aacgggctgt tctggtgttg ctagtttgtt    8280
atcagaatcg cagatccggc ttcagccggt ttgccggctg aaagcgctat tcttccaga    8340 attgccatga ttttttcccc acgggaggcg tcactggctc ccgtgttgtc ggcagctttg    8400
attcgataag cagcatcgcc tgtttcaggc tgtctatgtg tgactgttga gctgtaacaa    8460
gttgtctcag gtgttcaatt tcatgttcta gttgctttgt tttactggtt tcacctgttc    8520
tattaggtgt tacatgctgt tcatctgtta cattgtcgat ctgttcatgg tgaacagctt    8580
tgaatgcacc aaaaactcgt aaagctctg atgtatctat cttttttaca ccgttttcat    8640
ctgtgcatat ggacagtttt cccttttgata tgtaacggtg aacagttgtt ctactttttgt    8700 ttgttagtct tgatgcttca ctgatagata caagagccat aagaacctca gatccttccg    8760
tatttagcca gtatgttctc tagtgtggtt cgttgttttt gcgtgagcca tgagaacgaa    8820
ccattgagat catacttact ttgcatgtca ctcaaaaatt ttgcctcaaa actggtgagc    8880
tgaatttttg cagttaaagc atcgtgtagt gttttttctta gtccgttatg taggtaggaa    8940
tctgatgtaa tggttgttgg tatttttgtca ccattcattt ttatctggtt gttctcaagt    9000
tcggttacga gatccatttg tctatctagt tcaacttgga aaatcaacgt atcagtcggg    9060
cggcctcgct tatcaaccac caatttcata ttgctgtaag tgtttaaatc tttacttatt    9120
ggtttcaaaa cccattggtt aagccttttt aactcatggt agttattttc aagcattaac    9180
atgaacttaa attcatcaag gctaatctct atatttgcct tgtgagtttt cttttgtgtt    9240
agttctttta ataaccactc ataaatcctc atagagtatt tgttttcaaa agacttaaca    9300
tgttccagat tatatttttat gaattttttt aactggaaaa gataaggcaa tatctcttca    9360
ctaaaaacta attctaattt ttcgcttgag aacttggcat agtttgtcca ctggaaaatc    9420
tcaaagcctt taaccaaagg attcctgatt tccacagttc tcgtcatcag ctctctggtt    9480
gctttagcta atacaccata agcattttcc ctactgatgt tcatcatctg agcgtattgg    9540
ttataagtga acgataccgt ccgttctttc cttgtagggt tttcaatcgt ggggttgagt    9600
agtgccacac agcataaaat tagcttggtt tcatgctccg ttaagtcata gcgactaatc    9660
gctagttcat ttgctttgaa aacaactaat tcagacatac atctcaattg gtctaggtga    9720
ttttaatcac tataccaatt gagatgggct agtcaatgat aattactagt cctttttcctt    9780 tgagttgtgg gtatctgtaa attctgctag acctttgctg gaaaacttgt aaattctgct    9840
agaccctctg taaattccgc tagacctttg tgtgtttttt ttgtttatat tcaagtggtt    9900
ataatttata gaataaagaa agaataaaaa aagataaaaa gaatagatcc cagccctgtg    9960
tataactcac tactttagtc agttccgcag tattacaaaa ggatgtcgca aacgctgttt    10020
gctcctctac aaaacagacc ttaaaaccct aaaggcttaa gtagcaccct cgcaagctcg    10080
ggcaaatcgc tgaatattcc ttttgtctcc gaccatcagg cacctgagtc gctgtctttt    10140
tcgtgacatt cagttcgctg cgctcacggc tctggcagta aatgggggta aatggcacta    10200
caggcgcctt ttatggattc atgcaaggaa actacccata atacaagaaa agcccgtcac    10260
gggcttctca gggcgtttta tggcgggtct gctatgtggt gctatctgac tttttgctgt    10320
tcagcagttc ctgccctctg attttccagt ctgaccactt cggattatcc cgtgacaggt    10380
cattcagact ggctaatgca cccagtaagg cagcggtatc atcaacaggc tta    10433
```

```
<210> SEQ ID NO 25
<211> LENGTH: 10356
```

```
<212> TYPE: DNA
<213> ORGANISM: Artificial Sequence
<220> FEATURE:
<223> OTHER INFORMATION: Synthetic Construct

<400> SEQUENCE: 25
caagaaaaat gccccgctta cgcagggcat ccatttatta ctcaaccgta accgattttg      60
ccaggttacg cggctggtca acgtcggtgc ctttgatcag cgcgacatgg taagccagca     120
gctgcagcgg aacggtgtag aagatcggtg caatcacctc ttccacatgc ggcatctcga     180
tgatgtgcat gttatcgcta cttacaaaac ccgcatcctg atcggcgaag acatacaact     240
gaccgccacg cgcgcgaact tcttcaatgt tggatttcag tttttccagc aattcgttgt     300
tcggtgcaac aacaataacc ggcatatcgg catcaattag cgccagcgga ccgtgtttca     360
gttcgccagc agcgtaggct tcagcgtgaa tgtaagagat ctctttcaac ttcaatgcgc     420
cttccagcgc gattgggtac tgatcgccac ggcccaggaa cagcgcgtga tgtttgtcag     480
agaaatcttc tgccagcgct tcaatgcgtt tgtcctgaga cagcatctgc tcaatacggc     540
tcggcagcgc ctgcagacca tgcacgatgt catgttcaat ggaggcatcc agacctttca     600
ggcgagacag cttcgccacc agcatcaaca gcacagttaa ctgagtggtg aatgctttag     660
tggatgccac gccgatttct gtacccgcgt tggtcattag cgccagatcg gattcgcgca     720
ccagagaaga acccggaacg ttacagattg ccagtgaacc aaggtaaccc agctctttcg     780
acagacgcag gccagccagg gtatccgcgg tttcgccaga ctgtgacacg atcgcccttc     840
ccaacagttg cgcagcctat acgtacggca gtttaaggtt tacacctata aagagagag     900
ccgttatcgt ctgtttgtgg atgtacagag tgatattatt gacacgccgg ggcgacggat     960
ggtgatcccc ctggccagtg cacgtctgct gtcagataaa gtctcccgtg aactttaccc    1020
ggtggtgcat atcggggatg aaagctggcg catgatgacc accgatatgg ccagtgtgcc    1080
ggtctccgtt atcggggaag aagtggctga tctcagccac cgcgaaaatg acatcaaaaa    1140
cgccattaac ctgatgttct ggggaatata aatgtcaggc atgagattat caaaaaggat    1200
cttcacctag atccttttca cgtagaaagc cagtccgcag aaacggtgct gaccccggat    1260
gaatgtcagc tactgggcta tctggacaag ggaaaacgca agcgcaaaga gaaagcaggt    1320
agcttgcagt gggcttacat ggcgatagct agactgggcg gttttatgga cagcaagcga    1380
accggaattg ccagctgggg cgccctctgg taaggttggg aagccctgca agtaaactg     1440
gatggctttc tcgccgccaa ggatctgatg gcgcagggga tcaagctctg atcaagagac    1500
aggatgagga tcgtttcgca tgattgaaca agatggattg cacgcaggtt ctccggccgc    1560
ttgggtggag aggctattcg gctatgactg ggcacaacag acaatcggct gctctgatgc    1620
cgccgtgttc cggctgtcag cgcaggggcg cccggttctt tttgtcaaga ccgacctgtc    1680
cggtgccctg aatgaactgc aagacgaggc agcgcggcta tcgtggctgg ccacgacggg    1740
cgttccttgc gcagctgtgc tcgacgttgt cactgaagcg ggaagggact ggctgctatt    1800
gggcgaagtg ccggggcagg atctcctgtc atctcacctt gctcctgccg agaaagtatc    1860
catcatggct gatgcaatgc ggcggctgca tacgcttgat ccggctacct gcccattcga    1920
ccaccaagcg aaacatcgca tcgagcgagc acgtactcgg atggaagccg gtcttgtcga    1980
tcaggatgat ctggacgaag agcatcaggg gctcgcgcca gccgaactgt tcgccaggct    2040
caaggcgagc atgcccgacg cgaggatct cgtcgtgacc catggcgatg cctgcttgcc    2100
gaatatcatg gtggaaaatg gccgcttttc tggattcatc gactgtggcc ggctgggtgt    2160
```

```
ggcggaccgc tatcaggaca tagcgttggc tacccgtgat attgctgaag agcttggcgg    2220
cgaatgggct gaccgcttcc tcgtgcttta cggtatcgcc gctcccgatt cgcagcgcat    2280
cgccttctat cgccttcttg acgagttctt ctgaattatt aacgcttaca atttcctgat    2340
gcggtatttt ctccttacgc atctgtgcgg tatttcacac cgcatacagg tggcactttt    2400
cggggaaatg tgcgcggaac ccctatttgt ttatttttct aaatacattc aaatatgtat    2460
ccgctcatga acaataacc ctgataaatg cttcaataat agcacgtgag gagggccacc     2520
atggccaagt tgaccagtgc cgttccggtg ctcaccgcgc gcgacgtcgc cggagcggtc    2580
gagttctgga ccgaccggct cgggttctcc cctagtaacg gccgccagtg tgctggaatt    2640
caggcagttc aacctgttga tagtacgtac taagctctca tgtttcacgt actaagctct    2700
catgtttaac gtactaagct ctcatgttta cgaactaaaa ccctcatggc taacgtacta    2760
agctctcatg gctaacgtac taagctctca tgtttcacgt actaagctct catgtttgaa    2820
caataaaatt aatataaatc agcaacttaa atagcctcta aggttttaag ttttataaga    2880
aaaaaagaa tatataaggc ttttaaagct tttaaggttt aacggttgtg gacaacaagc     2940
cagggatgta acgcactgag aagcccttag agcctctcaa agcaattttc agtgacacag    3000
gaacacttaa cggctgacag cctgaattct gcagatatct gttttccac tcttcgttca     3060
ctttcgccag gtagctggtg aagacgaagg aagtcccgga gccatctgcg cggcgtacta    3120
cagcaatgtt ttgtgaaggc agtttcagac ccggattcag tttggcgatg gcttcatcat    3180
cccacttctt gattttgccc aggtagatgt cgccgagggt tttaccatcc agcaccagtt    3240
cgccagactt cagccctgga atgttaaccg ccagcaccac gccgccaatc acggtcggga    3300
actggaacag accttcctga gccagttttt cgtcagacag cggcgcgtca gaggcaccaa    3360
aatcaacggt attagcgata atctgttta cgccaccgga agaaccgata ccctggtagt     3420
taactttatt accggtttct ttctggtaag tgtcagccca tttggcatac accggcgcag    3480
ggaaggttgc acctgcacct gtcaggcttg cttctgcaaa cacagagaaa gcactcatcg    3540
ataaggtcgc ggcgacaaca gttgcgacgg tggtacgcat aactttcata atgtctcctg    3600
ggaggattca taaagcattg tttgttggct acgagaagca aaataggaca aacaggtgac    3660
agttatatgt aaggaatatg acagttttat gacagagaga taaagtcttc agtctgattt    3720
aaataagcgt tgatattcag tcaattacaa acattaataa cgaagagatg acagaaaaat    3780
tttcattctg tgacagagaa aaagtagccg aagatgacgg tttgtcacat ggagttggca    3840
ggatgtttga ttaaaagcaa ttaaccctca ctaaagggcg gccgcgaagt tcctattctc    3900
tagaaagtat aggaacttca ttctaccggg taggggaggc gcttttccca aggcagtctg    3960
gagcatgcgc tttagcagcc ccgctgggca cttggcgcta cacaagtggc ctctggcctc    4020
gcacacattc cacatccacc ggtaggcgcc aaccggctcc gttctttggt ggccccttcg    4080
cgccaccttc cactcctccc ctagtcagga agttcccccc cgccccgcag ctcgcgtcgt    4140
gcaggacgtg acaaatggaa gtagcacgtc tcactagtct cgtgcagatg gacagcaccg    4200
ctgagcaatg gaagcgggta ggcctttggg gcagcggcca atagcagctt tgctccttcg    4260
ctttctgggc tcagaggctg gaagggggtg gtccggggg cggctcagg gcgggctca      4320
ggggcgggc gggcgcccga aggtcctccg gaggcccggc attctgcacg cttcaaaagc    4380
gcacgtctgc cgcgctgttc tcctcttcct catctccggg cctttcgacc tgcagcagca    4440
cgtgttgaca attaatcatc ggcatagtat atcggcatag tataatacga caaggtgagg    4500
aactaaaacca tggagaaaaa aatcactgga tataccaccg ttgatatatc ccaatggcat    4560
```

```
cgtaaagaac atttttgaggc atttcagtca gttgctcaat gtacctataa ccagaccgtt   4620
cagctggata ttacggcctt tttaaagacc gtaaagaaaa ataagcacaa gttttatccg   4680
gcctttattc acattcttgc ccgcctgatg aatgctcatc cggaattccg tatggcaatg   4740
aaagacggtg agctggtgat atgggatagt gttcacccctt gttacaccgt tttccatgag   4800
caaactgaaa cgttttcatc gctctggagt gaataccacg acgatttccg gcagtttcta   4860
cacatatatt cgcaagatgt ggcgtgttac ggtgaaaacc tggcctattt ccctaaaggg   4920
tttattgaga atatgttttt cgtctcagcc aatccctggg tgagtttcac cagttttgat   4980
ttaaacgtgg ccaatatgga caacttcttc gcccccgttt tcaccatggg caaatattat   5040
acgcaaggcg acaaggtgct gatgccgctg gcgattcagg ttcatcatgc cgtttgtgat   5100
ggcttccatg tcggcagaat gcttaatgaa ttacaacagt actgcgatga gtggcagggc   5160
ggggcgtaag cgggactctg gggttcgaat aaagaccgac caagcgacgt ctgagagctc   5220
cctggcgaat tcgtaccaa taaaagagct ttattttcat gatctgtgtg ttggttttttg   5280
tgtgcggcgc ggaagttcct attctctaga aagtatagga acttcctcga gccctatagt   5340
gagtcgtatt agcccttgac gatgccacat cctgagcaaa taattcaacc actaattgtg   5400
agcggataac acaaggagga aacagctatg tcattaccgt tcttaacttc tgcaccggga   5460
aaggttatta ttttggtga acactctgct gtgtacaaca agcctgccgt cgctgctagt   5520
gtgtctgcgt tgagaaccta cctgctaata agcgagtcat ctgcaccaga tactattgaa   5580
ttggacttcc cggacattag ctttaatcat aagtggtcca tcaatgattt caatgccatc   5640
accgaggatc aagtaaactc ccaaaaattg gccaaggctc aacaagccac cgatggcttg   5700
tctcaggaac tcgttagtct tttggatccg ttgttagctc aactatccga atccttccac   5760
taccatgcag cgttttgttt cctgtatatg tttgtttgcc tatgcccca tgccaagaat    5820
attaagtttt ctttaaagtc tactttaccc atcggtgctg ggttgggctc aagcgcctct   5880
atttctgtat cactggcctt agctatggcc tacttggggg ggttaatagg atctaatgac   5940
ttggaaaagc tgtcagaaaa cgataagcat atagtgaatc aatgggcctt cataggtgaa   6000
aagtgtattc acggtacccc ttcaggaata gataacgctg tggccactta tggtaatgcc   6060
ctgctatttg aaaaagactc acataatgga acaataaaca caaacaattt taagttctta   6120
gatgatttcc cagccattcc aatgatccta acctatacta gaattccaag gtctacaaaa   6180
gatcttgttg ctcgcgttcg tgtgttggtc accgagaaat ttcctgaagt tatgaagcca   6240
attctagatg ccatgggtga atgtgcccta caaggcttag agatcatgac taagttaagt   6300
aaatgtaaag gcaccgatga cgaggctgta gaaactaata atgaactgta tgaacaacta   6360
ttggaattga taagaataaa tcatggactg cttgtctcaa tcggtgtttc tcatcctgga   6420
ttagaactta ttaaaaatct gagcgatgat ttgagaattg gctccacaaa acttaccggt   6480
gctggtggcg gcggttgctc tttgactttg ttacgaagag acattactca agagcaaatt   6540
gacagcttca aaaagaaatt gcaagatgat tttagttacg agacatttga aacagacttg   6600
ggtgggactg gctgctgttt gttaagcgca aaaaatttga ataaagatct taaaatcaaa   6660
tccctagtat tccaattatt tgaaaataaa actaccacaa agcaacaaat tgacgatcta   6720
ttattgccag gaaacacgaa tttaccatgg acttcataag ctaatttgcg ataggcctgc   6780
accccttaagg aggaaaaaaa catgtcagag ttgagagcct tcagtgcccc agggaaagcg   6840
ttactagctg gtggatattt agttttagat acaaaatatg aagcatttgt agtcggatta   6900
```

```
tcggcaagaa tgcatgctgt agcccatcct tacggttcat tgcaagggtc tgataagttt    6960
gaagtgcgtg tgaaaagtaa acaatttaaa gatggggagt ggctgtacca tataagtcct    7020
aaaagtggct tcattcctgt ttcgataggc ggatctaaga acccctttcat tgaaaaagtt   7080 atcgctaacg tatttagcta cttttaaacct aacatggacg actactgcaa tagaaacttg   7140
ttcgttattg atattttctc tgatgatgcc taccattctc aggaggatag cgttaccgaa    7200
catcgtggca acagaagatt gagttttcat tcgcacagaa ttgaagaagt tcccaaaaca    7260
gggctgggct cctcggcagg tttagtcaca gttttaacta cagctttggc ctccttttt    7320 gtatcggacc tggaaaataa tgtagacaaa tatagagaag ttattcataa tttagcacaa    7380
gttgctcatt gtcaagctca gggtaaaatt ggaagcgggt ttgatgtagc ggcggcagca    7440
tatggatcta tcagatatag aagattccca cccgcattaa tctctaattt gccagatatt    7500
ggaagtgcta cttacggcag taaactggcg catttggttg atgaagaaga ctggaatatt    7560
acgattaaaa gtaaccattt accttcggga ttaactttat ggatgggcga tattaagaat    7620
ggttcagaaa cagtaaaaact ggtccagaag gtaaaaaatt ggtatgattc gcatatgcca    7680
gaaagcttga aaatatatac agaactcgat catgcaaatt ctagatttat ggatggacta    7740
tctaaactag atcgcttaca cgagactcat gacgattaca gcgatcagat atttgagtct    7800
cttgagagga atgactgtac ctgtcaaaag tatcctgaaa tcacagaagt tagagatgca    7860
gttgccacaa ttagacgttc ctttagaaaa ataactaaag aatctggtgc cgatatcgaa    7920
cctcccgtac aaactagctt attggatgat gccagacct taaaaggagt tcttacttgc    7980
ttaatacctg gtgctggtgg ttatgacgcc attgcagtga ttactaagca agatgttgat    8040
cttagggctc aaaccgctaa tgacaaaaga ttttctaagg ttcaatggct ggatgtaact    8100
caggctgact ggggtgttag gaaagaaaaa gatccggaaa cttatcttga taataactt    8160 aaggtagctg catgcagaat tcgcccttaa ggaggaaaaa aaatgaccg tttacacagc    8220 atccgttacc gcacccgtca acatcgcaac ccttaagtat tggggaaaaa gggacacgaa    8280
gttgaatctg cccaccaatt cgtccatatc agtgacttta tcgcaagatg acctcagaac    8340
gttgacctct gcggctactg cacctgagtt tgaacgcgac actttgtggt taaatggaga    8400
accacacagc atcgacaatg aaagaactca aaattgtctg cgcgacctac gccaattaag    8460
aaaggaaatg gaatcgaagg acgcctcatt gcccacatta tctcaatgga actccacat    8520 tgtctccgaa ataactttc ctacagcagc tggtttagct tcctccgctg ctggctttgc    8580
tgcattggtc tctgcaattg ctaagttata ccaattacca cagtcaactt cagaaatatc    8640
tagaatagca agaaaggggt ctggttcagc ttgtagatcg ttgtttggcg atacgtggc    8700 ctggaaaatg gaaaagctg aagatggtca tgattccatg gcagtacaaa tcgcagacag    8760
ctctgactgg cctcagatga aagcttgtgt cctagttgtc agcgatatta aaaggatgt    8820 gagttccact cagggtatgc aattgaccgt ggcaacctcc gaactattta agaaagaat    8880 tgaacatgtc gtaccaaaga gatttgaagt catgcgtaaa gccattgttg aaaaagattt    8940
cgccaccttt gcaaaggaaa caatgatgga ttccaactct ttccatgcca catgtttgga    9000
ctctttccct ccaatattct acatgaatga cacttccaag cgtatcatca gttggtgcca    9060
caccattaat cagttttacg gagaaacaat cgttgcatac acgtttgatg caggtccaaa    9120
tgctgtgttg tactacttag ctgaaaaatga gtcgaaactc tttgcattta tctataaatt    9180
gtttggctct gttcctggat gggacaagaa atttactact gagcagcttg aggctttcaa    9240
ccatcaattt gaatcatcta actttactgc acgtgaattg gatcttgagt tgcaaaagga    9300
```

```
tgttgccaga gtgattttaa ctcaagtcgg ttcaggccca caagaaacaa acgaatcttt    9360
gattgacgca aagactggtc taccaaagga ataagatcaa ttcgctgcat cgcccttagg    9420
aggtaaaaaa aaatgactgc cgacaacaat agtatgcccc atggtgcagt atctagttac    9480
gccaaattag tgcaaaacca aacacctgaa gacattttgg aagagtttcc tgaaattatt    9540
ccattacaac aaagacctaa tacccgatct agtgagacgt caaatgacga agcggagaa    9600 acatgttttt ctggtcatga tgaggagcaa attaagttaa tgaatgaaaa ttgtattgtt    9660
ttggattggg acgataatgc tattggtgcc ggtaccaaga agtttgtca tttaatggaa    9720 aatattgaaa agggtttact acatcgtgca ttctccgtct ttattttcaa tgaacaaggt    9780
gaattacttt tacaacaaag agccactgaa aaataactt tccctgatct ttggactaac    9840
acatgctgct ctcatccact atgtattgat gacgaattag gtttgaaggg taagctagac    9900
gataagatta agggcgctat tactgcggcg gtgagaaaac tagatcatga attaggtatt    9960
ccagaagatg aaactaagac aagggggtaag tttcactttt taaacagaat ccattacatg   10020
gcaccaagca atgaaccatg gggtgaacat gaaattgatt acatcctatt ttataagatc   10080
aacgctaaag aaaacttgac tgtcaaccca aacgtcaatg aagttagaga cttcaaatgg   10140
gtttcaccaa atgatttgaa aactatgttt gctgacccaa gttacaagtt tacgccttgg   10200
tttaagatta tttgcgagaa ttacttattc aactggtggg agcaattaga tgacctttct   10260
gaagtggaaa atgacaggca aattcataga atgctataac aacgcgtcta caaataaaaa   10320
aggcacgtca gatgacgtgc cttttttctt ggggcc                              10356

<210> SEQ ID NO 26
<211> LENGTH: 6974
<212> TYPE: DNA
<213> ORGANISM: Artificial Sequence
<220> FEATURE:
<223> OTHER INFORMATION: Synthetic Construct

<400> SEQUENCE: 26
gtgcggccgc aagcttgtcg acggagctcg aattcggatc cctgcagtta gacatacatc     60
agctggttaa tcgggaaagg gtcaatcagc agcagtttga tgcggttttc agtcgcgtag    120
tctgggcgac ccagaccatc gccatactgg taggtgcagt gggaaacacg tgccatgtta    180
actgcgattt ccatgaacgc tttaggcagc agggtggagt cgctaacgcg ttcacgattc    240 atcttttttcc attcggcgtc gatcagttta cgcagttctt cgcgggcctg ttcctcgctg    300
gtaccatcgt tttcgtgcat gtagctaatg atagaattgg tagtctcgcc acgttccagc    360
tccgccgcag aggtggccag atcgttgcac aggcggaaga taacgcagct agaacgcacc    420
agaccatgga agtcggtcag ggaacgcagc gcgtggtcgg agatgtcttc ctgctgctgg    480
catacggaaa agtaagacgg cgccagcagc gctacaccgg aggaggaaac gctggcgttt    540
tccaggtact tggagaaagc cgggataatt ttgttgttgg accatttcgc tcttgcagaa    600
aaggctttgc acagttcacg ccagcttttc gtcagatagg acaggttgtt atgacctttc    660
tctttcagaa tagaataggg cgtgtcgtta acggtgttgt acagtgccag gaaacacagt    720
ttcatatagt ccggcagggt gttaatagcg ttaacgtccc agcgctctac agcatcggtg    780
aacagttgca gttcgtccag agtgccataa acgtcataca cgtcatcgat gatcgtcacc    840
agaccaaaca tttagtaac agctttgcga cattcaccaa actgcgggtc tggcgccata    900
cccagtgccc agaaataaac ttccatcagg cggtcgcgta caaaatccag tttgctagcc    960
```

```
aggcccatct cggtccacca gcgggacaga tcttgcagct ctttctggtg cagggtctgt   1020
accatgttaa aatccagctt cgccagctcc agcagcagct ggtgatgcgg ttctttcggt   1080
tcgtatttat ccaggaacca acgtgcctcc agacggtgca gacgctggtg atatggcagt   1140
tccagggcgt ggctcacttg ttctgcaacc ttggtattaa tgccttcttt caggttgttc   1200
ttcaggtggg tgatggaaaa ggtacgcgcc tcctccagca ggttctcacc ctcgaaaccc   1260
aggtaagacg cttcatacag gctcagcagg ccttggacgt cacctttcag ttcaccgctg   1320
aaaccacctt ctttatcctt gaaacgctca aaacatcct gagaaacctc gaaaccgtgc    1380
tgacgcagca gacggaaaga cagagcggtt gcgtgcaggt cagatttgtt cttttttgttt  1440
tcgtccagca gtacgatgtt ttccagggct ttaatgatgt ctttttcaaa tttgtaggtc   1500
agacccaggc gctgcacatc gtcgatcagc tccagcaggg acagcggctg ggtgtctaca   1560
cggttgatca tgcagcgaac ttcttcctcc agtttggtcg ctttctcctc cagcttttcc   1620
actttcaggt cgttctccag ggattgcagg aattcgaaat tccacaggtt tggctgatag   1680
tttgcggaac gacgggaatt atgctcgta atctgagtaa attgagaaga ggtcgcacac    1740
atggtatatc tccttcttaa agttaaacaa aattatttct agaggggaat tgttatccgc   1800
tcacaattcc cctatagtga gtcgtattaa tttcgcggga tcgagatctc gatcctctac   1860
gccggacgca tcgtggccgg catcaccggc gccacaggtg cggttgctgg cgcctatatc   1920
gccgacatca ccgatgggga agatcgggct cgccacttcg ggctcatgag cgcttgtttc   1980
ggcgtgggta tggtggcagg ccccgtggcc gggggactgt tgggcgccat ctccttgcat   2040
gcaccattcc ttgcggcggc ggtgctcaac ggcctcaacc tactactggg ctgcttccta   2100
atgcaggagt cgcataaggg agagcgtcga gatcccggac accatcgaat ggcgcaaaac   2160
ctttcgcggt atggcatgat agcgcccgga agagagtcaa ttcagggtgg tgaatgtgaa   2220
accagtaacg ttatacgatg tcgcagagta tgccggtgtc tcttatcaga ccgtttcccg   2280
cgtggtgaac caggccagcc acgtttctgc gaaaacgcgg gaaaagtgg aagcggcgat    2340
ggcggagctg aattacattc ccaaccgcgt ggcacaacaa ctggcgggca aacagtcgtt   2400
gctgattggc gttgccacct ccagtctggc cctgcacgcg ccgtcgcaaa ttgtcgcggc   2460
gattaaatct cgcgccgatc aactgggtgc cagcgtggtg gtgtcgatgg tagaacgaag   2520
cggcgtcgaa gcctgtaaag cggcggtgca caatcttctc gcgcaacgcg tcagtgggct   2580
gatcattaac tatccgctgg atgaccagga tgccattgct gtggaagctg cctgcactaa   2640
tgttccggcg ttatttcttg atgtctctga ccagacaccc atcaacagta ttattttctc   2700
ccatgaagac ggtacgcgac tgggcgtgga gcatctggtc gcattgggtc accagcaaat   2760
cgcgctgtta gcgggcccat taagttctgt ctcggcgcgt ctgcgtctgg ctggctggca   2820
taaatatctc actcgcaatc aaattcagcc gatagcggaa cgggaaggcg actggagtgc   2880
catgtccggt tttcaacaaa ccatgcaaat gctgaatgag gcatcgttcc cactgcgat    2940
gctggttgcc aacgatcaga tggcgctggg cgcaatgcgc gccattaccg agtccgggct   3000
gcgcgttggt gcggatatct cggtagtggg atacgacgat accgaagaca gctcatgtta   3060
tatcccgccg ttaaccacca tcaaacagga ttttcgcctg ctggggcaaa ccagcgtgga   3120
ccgcttgctg caactctctc agggccaggc ggtgaagggc aatcagctgt tgcccgtctc   3180
actggtgaaa agaaaaacca ccctggcgcc caatacgcaa accgcctctc ccgcgcgtt    3240
ggccgattca ttaatgcagc tggcacgaca ggtttcccga ctggaaagcg gcagtgagc    3300
gcaacgcaat taatgtaagt tagctcactc attaggcacc gggatctcga ccgatgccct   3360
```

```
tgagagcctt caacccagtc agctccttcc ggtgggcgcg gggcatgact atcgtcgccg   3420
cacttatgac tgtcttcttt atcatgcaac tcgtaggaca ggtgccggca gcgctctggg   3480
tcattttcgg cgaggaccgc tttcgctgga gcgcgacgat gatcggcctg tcgcttgcgg   3540
tattcggaat cttgcacgcc ctcgctcaag ccttcgtcac tggtcccgcc accaaacgtt   3600
tcggcgagaa gcaggccatt atcgccggca tggcggcccc acgggtgcgc atgatcgtgc   3660
tcctgtcgtt gaggacccgg ctaggctggc ggggttgcct tactggttag cagaatgaat   3720
caccgatacg cgagcgaacg tgaagcgact gctgctgcaa aacgtctgcg acctgagcaa   3780
caacatgaat ggtcttcggt ttccgtgttt cgtaaagtct ggaaacgcgg aagtcagcgc   3840
cctgcaccat tatgttccgg atctgcatcg caggatgctg ctggctaccc tgtggaacac   3900
ctacatctgt attaacgaag cgctggcatt gaccctgagt gattttctc tggtcccgcc    3960 gcatccatac cgccagttgt ttaccctcac aacgttccag taaccgggca tgttcatcat   4020
cagtaacccg tatcgtgagc atcctctctc gtttcatcgg tatcattacc cccatgaaca   4080
gaaatccccc ttacacggag gcatcagtga ccaaacagga aaaaccgcc cttaacatgg    4140 cccgctttat cagaagccag acattaacgc ttctggagaa actcaacgag ctggacgcgg   4200
atgaacaggc agacatctgt gaatcgcttc acgaccacgc tgatgagctt taccgcagct   4260
gcctcgcgcg tttcggtgat gacggtgaaa acctctgaca catgcagctc ccggagacgg   4320
tcacagcttg tctgtaagcg gatgccggga gcagacaagc ccgtcagggc gcgtcagcgg   4380
gtgttggcgg gtgtcgggc gcagccatga cccagtcacg tagcgatagc ggagtgtata    4440
ctggcttaac tatgcggcat cagagcagat tgtactgaga gtgcaccata tatgcggtgt   4500
gaaataccgc acagatgcgt aaggagaaaa taccgcatca ggcgctcttc cgcttcctcg   4560
ctcactgact cgctgcgctc ggtcgttcgg ctgcggcgag cggtatcagc tcactcaaag   4620
gcggtaatac ggttatccac agaatcaggg gataacgcag gaaagaacat gtgagcaaaa   4680
ggccagcaaa aggccaggaa ccgtaaaaag gccgcgttgc tggcgttttt ccataggctc   4740
cgcccccctg acgagcatca aaaaatcga cgctcaagtc agaggtggcg aaacccgaca    4800
ggactataaa gataccaggc gtttccccct ggaagctccc tcgtgcgctc tcctgttccg   4860
accctgccgc ttaccggata cctgtccgcc tttctccctt cgggaagcgt ggcgctttct   4920
catagctcac gctgtaggta tctcagttcg gtgtaggtcg ttcgctccaa gctgggctgt   4980
gtgcacgaac cccccgttca gcccgaccgc tgcgccttat ccggtaacta tcgtcttgag   5040
tccaacccgg taagacacga cttatcgcca ctggcagcag ccactggtaa caggattagc   5100
agagcgaggt atgtaggcgg tgctacagag ttcttgaagt ggtggcctaa ctacggctac   5160
actagaagga cagtatttgg tatctgcgct ctgctgaagc cagttacctt cggaaaaaga   5220
gttggtagct cttgatccgg caaacaaacc accgctggta gcggtggttt ttttgtttgc   5280
aagcagcaga ttacgcgcag aaaaaaagga tctcaagaag atcctttgat cttttctacg   5340
gggtctgacg ctcagtggaa cgaaaactca cgttaaggga ttttggtcat gaacaataaa   5400
actgtctgct tacataaaca gtaatacaag gggtgttatg agccatattc aacgggaaac   5460
gtcttgctct aggccgcgat taaattccaa catggatgct gatttatatg ggtataaatg   5520
ggctcgcgat aatgtcgggc aatcaggtgc gacaatctat cgattgtatg ggaagcccga   5580
tgcgccagag ttgtttctga acatggcaa aggtagcgtt gccaatgatg ttacagatga    5640
gatggtcaga ctaaactggc tgacggaatt tatgcctctt ccgaccatca agcattttat   5700
```

```
ccgtactcct gatgatgcat ggttactcac cactgcgatc cccgggaaaa cagcattcca    5760
ggtattagaa gaatatcctg attcaggtga aaatattgtt gatgcgctgg cagtgttcct    5820
gcgccggttg cattcgattc ctgtttgtaa ttgtcctttt aacagcgatc gcgtatttcg    5880
tctcgctcag gcgcaatcac gaatgaataa cggtttggtt gatgcgagtg attttgatga    5940
cgagcgtaat ggctggcctg ttgaacaagt ctggaaagaa atgcataaac ttttgccatt    6000
ctcaccggat tcagtcgtca ctcatggtga tttctcactt gataaccttg ttttgacga    6060
ggggaaatta ataggttgta ttgatgttgg acgagtcgga atcgcagacc gataccagga    6120
tcttgccatc ctatggaact gcctcggtga gttttctcct tcattacaga aacggctttt    6180
tcaaaaatat ggtattgata atcctgatat gaataaattg cagtttcatt tgatgctcga    6240
tgagtttttc taagaattaa ttcatgagcg gatacatatt tgaatgtatt tagaaaaata    6300
aacaaatagg ggttccgcgc acatttcccc gaaaagtgcc acctgaaatt gtaaacgtta    6360
atattttgtt aaaattcgcg ttaaattttt gttaaatcag ctcattttt aaccaatagg    6420
ccgaaatcgg caaaatccct tataaatcaa agaatagac cgagataggg ttgagtgttg    6480
ttccagtttg gaacaagagt ccactattaa agaacgtgga ctccaacgtc aaagggcgaa    6540
aaaccgtcta tcagggcgat ggcccactac gtgaaccatc accctaatca agttttttgg    6600
ggtcgaggtg ccgtaaagca ctaaatcgga acctaaagg agcccccga tttagagctt    6660
gacggggaaa gccggcgaac gtggcgagaa aggaagggaa gaaagcgaaa ggagcgggcg    6720
ctagggcgct ggcaagtgta gcggtcacgc tgcgcgtaac caccacccc gccgcgctta    6780
atgccgcct acagggcgcg tcccattcgc caatccggat atagttcctc ctttcagcaa    6840
aaaacccctc aagacccgtt tagaggcccc aaggggttat gctagttatt gctcagcggt    6900
ggcagcagcc aactcagctt cctttcgggc tttgttagca gccggatctc agtggtggtg    6960
gtggtggtgc tcga                                                      6974
```

<210> SEQ ID NO 27
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 27

```
gcggccgcgc ccttgacgat gccacatcct gagcaaataa ttcaaccact aattgtgagc      60
ggataacaca aggaggaaac agccatggta tcctgttctg cgccgggtaa gatttacctg     120
ttcggtgaac acgccgtagt ttatggcgaa actgcaattg cgtgtgcggt ggaactgcgt     180
acccgtgttc gcgcggaact caatgactct atcactattc agagccagat cggccgcacc     240
ggtctggatt tcgaaaagca cccttatgtg tctgcggtaa ttgagaaaat gcgcaaatct     300
attcctatta acggtgtttt cttgaccgtc gattccgaca tcccggtggg ctccggtctg     360
ggtagcagcg cagccgttac tatcgcgtct attggtgcgc tgaacgagct gttcggcttt     420
ggcctcagcc tgcaagaaat cgctaaactg ggccacgaaa tcgaaattaa agtacagggt     480
gccgcgtccc caaccgatac gtatgttct accttcggcg cgtggttac catcccggaa     540
cgtcgcaaac tgaaaactcc ggactgcggc attgtgattg gcgatacccg cgttttctcc     600
tccaccaaag agttagtagc taacgtacgt cagctgcgcg aaagctaccc ggatttgatc     660
gaaccgctga tgacctctat tggcaaaatc tctcgtatcg cgaacaact ggttctgtct     720
ggcgactacg catccatcgg ccgcctgatg aacgtcaacc agggtctcct ggacgccctg     780
```

```
ggcgttaaca tcttagaact gagccagctg atctattccg ctcgtgcggc aggtgcgttt    840
ggcgctaaaa tcacgggcgc tggcggcggt ggctgtatgg ttgcgctgac cgctccggaa    900
aaatgcaacc aagtggcaga agcggtagca ggcgctggcg gtaaagtgac tatcactaaa    960
ccgaccgagc aaggtctgaa agtagattaa gccttgactt aatagctgct tatttcgccc   1020
ttatggtacc tagtaggagg aaaaaaacat ggaaatgcgt caaccggctg tcgcaggtca   1080
attctaccca ctgcgttgcg agaacctgga aaacgaactg aaacgctgct cgaaggcct    1140
ggagatccgc gaacaagaag tgctgggcgc agtctgtccg cacgccggtt atatgtactc   1200
tggcaaagtt gcggcgcacg tctatgccac tctgccggaa gctgatacct acgtaatctt   1260
cggcccgaac cacaccggct acggtagccc tgtctctgtg agccgtgaaa cttggaagac   1320
cccgttgggc aatatcgatg ttgacctgga actggcggac ggcttcctgg gttccatcgt   1380
agatgcggat gaactcggtc acaaatacga acactctatc gaagttcagc tgccgtttct   1440
gcaataccgt tttgaacgcg atttcaaaat tctgccaatc tgcatgggta tgcaagacga   1500
agaaaccgcg gtcgaagtag gtaacctgct ggcggatctg atcagcgagt ccggtaaacg   1560
tgctgtgatc atcgcaagct ctgatttcac ccactatgag acggctgaac gtgccaaaga   1620
aatcgattcc gaagttattg attctatcct gaactttgac atctctggca tgtacgatcg   1680
cctgtatcgc cgtaacgcct ctgtttgcgg ttacggcccg atcaccgcta tgctgacggc   1740
aagcaaaaag ctgggcggct ctcgtgcgac tttgctgaaa tacgcaaaca gcggtgacgt   1800
gtccggtgat aaagacgctg tggtgggcta cgccgccatc atcgttgagt aagctgatta   1860
aaggttgaac agataggatt tcgtcatgga tcctacaagg aggaaaaaaa catgaatgct   1920
tctaatgaac cggtgattct gaaactgggt ggctctgcta ttaccgacaa aggtgcctac   1980
gaaggcgtag ttaaggaagc tgatttgctg cgcatcgcac aggaagttag cggtttccgt   2040
ggcaagatga tcgtggttca tggtgctggt agcttcggcc atacgtacgc gaagaaatac   2100
ggcctggacc gtaccttcga cccagagggc gcaattgtta ctcatgaatc tgttaaaaag   2160
ctcgcctcca agttgtagg tgctctgaat agcttcggcg tgcgtgctat cgcggtgcat   2220
cctatggact gcgcagtatg ccgtaacggt cgtatcgaaa cgatgtatct ggactccatc   2280
aagttaatgc tggaaaaagg tctggtgccg gttctgcacg gcgacgtcgc aatggatatt   2340
gaactgggca cttgtatcct gtccggtgat caaatcgttc cttacctggc caaagaactg   2400
ggtatctccc gcctcggcct gggcagcgca gaggatggtg tgctggatat ggagggcaaa   2460
cctgtaccgg aaatcacccc agaaactttc gaagagttcc gccactgcat cggtggttct   2520
ggttctactg atgtaaccgg tggcatgctg gcaaagtgc tggaacttct ggaattgagc   2580
aaaaattctt ccattactag ctacatttc aacgctggta agcagacaa catctaccgc   2640
tttctgaatg gtgagtccat cggcactcgc atcagcccgg acaagcgtgt ttaagctagt   2700
tattaaccta aatgctctaa accagttatg agctctacaa ggaggaaaaa aacatgatta   2760
acactaccag ccgccgcaaa attgaacacc tgaaactctg cgcagaatcc ccggttgaag   2820
cgcgtcaggt atctgccggc tttgaagacg ttactctgat ccaccgcgct ttaccggagc   2880
tgaacatgga tgaactggac ctcagcgttg atttcctggg taaacgcatc aaagcgccgt   2940
tcctgattgc gtctatcacg ggtggtcacc cagataccat cccggttaac gctgcgctgg   3000
cagctgctgc tgaggagctg ggtgttggca tcggcgttgg ctctcagcgc gcggccattg   3060
atgatccgag ccaggaagac agcttccgtg tagtgcgtga tgaagcccca gatgcgtttg   3120
```

```
tttatggcaa cgtcggcgca gcacagatcc gtcagtatgg tgttgaaggt gttgaaaaac    3180
tgatcgaaat gattgacgca gatgccttgg caatccacct gaactttctg caagaagcgg    3240
tccaaccgga aggtgaccgc gacgcgaccg gttgcctgga catgattacc gaaatttgct    3300
ctcagattaa aactccggta atcgtgaaag aaaccggtgc aggcattagc cgtgaagatg    3360
cgattctgtt ccagaaagct ggcgtgagcg caatcgacgt tggcggcgcg ggcggcacct    3420
cctgggctgg cgtcgaggtc taccgtgcta agaaagccg tgactctgtt agcgagcgtt    3480
taggtgagct gttttgggat tcggcattc cgacggtagc ttctctgatt gaatcccgcg    3540
tttccttgcc gctgatcgca accggcgta tccgtaacgg tctggacatt gctaaaagca    3600
tgctctcgg cgcaagcgct gccagcgccg ctctgccgtt cgttggtccg tccctggagg    3660
gcaaagaatc cgttgtacgt gtgctgagct gcatgctgga agaattaaa gcagcaatgt    3720
ttttgtgcgg ttgcggcaac atcaaagacc tgcacaactc tccagtagtg gtaactggtt    3780
ggacccgcga atacctggag cagcgcggtt ttaacgttaa ggacctctcc ctgccgggca    3840
acgctctgta agcttcaacg cgtctacaaa taaaaaggc acgtcagatg acgtgccttt    3900
tttcttgtct aga                                                       3913

<210> SEQ ID NO 28
<211> LENGTH: 6848
<212> TYPE: DNA
<213> ORGANISM: Artificial Sequence
<220> FEATURE:
<223> OTHER INFORMATION: Synthetic Construct

<400> SEQUENCE: 28
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgtgtgc     420
gacctcttct caatttactc agattaccga gcataattcc cgtcgttccg caaactatca     480
gccaaacctg tggaatttcg aattcctgca atccctggag aacgacctga agtggaaaa      540
gctggaggag aaagcgacca aactggagga agaagttcgc tgcatgatca accgtgtaga     600
cacccagccg ctgtccctgc tggagctgat cgacgatgtg cagcgcctgg gtctgaccta     660
caaatttgaa aaagacatca ttaaagccct ggaaaacatc gtactgctgg acgaaaacaa     720
aaagaacaaa tctgacctgc acgcaaccgc tctgtctttc cgtctgctgc gtcagcacgg     780
tttcgaggtt tctcaggatg ttttttgagcg tttcaaggat aaagaaggtg gtttcagcgg     840
tgaactgaaa ggtgacgtcc aaggcctgct gagcctgtat gaacgtcttc acctgggttt     900
cgagggtgag aacctgctgg aggaggcgcg tacctttcc atcacccacc tgaagaacaa     960
cctgaaagaa ggcattaata ccaaggttgc agaacaagtg agccacgccc tggaactgcc    1020
atatcaccag cgtctgcacc gtctggaggc acgttggttc ctggataaat acgaaccgaa    1080
agaaccgcat caccagctgc tgctggagct ggcgaagctg gattttaaca tggtacagac    1140
cctgcaccag aaagagctgc aagatctgtc ccgctggtgg accgagatgg gcctggctag    1200
caaactggat tttgtacgcg accgcctgat ggaagtttat ttctgggcac tgggtatggc    1260
```

```
gccagacccg cagtttggtg aatgtcgcaa agctgttact aaaatgtttg gtctggtgac    1320
gatcatcgat gacgtgtatg acgtttatgg cactctggac gaactgcaac tgttcaccga    1380
tgctgtagag cgctgggacg ttaacgctat taacaccctg ccggactata tgaaactgtg    1440
tttcctggca ctgtacaaca ccgttaacga cacgtcctat tctattctga agagaaaagg    1500
tcataacaac ctgtcctatc tgacgaaaag ctggcgtgaa ctgtgcaaag cctttctgca    1560
agaggcgaaa tggtccaaca acaaaattat cccggctttc tccaagtacc tggaaaacgc    1620
cagcgtttcc tcctccggtg tagcgctgct ggcgccgtct tacttttccg tatgccagca    1680
gcaggaagac atctccgacc acgcgctgcg ttccctgacc gacttccatg gtctggtgcg    1740
ttctagctgc gttatcttcc gcctgtgcaa cgatctggcc acctctgcgg cggagctgga    1800
acgtggcgag actaccaatt ctatcattag ctacatgcac gaaaacgatg gtaccagcga    1860
ggaacaggcc cgcgaagaac tgcgtaaact gatcgacgcc gaatggaaaa agatgaatcg    1920
tgaacgcgtt agcgactcca ccctgctgcc taaagcgttc atggaaatcg cagttaacat    1980
ggcacgtgtt tcccactgca cctaccagta tggcgatggt ctgggtcgcc cagactacgc    2040
gactgaaaac cgcatcaaac tgctgctgat tgaccctttc ccgattaacc agctgatgta    2100
tgtctaactg cataaaggag gtaaaaaaac atggtatcct gttctgcgcc gggtaagatt    2160
tacctgttcg gtgaacacgc cgtagtttat ggcgaaactg caattgcgtg tgcggtggaa    2220
ctgcgtaccc gtgttcgcgc ggaactcaat gactctatca ctattcagag ccagatcggc    2280
cgcaccggtc tggatttcga aaagcaccct tatgtgtctg cggtaattga aaaatgcgc     2340 aaatctattc ctattaacgg tgttttcttg accgtcgatt ccgacatccc ggtgggctcc    2400
ggtctgggta gcagcgcagc cgttactatc gcgtctattg gtgcgctgaa cgagctgttc    2460
ggctttggcc tcagcctgca agaaatcgct aaactgggcc acgaaatcga aattaaagta    2520
cagggtgccg cgtccccaac cgatacgtat gtttctacct tcggcggcgt ggttaccatc    2580
ccggaacgtc gcaaactgaa aactccggac tgcggcattg tgattggcga taccggcgtt    2640
ttctcctcca ccaaagagtt agtagctaac gtacgtcagc tgcgcgaaag ctacccggat    2700
ttgatcgaac cgctgatgac ctctattggc aaaatctctc gtatcggcga acaactggtt    2760
ctgtctggcg actacgcatc catcggccgc ctgatgaacg tcaaccaggg tctcctggac    2820
gccctgggcg ttaacatctt agaactgagc cagctgatct attccgctcg tcggcaggt    2880 gcgtttggcg ctaaaatcac gggcgctggc ggcggtggct gtatggttgc gctgaccgct    2940
ccggaaaaat gcaaccaagt ggcagaagcg gtagcaggcg ctggcggtaa agtgactatc    3000
actaaaccga ccgagcaagg tctgaaagta gattaaagtc tagttaaagt ttaaacggtc    3060
tccagcttgg ctgttttggc ggatgagaga agattttcag cctgatacag attaaatcag    3120
aacgcagaag cggtctgata aaacagaatt tgcctggcgg cagtagcgcg gtggtcccac    3180
ctgaccccat gccgaactca gaagtgaaac gccgtagcgc cgatggtagt gtggggtctc    3240
cccatgcgag agtagggaac tgccaggcat caaataaaac gaaaggctca gtcgaaagac    3300
tgggcctttc gttttatctg ttgtttgtcg gtgaacgctc tcctgagtag acaaatccg     3360 ccgggagcgg atttgaacgt tgcgaagcaa cggcccggag ggtggcgggc aggacgcccg    3420
ccataaactg ccaggcatca aattaagcag aaggccatcc tgacggatgg cctttttgcg    3480
tttctacaaa ctcttttttgt ttattttttct aaatacattc aaatatgtat ccgcttaacc    3540
ggaattgcca gctggggcgc cctctggtaa ggttgggaag ccctgcaaag taaactggat    3600
```

-continued

| | |
|---|---|
| ggctttctcg ccgccaagga tctgatggcg caggggatca agctctgatc aagagacagg | 3660 |
| atgaggatcg tttcgcatga ttgaacaaga tggattgcac gcaggttctc cggccgcttg | 3720 |
| ggtggagagg ctattcggct atgactgggc acaacagaca atcggctgct ctgatgccgc | 3780 |
| cgtgttccgg ctgtcagcgc aggggcgccc ggttcttttt gtcaagaccg acctgtccgg | 3840 |
| tgccctgaat gaactgcaag acgaggcagc gcggctatcg tggctggcca cgacgggcgt | 3900 |
| tccttgcgca gctgtgctcg acgttgtcac tgaagcggga agggactggc tgctattggg | 3960 |
| cgaagtgccg gggcaggatc tcctgtcatc tcaccttgct cctgccgaga agtatccat | 4020 |
| catggctgat gcaatgcggc ggctgcatac gcttgatccg gctacctgcc cattcgacca | 4080 |
| ccaagcgaaa catcgcatcg agcgagcacg tactcggatg aagccggtc ttgtcgatca | 4140 |
| ggatgatctg gacgaagagc atcagggct cgcgccagcc gaactgttcg ccaggctcaa | 4200 |
| ggcgagcatg cccgacggcg aggatctcgt cgtgacccat ggcgatgcct gcttgccgaa | 4260 |
| tatcatggtg aaaatggcc gcttttctgg attcatcgac tgtggccggc tgggtgtggc | 4320 |
| ggaccgctat caggacatag cgttggctac ccgtgatatt gctgaagagc ttggcggcga | 4380 |
| atgggctgac cgcttcctcg tgctttacgg tatcgccgct cccgattcgc agcgcatcgc | 4440 |
| cttctatcgc cttcttgacg agttcttctg acgcatgacc aaaatccctt aacgtgagtt | 4500 |
| ttcgttccac tgagcgtcag acccgtaga aagatcaaa ggatcttctt gagatccttt | 4560 |
| ttttctgcgc gtaatctgct gcttgcaaac aaaaaaacca ccgctaccag cggtggtttg | 4620 |
| tttgccggat caagagctac caactctttt tccgaaggta actggcttca gcagagcgca | 4680 |
| gataccaaat actgtccttc tagtgtagcc gtagttaggc caccacttca agaactctgt | 4740 |
| agcaccgcct acatacctcg ctctgctaat cctgttacca gtggctgctg ccagtggcga | 4800 |
| taagtcgtgt cttaccgggt tggactcaag acgatagtta ccggataagg cgcagcggtc | 4860 |
| gggctgaacg gggggttcgt gcacacagcc cagcttggag cgaacgacct acaccgaact | 4920 |
| gagataccta cagcgtgagc tatgagaaag cgccacgctt cccgaaggga aaaggcgga | 4980 |
| caggtatccg gtaagcggca gggtcggaac aggagagcgc acgagggagc ttccaggggg | 5040 |
| aaacgcctgg tatctttata gtcctgtcgg gtttcgccac ctctgacttg agcgtcgatt | 5100 |
| tttgtgatgc tcgtcagggg ggcggagcct atggaaaaac gccagcaacg cggccttttt | 5160 |
| acggttcctg gccttttgct ggccttttgc tcacatgttc tttcctgcgt tatcccctga | 5220 |
| ttctgtggat aaccgtatta ccgcctttga gtgagctgat accgctcgcc gcagccgaac | 5280 |
| gaccgagcgc agcgagtcag tgagcgagga agcggaagag cgcctgatgc ggtattttct | 5340 |
| ccttacgcat ctgtgcggta tttcacaccg catatggtgc actctcagta caatctgctc | 5400 |
| tgatgccgca tagttaagcc agtatacact ccgctatcgc tacgtgactg gtcatggct | 5460 |
| gcgccccgac acccgccaac acccgctgac gcgccctgac gggcttgtct gctcccggca | 5520 |
| tccgcttaca acaagctgt gaccgtctcc gggagctgca tgtgtcagag gttttcaccg | 5580 |
| tcatcaccga aacgcgcgag gcagcagatc aattcgcgcg cgaaggcgaa gcggcatgca | 5640 |
| tttacgttga caccatcgaa tggtgcaaaa ccttcgcgg tatggcatga tagcgcccgg | 5700 |
| aagagagtca attcagggtg gtgaatgtga accagtaac gttatacgat gtcgcagagt | 5760 |
| atgccggtgt ctcttatcag accgtttccc gcgtggtgaa ccaggccagc cacgtttctg | 5820 |
| cgaaaacgcg ggaaaaagtg gaagcggcga tggcggagct gaattacatt cccaaccgcg | 5880 |
| tggcacaaca actggcgggc aaacagtcgt tgctgattgg cgttgccacc tccagtctgg | 5940 |
| ccctgcacgc gccgtcgcaa attgtcgcgg cgattaaatc tcgcgccgat caactgggtg | 6000 |

-continued

```
ccagcgtggt ggtgtcgatg gtagaacgaa gcggcgtcga agcctgtaaa gcggcggtgc    6060
acaatcttct cgcgcaacgc gtcagtgggc tgatcattaa ctatccgctg gatgaccagg    6120
atgccattgc tgtggaagct gcctgcacta atgttccggc gttatttctt gatgtctctg    6180
accagacacc catcaacagt attattttct cccatgaaga cggtacgcga ctgggcgtgg    6240
agcatctggt cgcattgggt caccagcaaa tcgcgctgtt agcgggccca ttaagttctg    6300
tctcggcgcg tctgcgtctg gctggctggc ataaatatct cactcgcaat caaattcagc    6360
cgatagcgga acgggaaggc gactggagtg ccatgtccgg ttttcaacaa accatgcaaa    6420
tgctgaatga gggcatcgtt cccactgcga tgctggttgc caacgatcag atggcgctgg    6480
gcgcaatgcg cgccattacc gagtccgggc tgcgcgttgg tgcggatatc tcggtagtgg    6540
gatacgacga taccgaagac agctcatgtt atatcccgcc gtcaaccacc atcaaacagg    6600
attttcgcct gctggggcaa accagcgtgg accgcttgct gcaactctct cagggccagg    6660
cggtgaaggg caatcagctg ttgcccgtct cactggtgaa agaaaaacc accctggcgc    6720 ccaatacgca aaccgcctct ccccgcgcgt tggccgattc attaatgcag ctggcacgac    6780
aggtttcccg actggaaagc gggcagtgag cgcaacgcaa ttaatgtgag ttagcgcgaa    6840
ttgatctg                                                            6848
```

<210> SEQ ID NO 29
<211> LENGTH: 6647
<212> TYPE: DNA
<213> ORGANISM: Artificial Sequence
<220> FEATURE:
<223> OTHER INFORMATION: Synthetic Construct

<400> SEQUENCE: 29

```
aagggcgagc tcaacgatcc ggctgctaac aaagcccgaa aggaagctga gttggctgct      60
gccaccgctg agcaataact agcataaccc cttggggcct ctaaacgggt cttgaggagt     120 ttttgctga aaggaggaac tatatccgga tatcccgcaa gaggcccggc agtaccggca     180
taaccaagcc tatgcctaca gcatccaggt gacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata taatggtttt cttagacgtc     420
aggtggcact tttcggggaa atgtgcgcgg aaccctat tgtttatttt tctaaataca     480
ttcaaatatg tatccgctca tgagacaata accctgataa atgcttcaat aatattgaaa     540
aaggaagagt atgattgaac aagatggatt gcacgcaggt tctccggccg cttgggtgga     600
gaggctattc ggctatgact gggcacaact gacaatcggc tgctctgatg ccgccgtgtt     660
ccggctgtca gcgcaggggc gcccggttct ttttgtcaag accgacctgt ccggtgccct     720
gaatgaactg caggacgagg cagcgcggct atcgtggctg gccacgacgg gcgttccttg     780
cgcagctgtg ctcgacgttg tcactgaagc gggaagggac tggctgctat gggcgaagt     840 gccggggcag gatctcctgt catctcacct tgctcctgcc gagaaagtat ccatcatggc     900
tgatgcaatg cggcggctgc atacgcttga tccggctacc tgcccattcg accaccaagc     960
gaaacatcgc atcgagcggg cacgtactcg gatggaagcc ggtcttgtcg atcaggatga    1020
tctggacgaa gagcatcagg ggctcgcgcc agccgaactg ttcgccaggc tcaaggcgcg    1080 catgccccgac ggcgaggatc tcgtcgtgac acatggcgat gcctgcttgc cgaatatcat    1140
```

```
ggtggaaaat ggccgctttt ctggattcat cgactgtggc cggctgggtg tggcggaccg    1200
ctatcaggac atagcgttgg ctacccgtga tattgctgaa gagcttggcg gcgaatgggc    1260
tgaccgcttc ctcgtgcttt acggtatcgc cgctcccgat tcgcagcgca tcgccttcta    1320
tcgccttctt gacgagttct tctgagcggg actctgggt tcgaaatgac cgaccaagcg    1380
acgcctaact gtcagaccaa gtttactcat atatacttta gattgattta aaacttcatt    1440
tttaatttaa aaggatctag gtgaagatcc tttttgataa tctcatgacc aaaatccctt    1500
aacgtgagtt ttcgttccac tgagcgtcag accccgtaga aaagatcaaa ggatcttctt    1560
gagatccttt ttttctgcgc gtaatctgct gcttgcaaac aaaaaaacca ccgctaccag    1620
cggtggtttg tttgccggat caagagctac caactctttt tccgaaggta actggcttca    1680
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttaccgggt tggactcaag acgatagtta ccggataagg    1860
cgcagcggtc gggctgaacg gggggttcgt gcacacagcc cagcttggag cgaacgacct    1920
acaccgaact gagataccta cagcgtgagc tatgagaaag cgccacgctt cccgaaggga    1980
gaaaggcgga caggtatccg gtaagcggca gggtcggaac aggagagcgc acgagggagc    2040 ttccagggg aaacgcctgg tatctttata gtcctgtcgg gtttcgccac ctctgacttg    2100
agcgtcgatt tttgtgatgc tcgtcagggg ggcggagcct atgaaaaac gccagcaacg    2160 cggcctttt acggttcctg gcctttgct ggcctttgc tcacatgttc tttcctgcgt    2220 tatccctga ttctgtggat aaccgtatta ccgcctttga gtgagctgat accgctcgcc    2280
gcagccgaac gaccgagcgc agcgagtcag tgagcgagga agcggaagag cgcctgatgc    2340
ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctccaga    2700
agcgttaatg tctggcttct gataaagcgg gccatgttaa gggcggtttt ttcctgtttg    2760
gtcactgatg cctccgtgta agggggattt ctgttcatgg ggtaatgat accgatgaaa    2820 cgagagagga tgctcacgat acgggttact gatgatgaac atgcccggtt actgaacgt    2880 tgtgagggta aacaactggc ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag gcgctgact tccgcgtttc cagacttac    3060 gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctgagaa tggcggacgc gatggatatg    3300
ttctgccaag ggttggtttg cgcattcaca gttctccgca agaattgatt ggctccaatt    3360
cttggagtgg tgaatccgtt agcgaggtgc cgccggcttc cattcaggtc gaggtggccc    3420
ggctccatgc accgcgacgc aacgcgggga ggcagacaag gtatagggcg cgcctacaa    3480 tccatgccaa cccgttccat gtgctcgccg aggcggcata aatcgccgtg acgatcagcg    3540
```

-continued

```
gtccaatgat cgaagttagg ctggtaagag ccgcgagcga tccttgaagc tgtccctgat    3600
ggtcgtcatc tacctgcctg gacagcatgg cctgcaacgc gggcatcccg atgccgccgg    3660
aagcgagaag aatcataatg gggaaggcca tccagcctcg cgtcgcgaac gccagcaaga    3720
cgtagcccag cgcgtcggcc gccatgccgg cgataatggc ctgcttctcg ccgaaacgtt    3780
tggtggcggg accagtgacg aaggcttgag cgagggcgtg caagattccg aataccgcaa    3840
gcgacaggcc gatcatcgtc gcgctccagc gaaagcggtc ctcgccgaaa tgacccaga    3900 gcgctgccgg cacctgtcct acgagttgca tgataaagaa gacagtcata agtgcggcga    3960
cgatagtcat gccccgcgcc caccggaagg agctgactgg gttgaaggct ctcaagggca    4020
tcggtcgaga tcccggtgcc taatgagtga gctaacttac attaattgcg ttgcgctcac    4080
tgcccgcttt ccagtcggga aacctgtcgt gccagctgca ttaatgaatc ggccaacgcg    4140
cggggagagg cggtttgcgt attgggcgcc agggtggttt ttcttttcac cagtgagacg    4200
ggcaacagct gattgccctt caccgcctgg ccctgagaga gttgcagcaa gcggtccacg    4260
ctggtttgcc ccagcaggcg aaaatcctgt ttgatggtgg ttaacggcgg gatataacat    4320
gagctgtctt cggtatcgtc gtatcccact accgagatat ccgcaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acggcgcgtg cagggccaga ctggaggtgg caacgccaat cagcaacgac    4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tgtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc ccccggccac ggggcctgcc accataccca cgccgaaaca    5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580 aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catggtatcc tgttctgcgc    5760
cgggtaagat ttacctgttc ggtgaacacg ccgtagttta tggcgaaact gcaattgcgt    5820
gtgcggtgga actgcgtacc cgtgttcgcg cggaactcaa tgactctatc actattcaga    5880
```

| | |
|---|---|
| gccagatcgg ccgcaccggt ctggatttcg aaaagcaccc ttatgtgtct gcggtaattg | 5940 |
| agaaaatgcg caaatctatt cctattaacg gtgttttctt gaccgtcgat tccgacatcc | 6000 |
| cggtgggctc cggtctgggt agcagcgcag ccgttactat cgcgtctatt ggtgcgctga | 6060 |
| acgagctgtt cggctttggc ctcagcctgc aagaaatcgc taaactgggc cacgaaatcg | 6120 |
| aaattaaagt acagggtgcc gcgtccccaa ccgatacgta tgtttctacc ttcggcggcg | 6180 |
| tggttaccat cccggaacgt cgcaaactga aaactccgga ctgcggcatt gtgattggcg | 6240 |
| ataccggcgt tttctcctcc accaaagagt tagtagctaa cgtacgtcag ctgcgcgaaa | 6300 |
| gctacccgga tttgatcgaa ccgctgatga cctctattgg caaaatctct cgtatcggcg | 6360 |
| aacaactggt tctgtctggc gactacgcat ccatcggccg cctgatgaac gtcaaccagg | 6420 |
| gtctcctgga cgccctgggc gttaacatct tagaactgag ccagctgatc tattccgctc | 6480 |
| gtgcggcagg tgcgtttggc gctaaaatca cgggcgctgg cggcggtggc tgtatggttg | 6540 |
| cgctgaccgc tccggaaaaa tgcaaccaag tggcagaagc ggtagcaggc gctggcggta | 6600 |
| aagtgactat cactaaaccg accgagcaag gtctgaaagt agattaa | 6647 |

<210> SEQ ID NO 30
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 30

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta agggatttt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttattttc taaatacatt caaatatgta | 540 |
| tccgctcatg aattaattct tagaaaaact catcgagcat caaatgaaac tgcaatttat | 600 |
| tcatatcagg attatcaata ccatatttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga acgaaatac gcgatcgctg ttaaaaggac | 960 |
| aattacaaac aggaatcgaa tgcaaccggc gcaggaacac tgccagcgca tcaacaatat | 1020 |
| ttcacctga tcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |

-continued

```
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg actcaagac gatagttacc ggataaggcg    1800
cagcggtcgg gctgaacggg gggttcgtgc acacagccca gcttggagcg aacgacctac    1860
accgaactga atacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100 gccttttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg gggtaatga taccgatgaa    2760 acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
```

-continued

```
ccgcctggcc ctgagagagt tgcagcaagc ggtccacgct ggtttgcccc agcaggcgaa      3720
aatcctgttt gatggtggtt aacggcggga tataacatga gctgtcttcg gtatcgtcgt      3780
atcccactac cgagatatcc gcaccaacgc gcagcccgga ctcggtaatg gcgcgcattg      3840
cgcccagcgc catctgatcg ttggcaacca gcatcgcagt gggaacgatg ccctcattca      3900
gcatttgcat ggtttgttga aaaccggaca tggcactcca gtcgccttcc cgttccgcta      3960
tcggctgaat ttgattgcga gtgagatatt tatgccagcc agccagacgc agacgcgccg      4020
agacagaact taatgggccc gctaacagcg cgatttgctg gtgacccaat gcgaccagat      4080
gctccacgcc cagtcgcgta ccgtcttcat gggagaaaat aatactgttg atgggtgtct      4140
ggtcagagac atcaagaaat aacgccggaa cattagtgca ggcagcttcc acagcaatgg      4200
catcctggtc atccagcgga tagttaatga tcagcccact gacgcgttgc gcgagaagat      4260
tgtgcaccgc cgctttacag gcttcgacgc cgcttcgttc taccatcgac accaccacgc      4320
tggcacccag ttgatcggcg cgagatttaa tcgccgcgac aatttgcgac ggcgcgtgca      4380
gggccagact ggaggtggca acgccaatca gcaacgactg tttgcccgcc agttgttgtg      4440
ccacgcggtt gggaatgtaa ttcagctccg ccatcgccgc ttccactttt tcccgcgttt      4500
tcgcagaaac gtggctggcc tggttcacca cgcggggaaac ggtctgataa gagacaccgg      4560
catactctgc gacatcgtat aacgttactg gtttcacatt caccaccctg aattgactct      4620
cttccgggcg ctatcatgcc ataccgcgaa aggttttgcg ccattcgatg gtgtccggga      4680
tctcgacgct ctcccttatg cgactcctgc attaggaagc agcccagtag taggttgagg      4740
ccgttgagca ccgccgccgc aaggaatggt gcatgcaagg agatggcgcc caacagtccc      4800
ccggccacgg ggcctgccac catacccacg ccgaaacaag cgctcatgag cccgaagtgg      4860
cgagcccgat cttccccatc ggtgatgtcg gcgatatagg cgccagcaac cgcacctgtg      4920
gcgccggtga tgccggccac gatgcgtccg gcgtagagga tcgagatctc gatcccgcga      4980
aattaatacg actcactata ggggaattgt gagcggataa caattcccct ctagaaataa      5040
ttttgtttaa ctttaagaag gagatataca tatgcgttgt agcgtgtcca ccgaaaatgt      5100
gtctttcacc gaaactgaaa ccgaagctcg tcgttctgcg aactacgaac ctaacagctg      5160
ggactatgat tacctgctgt cctccgacac ggacgagtcc atcgaagtat acaaagacaa      5220
agcgaaaaag ctggaagccg aagttcgtcg cgagattaat aacgaaaaag cagaatttct      5280
gaccctgctg gaactgattg acaacgtcca gcgcctgggc ctgggttacc gtttcgagtc      5340
tgatatccgt ggtgcgctgg atcgcttcgt ttcctccggc ggcttcgatg cggtaaccaa      5400
gacttccctg cacggtacgg cactgtcttt ccgtctgctg cgtcaacacg ttttgaggt       5460
ttctcaggaa gcgttcagcg gcttcaaaga ccaaaacggc aacttcctgg agaacctgaa      5520
ggaagatatc aaagctatcc tgagcctgta cgaggccagc ttcctggctc tggaaggcga      5580
aaacatcctg gacgaggcga aggttttcgc aatctctcat ctgaaagaac tgtctgaaga      5640
aaagatcggt aaagagctgg cagaacaggt gaaccatgca ctggaactgc cactgcatcg      5700
ccgtactcag cgtctggaag cagtatggtc tatcgaggcc taccgtaaaa aggaggacgc      5760
gaatcaggtt ctgctggagc tggcaattct ggattacaac atgatccagt ctgtatacca      5820
gcgtgatctg cgtgaaacgt cccgttggtg gcgtcgtgtg ggtctggcga ccaaactgca      5880
cttttgctcgt gaccgcctga ttgagagctt ctactgggcc gtgggtgtag cattcgaacc      5940
gcaatactcc gactgccgta actccgtcgc aaaaatgttt tctttcgtaa ccattatcga      6000
cgatatctac gatgtatacg gcaccctgga cgaactggag ctgtttactg atgcagttga      6060
```

-continued

| | |
|---|---|
| gcgttgggac gtaaacgcca tcaacgacct gccggattac atgaaactgt gctttctggc | 6120 |
| tctgtataac actattaacg aaatcgccta cgacaacctg aaagataaag gtgagaacat | 6180 |
| cctgccgtat ctgaccaaag cctgggctga cctgtgcaac gctttcctgc aagaagccaa | 6240 |
| gtggctgtac aacaaatcta ctccgacctt tgacgactac ttcggcaacg catggaaatc | 6300 |
| ctcttctggc ccgctgcaac tggtgttcgc ttacttcgct gtcgtgcaga acattaaaaa | 6360 |
| ggaagagatc gaaaacctgc aaaaatacca tgacaccatc tctcgtcctt cccatatctt | 6420 |
| ccgtctgtgc aatgacctgg ctagcgcgtc tgcggaaatt gcgcgtggtg aaaccgcaaa | 6480 |
| tagcgtttct tgttacatgc gcactaaagg tatctccgaa gaactggcta ccgaaagcgt | 6540 |
| gatgaatctg atcgatgaaa cctggaaaaa gatgaacaag gaaaaactgg tggtagcct | 6600 |
| gttcgcgaaa ccgttcgtgg aaaccgcgat caacctggca cgtcaatctc actgcactta | 6660 |
| tcataacggc gacgcgcata cctctccgga tgagctgacc cgcaaacgcg ttctgtctgt | 6720 |
| aatcactgaa ccgattctgc cgtttgaacg ctaaggatcc gaattcgagc tccgtcgaca | 6780 |
| agcttgcggc cgcactcgag caccaccacc accaccactg agatccggct gctaacaaag | 6840 |
| cccgaaagga agctgagttg gctgctgcca ccgctgagca ataactagca taaccccttg | 6900 |
| gggcctctaa acgggtcttg aggggttttt tgctgaaagg aggaactata tccggat | 6957 |

<210> SEQ ID NO 31
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 31

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta taagggattt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttattttc taaatacatt caaatatgta | 540 |
| tccgctcatg aattaattct tagaaaaact catcgagcat caaatgaaac tgcaatttat | 600 |
| tcatatcagg attatcaata ccatattttt gaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga cgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |
| tggtgagtaa ccatgcatca tcaggagtac ggataaaatg cttgatggtc ggaagaggca | 1140 |

-continued

| | |
|---|---|
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa aatcccttaa | 1440 |
| cgtgagtttt cgttccactg agcgtcagac cccgtagaaa agatcaaagg atcttcttga | 1500 |
| gatcctttt ttctgcgcgt aatctgctgc ttgcaaacaa aaaaccacc gctaccagcg | 1560 |
| gtggtttgtt tgccggatca agagctacca actcttttc cgaaggtaac tggcttcagc | 1620 |
| agagcgcaga taccaaatac tgtccttcta gtgtagccgt agttaggcca ccacttcaag | 1680 |
| aactctgtag caccgcctac atacctcgct ctgctaatcc tgttaccagt ggctgctgcc | 1740 |
| agtggcgata agtcgtgtct taccggttg gactcaagac gatagttacc ggataaggcg | 1800 |
| cagcggtcgg gctgaacggg gggttcgtgc acacagccca gcttggagcg aacgacctac | 1860 |
| accgaactga gatacctaca gcgtgagcta tgagaaagcg ccacgcttcc cgaagggaga | 1920 |
| aaggcggaca ggtatccggt aagcggcagg gtcggaacag gagagcgcac gagggagctt | 1980 |
| ccagggggaa acgcctggta tctttatagt cctgtcgggt ttcgccacct ctgacttgag | 2040 |
| cgtcgatttt tgtgatgctc gtcagggggg cggagcctat ggaaaaacgc cagcaacgcg | 2100 |
| gcctttttac ggttcctggc cttttgctgg ccttttgctc acatgttctt cctgcgtta | 2160 |
| tcccctgatt ctgtggataa ccgtattacc gcctttgagt gagctgatac cgctcgccgc | 2220 |
| agccgaacga ccgagcgcag cgagtcagtg agcgaggaag cggaagagcg cctgatgcgg | 2280 |
| tattttctcc ttacgcatct gtgcggtatt tcacaccgca tatatggtgc actctcagta | 2340 |
| caatctgctc tgatgccgca tagttaagcc agtatacact ccgctatcgc tacgtgactg | 2400 |
| ggtcatggct gcgccccgac acccgccaac acccgctgac gcgccctgac gggcttgtct | 2460 |
| gctcccggca tccgcttaca gacaagctgt gaccgtctcc gggagctgca tgtgtcagag | 2520 |
| gttttcaccg tcatcaccga aacgcgcgag gcagctgcgg taaagctcat cagcgtggtc | 2580 |
| gtgaagcgat tcacagatgt ctgcctgttc atccgcgtcc agctcgttga gtttctccag | 2640 |
| aagcgttaat gtctggcttc tgataaagcg ggccatgtta agggcggttt tttcctgttt | 2700 |
| ggtcactgat gcctccgtgt aagggggatt tctgttcatg ggggtaatga taccgatgaa | 2760 |
| acgagagagg atgctcacga tacgggttac tgatgatgaa catgcccggt tactggaacg | 2820 |
| ttgtgagggt aaacaactgg cggtatggat gcggcgggac cagagaaaaa tcactcaggg | 2880 |
| tcaatgccag cgcttcgtta atacagatgt aggtgttcca gggtagcc agcagcatcc | 2940 |
| tgcgatgcag atccggaaca taatggtgca gggcgctgac ttccgcgttt ccagacttta | 3000 |
| cgaaacacgg aaaccgaaga ccattcatgt tgttgctcag gtcgcagacg ttttgcagca | 3060 |
| gcagtcgctt cacgttcgct cgcgtatcgg tgattcattc tgctaaccag taaggcaacc | 3120 |
| ccgccagcct agccgggtcc tcaacgacag gagcacgatc atgcgcaccc gtggggccgc | 3180 |
| catgccggcg ataatggcct gcttctcgcc gaaacgtttg gtggcgggac cagtgacgaa | 3240 |
| ggcttgagcg agggcgtgca agattccgaa taccgcaagc gacaggccga tcatcgtcgc | 3300 |
| gctccagcga aagcggtcct cgccgaaaat gacccagagc gctgccggca cctgtcctac | 3360 |
| gagttgcatg ataaagaaga cagtcataag tgcggcgacg atagtcatgc ccgcgccca | 3420 |
| ccggaaggag ctgactgggt tgaaggctct caagggcatc ggtcgagatc ccggtgccta | 3480 |
| atgagtgagc taacttacat taattgcgtt gcgctcactg cccgctttcc agtcgggaaa | 3540 |

```
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacgcggga tataacatga gctgtcttcg gtatcgtcgt    3780
atcccactac cgagatatcc gcaccaacgc gcagcccgga ctcggtaatg cgcgcattg    3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatataca tatgcgttgt agcgtgtcca ccgaaaatgt    5100
gtctttcacc gaaactgaaa ccgaaacgcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280
gaccctgccg gaactgattg acaacgtcca gcgcctgggc ctgggttacc gtttcgagtc    5340
tgatatccgt cgtgcgctgg atcgcttcgt ttcctccggc ggcttcgatg cggtaaccaa    5400
gacttccctg cacgcgacgg cactgtcttt ccgtctgctg cgtcaacacg gttttgaggt    5460
ttctcaggaa gcgttcagcg gcttcaaaga ccaaaacggc aacttcctga aaacctgaa    5520 ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagatctgg cagaacaggt gaaccatgca ctggaactgc cactgcatcg    5700
ccgtactcag cgtctggaag cagtatggtc tatcgaggcc taccgtaaaa aggaggacgc    5760
ggatcaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880
```

| | |
|---|---|
| ctttgctcgt gaccgcctga ttgagagctt ctactgggcc gtgggtgtag cattcgaacc | 5940 |
| gcaatactcc gactgccgta actccgtcgc aaaaatgttt tctttcgtaa ccattatcga | 6000 |
| cgatatctac gatgtatacg gcaccctgga cgaactggag ctgtttactg acgcagttga | 6060 |
| gcgttgggac gtaaacgcca tcgacgatct gccggattac atgaaactgt gctttctggc | 6120 |
| tctgtataac actattaacg aaatcgccta cgacaacctg aaagataaag gtgagaacat | 6180 |
| cctgccgtat ctgaccaaag cctgggctga cctgtgcaac gctttcctgc aagaagccaa | 6240 |
| gtggctgtac aacaaatcta ctccgacctt tgacgaatac ttcggcaacg catggaaatc | 6300 |
| ctcttctggc ccgctgcaac tggtgttcgc ttacttcgct gtcgtgcaga acattaaaaa | 6360 |
| ggaagagatc gataacctgc aaaaatacca tgacatcatc tctcgtcctt cccatatctt | 6420 |
| ccgtctgtgc aatgacctgg ctagcgcgtc tgcggaaatt gcgcgtggtg aaaccgcaaa | 6480 |
| tagcgtttct tgttacatgc gcactaaagg tatctccgaa gaactggcta ccgaaagcgt | 6540 |
| gatgaatctg atcgatgaaa cctggaaaaa gatgaacaag gaaaaactgg gtggtagcct | 6600 |
| gttcgcgaaa ccgttcgtgg aaaccgcgat caacctggca cgtcaatctc actgcactta | 6660 |
| tcataacggc gacgcgcata cctctccgga tgagctgacc cgcaaacgcg ttctgtctgt | 6720 |
| aatcactgaa ccgattctgc cgtttgaacg ctaaggatcc gaattcgagc tccgtcgaca | 6780 |
| agcttgcggc cgcactcgag caccaccacc accaccactg agatccggct gctaacaaag | 6840 |
| cccgaaagga agctgagttg gctgctgcca ccgctgagca taactagcaa taacccttg | 6900 |
| gggcctctaa acgggtcttg aggggttttt tgctgaaagg aggaactata tccggat | 6957 |

<210> SEQ ID NO 32
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 32

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta agggatttt gccgatttcg gcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg aattaattct tagaaaaact catcgagcat caaatgaaac tgcaatttat | 600 |
| tcatatcagg attatcaata ccatattttt gaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga gacgaaatac gcgatcgctg ttaaaaggac | 960 |
| aattacaaac aggaatcgaa tgcaaccggc gcaggaacac tgccagcgca tcaacaatat | 1020 |

```
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200 cttttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagactttta    3000 cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
```

```
gagttgcatg ataaagaaga cagtcataag tgcggcgacg atagtcatgc cccgcgccca   3420
ccggaaggag ctgactgggt tgaaggctct caagggcatc ggtcgagatc cggtgcctta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcgttgt agcgtgtcca ccgaaaatgt   5100
gtctttctct gaaactgaaa ccgaaacgcg tcgttctgcg aactacgaac ctaacagctg   5160
ggactatgat tacctgctgt cctccgacac ggacagtgcc atcgaagtac acaaagacaa   5220
agcgaaaaag ctggaagccg aagttcgtcg cgagattaat aacgaaaaag cagaatttct   5280
gaccctgctg gaactgattg acaacgtcca gcgcctgggc ctgggttacc gtttcgagtc   5340
tgatatccgt cgtgcgctgg atcgcttcgt ttcctccggc ggcttcgatg gcgtaaccaa   5400
gacttccctg cacggtacgg cactgtcttt ccgtctgctg cgtcaacacg gttttgaggt   5460
ttctcaggaa gcgttcagcg gcttcaaaga ccaaaacggc aacttcctgg agaacctgaa   5520
ggaagatatc aaagctatcc tgagcctgta cgaggccagc ttcctggctc tggaaggcga   5580
aaacatcctg gacgaggcga aggttttcgc aatctctcat ctgaaagaac tgtctgaaga   5640
aaagatcggt aaagagctgg cagaacaggt gtccatgtca ctggaactgc cactgcatcg   5700
ccgtactcag cgtctggaag cagtatggtc tatcgaggcc taccgtaaaa aggaggacgc   5760
```

```
gaaccaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880
ctttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggag ctgtttactg atgcagttga    6060
gcgttgggac gtaaacgcca tcaacgacct gccggattac atgaaactgt gctttctggc    6120
tctgtataac actattaacg aaatcgccta cgacaacctg aaagataaag gtgagaacat    6180
cctgccgtat ctgaccaaag cctgggctga cctgtgcaac gctttcctgc aagaagccaa    6240
gtggctgtac aacaaatcta ctccgacctt tgacgactac ttcggcaacg catggaaatc    6300
ctcttctggc ccgctgcaac tgatcttcgc ttacttcgct gtcgtgcaga acattaaaaa    6360
ggaagagatc gaaaacctgc aaaaatacca tgacatcatc tctcgtcctt cccatatctt    6420
ccgtctgtgc aatgacctgg ctagcgcgtc tgcggaaatt gcgcgtggtg aaaccgcaaa    6480
tagcgtttct tgttacatgc gcactaaagg tatctccgaa gaactggcta ccgaaagcgt    6540
gatgaatctg atcgatgaaa cctggaaaaa gatgaacaag gaaaaactgg gtggtagcct    6600
gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg ctaaggatcc gaattcgagc tccgtcgaca    6780
agcttgcggc cgcactcgag caccaccacc accaccactg agatccggct gctaacaaag    6840
cccgaaagga agctgagttg gctgctgcca ccgctgagca ataactagca taaccccttg    6900
gggcctctaa acgggtcttg agggttttt tgctgaaagg aggaactata tccggat      6957
```

<210> SEQ ID NO 33
<211> LENGTH: 560
<212> TYPE: PRT
<213> ORGANISM: Artificial Sequence
<220> FEATURE:
<223> OTHER INFORMATION: Synthetic Construct

<400> SEQUENCE: 33

```
Met Arg Cys Ser Val Ser Thr Glu Asn Val Ser Phe Ser Glu Thr Glu
 1               5                  10                  15

Thr Glu Thr Arg Arg Ser Ala Asn Tyr Glu Pro Asn Ser Trp Asp Tyr
             20                  25                  30

Asp Tyr Leu Leu Ser Ser Asp Thr Asp Glu Ser Ile Glu Val His Lys
         35                  40                  45

Asp Lys Ala Lys Lys Leu Glu Ala Glu Val Arg Arg Glu Ile Asn Asn
     50                  55                  60

Glu Lys Ala Glu Phe Leu Thr Leu Leu Glu Leu Ile Asp Asn Val Gln
 65                  70                  75                  80

Arg Leu Gly Leu Gly Tyr Arg Phe Glu Ser Asp Ile Arg Arg Ala Leu
                 85                  90                  95

Asp Arg Phe Val Ser Ser Gly Gly Phe Asp Gly Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
```

```
              145                 150                 155                 160
         Glu Ala Ser Phe Leu Ala Leu Glu Gly Glu Asn Ile Leu Asp Glu Ala
                         165                 170                 175
         Lys Val Phe Ala Ile Ser His Leu Lys Glu Leu Ser Glu Glu Lys Ile
                         180                 185                 190
         Gly Lys Glu Leu Ala Glu Gln Val Ser His Ala Leu Glu Leu Pro Leu
                         195                 200                 205
         His Arg Arg Thr Gln Arg Leu Glu Ala Val Trp Ser Ile Glu Ala Tyr
             210                 215                 220
         Arg Lys Lys Glu Asp Ala Asn Gln Val Leu Leu Glu Leu Ala Ile Leu
         225                 230                 235                 240
         Asp Tyr Asn Met Ile Gln Ser Val Tyr Gln Arg Asp Leu Arg Glu Thr
                         245                 250                 255
         Ser Arg Trp Trp Arg Arg Val Gly Leu Ala Thr Lys Leu His Phe Ala
                         260                 265                 270
         Arg Asp Arg Leu Ile Glu Ser Phe Tyr Trp Ala Val Gly Val Ala Phe
                         275                 280                 285
         Glu Pro Gln Tyr Ser Asp Cys Arg Asn Ser Val Ala Lys Met Phe Ser
                         290                 295                 300
         Phe Val Thr Ile Ile Asp Asp Ile Tyr Asp Val Tyr Gly Thr Leu Asp
         305                 310                 315                 320
         Glu Leu Glu Leu Phe Thr Asp Ala Val Glu Arg Trp Asp Val Asn Ala
                         325                 330                 335
         Ile Asn Asp Leu Pro Asp Tyr Met Lys Leu Cys Phe Leu Ala Leu Tyr
                         340                 345                 350
         Asn Thr Ile Asn Glu Ile Ala Tyr Asp Asn Leu Lys Asp Lys Gly Glu
                         355                 360                 365
         Asn Ile Leu Pro Tyr Leu Thr Lys Ala Trp Ala Asp Leu Cys Asn Ala
                         370                 375                 380
         Phe Leu Gln Glu Ala Lys Trp Leu Tyr Asn Lys Ser Thr Pro Thr Phe
         385                 390                 395                 400
         Asp Asp Tyr Phe Gly Asn Ala Trp Lys Ser Ser Gly Pro Leu Gln
                         405                 410                 415
         Leu Ile Phe Ala Tyr Phe Ala Val Val Gln Asn Ile Lys Lys Glu Glu
                         420                 425                 430
         Ile Glu Asn Leu Gln Lys Tyr His Asp Ile Ile Ser Arg Pro Ser His
                         435                 440                 445
         Ile Phe Arg Leu Cys Asn Asp Leu Ala Ser Ala Ser Ala Glu Ile Ala
                         450                 455                 460
         Arg Gly Glu Thr Ala Asn Ser Val Ser Cys Tyr Met Arg Thr Lys Gly
         465                 470                 475                 480
         Ile Ser Glu Glu Leu Ala Thr Glu Ser Val Met Asn Leu Ile Asp Glu
                         485                 490                 495
         Thr Trp Lys Lys Met Asn Lys Glu Lys Leu Gly Gly Ser Leu Phe Ala
                         500                 505                 510
         Lys Pro Phe Val Glu Thr Ala Ile Asn Leu Ala Arg Gln Ser His Cys
                         515                 520                 525
         Thr Tyr His Asn Gly Asp Ala His Thr Ser Pro Asp Glu Leu Thr Arg
                         530                 535                 540
         Lys Arg Val Leu Ser Val Ile Thr Glu Pro Ile Leu Pro Phe Glu Arg
         545                 550                 555                 560

<210> SEQ ID NO 34
```

<211> LENGTH: 6963
<212> TYPE: DNA
<213> ORGANISM: Artificial Sequence
<220> FEATURE:
<223> OTHER INFORMATION: Synthetic Construct

<400> SEQUENCE: 34

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttatttttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatcctttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |
| accgaactga | gatacctaca | gcgtgagcta | tgagaaagcg | ccacgcttcc | cgaagggaga | 1920 |
| aaggcggaca | ggtatccggt | aagcggcagg | gtcggaacag | gagagcgcac | gagggagctt | 1980 |
| ccagggggaa | acgcctggta | tctttatagt | cctgtcgggt | ttcgccacct | ctgacttgag | 2040 |
| cgtcgatttt | tgtgatgctc | gtcagggggg | cggagcctat | ggaaaaacgc | cagcaacgcg | 2100 |
| gcctttttac | ggttcctggc | cttttgctgg | ccttttgctc | acatgttctt | tcctgcgtta | 2160 |

```
tcccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac accgctgacg cgccctgacg ggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt tttcctgttt  2700
ggtcactgat gcctccgtgt aagggggatt tctgttcatg ggggtaatga taccgatgaa  2760
acgagagagg atgctcacga tacgggttac tgatgatgaa catgcccggt tactggaacg  2820
ttgtgagggt aaacaactgg cggtatggat gcggcgggac cagagaaaaa tcactcaggg  2880
tcaatgccag cgcttcgtta atacagatgt aggtgttcca cagggtagcc agcagcatcc  2940
tgcgatgcag atccggaaca taatggtgca gggcgctgac ttccgcgttt ccagacttta  3000
cgaaacacgg aaaccgaaga ccattcatgt tgttgctcag gtcgcagacg ttttgcagca  3060
gcagtcgctt cacgttcgct cgcgtatcgg tgattcattc tgctaaccag taaggcaacc  3120
ccgccagcct agccgggtcc tcaacgacag gagcacgatc atgcgcaccc gtggggccgc  3180
catgccggcg ataatggcct gcttctcgcc gaaacgtttg gtggcgggac cagtgacgaa  3240
ggcttgagcg agggcgtgca agattccgaa taccgcaagc gacaggccga tcatcgtcgc  3300
gctccagcga aagcggtcct cgccgaaaat gacccagagc gctgccggca cctgtcctac  3360
gagttgcatg ataaagaaga cagtcataag tgcggcgacg atagtcatgc cccgcgccca  3420
ccggaaggag ctgactgggt tgaaggctct caagggcatc ggtcgagatc ccggtgccta  3480
atgagtgagc taacttacat taattgcgtt gcgctcactg cccgctttcc agtcgggaaa  3540
cctgtcgtgc cagctgcatt aatgaatcgg ccaacgcgcg gggagaggcg gtttgcgtat  3600
tgggcgccag ggtggttttt cttttcacca gtgagacggg caacagctga ttgcccttca  3660
ccgcctggcc ctgagagagt tgcagcaagc ggtccacgct ggtttgcccc agcaggcgaa  3720
aatcctgttt gatggtggtt aacggcggga tataacatga gctgtcttcg gtatcgtcgt  3780
atcccactac cgagatatcc gcaccaacgc gcagcccgga ctcggtaatg gcgcgcattg  3840
cgcccagcgc catctgatcg ttggcaacca gcatcgcagt gggaacgatg ccctcattca  3900
gcatttgcat ggtttgttga aaaccggaca tggcactcca gtcgccttcc cgttccgcta  3960
tcggctgaat ttgattgcga gtgagatatt tatgccagcc agccagacgc agacgcgccg  4020
agacagaact taatgggccc gctaacagcg cgatttgctg gtgacccaat gcgaccagat  4080
gctccacgcc cagtcgcgta ccgtcttcat gggagaaaat aatactgttg atgggtgtct  4140
ggtcagagac atcaagaaat aacgccggaa cattagtgca ggcagcttcc acagcaatgg  4200
catcctggtc atccagcgga tagttaatga tcagcccact gacgcgttgc gcgagaagat  4260
tgtgcaccgc cgctttacag gcttcgacgc cgcttcgttc taccatcgac accaccacgc  4320
tggcacccag ttgatcggcg cgagatttaa tcgccgcgac aatttgcgac ggcgcgtgca  4380
gggccagact ggaggtggca acgccaatca gcaacgactg tttgcccgcc agttgttgtg  4440
ccacgcggtt gggaatgtaa ttcagctccg ccatcgccgc ttccactttt tcccgcgttt  4500
```

```
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc aacagtccc    4800 ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcatatg cgttgtagcg tgtccaccga    5100
aaatgtgtct ttcaccgaaa ctgaaaccga aacgcgtcgt tctgcgaact acgaacctaa    5160
cagctgggac tatgattacc tgctgtcctc cgacacggac gagtccatcg aagtatacaa    5220
agacaaagcg aaaaagctgg aagccgaagt tcgtcgcgag attaataacg aaaaagcaga    5280
atttctgacc ctgctggaac tgattgacaa cgtccagcgc ctgggcctgg gttaccgttt    5340
cgagtctgat atccgtcgtg cgctggatcg cttcgtttcc tccggcggct tcgatgcggt    5400
aaccaagact tccctgcacg cgacggcact gtctttccgt ctgctgcgtc aacacggttt    5460
tgaggtttct caggaagcgt tcagcggctt caaagaccaa aacggcaact tcctggagaa    5520
cctgaaggaa gatatcaaag ctatcctgag cctgtacgag gccagcttcc tggctctgga    5580
aggcgaaaac atcctggacg aggcgaaggt tttcgcaatc tctcatctga agaactgtc    5640 tgaagaaaag atcggtaaag atctggcaga acaggtgaac catgcactgg aactgccact    5700
gcatcgccgt actcagcgtc tggaagcagt actgtctatc gaggcctacc gtaaaaagga    5760
ggacgcggat caggttctgc tggagctggc aattctggat tacaacatga tccagtctgt    5820
ataccagcgt gatctgcgtg aaacgtcccg ttggtggcgt cgtgtgggtc tggcgaccaa    5880
actgcacttt gctcgtgacc gcctgattga gagcttctac tgggccgtgg gtgtagcatt    5940
cgaaccgcaa tactccgact gccgtaactc cgtcgcaaaa atgttttctt tcgtaaccat    6000
tatcgacgat atctacgatg tatacggcac cctggacgaa ctggagctgt ttactaacgc    6060
agttgagcgt tgggacgtaa acgccatcga cgatctgccg gattacatga aactgtgctt    6120
tctggctctg tataacacta ttaacgaaat cgcctacgac aacctgaaag aaaaaggtga    6180
gaacatcctg ccgtatctga ccaaagcctg ggctgacctg tgcaacgctt tcctgcaaga    6240
agccaagtgg ctgtacaaca aatctactcc gacctttgac gaatacttcg gcaacgcatg    6300
gaaatcctct tctggcccgc tgcaactggt gttcgcttac ttcgctgtcg tgcagaacat    6360
taaaaaggaa gagatcgaaa acctgcaaaa ataccatgac atcatctctc gtccttccca    6420
tatcttccgt ctgtgcaatg acctggctag cgcgtctgcg gaaattgcgc gtggtgaaac    6480
cgcaaatagc gtttcttgtt acatgcgcac taaaggtatc tccgaagaac tggctaccga    6540
aagcgtgatg aatctgatcg atgaaacctg gaaaagatg aacaaggaaa aactgggtgg    6600
tagcctgttc gcgaaaccgt tcgtggaaac cgcgatcaac ctggcacgtc aatctcactg    6660
cacttatcat aacggcgacg cgcataccte tccggatgag ctgacccgca aacgcgttct    6720
gtctgtaatc actgaaccga ttctgccgtt tgaacgctaa ggatccgaat tcgagctccg    6780
tcgacaagct tgcggccgca ctcgagcacc accaccacca ccactgagat ccggctgcta    6840
acaaagcccg aaaggaagct gagttggctg ctgccaccgc tgagcaataa ctagcataac    6900
```

-continued cccttggggc ctctaaacgg gtcttgaggg gttttttgct gaaaggagga actatatccg    6960
gat                                                                  6963

<210> SEQ ID NO 35
<211> LENGTH: 6966
<212> TYPE: DNA
<213> ORGANISM: Artificial Sequence
<220> FEATURE:
<223> OTHER INFORMATION: Synthetic Construct

<400> SEQUENCE: 35
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tcccctttagg   180 gttccgattt agtgctttac ggcacctcga ccccaaaaaa cttgattagg gtgatggttc     240
acgtagtggg ccatcgccct gatagacggt ttttcgccct ttgacgttgg agtccacgtt    300
ctttaatagt ggactcttgt tccaaactgg aacaacactc aaccctatct cggtctattc     360
ttttgattta tagggatttt tgccgatttc ggcctattgg ttaaaaaatg agctgattta    420
acaaaatttt aacgcgaatt ttaacaaaat attaacgttt acaatttcag gtggcacttt    480
tcggggaaat gtgcgcggaa cccctatttg tttatttttc taaatacatt caaatatgta     540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500 gatcctttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccgggttg gactcaagac gatagttacc ggataaggcg    1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920

```
aaggcggaca ggtatccggt aagcggcagg gtcggaacag gagagcgcac gagggagctt    1980
ccaggggaa acgcctggta tctttatagt cctgtcgggt ttcgccacct ctgacttgag     2040
cgtcgatttt tgtgatgctc gtcagggggg cggagcctat ggaaaaacgc cagcaacgcg    2100
gccttttac ggttcctggc cttttgctgg ccttttgctc acatgttctt tcctgcgtta     2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
```

```
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgtgctct gtttctaccg agaacgtttc    5100
cttcactgag acgaaaaccg aggcacgtcg tagcgcgaac tacgagccga atagctggga    5160
ctacgatttc ctgctgtctt ccgatactga cgaatctatt gaggtgtaca agacaaagc    5220 aaagaaactg gaggctgaag tgcgccgcga aattaacaac gagaaagctg aattcctgac    5280
tctgctggag ctgatcgata acgtacagcg cctgggtctg ggttaccgct tcgaatctga    5340
tatccgtcgc gcactggatc gtttcgtaag cagcggcggt ttcgatggcg tgaccaaaac    5400
gagcctgcac gctaccgcgc tgtccttccg tctgctgcgt cagcacggct tcgaagtttc    5460
tcaggaagca ttctccggtt tcaaagatca aaacggtaac ttcctggaaa acctgaaaga    5520
agacactaag gcgatcctga gcctgtatga ggcaagcttt ctggccctgg agggtgagaa    5580
catcctggat gaggcgcgcg tattctccat ctcccatctg aaagagctgt ctgaagagaa    5640
aatcggtaag gaactggcag agcaggttaa tcacgcactg gaactgccgc tgcatcgtcg    5700
tacccagcgt ctgaggcgg tttggtccat cgaagcgtac cgcaaaaagg aggatgctaa    5760
ccaggttctg ctggaactgg ccatcctgga ctacaacatg atccagtccg tttaccagcg    5820
tgatctgcgt gaaacctccc gttggtggcg ccgtgtgggc ctggcgacca aactgcactt    5880
cgctaaggac cgcctgattg agtcttttta ctgggcagtc ggcgttgcgt tcgaacctca    5940
gtattctgac tgccgtaaca gcgttgcgaa aatgttcagc ttcgttacta ttatcgacga    6000
catctacgac gtttacggta ctctggacga gctggaactg tttaccgacg ctgtcgaacg    6060
ttgggatgtt aacgccatca acgatctgcc tgactacatg aaactgtgct tcctggcact    6120
gtataacacg atcaacgaaa ttgcatacga caacctgaaa gacaaggtg aaaacatcct    6180 gccgtacctg actaaagcgt gggcggatct gtgtaacgct tttctgcaag aagcgaaatg    6240
gctgtataac aaatccactc cgacctttga cgattatttc ggcaatgcct ggaaatccag    6300
ctctggcccg ctgcaactga tcttcgctta ttttgcggtt gtccaaaaca tcaaaaagga    6360
ggaaattgaa aacctgcaaa ataccacga tatcattagc cgtccttctc atatctttcg    6420
cctgtgcaac gacctggcaa gcgcgtccgc agagatcgca cgtggcgaaa ccgctaactc    6480
tgtttcctgc tacatgcgca ccaagggcat ttccgaagag ctggcaaccg agagcgtaat    6540
gaatctgatc gacgaaacct gtaagaaaat gaacaaagaa aaactgggtg gctccctgtt    6600
cgctaaaccg ttcgtagaga ctgctattaa cctggcacgt cagagccact gcacctacca    6660
```

-continued

| | |
|---|---|
| caatggtgac gcacatacta gcccggatga actgactcgt aaacgtgtac tgtctgttat | 6720 |
| caccgaaccg attctgccgt tcgaacgtta actgcagctg gtaggatccg aattcgagct | 6780 |
| ccgtcgacaa gcttgcggcc gcactcgagc accaccacca ccaccactga gatccggctg | 6840 |
| ctaacaaagc ccgaaaggaa gctgagttgg ctgctgccac cgctgagcaa taactagcat | 6900 |
| aacccettgg ggcctctaaa cgggtcttga ggggttttt gctgaaagga ggaactatat | 6960 |
| ccggat | 6966 |

<210> SEQ ID NO 36
<211> LENGTH: 5679
<212> TYPE: DNA
<213> ORGANISM: Artificial Sequence
<220> FEATURE:
<223> OTHER INFORMATION: Synthetic Construct

<400> SEQUENCE: 36

| | |
|---|---|
| aagggcgaat actgcagata tccatcacac tggcggccgc tcgagcatgc atctagaggg | 60 |
| cccaattcgc cctatagtga gtcgtattac aattcactgg ccgtcgtttt acaacgtcgt | 120 |
| gactgggaaa accctggcgt tacccaactt aatcgccttg cagcacatcc cctttcgcc | 180 |
| agctggcgta atagcgaaga ggcccgcacc gatcgccctt cccaacagtt gcgcagcctg | 240 |
| aatggcgaat ggacgcgccc tgtagcggcg cattaagcgc ggcgggtgtg gtggttacgc | 300 |
| gcagcgtgac cgctacactt gccagcgccc tagcgcccgc tcctttcgct ttcttccctt | 360 |
| cctttctcgc cacgttcgcc ggctttcccc gtcaagctct aaatcggggg ctccctttag | 420 |
| ggttccgatt tagtgcttta cggcacctcg accccaaaaa acttgattag ggtgatggtt | 480 |
| cacgtagtgg gccatcgccc tgatagacgg ttttcgccc tttgacgttg gagtccacgt | 540 |
| tctttaatag tggactcttg ttccaaactg gaacaacact caaccctatc tcggtctatt | 600 |
| cttttgattt ataagggatt ttgccgattt cggcctattg gttaaaaaat gagctgattt | 660 |
| aacaaaaatt taacgcgaat tttaacaaaa ttcaggcgc aagggctgct aaaggaagcg | 720 |
| gaacacgtag aaagccagtc cgcagaaacg gtgctgaccc cggatgaatg tcagctactg | 780 |
| ggctatctgg acaagggaaa acgcaagcgc aaagagaaag caggtagctt gcagtgggct | 840 |
| tacatggcga tagctagact gggcggtttt atggacagca agcgaaccgg aattgccagc | 900 |
| tggggcgccc tctggtaagg ttgggaagcc ctgcaaagta actggatgg ctttcttgcc | 960 |
| gccaaggatc tgatggcgca ggggatcaag atctgatcaa gagacaggat gaggatcgtt | 1020 |
| tcgcatgatt gaacaagatg gattgcacgc aggttctccg gccgcttggg tggagaggct | 1080 |
| attcggctat gactgggcac aacagacaat cggctgctct gatgccgccg tgttccggct | 1140 |
| gtcagcgcag gggcgcccgg ttcttttttgt caagaccgac ctgtccggtg ccctgaatga | 1200 |
| actgcaggac gaggcagcgc ggctatcgtg gctggccacg acgggcgttc cttgcgcagc | 1260 |
| tgtgctcgac gttgtcactg aagcgggaag ggactggctg ctattgggcg aagtgccggg | 1320 |
| gcaggatccc ctgtcatccc accttgctcc tgccgagaaa gtatccatca tggctgatgc | 1380 |
| aatgcggcgg ctgcatacgc ttgatccggc tacctgccca ttcgaccacc aagcgaaaca | 1440 |
| tcgcatcgag cgagcacgta ctcggatgga agccggtctt gtcgatcagg atgatctgga | 1500 |
| cgaagagcat caggggctcg cgccagccga actgttcgcc aggctcaagg cgcgcatgcc | 1560 |
| cgacggcgag gatctcgtcg tgacccatgg cgatgcctgc ttgccgaata tcatggtgga | 1620 |
| aaatggccgc ttttctggat tcatcgactg tggccggctg ggtgtggcgg accgctatca | 1680 |
| ggacatagcg ttggctaccc gtgatattgc tgaagagctt ggcggcgaat gggctgaccg | 1740 |

```
cttcctcgtg ctttacggta tcgccgctcc cgattcgcag cgcatcgcct tctatcgcct    1800
tcttgacgag ttcttctgaa ttgaaaaagg aagagtatga gtattcaaca tttccgtgtc    1860
gcccttattc cctttttgc ggcattttgc cttcctgttt ttgctcaccc agaaacgctg     1920
gtgaaagtaa aagatgctga agatcagttg ggtgcacgag tgggttacat cgaactggat    1980
ctcaacagcg gtaagatcct tgagagtttt cgccccgaag aacgttttcc aatgatgagc    2040
acttttaaag ttctgctatg tggcgcggta ttatcccgta ttgacgccgg gcaagagcaa    2100
ctcggtcgcc gcatacacta ttctcagaat gacttggttg agtactcacc agtcacagaa    2160
aagcatctta cggatggcat gacagtaaga gaattatgca gtgctgccat aaccatgagt    2220
gataacactg cggccaactt acttctgaca acgatcggag gaccgaagga gctaaccgct    2280
tttttgcaca acatggggga tcatgtaact cgccttgatc gttgggaacc ggagctgaat    2340
gaagccatac caaacgacga gcgtgacacc acgatgcctg tagcaatggc aacaacgttg    2400
cgcaaactat taactggcga actacttact ctagcttccc ggcaacaatt aatagactgg    2460
atggaggcgg ataaagttgc aggaccactt ctgcgctcgg cccttccggc tggctggttt    2520
attgctgata atctggagcc cggtgagcgt gggtctcgcg gtatcattgc agcactgggg    2580
ccagatggta agccctcccg tatcgtagtt atctacacga cggggagtca ggcaactatg    2640
gatgaacgaa atagacagat cgctgagata ggtgcctcac tgattaagca ttggtaactg    2700
tcagaccaag tttactcata tatactttag attgatttaa aacttcattt ttaatttaaa    2760
aggatctagg tgaagatcct tttgataat ctcatgacca aaatcccta acgtgagttt    2820 tcgttccact gagcgtcaga ccccgtagaa aagatcaaag gatcttcttg agatccttt    2880 tttctgcgcg taatctgctg cttgcaaaca aaaaaaccac cgctaccagc ggtggttttgt  2940 ttgccggatc aagagctacc aactcttttt ccgaaggtaa ctggcttcag cagagcgcag   3000
ataccaaata ctgttcttct agtgtagccg tagttaggcc accacttcaa gaactctgta    3060
gcaccgccta catacctcgc tctgctaatc ctgttaccag tggctgctgc cagtggcgat    3120
aagtcgtgtc ttaccgggtt ggactcaaga cgatagttac cggataaggc gcagcggtcg    3180
ggctgaacgg ggggttcgtg cacacagccc agcttggagc gaacgaccta caccgaactg    3240
agatacctac agcgtgagct atgagaaagc gccacgcttc ccgaaggag aaaggcggac     3300 aggtatccgg taagcggcag ggtcggaaca ggagagcgca cgagggagct tccaggggga   3360
aacgcctggt atctttatag tcctgtcggg tttcgccacc tctgacttga gcgtcgattt    3420
ttgtgatgct cgtcaggggg gcggagccta tggaaaaacg ccagcaacgc ggcctttta    3480 cggttcctgg ccttttgctg gccttttgct cacatgttct ttcctgcgtt atccctgat    3540 tctgtggata accgtattac cgcctttgag tgagctgata ccgctcgccg cagccgaacg    3600
accgagcgca gcgagtcagt gagcgaggaa gcggaagagc gcccaatacg caaaccgcct    3660
ctccccgcgc gttggccgat tcattaatgc agctggcacg acaggtttcc cgactggaaa    3720
gcgggcagtg agcgcaacgc aattaatgtg agttagctca ctcattaggc accccaggct    3780
ttacacttta tgcttccggc tcgtatgttg tgtggaattg tgagcggata acaatttcac    3840
acaggaaaca gctatgacca tgattacgcc aagcttggta ccgagctcgg atccactagt    3900
aacggccgcc agtgtgctgg aattcgccct tgatcatgca ttcgccctta ggaggtaaaa    3960
aaacatgtgt gcgacctctt ctcaatttac tcagattacc gagcataatt cccgtcgttc    4020
cgcaaactat cagccaaacc tgtggaattt cgaattcctg caatccctgg agaacgacct    4080
```

| | |
|---|---|
| gaaagtggaa aagctggagg agaaagcgac caaactggag gaagaagttc gctgcatgat | 4140 |
| caaccgtgta gacacccagc cgctgtccct gctggagctg atcgacgatg tgcagcgcct | 4200 |
| gggtctgacc tacaaatttg aaaaagacat cattaaagcc ctggaaaaca tcgtactgct | 4260 |
| ggacgaaaac aaaaagaaca aatctgacct gcacgcaacc gctctgtctt ccgtctgct | 4320 |
| gcgtcagcac ggtttcgagg tttctcagga tgtttttgag cgtttcaagg ataaagaagg | 4380 |
| tggtttcagc ggtgaactga aggtgacgt ccaaggcctg ctgagcctgt atgaagcgtc | 4440 |
| ttacctgggt ttcgagggtg agaacctgct ggaggaggcg cgtaccttt ccatcaccca | 4500 |
| cctgaagaac aacctgaaag aaggcattaa taccaaggtt gcagaacaag tgagccacgc | 4560 |
| cctggaactg ccatatcacc agcgtctgca ccgtctggag gcacgttggt tcctggataa | 4620 |
| atacgaaccg aaagaaccgc atcaccagct gctgctggag ctggcgaagc tggatttaa | 4680 |
| catggtacag accctgcacc agaaagagct gcaagatctg tcccgctggt ggaccgagat | 4740 |
| gggcctggct agcaaactgg attttgtacg cgaccgcctg atggaagttt atttctgggc | 4800 |
| actgggtatg gcgccagacc cgcagtttgg tgaatgtcgc aaagctgtta ctaaaatgtt | 4860 |
| tggtctggtg acgatcatcg atgacgtgta tgacgtttat ggcactctgg acgaactgca | 4920 |
| actgttcacc gatgctgtag agcgctggga cgttaacgct attaacaccc tgccggacta | 4980 |
| tatgaaactg tgtttcctgg cactgtacaa caccgttaac gacacgtcct attctattct | 5040 |
| gaaagagaaa ggtcataaca acctgtccta tctgacgaaa agctggcgtg aactgtgcaa | 5100 |
| agcctttctg caagaggcga atggtccaa caacaaaatt atcccggctt tctccaagta | 5160 |
| cctgaaaaac gccagcgttt cctcctccgg tgtagcgctg ctggcgccgt cttactttc | 5220 |
| cgtatgccag cagcaggaag acatctccga ccacgcgctg agttccctga ccgacttcca | 5280 |
| tggtctggtg cgttctagct gcgttatctt ccgcctgtgc aacgatctgg ccacctctgc | 5340 |
| ggcggagctg gaacgtggcg agactaccaa ttctatcatt agctacatgc acgaaaacga | 5400 |
| tggtaccagc gaggaacagg cccgcgaaga actgcgtaaa ctgatcgacg ccgaatggaa | 5460 |
| aaagatgaat cgtgaacgcg ttagcgactc caccctgctg cctaaagcgt tcatggaaat | 5520 |
| cgcagttaac atggcacgtg tttcccactg cacctaccag tatggcgatg gtctgggtcg | 5580 |
| cccagactac gcgactgaaa accgcatcaa actgctgctg attgacccctt tcccgattaa | 5640 |
| ccagctgatg tatgtctaac tgcagggatc cgtcgaccg | 5679 |

<210> SEQ ID NO 37
<211> LENGTH: 6974
<212> TYPE: DNA
<213> ORGANISM: Artificial Sequence
<220> FEATURE:
<223> OTHER INFORMATION: Synthetic Construct

<400> SEQUENCE: 37

| | |
|---|---|
| gtgcggccgc aagcttgtcg acggagctcg aattcggatc cctgcagtta gacatacatc | 60 |
| agctggttaa tcgggaaagg gtcaatcagc agcagtttga tgcggttttc agtcgcgtag | 120 |
| tctgggcgac ccagaccatc gccatactgg taggtgcagt gggaaacacg tgccatgtta | 180 |
| actgcgattt ccatgaacgc tttaggcagc agggtgagt cgctaacgcg ttcacgattc | 240 |
| atctttttcc attcggcgtc gatcagttta cgcagttctt cgcgggcctg ttcctcgctg | 300 |
| gtaccatcgt tttcgtgcat gtagctaatg atagaattgg tagtctcgcc acgttccagc | 360 |
| tccgccgcag aggtggccag atcgttgcac aggcggaaga taacgcagct agaacgcacc | 420 |
| agaccatgga agtcggtcag ggaacgcagc gcgtggtcgg agatgtcttc ctgctgctgg | 480 |

-continued

```
catacggaaa agtaagacgg cgccagcagc gctacaccgg aggaggaaac gctggcgttt      540
tccaggtact tggagaaagc cgggataatt ttgttgttgg accatttcgc ctcttgcaga      600
aaggctttgc acagttcacg ccagcttttc gtcagatagg acaggttgtt atgacctttc      660
tctttcagaa tagaatagga cgtgtcgtta acggtgttgt acagtgccag gaaacacagt      720
ttcatatagt ccggcagggt gttaatagcg ttaacgtccc agcgctctac agcatcggtg      780
aacagttgca gttcgtccag agtgccataa acgtcataca cgtcatcgat gatcgtcacc      840
agaccaaaca ttttagtaac agcattgcga cattcaccaa actgcgggtc tggcgccata      900
cccagtgccc agaaataaac ttccatcagg cggtcgcgta caaaatccag tttgctagcc      960
aggcccatct cggtccacca gcgggacaga tcttgcagct cttctggtg cagggtctgt     1020 accatgttaa atccagcttc cgccagctcc agcagcagct ggtgatgcgg ttctttcggt     1080
tcgtatttat ccaggaacca acgtgcctcc agacggtgca gacgctggtg atatggcagt     1140
tccagggcgt ggctcacttg ttctgcaacc ttggtattaa tgccttcttt caggttgttc     1200
ttcaggtggg tgatggaaaa ggtacgcgcc tcctccagca ggttctcacc ctcgaaaccc     1260
aggtaagacg cttcatacag gctcagcagg ccttggacgt caccttcag ttcaccgctg     1320 aaaccaccta ctttaacctt gaaacgcaca aaaacatcct gagaaacctc gaaaccgtgc     1380
tgacgcagca gacggaaaga cagagcggtt cgtgcaggt cagatttgtt cttttgttt     1440 tcgtccagca gtacgacgtt ttccagggct ttaatgatgt ctttttcaaa tttgtaggtc     1500
agacccaggc gctgcacatc gtcgatcagc tccagcaggg acagcggctg ggtgtctaca     1560
cggttgatca tgcagcgaac ttcttcctcc agtttggtcg ctttctcctc cagcttttcc     1620
actttcaggt cgttctccag ggattgcagg aattcgaaat tccacaggtt tggctgatag     1680
tttgcggaac gacgggaatt atgctcggta atctgagtaa attgagaaga ggtcgcacac     1740
atggtatatc tccttcttaa agttaaacaa aattatttct agaggggaat tgttatccgc     1800
tcacaattcc cctatagtga gtcgtattaa tttcgcggga tcgagatctc gatcctctac     1860
gccggacgca tcgtggccgg catcaccggc gccacaggtg cggttgctgg cgcctatatc     1920
gccgacatca ccgatgggga agatcgggct cgccacttcg gctcatgag cgcttgtttc     1980 ggcgtgggta tggtgcagg ccccgtggcc gggggactgt tgggcgccat ctccttgcat     2040
gcaccattcc ttgcggcggc ggtgctcaac ggcctcaacc tactactggg ctgcttccta     2100
atgcaggagt cgcataaggg agagcgtcga tcccggac accatcgaat ggcgcaaaac     2160
ctttcgcggt atggcatgat agcgcccgga agagagtcaa ttcagggtgg tgaatgtgaa     2220
accagtaacg ttatacgatg tcgcagagca tgccggtgtc tcttatcaga ccgtttcccg     2280
cgtggtgaac caggccagcc acgtttctgc gaaaacgcgg gaaaagtgg aagcggcgat     2340 ggcggagctg aattacattc ccaaccgcgt ggcacaacaa ctggcgggca aacagtcgtt     2400
gctgattggc gtagccacct ccagtctggc cctgcacgcg ccgtcgcaaa ttgtcgcggc     2460
gattaaatct cgcgccgatc aactgggtgc cagcgtggtg gtgtcgatgg tagaacgaag     2520
cggcgtcgaa gcctgtaaag cggcggtgca caatcttctc gcgcaacgcg tcagtgggct     2580
gatcattaac tatccgctgg atgaccagga tgccattgct gtggaagctg cctgcactaa     2640
tgttccggcg ttatttcttg atgtctctga ccagacaccc atcaacagta ttattttctc     2700
ccatgaagac ggtacgcgac tgggcgtgga gcatctggtc gcattgggtc accagcaaat     2760
cgcgctgtta gcgggcccat taagttctgt ctcggcgcgt ctgcgtctgg ctggctggca     2820
```

```
taaatatctc actcgcaatc aaattcagcc gatagcggaa cgggaaggcg actggagtgc    2880
catgtccggt tttcaacaaa ccatgcaaat gctgaatgag ggcatcgttc ccactgcgat    2940
gctggttgcc aacgatcaga tggcgctggg cgcaatgcgc gccattaccg agtccgggct    3000
gcgcgttggt gcggatatct cggtagtggg atacgacgat accgaagaca gctcatgtta    3060
tatcccgccg ttaaccacca tcaaacagga ttttcgcctg ctggggcaaa ccagcgtgga    3120
ccgcttgctg caactctctc agggccaggc ggtgaagggc aatcagctgt tgcccgtctc    3180
actggtgaaa agaaaaacca ccctggcgcc caatacgcaa accgcctctc cccgcgcgtt    3240
ggccgattca ttaatgcagc tggcacgaca ggtttcccga ctggaaagcg ggcagtgagc    3300
gcaacgcaat taatgtaagt tagctcactc attaggcacc gggatctcga ccgatgccct    3360
tgagagcctt caacccagtc agctccttcc ggtgggcgcg gggcatgact atcgtcgccg    3420
cacttatgac tgtcttcttt atcatgcaac tcgtaggaca ggtgccggca gcgctctggg    3480
tcattttcgg cgaggaccgc tttcgctgga gcgcgacgat gatcggcctg tcgcttgcgg    3540
tattcggaat cttgcacgcc ctcgctcaag ccttcgtcac tggtcccgcc accaaacgtt    3600
tcggcgagaa gcaggccatt atcgccggca tggcggcccc acgggtgcgc atgatcgtgc    3660
tcctgtcgtt gaggacccgg ctaggctggc ggggttgcct tactggttag cagaatgaat    3720
caccgatacg cgagcgaacg tgaagcgact gctgctgcaa aacgtctgcg acctgagcaa    3780
caacatgaat ggtcttcggt ttccgtgttt cgtaaagtct ggaaacgcgg aagtcagcgc    3840
cctgcaccat tatgttccgg atctgcatcg caggatgctg ctggctaccc tgtggaacac    3900
ctacatctgt attaacgaag cgctggcatt gaccctgagt gattttctc tggtcccgcc     3960
gcatccatac cgccagttgt ttaccctcac aacgttccag taaccgggca tgttcatcat    4020
cagtaacccg tatcgtgagc atcctctctc gtttcatcgg tatcattacc cccatgaaca    4080
gaaatccccc ttacacggag gcatcagtga ccaaacagga aaaaccgcc cttaacatgg     4140
cccgctttat cagaagccag acattaacgc ttctggagaa actcaacgag ctggacgcgg    4200
atgaacaggc agacatctgt gaatcgcttc acgaccacgc tgatgagctt taccgcagct    4260
gcctcgcgcg tttcggtgat gacggtgaaa acctctgaca catgcagctc ccggagacgg    4320
tcacagcttg tctgtaagcg gatgccggga gcagacaagc ccgtcagggc gcgtcagcgg    4380
gtgttggcgg gtgtcgggc gcagccatga cccagtcacg tagcgatagc ggagtgtata     4440
ctggcttaac tatgcggcat cagagcagat tgtactgaga gtgcaccata tatgcggtgt    4500
gaaataccgc acagatgcgt aaggagaaaa taccgcatca ggcgctcttc cgcttcctcg    4560
ctcactgact cgctgcgctc ggtcgttcgg ctgcggcgag cggtatcagc tcactcaaag    4620
gcggtaatac ggttatccac agaatcaggg gataacgcag gaaagaacat gtgagcaaaa    4680
ggccagcaaa aggccaggaa ccgtaaaaag gccgcgttgc tggcgttttt ccataggctc    4740
cgcccccctg acgagcatca caaaaatcga cgctcaagtc agaggtggcg aaacccgaca    4800
ggactataaa gataccaggc gtttccccct ggaagctccc tcgtgcgctc tcctgttccg    4860
accctgccgc ttaccggata cctgtccgcc tttctccctt cgggaagcgt ggcgctttct    4920
catagctcac gccgtaggta tctcagttcg gtgtaggtcg atcgctccaa gctgggctgt    4980
gtgcacgaac cccccgttca gcccgaccgc tgcgccttat ccggtaacta tcgtcttgag    5040
tccaacccgg taagacacga cttatcgcca ctggcagcag ccactggtaa caggattagc    5100
agagcgaggt atgtaggcgg tgctacagag ttcttgaagt ggtggcctaa ctacggctac    5160
actagaagga cagtatttgg tatctgcgct ctgctgaagc cagttacctt cggaaaaaga    5220
```

```
gttggtagct cttgatccgg caaacaaacc accgctggta gcggtggttt ttttgtttgc    5280
aagcagcaga ttacgcgcag aaaaaaagga tctcaagaag atcctttgat cttttctacg    5340
gggtctgacg ctcagtggaa cgaaaactca cgttaaggga ttttggtcat gaacaataaa    5400
actgtctgct tacataaaca gtaatacaag gggtgttatg agccatattc aacgggaaac    5460
gtcttgctct aggccgcgat taaattccaa catggatgct gatttatatg ggtataaatg    5520
ggctcgcgat aatgtcgggc aatcaggtgc gacaatctat cgattgtatg ggaagcccga    5580
tgcgccagag ttgtttctga acatggcaa aggtagcgtt gccaatgatg ttacagatga    5640
gatggtcaga ctaaactggc tgacggaatt tatgcctctt ccgaccatca agcattttat    5700
ccgtactcct gatgatgcat ggttactcac cactgcgatc cccgggaaaa cagcattcca    5760
ggtattagaa gaatatcctg attcaggtga aaatattgtt gatgcgctgg cagtgttcct    5820
gcgccggttg cattcgattc ctgtttgtaa ttgtcctttt aacagcgatc gcgtatttcg    5880
tctcgctcag gcgcaatcac gaatgaataa cggtttggtt gatgcgagtg attttgatga    5940
cgagcgtaat ggctggcctg ttgaacaagt ctggaaagaa atgcataaac ttttgccatt    6000
ctcaccggat tcagtcgtca ctcatggtga tttctcactt gataaccta ttttgacga    6060 ggggaaatta ataggttgta ttgatgttgg acgagtcgga atcgcagacc gataccagga    6120
tcttgccatc ctatggaact gcctcggtga gttttctcct tcattacaga aacggctttt    6180
tcaaaaatat ggtattgata atcctgatat gaataaattg cagtttcatt tgatgctcga    6240 tgagttttc taagaattaa ttcatgagcg gatacatatt tgaatgtatt tagaaaaata    6300
aacaaatagg ggttccgcgc acatttcccc gaaaagtgcc acctgaaatt gtaaacgtta    6360
atattttgtt aaaattcgcg ttaaattttt gttaaatcag ctcattttt aaccaatagg    6420 ccgaaatcgg caaaatccct tataaatcaa aagaatagac cgagataggg ttgagtgttg    6480
ttccagtttg gaacaagagt ccactattaa agaacgtgga ctccaacgtc aaagggcgaa    6540
aaaccgtcta tcagggcgat ggcccactac gtgaaccatc accctaatca agttttttgg    6600
ggtcgaggtg ccgtaaagca ctaaatcgga accctaaagg agcccccga tttagagctt    6660 gacggggaaa gccggcgaac gtggcgagaa aggaagggaa gaaagcgaaa ggagcgggcg    6720
ctagggcgct ggcaagtgta gcggtcacgc tgcgcgtaac caccacaccc gccgcgctta    6780
atgcgccgct acagggcgcg tcccattcgc caatccggat atagttcctc ctttcagcaa    6840 aaaaccctc aagacccgtt tagaggcccc aaggggttat cgtagttatt gctcagcggt    6900
ggcagcagcc aactcagctt cctttcgggc tttgttagca gccggatctc agtggtggtg    6960
gtggtggtgc tcga                                                      6974
```

<210> SEQ ID NO 38
<211> LENGTH: 1719
<212> TYPE: DNA
<213> ORGANISM: Artificial Sequence
<220> FEATURE:
<223> OTHER INFORMATION: Synthetic Construct

<400> SEQUENCE: 38

```
gaattcaaaa tgtgtgcaac ttcatcccaa ttcactcaaa tcacagagca taattctaga      60
cgttcagcta actaccaacc aaatctgtgg aattttgaat ttcttcaatc ccttgaaaat     120
gatttgaaag tggaaaagtt ggaggaaaaa gccacaaaac tagaggaaga agttagatgt     180
atgataaaca gagtagatac acaacctctg tcactactag aattgattga cgatgtccag     240
```

| | |
|---|---:|
| aggctgggtt taacatataa gttcgaaaag gatataatca aagccttaga aaacatagtc | 300 |
| cttctagatg aaaacaagaa gaataagtct gacttgcacg caaccgctct gagttttaga | 360 |
| ttgctgagac aacatggttt tgaagtaagt caagatgtgt ttgaaaggtt caaagacaaa | 420 |
| gagggaggat tctcaggaga attaaaggga gatgtgcagg gtctgttgtc attgtacgag | 480 |
| gccagttatt tgggggttga aggggaaaat ctactagagg aggccagaac cttctctata | 540 |
| acccatctga agaataactt gaagaaggc atcaatacaa aagtggctga acaagtttca | 600 |
| catgcattgg aattgcccta ccaccaaaga cttcatagac ttgaagccag atggttttg | 660 |
| gacaagtatg aaccaaagga gcctcaccat caacttttat tggaattagc aaaactggat | 720 |
| tttaacatgg ttcagacatt acaccagaaa gaattgcagg acctatcaag atggtggacg | 780 |
| gagatgggtt tagccagcaa gttagatttc gttagagata gattgatgga agtttacttt | 840 |
| tgggcactgg gaatggcacc agatcctcaa tttggtgaat gtagaaaggc agttacaaag | 900 |
| atgtttggtc tagtaacaat cattgatgat gtttatgatg tgtacggaac tttggatgaa | 960 |
| ttacaactat tcaccgacgc agttgaacgt tgggatgtaa acgcaataaa cacgttgcct | 1020 |
| gattatatga agctgtgttt tctggcattg tacaacacag tcaatgacac ttcttactcc | 1080 |
| attttaaagg agaaagggca taacaatcta tcctatttga caaaatcatg gagggagtta | 1140 |
| tgcaaagcat tccttcaaga agctaagtgg tctaacaata agataatccc agcattctcc | 1200 |
| aagtatcttg aaaacgcttc cgtatcctcc tccggtgtgg ccctactagc accatcatat | 1260 |
| ttttccgtct gccagcagca ggaagatatc tctgatcatg ctttgagatc cttaacagat | 1320 |
| tttcatggtc tagtcagatc ctcttgcgtg attttcagat tgtgcaatga tttggctact | 1380 |
| tcagccgcag agttagagag gggtgaaacc acgaactcaa ttattagtta tatgcacgag | 1440 |
| aatgatggaa catccgaaga acaagcccgt gaagaattaa gaaaactgat cgatgctgaa | 1500 |
| tggaagaaga tgaatagaga aagagtttcc gacagcactt tgctgcctaa ggcattcatg | 1560 |
| gagatagctg ttaacatggc tagggtttca cactgtacat accaaatcgg ggacggtctt | 1620 |
| ggaaggcccg actacgccac tgaaaataga attaaactgc tactgattga tccttttccc | 1680 |
| attaaccagt taatgtacgt gtaataggga tccgaattc | 1719 |

<210> SEQ ID NO 39
<211> LENGTH: 7658
<212> TYPE: DNA
<213> ORGANISM: Artificial Sequence
<220> FEATURE:
<223> OTHER INFORMATION: Synthetic Construct

<400> SEQUENCE: 39

| | |
|---|---:|
| acggattaga agccgccgag cgggtgacag ccctccgaag gaagactctc ctccgtgcgt | 60 |
| cctcgtcttc accggtcgcg ttcctgaaac gcagatgtgc ctcgcgccgc actgctccga | 120 |
| acaataaaga ttctacaata ctagctttta tggttatgaa gaggaaaaat tggcagtaac | 180 |
| ctggccccac aaaccttcaa atgaacgaat caaattaaca accataggat gataatgcga | 240 |
| ttagtttttt agccttattt ctggggtaat taatcagcga agcgatgatt tttgatctat | 300 |
| taacagatat ataaatgcaa aaactgcata accactttaa ctaatacttt caacattttc | 360 |
| ggtttgtatt acttcttatt caaatgtaat aaaagtatca acaaaaaatt gttaatatac | 420 |
| ctctatactt taacgtcaag gagaaaaaac cccggatcgg actactagca gctgtaatac | 480 |
| gactcactat agggaatatt aagctatcaa acaagtttgt acaaaaaagc aggctgaatt | 540 |
| caaaatgtgt gcaacttcat cccaattcac tcaaatcaca gagcataatt ctagacgttc | 600 |

```
agctaactac caaccaaatc tgtggaattt tgaatttctt caatcccttg aaaatgattt      660
gaaagtggaa aagttggagg aaaaagccac aaaactagag gaagaagtta gatgtatgat      720
aaacagagta gatacacaac ctctgtcact actagaattg attgacgatg tccagaggct      780
gggtttaaca tataagttcg aaaaggatat aatcaaagcc ttagaaaaca tagtccttct      840
agatgaaaac aagaagaata agtctgactt gcacgcaacc gctctgagtt ttagattgct      900
gagacaacat ggttttgaag taagtcaaga tgtgtttgaa aggttcaaag acaaagaggg      960
aggattctca ggagaattaa agggagatgt gcagggtctg ttgtcattgt acgaggccag     1020
ttatttgggg tttgaagggg aaaatctact agaggaggcc agaaccttct ctataaccca     1080
tctgaagaat aacttgaaag aaggcatcaa tacaaaagtg gctgaacaag tttcacatgc     1140
attggaattg ccctaccacc aaagacttca tagacttgaa gccagatggt ttttggacaa     1200
gtatgaacca aaggagcctc accatcaact tttattggaa ttagcaaaac tggattttaa     1260
catggttcag acattacacc agaaagaatt gcaggaccta tcaagatggt ggacggagat     1320
gggtttagcc agcaagttag atttcgttag agatagattg atggaagttt acttttgggc     1380
actgggaatg gcaccagatc ctcaatttgg tgaatgtaga aaggcagtta caaagatgtt     1440
tggtctagta acaatcattg atgatgttta tgatgtgtac ggaactttgg atgaattaca     1500
actattcacc gacgcagttg aacgttggga tgtaaacgca ataaacacgt tgcctgatta     1560
tatgaagctg tgttttctgg cattgtacaa cacagtcaat gacacttctt actccatttt     1620
aaaggagaaa gggcataaca atctatccta tttgacaaaa tcatggaggg agttatgcaa     1680
agcattcctt caagaagcta gtggtctaa caataagata atcccagcat tctccaagta     1740
tcttgaaaac gcttccgtat cctcctccgg tgtggcccta ctagcaccat catatttttc     1800
cgtctgccag cagcaggaag atatctctga tcatgctttg agatccttaa cagattttca     1860
tggtctagtc agatcctctt gcgtgatttt cagattgtgc aatgatttgg ctacttcagc     1920
cgcagagtta gagaggggtg aaaccacgaa ctcaattatt agttatatgc acgagaatga     1980
tggaacatcc gaagaacaag cccgtgaaga attaagaaaa ctgatcgatg ctgaatggaa     2040
gaagatgaat agagaaagag tttccgacag cactttgctg cctaaagcat tcatggagat     2100
agctgttaac atggctaggg tttcacactg tacataccaa tacggggacg gtcttggaag     2160
gcccgactac gccactgaaa atagaattaa actgctactg attgatcctt tccccattaa     2220
ccagttaatg tacgtgtaat agggatccga attcacccag ctttcttgta caaagtggtt     2280
cgatctagag ggcccttcga aggtaagcct atccctaacc ctctcctcgg tctcgattct     2340
acgcgtaccg gtcatcatca ccatcaccat tgagtttaaa cccgctgatc ctagagggcc     2400
gcatcatgta attagttatg tcacgcttac attcacgccc tccccccaca tccgctctaa     2460
ccgaaaagga aggagttaga aacctgaag tctaggtccc tatttatttt tttatagtta     2520
tgttagtatt aagaacgtta tttatatttc aaatttttct ttttttttctg tacagacgcg     2580 tgtacgcatg taacattata ctgaaaacct tgcttgagaa ggttttggga cgctcgaagg     2640
ctttaatttg caagctgcgg ccctgcatta atgaatcggc caacgcgcgg ggagaggcgg     2700
tttgcgtatt gggcgctctt ccgcttcctc gctcactgac tcgctgcgct cggtcgttcg     2760
gctgcggcga gcggtatcag ctcactcaaa ggcggtaata cggttatcca cagaatcagg     2820
ggataacgca ggaaagaaca tgtgagcaaa aggccagcaa aagccaggaa ccgtaaaaa     2880 ggccgcgttg ctggcgtttt tccataggct ccgcccccct gacgagcatc acaaaaatcg     2940
```

```
acgctcaagt cagaggtggc gaaacccgac aggactataa agataccagg cgtttccccc    3000
tggaagctcc ctcgtgcgct ctcctgttcc gaccctgccg cttaccggat acctgtccgc    3060
ctttctccct tcgggaagcg tggcgctttc tcatagctca cgctgtaggt atctcagttc    3120
ggtgtaggtc gttcgctcca agctgggctg tgtgcacgaa ccccccgttc agcccgaccg    3180
ctgcgcctta tccggtaact atcgtcttga gtccaacccg gtaagacacg acttatcgcc    3240
actggcagca gccactggta acaggattag cagagcgagg tatgtaggcg gtgctacaga    3300
gttcttgaag tggtggccta actacggcta cactagaagg acagtatttg gtatctgcgc    3360
tctgctgaag ccagttacct tcggaaaaag agttggtagc tcttgatccg gcaaacaaac    3420
caccgctggt agcggtggtt ttttttgtttg caagcagcag attacgcgca gaaaaaaagg    3480
atctcaagaa gatcctttga tcttttctac ggggtctgac gctcagtgga acgaaaactc    3540
acgttaaggg attttggtca tgagattatc aaaaaggatc ttcacctaga tccttttaaa    3600
ttaaaaatga agttttaaat caatctaaag tatatatgag taaacttggt ctgacagtta    3660
ccaatgctta atcagtgagg cacctatctc agcgatctgt ctatttcgtt catccatagt    3720
tgcctgactc cccgtcgtgt agataactac gatacgggag cgcttaccat ctggccccag    3780
tgctgcaatg ataccgcgag acccacgctc accggctcca gatttatcag caataaacca    3840
gccagccgga agggccgagc gcagaagtgg tcctgcaact ttatccgcct ccatccagtc    3900
tattaattgt tgccgggaag ctagagtaag tagttcgcca gttaatagtt tgcgcaacgt    3960
tgttggcatt gctacaggca tcgtggtgtc actctcgtcg tttggtatgg cttcattcag    4020
ctccggttcc caacgatcaa ggcgagttac atgatccccc atgttgtgca aaaaagcggt    4080
tagctccttc ggtcctccga tcgttgtcag aagtaagttg gccgcagtgt tatcactcat    4140
ggttatggca gcactgcata attctcttac tgtcatgcca tccgtaagat gcttttctgt    4200
gactggtgag tactcaacca agtcattctg agaatagtgt atgcggcgac cgagttgctc    4260
ttgcccggcg tcaatacggg ataatagtgt atcacatagc agaactttaa aagtgctcat    4320
cattggaaaa cgttcttcgg ggcgaaaact ctcaaggatc ttaccgctgt tgagatccag    4380
ttcgatgtaa cccactcgtg cacccaactg atcttcagca tcttttactt tcaccagcgt    4440
ttctgggtga gcaaaaacag gaaggcaaaa tgccgcaaaa aagggaataa gggcgacacg    4500
gaaatgttga atactcatac tcttcctttt tcaatgggta ataactgata taattaaatt    4560
gaagctctaa tttgtgagtt tagtatacat gcatttactt ataatacagt tttttagttt    4620
tgctggccgc atcttctcaa atatgcttcc cagcctgctt ttctgtaacg ttcaccctct    4680
accttagcat cccttccctt tgcaaatagt cctcttccaa caataataat gtcagatcct    4740
gtagagacca catcatccac ggttctatac tgttgaccca atgcgtctcc cttgtcatct    4800
aaacccacac cgggtgtcat aatcaaccaa tcgtaacctt catctcttcc acccatgtct    4860
ctttgagcaa taaagccgat aacaaaatct ttgtcgctct tcgcaatgtc aacagtaccc    4920
ttagtatatt ctccagtaga tagggagccc ttgcatgaca attctgctaa catcaaaagg    4980
cctctaggtt cctttgttac ttcttctgcc gcctgcttca aaccgctaac aatacctggg    5040
cccaccacac cgtgtgcatt cgtaatgtct gcccattctg ctattctgta tacacccgca    5100
gagtactgca atttgactgt attaccaatg tcagcaaatt ttctgtcttc gaagagtaaa    5160
aaattgtact ggcggataa tgcctttagc ggcttaactg tgccctccat ggaaaaatca    5220
gtcaagatat ccacatgtgt ttttagtaaa caaattttgg gacctaatgc ttcaactaac    5280
tccagtaatt ccttggtggt acgaacatcc aatgaagcac acaagtttgt ttgcttttcg    5340
```

```
tgcatgatat taaatagctt ggcagcaaca ggactaggat gagtagcagc acgttccttA    5400
tatgtagctt tcgacatgat ttatcttcgt ttcctgcagg tttttgttct gtgcagttgg    5460
gttaagaata ctgggcaatt tcatgtttct tcaacactac atatgcgtat atataccaat    5520
ctaagtctgt gctccttcct tcgttcttcc ttctgttcgg agattaccga atcaaaaaaa    5580
tttcaaagaa accgaaatca aaaaaagaa taaaaaaaa atgatgaatt gaattgaaaa      5640
gctagcttat cgatgataag ctgtcaaaga tgagaattaa ttccacggac tatagactat    5700
actagatact ccgtctactg tacgatacac ttccgctcag gtccttgtcc tttaacgagg    5760
ccttaccact cttttgttac tctattgatc cagctcagca aaggcagtgt gatctaagat    5820
tctatcttcg cgatgtagta aaactagcta gaccgagaaa gagactagaa atgcaaaagg    5880
cacttctaca atggctgcca tcattattat ccgatgtgac gctgcagctt ctcaatgata    5940
ttcgaatacg ctttgaggag atacagccta atatccgaca aactgtttta cagatttacg    6000
atcgtacttg ttacccatca ttgaattttg aacatccgaa cctgggagtt ttccctgaaa    6060
cagatagtat atttgaacct gtataataat atatagtcta gcgctttacg aagacaatg     6120
tatgtatttc ggttcctgga gaaactattg catctattgc ataggtaatc ttgcacgtcg    6180
catccccggt tcattttctg cgtttccatc ttgcacttca atagcatatc tttgttaacg    6240
aagcatctgt gcttcatttt gtagaacaaa aatgcaacgc gagagcgcta attttcaaa     6300
caaagaatct gagctgcatt tttacagaac agaaatgcaa cgcgaaagcg ctattttacc    6360
aacgaagaat ctgtgcttca tttttgtaaa acaaaaatgc aacgcgacga gagcgctaat    6420
ttttcaaaca aagaatctga gctgcatttt tacagaacag aaatgcaacg cgagagcgct    6480
attttaccaa caaagaatct atacttcttt tttgttctac aaaaatgcat cccgagagcg    6540
ctatttttct aacaaagcat cttagattac tttttttctc ctttgtgcgc tctataatgc    6600
agtctcttga taactttttg cactgtaggt ccgttaaggt tagaagaagg ctactttggt    6660
gtctatttc tcttccataa aaaaagcctg actccacttc ccgcgtttac tgattactag     6720
cgaagctgcg ggtgcatttt ttcaagataa aggcatcccc gattatattc tataccgatg    6780
tggattgcgc atactttgtg aacagaaagt gatagcgttg atgattcttc attggtcaga    6840
aaattatgaa cggtttcttc tatttgtct ctatatacta cgtataggaa atgtttacat      6900
tttcgtattg ttttcgattc actctatgaa tagttcttac tacaattttt ttgtctaaag    6960
agtaatacta gagataaaca taaaaaatgt agaggtcgag tttagatgca agttcaagga    7020
gcgaaaggtg gatgggtagg ttatataggg atatagcaca gagatatata gcaaagagat    7080
actttgagc aatgtttgtg gaagcggtat tcgcaatggg aagctccacc ccggttgata     7140
atcagaaaag ccccaaaaac aggaagattg tataagcaaa tatttaaatt gtaaacgtta    7200
atattttgtt aaaattcgcg ttaaattttt gttaaatcag ctcatttttt aacgaatagc    7260
ccgaaatcgg caaaatccct tataaatcaa agaatagac cgagataggg ttgagtgttg     7320
ttccagtttc caacaagagt ccactattaa agaacgtgga ctccaacgtc aaagggcgaa    7380
aaagggtcta tcagggcgat ggcccactac gtgaaccatc acctaatca gttttttgg      7440
ggtcgaggtg ccgtaaagca gtaaatcgga agggtaaacg atgcccca tttagagctt      7500
gacggggaaa gccggcgaac gtggcgagaa aggaagggaa gaaagcgaaa ggagcggggg    7560
ctagggcggt gggaagtgta gggtcacgc tgggcgtaac caccacaccc gccgcgctta     7620
atggggcgct acagggcgcg tgggatgat ccactagt                              7658
```

<210> SEQ ID NO 40
<211> LENGTH: 1746
<212> TYPE: DNA
<213> ORGANISM: Artificial Sequence
<220> FEATURE:
<223> OTHER INFORMATION: Synthetic Construct

<400> SEQUENCE: 40

| | | | | | |
|---|---|---|---|---|---|
| catcttaagc | ttgtttaact | ttaagaagga | gatatacata | tgtgcgccac | cagcagccag | 60 |
| ttcacccaga | tcaccgagca | taatagccgt | cggtccgcga | actaccagcc | caacctgtgg | 120 |
| aacttcgagt | tcctgcagag | cctggaaaac | gacctgaagg | tggagaagct | cgaagagaag | 180 |
| gccaccaagc | tggaggagga | ggtgcgttgc | atgatcaacc | gggtggacac | ccagcccctg | 240 |
| agcctgctgg | agctcatcga | cgacgtgcag | cgcctgggcc | tgacctacaa | gtttgagaaa | 300 |
| gatatcatca | aggcgctgga | gaacatcgtc | ctgctggacg | agaataagaa | gaacaaaagc | 360 |
| gatctgcacg | cgaccgccct | gagcttccgc | ctgctgcggc | agcatggctt | tgaggtgagc | 420 |
| caggacgtgt | tcgagcgctt | caaggacaaa | gaaggggggct | tctccgggga | actgaagggt | 480 |
| gacgtgcagg | gcctgctgag | cctgtacgag | gccagctatc | tcggtttcga | aggcgaaaat | 540 |
| ctgctggagg | aggcccgtac | cttcagcatc | acccatctga | agaacaacct | caaggagggg | 600 |
| atcaacacga | aggtggccga | gcaggtgtcc | cacgcgctgg | agctgccgta | tcatcaacgc | 660 |
| ctgcaccgcc | tggaggcgcg | gtggtttctg | gacaagtacg | aacccaagga | gccgcatcac | 720 |
| cagctgctgc | tggaactggc | caaactcgat | ttcaacatgg | tccagaccct | gcaccaaaaa | 780 |
| gagctgcagg | acctgagccg | tggtggacc | gagatgggcc | tcgccagcaa | gctggatttc | 840 |
| gtgcgggacc | gcctgatgga | agtgtacttc | tgggcgctgg | gcatggcgcc | ggacccgcag | 900 |
| ttcggcgaat | gccgcaaggc | cgtcaccaag | atgttcggtc | tggtcaccat | tatcgatgac | 960 |
| gtctatgacg | tgtacggtac | cctggacgaa | ctgcagctct | tcaccgacgc | ggtggaacgc | 1020 |
| tgggacgtga | acgccatcaa | cacgctgccc | gactatatga | agctgtgctt | cctggccctg | 1080 |
| tacaacaccg | tgaacgacac | gtcctactcc | atcctgaagg | agaagggcca | caataacctg | 1140 |
| agctatctga | ccaaaagctg | gcgcgaactg | tgcaaggcct | tcctgcaaga | agccaagtgg | 1200 |
| agcaataaca | agatcatccc | cgccttcagc | aagtacctgg | agaacgccag | cgtgtcctcc | 1260 |
| agcgggggtcg | cgctgctggc | gccgagctac | ttctcggtct | gccagcagca | ggaagatatc | 1320 |
| tcggaccacg | ccctccgctc | cctgaccgac | ttccacggcc | tggtgcgctc | gtcctgcgtg | 1380 |
| atctttcggc | tgtgcaacga | tctggcgacc | tcggcggcgg | aactcgaacg | cggcgaaacc | 1440 |
| accaacagca | tcatcagcta | catgcacgag | aacgacggca | cgagcgagga | acaggcccgc | 1500 |
| gaagagctgc | gcaagctgat | cgacgccgag | tggaagaaaa | tgaaccgcga | gcgcgtgtcg | 1560 |
| gacagcaccc | tgctgccgaa | ggcgttcatg | gagatcgccg | tgaacatggc | ccgcgtgagc | 1620 |
| cactgcacct | accaatatgg | ggacgggctg | ggccgcccgg | attacgccac | cgagaaccgc | 1680 |
| atcaagctgc | tgctcatcga | cccgttcccc | atcaaccagc | tgatgtacgt | gtgaggatcc | 1740 |
| cgtaac | | | | | | 1746 |

<210> SEQ ID NO 41
<211> LENGTH: 4768
<212> TYPE: DNA
<213> ORGANISM: Artificial Sequence
<220> FEATURE:
<223> OTHER INFORMATION: Synthetic Construct

<400> SEQUENCE: 41

-continued

```
ctcgggccgt ctcttgggct tgatcggcct tcttgcgcat ctcacgcgct cctgcggcgg      60
cctgtagggc aggctcatac ccctgccgaa ccgcttttgt cagccggtcg ccacggctt      120
ccggcgtctc aacgcgcttt gagattccca gcttttcggc caatccctgc ggtgcatagg     180
cgcgtggctc gaccgcttgc gggctgatgg tgacgtggcc cactggtggc cgctccaggg     240
cctcgtagaa cgcctgaatg cgcgtgtgac gtgccttgct gccctcgatg ccccgttgca     300
gccctagatc ggccacagcg gccgcaaacg tggtctggtc gcgggtcatc tgcgctttgt     360
tgccgatgaa ctccttggcc gacagcctgc cgtcctgcgt cagcggcacc acgaacgcgg     420
tcatgtgcgg gctggtttcg tcacggtgga tgctggccgt cacgatgcga tccgccccgt     480
acttgtccgc cagccacttg tgcgccttct cgaagaacgc cgcctgctgt tcttggctgg     540
ccgacttcca ccattccggg ctggccgtca tgacgtactc gaccgccaac acagcgtcct     600
tgcgccgctt ctctggcagc aactcgcgca gtcggcccat cgcttcatcg gtgctgctgg     660
ccgcccagtg ctcgttctct ggcgtcctgc tggcgtcagc gttgggcgtc tcgcgctcgc     720
ggtaggcgtg cttgagactg gccgccacgt tgcccatttt cgccagcttc ttgcatcgca     780
tgatcgcgta tgccgccatg cctgcccctc ccttttggtg tccaaccggc tcgacggggg     840
cagcgcaagg cggtgcctcc ggcgggccac tcaatgcttg agtatactca ctagactttg     900
cttcgcaaag tcgtgaccgc ctacggcggc tgcggcgccc tacgggcttg ctctccgggc     960
ttcgccctgc gcggtcgctg cgctcccttg ccagcccgtg gatatgtgga cgatggccgc    1020
gagcggccac cggctggctc gcttcgctcg gcccgtggac aaccctgctg acaagctga     1080
tggacaggct gcgcctgccc acgagcttga ccacagggat tgcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt gggggcagtc gaaggcgaag cccgcccgcc    1380
tgccccccga gcctcacggc ggcgagtgcg ggggttccaa gggggcagcg ccaccttggg    1440
caaggccgaa ggccgcgcag tcgatcaaca agccccggag gggccacttt ttgccggagg    1500
gggagccgcg ccgaaggcgt gggggaaccc cgcaggggtg cccttctttg ggcaccaaag    1560
aactagatat agggcgaaat gcgaaagact taaaaatcaa caacttaaaa aaggggggta    1620
cgcaacagct cattgcggca ccccccgcaa tagctcattg cgtaggttaa agaaaatctg    1680
taattgactg ccacttttac gcaacgcata attgttgtcg cgctgccgaa aagttgcagc    1740
tgattgcgca tggtgccgca accgtgcggc accctaccgc atggagataa gcatggccac    1800
gcagtccaga gaaatcggca ttcaagccaa gaacaagccc ggtcactggg tgcaaacgga    1860
acgcaaagcg catgaggcgt gggccgggct tattgcgagg aaacccacgg cggcaatgct    1920
gctgcatcac ctcgtggcgc agatgggcca ccagaacgcc gtggtggtca gccagaagac    1980
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
tgccgccgtg gtggttgatc acgacgacca ggacgaatcg ctgttggggc atggcgacct    2220
gcgccgcatc ccgaccctgt atccgggcga gcagcaacta ccgaccggcc ccggcgagga    2280
gccgccagc cagcccggca ttccgggcat ggaaccagac ctgccagcct tgaccgaaac    2340
```

```
ggaggaatgg gaacggcgcg ggcagcagcg cctgccgatg cccgatgagc cgtgtttttct   2400
ggacgatggc gagccgttgg agccgccgac acgggtcacg ctgccgcgcc ggtagcactt    2460
gggttgcgca gcaacccgta agtgcgctgt tccagactat cggctgtagc cgcctcgccg    2520
ccctatacct tgtctgcctc cccgcgttgc gtcgcggtgc atggagccgg ccacctcga    2580
cctgaatgga agccggcggc acctcgctaa cggattcacc gttttatca ggctctggga    2640
ggcagaataa atgatcatat cgtcaattat tacctccacg gggagagcct gagcaaactg    2700
gcctcaggca tttgagaagc acacggtcac actgcttccg gtagtcaata aaccggtaaa    2760
ccagcaatag acataagcgg ctatttaacg accctgccct gaaccgacga ccgggtcgaa    2820
tttgctttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagaactagt ggatccccg ggctgcagga attcgatatc aagcttatcg ataccgtcga    3300
cctcgagggg gggcccggta cccagctttt gttcccttta gtgagggtta attgcgcgct    3360
tggcgtaatc atggtcatag ctgtttcctg tgtgaaattg ttatccgctc acaattccac    3420
acaacatacg agccggaagc ataaagtgta aagcctgggg tgcctaatga gtgagctaac    3480
tcacattaat tgcgttgcgc tcactgcccg ctttccagtc gggaaacctg tcgtgccagc    3540
tgcattaatg aatcggccaa cgcgcgggga gaggcggttt gcgtattggg cgcatgcata    3600
aaaactgttg taattcatta agcattctgc cgacatggaa gccatcacaa acggcatgat    3660
gaacctgaat cgccagcggc atcagcacct tgtcgccttg cgtataatat ttgcccatgg    3720
acgcacaccg tggaaacgga tgaaggcacg aacccagttg acataagcct gttcggttcg    3780
taaactgtaa tgcaagtagc gtatgcgctc acgcaactgg tccagaacct tgaccgaacg    3840
cagcggtggt aacggcgcag tggcggtttt catggcttgt tatgactgtt tttttgtaca    3900
gtctatgcct cgggcatcca agcagcaagc gcgttacgcc gtgggtcgat gtttgatgtt    3960
atggagcagc aacgatgtta cgcagcagca acgatgttac gcagcagggc agtcgcccta    4020
aaacaaagtt aggtggctca agtatgggca tcattcgcac atgtaggctc ggccctgacc    4080
aagtcaaatc catgcgggct gctcttgatc ttttcggtcg tgagttcgga gacgtagcca    4140
cctactccca acatcagccg gactccgatt acctcgggaa cttgctccgt agtaagacat    4200
tcatcgcgct tgctgccttc gaccaagaag cggttgttgg cgctctcgcg gcttacgttc    4260
tgcccaggtt tgagcagccg cgtagtgaga tctatatcta tgatctcgca gtctccggcg    4320
agcaccggag gcagggcatt gccaccgcgc tcatcaatct cctcaagcat gaggccaacg    4380
cgcttggtgc ttatgtgatc tacgtgcaag cagattacgg tgacgatccc gcagtggctc    4440
tctatacaaa gttgggcata cggaagaag tgatgcactt tgatatcgac ccaagtaccg    4500
ccacctaaca attcgttcaa gccgagatcg gcttcccggc cgcggagttg ttcggtaaat    4560
tgtcacaacg ccgccaggtg gcacttttcg gggaaatgtg cgcgcccgcg ttcctgctgg    4620
cgctgggcct gtttctggcg ctggacttcc cgctgttccg tcagcagctt ttcgcccacg    4680
gccttgatga tcgcggcggc cttggcctgc atatcccgat tcaacggccc cagggcgtcc    4740
```

-continued agaacgggct tcaggcgctc ccgaaggt              4768

<210> SEQ ID NO 42
<211> LENGTH: 6466
<212> TYPE: DNA
<213> ORGANISM: Artificial Sequence
<220> FEATURE:
<223> OTHER INFORMATION: Synthetic Construct

<400> SEQUENCE: 42

```
ctcgggccgt ctcttgggct tgatcggcct tcttgcgcat ctcacgcgct cctgcggcgg       60
cctgtagggc aggctcatac ccctgccgaa ccgcttttgt cagccggtcg gccacggctt      120
ccggcgtctc aacgcgcttt gagattccca gcttttcggc caatccctgc ggtgcatagg      180
cgcgtggctc gaccgcttgc gggctgatgg tgacgtggcc cactggtggc cgctccaggg      240
cctcgtagaa cgcctgaatg cgcgtgtgac gtgccttgct gccctcgatg ccccgttgca      300
gccctagatc ggccacagcg gccgcaaacg tggtctggtc gcgggtcatc tgcgctttgt      360
tgccgatgaa ctccttggcc gacagcctgc cgtcctgcgt cagcggcacc acgaacgcgg      420
tcatgtgcgg gctggtttcg tcacggtgga tgctggccgt cacgatgcga tccgccccgt      480
acttgtccgc cagccacttg tgcgccttct cgaagaacgc cgcctgctgt tcttggctgg      540
ccgacttcca ccattccggg ctggccgtca tgacgtactc gaccgccaac acagcgtcct      600
tgcgccgctt ctctggcagc aactcgcgca gtcggcccat cgcttcatcg gtgctgctgg      660
ccgcccagtg ctcgttctct ggcgtcctgc tggcgtcagc gttgggcgtc tcgcgctcgc      720
ggtaggcgtg cttgagactg gccgccacgt tgcccatttt cgccagcttc ttgcatcgca      780
tgatcgcgta tgccgccatg cctgcccctc ccttttggtg tccaaccggc tcgacggggg      840
cagcgcaagg cggtgcctcc ggcgggccac tcaatgcttg agtatactca ctagactttg      900
cttcgcaaag tcgtgaccgc ctacggcggc tgcggcgccc tacgggcttg ctctccgggc      960
ttcgccctgc gcggtcgctg cgctcccttg ccagcccgtg gatatgtgga cgatggccgc     1020
gagcggccac cggctggctc gcttcgctcg gccgtggac aaccctgctg gacaagctga     1080
tggacaggct gcgcctgccc acgagcttga ccacagggat tgcccaccgg ctacccagcc     1140
ttcgaccaca tacccaccgg ctccaactgc gcggcctgcg gccttgcccc atcaattttt     1200
ttaattttct ctgggaaaa gcctccggcc tgcggcctgc gcgcttcgct tgccggttgg     1260
acaccaagtg gaaggcgggt caaggctcgc gcagcgaccg cgcagcggct tggccttgac     1320
gcgcctggaa cgacccaagc ctatgcgagt gggggcagtc gaaggcgaag cccgcccgcc     1380
tgcccccga gcctcacggc ggcgagtgcg ggggttccaa gggggcagcg ccaccttggg     1440
caaggccgaa ggccgcgcag tcgatcaaca agccccggag gggccacttt ttgccggagg     1500
gggagccgcg ccgaaggcgt gggggaaccc cgcagggtg cccttctttg ggcaccaaag     1560
aactagatat agggcgaaat gcgaaagact taaaaatcaa caacttaaaa aagggggta     1620
cgcaacagct cattgcggca ccccccgcaa tagctcattg cgtaggttaa agaaaatctg     1680
taattgactg ccacttttac gcaacgcata attgttgtcg cgctgccgaa aagttgcagc     1740
tgattgcgca tggtgccgca accgtgcggc accctaccgc atggagataa gcatggccac     1800
gcagtccaga gaaatcggca ttcaagccaa gaacaagccc ggtcactggg tgcaaacgga     1860
acgcaaagcg catgaggcgt gggccgggct tattgcgagg aaacccacgg cggcaatgct     1920
gctgcatcac ctcgtggcgc agatgggcca ccagaacgcc gtggtggtca gccagaagac     1980
```

```
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
tgccgccgtg gtggttgatc acgacgacca ggacgaatcg ctgttggggc atggcgacct    2220
gcgccgcatc ccgaccctgt atccgggcga gcagcaacta ccgaccggcc ccggcgagga    2280
gccgcccagc cagcccggca ttccgggcat ggaaccagac ctgccagcct tgaccgaaac    2340
ggaggaatgg gaacggcgcg ggcagcagcg cctgccgatg cccgatgagc cgtgttttct    2400
ggacgatggc gagccgttgg agccgccgac acgggtcacg ctgccgcgcc ggtagcactt    2460
gggttgcgca gcaacccgta agtgcgctgt tccagactat cggctgtagc cgcctcgccg    2520
ccctatacct tgtctgcctc cccgcgttgc gtcgcggtgc atggagccgg ccacctcga    2580
cctgaatgga agccggcggc acctcgctaa cggattcacc gttttatca ggctctggga    2640
ggcagaataa atgatcatat cgtcaattat tacctccacg gggagagcct gagcaaactg    2700
gcctcaggca tttgagaagc acacggtcac actgcttccg gtagtcaata aaccggtaaa    2760
ccagcaatag acataagcgg ctatttaacg accctgccct gaaccgacga ccgggtcgaa    2820
tttgcttttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagaactagt ggatcctcac acgtacatca gctggttgat ggggaacggg tcgatgagca    3300
gcagcttgat gcggttctcg gtggcgtaat ccgggcggcc cagcccgtcc ccatattggt    3360
aggtgcagtg gctcacgcgg gccatgttca cggcgatctc catgaacgcc ttcggcagca    3420
gggtgctgtc cgacacgcgc tcgcggttca tttctcttcca ctcggcgtcg atcagcttgc    3480
gcagctcttc gcgggcctgt tcctcgctcg tgccgtcgtt ctcgtgcatg tagctgatga    3540
tgctgttggt ggtttcgccg cgttcgagtt ccgccgccga ggtcgccaga tcgttgcaca    3600
gccgaaagat cacgcaggac gagcgcacca ggccgtggaa gtcggtcagg gagcggaggg    3660
cgtggtccga gatatcttcc tgctgctggc agaccgagaa gtagctcggc gccagcagcg    3720
cgaccccgct ggaggacacg ctggcgttct ccaggtactt gctgaaggcg gggatgatct    3780
tgttattgct ccacttggct tcttgcagga aggccttgca cagttcgcgc agcttttggg    3840
tcagatagct caggttattg tggcccttct ccttcaggat ggagtaggac gtgtcgttca    3900
cggtgttgta cagggccagg aagcacagct tcatatagtc gggcagcgtg ttgatggcgt    3960
tcacgtccca gcgttccacc gcgtcggtga agagctgcag ttcgtccagg gtaccgtaca    4020
cgtcatagac gtcatcgata atggtgacca gaccgaacat cttggtgacg gccttgcggc    4080
attcgccgaa ctgcgggtcc ggcgccatgc ccagcgccca gaagtacact tccatcaggc    4140
ggtcccgcac gaaatccagc ttgctggcga ggcccatctc ggtccaccac cggctcaggt    4200
cctgcagctc ttttttggtgc agggtctgga ccatgttgaa atcgagtttg gccagttcca    4260
gcagcagctg tgatgcggc tccttgggtt cgtacttgtc cagaaccac cgcgcctcca    4320
ggcggtgcag gcgttgatga tacggcagct ccagcgcgtg ggacacctgc tcggccacct    4380
```

```
tcgtgttgat cccctccttg aggttgttct tcagatgggt gatgctgaag gtacgggcct    4440
cctccagcag attttcgcct tcgaaaccga gatagctggc ctcgtacagg ctcagcaggc    4500
cctgcacgtc acccttcagt tccccggaga agccccttc tttgtccttg aagcgctcga     4560
acacgtcctg gctcacctca aagccatgct gccgcagcag gcggaagctc agggcggtcg    4620
cgtgcagatc gcttttgttc ttcttattct cgtccagcag gacgatgttc tccagcgcct    4680
tgatgatatc tttctcaaac ttgtaggtca ggcccaggcg ctgcacgtcg tcgatgagct    4740
ccagcaggct caggggctgg gtgtccaccc ggttgatcat gcaacgcacc tcctcctcca    4800
gcttggtggc cttctcttcg agcttctcca ccttcaggtc gttttccagg ctctgcagga    4860
actcgaagtt ccacaggttg ggctggtagt tcgcggaccg acggctatta tgctcggtga    4920
tctgggtgaa ctggctgctg gtggcgcaca tatgtatatc tccttcttaa agttaaacaa    4980
gcttatcgat accgtcgacc tcgaggggg gcccggtacc cagcttttgt tccctttagt     5040
gagggttaat tgcgcgcttg gcgtaatcat ggtcatagct gtttcctgtg tgaaattgtt    5100
atccgctcac aattccacac aacatacgag ccggaagcat aaagtgtaaa gcctggggtg    5160
cctaatgagt gagctaactc acattaattg cgttgcgctc actgcccgct ttccagtcgg    5220
gaaacctgtc gtgccagctg cattaatgaa tcggccaacg cgcggggaga ggcggtttgc    5280
gtattgggcg catgcataaa aactgttgta attcattaag cattctgccg acatggaagc    5340
catcacaaac ggcatgatga acctgaatcg ccagcggcat cagcaccttg tcgccttgcg    5400
tataatattt gcccatggac gcacaccgtg gaaacggatg aaggcacgaa cccagttgac    5460
ataagcctgt tcggttcgta aactgtaatg caagtagcgt atgcgctcac gcaactggtc    5520
cagaaccttg accgaacgca gcggtggtaa cggcgcagtg gcggttttca tggcttgtta    5580
tgactgtttt tttgtacagt ctatgcctcg ggcatccaag cagcaagcgc gttacgccgt    5640
gggtcgatgt ttgatgttat ggagcagcaa cgatgttacg cagcagcaac gatgttacgc    5700
agcagggcag tcgccctaaa acaaagttag gtggctcaag tatgggcatc attcgcacat    5760
gtaggctcgg ccctgaccaa gtcaaatcca tgcgggctgc tcttgatctt ttcggtcgtg    5820
agttcggaga cgtagccacc tactcccaac atcagccgga ctccgattac ctcgggaact    5880
tgctccgtag taagacattc atcgcgcttg ctgccttcga ccaagaagcg gttgttggcg    5940
ctctcgcggc ttacgttctg cccaggtttg agcagccgcg tagtgagatc tatatctatg    6000
atctcgcagt ctccggcgag caccggaggc agggcattgc caccgcgctc atcaatctcc    6060
tcaagcatga ggccaacgcg cttggtgctt atgtgatcta cgtgcaagca gattacggtg    6120
acgatcccgc agtggctctc tatacaaagt tgggcatacg gaagaagtg atgcactttg     6180 atatcgaccc aagtaccgcc acctaacaat tcgttcaagc cgagatcggc ttcccggccg    6240
cggagttgtt cggtaaattg tcacaacgcc gccaggtggc acttttcggg gaaatgtgcg    6300
cgcccgcgtt cctgctggcg ctgggcctgt ttctggcgct ggacttcccg ctgttccgtc    6360
agcagctttt cgcccacggc cttgatgatc gcggcggcct tggcctgcat atcccgattc    6420
aacggcccca gggcgtccag aacgggcttc aggcgctccc gaaggt                   6466
```

<210> SEQ ID NO 43
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 43

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccttagg       180
gttccgattt agtgctttac ggcacctcga ccccaaaaaa cttgattagg gtgatggttc     240
acgtagtggg ccatcgccct gatagacggt ttttcgccct tgacgttgg agtccacgtt     300
ctttaatagt ggactcttgt tccaaactgg aacaacactc aaccctatct cggtctattc     360
ttttgattta aagggatt tgccgatttc ggcctattgg ttaaaaaatg agctgattta      420
acaaaatt aacgcgaatt ttaacaaaat attaacgttt acaatttcag gtggcacttt       480
tcggggaaat gtgcgcggaa ccctatttg tttatttttc taaatacatt caaatatgta      540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga      780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga acgaaatac gcgatcgctg ttaaaaggac      960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaatg cttgatggtc ggaagaggca     1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgttatg taagcagaca gttttattgt tcatgaccaa atcccttaa     1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttt cgaaggtaac tggcttcagc     1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggtg gactcaagac gatagttacc ggataaggcg     1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggg cggagcctat ggaaaaacgc cagcaacgcg     2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tatttctcc ttacgcatct gtgcggtatt tcacaccgca tatatggtgc actctcagta    2340
```

-continued

```
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
```

```
tctcgacgct ctcccttatg cgactcctgc attaggaagc agcccagtag taggttgagg      4740
ccgttgagca ccgccgccgc aaggaatggt gcatgcaagg agatggcgcc caacagtccc      4800
ccggccacgg ggcctgccac catacccacg ccgaaacaag cgctcatgag cccgaagtgg      4860
cgagcccgat cttccccatc ggtgatgtcg gcgatatagg cgccagcaac cgcacctgtg      4920
gcgccggtga tgccggccac gatgcgtccg gcgtagagga tcgagatctc gatcccgcga      4980
aattaatacg actcactata ggggaattgt gagcggataa caattcccct ctagaaataa      5040
ttttgtttaa ctttaagaag gagatataca tatgcgttgt agcgtgtcca ccgaaaatgt      5100
gtctttcacc gaaactgaaa ccgaagctcg tcgttctgcg aactacgaac ctaacagctg      5160
ggactatgat tacctgctgt cctccgacac ggacgagtcc atcgaagtat acaaagacaa      5220
agcgaaaaag ctggaagccg aagttcgtcg cgagattaat aacgaaaaag cagaatttct      5280
gaccctgctg gaactgattg acaacgtcca gcgcctgggc ctgggttacc gtttcgagtc      5340
tgatatccgt ggtgcgctgg atcgcttcgt ttcctccggc ggcttcgatg cggtaaccaa      5400
gacttccctg cacggtacgg cactgtcttt ccgtctgctg cgtcaacacg gttttgaggt      5460
ttctcaggaa gcgttcagcg gcttcaaaga ccaaaacggc aacttcctgg agaacctgaa      5520
ggaagatatc aaagctatcc tgagcctgta cgaggccagc ttcctggctc tggaaggcga      5580
aaacatcctg gacgaggcga aggttttcgc aatctctcat ctgaaagaac tgtctgaaga      5640
aaagatcggt aaagagctgg cagaacaggt gaaccatgca ctggaactgc cactgcatcg      5700
ccgtactcag cgtctggaag cagtatggtc tatcgaggcc taccgtaaaa aggaggacgc      5760
gaatcaggtt ctgctggagc tggcaattct ggattacaac atgatccagt ctgtatacca      5820
gcgtgatctg cgtgaaacgt cccgttggtg gcgtcgtgtg ggtctggcga ccaaactgca      5880 cttgctcgt gaccgcctga ttgagagctt ctactgggcc gtgggtgtag cattcgaacc      5940
gcaatactcc gactgccgta actccgtcgc aaaaatgttt tctttcgtaa ccattatcga      6000
cgatatctac gatgtatacg gcaccctgga cgaactggag ctgtttactg atgcagttga      6060
gcgttgggac gtaaacgcca tcaacgacct gccggattac atgaaactgt gctttctggc      6120
tctgtataac actattaacg aaatcgccta cgacaacctg aaagataaag gtgagaacat      6180
cctgccgtat ctgaccaaag cctgggctga cctgtgcaac gctttcctgc aagaagccaa      6240
gtggctgtac aacaaatcta ctccgacctt tgacgactac ttcggcaacg catggaaatc      6300
ctcttctggc ccgctgcaac tggtgttcgc ttacttcgct gtcgtgcaga acattaaaaa      6360
ggaagagatc gaaaacctgc aaaaatacca tgacaccatc tctcgtccta cccatatctt      6420
ccgtctgtgc aatgacctgg ctagcgcgtc tgcggaaatt gcgcgtggtg aaaccgcaaa      6480 tagcgttct tgttacatgc gcactaaagg tatctccgaa gaactggcta ccgaaagcgt      6540
gatgaatctg atcgatgaaa cctggaaaaa gatgaacaag gaaaaactgg gtggtagcct      6600
gttcgcgaaa ccgttcgtgg aaaccgcgat caacctggca cgtcaatctc actgcactta      6660
tcataacggc gacgcgcata cctctccgga tgagctgacc cgcaaacgcg ttctgtctgt      6720
aatcactgaa ccgattctgc cgtttgaacg ctaaggatcc gaattcgagc tccgtcgaca      6780
agcttgcggc cgcactcgag caccaccacc accaccactg agatccggct gctaacaaag      6840
cccgaaagga agctgagttg gctgctgcca ccgctgagca ataactagca taaccccttg      6900
gggcctctaa acgggtcttg aggggttttt tgctgaaagg aggaactata tccggat      6957
```

<210> SEQ ID NO 44
<211> LENGTH: 6068

<212> TYPE: DNA
<213> ORGANISM: Artificial Sequence
<220> FEATURE:
<223> OTHER INFORMATION: Synthetic Construct

<400> SEQUENCE: 44

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat aatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgagatg     420
tagcgtgtcc accgaaaatg tgtctttcac cgaaactgaa accgaagctc gtcgttctgc     480
gaactacgaa cctaacagct gggactatga ttacctgctg tcctccgaca cggacgagtc     540
catcgaagta tacaaagaca agcgaaaaa gctggaagcc gaagttcgtc gcgagattaa     600
taacgaaaaa gcagaatttc tgaccctgct ggaactgatt gacaacgtcc agcgcctggg     660
cctgggttac cgtttcgagt ctgatatccg tggtgcgctg gatcgcttcg tttcctccgg     720
cggcttcgat gcggtaacca agacttccct gcacggtacg gcactgtctt tccgtctgct     780
gcgtcaacac ggttttgagg tttctcagga agcgttcagc ggcttcaaag accaaaacgg     840
caacttcctg gagaacctga aggaagatat caaagctatc ctgagcctgt acgaggccag     900
cttcctggct ctggaaggcg aaaacatcct ggacgaggcg aaggttttcg caatctctca     960
tctgaaagaa ctgtctgaag aaagatcgg taaagagctg gcagaacagg tgaaccatgc    1020
actgaaactg ccactgcatc gccgtactca gcgtctggaa gcagtatggt ctatcgaggc    1080
ctaccgtaaa aaggaggacg cgaatcaggt tctgctggag ctggcaattc tggattacaa    1140
catgatccag tctgtatacc agcgtgatct gcgtgaaacg tcccgttggt ggcgtcgtgt    1200
gggtctggcg accaaactgc actttgctcg tgaccgcctg attgagagct ctactgggc    1260
cgtgggtgta gcattcgaac cgcaatactc cgactgccgt aactccgtcg caaaaatgtt    1320
ttctttcgta accattatcg acgatatcta cgatgtatac ggcacccctgg acgaactgga    1380
gctgtttact gatgcagttg agcgttggga cgtaaacgcc atcaacgacc tgccggatta    1440
catgaaactg tgctttctgg ctctgtataa cactattaac gaaatcgcct acgacaacct    1500
gaaagataaa ggtgagaaca tcctgccgta tctgaccaaa gcctgggctg acctgtgcaa    1560
cgctttcctg caagaagcca agtggctgta caacaaatct actccgacct ttgacgacta    1620
cttcggcaac gcatggaaat cctcttctgg cccgctgcaa ctggtgttcg cttacttcgc    1680
tgtcgtgcag aacattaaaa aggaagagat cgaaaacctg caaaaatacc atgacaccat    1740
ctctcgtcct tcccatatct tccgtctgtg caatgacctg gctagcgcgt ctgcggaaat    1800
tgcgcgtggt gaaaccgcaa atagcgtttc ttgttacatg cgcactaaag gtatctccga    1860
agaactggct accgaaagcg tgatgaatct gatcgatgaa acctggaaaa agatgaacaa    1920
ggaaaaactg ggtggtagcc tgttcgcgaa accgttcgtg gaaccgcgca tcaacctggc    1980
acgtcaatct cactgcactt atcataacgg cgacgcgcat acctctccgg atgagctgac    2040
ccgcaaacgc gttctgtctg taatcactga accgattctg ccgtttgaac gctaactgca    2100
gctggtacca tatgggaatt cgaagctttc tagaacaaaa actcatctca gaagaggatc    2160
```

```
tgaatagcgc cgtcgaccat catcatcatc atcattgagt ttaaacggtc tccagcttgg     2220
ctgttttggc ggatgagaga agattttcag cctgatacag attaaatcag aacgcagaag     2280
cggtctgata aaacagaatt tgcctggcgg cagtagcgcg gtggtcccac ctgaccccat     2340
gccgaactca gaagtgaaac gccgtagcgc cgatggtagt gtggggtctc cccatgcgag     2400
agtagggaac tgccaggcat caaataaaac gaaaggctca gtcgaaagac tgggcctttc     2460
gttttatctg ttgtttgtcg gtgaacgctc tcctgagtag acaaatccg ccgggagcgg      2520 atttgaacgt tgcgaagcaa cggcccggag ggtggcgggc aggacgcccg ccataaactg     2580
ccaggcatca aattaagcag aaggccatcc tgacggatgg cctttttgcg tttctacaaa     2640 ctcttttttgt ttatttttct aaatacattc aaatatgtat ccgctcatga gacaataacc    2700
ctgataaatg cttcaataat attgaaaaag gaagagtatg agtattcaac atttccgtgt     2760
cgcccttatt ccctttttttg cggcattttg ccttcctgtt tttgctcacc cagaaacgct    2820
ggtgaaagta aaagatgctg aagatcagtt gggtgcacga gtgggttaca tcgaactgga    2880
tctcaacagc ggtaagatcc ttgagagttt tcgccccgaa gaacgttttc caatgatgag     2940
cacttttaaa gttctgctat gtggcgcggt attatcccgt gttgacgccg ggcaagagca    3000
actcggtcgc cgcatacact attctcagaa tgacttggtt gagtactcac cagtcacaga     3060
aaagcatctt acggatggca tgacagtaag agaattatgc agtgctgcca taaccatgag    3120
tgataacact gcggccaact tacttctgac aacgatcgga ggaccgaagg agctaaccgc    3180
ttttttgcac aacatggggg atcatgtaac tcgccttgat cgttgggaac cggagctgaa    3240
tgaagccata ccaaacgacg agcgtgacac cacgatgcct gtagcaatgg caacaacgtt    3300
gcgcaaacta ttaactggcg aactacttac tctagcttcc cggcaacaat aatagactg     3360 gatgaggcg gataaagttg caggaccact tctgcgctcg gcccttccgg ctggctggtt     3420
tattgctgat aaatctggag ccggtgagcg tgggtctcgc ggtatcattg cagcactggg    3480
gccagatggt aagccctccc gtatcgtagt tatctacacg acggggagtc aggcaactat    3540
ggatgaacga aatagacaga tcgctgagat aggtgcctca ctgattaagc attggtaact    3600
gtcagaccaa gtttactcat atatacttta gattgattta aaacttcatt tttaatttaa    3660
aaggatctag gtgaagatcc tttttgataa tctcatgacc aaaatccctt aacgtgagtt    3720
ttcgttccac tgagcgtcag accccgtaga aaagatcaaa ggatcttctt gagatccttt    3780
ttttctgcgc gtaatctgct gcttgcaaac aaaaaaacca ccgctaccag cggtggtttg    3840
tttgccggat caagagctac caactctttt tccgaaggta actggcttca gcagagcgca    3900
gataccaaat actgtccttc tagtgtagcc gtagttaggc caccacttca agaactctgt    3960
agcaccgcct acatacctcg ctctgctaat cctgttacca gtggctgctg ccagtggcga    4020
taagtcgtgt cttaccgggt tggactcaag acgatagtta ccggataagg cgcagcggtc    4080
gggctgaacg gggggttcgt gcacacagcc cagcttggag cgaacgacct acaccgaact    4140
gagataccta cagcgtgagc tatgagaaag cgccacgctt cccgaaggga aaaggcgga    4200 caggtatccg gtaagcggca gggtcggaac aggagagcgc acgagggagc ttccaggggg    4260
aaacgcctgg tatctttata gtcctgtcgg gtttcgccac ctctgacttg agcgtcgatt    4320
tttgtgatgc tcgtcagggg ggcggagcct atggaaaaac gccagcaacg cggccttttt    4380
acggttcctg gccttttgct ggccttttgc tcacatgttc tttcctgcgt tatcccctga    4440
ttctgtggat aaccgtatta ccgcctttga gtgagctgat accgctcgcc gcagccgaac    4500
gaccgagcgc agcgagtcag tgagcgagga agcggaagag cgcctgatgc ggtattttct    4560
```

| | |
|---|---|
| ccttacgcat ctgtgcggta tttcacaccg catatggtgc actctcagta caatctgctc | 4620 |
| tgatgccgca tagttaagcc agtatacact ccgctatcgc tacgtgactg ggtcatggct | 4680 |
| gcgccccgac acccgccaac acccgctgac gcgccctgac gggcttgtct gctcccggca | 4740 |
| tccgcttaca gacaagctgt gaccgtctcc gggagctgca tgtgtcagag gttttcaccg | 4800 |
| tcatcaccga aacgcgcgag gcagcagatc aattcgcgcg cgaaggcgaa gcggcatgca | 4860 |
| tttacgttga caccatcgaa tggtgcaaaa cctttcgcgg tatggcatga tagcgcccgg | 4920 |
| aagagagtca attcagggtg gtgaatgtga aaccagtaac gttatacgat gtcgcagagt | 4980 |
| atgccggtgt ctcttatcag accgtttccc gcgtggtgaa ccaggccagc cacgtttctg | 5040 |
| cgaaaacgcg ggaaaaagtg gaagcggcga tggcggagct gaattacatt cccaaccgcg | 5100 |
| tggcacaaca actggcgggc aaacagtcgt tgctgattgg cgttgccacc tccagtctgg | 5160 |
| ccctgcacgc gccgtcgcaa attgtcgcgg cgattaaatc tcgcgccgat caactgggtg | 5220 |
| ccagcgtggt ggtgtcgatg gtagaacgaa gcggcgtcga agcctgtaaa gcggcggtgc | 5280 |
| acaatcttct cgcgcaacgc gtcagtgggc tgatcattaa ctatccgctg gatgaccagg | 5340 |
| atgccattgc tgtggaagct gcctgcacta atgttccggc gttatttctt gatgtctctg | 5400 |
| accagacacc catcaacagt attatttttct cccatgaaga cggtacgcga ctgggcgtgg | 5460 |
| agcatctggt cgcattgggt caccagcaaa tcgcgctgtt agcgggccca ttaagttctg | 5520 |
| tctcggcgcg tctgcgtctg gctggctggc ataaatatct cactcgcaat caaattcagc | 5580 |
| cgatagcgga acgggaaggc gactggagtg ccatgtccgg ttttcaacaa accatgcaaa | 5640 |
| tgctgaatga gggcatcgtt cccactgcga tgctggttgc caacgatcag atggcgctgg | 5700 |
| gcgcaatgcg cgccattacc gagtccgggc tgcgcgttgg tgcggatatc tcggtagtgg | 5760 |
| gatacgacga taccgaagac agctcatgtt atatcccgcc gtcaaccacc atcaaacagg | 5820 |
| attttcgcct gctggggcaa accagcgtgg accgcttgct gcaactctct cagggccagg | 5880 |
| cggtgaaggg caatcagctg ttgcccgtct cactggtgaa aagaaaaacc accctggcgc | 5940 |
| ccaatacgca aaccgcctct ccccgcgcgt tggccgattc attaatgcag ctggcacgac | 6000 |
| aggtttcccg actggaaagc gggcagtgag cgcaacgcaa ttaatgtgag ttagcgcgaa | 6060 |
| ttgatctg | 6068 |

<210> SEQ ID NO 45
<211> LENGTH: 6906
<212> TYPE: DNA
<213> ORGANISM: Artificial Sequence
<220> FEATURE:
<223> OTHER INFORMATION: Synthetic Construct

<400> SEQUENCE: 45

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatgagatg | 420 |
| tagcgtgtcc accgaaaatg tgtctttcac cgaaactgaa accgaagctc gtcgttctgc | 480 |

```
gaactacgaa cctaacagct gggactatga ttacctgctg tcctccgaca cggacgagtc      540
catcgaagta tacaaagaca aagcgaaaaa gctggaagcc gaagttcgtc gcgagattaa      600
taacgaaaaa gcagaatttc tgaccctgct ggaactgatt gacaacgtcc agcgcctggg      660
cctgggttac cgtttcgagt ctgatatccg tggtgcgctg gatcgcttcg tttcctccgg      720
cggcttcgat gcggtaacca agacttccct gcacggtacg gcactgtctt ccgtctgct       780 gcgtcaacac ggttttgagg tttctcagga agcgttcagc ggcttcaaag accaaaacgg      840
caacttcctg gagaacctga aggaagatat caaagctatc ctgagcctgt acgaggccag      900
cttcctggct ctggaaggcg aaaacatcct ggacgaggcg aaggttttcg caatctctca      960
tctgaaagaa ctgtctgaag aaaagatcgg taaagagctg gcagaacagg tgaaccatgc     1020
actggaactg ccactgcatc gccgtactca gcgtctggaa gcagtatggt ctatcgaggc     1080
ctaccgtaaa aaggaggacg cgaatcaggt tctgctggag ctggcaattc tggattacaa     1140
catgatccag tctgtatacc agcgtgatct gcgtgaaacg tcccgttggt ggcgtcgtgt     1200
gggtctggcg accaaactgc actttgctcg tgaccgcctg attgagagct ctactgggc      1260 cgtgggtgta gcattcgaac cgcaatactc cgactgccgt aactccgtcg caaaaatgtt     1320
ttctttcgta accattatcg acgatatcta cgatgtatac ggcaccctgg acgaactgga     1380
gctgtttact gatgcagttg agcgttggga cgtaaacgcc atcaacgacc tgccggatta     1440
catgaaactg tgctttctgg ctctgtataa cactattaac gaaatcgcct acgacaacct     1500
gaaagataaa ggtgagaaca tcctgccgta tctgaccaaa gcctgggctg acctgtgcaa     1560
cgctttcctg caagaagcca gtggctgta caacaaatct actccgacct ttgacgacta      1620
cttcggcaac gcatggaaat cctcttctgg cccgctgcaa ctggtgttcg cttacttcgc     1680
tgtcgtgcag aacattaaaa aggaagagat cgaaaacctg caaaaatacc atgacaccat     1740
ctctcgtcct tcccatatct tccgtctgtg caatgacctg gctagcgcgt ctgcggaaat     1800
tgcgcgtggt gaaaccgcaa atagcgtttc ttgttacatg cgcactaaag gtatctccga     1860
agaactggct accgaaagcg tgatgaatct gatcgatgaa acctggaaaa agatgaacaa     1920
ggaaaaactg ggtggtagcc tgttcgcgaa accgttcgtg gaaaccgcga tcaacctggc     1980
acgtcaatct cactgcactt atcataacgg cgacgcgcat acctctccgg atgagctgac     2040
ccgcaaacgc gttctgtctg taatcactga accgattctg ccgtttgaac gctaactgca     2100
taaaggaggt aaaaaaacat ggtatcctgt tctgcgccgg gtaagattta cctgttcggt     2160
gaacacgccg tagtttatgg cgaaactgca attgcgtgtg cggtggaact gcgtacccgt     2220
gttcgcgcgg aactcaatga ctctatcact attcagagcc agatcggccg caccggtctg     2280
gatttcgaaa agcacccctta tgtgtctgcg gtaattgaga aaatgcgcaa atctattcct     2340
attaacggtg ttttcttgac cgtcgattcc gacatcccgg tgggctccgg tctgggtagc     2400
agcgcagccg ttactatcgc gtctattggt gcgctgaacg agctgttcgg cttttggcctc     2460 agcctgcaag aaatcgctaa actgggccac gaaatcgaaa ttaaagtaca gggtgccgcg     2520
tccccaaccg atacgtatgt ttctaccttc ggcggcgtgg ttaccatccc ggaacgtcgc     2580
aaactgaaaa ctccggactg cggcattgtg attggcgata ccggcgtttt ctcctccacc     2640
aaagagttag tagctaacgt acgtcagctg cgcgaaagct acccggattt gatcgaaccg     2700
ctgatgacct ctattggcaa aatctctcgt atcggcgaac aactggttct gtctggcgac     2760
tacgcatcca tcggccgcct gatgaacgtc aaccagggtc tcctgacgc cctgggcgtt      2820 aacatcttag aactgagcca gctgatctat tccgctcgtg cggcaggtgc gtttggcgct     2880
```

```
aaaatcacgg gcgctggcgg cggtggctgt atggttgcgc tgaccgctcc ggaaaaatgc   2940
aaccaagtgg cagaagcggt agcaggcgct ggcggtaaag tgactatcac taaaccgacc   3000
gagcaaggtc tgaaagtaga ttaaagtcta gttaaagttt aaacggtctc cagcttggct   3060
gttttggcgg atgagagaag attttcagcc tgatacagat taaatcagaa cgcagaagcg   3120
gtctgataaa acagaatttg cctggcggca gtagcgcggt ggtcccacct gaccccatgc   3180
cgaactcaga agtgaaacgc cgtagcgccg atggtagtgt ggggtctccc catgcgagag   3240
tagggaactg ccaggcatca ataaaacga aaggctcagt cgaaagactg gcctttcgt    3300
tttatctgtt gtttgtcggt gaacgctctc ctgagtagga caaatccgcc gggagcggat   3360
ttgaacgttg cgaagcaacg gcccggaggg tggcgggcag gacgcccgcc ataaactgcc   3420
aggcatcaaa ttaagcagaa ggccatcctg acggatggcc ttttgcgtt tctacaaact   3480
cttttttgttt attttctaa atacattcaa atatgtatcc gctcatgaga caataaccct   3540
gataaatgct tcaataatat tgaaaaagga agagtatgag tattcaacat ttccgtgtcg   3600
cccttattcc cttttttgcg gcattttgcc ttcctgtttt tgctcaccca gaaacgctgg   3660
tgaaagtaaa agatgctgaa gatcagttgg gtgcacgagt gggttacatc gaactggatc   3720
tcaacagcgg taagatcctt gagagttttc gccccgaaga acgttttcca atgatgagca   3780
cttttaaagt tctgctatgt ggcgcggtat tatcccgtgt tgacgccggg caagagcaac   3840
tcggtcgccg catacactat tctcagaatg acttggttga gtactcacca gtcacagaaa   3900
agcatcttac ggatggcatg acagtaagag aattatgcag tgctgccata accatgagtg   3960
ataacactgc ggccaactta cttctgacaa cgatcggagg accgaaggag ctaaccgctt   4020
ttttgcacaa catgggggat catgtaactc gccttgatcg ttgggaaccg gagctgaatg   4080
aagccatacc aaacgacgag cgtgacacca cgatgcctgt agcaatggca acaacgttgc   4140
gcaaactatt aactggcgaa ctacttactc tagcttcccg gcaacaatta atagactgga   4200
tggaggcgga taaagttgca ggaccacttc tgcgctcggc ccttccggct ggctggttta   4260
ttgctgataa atctggagcc ggtgagcgtg ggtctcgcgg tatcattgca gcactggggc   4320
cagatggtaa gccctcccgt atcgtagtta tctacacgac ggggagtcag gcaactatgg   4380
atgaacgaaa tagacagatc gctgagatag gtgcctcact gattaagcat tggtaactgt   4440
cagaccaagt ttactcatat atactttaga ttgatttaaa acttcatttt taatttaaaa   4500
ggatctaggt gaagatcctt tttgataatc tcatgaccaa aatcccttaa cgtgagtttt   4560
cgttccactg agcgtcagac cccgtagaaa agatcaaagg atcttcttga gatccttttt   4620
ttctgcgcgt aatctgctgc ttgcaaacaa aaaaaccacc gctaccagcg gtggtttgtt   4680
tgccggatca agagctacca actctttttc cgaaggtaac tggcttcagc agagcgcaga   4740
taccaaatac tgtccttcta gtgtagccgt agttaggcca ccacttcaag aactctgtag   4800
caccgcctac atacctcgct ctgctaatcc tgttaccagt ggctgctgcc agtggcgata   4860
agtcgtgtct taccgggttg gactcaagac gatagttacc ggataaggcg cagcggtcgg   4920
gctgaacggg gggttcgtgc acacagccca gcttggagcg aacgacctac accgaactga   4980
gatacctaca gcgtgagcta tgagaaagcg ccacgcttcc cgaagggaga aaggcggaca   5040
ggtatccggt aagcggcagg gtcggaacag gagagcgcac gagggagctt ccagggggaa   5100
acgcctggta tctttatagt cctgtcgggt ttcgccacct ctgacttgag cgtcgatttt   5160
tgtgatgctc gtcaggggggg cggagcctat ggaaaaacgc cagcaacgcg gcctttttac   5220
```

| | |
|---|---|
| ggttcctggc cttttgctgg ccttttgctc acatgttctt tcctgcgtta tccctgatt | 5280 |
| ctgtggataa ccgtattacc gcctttgagt gagctgatac cgctcgccgc agccgaacga | 5340 |
| ccgagcgcag cgagtcagtg agcgaggaag cggaagagcg cctgatgcgg tattttctcc | 5400 |
| ttacgcatct gtgcggtatt tcacaccgca tatggtgcac tctcagtaca atctgctctg | 5460 |
| atgccgcata gttaagccag tatacactcc gctatcgcta cgtgactggg tcatggctgc | 5520 |
| gccccgacac ccgccaacac ccgctgacgc gccctgacgg gcttgtctgc tcccggcatc | 5580 |
| cgcttacaga caagctgtga ccgtctccgg gagctgcatg tgtcagaggt tttcaccgtc | 5640 |
| atcaccgaaa cgcgcgaggc agcagatcaa ttcgcgcgcg aaggcgaagc ggcatgcatt | 5700 |
| tacgttgaca ccatcgaatg gtgcaaaacc tttcgcggta tggcatgata gcgcccggaa | 5760 |
| gagagtcaat tcagggtggt gaatgtgaaa ccagtaacgt tatacgatgt cgcagagtat | 5820 |
| gccggtgtct cttatcagac cgtttcccgc gtggtgaacc aggccagcca cgtttctgcg | 5880 |
| aaaacgcggg aaaaagtgga agcggcgatg gcggagctga attacattcc caaccgcgtg | 5940 |
| gcacaacaac tggcgggcaa acagtcgttg ctgattggcg ttgccacctc cagtctggcc | 6000 |
| ctgcacgcgc cgtcgcaaat tgtcgcggcg attaaatctc gcgccgatca actgggtgcc | 6060 |
| agcgtggtgg tgtcgatggt agaacgaagc ggcgtcgaag cctgtaaagc ggcggtgcac | 6120 |
| aatcttctcg cgcaacgcgt cagtgggctg atcattaact atccgctgga tgaccaggat | 6180 |
| gccattgctg tggaagctgc ctgcactaat gttccggcgt tatttcttga tgtctctgac | 6240 |
| cagacaccca tcaacagtat tattttctcc catgaagacg gtacgcgact gggcgtggag | 6300 |
| catctggtcg cattgggtca ccagcaaatc gcgctgttag cgggcccatt aagttctgtc | 6360 |
| tcggcgcgtc tgcgtctggc tggctggcat aaatatctca ctcgcaatca aattcagccg | 6420 |
| atagcggaac gggaaggcga ctggagtgcc atgtccggtt ttcaacaaac catgcaaatg | 6480 |
| ctgaatgagg gcatcgttcc cactgcgatg ctggttgcca acgatcagat ggcgctgggc | 6540 |
| gcaatgcgcg ccattaccga gtccgggctg cgcgttggtg cggatatctc ggtagtggga | 6600 |
| tacgacgata ccgaagacag ctcatgttat atcccgccgt caaccaccat caaacaggat | 6660 |
| tttcgcctgc tggggcaaac cagcgtggac cgcttgctgc aactctctca gggccaggcg | 6720 |
| gtgaagggca atcagctgtt gcccgtctca ctggtgaaaa gaaaaaccac cctggcgccc | 6780 |
| aatacgcaaa ccgcctctcc ccgcgcgttg gccgattcat taatgcagct ggcacgacag | 6840 |
| gtttcccgac tggaaagcgg gcagtgagcg caacgcaatt aatgtgagtt agcgcgaatt | 6900 |
| gatctg | 6906 |

<210> SEQ ID NO 46
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 46

| | |
|---|---|
| gcggccgcgc ccttgacgat gccacatcct gagcaaataa ttcaaccact aattgtgagc | 60 |
| ggataacaca aggaggaaac agccatggta tcctgttctg cgccgggtaa gatttacctg | 120 |
| ttcggtgaac acgccgtagt ttatggcgaa actgcaattg cgtgtgcggt ggaactgcgt | 180 |
| acccgtgttc gcgcggaact caatgactct atcactattc agagccgat cggccgcacc | 240 |
| ggtctggatt tcgaaaagca cccttatgtg tctgcggtaa ttgagaaaat gcgcaaatct | 300 |
| attcctatta acggtgtttt cttgaccgtc gattccgaca tcccggtggg ctccggtctg | 360 |

-continued

```
ggtagcagcg cagccgttac tatcgcgtct attggtgcgc tgaacgagct gttcggcttt      420
ggcctcagcc tgcaagaaat cgctaaactg ggccacgaaa tcgaaattaa agtacagggt      480
gccgcgtccc caaccgatac gtatgtttct accttcggcg cgtggttac catcccggaa       540 cgtcgcaaac tgaaaactcc ggactgcggc attgtgattg cgataccgg cgttttctcc       600 tccaccaaag agttagtagc taacgtacgt cagctgcgcg aaagctaccc ggatttgatc      660
gaaccgctga tgacctctat tggcaaaatc tctcgtatcg cgaacaact ggttctgtct       720 ggcgactacg catccatcgg ccgcctgatg aacgtcaacc agggtctcct ggacgccctg      780
ggcgttaaca tcttagaact gagccagctg atctattccg ctcgtgcggc aggtgcgttt     840
ggcgctaaaa tcacgggcgc tggcggcggt ggctgtatgg ttgcgctgac cgctccggaa     900
aaatgcaacc aagtggcaga gcggtagca ggcgctggcg gtaaagtgac tatcactaaa      960
ccgaccgagc aaggtctgaa agtagattaa gccttgactt aatagctgct tatttcgccc    1020
ttatggtacc tagtaggagg aaaaaaacat ggaaatgcgt caaccggctg tcgcaggtca    1080
attctaccca ctgcgttgcg agaacctgga aaacgaactg aaacgctgct tcgaaggcct    1140
ggagatccgc gaacaagaag tgctgggcgc agtctgtccg cacgccggtt atatgtactc    1200
tggcaaagtt gcggcgcacg tctatgccac tctgccggaa gctgatacct acgtaatctt    1260
cggcccgaac cacaccggct acggtagccc tgtctctgtg agccgtgaaa cttggaagac    1320
cccgttgggc aatatcgatg ttgacctgga actggcggac ggcttcctgg ttccatcgt     1380 agatgcggat gaactcggtc acaaatacga acactctatc gaagttcagc tgccgtttct    1440
gcaataccgt tttgaacgcg atttcaaaat tctgccaatc tgcatgggta tgcaagacga    1500
agaaaccgcg gtcgaagtag gtaacctgct ggcggatctg atcagcgagt ccggtaaacg    1560
tgctgtgatc atcgcaagct ctgatttcac ccactatgag acggctgaac gtgccaaaga    1620
aatcgattcc gaagttattg attctatcct gaactttgac atctctggca tgtacgatcg    1680
cctgtatcgc cgtaacgcct ctgtttgcgg ttacggcccg atcaccgcta tgctgacggc    1740
aagcaaaaag ctgggcggct ctcgtgcgac tttgctgaaa tacgcaaaca gcggtgacgt    1800
gtccggtgat aaagacgctg tggtgggcta cgccgccatc atcgttgagt aagctgatta    1860
aaggttgaac agataggatt tcgtcatgga tcctacaagg aggaaaaaaa catgaatgct    1920
tctaatgaac cggtgattct gaaactgggt ggctctgcta ttaccgacaa aggtgcctac    1980
gaaggcgtag ttaaggaagc tgatttgctg cgcatcgcac aggaagttag cggtttccgt    2040
ggcaagatga tcgtggttca tggtgctggt agcttcggcc atacgtacgc gaagaaatac    2100
ggcctggacc gtaccttcga cccagagggc gcaattgtta ctcatgaatc tgttaaaaag    2160
ctcgcctcca agttgtaggt tgctctgaat agcttcggcg tgcgtgctat cgcggtgcat    2220
cctatggact gcgcagtatg ccgtaacggt cgtatcgaaa cgatgtatct ggactccatc    2280
aagttaatgc tggaaaaagg tctggtgccg gttctgcacg cgacgtcgc aatggatatt     2340 gaactgggca cttgtatcct gtccggtgat caaatcgttc cttacctggc caaagaactg    2400
ggtatctccc gcctcggcct gggcagcgca gaggatggtg tgctggatat ggagggcaaa    2460
cctgtaccgg aaatcacccc agaaactttc gaagagttcc gccactgcat cggtggttct    2520
ggttctactg atgtaaccgg tggcatgctg ggcaaagtgc tggaacttct ggaattgagc    2580
aaaaattctt ccattactag ctacattttc aacgctggta agcagacaa catctaccgc     2640 tttctgaatg gtgagtccat cggcactcgc atcagcccgg acaagcgtgt ttaagctagt    2700
```

-continued

```
tattaaccta aatgctctaa accagttatg agctctacaa ggaggaaaaa aacatgatta    2760
acactaccag ccgccgcaaa attgaacacc tgaaactctg cgcagaatcc ccggttgaag    2820
cgcgtcaggt atctgccggc tttgaagacg ttactctgat ccaccgcgct ttaccggagc    2880
tgaacatgga tgaactggac ctcagcgttg atttcctggg taaacgcatc aaagcgccgt    2940
tcctgattgc gtctatcacg ggtggtcacc cagataccat cccggttaac gctgcgctgg    3000
cagctgctgc tgaggagctg ggtgttggca tcggcgttgg ctctcagcgc gcggccattg    3060
atgatccgag ccaggaagac agcttccgtg tagtgcgtga tgaagcccca gatgcgtttg    3120
tttatggcaa cgtcggcgca gcacagatcc gtcagtatgg tgttgaaggt gttgaaaaac    3180
tgatcgaaat gattgacgca gatgccttgg caatccacct gaactttctg caagaagcgg    3240
tccaaccgga aggtgaccgc gacgcgaccg gttgcctgga catgattacc gaaatttgct    3300
ctcagattaa aactccggta atcgtgaaag aaaccggtgc aggcattagc cgtgaagatg    3360
cgattctgtt ccagaaagct ggcgtgagcg caatcgacgt tggcggcgcg ggcggcacct    3420
cctgggctgg cgtcgaggtc taccgtgcta agaaagccg tgactctgtt agcgagcgtt    3480
taggtgagct gttttgggat tcggcattc cgacggtagc ttctctgatt gaatcccgcg    3540
tttccttgcc gctgatcgca accggcggta tccgtaacgg tctggacatt gctaaaagca    3600
ttgctctcgg cgcaagcgct gccagcgccg ctctgccgtt cgttggtccg tccctggagg    3660
gcaaagaatc cgttgtacgt gtgctgagct gcatgctgga agaatttaaa gcagcaatgt    3720
ttttgtgcgg ttgcggcaac atcaaagacc tgcacaactc tccagtagtg gtaactggtt    3780
ggacccgcga ataccggag cagcgcggtt ttaacgttaa ggacctctcc ctgccgggca    3840
acgctctgta agcttcaacg cgtctacaaa taaaaaggc acgtcagatg acgtgccttt    3900
tttcttgtct aga                                                      3913
```

<210> SEQ ID NO 47
<211> LENGTH: 6647
<212> TYPE: DNA
<213> ORGANISM: Artificial Sequence
<220> FEATURE:
<223> OTHER INFORMATION: Synthetic Construct

<400> SEQUENCE: 47

```
aagggcgagc tcaacgatcc ggctgctaac aaagcccgaa aggaagctga gttggctgct      60
gccaccgctg agcaataact agcataaccc cttggggcct ctaaacgggt cttgaggagt     120
tttttgctga aaggaggaac tatatccgga tatcccgcaa gaggcccggc agtaccggca     180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata ataatggttt cttagacgtc     420
aggtggcact tttcggggaa atgtgcgcgg aaccctatt tgtttattt tctaaataca     480 ttcaaatatg tatccgctca tgagacaata accctgataa atgcttcaat aatattgaaa     540
aaggaagagt atgattgaac aagatggatt gcacgcaggt tctccggccg cttgggtgga     600
gaggctattc ggctatgact gggcacaact gacaatcggc tgctctgatg ccgccgtgtt     660
ccggctgtca gcgcaggggc gcccggttct ttttgtcaag accgacctgt ccggtgccct     720
gaatgaactg caggacgagg cagcgcggct atcgtggctg gccacgacgg cgttccttg     780 cgcagctgtg ctcgacgttg tcactgaagc gggaagggac tggctgctat gggcgaagt     840
```

-continued

```
gccggggcag gatcctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtgaaaat ggccgctttt ctggattcat cgactgtggc cggctgggtg tggcggaccg    1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc ttttgataa tctcatgacc aaaatccctt    1500
aacgtgagtt ttcgttccac tgagcgtcag accccgtaga aagatcaaa ggatcttctt    1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccagggg aaacgcctgg tatctttata gtcctgtcgg gtttcgccac ctctgacttg    2100
agcgtcgatt tttgtgatgc tcgtcagggg gcggagcct atggaaaaac gccagcaacg    2160
cggccttttt acggttcctg ccttttgct ggccttttgc tcacatgttc tttcctgcgt    2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg ccatgttaa gggcggtttt tcctgtttg    2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag gccgctgact ccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
```

```
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata atcgccgtg acgatcagcg    3540 gtccaatgat cgaagttagg ctggtaagag ccgcgagcga tccttgaagc tgtccctgat   3600
ggtcgtcatc tacctgcctg acagcatgg cctgcaacgc gggcatcccg atgccgccgg    3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg caccctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
acaatttgcg acggcgcgtg cagggccaga ctggaggtgg caacgccaat cagcaacgac   4980
tgtttgcccg ccagttgttg tgccacgcgg ttgggaatgt aattcagctc cgccatcgcc   5040
gcttccactt tttcccgcgt tttcgcagaa acgtggctgg cctggttcac cacgcgggaa   5100
acggtctgat aagagacacc ggcatactct gcgacatcgt ataacgttac tggtttcaca   5160
ttcaccaccc tgaattgact ctcttccggg cgctatcatg ccataccgcg aaaggttttg   5220
cgccattcga tggtgtccgg gatctcgacg ctctccctta tgcgactcct gcattaggaa   5280
gcagcccagt agtaggttga ggccgttgag caccgccgcc gcaaggaatg gtgcatgcaa   5340
ggagatggcg cccaacagtc cccccggccac ggggcctgcc accatacccca gccgaaaca   5400 agcgctcatg agcccgaagt ggcgagcccg atcttcccca tcggtgatgt cggcgatata   5460
ggcgccagca accgcacctg tggcgccggt gatgccggcc acgatgcgtc cggcgtagag   5520
gatcgagatc tcgatcccgc gaaattaata cgactcacta tagggaatt gtgagcggat   5580
```

```
aacaattccc ctctagaaat aattttgttt aactttaaga aggagatata catatgcggg      5640
gttctcatca tcatcatcat catggtatgg ctagcatgac tggtggacag caaatgggtc      5700
gggatctgta cgacgatgac gataaggatc atcccttcac catggtatcc tgttctgcgc      5760
cgggtaagat ttacctgttc ggtgaacacg ccgtagttta tggcgaaact gcaattgcgt      5820
gtgcggtgga actgcgtacc cgtgttcgcg cggaactcaa tgactctatc actattcaga      5880
gccagatcgg ccgcaccggt ctggatttcg aaaagcaccc ttatgtgtct gcggtaattg      5940
agaaaatgcg caaatctatt cctattaacg gtgttttctt gaccgtcgat tccgacatcc      6000
cggtgggctc cggtctgggt agcagcgcag ccgttactat cgcgtctatt ggtgcgctga      6060
acgagctgtt cggctttggc ctcagcctgc aagaaatcgc taaactgggc cacgaaatcg      6120
aaattaaagt acagggtgcc gcgtccccaa ccgatacgta tgtttctacc ttcggcggcg      6180
tggttaccat cccggaacgt cgcaaactga aaactccgga ctgcggcatt gtgattggcg      6240
ataccggcgt tttctcctcc accaaagagt tagtagctaa cgtacgtcag ctgcgcgaaa      6300
gctacccgga tttgatcgaa ccgctgatga cctctattgg caaaatctct cgtatcggcg      6360
aacaactggt tctgtctggc gactacgcat ccatcggccg cctgatgaac gtcaaccagg      6420
gtctcctgga cgccctgggc gttaacatct tagaactgag ccagctgatc tattccgctc      6480
gtgcggcagg tgcgtttggc gctaaaatca cgggcgctgg cggcggtggc tgtatggttg      6540
cgctgaccgc tccggaaaaa tgcaaccaag tggcagaagc ggtagcaggc gctggcggta      6600
aagtgactat cactaaaccg accgagcaag gtctgaaagt agattaa                   6647
```

<210> SEQ ID NO 48
<211> LENGTH: 7519
<212> TYPE: DNA
<213> ORGANISM: Artificial Sequence
<220> FEATURE:
<223> OTHER INFORMATION: Synthetic Construct

<400> SEQUENCE: 48

```
ctcgggccgt ctcttgggct tgatcggcct tcttgcgcat ctcacgcgct cctgcggcgg       60
cctgtagggc aggctcatac ccctgccgaa ccgcttttgt cagccggtcg gccacggctt      120
ccggcgtctc aacgcgcttt gagattccca gcttttcggc caatccctgc ggtgcatagg      180
cgcgtggctc gaccgcttgc gggctgatgg tgacgtggcc cactggtggc cgctccaggg      240
cctcgtagaa cgcctgaatg cgcgtgtgac gtgccttgct gccctcgatg ccccgttgca      300
gccctagatc ggccacagcg gccgcaaacg tggtctggtc gcgggtcatc tgcgctttgt      360
tgccgatgaa ctccttggcc gacagcctgc cgtcctgcgt cagcggcacc acgaacgcgg      420
tcatgtgcgg gctggtttcg tcacggtgga tgctggccgt cacgatgcga tccgccccgt      480
acttgtccgc cagccacttg tgcgccttct cgaagaacgc cgcctgctgt tcttggctgg      540
ccgacttcca ccattccggg ctggccgtca tgacgtactc gaccgccaac acagcgtcct      600
tgcgccgctt ctctggcagc aactcgcgca gtcggcccat cgcttcatcg gtgctgctgg      660
ccgcccagtg ctcgttctct ggcgtcctgc tgggcgtcagc gttgggcgtc tcgcgctcgc      720
ggtaggcgtg cttgagactg gccgccacgt tgccatttt cgccagcttc ttgcatcgca      780
tgatcgcgta tgccgccatg cctgccctc ccttttggtg tccaaccggc tcgacggggg      840
cagcgcaagg cggtgcctcc ggcgggccac tcaatgcttg agtatactca ctagactttg      900
cttcgcaaag tcgtgaccgc ctacggcggc tgcggcgccc tacgggcttg ctctccgggc      960
```

-continued

```
ttcgccctgc gcggtcgctg cgctcccttg ccagcccgtg gatatgtgga cgatggccgc    1020
gagcggccac cggctggctc gcttcgctcg gcccgtggac aaccctgctg gacaagctga    1080
tggacaggct gcgcctgccc acgagcttga ccacagggat tgcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt gggggcagtc gaaggcgaag cccgcccgcc    1380 tgcccccccga gcctcacggc ggcgagtgcg ggggttccaa gggggcagcg ccaccttggg    1440
caaggccgaa ggccgcgcag tcgatcaaca agccccggag gggccacttt tgccggagg     1500 gggagccgcg ccgaaggcgt gggggaaccc cgcaggggtg cccttctttg gcaccaaag     1560 aactagatat agggcgaaat gcgaaagact aaaaatcaa caacttaaaa aagggggta     1620 cgcaacagct cattgcggca ccccccgcaa tagctcattg cgtaggttaa agaaaatctg    1680
taattgactg ccacttttac gcaacgcata attgttgtcg cgctgccgaa aagttgcagc    1740
tgattgcgca tggtgccgca accgtgcggc accctaccgc atggagataa gcatggccac    1800
gcagtccaga gaaatcggca ttcaagccaa gaacaagccc ggtcactggg tgcaaacgga    1860
acgcaaagcg catgaggcgt gggccgggct tattgcgagg aaacccacgg cggcaatgct    1920
gctgcatcac ctcgtggcgc agatgggcca ccagaacgcc gtggtggtca gccagaagac    1980
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
tgccgccgtg gtggttgatc acgacgacca ggacgaatcg ctgttggggc atggcgacct    2220
gcgccgcatc ccgaccctgt atccgggcga gcagcaacta ccgaccggcc ccggcgagga    2280
gccgcccagc cagcccggca ttccgggcat ggaaccagac ctgccagcct tgaccgaaac    2340
ggaggaatgg gaacggcgcg ggcagcagcg cctgccgatg cccgatgagc cgtgttttct    2400
ggacgatggc gagccgttgg agccgccgac acgggtcacg ctgccgcgcc ggtagcactt    2460
gggttgcgca gcaacccgta agtgcgctgt tccagactat cggctgtagc cgcctcgccg    2520
ccctatacct tgtctgcctc cccgcgttgc gtcgcggtgc atggagccgg gccacctcga    2580
cctgaatgga agccggcggc acctcgctaa cggattcacc gttttatca ggctctggga    2640 ggcagaataa atgatcatat cgtcaattat tacctccacg gggagagcct gagcaaactg    2700
gcctcaggca tttgagaagc acacggtcac actgcttccg gtagtcaata aaccggtaaa    2760
ccagcaatag acataagcgg ctatttaacg accctgccct gaaccgacga ccgggtcgaa    2820
tttgctttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagaactagt ggatccccg gctgcatgc tcgagcggcc gccagtgtga tggatatctg    3300
cagaattcgc ccttcttgat atcttagtgt gcgttaacca ccacccacat tggtccctgc    3360
```

```
ccgaccgcat agcggccttt ttcatgcagt agcccctgct cgccaacaat ttcgtatacc    3420
gagatgtggt gagattttgt cccggcggca atcagatact tgccgctgtg atcaacattg    3480
aagccgcgcg gctgggtttc cgttggctgg aagccttctt tactcaacac gctgccatct    3540
tccgaaacgc tgaaaacggt aatcaggctg gcggtacggt cgcaggcgta taaatggcga    3600
ccatccgggg tgatatgaat atcagccgcc aacgggtgt cggagaagtt ttccggcatc     3660
atatccagcg tctggacaca ttcgatatta ccgtgcggat ctttcagttc ccagacatcc    3720
actgagctgt ttaactcatt gacgcaatac gcatattgtt cgtttggatg gaataccata    3780
tgacgcgggc cggccccttc aacggtggtc acttccgcag ggtcctgcgc cacgagatga    3840
ccatcatcgc tgaccgtaaa caggcaaatg cgatcctgct taatgccgg aacccacagc     3900
gtacggttgt ccggtgagat attggcggaa tggcaaccgt ccagcccctc gaccacatcg    3960
acgacgccca ctggcaggcc atcttccaga cgcgttacgc tcacgttacc cgcattgtaa    4020
gaacctacaa agacaaactg cccctggtga tcggtggaaa tatgcgtcgg actcccggc    4080
agcgcagact ctgcggcaaa ggtcagtgcg ccatcgtccg gggcgatacg atacgccagg    4140
acgcgaaact cagggcgaac accaacatag agataacgtt tgtccgggct gaccaccatc    4200
ggctgcacct gccccggcac atcgacaacc tgtgtcagcg tcagtgcgcc ttcatgattc    4260
agattccaga cgtgaatttg ctggctctca gggctggcga tataaactgt ttgcttcatg    4320
aatgctcctt tgggttacct ccgggaaacg cggttgattt gtttagtggt tgaattattt    4380
gctcaggatg tggcatagtc aagggcgtga cggctcgcta atacaactca ctataggggct   4440
cgaggaagtt cctatacttt ctagagaata ggaacttccg cgccgcacac aaaaaccaac    4500
acacagatca tgaaaataaa gctcttttat tggtaccgaa ttcgccaggg agctctcaga    4560
cgtcgcttgg tcggtctta ttcgaacccc agagtcccgc ttacgccccg ccctgccact     4620
catcgcagta ctgttgtaat tcattaagca ttctgccgac atggaagcca tcacaaacgg    4680
catgatgaac ctgaatcgcc agcggcatca gcaccttgtc gccttgcgta taatatttgc    4740
ccatggtgaa aacgggggcg aagaagttgt ccatattggc cacgtttaaa tcaaaactgg    4800
tgaaactcac ccagggattg gctgagacga aaaacatatt ctcaataaac cctttaggga    4860
aataggccag ttttcaccg taacacgcca catcttgcga atatatgtgt agaaactgcc     4920
ggaaatcgtc gtggtattca ctccagagcg atgaaaacgt ttcagtttgc tcatggaaaa    4980
cggtgtaaca agggtgaaca ctatcccata tcaccagctc accgtctttc attgccatac    5040
ggaattccgg atgagcattc atcaggcggg caagaatgtg aataaaggcc ggataaaact    5100
tgtgcttatt tttctttacg gtcttaaaa aggccgtaat atccagctga acggtctggt     5160
tataggtaca ttgagcaact gactgaaatg cctcaaaatg ttctttacga tgccattggg    5220
atatatcaac ggtggtatat ccagtgattt ttttctccat ggtttagttc ctcaccttgt    5280
cgtattatac tatgccgata tactatgccg atgattaatt gtcaacacgt gctgctgcag    5340
gtcgaaaggc ccggagatga ggaagaggag aacagcgcgg cagacgtgcg cttttgaagc    5400
gtgcagaatg ccgggcctcc ggaggaccttt cgggcgcccg cccgcccct gagcccgccc    5460
ctgagcccgc ccccggaccc accccttccc agcctctgag cccagaaagc gaaggagcaa    5520
agctgctatt ggccgctgcc ccaaaggcct acccgcttcc attgctcagc ggtgctgtcc    5580
atctgcacga gactagtgag acgtgctact tccatttgtc acgtcctgca cgacgcgagc    5640
tgcggggcgg gggggaactt cctgactagg ggaggagtgg aaggtggcgc gaaggggcca    5700
```

| | |
|---|---:|
| ccaaagaacg gagccggttg gcgcctaccg gtggatgtgg aatgtgtgcg aggccagagg | 5760 |
| ccacttgtgt agcgccaagt gcccagcggg gctgctaaag cgcatgctcc agactgcctt | 5820 |
| gggaaaagcg cctcccctac ccggtagaat gaagttccta cactttctag agaataggaa | 5880 |
| cttcgcggcc gcccttttagt gagggttaat tcaactgact gtaacagcta aaattagtcg | 5940 |
| cttttggcgg taagggcgaa ttccagcaca ctggcggccg ttactagtgg atccgagctc | 6000 |
| ggtaccaagc ttgatgcagg aattcgatat caagcttatc gataccgtcg acctcgaggg | 6060 |
| ggggcccggt acccagcttt tgttcccttt agtgagggtt aattgcgcgc ttggcgtaat | 6120 |
| catggtcata gctgtttcct gtgtgaaatt gttatccgct cacaattcca cacaacatac | 6180 |
| gagccggaag cataaagtgt aaagcctggg gtgcctaatg agtgagctaa ctcacattaa | 6240 |
| ttgcgttgcg ctcactgccc gctttccagt cgggaaacct gtcgtgccag ctgcattaat | 6300 |
| gaatcggcca acgcgcgggg agaggcggtt tgcgtattgg gcgcatgcat aaaaactgtt | 6360 |
| gtaattcatt aagcattctg ccgacatgga agccatcaca aacggcatga tgaacctgaa | 6420 |
| tcgccagcgg catcagcacc ttgtcgcctt gcgtataata tttgcccatg gacgcacacc | 6480 |
| gtggaaacgg atgaaggcac gaacccagtt gacataagcc tgttcggttc gtaaactgta | 6540 |
| atgcaagtag cgtatgcgct cacgcaactg gtccagaacc ttgaccgaac gcagcggtgg | 6600 |
| taacggcgca gtggcggttt tcatggcttg ttatgactgt ttttttgtac agtctatgcc | 6660 |
| tcgggcatcc aagcagcaag cgcgttacgc cgtgggtcga tgtttgatgt tatggagcag | 6720 |
| caacgatgtt acgcagcagc aacgatgtta cgcagcaggg cagtcgccct aaaacaaagt | 6780 |
| taggtggctc aagtatgggc atcattcgca catgtaggct cggccctgac caagtcaaat | 6840 |
| ccatgcgggc tgctcttgat cttttcggtc gtgagttcgg agacgtagcc acctactccc | 6900 |
| aacatcagcc ggactccgat tacctcggga acttgctccg tagtaagaca ttcatcgcgc | 6960 |
| ttgctgcctt cgaccaagaa gcggttgttg gcgctctcgc ggcttacgtt ctgcccaggt | 7020 |
| ttgagcagcc gcgtagtgag atctatatct atgatctcgc agtctccggc gagcaccgga | 7080 |
| ggcagggcat tgccaccgcg ctcatcaatc tcctcaagca tgaggccaac gcgcttggtg | 7140 |
| cttatgtgat ctacgtgcaa gcagattacg gtgacgatcc cgcagtggct ctctatacaa | 7200 |
| agttgggcat acgggaagaa gtgatgcact ttgatatcga cccaagtacc gccacctaac | 7260 |
| aattcgttca agccgagatc ggcttcccgg ccgcggagtt gttcggtaaa ttgtcacaac | 7320 |
| gccgccaggt ggcacttttc ggggaaatgt gcgcgcccgc gttcctgctg gcgctgggcc | 7380 |
| tgtttctggc gctggacttc ccgctgttcc gtcagcagct tttcgcccac ggccttgatg | 7440 |
| atcgcggcgg ccttggcctg catatcccga ttcaacggcc caggcgtc cagaacgggc | 7500 |
| ttcaggcgct cccgaaggt | 7519 |

<210> SEQ ID NO 49
<211> LENGTH: 37
<212> TYPE: DNA
<213> ORGANISM: Artificial Sequence
<220> FEATURE:
<223> OTHER INFORMATION: Synthetic Construct

<400> SEQUENCE: 49

| | |
|---|---:|
| cgtgagatca tatgtgtgcg acctcttctc aatttac | 37 |

<210> SEQ ID NO 50
<211> LENGTH: 38
<212> TYPE: DNA
<213> ORGANISM: Artificial Sequence

```
<220> FEATURE:
<223> OTHER INFORMATION: Synthetic Construct

<400> SEQUENCE: 50
cggtcgacgg atccctgcag ttagacatac atcagctg                              38

<210> SEQ ID NO 51
<211> LENGTH: 41
<212> TYPE: DNA
<213> ORGANISM: Artificial Sequence
<220> FEATURE:
<223> OTHER INFORMATION: Synthetic Construct

<400> SEQUENCE: 51
catatgaaag cttgtatcga ttaaataagg aggaataaac c                          41

<210> SEQ ID NO 52
<211> LENGTH: 60
<212> TYPE: DNA
<213> ORGANISM: Artificial Sequence
<220> FEATURE:
<223> OTHER INFORMATION: Synthetic Construct

<400> SEQUENCE: 52
gatcatgcat tcgcccttag gaggtaaaaa aacatgtgtg cgacctcttc tcaatttact      60

<210> SEQ ID NO 53
<211> LENGTH: 31
<212> TYPE: DNA
<213> ORGANISM: Artificial Sequence
<220> FEATURE:
<223> OTHER INFORMATION: Synthetic Construct

<400> SEQUENCE: 53
gacatcaatt gctccatttt cttctgctat c                                     31

<210> SEQ ID NO 54
<211> LENGTH: 41
<212> TYPE: DNA
<213> ORGANISM: Artificial Sequence
<220> FEATURE:
<223> OTHER INFORMATION: Synthetic Construct

<400> SEQUENCE: 54
attgagaaga ggtcgcacac actctttacc ctctcctttt a                          41

<210> SEQ ID NO 55
<211> LENGTH: 41
<212> TYPE: DNA
<213> ORGANISM: Artificial Sequence
<220> FEATURE:
<223> OTHER INFORMATION: Synthetic Construct

<400> SEQUENCE: 55
taaaaggaga gggtaaagag tgtgtgcgac ctcttctcaa t                          41

<210> SEQ ID NO 56
<211> LENGTH: 41
<212> TYPE: DNA
<213> ORGANISM: Artificial Sequence
<220> FEATURE:
<223> OTHER INFORMATION: Synthetic Construct

<400> SEQUENCE: 56
ccaaggccgg ttttttttag acatacatca gctggttaat c                          41
```

<210> SEQ ID NO 57
<211> LENGTH: 41
<212> TYPE: DNA
<213> ORGANISM: Artificial Sequence
<220> FEATURE:
<223> OTHER INFORMATION: Synthetic Construct

<400> SEQUENCE: 57
gattaaccag ctgatgtatg tctaaaaaaa accggccttg g                41

<210> SEQ ID NO 58
<211> LENGTH: 32
<212> TYPE: DNA
<213> ORGANISM: Artificial Sequence
<220> FEATURE:
<223> OTHER INFORMATION: Synthetic Construct

<400> SEQUENCE: 58
gacatgacgg atccgattac gaatgccgtc tc                          32

<210> SEQ ID NO 59
<211> LENGTH: 27
<212> TYPE: DNA
<213> ORGANISM: Artificial Sequence
<220> FEATURE:
<223> OTHER INFORMATION: Synthetic Construct

<400> SEQUENCE: 59
gacatgaatt cctccatttt cttctgc                                27

<210> SEQ ID NO 60
<211> LENGTH: 20
<212> TYPE: DNA
<213> ORGANISM: Artificial Sequence
<220> FEATURE:
<223> OTHER INFORMATION: Synthetic Construct

<400> SEQUENCE: 60
aggagagggt aaagagtgag                                        20

<210> SEQ ID NO 61
<211> LENGTH: 22
<212> TYPE: DNA
<213> ORGANISM: Artificial Sequence
<220> FEATURE:
<223> OTHER INFORMATION: Synthetic Construct

<400> SEQUENCE: 61
cttttccatc acccacctga ag                                     22

<210> SEQ ID NO 62
<211> LENGTH: 28
<212> TYPE: DNA
<213> ORGANISM: Artificial Sequence
<220> FEATURE:
<223> OTHER INFORMATION: Synthetic Construct

<400> SEQUENCE: 62
ggcgaaatgg tccaacaaca aaattatc                               28

<210> SEQ ID NO 63
<211> LENGTH: 40
<212> TYPE: DNA
<213> ORGANISM: Artificial Sequence
<220> FEATURE:
<223> OTHER INFORMATION: Synthetic Construct

<400> SEQUENCE: 63
gcttatggat cctctagact attacacgta catcaattgg                           40

<210> SEQ ID NO 64
<211> LENGTH: 30
<212> TYPE: DNA
<213> ORGANISM: Artificial Sequence
<220> FEATURE:
<223> OTHER INFORMATION: Synthetic Construct

<400> SEQUENCE: 64
caccatgtgt gcaacctcct cccagtttac                                      30

<210> SEQ ID NO 65
<211> LENGTH: 51
<212> TYPE: DNA
<213> ORGANISM: Artificial Sequence
<220> FEATURE:
<223> OTHER INFORMATION: Synthetic Construct

<400> SEQUENCE: 65
ggtgaattca gtctactggg gattcccaaa tctatatata ctgcaggtga c              51

<210> SEQ ID NO 66
<211> LENGTH: 23
<212> TYPE: DNA
<213> ORGANISM: Artificial Sequence
<220> FEATURE:
<223> OTHER INFORMATION: Synthetic Construct

<400> SEQUENCE: 66
gcaggtggga aactatgcac tcc                                             23

<210> SEQ ID NO 67
<211> LENGTH: 36
<212> TYPE: DNA
<213> ORGANISM: Artificial Sequence
<220> FEATURE:
<223> OTHER INFORMATION: Synthetic Construct

<400> SEQUENCE: 67
cctgaattct gttggattgg aggattggat agtggg                               36

<210> SEQ ID NO 68
<211> LENGTH: 30
<212> TYPE: DNA
<213> ORGANISM: Artificial Sequence
<220> FEATURE:
<223> OTHER INFORMATION: Synthetic Construct

<400> SEQUENCE: 68
ggtgtcgacg tacggtcgag cttattgacc                                      30

<210> SEQ ID NO 69
<211> LENGTH: 32
<212> TYPE: DNA
<213> ORGANISM: Artificial Sequence
<220> FEATURE:
<223> OTHER INFORMATION: Synthetic Construct

<400> SEQUENCE: 69
ggtgggcccg cattttgcca cctacaagcc ag                                   32

<210> SEQ ID NO 70

```
<211> LENGTH: 40
<212> TYPE: DNA
<213> ORGANISM: Artificial Sequence
<220> FEATURE:
<223> OTHER INFORMATION: Synthetic Construct

<400> SEQUENCE: 70
ggtgaattct agaggatccc aacgctgttg cctacaacgg                    40

<210> SEQ ID NO 71
<211> LENGTH: 36
<212> TYPE: DNA
<213> ORGANISM: Artificial Sequence
<220> FEATURE:
<223> OTHER INFORMATION: Synthetic Construct

<400> SEQUENCE: 71
ggtgcggccg ctgtctggac ctggtgagtt tccccg                        36

<210> SEQ ID NO 72
<211> LENGTH: 37
<212> TYPE: DNA
<213> ORGANISM: Artificial Sequence
<220> FEATURE:
<223> OTHER INFORMATION: Synthetic Construct

<400> SEQUENCE: 72
ggtgggccca ttaaatcagt tatcgtttat ttgatag                       37

<210> SEQ ID NO 73
<211> LENGTH: 35
<212> TYPE: DNA
<213> ORGANISM: Artificial Sequence
<220> FEATURE:
<223> OTHER INFORMATION: Synthetic Construct

<400> SEQUENCE: 73
ggtgaccagc aagtccatgg gtggtttgat catgg                         35

<210> SEQ ID NO 74
<211> LENGTH: 35
<212> TYPE: DNA
<213> ORGANISM: Artificial Sequence
<220> FEATURE:
<223> OTHER INFORMATION: Synthetic Construct

<400> SEQUENCE: 74
ggtgcggccg cctttggagt acgactccaa ctatg                         35

<210> SEQ ID NO 75
<211> LENGTH: 31
<212> TYPE: DNA
<213> ORGANISM: Artificial Sequence
<220> FEATURE:
<223> OTHER INFORMATION: Synthetic Construct

<400> SEQUENCE: 75
gcggccgcag actaaattta tttcagtctc c                             31

<210> SEQ ID NO 76
<211> LENGTH: 28
<212> TYPE: DNA
<213> ORGANISM: Artificial Sequence
<220> FEATURE:
<223> OTHER INFORMATION: Synthetic Construct

<400> SEQUENCE: 76
```
gatcaagctt aaccggaatt gccagctg                                           28

<210> SEQ ID NO 77
<211> LENGTH: 33
<212> TYPE: DNA
<213> ORGANISM: Artificial Sequence
<220> FEATURE:
<223> OTHER INFORMATION: Synthetic Construct

<400> SEQUENCE: 77
gatccgatcg tcagaagaac tcgtcaagaa ggc                                     33

<210> SEQ ID NO 78
<211> LENGTH: 38
<212> TYPE: DNA
<213> ORGANISM: Artificial Sequence
<220> FEATURE:
<223> OTHER INFORMATION: Synthetic Construct

<400> SEQUENCE: 78
catcaatgca tcgcccttag gaggtaaaaa aaaatgac                                38

<210> SEQ ID NO 79
<211> LENGTH: 26
<212> TYPE: DNA
<213> ORGANISM: Artificial Sequence
<220> FEATURE:
<223> OTHER INFORMATION: Synthetic Construct

<400> SEQUENCE: 79
ccttctgcag gacgcgttgt tatagc                                             26

<210> SEQ ID NO 80
<211> LENGTH: 60
<212> TYPE: DNA
<213> ORGANISM: Artificial Sequence
<220> FEATURE:
<223> OTHER INFORMATION: Synthetic Construct

<400> SEQUENCE: 80
gatcatgcat tcgcccttag gaggtaaaaa aacatgagtt ttgatattgc caaatacccg        60

<210> SEQ ID NO 81
<211> LENGTH: 31
<212> TYPE: DNA
<213> ORGANISM: Artificial Sequence
<220> FEATURE:
<223> OTHER INFORMATION: Synthetic Construct

<400> SEQUENCE: 81
catgctgcag ttatgccagc caggccttga t                                       31

<210> SEQ ID NO 82
<211> LENGTH: 7
<212> TYPE: DNA
<213> ORGANISM: Artificial Sequence
<220> FEATURE:
<223> OTHER INFORMATION: Synthetic Construct

<400> SEQUENCE: 82 aggaggt                                                                   7

<210> SEQ ID NO 83
<211> LENGTH: 7
<212> TYPE: DNA

```
<213> ORGANISM: Artificial Sequence
<220> FEATURE:
<223> OTHER INFORMATION: Synthetic Construct

<400> SEQUENCE: 83 aaggagg                                                                       7

<210> SEQ ID NO 84
<211> LENGTH: 41
<212> TYPE: DNA
<213> ORGANISM: Artificial Sequence
<220> FEATURE:
<223> OTHER INFORMATION: Synthetic Construct

<400> SEQUENCE: 84
aggaggtaaa aaaacatgtc attaccgttc ttaacttctg c                                 41

<210> SEQ ID NO 85
<211> LENGTH: 52
<212> TYPE: DNA
<213> ORGANISM: Artificial Sequence
<220> FEATURE:
<223> OTHER INFORMATION: Synthetic Construct

<400> SEQUENCE: 85
atggctgcag gcctatcgca aattagctta tgaagtccat ggtaaattcg tg                     52

<210> SEQ ID NO 86
<211> LENGTH: 23
<212> TYPE: DNA
<213> ORGANISM: Artificial Sequence
<220> FEATURE:
<223> OTHER INFORMATION: Synthetic Construct

<400> SEQUENCE: 86
gaattcgccc ttctgcagct acc                                                    23

<210> SEQ ID NO 87
<211> LENGTH: 38
<212> TYPE: DNA
<213> ORGANISM: Artificial Sequence
<220> FEATURE:
<223> OTHER INFORMATION: Synthetic Construct

<400> SEQUENCE: 87
cgactggtgc acccttaagg aggaaaaaaa catgtcag                                    38

<210> SEQ ID NO 88
<211> LENGTH: 25
<212> TYPE: DNA
<213> ORGANISM: Artificial Sequence
<220> FEATURE:
<223> OTHER INFORMATION: Synthetic Construct

<400> SEQUENCE: 88
gtgctggaat tcgcccttct gcagc                                                  25

<210> SEQ ID NO 89
<211> LENGTH: 32
<212> TYPE: DNA
<213> ORGANISM: Artificial Sequence
<220> FEATURE:
<223> OTHER INFORMATION: Synthetic Construct

<400> SEQUENCE: 89
gtagatgcat gcagaattcg cccttaagga gg                                          32
```

<210> SEQ ID NO 90
<211> LENGTH: 25
<212> TYPE: DNA
<213> ORGANISM: Artificial Sequence
<220> FEATURE:
<223> OTHER INFORMATION: Synthetic Construct

<400> SEQUENCE: 90
gtgtgatgga tatctgcaga attcg                                    25

<210> SEQ ID NO 91
<211> LENGTH: 36
<212> TYPE: DNA
<213> ORGANISM: Artificial Sequence
<220> FEATURE:
<223> OTHER INFORMATION: Synthetic Construct

<400> SEQUENCE: 91
catcaatgca tcgcccttag gaggtaaaaa aacatg                        36

<210> SEQ ID NO 92

<400> SEQUENCE: 92

000

<210> SEQ ID NO 93
<211> LENGTH: 50
<212> TYPE: DNA
<213> ORGANISM: Artificial Sequence
<220> FEATURE:
<223> OTHER INFORMATION: Synthetic Construct

<400> SEQUENCE: 93
gagacatgag ctcaggaggt aaaaaaacat gaaaacagta gttattattg         50

<210> SEQ ID NO 94
<211> LENGTH: 54
<212> TYPE: DNA
<213> ORGANISM: Artificial Sequence
<220> FEATURE:
<223> OTHER INFORMATION: Synthetic Construct

<400> SEQUENCE: 94
tttatcaatc ccaattgtca tgttttttta cctcctttat tgttttctta aatc    54

<210> SEQ ID NO 95
<211> LENGTH: 54
<212> TYPE: DNA
<213> ORGANISM: Artificial Sequence
<220> FEATURE:
<223> OTHER INFORMATION: Synthetic Construct

<400> SEQUENCE: 95
gatttaagaa aacaataaag gaggtaaaaa aacatgacaa ttgggattga taaa    54

<210> SEQ ID NO 96
<211> LENGTH: 40
<212> TYPE: DNA
<213> ORGANISM: Artificial Sequence
<220> FEATURE:
<223> OTHER INFORMATION: Synthetic Construct

<400> SEQUENCE: 96
gacatgacat agatctttag tttcgataag aacgaacggt                    40

<210> SEQ ID NO 97
<211> LENGTH: 26
<212> TYPE: DNA
<213> ORGANISM: Artificial Sequence
<220> FEATURE:
<223> OTHER INFORMATION: Synthetic Construct

<400> SEQUENCE: 97
atgaaaacag tagttattat tgatgc                                26

<210> SEQ ID NO 98
<211> LENGTH: 33
<212> TYPE: DNA
<213> ORGANISM: Artificial Sequence
<220> FEATURE:
<223> OTHER INFORMATION: Synthetic Construct

<400> SEQUENCE: 98
atgttattgt tttcttaaat catttaaaat agc                         33

<210> SEQ ID NO 99
<211> LENGTH: 26
<212> TYPE: DNA
<213> ORGANISM: Artificial Sequence
<220> FEATURE:
<223> OTHER INFORMATION: Synthetic Construct

<400> SEQUENCE: 99
atgacaattg ggattgataa aattag                                26

<210> SEQ ID NO 100
<211> LENGTH: 24
<212> TYPE: DNA
<213> ORGANISM: Artificial Sequence
<220> FEATURE:
<223> OTHER INFORMATION: Synthetic Construct

<400> SEQUENCE: 100
ttagtttcga taagaacgaa cggt                                  24

<210> SEQ ID NO 101
<211> LENGTH: 23
<212> TYPE: DNA
<213> ORGANISM: Artificial Sequence
<220> FEATURE:
<223> OTHER INFORMATION: Synthetic Construct

<400> SEQUENCE: 101
gaaatagccc cattagaagt atc                                   23

<210> SEQ ID NO 102
<211> LENGTH: 24
<212> TYPE: DNA
<213> ORGANISM: Artificial Sequence
<220> FEATURE:
<223> OTHER INFORMATION: Synthetic Construct

<400> SEQUENCE: 102
ttgccaatca tatgattgaa aatc                                  24

<210> SEQ ID NO 103
<211> LENGTH: 25
<212> TYPE: DNA
<213> ORGANISM: Artificial Sequence
<220> FEATURE:

<223> OTHER INFORMATION: Synthetic Construct

<400> SEQUENCE: 103
gctatgcttc attagatcct tatcg                                                  25

<210> SEQ ID NO 104
<211> LENGTH: 25
<212> TYPE: DNA
<213> ORGANISM: Artificial Sequence
<220> FEATURE:
<223> OTHER INFORMATION: Synthetic Construct

<400> SEQUENCE: 104
gaaacctaca tccaatcttt tgccc                                                  25

<210> SEQ ID NO 105
<211> LENGTH: 31
<212> TYPE: DNA
<213> ORGANISM: Artificial Sequence
<220> FEATURE:
<223> OTHER INFORMATION: Synthetic Construct

<400> SEQUENCE: 105
cttgatgcat cctgcattcg cccttaggag g                                           31

<210> SEQ ID NO 106
<211> LENGTH: 23
<212> TYPE: DNA
<213> ORGANISM: Artificial Sequence
<220> FEATURE:
<223> OTHER INFORMATION: Synthetic Construct

<400> SEQUENCE: 106
ccaggcaaat tctgttttat cag                                                    23

<210> SEQ ID NO 107
<211> LENGTH: 43
<212> TYPE: DNA
<213> ORGANISM: Artificial Sequence
<220> FEATURE:
<223> OTHER INFORMATION: Synthetic Construct

<400> SEQUENCE: 107
gcatgctcga gcggccgctt ttaatcaaac atcctgccaa ctc                              43

<210> SEQ ID NO 108
<211> LENGTH: 37
<212> TYPE: DNA
<213> ORGANISM: Artificial Sequence
<220> FEATURE:
<223> OTHER INFORMATION: Synthetic Construct

<400> SEQUENCE: 108
gatcgaaggg cgatcgtgtc acagtctggc gaaaccg                                     37

<210> SEQ ID NO 109
<211> LENGTH: 43
<212> TYPE: DNA
<213> ORGANISM: Artificial Sequence
<220> FEATURE:
<223> OTHER INFORMATION: Synthetic Construct

<400> SEQUENCE: 109
ctgaattctg cagatatctg tttttccact cttcgttcac ttt                              43

```
<210> SEQ ID NO 110
<211> LENGTH: 33
<212> TYPE: DNA
<213> ORGANISM: Artificial Sequence
<220> FEATURE:
<223> OTHER INFORMATION: Synthetic Construct

<400> SEQUENCE: 110
tctagagggc caagaaaaaa tgccccgctt acg                                    33

<210> SEQ ID NO 111
<211> LENGTH: 111
<212> TYPE: DNA
<213> ORGANISM: Artificial Sequence
<220> FEATURE:
<223> OTHER INFORMATION: Synthetic Construct

<400> SEQUENCE: 111
gatcgcggcc gcgcccttga cgatgccaca tcctgagcaa ataattcaac cactaattgt      60
gagcggataa cacaaggagg aaacagctat gtcattaccg ttcttaactt c               111

<210> SEQ ID NO 112
<211> LENGTH: 75
<212> TYPE: DNA
<213> ORGANISM: Artificial Sequence
<220> FEATURE:
<223> OTHER INFORMATION: Synthetic Construct

<400> SEQUENCE: 112
gatcgggccc caagaaaaaa ggcacgtcat ctgacgtgcc ttttttattt gtagacgcgt      60
tgttatagca ttcta                                                       75

<210> SEQ ID NO 113
<211> LENGTH: 81
<212> TYPE: DNA
<213> ORGANISM: Artificial Sequence
<220> FEATURE:
<223> OTHER INFORMATION: Synthetic Construct

<400> SEQUENCE: 113
aaagtagccg aagatgacgg tttgtcacat ggagttggca ggatgtttga ttaaaagcaa      60
ttaaccctca ctaaagggcg g                                                81

<210> SEQ ID NO 114
<211> LENGTH: 160
<212> TYPE: DNA
<213> ORGANISM: Artificial Sequence
<220> FEATURE:
<223> OTHER INFORMATION: Synthetic Construct

<400> SEQUENCE: 114
agagtgttca ccaaaaataa taacctttcc cggtgcagaa gttaagaacg gtaatgacat      60 agctgttttcc tccttgtgtt atccgctcac aattagtggt tgaattattt gctcaggatg    120
tggcatcgtc aagggctaat acgactcact atagggctcg                           160

<210> SEQ ID NO 115
<211> LENGTH: 27
<212> TYPE: DNA
<213> ORGANISM: Artificial Sequence
<220> FEATURE:
<223> OTHER INFORMATION: Synthetic Construct

<400> SEQUENCE: 115
```

```
gacatctgca gctccatttt cttctgc                                            27

<210> SEQ ID NO 116
<211> LENGTH: 42
<212> TYPE: DNA
<213> ORGANISM: Artificial Sequence
<220> FEATURE:
<223> OTHER INFORMATION: Synthetic Construct

<400> SEQUENCE: 116
caataataac tactgttttc actctttacc ctctcctttt aa                           42

<210> SEQ ID NO 117
<211> LENGTH: 42
<212> TYPE: DNA
<213> ORGANISM: Artificial Sequence
<220> FEATURE:
<223> OTHER INFORMATION: Synthetic Construct

<400> SEQUENCE: 117
ttaaaaggag agggtaaaga gtgaaaacag tagttattat tg                           42

<210> SEQ ID NO 118
<211> LENGTH: 45
<212> TYPE: DNA
<213> ORGANISM: Artificial Sequence
<220> FEATURE:
<223> OTHER INFORMATION: Synthetic Construct

<400> SEQUENCE: 118
cggggccaag gccggttttt tttagtttcg ataagaacga acggt                        45

<210> SEQ ID NO 119
<211> LENGTH: 45
<212> TYPE: DNA
<213> ORGANISM: Artificial Sequence
<220> FEATURE:
<223> OTHER INFORMATION: Synthetic Construct

<400> SEQUENCE: 119
accgttcgtt cttatcgaaa ctaaaaaaaa ccggccttgg ccccg                        45

<210> SEQ ID NO 120
<211> LENGTH: 22
<212> TYPE: DNA
<213> ORGANISM: Artificial Sequence
<220> FEATURE:
<223> OTHER INFORMATION: Synthetic Construct

<400> SEQUENCE: 120
caccatggta tcctgttctg cg                                                 22

<210> SEQ ID NO 121
<211> LENGTH: 22
<212> TYPE: DNA
<213> ORGANISM: Artificial Sequence
<220> FEATURE:
<223> OTHER INFORMATION: Synthetic Construct

<400> SEQUENCE: 121
ttaatctact ttcagaccctt gc                                                22

<210> SEQ ID NO 122
<211> LENGTH: 66
<212> TYPE: DNA
<213> ORGANISM: Artificial Sequence
```

<220> FEATURE:
<223> OTHER INFORMATION: Synthetic Construct

<400> SEQUENCE: 122
gcgaacgatg cataaaggag gtaaaaaaac atggtatcct gttctgcgcc gggtaagatt    60
tacctg    66

<210> SEQ ID NO 123
<211> LENGTH: 48
<212> TYPE: DNA
<213> ORGANISM: Artificial Sequence
<220> FEATURE:
<223> OTHER INFORMATION: Synthetic Construct

<400> SEQUENCE: 123
gggcccgttt aaactttaac tagactttaa tctactttca gaccttgc    48

<210> SEQ ID NO 124
<211> LENGTH: 20
<212> TYPE: DNA
<213> ORGANISM: Artificial Sequence
<220> FEATURE:
<223> OTHER INFORMATION: Synthetic Construct

<400> SEQUENCE: 124
caccaaagac ttcatagact    20

<210> SEQ ID NO 125
<211> LENGTH: 20
<212> TYPE: DNA
<213> ORGANISM: Artificial Sequence
<220> FEATURE:
<223> OTHER INFORMATION: Synthetic Construct

<400> SEQUENCE: 125
agagatatct tcctgctgct    20

<210> SEQ ID NO 126
<211> LENGTH: 20
<212> TYPE: DNA
<213> ORGANISM: Artificial Sequence
<220> FEATURE:
<223> OTHER INFORMATION: Synthetic Construct

<400> SEQUENCE: 126
taatacgact cactataggg    20

<210> SEQ ID NO 127
<211> LENGTH: 19
<212> TYPE: DNA
<213> ORGANISM: Artificial Sequence
<220> FEATURE:
<223> OTHER INFORMATION: Synthetic Construct

<400> SEQUENCE: 127
accaattgca cccggcaga    19

<210> SEQ ID NO 128
<211> LENGTH: 21
<212> TYPE: DNA
<213> ORGANISM: Artificial Sequence
<220> FEATURE:
<223> OTHER INFORMATION: Synthetic Construct

<400> SEQUENCE: 128
gctaaagcgc atgctccaga c                                             21

<210> SEQ ID NO 129
<211> LENGTH: 19
<212> TYPE: DNA
<213> ORGANISM: Artificial Sequence
<220> FEATURE:
<223> OTHER INFORMATION: Synthetic Construct

<400> SEQUENCE: 129
gactggcctc agatgaaag                                                19

<210> SEQ ID NO 130
<211> LENGTH: 20
<212> TYPE: DNA
<213> ORGANISM: Artificial Sequence
<220> FEATURE:
<223> OTHER INFORMATION: Synthetic Construct

<400> SEQUENCE: 130
caaacatgtg gcatggaaag                                               20

<210> SEQ ID NO 131
<211> LENGTH: 52
<212> TYPE: DNA
<213> ORGANISM: Artificial Sequence
<220> FEATURE:
<223> OTHER INFORMATION: Synthetic Construct

<400> SEQUENCE: 131
gggcccgttt aaactttaac tagactctgc agttagcgtt caaacggcag aa           52

<210> SEQ ID NO 132
<211> LENGTH: 38
<212> TYPE: DNA
<213> ORGANISM: Artificial Sequence
<220> FEATURE:
<223> OTHER INFORMATION: Synthetic Construct

<400> SEQUENCE: 132
cgcatgcatg tcatgagatg tagcgtgtcc accgaaaa                           38

<210> SEQ ID NO 133
<211> LENGTH: 22
<212> TYPE: DNA
<213> ORGANISM: Artificial Sequence
<220> FEATURE:
<223> OTHER INFORMATION: Synthetic Construct

<400> SEQUENCE: 133
acaatttcac acaggaaaca gc                                            22

<210> SEQ ID NO 134
<211> LENGTH: 22
<212> TYPE: DNA
<213> ORGANISM: Artificial Sequence
<220> FEATURE:
<223> OTHER INFORMATION: Synthetic Construct

<400> SEQUENCE: 134
gcactgtctt tccgtctgct gc                                            22

<210> SEQ ID NO 135

<400> SEQUENCE: 135

000

<210> SEQ ID NO 136
<400> SEQUENCE: 136

000

<210> SEQ ID NO 137
<211> LENGTH: 24
<212> TYPE: DNA
<213> ORGANISM: Artificial Sequence
<220> FEATURE:
<223> OTHER INFORMATION: Synthetic Construct

<400> SEQUENCE: 137
gatagtaacg gctgcgctgc tacc    24

<210> SEQ ID NO 138
<211> LENGTH: 23
<212> TYPE: DNA
<213> ORGANISM: Artificial Sequence
<220> FEATURE:
<223> OTHER INFORMATION: Synthetic Construct

<400> SEQUENCE: 138
gacagcttat catcgactgc acg    23

<210> SEQ ID NO 139
<211> LENGTH: 67
<212> TYPE: DNA
<213> ORGANISM: Artificial Sequence
<220> FEATURE:
<223> OTHER INFORMATION: Synthetic Construct

<400> SEQUENCE: 139
accgccaaaa gcgactaatt ttagctgtta cagtcagttg aattaaccct cactaaaggg    60
cggccgc    67

<210> SEQ ID NO 140
<211> LENGTH: 152
<212> TYPE: DNA
<213> ORGANISM: Artificial Sequence
<220> FEATURE:
<223> OTHER INFORMATION: Synthetic Construct

<400> SEQUENCE: 140
gctggcgata taaactgttt gcttcatgaa tgctcctttg ggttacctcc gggaaacgcg    60
gttgatttgt ttagtggttg aattatttgc tcaggatgtg gcatagtcaa gggcgtgacg    120
gctcgctaat acgactcact atagggctcg ag    152

<210> SEQ ID NO 141
<211> LENGTH: 26
<212> TYPE: DNA
<213> ORGANISM: Artificial Sequence
<220> FEATURE:
<223> OTHER INFORMATION: Synthetic Construct

<400> SEQUENCE: 141
accgccaaaa gcgactaatt ttagct    26

<210> SEQ ID NO 142
<211> LENGTH: 30
<212> TYPE: DNA

```
<213> ORGANISM: Artificial Sequence
<220> FEATURE:
<223> OTHER INFORMATION: Synthetic Construct

<400> SEQUENCE: 142
cttgatatct tagtgtgcgt taaccaccac                                           30

<210> SEQ ID NO 143
<211> LENGTH: 21
<212> TYPE: DNA
<213> ORGANISM: Artificial Sequence
<220> FEATURE:
<223> OTHER INFORMATION: Synthetic Construct

<400> SEQUENCE: 143
cgtgaatttg ctggctctca g                                                   21

<210> SEQ ID NO 144
<211> LENGTH: 21
<212> TYPE: DNA
<213> ORGANISM: Artificial Sequence
<220> FEATURE:
<223> OTHER INFORMATION: Synthetic Construct

<400> SEQUENCE: 144
ggtttagttc ctcaccttgt c                                                   21

<210> SEQ ID NO 145
<211> LENGTH: 21
<212> TYPE: DNA
<213> ORGANISM: Artificial Sequence
<220> FEATURE:
<223> OTHER INFORMATION: Synthetic Construct

<400> SEQUENCE: 145
actgaaacgt tttcatcgct c                                                   21

<210> SEQ ID NO 146
<211> LENGTH: 112
<212> TYPE: DNA
<213> ORGANISM: Artificial Sequence
<220> FEATURE:
<223> OTHER INFORMATION: Synthetic Construct

<400> SEQUENCE: 146
gttactacta gtgttgacaa ttaatcatcc ggctcgtata atgtgtggaa ttgtgagcgg         60
ataacaattt aggaggaaaa aaaaatgagt tatactgtcg gtacctattt ag                112

<210> SEQ ID NO 147
<211> LENGTH: 39
<212> TYPE: DNA
<213> ORGANISM: Artificial Sequence
<220> FEATURE:
<223> OTHER INFORMATION: Synthetic Construct

<400> SEQUENCE: 147
gttagatctg caggtttatt taaaaactag aggagcttg                                39

<210> SEQ ID NO 148
<211> LENGTH: 6548
<212> TYPE: DNA
<213> ORGANISM: Artificial Sequence
<220> FEATURE:
<223> OTHER INFORMATION: Synthetic Construct

<400> SEQUENCE: 148
```

```
ctcgggccgt ctcttgggct tgatcggcct tcttgcgcat ctcacgcgct cctgcggcgg      60
cctgtagggc aggctcatac ccctgccgaa ccgcttttgt cagccggtcg gccacggctt     120
ccggcgtctc aacgcgcttt gagattccca gcttttcggc caatccctgc ggtgcatagg     180
cgcgtggctc gaccgcttgc gggctgatgg tgacgtggcc cactggtggc cgctccaggg     240
cctcgtagaa cgcctgaatg cgcgtgtgac gtgccttgct gccctcgatg ccccgttgca     300
gccctagatc ggccacagcg gccgcaaacg tggtctggtc gcgggtcatc tgcgctttgt     360
tgccgatgaa ctccttggcc gacagcctgc cgtcctgcgt cagcggcacc acgaacgcgg     420
tcatgtgcgg gctggtttcg tcacggtgga tgctggccgt cacgatgcga tccgccccgt     480
acttgtccgc cagccacttg tgcgccttct cgaagaacgc cgcctgctgt tcttggctgg     540
ccgacttcca ccattccggg ctggccgtca tgacgtactc gaccgccaac acagcgtcct     600
tgcgccgctt ctctggcagc aactcgcgca gtcggcccat cgcttcatcg gtgctgctgg     660
ccgcccagtg ctcgttctct ggcgtcctgc tggcgtcagc gttgggcgtc tcgcgctcgc     720
ggtaggcgtg cttgagactg gccgccacgt tgcccatttt cgccagcttc ttgcatcgca     780
tgatcgcgta tgccgccatg cctgcccctc ccttttggtg tccaaccggc tcgacggggg     840
cagcgcaagg cggtgcctcc ggcgggccac tcaatgcttg agtatactca ctagactttg     900
cttcgcaaag tcgtgaccgc ctacggcggc tgcggcgccc tacgggcttg ctctccgggc     960
ttcgccctgc gcggtcgctg cgctcccttg ccagcccgtg gatatgtgga cgatggccgc    1020
gagcggccac cggctggctc gcttcgctcg gcccgtggac aaccctgctg acaagctga    1080
tggacaggct gcgcctgccc acgagcttga ccacagggat tgcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt gggggcagtc gaaggcgaag cccgcccgcc    1380
tgccccccga gcctcacggc ggcgagtgcg ggggttccaa gggggcagcg ccaccttggg    1440
caaggccgaa ggccgcgcag tcgatcaaca agccccggag gggccacttt ttgccggagg    1500
gggagccgcg ccgaaggcgt gggggaaccc cgcaggggtg cccttctttg ggcaccaaag    1560
aactagatat agggcgaaat gcgaaagact taaaaatcaa caacttaaaa aaggggggta    1620
cgcaacagct cattgcggca ccccccgcaa tagctcattg cgtaggttaa agaaaatctg    1680
taattgactg ccacttttac gcaacgcata attgttgtcg cgctgccgaa aagttgcagc    1740
tgattgcgca tggtgccgca accgtgcggc accctaccgc atggagataa gcatggccac    1800
gcagtccaga gaaatcggca ttcaagccaa gaacaagccc ggtcactggg tgcaaacgga    1860
acgcaaagcg catgaggcgt gggccgggct tattgcgagg aaacccacgg cggcaatgct    1920
gctgcatcac ctcgtggcgc agatgggcca ccagaacgcc gtggtggtca gccagaagac    1980
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
tgccgccgtg gtggttgatc acgacgacca ggacgaatcg ctgttggggc atggcgacct    2220
gcgccgcatc ccgaccctgt atccgggcga gcagcaacta ccgaccggcc ccggcgagga    2280
gccgcccagc cagcccggca ttccgggcat ggaaccagac ctgccagcct tgaccgaaac    2340
```

```
ggaggaatgg gaacggcgcg ggcagcagcg cctgccgatg cccgatgagc cgtgttttct    2400
ggacgatggc gagccgttgg agccgccgac acgggtcacg ctgccgcgcc ggtagcactt    2460
gggttgcgca gcaacccgta agtgcgctgt tccagactat cggctgtagc cgcctcgccg    2520
ccctataccl tgtctgcctc cccgcgttgc gtcgcggtgc atggagccgg ccacctcga    2580
cctgaatgga agccggcggc acctcgctaa cggattcacc gtttttatca ggctctggga    2640
ggcagaataa atgatcatat cgtcaattat tacctccacg gggagagcct gagcaaactg    2700
gcctcaggca tttgagaagc acacggtcac actgcttccg gtagtcaata aaccggtaaa    2760
ccagcaatag acataagcgg ctatttaacg accctgccct gaaccgacga ccgggtcgaa    2820
tttgctttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagaactagt gttgacaatt aatcatccgg ctcgtataat gtgtggaatt gtgagcggat    3300
aacaatttag gaggaaaaaa aaatgagtta tactgtcggt acctatttag cggagcggct    3360
tgtccagatt ggtctcaagc atcacttcgc agtcgcgggc gactacaacc tcgtccttct    3420
tgacaacctg cttttgaaca aaaacatgga gcaggtttat tgctgtaacg aactgaactg    3480
cggtttcagt gcagaaggtt atgctcgtgc caaaggcgca gcagcagccg tcgttaccta    3540
cagcgtcggt gcgcttttccg catttgatgc tatcggtggc gcctatgcag aaaaccttcc    3600
ggttatcctg atctccggtg ctccgaacaa caatgatcac gctgctggtc acgtgttgca    3660
tcacgctctt ggcaaaaccg actatcacta tcagttggaa atggccaaga acatcacggc    3720
cgccgctgaa gcgatttaca ccccggaaga agctccggct aaaatcgatc acgtgattaa    3780
aactgctctt cgtgagaaga agccggttta tctcgaaatc gcttgcaaca ttgcttccat    3840
gccctgcgcc gctcctggac cggcaagcgc attgttcaat gacgaagcca gcgacgaagc    3900
ttctttgaat gcagcggttg aagaaaccct gaaattcatc gccaaccgcg acaaagttgc    3960
cgtcctcgtc ggcagcaagc tgcgcgcagc tggtgctgaa gaagctgctg tcaaatttgc    4020
tgatgctctc ggtggcgcag ttgctaccat ggctgctgca aaaagcttct cccagaaga    4080
aaacccgcat tacatcggca cctcatgggg tgaagtcagc tatccgggcg ttgaaaagac    4140
gatgaaagaa gccgatgcgg ttatcgctct ggctcctgtc ttcaacgact actccaccac    4200
tggttggacg gatattcctg atcctaagaa actggttctc gctgaaccgc gttctgtcgt    4260
cgttaacggc attcgcttcc ccagcgtcca tctgaaagac tatctgaccc gtttggctca    4320
gaaagtttcc aagaaaaccg gtgcattgga cttcttcaaa tccctcaatg caggtgaact    4380
gaagaaagcc gctccggctg atccgagtgc tccgttggtc aacgcagaaa tcgcccgtca    4440
ggtcgaagct cttctgaccc cgaacacgac ggttattgct gaaacggtg actcttggtt    4500
caatgctcag cgcatgaagc tcccgaacgg tgctcgcgtt gaatatgaaa tgcagtgggg    4560
tcacattggt tggtccgttc ctgccgcctt cggttatgcc gtcggtgctc cggaacgtcg    4620
caacatcctg atggttggtg atggttcctt ccagctgacg gctcaggaag tcgctcagat    4680
ggttcgcctg aaactgccgg ttatcatctt cttgatcaat aactatggtt acaccatcga    4740
```

-continued

```
agttatgatc catgatggtc cgtacaacaa catcaagaac tgggattatg ccggtctgat    4800
ggaagtgttc aacggtaacg gtggttatga cagcggtgct ggtaaaggcc tgaaggctaa    4860
aaccggtggc gaactggcag aagctatcaa ggttgctctg gcaaacaccg acggcccaac    4920
cctgatcgaa tgcttcatcg gtcgtgaaga ctgcactgaa gaattggtca atggggtaa    4980
gcgcgttgct gccgccaaca gccgtaagcc tgttaacaag ctcctctagt ttttaaataa    5040
acctgcagga attcgatatc aagcttatcg ataccgtcga cctcgagggg gggcccggta    5100
cccagctttt gttcccttta gtgagggtta attgcgcgct tggcgtaatc atggtcatag    5160
ctgtttcctg tgtgaaattg ttatccgctc acaattccac acaacatacg agccggaagc    5220
ataaagtgta aagcctgggg tgcctaatga gtgagctaac tcacattaat tgcgttgcgc    5280
tcactgcccg ctttccagtc gggaaacctg tcgtgccagc tgcattaatg aatcggccaa    5340
cgcgcgggga gaggcggttt gcgtattggg cgcatgcata aaaactgttg taattcatta    5400
agcattctgc cgacatggaa gccatcacaa acggcatgat gaacctgaat cgccagcggc    5460
atcagcacct tgtcgccttg cgtataatat ttgcccatgg acgcacaccg tggaaacgga    5520
tgaaggcacg aacccagttg acataagcct gttcggttcg taaactgtaa tgcaagtagc    5580
gtatgcgctc acgcaactgg tccagaacct tgaccgaacg cagcggtggt aacggcgcag    5640
tggcggtttt catggcttgt tatgactgtt ttttgtaca gtctatgcct cgggcatcca    5700
agcagcaagc gcgttacgcc gtgggtcgat gtttgatgtt atggagcagc aacgatgtta    5760
cgcagcagca acgatgttac gcagcagggc agtcgcccta aaacaaagtt aggtggctca    5820
agtatgggca tcattcgcac atgtaggctc ggccctgacc aagtcaaatc catgcgggct    5880
gctcttgatc ttttcggtcg tgagttcgga gacgtagcca cctactccca acatcagccg    5940
gactccgatt acctcgggaa cttgctccgt agtaagacat tcatcgcgct tgctgccttc    6000
gaccaagaag cggttgttgg cgctctcgcg gcttacgttc tgcccaggtt tgagcagccg    6060
cgtagtgaga tctatatcta tgatctcgca gtctccggcg agcaccggag gcagggcatt    6120
gccaccgcgc tcatcaatct cctcaagcat gaggccaacg cgcttggtgc ttatgtgatc    6180
tacgtgcaag cagattacgg tgacgatccc gcagtggctc tctatacaaa gttgggcata    6240
cgggaagaag tgatgcactt tgatatcgac ccaagtaccg ccacctaaca attcgttcaa    6300
gccgagatcg gcttcccggc cgcggagttg ttcggtaaat tgtcacaacg ccgccaggtg    6360
gcactttcg gggaaatgtg cgcgcccgcg ttcctgctgg cgctgggcct gtttctggcg    6420
ctggacttcc cgctgttccg tcagcagctt ttcgcccacg gccttgatga tcgcggcggc    6480
cttggcctgc atatcccgat tcaacggccc cagggcgtcc agaacgggct tcaggcgctc    6540
ccgaaggt                                                             6548
```

<210> SEQ ID NO 149
<211> LENGTH: 35
<212> TYPE: DNA
<213> ORGANISM: Artificial Sequence
<220> FEATURE:
<223> OTHER INFORMATION: Synthetic Construct

<400> SEQUENCE: 149

```
gaaactgaaa cccatatgga agctcgtcgt tctgc                                 35
```

<210> SEQ ID NO 150
<211> LENGTH: 44
<212> TYPE: DNA

```
<213> ORGANISM: Artificial Sequence
<220> FEATURE:
<223> OTHER INFORMATION: Synthetic Construct

<400> SEQUENCE: 150
cccgcgctta ctcgaggcgt tcaaacggca gaatcggttc agtg                    44

<210> SEQ ID NO 151
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 151
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aacccatatct cggtctattc     360 ttttgattta agggattt tgccgatttc ggcctattgg ttaaaaaatg agctgattta       420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga     780 aatcaccatg agtgacgact gaatccggtg agaatggcaa aagtttatgc atttcttttcc     840 agacttgttc aacaggccag ccattacgct cgtcatcaaa atcactcgca tcaaccaaac     900
cgttattcat tcgtgattgc gcctgagcga cgaaatac gcgatcgctg ttaaaaggac        960
aattacaaac aggaatcgaa tgcaaccggc gcaggaacac tgccagcgca tcaacaatat    1020
tttcacctga tcaggatat tcttctaata cctggaatgc tgtttttccccg gggatcgcag    1080 tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500 gatcctttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccgggttg gactcaagac gatagttacc ggataaggcg    1800
cagcggtcgg gctgaacggg gggttcgtgc acacagccca gcttggagcg aacgacctac    1860
```

-continued

```
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggg cggagcctat ggaaaaacgc cagcaacgcg     2100 gccttttac ggttcctggc cttttgctgg cctttgctc acatgttctt tcctgcgtta      2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
```

```
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacagagc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttcttttcgt    5940 aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgcacca tctctcgtcc    6360 ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga acctgaaa aagatgaaca ggaaaaact     6540 gggtggtagc ctgttcgcga aaccgttcgt ggaaaccgcg atcaacctgg cacgtcaatc    6600
```

```
tcactgcact tatcataacg gcgacgcgca tacctctccg gatgagctga cccgcaaacg    6660
cgttctgtct gtaatcactg aaccgattct gccgtttgaa cgctaaggat ccgaattcga    6720
gctccgtcga caagcttgcg gccgcactcg agcaccacca ccaccaccac tgagatccgg    6780
ctgctaacaa agcccgaaag gaagctgagt tggctgctgc caccgctgag caataactag    6840
cataacccct tggggcctct aaacgggtct tgaggggttt tttgctgaaa ggaggaacta    6900
tatccggat                                                           6909

<210> SEQ ID NO 152
<211> LENGTH: 30
<212> TYPE: DNA
<213> ORGANISM: Artificial Sequence
<220> FEATURE:
<223> OTHER INFORMATION: Synthetic Construct

<400> SEQUENCE: 152
gatcggatcc attcgccctt aggaggtaaa                                      30

<210> SEQ ID NO 153
<211> LENGTH: 40
<212> TYPE: DNA
<213> ORGANISM: Artificial Sequence
<220> FEATURE:
<223> OTHER INFORMATION: Synthetic Construct

<400> SEQUENCE: 153
gatcgcggcc gccagctgca ggacgcgttg ttatagcatt                           40

<210> SEQ ID NO 154
<211> LENGTH: 9685
<212> TYPE: DNA
<213> ORGANISM: Artificial Sequence
<220> FEATURE:
<223> OTHER INFORMATION: Synthetic Construct

<400> SEQUENCE: 154
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggggc tccctttagg    180 gttccgattt agtgctttac ggcacctcga ccccaaaaaa cttgattagg gtgatggttc     240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta agggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
```

-continued

```
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg caacgctac     1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc     1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gccttttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tatttttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac accccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag tcgcagacg ttttgcagca     3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
```

```
gagttgcatg ataaagaaga cagtcataag tgcggcgacg atagtcatgc cccgcgccca   3420
ccggaaggag ctgactgggt tgaaggctct caagggcatc ggtcgagatc cggtgccta    3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggtttcgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaagatcg gtaaagagct ggcagaacag gtgaaccatg cactggaact   5640
gccactgcat cgccgtactc agcgtctgga agcagtatgg tctatcgagg cctaccgtaa   5700
```

```
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccgca aatagcgttt cttgttacat gcgcactaaa ggtatctccg aagaactggc   6480
taccgaaagc gtgatgaatc tgatcgatga aacctggaaa aagatgaaca aggaaaaact   6540
gggtggtagc ctgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatcactg aaccgattct gccgtttgaa cgctaaggat ccattcgccc   6720
ttaggaggta aaaaaacatg agttttgata ttgccaaata cccgaccctg gcactggtcg   6780
actccacccc ggagttacga ctgttgccga aagagagttt accgaaactc tgcgacgaac   6840
tgcgccgcta tttactcgac agcgtgagcc gttccagcgg cacttcgcc tccgggctgg   6900 gcacggtcga actgaccgtg gcgctgcact atgtctacaa cacccgtttt gaccaattga   6960
tttgggatgt ggggcatcag gcttatccgc ataaaatttt gaccggacgc cgcgacaaaa   7020
tcggcaccat ccgtcagaaa ggcggtctgc acccgttccc gtggcgcggc gaaagcgaat   7080
atgacgtatt aagcgtcggg cattcatcaa cctccatcag tgccggaatt ggtattgcgg   7140
ttgctgccga aaaagaaggc aaaaatcgcc gcaccgtctg tgtcattggc gatgcgcga   7200 ttaccgcagg catggcgttt gaagcgatga atcacgcggg cgatatccgt cctgatatgc   7260
tggtgattct caacgacaat gaaatgtcga tttccgaaaa tgtcggcgcg ctcaacaacc   7320
atctggcaca gctgctttcc ggtaagcttt actcttcact gcgcgaaggc gggaaaaaag   7380
ttttctctgg cgtgccgcca attaaagagc tgctcaaacg caccgaagaa catattaaag   7440
gcatggtagt gcctggcacg ttgtttgaag agctgggctt taactacatc ggcccggtgg   7500
acggtcacga tgtgctgggg cttatcacca cgctaaagaa catgcgcgac ctgaaaggcc   7560
cgcagttcct gcatatcatg accaaaaaag gtcgtggtta tgaaccggca gaaaaagacc   7620
cgatcacttt ccacgccgtg cctaaatttg atccctccag cggttgtttg ccgaaaagta   7680
gcggcggttt gccgagctat tcaaaaatct ttggcgactg gttgtgcgaa acggcagcga   7740
aagacaacaa gctgatggcg attactccgg cgatgcgtga aggttccggc atggtcgagt   7800
tttcacgtaa attcccggat cgctacttcg acgtggcaat gccgagcaa cacgcggtga   7860 cctttgctgc gggtctggcg attggtgggt acaaacccat tgtcgcgatt tactccactt   7920
tcctgcaacg cgcctatgat caggtgctgc atgacgtggc gattcaaaag cttccggtcc   7980
tgttcgccat cgaccgcgcg ggcattgttg gtgctgacgg tcaaacccat cagggtgctt   8040
ttgatctctc ttacctgcgc tgcataccgg aaatggtcat tatgacccccg agcgatgaaa   8100
```

```
acgaatgtcg ccagatgctc tataccggct atcactataa cgatggcccg tcagcggtgc    8160
gctacccgcg tggcaacgcg gtcggcgtgg aactgacgcc gctggaaaaa ctaccaattg    8220
gcaaaggcat tgtgaagcgt cgtggcgaga actggcgat ccttaacttt ggtacgctga    8280
tgccagaagc ggcgaaagtc gccgaatcgc tgaacgccac gctggtcgat atgcgttttg    8340
tgaaaccgct tgatgaagcg ttaattctgg aaatggccgc cagccatgaa gcgctggtca    8400
ccgtagaaga aaacgccatt atgggcggcg caggcagcgg cgtgaacgaa gtgctgatgg    8460
cccatcgtaa accagtaccc gtgctgaaca ttggcctgcc ggacttcttt attccgcaag    8520
gaactcagga gaaatgcgc gccgaactcg gcctcgatgc cgctggtatg gaagccaaaa    8580
tcaaggcctg gctggcataa ctgcatcgcc cttaggaggt aaaaaaaaat gactgccgac    8640
aacaatagta tgccccatgg tgcagtatct agttacgcca aattagtgca aaaccaaaca    8700
cctgaagaca tttttggaaga gtttcctgaa attattccat tacaacaaag acctaatacc    8760
cgatctagtg agacgtcaaa tgacgaaagc ggagaaacat gtttttctgg tcatgatgag    8820
gagcaaatta agttaatgaa tgaaaattgt attgttttgg attgggacga taatgctatt    8880
ggtgccggta ccaagaaagt ttgtcattta atggaaaata ttgaaaaggg tttactacat    8940
cgtgcattct ccgtctttat tttcaatgaa caaggtgaat tacttttaca acaaagagcc    9000
actgaaaaaa taactttccc tgatctttgg actaacacat gctgctctca tccactatgt    9060
attgatgacg aattaggttt gaagggtaag ctagacgata agattaaggg cgctattact    9120
gcggcggtga aaaactaga tcatgaatta ggtattccag aagatgaaac taagacaagg    9180
ggtaagtttc actttttaaa cagaatccat tacatggcac caagcaatga accatggggt    9240
gaacatgaaa ttgattacat cctatttat aagatcaacg ctaaagaaaa cttgactgtc    9300
aacccaaacg tcaatgaagt tagagacttc aaatgggttt caccaaatga tttgaaaact    9360
atgtttgctg acccaagtta caagtttacg ccttggttta agattatttg cgagaattac    9420
ttattcaact ggtgggagca attagatgac cttttctgaag tggaaaatga caggcaaatt    9480
catagaatgc tataacaacg cgtcctgcag ctggcggccg cactcgagca ccaccaccac    9540
caccactgag atccggctgc taacaaagcc cgaaggaag ctgagttggc tgctgccacc    9600
gctgagcaat aactagcata accccttggg gcctctaaac gggtcttgag ggttttttg    9660 ctgaaaggag gaactatatc cggat                                          9685

<210> SEQ ID NO 155
<211> LENGTH: 35
<212> TYPE: DNA
<213> ORGANISM: Artificial Sequence
<220> FEATURE:
<223> OTHER INFORMATION: Synthetic Construct

<400> SEQUENCE: 155
ctaaactcta gagctcatga tcgcggcatg ttctg                                35

<210> SEQ ID NO 156
<211> LENGTH: 52
<212> TYPE: DNA
<213> ORGANISM: Artificial Sequence
<220> FEATURE:
<223> OTHER INFORMATION: Synthetic Construct

<400> SEQUENCE: 156
gcagaacgac gagcttcggt cattgcttac tccatatatt caaaacacta tg            52
```

<210> SEQ ID NO 157
<211> LENGTH: 36
<212> TYPE: DNA
<213> ORGANISM: Artificial Sequence
<220> FEATURE:
<223> OTHER INFORMATION: Synthetic Construct

<400> SEQUENCE: 157
ctacgactgc agccggatat agttcctcct ttcagc                                36

<210> SEQ ID NO 158
<211> LENGTH: 52
<212> TYPE: DNA
<213> ORGANISM: Artificial Sequence
<220> FEATURE:
<223> OTHER INFORMATION: Synthetic Construct

<400> SEQUENCE: 158
catagtgttt tgaatatatg gagtaagcaa tgaccgaagc tcgtcgttct gc              52

<210> SEQ ID NO 159
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 159
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggc tccctttagg       180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta       420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttcttccc    840
agacttgttc aacaggccag ccattacgct cgtcatcaaa atcactcgca tcaaccaaac    900
cgttattcat tcgtgattgc gcctgagcga cgaaatac gcgatcgctg ttaaaaggac       960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380

```
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctcagagagt tgcagcaagc ggtccacgct ggtttgcccc agcaggcgaa   3720
```

```
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgaccgaa gctcgtcgtt ctgcgaacta    5100
cgaacctaac agctgggact atgattacct gctgtcctcc gacacggacg agtccatcga    5160
agtatacaaa gacaaagcga aaaagctgga agccgaagtt cgtcgcgaga ttaataacga    5220
aaaagcagaa tttctgaccc tgctggaact gattgacaac gtccagcgcc tgggcctggg    5280
ttaccgtttc gagtctgata tccgtggtgc gctggatcgc ttcgtttcct ccggcggctt    5340
cgatgcggta accaagactt ccctgcacgg tacggcactg tctttccgtc tgctgcgtca    5400
acacggtttt gaggtttctc aggaagcgtt cagcggcttc aaagaccaaa acggcaactt    5460
cctggagaac ctgaaggaag atatcaaagc tatcctgagc ctgtacgagg ccagcttcct    5520
ggctctggaa ggcgaaaaca tcctggacga ggcgaaggtt ttcgcaatct ctcatctgaa    5580
agaactgtct gaagaaaaga tcggtaaaga gctggcagaa caggtgaacc atgcactgga    5640
actgccactg catcgccgta ctcagcgtct ggaagcagta tggtctatcg aggcctaccg    5700
taaaaaggag gacgcgaatc aggttctgct ggagctggca attctggatt acaacatgat    5760
ccagtctgta taccagcgtg atctgcgtga aacgtcccgt tggtggcgtc gtgtgggtct    5820
ggcgaccaaa ctgcactttg ctcgtgaccg cctgattgag agcttctact gggcgtggg    5880
tgtagcattc gaaccgcaat actccgactg ccgtaactcc gtcgcaaaaa tgttttcttt    5940
cgtaaccatt atcgacgata tctacgatgt atacggcacc ctggacgaac tggagctgtt    6000
tactgatgca gttgagcgtt gggacgtaaa cgccatcaac gacctgccgg attacatgaa    6060
actgtgcttt ctggctctgt ataacactat taacgaaatc gcctacgaca acctgaaaga    6120
```

```
taaaggtgag aacatcctgc cgtatctgac caaagcctgg gctgacctgt gcaacgcttt      6180
cctgcaagaa gccaagtggc tgtacaacaa atctactccg acctttgacg actacttcgg      6240
caacgcatgg aaatcctctt ctggcccgct gcaactggtg ttcgcttact tcgctgtcgt      6300
gcagaacatt aaaaaggaag agatcgaaaa cctgcaaaaa taccatgaca ccatctctcg      6360
tccttcccat atcttccgtc tgtgcaatga cctggctagc gcgtctgcgg aaattgcgcg      6420
tggtgaaacc gcaaatagcg tttcttgtta catgcgcact aaaggtatct ccgaagaact      6480
ggctaccgaa agcgtgatga atctgatcga tgaaacctgg aaaaagatga caaggaaaa       6540 actgggtggt agcctgttcg cgaaaccgtt cgtggaaacc gcgatcaacc tggcacgtca      6600
atctcactgc acttatcata acggcgacgc gcatacctct ccggatgagc tgacccgcaa      6660
acgcgttctg tctgtaatca ctgaaccgat tctgccgttt gaacgctaag gatccgaatt      6720
cgagctccgt cgacaagctt gcggccgcac tcgagcacca ccaccaccac cactgagatc      6780
cggctgctaa caaagcccga aggaagctg agttggctgc tgccaccgct gagcaataac        6840
tagcataacc ccttggggcc tctaaacggg tcttgagggg ttttttgctg aaaggaggaa      6900
ctatatccgg at                                                          6912

<210> SEQ ID NO 160
<211> LENGTH: 6550
<212> TYPE: DNA
<213> ORGANISM: Artificial Sequence
<220> FEATURE:
<223> OTHER INFORMATION: Synthetic Construct

<400> SEQUENCE: 160
gccctcgatg ccccgttgca gccctagatc ggccacagcg gccgcaaacg tggtctggtc        60
gcgggtcatc tgcgctttgt tgccgatgaa ctccttggcc gacagcctgc cgtcctgcgt       120
cagcggcacc acgaacgcgg tcatgtgcgg gctggtttcg tcacggtgga tgctggccgt       180
cacgatgcga tccgccccgt acttgtccgc cagccacttg tgcgccttct cgaagaacgc       240
cgcctgctgt tcttggctgg ccgacttcca ccattccggg ctggccgtca tgacgtactc       300
gaccgccaac acagcgtcct tgcgccgctt ctctggcagc aactcgcgca gtcggcccat       360
cgcttcatcg gtgctgctgg ccgcccagtg ctcgttctct ggcgtcctgc tggcgtcagc       420
gttgggcgtc tcgcgctcgc ggtaggcgtg cttgagactg gccgccacgt tgcccatttt       480
cgccagcttc ttgcatcgca tgatcgcgta tgccgccatg cctgcccctc ccttttggtg       540
tccaaccggc tcgacggggg cagcgcaagg cggtgcctcc ggcgggccac tcaatgcttg       600
agtatactca ctagactttg cttcgcaaag tcgtgaccgc ctacggcggc tgcggcgccc       660
tacgggcttg ctctccgggc ttcgccctgc gcggtcgctg cgctcccttg ccagcccgtg       720
gatatgtgga cgatggccgc gagcggccac cggctggctc gcttcgctcg gcccgtggac       780
aaccctgctg gacaagctga tggacaggct gcgcctgccc acgagcttga ccacagggat       840
tgcccaccgg ctacccagcc ttcgaccaca tacccaccgg ctccaactgc gcggcctgcg       900
gccttgcccc atcaattttt ttaattttct ctggggaaaa gcctccggcc tgcggcctgc       960
gcgcttcgct tgccggttgg acaccaagtg aaggcgggt caaggctcgc gcagcgaccg       1020
cgcagcggct tggccttgac gcgcctggaa cgacccaagc ctatgcgagt gggggcagtc      1080
gaaggcgaag cccgccgcc tgcccccga gcctcacggc ggcgagtgcg ggggttccaa         1140
gggggcagcg ccaccttggg caaggccgaa ggccgcgcag tcgatcaaca agccccggag      1200
```

```
gggccacttt ttgccggagg gggagccgcg ccgaaggcgt gggggaaccc cgcagggtg    1260 cccttctttg ggcaccaaag aactagatat agggcgaaat gcgaaagact taaaaatcaa   1320
caacttaaaa aaggggggta cgcaacagct cattgcggca cccccgcaa tagctcattg    1380 cgtaggttaa agaaaatctg taattgactg ccacttttac gcaacgcata attgttgtcg   1440
cgctgccgaa aagttgcagc tgattgcgca tggtgccgca accgtgcggc accctaccgc   1500
atggagataa gcatggccac gcagtccaga gaaatcggca ttcaagccaa gaacaagccc   1560
ggtcactggg tgcaaacgga acgcaaagcg catgaggcgt gggccgggct tattgcgagg   1620
aaacccacgg cggcaatgct gctgcatcac ctcgtggcgc agatgggcca ccagaacgcc   1680
gtggtggtca gccagaagac acttccaag ctcatcggac gttctttgcg gacggtccaa    1740
tacgcagtca aggacttggt ggccgagcgc tggatctccg tcgtgaagct caacggcccc   1800
ggcaccgtgt cggcctacgt ggtcaatgac cgcgtggcgt ggggccagcc ccgcgaccag   1860
ttgcgcctgt cggtgttcag tgccgccgtg gtggttgatc acgacgacca ggacgaatcg   1920
ctgttggggc atggcgacct cgccgcatc ccgaccctgt atccgggcga gcagcaacta    1980
ccgaccggcc ccggcgagga ccgcccagc cagcccggca ttccgggcat ggaaccagac    2040
ctgccagcct tgaccgaaac ggaggaatgg gaacggcgcg ggcagcagcg cctgccgatg   2100
cccgatgagc cgtgttttct ggacgatggc gagccgttgg agccgccgac acgggtcacg   2160
ctgccgcgcc ggtagcactt gggttgcgca gcaacccgta agtgcgctgt tccagactat   2220
cggctgtagc cgcctcgccg ccctatacct tgtctgcctc ccgcgttgc gtcgcggtgc    2280 atggagccgg gccacctcga cctgaatgga agccggcggc acctcgctaa cggattcacc   2340
gtttttatca ggctctggga ggcagaataa atgatcatat cgtcaattat tacctccacg   2400
gggagagcct gagcaaactg gcctcaggca tttgagaagc acacggtcac actgcttccg   2460
gtagtcaata aaccggtaaa ccagcaatag acataagcgg ctatttaacg accctgccct   2520
gaaccgacga ccgggtcgaa tttgcttcg aatttctgcc attcatccgc ttattatcac    2580
ttattcaggc gtagcaccag gcgtttaagg gcaccaataa ctgccttaaa aaaattacgc   2640
cccgccctgc cactcatcgc agtcggccta ttggttaaaa aatgagctga tttaacaaaa   2700
atttaacgcg aattttaaca aaatattaac gcttacaatt tccattcgcc attcaggctg   2760
cgcaactgtt gggaagggcg atcggtgcgg gcctcttcgc tattacgcca gctggcgaaa   2820
gggggatgtg ctgcaaggcg attaagttgg gtaacgccag ggttttccca gtcacgacgt   2880
tgtaaaacga cggccagtga gcgcgcgtaa tacgactcac tatagggcga attggagctc   2940
caccgcggtg gcggccgctc tagagctcat gatcgcggca tgttctgata ttttttcctct  3000 aaaaaagata aaaagtcttt tcgcttcggc agaagaggtt catcatgaac aaaaaattcgg   3060 cattttttaaa aatgcctata gctaaatccg gaacgacact ttagaggttt ctgggtcatc   3120
ctgattcaga catagtgttt tgaatatatg gagtaagcaa tgatgaccga agctcgtcgt   3180
tctgcgaact acgaacctaa cagctgggac tatgattacc tgctgtcctc cgacacggac   3240
gagtccatcg aagtatacaa agacaaagcg aaaaagctgg aagccgaagt tcgtcgcgag   3300
attaataacg aaaagcaga atttctgacc ctgctggaac tgattgacaa cgtccagcgc   3360
ctgggcctgg gttaccgttt cgagtctgat atccgtggtg cgctggatcg cttcgtttcc   3420
tccggcggct tcgatgcggt aaccaagact tccctgcacg gtacggcact gtctttccgt   3480
ctgctgcgtc aacacggttt tgaggtttct caggaagcgt tcagcggctt caaagaccaa   3540
aacggcaact tcctggagaa cctgaaggaa gatatcaaag ctatcctgag cctgtacgag   3600
```

```
gccagcttcc tggctctgga aggcgaaaac atcctggacg aggcgaaggt tttcgcaatc      3660
tctcatctga aagaactgtc tgaagaaaag atcggtaaag agctggcaga acaggtgaac      3720
catgcactgg aactgccact gcatcgccgt actcagcgtc tggaagcagt atggtctatc      3780
gaggcctacc gtaaaaagga ggacgcgaat caggttctgc tggagctggc aattctggat      3840
tacaacatga tccagtctgt ataccagcgt gatctgcgtg aaacgtcccg ttggtggcgt      3900
cgtgtgggtc tggcgaccaa actgcacttt gctcgtgacc gcctgattga gagcttctac      3960
tgggccgtgg gtgtagcatt cgaaccgcaa tactccgact gccgtaactc cgtcgcaaaa      4020 atgtttctt tcgtaaccat tatcgacgat atctacgatg tatacggcac cctggacgaa      4080
ctggagctgt ttactgatgc agttgagcgt tgggacgtaa acgccatcaa cgacctgccg      4140
gattacatga aactgtgctt tctggctctg tataacacta ttaacgaaat cgcctacgac      4200
aacctgaaag ataaaggtga aacatcctg ccgtatctga ccaaagcctg gctgaccctg      4260
tgcaacgctt cctgcaaga agccaagtgg ctgtacaaca aatctactcc gacctttgac      4320
gactacttcg gcaacgcatg gaaatcctct tctggcccgc tgcaactggt gttcgcttac      4380
ttcgctgtcg tgcagaacat taaaaaggaa gagatcgaaa acctgcaaaa ataccatgac      4440
accatctctc gtccttccca tatcttccgt ctgtgcaatg acctggctag cgcgtctgcg      4500
gaaattgcgc gtggtgaaac cgcaaatagc gtttcttgtt acatgcgcac taaaggtatc      4560
tccgaagaac tggctaccga aagcgtgatg aatctgatcg atgaaacctg gaaaagatg      4620 aacaaggaaa aactgggtgg tagcctgttc gcgaaaccgt tcgtggaaac cgcgatcaac      4680
ctggcacgtc aatctcactg cacttatcat aacggcgacg cgcataccte tccggatgag      4740 ctgacccgca aacgcgttct gtctgtaatc actgaaccga ttctgccgtt tgaacgctaa      4800
ggatccgaat tcgagctccg tcgacctgca ggaattcgat atcaagctta tcgataccgt      4860
cgacctcgag ggggggcccg gtacccagct ttttgttccct ttagtgaggg ttaattgcgc      4920
gcttggcgta atcatggtca tagctgtttc ctgtgtgaaa ttgttatccg ctcacaattc      4980
cacacaacat acgagccgga agcataaagt gtaaagcctg gggtgcctaa tgagtgagct      5040
aactcacatt aattgcgttg cgctcactgc ccgctttcca gtcgggaaac ctgtcgtgcc      5100
agctgcatta atgaatcggc caacgcgcgg ggagaggcgg tttgcgtatt gggcgcatgc      5160
ataaaaactg ttgtaattca ttaagcattc tgccgacatg gaagccatca caacggcat      5220 gatgaacctg aatcgccagc ggcatcagca ccttgtcgcc ttgcgtataa tatttgccca      5280
tggtgaaaac gggggcgaag aagttgtcca tattggccac gtttaaatca aaactggtga      5340
aactcaccca gggattggct gagacgaaaa acatattctc aataaaccct ttagggaaat      5400
aggccaggtt ttcaccgtaa cacgccacat cttgcgaata tatgtgtaga aactgccgga      5460
aatcgtcgtg gtattcactc cagagcgatg aaaacgtttc agtttgctca tggaaaacgg      5520
tgtaacaagg gtgaacacta tcccatatca ccagctcacc gtctttcatt gccatacgga      5580
attccggatg agcattcatc aggcgggcaa gaatgtgaat aaaggccgga taaaacttgt      5640
gcttattttt ctttacggtc tttaaaaagg ccgtaatatc cagctgaacg gtctggttat      5700
aggtacattg agcaactgac tgaaatgcct caaaatgttc tttacgatgc cattgggata      5760
tatcaacggt ggtatatcca gtgatttttt tctccatttt agcttcctta gctcctgaaa      5820
atctcgataa ctcaaaaaat acgcccggta gtgatcttat ttcattatgg tgaaagttgg      5880
aacctcttac gtgccgatca acgtctcatt ttcgccaaaa gttggcccag gcttcccgg      5940
```

| | |
|---|---|
| tatcaacagg gacaccagga tttatttatt ctgcgaagtg atcttccgtc acaggtattt | 6000 |
| attcgaagac gaaagggcct cgtgatacgc ctatttttat aggttaatgt catgataata | 6060 |
| atggtttctt agacgtcagg tggcactttt cggggaaatg tgcgcgcccg cgttcctgct | 6120 |
| ggcgctgggc ctgtttctgg cgctggactt cccgctgttc cgtcagcagc ttttcgccca | 6180 |
| cggccttgat gatcgcggcg gccttggcct gcatatcccg attcaacggc cccagggcgt | 6240 |
| ccagaacggg cttcaggcgc tcccgaaggt ctcgggccgt ctcttgggct tgatcggcct | 6300 |
| tcttgcgcat ctcacgcgct cctgcggcgg cctgtagggc aggctcatac ccctgccgaa | 6360 |
| ccgcttttgt cagccggtcg gccacggctt ccggcgtctc aacgcgcttt gagattccca | 6420 |
| gcttttcggc caatccctgc ggtgcatagg cgcgtggctc gaccgcttgc gggctgatgg | 6480 |
| tgacgtggcc cactggtggc cgctccaggg cctcgtagaa cgcctgaatg cgcgtgtgac | 6540 |
| gtgccttgct | 6550 |

<210> SEQ ID NO 161
<211> LENGTH: 8911
<212> TYPE: DNA
<213> ORGANISM: Artificial Sequence
<220> FEATURE:
<223> OTHER INFORMATION: Synthetic Construct

<400> SEQUENCE: 161

| | |
|---|---|
| accttcggga gcgcctgaag cccgttctgg acgccctggg gccgttgaat cgggatatgc | 60 |
| aggccaaggc cgccgcgatc atcaaggccg tgggcgaaaa gctgctgacg gaacagcggg | 120 |
| aagtccagcg ccagaaacag gcccagcgcc agcaggaacg cgggcgcgca catttccccg | 180 |
| aaaagtgcca cctggcggcg ttgtgacaat ttaccgaaca actccgcggc cgggaagccg | 240 |
| atctcggctt gaacgaattg ttaggtggcg gtacttgggt cgatatcaaa gtgcatcact | 300 |
| tcttcccgta tgcccaactt tgtatagaga gccactgcgg gatcgtcacc gtaatctgct | 360 |
| tgcacgtaga tcacataagc accaagcgcg ttggcctcat gcttgaggag attgatgagc | 420 |
| gcggtggcaa tgccctgcct ccggtgctcg ccggagactg cgagatcata gatatagatc | 480 |
| tcactacgcg gctgctcaaa cctgggcaga acgtaagccg cgagagcgcc aacaaccgct | 540 |
| tcttggtcga aggcagcaag cgcgatgaat gtcttactac ggagcaagtt cccgaggtaa | 600 |
| tcggagtccg gctgatgttg ggagtaggtg gctacgtctc cgaactcacg accgaaaaga | 660 |
| tcaagagcag cccgcatgga tttgacttgg tcagggccga gcctacatgt gcgaatgatg | 720 |
| cccatacttg agccacctaa cttttgtttta gggcgactgc cctgctgcgt aacatcgttg | 780 |
| ctgctgcgta acatcgttgc tgctccataa catcaaacat cgacccacgg cgtaacgcgc | 840 |
| ttgctgcttg gatgcccgag gcatagactg tacaaaaaaa cagtcataac aagccatgaa | 900 |
| aaccgccact gcgccgttac caccgctgcg ttcggtcaag gttctggacc agttgcgtga | 960 |
| gcgcatacgc tacttgcatt acagtttacg aaccgaacag gcttatgtca actgggttcg | 1020 |
| tgccttcatc cgtttccacg gtgtgcgtcc atgggcaaat attatacgca aggcgacaag | 1080 |
| gtgctgatgc cgctggcgat tcaggttcat catgccgttt gtgatggctt ccatgtcggc | 1140 |
| agaatgctta atgaattaca acagttttta tgcatgcgcc caatacgcaa accgcctctc | 1200 |
| cccgcgcgtt ggccgattca ttaatgcagc tggcacgaca ggtttcccga ctggaaagcg | 1260 |
| ggcagtgagc gcaacgcaat taatgtgagt tagctcactc attaggcacc ccaggcttta | 1320 |
| cactttatgc ttccggctcg tatgttgtgt ggaattgtga gcggataaca atttcacaca | 1380 |
| ggaaacagct atgaccatga ttacgccaag cgcgcaatta accctcacta aagggaacaa | 1440 |

```
aagctgggta ccgggccccc cctcgagctg ttgacaatta atcatccggc tcgtataatg   1500
tgtggaattg tgagcggata caatttcac acaggaaaca gcgccgctga gaaaaagcga    1560
agcggcactg ctctttaaca atttatcaga caatctgtgt gggcactcga ccggaattat   1620
cgattaactt tattattaaa aattaaagag gtatatatta atgtatcgat taaataagga   1680
ggaataaacc atggatccga gctcaggagg taaaaaaaca tgaaaacagt agttattatt   1740
gatgcattac gaacaccaat tggaaaatat aaaggcagct taagtcaagt aagtgccgta   1800
gacttaggaa cacatgttac aacacaactt ttaaaaagac attccactat ttctgaagaa   1860
attgatcaag taatctttgg aaatgtttta caagctggaa atggccaaaa tcccgcacga   1920
caaatagcaa taaacagcgg tttgtctcat gaaattcccg caatgacggt taatgaggtc   1980
tgcggatcag gaatgaaggc cgttattttg gcgaaacaat tgattcaatt aggagaagcg   2040
gaagttttaa ttgctggcgg gattgagaat atgtcccaag cacctaaatt acaacgtttt   2100
aattacgaaa cagaaagcta cgatgcgcct ttttctagta tgatgtatga tggattaacg   2160
gatgccttta gtggtcaggc aatgggctta actgctgaaa atgtggccga aaagtatcat   2220
gtaactagag aagagcaaga tcaattttct gtacattcac aattaaaagc agctcaagca   2280
caagcagaag ggatattcgc tgacgaaata gccccattag aagtatcagg aacgcttgtg   2340
gagaaagatg aagggattcg ccctaattcg agcgttgaga agctaggaac gcttaaaaca   2400
gtttttaaag aagacggtac tgtaacagca gggaatgcat caaccattaa tgatggggct   2460
tctgctttga ttattgcttc acaagaatat gccgaagcac acggtcttcc ttatttagct   2520
attattcgag acagtgtgga agtcggtatt gatccagcct atatgggaat tcgccgattc   2580
aaagccattc aaaaactgtt agcgcgcaat caacttacta cggaagaaat tgatctgtat   2640
gaaatcaacg aagcatttgc agcaacttca atcgtggtcc aaagagaact ggctttacca   2700
gaggaaaagg tcaacattta tggtggcggt atttcattag gtcatgcgat tggtgccaca   2760
ggtgctcgtt tattaacgag tttaagttat caattaaatc aaaaagaaaa gaaatatgga   2820
gtggcttctt tatgtatcgg cggtggctta ggactcgcta tgctactaga gagacctcag   2880
caaaaaaaaa acagccgatt ttatcaaatg agtcctgagg aacgcctggc ttctcttctt   2940
aatgaaggcc agatttctgc tgatacaaaa aaagaatttg aaaatacggc tttatcttcg   3000
cagattgcca atcatatgat tgaaaatcaa atcagtgaaa cagaagtgcc gatgggcgtt   3060
ggcttacatt taacagtgga cgaaactgat tatttggtac caatggcgac agaagagccc   3120
tcagttattg cggcttttgag taatggtgca aaaatagcac aaggatttaa acagtgaat   3180 caacaacgct taatgcgtgg acaaatcgtt ttttacgatg ttgcagatcc cgagtcattg   3240
attgataaac tacaagtaag agaagcggaa gttttttcaac aagcagagtt aagttatcca   3300
tctatcgtta acggggcgg cggcttaaga gatttgcaat atcgtacttt tgatgaatca   3360
tttgtatctg tcgactttt agtagatgtt aaggatgcaa tggggcaaa tatcgttaac   3420 gctatgttgg aaggtgtggc cgagttgttc cgtgaatggt ttgcggagca aaagatttta   3480
ttcagtattt taagtaatta tgccacggag tcggttgtta cgatgaaaac ggctattcca   3540
gtttcacgtt taagtaaggg gagcaatggc cgggaaattc ctgaaaaaat tgttttagct   3600
tcacgctatg cttcattaga tccttatcgg gcagtcacgc ataacaaagg aatcatgaat   3660
ggcattgaag ctgtagtttt agctacagga aatgatacac gcgctgttag cgcttcttgt   3720
catgcttttg cggtgaagga aggtcgctac caaggcttga ctagttggac gctggatggc   3780
```

```
gaacaactaa ttggtgaaat tcagttccg cttgctttag ccacggttgg cggtgccaca    3840
aaagtcttac ctaaatctca agcagctgct gatttgttag cagtgacgga tgcaaaagaa    3900
ctaagtcgag tagtagcggc tgttggtttg gcacaaaatt tagcggcgtt acgggcctta    3960
gtctctgaag gaattcaaaa aggacacatg gctctacaag cacgttcttt agcgatgacg    4020
gtcggagcta ctggtaaaga agttgaggca gtcgctcaac aattaaaacg tcaaaaaacg    4080
atgaaccaag accgagccat ggctatttta aatgatttaa gaaaacaata aaggaggtaa    4140
aaaaacatga caattgggat tgataaaatt agttttttg tgcccccttta ttatattgat    4200 atgacggcac tggctgaagc cagaaatgta gaccctggaa aatttcatat tggtattggg    4260
caagaccaaa tggcggtgaa cccaatcagc caagatattg tgacatttgc agccaatgcc    4320
gcagaagcga tcttgaccaa agaagataaa gaggccattg atatggtgat tgtcgggact    4380
gagtccagta tcgatgagtc aaaagcggcc gcagttgtct tacatcgttt aatggggatt    4440 caaccttcg ctcgctcttt cgaaatcaag gaagcttgtt acggagcaac agcaggctta    4500
cagttagcta agaatcacgt agccttacat ccagataaaa aagtcttggt cgtagcggca    4560
gatattgcaa aatatggctt aaattctggc ggtgagccta cacaaggagc tggggcggtt    4620
gcaatgttag ttgctagtga accgcgcatt ttggctttaa aagaggataa tgtgatgctg    4680
acgcaagata tctatgactt ttggcgtcca acaggccacc cgtatcctat ggtcgatggt    4740
cctttgtcaa acgaaaccta catccaatct tttgcccaag tctgggatga acataaaaaa    4800
cgaaccggtc ttgattttgc agattatgat gctttagcgt tccatattcc ttacacaaaa    4860
atgggcaaaa aagccttatt agcaaaaatc tccgaccaaa ctgaagcaga acaggaacga    4920
attttagccc gttatgaaga aagtatcgtc tatagtcgtc gcgtaggaaa cttgtatacg    4980
ggttcacttt atctgggact catttccctt ttagaaaatg caacgacttt aaccgcaggc    5040
aatcaaattg gttattcag ttatggttct ggtgctgtcg ctgaattttt cactggtgaa    5100
ttagtagctg gttatcaaaa tcatttacaa aaagaaactc atttagcact gctgataat    5160 cggacagaac tttctatcgc tgaatatgaa gccatgtttg cagaaacttt agacacagac    5220
attgatcaaa cgttagaaga tgaattaaaa tatagtattt ctgctattaa taataccgtt    5280
cgttcttatc gaaactaaag atctgcagct ggtaccatat gggaattcga agcttgggcc    5340
cgaacaaaaa ctcatctcag aagaggatct gaatagcgcc gtcgaccatc atcatcatca    5400
tcattgagtt taaacggtct ccagcttggc tgttttggcg gatgagagaa gattttcagc    5460
ctgatacaga ttaaatcaga acgcagaagc ggtctgataa acagaatttg cctggcggc    5520 agtagcgcgg tggtcccacc tgaccccatg ccgaactcag aagtgaaacg ccgtagcgcc    5580
gatggtagtg tggggtctcc ccatgcgaga gtagggaact gccaggcatc aaataaaacg    5640
aaaggctcag tcgaaagact gggcctttct agagcggccg ccaccgcggt ggagctccaa    5700
ttcgccctat agtgagtcgt attacgcgcg ctcactggcc gtcgttttac aacgtcgtga    5760
ctgggaaaac cctggcgtta cccaacttaa tcgccttgca gcacatcccc ctttcgccag    5820
ctggcgtaat agcgaagagg cccgcaccga tcgcccttcc caacagttgc gcagcctgaa    5880
tggcgaatgg aaattgtaag cgttaatatt ttgttaaaat tcgcgttaaa ttttgttaa    5940 atcagctcat tttttaacca ataggccgac tgcgatgagt ggcagggcgg ggcgtaattt    6000
ttttaaggca gttattggtg cccttaaacg cctggtgcta cgcctgaata agtgataata    6060
agcggatgaa tggcagaaat tcgaaagcaa attcgacccg tcgtcggtt cagggcaggg    6120 tcgttaaata gccgcttatg tctattgctg gtttaccggt ttattgacta ccggaagcag    6180
```

```
tgtgaccgtg tgcttctcaa atgcctgagg ccagtttgct caggctctcc ccgtggaggt    6240
aataattgac gatatgatca tttattctgc ctcccagagc ctgataaaaa cggtgaatcc    6300
gttagcgagg tgccgccggc ttccattcag gtcgaggtgg cccggctcca tgcaccgcga    6360
cgcaacgcgc ggaggcagac aaggtatagg gcggcgaggc ggctacagcc gatagtctgg    6420
aacagcgcac ttacggggttg ctgcgcaacc caagtgctac cggcgcggca gcgtgacccg    6480
tgtcggcggc tccaacggct cgccatcgtc cagaaaacac ggctcatcgg gcatcggcag    6540
gcgctgctgc ccgcgccgtt cccattcctc cgtttcggtc aaggctggca ggtctggttc    6600
catgcccgga atgccgggct ggctgggcgg ctcctcgccg gggccggtcg gtagttgctg    6660
ctcgcccgga tacagggtcg ggatgcggcg caggtcgcca tgccccaaca gcgattcgtc    6720
ctggtcgtcg tgatcaacca ccacggcggc actgaacacc gacaggcgca actggtcgcg    6780
gggctggccc cacgccacgc ggtcattgac cacgtaggcc gacacggtgc cggggccgtt    6840
gagcttcacg acggagatcc agcgctcggc caccaagtcc ttgactgcgt attggaccgt    6900
ccgcaaagaa cgtccgatga gcttggaaag tgtcttctgg ctgaccacca cggcgttctg    6960
gtggcccatc tgcgccacga ggtgatgcag cagcattgcc gccgtgggtt tcctcgcaat    7020
aagcccggcc cacgcctcat gcgctttgcg ttccgtttgc acccagtgac cgggcttgtt    7080
cttggcttga atgccgattt ctctggactg cgtggccatg cttatctcca tgcggtaggg    7140
tgccgcacgg ttgcggcacc atgcgcaatc agctgcaact tttcggcagc gcgacaacaa    7200
ttatgcgttg cgtaaaagtg gcagtcaatt acagatttc tttaacctac gcaatgagct    7260
attgcggggg gtgccgcaat gagctgttgc gtaccccct tttttaagtt gttgattttt    7320
aagtcttccg catttcgccc tatatctagt tctttggtgc ccaaagaagg gcacccctgc    7380
ggggttcccc cacgccttcg gcgcggctcc ccctccggca aaaagtggcc cctccggggc    7440
ttgttgatcg actgcgcggc cttcggcctt gcccaaggtg gcgctgcccc cttggaaccc    7500
ccgcactcgc cgccgtgagg ctcgggggggc aggcgggcgg gcttcgcctt cgactgcccc    7560
cactcgcata ggcttgggtc gttccaggcg cgtcaaggcc aagccgctgc gcggtcgctg    7620
cgcgagcctt gacccgcctt ccacttggtg tccaaccggc aagcgaagcg cgcaggccgc    7680
aggccggagg cttttcccca gagaaaatta aaaaaattga tggggcaagg ccgcaggccg    7740
cgcagttgga gccggtgggt atgtggtcga aggctgggta gccggtgggc aatccctgtg    7800
gtcaagctcg tgggcaggcg cagcctgtcc atcagcttgt ccagcagggt tgtccacggg    7860
ccgagcgaag cgagccagcc ggtggccgct cgcggccatc gtccacatat ccacgggctg    7920
gcaagggagc gcagcgaccg cgcagggcga agcccggaga gcaagcccgt agggcgccgc    7980
agccgccgta ggcggtcacg actttgcgaa gcaaagtcta gtgagtatac tcaagcattg    8040
agtggcccgc cggaggcacc gccttgcgct gccccgtcg agccggttgg acaccaaaag    8100
ggaggggcag gcatggcggc atacgcgatc atgcgatgca agaagctggc gaaaatgggc    8160
aacgtggcgg ccagtctcaa gcacgcctac cgcgagcgcg agacgcccaa cgctgacgcc    8220
agcaggacgc cagagaacga gcactgggcg gccagcagca ccgatgaagc gatgggccga    8280
ctgcgcgagt tgctgccaga gaagcggcgc aaggacgctg tgttggcggt cgagtacgtc    8340
atgacggcca gcccggaatg gtggaagtcg gccagccaag aacagcaggc ggcgttcttc    8400
gagaaggcgc acaagtggct ggcggacaag tacgggcgg atcgcatcgt gacgccagc    8460 atccaccgtg acgaaaccag cccgcacatg accgcgttcg tggtgccgct gacgcaggac    8520
```

```
ggcaggctgt cggccaagga gttcatcggc aacaaagcgc agatgacccg cgaccagacc    8580
acgtttgcgg ccgctgtggc cgatctaggg ctgcaacggg gcatcgaggg cagcaaggca    8640
cgtcacacgc gcattcaggc gttctacgag ccctggagc ggccaccagt gggccacgtc     8700
accatcagcc cgcaagcggt cgagccacgc gcctatgcac cgcagggatt ggccgaaaag    8760
ctgggaatct caaagcgcgt tgagacgccg gaagccgtgg ccgaccggct gacaaaagcg    8820
gttcggcagg gtatgagcc tgccctacag gccgccgcag gagcgcgtga gatgcgcaag     8880
aaggccgatc aagcccaaga gacggcccga g                                    8911
```

<210> SEQ ID NO 162
<211> LENGTH: 13012
<212> TYPE: DNA
<213> ORGANISM: Artificial Sequence
<220> FEATURE:
<223> OTHER INFORMATION: Synthetic Construct

<400> SEQUENCE: 162

```
ctagagtata catttaaatg gtaccctcta gtcaaggcct taagtgagtc gtattacgga      60
ctggccgtcg ttttacaacg tcgtgactgg gaaaaccctg gcgttaccca acttaatcgc    120
cttgcagcac atccccttt cgccagctgg cgtaatagcg aagaggcccg caccgatcgc     180
ccttcccaac agttgcgcag cctgaatggc gaatggcgcc tgatgcggta ttttctcctt    240
acgcatctgt gcggtatttc acaccgcata tggtgcactc tcagtacaat ctgctctgat    300
gccgcatagt taagccagcc ccgacacccg ccaacacccg ctgacgagct tagtaaagcc    360
ctcgctagat tttaatgcgg atgttgcgat tacttcgcca actattgcga taacaagaaa    420
aagccagcct ttcatgatat atctcccaat ttgtgtaggg cttattatgc acgcttaaaa    480
ataataaaag cagacttgac ctgatagttt ggctgtgagc aattatgtgc ttagtgcatc    540
taacgcttga gttaagccgc gccgcgaagc ggcgtcggct tgaacgaatt gttagacatt    600
atttgccgac taccttggtg atctcgcctt tcacgtagtg gacaaattct tccaactgat    660
ctgcgcgcga ggccaagcga tcttcttctt gtccaagata agcctgtcta gcttcaagta    720
tgacgggctg atactgggcc ggcaggcgct ccattgccca gtcggcagcg acatccttcg    780
gcgcgatttt gccggttact gcgctgtacc aaatgcggga caacgtaagc actacatttc    840
gctcatcgcc agcccagtcg gcggcgagt tccatagcgt taaggtttca tttagcgcct    900
caaatagatc ctgttcagga accggatcaa agagttcctc cgccgctgga cctaccaagg    960
caacgctatg ttctcttgct tttgtcagca agatagccag atcaatgtcg atcgtggctg    1020
gctcgaagat acctgcaaga atgtcattgc gctgccattc tccaaattgc agttcgcgct    1080
tagctggata cgccacggaa tgatgtcgt cgtgcacaac aatggtgact tctacagcgc     1140
ggagaatctc gctctctcca ggggaagccg aagtttccaa aaggtcgttg atcaaagctc    1200
gccgcgttgt ttcatcaagc cttacggtca ccgtaaccag caaatcaata tcactgtgtg    1260
gcttcaggcc gccatccact gcggagccgt acaaatgtac ggccagcaac gtcggttcga    1320
gatggcgctc gatgacgcca actacctctg atagttgagt cgatacttcg gcgatcaccg    1380
cttccctcat gatgtttaac tttgttttag ggcgactgcc ctgctgcgta acatcgttgc    1440
tgctccataa catcaaacat cgacccacgg cgtaacgcgc ttgctgcttg gatgcccgag    1500
gcatagactg taccccaaaa aaacagtcat aacaagccat gaaaaccgcc actgcgccgt    1560
taccaccgct gcgttcggtc aaggttctgg accagttgcg tgagcgcata cgctacttgc    1620
attacagctt acgaaccgaa caggcttatg tccactgggt tcgtgccttc atccgtttcc    1680
```

```
acggtgtgcg tcacccggca accttgggca gcagcgaagt cgaggcattt ctgtcctggc    1740
tggcgaacga gcgcaaggtt tcggtctcca cgcatcgtca ggcattggcg gccttgctgt    1800
tcttctacgg caaggtgctg tgcacggatc tgccctggct tcaggagatc ggaagacctc    1860
ggccgtcgcg gcgcttgccg gtggtgctga ccccggatga agtggttcgc atcctcggtt    1920
ttctggaagg cgagcatcgt ttgttcgccc agcttctgta tggaacgggc atgcggatca    1980
gtgagggttt gcaactgcgg gtcaaggatc tggatttcga tcacggcacg atcatcgtgc    2040
gggagggcaa gggctccaag gatcgggcct tgatgttacc cgagagcttg gcacccagcc    2100
tgcgcgagca gggaattaa ttcccacggg ttttgctgcc cgcaaacggg ctgttctggt    2160
gttgctagtt tgttatcaga atcgcagatc cggcttcagc cggtttgccg gctgaaagcg    2220
ctatttcttc cagaattgcc atgatttttt ccccacggga ggcgtcactg gctcccgtgt    2280
tgtcggcagc tttgattcga taagcagcat cgcctgtttc aggctgtcta tgtgtgactg    2340
ttgagctgta acaagttgtc tcaggtgttc aatttcatgt tctagttgct ttgttttact    2400
ggtttcacct gttctattag gtgttacatg ctgttcatct gttacattgt cgatctgttc    2460
atggtgaaca gctttgaatg caccaaaaac tcgtaaaagc tctgatgtat ctatcttttt    2520
tacaccgttt tcatctgtgc atatggacag ttttcccttt gatatgtaac ggtgaacagt    2580
tgttctactt tgtttgtta gtcttgatgc ttcactgata gatacaagag ccataagaac    2640
ctcagatcct tccgtattta gccagtatgt tctctagtgt ggttcgttgt ttttgcgtga    2700
gccatgagaa cgaaccattg agatcatact tactttgcat gtcactcaaa aattttgcct    2760
caaaactggt gagctgaatt tttgcagtta aagcatcgtg tagtgttttt cttagtccgt    2820
tatgtaggta ggaatctgat gtaatggttg ttggtatttt gtcaccattc atttttatct    2880
ggttgttctc aagttcggtt acgagatcca tttgtctatc tagttcaact tggaaaatca    2940
acgtatcagt cgggcggcct cgcttatcaa ccaccaattt catattgctg taagtgttta    3000
aatctttact tattggtttc aaaacccatt ggttaagcct tttaaactca tggtagttat    3060
tttcaagcat taacatgaac ttaaattcat caaggctaat ctctatattt gccttgtgag    3120
ttttcttttg tgttagttct tttaataacc actcataaat cctcatagag tatttgtttt    3180
caaaagactt aacatgttcc agattatatt ttatgaattt ttttaactgg aaaagataag    3240
gcaatatctc ttcactaaaa actaattcta attttttcgct tgagaacttg gcatagtttg    3300
tccactggaa aatctcaaag cctttaacca aaggattcct gatttccaca gttctcgtca    3360
tcagctctct ggttgcttta gctaatacac cataagcatt ttccctactg atgttcatca    3420
tctgagcgta ttggttataa gtgaacgata ccgtccgttc tttccttgta gggttttcaa    3480
tcgtggggtt gagtagtgcc acacagcata aaattagctt ggtttcatgc tccgttaagt    3540
catagcgact aatcgctagt tcatttgctt tgaaaacaac taattcagac atacatctca    3600
attggtctag gtgattttaa tcactatacc aattgagatg ggctagtcaa tgataattac    3660
tagtcctttt cctttgagtt gtgggtatct gtaaattctg ctagacccttt gctggaaaac    3720
ttgtaaattc tgctagaccc tctgtaaatt ccgctagacc tttgtgtgtt tttttgttt    3780
atattcaagt ggtataatt tatagaataa agaaagaata aaaaaagata aaagaatag    3840
atcccagccc tgtgtataac tcactacttt agtcagttcc gcagtattac aaaaggatgt    3900
cgcaaacgct gtttgctcct ctacaaaaca gaccttaaaa ccctaaaggc ttaagtagca    3960
ccctcgcaag ctcgggcaaa tcgctgaata ttccttttgt ctccgaccat caggcacctg    4020
```

```
agtcgctgtc tttttcgtga cattcagttc gctgcgctca cggctctggc agtgaatggg    4080
ggtaaatggc actacaggcg cctttttatgg attcatgcaa ggaaactacc cataatacaa   4140
gaaaagcccg tcacgggctt ctcagggcgt tttatggcgg gtctgctatg tggtgctatc    4200
tgacttttg  ctgttcagca gttcctgccc tctgattttc cagtctgacc acttcggatt    4260
atcccgtgac aggtcattca gactggctaa tgcacccagt aaggcagcgg tatcatcaac    4320
aggcttaccc gtcttactgt cgggaattca tttaaatagt caaaagcctc cgaccggagg    4380
cttttgactg ctaggcgatc tgtgctgttt gccacggtat gcagcaccag cgcgagatta    4440
tgggctcgca cgctcgactg tcggacgggg cactggaac  gagaagtcag gcgagccgtc    4500
acgcccttga caatgccaca tcctgagcaa ataattcaac cactaaacaa atcaaccgcg    4560
tttcccggag gtaaccaagc ttgcgggaga gaatgatgaa caagagccaa caagttcaga    4620
caatcaccct ggccgccgcc cagcaaatgg cggcggcggt ggaaaaaaaa gccactgaga    4680
tcaacgtggc ggtggtgttt tccgtagttg accgcggagg caacacgctg cttatccagc    4740
ggatggacga ggccttcgtc tccagctgcg atatttccct gaataaagcc tggagcgcct    4800
gcagcctgaa gcaaggtacc catgaaatta cgtcagcggt ccagccagga caatctctgt    4860
acggtctgca gctaaccaac caacagcgaa ttattatttt tggcggcggc ctgccagtta    4920
tttttaatga gcaggtaatt ggcgccgtcg gcgttagcgg cggtacgggtc gagcaggatc   4980
aattattagc ccagtgcgcc ctggattgtt tttccgcatt ataacctgaa gcgagaaggt    5040
atattatgag ctatcgtatg ttccgccagg cattctgagt gttaacgagg ggaccgtcat    5100
gtcgcttttca ccgccaggcg tacgcctgtt ttacgatccg cgcgggcacc atgccggcgc   5160
catcaatgag ctgtgctggg ggctggagga gcaggggtc  ccctgccaga ccataaccta    5220
tgacggaggc ggtgacgccg ctgcgctggg cgccctggcg ccagaagct  cgcccctgcg    5280
ggtgggtatc gggctcagcg cgtccggcga gatagccctc actcatgccc agctgccggc    5340
ggacgcgccg ctggctaccg gacacgtcac cgatagcgac gatcaactgc gtacgctcgg    5400
cgccaacgcc gggcagctgg ttaaagtcct gccgttaagt gagagaaact gaactggcct    5460
agcaaaacaca gaaaaaagcc cgcacctgac agtgcgggct tttttttttcc taggcgatct   5520
gtgctgtttg ccacggtatg cagcaccagc gcgagattat gggctcgcac gctcgactgt    5580
cggacggggg cactgaacg  agaagtcagg cgagccgtca cgcccttgac aatgccacat    5640
cctgagcaaa taattcaacc actaaacaaa tcaaccgcgt ttcccggagg taaccaagct    5700
tcaccttttg agccgatgaa caatgaaaag atcaaaacga tttgcagtac tggcccagcg    5760
ccccgtcaat caggacgggc tgattggcga gtggcctgaa gagggggctga tcgccatgga   5820
cagccccttt gacccggtct cttcagtaaa agtggacaac ggtctgatcg tcgaactgga    5880
cggcaaacgc cgggaccagt ttgacatgat cgaccgattt atcgccgatt acgcgatcaa    5940
cgttgagcgc acagagcagg caatgcgcct ggaggcggtg gaaatagccc gtatgctggt    6000
ggatattcac gtcagccggg aggagatcat tgccatcact accgccatca cgccggccaa    6060
agcggtcgag gtgatggcgc agatgaacgt ggtggagatg atgatggcgc tgcagaagat    6120
gcgtgcccgc cggacccct  ccaaccagtg ccacgtcacc aatctcaaag ataatccggt    6180
gcagattgcc gctgacgccg ccgaggccgg gatccgcggc ttctcagaac aggagaccac    6240
ggtcggtatc gcgcgctacg cgccgtttaa cgccctggcg ctgttggtcg gttcgcagtg    6300
cggccgcccc ggcgtgttga cgcagtgctc ggtggaagag gccaccgagc tggagctggg    6360
catgcgtggc ttaaccagct acgccgagac ggtgtcggtc tacggcaccg aagcggtatt    6420
```

```
taccgacggc gatgatacgc cgtggtcaaa ggcgttcctc gcctcggcct acgcctcccg    6480
cgggttgaaa atgcgctaca cctccggcac cggatccgaa gcgctgatgg gctattcgga    6540
gagcaagtcg atgctctacc tcgaatcgcg ctgcatcttc attactaaag gcgccggggt    6600
tcagggactg caaaacggcg cggtgagctg tatcggcatg accggcgctg tgccgtcggg    6660
cattcgggcg gtgctggcgg aaaacctgat cgcctctatg ctcgacctcg aagtggcgtc    6720
cgccaacgac cagactttct cccactcgga tattcgccgc accgcgcgca ccctgatgca    6780
gatgctgccg ggcaccgact ttattttctc cggctacagc gcggtgccga actacgacaa    6840
catgttcgcc ggctcgaact tcgatgcgga agattttgat gattacaaca tcctgcagcg    6900
tgacctgatg gttgacggcg gcctgcgtcc ggtgaccgag gcggaaacca ttgccattcg    6960
ccagaaagcg gcgcgggcga tccaggcggt tttccgcgag ctggggctgc cgccaatcgc    7020
cgacgaggag gtggaggccg ccacctacgc gcacggcagc aacgagatgc cgccgcgtaa    7080
cgtggtggag gatctgagtg cggtggaaga gatgatgaag cgcaacatca ccggcctcga    7140
tattgtcggc gcgctgagcc gcagcggctt tgaggatatc gccagcaata ttctcaatat    7200
gctgcgccag cgggtcaccg gcgattacct gcagacctcg gccattctcg atcggcagtt    7260
cgaggtggtg agtgcggtca acgacatcaa tgactatcag gggccgggca ccggctatcg    7320
catctctgcc gaacgctggg cggagatcaa aaatattccg ggcgtggttc agcccgacac    7380
cattgaataa ggcggtattc ctgtgcaaca gacaacccaa attcagccct cttttaccct    7440
gaaaacccgc gagggcgggg tagcttctgc cgatgaacgc gccgatgaag tggtgatcgg    7500
cgtcggccct gccttcgata acaccagca tcacactctg atcgatatgc cccatggcgc    7560
gatcctcaaa gagctgattg ccggggtgga agaagagggg cttcacgccc gggtggtgcg    7620
cattctgcgc acgtccgacg tctcctttat ggcctgggat gcggccaacc tgagcggctc    7680
ggggatcggc atcggtatcc agtcgaaggg gaccacggtc atccatcagc gcgatctgct    7740
gccgctcagc aacctggagc tgttctccca ggcgccgctg ctgacgctgg agacctaccg    7800
gcagattggc aaaaacgctg cgcgctatgc gcgcaaagag tcaccttcgc cggtgccggt    7860
ggtgaacgat cagatggtgc ggccgaaatt tatggccaaa gccgcgctat ttcatatcaa    7920
agagaccaaa catgtggtgc aggacgccga gcccgtcacc ctgcacatcg acttagtaag    7980
ggagtgacca tgagcgagaa aaccatgcgc gtgcaggatt atccgttagc cacccgctgc    8040
ccggagcata tcctgacgcc taccggcaaa ccattgaccg atattaccct cgagaaggtg    8100
ctctctggcg aggtgggccc gcaggatgtg cggatctccc gccagaccct tgagtaccag    8160
gcgcagattg ccgagcagat gcagcgccat gcggtggcgc gcaatttccg ccgcgcggcg    8220
gagcttatcg ccattcctga cgagcgcatt ctggctatct ataacgcgct gcgcccgttc    8280
cgctcctcgc aggcggagct gctggcgatc gccgacgagc tggagcacac ctggcatgcg    8340
acagtgaatg ccgcctttgt ccgggagtcg gcggaagtgt atcagcagcg gcataagctg    8400
cgtaaaggaa gctaagcgga ggtcagcatg ccgttaatag ccgggattga tatcggcaac    8460
gccaccaccg aggtggcgct ggcgtccgac tacccgcagg cgagggcgtt tgttgccagc    8520
gggatcgtcg cgacgacggg catgaaaggg acgcgggaca atatcgccgg accctcgcc    8580 gcgctggagc aggccctggc gaaaacaccg tggtcgatga gcgatgtctc tcgcatctat    8640
cttaacgaag ccgcgccggt gattggcgat gtggcgatgg agaccatcac cgagaccatt    8700
atcaccgaat cgaccatgat cggtcataac ccgcagacgc cgggcggggt gggcgttggc    8760
```

```
gtggggacga ctatcgccct cgggcggctg gcgacgctgc cggcggcgca gtatgccgag   8820
gggtggatcg tactgattga cgacgccgtc gatttccttg acgccgtgtg gtggctcaat   8880
gaggcgctcg accgggggat caacgtggtg gcggcgatcc tcaaaaagga cgacggcgtg   8940
ctggtgaaca accgcctgcg taaaaccctg ccggtggtgg atgaagtgac gctgctggag   9000
caggtccccg aggggtaat ggcggcggtg gaagtggccg cgccgggcca ggtggtgcgg   9060
atcctgtcga atccctacgg gatcgccacc ttcttcgggc taagcccgga agagacccag   9120
gccatcgtcc ccatcgcccg cgccctgatt ggcaaccgtt ccgcggtggt gctcaagacc   9180 ccgcagggggg atgtgcagtc gcgggtgatc ccggcgggca acctctacat tagcggcgaa   9240
aagcgccgcg gagaggccga tgtcgccgag ggcgcggaag ccatcatgca ggcgatgagc   9300
gcctgcgctc cggtacgcga catccgcggc gaacccggca cccacgccgg cggcatgctt   9360
gagcgggtgc gcaaggtaat ggcgtccctg accggccatg agatgagcgc gatatacatc   9420
caggatctgc tggcggtgga tacgtttatt ccgcgcaagg tgcagggcgg gatggccggc   9480
gagtgcgcca tggagaatgc cgtcgggatg gcggcgatgg tgaaagcgga tcgtctgcaa   9540
atgcaggtta tcgcccgcga actgagcgcc cgactgcaga ccgaggtggt ggtgggcggc   9600
gtggaggcca acatggccat cgccgggggcg ttaaccactc ccggctgtgc ggcgccgctg   9660
gcgatcctcg acctcggcgc cggctcgacg gatgcggcga tcgtcaacgc ggaggggcag   9720
ataacggcgg tccatctcgc cggggcgggg aatatggtca gcctgttgat taaaaccgag   9780
ctgggcctcg aggatctttc gctggcggaa gcgataaaaa aatacccgct ggccaaagtg   9840
gaaagcctgt tcagtattcg tcacgagaat ggcgcggtgg agttctttcg ggaagccctc   9900
agcccggcgg tgttcgccaa agtggtgtac atcaaggagg gcgaactggt gccgatcgat   9960
aacgccagcc cgctggaaaa aattcgtctc gtgcgccggc aggcgaaaga gaaagtgttt  10020
gtcaccaact gcctgcgcgc gctgcgccag gtctcacccg gcggttccat tcgcgatatc  10080
gcctttgtgg tgctggtggg cggctcatcg ctggactttg agatcccgca gcttatcacg  10140
gaagccttgt cgcactatgg cgtggtcgcc gggcagggca atattcgggg aacagaaggg  10200
ccgcgcaatg cggtcgccac cgggctgcta ctggccggtc aggcgaatta acgggcgct  10260 cgcgccagcc tctaggtaca aataaaaaag gcacgtcaga tgacgtgcct tttttcttgt  10320
ctagcgtgca ccaatgcttc tggcgtcagg cagccatcgg aagctgtggt atggctgtgc  10380
aggtcgtaaa tcactgcata attcgtgtcg ctcaaggcgc actcccgttc tggataatgt  10440 ttttttgcgcc gacatcataa cggttctggc aaatattctg aaatgagctg ttgacaatta  10500
atcatccggc tcgtataatg tgtggaattg tgagcggata caatttcac acaggaaaca  10560 gaccatgact agtaaggagg acaattccat ggctgctgct gctgatagat taaacttaac  10620
ttccggccac ttgaatgctg gtagaaagag aagttcctct tctgtttctt tgaaggctgc  10680
cgaaaagcct ttcaaggtta ctgtgattgg atctggtaac tggggactac ctattgccaa  10740
ggtggttgcc gaaaattgta agggataccc agaagttttc gctccaatag tacaaatgtg  10800
ggtgttcgaa gaagagatca atggtgaaaa attgactgaa atcataaata ctagacatca  10860
aaacgtgaaa tacttgcctg gcatcactct acccgacaat ttggttgcta atccagactt  10920
gattgattca gtcaaggatg tcgacatcat cgttttcaac attccacatc aatttttgcc  10980
ccgtatctgt agccaattga aaggtcatgt tgattcacac gtcagagcta tctcctgtct  11040
aaagggtttt gaagttggtg ctaaaggtgt ccaattgcta tcctcttaca tcactgagga  11100
actaggtatt caatgtggtg ctctatctgg tgctaacatt gccaccgaag tcgctcaaga  11160
```

```
acactggtct gaaacaacag ttgcttacca cattccaaag gatttcgagg gcgagggcaa    11220
ggacgtcgac cataaggttc taaaggcctt gttccacaga ccttacttcc acgttagtgt    11280
catcgaagat gttgctggta tctccatctg tggtgctttg aagaacgttg ttgccttagg    11340
ttgtggtttc gtcgaaggtc taggctgggg taacaacgct tctgctgcca tccaaagagt    11400
cggtttgggt gagatcatca gattcggtca aatgtttttc ccagaatcta gagaagaaac    11460
atactaccaa gagtctgctg gtgttgctga tttgatcacc acctgcgctg gtggtagaaa    11520
cgtcaaggtt gctaggctaa tggctacttc tggtaaggac gcctgggaat gtgaaaagga    11580
gttgttgaat ggccaatccg ctcaaggttt aattacctgc aaagaagttc acgaatggtt    11640
ggaaacatgt ggctctgtcg aagacttccc attatttgaa gccgtatacc aaatcgttta    11700
caacaactac ccaatgaaga acctgccgga catgattgaa gaattagatc tacatgaaga    11760
ttagatttat tggatccagg aaacagacta gaattatggg attgactact aaacctctat    11820
cttggaaagt taacgccgct ttgttcgacg tcgacggtac cattatcatc tctcaaccag    11880
ccattgctgc attctggagg gatttcggta aggacaaacc ttatttcgat gctgaacacg    11940
ttatccaagt ctcgcatggt tggagaacgt ttgatgccat tgctaagttc gctccagact    12000
ttgccaatga agagtatgtt aacaaattag aagctgaaat tccggtcaag tacggtgaaa    12060
aatccattga gtcccaggt gcagttaagc tgtgcaacgc tttgaacgct ctaccaaaag    12120
agaaatgggc tgtggcaact tccggtaccc gtgatatggc acaaaaatgg ttcgagcatc    12180
tgggaatcag gagaccaaag tacttcatta ccgctaatga tgtcaaacag ggtaagcctc    12240
atccagaacc atatctgaag ggcaggaatg gcttaggata tccgatcaat gagcaagacc    12300
cttccaaatc taaggtagta gtatttgaag acgctccagc aggtattgcc gccggaaaag    12360
ccgccggttg taagatcatt ggtattgcca ctactttcga cttggacttc ctaaaggaaa    12420
aaggctgtga catcattgtc aaaaaccacg aatccatcag agttggcggc tacaatgccg    12480
aaacagacga agttgaattc atttttgacg actacttata tgctaaggac gatctgttga    12540
aatggtaacc cgggctgcag gcatgcaagc ttggctgttt tggcggatga gagaagattt    12600
tcagcctgat acagattaaa tcagaacgca gaagcggtct gataaaacag aatttgcctg    12660
gcggcagtag cgcggtggtc ccacctgacc ccatgccgaa ctcagaagtg aaacgccgta    12720
gcgccgatgg tagtgtgggg tctccccatg cgagagtagg gaactgccag gcatcaaata    12780
aaacgaaagg ctcagtcgaa agactgggcc tttcgtttta tctgttgttt gtcggtgaac    12840
gctctcctga gtaggacaaa tccgccggga gcggatttga acgttgcgaa gcaacggccc    12900
ggagggtggc gggcaggacg cccgccataa actgccaggc atcaaattaa gcagaaggcc    12960
atcctgacgg atggcctttt tgcgtttcta caaactccag ctggatcggg cg             13012
```

<210> SEQ ID NO 163
<211> LENGTH: 13012
<212> TYPE: DNA
<213> ORGANISM: Artificial Sequence
<220> FEATURE:
<223> OTHER INFORMATION: Synthetic Construct

<400> SEQUENCE: 163

```
ctagagtata catttaaatg gtaccctcta gtcaaggcct taagtgagtc gtattacgga      60
ctggccgtcg ttttacaacg tcgtgactgg gaaaaccctg gcgttaccca acttaatcgc     120
cttgcagcac atccccccttt cgccagctgg cgtaatagcg aagaggcccg caccgatcgc     180
```

```
ccttcccaac agttgcgcag cctgaatggc gaatggcgcc tgatgcggta ttttctcctt    240
acgcatctgt gcggtatttc acaccgcata tggtgcactc tcagtacaat ctgctctgat    300
gccgcatagt taagccagcc ccgacacccg ccaacacccg ctgacgagct tagtaaagcc    360
ctcgctagat tttaatgcgg atgttgcgat tacttcgcca actattgcga taacaagaaa    420
aagccagcct ttcatgatat atctcccaat ttgtgtaggg cttattatgc acgcttaaaa    480
ataataaaag cagacttgac ctgatagttt ggctgtgagc aattatgtgc ttagtgcatc    540
taacgcttga gttaagccgc gccgcgaagc ggcgtcggct tgaacgaatt gttagacatt    600
atttgccgac taccttggtg atctcgcctt tcacgtagtg acaaattct tccaactgat     660
ctgcgcgcga ggccaagcga tcttcttctt gtccaagata agcctgtcta gcttcaagta    720
tgacgggctg atactgggcc ggcaggcgct ccattgccca gtcggcagcg acatccttcg    780
gcgcgatttt gccggttact cgctgtacc aaatgcggga caacgtaagc actacatttc     840
gctcatcgcc agcccagtcg ggcggcgagt tccatagcgt taaggtttca tttagcgcct    900
caaatagatc ctgttcagga accggatcaa agagttcctc cgccgctgga cctaccaagg    960
caacgctatg ttctcttgct tttgtcagca agatagccag atcaatgtcg atcgtggctg   1020
gctcgaagat acctgcaaga atgtcattgc gctgccattc tccaaattgc agttcgcgct   1080
tagctggata acgccacgga atgatgtcgt cgtgcacaac aatggtgact tctacagcgc   1140
ggagaatctc gctctctcca ggggaagccg aagtttccaa aaggtcgttg atcaaagctc   1200
gccgcgttgt tcatcaagc cttacggtca ccgtaaccag caaatcaata tcactgtgtg    1260
gcttcaggcc gccatccact gcggagccgt acaaatgtac ggccagcaac gtcggttcga   1320
gatggcgctc gatgacgcca actacctctg atagttgagt cgatacttcg gcgatcaccg   1380
cttccctcat gatgtttaac tttgttttag ggcgactgcc ctgctgcgta acatcgttgc   1440
tgctccataa catcaaacat cgacccacgg cgtaacgcgc ttgctgcttg gatgcccgag   1500
gcatagactg taccccaaaa aaacagtcat aacaagccat gaaaaccgcc actgcgccgt   1560
taccaccgct gcgttcggtc aaggttctgg accagttgcg tgagcgcata cgctacttgc   1620
attacagctt acgaaccgaa caggcttatg tccactgggt tcgtgccttc atccgtttcc   1680
acggtgtgcg tcacccggca accttgggca gcagcgaagt cgaggcattt ctgtcctggc   1740
tggcgaacga gcgcaaggtt tcggtctcca cgcatcgtca ggcattggcg ccttgctgt   1800
tcttctacgg caaggtgctg tgcacggatc tgccctggct tcaggagatc ggaagacctc   1860
ggccgtcgcg gcgcttgccg gtggtgctga ccccggatga agtggttcgc atcctcggtt   1920
ttctggaagg cgagcatcgt tgttcgccc agcttctgta tggaacgggc atgcggatca   1980
gtgagggttt gcaactgcgg gtcaaggatc tggatttcga tcacggcacg atcatcgtgc   2040
gggagggcaa gggctccaag gatcgggcct tgatgttacc cgagagcttg gcacccagcc   2100
tgcgcgagca ggggaattaa ttcccacggg ttttgctgcc cgcaaacggg ctgttctggt   2160
gttgctagtt tgttatcaga atcgcagatc cggcttcagc cggtttgccg gctgaaagcg   2220
ctatttcttc cagaattgcc atgatttttt ccccacggga ggcgtcactg gctcccgtgt   2280
tgtcggcagc tttgattcga taagcagcat cgcctgtttc aggctgtcta tgtgactg    2340
ttgagctgta acaagttgtc tcaggtgttc aatttcatgt tctagttgct ttgttttact   2400
ggtttcacct gttctattag gtgttacatg ctgttcatct gttacattgt cgatctgttc   2460
atggtgaaca gctttgaatg caccaaaaac tcgtaaaagc tctgatgtat ctatcttttt   2520
tacaccgttt tcatctgtgc atatggacag ttttcccttt gatatgtaac ggtgaacagt   2580
```

-continued

```
tgttctactt ttgtttgtta gtcttgatgc ttcactgata gatacaagag ccataagaac    2640
ctcagatcct tccgtattta gccagtatgt tctctagtgt ggttcgttgt ttttgcgtga    2700
gccatgagaa cgaaccattg agatcatact tactttgcat gtcactcaaa aattttgcct    2760
caaaactggt gagctgaatt tttgcagtta aagcatcgtg tagtgttttt cttagtccgt    2820
tatgtaggta ggaatctgat gtaatggttg ttggtatttt gtcaccattc attttatct    2880 ggttgttctc aagttcggtt acgagatcca tttgtctatc tagttcaact tggaaaatca    2940
acgtatcagt cgggcggcct cgcttatcaa ccaccaattt catattgctg taagtgttta    3000
aatctttact tattggtttc aaacccatt ggttaagcct tttaaactca tggtagttat    3060
tttcaagcat taacatgaac ttaaattcat caaggctaat ctctatattt gccttgtgag    3120
ttttcttttg tgttagttct tttaataacc actcataaat cctcatagag tatttgtttt    3180
caaaagactt aacatgttcc agattatatt ttatgaattt ttttaactgg aaaagataag    3240
gcaatatctc ttcactaaaa actaattcta attttctcgct tgagaacttg gcatagtttg    3300
tccactggaa aatctcaaag cctttaacca aaggattcct gatttccaca gttctcgtca    3360
tcagctctct ggttgcttta gctaatacac cataagcatt ttccctactg atgttcatca    3420
tctgagcgta ttggttataa gtgaacgata ccgtccgttc tttccttgta gggttttcaa    3480 tcgtgggggtt gagtagtgcc acacagcata aaattagctt ggtttcatgc tccgttaagt    3540
catagcgact aatcgctagt tcatttgctt tgaaaacaac taattcagac atacatctca    3600
attggtctag gtgattttaa tcactatacc aattgagatg ggctagtcaa tgataattac    3660 tagtccttt cctttgagtt gtgggtatct gtaaattctg ctagacctt gctggaaaac    3720 ttgtaaattc tgctagaccc tctgtaaatt ccgctagacc tttgtgtgtt tttttgttt    3780 atattcaagt ggttataatt tatagaataa agaaagaata aaaaaagata aaagaatag    3840 atcccagccc tgtgtataac tcactacttt agtcagttcc gcagtattac aaaaggatgt    3900
cgcaaacgct gtttgctcct ctacaaaaca gaccttaaaa ccctaaaggc ttaagtagca    3960
ccctcgcaag ctcgggcaaa tcgctgaata ttccttttgt ctccgaccat caggcacctg    4020
agtcgctgtc ttttcgtga cattcagttc gctgcgctca cggctctggc agtgaatggg    4080
ggtaaatggc actacaggcg ccttttatgg attcatgcaa ggaaactacc cataatacaa    4140
gaaaagcccg tcacgggctt ctcagggcgt tttatggcgg gtctgctatg tggtgctatc    4200 tgacttttg ctgttcagca gttcctgccc tctgattttc cagtctgacc acttcggatt    4260
atcccgtgac aggtcattca gactggctaa tgcacccagt aaggcagcgg tatcatcaac    4320
aggcttaccc gtcttactgt cgggaattca tttaaatagt caaaagcctc cgaccggagg    4380
cttttgactg ctaggcgatc tgtgctgttt gccacggtat gcagcaccag cgcgagatta    4440
tgggctcgca cgctcgactg tcggacgggg gcactggaac gagaagtcag gcgagccgtc    4500
acgcccttga caatgccaca tcctgagcaa ataattcaac cactaaacaa atcaaccgcg    4560
tttcccggag gtaaccaagc ttgcgggaga gaatgatgaa caagagccaa caagttcaga    4620
caatcaccct ggccgccgcc cagcaaatgg cggcggcggt ggaaaaaaaa gccactgaga    4680
tcaacgtggc ggtggtgttt tccgtagttg accgcggagg caacacgctg cttatccagc    4740
ggatggacga ggccttcgtc tccagctgcg atatttccct gaataaagcc tggagcgcct    4800
gcagcctgaa gcaaggtacc catgaaatta cgtcagcggt ccagccagga caatctctgt    4860
acggtctgca gctaaccaac caacagcgaa ttattatttt tggcggcggc ctgccagtta    4920
```

-continued

```
tttttaatga gcaggtaatt ggcgccgtcg gcgttagcgg cggtacggtc gagcaggatc    4980
aattattagc ccagtgcgcc ctggattgtt tttccgcatt ataacctgaa gcgagaaggt    5040
atattatgag ctatcgtatg ttccgccagg cattctgagt gttaacgagg ggaccgtcat    5100
gtcgctttca ccgccaggcg tacgcctgtt ttacgatccg cgcgggcacc atgccggcgc    5160
catcaatgag ctgtgctggg ggctggagga gcaggggtc ccctgccaga ccataaccta    5220
tgacggaggc ggtgacgccg ctgcgctggg cgccctggcg gccagaagct cgcccctgcg    5280
ggtgggtatc gggctcagcg cgtccggcga gatagccctc actcatgccc agctgccggc    5340
ggacgcgccg ctggctaccg gacacgtcac cgatagcgac gatcaactgc gtacgctcgg    5400
cgccaacgcc gggcagctgg ttaaagtcct gccgttaagt gagagaaact gaactggcct    5460
agcaaacaca gaaaaaagcc cgcacctgac agtgcgggct ttttttttcc taggcgatct    5520
gtgctgtttg ccacggtatg cagcaccagc gcgagattat gggctcgcac gctcgactgt    5580
cggacggggg cactggaacg agaagtcagg cgagccgtca cgcccttgac aatgccacat    5640
cctgagcaaa taattcaacc actaaacaaa tcaaccgcgt ttcccggagg taaccaagct    5700
tcaccttttg agccgatgaa caatgaaaag atcaaaacga tttgcagtac tggcccagcg    5760
ccccgtcaat caggacgggc tgattggcga gtggcctgaa gaggggctga tcgccatgga    5820
cagccccttt gacccggtct cttcagtaaa agtggacaac ggtctgatcg tcgaactgga    5880
cggcaaacgc cgggaccagt ttgacatgat cgaccgattt atcgcgcatt acgcgatcaa    5940
cgttgagcgc acagagcagg caatgcgcct ggaggcggtg gaaatagccc gtatgctggt    6000
ggatattcac gtcagccggg aggagatcat tgccatcact accgccatca cgccggccaa    6060
agcggtcgag gtgatggcgc agatgaacgt ggtggagatg atgatggcgc tgcagaagat    6120
gcgtgccccg cggaccccct ccaaccagtg ccacgtcacc aatctcaaag ataatccggt    6180
gcagattgcc gctgacgccg ccgaggccgg gatccgcggc ttctcagaac aggagaccac    6240
ggtcggtatc gcgcgctacg cgccgtttaa cgccctggcg ctgttggtcg gttcgcagtg    6300
cggccgcccc ggcgtgttga cgcagtgctc ggtggaagag gccaccgagc tggagctggg    6360
catgcgtggc ttaaccagct acgccgagac ggtgtcggtc tacggcaccg aagcggtatt    6420
taccgacggc gatgatacgc cgtggtcaaa ggcgttcctc gcctcggcct acgcctcccg    6480
cgggttgaaa atgcgctaca cctccggcac cggatccgaa cgctgatgg gctattcgga    6540 gagcaagtcg atgctctacc tcgaatcgcg ctgcatcttc attactaaag gcgccggggt    6600
tcagggactg caaaacggcg cggtgagctg tatcggcatg accggcgctg tgccgtcggg    6660
cattcgggcg gtgctggcgg aaaacctgat cgcctctatg ctcgacctcg aagtggcgtc    6720
cgccaacgac cagactttct cccactcgga tattcgccgc accgcgcgca ccctgatgca    6780
gatgctgccg ggcaccgact ttattttctc cggctacagc gcggtgccga actacgacaa    6840
catgttcgcc ggctcgaact tcgatgcgga agattttgat gattacaaca tcctgcagcg    6900
tgacctgatg gttgacggcg gcctgcgtcc ggtgaccgag gcggaaacca ttgccattcg    6960
ccagaaagcg gcgcgggcga tccaggcggt tttccgcgag ctggggctgc gccaatcgc    7020 cgacgaggag gtgaggccg ccacctacgc gcacggcagc aacgagatgc gccgcgtaa    7080 cgtggtggag atctgagtg cggtggaaga gatgatgaag cgcaacatca ccggcctcga    7140
tattgtcggc gcgctgagcc gcagcggctt tgaggatatc gccagcaata ttctcaatat    7200
gctgcgccag cgggtcaccg gcgattacct gcagacctcg gccattttcg atcggcagtt    7260
cgaggtggtg agtgcggtca acgacatcaa tgactatcag gggccgggca ccggctatcg    7320
```

```
catctctgcc gaacgctggg cggagatcaa aaatattccg ggcgtggttc agcccgacac    7380
cattgaacaa ggcggtattc ctgtgcaaca gacaacccaa attcagccct cttttaccct    7440
gaaaacccgc gagggcgggg tagcttctgc cgatgaacgc gccgatgaag tggtgatcgg    7500
cgtcggccct gccttcgata aacaccagca tcacactctg atcgatatgc ccatggcgc     7560 gatcctcaaa gagctgattg ccggggtgga agaagagggg cttcacgccc gggtggtgcg    7620
cattctgcgc acgtccgacg tctcctttat ggcctgggat gcggccaacc tgagcggctc    7680
ggggatcggc atcggtatcc agtcgaaggg gaccacggtc atccatcagc gcgatctgct    7740
gccgctcagc aacctggagc tgttctccca ggcgccgctg ctgacgctgg agacctaccg    7800
gcagattggc aaaaacgctg cgcgctatgc gcgcaaagag tcaccttcgc cggtgccggt    7860
ggtgaacgat cagatggtgc ggccgaaatt tatggccaaa gccgcgctat ttcatatcaa    7920
agagaccaaa catgtggtgc aggacgccga gcccgtcacc ctgcacatcg acttagtaag    7980
ggagtgacca tgagcgagaa aaccatgcgc gtgcaggatt atccgttagc cacccgctgc    8040
ccggagcata tcctgacgcc taccggcaaa ccattgaccg atattaccct cgagaaggtg    8100
ctctctggcg aggtgggccc gcaggatgtg cggatctccc gccagaccct tgagtaccag    8160
gcgcagattg ccgagcagat gcagcgccat gcggtggcgc gcaatttccg ccgcgcggcg    8220
gagcttatcg ccattcctga cgagcgcatt ctggctatct ataacgcgct gcgcccgttc    8280
cgctcctcgc aggcggagct gctggcgatc gccgacgagc tggagcacac ctggcatgcg    8340
acagtgaatg ccgcctttgt ccgggagtcg gcggaagtgt atcagcagcg gcataagctg    8400
cgtaaaggaa gctaagcgga ggtcagcatg ccgttaatag ccgggattga tatcggcaac    8460
gccaccaccg aggtggcgct ggcgtccgac tacccgcagg cgagggcgtt tgttgccagc    8520
gggatcgtcg cgacgacggg catgaaaggg acgcgggaca atatcgccgg gaccctcgcc    8580
gcgctggagc aggccctggc gaaaacaccg tggtcgatga gcgatgtctc tcgcatctat    8640
cttaacgaag ccgcgccggt gattggcgat gtggcgatgg agaccatcac cgagaccatt    8700
atcaccgaat cgaccatgat cggtcataac ccgcagacgc cggcgggggt gggcgttggc    8760
gtggggacga ctatcgccct cgggcggctg gcgacgctgc cggcggcgca gtatgccgag    8820
gggtggatcg tactgattga cgacgccgtc gatttccttg acgccgtgtg gtggctcaat    8880
gaggcgctcg accggggggat caacgtggtg gcggcgatcc tcaaaaagga cgacggcgtg    8940
ctggtgaaca accgcctgcg taaaaccctg ccggtggtgg atgaagtgac gctgctggag    9000
caggtccccg aggggggtaat ggcggcggtg gaagtggccg cgccgggcca ggtggtgcgg    9060
atcctgtcga atccctacgg gatcgccacc ttcttcgggc taagcccgga agagacccag    9120
gccatcgtcc ccatcgcccg cgccctgatt ggcaaccgtt ccgcggtggt gctcaagacc    9180 ccgcagggggg atgtgcagtc gcgggtgatc ccggcgggca acctctacat tagcggcgaa    9240
aagcgccgcg gagaggccga tgtcgccgag ggcgcggaag ccatcatgca ggcgatgagc    9300
gcctgcgctc cggtacgcga catccgcggc gaaccgggca cccacgccgg cggcatgctt    9360
gagcgggtgc gcaaggtaat ggcgtccctg accggccatg agatgagcgc gatatacatc    9420
caggatctgc tggcggtgga tacgtttatt ccgcgcaagg tgcagggcgg gatggccggc    9480
gagtgcgcca tggagaatgc cgtcgggatg gcggcgatgg tgaaagcgga tcgtctgcaa    9540
atgcaggtta tcgcccgcga actgagcgcc cgactgcaga ccgaggtggt ggtgggcggc    9600
gtggaggcca acatggccat cgccggggcg ttaaccactc ccggctgtgc ggcgccgctg    9660
```

|  |  |  |  |  |  |
|---|---|---|---|---|---|
| gcgatcctcg | acctcggcgc | cggctcgacg | gatgcggcga | tcgtcaacgc | ggaggggcag | 9720 |
| ataacggcgg | tccatctcgc | cggggcgggg | aatatggtca | gcctgttgat | taaaaccgag | 9780 |
| ctgggcctcg | aggatctttc | gctggcggaa | gcgataaaaa | aatacccgct | ggccaaagtg | 9840 |
| gaaagcctgt | tcagtattcg | tcacgagaat | ggcgcggtgg | agttctttcg | ggaagccctc | 9900 |
| agcccggcgg | tgttcgccaa | agtggtgtac | atcaaggagg | gcgaactggt | gccgatcgat | 9960 |
| aacgccagcc | cgctggaaaa | aattcgtctc | gtgcgccggc | aggcgaaaga | gaaagtgttt | 10020 |
| gtcaccaact | gcctgcgcgc | gctgcgccag | gtctcacccg | gcggttccat | tcgcgatatc | 10080 |
| gcctttgtgg | tgctggtggg | cggctcatcg | ctggactttg | agatcccgca | gcttatcacg | 10140 |
| gaagccttgt | cgcactatgg | cgtggtcgcc | gggcagggca | atattcgggg | aacagaaggg | 10200 |
| ccgcgcaatg | cggtcgccac | cgggctgcta | ctggccggtc | aggcgaatta | aacgggcgct | 10260 |
| cgcgccagcc | tctaggtaca | aataaaaaag | gcacgtcaga | tgacgtgcct | tttttcttgt | 10320 |
| ctagcgtgca | ccaatgcttc | tggcgtcagg | cagccatcgg | aagctgtggt | atggctgtgc | 10380 |
| aggtcgtaaa | tcactgcata | attcgtgtcg | ctcaaggcgc | actcccgttc | tggataatgt | 10440 |
| tttttgcgcc | gacatcataa | cggttctggc | aaatattctg | aaatgagctg | ttgacaatta | 10500 |
| atcatccggc | tcgtataatg | tgtggaattg | tgagcggata | acaatttcac | acaggaaaca | 10560 |
| gaccatgact | agtaaggagg | acaattccat | ggctgctgct | gctgatagat | taaacttaac | 10620 |
| ttccggccac | ttgaatgctg | gtagaaagag | aagttcctct | tctgtttctt | tgaaggctgc | 10680 |
| cgaaaagcct | ttcaaggtta | ctgtgattgg | atctggtaac | tggggtacta | ctattgccaa | 10740 |
| ggtggttgcc | gaaaattgta | agggataccc | agaagttttc | gctccaatag | tacaaatgtg | 10800 |
| ggtgttcgaa | gaagagatca | atggtgaaaa | attgactgaa | atcataaata | ctagacatca | 10860 |
| aaacgtgaaa | tacttgcctg | gcatcactct | acccgacaat | ttggttgcta | atccagactt | 10920 |
| gattgattca | gtcaaggatg | tcgacatcat | cgttttcaac | attccacatc | aattttttgcc | 10980 |
| ccgtatctgt | agccaattga | aaggtcatgt | tgattcacac | gtcagagcta | tctcctgtct | 11040 |
| aaagggtttt | gaagttggtg | ctaaaggtgt | ccaattgcta | tcctcttaca | tcactgagga | 11100 |
| actaggtatt | caatgtggtg | ctctatctgg | tgctaacatt | gccaccgaag | tcgctcaaga | 11160 |
| acactggtct | gaaacaacag | ttgcttacca | cattccaaag | gatttcagag | gcgagggcaa | 11220 |
| ggacgtcgac | cataaggttc | taaaggcctt | gttccacaga | ccttacttcc | acgttagtgt | 11280 |
| catcgaagat | gttgctggta | tctccatctg | tggtgctttg | aagaacgttg | ttgccttagg | 11340 |
| ttgtggtttc | gtcgaaggtc | taggctgggg | taacaacgct | tctgctgcca | tccaaagagt | 11400 |
| cggtttgggt | gagatcatca | gattcggtca | aatgttttc | ccagaatcta | gagaagaaac | 11460 |
| atactaccaa | gagtctgctg | gtgttgctga | tttgatcacc | acctgcgctg | gtggtagaaa | 11520 |
| cgtcaaggtt | gctaggctaa | tggctacttc | tggtaaggac | gcctgggaat | gtgaaaagga | 11580 |
| gttgttgaat | ggccaatccg | ctcaaggttt | aattacctgc | aaagaagttc | acgaatggtt | 11640 |
| ggaaacatgt | ggctctgtcg | aagacttccc | attatttgaa | gccgtatacc | aaatcgttta | 11700 |
| caacaactac | ccaatgaaga | acctgccgga | catgattgaa | gaattagatc | tacatgaaga | 11760 |
| ttagatttat | tggatccagg | aaacagacta | gaattatggg | attgactact | aaacctctat | 11820 |
| cttttgaaagt | taacgccgct | tgttcgacg | tcgacggtac | cattatcatc | tctcaaccag | 11880 |
| ccattgctgc | attctggagg | gatttcggta | aggacaaacc | ttatttcgat | gctgaacacg | 11940 |
| ttatccaagt | ctcgcatggt | tggagaacgt | ttgatgccat | tgctaagttc | gctccagact | 12000 |
| ttgccaatga | agagtatgtt | aacaaattag | aagctgaaat | tccggtcaag | tacggtgaaa | 12060 |

-continued

```
aatccattga agtcccaggt gcagttaagc tgtgcaacgc tttgaacgct ctaccaaaag    12120
agaaatgggc tgtggcaact tccggtaccc gtgatatggc acaaaaatgg ttcgagcatc    12180
tgggaatcag gagaccaaag tacttcatta ccgctaatga tgtcaaacag ggtaagcctc    12240
atccagaacc atatctgaag ggcaggaatg cttaggata tccgatcaat gagcaagacc     12300
cttccaaatc taaggtagta gtatttgaag acgctccagc aggtattgcc gccggaaaag    12360
ccgccggttg taagatcatt ggtattgcca ctactttcga cttggacttc ctaaaggaaa    12420
aaggctgtga catcattgtc aaaaaccacg aatccatcag agttggcggc tacaatgccg    12480
aaacagacga agttgaattc attttgacg actacttata tgctaaggac gatctgttga    12540
aatggtaacc cgggctgcag gcatgcaagc ttggctgttt tggcggatga gagaagattt    12600
tcagcctgat acagattaaa tcagaacgca gaagcggtct gataaaacag aatttgcctg    12660
gcggcagtag cgcggtggtc ccacctgacc ccatgccgaa ctcagaagtg aaacgccgta    12720
gcgccgatgg tagtgtgggg tctccccatg cgagagtagg gaactgccag gcatcaaata    12780
aaacgaaagg ctcagtcgaa agactgggcc tttcgtttta tctgttgttt gtcggtgaac    12840
gctctcctga gtaggacaaa tccgccggga gcggatttga acgttgcgaa gcaacggccc    12900
ggagggtggc gggcaggacg cccgccataa actgccaggc atcaaattaa gcagaaggcc    12960
atcctgacgg atggcctttt tgcgtttcta caaactccag ctggatcggg cg            13012
```

<210> SEQ ID NO 164
<211> LENGTH: 34
<212> TYPE: DNA
<213> ORGANISM: Artificial Sequence
<220> FEATURE:
<223> OTHER INFORMATION: Synthetic Construct

<400> SEQUENCE: 164

```
atgctcgagc tgttgacaat taatcatccg gctc                                 34
```

<210> SEQ ID NO 165
<211> LENGTH: 33
<212> TYPE: DNA
<213> ORGANISM: Artificial Sequence
<220> FEATURE:
<223> OTHER INFORMATION: Synthetic Construct

<400> SEQUENCE: 165

```
cgatctagaa aggcccagtc tttcgactga gcc                                  33
```

<210> SEQ ID NO 166
<211> LENGTH: 22
<212> TYPE: DNA
<213> ORGANISM: Artificial Sequence
<220> FEATURE:
<223> OTHER INFORMATION: Synthetic Construct

<400> SEQUENCE: 166

```
ggattttggc catttccagc tt                                              22
```

<210> SEQ ID NO 167

<400> SEQUENCE: 167

000

<210> SEQ ID NO 168
<211> LENGTH: 20

<212> TYPE: DNA
<213> ORGANISM: Artificial Sequence
<220> FEATURE:
<223> OTHER INFORMATION: Synthetic Construct

<400> SEQUENCE: 168
cttaaatcat ttaaaatagc            20

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175
<211> LENGTH: 22
<212> TYPE: DNA
<213> ORGANISM: Artificial Sequence
<220> FEATURE:
<223> OTHER INFORMATION: Synthetic Construct

<400> SEQUENCE: 175
gctctgaata gtgatagagt ca            22

<210> SEQ ID NO 176
<211> LENGTH: 199
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 112
<223> OTHER INFORMATION: n = any nucleotide

<400> SEQUENCE: 176
taaatcttac ccggcgcaga acaggatacc atgtttttt acctcctttg caccttcatg            60

```
gtggtcagtg cgtcctgctg atgtgctcag tatcaccgcc agtggtattt angtcaacac    120
cgccagagat aatttatcac cgcagatggt tatctgtatg ttttttatat gaatttaata    180
cgactcacta tagggctcg                                                 199

<210> SEQ ID NO 177
<211> LENGTH: 24
<212> TYPE: DNA
<213> ORGANISM: Artificial Sequence
<220> FEATURE:
<223> OTHER INFORMATION: Synthetic Construct

<400> SEQUENCE: 177
aaagaccgac caagcgacgt ctga                                            24

<210> SEQ ID NO 178
<211> LENGTH: 445
<212> TYPE: DNA
<213> ORGANISM: Artificial Sequence
<220> FEATURE:
<223> OTHER INFORMATION: Synthetic Construct

<400> SEQUENCE: 178
aaagaccgac caagcgacgt ctgagagctc cctggcgaat tcggtaccaa taaaagagct     60
ttattttcat gatctgtgtg ttggttttg tgtgcggcgc ggaagttcct attctctaga    120
aagtatagga acttcctcga gccctatagt gagtcgtatt aaattcatat aaaaaacata    180
cagataacca tctgcggtga taaattatct ctggcggtgt tgacataaat accactggcg    240
gtgatactga gcacatcagc aggacgcact gaccaccatg aagtgcaaa ggaggtaaaa     300 aaacatggta tcctgttctg cgccgggtaa gatttacctg ttcggtgaac acgccgtagt    360
ttatggcgaa actgcaattg cgtgtgcggt ggaactgcgt acccgtgttc gcgcggaact    420
caatgactct atcactattc agagc                                          445

<210> SEQ ID NO 179
<211> LENGTH: 445
<212> TYPE: DNA
<213> ORGANISM: Artificial Sequence
<220> FEATURE:
<223> OTHER INFORMATION: Synthetic Construct

<400> SEQUENCE: 179
aaagaccgac caagcgacgt ctgagagctc cctggcgaat tcggtaccaa taaaagagct     60
ttattttcat gatctgtgtg ttggttttg tgtgcggcgc ggaagttcct attctctaga    120
aagtatagga acttcctcga gccctatagt gagtcgtatt aaattcatat aaaaaacata    180
cagataacca tctgcggtga taaattatct ctggcggtgt tgacctaaat accactggcg    240
gtgatactga gcacatcagc aggacgcact gaccaccatg aagtgcaaa ggaggtaaaa     300 aaacatggta tcctgttctg cgccgggtaa gatttacctg ttcggtgaac acgccgtagt    360
ttatggcgaa actgcaattg cgtgtgcggt ggaactgcgt acccgtgttc gcgcggaact    420
caatgactct atcactattc agagc                                          445

<210> SEQ ID NO 180
<211> LENGTH: 442
<212> TYPE: DNA
<213> ORGANISM: Artificial Sequence
<220> FEATURE:
<223> OTHER INFORMATION: Synthetic Construct

<400> SEQUENCE: 180
```

```
aaagaccgac caagcgacgt ctgagagctc cctggcgaat tcggtaccaa taaaagagct    60
ttattttcat gatctgtgtg ttggttttg tgtgcggcgc ggaagttcct attctctaga    120
aagtatagga acttcctcga gccctatagt gagtcgtatt aaattcatat aaaaaacata    180
cagataacca tctgcggtga taaattatct ctggcggtgt tgacctaaat accactggcg    240
gtgatactga gcacatcagc aggacgcact gaccaccatg aaggtgcaaa ggtaaaaaaa    300
catggtatcc tgttctgcgc cgggtaagat ttacctgttc ggtgaacacg ccgtagttta    360
tggcgaaact gcaattgcgt gtgcggtgga actgcgtacc cgtgttcgcg cggaactcaa    420
tgactctatc actattcaga gc    442
```

<210> SEQ ID NO 181
<211> LENGTH: 445
<212> TYPE: DNA
<213> ORGANISM: Artificial Sequence
<220> FEATURE:
<223> OTHER INFORMATION: Synthetic Construct

<400> SEQUENCE: 181

```
aaagaccgac caagcgacgt ctgagagctc cctggcgaat tcggtaccaa taaaagagct    60
ttattttcat gatctgtgtg ttggttttg tgtgcggcgc ggaagttcct attctctaga    120
aagtatagga acttcctcga gccctatagt gagtcgtatt aaattcatat aaaaaacata    180
cagataacca tctgcggtga taaattatct ctggcggtgt tgacgtaaat accactggcg    240
gtgatactga gcacatcagc aggacgcact gaccaccatg aaggtgcaaa ggaggtaaaa    300
aaacatggta tcctgttctg cgccgggtaa gatttacctg ttcggtgaac acgccgtagt    360
ttatggcgaa actgcaattg cgtgtgcggt ggaactgcgt acccgtgttc gcgcggaact    420
caatgactct atcactattc agagc    445
```

<210> SEQ ID NO 182
<211> LENGTH: 22
<212> TYPE: DNA
<213> ORGANISM: Artificial Sequence
<220> FEATURE:
<223> OTHER INFORMATION: Synthetic Construct

<400> SEQUENCE: 182

```
gctattctga tggggctgat cc    22
```

<210> SEQ ID NO 183
<211> LENGTH: 22
<212> TYPE: DNA
<213> ORGANISM: Artificial Sequence
<220> FEATURE:
<223> OTHER INFORMATION: Synthetic Construct

<400> SEQUENCE: 183

```
gcctttatcg cctactgcca gc    22
```

<210> SEQ ID NO 184
<211> LENGTH: 24
<212> TYPE: DNA
<213> ORGANISM: Artificial Sequence
<220> FEATURE:
<223> OTHER INFORMATION: Synthetic Construct

<400> SEQUENCE: 184

```
cgtagcgcat caggcaattt tgcg    24
```

```
<210> SEQ ID NO 185
<211> LENGTH: 23
<212> TYPE: DNA
<213> ORGANISM: Artificial Sequence
<220> FEATURE:
<223> OTHER INFORMATION: Synthetic Construct

<400> SEQUENCE: 185
gtgacttccg aaggtctggc agc                                              23

<210> SEQ ID NO 186
<211> LENGTH: 18
<212> TYPE: DNA
<213> ORGANISM: Artificial Sequence
<220> FEATURE:
<223> OTHER INFORMATION: Synthetic Construct

<400> SEQUENCE: 186
gacgctttcg ccaagtca                                                    18

<210> SEQ ID NO 187
<211> LENGTH: 21
<212> TYPE: DNA
<213> ORGANISM: Artificial Sequence
<220> FEATURE:
<223> OTHER INFORMATION: Synthetic Construct

<400> SEQUENCE: 187
gtcaggctgg aatactcttc g                                                21

<210> SEQ ID NO 188
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4, 5, 6, 7, 8, 9
<223> OTHER INFORMATION: n = any nucleotide

<400> SEQUENCE: 188
ccannnnnnt gg                                                          12
```